(12) United States Patent
Yoshida et al.

(10) Patent No.: US 7,074,801 B1
(45) Date of Patent: Jul. 11, 2006

(54) NITROGEN-CONTAINING CONDENSED CYCLIC COMPOUND HAVING A PYRAZOLYL GROUP AS A SUBSTITUENT GROUP AND PHARMACEUTICAL COMPOSITION THEREOF

(75) Inventors: Ichiro Yoshida, Ibaraki (JP); Naoki Yoneda, Ibaraki (JP); Yoshiaki Ohashi, Ibaraki (JP); Shuichi Suzuki, Ibaraki (JP); Mitsuaki Miyamoto, Ibaraki (JP); Futoshi Miyazaki, Ibaraki (JP); Hidenori Seshimo, Saitama (JP); Junichi Kamata, Ibaraki (JP); Yasutaka Takase, Ibaraki (JP); Manabu Shirato, Ibaraki (JP); Daiya Shimokubo, Ibaraki (JP); Yoshinori Sakuma, Ibaraki (JP); Hiromitsu Yokohama, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 94 days.

(21) Appl. No.: 10/475,585

(22) PCT Filed: Apr. 25, 2002

(86) PCT No.: PCT/JP02/04156

§ 371 (c)(1),
(2), (4) Date: Oct. 23, 2003

(87) PCT Pub. No.: WO02/088107

PCT Pub. Date: Nov. 7, 2002

(30) Foreign Application Priority Data

Apr. 26, 2001 (JP) ............................. 2001-129959

(51) Int. Cl.
A61K 31/517 (2006.01)
A61K 31/4725 (2006.01)
C07D 417/04 (2006.01)
C07D 401/14 (2006.01)
C07D 217/02 (2006.01)

(52) U.S. Cl. ................ 514/266.23; 514/307; 514/314; 546/118; 546/121; 546/122; 546/144; 546/167

(58) Field of Classification Search ................ 546/121, 546/122, 167, 144, 118; 514/266.23, 307, 514/314
See application file for complete search history.

(56) References Cited

U.S. PATENT DOCUMENTS

| 5,232,939 | A | | 8/1993 | Terada et al. |
| 5,932,576 | A | | 8/1999 | Anantanarayan et al. |
| 6,156,766 | A | * | 12/2000 | Arita et al. ................. 514/300 |
| 6,214,807 | B1 | * | 4/2001 | Zablocki et al. .............. 514/46 |
| 6,352,989 | B1 | * | 3/2002 | Miyazaki et al. ...... 514/266.21 |
| 6,448,281 | B1 | * | 9/2002 | Beaulieu et al. .............. 514/394 |
| 6,664,395 | B1 | * | 12/2003 | Letavic et al. ............... 544/405 |
| 6,710,054 | B1 | * | 3/2004 | Nakao et al. ................ 514/303 |
| 6,770,634 | B1 | * | 8/2004 | Zablocki et al. .............. 514/46 |
| 6,897,230 | B1 | * | 5/2005 | Fukuda et al. ............... 514/376 |
| 2001/0044445 | A1 | * | 11/2001 | Bamaung et al. ............ 514/277 |
| 2002/0012946 | A1 | * | 1/2002 | Belardinelli et al. ......... 435/7.1 |
| 2002/0077329 | A1 | * | 6/2002 | Audoly et al. ......... 514/263.35 |
| 2003/0078232 | A1 | * | 4/2003 | Elzein et al. .................. 514/46 |
| 2003/0092749 | A1 | * | 5/2003 | Dombroski et al. ........ 514/365 |
| 2003/0125367 | A1 | * | 7/2003 | Fukuda et al. ............... 514/376 |

FOREIGN PATENT DOCUMENTS

| EP | 656359 A1 | 6/1995 |
| EP | 791594 A2 | 8/1997 |
| JP | 58-41897 A | 3/1983 |
| WO | WO 96/03385 A1 | 2/1996 |
| WO | WO 96/20954 A2 | 7/1996 |
| WO | WO 98/41090 A1 | 9/1998 |
| WO | WO 98/52940 A1 | 11/1998 |
| WO | WO 98/52941 A1 | 11/1998 |
| WO | WO 00/31063 A1 | 6/2000 |
| WO | WO 00/78778 A2 | 12/2000 |
| WO | WO 01/62979 A2 | 8/2001 |
| WO | WO 02/14321 A1 | 2/2002 |

(Continued)

OTHER PUBLICATIONS

Zablocki, J. et al., "2-Substituted Pi System Derivatives of Adenosine That Are Coronary Vasodilators" Nucleosides, Nucleotides & Nucleic Acids, vol. 20(4-7): 343-360 (Apr.-Jul. 2001)(available on-line Mar. 31, 2001) at p. 350, Table 4 (cmpd 31 "CVT-3033").*

(Continued)

*Primary Examiner*—Kamal A. Saeed
*Assistant Examiner*—Anthony J. Paviglianiti
(74) *Attorney, Agent, or Firm*—Birch, Stewart, Kolasch & Birch, LLP

(57) ABSTRACT

The present invention discloses compounds and compositions of formula (I):

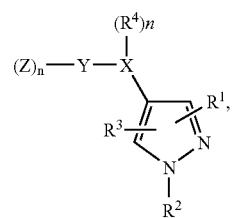

having inhibitory activity on activation of STAT6, wherein X represents quinoline, isoquinoline, quinazoline or imidazopyridine; Y represents phenyl, piperazine, pyridine, thiophene, thiazole, oxathiazole or oxathiadiazole; and variables Z, n, $R^1$, $R^2$, $R^3$ and $R^4$ are as defined in the claims.

17 Claims, No Drawings

FOREIGN PATENT DOCUMENTS

| WO | WO 2003051833 A2 * | 6/2003 |
|---|---|---|
| WO | WO 2003070723 A1 * | 8/2003 |

OTHER PUBLICATIONS

Zhenhai Gao, et al., "Novel Short-Acting A2A Adenosine Receptor Agonists for Coronary Vasodilation," J. Pharmacology and Experimental Therapeutics, vol. 298:209-218 (Jul. 2001) at p. 218 lines 37-38 (CVT-3033), lines 39-40 (CVT-3032), lines 46-47 (CVT-3126).*

Magn. Reson. Chem., vol. 34, No. 4, pp. 318-323 (1996), Cudero, J. et al.

Chemical Abstracts, vol. 120, abs. No. 54498, Jonas, R. et al.

Chemical Abstracts, vol. 119, abs. No. 8730, Awad, IMA.

Chemical Abstracts, vol. 117, abs. No. 13117, Awad, IMA.

Phosphorus Sulfur Silicon Relat. Elem., vol. 66, No. 1-4, pp. 29-35 (1992), Ismail, N. et al.

Tetrahedron Lett., vol. 32, No. 50, pp. 7415-7418 (1991), Hamamichi, N.

Indian J. Chem., Sect. B, vol. 30B, No. 3, pp. 371-374 (1991), Essawy, S.A.

Chemical Abstracts, vol. 114, abs. No. 207112, Awad, I. M. A.

Chem. Pham. Bull., vol. 38, No. 7, pp. 2018-2019 (1990), Hamamichi, N. et al.

Mosmann et al., The Journal of Immunology, vol. 136, No. 7, 2348-2357, Apr. 1, 1986.

Darnell, Jr. et al., Science, vol. 264, 1415-1421, Jun. 3, 1994.

Quelle et al., Molecular and Cellular Biology, vol. 15, No. 6, 3336-3343, Jun. 1995.

Izuhara et al., The Journal of Biological Chemistry, vol. 271, No. 2, 619-622, Jan. 12, 1996.

T. Akimoto et al., J. Exp. Med., vol. 187, No. 9, 1537-1542, May 4, 1998.

D. Kuperman et al., J. Exp. Med., vol. 187, No. 6, 939-948, Mar. 16, 1998.

* cited by examiner

NITROGEN-CONTAINING CONDENSED CYCLIC COMPOUND HAVING A PYRAZOLYL GROUP AS A SUBSTITUENT GROUP AND PHARMACEUTICAL COMPOSITION THEREOF

This application is the national phase under 35 U.S.C. § 371 of PCT International Application No. PCT/JP02/04156 which has an International filing date of Apr. 25, 2002, which designated the United States of America.

TECHNICAL FIELD

The present invention relates to a novel nitrogen-containing condensed cyclic compound having an inhibitory action on activation of STAT6.

PRIOR ART

The degree of onset of allergic diseases (for example bronchial asthma, atopic dermatitis, pollinosis, etc.) is raising mainly on advanced nations, and these diseases come to be a socially important problem. By extensive study in recent years, it is recognized that allergic inflammations caused by immunocompetent cells are a fundamental morbid state of allergic diseases. Lymphocytes called helper T cells play an important role in balance/homeostasis in the immune system, and are classified into helper I type T cells (Th1) and helper II type T cells (Th2), depending on a pattern of cytokine secreted (Mosmann et al., J. Immunol. 136:2348, 1986). It is known that Th1 cells are involved in cellular immune response, and also that Th2 cells produce cytokines such as interleukin (IL)-4, IL-5, IL-10 and IL-13, to activate humoral immune response. It is reported that the balance between Th1 and Th2 in patients with allergic diseases such as bronchial asthma, atopic dermatitis, etc. inclines Th2 to predominance in many cases. Cytokines such as IL-5, IL-3, etc. secreted from Th2 act on eosinophils, to promote their infiltration, and thus Th2 predominance is regarded as one factor causing not only immediate type allergic reaction but also delayed type allergic reaction.

Many allergic diseases are IgE-dependent allergies. Immunologically, a definite correlation between a disease such as asthma or atopic dermatitis and total IgE level in serum or antigen-specific IgE antibody level. It is estimated that antigen-specific IgE produced by B cells upon sensitization with allergen binds to high-affinity IgE receptor on mast cells, and the degranulation of the mast cells, upon being exposed again to allergen, is triggered by the binding of the allergen to IgE, to induce immediate type allergic diseases. IL-4 and IL-13 i.e. cytokines produced by Th2 cells play a major role in activation of B cells producing IgE antibody, class switch of B cell, growth of mast cells, and promotion of histamine secretion. It is also estimated that the Th2 type cytokines play a major role in activation of Th2 cells themselves, and it is reported that for example IL-4 acts on differentiation of peripheral naïve T cells into Th2, to form a state of Th2 predominance, and Th2 itself also induces immune reaction by secretion of IL-4 and IL-13. Thus, Th2 cells and IgE antibody participate closely in allergic inflammations in bronchial asthma, and especially Th2 cells are notified as cells regulating allergic reaction.

At present, steroid inhalations come to be used as a base drug in clinical therapy of bronchial asthma, and there are cases where use of oral steroids is unavoidable in control of morbid states, or inhalations are not suitable because of inadequate respiratory functions. On one hand, steroids have the problem of side effects, and thus administration thereof to infants and old people poor in resistance should be careful, and even for oral steroids, there are some patients with hardly controlled steroid resistance. Further, steroids are often used in therapy of atopic dermatitis, but long-term administration should be careful because of the problem of side effects.

The STAT (signal transducer and activator of transcription) family members are intracellular proteins containing an SH2 (Src homology 2) region and play fundamental roles in relaying intracellular signals elicited by cytokines into a nucleus (Darnell J. et al., Science, 264, 1415–1421 (1994)), and these proteins themselves function as transcriptional factors. Among STAT proteins, STAT6 is known as an important transcriptional factor transmitting signals of IL-4 and IL-13 (Quelle F W et al., Mol. Cell. Biol, 15, 3336 (1995)), and blocking of a signal transduction pathway via STAT6 is considered very effective in invalidating the action of IL-4 and IL-13. For example, it is reported that when STAT6 is inhibited, the up-regulation of IgE receptor is inhibited (Izuhara K., J. Biol. Chem. 271, 619 (1996)). Further, it is reported that respiratory-tract inflammations accompanied by infiltration with eosinophils by sensitization with an antigen, and an increase in respiratory-tract hypersensitivity, are not recognized in STAT6 knockout mice (Arimoto, T et al., J. Exp. Med., 187, 16537, 1998; Kuperman D et al., J. Exp. Med., 187, 939, 1998). Accordingly, a compound having an inhibitory action on activation of STAT6 can be expected to break in many aspects a complicated chain participating in onset and progress of allergic diseases (for example bronchial asthma, allergic rhinitis, atopic dermatitis, etc.) and to be useful in treatment and prevention of allergic diseases. In particular, use of an STAT6 activation inhibitor in treatment of bronchial asthma is expected to bring about various actions based on blocking of signals of IL-4 and IL-13, such as inhibitory action on production of IgE antibody and antiinflammatory action, and expected to not only exhibit effects in a broad range from atopic to inflammatory diseases but also provide a new therapeutic method for steroid-resistant patients.

Further, the STAT6 activation inhibitor also acts on the balance and regulation in the immune system, and can thus be expected to be useful in prevention and treatment of autoimmune diseases, various infections, acquired immunodeficiency syndrome (AIDS), malignant tumors etc.

(1) There are for example the following reports on STAT protein, particularly on STAT6.

1) Antibody selective for a functional domain of STAT protein (WO96/20954);
2) Method of stimulating a rate and/or an amount of cellular growth, cell adhesion, apoptosis, cellular death etc., which comprises changing a receptor/tyrosine phosphatase-STAT pathway in cells (WO98/41090); and
3) Method of treating an allergic reaction in a patient, characterized by administering, into a patient, a therapeutically active amount of a compound having specificity for STAT6 SH2 region, said compound binding to the STAT6 SH2 region with binding affinity that is at least 50 times as high as that of binding affinity for human STAT5 SH2 region.

(2) On compounds having an inhibitory action on activation of STAT6, there are, for example, the following reports: 1) JP-A 10-175964, 2) JP-A 10-175965, 3) JP-A 11-106340, 4) JP-A 11-116481, 5) JP-A 2000-229959. However, there is no report on pyrazole compounds.

On the other hand, (3) there are the following reports on pyrazole derivatives.

1) A compound represented by the following formula, or a pharmacologically acceptable salt thereof:

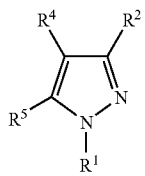

wherein R¹ is a group selected from hydride, alkyl, alkenyl, etc.; R² and R³ are groups selected independently from aryl, cycloalkyl, cycloalkenyl and heterocycle, and one of R² and R³ is substituted with an alkylsulfonyl group etc.; and R⁴ represents a group selected from hydride, alkyl, haloalkyl, cyano, acyl, alkoxy etc. (WO96/03385);

2) A compound represented by the following formula, or a pharmacologically acceptable salt thereof:

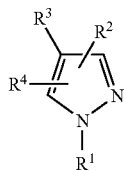

wherein R¹ is a group selected from hydride, alkyl, alkenyl, etc.; R² is a group selected from hydride, halogen, alkyl, alkenyl, alkynyl, aryl, etc.; R³ is a group selected from pyridinyl, pyrimidinyl, quinolyl, purinyl group etc.; and R⁴ is a group selected from hydride, alkyl, alkenyl etc. (WO98/52940);

3) A compound represented by the following formula, or a pharmacologically acceptable salt thereof:

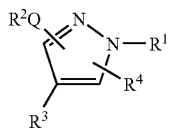

wherein R¹ is a group selected from hydride, alkyl, cycloalkyl, etc.; Q is a group selected from oxy, thio, alkylene, alkenylene, etc.; R² is an aryl group which may be substituted halo, alkyl etc.; R³ is a heteroaryl group which may be substituted halo, alkyl, alkoxy, alkylthio, etc.; and R⁴ is a group selected from hydride, alkyl, aryl etc. (WO98/52941); and 4) WO00/31063; 5) WO00/39116; 6) WO00/75131; and 7) JP-A 8-183787.

However, none of the pyrazole derivatives are provided with a description or suggestion of the relationship thereof with STAT6. Further, there is no description of compounds having a nitrogen-containing complex aromatic heterocyclic group added to the 4-position of the pyrazole ring, said aromatic group being substituted with a cyclic group such as a cycloalkyl group, aromatic group or a non-aromatic heterocyclic group.

The compound having an inhibitory action on activation of STAT6 can be expected to exhibit various actions such as inhibition of IgE antibody production, anti-inflammatory action, etc. by blocking IL-4 and IL-13 signals. Further, the compound having an inhibitory action on activation of STAT6 can not only exhibit effects of preventing and treating a broad range of diseases from atopic to inflammatory diseases but also provide a new therapeutic method for steroid-resistant patients by enabling a reduction in the amount of steroids having possible side effects. Accordingly, the compound having an inhibitory action on activation of STAT6 is desired as a medicine as a substitute for conventional therapeutic medicines such as steroids for allergic diseases, but none of the compound having an excellent inhibitory action on activation of STAT6 and acting clinically and effectively with sufficient pharmacological activity, safety and movement in the body as a pharmaceutical preparation has been found.

DISCLOSURE OF THE INVENTION

In view of the foregoing, the present inventors made extensive study for the purpose of providing a compound having a more excellent inhibitory action on activation of STAT6 and pharmaceutical composition thereof, and as a result, they found that the "nitrogen-containing condensed cyclic compound having a pyrazolyl group as a substituent group and a pharmaceutical composition thereof" having a novel structure have an excellent inhibitory action on activation of STAT6, and the present invention was thereby completed.

The present invention relates to:

1) a compound represented by the following formula (I), or a salt thereof or a hydrate thereof:

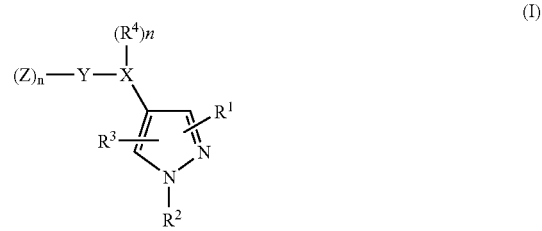

(wherein X represents a nitrogen-containing condensed aromatic heterocyclic group and has $(R^4)_n$ as substituent groups whereupon n is 0, 1, 2 or 3, and the substituent groups $(R^4)_n$ independently represent a hydrogen atom, halogen atom, cyano group, hydroxyl group, amino group, $C_{1-6}$alkyl group, halogenated $C_{1-6}$alkyl group, $C_{2-6}$ alkenyl group, $C_{1-6}$ alkylsulfonyl group, $C_{1-6}$ alkylsulfonylamino group, $C_{1-6}$ alkylsulfinyl group, N—($C_{1-6}$ alkyl)amino group, N,N-di($C_{1-6}$ alkyl)amino group, $C_{1-6}$ alkoxy group, $C_{1-6}$ alkylsulfanyl group, carbamoyl group, N—($C_{1-6}$ alkyl)carbamoyl group, N,N-di($C_{1-6}$ alkyl)carbamoyl group, sulfamoyl group, phenyl group, heteroaryl group, phenoxy group, heteroallyloxy group, phenyl $C_{1-6}$ alkylamino group or heteroaryl $C_{1-6}$ alkylamino group, which is bound to an atom constituting X;

Y represents a $C_{3-8}$ cycloalkyl group, a $C_{4-8}$ cycloalkenyl group, a 5- to 14-membered non-aromatic heterocyclic group, a $C_{6-14}$ aromatic hydrocarbon cyclic group, a 5- to 14-membered aromatic heterocyclic group, a condensed cyclic group consisting of a benzene ring and a 5- to 7-membered non-aromatic ring, or a condensed cyclic group consisting of a 5- to 6-membered aromatic heterocyclic ring and a 5- to 7-membered non-aromatic ring;

(Z)n are n (Z) groups bound to Y, whereupon n is 0, 1, 2 or 3, Z groups are bound to an atom constituting the cyclic group Y and independently represent a group selected from (1) hydrogen atom, (2) amino group, (3) halogen atom, (4) hydroxyl group, (5) nitro group, (6) cyano group, (7) azido group, (8) formyl group, (9) hydroxyamino group, (10) sulfamoyl group, (11) guanodino group, (12) oxo group, (13) $C_{2-6}$ alkenyl group, (14) $C_{1-6}$ alkoxy group, (15) $C_{1-6}$ alkyl hydroxyamino group, (16) halogenated $C_{1-6}$alkyl group, (17) halogenated $C_{2-6}$ alkenyl group, (18) formula $-M^1-M^2-M^3$ wherein:

$M^1$ and $M^2$ each represent a single bond, $-(CH_2)_m-$, $-CHR^5CHR^6-$, $-(CH_2)_m-CR^5R^6-(CH_2)_n-$, $-CR^5=CR^6-$, $-C\equiv C-$, $-CR^5=CR^6-CO-$, $-(CH_2)_m-O-(CH_2)_n-$, $-O-(CH_2)_n-CR^5R^6-$, $-(CH_2)_m-S-(CH_2)_n-$, $-SO(CH_2)_m-$, $-SO_2(CH_2)_m-$, $-CO(CH_2)_m-$, $-COO-$, $-CONR^7-$, $-CONR^7CHR^8-$, $CONR^7-CR^5R^6-$, $-CONR^7-(CH_2)_m-$, $-NR^7-$, $-NR^7CO-CR^5R^6-$, $-NR^7CO-CR^5R^6-CO-$, $-NR^7CO-(CH_2)_m-$, $-NR^7SO_2(CH_2)_m-$, $-SO_2NR^7-(CH_2)_m-$, $-SO_2NR^7-CR^5R^6-$, $-NR^7CONR^8-$, or $-NR^7CSNR^8-$ whereupon n and m are independently 0, 1, 2 or 3, or (19) a group selected from (a) $C_{6-14}$ aromatic hydrocarbon cyclic group, (b) $C_{3-14}$cycloalkyl group, (c) $C_{4-14}$ cycloalkenyl group, (d) 5- to 14-membered aromatic heterocyclic group, or (e) 4- to 14-membered non-aromatic heterocyclic group, each of which may be substituted with 4 or less groups selected from the substituent group Q, $M^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) $-OR^7$, (xviv) $-NR^7R^8$, (xx) $-NR^7COR^8$, (xxi) $-COR^7$, (xxii) $-CONR^7R^8$, (xxiii) $-SOR^7$, (xxiv) $-SO_2R^7$, (xxv) $-NR^7SO_2R^8$, (xxvi) $-SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

the substituent group Q represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, $-OR^7$, $-OCH_2CONR^7R^8$, $-NR^7R^8$, $-NR^7COR^8$, $-COR^7$, $-CONR^7R^8$, $-SOR^7$, $-SO_2R^7$, $-NR^7SO_2R^8$, $-SO_2NR^7R^8$, methylene dioxy group or ethylene dioxy group;

$R^1$ represents (1) hydrogen atom, (2) halogen atom, (3) hydroxyl group, (4) nitro group, (5) cyano group, (6) halogenated $C_{1-6}$ alkyl group, (7) $C_{2-6}$ alkyl group substituted with a hydroxyl or cyano group, (8) $C_{2-6}$ alkenyl group, or (9) formula $-L^1-L^2-L^3$ whereupon 1) $-L^1$ represents a single bond, $-(CH_2)_m-$, $-(CH_2)_m-CR^5R^6-(CH_2)_n-$, $-CR^5=CR^6-$, $-CH=CR^5-CO-$, $-(CH_2)_m-O-(CH_2)_n-$, $-CO(CH_2)_m-$, $-COO-$, $-NR^7-$, $-CO-NR^7-$, $-NR^7CO-$, $-NR^7CO-(CH_2)_m-$, $-NR^7CONR^8-$, whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

2) $L^2$ represents a single bond, $-(CH_2)_m-$, $-CR^5R^6-$, $-(CH_2)_m-CR^5R^6-(CH_2)_n-$, $-CR^5=CR^6-$, $-C\equiv C-$, $-CR=CR^5-CO-$, $-O-$, $-S-$, $-SO-$, $-SO_2-$, $-SO_2-(CH_2)_m-$, $-(CH_2)_m-O-(CH_2)_n-$, $-O-(CH_2)_n-CR^5R^6-$, $-CO-(CH_2)_m-$, $-COO-$, $-NR^7-$, $-CO-NR^7-$, $-CO-NR^7-(CH_2)_m-$, $-NR^7CO-$, $-NR^7CO-(CH_2)_m-$, $-NR^7SO_2-$, $-SO_2NR^7-$, $-NR^7CONR^8-$, or $-NR^7CSNR^8-$ whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group which may be substituted with 4 or less substituent groups selected from the substituent group Q;

3) $L^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$alkenyl group, (xv) $C_{2-6}$ alkynyl group, (xvi) halogenated $C_{2-6}$ alkenyl group, (xvii) halogenated $C_{1-6}$ alkoxy group, (xviii) $-OR^7$, (xviv) $-NR^7R^8$, (xx) $-NR^7COR^8$, (xxi) $-COR^7$, (xxii) $-CONR^7R^8$, (xxiii) $-SOR^7$, (xxiv) $-SO_2R^7$, (xxv) $-NR^7SO_2R^8$, (xxvi) $-SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

$R^2$ represents a hydrogen atom or a group for protecting pyrazole nitrogen, $R^3$ represents a hydrogen atom, halogen atom, cyano group, amino group, $C_{1-4}$ alkyl group or halogenated $C_{1-4}$ alkyl group, the above-mentioned $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and the above-mentioned $R^7$ and $R^8$ are the same or different and each represent a hydrogen atom, $C_{1-6}$ alkyl group, halogenated C$_{1-6}$ alkyl group, C$_{3-8}$ cycloalkyl group, phenyl group or 5- to 6-membered aromatic heterocyclic group);

2) the compound according to 1), a salt thereof or a hydrate of them, wherein in the formula (I), X is a nitrogen-containing condensed aromatic heterocyclic group represented by the formula (II):

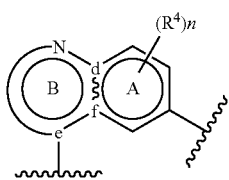

(II)

(wherein rings A and B are combined to form a 9- to 10-membered nitrogen-containing condensed aromatic heterocyclic group, and have (R$^4$)$_n$ as substituent groups, whereupon n in the substituent groups (R$^4$)$_n$ is 0, 1 or 2, the substituent groups R$^4$ independently represent a hydrogen atom, halogen atom, cyano group, hydroxyl group, amino group, C$_{1-6}$alkyl group, halogenated C$_{1-6}$alkyl group, C$_{2-6}$ alkenyl group, C$_{1-6}$ alkylsulfonyl group, C$_{1-6}$ alkylsulfonylamino group, C$_{1-6}$ alkylsulfinyl group, N—(C$_{1-6}$ alkyl)amino group, N,N-di(C$_{1-6}$ alkyl)amino group, C$_{1-6}$ alkoxy group, C$_{1-6}$ alkylthio group, carbamoyl group, N—(C$_{1-6}$ alkyl)carbamoyl group, N,N-di(C$_{1-6}$ alkyl)carbamoyl group, sulfamoyl group, phenyl group, heteroaryl group, phenoxy group, heteroaryloxy group, phenyl C$_{1-6}$ alkylamino group or heteroaryl C$_{1-6}$ alkylamino group, each of which is bound to an atom constituting ring A and/or ring B, provided that when the 10-membered nitrogen-containing condensed aromatic heterocyclic group formed by the rings A and B is a quinazoline ring, and simultaneously R$^4$ is an amino group, N—(C$_{1-6}$alkyl)amino group and/or N,N-di(C$_{1-6}$ alkyl)amino group, R$^4$ is not bound to the atom at the 2-position of the quinazolinyl ring, the ring A represents a 6-membered aromatic hydrocarbon cyclic group or a 6-membered aromatic heterocyclic group;

the ring B represents a 5- or 6-membered nitrogen-containing aromatic heterocyclic group, and may contain 1, 2 or 3 heteroatoms selected from a nitrogen atom, an oxygen atom and a sulfur atom, d, f and e are adjacent in this order, are the same or different and represent a carbon atom or a nitrogen atom, provided that d and e do not simultaneously represent a nitrogen atom, and when e represents a nitrogen atom, d and f each represent a carbon atom, and the ring A binds to the 4-position of the pyrazole ring, and the ring B binds via e to Y in the formula (I));

3) the compound according to 1) or 2), a salt thereof or a hydrate of them, wherein in the formula (I), X is an imidazo[1,2-a]pyridine cyclic group, benzimidazole cyclic group, quinazoline cyclic group, quinoline cyclic group, or 2,1-benzisoxazole cyclic ring;

4) the compound according to 2) or 3), a salt thereof or a hydrate of them wherein in the formula (II), n in the substituent groups (R$^4$)$_n$ is 0, 1 or 2, and the substituent groups R$^4$ independently represent a hydrogen atom, halogen atom, cyano group, hydroxyl group, amino group, a C$_{1-6}$ alkyl group, a halogenated C$_{1-6}$ alkyl group, an N—(C$_{1-6}$ alkyl)amino group or a C$_{1-6}$ alkoxy group;

5) the compound according to 1) or 2), a salt thereof or a hydrate of them, wherein in the formula (I), X is an imidazo[1,2-a]pyridine cyclic group, benzimidazole cyclic group, quinazoline cyclic group, quinoline cyclic group, or 2,1-benzisoxazole cyclic ring, n in the substituent groups (R$^4$)$_n$ is 0, 1 or 2, and the substituent groups R$^4$ independently represent a hydrogen atom, halogen atom, cyano group, hydroxyl group, amino group, a C$_{1-6}$alkyl group, a halogenated C$_{1-6}$alkyl group, an N—(C$_{1-6}$ alkyl)amino group or a C$_{1-6}$ alkoxy group, and Y is a C$_{5-6}$ cycloalkyl group, C$_{5-7}$ cycloalkenyl group, phenyl group, naphthyl group, monocyclic or bicyclic 5- to 10-membered non-aromatic heterocyclic group, monocyclic or bicyclic 5- to 14-membered aromatic heterocyclic group, a condensed cyclic group of a benzene ring and a 5- to 7-membered non-aromatic ring, or a condensed cyclic group of a 5- to 6-membered aromatic heterocyclic ring and a 5- to 7-membered non-aromatic ring;

6) the compound according to 4) or 5), a salt thereof or a hydrate of them, wherein in the formula (I), R$^2$ is a hydrogen atom, trityl group, tetrahydropyranyl group, t-butyldimethylsilyl group, t-butoxycarbonyl group or pivaloyloxymethyl group, R$^3$ is a hydrogen atom, n in the substituent groups (R$^4$)$_n$ is 0, 1 or 2, and the substituent groups R$^4$ independently represent a hydrogen atom, halogen atom, cyano group, carbamoyl group, C$_{1-6}$ alkyl group or halogenated C$_{1-6}$ alkyl group;

7) the compound according to 5) or 6), a salt thereof or a hydrate thereof, wherein in the formula (I), X is an imidazo[1,2-a]pyridine cyclic group, benzimidazole cyclic group, quinazoline cyclic group, quinoline cyclic group, or 2,1-benzisoxazole cyclic ring, Y is a 5- to 7-membered cyclic group containing 0, 1 or 2 nitrogen atoms, which is saturated or has one double bond in the cycle, a phenyl group, a monocyclic or bicyclic 5- to 14-membered aromatic heterocyclic ring, and binds to X via a carbon or nitrogen atom on Y, n in the substituent groups (R$^4$) n is 0, 1 or 2, the substituent groups R$^4$ independently represent a hydrogen atom, halogen atom, carbamoyl group or C$_{1-6}$ alkyl group, R$^2$ is a hydrogen atom or trityl group, and R$^3$ is a hydrogen atom;

8) the compound according to any one of 5) to 7), a salt thereof or a hydrate thereof, wherein R$^1$ represents (1) hydrogen, (2) halogen atom, (3) nitro group, (4) cyano group, (5) C$_{1-6}$alkyl group, (6) C$_{2-6}$ alkenyl group, (7) halogenated C$_{1-6}$ alkyl group, (8) C$_{2-6}$alkenyl group substituted with a hydroxyl or cyano group, (9)—CONR$^7$R$^8$, (10) —NR$^7$R$^8$, (11) —(CH$_2$)$_m$R$^9$, (12) —(CH$_2$)$_m$—O—(CH$_2$)$_n$—R$^9$, (13)—COOR$^7$ whereupon n and m independently represent 0, 1, 2 or 3, R$^7$ and R$^8$ are the same or different and each represent a hydrogen atom, C$_{1-6}$ alkyl group or C$_{3-8}$ cycloalkyl group, and R$^9$ groups are the same or different and represent a hydrogen atom, C$_{1-6}$ alkyl group, hydroxyl group, cyano group, or 1) C$_{3-8}$ cycloalkyl group, 2) C$_{4-8}$ cycloalkenyl group, 3) phenyl group, 4) 5- to 10-membered non-aromatic heterocyclic group, 5) 5- to 6-membered aromatic heterocyclic ring, each of which may be substituted with 4 or less groups selected independently from the substituent group $P^1$, or (14) (a) $C_{3-8}$ cycloalkyl group, (b) $C_{3-8}$ cycloalkenyl group, (c) 5- to 10-membered non-aromatic heterocyclic group, (d) phenyl group or (e) 5- to 10-membered aromatic heterocyclic group which may be arbitrarily substittued with 3 or less groups selected independently from the substituent group $P^1$ and with 1 or less group selected independently from the substituent group $P^2$, the above-mentioned substituent group $P^1$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, $-OR^7$, $-NR^7R^8-$, $-NR^7COR^8$, $-COR^7$, $-CONR^7R^8$, $-SOR^7$, $-SO_2R^7$, $-NR^7SO_2R^8$, or $-SO_2NR^7R^8$, whereupon $R^7$ and $R^8$ are the same or different and each represent a hydrogen atom, $C_{1-6}$ alkyl group or $C_{3-8}$ cycloalkyl group, and the substituent group $P^2$ represents $-CH_2NR^7R^8$, $-OCH_2CONR^7R^8$, $-O-(CH_2)_m-R^{10}-$, $-NR^7COR^{10}$, $NR^7COOR^{10}$, $C_{3-7}$ cycloalkyl group, $C_{4-7}$ cycloalkenyl group, phenyl group, 5- to 6-membered aromatic heterocyclic group, 5- to 7-membered non-aromatic heterocyclic group, $C_{3-7}$ cycloalkyloxy group, phenoxy group, heteroallyloxy group, methylene dioxy group or ethylene dioxy group, whereupon m is 0, 1, 2 or 3, $R^7$ and $R^8$ are the same or different and each represent a hydrogen atom, $C_{1-6}$ alkyl group or $C_{3-8}$ cycloalkyl group, $R^{10}$ represents a hydrogen atom, $C_{1-6}$ alkyl group, $C_{3-8}$ cycloalkyl group, phenyl group, 5- to 10-membered non-aromatic heterocyclic group, or 5- to 6-membered aromatic heterocyclic group;

9) the compound according to any one of 5) to 8), a salt thereof or a hydrate thereof, wherein in the formula (I), $(Z)n$ represent n $(Z)$ groups bound to Y, n is 0, 1, 2 or 3, Z groups independently represent (1) hydrogen atom, (2) amino group, (3) halogen atom, (4) hydroxyl group, (5) nitro group, (6) cyano group, (7) azido group, (8) formyl group, (9) hydroxy amino group, (10) sulfamoyl group, (11) guanodino group, (12) oxo group, (13) $C_{2-6}$ alkenyl group, (14) $C_{1-6}$ alkoxy group, (15) $C_{1-6}$ alkyl hydroxy amino group, (16) halogenated $C_{1-6}$ alkyl group, (17) halogenated $C_{2-6}$ alkenyl group, (18) $C_{3-6}$ alkynyl group, (19) formula $-J-R^{11}$ wherein J is a single bond, $-(CH_2)_m-$, $-CHR^5CHR^6-$, $-(CH_2)m-CR^5R^6-(CH_2)_n-$, $-CR^5=CR^6-$, $-C\equiv C-CR^5=CR^6-CO-$, $-(CH_2)_m-O-(CH_2)_n-$, $-O-(CH_2)_n-CR^5R^6-$, $-(CH_2)_m-S-(CH_2)_n-$, $-SO(CH_2)_m-$, $-SO_2(CH_2)_m-$, $-CO(CH_2)_m-$, $-COO-$, $-$, $CONR^7-$, $-CONR^7CHR^5-$, $-CONR^7-CR^5R^6-$, $-CONR^7-(CH_2)_m-$, $-NR^7-$, $NR^7CO-CR^5R^6-$, $NR^7CO-CR^5R^6-CO-$, $-NR^7CO-(CH_2)_m-$, $-NR^7SO_2(CH_2)_m-$, $-SO_2NR^7-(CH_2)_m-$, $-SO_2NR^7-CR^5R^6-$, $-NR^7CONR^8-$, or $-NR^7CSNR^8-$ whereupon n and m are independently 0, 1, 2 or 3, or $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and $R^7$ and $R^8$ are the same or different and each represent a hydrogen atom, $C_{1-6}$ alkyl group or $C_{3-8}$ cycloalkyl group, $R^{11}$ represents a hydrogen atom, halogen atom, hydroxyl group, cyano group, carboxyl group, $C_{1-6}$ alkyl group, $C_{1-6}$ alkoxy group, halogenated $C_{1-6}$ alkyl group, $C_{3-8}$ cycloalkyl group, $C_{3-8}$ cycloalkenyl group, phenyl group, 5- to 6-membered aromatic heterocyclic group or 5- to 6-membered non-aromatic heterocyclic group, provided that each of the $C_{3-8}$ cycloalkyl group, $C_{3-8}$ cycloalkenyl group, phenyl group, 5- to 6-membered aromatic heterocyclic group and 5- to 6-membered non-aromatic heterocyclic group may be arbitrarily substituted with 3 or less substituent groups selected independently from the substituent group $P^3$ and with 1 or less substituent group selected independently from the substituent group $P^4$, the above-mentioned substituent group $P^3$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, $-OR^7$, $-NR^7R^8$, $-NR^7COR^8$, $-COR^7$, $-CONR^7R^6$, $-SOR^7$, $-SO_2R^7$, $-NR^7SO_2R^8$, or $-SO_2NR^7R^8$, whereupon $R^7$ and $R^8$ are the same or different and each represent a hydrogen atom, $C_{1-6}$ alkyl group or $C_{3-8}$ cycloalkyl group, and the substituent group $P^4$ represents a $C_{3-7}$ cycloalkyl group, $C_{4-7}$ cycloalkenyl group, phenyl group, 5- to 6-membered aromatic heterocyclic group, 5- to 7-membered non-aromatic heterocyclic group, $C_{3-7}$ cycloalkyloxy group, phenoxy group, heteroaryloxy group, methylene dioxy group or ethylene dioxy group, each of which is a group binding to the cyclic group Y;

10) the compound according to any one of 5) to 9), a salt thereof or a hydrate of them, wherein in the formula (I), $R^1$ is (1) hydrogen, (2) halogen atom, (3) nitro group, (4) cyano group, (5) $C_{1-6}$ alkyl group, (6) $C_{2-6}$ alkenyl group, (7) halogenated $C_{1-6}$ alkyl group, (8) phenyl group, (9) 5- to 6-membered aromatic heterocyclic group, (10) 5- to 7-membered non-aromatic heterocyclic group, provided that (8) phenyl group, (9) 5- to 6-membered aromatic heterocyclic group and (10) 5- to 7-membered non-aromatic heterocyclic group may be substituted arbitrarily with 3 or less substituent groups selected independently from the substituent group $P^5$ and with 1 or less substituent group selected independently from the substituent group $P^6$, the substituent group $P^5$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, $-OR^7$, $-OCH_2CONR^7R^8$, $-NR^7R^8$, $-NR^7COR^8$, $-COR^7$, $-CONR^7R^8$, $-SOR^7-$, $SO_2R^8$, $-NR^7SO_2R^8$ or $-SO^2NR^7R^8$ whereupon $R^7$ and $R^8$ are the same or different and each represent a hydrogen atom, $C_{1-6}$ alkyl group or $C_{3-8}$ cycloalkyl group, the substituent group $P^6$ represents a $C_{3-7}$ cycloalkyl group, $C_{4-7}$ cycloalkenyl group, phenyl group, 5- to 6-membered aromatic heterocyclic group, 5- to 7-membered non-aromatic heterocyclic group, C$_{3-7}$ cycloalkyloxy group, phenoxy group, heteroaryloxy group, methylene dioxy group or ethylene dioxy group; and R$^2$, R$^3$ and R$^4$ are hydrogen atoms;

11) the compound according to any one of 1) to 10), a salt thereof or a hydrate of them, wherein in the formula (I), X is an imidazo[1,2-a]pyridine cyclic group, and Y is a phenyl group, pyridyl group, thienyl group, thiazolyl group, pyrazolyl group, 1,2,4-thiadiazolyl group, 1,2,4-oxadiazolyl group, 1,3,4-thiadiazolyl group, 1,3,4-oxadiazolyl group or benzothiazolyl group;

12) the compound according to any one of 1) to 10), a salt thereof or a hydrate of them, wherein in the formula (I), X is a quinazoline cyclic group, and Y is a phenyl group, pyridyl group, thienyl group, furyl group, imidazolyl group, pyrazolyl group, 1,3,4-thiadiazolyl group, 1,3,4-oxadiazolyl group, piperidinyl group, piperazinyl group or homopiperazinyl group;

13) the compound according to 1) represented by the formula (I), a salt thereof or a hydrate thereof, wherein the compound is the one selected from: 6-[3-(4-fluorophenyl)-1H-4-pyrazolyl]-3-[5-(methylsulfonyl)-2-thienyl]imidazo[1,2-a]pyridine hydrochloride, 6-[3-(2,4-difluorophenyl)-1H-pyrazol-4-yl]-3-(5-methylsulfonylthiophen-2-yl)imidazo[1,2-a]pyridine, 6-[3-(2,6-difluorophenyl)-1H-pyrazol-4-yl]-3-(5-methylsulfonylthiazol-2-yl)imidazo[1,2-a]pyridine, 3-(5-cyclopropyl[1,3,4]oxadiazol-2-yl)-6-[3-(2,4-difluorophenyl)-1H-pyrazol-4-yl]imidazo[1,2-a] pyridine, 6-[3-(2,4-difluorophenyl)-1H-pyrazol-4-yl]-3-(5-methoxy-[1,3,4]oxadiazol-2-yl)imidazo[1,2-a]pyridine, 6-[3-(2,6-difluorophenyl)-1H-pyrazol-4-yl]-3-(5-methoxy[1,2,4]-oxadiazol-3-yl)imidazo[1,2-a] pyridine, 3-(5-cyclopropyl-[1,2,4]oxadiazol-3-yl)-6-[3-(4-fluorophenyl)-1H-4-pyrazolyl]-imidazo[1,2-a] pyridine hydrochloride, 3-(5-cyclopropyl-[1,2,4]oxadiazol-3-yl)-6-[3-(2,4-difluorophenyl)-1H-4-pyrazolyl]-imidazo[1,2-a]pyridine trihydrochloride, 3-(5-cyclopropyl-[1,2,4]oxadiazol-3-yl)-6-[3-(2-fluoro-4-methoxyphenyl)-1H-4-pyrazolyl]-imidazo[1,2-a]pyridine trihydrochloride, 3-(5-cyclopropyl-[1,2,4]oxadiazol-3-yl)-6-[3-(2-fluorophenyl)-1H-4-pyrazolyl]-imidazo[1,2-a]pyridine trihydrochloride, 6-[3-(4-cyclopentyloxy-2-fluorophenyl)-1H-4-pyrazolyl]-3-(5-cyclopropyl-[1,2,4]oxadiazol-3-yl)-imidazo[1,2-a]-pyridine trihydrochloride, 3-(5-cyclopropyl-[1,2,4]-oxadiazol-3-yl)-6-[3-(2,6-difluorophenyl)-1H-4-pyrazolyl]-imidazo[1,2-a]pyridine trihydrochloride, 6-[3-(2,4-difluorophenyl)-1H-4-pyrazolyl]-3-(5-difluoromethyl-[1,2,4]oxadiazol-3-yl)-imidazo[1,2-a]pyridine trihydrochloride, 3-(5-difluoromethyl-[1,2,4]oxadiazol-3-yl)-6-[3-(2-fluorophenyl)-1H-4-pyrazolyl]-imidazo[1,2-a]-pyridine trihydrochloride, 6-[3-(2,6-difluorophenyl)-1H-4-pyrazolyl]-3-(5-difluoromethyl-[1,2,4]oxadiazol-3-yl)-imidazo[1,2-a]pyridine trihydrochloride, N1-[(1S)-2-(4-fluorophenyl)-1-methyl-2-oxoethyl]-2-fluoro-4-[6-(1H-4-pyrazolyl)imidazo[1,2-a]pyridin-3-yl] benzamide hydrochloride, N1-(2,4-difluorophenyl)-2-fluoro-4-[6-(1H-4-pyrazolyl)imidazo[1,2-a]pyridin-3-yl]benzamide hydrochloride, N1-(5-chloro-2-pyridyl)-2-fluoro-4-[6-(1H-4-pyrazolyl)imidazo[1,2-a]pyridin-3-yl]benzamide dihydrochloride, N1-(4-methyl-2-pyridyl)-2-fluoro-4-[6-(1H-4-pyrazolyl)imidazo[1,2-a] pyridin-3-yl]benzamide dihydrochloride, N1-(2,4-difluorophenyl)-2-chloro-4-[6-(1H-4-pyrazolyl) imidazo[1,2-a]pyridin-3-yl]benzamide hydrochloride, N1-(5-vinyl-2-pyridyl)-2-fluoro-4-[6-(1H-4-pyrazolyl) imidazo[1,2-a]pyridin-3-yl]benzamide dihydrochloride, N1-(5-ethyl-2-pyridyl)-2-fluoro-4-[6-(1H-4-pyrazolyl)imidazo[1,2-a]pyridin-3-yl]benzamide dihydrochloride, 6-[3-(4-fluorophenyl)-1H-4-pyrazolyl]-4-[5-(methylsulfonyl)-2-thienyl]quinazoline dihydrochloride, 6-[3-(2,4-difluorophenyl)-1H-pyrazol-4-yl]-4-(5-methylsulfonylthiophen-2-yl) quinazoline, 6-[3-(4-chloro-2-fluorophenyl)-1H-pyrazol-4-yl]-4-(5-methylsulfonylthiazol-2-yl) quinazoline, 4-(5-cyclopropyl[1,3,4]oxadiazol-2-yl)-6-[3-(2,4-difluorophenyl)-1H-pyrazol-4-yl] quinazoline, 4-(5-cyclopropyl[1,3,4]thiadiazol-2-yl)-6-[3-(2,4-difluorophenyl)-1H-pyrazol-4-yl] quinazoline, 6-[3-(2,6-difluorophenyl)-1H-pyrazol-4-yl]-4-(5-methoxy[1,3,4]-oxadiazol-2-yl) quinazoline, 6-(1H-pyrazol-4-yl)-4-(4-m-tolylpiperazin-1-yl)-quinazoline tri-trifluoroacetate, 4-[4-(3-methylsulfonylphenyl) piperazin-1-yl]-6-(1H-pyrazol-4-yl)quinazoline tri-trifluoroacetate, and 4-[4-(3-cyclopropylsulfonylphenyl)piperazin-1-yl]-6-(1H-pyrazol-4-yl)quinazoline tri-trifluoroacetate;

14) a compound useful for synthesizing the compound represented by the formula (I) in 1) to 13), which is represented by the formula (III):

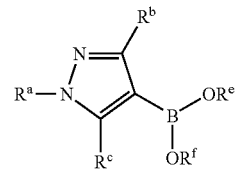

(III)

(wherein R$^a$ represents a trityl group, tetrahydropyranyl group, t-butyldimethylsilyl group, trimethylsilylethoxysilyl group, t-butoxycarbonyl group or pivaloyloxymethyl group, R$^b$ is (1) chlorine, (2) nitro group, (3) cyano group, (4) C$_{1-6}$ alkyl group, (5) C$_{2-6}$ alkenyl group, (6) C$_{1-6}$ alkyl group substituted with 3 or less fluorine atoms, (7) C$_{1-6}$ alkyl group substituted with a hydroxyl group, (8) C$_{1-3}$ alkyl carboxylate, or (9) formula —W—R$^{b1}$ wherein W represents 1) phenyl group, 2) 5- to 6-membered aromatic heterocyclic group or 3) 5- to 6-membered non-aromatic heterocyclic group, each of which may be arbitrarily substituted with 3 or less substituent groups selected from the substituent group Q$^7$, and R$^{b1}$ represents (i) hydrogen atom, (ii) halogen atom, (iii) nitro group, (iv) cyano group, (v) C$_{2-6}$ alkenyl group, (vi) C$_{1-6}$ alkoxy group, (vii) halogenated C$_{1-6}$ alkoxy group, (viii) C$_{1-3}$ alkoxy C$_{1-3}$ alkyloxy group, and (viv) (a) C$_{3-8}$ cycloalkyl group, (c) 5- to 7-membered non-aromatic heterocyclic group, (d) phenyl group, (e) 5- to 6-membered aromatic heterocyclic group, (f) phenoxy group, (g) heteroallyoxy group, (h) C$_{3-8}$ cycloalkyloxy group, each of which may be substituted with 3 or less groups selected from the substituent group Q$^7$, Q$^7$ represents (1) halogen atom, (2) nitro group, (3) cyano group, (4) C$_{1-6}$ alkyl group, (5) C$_{2-6}$ alkenyl group, (6) C$_{1-6}$ alkyl group substituted with 3 or less fluorine atoms, (7) C$_{1-6}$ alkyl group substituted with a hydroxyl group, or (8) C$_{1-3}$ alkyl carboxylate, R$^e$ and R$^f$ each represent a hydrogen atom or C$_{1-3}$ alkyl group, or R$^e$ and R$^f$ are combined to form a propylene chain or a tetramethylethylene chain, which together with a boron atom and an oxygen atom, forms a cyclic borate);

15) a pharmaceutical composition comprising a compound represented by the following formula (I), a salt thereof or a hydrate of them, and a pharmaceutically acceptable carrier:

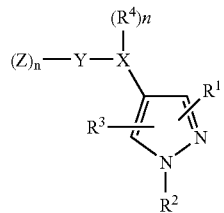
(I)

(in the formula, X represents a nitrogen-containing condensed aromatic heterocyclic group and has $(R^4)_n$ as substituent groups whereupon n is 0, 1, 2 or 3, and the substituent groups $R^4$ independently represent a hydrogen atom, halogen atom, cyano group, hydroxyl group, amino group, $C_{1-6}$alkyl group, halogenated $C_{1-6}$ alkyl group, $C_{2-6}$ alkenyl group, $C_{1-6}$ alkylsulfonyl group, $C_{1-6}$ alkylsulfonylamino group, $C_{1-6}$ alkylsulfinyl group, $N-(C_{1-6}$ alkyl)amino group, N,N-di($C_{1-6}$ alkyl)amino group, $C_{1-6}$ alkoxy group, $C_{1-6}$ alkylsulfanyl group, carbamoyl group, $N-(C_{1-6}$ alkyl)carbamoyl group, N,N-di($C_{1-6}$ alkyl)carbamoyl group, sulfamoyl group, phenyl group, heteroaryl group, phenoxy group, heteroallyloxy group, phenyl $C_{1-6}$ alkylamino group or heteroaryl $C_{1-6}$ alkylamino group, which is bound to an atom constituting X;

Y represents a $C_{3-8}$ cycloalkyl group, a $C_{4-8}$ cycloalkenyl group, a 5- to 14-membered non-aromatic heterocyclic group, a $C_{6-14}$ aromatic hydrocarbon cyclic group, a 5- to 14-membered aromatic hetero cyclic group, a condensed cyclic group consisting of a benzene ring and a 5- to 7-membered non-aromatic ring, or a condensed cyclic group consisting of a 5- to 6-membered aromatic heterocyclic ring and a 5- to 7-membered non-aromatic ring;

$(Z)n$ are n (Z) groups bound to Y, whereupon n is 0, 1, 2 or 3, Z groups are bound to an atom constituting the cyclic group Y and independently represent a group selected from (1) hydrogen atom, (2) amino group, (3) halogen atom, (4) hydroxyl group, (5) nitro group, (6) cyano group, (7) azido group, (8) formyl group, (9) hydroxyamino group, (10) sulfamoyl group, (11) guanodino group, (12) oxo group, (13) $C_{2-6}$ alkenyl group, (14) $C_{1-6}$ alkoxy group, (15) $C_{1-6}$ alkyl hydroxyamino group, (16) halogenated $C_{1-6}$alkyl group, (17) halogenated $C_{2-6}$alkenyl group, (18) formula $-M^1-M^2-M^3$ wherein:

$M^1$ and $M^2$ each represent a single bond, $-(CH_2)_m-$, $-CHR^5CHR^6-$, $-(CH_2)_m-CR^5R^6-(CH_2)_n-$, $-CR^5=CR^6-$, $-C\equiv C-$, $-CR^5=CR^6-CO-$, $-(CH_2)_m-O-(CH_2)_n-$, $-O-(CH_2)_n-CR^5R^6-$, $-(CH_2)_m-S-(CH_2)_n-$, $-SO(CH_2)_m-$, $-SO_2(CH_2)_m-$, $-CO(CH_2)_m-$, $-COO-$, $-CONR^7-$, $-CONR^7CHR^8-$, $-CONR^7-CR^5R^6-$, $-CONR^7-(CH_2)_m-$, $-NR^7-$, $-NR^7CO-CR^5R^6-$, $-NR^7CO-CR^5R^6-CO-$, $-NR^7CO-(CH_2)_m-$, $-NR^7SO_2(CH_2)_m-$, $-SO_2NR^7-(CH_2)_m-$, $-SO_2NR^7-CR^5R^6-$, $-NR^7CONR^8-$, or $-NR^7CSNR^8-$ whereupon n and m are independently 0, 1, 2 or 3, or (19) a group selected from (a) $C_{6-14}$ aromatic hydrocarbon cyclic group, (b) $C_{3-14}$ cycloalkyl group, (c) $C_{4-14}$ cycloalkenyl group, (d) 5- to 14-membered aromatic heterocyclic group, or (e) 4- to 14-membered non-aromatic heterocyclic group, each of which may be substituted with 4 or less groups selected from the substituent group Q, $M^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) $-OR^7$, (xviv) $-NR^7R^8$, (xx) $-NR^7COR^8$, (xxi) $-COR^7$, (xxii) $-CONR^7R^8$, (xxiii) $-SOR^7$, (xxiv) $-SO_2R^7$, (xxv) $-NR^7SO_2R^8$, (xxvi) $-SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

the substituent group Q represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, $-OR^7$, $-OCH_2CONR^7R^8$, $-NR^7R^8$, $-NR^7COR^8$, $-COR^7$, $-CONR^7R^8$, $-SOR^7$, $-SO_2R^7$, $-NR^7SO_2R^8$, $-SO_2NR^7R^8$, methylene dioxy group or ethylene dioxy group (wherein $R^7$ and $R^8$ are the same as or different from each other and each represents a hydrogen atom, a $C_{1-6}$ alkyl group or a $C_{3-8}$ cyloalkyl group);

$R^1$ represents (1) hydrogen atom, (2) halogen atom, (3) hydroxyl group, (4) nitro group, (5) cyano group, (6) halogenated $C_{1-6}$ alkyl group, (7) $C_{2-6}$ alkyl group substituted with a hydroxyl or cyano group, (8) $C_{2-6}$ alkenyl group, or (9) formula $-L^1-L^2-L^3$ whereupon 1) $-L^1$ represents a single bond, $-(CH_2)_m-$, $-(CH_2)$ m$-CR^5R^6$ $-(CH_2)_n-$, $-CR^5=CR^6-$, $-CH=CR^5-CO-$, $-(CH_2)_m-O-(CH_2)_n-$, $-CO(CH_2)_m-$, $-COO-$, $-NR^7-$, $-CO-NR^7-$, $-NR^7CO-$, $-NR^7CO-(CH_2)_m-$, $-NR^7CONR^8-$, whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

2) $L^2$ represents a single bond, $-(CH_2)_m-$, $-CR^5R^6-$, $-(CH_2)_m-CR^5R^6-(CH_2)_n-$, $-CR^5=CR^6-$, $-C\equiv C-$, $-CR=CR^5-CO-$, $-O-$, $-S-$, $-SO-$, $-SO_2-$, $-SO_2-(CH_2)_m-$, $-(CH_2)_m-O-(CH_2)_n-$, $-O-(CH_2)_n-CR^5R^6-$, $-CO-(CH_2)_m-$, $-COO-$, $-NR^7-$, $-CO-NR^7-$, $-CO-NR^7(CH_2)_m-$, $-NR^7CO-$, $-NR^7CO-(CH_2)_m-$, $-NR^7SO_2-$, $-SO_2NR^7-$, —NR⁷CONR⁸—, or —NR⁷CSNR⁸— whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

3) $L^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii)—OR⁷, (xviv) —NR⁷R⁸, (xx) —NR⁷COR⁸, (xxi) —COR⁷, (xxii) —CONR⁷R⁸, (xxiii) —SOR⁷, (xxiv) —SO₂R⁷, (xxv) —NR⁷SO₂R⁸, (xxvi) —SO₂NR⁷R⁸, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, each of which may be substituted with 4 or less groups selected from the substituent group Q;

$R^2$ represents a hydrogen atom;

$R^3$ represents a hydrogen atom, halogen atom, cyano group, amino group, $C_{1-4}$ alkyl group or halogenated $C_{1-4}$ alkyl group, the above-mentioned $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and the above-mentioned $R^7$ and $R^8$ are the same or different and each represent a hydrogen atom, $C_{1-6}$ alkyl group, halogenated $C_{1-6}$ alkyl group, $C_{3-8}$ cycloalkyl group, phenyl group or 5- to 6-membered aromatic heterocyclic group);

16) the pharmaceutical composition according to 15), wherein in the formula (I), X is a nitrogen-containing condensed aromatic heterocyclic group represented by the following formula (II):

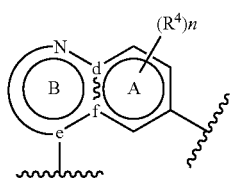

(II)

(in the formula (II), rings A and B are combined to form a 9- to 10-membered nitrogen-containing condensed aromatic heterocyclic group, and have $(R^4)_n$ as substituent groups, whereupon n in the substituent groups $(R^4)_n$ is 0, 1 or 2, the substituent groups $R^4$ independently represent a hydrogen atom, halogen atom, cyano group, hydroxyl group, amino group, $C_{1-6}$alkyl group, halogenated $C_{1-6}$ alkyl group, $C_{2-6}$ alkenyl group, $C_{1-6}$ alkylsulfonyl group, $C_{1-6}$ alkylsulfonylamino group, $C_{1-6}$ alkylsulfinyl group, N—($C_{1-6}$ alkyl)amino group, N,N-di($C_{1-6}$ alkyl)amino group, $C_{1-6}$ alkoxy group, $C_{1-6}$ alkylthio group, carbamoyl group, N—($C_{1-6}$ alkyl)carbamoyl group, N,N-di($C_{1-6}$ alkyl)carbamoyl group, sulfamoyl group, phenyl group, heteroaryl group, phenoxy group, heteroaryloxy group, phenyl $C_{1-6}$ alkylamino group or heteroaryl $C_{1-6}$ alkylamino group, each of which is bound to an atom constituting ring A and/or ring B, provided that when the 10-membered nitrogen-containing condensed aromatic heterocyclic group formed by the rings A and B is a quinazoline ring, and simultaneously $R^4$ is an amino group, N—($C_{1-6}$ alkyl)amino group and/or N,N-di($C_{1-6}$ alkyl) amino group, $R^4$ is not bound to the atom at the 2-position of the quinazolinyl ring, the ring A represents a 6-membered aromatic hydrocarbon cyclic group or a 6-membered aromatic heterocyclic group;

the ring B represents a 5- or 6-membered nitrogen-containing aromatic heterocyclic group, and may contain 1, 2 or 3 heteroatoms selected from a nitrogen atom, an oxygen atom and a sulfur atom, d, f and e are adjacent in this order, are the same or different and represent a carbon atom or a nitrogen atom, provided that d and e do not simultaneously represent a nitrogen atom, and when e represents a nitrogen atom, d and f each represent a carbon atom, and the ring A binds to the 4-position of the pyrazole ring, and the ring B binds via e to Y in the formula (I));

17) the pharmaceutical composition according to 15) or 16), which is an STAT6 activation inhibitor;

18) the pharmaceutical composition according to 15) or 16), which is an IL-4 and/or IL-13 signal transduction inhibitor;

19) the pharmaceutical composition according to any one of 15) to 18), which is a prophylactic or therapeutic agent for allergic diseases;

20) the pharmaceutical composition according to any one of 15) to 18), which is a prophylactic or therapeutic agent for allergic rhinitis;

21) the pharmaceutical composition according to any one of 15) to 18), which is a prophylactic or therapeutic agent for bronchial asthma;

22) the pharmaceutical composition according to any one of 15) to 18), which is a prophylactic or therapeutic agent for atopic dermatitis;

23) the pharmaceutical composition according to any one of 15) to 18), which is a prophylactic or therapeutic agent for pollinosis, digestive organ allergies, hives, hypersensitivity pneumonitis, pulmonary Aspergillosis, eosinophil leukemia, parasitism, eosinophilia, eosinophil pneumonia, and/or eosinophil gastroenteritis;

24) the pharmaceutical composition according to any one of 15) to 18), which is an improver for an allergic constitution;

25) the pharmaceutical composition according to 15) or 16), which is a prophylactic or therapeutic agent for autoimmune diseases, systemic erythematosus, viral infections, bacterial infections, obesity, bulimia, malignant tumors or acquired immunodeficiency syndrome (AIDS);

26) a method of preventing and treating diseases against which (a) an inhibitory action on activation of STAT6 and/or (b) an inhibitory action on transduction of IL-4 and/or IL-13 signals is effective, which comprises administering a pharmacologically active amount of the compound according to any one of 1) to 13) represented by the formula (I), a salt thereof or a hydrate of them to a patient; and 27) use of a pharmacologically active amount of the compound according to any one of 1) to 13) represented by the formula (I), a salt thereof or a hydrate of them, for producing a prophylactic or therapeutic agent for diseases against which (a) an inhibitory action on activation of STAT6 and/or (b) an inhibitory action on transduction of IL-4 and/or IL-13 signals is effective.

The present invention provides a method of preventing and treating allergic diseases, which comprises administering a pharmacologically active amount of a compound represented by the formula (I), or a salt thereof or a hydrate thereof described in any of the above-mentioned 1) to 13) to a patient. The present invention also provides use of a pharmacologically active amount of a compound represented by the formula (I), or a salt thereof or a hydrate thereof described in any of the above-mentioned 1) to 13) in producing a prophylactic and therapeutic agent for allergic diseases. Further, the present invention provides a method of preventing and treating autoimmune diseases, systemic erythematosus, viral infections, bacterial infections, obesity, bulimia, malignant tumors, and acquired immunodeficiency syndrome (AIDS), which comprises administering a pharmacologically active amount of a compound represented by the general formula (I), or a salt thereof or a hydrate thereof described in any of the above-mentioned 1) to 13) to a patient. Furthermore, the present invention provides use of a pharmacologically active amount of a compound represented by the general formula (I), or a salt thereof or a hydrate thereof described in any of the above-mentioned 1) to 13) in producing a prophylactic and therapeutic agent for autoimmune diseases, systemic erythematosus, viral infections, bacterial infections, obesity, bulimia, malignant tumors, or acquired immunodeficiency syndrome (AIDS).

The structural formulae of the compound in the present specification may, for convenience' sake, indicate a certain isomer, but this invention encompasses all possible isomers which can occur in the structures of the compound, for example geometric isomer, optical isomer based on asymmetrical carbon, stereoisomer and tautomer, as well as a mixture of such isomers, and the compound of the invention may be any isomers or a mixture thereof without limitation to the formulae shown for convenience' sake. In the compound, there may be crystal polymorphism, and the compound is not limited and may be in a single crystal form or a mixed crystal form. The compound (I) of the present invention and salts thereof may be anhydrides or hydrates.

Salts or hydrates of the compound of the present invention are preferably pharmacologically acceptable salts.

Now, the terms used in the present invention are described.

The "nitrogen-containing condensed aromatic heterocyclic group" represented by X refers to a bicyclic or tricyclic condensed aromatic heterocyclic group containing at least one nitrogen atom, which may contain a heteroatom selected from the group consisting of a sulfur atom and an oxygen atom and may be substituted with a substituent group. The nitrogen-containing condensed aromatic heterocyclic group includes, for example, an optionally substituted benzotriazolyl group, benzimidazolyl group, indolyl group, isoindolyl group, indolizinyl group, purinyl group, indazolyl group, quinolyl group, isoquinolyl group, quinolyl group, quinolizyl group, naphthyridinyl group, quinoxalyl group, quinazolinyl group, cinnolinyl group, puteridinyl group, imidazotriazinyl group, pyrazinopyridazinyl group, acridinyl group, phenanthridinyl group, carbazolyl group, carbazolinyl group, pyrimidinyl group, phenanthrolinyl group, phenacynyl group, imidazopyridinyl group, imidazopyrimidinyl group, pyrazolopyridinyl group, pyrazolopyridinyl group, benzothiazolyl group, benzimidazolyl group, benzthiadiazolyl group, phenothiazinyl group, isoxazolyl group, furazanyl group, phenoxazinyl group, oxazolyl group, benzisoxazolyl group, isoxazoyl group, benzoxazolyl group, oxadiazolyl group, pyrazoloxazolyl group, imidazothiazolyl group, thienofuranyl group, furopyrrolyl group, pyridoxazinyl group etc., preferably a group represented by the general formula (II), and more preferable X is an imidazo[1,2-a]pyridine ring (imidazo[1,2-a]pyridinyl group), benzimidazole ring (benzimidazolyl group), quinazoline ring (quinazolinyl group), quinoline ring (quinolyl group), and 2,1-benzisoxazole ring (2,1-benzisoxazolyl group).

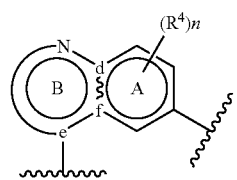

(II)

The "$C_{3-8}$ cycloalkyl group" refers to a cycloalkyl group composed of 3 to 8 carbon atoms, and examples thereof include a cyclopropyl group, cyclobutyl group, cyclopentyl group, cyclohexyl group, cycloheptyl group, cyclooctyl group, etc.

The "$C_{3-8}$ cycloalkenyl group" refers to a $C_{3-8}$ cycloalkenyl group composed of 3 to 8 carbon atoms, and examples there of include cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl, 1,3,6-cyclooctatrien-6-yl group, etc.

The "5- to 14-membered non-aromatic heterocyclic group" refers to a monocyclic, bicyclic or tricyclic, 5- to 14-membered non-aromatic heterocyclic group containing at least one heteroatom selected from the group consisting of a nitrogen atom, a sulfur atom and an oxygen atom. Specific examples of this group include a pyrrolidinyl group, piperidyl group, 1,2,3,6-tetrahydropyridine, piperazinyl group, homopiperazinyl group, morpholinyl group, thiomorphonyl group, tetrahydrofuryl group, tetrahydropyranyl group, aziridinyl group, oxiranyl group, oxathioranyl group, tetrahydroisothiazole group etc. The non-aromatic heterocyclic group includes a thiomorphonyl-1,1-dioxide group, tetrahydroisothiazole-1,1-dioxide group, a group derived from a pyridone ring, and a non-aromatic condensed ring (for example, a group derived from a phthalimide ring, succinimide ring etc.)

The "5- to 7-membered non-aromatic ring" refers to a cycloalkyl group composed of 5 to 7 carbon atoms, a cycloalkenyl group composed of 5 to 7 carbon atoms or a monocyclic 5- to 7-membered non-aromatic heterocyclic group containing at least one nitrogen atom, sulfur atom and oxygen atom.

The "$C_{6-14}$ aromatic hydrocarbon cyclic group" refers to an aromatic hydrocarbon cyclic group composed of 6 to 14 carbon atoms, and includes a monocyclic group and a condensed ring such as bicyclic group, tricyclic group, etc. Specific examples of this group include a phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, benzocyclooctenyl group, etc.

The "5- to 14-membered aromatic heterocyclic group", "heteroaryl group" and "heteroaryl" refer to a monocyclic, bicyclic or tricyclic, 5- to 14-membered aromatic heterocyclic group containing at least one heteroatom selected from the group consisting of a nitrogen atom, a sulfur atom and an oxygen atom. Specific examples of this group include nitrogen-containing aromatic heterocyclic groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, puteridinyl group, imidazotriazinyl group, pyrazinopyridazinyl group, acridinyl group, phenanthridinyl group, carbazolyl group, carbazolynyl group, pyrimidinyl group, phenanthrolinyl group, phenacynyl group, imidazopyridinyl group, imidazopyrimidinyl group, pyrazolopyridinyl group, pyrazolopyridinyl group, etc.; sulfur-containing aromatic heterocyclic groups such as thienyl group, benzothienyl group, etc.; oxygen-containing aromatic heterocyclic groups such as furyl group, pyranyl group, cyclopentapyranyl group, benzofuryl group, isobenzofuryl group, etc.; and aromatic heterocyclic group containing two or more heteroatoms, such as thiazolyl group, isothiazolyl group, thiadiazoyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazoloxazolyl group, imidazothiazolyl group, thienofuranyl group, furopyrrolyl group, pyridoxazinyl group, etc.

The "halogen atom" is, for example, a fluorine atom, chlorine atom, bromine atom, iodine atom or the like, preferably a fluorine atom, chlorine atom or bromine atom.

The "$C_{1-6}$ alkyl group" refers to a linear or branched alkyl group containing 1 to 6 carbon groups, and examples thereof include a methyl group, ethyl group, n-propyl group, iso-propyl group, n-butyl group, iso-butyl group, sec-butyl group, tert-butyl group, n-pentyl group, 1,1-dimethyl propyl group, 1,2-dimethyl propyl group, 2,2-dimethyl propyl group, 1-ethyl propyl group, 2-ethyl propyl group, n-hexyl group, 1-methyl-2-ethyl propyl group, 1-ethyl-2-methyl propyl group, 1,1,2-trimethyl propyl group, 1-propyl propyl group, 1-methyl butyl group, 2-methyl butyl group, 1,1,-dimethyl butyl group, 1,2-dimethyl butyl group, 2,2-dimethyl butyl group, 1,3-dimethyl butyl group, 2,3-dimethyl butyl group, 2-ethyl butyl group, 2-methyl pentyl group, 3-methyl pentyl group, etc., more preferably a methyl group, ethyl group, n-propyl group, iso-propyl group, n-butyl group, iso-butyl group, sec-butyl group, tert-butyl group, n-pentyl group etc.

The "$C_{2-6}$ alkenyl group" refers to a linear or branched alkenyl group containing 2 to 6 carbon atoms, and examples thereof include a vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group, etc.

The "$C_{2-6}$ alkynyl group" refers to an alkynyl group containing 2 to 6 carbon atoms, and preferable examples thereof include an ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group, 1,6-hexanediynyl group, etc.

The "halogenated $C_{1-6}$ alkyl group" refers to a linear or branched alkyl group containing 1 to 6 carbon atoms and substituted with a fluorine atom, chlorine atom, bromine atom or iodine atom, and preferable examples thereof include a fluoromethyl group, difluoromethyl group, trifluoromethyl group, chloromethyl group, bromomethyl group, tetrafluoroethyl group, 2,2,2-trifluoroethyl group, 2-chloroethyl group, etc.

The "$C_{1-6}$ alkoxy group" refers to a linear or branched alkoxy group containing 1 to 6 carbon atoms, and preferable examples thereof include a methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethyl propyloxy group, 1,2-dimethyl propoxy group, 2,2-dimethyl propyloxy group, 2-ethyl propoxy group, 1-methyl-2-ethyl propoxy group, 1-ethyl-2-methyl propoxy group, 1,1,2-trimethyl propoxy group, 1,1,2-trimethyl propoxy group, 1,1-dimethyl butoxy group, 1,2-dimethyl butoxy group, 2,2-dimethyl butoxy group, 2,3-dimethyl butyloxy group, 1,3-dimethyl butyloxy group, 2-ethyl butoxy group, 1,3-dimethyl butoxy group, 2-methyl pentoxy group, 3-methyl pentoxy group, hexyloxy group, etc.

The "halogenated $C_{1-6}$ alkoxy group" refers to a linear or branched alkoxy group containing 1 to 6 carbon atoms whose alkyl-moiety hydrogen atom is substituted with a fluorine atom, chlorine atom, bromine atom or iodine atom, and preferable examples thereof include a fluoromethyloxy group, difluoromethoxy group, trifluoromethoxy group, tetrafluoroethoxy group etc.

The "pyrazole-protecting group" is not particularly limited, and insofar as it is any group usually known in organic synthesis as a group for protecting nitrogen in a pyrazole ring, and examples thereof include a substituted or unsubstituted alkanoyl group such as formyl group, acetyl group, chloroacetyl group, dichloroacetyl group, propionyl group, phenylacetyl group, phenoxyacetyl group, thienylacetyl group etc.; a substituted or unsubstituted lower oxy carbonyl group such as benzyloxy carbonyl group, t-butoxy carbonyl group, p-nitrobenzyloxy carbonyl group etc.; alkanoyloxy alkyl group such as isobutanoyloxy methyl group, pivaloyloxy methyl group, pivaloyloxy ethyl group etc.; cycloalkyl carbonyl oxy alkyl group such as cyclohexane carbonyloxy methyl group, cyclohexane carbonyloxy ethyl group etc.; substituted lower alkyl group such as t-butyl group, 2,2,2-trichloroethyl group, trityl group, p-methoxybenzyl group, p-nitrobenzyl group, diphenyl methyl group etc.; substituted silyl group such as trimethyl silyl group, t-butyldimethylsilyl group etc.; substituted silyl alkoxyalkyl group such as trimethyl silyl methoxy methyl group, t-butyl dimethyl silyl methoxy methyl group, t-butyl dimethyl silyl ethoxy methyl group etc.; substituted or unsubstituted benzylidene group such as benzylidene group, salicylidene group, p-nitrobenzylidene group, m-chlorobenzylidene group, 3,5-di(t-butyl)-4-hydroxybenzylidene group; and tetrahydropyranyl group.

In the present specification, the term "hetero" refers specifically to an oxygen atom, sulfur atom, nitrogen-atom, phosphorus, arsenic, antimony, silicon, germanium, tin, lead, boron and mercury, preferably an oxygen atom, sulfur atom, nitrogen atom and phosphorus, more preferably an oxygen atom, sulfur atom and nitrogen atom.

The "salts" used in the present specification is not particularly limited insofar as these are pharmacologically acceptable salts formed from the compound of the present invention, and examples thereof include addition salts of inorganic acids such as hydrochloride, sulfate, carbonate, bicarbonate, hydrobromate, hydroiodate etc.; addition salts of organic carboxylic acids such as acetate, maleate, lactate, tartrate, trifluoroacetete etc.; addition salts of organic sulfonic acid such as methane sulfonate, hydroxymethane sulfonate, hydroxyethane sulfonate, benzene sulfonate, toluene sulfonate, taurine salt, etc.; addition salts of amines such as trimethylamine salt, triethylamine salt, pyridine salt, procaine salt, picoline salt, dicyclohexylamine salt, N,N'-dibenzylethylene diamine salt, N-methyl glucamine salt, diethanol amine salt, triethanol amine salt, tris (hydroxymethylamino) methane salt, phenethyl benzyl amine salt etc.; addition salts of alkali metals, such as sodium salt, potassium salt etc.; and addition salts of amino acids, such as arginine salt, lysine salt, serine salt, glycine salt, aspartate, glutamate, etc.

The compound represented by the general formula (I) in this invention, or a salt thereof or a hydrate thereof can be synthesized by a conventional method, for example by any of Production Methods A to E below.

The compound of the general formula (I) wherein X (nitrogen-containing condensed aromatic heterocyclic group) is an imidazo[1,2-a]pyridine ring can be synthesized by Production Method A.

Production Method A

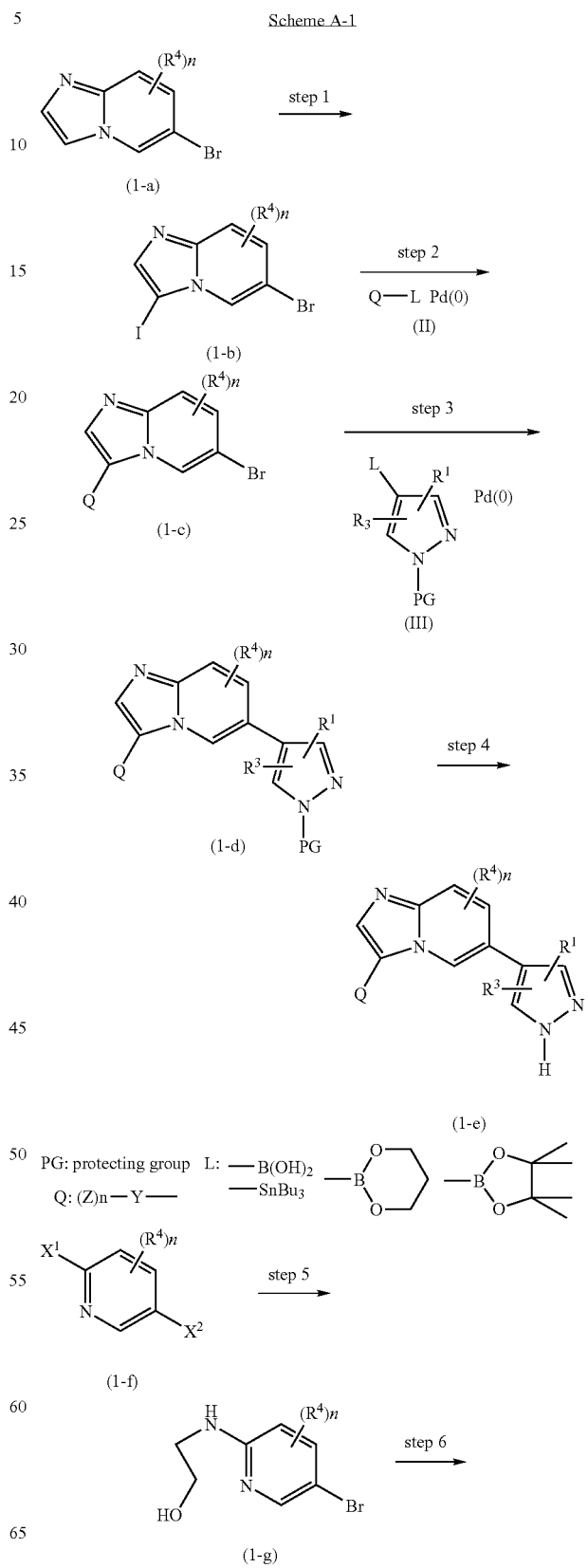

-continued

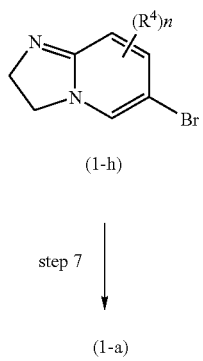

(1-h)

step 7

(1-a)

X$^1$: Cl or Br
X$^2$: H or Br

In the reaction scheme, each symbol represents the same group as defined above. However, Q represents ring Y [(Z)n—Y—] which may be arbitrarily substituted with the above-defined (Z)n (=substituent groups Z wherein n is 0, 1, 2 or 3), the ring Y represents an aryl group or heteroaryl group. PG represents an amino group-protecting group such as a trityl group, tetrahydropyranyl group etc., and L represents trialkyl tin, boric acid, or a group represented by cyclic or non-cyclic borate. X$^1$ represents a chloro or bromo group, and X$^2$ represents a hydrogen atom or bromo group.

(1-a) can be synthesized according to a method described in M. Yamanaka et al., Chem. Pharm. Bull., 39, 1556 (1991) or a method of synthesizing it from (1-f) through steps 5 to 7 described later.

Step 1 is a method of position-selectively halogenating Compound (1-a). (1-b) can be obtained by adding N-iodosuccinimide in a solvent such as dimethyl formamide, alcohol, dichloromethane or chloroform under ice-cooling to a temperature of up to 60° C. These solvents may contain water.

Step 2 is a step of introducing ring Q (ring Y [(Z)n-Y—] which may be arbitrarily substituted by the above-defined (Z)n) by cross-coupling Q—L with the imidazopyridine ring in the presence of a palladium (0) catalyst by Suzuki reaction or Stille reaction. Preferable examples of the Pd catalyst include, but are not limited to, catalysts such as tetrakistriphenylphosphine palladium, dichlorobis(tri-o-tolylphoshine) palladium and dichloro[1,1'-bis(diphenylphosphino)ferrocene palladium and catalysts such as a combination of trisdibenzylidene acetone dipalladium (Pd$_2$(dba)$_3$) or palladium acetate and various phosphine ligands such as tri-t-butyl phosphine and 2-(di-t-butylphoshino)diphenyl. By using Q—L in a ratio of 0.9–1.2 to (1-b) while regulating the reaction temperature, Q—L can be reacted position-selectively with iodine in (1-b), to introduce the ring Q. When Q—L is a trialkyl tin derivative such as tributyl tin, (1-c) can be obtained by heating in the presence of the palladium catalyst at 60 to 180° C. in a reaction solvent such as xylene, toluene, N,N-dimethylformamide, or 1,4-dioxane or a solvent mixture thereof, preferably at 70 to 120° C. under nitrogen atmosphere. Further, cesium fluoride, potassium fluoride, lithium chloride, tetrabutyl ammonium chloride or cuprous iodide can also be added as additives. When Q—L is a boric acid derivative, (1-c) can be obtained by heating at 60 to 120° C. under nitrogen atmosphere or by heating under reflux, in the presence of the palladium catalyst in a mixture consisting of a solvent selected from 1,2-dimethoxyethane, ethanol, toluene, 1,4-dioxane and tetrahydrofuran or a solvent mixture thereof and an aqueous solution of potassium carbonate, sodium carbonate, potassium phosphate, barium sulfate or potassium fluoride. When Q—L is a borate derivative, (1-c) can be obtained by heating in the presence of the palladium catalyst at 70 to 180° C. in the presence of an in organic base such as potassium carbonate, sodium carbonate, potassium phosphate and barium sulfate in a solvent such as 1,4-dioxane, tetrahydrofuran, N,N-dimethylformamide etc., preferably at 80 to 120° C. under nitrogen atmosphere.

Step 3 is a reaction of introducing the pyrazole derivative represented by the formula (III) into the imidazopyridine ring. The reaction conditions are the same as in step 2.

Step 4 is a step of removing the protecting group on the pyrazole ring. The pyrazole ring is deprotected by reaction with 0.5 to 5 N aqueous hydrochloric acid in a solvent such as 1,4-dioxane, tetrahydrofuran or methanol or a solvent mixture thereof or by reaction with 0.5 to 5 N hydrochloric acid/methanol, hydrochloric acid/ethanol or hydrochloric acid/ethyl acetate in the solvent mixture, or by heating at room temperature to 50° C. with trifluoroacetic acid in a dichloromethane solvent, whereby (1-e) can be obtained.

The starting material (1-a) can also be synthesized in the following manner.

Step 5 is a method of substituting Compound (1-f) with 2-aminoethanol. By heating at 80 to 130° C. with or without a solvent such as dimethyl sulfoxide or alcohol, (1-g) can be obtained. When Compound (1-f) wherein X$^2$ is a hydrogen atom [X$^2$=H], a brominating step is additionally carried out. That is, (1-f) is reacted with a brominating agent such as bromine or N-bromosuccinimide under ice-cooling to room temperature in a solvent such as N,N-dimethylformamide, alcohol, acetonitrile etc., whereby (1-g) can be obtained.

Step 6 is a method of constructing a dihydroimidazopyridine ring by cyclization reaction. By reaction with thionyl chloride under ice-cooling to room temperature in an inert solvent such as toluene or xylene and subsequent reaction under heating at 100° C. or under reflux, (1-h) can be obtained.

Step 7 is a method of synthesizing an imidazopyridine ring by oxidation reaction. Compound (1-h) is reacted with 2,3-dichloro-5,6-dicyano-1,4-benzoquinone at room temperature or by heating under reflux, in a solvent such as tetrahydrofuran, diethyl ether or 1,4-dioxane, whereby (1-a) can be obtained. Alternatively, (1-a) can be obtained by reacting manganese dioxide with (1-h) under heating reflux in a solvent such as acetone, toluene or chloroform.

When the substituent group Q at the 3-position of the imidazo[1,2-a]pyridine ring of Compound (1-c) in the scheme A-1 is a 1,2,4-oxadiazole ring, 1,3,4-oxadiazole ring or 1,3,4-thiadiazole ring, each of which has a substituent group, Compound (1-c) can be synthesized according to schemes A-2, A-4 and A-5.

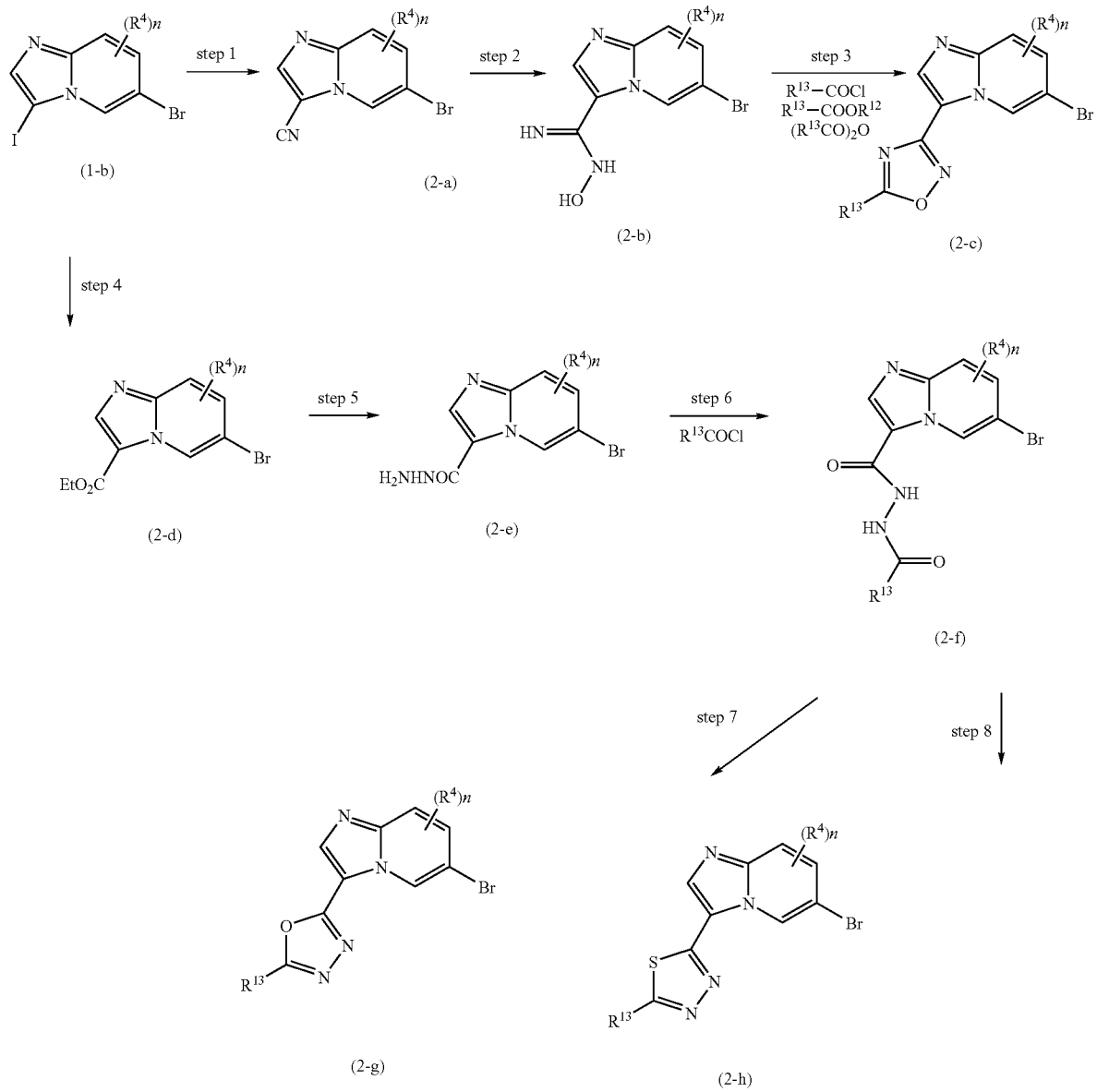

Scheme A-2

In the reaction schemes, each symbol represents the same group as defined above. However, $R^{12}$ represents a lower alkyl or a hydrogen atom, $R^{13}$ represents an optionally substituted alkyl group, an optionally substituted $C_{3-8}$ cycloalkyl group, an optionally substituted aryl group or an optionally substituted heteroaryl group.

The 1,2,4-oxadiazole ring can be synthesized from (1-b) by the reactions in steps 1 to 3.

Step 1 is a method of position-selectively introducing a cyano group, in which Compound (1-b) is reacted with isopropyl magnesium bromide at a temperature from 0° C. to room temperature in a solvent such as diethyl ether or tetrahydrofuran to prepare a Grignard reagent which is then reacted at the same temperature with p-toluenesulfonyl cyanide, whereby (2-a) can be obtained.

Step 2 is a method of synthesizing hydroxy amidine. Compound (2-a) is reacted with hydroxylamine hydrochloride by heating under reflux in the presence of potassium t-butyl oxide in a solvent mixture of toluene and alcohol, whereby (2-b) can be obtained.

Step 3 is a method of constructing a 1,2,4-oxadiazole ring, in which one of the following 3 methods can be used depending on the type of the substituent group $R^{13}$. The first method is a method according to A. R. Gangloff et al., Tetrahydron Letters, 42, 1441 (2001), and various acid chlorides [$R^{13}$—COCl] or acid anhydrides [($R^{13}$—CO)O] are allowed to act at 0° C. to room temperature on (2-b) in the presence of an organic amine such as N,N-diisopropyl ethylamine or triethylamine in a solvent such as tetrahydrofuran, N,N-dimethylformamide, acetonitrile, dichloromethane or chloroform thereby acylating the hydroxyl group, followed by heating from room temperature to a temperature causing reflux with tetrabutyl ammonium fluoride in a tetrahydrofuran solvent, whereby (2-c) can be obtained. The second method involves allowing sodium hydride to act on (2-b) at room temperature to 50° C. in a tetrahydrofuran solvent and then reacting the product with an ester [$R^{13}$—$COOR^{12}$] by heating under reflux to give (2-c). The third method is a method described in R. F. Poulain et al., Tetrahedron Letters, 42, 1495 (2001), and a carboxylic acid [$R^{13}$—COOH] and (2-b) are subjected to esterification under condensation reactions and then to cyclization reaction under heating, whereby (2-c) can be obtained.

The 1,3,4-oxadiazole ring can be synthesized from (1-b) by the reactions in steps 4 to 7.

Step 4 is a step of selectively converting iodine in (1-b) into an ethyl ester, in which (1-b) is treated with isopropyl magnesium halide in an anhydrous solvent such as diethyl ether and tetrahydrofuran, to prepare a Grignard reagent which is then reacted with ethyl chlorocarbonate or diethyl carbonate, whereby (2-d) can be obtained.

Step 5 is a step of converting the ester in (2-d) into a hydrazinoester, in which (2-d) and hydrazine monohydrate are heated from room temperature to 150° C. in an alcohol such as methanol, ethanol etc. or an organic solvent such as benzene or ethyl acetate or in the absence of a solvent, to give (2-e) Step 6 is a step of acylating the terminal amino group of the hydrazino group in (2-e). (2-e) is reacted with an acid chloride [$R^{13}$—COCl] at −50° C. to 100° C. in the presence of a base such as sodium bicarbonate, triethylamine or pyridine in a solvent such as N,N-dimethylformamide, tetrahydrofuran, pyridine or dichloromethane, whereby (2-f) can be obtained.

Step 7 is a step of constructing a 1,3,4-oxadiazole ring from (2-f). (2-f) is reacted with phosphorus oxychloride in a solvent such as acetonitrile or in the absence of a solvent, or reacted with trifluoromethane sulfonic anhydride in the presence of a base such as pyridine, triethylamine etc. in a solvent such as dichloromethane, tetrahydrofuran etc., whereby (2-g) can be obtained.

The 1,3,4-thiadiazole ring can be synthesized from (2-f) by the reaction in step 8.

Step 8 is a step of forming a 1,3,4-thiadiazole ring, wherein (2-h) can be obtained by reacting (2-f) with a Lawsson reagent at 80 to 140° C. in a solvent such as benzene, toluene, xylene etc.

Each of (2-c), (2-g) and (2-h) is reacted in the same manner as in the steps 3 and 4 in the scheme A-1, whereby the compounds of the general formula (I) wherein the ring Y is 1,2-oxadiazole, 1,3,4-oxadiazole or 1,3,4-thiadiazole can be obtained.

(2-a) in the scheme A-2 can also be synthesized by the method in scheme A-3.

Scheme A-3

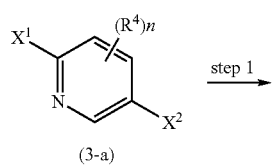

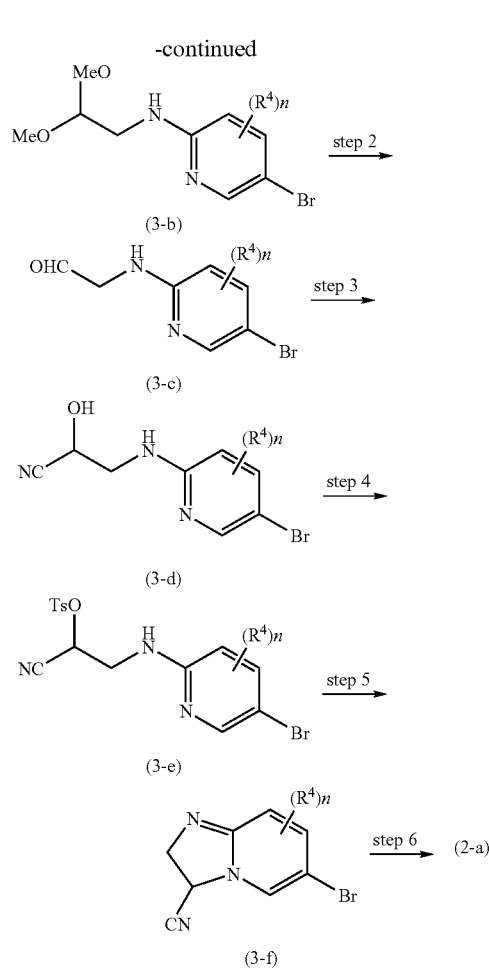

$X^1$ = Cl or Br
$X^2$ = H or Br

In the reaction scheme, each symbol represents the same group as defined above.

According to a method described in D. E. Podhorez et al., J. Heterocyclic Chem., 28, 971 (1991), (2-a) can be synthesized from (3-a).

Step 1 is a method of substituting Compound (3-a) with aminoacetaldehyde dimethyl acetal. By heating at 80° C. to 130° C. in the absence of a solvent or in a solvent such as dimethyl sulfoxide or alcohol, (3-b) can be obtained. When Compound (3-a) wherein $X^2$ is a hydrogen atom [$X^2$=H] is used, a brominating step is further conducted. That is, (3-b) can be obtained by acting a bromating agent such as bromine or N-bromosuccinimide in a solvent such as N,N-dimethylformamide, alcohol, acetonitrile etc. under conditions of ice-cooling or room temperature.

Step 2 is a method of hydrolyzing the acetal under acidic conditions. Compound (3-b) is reacted with 0.5 to 5 N hydrochloric acid at room temperature to 70° C. in a solvent such as tetrahydrofuran, diethyl ether or alcohol, whereby (3-c) can be obtained.

Step 3 is a method of introducing a cyano group to synthesize cyanohydrin. Compound (3-c) is reacted at 0° C. to room temperature with an organic solvent solution of diethyl aluminum cyanide in a solvent such as tetrahydrofuran, diethyl ether or toluene, whereby (3-d) can be obtained.

Step 4 is a method of introducing a p-toluene sulfonyl group into the hydroxyl group. Compound (3-d) is reacted with p-toluene sulfonyl chloride at 0° C. to room temperature in the presence of an organic amine such as N,N-diisopropyl ethylamine or triethylamine in a solvent such as tetrahydrofuran, N,N-dimethylformamide, acetonitrile, dichloromethane or chloroform, whereby (3-e) can be obtained.

Step 5 is a method of constructing a dihydroimidazopyridine ring by cyclization reaction. Compound (3-e) is heated under reflux in a solvent such as tetrahydrofuran, N,N-dimethylformamide, acetonitrile or toluene, whereby (3-f) can be obtained.

Step 6 is a method of synthesizing imidazopyridine by oxidation reaction. Compound (3-f) is reacted with 2,3-dichloro-5,6-dicyano-1,4-benzoquinone at room temperature or at a temperature under heating reflux, in a solvent such as tetrahydrofuran, diethyl ether or 1,4-dioxane, whereby (2-a) can be obtained. Alternatively, (3-f) may be reacted with manganese dioxide by heating under reflux in a solvent such as acetone, toluene or chloroform, whereby (2-a) can be obtained.

The compounds of the general formula (1-c) in the scheme A-1, wherein the substituent group Q at the 3-position of the imidazo[1,2-a]pyridine ring is a 1,2,4-oxadiazole ring, 1,3,4-oxadiazole ring, 1,3,4-thiadiazole ring or 1,3,4-triazole ring, each of which is substituted with an alkylsulfanyl group, can be synthesized according to scheme A-4.

Scheme A-4

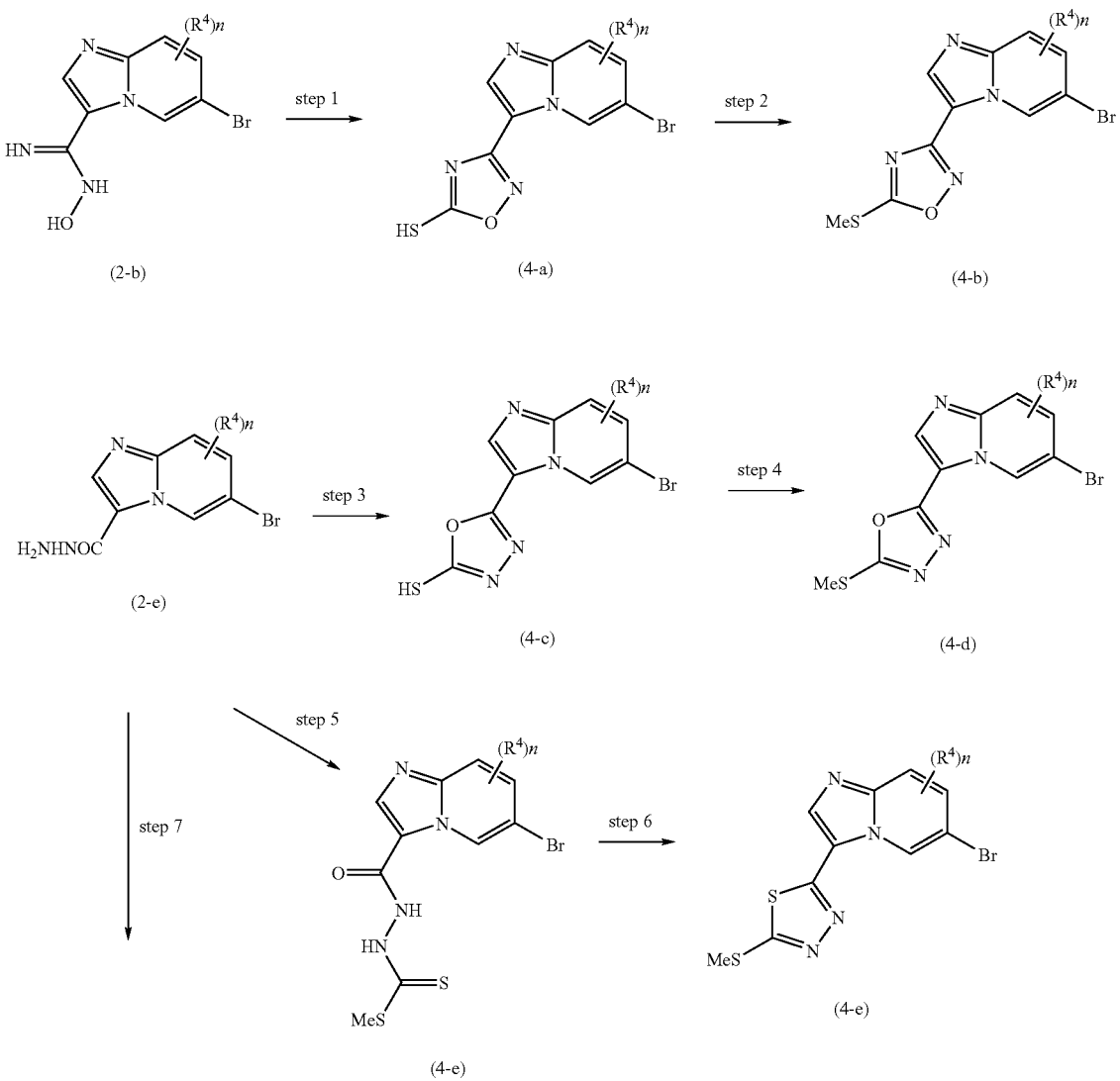

-continued

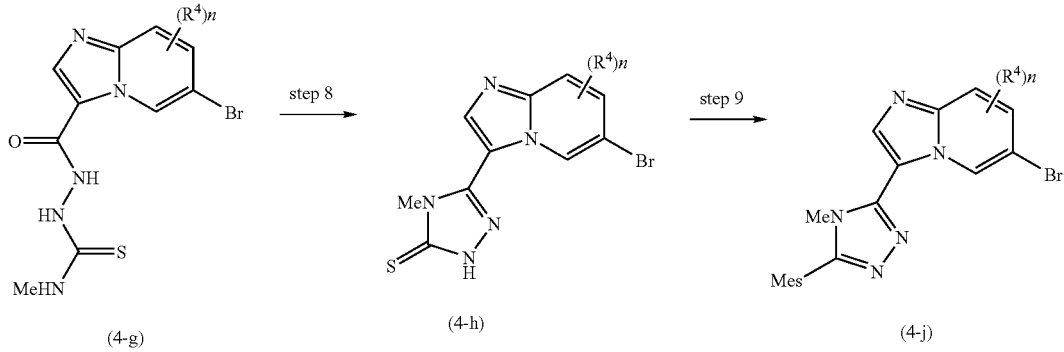

In the reaction scheme, each symbol represents the same group as defined above.

Step 1 is a step of converting (2-b) into a 1,2,4-oxadiazole ring having a thiol group at the 5-position. (2-b) is heated under reflux in the presence of carbon disulfide and a base such as sodium hydroxide, potassium hydroxide etc. in a solvent such as hydrous methanol or ethanol, whereby (4-a) can be obtained.

Step 2 is a step of converting the thiol group in (4-a) into a methylsulfanyl group, wherein (4-a) is reacted at 0° C. to room temperature with methyl iodide in the presence of base such as potassium carbonate or sodium hydride in a solvent such as N,N-dimethylformamide or tetrahydrofuran, whereby (4-b) can be obtained. By reacting (4-a) with an optionally substituted alkyl halide in place of methyl iodide, the corresponding alkyl sulfanyl group can be introduced.

Steps 3 and 4 are the same reactions as in steps 1 and 2 respectively, and when (4-e) is used as the starting material, the 1,3,4-oxadiazole ring (4-c) having a thiol group at the 5-position can be obtained in step 3, and (4-d) can be obtained by alkylating the thiol group in step 4.

Step 5 is a step of converting the hydrazino group in (4-e) into a thiosemicarbazide group. (4-e) is reacted with carbon disulfide at 0° C. to room temperature in the presence of a base such as potassium hydroxide, sodium hydroxide etc. in a solvent such as methanol, ethanol etc., and then treated with methyl iodide, whereby (4-e) can be obtained.

Step 6 is a step of constructing a 1,3,4-thiadiazole ring by dehydrating condensation reaction of (4-e). By heating (4-e) together with a dehydrating agent such as p-toluenesulfonic acid monohydrate under reflux in a solvent such as benzene, toluene etc., (4-f) can be obtained.

Step 7 is a step of converting the hydrazino group in (4-e) into a thiosemicarbazide group, in which (4-e) is reacted at room temperature to 80° C. with methyl isocyanate in the presence or absence of a base such as potassium hydroxide, sodium hydroxide etc. in a solvent such as methanol, ethanol etc., whereby (4-g) can be obtained.

Step 8 is a step of constructing a 1,2,4-triazole ring from (4-g). By heating (4-g) under reflux in an aqueous sodium carbonate solution, (4-h) can be obtained.

Step 9 is a step of converting the thiol group into a methylsulfanyl group, and is identical with step 2. By reaction with methyl iodide, (4-i) is obtained, and by reaction with various kinds of alkyl halides, their corresponding alkylsulfanyl group can be obtained.

(4-b), (4-d), (4-f) and (4-i) are reacted in the same manner as in steps 3 and 4 in the scheme A-1, whereby the compounds of the general formula (I) wherein the ring Y is 1,2,4-oxadiazole, 1,3,4-oxadiazole, 1,3,4-thiadiazole or 1,3,4-triazole, each of which is substituted with an alkylsulfanyl group, can be obtained.

The compounds of the general formula (1-c) in the scheme A-1, wherein the substituent group Q at the 3-position of the imidazo[1,2-a]pyridine ring is a 1,2,4-oxadiazole ring, 1,3,4-oxadiazole ring, 1,3,4-thiadiazole ring and 1,3,4-triazole ring, each of which is substituted with an alkoxy or amino group, can be synthesized according to scheme A-5.

Scheme A-5

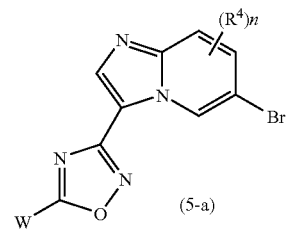

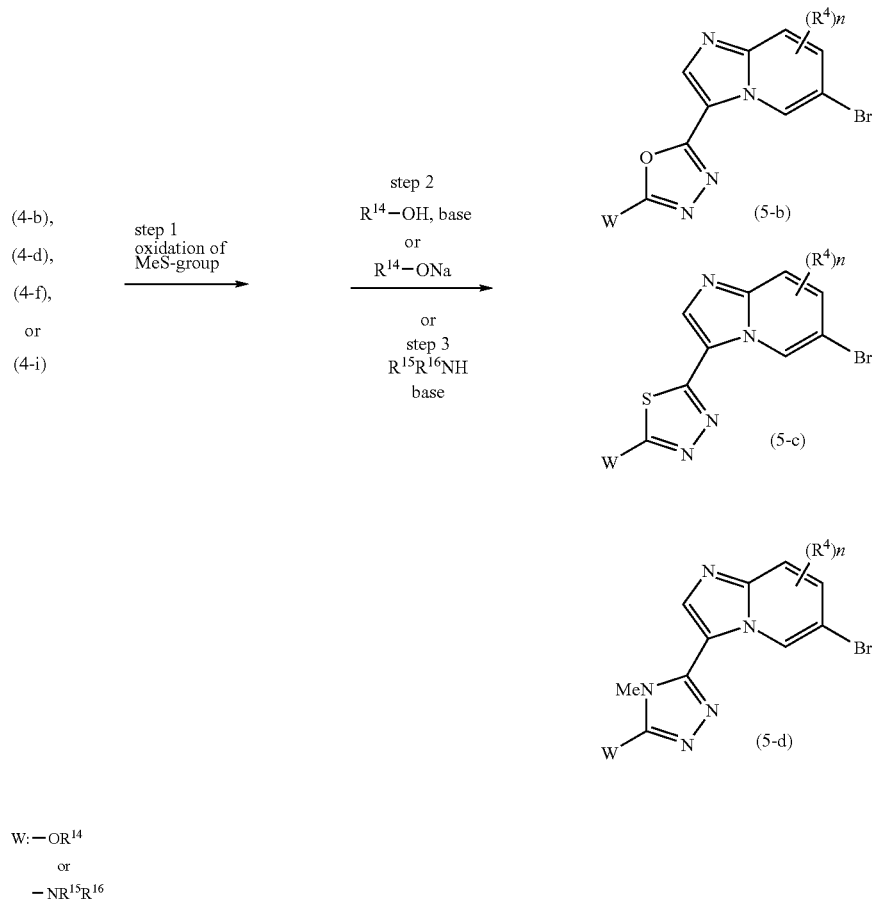

In the reaction scheme, each symbol represents the same group as defined above. However, W represents $OR^{14}$ or $NR^{15}R^{16}$. $R^{14}$ and $R^{15}$ each represent an optionally substituted alkyl group, an optionally substituted $C_{3-8}$ cycloalkyl group, an optionally substituted aryl group or an optionally substituted heteroaryl group, and $R^{16}$ is a hydrogen atom, a lower alkyl or an optionally substituted $C_{3-8}$ cycloalkyl group. In $NR^{15}R^{16}$, $R^{15}$ and $R^6$ may be combined to form a heterocyclic ring.

Step 1 is a step of oxidizing the methylsulfanyl group in the general formulae (4-b), (4-d), (4-f) and (4-i) in the scheme A-4 into a methylsulfinyl group or methanesulfonyl group, and by reaction with m-chloroperbenzoic acid at 0° C. to room temperature in a halogenated hydrocarbon solvent such as dichloromethane, dichloroethane etc. or by oxidization with oxone in water-containing methanol or water-containing tetrahydrofuran, the corresponding methanesulfinyl or methanesulfonyl compound to the starting material is obtained. Either oxide can be used in the subsequent step.

Steps 2 and 3 are steps of substituting the methanesulfinyl group or methanesulfonyl group obtained in step 1 with an alkoxy group ($OR^{14}$) or an amine ($NR^{15}R^{16}$). Step 2 is a step of reacting $R^{14}$—OH at room temperature to 70° C. in the presence of a base such as methylamine, triethylamine etc. in a solvent such as alcohol or tetrahydrofuran, whereby ether (5-a), (5-b), (5-c) or (5-d) corresponding to the starting material can be obtained. Alternatively, the desired product can be obtained in a solvent such as N,N-dimethylformamide or alcohol by reacting $R^{14}$—OH and sodium alkoxide prepared from sodium hydride.

Step 3 is a reaction of reacting an amine ($R^{15}R^{16}NH$) at room temperature to 70° C. in the presence of a base such as methylamine, triethylamine etc. in a solvent such as alcohol or tetrahydrofuran, whereby the amine (5-a), (5-b), (5-c) or (5-d) corresponding to the starting material can be obtained.

(5-a), (5-b), (5-c) and (5-d) are reacted in the same manner as in steps 3 and 4 in the scheme A-1, whereby the compounds of the general formula (I) wherein the ring Y is 1,2,4-oxadiazole, 1,3,4-oxadiazole, 1,3,4-thiadiazole or 1,3,4-triazole substituted with an alkoxy group or an amide derivative can be obtained.

The compounds of the general formula (1-d) in the scheme A-1, wherein the substituent group Q at the 3-position of the imidazo[1,2-a]pyridine ring can be represented by a 1,2,4-oxadiazole ring substituted with an alkylsulfanyl group, alkoxy group or amino group can also be synthesized by the method shown in scheme A-6.

Scheme A-6

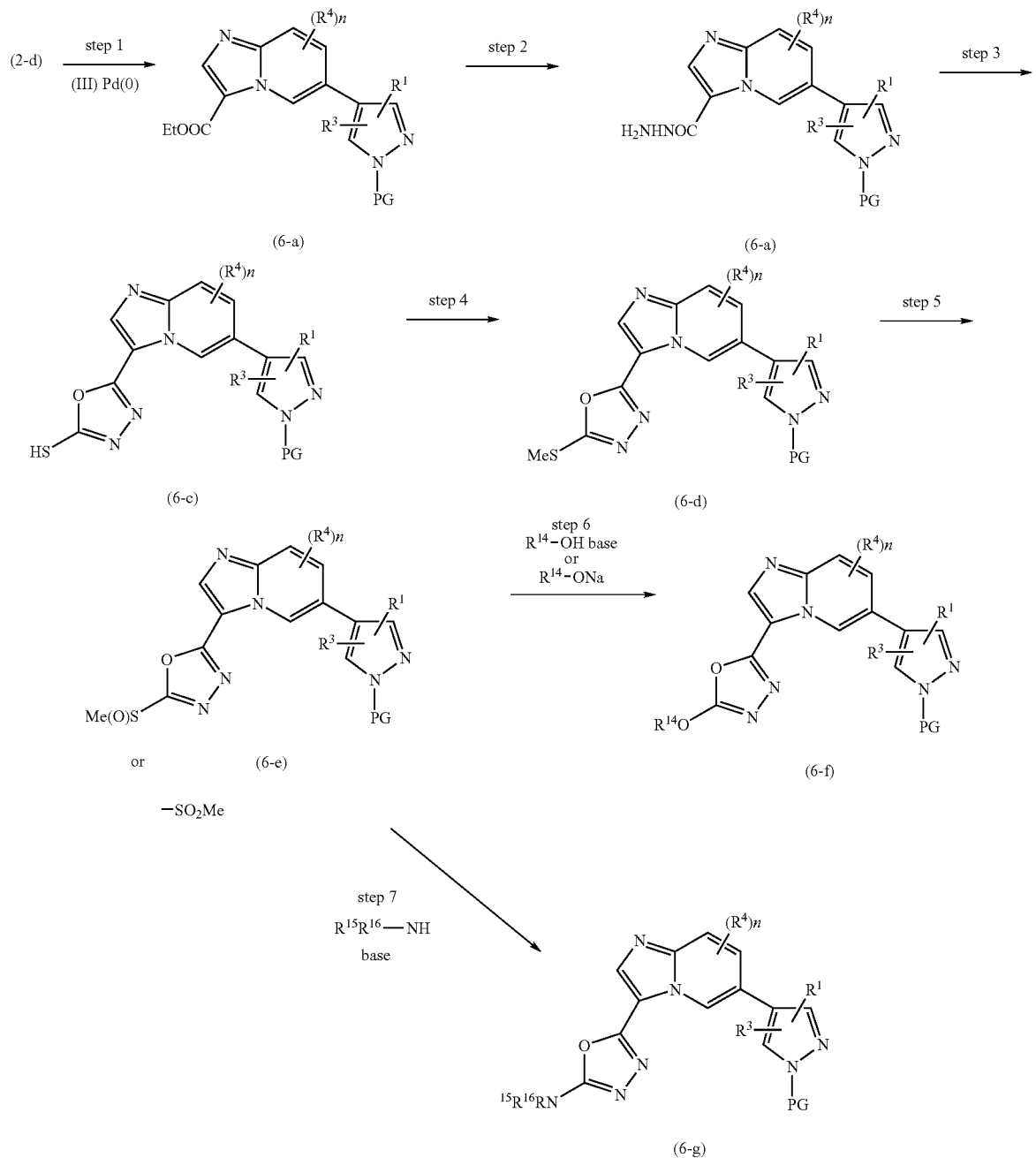

In the scheme, each symbol represents the same group as defined above. However, $R^{14}$ and $R^{15}$ each represent an optionally substituted alkyl group, an optionally substituted $C_{3-8}$ cycloalkyl group, an optionally substituted aryl group or an optionally substituted heteroaryl group, and $R^{16}$ is a hydrogen atom, a lower alkyl group or an optionally substituted $C_{3-8}$ cycloalkyl group. In $NR^{15}R^{16}$, $R^{15}$ and $R^{16}$ may be combined to form a heterocyclic ring. PG represents a protective group such as a trityl group, tetrahydropyranyl group etc., and (III) represents the structural formula shown in the scheme A-1.

Step 1 is the same reaction as in step 3 in the scheme A-1, and by cross-coupling (2-d) in the scheme A-2 with (III), (6-a) can be obtained.

Step 2 corresponds to step 5 in the scheme A-7, and steps 3 and 4 are steps which are identical with steps 3 and 4 in the scheme A-4, respectively. (6-a) can be converted in steps 2, 3 and 4 into (6-d) having a 1,2,4-oxadiazole ring substituted with an alkylsulfanyl group. Step 5 is a step of oxidizing the methanesulfanyl group, which is carried out under the same conditions as in step 4 in the scheme A-4, to give (6-e). Step 6 is a reaction step of substituting the methanesulfinyl group or methylsulfonyl group in (6-e) with an alkoxy group ($R^1 4O$ group), and by the same reaction as in step 2 in the scheme A-5, Compound (6-f) having a 1, 2, 4-dioxadiazole ring substituted with the $R^{14}O$ group can be obtained. Step 7 is a step of substitution with an amino group ($R^{15}R^{16}N$ group), and Compound (6-g) having a 1,2,4-oxadiazole ring substituted with $R^{15}R^{16}N$ can be obtained from (6-e) by the same reaction as in step 3 in the scheme A-5. (6-d), (6-f) and (6-g) can be subjected to deprotection of pyrazole by the same method as in step 4 in the scheme A-1, whereby the compounds of the general formula (1-e) in the scheme A-1, wherein the substituent group Q at the 3-position of the imidazo[1,2-a]pyridine ring can be represented by a 1,2,4-oxadiazole ring substituted with an alkylsulfanyl group, $R^{14}O$ group or $R^{15}R^{16}N$ group can be obtained.

The compounds represented by the general formula (1-d) in the scheme A-1 can also be synthesized by a method in scheme A-7 or A-8.

bromine in a solvent such as dimethylformamide, alcohol, water, acetic acid etc. under ice-cooling. This reaction can also be carried out in the presence of a base such as sodium bicarbonate or potassium bicarbonate. Step 3 can be carried out in the same manner as in step 2 in the scheme A-1, but when the halogen atom at the 3-position of the imidazopyridine ring in (7-b) is chlorine, coupling reaction using 2-(di-t-butylphosphino)diphenyl as a ligand for the palladium catalyst can be carried out at room temperature to a temperature of 80° C. by a method described in J. P. Wolfe and S. L. Buchwald, Angew. Chem. Int. Ed. 1999, 38, 2413.

Alternatively, the compounds represented by the general formula (1-e) in the scheme A-1 can be obtained by deprotecting (7-b) in the same method as in step 4 in the scheme A-1 and then cross-coupling the product under the same conditions as in the method in step 2 in the scheme A-1.

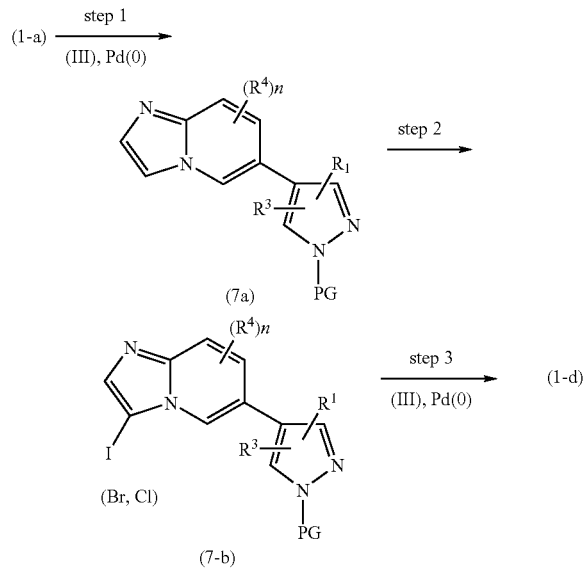

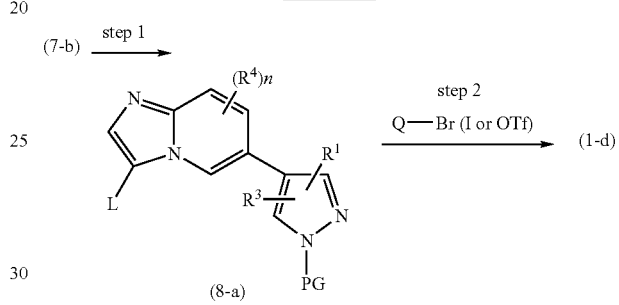

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group or heteroaryl group. PG represents a protecting group such as a trityl group, tetrahydropyranyl group etc., and (II) and (III) refer to the structural formulae shown in the scheme A-1.

This method is a method wherein the imidazopyridine ring is bound to the pyrazole ring to give (7-a), and then the ring Y [(Z)n-Y—] which may be arbitrarily substituted with (Z)n is introduced into the imidazopyridine ring. Step 1 can be carried out in the same manner as step 3 in the scheme A-1. Step 2 is a step of halogenating the 3-position of the imidazopyridine ring, and the corresponding iodide, bromide or chloride (7-b) can be obtained by adding a 1- to 1.2-fold excess of N-iodosuccinimide, N-bromosuccinimide or N-chlorosuccinimide in a solvent such as dimethylformamide, alcohol, dichloromethane or chloroform under ice-cooling or a temperature up to 60° C. These solvents may also contain water. Alternatively, the iodide or bromide can be obtained by adding a 1- to 1.2-fold excess of iodine or In the reaction scheme, each symbol represents the same group as defined above. However, Q represents ring Y [(Z)n-Y—] which may be arbitrarily substituted with the above-defined (Z) n (=substituent groups Z wherein n is 0, 1, 2 or 3), and the ring Y represents an aryl group, a heteroaryl group, or a non-aromatic cyclocyclic group having a double bond in the cycle. When the ring Y represents a non-aromatic cyclocylic group having a double bond in the cycle, the binding position of Br, I or OTf in Q—Br (I, OTf) shall be that of a vinyl type substituent group. PG represents a protecting group such as a trityl group, tetrahydropyranyl group etc., and L represents a group represented by trialkyl tin, boric acid, or cyclic or non-cyclic borate.

The method in the scheme A-8 is a method wherein a trialkyl tin derivative, boric acid derivative or borate derivative (8-a) of the imidazopyridine ring is synthesized and reacted with a halide or triflate of Q [ring Y ((Z)n-Y—) which may be arbitrarily substituted with (Z)n], that is, (Z)n-Y—Br (I, OTf). By this method, the compound represented by the general formula (1-d) in the scheme A-1, wherein the ring Y is a non-aromatic cyclocyclic group, can also be synthesized.

Step 1 is (1) a process of preparing a Grignard reagent by lithiolation of (7-b) with n-butyl lithium or transmetallation thereof with isopropyl magnesium halide and then adding tri-n-butyl tin chloride to synthesize a tributyl tin derivative, (2) a process of heating (7-b) together with bis (tri-n-butyl tin) in the presence of tetrakistriphenyl phosphine palladium in a toluene or xylene solution to synthesize a tributyl tin derivative, (3) a process of preparing a Grignard reagent by lithiolation of (7-b) with n-butyl lithium or by adding isopropyl magnesium halide, then adding triisopropyl boronate, and hydrolyzing the product to synthesize a boric acid derivative, or (4) a process of synthesizing a boronate by a method described in T. Ishiyama et al., J. Org. Chem., 60, 7508 (1995).

Step 2 is a step of cross-coupling the imidazopyridine ring with Q-Br (I, OTf), in which (1-d) can be synthesized under the same conditions as in step 2 in the scheme A-1.

Alternatively, the pyrazole ring can be constructed through the route shown in the scheme A-8 from the imidazo[1,2-a]pyridine carboxy aldehyde (9-a) as the starting material by a method disclosed in JP-A 8-183787.

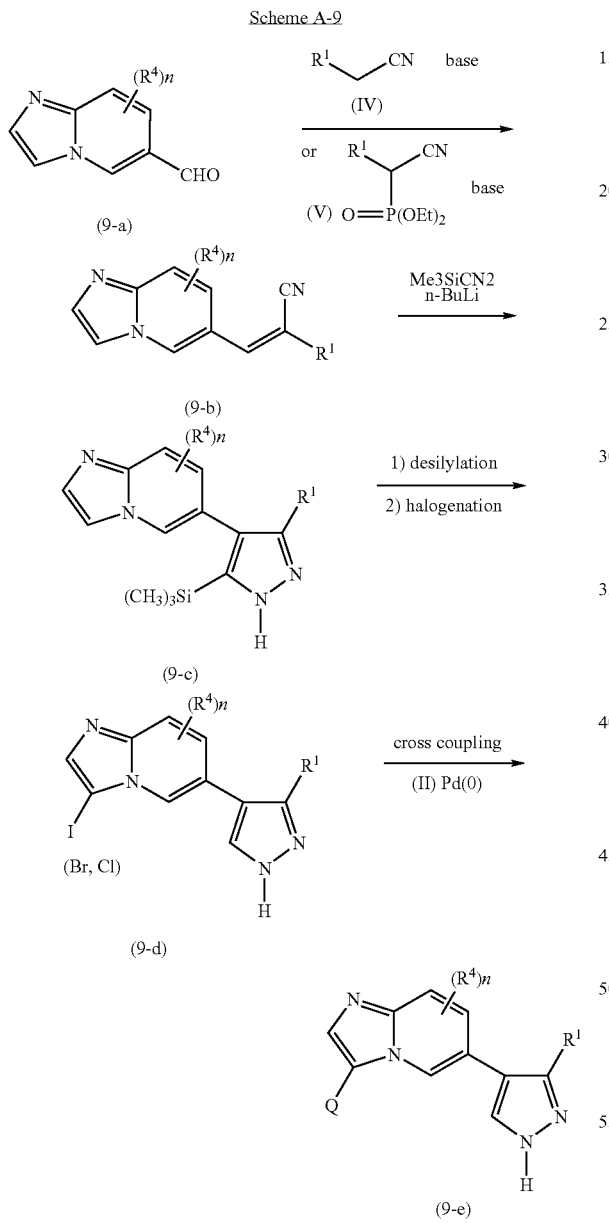

In this method, the aldehyde (9-a) is reacted with (IV) in the presence of a base such as sodium hydride or sodium methoxide in a solvent not inhibiting the reaction, such as N,N-dimethylformamide, tetrahydrofuran or alcohol, or the aldehyde (9-a) is subjected to Wittig reaction with a compound represented by (V), to synthesize an olefin (9-b), followed by reacting (9-b) at low temperatures with n-butyl lithium and trimethylsilyl diazomethane by a method descried in T. Aoyama et al., Tetrahedron Letters, 25, 433 (1984), to construct a pyrazole ring (9-c). The desilylation for synthesis of (9-d) can be accomplished by a usual method, for example by treatment with tetrabutyl ammonium fluoride. The halogenation can be carried out in the same manner as in step 1 in the scheme A-1. Whichever of the desilylation or halogenation is first conducted, (9-d) can be obtained. The reaction for introduction of the ring Q by cross-coupling of (9-d) can be carried out under the same conditions as in step 2 in the scheme A-1.

When X (nitrogen-containing condensed aromatic heterocyclic group) in the general formula (I) is a benzimidazole ring, Production Method B can be used for synthesis.

Production Method B

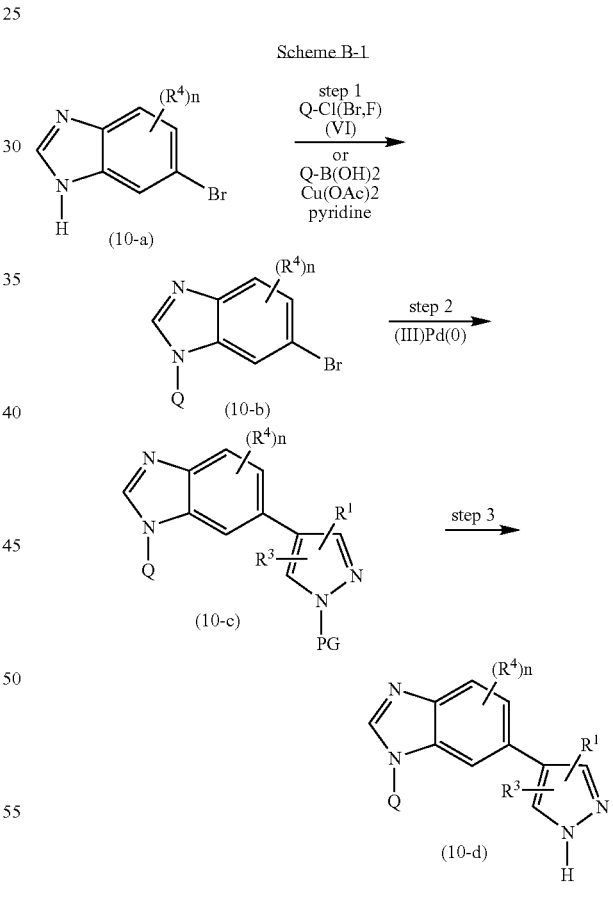

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group or heteroaryl group. (II) refers to the structural formula shown in the scheme A-1.

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group or heteroaryl group. (III) refers to the structural formula defined in the scheme A-1, and PG represents a protecting group such as a trityl group, tetrahydropyranyl group etc.

Step 1 is a step of introducing Q (ring Y[(Z)n-Y—]) which may be arbitrarily substituted with (Z)n) into nitrogen of the benzimidazole. When the ring Y has an electron-withdrawing substituent group such as a nitro group, carbonyl group etc. or when the ring Y is an electron-deficient ring such as pyridine, (10-b) can be synthesized by heating (10-a) and an aryl halide or heteroaryl halide (VI) at room temperature to 18° C., preferably at 60 to 140° C., in the presence of a base such as triethylamine or potassium carbonate in a solvent such as N,N-dimethylformamide or dimethyl sulfoxide.

Alternatively, (10-b) can be synthesized by reacting (10-a) with arylboronic acid Q—B(OH)$_2$, Cu(OAc)$_2$ and a base such as pyridine at room temperature to 60° C., according to a method of P. Y. S. Lam et al., Tetrahedron Letters 39, 2941 (1998). The reaction product is obtained as a mixture of (10-b) and its positional isomers, and can be separated by purification on a column after the reaction in step 1 or by purification on a column in step 2.

Step 2 is a step of coupling (10-b) with a pyrazole derivative (III) by a palladium catalyst, and step 3 is a step of deprotecting the pyrazole-protecting group, and the respective steps can be carried out in the same manner as in steps 3 and 4 in the scheme A-1, respectively. By these steps, the compounds represented by the general formulae (10-c) and (10-d) can be obtained.

(10-c) can also be synthesized through the route shown in the scheme B-2.

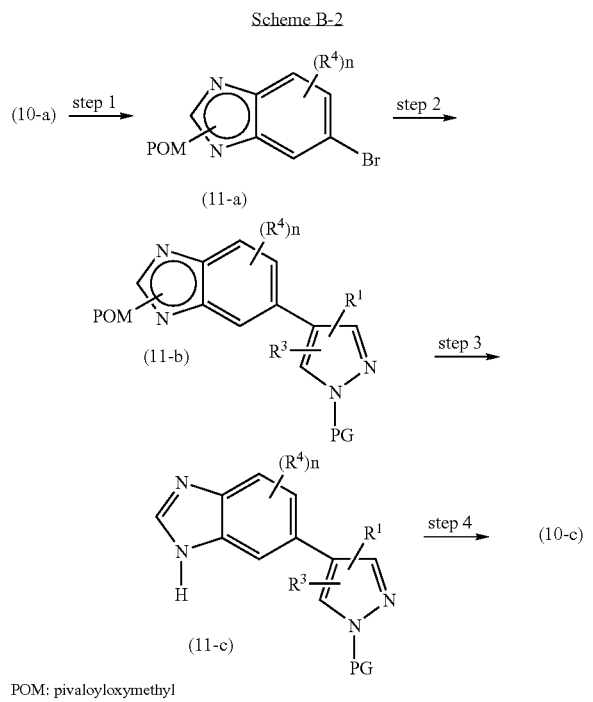

Scheme B-2

POM: pivaloyloxymethyl

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group or heteroaryl group. PG represents an amino group-protecting group such as a trityl group, tetrahydropyranyl group etc. POM represents a pivaloyloxymethyl group.

Step 1 is a step of protecting nitrogen of the benzimidazole with a pivaloyloxymethyl group. (11-a) can be synthesized by reacting (10-a) with pivaloyloxymethyl chloride in the presence of a base such as triethylamine or potassium carbonate in a solvent such as N,N-dimethylformamide.

Step 2 is a step identical with step 3 in the scheme A-1.

Step 3 is a step of deprotecting the pivaloyloxy methyl group, in which the group is hydrolyzed by reaction with an aqueous alkaline solution of sodium hydroxide, potassium hydroxide or lithium hydroxide in a solvent such as alcohol or tetrahydrofuran.

Step 4 is a step of introducing the substituent group Q into the benzimidazole to give (10-c), and this step can be carried out in the same manner as in step 1 in the scheme B-1, starting from (11-c), an aryl halide or heteroaryl halide represented by Q—Cl (Br, F) or an aryl boronic acid and heteroaryl boronic acid represented by Q—B(OH)$_2$. The positional isomers of (10-c) formed by the reaction can be separated by purification procedures with a column.

The compound of the general formula (10-b) in the scheme B-1 can also be synthesized by the route shown in the scheme B-3.

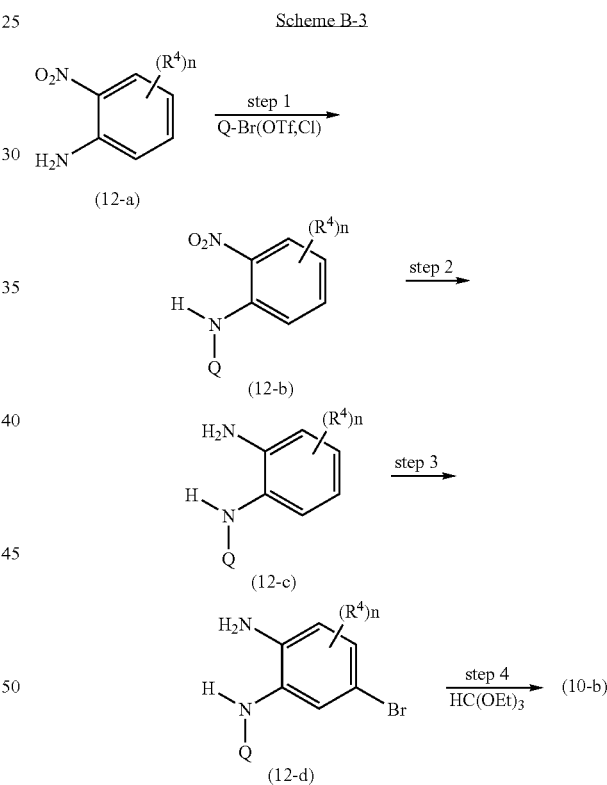

Scheme B-3

In the reaction scheme, each symbol represents the same group as defined above. However, Q represents ring Y [(Z)n-Y—] which may be arbitrarily substituted with the above-defined (Z) n (=substituent groups Z wherein n is 0, 1, 2 or 3), and the ring Y represents an aryl group or heteroaryl group.

Step 1 is a reaction of aminating Q [aryl halide (or triflate) or heteroaryl halide (or triflate)] with (12-a). This reaction can be carried out according to a method described in S. L. Buchwald et al., J. Org. Chem. 65, 1144–1157 (2000), J. Org. Chem. 65, 1158–1174 (2000) or M. Nishiyama et al., Tetrahydron Letters 39, 617–620 (1998). The palladium catalyst includes, but is not limited to, catalyst systems comprising trisdibenzylidene acetone dipalladium [Pd$_2$(dba)$_3$] or palladium acetate combined with a ligand selected from tri-t-butyl phosphine, 2-(di-t-butylphosphino)diphenyl and 2,2'-bis(diphenylphoshino)-1,1'-binaphthyl (BINAP). The usable base includes cesium carbonate, t-butoxy sodium and potassium phosphate. (12-b) can be obtained by heating (12-a) and Q—Br (Cl or OTf) at 60 to 140° C. in the presence of the palladium catalyst and the base in a solvent such as toluene, xylene, 1,2-dimethoxyethane or 1,4-dioxane.

Step 2 is reduction of the nitro group, in which (12-b) is heated under stirring at 50° C. to a reflux temperature with iron powder in the presence of ammonium chloride in a solvent such as methanol, ethanol or water or in a solvent mixture thereof, or is catalytically reduced with palladium-carbon, platinum, or Raney nickel as the catalyst in a solvent such as methanol, ethanol or ethyl acetate under hydrogen atmosphere, whereby (12-c) can be obtained.

Step 3 is a bromating step in which (12-c) can be obtained by adding N-bromosuccinimide under ice-cooling to room temperature in a solvent such as N,N-dimethylformamide, methanol or ethanol.

Step 4 is a step of constructing a benzimidazole ring, in which (12-d), together with ethyl o-formate or methyl o-formate, is heated under reflux to give (10-d).

The compounds represented by the general formula (10-b) in the scheme B-1 can also be synthesized by the method shown in the scheme B-4. By this synthesis method, the compound of the general formula (I) wherein X (nitrogen-containing condensed aromatic heterocyclic ring) is benzimidazole, and the ring Y is a non-aromatic cyclocyclic ring, can be obtained.

Scheme B-4

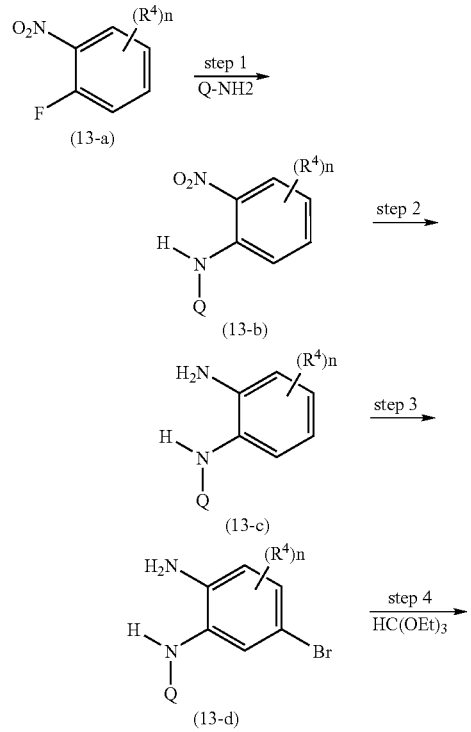

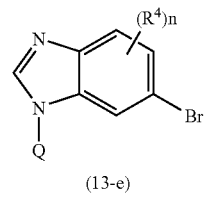

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group, a heteroaryl group, or a non-aromatic cyclocyclic group.

Step 1 shows a step of aminating, with Q-NH$_2$, the 1-fluoro-2-nitrobenzene derivative which may arbitrarily have substituent groups (R$^4$)$_n$ (n=0, 1 or 2). When Q is a nitrogen-containing non-aromatic cyclocyclic group such as 4-amino piperazine or 3-amino-8-azabicyclo[3,2,1]octane, hydrogen in the secondary amine in the ring shall be substituted with the substituent group Z. (13-a) and Q-NH$_2$ are heated at 80 to 120° C. in the presence of a base such as potassium carbonate, sodium hydride or triethylamine in a solvent such as N,N-dimethylformamide or dimethyl sulfoxide, whereby (13-b) is obtained.

Steps 2, 3 and 4 are reactions steps identical with steps 2, 3 and 4 in the scheme B-3 respectively. By these steps, (13-c), (13-d) and (13-e) are obtained from (13-b). When the ring Y is an aryl group or heteroaryl group, (13-e) is identical with the general formula (10-b) in the scheme B-1. By steps identical with the steps 2 and 3 in the scheme B-1, the compound of the general formula (10-d) in the scheme B-1 can be obtained from (13-e).

The compound of the general formula (I) wherein X (nitrogen-containing condensed aromatic heterocyclic group) is benzimidazole having a substituent group at the 2-position can be synthesized according to the scheme B-5 or B-6.

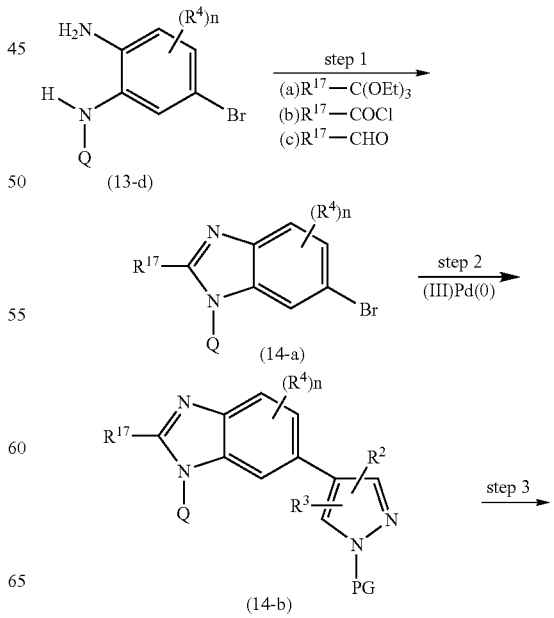

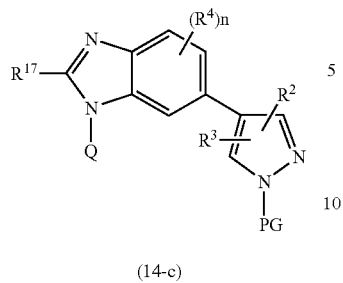

(14-c)

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group, a heteroaryl group, or a non-aromatic cyclocyclic group. $R^{17}$ represents an optionally substituted alkyl group, an optionally substituted $C_{3-8}$ cycloalkyl group, an optionally substituted aryl group or an optionally substituted heteroaryl group.

Step 1 is a method of synthesizing, from (13-d), (14-a) substituted with $R^{17}$ at the 2-position of benzimidazole, and (14-a) can be synthesized by reaction with a carboxylic acid ($R^{17}$—COOH) and a derivative thereof. The major synthesis method includes (a) a method of heating with $R^{17}$—C(O-lower alkyl group) 3 under reflux, (b) a method which comprises reacting an acid chloride ($R^{17}$—COCl) in the presence of a base such as triethylamine in a solvent such as dichloromethane, tetrahydrofuran and pyridine (c) to form an amide of (14-a) with $R^{17}$—COOH and heating the product in the presence of an acid catalyst such as p-toluenesulfonic acid in toluene or benzene as the solvent, to dehydrate it to form a condensed ring, and (c) a method of dehydrating cyclization by heating together with an aldehyde ($R^{17}$—CHO) in the presence of an acid catalyst such as hydrochloric acid or sulfuric acid in an alcohol solvent.

Step 2 is a coupling reaction of (14-a) with the structural formula (III) shown in the scheme A-1 in the presence of palladium as the catalyst, and (14-b) can be obtained by the same reaction as in step 2 in the scheme B-1.

Step 3 is a step of deprotecting the pyrazole, and the compound represented by the general formula (14-c) can be obtained by the same method as in step 3 in the scheme B-1.

The compound of the general formula (I) wherein X (nitrogen-containing condensed aromatic heterocyclic group) is benzimidazole substituted at the 2-position with a substituent group such as a sulfanyl group, alkoxy group or amino group can also be synthesized according to the scheme B-6.

Scheme B-6

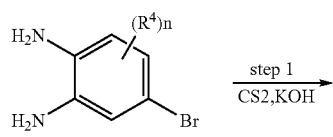

(15-a)

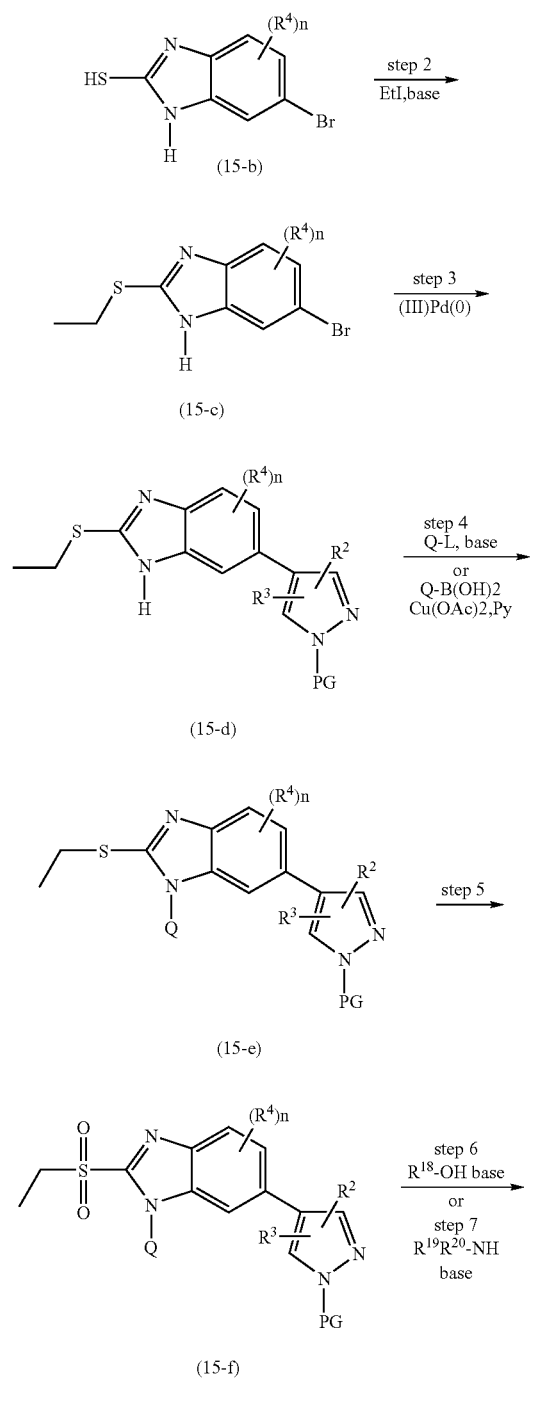

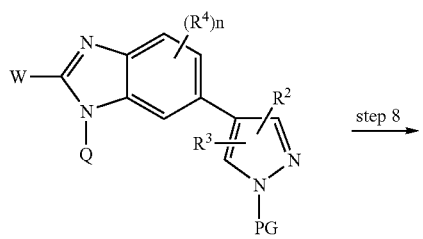

-continued

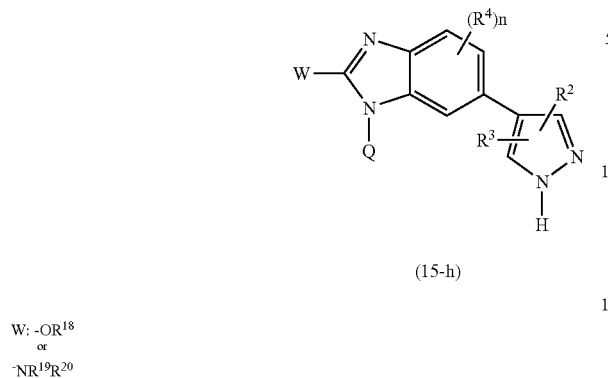

(15-h)

W: -OR¹⁸
or
-NR¹⁹R²⁰

In the reaction scheme, each symbol represents the same group as defined above. However, Q represents ring Y [(Z)n-Y—] which may be arbitrarily substituted with the above-defined (Z)n (=substituent groups Z wherein n is 0, 1, 2 or 3), and the ring Y represents an aryl group or a heteroaryl group. W represents OR¹⁸ or NR¹⁹R²⁰. R¹⁸ and R¹⁹ each represent an optionally substituted alkyl group, an optionally substituted $C_{3-8}$ cycloalkyl group, an optionally substituted aryl group or an optionally substituted heteroaryl group, and R²⁰ is a hydrogen atom, a lower alkyl or an optionally substituted $C_{3-8}$ cycloalkyl group. In NR¹⁹R²⁰, R¹⁹ and R²⁰ may be combined to form a heterocyclic ring.

Step 1 is a step of synthesizing benzimidazole having a thiol group at the 2-position, and (15-b) is obtained by heating (15-a) together with carbon disulfide and potassium hydroxide in methanol or ethanol. Step 2 is a step of alkylating the thiol to synthesize a thioether, in which (15-c) is obtained by reacting (15-b) with ethyl iodide under ice-cooling or at room temperature in the presence of a base such as sodium hydride in N,N-dimethylformamide. Steps 3 and 4 are respectively steps identical with steps 2 and 1 in the scheme B-1, to give (15-d) and (15-e) respectively.

Step 5 is a step of oxidizing the alkylsulfanyl group into an alkylsulfonyl group, and this step can be carried out in the same manner as in step 1 in the scheme A-5. By oxidization of (15-e), (15-f) is obtained.

Steps 6 and 7 show, respectively, steps of substituting the ethenesulfonyl group in (15-f) with an alkoxy group (OR¹⁸) or an amine (NR¹⁹R²⁰). Step 6 shows the same reaction conditions as in step 2 in the scheme A-5, to convert (15-f) into ether (15-g) wherein W is OR¹⁸.

Step 7 shows the same reaction conditions as in step 3 in the scheme A-5, to convert (15-f) into amine derivative (15-g) wherein W is NR¹⁹R²⁰.

Step 8 is a step of deprotecting the pyrazole, and this step can be carried out in the same manner as in step 3 in the scheme B-1, to give (15-h).

The compounds of the general formula (I) wherein X (nitrogen-containing condensed aromatic heterocyclic group) is quinazoline or quinoline can be synthesized according to Production Method C.

Production Method C

Scheme C-1

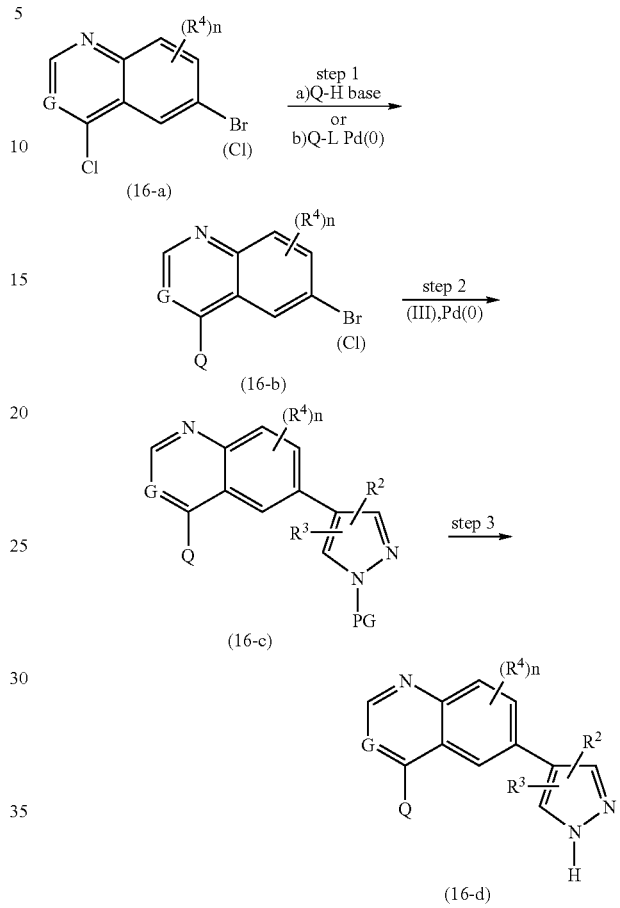

In the reaction scheme, each symbol represents the same group as defined above. However, G represents N or CH, and Q represents ring Y [(Z)n-Y—] which may be arbitrarily substituted with the above-defined (Z)n (=substituent groups Z wherein n is 0, 1, 2 or 3). (III) refers to the structural formula of the pyrazole derivative shown in the scheme A-1. PG represents a protecting group such as a trityl group, tetrahydropyranyl group etc., and L represents a group represented by trialkyl tin, boric acid, or cyclic or non-cyclic borate.

Step 1 is a step of introducing the substituent group Q into (16-a). When Q—H is a cyclic amine derivative such as piperidine, piperazine or homopiperazine, (16-b) is synthesized by method 1) in step 1, or in the case of cross-coupling with Q—L, (16-b) is synthesized by method 2) in step 1. The method 1) in step 1 is a reaction wherein (16-b) is obtained by reacting Q—H with (16-a) at room temperature or under heating to a temperature up to 150° C. in the presence of a base such as potassium carbonate or triethylamine in a solvent not inhibiting the reaction, such as N,N-dimethylformamide, N-methylpyrrolidone or dimethyl sulfoxide. The method 2) in the step 1 is the same reaction as in step 2 in the scheme A-1, and by coupling (16-a) with Q—L under suitable temperature control in the presence of palladium catalyst, Q can be introduced selectively into the 4-position of the quinazoline ring. This method can be applied to the case where the structural formula (16-a) is quinazoline (G=N).

Step 2 is a step of palladium-catalyzed cross-coupling reaction of (16-b) with the pyrazole derivative (III), to give (16-c) by the same method as in step 3 in A-1. Step 3 is a step of deprotecting the pyrazole-protecting group, to give (16-d) by the same reaction as in step 4 in the scheme A-1.

(16-c) can also be synthesized according to the route shown in the scheme C-2.

In the reaction scheme, each symbol represents the same group as defined above. However, G represents N or CH, and Q represents ring Y [(Z)n-Y—] which may be arbitrarily substituted with the above-defined (Z)n (=substituent groups Z wherein n is 0, 1, 2 or 3). (III) refers to the structural formula of the pyrazole derivative shown in the scheme A-1. PG represents a protecting group such as a trityl group, tetrahydropyranyl group etc., and L represents a group represented by trialkyl tin, boric acid, or cyclic or non-cyclic borate.

This is a method of previously binding a pyrazole ring to (17-a) as the starting material and then introducing the substituent group Q.

Step 1 is the same reaction as in step 3 in the scheme A-1, whereby (17-b) can be obtained.

Step 2 is a reaction for converting the hydroxyl group in (17-b) into a triflate group, and by reaction with trifluoromethanesulfonic anhydride at −70° C. to a temperature up to 20° C. or by reaction with N-phenyl-bis(trifluoromethane sulfonimide) in the presence of a base such as triethylamine or sodium hydride, (17-c) can be obtained.

Step 3 is a method of introducing the substituent group Q into (17-c), and is the same step as in 1) or 2) in step 1 in the scheme C-1. In this case, this step can also be applied regardless of whether (17-a) is a quinazoline ring (G=N) or a quinoline ring (G=CH), whereby (16-c) can be synthesized.

The compounds of the general formula (I) wherein X (nitrogen-containing condensed aromatic heterocyclic group) is a quinazoline ring and Y is a 1,3,4-oxadiazole ring or 1,3,4-thiadiazole ring can be synthesized according to the route in the scheme C-3.

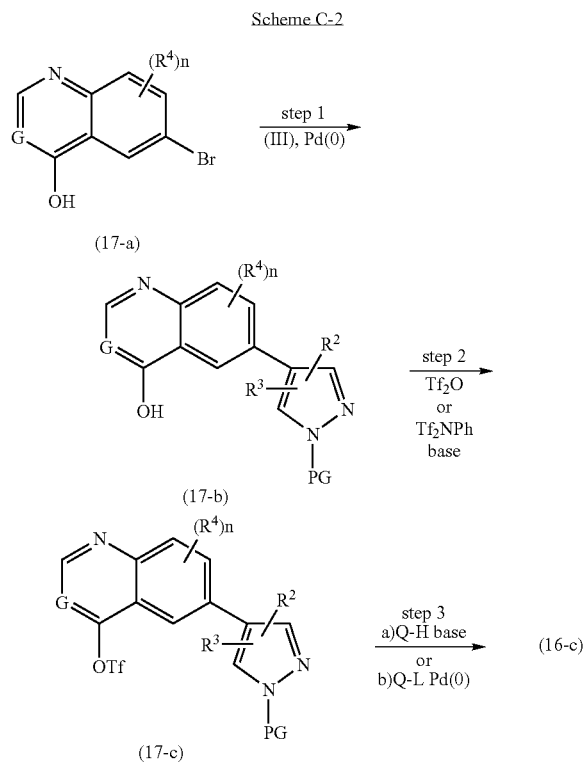

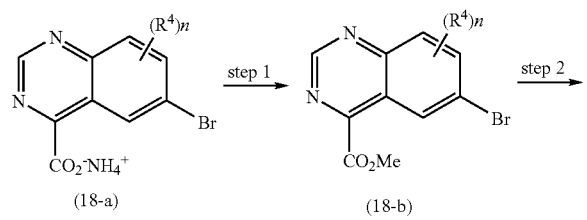

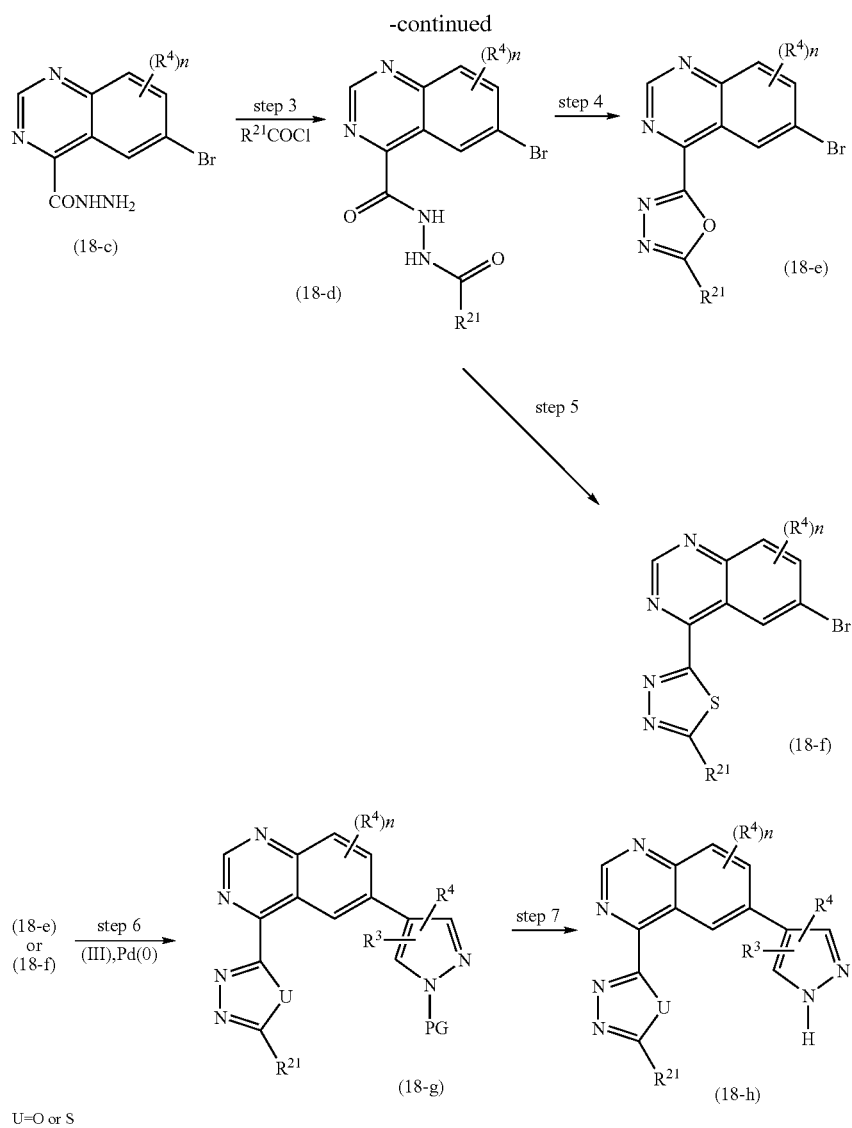

U=O or S

In the reaction scheme, each symbol represents the same group as defined above. However, Q represents ring Y[(Z)n-Y—] which may be arbitrarily substituted with the above-defined (Z)n (=substituent groups Z wherein n is 0, 1, 2 or 3). U represents O or S. (III) refers to the structural formula of the pyrazole derivative shown in the scheme A-1. $R^{21}$ represents an op s tionally substituted alkyl group, an optionally substituted $C_{3-8}$ cycloalkyl group, an optionally substituted aryl group or an optionally substituted heteroaryl group. PG represents a protecting group such as a trityl group, tetrahydropyranyl group etc.

(18-a) can be synthesized according to a method described in W. L. F. Armarego et al., J. Chem. Soc. (B), 452 (1967).

Step 1 is a step of converting the ammonium carboxylate of (18-a) into the corresponding methyl carbonate. (18-b) can be obtained by heating (18-a) in methanol under reflux in the presence of a catalytic amount of sulfuric acid.

Steps 2 and 3 are carried out under the same conditions as in the steps 5 and 6 in the scheme A-2, to give the compounds represented by the general formulae (18-c) and (18-d) respectively.

Step 4 is a step of cyclizing a 1,3,4-oxadiazole ring in (18-d), and this step is carried out in the same manner as in step 7 in the scheme A-2, to give (18-e).

Step 5 is a step of cyclizing a 1,3,4-thiadiazole ring in (18-d), and this step is carried out under the same conditions as in step 8 in the scheme A-2, to give (18-f).

Step 6 is a step of palladium-catalyzed cross-coupling reaction of (18-e) or (18-f) with the pyrazole derivative (III), and step 7 is a step of deprotecting the pyrazole-protecting group, and the respective groups are carried out according to the same methods as in steps 3 and 4 in the scheme A-1, respectively. The compounds represented by the general formulae (18-g) and (18-h) can be obtained in steps 6 and 7, respectively.

The compounds of the general formulae (18-e) and (18-f) in the scheme C-3, wherein the substituent group $R^{21}$ is a sulfanyl group, alkoxy group or amino group, can be synthesized according to the scheme C-4.

methyl iodide. These steps can be carried out in the same manner as in steps 3 and 4 in the scheme A-4, to give (19-b).

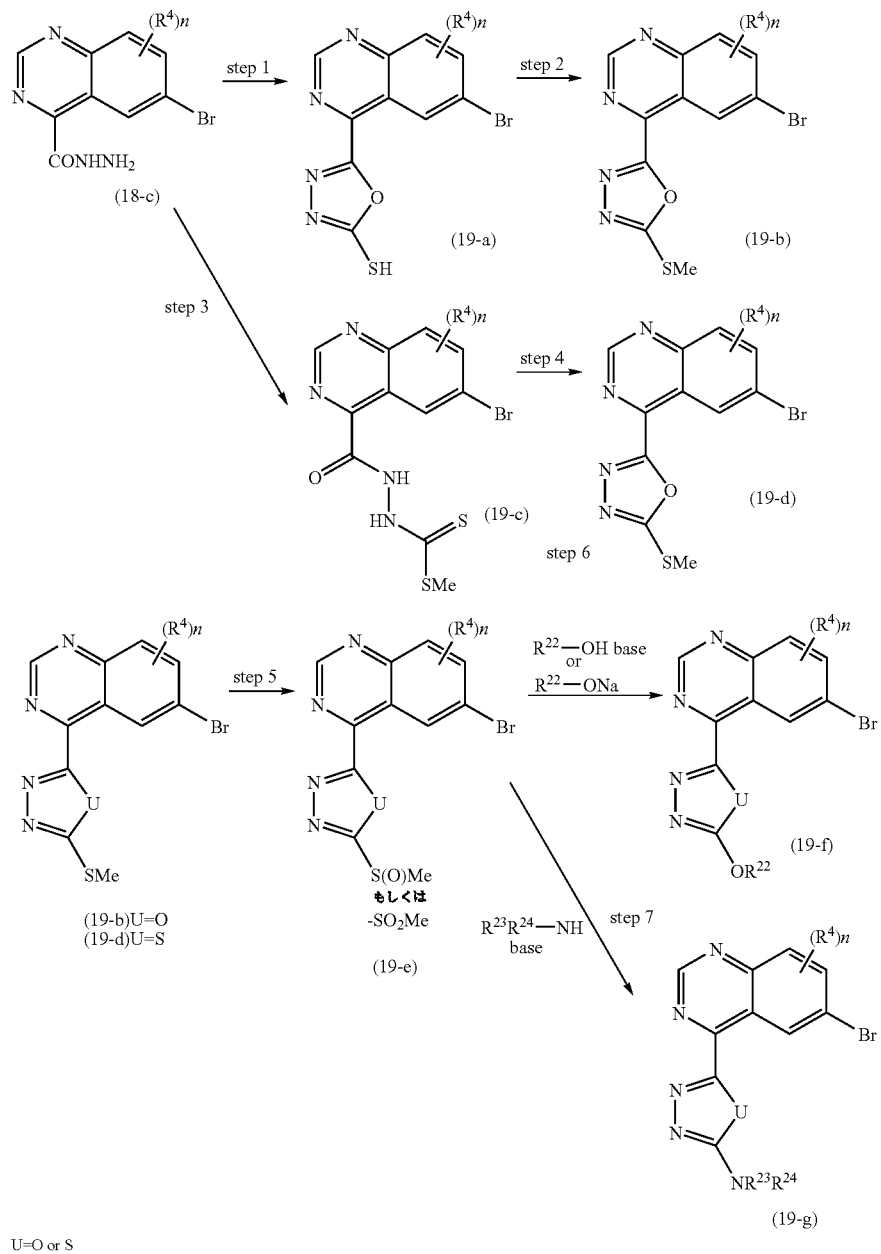

U=O or S

In the reaction scheme, each symbol represents the same group as defined above. However, U represents oxygen or sulfur, $R^{22}$ and $R^{23}$ each represent an optionally substituted alkyl group, an optionally substituted $C_{3-8}$ cycloalkyl group, an optionally substituted aryl group or an optionally substituted heteroaryl group, and $R^{24}$ represents a hydrogen atom, a lower alkyl or an optionally substituted $C_{3-8}$cycloalkyl group. In $NR^{23}R^{24}$, $R^{23}$ and $R^{24}$ may be combined to form a heterocyclic ring.

Step 1 is a step of converting (18-c) in the scheme C-3 into a 1,2,4-oxadiazole ring having a thiol group at the 5-position, and step 2 is a step of methylating the thiol group with By reaction with an optionally substituted alkyl halide in place of methyl iodide in step 2, the corresponding alkyl sulfanyl group can be introduced.

Steps 3 and 4 are steps of constructing a 1,2,4-thiadiazole ring having a thiol group at the 5-position, and these steps can be carried out under the same conditions as in the steps 5 and 6 in the scheme A-4, to give (19-d).

Step 5 is a step of oxidizing the methanesulfanyl group in (19-b) or (19-d), and this step be carried out under the same conditions as in step 1 in the scheme A-5, wherein depending on the degree of oxidation, a methanesulfinyl group or methylsulfonyl group (19-e) corresponding to the starting material can be obtained. Both the methanesulfinyl group and methylsulfonyl group can be used in the subsequent substitution reaction.

Step 6 shows a step of substitution with an alkoxy group, in which a 1,2,4-oxadiazole ring substituted with an alkoxy group, and a 1,2,4-thiadiazole ring (19-f), can be obtained under the same conditions as in step 2 in the scheme A-5.

Step 7 is a step of substitution with an amino group, in which a 1,2,4-oxadiazole ring substituted with an amino group, and a 1,2,4-thiadiazole ring (19-g), can be obtained under the same conditions as in step 3 in the scheme A-5.

(19-b), (19-d), (19-f) and (19-g) can be subjected to coupling reaction with the pyrazole derivative (III) under the same conditions as in steps 6 and 7 in the scheme C-3 and then to deprotection of the pyrazole-protecting group, whereby the compounds of the general formula (I) wherein X is quinazoline, and the ring Y is a 1,2,4-oxadiazole ring or a 1,2,4-thiadiazole ring, each of which is substituted with an alkylsulfanyl group, an alkoxy group or an amino group can be obtained.

The compounds of the general formula (I) wherein X (nitrogen-containing condensed aromatic heterocyclic group) is 2,1-benzoisoxazole can be synthesized according to Production Method D.

Production Method D

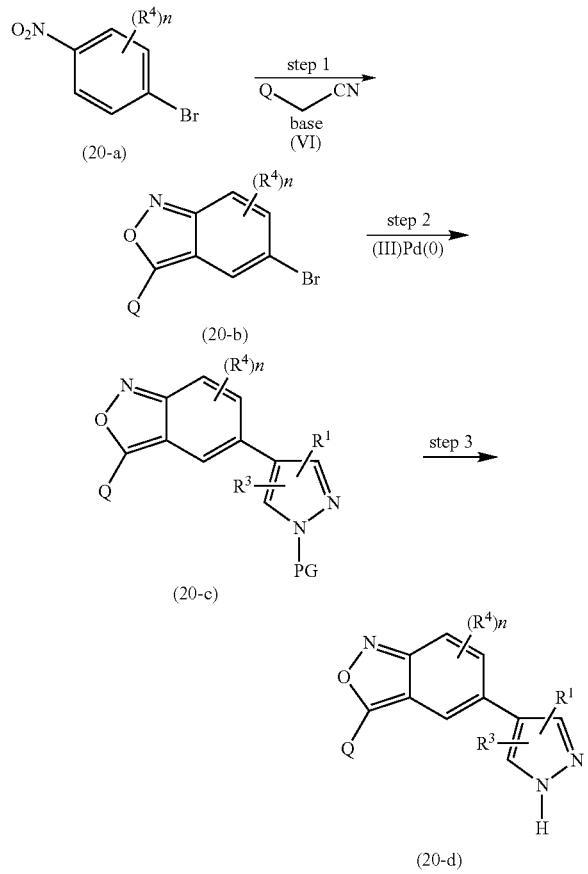

In the reaction scheme, each symbol represents the same group as defined above. PG represents a protecting group such as a trityl group, tetrahydropyranyl group etc., and (III) refers to the structural formula shown in the scheme A-1. Q represents ring Y[(Z)n-Y—] which may be arbitrarily substituted with the above-defined (Z)n (=substituent groups Z wherein n is 0, 1, 2 or 3), and Q in the structural formula (VI) represents an aryl group or heteroaryl group.

Step 1 is a step of synthesizing a benzoisoxazole ring containing Q, according to a method described in J. S. Baum et al., J. Org. Chem., 52, 2983 (1987).

(20-b) can be obtained by reacting (20-a) with (VI) under ice-cooling or at a temperature of up to 40° C. in the presence of a base such as potassium t-butoxide, sodium methoxide or potassium hydroxide in an alcohol such as t-butanol or methanol or in a solvent mixture of an alcohol and tetrahydrofuran. Steps 2 and 3 indicate the same reactions as in steps 3 and 4 shown in the scheme A-1, respectively.

The pyrazole derivative (III) substituted with R1 or R3 at the 3- or 5-position, which is used in Production Methods A, B, C and D, can be synthesized according to Production Method E.

Production Method E

The pyrazole having an optionally substituted aryl group or an optionally substituted heteroaryl group at the 3-position, having a protective group at the 1-position and being substituted with a halogen atom at the 4-position, can be synthesized according to the scheme E-1.

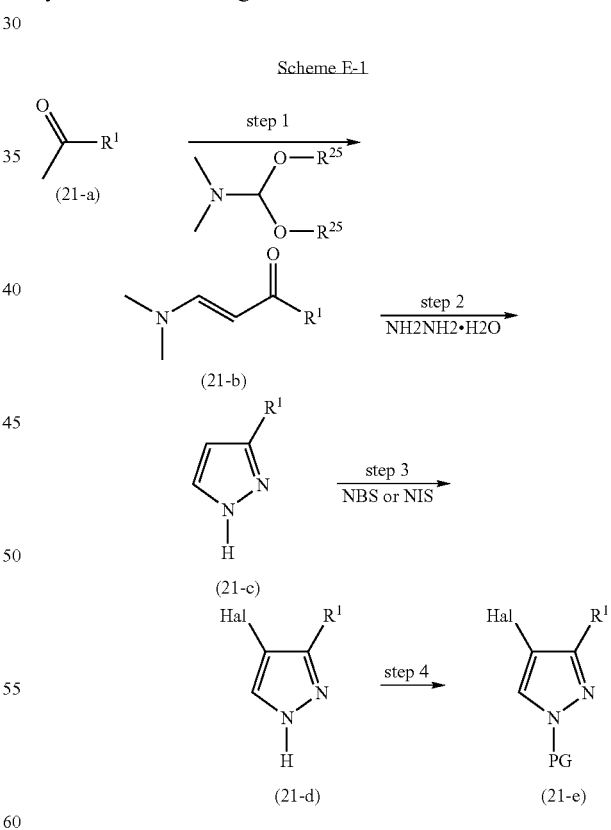

In the reaction scheme, $R^1$ represents an optionally substituted aryl group or an optionally substituted heteroaryl group, and $R^{25}$ represents a lower alkyl group. PG represents a protecting group such as a trityl group, tetrahydropyranyl group etc., and Hal represents a halogen atom such as bromine or iodine.

Step 1 is a step of heating (21-a) and N,N-dimethylformamide dimethyl acetal or N,N-dimethylformamide diethyl acetal at 80° C. or at a temperature of up to reflux temperature, to give (21-b).

Step 2 is a step of reacting hydrazine monohydrate with (21-b) to construct a pyrazole ring. (21-c) is obtained (a) by heating together with hydrazine monohydrate in ethanol under reflux or (b) by stirring under ice-cooling or at a temperature of up to room temperature in a solvent such as methanol or ethanol with a small amount of acetic acid.

Step 3 is a step of halogenating the 4-position of pyrazole, in which (21-d) is obtained by reacting (21-c) at 0 to 100° C. in a solvent such as N,N-dimethylformamide with N-bromosuccinimide or N-iodosuccinimide added.

Step 4 is a step of introducing a protecting group into the pyrazole, and this step can be carried out under generally known suitable conditions depending on the type of the protecting group. When e.g. a trityl group is to be introduced, (21-d) is reacted at room temperature to 100° C. in the presence of a base such as triethylamine in N,N-dimethylformamide as the solvent, whereby (21-e) can be obtained. When a tetrahydropyranyl group is to be introduced, (21-d) is reacted with an acid catalyst such as 3,4-dihydro-2H-pyran, p-toluenesulfonic acid etc. in a solvent such as tetrahydrofuran at room temperature to 50° C., whereby (21-e) can be obtained. Positional isomers formed by introducing the protecting group can be separated by purification using silica gel column chromatography or by recrystallization. Whichever of the step of halogenating (21-c) and the step of introducing the substituent group is first conducted, (21-e) can be obtained; for example, it can be obtained by introducing the protecting group into (21-c) by the method in step 4 and subsequent halogenation by the method in step 3.

Pyrazole substituted at the 3-position with a substituent group other than an aryl or heteroaryl group, having a protecting group at the 1-position, and substituted with a halogen atom at the 4-position can be synthesized according to the scheme E-2 or E-3.

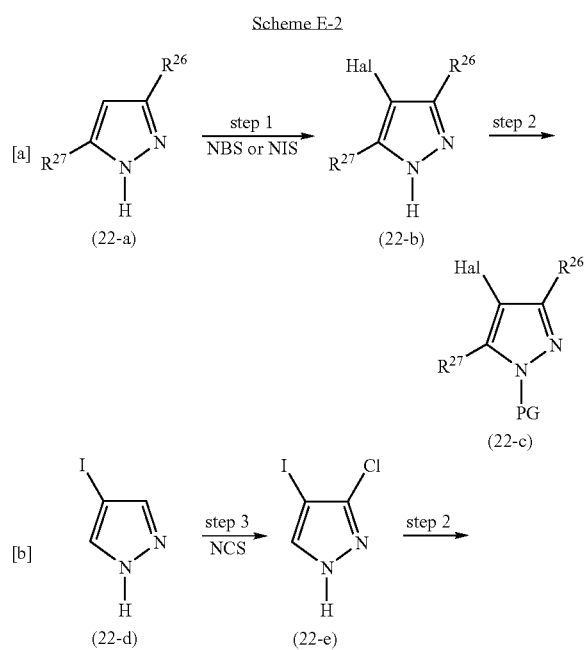

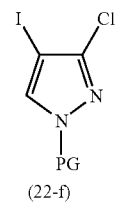

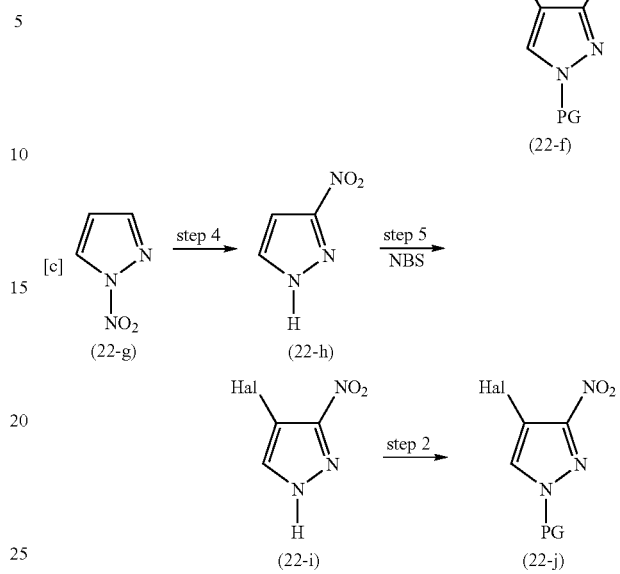

In the reaction schemes, $R^{26}$ and $R^{27}$ each represent an optionally branched lower alkyl group. PG represents a protecting group such as a trityl group, tetrahydropyranyl group etc., and Hal represents a halogen such as bromine or iodine.

The above schemes show methods of synthesizing pyrazole derivatives which have a protective group at the 1-position of the pyrazole, are substituted with a halogen atom at the 4-position, and have [a]alkyl group, [b] halogen atom and [c] nitro group at the 3-position.

For [a], step 1 is a step of halogenating the 4-position of pyrazole, and step 2 is a step of introducing a protecting group, in which the same reactions as in steps 3 and 4 in the scheme E-1 are carried out to give (22-c). Regardless of the type of the substituent group at the 3-position of pyrazole, the method of introducing the protecting group can be carried out in the same manner as in step 2.

Step 3 for [b] is a step of chlorinating the 3-position of pyrazole, in which (22-d) is heated together with N-chlorosuccinimide at 60 to 80° C. in N,N-dimethylformamide to give (22-e), followed by introducing a protecting group into it to give (22-f).

Step 4 for [c] is a step of nitrating the 3-position of pyrazole, and this step is carried out according to a method described in Janssen et al., J. Org. Chem., 36, 3081 (1971). That is, a commercial compound (22-g) is heated at 140 to 150° C. in anisole, to give a compound (22-h) whose nitro group is rearranged. Step 5 is a step of halogenating the 4-position of pyrazole, and this step can be carried out in the same manner as in step 1. In step 2, a protecting group can be introduced to give (22-j).

Pyrazole having a carboxylate or a derivative thereof at the 3-position, having a protecting group at the 1-position and being substituted with a halogen atom at the 4-position can be synthesized according to the scheme E-3.

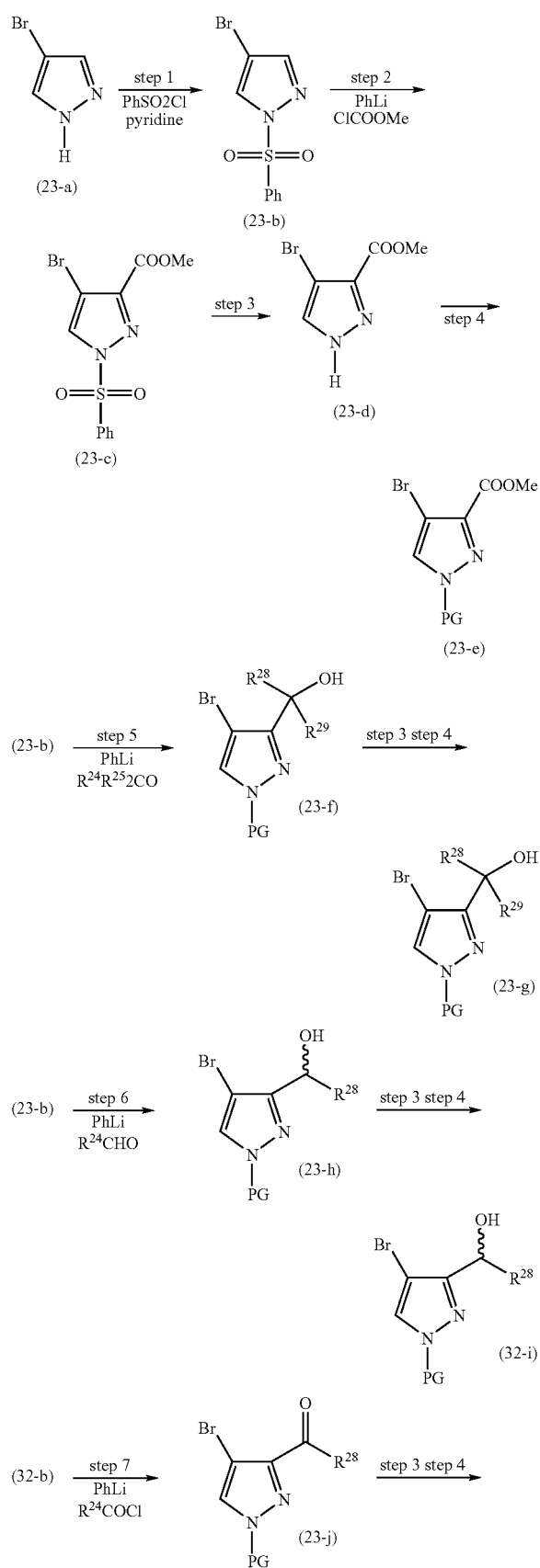

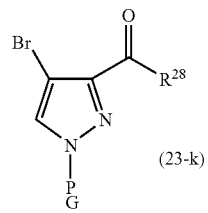

(23-k)

In the reaction scheme, $R^{28}$ and $R^{29}$ each represent an aryl or heteroaryl group which may be substituted with a lower alkyl group, a halogen atom or a lower alkoxy group. PG represents a protecting group such as a trityl group, tetrahydropyranyl group etc.

(23-e) can be synthesized according to a method described in M. D. Erion and M. Rydzewsk, Nucleosides & Nucleotides, 16, 315–337 (1997).

Step 1 is a step of protecting the 1-position of pyrazole in (23-a) with a benzene sulfonyl group, in which (23-a) is heated together with benzenesulfonyl chloride in the presence of a base to give (23-b).

Step 2 is a step of lithiolating the 5-position of pyrazole in (23-b) with phenyl lithium or t-butyl lithium at –70° C. to 0° C. in anhydrous ether and then reacting the product with methyl chlorocarbonate at –70° C. to 0° C. to introduce a methoxycarbonyl group, whereby (23-c) can be obtained.

Step 3 is a reaction for deprotecting the benzenesulfonyl group, in which (23-c) is heated together with an alkali or a water-containing solvent, to give (23-d). In step 4, a suitable protecting group can be introduced to give (23-e).

Steps 5, 6 and 7 are steps of lithiolating (23-b) and then reacting the product with (a) ketone $R^{24}R^{25}CO$, (b) aldehyde $R^{24}CHO$, and (c) acid chloride $R^{24}COCl$, respectively. (23-g), (23-i) and (23-k) are obtained respectively by conversion of the protecting groups on the respective products (23-f), (23-h) and (23-j) under the same conditions as in steps 3 and 4, followed by step 8 (deprotection) and step 2 (introduction of protecting group) in the same manner as in [d].

The pyrazole derivative (III) used in Production Method A, B, C or D can be synthesized according to scheme E-4 from pyrazole substituted at the 4-position with a halogen atom synthesized according to schemes E-1, E-2 and E-3.

Scheme E-4

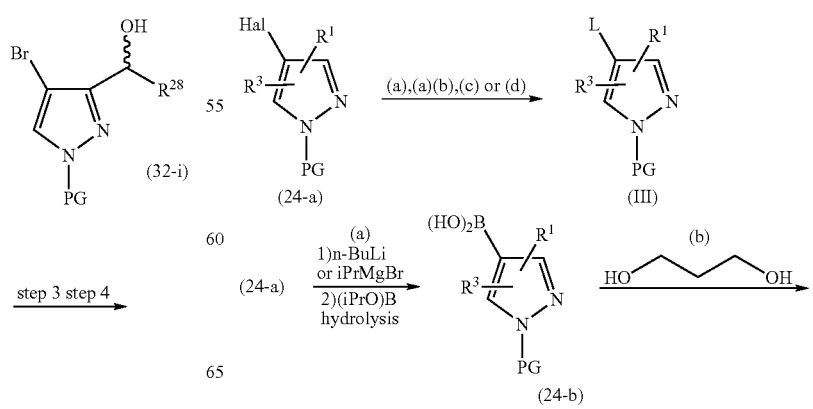

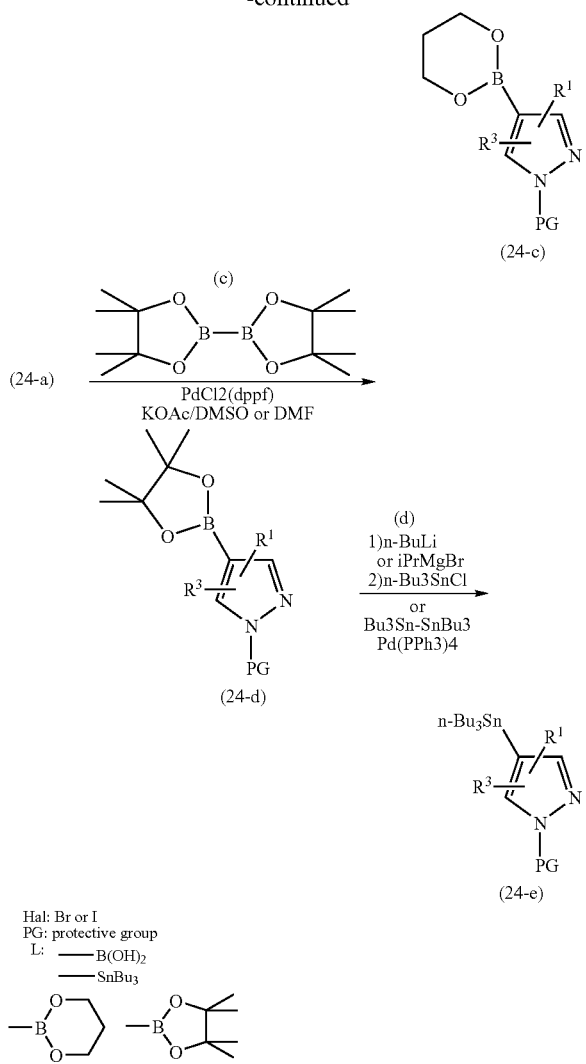

In the reaction scheme, each symbol represents the same group as defined above. PG represents a protecting group such as a trityl group, tetrahydropyranyl group etc., and Hal represents a bromine or iodine atom. L represents trialkyl tin, boric acid, or a cyclic or non-cyclic boronate.

The compounds represented by the general formula (24-a), which are substituted with a halogen atom at the 3-position of pyrazole, can be converted into boronic acid, boronate or trialkyl tin derivatives represented by the general formula (III) The boronic acid can be synthesized by method (a), the boronate by methods (a) and (b) or by method (c), and the trialkyl tin by method (d).

The method (a) is a method of treating (24-a) with n-butyl lithium or isopropyl magnesium bromide, then reacting it with triisopropyl borate and hydrolyzing the ester with water or aqueous ammonium chloride to give boronic acid (24-b).

The method (b) is a method of reacting the boronic acid (24-b) with 1,3-propane diol in a solvent such as dichloromethane or diethyl ether to synthesize the boronate (24-c).

The method (c) is a method of synthesizing the boronate (24-f) directly from (24-a), and this method can be carried out according to a method described in Miyaura et al., J. Org. Chem., 60, 7508–7510 (1995). That is, (24-a), bis(pinacolate)diboron, a weak base such as potassium acetate, and a palladium catalyst such as dichloro[1,1'-bis(diphenylphosphino)ferrocene]palladium (PdCl$_2$(dppf)) are heated in a solvent such as N,N-dimethylformamide or dimethyl sulfoxide to give (24-d).

The method (d) is a method of synthesizing tri-n-butyl tin derivative (24-e), in which (24-a) is treated with n-butyl lithium or isopropyl magnesium bromide at −70° C. to room temperature and then reacted with tri-n-butyl tin chloride to give (24-e). Alternatively, (24-a) is heated together with bis(tri-n-butyl tin) at 60 to 140° C. in the presence of tetrakis(triphenylphosphine)palladium as the catalyst in toluene or xylene as the solvent to give (24-e).

After the above reactions, the product can be purified by column chromatography using e.g. silica gel or absorptive resin and by recrystallization from a suitable solvent by a usual treatment method.

The dose of the pharmaceutical preparation of the present invention is varied depending on the severeness of symptoms, age, sex, body weight, administration form, and the type of disease, and usually the pharmaceutical preparation is administered daily in one portion or in divided portions into a man in a dose of 100 μg to 10 g/day.

The administration form of the pharmaceutical preparation according to the present invention is not particularly limited, and the pharmaceutical preparation can be administered orally or parenterally by a conventionally used method.

To prepare the pharmaceutical preparation, ordinarily used excipients, binders, lubricants, coloring agents, taste and odor correctives and if necessary stabilizers, emulsifiers, absorption promoters and surfactants can be used, and ingredients used generally as starting materials for pharmaceutical preparations can be blended in a usual manner for manufacturing.

These ingredients include e.g. sugars (lactose, glucose, sucrose etc.), sugar alcohols (mannitol, erythritol etc.), silicic acid (silicic anhydride, magnesium metasilicate aluminate, etc.), animal and vegetable oils (soybean oil, synthetic glyceride etc.), hydrocarbons (liquid paraffin, squalene, solid paraffin etc.) ester oils (octyldodecyl myristate, isopropyl myristate etc.), higher alcohols (cetostearyl alcohol, behenyl alcohol etc.), silicon oil, surfactants (polyoxyethylene fatty ester, sorbitan fatty ester, glycerin fatty ester, polyoxyethylene sorbitan fatty ester, polyoxyethylene hardened castor oil, polyoxyethylene polyoxypropylene block copolymer etc.), water-soluble polymers (hydroxy propyl cellulose, hydroxy propyl methyl cellulose, carboxyvinyl polymer, polyvinyl pyrrolidone, methyl cellulose etc.) and polyvalent alcohols (glycerin, propylene glycol, dipropylene glycol, sorbitol etc.). If necessary, lower alcohols (ethanol, isopropanol etc.) and pure water are added, and for pH adjustment, inorganic acids (hydrochloric acid, phosphoric acid etc.), alkali metal salts of inorganic acids (sodium phosphate, etc.), inorganic bases (sodium hydroxide, etc.), organic acids (lower fatty acids, citric acid, lactic acid, etc.), alkali metal salts of organic acids (sodium citrate, sodium lactate) and organic bases (arginine, ethanolamine, etc.) can be used. If necessary, a preservative, an antioxidant etc. can be added.

According to the present invention, there can be provided a compound having a more excellent inhibitory action on activation of STAT6 and a pharmaceutical composition thereof. Pharmacological experimental examples showing significant effects are shown below.

EXPERIMENTAL EXAMPLES

The inhibitory action of the present compound on activation of STAT6 was evaluated according to the following experiments.

1) Construction of a STAT6 Reporter Gene

An oligonucleotide of SEQ ID NO:1 in which three STAT6-binding regions on a human immunoglobulin germline E gene promoter had been linked was mixed with its complementary chain, thermally denatured and annealed, and 5'- and 3'-ends thereof were cleaved with restriction enzymes Kpn I (Code No. 1068A, Takara Shuzo) and Xba I (Code No. 1093A, Takara Shuzo) respectively, and the resulting fragment was cloned into a Kpn I/Xba I site of pUG-BGH-PLAP vector (described in Molecular Pharmacology, 49:860–873, 1996). To induce a basic transcriptional factor, a TK promoter region of herpes virus was cloned into an Xba I/Hind III (Code No. 1060A, Takara Shuzo) site of the pUG-BGH-PLAP vector. To obtain a stably expressing cell strain, a neomycin resistance gene (PGK-neo expression cassette) was integrated with an Sal I (Code No. 1080A, Takara Shuzo) of this vector. Cloning of the TK promoter and PGK-neo expression cassette was carried out according to Molecular Pharmacology, 49:860–873, 1996.

(SEQ ID NO:1)

5'-AGC<u>GGTACC</u>TCGACTTCCCAAGAACAGAATCGACTTCCCAAGAACAGAATCGACTT
CCCAAGAACAGAA<u>TCTAGA</u>GCT-3'

The underlined sites are a Kpn I recognition site and Xba I recognition site respectively.

2) Construction of an STAT6 Expression Vector

An oligonucleotide of SEQ ID NO:2 containing an initiation codon of STAT6 gene and an oligonucleotide of SEQ ID NO:3 containing a stop codon were used, and total RNA was prepared from human peripheral blood cells by using RNeasy Mini kit (Code No. 74104, OIAGEN). Then, cDNA was prepared by reverse transcription reaction using Takara RNA LA PCR kit (Code No. RR012A, Takara Shuzo) and then subjected to PCR reaction with primers of SEQ ID NOS:2 and 3, to amplify the STAT6 gene.

(SEQ ID NO:2) 5'-CG<u>GAATTC</u>ATGTCTCTGTGGGGTCTGGTCTCCA-3'

The underlined site is an EcoR I recognition site.

(SEQ ID NO:3) 5'-CC<u>GCTCGAG</u>TCACCAACTGGGGTTGGCCCTTAGG-3'

The underlined site is an Xho I recognition site.

The PCR product was digested with EcoR I (Code No. 1040A, Takara Shuzo) and Xho I (1094A, Takara Shuzo), and the digested fragment was isolated on an agarose gel. The isolated fragment was integrated into a vector fragment obtained by digesting pcDNA3.1 (+) (Code No. U790-20, Invitrogen) vector with EcoRI/Xho I.

3) Introduction of the Gene and Preparation of a Stably Expressing Cell Strain

Human fetal kidney-derived 293 cells (American Type Culture Collection), $3.0 \times 10^5$ cells, were spread on a Falcon tissue culture 6-well plate (Code No. 35-3046, Becton Dickinson) and cultured overnight. 1.5 µg of the prepared STAT6 reporter gene, 1.5 µg of the STAT6 gene and 20 µl of lipofectamine (Code No. 18324-012, GIBCO BRL) were mixed in 0.3 ml OPTI-MEM medium (Code No. 31985-070) and left at room temperature for 20 minutes. Thereafter, 1.2 ml OPTI-MEM medium was further added to the cells washed with OPTI-MEM medium not containing fetal bovine serum, and the cells were cultured for 2 hours. 1.5 ml medium containing fetal bovine serum was added thereto, and the cells were cultured for additional 19 hours. The medium was exchanged with a fresh one, and Geneticin (Code No. G-5013, SIGMA) was added at a concentration of 1 mg/ml, and the cells were cultured, and chemical-resistant cells were selected. The resulting chemical-resistant cells were floated in a medium containing 1 mg/ml Geneticin, then spread at a density of 0.5 cell/well on a 96-well microplate (Code No. 35-3072, Becton Dickinson) and cloned to give a clone expressing alkali phosphatase in response to IL-4.

4) Inhibitory Test on STAT6 Activation

The cells stably expressing the STAT6 gene and STAT6 reporter gene and expressing alkali phosphatase in response to IL-4 were spread at a density of 5000 cells/180 µl/well on a 96-well microplate (Code No. 35-3072, Becton Dickinson) and cultured overnight. On the next day, 10 mM of the present compound (used after dissolved in dimethyl sulfoxide and diluted to a dimethyl sulfoxide concentration of 0.1% or less with a medium), and 1 ng/ml human recombinant IL-4 (Code No. 407635, CALBIOCHEM) were added to a final volume of 200 µl/well and cultured for 16 hours, and the supernatant was recovered, and the recovered solution was treated at 65° C. for 10 minutes. Then, 100 µl carbonate buffer (16 mM $NaHCO_3$, 12 mM $Na_2CO_3$, 0.8 mM $MgSO_4$) was added to each well of a fluorescence measurement black plate (Code No. TS-1001, Dainippon Seiyaku), and 10 µl of the thermally treated culture supernatant was added to each well. Further, 50 µl Lumistain (Code No. R02-ES, K.K. Genome Science Kenkyusho) was added to each well and left at room temperature for 1 hour. The alkali phosphatase activity was measured by using MicroLumat (EG&G BERTHOLD).

Assuming that the alkali phosphatase activity induced by stimulation with IL-4 in the absence of the present compound was 100%, the degree of inhibition (%) of the present compound was calculated according to the equation below, and the concentration of the present compound ($IC_{50}$) at which the alkali phosphatase activity induced by IL-4 was inhibited by 50% was determined.

Degree of inhibition (%)=$(E-B)/(C-B) \times 100$

E: Alkali phosphatase activity induced by stimulation with IL-4 in the presence of the present compound C: Alkali phosphatase activity induced by stimulation with IL-4 in the absence of the present compound B: Alkali phosphatase activity induced without stimulation, in the absence of the present compound Tables 1 and 2 show the concentration of the present compound ($IC_{50}$) at which the alkali phosphatase activity induced by IL-4 was inhibited by 50%.

TABLE 1

| Ex. No. | Inhibitory activity IC$_{50}$ |
|---|---|
| 70 | ++ |
| 71 | ++ |
| 77 | +++ |
| 78 | +++ |
| 87 | +++ |
| 92 | +++ |
| 101 | ++ |
| 102 | ++ |
| 108 | +++ |
| 109 | +++ |
| 115 | +++ |
| 120 | +++ |
| 148 | +++ |
| 203 | ++ |
| 212 | +++ |
| 224 | +++ |
| 227 | ++ |
| 230 | +++ |
| 239 | +++ |
| 254 | ++ |
| 261 | + |
| 265 | ++ |
| 287 | ++ |
| 534 | +++ |
| 539 | +++ |
| 549 | +++ |
| 555 | +++ |
| 556 | +++ |
| 561 | +++ |
| 562 | +++ |
| 557 | +++ |
| 576 | +++ |
| 580 | +++ |
| 583 | +++ |
| 584 | +++ |
| 605 | +++ |
| 589 | +++ |
| 592 | +++ |
| 596 | +++ |
| 598 | +++ |
| 601 | +++ |
| 622 | +++ |
| 623 | +++ |
| 626 | +++ |
| 628 | +++ |
| 629 | +++ |
| 632 | ++ |
| 644 | +++ |
| 648 | ++ |
| 652 | +++ |
| 655 | ++ |
| 661 | +++ |
| 663 | +++ |
| 669 | +++ |
| 670 | ++ |
| 672 | +++ |
| 674 | +++ |
| 676 | ++ |
| 678 | +++ |
| 680 | +++ |
| 681 | +++ |
| 688 | +++ |
| 689 | +++ |
| 697 | ++ |
| 698 | ++ |
| 699 | ++ |

The inhibitory activity (IC$_{50}$) in the above table is expressed as follows:
+++: IC$_{50}$ value of less than 10 nM,
++: IC$_{50}$ value of 10 nM (inclusive) to 100 nM (exclusive),
+: IC$_{50}$ value of 100 nM (inclusive) to 1 µM (exclusive).

TABLE 2

| Ex. No. | Inhibitory activity IC$_{50}$ | Ex. No. | Inhibitory activity IC$_{50}$ |
|---|---|---|---|
| 700 | ++ | 903 | +++ |
| 701 | ++ | 904 | + |
| 705 | ++ | 905 | + |
| 706 | +++ | 906 | + |
| 707 | ++ | 907 | ++ |
| 712 | +++ | 908 | +++ |
| 725 | +++ | 909 | ++ |
| 727 | +++ | 910 | +++ |
| 728 | +++ | 911 | +++ |
| 729 | +++ | 913 | +++ |
| 845 | +++ | 914 | +++ |
| 850 | + | 921 | +++ |
| 855 | +++ | 923 | +++ |
| 856 | + | 936 | +++ |
| 866 | ++ | 934 | +++ |
| 869 | ++ | 946 | +++ |
| 872 | ++ | 951 | ++ |
| 873 | + | 952 | +++ |
| 876 | ++ | 955 | +++ |
| 880 | ++ | 957 | ++ |
| 883 | +++ | 963 | +++ |
| 896 | +++ | 964 | +++ |
| 887 | ++ | 967 | +++ |
| 889 | ++ | 971 | + |
| 890 | +++ | 976 | +++ |
| 892 | ++ | 978 | +++ |
| 895 | +++ | 993 | ++ |
| 894 | +++ | 1000 | +++ |
| 897 | +++ | 1002 | ++ |
| 899 | +++ | 1007 | ++ |
| 900 | ++ | 1032 | ++ |
| 901 | + | 1034 | ++ |
| 902 | +++ | 1070 | ++ |

The inhibitory activity (IC$_{50}$) in the above table is expressed as follows:
+++: IC$_{50}$ value of less than 10 nM,
++: IC$_{50}$ value of 10 nM (inclusive) to 100 nM (exclusive),
+: IC$_{50}$ value of 100 nM (inclusive) to 1 µM (exclusive).

As shown in Tables 1 and 2, the concentrations of the present compounds (IC$_{50}$) at which alkali phosphatase was inhibited by 50% were very low.

It is evident that the present compounds have extremely excellent inhibitory actions on transduction of IL-4 signal and on activation of STAT6.

PRODUCTION EXAMPLES

Production Example 1

3-(4-Fluorophenyl)-1H-pyrazole 25 g 4'-fluoroacetophenone and 24 g N,N-dimethylformamide dimethyl acetal were heated for 6 hours under reflux, concentrated and evaporated into dryness to give 34.3 g of a reddish brown solid. The product was dissolved in 15 mL ethanol, and 9.9 mL hydrazine monohydrate was added thereto and heated at 70° C. for 2 hours. The reaction solution was poured into water, extracted with ethyl acetate and dried over magnesium sulfate, and the solvent was evaporated. The product was recrystallized from ethyl acetate and hexane to give 24.5 g pale yellow crystals.

$^1$H-NMR (CDCl$_3$)

δ: 6.57(d, J=2.4 Hz, 1H), 7.05–7.12(m, 2H), 7.60(d, J=2.4 Hz, 1H), 7.70–7.76(m, 2H)

Production Example 2

3-[4-(Methylsulfanyl)phenyl]-1H-pyrazole 8.5 g of the title compound (colorless crystals) was obtained from 10 g 4-(methylthio)acetophenone in the same manner as in Production Example 1.

$^1$H-NMR (CDCl$_3$)

δ: 2.52(s, 3H), 6.59(d, J=2.4 Hz, 1H), 7.30 (dt, J=8.8, 2 Hz, 2H), 7.61(d, J=2.4 Hz, 1H), 7.68(brd, J=8.4 Hz, 2H)

Production Example 3

3-(4-Methoxyphenyl)-1H-pyrazole 24.6 g 4'-methoxyacetophenone and 43.5 mL N,N-dimethylformamide dimethyl acetal were heated for 24 hours under reflux, concentrated into dryness and recrystallized from ethyl acetate/hexane to give 12.9 g pale yellow solid. The product was dissolved in 130 mL ethanol, and 5.4 mL acetic acid and 4.6 mL hydrazine monohydrate were added thereto under ice-cooling and stirred overnight at room temperature. After removing methanol, a sodium bicarbonate solution was added thereto, and the reaction solution was extracted with ethyl acetate. The organic layer was dried over magnesium sulfate and then purified by NH silica gel column chromatography (ethyl acetate/hexane) to give 8.5 g of the title compound (colorless solid.

$^1$H-NMR (DMSO-d$_6$)

δ: 3.75(s, 3H), 6.58(s, 1H), 6.94(d, J=8.6 Hz, 2H), 7.65–7.77(m, 3H)

Production Example 4

3-(4-Chlorophenyl)-1H-pyrazole 22.5 g of the title compound (colorless solid) was obtained from 26.2 g 4'-chloroacetophenone in the same manner as in Production Example 3.

$^1$H-NMR (DMSO-d$_6$)

δ: 6.72(d, J=2.0 Hz, 1H), 7.44(d, J=8.0 Hz, 2H), 7.70–7.88(m, 3H)

Production Example 5

3-(3,4-Dimethoxyphenyl)-1H-pyrazole 17.5 g of the title compound (colorless solid) was obtained from 24 g 3',4'-dimethoxyacetophenone in the same manner as in Production Example 3.

$^1$H-NMR (DMSO-d$_6$)

δ: 3.73(s, 3H), 3.77(s, 3H), 6.60(s, 1H), 6.95(d, J=8.4 Hz, 1H), 7.28(d, J=8.4 Hz, 1H), 7.35(s, 1H), 7.62(s, 1H)

Production Example 6

4-(1H-3-Pyrazolyl)benzonitrile 8.5 g of the title compound (colorless solid) was obtained from 10 g 4-acetylbenzonitrile in the same manner as in Production Example 3.

$^1$H-NMR (CDCl$_3$)

δ: 6.71(d, J=2.4 Hz, 1H), 7.66(d, J=2.4 Hz, 1H), 7.68–7.72(m, 2H), 7.89–7.93(m, 2H)

Production Example 7

3-(1H-3-Pyrazolyl)benzonitrile 3.8 g of the title compound (colorless solid) was obtained from 5.1 g 3-acetylbenzonitrile in the same manner as in Production Example 3.

$^1$H-NMR (CDCl$_3$)

δ: 6.67(s, 1H), 7.48–7.55(m, 1H), 7.60(d, J=8.6 Hz, 1H), 7.66(s, 1H), 8.04(d, J=8.6 Hz, 1H), 8.09 (s, 1H)

Production Example 8

4-Bromo-3-(4-fluorophenyl)-1H-pyrazole 24 g 3-(4-fluorophenyl)pyrazole was dissolved in 150 mL N,N-dimethylformamide, then 28 g N-bromosuccinimide was added thereto little by little, and the mixture was stirred for 2 hours. An aqueous sodium thiosulfate solution and an aqueous sodium dicarbonate solution were added thereto and stirred for 1 hour, and the formed solid was collected by filtration. The product was dissolved in ethyl acetate, dried over magnesium sulfate, and then purified by silica gel column chromatography (ethyl acetate). The resulting solid was crystallized from diethyl ether/hexane, to give 33.6 g colorless crystals.

$^1$H-NMR (CDCl$_3$)

δ: 7.10–7.17(m, 2H), 7.62(d, J=2.4 Hz, 1H), 7.73–7.79(m, 2H)

Production Example 9

4-Bromo-3-[4-(methylsulfanyl)phenyl)-1H-pyrazole 8.9 g of the title compound (colorless crystals) was obtained from 8.5 g 3-[4-(methylsulfanyl) phenyl)-1H-pyrazole in the same manner as in Production Example 8.

$^1$H-NMR (CDCl$_3$)

δ: 2.53(s, 3H), 7.33(dt, J=8.4, 2.4 Hz, 2H), 7.64(s, 1H), 7.70(dt, J=8.4, 2.4 Hz, 2H)

Production Example 10

4-Bromo-3-(4-methoxyphenyl)-1H-pyrazole 17.5 g of the title compound (colorless crystals) was obtained from 10.8 g 3-(4-methyoxyphenyl)-1H-pyrazole (reaction time: 24 hours) in the same manner as in Production Example 8.

$^1$H-NMR (CDCl$_3$)

δ: 3.83(s, 3H), 6.92(d, J=8.6 Hz, H), 7.54(s, 1H), 7.66(d, J=8.6 Hz, 2H)

Production Example 11

4-Bromo-3-(4-chlorophenyl)-1H-pyrazole

Solid obtained from 222.5 g 3-(4-chlorophenyl)-1H-pyrazole in the same manner as in Production Example 8 was purified by silica gel column chromatography (hexane/ethylacetate) to give 27.6 g of the title compound (colorless crystals).

$^1$H-NMR (DMSO-d$_6$)

δ: 7.53(d, J=8.6 Hz, 2H), 7.81(d, J=8.6 Hz, 2H), 7.97(br, 1H)

Production Example 12

4-Bromo-3-(3,4-dimethoxyphenyl)-1H-pyrazole 16.8 g of the title compound (colorless crystals; recrystallization solvent, methanol/ethyl acetate) was obtained from 17.5 g 3-(3,4-dimethoxyphenyl)-1H-pyrazole in the same manner as in Production Example 8.

$^1$H-NMR (CDCl$_3$)

δ: 3.91(s, 3H), 3.92(s, 3H), 6.93(d, J=8.4 Hz, 1H), 7.30–7.36(m, 2H), 7.61(s, 1H)

Production Example 13

4-(4-Iodo-1H-3-pyrazolyl)benzonitrile 6.82 g of the title compound was obtained as colorless crystals from 4.25 g 4-(1H-3-pyrazolyl)benzonitrile and 6 g N-iodosuccinimide in the same manner as in Production Example 8.

$^1$H-NMR (CDCl$_3$)

δ: 7.73–7.77(m, 2H), 7.74(s, 1H), 7.96–8.00(m, 2H)

Production Example 14

3-(4-Iodo-1H-3-pyrazolyl)benzonitrile 6.98 g of the title compound was obtained from 3.77 g 3-(1H-3-pyrazolyl)benzonitrile and 7.97 g N-iodosuccinimide in the same manner as in Production Example 14.

$^1$H-NMR (CDCl$_3$)

δ: 7.53–7.60(m, 1H), 7.67(d, J=8.6 Hz, 1H), 7.72(s, 1H), 8.01–8.13(m, 2H)

Production Example 15

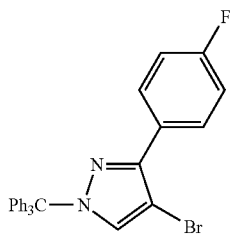

4-Bromo-3-(4-fluorophenyl)-1-trityl-1H-pyrazole 33.6 g 4-bromo-3-(4-fluorophenyl)-1H-pyrazole, 25.4 mL triethylamine and 45 g triphenyl methyl chloride were heated at 70° C. for 5 hours in 200 mL N,N-dimethylformamide. Ethyl acetate was added thereto, and formed precipitates were removed by filtration. The filtrate was concentrated and then purified by NH silica gel column chromatography (hexane/dichloromethane/ethyl acetate) to give 46.7 g colorless crystals.

$^1$H-NMR (DMSO-d$_6$)

δ: 7.08–7.13(m, 6H), 7.23–7.30(m, 2H), 7.34–7.41(m, 9H), 7.58(s, 1H), 7.74–7.79(m, 2H)

Production Example 16

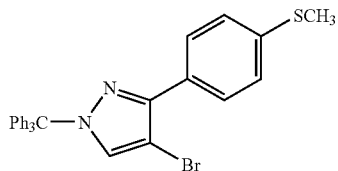

4-Bromo-3-[4-(methylsulfanyl)phenyl]-1-trityl-1H-pyrazole 13.5 g of the title compound (colorless solid) was obtained from 7.7 g 4-bromo-3-[4-(methylsulfanyl)phenyl]pyrazole in the same manner as in Production Example 15.

$^1$H-NMR (CDCl$_3$)

δ: 2.49(s, 1H), 7.15–7.20(m, 6H), 7.24–7.28(m, 2H), 7.30–7.34(m, 9H), 7.36(s, 1H) 7.81–7.85(m, 2H)

Production Example 17

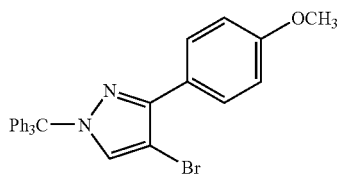

4-Bromo-3-(4-methoxyphenyl)-1-trityl-1H-pyrazole 17.0 g of the title compound (colorless solid) was obtained from 17.5 g 4-bromo-3-(4-methoxyphenyl)-1H-pyrazole by the same method as in Production Example 15 (eluent in silica gel chromatography: hexane/ethyl acetate).

$^1$H-NMR(CDCl$_3$)

δ: 3.81(s, 3H), 6.89–6.94(m, 2H), 7.16–7.21(m, 6H), 7.26–7.34(m, 9H), 7.35(s, 1H), 7.80–7.85(m, 2H)

Production Example 18

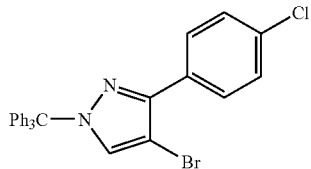

4-Bromo-3-(4-chlorophenyl)-1-trityl-1H-pyrazole 36.8 g of the title compound (colorless crystals; recrystallization solvent, hexane/ethyl acetate) was obtained from 27.6 g 4-bromo-3-(4-chlorophenyl)-1H-pyrazole by the same method as in Production Example 15.

$^1$H-NMR(CDCl$_3$)

δ: 7.15–7.20(m, 6H), 7.30–7.36(m, 11H), 7.38(s, 1H), 7.81–7.86(m, 2H)

Production Example 19

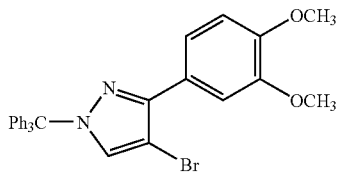

4-Bromo-3-(3,4-dimethoxyphenyl)-1-trityl-1H-pyrazole 15.0 g of the title compound (colorless solid) was obtained from 16.8 g 4-bromo-3-(3,4-dimethylphenyl)-1H-pyrazole by the same method as in Production Example 15 (eluent in silica gel chromatography: dichloromethane/ethyl acetate).

$^1$H-NMR (CDCl$_3$)

δ: 3.88(s, 6H), 6.89(d, J=8.4 Hz, 1H), 7.16–7.22(m, 6H), 7.30–7.35(m, 9H), 7.36(s, 1H), 7.45(d, J=2.0 Hz, 1H), 7.49(dd, J=8.4, 2.0 Hz, 1H)

Production Example 20

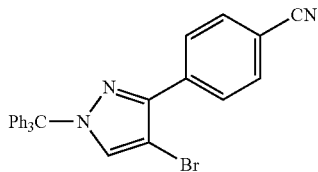

4-(4-Iodo-1-trityl-1H-3-pyrazolyl)benzonitrile 10 g of the title compound was obtained as crystals from 6.8 g 4-(4-iodo-1H-3-pyrazolyl)benzonitrile by the same method as in Production Example 15.

$^1$H-NMR (CDCl$_3$)

δ: 7.14–7.20(m, 6H), 7.28–7.36(m, 9H), 7.46(s, 1H), 7.64–7.68(m, 2H), 7.99–8.03(m, 2H)

Production Example 21

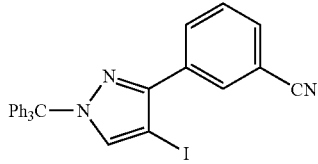

3-(4-Iodo-1-trityl-1H-3-pyrazolyl)benzonitrile 7.98 g of the title compound was obtained from 6.98 g 3-(4-iodo-1H-3-pyrazolyl)benzonitrile by the same method as in Production Example 15.

$^1$H-NMR (DMSO-d$_6$)

δ: 7.07–7.12(m, 6H), 7.33–7.41(m, 9H), 7.56(s, 1H), 7.66(dt, J=8.0, 0.6 Hz, 1H), 7.86(dt, J=8.0, 1.6 Hz, 1H), 8.03(dt, J=8.0, 1.6 Hz, 1H), 8.08(dt, J=1.6, 0.6 Hz, 1H)

Production Example 22

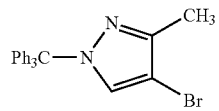

4-Bromo-3-methyl-1-trityl-1H-pyrazole 31.9 g of the title compound (colorless crystals; recrystallization solvent, ethyl acetate) was obtained from 15.3 g 4-bromo-3-methyl-1H-pyrazole by the same method as in Production Example 15.

Production Example 23

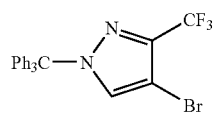

4-Bromo-3-trifluoromethyl-1-trityl-1H-pyrazole 20.9 g of the title compound was obtained as colorless crystals from 11.6 g 4-bromo-3-trifluoromethyl-1H-pyrazole by the same method as in Production Example 15.

$^1$H-NMR (CDCl$_3$)

δ: 7.09(m, 6H), 7.33(m, 9H), 7.38(s, 1H)

Production Example 24

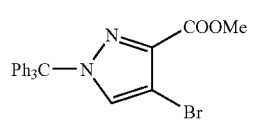

Methyl 4-bromo-1-trityl-1H-3-pyrazole carboxylate 5.29 g of the title compound (colorless crystals; recrystallization solvent, dichloromethane/hexane) was obtained by the same method as in Production Example 15 from 4.5 g 4-bromo-1H-3-pyrazole carboxylate synthesized by a method described by M. D. Erion, R. M. Rydzewski: Nucleoside & Nucleotide, 16, 315 (1997).

$^1$H-NMR (CDCl$_3$)

δ: 3.88(s, 3H), 7.09–7.14(m, 6H), 7.29–7.36(m, 9H), 7.38(s, 1H)

Production Example 25

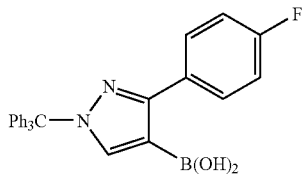

3-(4-Fluorophenyl)-1-trityl-1H-4-pyrazolylboronic acid 47.5 g 4-bromo-3-(4-fluorophenyl)-1-trityl-1H-pyrazole was dissolved in 400 mL anhydrous tetrahydrofuran, and then 40.7 mL solution of 1.6 M n-butyl lithium in hexane was added dropwise thereto at −70° C. The mixture was stirred for 30 minutes, 17.2 mL triisopropyl borate was added dropwise thereto, and the mixture was stirred at −70° C. for 1 hour and at −40° C. for 1 hour. The temperature was increased to 0° C., 50 mL aqueous saturated ammonium chloride solution was added thereto and stirred for 30 minutes, and water was added to the reaction solution which was then extracted with ethyl acetate. The extract was dried over magnesium sulfate, the solvent was removed under reduced pressure, and upon addition of toluene to the resulting oil, colorless crystals were formed. The crystals were collected by filtration, to give 31 g of the title compound.

$^1$H-NMR (DMSO-$d_6$)

δ: 6.70–6.77(m, 2H), 7.05–7.11(m, 6H), 7.15(d, J=0.8 Hz, 1H), 7.22(d, J=0.8 Hz, 1H), 7.28–7.36(m, 9H), 7.41(s, 1H), 7.72–7.78(m, 2H)

Production Example 26

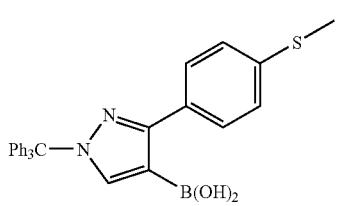

3-[4-(Methylsulfanyl)phenyl]-1-trityl-1H-4-pyrazolylboronic acid 8.5 g of the title compound was obtained as colorless crystals from 10 g 4-bromo-3-[4-(methylsulfanyl)phenyl]-trityl-1H-pyrazole in the same manner as in Production Example 25.

$^1$H-NMR (DMSO-$d_6$)

δ: 2.31(s, 3H), 6.88(dt, J=8.8, 2.0 Hz, 2H), 7.05–7.11(m, 6H), 7.13–7.17(m, 1H), 7.21–7.24(m, 1H), 7.27–7.36(m, 9H), 7.43(s, 1H), 7.72(dt, J=8.8, 2.0 Hz, 2H)

Production Example 27

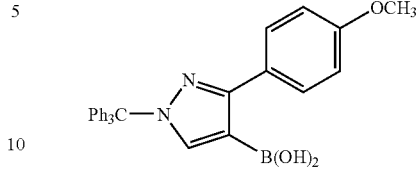

3-(4-Methoxyphenyl)-1-trityl-1H-4-pyrazolylboronic acid 4.8 g of the title compound (colorless crystals) was obtained from 17 g 4-bromo-3-(4-methoxyphenyl)-1-trityl-1H-pyrazole in the same manner as in Production Example 25.

$^1$H-NMR (DMSO-$d_6$)

δ: 3.72(s, 3H), 6.87(d, J=8.6 Hz, 2H), 7.06–7.40(m, 17H), 7.66(d, J=8.6 Hz, 2H), 7.68(s, 1H)

Production Example 28

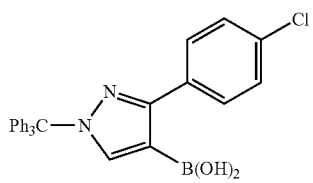

3-(4-Chlorophenyl)-1-trityl-1H-4-pyrazolylboronic acid 24.2 g of the title compound (amorphous) was obtained from 24.9 g 4-bromo-3-(4-chlorophenyl)-1-trityl-1H-pyrazole in the same manner as in Production Example 25.

$^1$H-NMR (DMSO-$d_6$)

δ: 6.99(d, J=8.6 Hz, 2H), 7.06–7.12(m, 6H), 7.26–7.40(m, 10H), 7.43(s, 1H), 7.74(d, J=8.8 Hz, 1H), 7.78(d, J=8.6 Hz, 2H)

Production Example 29

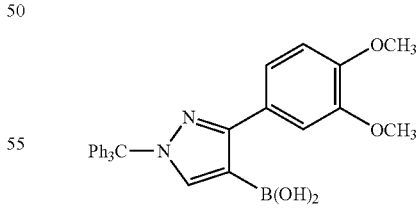

3-(3,4-Dimethoxyphenyl)-1-trityl-1H-4-pyrazolylboronic acid 9.5 g of the title compound (colorless crystals) was obtained from 15 g 4-bromo-3-(3,4-dimethoxyphenyl)-1-trityl-1H-pyrazole in the same manner as in Production Example 25.

$^1$H-NMR (DMSO-$d_6$)

δ: 3.71(s, 3H), 3.72(s, 3H), 6.89(d, J=8.4 Hz, 1H), 7.04–7.40(m, 18H), 7.51(d, J=1.6 Hz, 1H), 7.68(s, 1H)

Production Example 30

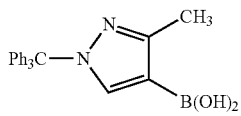

3-Methyl-1-trityl-1H-4-pyrazolylboronic acid 13.6 g 4-bromo-3-methyl-1-trityl-1H-pyrazole was reacted in the same manner as in Production Example 25, and then the product was crystallized from tetrahydrofuran, 2-propanol and water, to give 12.5 g of the title compound as colorless crystals.
$^1$H-NMR (DMSO-$d_6$)
δ: 2.22(d, J=3.0 Hz, 3H), 6.99–7.05(m, 6H), 7.28–7.37(m, 9H), 7.60(s, 1H), 7.71(d, J=3.0 Hz, 1H), 8.25(s, 1H)

Production Example 31

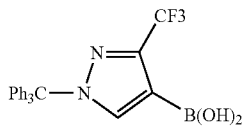

3-Trifluoromethyl-1-trityl-1H-4-pyrazolylboronic acid 11.4 g of the title compound was obtained as colorless crystals from 13.7 g 4-bromo-3-trifluoromethyl-1-trityl-1H-pyrazole (compound in Production Example 23) in the same manner as in Production Example 25.
$^1$H-NMR (CDCl$_3$)
δ: 4.68(s, 1H), 7.10(m, 6H), 7.31(m, 9H), 7.72(s, 1H), 7.87(s, 1H)

Production Example 32

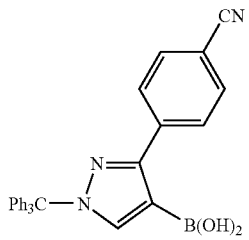

3-(4-Cyanophenyl)-1-trityl-1H-4-pyrazolylboronic acid 17.2 mL of 0.75 M isopropyl magnesium bromide was added dropwise at –40° C. into a solution of 6 g 4-(4-iodo-1-trityl-1H-3-pyrazolyl)benzonitrile in tetrahydrofuran, and the mixture was stirred for 30 minutes. Subsequently, 3.3 mL triisopropyl borate was added dropwise thereto at –40° C. ad stirred at –10° C. for 2 hours. The temperature of the reaction mixture was raised to room temperature, 20 mL saturated ammonium chloride solution was added thereto, and the mixture was stirred for 30 minutes. After extraction with ethyl acetate, the organic layer was washed with water and brine and dried over magnesium sulfate, and the solvent was removed. By recrystallization from toluene/hexane (2:1), 3.45 g of the title compound was obtained as colorless crystals.
$^1$H-NMR (DMSO-$d_6$)
δ: 7.05–7.11(m, 6H), 7.13–7.17(m, 1H), 7.20–7.24(m, 1H), 7.29–7.38(m, 11H), 7.43(s, 1H), 7.94(dt, J=8.4, 2.0 Hz, 2H)

Production Example 33

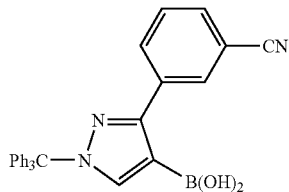

3-(3-Cyanophenyl)-1-trityl-1H-4-pyrazolylboronic acid 0.78 g of the title compound (colorless crystals) was obtained from 2.0 g 3-(4-iodo-1-trityl-1H-3-pyrazolyl)benzonitrile in the same manner as in Production Example 32.
$^1$H-NMR (DMSO-$d_6$)
δ: 7.05–7.12(m, 6H), 7.28–7.41(m, 10H), 7.53(t, J=7.8 Hz, 1H), 7.73(dt, J=1.6, 7.8 Hz, 1H), 7.84(s, 1H), 7.97(br, 1H), 8.01(dt, J=7.8, 1.6 Hz, 1H), 8.17(s, 1H)

Production Example 34

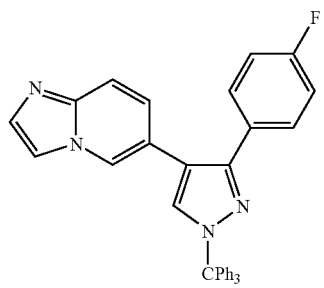

6-[3-(4-Fluorophenyl)-1-trityl-1H-pyrazolyl]imidazo[1,2-a]-pyridine 2.2 g 6-bromoimidazo[1,2-a]pyridine, 6 g 3-(4-fluorophenyl)-1-trityl-1H-4-pyrazolylboronic acid (compound in Production Example 25), and 647 mg tetrakistriphenyl phosphine palladium were heated in a solution mixture of 30 mL ethanol, 30 mL toluene and 17 mL of 2 N aqueous sodium carbonate at 80° C. for 2 hours in a stream of nitrogen. The reaction solution was cooled to room temperature, ethyl acetate was added thereto, and the organic layer was dried over magnesium sulfate. After filtration, the organic solvent was evaporated, and the residue was dissolved in dichloromethane and purified by NH silica gel (hexane/ethylacetate). The resulting solid was recrystallized from ethyl acetate/hexane, to give 4.65 g of the title compound as colorless crystals.

$^1$H-NMR (CDCl$_3$)

δ: 6.93–7.00(m, 2H), 7.02(dd, J=9.2, 2.0 Hz, 1H), 7.21–7.28(m, 6H), 7.32–7.37(m, 9H), 7.40(s, 1H), 7.44–7.49(m, 2H), 7.49(dd, J=1.6, 0.8 Hz, 1H), 7.53(dt, J=9.2, 0.8 Hz, 1H), 7.66(d, J=1.6 Hz, 1H), 8.01(dd, J=2.0, 0.8 Hz, 1H)

Production Example 35

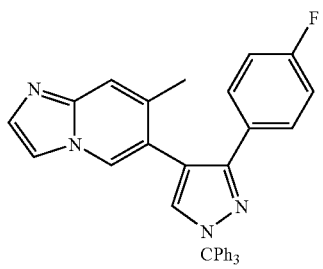

6-[3-(4-Fluorophenyl)-1-trityl-1H-4-pyrazolyl]-7-methylimidazo[1,2-a]pyridine 1.85 g of the title compound (colorless crystals; recrystallization solvent, ethyl acetate/diethyl ether) was obtained from 1.2 g 6-bromo-7-methylimidazo[1,2-a]pyridine and 3.06 g 3-(4-fluorophenyl)-1-trityl-1H-4-pyrazolylboronic acid (compound in Production Example 25) in the same manner as in Production Example 34.

$^1$H-NMR (CDCl$_3$)

δ: 2.02(s, 3H), 6.86–6.92(m, 2H), 7.22–7.29(m, 6H), 7.28(s, 1H), 7.32–7.37(m, 9H), 7.40–7.45(m, 2H), 7.46(d, J=0.8, 1H), 7.47(dd, J=1.6, 0.8 Hz, 1H), 7.57(d, J=1.6 Hz, 1H), 8.00(s, 1H)

Production Example 36

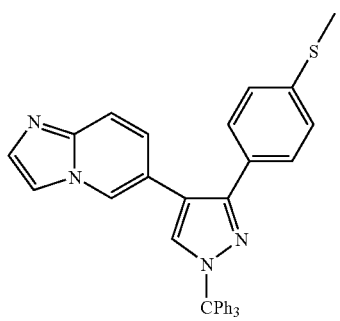

6-{3-[4-(Methylsulfanyl)phenyl]-1-trityl-1H-4-pyrazolyl}imidazo[1,2-a]pyridine 4 g of the title compound was obtained as an amorphous from 1.5 g 6-bromoimidazo[1,2-a]pyridine and 4 g 3-[4-(methylsulfanyl)phenyl]-1-trityl-1H-4-pyrazolylboronic acid (compound in Production Example 26) in the same manner as in Production Example 34.

$^1$H-NMR (CDCl$_3$)

δ: 2.46(s, 3H), 7.05(dd, J=9.2, 2.0 Hz, 1H), 7.15(dt, J=8.8, 2.0 Hz, 2H), 7.22–7.28(m, 6H), 7.31–7.36(m, 9H), 7.39(s, 1H), 7.43(dt, J=8.8, 2.0 Hz, 2H), 7.49(dd, J=1.2, 0.8 Hz, 1H), 7.53(dt, J=9.2, 0.8 Hz, 1H), 7.60(d, J=1.2 Hz, 1H), 8.03(dd, J=2.0, 0.8 Hz, 1H)

Production Example 37

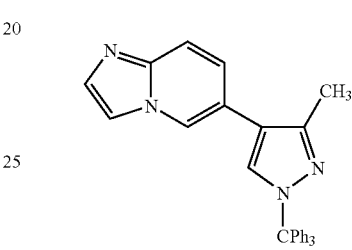

6-(3-Methyl-1-trityl-1H-4-pyrazolyl)imidazo[1,2-a]pyridine 2.94 g of the title compound was obtained as colorless crystals from 1.9 g 6-bromoimidazo[1,2-a]pyridine and 4.4 g 3-methyl-1-trityl-1H-4-pyrazolylboronic acid (compound in Production Example 30) by the same method as in Production Example 34.

$^1$H-NMR (DMSO-d$_6$)

δ: 2.33(s, 3H), 7.09–7.14(m, 6H), 7.26(dd, J=9.1, 1.8 Hz, 1H), 7.30–7.40(m, 9H), 7.51(d, J=9.1 Hz, 1H), 7.49–7.54(m, 1H), 7.59(br, 1H), 7.89(brs, 1H), 8.61(brs, 1H)

Production Example 38

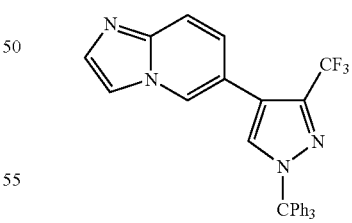

6-(3-Trifluoromethyl-1-trityl-1H-4-pyrazolyl)imidazo-[1,2-a]pyridine 226 mg of the title compound (pale yellow amorphous) was obtained from 88 mg 6-bromoimidazo[1,2-a]pyridine and 245 mg 3-trifluoromethyl-1-trityl-1H-4-pyrazolylboronic acid (compound in Production Example 31) by the same reaction as in Production Example 34.

¹H-NMR (CDCl₃)

δ: 7.14(m, 7H), 7.35(m, 9H), 7.46(d, J=1.6 Hz, 1H), 7.58(m, 1H), 7.61(dd, J=9.2, 0.8 Hz, 1H), 7.64(d, J=1.6 Hz, 1H), 8.16(dd, J=1.6, 0.8 Hz, 1H)

Production Example 39

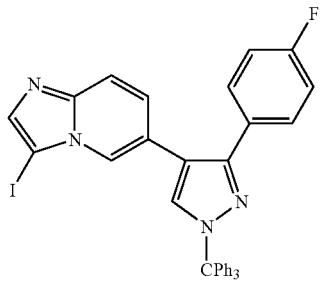

6-[3-(4-Fluorophenyl)-1-trityl-1H-4-pyrazolyl]-3-iodoimidazo[1,2-a]pyridine 5 g 6-[3-(4-fluorophenyl)-1-trityl-1H-pyrazolyl]imidazo[1,2-a]pyridine obtained in Production Example 34 was dissolved in 50 mL N,N-dimethylformamide, then 2.3 g N-iodosuccinimide was added thereto little by little at room temperature, and the mixture was stirred for 1 hour. An aqueous sodium thiosulfate solution and an aqueous sodium dicarbonate solution were added thereto and stirred for 1 hour, the reaction solution was extracted with ethyl acetate, the extract was washed with water, and the organic layer was dried over magnesium sulfate. The organic layer was purified by passing it through an NH silica gel column, and then recrystallized from ethyl acetate/hexane, to give 6 g of the title compound as colorless crystals.

¹H-NMR (CDCl₃)

δ: 6.95–7.02(m, 2H), 7.08(dd, J=9.2, 1.6 Hz, 1H), 7.23–7.29(m, 6H), 7.33–7.38(m, 9H) 7.43–7.49(m, 2H), 7.48(s, 1H), 7.50(dt, J=9.2, 0.8 Hz, 1H), 7.67(s, 1H), 7.97 (dd, J=1.6, 0.8 Hz, 1H)

Production Example 40

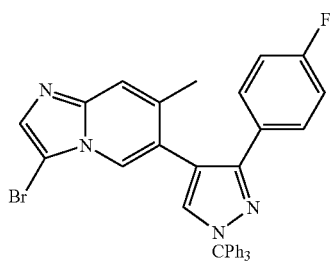

3-Bromo-6-[3-(4-fluorophenyl)-1-trityl-1H-4-pyrazolyl]-7-methylimidazo[1,2-a]pyridine 1.44 g of the title compound was obtained as colorless crystals from 1.5 g 6-[3-(4-fluorophenyl)-1-trityl-1H-4-pyrazolyl]-7-methylimidazo[1,2-a]pyridine (compound in Production Example 35) and 0.57 g N-bromosuccinimide in the same manner as in Production Example 39.

¹H-NMR (CDCl₃)

δ: 2.02(s, 3H), 6.87–6.93(m, 2H), 7.23–7.29(m, 6H), 7.32(s, 1H), 7.33–7.37(m, 9H) 7.38–7.43(m, 2H), 7.46(s, 1H), 7.57(s, 1H), 7.96(s, 1H)

Production Example 41

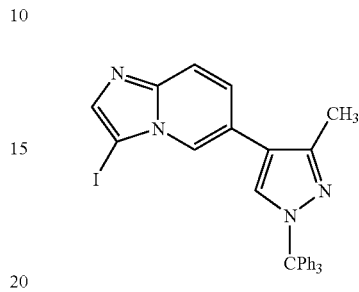

3-Iodo-6-(3-methyl-1-trityl-1H-4-pyrazolyl)imidazo[1,2-a]pyridine 3.03 g of the title compound was obtained as colorless crystals from 2.84 g 6-(3-methyl-1-trityl-1H-4-pyrazolyl)imidazo[1,2-a]pyridine (compound in Production Example 37) and 1.54 g N-iodosuccinimide in the same manner as in Production Example 39.

¹H-NMR (CDCl₃)

δ: 2.46(s, 3H), 7.18–7.24(m, 8H), 7.31–7.36(m, 9H), 7.45(s, 1H), 7.56(dt, J=9.2, 1.2 Hz, 1H), 7.68(s, 1H), 8.10 (dd, J=1.6, 1.2 Hz, 1H)

Production Example 42

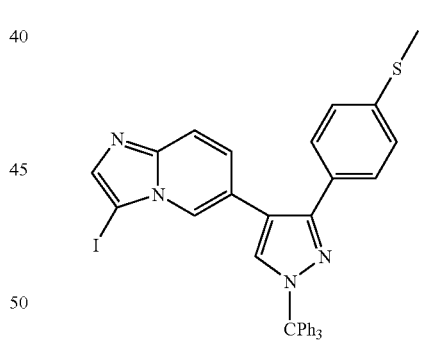

3-Iodo-6-{3-[4-(methylsulfanyl)phenyl]-1-trityl-1H-4-pyrazolyl}imidazo[1,2-a]pyridine 2.7 g of the title compound was obtained as a colorless amorphous from 2.3 g 6-{3-[4-(methylsulfanyl)phenyl]-1-trityl-1H-4-pyrazolyl}imidazo[1,2-a]pyridine (compound in Production Example 36) and 0.99 g N-iodosuccinimide in the same manner as in Production Example 39.

¹H-NMR (CDCl₃)

δ: 2.45(s, 3H), 7.10(dd, J=9.2, 1.6 Hz, 1H), 7.17(dt, J=8.8, 2.0 Hz, 2H), 7.24–7.30(m, 6H), 7.32–7.37(m, 9H), 7.41(dt, J=8.8, 2.0 Hz, 2H), 7.46(s, 1H), 7.50(dd, J=9.2, 0.8 Hz, 1H), 7.66(s, 1H), 7.98(dd, J=1.6, 0.8 Hz, 1H)

Production Example 43

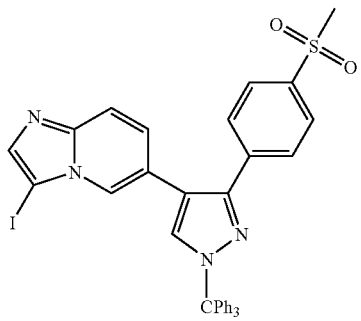

3-Iodo-6-{3-[4-(methylsulfonyl)phenyl]-1-trityl-1H-4-pyrazolyl}imidazo[1,2-a]pyridine 1.7 g 3-iodo-6-{3-[4-(methylsulfanyl)phenyl]-1-trityl-1H-4-pyrazolyl}imidazo[1,2-a]pyridine obtained in Example 42 was dissolved in a solvent mixture of 30 mL tetrahydrofuran and 30 mL methanol, and then 20 mL aqueous solution of 3.1 g oxone was added in divided portions thereto. The mixture was stirred at room temperature for 2 hours, then water was added thereto, and the reaction solution was extracted with ethyl acetate and dried over magnesium sulfate. The product was purified by NH silica gel (hexane/ethyl acetate) to give 1.67 g of the title compound as a colorless amorphous.

$^1$H-NMR (CDCl$_3$)

δ: 3.03(s, 3H), 7.07(dd, J=9.2, 1.6 Hz, 1H), 7.23–7.28(m, 6H), 7.35–7.39(m, 9H), 7.52(s, 1H), 7.54(dd, J=9.2, 0.8 Hz, 1H), 7.69(s, 1H), 7.70(dt, J=8.8, 2.0 Hz, 2H), 7.85(dt, J=8.8, 2.0 Hz, 2H), 7.98(dd, J=1.6, 0.8 Hz, 1H)

Production Example 44

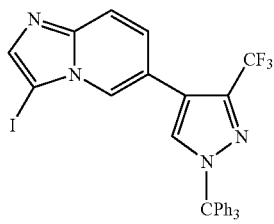

3-Iodo-6-(3-trifluoromethyl-1-trityl-1H-4-pyrazolyl)imidazo[1,2-a]pyridine 251 mg of the title compound (colorless crystals) was obtained from 222 mg 6-(3-trifluoromethyl-1-trityl-1H-4-pyrazolyl)imidazo[1,2-a]pyridine obtained in Production Example 38 and 111 mg N-iodosuccinimide.

$^1$H-NMR (CDCl$_3$)

δ: 7.14(m, 7H), 7.35(m, 9H), 7.50(d, J=0.8 Hz, 1H), 7.61(dd, J=9.2, 1.2 Hz, 1H), 7.71(s, 1H), 8.16(dd, J=2.0, 1.2 Hz, 1H)

Production Example 45

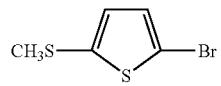

2-Bromo-5-(methylsulfanyl)thiophene 3 g 2-(methylsulfanyl)thiophene was dissolved in 20 mL N,N-dimethylformamide, and 4.23 g N-bromosuccinimide was added in divided portions thereto under ice-cooling. The mixture was stirred for 1 hour, then an aqueous sodium thiosulfate solution and an aqueous sodium bicarbonate solution water were added thereto, and the reaction solution was extracted with ethyl acetate and washed with water. The product was dried over magnesium sulfate and purified by silica gel (hexane/ethyl acetate) to give 4.54 g of the title compound (oil).

$^1$H-NMR (CDCl$_3$)

δ: 2.44(s, 3H), 6.87(d, J=4.0 Hz, 1H), 6.91(d, J=4.0 Hz, 1H)

Production Example 46

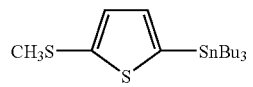

Tributyl[5-(methylsulfanyl)-2-thienyl]stannane 4.5 g 2-bromo-5-(methylsulfanyl)thiophene obtained in Production Example 45 was dissolved in 50 mL dry diethyl ether, and 14.6 mL n-butyl lithium (1.59 M hexane solution) was added dropwise thereto at −70° C. The mixture was stirred for 1 hour, then 6.26 mL tributyltin (IV) chloride was added dropwise thereto and stirred for 30 minutes. The temperature of the reaction solution was raised to room temperature, then water was added to the reaction solution which was then extracted with diethyl ether and dried over magnesium sulfate. The reaction product was purified by neutral alumina (solvent: diethyl ether) to give 9.65 g of the title compound as an oil.

$^1$H-NMR (CDCl$_3$)

δ: 0.89(t, J=7.2 Hz, 9H), 1.06–1.12(m, 6H), 1.33(sext, J=7.2 Hz, 6H), 1.51–1.60(m, 6H) 2.50(s, 1H), 7.02(d, J=3.4 Hz, 1H), 7.15(d, J=3.4 Hz, 1H)

Production Example 47

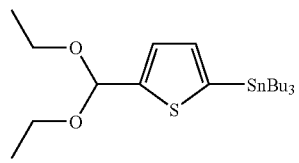

Tributyl[5-(diethoxymethyl)-2-thienyl]stannane 17.1 g of the title compound was obtained as an oil from 8 g 5-bromo-2-thiophenecarboxyaldehyde diethyl acetal in the same manner as in Production Example 46.

$^1$H-NMR (CDCl$_3$)

δ: 0.89(t, J=7.2 Hz, 9H), 1.05–1.1(m, 6H), 1.25(t, J=6.8 Hz, 6H), 1.27–1.38(m, 6H) 1.50–1.60(m, 6H), 3.54–3.72(m, 4H), 5.78(d, J=0.8H, 1H), 7.04(d, J=3.4 Hz, 1H), 7.18(dd, J=3.4, 0.8 Hz, 1H)

Production Example 48

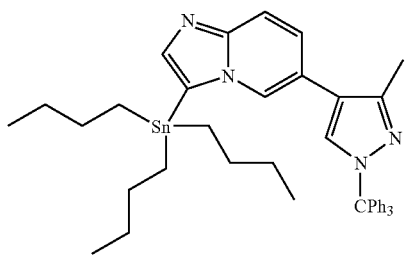

6-(3-Methyl-1-trityl-1H-4-pyrazolyl)-3-(1,1,1-tributylstannyl)imidazo[1,2-a]pyridine 1.17 mL n-butyl lithium (1.5 M hexane solution) was added dropwise at −70° C. to a tetrahydrofuran solution of 906 mg 3-iodo-6-(3-methyl-1-trityl-1H-4-pyrazolyl)imidazo[1,2-a]pyridine obtained in Production Example 41, then the mixture was stirred for 30 minutes, and 0.07 mL tributyltin chloride was added thereto and stirred for 1 hour. An aqueous saturated antimony chloride solution was added to the reaction solution which was then extracted with ethyl acetate and purified by NH silica gel chromatography (hexane/ethyl acetate) to give 500 mg of the title compound as an oil.

$^1$H-NMR (CDCl$_3$)

δ: 0.91(t, J=7.2 Hz, 9H), 1.07–1.15(m, 6H), 1.34(sext. J=7.2 Hz, 6H), 1.53–1.65(m, 6H), 2.41(s, 3H), 7.16(dd, J=9.6, 1.2 Hz, 1H), 7.17–7.24(m, 6H), 7.30–7.37(m, 9H), 7.93(s, 1H), 7.56(s, 1H), 7.58(dd, J=9.6, 0.8 Hz, 1H), 8.10(dd, J=1.2, 0.8 Hz, 1)

Production Example 49

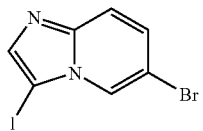

6-Bromo-3-iodoimidazo[1,2-a]pyridine 10.7 g N-iodosuccinimide was added in divided portions to 100 mL solution of 9 g 6-bromoimidazo[1,2-a]pyridine in N,N-dimethylformamide, and the mixture was stirred for 2 hours. An aqueous sodium thiosulfate solution was added thereto and stirred for 1 hour, water was added thereto, and the formed crystals were collected by filtration. The product was recrystallized from tetrahydrofuran/ethanol to give 13.5 g of the title compound (colorless crystals).

$^1$H-NMR (CDCl$_3$)

δ: 7.29(dd, J=9.2, 2.0 Hz, 1H), 7.51(dd, J=9.2, 0.8 Hz, 1H), 7.70(s, 1H), 8.28(dd, J=2.0, 0.8 Hz, 1H)

Production Example 50

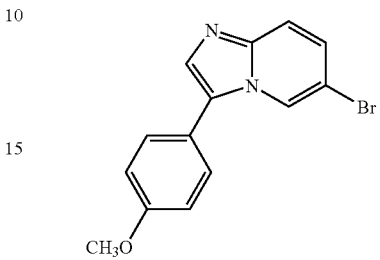

6-Bromo-3-(4-methoxyphenyl)imidazo[1,2-a]pyridine 0.81 mL 1,3-propane diol was added to a suspension of 1.69 g 4-methoxyphenylboronic acid in 15 mL diethyl ether, and the mixture was stirred a room temperature for 1 hour. Formed water was removed, and the organic solvent was evaporated, whereby an oil was obtained. 2.7 g 6-bromo-3-iodoimidazo[1,2-a]pyridine (compound in Production Example 49), 3.5 g potassium phosphate, 483 mg tetrakistriphenyl phosphine palladium and 40 mL N,N-dimethylformamide were added thereto and heated at 90° C. for 3 hours under nitrogen atmosphere. Insolubles were filtered off, the solvent was removed, and the residue was purified by NH silica gel column chromatography (hexane/ethyl acetate) to give 2 g of the title compound as an oil.

$^1$H-NMR (CDCl$_3$)

δ: 3.89(s, 3H), 7.07(dt, J=8.8, 2.0 Hz, 2H), 7.25(dd, J=9.2, 1.6 Hz, 1H), 7.45(dt, J=8.8, 2.0 Hz, 2H), 7.59(dd, J=9.2, 0.8 Hz, 1H), 7.63(s, 1H), 7.98(dd, J=1.6, 0.8 Hz, 1H) MS m/e (ESI)303 (MH$^+$)

Production Example 51

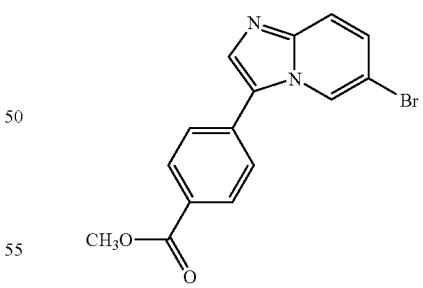

Methyl 4-(6-bromoimidazo[1,2-a]pyridin-3-yl)benzoate 2.3 g methyl 4-(4,4,5,5-tetramethyl-1,3,2-dioxaborolan-2-yl)benzoate prepared according to T. Ishiyama et al., J. Org. Chem., 60, 7508 (1995), 2.0 g 6-bromo-3-iodoimidazo [1,2-a]pyridine (compound in Production Example 49), 2.5 g potassium phosphate, 360 mg tetrakistriphenyl phosphine palladium and 30 mL N,N-dimethylformamide were heated at 100° C. under nitrogen atmosphere. Insolubles were filtered off, the solvent was removed, and the residue was purified by NH silica gel column chromatography (hexane/ethyl acetate) and recrystallized from ethyl acetate to give 1.39 g of the title compound (colorless crystals).

¹H-NMR (CDCl₃)

δ: 3.97(s, 3H), 7.32(dd, J=9.6, 2.0 Hz, 1H), 7.62(d, J=9.6 Hz, 1H), 7.65(dt, J=8.8, 2.0 Hz, 2H), 7.79(br.s, 1H), 8.21(dt, J=8.8, 2.0 Hz, 2H), 8.50(br.s, 1H)

Production Example 52

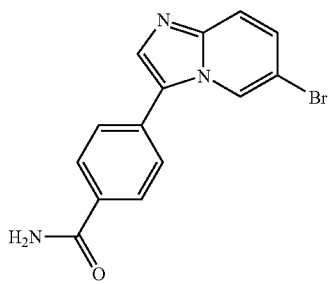

4-(6-Bromoimidazo[1,2-a]pyridin-3-yl)benzamide 228 mg of the title compound was obtained as colorless crystals in the same manner as in Production Example 51 from 1.31 g 4-(4,4,5,5-tetramethyl-1,3,2-dioxaborolan-2-yl)benzamide and 1 g 6-bromo-3-iodoimidazo[1,2-a]pyridine (compound in Production Example 49).

¹H-NMR (CDCl₃)

δ: 5.75(br.s, 1H), 6.18(br.s, 1H), 7.31(dd, J=9.6, 1.6 Hz, 1H), 7.61(d, J=9.6 Hz, 1H), 7.66(d, J=8.8, 2H), 7.76(s, 1H), 7.99(d, J=8.8, 2H), 8.47(dd, J=1.6, 0.4 Hz, 1H)

Production Example 53

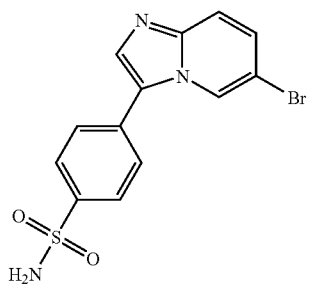

4-(6-Bromoimidazo[1,2-a]pyridin-3-yl)-1-benzene sulfonamide 187 mg of the title compound was obtained as colorless crystals (recrystallized from ethyl acetate/methanol) from 900 mg 4-(4,4,5,5-tetramethyl-1,3,2-dioxaborolan-2-yl)benzene sulfonamide and 646 mg 6-bromo-3-iodoimidazo[1,2-a]pyridine (compound in Production Example 49).

MS m/e (ESI) 352 (MH⁺)

Production Example 54

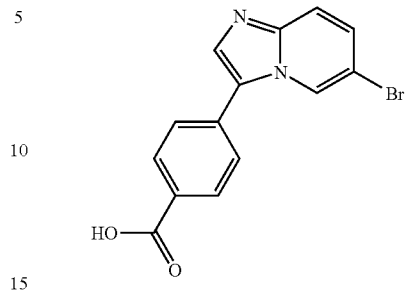

4-(6-Bromoimidazo[1,2-a]pyridin-3-yl)benzoic acid 1.39 g methyl 4-(6-bromoimidazo[1,2-a]pyridin-3-yl)benzoate obtained in Production Example 51 was dissolved in 20 mL tetrahydrofuran and 10 mL methanol, then 4 mL of 2 N aqueous sodium hydroxide was added thereto, and the mixture was stirred at room temperature for 2 hours. After neutralization with 2 N hydrochloric acid, water was added thereto and the precipitated crystals were collected by filtration and washed with ethanol to give 1.21 g of the title compound (colorless crystals).

¹H-NMR (DMSO-d₆)

δ: 7.45(dd, J=9.6, 2.0 Hz, 1H), 7.67(dd, J=9.6, 0.8 Hz, 1H), 7.83(dt, J=8.4, 2.0 Hz, 2H) 7.92(s, 1H), 8.07(dt, J=8.4, 2.0 Hz, 2H), 8.76(dd, J=2.0, 0.8 Hz, 1H)

Production Example 55

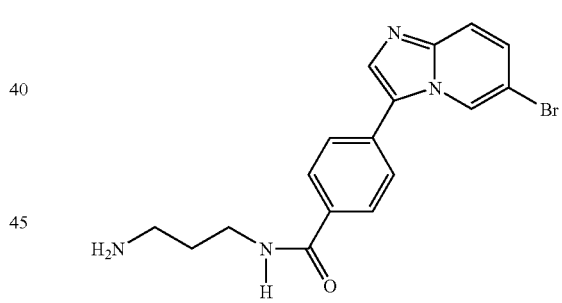

N1-(3-Aminopropyl)-4-(6-bromoimidazo[1,2-a]pyridin-3-yl)benzamide 500 mg 4-(6-bromoimidazo[1,2-a]pyridin-3-yl)benzoic acid obtained in Production Example 54, 302 mg t-butyl-N-(3-aminopropyl)carbamate, 317 mg 1-ethyl-3-(3-dimethylaminopropyl)carbodiimide hydrochloride and 224 mg 1-oxybenzotriazole were left overnight in N,N-dimethylformamide at room temperature. After the solvent was removed, the residue was purified by NH silica gel (ethyl acetate) to give 730 mg colorless amorphous. 440 mg of this product was dissolved in 15 mL trifluoroacetic acid and left at room temperature for 1 hour. The trifluoroacetic acid was removed, then an aqueous sodium bicarbonate solution was added thereto, and the precipitated crystals were collected by filtration. The product was recrystallized from ethanol to give 264 mg of the title compound as colorless crystals.

¹H-NMR (DMSO-d₆)

δ: 1.60(quint, J=6.8 Hz, 2H), 2.59(t, J=6.8 Hz, 2H), 3.29 (br. s, 2H), 3.30–3.36(m, 2H), 7.42(dd, J=9.6, 1.6 Hz, 1H), 7.67(dd, J=9.6 0.8 Hz, 1H), 7.78(dt, J=8.8, 2.0 Hz, 2H), 7.88(s, 1H), 8.65(t, J=6.8 Hz, 1H), 8.47(dd, J=1.6, 0.8 Hz, 1H)

Production Example 56

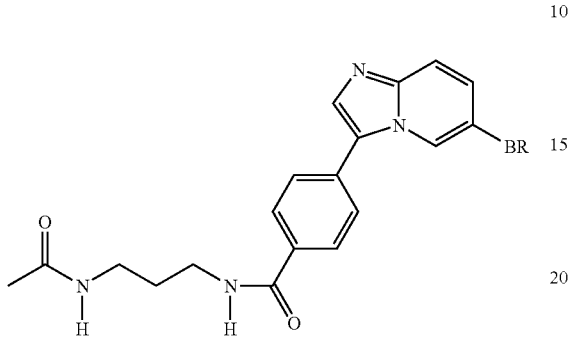

N1-[3-(Acetylamino)propyl]-4-(6-imidazo[1,2-a]pyridin-3-yl)benzamide 0.025 mL acetic anhydride was added to a solution of 50 mg N-1-(3-aminopropyl)-4-(6-bromoimidazo[1,2-a]pyridin-3-yl)benzamide obtained in Production Example 55 in 0.5 mL pyridine under ice-cooling, and the mixture was stirred for 1 hour. Water was added thereto, and the precipitated crystals were collected by filtration and dried to give 38 mg of the title compound (colorless crystals).

¹H-NMR (DMSO-d₆)

δ: 1.64(quint, 6.8 Hz, 2H), 1.80(s, 3H), 3.08 (q, 6.8 Hz, 2H), 3.28(q. 6.8 Hz, 2H), 7.44(dd, 9.6, 1.6 Hz, 1H), 7.67(dd, J=9.6, 0.8 Hz, 1H), 7.79(dt, J=8.4, 2.0 Hz, 2H), 7.87(t, J=5.6 Hz, 1H), 7.88(s, 1H), 7.99(dt, J=8.4, 2.0 Hz, 2H), 8.56(t, J=5.6 Hz 1H), 8.71(dd, J=1.6, 0.8 Hz, 1H)

Production Example 57

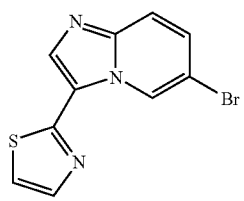

2-(6-Bromoimidazo[1,2-a]pyridin-3-yl)-1,3-thiazole 4.3 g 2-(1,1,1-tributylstannyl)-1,3-thiazole, 3.23 g 6-bromo-3-iodoimidazo[1,2-a]pyridine (compound in Production Example 49) and 578 mg tetrakistriphenyl phosphine palladium were heated at 110° C. for 10 hours in xylene. The solvent was removed, and the residue was purified by an NH silica gel column (solvent: hexane/dichloromethane/ethyl acetate) and recrystallized from ethyl acetate to give 2.06 g of the title compound as colorless crystals.

¹H-NMR (CDCl₃)

δ: 7.30(d, J=3.2 Hz, 1H), 7.41(dd, J=9.6, 1.6 Hz, 1H), 7.61(dd, J=9.6, 0.4 Hz, 1H), 7.90(d, J=3.2 Hz, 1H), 8.12(s, 1H), 9.91(dd, J=1.6, 0.4 Hz, 1H)

Production Example 58

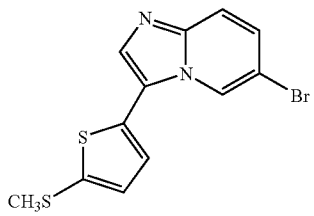

6-Bromo-3-[5-(methylsulfanyl)-2-thienyl]imidazo[1,2-a]pyridine 2 g of the title compound was obtained as a yellow oil from 4.65 g tributyl[5-(methylsulfanyl)-2-thienyl]stannane (compound in Production Example 46) and 3.10 g 6-bromo-3-iodoimidazo[1,2-a]pyridine (compound in Production Example 49).

¹H-NMR (CDCl₃)

δ: 2.57(s, 3H), 7.13(d, J=3.6 Hz, 1H), 7.15(d, J=3.6 Hz, 1H), 7.29(dd, J=9.6, 1.6 Hz, 1H), 7.56(dd, J=9.6, 0.8 Hz, 1H), 7.72(s, 1H), 8.49(dd, J=1.6, 0.8 Hz, 1H)

Production Example 59

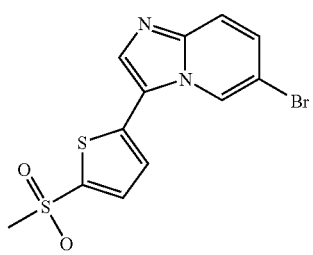

6-Bromo-3-[5-(methylsulfonyl)-2-thienyl]imidazo[1,2-a]pyridine 14 mL aqueous solution of 5.84 g oxone was added to a solution of 1.5 g6-bromo-3-[5-(methylsulfanyl)-2-thienyl]imidazo[1,2-a]pyridine obtained in Production Example 58 in a solvent mixture of 20 mL tetrahydrofuran and 20 mL methanol, and the mixture was stirred for 5 hours. The reaction solution was treated with an aqueous sodium bicarbonate solution and an aqueous sodium thiosulfate solution, then extracted with ethyl acetate and dried over magnesium sulfate. The residue was purified by NH silica gel column chromatography (ethyl acetate) to give 461 mg of the title compound as a yellow solid.

¹H-NMR (CDCl₃)

δ: 3.27(s, 3H), 7.33(d, J=3.6 Hz, 1H), 7.38(dd, J=9.6, 2.0 Hz, 1H), 7.56(dd, J=9.6, 0.8 Hz, 1H), 7.81(d, J=3.6 Hz, 1H), 7.86(s, 1H), 8.52(dd, J=1.6, 0.8 Hz, 1H)

Production Example 60

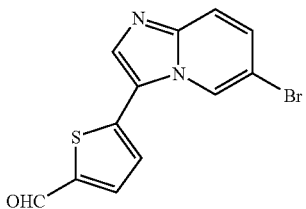

5-(6-Bromoimidazo[1,2-a]pyridin-3-yl)-2-thiophene carboxy aldehyde 4.2 g 6-bromo-3-[5-(diethoxymethyl)-2-thienyl]imidazo[1,2-a]pyridine was obtained as a brown oil in the same manner as in Production Example 57 from 7 g tributyl[5-(diethoxymethyl)-2-thienyl]stannane (compound in Production Example 47) and 4 g 6-bromo-3-iodoimidazo[1,2-a]pyridine (compound in Production Example 49).

4 g 6-bromo-3-[5-(diethoxymethyl)-2-thienyl]imidazo[1,2-a]pyridine was dissolved in 20 mL tetrahydrofuran and 20 mL methanol, then 5 mL of 2 N hydrochloric acid was added thereto, and the mixture was stirred at room temperature for 1 hour. The reaction solution was adjusted to pH 11 with an aqueous sodium bicarbonate solution and extracted with dichloromethane. The extract was purified by silica gel column chromatography (dichloromethane/ethyl acetate) to give 2.3 g of the title compound as yellow crystals.

$^1$H-NMR (CDCl$_3$)

δ: 7.38(dd, J=9.6, 1.6 Hz, 1H), 7.43(d, J=3.6 Hz, 1H), 7.63(dd, J=9.6, 0.8 Hz, 1H), 7.86(d, J=3.6 Hz, 1H), 7.93(s, 1H), 8.64(dd, J=1.6, 0.8 Hz, 1H), 7.96(s, 1H)

Production Example 61

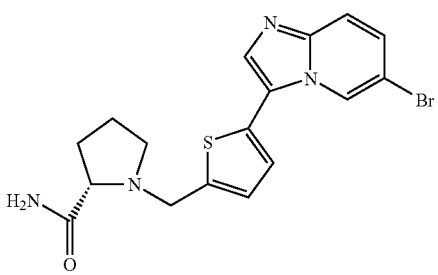

(2S)-1-{[5-(6-Bromoimidazo[1,2-a]pyridin-3-yl)-2-thienyl]methyl}tetrahydro-1H-2-pyrrole carboxyamide 0.06 mL acetic acid and 276 mg sodium triacetoxy borohydride were added to a solution of 300 mg 5-(6-bromoimidazo[1,2-a]pyridin-3-yl)-2-thiophene carboxy aldehyde obtained in Production Example 60 and 126 mg L-proline amide in tetrahydrofuran, and the mixture was stirred at room temperature for 12 hours under nitrogen atmosphere. After an aqueous solution of sodium bicarbonate was added, the reaction solution was extracted with ethyl acetate and dried over magnesium sulfate. After the solvent was removed, the residue was crystallized from ethyl acetate/methanol/diethyl ether to give 315 mg of the title compound as colorless crystals.

$^1$H-NMR (CDCl$_3$)

δ: 1.80–1.90(m, 1H), 1.94–2.05(m, 1H), 2.22–2.33(m, 1H), 2.45–2.55(m, 1H), 3.20–3.34(m, 2H), 3.86(d, J=14.0 Hz, 1H), 4.12(d, J=14.0 Hz, 1H), 5.39(s, 1H), 7.02(d, J=3.6 Hz, 1H), 7.13(d, J=3.6 Hz, 1H), 7.20–7.30(br.s, 2H), 7.29 (dd, J=9.6, 2.0 Hz, 1H), 7.58(dd, J=9.6, 0.8 Hz, 1H), 7.72(s, 1H), 8.49(dd, J=2.0, 0.8 Hz, 1H)

Production Example 62

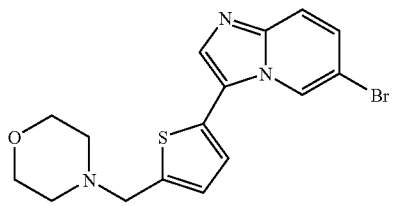

4-{[5-(6-Bromoimidazo[1,2-a]pyridin-3-yl)-2-thienyl]methyl}morpholine

The title compound, 310 mg, was obtained as colorless crystals from 300 mg 5-(6-bromoimidazo[1,2-a]pyridin-3-yl)-2-thiophene carboxy aldehyde (compound in Production Example 60) and 90 mg morpholine in the same manner as in Production Example 61.

$^1$H-NMR (CDCl$_3$)

δ: 2.57 (br. s, 4H), 3.73–3.79(m, 6H), 7.02(d, J=3.6 Hz, 1H), 7.13(d, J=3.6 Hz, 1H), 7.28(dd, J=9.6, 2.0 Hz, 1H), 7.56(dd, J=9.6, 0.4 Hz, 1H), 7.72(s, 1H), 8.49(dd, J=2.0, 0.4 Hz, 1H)

Production Example 63

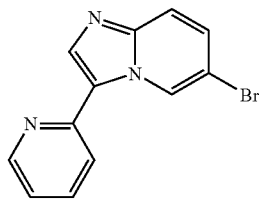

6-Bromo-3-(2-pyridyl)imidazo[1,2-a]pyridine

The title compound, 784 mg, was obtained as white crystals from 1.29 g 6-bromo-3-iodoimidazo[1,2-a]pyridine (compound in Production Example 49) and 1.77 g 2-(tri-n-butylstannyl)-pyridine in the same manner as in Production Example 57.

$^1$H-NMR (CDCl$_3$)

δ: 7.19(ddd, J=4.8, 2.0, 2.0 Hz, 1H), 7.36(dd, J=9.6, 2.0 Hz, 1H), 7.59(dd, J=9.6, 0.8 Hz, 1H), 7.75(m, 2H), 8.13(s, 1H), 8.29 (1H, dd, J=2.0, 0.8 Hz, 1H), 10.16(brs, 1H)

Production Example 64

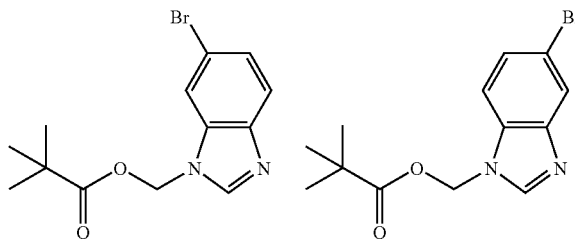

Mixture of (6-bromo-1H-benzo[d]imidazol-1-yl)methyl pivalate and (5-bromo-1H-benzo[d]imidazol-1-yl)methyl pivalate in a ratio of 1:1

0.76 g of 6-bromo-1H-benzo[d]imidazole was dissolved in 10 mL N,N-dimethylformamide, and 0.61 mL chloromethyl pivalate and 0.69 g potassium carbonate were added thereto, and the mixture was stirred at room temperature for one day under nitrogen atmosphere. After water and an aqueous saturated solution of ammonium chloride were added, the reaction solution was extracted with ethyl acetate, and the organic layer was washed with brine and dried over sodium sulfate. The solvent was evaporated, whereby 1.17 g of the title compound was obtained as a pale skin-colored solid.

$^1$H-NMR (CDCl$_3$)

δ: 1.14(s, 4.5H), 1.16(s, 4.5H), 6.07(s, 1H), 6.09(s, 1H), 7.42–7.48(m, 1.5H), 7.65–7.73(m, 1H), 7.95–7.97(m, 0.5H), 8.07(s, 0.5H), 8.08(s, 0.5H)

Production Example 65

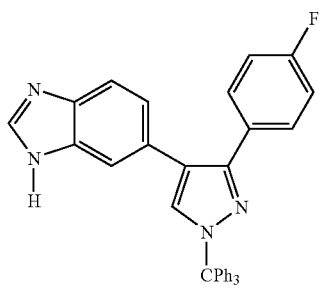

6-[3-(4-Fluorophenyl)-1-trityl-1H-4-pyrazolyl]-1H-benzo[d]imidazole 0.88 g mixture of {6-[3-(4-fluorophenyl)-1-trityl-1H-4-pyrazolyl]-1H-benzo[d]imidazol-1-yl}methyl pivalate and {5-[3-(4-fluorophenyl)-1-trityl-1H-4-pyrazolyl]-1H-benzo[d]imidazol-1-yl}methyl pivalate in a ratio of 1:1 was obtained as a colorless amorphous by the same method as in Production Example 34 from 0.6 g mixture of (6-bromo-1H-benzo[d]imidazol-1-yl)methyl pivalate and (5-bromo-1H-benzo[d]imidazol-1-yl)methyl pivalate in a ratio of 1:1 obtained in Production Example 64 and 1.3 g of 3-(4-fluorophenyl)-1-trityl-1H-4-pyrazolylboronic acid (compound in Production Example 25). The product was dissolved in 10 mL methanol, and 84 mg sodium hydride was added thereto, and the mixture was stirred at room temperature for 1.5 hours. After water was added, the reaction solution was extracted with diethyl ether, and the organic layer was washed with brine and dried over sodium sulfate. The solvent was evaporated, and then the residue was purified by silica gel chromatography (ethyl acetate/methanol) to give 0.64 g of the title compound as a colorless amorphous.

$^1$H-NMR (CDCl$_3$)

δ: 6.84–6.91(m, 2H), 7.12–7.46(m, 21H), 7.91–7.95(m, 1H)

MS m/e(ESI) 521(MH$^+$)

Production Example 66

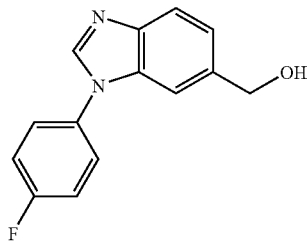

[1-(4-Fluorophenyl)-1H-benzo[d]imidazol-6-yl]methanol

A mixture of 5 g methyl 1H-benzo[d] imidazole-6-carboxylate, 7.9 g 4-fluorophenylboronic acid, 7.7 g copper (II) acetate, 4.6 mL pyridine, 10.5 g 4 Å molecular sieves and 100 mL dry dichloromethane was stirred at room temperature for 24 hours. The mixture was filtered through Celite, the solvent was evaporated, and the residue was purified by silica gel chromatography (hexane/ethyl acetate) to give 4.4 g of 1-(4-fluorophenyl)-1H-benzo[d]imidazole-6-carboxylate as colorless crystals. This product was dissolved in 45 mL tetrahydrofuran, and 0.62 g lithium aluminum hydride was added thereto with stirring under ice-cooling and stirred at room temperature for 4 hours under nitrogen atmosphere. The reaction solution was added to iced water and extracted with ethyl acetate, and the organic layer was washed with brine and dried over sodium sulfate. After the solvent was evaporated, the residue was purified by silica gel chromatography (hexane/ethyl acetate) to give 1.24 g of the title compound as colorless crystals.

$^1$H-NMR (DMSO-d$_6$)

δ: 4.45–4.65(br, 2H), 5.20–5.25(m, 1H), 7.23(d, J=8.4 Hz, 1H), 7.43–7.52(m, 3H), 7.66–7.74(m, 3H), 8.46(d, J=1.6 Hz, 1H)

Production Example 67

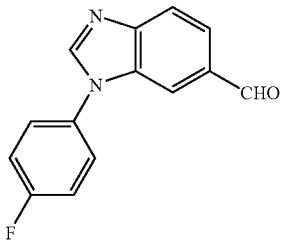

1-(4-Fluorophenyl)-1H-benzo[d]imidazole-6-carboaldehyde 1.88 g [1-(4-fluorophenyl)-1H-benzo[d]imidazol-6-yl] methanol obtained in Production Example 66 and 8.1 g manganese dioxide were stirred in 80 mL acetone at room temperature for 8 hours. The reaction mixture was filtered through Celite, and the solvent was evaporated, whereby 1.62 g of the title compound was obtained as colorless crystals.

$^1$H-NMR (DMSO-$d_6$)

δ: 7.48–7.54(m, 2H), 7.77–7.82(m, 2H), 7.85(dd, J=8.4, 1.6 Hz, 1H), 7.93(d, J=8.4 Hz, 1H), 8.10–8.13(m, 1H), 8.79(s, 1H), 10.05(s, 1H)

Production Example 68

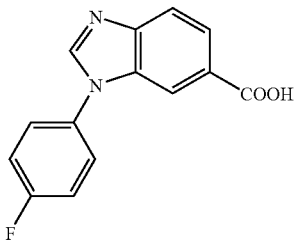

1-(4-Fluorophenyl)-1H-benzo[d]imidazole-6-carboxylic acid 1.62 g of 1-(4-fluorophenyl)-1H-benzo[d]imidazole-6-carboaldehyde obtained in Production Example 67 was dissolved in 33 mL dimethylacetamide, and 16.5 mL water, 5.25 g sodium chlorite, 5.26 g sodium dihydrogen phosphate-dihydrate and 3.44 mL 2-methyl-2-butene were added thereto and stirred at room temperature for 1 hour. After water and 1 N aqueous hydrochloric acid were added, the reaction mixture was extracted with ethyl acetate. The organic layer was washed with an aqueous solution of sodium thiosulfate and brine, and dried over sodium sulfate. The solvent was evaporated to give 0.42 g of the title compound as colorless crystals.

$^1$H-NMR (DMSO-$d_6$)

δ: 7.48–7.54(m, 2H), 7.74–7.79(m, 2H), 7.84(d, J=8.8 Hz, 1H), 7.90(dd, J=8.8, 1.6 Hz, 1H), 8.05(d, J=1.6 Hz, 1H), 8.71(s, 1H)

Production Example 69

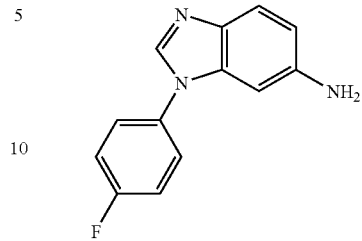

1-(4-Fluorophenyl)-1H-benzo[d]imidazol-6-amine 0.38 g 1-(4-fluorophenyl)-1H-benzo[d]imidazole-6-carboxylic acid obtained in Production Example 68, 15 mL t-butanol, 0.25 mL triethylamine and 0.38 mL diphenylphosphoryl azide were heated for 2.5 hours under reflux. After water, an aqueous saturated solution of sodium bicarbonate and an aqueous saturated solution of ammonium chloride were added, the reaction mixture was extracted with ethyl acetate. The organic layer was washed with brine and dried over sodium sulfate. After the solvent was evaporated, the residue was purified by silica gel chromatography (hexane/ethyl acetate) to give 0.17 g t-butyl N-[1-(4-fluorophenyl)-1H-benzo[d]imidazol-6-yl] carbamate. This product was, dissolved in 4 mL dichloromethane, then 4 mL trifluoroacetic acid was added thereto, and the mixture was stirred at room temperature for 1 hour. After water was added, the reaction mixture was neutralized with an aqueous saturated solution of sodium bicarbonate and then extracted with dichloromethane, and the organic layer was dried over sodium sulfate. The solvent was evaporated to give 0.11 g of the title compound as a pale brown oil.

$^1$H-NMR (DMSO-$d_6$)

δ: 5.06(br, 2H), 6.55–6.67(m, 2H), 7.33–7.47(m, 3H), 7.58–7.65(m, 2H), 8.10(s, 1H)

Production Example 70

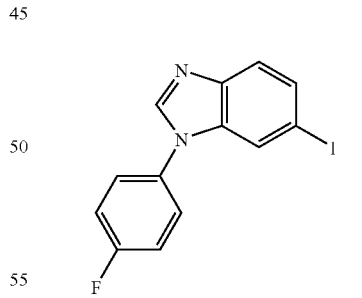

1-(4-Fluorophenyl)-6-iodo-1H-benzo[d]imidazole

A mixture of 0.11 g of 1-(4-fluorophenyl)-1H-benzo[d] imidazol-6-amine obtained in Production Example 69, 94 mg copper (I) iodide, 0.2 mL methylene iodide, 0.2 mL isoamyl nitrite and 4 mL tetrahydrofuran was heated for 6 hours under reflux. The reaction mixture was filtered through Celite, the solvent was evaporated, and then the residue was purified by silica gel chromatography (hexane/ ethyl acetate) to give 72 mg of the title compound as yellow crystals.

¹H-NMR (DMSO-d₆)

δ: 7.40–7.50(m, 2H), 7.50–7.60(m, 2H), 7.66–7.75(m, 2H), 7.83(s, 1H), 8.47(s, 1H)

Production Example 71

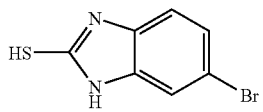

6-Bromo-1H-benzo[d]imidazole-2-thiol 6.7 g of 4-bromo-1,2-benzenediamine obtained by reducing 5-bromo-2-nitroaniline was dissolved in 50 mL methanol, then 4.4 mL carbon disulfide was added thereto, a solution of 1.3 g potassium hydroxide in 40 mL ethanol was added little by little thereto, and the mixture was heated for 3.5 hours under reflux. The reaction mixture was made weakly acidic by adding iced water and acetic acid, and the precipitated crystals were filtered and washed with water to give 7.1 g of the title compound as colorless crystals.

¹H-NMR (DMSO-d₆)

δ: 7.06(d, J=9.2 Hz, 1H), 7.23–7.27(m, 2H)

Production Example 72

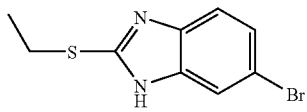

6-Bromo-2-(ethylsulfanyl)-1H-benzo[d]imidazole 8.0 g of 6-bromo-1H-benzo [d] imidazole-2-thiol obtained in Production Example 17 was dissolved in 85 mL N,N-dimethylformamide, 1.46 g sodium hydride was added thereto under ice-cooling, the mixture was stirred for 15 minutes, 3.0 mL ethyl iodide was added thereto, and the mixture was stirred under ice-cooling for 1 hour. Water was added to the reaction mixture which was then extracted with ethyl acetate. The organic layer was washed with water and brine and dried over sodium sulfate. The solvent was evaporated, and the residue was purified by silica gel chromatography (hexane/ethyl acetate) to give 8.1 g of the title compound as skin-colored crystals.

¹H-NMR (DMSO-d₆)

δ: 1.33(t, J=9.0 Hz, 3H), 3.25 (q, J=9.0 Hz, 2H), 7.20(d, J=9.2 Hz, 1H), 7.34(d, J=9.2 Hz, 1H), 7.59(s, 1H)

Production Example 73

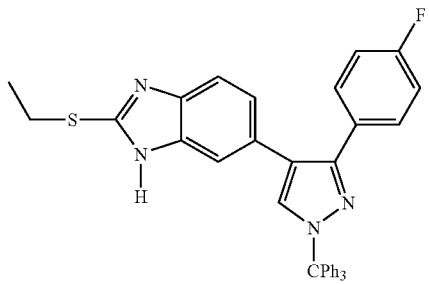

2-(Ethylsulfanyl)-6-[3-(4-fluorophenyl)-1-trityl-1H-4-pyrazolyl]-1H-benzo[d]imidazole 11.8 g mixture of [6-bromo-2-(ethylsulfanyl)-1H-benzo[d]imidazol-1-yl]methyl pivalate and [5-bromo-2-(ethylsulfanyl)-1H-benzo[d]imidazol-1-yl]methyl pivalate in a ratio of 1:1 was obtained as pale yellow solid by the same method as in Production Example 64 from 8.1 g 6-bromo-2-(ethylsulfanyl)-1H-benzo[d]imidazole obtained in Production Example 72. 7.2 g of the title compound was obtained as a colorless amorphous by the same method as in Production Example 65 from 6.9 g of the above product and 10 g 3-(4-fluorophenyl)-1-trityl-1H-4-pyrazolylboronic acid (compound in Production Example 25).

¹H-NMR (CDCl₃)

δ: 1.38(t, J=9.0 Hz, 3H), 3.25 (q, J=9.0 Hz, 2H), 6.84–6.9 (m, 2H), 7.00–7.07(m, 2H), 7.22–7.33(m, 16H), 7.37(s, 1H), 7.40–7.45(m, 2H)

Production Example 74

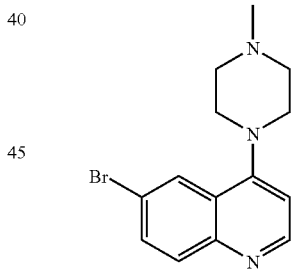

6-Bromo-4-(4-methylpiperazin-1-yl)quinoline

A mixture of 485 mg 6-bromo-4-chloroquinoline, 1.1 mL N-methyl piperazine, 415 mg potassium carbonate and 10 mL N,N-dimethylformamide was stirred at 130° C. for 8 hours. Ethyl acetate and water were added to the reaction solution, and the organic layer was separated. The organic layer was washed with water and brine and dried over anhydrous magnesium sulfate. The drying agent was filtered off, and the filtrate was evaporated. The residue was purified by silica gel column chromatography (hexane/ethyl acetate) to give 502 mg of the title compound as pale yellow crystals.

¹H-NMR (CDCl₃)

δ: 2.44(s, 3H), 2.73(m, 4H), 3.25(m, 4H), 6.88(d, J=5.2 Hz, 1H), 7.71(dd, J=8.8, 2.0 Hz, 1H), 7.91(d, J=8.8 Hz, 1H), 8.14(d, J=2.0 Hz, 1H), 8.72(d, J=5.2 Hz, 1H)

Production Example 75

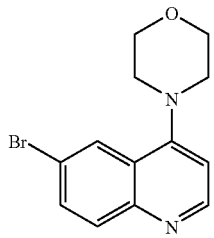

4-(6-Bromo-4-quinolyl) morpholine 122 mg 6-bromo-4-chloroquinoline and 0.13 mL morpholine were reacted by the same method as in Production Example 74 to give 68 mg of the title compound as a colorless oil.

$^1$H-NMR (CDCl$_3$)

δ: 3.21(m, 4H), 4.00(m, 4H), 6.88(d, J=5.2 Hz, 1H), 7.72(dd, J=8.8, 2.0 Hz, 1H), 7.92(d, J=8.8 Hz, 1H), 8.16(d, J=2.0 Hz, 1H), 8.77(d, J=5.2 Hz, 1H)

Production Example 76

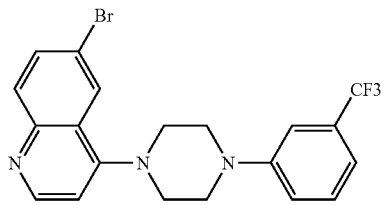

6-Bromo-4-[4-(3-trifluoromethylphenyl)piperazin-1-yl]quinoline 243 mg 6-bromo-4-chloroquinoline and 691 mg 1-[3-(triphenylmethyl)phenyl]piperazine were reacted by the same method as in Production Example 74 to give 188 mg of the title compound as a pale yellow amorphous.

$^1$H-NMR (CDCl$_3$)

δ: 3.38(m, 4H), 3.54(m, 4H), 6.94(d, J=4.8 Hz, 1H), 7.16(m, 2H), 7.22(s, 1H), 7.41(t, J=8.0 Hz, 1H), 7.75(dd, J=9.2, 2.4 Hz), 7.95(d, J=9.2 Hz, 1H), 8.21(d, J=2.4 Hz, 1H), 8.77(d, J=4.8 Hz, 1H)

Production Example 77

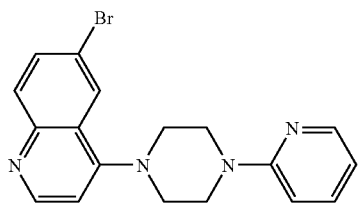

6-Bromo-4-[4-(2-pyridyl)piperazin-1-yl]quinoline 291 mg 6-bromo-4-chloroquinoline and 0.91 mL 4-(2-pyridyl)piperazine were reacted by the same method as in Production Example 74 to give 373 mg of the title compound as a colorless oil.

$^1$H-NMR (CDCl$_3$)

δ: 3.33(m, 4H), 3.83(m, 4H), 6.71(m, 1H), 6.76(dd, J=8.8, 2.0 Hz, 1H), 6.92(d, J=4.8 Hz, 1H), 7.55 (td, J=8.8, 2.0 Hz, 1H), 7.74(dd, J=8.8, 2.0 Hz, 1H), 7.92(d, J=8.8)Hz, 1H), 8.23(d, J=2.0 Hz, 1H), 8.25(m, 1H), 8.75(d, J=4.8 Hz, 1H)

Production Example 78

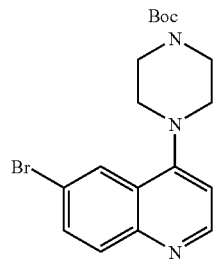

t-Butyl 4-(6-bromo-4-quinolyl)-1-piperazine carboxylate

A mixture of 243 mg 6-bromo-4-chloroquinoline, 373 mg t-butyl 1-piperazine carboxylate, 0.28 mL triethylamine and 10 mL dimethyl sulfoxide was stirred at 80° C. overnight. Ethyl acetate and water were added to the reaction solution, and the organic layer was separated, washed twice with water and then with brine and dried over anhydrous magnesium sulfate. The drying agent was filtered off, and the filtrate was evaporated. The residue was purified by silica gel column chromatography (hexane/ethyl acetate) to give 282 mg of the title compound as a pale yellow oil.

$^1$H-NMR (CDCl$_3$)

δ: 1.50(s, 9H), 3.16(m, 4H), 3.53(m, 4H), 6.87(d, J=5.2 Hz, 1H), 7.73(dd, J=8.8, 2.0 Hz, 1H), 7.93(d, J=8.8 Hz, 1H), 8.15(d, J=2.0 Hz, 1H), 8.73(d, J=5.2 Hz, 1H)

Production Example 79

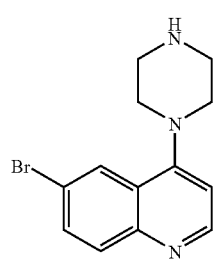

6-Bromo-4-piperazin-1-yl-quinoline

A mixture of 197 mg t-butyl 4-(6-bromo-4-quinolyl)-1-piperazine carboxylate obtained in Production Example 78, 2 mL trifluoroacetic acid and 3 mL dichloromethane was stirred at room temperature overnight. The reaction solution was cooled and basified with 5 N aqueous sodium hydroxide. Then, ethyl acetate and water were added thereto, and the organic layer was separated. The aqueous layer was extracted with ethyl acetate, and the combined organic layer was washed with brine and dried over an hydrous magnesium sulfate. The drying agent was filtered off, and the filtrate was evaporated, to give 157 mg of the title compound as a pale yellow oil.

$^1$H-NMR (CDCl$_3$)

δ: 3.18(s, 8H), 6.87(d, J=5.2 Hz, 1H), 7.71(dd, J=8.8, 2.0 Hz, 1H), 7.92(d, J=8.8 Hz, 1H), 8.16(d, J=2.0 Hz, 1H), 8.73(d, J=5.2 Hz, 1H)

Production Example 80

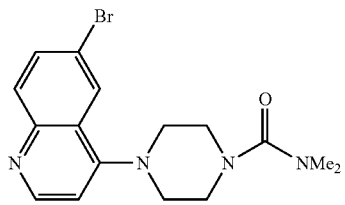

N,N-Dimethyl-4-(6-bromo-4-quinolyl)-1-piperazine carboxamide

While 5 mL solution of 72 mg of 6-bromo-4-piperazin-1-yl-quinoline obtained in Production Example 79 and 75 mg triethylamine in dichloromethane was stirred in a stream of nitrogen, 34 μL N,N-dimethylcarbamoyl chloride was added thereto. Then, the mixture was stirred at room temperature for 1 hour. Ethyl acetate and water were added thereto, and the organic layer was separated, washed with water and brine and dried over an hydrous magnesium sulfate. The drying agent was filtered off, and the filtrate was evaporated, and the residue was purified by silica gel column chromatography (hexane/ethyl acetate), to give 70 mg of the title compound as a colorless oil.

$^1$H-NMR (CDCl$_3$)

δ: 2.90(s, 6H), 3.22(m, 4H), 3.54(m, 4H), 6.87(d, J=5.2 Hz, 1H), 7.73(dd, J=8.8, 2.0 Hz, 1H), 7.93(d, J=8.8 Hz, 1H), 8.16(d, J=2.0 Hz, 1H), 8.74(d, J=5.2 Hz, 1H)

Production Example 81

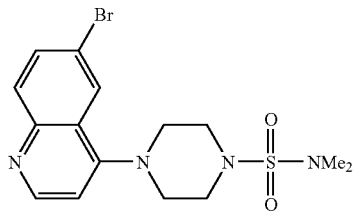

N,N-Dimethyl-4-(6-bromo-4-quinolyl)-1-piperazine sulfonamide 72 mg 6-bromo-4-piperazin-1-yl-quinoline obtained in Production Example 78 and 45 μL N,N-dimethylcarbamoyl chloride were reacted by the same method as in Production Example 80, to give 71 mg of the title compound as a colorless oil.

$^1$H-NMR (CDCl$_3$)

δ: 2.91(s, 6H), 3.25(m, 4H), 3.55(m, 4H), 6.89(d, J=4.8 Hz, 1H), 7.74(dd, J=8.8, 2.0 Hz, 1H), 7.94(d, J=8.8 Hz, 1H), 8.12(d, J=2.0 Hz, 1H), 8.75(d, J=5.2 Hz, 1H)

Production Example 82

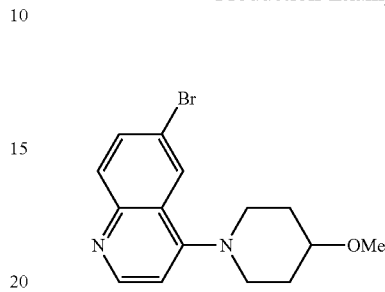

1-(6-Bromo-4-quinolyl)-4-piperidyl methyl ether

A mixture of 500 mg 6-bromo-4-chloroquinoline, 330 mg 4-methoxypiperidine monohydrochloride, 0.57 mL triethylamine and 10 mL N,N-dimethylformamide was stirred at 130° C. for 8 hours. Ethyl acetate and water were added to the reaction solution, and the organic layer was separated. The organic layer was washed with water and brine and dried over sodium sulfate, and the solvent was evaporated. The residue was purified by silica gel column chromatography (hexane/ethyl acetate) to give 516 mg of the title compound as a pale yellow oil.

$^1$H-NMR (CDCl$_3$)

δ: 1.85–1.98(m, 2H), 2.08–2.20(m, 2H), 2.97–3.08(m, 2H), 3.38–3.55(m, 6H), 6.85(d, J=5.0 Hz, 1H), 7.70(d, J=8.6 Hz, 1H), 7.90(d, J=8.6 Hz, 1H), 8.12(s, 1H), 8.69(d, J=5.0 Hz, 1H)

Production Example 83

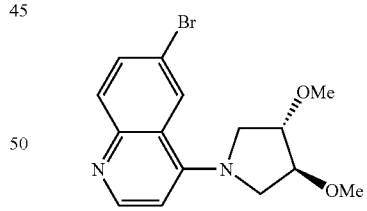

6-Bromo-4-[(3S,4S)-3,4-dimethoxytetrahydro-1H-1-pyrrolyl]quinoline 697 mg 6-bromo-4-chloroquinoline and 482 mg (3S,4S)-3,4-dimethoxytetrahydro-1H pyrrole monohydrochloride were reacted by the same method as in Production Example 82, to give 346 mg of the title compound as pale brown crystals.

$^1$H-NMR (CDCl$_3$)

δ: 3.42(s, 6H), 3.60(d, J=8.6 Hz, 2H), 3.90–4.00(m, 4H), 6.50(d, J=5.0 Hz, 1H), 7.65(d, J=8.2 Hz, 1H), 7.86(d, J=8.2 Hz, 1H), 8.31(s, 1H), 8.51(d, J=5.0 Hz, 1H)

Production Example 84

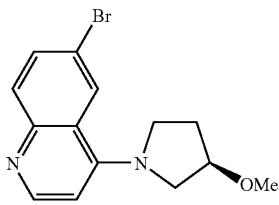

6-Bromo-4-[(3R)-3-methoxytetrahydro-1H-1-pyrrolyl]quinoline 500 mg 6-bromo-4-chloroquinoline and 300 mg (3R)-3-methoxy pyrrolidine monohydrochloride were reacted by the same method as in Production Example 82, to give 284 mg of the title compound as a yellow oil.

$^1$H-NMR (CDCl$_3$)

δ: 2.00–2.15(m, 1H), 2.20–2.30(m, 1H), 3.39(s, 3H), 3.60–3.71(m, 2H), 3.83–3.92(m, 2H), 4.10–4.16(m, 1H), 6.47(d, J=7.4 Hz, 1H), 7.64(d, J=8.4 Hz, 1H), 7.83(d, J=8.4 Hz, 1H), 8.33(s, 1H), 8.48(d, J=7.4 Hz, 1H)

Production Example 85

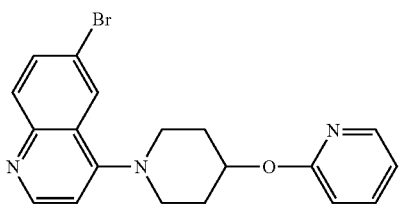

6-Bromo-4-[4-(2-pyridyloxy)piperidino]quinoline 500 mg 6-bromo-4-chloroquinoline and 540 mg 2-(4-piperidyloxy) pyridine dihydrochloride were reacted by the same method as in Production Example 82, to give 629 mg of the title compound as an orange oil.

$^1$H-NMR (CDCl$_3$)

δ: 2.08–2.16(m, 2H), 2.28–2.35(m, 2H), 3.14–3.20(m, 2H), 3.45–3.55(m, 2H), 5.33–5.40(m, 1H), 6.74–6.79(m, 1H), 6.84–6.88(m, 1H), 6.90(d, J=4.8 Hz, 1H), 7.56–7.62(m, 1H), 7.72(dd, J=8.8, 2.2 Hz, 1H), 7.92(d, J=8.8 Hz, 1H), 8.14–8.19(m, 2H), 8.72(d, J=4.8 Hz, 1H)

Production Example 86

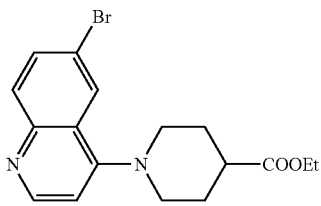

Ethyl 1-(6-bromo-4-quinolyl)-4-piperidine carboxylate 500 mg 6-bromo-4-chloroquinoline and 340 mg ethyl 4-piperidine carboxylate were reacted by the same method as in Production Example 74, to give 480 mg of the title compound as a yellow oil.

$^1$H-NMR (CDCl$_3$)

δ: 1.30(t, J=8.8 Hz, 3H), 2.01–2.20(m, 4H), 2.50–2.62(m, 1H), 2.85–2.95(m, 2H), 3.52–3.60(m, 2H), 4.22 (q, J=8.8 Hz, 2H), 6.85(d, J=4.8 Hz, 1H), 7.72(d, J=8.8 Hz, 1H), 7.92(d, J=8.8 Hz, 1H), 8.13(s, 1H), 8.71(d, J=4.8 Hz, 1H)

Production Example 87

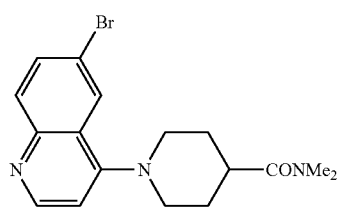

N4,N4-Dimethyl-1-(6-bromo-4-quinolyl)-4-piperidine carboxamide 480 mg ethyl 1-(6-bromo-4-quinolyl)-4-piperidine carboxylate obtained in Production Example 86 was dissolved in 10 mL ethanol, then a solution of 110 mg lithium hydroxide in 5 mL water was added thereto, and the mixture was stirred at 85° C. for 8 hours. After water was added, the solution was made weakly acidic and the resulting crystals were filtered and washed with diethyl ether to give 280 mg 1-(6-bromo-4-quinolyl)-4-piperidine carboxylic acid as colorless crystals. This product was dissolved in 4 mL tetrahydrofuran, and 0.17 mL triethylamine and 0.064 mL isobutyl chlorocarbonate were added thereto under stirring with cooling on ice and stirred under nitrogen atmosphere for 1 hour. 4 mL of 50% aqueous dimethylamine was added thereto and stirred at room temperature for 1.5 hours. After water was added, the reaction mixture was extracted with ethyl acetate, and the solvent was evaporated. The residue was purified by silica gel column chromatography (ethyl acetate/methanol), to give 81 mg of the title compound as a pale yellow amorphous.

$^1$H-NMR (CDCl$_3$)

δ: 1.87–1.98(m, 2H), 2.13–2.25(m, 2H), 2.72–2.93(m, 3H), 3.00(s, 3H), 3.12(s, 3H), 3.60–3.68(m, 2H), 6.85(d, J=4.8 Hz, 1H), 7.71(d, J=8.8 Hz, 1H), 7.91(d, J=8.8 Hz, 1H), 8.16(s, 1H), 8.71(d, J=4.8 Hz, 1H)

Production Example 88

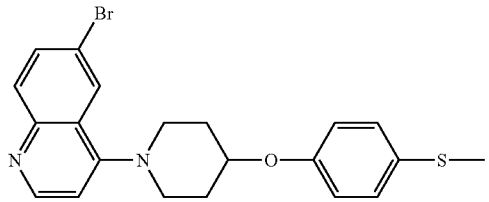

6-Bromo-4-{4-[4-(methylsulfanyl)phenoxy]
piperidino}quinoline 420 mg 6-bromo-4-chloroquinoline and 473 mg 4-[4-(methylsulfanyl)phenoxy]piperidine monohydrochloride were reacted by the same method as in Production Example 82, to give 494 mg of the title compounds a brown oil.

$^1$H-NMR (CDCl$_3$)

δ: 2.05–2.17(m, 2H), 2.20–2.30(m, 2H), 2.46(s, 3H), 3.10–3.20(m, 2H), 3.40–3.49(m, 2H), 4.51–4.61(m, 1H), 6.87–6.94(m, 3H), 7.26–7.30(m, 2H), 7.73(d, J=8.8 Hz, 1H), 7.91(d, J=8.8 Hz, 1H), 8.13(s, 1H), 8.72(d, J=4.8 Hz, 1H)

Production Example 89

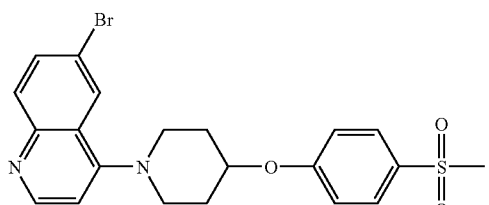

6-Bromo-4-{4-[4-(methylsulfonyl)phenoxy]
piperidino}quinoline 424 mg of the title compound was obtained as a pale yellow amorphous by the same method as in Production Example 43 from 494 mg 6-bromo-4-{4-[4-(methylsulfanyl)phenoxy]piperidino}-quinoline obtained in Production Example 88 and 1.42 g oxone.

$^1$H-NMR (CDCl$_3$)

δ: 1.90–2.02(m, 2H), 2.17–2.27(m, 2H), 3.04(s, 3H), 3.05–3.48(m, 4H), 4.83–4.91(m, 1H), 7.08(d, J=4.8 Hz, 1H), 7.20–7.27(m, 2H), 7.80–7.90(m, 4H), 8.11(s, 1H), 8.70(d, J=4.8 Hz, 1H)

MS m/e(ESI) 462(MH$^+$)

Production Example 90

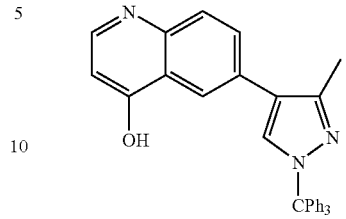

6-(3-Methyl-1-trityl-1H-4-pyrazolyl)-4-quinolinol

While a mixture of 1.79 g 6-bromo-4-quinolinol, 3.83 g 3-methyl-1H-4-pyrazolylboronic acid, 4.8 g sodium carbonate, 30 mL toluene and 60 mL ethanol was stirred in a stream of nitrogen, 280 mg tetrakis (triphenylphosphine) palladium was added thereto, and then this mixture was heated for 6 hours under reflux in a stream of nitrogen. The reaction solution was cooled to room temperature, then ethyl acetate and water were added, and the organic layer was separated. The organic layer was evaporated, and methanol and toluene were added to the residues which were then subjected to azeotropic distillation, ethyl acetate was added thereto, and the resulting crystals were collected. The crystals were dried in hot air at 60° C. for 20 hours, whereby 3.14 g of the title compound was obtained as pale reddish brown crystals.

$^1$H-NMR (CDCl$_3$)

δ: 2.40(s, 3H), 6.26(d, J=7.2 Hz, 1H), 7.20(m, 7H), 7.30(m, 9H), 7.49(m, 2H), 7.59(dd, J=8.8, 2.0 Hz, 1H), 8.30(d, J=2.0 Hz, 1H), 9.95(brs, 1H)

Production Example 91

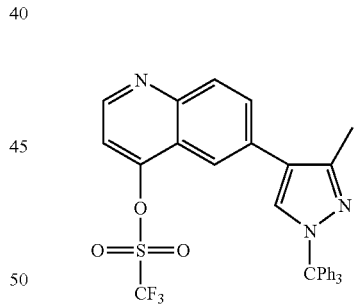

6-(3-Methyl-1-trityl-1H-pyrazolyl)-4-quinolyl
trifluoromethane sulfonate

While 30 mL suspension of 1 g sodium hydride (about 60%) in N,N-dimethylformamide was stirred in a stream of nitrogen at room temperature, 50 ml solution of 3.91 g 6-(3-methyl-1-trityl-1H-4-pyrazolyl)-4-quinolinol obtained in Production Example 90 in N,N-dimethylformamide was added thereto little by little. Then, the reaction solution was stirred at 40° C. for 30 minutes and cooled to room temperature, and 6 g N-phenyltrifluoromethane sulfonimide was added in a solid form and stirred for 1 hour. The reaction solution was cooled, then ethyl acetate, an aqueous saturated solution of sodium bicarbonate and water were added thereto, and the organic layer was separated. The organic layer was washed with water and then with brine and dried over anhydrous magnesium sulfate. The drying agent was filtered off, and after the filtrate was evaporated, the residue was purified by silica gel column chromatography (hexane/ethyl acetate) to give 3.57 g of the title compound as a colorless amorphous.

$^1$H-NMR (CDCl$_3$)

δ: 2.54(s, 3H), 7.26(m, 7H), 7.34(m, 8H), 7.39(d, J=5.2 Hz, 1H), 7.57(s, 1H), 7.82(dd, J=8.8, 2.0 Hz, 1H), 8.02(d, J=2.0 Hz, 1H), 8.13(d, J=8.8 Hz, 1H), 8.89(d, J=5.2 Hz, 1H)

Production Example 92

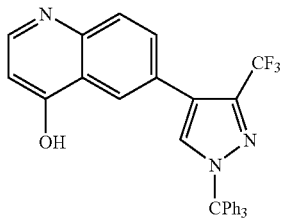

6-(3-Trifluoromethyl-1-trityl-1H-4-pyrazolyl)-4-quinolinol 840 mg of the title compound was obtained as pale yellow crystals from 448 mg 6-bromo-4-quinolinol and 1.01 g 3-trifluoromethyl-1H-4-pyrazolylboronic acid by the same method as in Production Example 90.

$^1$H-NMR (CDCl$_3$)

δ: 6.28(d, J=7.6 Hz, 1H), 7.15(m, 7H), 7.32(m, 8H), 7.44(d, J=8.8 Hz, 1H), 7.53(d, J=0.8 Hz, 1H), 7.62(d, J=7.6 Hz, 1H), 7.67(dd, J=8.8, 2.0 Hz, 1H), 8.29(d, J=2.0 Hz, 1H)

Production Example 93

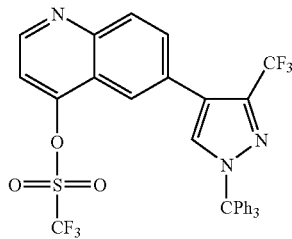

6-(3-Trifluoromethyl-1-trityl-1H-4-pyrazolyl)-4-quinolyl trifluoromethane sulfonate 840 mg 6-(3-trifluoromethyl-1-trityl-1H-4-pyrazolyl)-4-quinolinol obtained in Production Example 94 and 864 mg N-phenyltrifluoromethane sulfonimide were reacted in the same manner as in Production Example 91, to give 525 mg of the title compound as a colorless amorphous.

$^1$H-NMR (CDCl$_3$)

δ: 7.18(m, 7H), 7.36(m, 8H), 7.43(d, J=5.2 Hz, 1H), 7.56(s, 1H), 7.84(dd, J=8.8, 2.0 Hz, 1H), 8.06(d, J=2.0 Hz, 1H), 8.17(d, J=8.8 Hz, 1H), 8.95(d, J=5.2 Hz, 1H)

Production Example 94

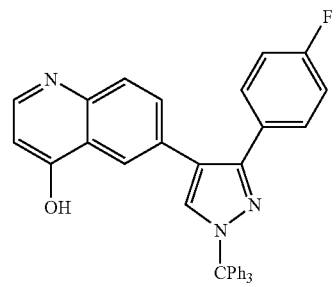

6-[3-(4-Fluorophenyl)-1-trityl-1H-4-pyrazolyl]-4-quinolinol 560 mg 6-bromo-4-quinolinol and 1.68 g 3-(4-fluorophenyl-1-trityl-1H-4-pyrazolylboronic acid were reacted in the same manner as in Production Example 90, to give 1.4 g of the title compound as white crystals.

$^1$H-NMR (CDCl$_3$)

δ: 6.23(d, J=7.2 Hz, 1H), 6.85(t, J=8.8 Hz, 2H), 7.15–7.38 (m, 19H), 7.46(m, 1H), 7.50(s, 1H), 8.27(d, J=1.6 Hz, 1H), 10.65(br, 1H)

Production Example 95

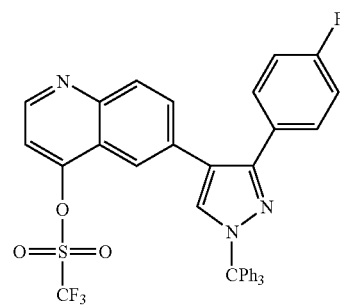

6-[3-(4-Fluorophenyl)-1-trityl-1H-4-pyrazolyl]-4-quinolyl trifluoromethane sulfonate 548 mg 6-[3-(4-fluorophenyl)-1-trityl-1H-4-pyrazolyl]-4-quinolinol obtained in Production Example 94 and 536 mg N-phenyltrifluoromethane sulfonimide were reacted in the same manner as in Production Example 91, to give 539 mg of the title compound as a colorless amorphous.

$^1$H-NMR (CDCl$_3$)

δ: 6.98(m, 2H), 7.28(m, 7H), 7.35(m, 9H), 7.43(m, 2H), 7.53(s, 1H), 7.69(dd, J=8.8, 2.0 Hz, 1H), 7.87(d, J=2.0 Hz, 1H), 8.06(d, J=8.8 Hz, 1H), 8.90(d, J=5.2 Hz, 1H)

Production Example 96

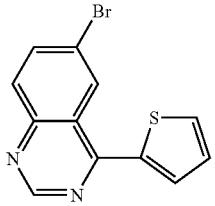

6-Bromo-4-(2-thienyl)quinazoline 0.6 g 6-bromo-4-chloroquinazoline was dissolved in 18 mL toluene, and 0.82 mL tri-n-butyl(2-thienyl)stannane and 0.14 g tetrakis (triphenylphosphine)palladium (0) were added thereto and stirred at 80° C. for 24 hours under nitrogen atmosphere. After the solvent was evaporated, the residue was purified by silica gel chromatography (hexane/ethyl acetate), to give 0.29 g of the title compound as yellow crystals.

$^1$H-NMR (CDCl$_3$)

δ: 7.30(t, J=4.4 Hz, 1H), 7.70(d, J=5.2 Hz, 1H), 7.85(d, J=3.6 Hz, 1H), 7.97–8.00(m, 2H), 8.66(m, 1H), 9.28(s, 1H)

Production Example 97

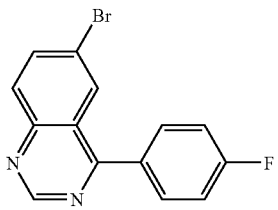

6-Bromo-4-(4-fluorophenyl)quinazoline 0.25 g of the title compound was obtained as colorless crystals from 1.2 g 6-bromo-4-chloroquinazoline and 1.99 mL 4-fluoro-(tri-n-butylstannyl) benzene by the same method as in Example 96.

$^1$H-NMR (CDCl$_3$)

δ: 7.46(t, J=8.6 Hz, 2H), 7.85(d, J=5.4 Hz, 1H), 7.87(d, J=5.4 Hz, 1H), 8.04(d, J=8.4 Hz, 1H), 8.13–8.19(m, 2H), 9.37(s, 1H)

Production Example 98

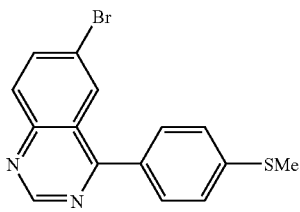

6-Bromo-4-[4-(methylsulfanyl)phenyl]quinazoline 0.83 g 4-(methylthio)phenylboronic acid was dissolved in 10 mL diethylether, and 0.36 mL 1,3-propanediol was added thereto and stirred at room temperature for 1 hour. Formed water was removed by decantation, toluene was added to the reaction solution, and the solvent was evaporated. To the resulting oil were added 20 mL N,N-dimethylformamide, 1.1 g 6-bromo-4-chloroquinazoline, 0.26 g tetrakis(triphenylphosphine) palladium (0) and 1.44 g potassium phosphate, and the mixture was stirred at 70° C. for 5 hours under nitrogen atmosphere. After water was added, the reaction solution was extracted with ethyl acetate, and the organic layer was washed with brine and dried over sodium sulfate. The solvent was evaporated, and the residue was purified by silica gel column chromatography (hexane/ethyl acetate) to give 0.62 g of the title compound as colorless crystals.

$^1$H-NMR (DMSO-d$_6$)

δ: 2.56(s, 3H), 7.49(d, J=8.6 Hz, 2H), 7.76(d, J=8.6 Hz, 2H), 8.03(d, J=8.8 Hz, 1H), 8.17(dd, J=8.8, 2.2 Hz, 1H), 8.20(d, J=2.2 Hz, 1H), 9.36(s, 1H)

Production Example 99

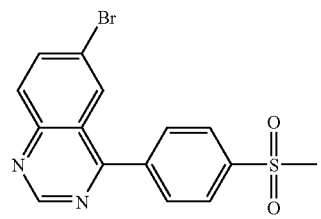

6-Bromo-4-[4-(methylsulfonyl)phenyl] quinazoline 0.51 g of the title compound was obtained as pale skin-colored crystals by the same method as in Production Example 43 from 0.62 g 6-bromo-4-[4-(methylsulfanyl)phenyl]quinazoline obtained in Production Example 98 and 2.3 g oxone.

$^1$H-NMR (DMSO-d$_6$)

δ: 3.33(m, 3H), 8.03–8.23(m, 8H), 9.44(s, 1H)

Production Example 100

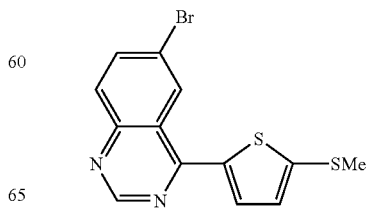

6-Bromo-4-[5-(methylsulfanyl)-2-thienyl]quinazoline 0.89 g of the title compound was obtained as yellow crystals by the same method as in Production Example 96 from 1.0 g 6-bromo-4-chloroquinazoline and 1.8 g tributyl [5-(methylsulfanyl)-2-thienyl]stannane obtained in Production Example 46.

$^1$H-NMR (DMSO-$d_6$)
δ: 2.65(s, 3H), 7.23(d, J=4.0 Hz, 1H), 7.96(d, J=9.2 Hz, 1H), 8.03(d, J=4.0 Hz, 1H), 8.15(dd, J=9.2, 2.0 Hz, 1H), 8.60(br, 1H), 9.17(s, 1H)

Production Example 101

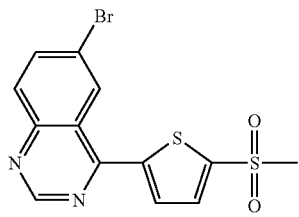

6-Bromo-4-[5-(methylsulfonyl)-2-thienyl]quinazoline

From 0.89 g 6-bromo-4-[5-(methylsulfanyl)-2-thienyl]quinazoline obtained in Production Example 100, 0.81 g of the title compound was obtained as dark orange crystals by oxidizing its methyl sulfanyl group in the same manner as in Production Example 43.

$^1$H-NMR (DMSO-$d_6$)
δ: 3.47(s, 3H), 7.96(d, J=4.2 Hz, 1H), 8.05(d, J=9.0 Hz, 1H), 8.20(d, J=4.2 Hz, 1H), 8.23(dd, J=9.0, 2.0 Hz, 1H), 8.62(d, J=2.0 Hz, 1H), 9.35(s, 1H)

Production Example 102

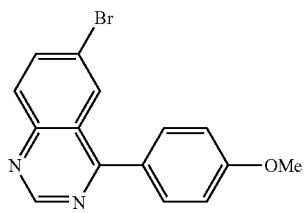

6-Bromo-4-(4-methoxyphenyl)quinazoline 0.17 g of the title compound was obtained as colorless crystals by the same method as in Production Example 98 from 0.23 g 4-methoxyphenylboronic acid and 0.3 g 6-bromo-4-chloroquinazoline.

$^1$H-NMR (DMSO-$d_6$)
δ: 3.86(s, 3H), 7.18(d, J=6.6 Hz, 2H), 7.79(d, J=6.6 Hz, 2H), 8.01(d, J=8.8 Hz, 1H), 8.15(dd, J=8.8, 2.4 Hz, 1H), 8.21(d, J=2.4 Hz, 1H), 9.33(s, 1H)

Production Example 103

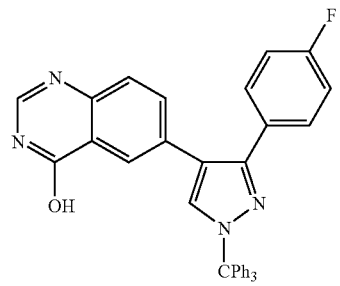

6-[3-(4-Fluorophenyl)-1-trityl-1H-4-pyrazolyl]-4-quinazolinol 44 mg of the title compound was obtained as colorless crystals by the same method as in Production Example 90 from 100 mg 6-bromo-4-quinazolinol and 400 mg 3-(4-fluorophenyl)-1-trityl-1H-4-pyrazolylboronic acid (compound in Production Example 25).

$^1$H-NMR (DMSO-$d_6$)
δ: 7.13–7.21(m, 8H), 7.32–7.42(m, 11H), 7.55–7.60(m, 2H), 7.65(s, 1H), 7.92(dd, J=2.3, 0.4 Hz, 1H), 8.05(s, 1H)

Production Example 104

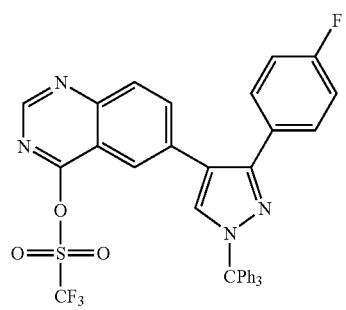

6-[3-(4-Fluorophenyl)-1-trityl-1H-4-pyrazolyl]-4-quinazolinyl trifluoromethane sulfonate 0.39 g of the title compound was obtained as a yellow oil by the same method as in Production Example 91 from 0.73 g 6-[3-(4-fluorophenyl)-1-trityl-1H-4-pyrazolyl]-4-quinazolinol obtained in Production Example 103 and 0.57 g N-phenyltrifluoromethane sulfonimide.

$^1$H-NMR (DMSO-$d_6$)
δ: 7.13–7.45(m, 19H), 7.65–7.80(m, 3H), 8.03(s, 1H), 8.46(s, 1H)

Production Example 105

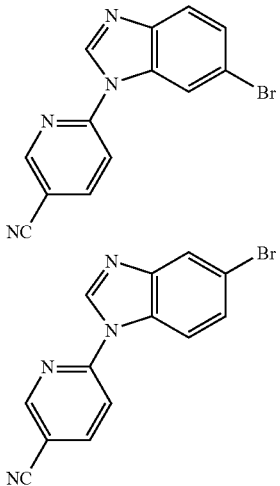

Mixture of 6-(6-bromo-1H-benzo[d]imidazol-1-yl)-
3-pyridyl cyanide and 6-(5-bromo-1H-benzo[d]imi-
dazol-1-yl)-3-pyridyl cyanide in a ratio of 1:1

A mixture of 2 g 5-bromo-1H-benzo[d]imidazole, 1.39 g 6-chloro-3-pyridyl cyanide, 2.81 g potassium carbonate and 20 mL N,N-dimethylformamide was stirred at 100° C. for 4 hours under nitrogen atmosphere. After water was added, the reaction mixture was extracted with ethyl acetate, and the organic layer was washed with water and brine and dried over sodium sulfate. The solvent was evaporated, to give 2.85 g of the title compound as a pale skin-colored solid.

$^1$H-NMR (DMSO-d$_6$)

δ: 7.50(dd, J=8.6, 2.0 Hz, 0.5H), 7.54(dd, J=8.6, 2.0 Hz, 0.5H), 7.72(d, J=8.6 Hz, 0.5H), 7.97(d, J=2.0 Hz, 0.5H), 8.17(dd, J=8.8, 2.6 Hz, 0.5H), 8.18(dd, J=8.8, 2.6 Hz, 0.5H), 8.34(d, J=8.6 Hz, 0.5H), 8.54(dd, J=8.8, 0.8 Hz, 0.5H), 8.55(dd, J=8.8, 0.8 Hz, 0.5H), 8.60(d, J=2.0 Hz, 0.5H), 9.06(dd, J=2.6, 0.8 Hz, 0.5H), 9.09(dd, J=2.6, 0.8 Hz, 0.5H), 9.13(s, 0.5H), 9.14(s, 0.5H)

Production Example 106

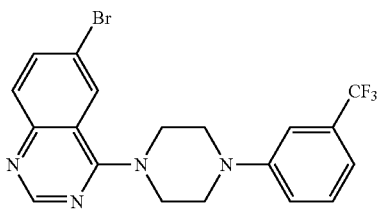

6-Bromo-4-{4-[3-(trifluoromethyl)phenyl]piperazin-
1-yl}quinazoline

A mixture of 300 mg 6-bromo-4-chloroquinazoline, 350 mg 1-[3-(trifluoromethyl)phenyl]piperazine, 0.18 mL triethylamine and 5 mL N,N-dimethylformamide was stirred at room temperature for 4 hours. After the solvent was evaporated, the residue was purified by silica gel column chromatography (hexane/ethyl acetate) to give a yellow oil. This product was crystallized from diethyl ether to give 360 mg of the title compound as pale yellow crystals.

$^1$H-NMR (CDCl$_3$)

δ: 3.45–3.50(m, 4H), 3.93–3.97(m, 4H), 7.11–7.20(m, 3H), 7.41(t, J=8.0 Hz, 1H), 7.81(dd, J=8.8, 0.4 Hz, 1H), 7.84(dd, J=8.8, 2.0 Hz, 1H), 8.08(dd, J=2.0, 0.4 Hz, 1H), 8.78(s, 1H)

Production Example 107

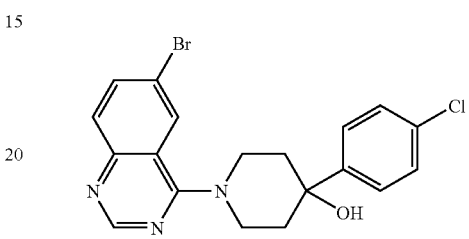

1-(6-Bromo-4-quinazolinyl)-4-(4-chlorophenyl)-4-
piperidinol 500 mg of the title compound was obtained as colorless crystals from 300 mg 6-bromo-4-chloroquinazoline and 417 mg 4-(4-chlorophenyl)-4-piperidinol by the same method as in Production Example 106.

$^1$H-NMR (CDCl$_3$)

δ: 1.88–1.96(m, 2H), 2.23–2.34(m, 2H), 3.68–3.78(m, 2H), 4.24–4.33(m, 2H), 7.36(dt, J=8.8, 2.0 Hz, 2H), 7.48(dt, J=8.8, 2.0 Hz, 2H), 7.77(d, J=8.8 Hz, 1H), 7.81(dd, J=8.8, 2.0 Hz, 1H), 8.05(d, J=2.0 Hz, 1H), 8.72(s, 1H)

Production Example 108

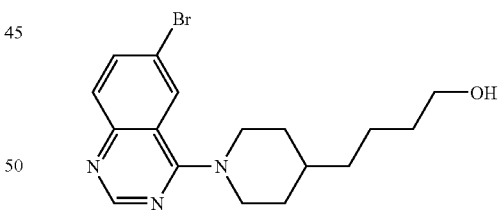

4-[1-(6-Bromo-4-quinazolinyl)-4-piperidyl]-1-butanol 349 mg of the title compound was obtained as a pale brown solid from 315 mg 6-bromo-4-chloroquinazoline and 310 mg 4-(4-piperidyl)-1-butanol by the same method as in Production Example 106.

$^1$H-NMR (CDCl$_3$)

δ: 1.32–1.50(m, 5H), 1.52–1.70(m, 4H), 1.89(dd, J=10.0, 2.0 Hz, 2H), 3.13(dt, J=13.2, 2.0 Hz, 2H), 3.68(t, J=6.8 Hz, 2H), 4.34(d, J=13.2 Hz, 2H), 7.76–7.80(m, 2H), 7.98(d, J=2.0 Hz, 1H), 8.69(s, 1H)

Production Example 109

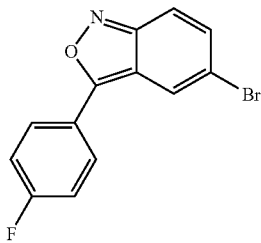

5-Bromo-3-(4-fluorophenyl)benzo[c]isoxazole 13 g 1-bromo-4-nitrobenzene, 7.68 mL 2-(4-fluorophenyl)acetonitrile and 3.9 g sodium hydroxide were stirred in 130 mL ethanol at 40° C. for 24 hours. After the reaction solution was left and cooled, water was added thereto and the reaction solution was extracted with ethylacetate. The organic solvent was washed with brine and dried over sodium sulfate. The solvent was evaporated, and the residue was purified by silica gel column chromatography (hexane/ethyl acetate) and then recrystallized from hexane/ethyl acetate to give 2.9 g of the title compound as pale brown crystals.

$^1$H-NMR(CDCl$_3$)

δ: 7.25–7.31(m, 2H), 7.38(dd, J=9.5, 1.6 Hz, 1H), 7.53 (dd, J=9.5, 0.8 Hz, 1H), 7.96–8.05(m, 3H)

Production Example 110

5-(1H-3-pyrazolyl)-2-thiophene carbonitrile 3.78 g of the title compound (yellow solid) was obtained from 4.2 g of 5-acetylthiophene-2-carbonitrile by the same method as in Production Example 3.

$^1$H-NMR (DMSO-d$_6$)

δ: 6.80(d, J=2.2 Hz, 1H), 7.53(d, J=4.2 Hz, 1H), 7.85(d, J=2.2 Hz, 1H), 7.91(d, J=4.2 Hz, 1H)

Production Example 111

Methyl 5-(1H-3-pyrazolyl)-2-thiophene carboxylate 27.4 g of the title compound (pale skin-colored solid) was obtained from 25.7 g of methyl 5-acetyl-2-thiophene carboxylate by the same method as in Production Example 3.

$^1$H-NMR (CDCl$_3$)

δ: 3.91(s, 3H), 6.60(d, J=2.4 Hz, 1H), 7.32(d, J=3.8 Hz, 1H), 7.66(d, J=2.4 Hz, 1H), 7.76(d, J=3.8 Hz, 1H)

Production Example 112

5-(4-Iodo-1H-3-pyrazolyl)-2-thiophene carbonitrile 5.72 g of the title compound was obtained as pale yellow crystals from 3.78 g of 5-(1H-3-pyrazolyl)-2-thiophene carbonitrile and 5.2 g N-iodosuccinimide by the same method as in Production Example 8.

$^1$H-NMR (DMSO-d$_6$)

δ: 7.77(d, J=4.0 Hz, 1H), 7.96(d, J=4.0 Hz, 1H), 8.09(s, 1H)

Production Example 113

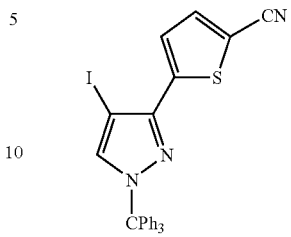

5-(4-Iodo-1-trityl-1H-3-pyrazolyl)-2-thiophene carbonitrile 7.34 g of the title compound was obtained as a colorless solid from 5.72 g of 5-(4-iodo-1H-3-pyrazolyl)-2-thiophene carbonitrile by the same method as in Production Example 15.

$^1$H-NMR (DMSO-d$_6$)

δ: 7.03–7.10(m, 6H), 7.33–7.41(m, 9H), 7.59(s, 1H), 7.74(d, J=4.0 Hz, 1H), 7.94(d, J=4.0 Hz, 1H)

Production Example 114

Methyl 5-(1-trityl-1H-3-pyrazolyl)-2-thiophene carboxylate 44.7 g of the title compound was obtained as pale yellow crystals from 27.4 g of methyl 5-(1H-3-pyrazolyl)-2-thiophene carboxylate by the same method as in Production Example 15.

$^1$H-NMR(CDCl$_3$)

δ: 3.86(s, 3H), 6.48(d, J=2.6 Hz, 1H), 7.16–7.21(m, 6H), 7.27(d, J=4.0 Hz, 1H), 7.28(d, J=2.6 Hz, 1H), 7.28–7.34(m, 9H), 7.71(d, J=4.0 Hz, 1H)

Production Example 115

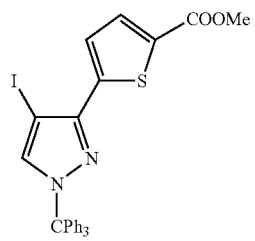

Methyl 5-(4-iodo-1-trityl-1H-3-pyrazolyl)-2-thiophene carboxylate 20 g methyl 5-(1-trityl-1H-3-pyrazolyl)-2-thiophene carboxylate and 10.6 g N-iodosuccinimide were stirred in 200 mL N,N-dimethylformamide at 80° C. for 24 hours. Additional N-iodosuccinimide, 10.6 g, was added thereto and stirred at 80° C. for 24 hours, and then an aqueous solution of sodium thiosulfate and an aqueous solution of sodium bicarbonate were added thereto and stirred for 1 hour, and the formed solid was collected by filtration. The solid was ¹H-NMR (CDCl₃)

δ: 1.32(s, 12H), 3.85(s, 3H), 7.13–7.19(m, 6H), 7.28–7.34 (m, 9H), 7.69(s, 1H), 7.71(d, J=4.0 Hz, 1H), 7.98(d, J=4.0 Hz, 1H)

Production Example 118

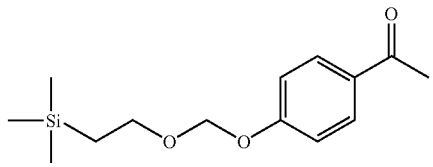

1-[4-(2-Trimethylsilanylethoxymethoxy)phenyl] ethanone

While 30 mL solution of 2.72 g 4-hydroxyacetophenone and 5.2 mL diisopropyl ethylamine in dichloromethane was stirred under ice-cooling in a stream of nitrogen, 4.2 mL 2-(trimethylsilyl)ethoxymethyl chloride was added thereto. Then, the reaction solution was stirred at room temperature for 4 hours. The reaction solution was evaporated, then ethyl acetate and water were added to the residue, the organic layer was separated, washed with brine and dried over anhydrous sodium sulfate. The drying agent was filtered off, the filtrate was concentrated, and the resulting residue was purified by silica gel column chromatography (hexane/ethyl acetate) to give 5.22 g of the title compound as a colorless oil.

¹H-NMR (CDCl₃)

δ: 0.05(s, 9H), 1.95(m, 2H), 2.57(s, 3H), 3.76(m, 2H), 5.28(s, 2H), 7.08(m, 2H), 7.94(m, 2H)

Production Example 119

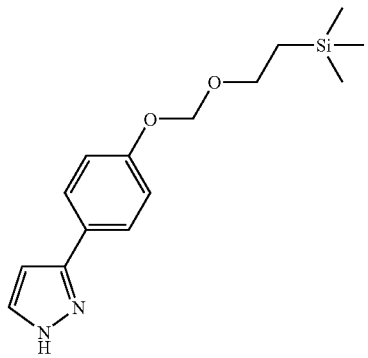

3-[4-(2-Trimethylsilanylethoxymethoxy)phenyl]-1H-pyrazole 5.22 g of the title compound was obtained as pale reddish brown oil from 5.22 g 1-[4-(2-trimethylsilanylethoxymethoxy)-phenyl]ethanone (compound in Production Example 118) by the same method as in Production Example 3.

¹H-NMR (CDCl₃)

δ: 0.05(s, 9H), 0.96(m, 2H), 3.76(m, 2H), 5.24(s, 2H), 6.54(d, J=2.0 Hz, 1H), 7.09(m, 2H), 7.59(d, J=2.0 Hz, 1H), 7.66(m, 2H)

dissolved in dichloromethane and dried over magnesium sulfate, and the solvent was removed, whereby 24.5 g of the title compound was obtained as colorless crystals.

¹H-NMR (CDCl₃)

δ: 3.87(d, J=0.4 Hz, 3H), 7.13–7.19(m, 6H), 7.29(d, J=4.0 Hz, 1H), 7.30–7.36(m, 9H), 7.40(d, J=0.4 Hz, 1H), 7.73(d, J=4.0 Hz, 1H)

Production Example 116

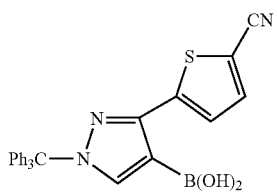

3-(5-Cyano-2-thienyl)-1-trityl-1H-4-pyrazolylboronic acid 1.22 g of the title compound (colorless crystals) was obtained from 3.5 g of 5-(4-iodo-1-trityl-1H-3-pyrazolyl)-2-thiophene carbonitrile in the same manner as in Production Example 32.

¹H-NMR (DMSO-d₆)

δ: 7.03–7.10(m, 6H), 7.30–7.41(m, 10H), 7.85(d, J=4.0 Hz, 1H), 7.89(s, 1H), 8.06(d, J=4.0 Hz, 1H), 8.20(br, 1H)

Production Example 117

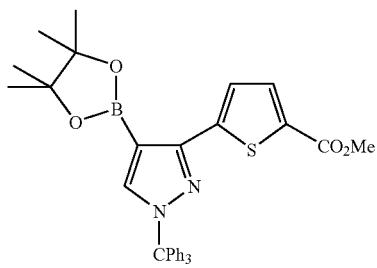

Methyl 5-[4-(4,4,5,5-tetramethyl-1,3,2-dioxaborolan-2-yl)-1-trityl-1H-3-pyrazolyl]-2-thiophen carboxylate 10 g methyl 5-(4-iodo-1-trityl-1H-3-pyrazolyl)-2-thiophen carboxylate, 5.7 g bis(pinacolate) diboron, 0.7 g [1,1'-bis(diphenylphosphino)ferrocene] dichloropalladium (II), 0.7 g dichloromethane adduct (1:1) and 5.1 g potassium acetate were stirred in 250 mL dimethyl sulfoxide at 80° C. for 4 hours. Additional bis(pinacolate) diboron, 3 g, was added thereto and stirred for 24 hours. Water and ethyl acetate were added thereto, the reaction mixture was filtered thorough Celite, and the filtrate was extracted with ethyl acetate. The organic layer was dried over magnesium sulfate and then purified by silica gel column chromatography to give 2.73 g of the title compound (colorless crystals; recrystallization solvent, diethyl ether/hexane).

Production Example 120

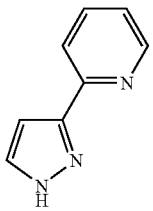

2-(1H-Pyrazol-3-yl)pyridine 6.61 g of the title compound was obtained as yellowish brown crystals from 6.06 g 2-acetyl pyridine by the same method as in Production Example 3.
$^1$H-NMR (CDCl$_3$)
δ: 6.80(d, J=2.0 Hz, 1H), 7.24(m, 1H), 7.66(d, J=2.0 Hz, 1H), 7.74(m, 2H), 8.68(m, 1H)

Production Example 121

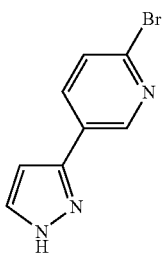

2-Bromo-5-(1H-pyrazol-3-yl)pyridine 3.14 g of the title compound was obtained as yellowish brown crystals from 3.58 g 3-acetyl-6-bromopyridine by the same method as in Production Example 3.
$^1$H-NMR (CDCl$_3$)
δ: 6.66(d, J=2.4 Hz, 1H), 7.52(d, J=8.0 Hz, 1H), 7.66(d, J=2.4 Hz, 1H), 7.96(dd, J=8.0, 2.4 Hz, 1H), 8.79(d, J=2.4 Hz, 1H)

Production Example 122

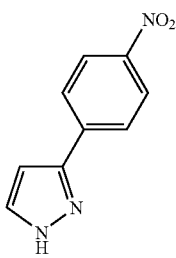

3-(4-Nitrophenyl)-1H-pyrazole 7.55 g of the title compound was obtained as yellowish brown crystals from 8.26 g 4'-nitroacetophenone by the same method as in Production Example 3.
$^1$H-NMR (CDCl$_3$)
δ: 6.75(d, J=2.0 Hz, 1H), 7.68(d, J=2.0 Hz, 1H), 7.97(d, J=8.8 Hz, 2H), 8.28(d, J=8.8 Hz, 2H)

Production Example 123

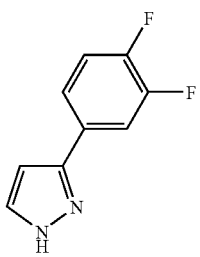

3-(3,4-Difluorophenyl)-1H-pyrazole 5.05 g of the title compound was obtained as pale yellow crystals from 4.68 g 3',4'-difluoroacetophenone by the same method as in Production Example 3.
$^1$H-NMR (CDCl$_3$)
δ: 6.56(d, J=2.0 Hz, 1H), 7.18(m, 1H), 7.48(m, 1H), 7.60(m, 2H)

Production Example 124

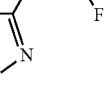

3-(2,4-Difluorophenyl)-1H-pyrazole 5.76 g of the title compound was obtained as pale brown crystals from 4.68 g 2',4'-difluoroacetophenone by the same method as in Production Example 3.
$^1$H-NMR (CDCl$_3$)
δ: 6.69(d, J=2.0 Hz, 1H), 6.93(m, 2H), 7.64(d, J=2.0 Hz, 1H), 7.83(m, 1H)

Production Example 125

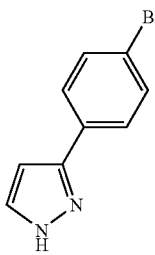

3-(4-Bromophenyl)-1H-pyrazole 16.74-g of the title compound was obtained as pale yellow crystals from 17.28 g 4'-bromoacetophenone by the same method as in Production Example 3.

$^1$H-NMR (CDCl$_3$)

δ: 6.60(d, J=2.0 Hz, 1H), 7.51(d, J=8.8 Hz, 2H), 7.63(m, 3H)

Production Example 126

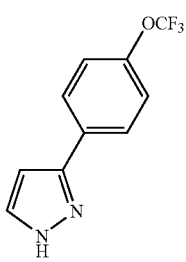

3-p-Tolyl-1H-pyrazole 4.59 g of the title compound was obtained as a reddish brown oil from 4.03 g 4'-methylacetophenone by the same method as in Production Example 3.

$^1$H-NMR (CDCl$_3$)

δ: 2.38(s, 3H), 6.57(d, J=2.4 Hz, 1H), 7.22(d, J=8.8 Hz, 2H), 7.60(d, J=2.4 Hz, 1H), 7.63(d, J=8.8 Hz, 2H)

Production Example 127

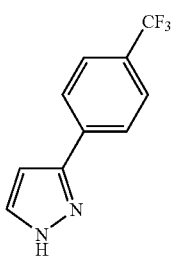

3-(4-Trifluoromethylphenyl)-1H-pyrazole 5.82 g of the title compound was obtained as pale reddish brown crystals from 5.12 g 4'-(trifluoromethyl)acetophenone by the same method as in Production Example 3.

$^1$H-NMR (CDCl$_3$)

δ: 6.69(d, J=2.4 Hz, 1H), 7.66(m, 3H), 7.90(d, J=8.8 Hz, 2H)

Production Example 128

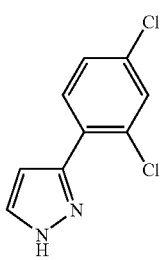

3-(4-Trifluoromethyoxyphenyl)-1H-pyrazole 6.86 g of the title compound was obtained as pale reddish brown crystals from 5.62 g 4'-(trifluoromethoxy)acetophenone by the same method as in Production Example 3.

$^1$H-NMR (CDCl$_3$)

δ: 6.62(d, J=2.4 Hz, 1H), 7.25(m, 2H), 7.62(d, J=2.4 Hz, 2H), 7.79(m, 2H)

Production Example 129

3-(2,4-Dichlorophenyl)-1H-pyrazole 7.1 g of the title compound was obtained as pale brown crystals from 5.67 g 2',4'-dichloroacetophenone by the same method as in Production Example 3.

$^1$H-NMR (CDCl$_3$)

δ: 6.76(d, J=2.4 Hz, 1H), 7.28(dd, J=8.4, 2.0 Hz, 1H), 7.49(d, J=2.4 Hz, 1H), 7.64(m, 2H)

Production Example 130

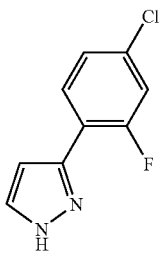

3-(4-Chloro-2-fluorophenyl)-1H-pyrazole 14.39 g of the title compound was obtained as reddish white crystals from 12.51 g 4'-chloro-2'-fluoroacetophenone by the same method as in Production Example 3.

$^1$H-NMR (CDCl$_3$)

δ: 6.73(t, J=2.4 Hz, 1H), 7.20(m, 2H), 7.65(d, J=2.4 Hz, 1H), 7.81 (td, J=8.0, 0.8 Hz, 1H)

Production Example 131

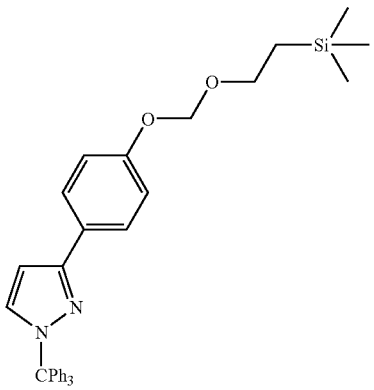

3-[4-(2-Trimethylsilanylethoxymethoxy)phenyl]-1-trityl-1H-pyrazole 9.45 g of the title compound was obtained as a pale brown oil from 5.22 g 3-[4-(2-trimethylsilanylethoxymethoxy)phenyl]-1H-pyrazole (compound in Production Example 119) was obtained by the same method as in Production Example 15.

$^1$H-NMR (CDCl$_3$)

δ: 0.05(s, 9H), 0.96(m, 2H), 3.76(m, 2H), 5.23(s, 2H), 6.47(d, J=2.0 Hz, 1H), 7.03(m, 2H), 7.20(m, 6H), 7.31(m, 10H), 7.73(m, 2H)

Production Example 132

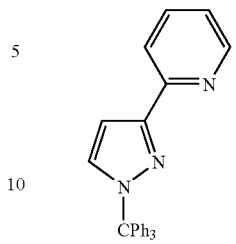

2-(1-Trityl-1H-pyrazol-3-yl)pyridine 12.61 g of the title compound was obtained as pale brown crystals from 6.61 g 2-(1H-pyrazol-3-yl)pyridine (compound in Production Example 120) by the same method as in Production Example 15.

$^1$H-NMR (CDCl$_3$)

δ: 6.93(d, J=2.0 Hz, 1H), 7.13–7.40(m, 17H), 7.64(ddd, J=7.6, 7.6, 1.6 Hz, 1H), 7.96(d, J=7.6 Hz, 1H), 8.59(m, 1H)

Production Example 133

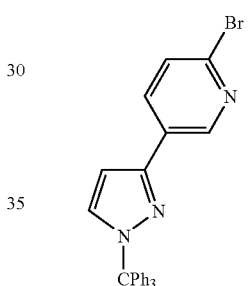

2-Bromo-5-(1-trityl-1H-pyrazol-3-yl)pyridine 6.74 g of the title compound was obtained as pale brown crystals from 3.14 g 5-bromo-2-(1H-pyrazol-3-yl)pyridine (compound in Production Example 121) by the same method as in Production Example 15.

$^1$H-NMR (CDCl$_3$)

δ: 6.57(d, J=2.4 Hz, 1H), 7.19(m, 6H), 7.32(m, 9H), 7.35(d, J=2.4 Hz, 1H), 7.44(dd, J=8.4, 0.8 Hz, 1H), 7.94(dd, J=8.4, 2.4 Hz, 1H), 8.72(dd, J=2.4, 0.8 Hz, 1H)

Production Example 134

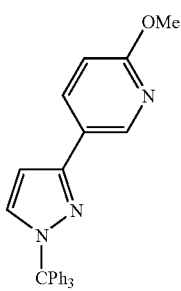

2-Methoxy-5-(1-trityl-1H-pyrazol-3-yl)pyridine

A mixture of 933 mg 2-bromo-5-(1-trityl-1H-pyrazol-3-yl)pyridine (compound in Production Example 133), 2.3 mL sodium methoxide (25% methanol solution), 5 mL methanol and 15 mL N,N-dimethylformamide was stirred overnight at 100° C. Ethyl acetate, tetrahydrofuran and water were added to the reaction solution, and the organic layer was separated, washed twice with water and then with brine and dried over anhydrous sodium sulfate. The drying agent was filtered off, and the filtrate was evaporated. 819 mg crude product of the title compound was obtained as pale brown crystals.
$^1$H-NMR (CDCl$_3$)
δ: 3.93(s, 3H), 6.48(d, J=2.4 Hz, 1H), 6.73(dd, J=8.4, 0.8 Hz, 1H), 7.20(m, 6H), 7.31(m, 10H), 7.98(dd, J=8.4, 2.4 Hz, 1H), 8.55(dd, J=2.4, 0.8 Hz, 1H)

Production Example 135

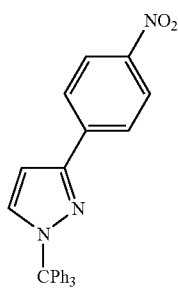

3-(4-Nitrophenyl)-1-trityl-1H-pyrazole 15.52 g of the title compound was obtained as pale brown crystals from 7.55 g 3-(4-nitrophenyl)-1H-pyrazole (compound in Production Example 122) by the same method as in Production Example 15.
$^1$H-NMR (CDCl$_3$)
δ: 6.65(d, J=2.0 Hz, 1H), 7.18(m, 6H), 7.33(m, 9H), 7.38(d, J=2.0 Hz, 1H), 7.92(d, J=8.8 Hz, 2H), 8.20(d, J=8.8 Hz, 2H)

Production Example 136

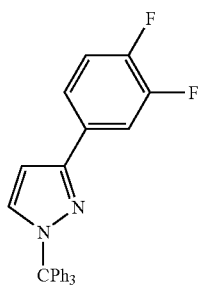

3-(3,4-Difluorophenyl)-1-trityl-1H-pyrazole 2.58 g of the title compound was obtained as pale brown crystals from 5.05 g 3-(3,4-difluorophenyl)-1H-pyrazole (compound in Production Example 123) by the same method as in Production Example 15.
$^1$H-NMR (CDCl$_3$)
δ: 6.47(d, J=2.0 Hz, 1H), 7.11(m, 1H), 7.17(m, 6H), 7.30(m, 10H), 7.46(m, 1H), 7.58(m, 1H)

Production Example 137

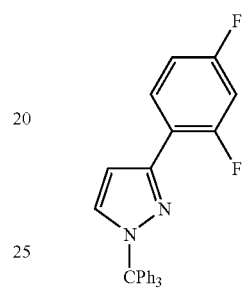

3-(2,4-Difluorophenyl)-1-trityl-1H-pyrazole 7.54 g of the title compound was obtained as pale brown crystals from 5.76 g 3-(2,4-difluorophenyl)-1H-pyrazole (compound in Production Example 124) by the same method as in Production Example 15.
$^1$H-NMR (CDCl$_3$)
δ: 6.65(d, J=2.4 Hz, 1H), 6.84(m, 2H), 7.20(m, 6H), 7.31(m, 10H), 7.91(m, 1H)

Production Example 138

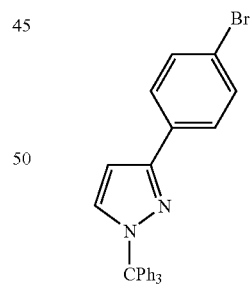

3-(4-Bromophenyl)-1-trityl-1H-pyrazole 32.71 g of the title compound was obtained as pale brown crystals from 6.74 g 3-(4-bromophenyl)-1H-pyrazole (compound in Production Example 125) by the same method as in Production Example 15.
$^1$H-NMR (CDCl$_3$)
δ: 6.51(d, J=2.4 Hz, 1H), 7.20(m, 6H), 7.29(m, 10H), 7.45(d, J=8.8 Hz, 2H), 7.65(d, J=8.8 Hz, 2H)

Production Example 139

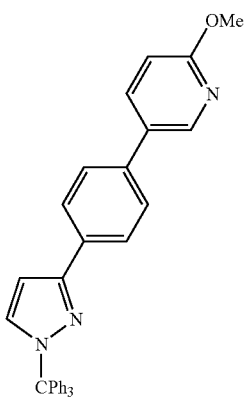

2-Methoxy-5-[4-(1-trityl-1H-pyrazol-3-yl)phenyl]pyridine 1.02 g of the title compound was obtained as a white solid by the same reaction as in Production Example 34 from 2.23 g 3-(4-bromophenyl)-1-trityl-1H-pyrazole (compound in Production Example 138) and 1.1 g 2-methoxy-5-pyridylboronic acid.

$^1$H-NMR (CDCl$_3$)

δ: 3.98(s, 3H), 6.58(d, J=2.4 Hz, 1H), 6.82(dd, J=8.4, 0.8 Hz, 1H), 7.22(m, 6H), 7.32(m, 10H), 7.52(d, J=8.4 Hz, 2H), 7.80(dd, J=8.4, 2.4 Hz, 1H), 7.87(d, J=8.4 Hz, 2H), 8.40(dd, J=2.4, 0.8 Hz, 1H)

Production Example 140

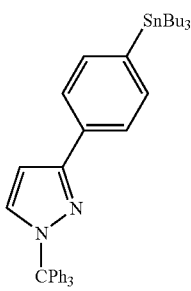

3-(4-Tributylstannylphenyl)-1-trityl-1H-pyrazole 15.2 g crude product of the title compound was obtained as a reddish brown oil from 9.31 g 3-(4-bromophenyl)-1-trityl-1H-pyrazole (compound in Production Example 138) by the same method as in Production Example 46. This product was used in the following reaction without purification.

Production Example 141

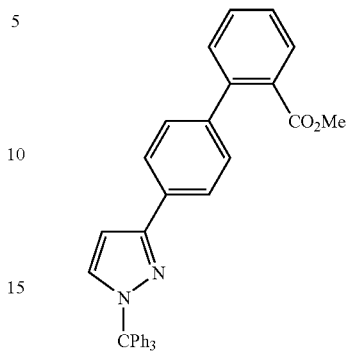

Methyl 4'-(1-trityl-1H-pyrazol-3-yl) biphenyl-2-carboxylate 1.56 g of the title compound was obtained as white crystals from 4.46 g 3-(4-tributylstannylphenyl)-1-trityl-1H-pyrazole (compound in Production Example 140) and 645 mg methyl 2-bromobenzoate in the same manner as in Production Example 57.

$^1$H-NMR (CDCl$_3$)

δ: 3.66(s, 3H), 6.57(d, J=2.4 Hz, 1H), 7.22(m, 6H), 7.31(m, 12H), 7.39(m, 2H), 7.52(ddd, J=7.6, 7.6, 1.2 Hz, 1H), 7.83(m, 3H)

Production Example 142

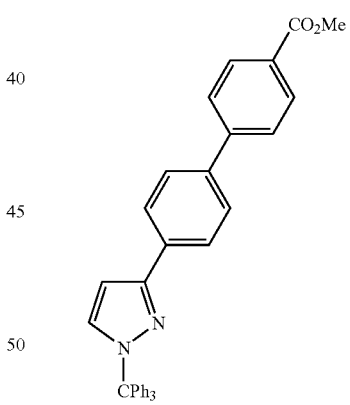

Methyl 4'-(1-trityl-1H-pyrazol-3-yl)biphenyl-4-carboxylate 1.16 g of the title compound was obtained as pale yellow crystals from 3.65 g 3-(4-tributylstannylphenyl)-1-trityl-1H-pyrazole (compound in Production Example 140) and 645 mg methyl 4-bromobenzoate by the same method as in Production Example 57.

$^1$H-NMR (CDCl$_3$)

δ: 3.93(s, 3H), 6.59(d, J=2.4 Hz, 1H), 7.23(m, 6H), 7.32(m, 10H), 7.63(d, J=8.8 Hz, 2H), 7.68(d, J=8.8 Hz, 2H), 7.90(d, J=8.8 Hz, 2H), 8.10(d, J=8.8 Hz, 2H)

Production Example 143

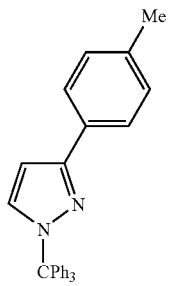

3-p-Tolyl-1-trityl-1H-pyrazole 6.94 g of the title compound was obtained as pale brown crystals from 4.59 g 3-p-tolyl-1H-pyrazole (compound in Production Example 126) by the same method as in Production Example 15.

$^1$H-NMR (CDCl$_3$)

δ: 2.35(s, 3H), 6.50(d, J=2.4 Hz, 1H), 7.16(d, J=8.0 Hz, 2H), 7.21(m, 6H), 7.27(d, J=2.4 Hz, 1H), 7.30(m, 9H), 7.69(d, J=8.0 Hz, 2H)

Production Example 144

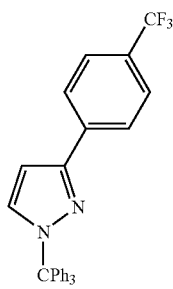

3-(4-Trifluoromethylphenyl)-1-trityl-1H-pyrazole 6.48 g of the title compound was obtained as pale brown crystals from 5.82 g 3-(4-trifluoromethylphenyl)-1H-pyrazole (compound in Production Example 127) by the same method as in Production Example 15.

$^1$H-NMR (CDCl$_3$)

δ: 6.59(d, J=2.4 Hz, 1H), 7.20(m, 6H), 7.32(m, 9H), 7.34(d, J=2.4 Hz, 1H), 7.59(d, J=8.4 Hz, 2H), 7.89(d, J=8.4 Hz, 2H)

Production Example 145

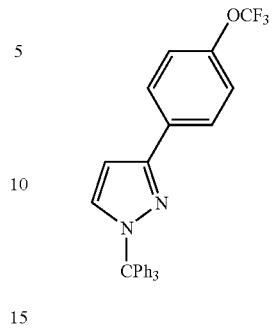

3-(4-Trifluoromethoxyphenyl)-1-trityl-1H-pyrazole 12.44 g of the title compound was obtained as pale yellow crystals from 6.86 g 3-(4-trifluoromethoxyphenyl)-1H-pyrazole (compound in Production Example 128) by the same method as in Production Example 15.

$^1$H-NMR (CDCl$_3$)

δ: 6.52(d, J=2.4 Hz, 1H), 7.19(m, 8H), 7.31(m, 10H), 7.80(d, J=8.8 Hz, 2H)

Production Example 146

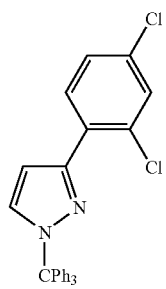

3-(2,4-Dichlorophenyl)-1-trityl-1H-pyrazole 8.39 g of the title compound was obtained as pale brown crystals from 7.10 g 3-(2,4-dichlorophenyl)-1H-pyrazole (compound in Production Example 129) by the same method as in Production Example 15.

$^1$H-NMR (CDCl$_3$)

δ: 6.77(d, J=2.8 Hz, 1H), 7.19(m, 7H), 7.32(m, 9H), 7.34(d, J=2.8 Hz, 1H), 7.42(d, J=2.0 Hz, 1H), 7.69(d, J=8.4 Hz, 1H)

Production Example 147

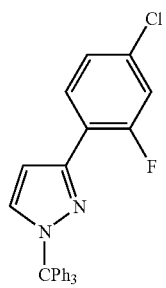

3-(4-Chloro-2-fluorophenyl)-1-trityl-1H-pyrazole 11.08 g of the title compound was obtained as pale brown crystals from 14.39 g 3-(4-chloro-2-fluorophenyl)-1H-pyrazole (compound in Production Example 130) by the same method as in Production Example 15.

$^1$H-NMR (CDCl$_3$)

δ: 6.67(m, 1H), 7.09(ddd, J=8.4, 2.0,0.4 Hz, 1H), 7.13(dd, J=11.2, 2.0 Hz, 1H), 7.18(m, 6H), 7.32(m, 10H), 7.89(t, J=8.4 Hz, 1H)

Production Example 148

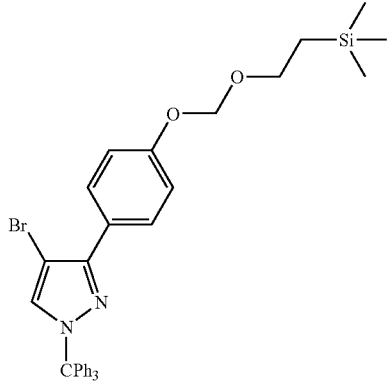

4-Bromo-3-[4-(2-Trimethylsilanylethoxymethoxy) phenyl]-1-trityl-1H-pyrazole 10.05 g of the title compound was obtained as a pale yellow oil from 9.45 g 3-[4-(2-trimethylsilanylethoxymethoxy)phenyl-]-1-trityl-1H-pyrazole (compound in Production Example 131) by the same method as in Production Example 8.

$^1$H-NMR (CDCl$_3$)

δ: 0.05(s, 9H), 0.96(m, 2H), 3.74(m, 2H), 5.24(s, 2H), 7.04(d, J=8.8 Hz, 2H), 7.16(m, 6H), 7.33(m, 10H), 7.80(d, J=8.8 Hz, 2H)

Production Example 149

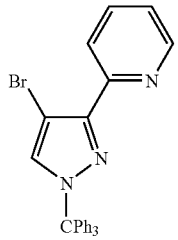

2-(4-Bromo-1-trityl-1H-pyrazol-3-yl)pyridine 13.13 g of the title compound was obtained as pale yellow crystals from 12.61 g 2-(1-trityl-1H-pyrazol-3-yl)pyridine (compound in Production Example 132) by the same method as in Production Example 8.

$^1$H-NMR (CDCl$_3$)

δ: 7.20(m, 7H), 7.30(m, 9H), 7.43(s, 1H), 7.66(ddd, J=7.6, 7.6, 1.6 Hz, 1H), 7.81(d, J=8.0 Hz, 1H), 8.69(m, 1H)

Production Example 150

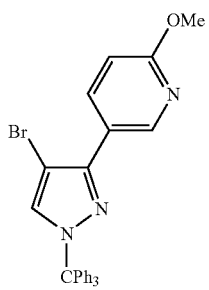

5-(4-Bromo-1-trityl-1H-pyrazol-3-yl)-2-methoxy pyridine 646 mg of the title compound was obtained as pale brown crystals from 817 mg 2-methoxy-5-(1-trityl-1H-pyrazol-3-yl)pyridine (compound in Production Example 134) by the same method as in Production Example 8.

$^1$H-NMR (CDCl$_3$)

δ: 3.96(s, 3H), 6.75(dd, J=8.8, 0.4 Hz, 1H), 7.17(m, 6H), 7.32(m, 9H), 7.39(s, 1H), 8.04(dd, J=8.4, 2.4 Hz, 1H), 8.72(dd, J=2.4, 0.4 Hz, 1H)

Production Example 151

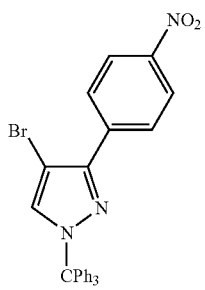

4-Bromo-3-(4-nitrophenyl)-1-trityl-1H-pyrazole 5.42 g of the title compound was obtained as pale brown crystals from 4.66 g 3-(4-nitrophenyl)-1-trityl-1H-pyrazole (compound in Production Example 135) by the same method as in Production Example 8.

$^1$H-NMR (CDCl$_3$)

δ: 7.15(m, 6H), 7.33(m, 9H), 7.45(s, 1H), 8.10(d, J=8.8 Hz, 2H), 8.23(d, J=8.8 Hz, 2H)

Production Example 152

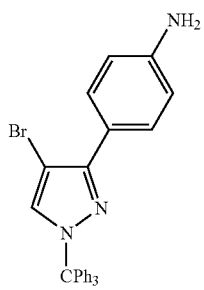

4-(4-Bromo-1-trityl-1H-pyrazol-3-yl)phenylamine

While a mixture of 2.08 g iron powder, 192 mg ammonium chloride, 50 mL ethanol and 18 mL water was stirred at 50° C., 5.42 g 4-bromo-3-(4-nitrophenyl)-1-trityl-1H-pyrazole (compound in Production Example 151) in a solid form was added thereto little by little. Then, this reaction solution was heated for 3 hours under reflux. Insolubles were filtered off, and the filtrate was evaporated. Ethyl acetate and tetrahydrofuran were added to the residue which were then washed with water and brine and dried over anhydrous sodium sulfate. The drying agent was filtered off, and the filtrate was evaporated. 5.32 g crude product of the title compound was obtained as a pale yellowish brown amorphous.

$^1$H-NMR (CDCl$_3$)

δ: 3.70(br, 2H), 6.68(d, J=8.8 Hz, 2H), 7.20(m, 6H), 7.30(m, 1H), 7.70(m, 2H)

Production Example 153

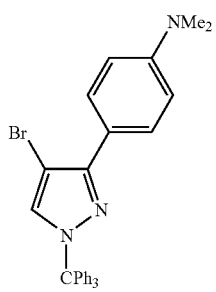

[4-(4-Bromo-1-trityl-1H-pyrazol-3-yl)phenyl]dimethylamine 2.54 g sodium triacetoxy borohydride was added little by little at room temperature to a mixture of 1.44 g 4-(4-bromo-1-trityl-1H-pyrazol-3-yl)phenylamine (compound in Production Example 152), 0.61 mL of 37% formamide and 40 mL 1,2-dichloroethane, and the mixture was stirred for 3 days. Ethyl acetate and an aqueous saturated sodium bicarbonate solution were added to the reaction solution and stirred, then water was added thereto, and the organic layer was separated. The organic layer was washed with brine and dried over anhydrous sodium sulfate. The drying agent was filtered off, and the filtrate was evaporated, and diisopropyl ether was added to the resulting residues which were then triturated, and the crystals were collected by filtration. The crystals were dried over a vacuum pump, to give 1.18 g of the title compound as pale brown crystals.

$^1$H-NMR (CDCl$_3$)

δ: 2.97(s, 6H), 6.63(d, J=8.8 Hz, 2H), 7.18(m, 6H), 7.31(m, 10H), 7.80(d, J=8.8 Hz, 2H)

Production Example 154

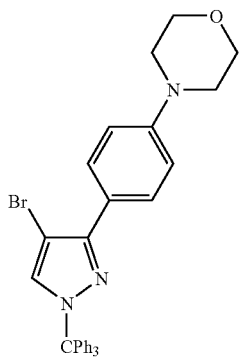

4-[4-(4-Bromo-1-trityl-1H-pyrazol-3-yl)phenyl]morpholine

A mixture of 2.4 g 4-(4-bromo-1-trityl-1H-pyrazol-3-yl)phenylamine (compound in Production Example 152), 0.7 mL 2-bromoethyl ether, 80 mg sodium iodide, 1.52 g potassium carbonate and 50 mL N,N-dimethylformamide was stirred at 80° C. for 3 days. Ethyl acetate and water were added to the reaction solution, then water was added thereto, and the organic layer was separated, washed with an aqueous saturated solution of sodium bicarbonate, water and brine and dried over anhydrous sodium sulfate. The drying agent was filtered off, and the filtrate was evaporated. The resulting residue was purified by NH silica gel column chromatography (ethyl acetate/hexane) to give 1.21 g of the title compound as a pale yellow amorphous.

$^1$H-NMR (CDCl$_3$)

δ: 3.18(t, J=4.8 Hz, 4H), 3.86(t, J=4.8 Hz, 4H), 6.92(d, J=8.8 Hz, 2H), 7.18(m, 6H), 7.31(m, 10H), 7.82(d, J=8.8 Hz, 2H)

Production Example 155

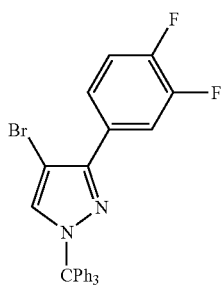

4-Bromo-3-(3,4-difluorophenyl)-1-trityl-1H-pyrazole 2.61 g of the title compound was obtained as white crystals from 2.58 g 3-(3,4-difluorophenyl)-1-trityl-1H-pyrazole (compound in Production Example 136) by the same method as in Production Example 8.

$^1$H-NMR (CDCl$_3$)
δ: 7.15(m, 7H), 7.33(m, 9H), 7.40(s, 1H), 7.65(m, 1H), 7.72(m, 1H)

Production Example 156

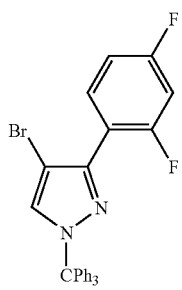

4-Bromo-3-(2,4-difluorophenyl)-1-trityl-1H-pyrazole 8.44 g of the title compound was obtained as pale brown crystals from 7.53 g 3-(2,4-difluorophenyl)-1-trityl-1H-pyrazole (compound in Production Example 137) by the same method as in Production Example 8.

$^1$H-NMR (CDCl$_3$)
δ: 6.88(m, 2H), 7.18(m, 6H), 7.31(m, 9H), 7.40(s, 1H), 7.43(m, 1H)

Production Example 157

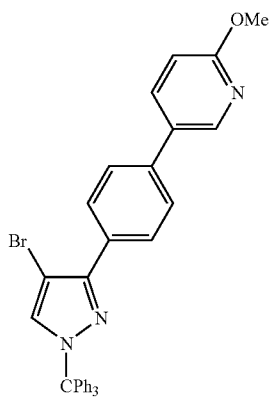

5-[4-(4-Bromo-1-trityl-1H-pyrazol-3-yl)phenyl]-2-methoxypyridine 1.15 g of the title compound was obtained as a colorless amorphous from 1.02 g 2-methoxy-5-[4-(1-trityl-1H-pyrazol-3-yl)phenyl]pyridine (compound in Production Example 139) by the same method as in Production Example 8.

$^1$H-NMR (CDCl$_3$)
δ: 3.98(s, 3H), 6.82(dd, J=8.8, 0.8 Hz, 1H), 7.20(m, 6H), 7.33(m, 9H), 7.40(s, 1H), 7.55(d, J=8.8 Hz, 2H), 7.81(dd, J=8.8, 2.4 Hz, 1H), 7.99(d, J=8.8 Hz, 2H), 8.41(dd, J=2.4, 0.8 Hz, 1H)

Production Example 158

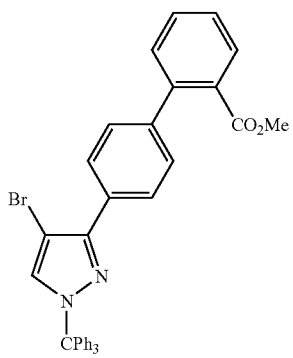

Methyl 4'-(4-bromo-1-trityl-1H-pyrazol-3-yl)biphenyl]-2-carboxylate 1.67 g of the title compound was obtained as a pale yellow amorphous from 1.56 g methyl 4'-(1-trityl-pyrazol-3-yl)biphenyl-2-carboxylate (compound in Production Example 141) by the same method as in Production Example 8.

$^1$H-NMR (CDCl$_3$)
δ: 3.67(s, 3H), 7.21(m, 6H), 7.33(m, 11H), 7.40(m, 3H), 7.53(ddd, J=7.6, 7.6, 1.6 Hz, 1H), 7.82(dd, J=7.6, 1.2 Hz, 1H), 7.96(d, J=8.8 Hz, 2H)

Production Example 159

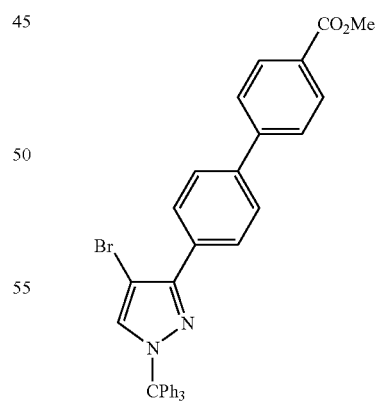

Methyl 4'-(4-bromo-1-trityl-1H-pyrazol-3-yl)biphenyl-4-carboxylate 1.24 g of the title compound was obtained as a colorless amorphous from 1.15 g methyl 4'-(1-tritylpyrazol-3-yl)bi phenyl-4-carboxylate (compound in Production Example 142) by the same method as in Production Example 8.

$^1$H-NMR (CDCl$_3$)

δ: 3.94(s, 3H), 7.20(m, 6H), 7.33(m, 9H), 7.41(s, 1H), 7.65(d, J=8.8 Hz, 2H), 7.68(d, J=8.8 Hz, 2H), 8.02(d, J=8.4 Hz, 2H), 8.10(d, J=8.4 Hz, 2H)

Production Example 160

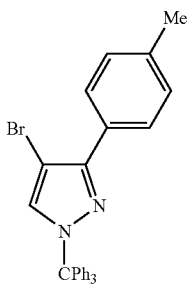

4-Bromo-3-p-tolyl-1-trityl-1H-pyrazole 7.97 g of the title compound was obtained as pale brown crystals from 6.94 g 3-p-tolyl-1-trityl-1H-pyrazole (compound in Production Example 143) by the same method as in Production Example 8.

$^1$H-NMR (CDCl$_3$)

δ: 2.36(s, 3H), 7.19(m, 8H), 7.31(m, 9H), 7.34(s, 1H), 7.77(d, J=8.0 Hz, 2H)

Production Example 161

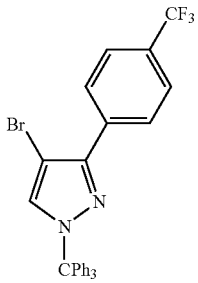

4-Bromo-3-(4-trifluoromethylphenyl)-1-trityl-1H-pyrazole 7.53 g of the title compound was obtained as pale brown crystals from 6.48 g 3-(4-trifluoromethylphenyl)-1-trityl-1H-pyrazole (compound in Production Example 144) by the same method as in Production Example 8.

$^1$H-NMR (CDCl$_3$)

δ: 7.17(m, 6H), 7.31(m, 9H), 7.40(s, 1H), 7.63(d, J=8.4 Hz, 2H), 8.03(d, J=8.4 Hz, 2H)

Production Example 162

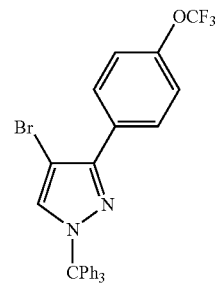

4-Bromo-3-(4-trifluoromethoxyphenyl)-1-trityl-1H-pyrazole 13.9 g of the title compound was obtained as pale brown crystals from 12.44 g 3-(4-trifluoromethoxyphenyl)-1-trityl-1H-pyrazole (compound in Production Example 145) by the same method as in Production Example 8.

$^1$H-NMR (CDCl$_3$)

δ: 7.16(m, 6H), 7.20(d, J=8.8 Hz, 2H), 7.31(m, 9H), 7.40(s, 1H), 7.92(d, J=8.8 Hz, 2H)

Production Example 163

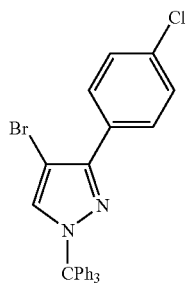

4-Bromo-3-(2,4-dichlorophenyl)-1-trityl-1H-pyrazole 9.41 g of the title compound was obtained as pale brown crystals from 8.39 g 3-(2,4-dichlorophenyl)-1-trityl-1H-pyrazole (compound in Production Example 146) by the same method as in Production Example 8.

$^1$H-NMR (CDCl$_3$)

δ: 7.19(m, 6H), 7.25(dd, J=8.4, 2.0 Hz, 1H), 7.32(m, 10H), 7.43(s, 1H), 7.46(d, J=2.0 Hz, 1H)

Production Example 164

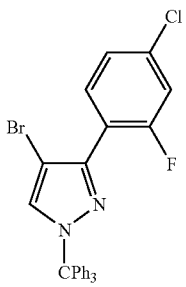

4-Bromo-3-(4-chloro-2-fluorophenyl)-1-trityl-1H-pyrazole 11.93 g of the title compound was obtained as pale brown crystals from 11.08 g 3-(4-chloro-2-fluorophenyl)-1-trityl-1H-pyrazole (compound in Production Example 147) by the same method as in Production Example 8.

$^1$H-NMR (CDCl$_3$)

δ: 7.17(m, 8H), 7.33(m, 9H), 7.41(m, 2H)

Production Example 165

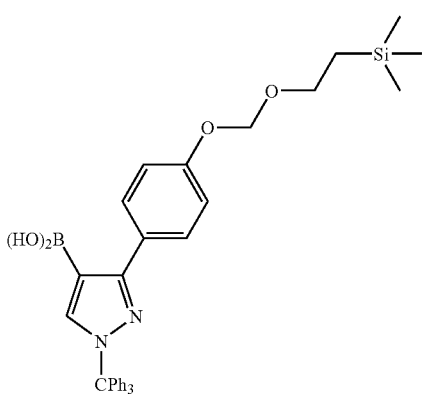

3-[4-(2-Trimethylsilanylethoxymethoxy)phenyl]-1-trityl-1H-4-pyrazolylboronic acid 3.72 g crude product of the title compound was obtained as a colorless amorphous compound from 4.1 g 4-bromo-3-[4-(2-trimethylsilanylethoxymethoxy)phenyl]-1-trityl-1H-pyrazole (compound in Production Example 148) in the same manner as in Production Example 25. This product was used in the subsequent reaction without purification.

Production Example 166

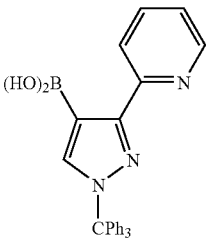

3-(2-Pyridyl)-1-trityl-1H-4-pyrazolylboronic acid 3.75 g crude product of the title compound was obtained as pale brown crystals from 4.66 g 2-(4-bromo-1-trityl-1H-pyrazol-3-yl)pyridine (compound in Production Example 149) in the same manner as in Production Example 25. This product was used in the subsequent reaction without purification.

$^1$H-NMR (CDCl$_3$)

δ: 7.12–7.40(m, 18H), 7.72(ddd, J=7.6, 7.6, 2.0 Hz, 1H), 7.80(s, 1H), 8.16(d, J=8.0 Hz, 1H), 8.49(dt, J=5.2, 0.8 Hz, 1H)

Production Example 167

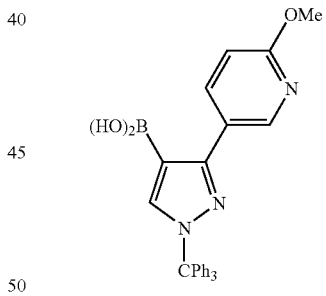

3-(2-Methoxypyridin-5-yl)-1-trityl-1H-4-pyrazolyl-boronic acid 728 mg crude product of the title compound was obtained as pale brown crystals from 644 mg 5-(4-bromo-1-trityl-1H-pyrazol-3-yl)-2-methoxy pyridine (compound in Production Example 150) in the same manner as in Production Example 25. This product was used in the subsequent reaction without purification.

$^1$H-NMR (CDCl$_3$)

δ: 3.94(s, 3H), 4.35(brs, 2H), 6.76(dd, J=8.4, 0.8 Hz, 1H), 7.17(m, 6H), 7.31(m, 9H), 7.68(s, 1H), 7.83(dd, J=8.4, 2.4 Hz, 1H), 8.44(d, J=2.0 Hz, 1H)

Production Example 168

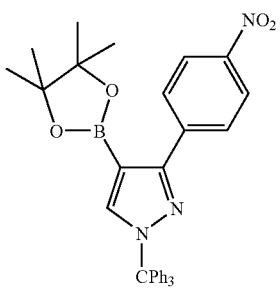

3-(4-Nitrophenyl)-4-(4,4,5,5-tetramethyl-1,3,2-dioxaborolan-2-yl)-1-trityl-1H-pyrazole While a mixture of 1.52 g bis(pinacolate) diboron, 1.47 g potassium acetate, 206 mg [1,1'-bis(diphenylphosphino)ferrocene] dichloropalladium (II) and 20 mL N,N-dimethylformamide was stirred at room temperature in a stream of nitrogen, 20 mL suspension of 2.55 g 4-bromo-3-(4-nitrophenyl)-1-trityl-1H-pyrazole (compound in Production Example 151) in N,N-dimethylformamide was added thereto, and then the mixture was stirred at 85° C. for 5 hours. The reaction solution was partitioned by adding ethyl acetate and water. Insolubles in the organic layer were filtered off, and the filtrate was washed twice with water and then with brine and dried over anhydrous sodium sulfate. The drying agent was filtered off, and the filtrate was evaporated. The resulting residue was purified by silica gel column chromatography (ethyl acetate/hexane) to give 1.05 g of the title compound as white crystals.

$^1$H-NMR (CDCl$_3$)
δ: 1.30(s, 12H), 7.15(m, 6H), 7.33(m, 9H), 7.76(s, 1H), 8.14 (q, J=8.8 Hz, 4H)

Production Example 169

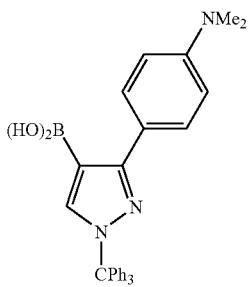

3-(4-Dimethylaminophenyl)-1-trityl-1H-4-pyrazolylboronic acid 1.06 g crude product of the title compound was obtained as pale brown crystals from 1.18 g [4-(4-bromo-1-trityl-1H-pyrazol-3-yl)phenyl]dimethylamine (compound in Production Example 153) in the same manner as in Production Example 25. This product was used in the subsequent reaction without purification.

$^1$H-NMR (CDCl$_3$)
δ: 2.96(s, 3H), 4.35(brs, 1H), 7.13–7.36(m, 15H), 6.75(d, J=8.8 Hz, 2H), 7.44(d, J=8.8 Hz, 2H), 7.66(s, 1H)

Production Example 170

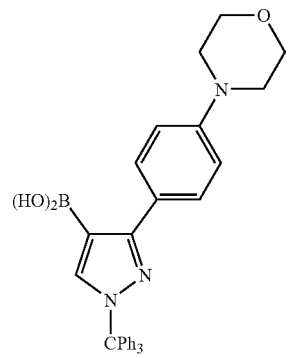

3-[4-(Morpholine-4-yl)phenyl]-1-trityl-1H-4-pyrazolylboronic acid 1.32 g crude product of the title compound was obtained as pale brown crystals from 1.49 g 4-[4-(4-bromo-1-trityl-1H-pyrazol-3-yl)phenyl]morpholine (compound in Production Example 154) in the same manner as in Production Example 25. This product was used in the subsequent reaction without purification.

$^1$H-NMR (CDCl$_3$)
δ: 3.15(t, J=4.8 Hz, 4H), 3.83(t, J=4.8 Hz, 4H), 4.37(s, 2H), 6.93(d, J=8.8 Hz, 2H), 7.12–7.40(m, 15H), 7.49(d, J=8.8 Hz, 2H), 7.67(s, 1H)

Production Example 171

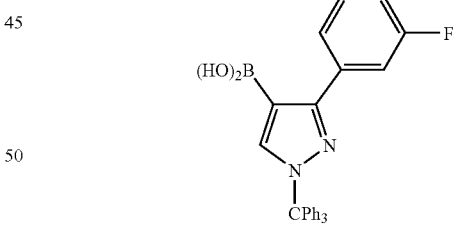

3-(3,4-Difluorophenyl)-1-trityl-1H-4-pyrazolylboronic acid 2.52 g crude product of the title compound was obtained as a pale brown amorphous from 2.61 g 4-bromo-3-(3,4-difluorophenyl)-1-trityl-1H-pyrazole (compound in Production Example 155) in the same manner as in Production Example 25. This product was used in the subsequent reaction without purification.

$^1$H-NMR (CDCl$_3$)
δ: 4.33(s, 1H), 7.12–7.38(m, 16H), 7.47(m, 2H), 7.66(s, 1H), 7.68(s, 1H)

Production Example 172

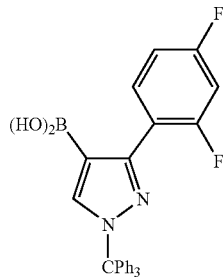

3-(2,4-Difluorophenyl)-1-trityl-1H-4-pyrazolylboronic acid 3.19 g crude product of the title compound was obtained as a pale brown amorphous from 3.5 g 4-bromo-3-(2,4-difluorophenyl)-1-trityl-1H-pyrazole (compound in Production Example 156) in the same manner as in Production Example 25. This product was used in the subsequent reaction without purification.

Production Example 173

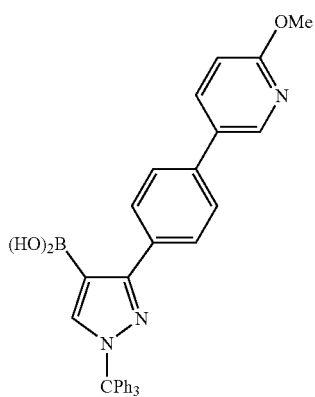

3-[4-(6-Methoxypyridin-3-yl)phenyl]-1-trityl-1H-pyrazolylboronic acid 1.01 g crude product of the title compound was obtained as a pale yellow amorphous from 1.15 g 5-[4-(4-bromo-1-trityl-1H-pyrazol-3-yl)phenyl]-2-methoxypyridine (compound in Production Example 157) in the same manner as in Production Example 25. This product was used in the subsequent reaction without purification.

$^1$H-NMR (CDCl$_3$)

δ: 3.97(s, 3H), 4.55(s, 1H), 6.82(dd, J=8.4, 0.8 Hz, 1H), 7.18–7.36(m, 15H), 7.56(d, J=8.4 Hz, 2H), 7.69(d, J=8.4 Hz, 2H), 7.72(s, 1H), 7.80(dd, J=8.4, 2.4 Hz, 1H), 8.40(dd, J=2.4, 0.8 Hz, 1H)

Production Example 174

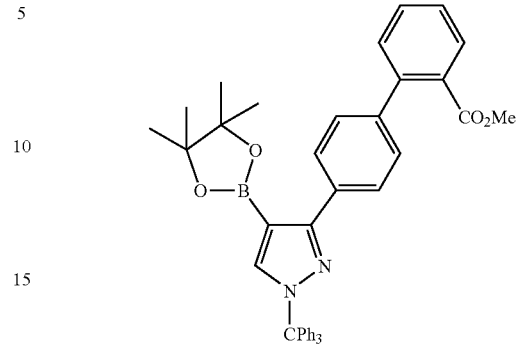

Methyl 4'-[4-(4,4,5,5-tetramethyl-1,3,2-dioxaborolan-2-yl)-1-trityl-1H-pyrazol-3-yl]biphenyl-2-carboxylate 847 mg of the title compound was obtained as a colorless amorphous from 1.66 g methyl 4'-(4-bromo-1-trityl-1H-pyrazol-3-yl)biphenyl]-2-carboxylate (compound in Production Example 158) in the same manner as in Production Example 168.

$^1$H-NMR (CDCl$_3$)

δ: 1.30(s, 12H), 3.65(s, 3H), 7.20(m, 6H), 7.28(d, J=8.8 Hz, 2H), 7.30(m, 9H), 7.39(m, 2H), 7.51(ddd, J=7.6, 7.6, 1.6 Hz, 1H), 7.79(dd, J=7.6, 1.6 Hz, 1H), 7.97(d, J=8.8 Hz, 2H)

Production Example 175

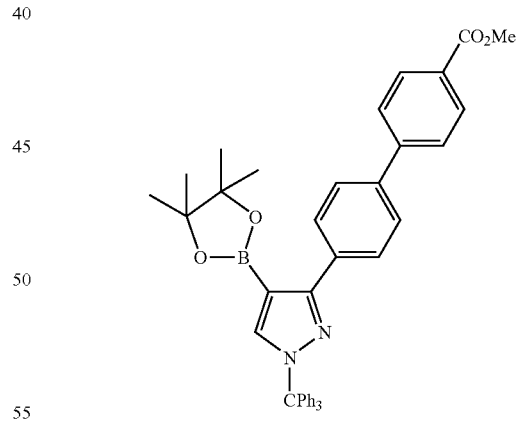

Methyl 4'-[4-(4,4,5,5-tetramethyl-1,3,2-dioxaborolan-2-yl)-1-trityl-1H-pyrazol-3-yl]biphenyl-4-carboxylate 240 mg of the title compound was obtained as a colorless amorphous from 1.24 g methyl 4'-(4-bromo-1-trityl-1H-pyrazol-3-yl)biphenyl-4-carboxylate (compound in Production Example 159) in the same manner as in Production Example 168.

¹H-NMR (CDCl₃)

δ: 1.30(s, 12H), 3.93(s, 3H), 7.20(m, 6H), 7.30(m, 9H), 7.60(d, J=8.8 Hz, 2H), 7.69(d, J=8.8 Hz, 2H), 7.73(s, 1H), 8.04(d, J=8.8 Hz, 2H), 8.09(d, J=8.8 Hz, 2H)

Production Example 176

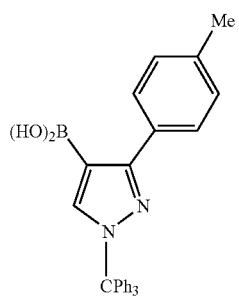

3-p-Tolyl-1-trityl-1H-4-pyrazolylboronic acid 3.23 g crude product of the title compound was obtained as a pale brown amorphous from 3.36 g 4-bromo-3-p-tolyl-1-trityl-1H-pyrazole (compound in Production Example 160) in the same manner as in Production Example 25. This product was used in the subsequent reaction without purification.

¹H-NMR (CDCl₃)

δ: 2.36(s, 3H), 4.36(s, 2H), 7.13–7.36(m, 17H), 7.47(d, J=8.0 Hz, 2H), 7.69(s, 1H)

Production Example 177

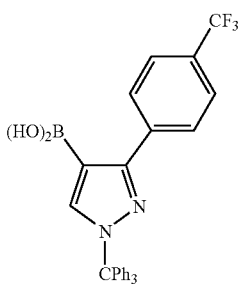

3-(4-Trifluoromethylphenyl)-1-trityl-1H-4-pyrazolylboronic acid 3.6 g crude product of the title compound was obtained as a pale brown amorphous from 3.73 g 4-bromo-3-(4-trifluoromethylphenyl)-1-trityl-1H-pyrazole (compound in Production Example 161) in the same manner as in Production Example 25. This product was used in the subsequent reaction without purification.

¹H-NMR (CDCl₃)

δ: 4.32(s, 1H), 7.13–7.38(m, 15H), 7.65(d, J=8.0 Hz, 2H), 7.71(s, 1H), 7.77(d, J=8.0 Hz, 2H)

Production Example 178

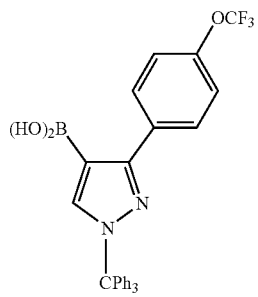

3-(4-Trifluoromethoxylphenyl)-1-trityl-1H-4-pyrazolylboronic acid 3.78 g crude product of the title compound was obtained as a pale brown amorphous from 3.85 g 4-bromo-3-(4-trifluoromethoxylphenyl)-1-trityl-1H-pyrazole (compound in Production Example 162) in the same manner as in Production Example 25. This product was used in the subsequent reaction without purification.

¹H-NMR (CDCl₃)

δ: 4.30(s, 2H), 7.14–7.38(m, 17H), 7.66(d, J=8.4 Hz, 2H), 7.70(s, 1H)

Production Example 179

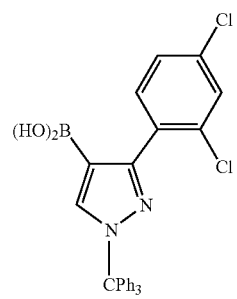

3-(2,4-Dichlorophenyl)-1-trityl-1H-4-pyrazolylboronic acid 3.29 g crude product of the title compound was obtained as a pale brown amorphous from 3.74 g 4-bromo-3-(2,4-dichlorophenyl)-1-trityl-1H-pyrazole (compound in Production Example 163) in the same manner as in Production Example 25. This product was used in the subsequent reaction without purification.

¹H-NMR (CDCl₃)

δ: 4.08(s, 1H), 7.14–7.36(m, 18H), 7.73(s, 1H)

Production Example 180

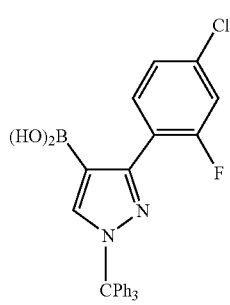

3-(4-Chloro-2-fluorophenyl)-1-trityl-1H-4-pyrazolylboronic acid 3.46 g crude product of the title compound was obtained as a pale brown amorphous from 3.62 g 4-bromo-3-(4-chloro-2-fluorophenyl)-1-trityl-1H-pyrazole (compound in Production Example 164) in the same-manner as in Production Example 25. This product was used in the subsequent reaction without purification.

$^1$H-NMR (CDCl$_3$)

δ: 4.24(s, 1H), 7.14–7.38(m, 18H), 7.42(d, J=8.4 Hz, 1H), 7.69(s, 1H)

Production Example 181

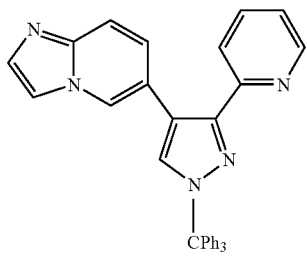

6-[3-(Pyridin-2-yl)-1-trityl-1H-pyrazol-4-yl]imidazo[1,2-a]pyridine 233 mg of the title compound was obtained as a colorless amorphous from 79 mg of 6-bromoimidazo[1,2-a]pyridine and 345 mg of 3-(2-pyridyl)-1-trityl-1H-4-pyrazolylboronic acid (compound in Production Example 166) by the same reaction as in Production Example 34.

$^1$H-NMR (CDCl$_3$)

δ: 7.12(dd, J=9.6, 1.6 Hz, 1H), 7.18(m, 2H), 7.22–7.38(m, 15H), 7.47(s, 1H), 7.50(s, 1H), 7.57(d, J=1.6 Hz, 1H), 7.66(ddd, J=7.6, 7.6, 1.6 Hz, 1H), 7.78(m, 1H), 8.36(d, J=1.6 Hz, 1H), 8.46(m, 1H)

Production Example 182

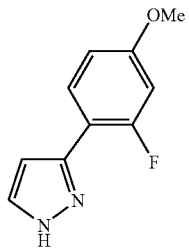

3-(2-Fluoro-4-methoxyphenyl)-1H-pyrazole 3.69 g of the title compound (yellow oil) was obtained from 5.08 g of 2'-fluoro-4'-methoxyacetophenone by the same method as in Production Example 3.

$^1$H-NMR (CDCl$_3$)

δ: 3.84(s, 3H), 6.63(dd, J=2.0, 2.0 Hz, 1H), 6.72(dd, J=13.2, 2.4 Hz, 1H), 6.78(dd, J=8.8, 2.4 Hz, 1H), 7.63(d, J=2.0 Hz, 1H), 7.70(dd, J=8.8, 8.8 Hz, 1H)

Production Example 183

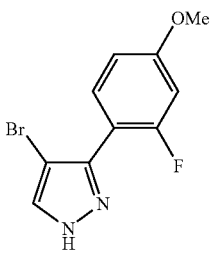

4-Bromo-3-(2-fluoro-4-methoxyphenyl)-1H-pyrazole 4.62 g of the title compound (colorless crystals) was obtained from 3.69 g of 3-(2-fluoro-4-methoxyphenyl)-1H-pyrazole in the same manner as in Production Example 8.

$^1$H-NMR (CDCl$_3$)

δ: 3.89(s, 3H), 6.74(dd, J=13.2, 2.4 Hz, 1H), 6.81(ddd, J=8.8, 2.4, 0.4 Hz, 1H), 7.63(s, 1H), 7.79(dd, J=8.8, 8.8 Hz, 1H)

Production Example 184

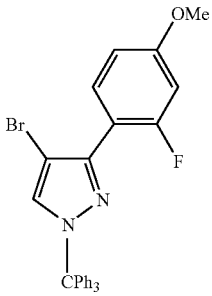

4-Bromo-3-(2-fluoro-4-methoxyphenyl)-1-trityl-1H-pyrazole 7.72 g of the title compound (colorless solid) was obtained from 4.62 g of 4-bromo-3-(2-fluoro-4-methoxyphenyl)-1H-pyrazole by the same method as in Production Example 15.

$^1$H-NMR (CDCl$_3$)

δ: 3.81(s, 3H), 6.65–6.73(m, 2H), 7.15–7.38(m, 16H), 7.39(s, 1H)

Production Example 185

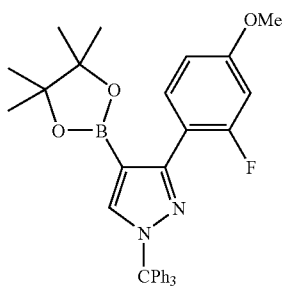

3-(2-Fluoro-4-methoxyphenyl)-4-(4,4,5,5-tetramethyl-[1,3,2]dioxaborolan-2-yl)-1-trityl-1H-pyrazole A solution of 1.0 g 4-bromo-3-(2-fluoro-4-methoxyphenyl)-1-trityl-1H-pyrazole obtained in Production Example 184, 0.58 g potassium acetate, 0.65 g bis(pinacolate)diboron, and 80 mg 1,1'-[bis(diphenylphosphino)ferrocene]dichloropalladium (II) in 9 ml dimethyl sulfoxide was heated at 80° C. for 5 hours under nitrogen atmosphere. Water and ethyl acetate were added thereto, the reaction mixture was filtered through Celite, and the organic layer was washed with water and brine. The reaction solution was dried over anhydrous sodium sulfate, the solvent was removed, and the resulting residue was purified by silica gel column chromatography (hexane/ethyl acetate) to give 227 mg of the title compound (colorless crystals).

$^1$H-NMR (CDCl$_3$)

δ: 1.24(s, 6H), 1.26(s, 6H), 3.80(s, 3H), 6.61(dd, J=12.0, 2.4 Hz, 1H), 6.65(dd, J=7.6, 2.4 Hz, 1H), 7.15–7.37(m, 15H), 7.41(dd, J=8.0, 8.0 Hz, 1H), 7.65(s, 1H)

Production Example 186

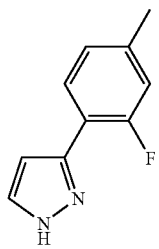

3-(2-Fluoro-4-methylphenyl)-1H-pyrazole 54 mL solution of 5.0 g 1-bromo-2-fluoro-4-methylbenzene, 10 g tributyl(1-ethoxyvinyl)tin and 1.53 g tetrakis (triphenylphosphine) palladium in toluene was heated at 120° C. for 2 hours. After cooling to room temperature, the reaction mixture was diluted with ethyl acetate, 10% aqueous potassium fluoride solution was added thereto and stirred for 30 minutes, and formed insolubles were filtered off through Celite. The organic layer was washed with water, then hydrolyzed by vigorously stirring it together with 5 N aqueous hydrochloric acid, and the organic layer was further washed with water and brine. The solution was dried over anhydrous sodium sulfate, then the solvent was removed, and the resulting residue was purified by silica gel column chromatography (hexane/ethyl acetate) to give 4.61 g of 2'-fluoro-4'-methylacetophenone (yellow oil) as a crude product. From 4.61 g crude 2'-fluoro-4'-methylacetophenone, 4.1 g of the title compound (yellow oil) was obtained by the same method as in Production Example 3.

$^1$H-NMR (CDCl$_3$)

δ: 2.32(d, J=1.2 Hz, 3H), 6.56(d, J=2.4 Hz, 1H), 7.04(dd, J=8.8, 8.8 Hz, 1H), 7.39–7.45(m, 1H), 7.50–7.57(m, 1H), 7.61(d, J=2.4 Hz, 1H)

Production Example 187

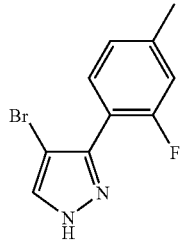

4-Bromo-3-(2-fluoro-4-methylphenyl)-1H-pyrazole 5.0 g of the title compound (yellow oil) was obtained from 4.1 g of 3-(2-fluoro-4-methylphenyl)-1H-pyrazole in the same manner as in Production Example 8.

$^1$H-NMR (CDCl$_3$)

δ: 2.33(s, 3H), 7.08(dd, J=8.8, 8.8 Hz, 1H), 7.53–7.61(m, 2H), 7.62(s, 1H)

Production Example 188

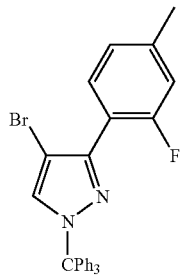

4-Bromo-3-(2-fluoro-4-methylphenyl)-1-trityl-1H-pyrazole 5.53 g of the title compound (colorless solid) was obtained from 5.0 g of 4-bromo-3-(2-fluoro-4-methylphenyl)-1H-pyrazole in the same manner as in Production Example 15.

$^1$H-NMR (CDCl$_3$)

δ: 2.28(s, 3H), 7.00(dd, J=8.8, 8.8 Hz, 1H), 7.14–7.40(m, 17H), 7.64–7.69(m, 1H)

Production Example 189

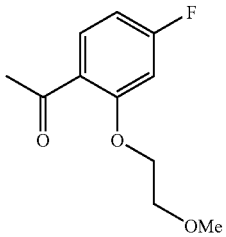

4'-Fluoro-2'-(2-methoxyethoxy)acetophenone

A solution of 1.75 g 2-methoxy ethanol in tetrahydrofuran (23 mL) was added dropwise to a suspension of 0.84 g of 60% sodium hydride in tetrahydrofuran (21 mL), and subsequently a solution of 3.0 g 2',4'-difluoroacetophenone in tetrahydrofuran (19 mL) was added dropwise thereto. The temperature of the mixture was increased to room temperature, then the mixture was stirred for 24 hours, water was carefully added thereto, and the reaction mixture was extracted with ethyl acetate. The organic layer was washed with brine and then dried over anhydrous sodium sulfate, the solvent was removed, and the resulting residue was purified by silica gel column chromatography (hexane/ethyl acetate) to give 2.84 g of the title compound (yellow oil).

$^1$H-NMR (CDCl$_3$)

δ: 2.63(s, 3H), 3.44(s, 3H), 3.78–3.83(m, 2H), 4.16–4.21(m, 2H), 6.61–6.74(m, 2H), 7.83(dd, J=8.8, 7.2 Hz, 1H)

Production Example 190

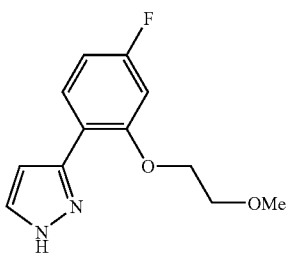

3-[4-Fluoro-2-(2-methoxyethoxy)phenyl]-1H-pyrazole 2.81 g of the title compound (yellow oil) was obtained from 2.84 g of 4'-fluoro-2'-(2-methoxyethoxy)acetophenone by the same method as in Production Example 3.

$^1$H-NMR (CDCl$_3$)

δ: 3.58(s, 3H), 3.82–3.91(m, 2H), 4.24–4.32(m, 2H), 6.57(d, J=2.0 Hz, 1H), 6.70–6.82(m, 2H), 7.59(d, J=2.0 Hz, 1H), 7.62(dd, J=8.8, 6.8 Hz, 1H)

Production Example 191

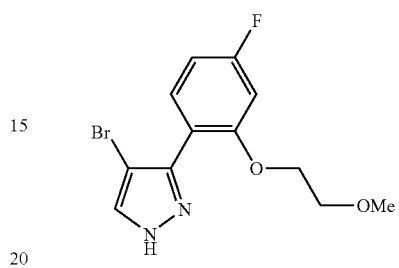

4-Bromo-3-[4-fluoro-2-(2-methoxyethoxy)phenyl]-1H-pyrazole 3.97 g of the title compound (yellow oil) was obtained from 2.81 g of 3-[4-fluoro-2-(2-methoxyethoxy)phenyl]-1H-pyrazole in the same manner as in Production Example 8.

$^1$H-NMR (CDCl$_3$)

δ: 3.57(s, 3H), 3.75–3.90(m, 2H), 4.20–4.35(m, 2H), 6.74(dd, J=10.4, 2.4 Hz, 1H), 6.82(dd, J=6.8, 2.4 Hz, 1H), 7.58(s, 1H), 8.05(dd, J=8.8, 6.8 Hz, 1H)

Production Example 192

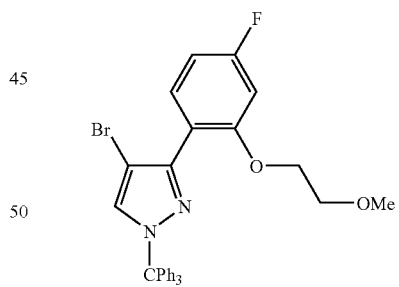

4-Bromo-3-[4-fluoro-2-(2-methoxyethoxy)phenyl]-1-trityl-1H-pyrazole 4.64 g of the title compound (colorless solid) was obtained from 3.97 g of 4-bromo-3-[4-fluoro-2-(2-methoxyethoxy)phenyl]-1H-pyrazole by the same method as in Production Example 15.

$^1$H-NMR (CDCl$_3$)

δ: 3.33(s, 3H), 3.67(t, J=5.2 Hz, 2H), 4.08(t, J=5.2 Hz, 2H), 6.54–6.72(m, 2H), 7.15–7.36(m, 16H), 7.37(s, 1H)

Production Example 193

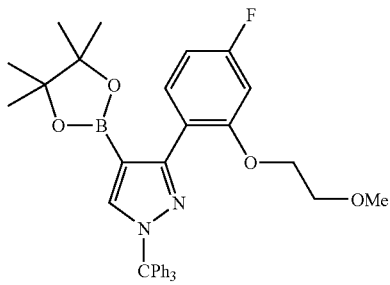

3-[4-Fluoro-2-(2-methoxyethoxy)phenyl]-4-(4,4,5,5-tetramethyl-[1,3,2]dioxaborolan-2-yl)-1-trityl-1H-pyrazole 400 mg of the title compound was obtained from 1.5 g of 4-bromo-3-[4-fluoro-2-(2-methoxyethoxy)phenyl]-1-trityl-1H-pyrazole in the same manner as in Production Example 185.

$^1$H-NMR (CDCl$_3$)

δ: 1.18(s, 6H), 1.26(s, 6H), 3.28(s, 3H), 3.55(t, J=5.2 Hz, 2H), 3.96(t, J=5.2 Hz, 2H), 6.60–6.70(m, 2H), 7.15–7.38(m, 16H), 7.66(s, 1H)

Production Example 194

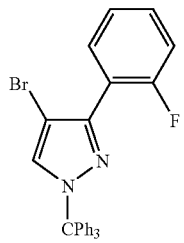

3-(2-Fluorophenyl)-1H-pyrazole 4.17 g of the title compound (yellow oil) was obtained from 3.25 g of 2'-fluoroacetophenone by the same method as in Production Example 3.

$^1$H-NMR (CDCl$_3$)

δ: 6.74(dd, J=2.0, 2.0 Hz, 1H), 7.17(ddd, J=11.6, 8.0, 1.2 Hz, 1H), 7.21(ddd, J=7.6, 7.6, 1.2 Hz, 1H), 7.28–7.34(m, 1H), 7.66(d, J=2.0 Hz, 1H), 7.82(ddd, J=7.6, 7.6, 1.6 Hz, 1H)

Production Example 195

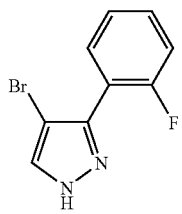

4-Bromo-3-(2-fluorophenyl)-1H-pyrazole 6.04 g of the title compound (yellow oil) was obtained from 4.17 g of 3-(2-fluorophenyl)-1H-pyrazole in the same manner as in Production Example 8.

$^1$H-NMR (CDCl$_3$)

δ: 7.21(ddd, J=11.2, 8.0, 1.2 Hz, 1H), 7.27(ddd, J=8.0, 8.0, 1.2 Hz, 1H), 7.39–7.45(m, 1H), 7.67(s, 1H), 7.89(ddd, J=8.0, 8.0, 1.6 Hz, 1H)

Production Example 196

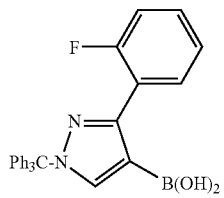

4-Bromo-3-(2-fluorophenyl)-1-trityl-1H-pyrazole 7.41 g of the title compound (slightly yellow solid) was obtained from 6.04 g of 4-bromo-3-(2-fluorophenyl)-1H-pyrazole in the same manner as in Production Example 15.

$^1$H-NMR (CDCl$_3$)

δ: 7.09–7.40(m, 18H), 7.42(s, 1H), 7.47(ddd, J=7.6, 7.6, 1.6 Hz, 1H)

Production Example 197

3-(2-Fluorophenyl)-1-trityl-1H-4-pyrazolylboronic acid 0.79 g of the title compound (colorless amorphous) was obtained from 2.0 g of 4-bromo-3-(2-fluorophenyl)-1-trityl-1H-pyrazole in the same manner as in Production Example 25.

$^1$H-NMR (CDCl$_3$)

δ: 4.23(d, J=1.2 Hz, 1H), 7.11–7.41(m, 18H), 7.46(ddd, J=7.6, 7.6, 1.6 Hz, 1H), 7.71(s, 1H)

Production Example 198

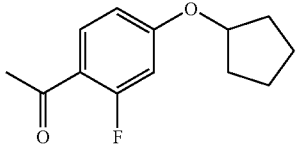

4'-Cyclopentyloxy-2'-fluoroacetophenone

A suspension of 2.5 g 4'-hydroxy-2'-fluoroacetophenone, 2.0 mL cyclopentane bromide and 7.9 g cesium carbonate in acetonitrile (35 mL) was heated for 1 hour under reflux and then heated at 70° C. for 15 hours. Further, 1.0 mL cyclopentane bromide was added thereto, and the mixture was heated for 3 hours under reflux. The reaction mixture was diluted with ethyl acetate, washed with water and brine and dried over anhydrous sodium sulfate, and the solvent was removed, whereby 3.65 g of the title compound in a crude state (yellow oil) was obtained.

$^1$H-NMR (CDCl$_3$)

δ: 1.57–2.00(m, 8H), 2.58(d, J=5.2 Hz, 3H), 4.75–4.83(m, 1H), 6.57(dd, J=13.2, 2.4 Hz, 1H), 6.70(dd, J=8.8, 2.4 Hz, 1H), 7.85(dd, J=8.8, 8.8 Hz, 1H)

Production Example 199

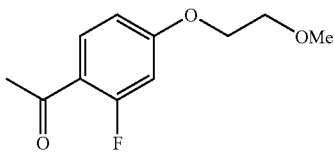

2'-Fluoro-4'-(2-methoxyethoxy)acetophenone 3.27 g of the title compound (yellow oil) was obtained from 2.52 g of 4'-hydroxy-2'-fluoroacetophenone and 1.9 mL 2-bromoethyl methyl ether in the same manner as in Production Example 198.

$^1$H-NMR (CDCl$_3$)

δ: 2.59(d, J=5.2 Hz, 3H), 3.45(s, 3H), 3.74–3.79(m, 2H), 4.13–4.19(m, 2H), 6.55(dd, J=13.2, 2.4 Hz, 1H), 6.76(dd, J=8.8, 2.4 Hz, 1H), 7.87(dd, J=8.8, 8.8 Hz, 1H)

Production Example 200

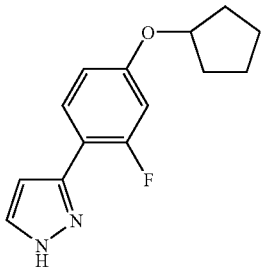

3-(4-Cyclopentyloxy-2-fluorophenyl)-1H-pyrazole 3.47 g of the title compound (yellow oil) was obtained from 3.65 g of 4'-cyclopentyloxy-2'-fluoroacetophenone by the same method as in Production Example 3.

$^1$H-NMR (CDCl$_3$)

δ: 1.58–1.99(m, 8H), 4.72–4.82(m, 1H), 6.61(dd, J=2.0, 2.0 Hz, 1H), 6.68(dd, J=13.6, 2.4 Hz, 1H), 6.73(dd, J=8.8, 2.4 Hz, 1H), 7.59–7.71(m, 2H)

Production Example 201

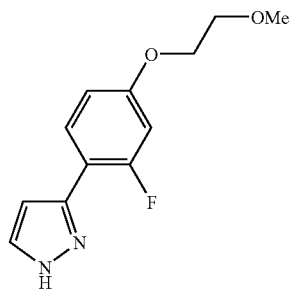

3-[2-Fluoro-4-(2-methoxyethoxy)phenyl]-1H-pyrazole 3.48 g of the title compound (yellow oil) was obtained from 3.27 g of 2'-fluoro-4'-(2-methoxyethoxy)acetophenone by the same method as in Production Example 3.

$^1$H-NMR (CDCl$_3$)

δ: 3.46(s, 3H), 3.74–3.79(m, 2H), 4.12–4.17(m, 2H), 6.63(dd, J=2.0, 2.0 Hz, 1H), 6.74(dd, J=13.6, 2.4 Hz, 1H), 6.80(dd, J=8.8, 2.4 Hz, 1H), 7.62(d, J=2.0 Hz, 1H), 7.69(dd, J=8.8, 8.8 Hz, 1H)

Production Example 202

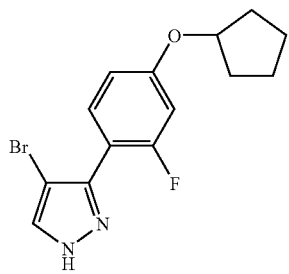

4-Bromo-3-(4-cyclopentyloxy-2-fluorophenyl)-1H-pyrazole 5.42 g of the title compound in a crude state (yellow oil) was obtained from 3.47 g of 3-(4-cyclopentyloxy-2-fluorophenyl)-1H-pyrazole in the same manner as in Production Example 8.

$^1$H-NMR (CDCl$_3$)

δ: 1.50–2.02(m, 8H), 4.74–4.85(m, 1H), 6.70(dd, J=13.2, 2.4 Hz, 1H), 6.77(dd, J=8.8, 2.4 Hz, 1H), 7.62(s, 1H), 7.77(dd, J=8.8, 8.8 Hz, 1H)

Production Example 203

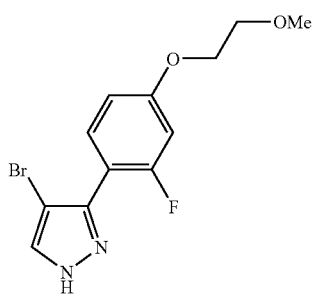

4-Bromo-3-[2-fluoro-4-(2-methoxyethoxy)phenyl]-1H-pyrazole 5.01 g of the title compound in a crude state (yellow oil) was obtained from 3.48 g of 3-[2-fluoro-4-(2-methoxyethoxy)phenyl]-1H-pyrazole in the same manner as in Production Example 8.

$^1$H-NMR (CDCl$_3$)

δ: 3.46(s, 3H), 3.74–3.80(m, 2H), 4.13–4.18(m, 2H), 6.78(dd, J=13.2, 2.4 Hz, 1H), 6.84(dd, J=8.8, 2.4 Hz, 1H), 7.63(s, 1H), 7.80(dd, J=8.8, 8.8 Hz, 1H)

Production Example 204

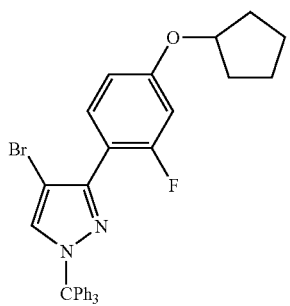

4-Bromo-3-(4-cyclopentyloxy-2-fluorophenyl)-1-trityl-1H-pyrazole 5.52 g of the title compound (slightly yellow solid) was obtained from 5.42 g of 4-bromo-3-(4-cyclopentyloxy-2-fluorophenyl]-1H-pyrazole by the same method as in Production Example 15.

$^1$H-NMR (CDCl$_3$)

δ: 1.45–1.98(m, 8H), 4.70–4.78(m, 1H), 6.61–6.69(m, 2H), 7.14–7.37(m, 16H), 7.38(s, 1H)

Production Example 205

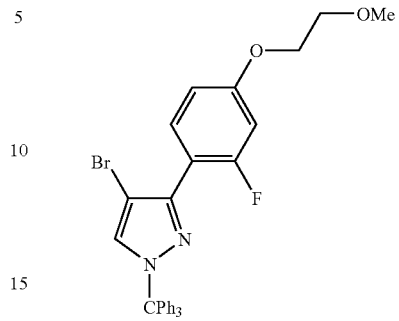

4-Bromo-3-[2-fluoro-4-(2-methoxyethoxy)phenyl]-1-trityl-1H-pyrazole 3.79 g of the title compound (colorless amorphous) was obtained from 5.01 g of 4-bromo-3-[2-fluoro-4-(2-methoxyethoxy)phenyl]-1H-pyrazole by the same method as in Production Example 15.

$^1$H-NMR (CDCl$_3$)

δ: 3.45(s, 3H), 3.72–3.77(m, 2H), 4.09–4.14(m, 2H), 6.67–6.76(m, 2H), 7.02–7.42(m, 17H)

Production Example 206

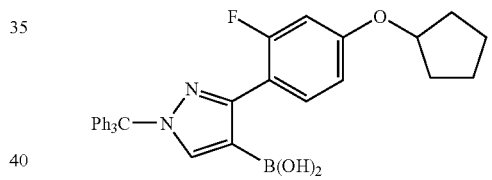

3-(4-Cyclopentyloxy-2-fluorophenyl)-1-trityl-1H-4-pyrazolylboronic acid 118 mg of the title compound (pale yellow amorphous) was obtained from 500 mg of 4-bromo-3-(4-cyclopentyloxy-2-fluorophenyl)-1-trityl-1H-pyrazole in the same manner as in Production Example 25.

$^1$H-NMR (CDCl$_3$)

δ: 1.45–1.98(m, 8H), 4.70–4.78(m, 1H), 6.62–6.71(m, 2H), 7.14–7.41(m, 16H), 7.69(s, 1H)

Production Example 207

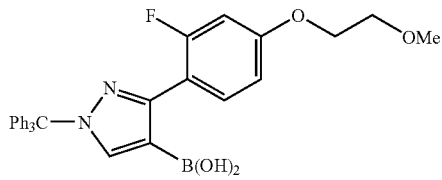

3-[2-Fluoro-4-(2-methoxyethoxy)phenyl]-1-trityl-1H-4-pyrazolylboronic acid 147 mg of the title compound (colorless amorphous) was obtained from 500 mg of 4-bromo-3-[2-fluoro-4-(2-methoxyethoxy)phenyl]-1-trityl-1H-pyrazole in the same manner as in Production Example 25.

$^1$H-NMR (CDCl$_3$)

δ: 3.45(s, 3H), 3.68–3.80(m, 2H), 4.08–4.18(m, 2H), 6.67–6.80(m, 2H), 7.10–7.41(m, 16H), 7.69(s, 1H)

Production Example 208

3-(2,6-Difluorophenyl)-1H-pyrazole 5.62 g of the title compound (yellow solid) was obtained from 5.0 g of 2',6'-difluoroacetophenone by the same method as in Production Example 3.

$^1$H-NMR (CDCl$_3$)

δ: 6.83(dd, J=4.4, 2.0 Hz, 1H), 6.99–7.08(m, 2H), 7.28 (dddd, J=8.0, 8.0, 6.0, 6.0 Hz, 1H), 7.71(d, J=2.0 Hz, 1H)

Production Example 209

4-Bromo-3-(2,6-difluorophenyl)-1H-pyrazole 10.11 g of the title compound in a crude state (yellow oil) was obtained from 5.62 g of 3-(2,6-difluorophenyl)-1H-pyrazole in the same manner as in Production Example 8.

$^1$H-NMR (CDCl$_3$)

δ: 6.99–7.07(m, 2H), 7.42 (dddd, J=8.4, 8.4, 6.4, 6.4 Hz, 1H), 7.72(s, 1H)

Production Example 210

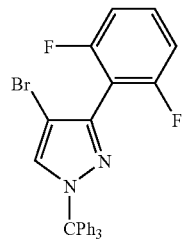

4-Bromo-3-(2,6-difluorophenyl)-1-trityl-1H-pyrazole 9.84 g of the title compound (slightly yellow solid) was obtained from 10.11 g of 4-bromo-3-(2,6-difluorophenyl)-1H-pyrazole by the same method as in Production Example 15.

$^1$H-NMR (CDCl$_3$)

δ: 6.90–6.98(m, 2H), 7.11–7.38(m, 16H), 7.45(s, 1H)

Production Example 211

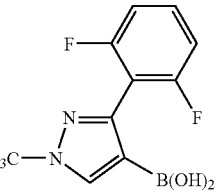

3-(2,6-Difluorophenyl)-1-trityl-1H-4-pyrazolylboronic acid 1.0 g of the title compound (colorless crystals) was obtained from 3.0 g of 4-bromo-3-(2,6-difluorophenyl)-1-trityl-1H-pyrazole in the same manner as in Production Example 25.

$^1$H-NMR (CDCl$_3$)

δ: 4.19(s, 1H), 6.92–7.00(m, 2H), 7.12–7.38(m, 16H), 7.73(s, 1H)

Production Example 212

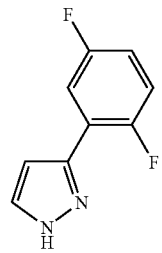

3-(2,5-Difluorophenyl)-1H-pyrazole 5.64 g of the title compound (yellow solid) was obtained from 5.2 g of 2',5'-difluoroacetophenone by the same method as in Production Example 3.

$^1$H-NMR (CDCl$_3$)

δ: 6.71–6.83(m, 1H), 6.92–7.03(m, 1H), 7.06–7.17(m, 1H), 7.48–7.63(m, 1H), 7.66(d, J=2.4 Hz, 1H)

Production Example 213

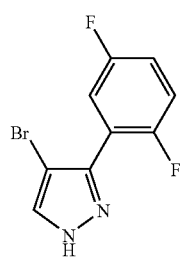

4-Bromo-3-(2,5-difluorophenyl)-1H-pyrazole 11.83 g of the title compound in a crude state (yellow oil) was obtained from 5.64 g of 3-(2,5-difluorophenyl)-1H-pyrazole in the same manner as in Production Example 8.

$^1$H-NMR (CDCl$_3$)

δ: 7.05–7.22(m, 2H), 7.50–7.66(m, 1H), 7.68(s, 1H)

Production Example 214

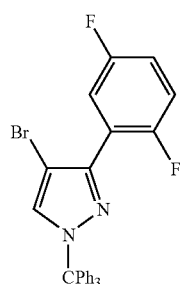

4-Bromo-3-(2,5-difluorophenyl)-1-trityl-1H-pyrazole 6.07 g of the title compound (slightly yellow solid) was obtained from 11.53 g of 4-bromo-3-(2,5-difluorophenyl)-1H-pyrazole by the same method as in Production Example 15.

$^1$H-NMR (CDCl$_3$)

δ: 6.90–7.12(m, 2H), 7.13–7.40(m, 16H), 7.42(s, 1H)

Production Example 215

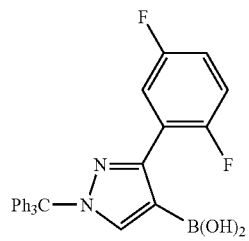

3-(2,5-Difluorophenyl)-1-trityl-1H-4-pyrazolylboronic acid 1.68 g of the title compound (pale brown crystals) was obtained from 6.07 g of 4-bromo-3-(2,5-difluorophenyl)-1-trityl-1H-pyrazole in the same manner as in Production Example 25.

$^1$H-NMR (CDCl$_3$)

δ: 4.16(s, 1H), 6.90–7.40(m, 18H), 7.70(s, 1H)

Production Example 216

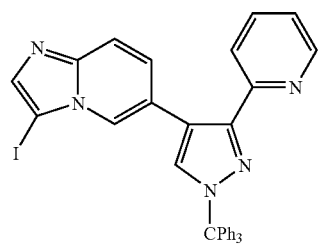

3-Iodo-6-[3-(pyridin-2-yl)-1-trityl-1H-pyrazol-4-yl]imidazo[1,2-a]pyridine 218 mg of the title compound was obtained as a colorless amorphous from 231 mg of 6-[3-(pyridin-2-yl)-1-trityl-1H-pyrazol-4-yl]imidazo[1,2-a]pyridine (compound in Production Example 181) by the same reaction as in Production Example 39.

$^1$H-NMR (CDCl$_3$)

δ: 7.12(dd, J=9.2, 1.6 Hz, 1H), 7.20(m, 1H), 7.23–7.38(m, 15H), 7.46(dd, J=9.2, 1.2 Hz, 1H), 7.56(s, 1H), 7.64(s, 1H), 7.67(ddd, J=8.0, 8.0, 2.0 Hz, 1H), 7.79(dt, J=8.0, 1.2 Hz, 1H), 8.55(m, 1H), 8.68(dd, J=1.6, 1.2 Hz, 1H)

Production Example 217

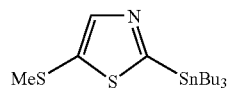

5-Methylsulfanyl-2-tributylstannylthiazole 2.96 g crude product of the title compound was obtained as dark green oil from 979 mg 5-methylsulfanylthiazole [compound described by D. S. Noyce, S. A. Fike in J. Org. Chem., 38, 3318 (1973)] under the same conditions as in Production Example 46. This product was used in the subsequent reaction without purification.

Production Example 218

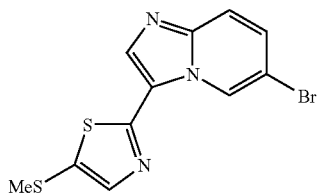

6-Bromo-3-(5-methylsulfanylthiazol-2-yl)imidazo[1,2-a]-pyridine 538 mg of the title compound was obtained as white crystals from 1.5 g of 5-methylsulfanyl-2-tributylstannylthiazole (compound in Production Example 217) and 1.32 g of 6-bromo-3-iodoimidazo[1,2-a]pyridine (compound in Production Example 49) by the same reaction as in Production Example 57.

$^1$H-NMR (CDCl$_3$)

δ: 2.54(s, 3H), 7.42(dd, J=9.6, 2.0 Hz, 1H), 7.61(dd, J=9.6, 0.8 Hz, 1H), 7.74(s, 1H), 8.06(s, 1H), 9.82(dd, J=2.0, 0.8 Hz, 1H)

Production Example 219

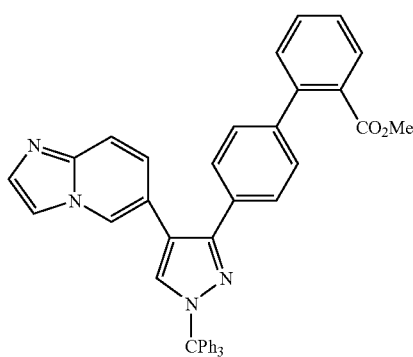

Methyl 4'-(4-imidazo[1,2-a]pyridin-6-yl-1-trityl-1H-pyrazol-3-yl)biphenyl-2-carboxylate 144 mg of the title compound was obtained as a pale brown amorphous from 217 mg of 6-bromoimidazo[1,2-a]pyridine and 845 mg of methyl 4'-[4-(4,4,5,5-tetramethyl-1,3,2-dioxaborolan-2-yl)-1-trityl-1H-pyrazol-3-yl]biphenyl-2-carboxylate (compound in Production Example 174) by the same reaction as in Production Example 51.

$^1$H-NMR (CDCl$_3$)

δ: 3.66(s, 3H), 7.10(dd, J=9.2, 1.6 Hz, 1H), 7.23(d, J=8.4 Hz, 2H), 7.27(m, 6H), 7.35(m, 9H), 7.42(s, 1H), 7.44–7.58 (m, 5H), 7.60(d, J=1.2 Hz, 1H), 7.66(m, 2H), 7.66(dd, J=7.6, 1.6 Hz, 1H), 8.05(dd, J=1.6, 0.8 Hz, 1H)

Production Example 220

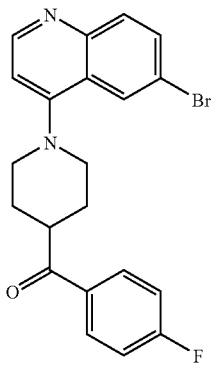

[1-(6-Bromoquinolin-4-yl)piperidin-4-yl]-(4-fluorophenyl)methanone 43 mg of the title compound was obtained from 120 mg of 6-bromo-4-chloroquinoline and 130 mg of (4-fluorophenyl)-piperidin-4-yl-methanone hydrochloride in the same manner as in Production Example 82.

$^1$H-NMR(CDCl$_3$)

δ: 2.05–2.24(m, 4H), 2.97–3.05(m, 2H), 3.44–3.59(m, 1H), 3.62–3.70(m, 2H), 6.89(d, J=5.0 Hz, 1H), 7.16–7.21(m, 2H), 7.72(dd, J=9.2, 2.4 Hz, 1H), 7.92(d, J=9.2 Hz, 1H), 8.01–8.06(m, 2H), 8.15(d, J=2.4 Hz, 1H), 8.73(d, J=5.0 Hz, 1H)

Production Example 221

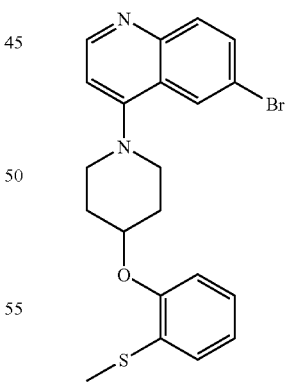

6-Bromo-4-[4-(2-methylsulfanylphenoxy)piperidin-1-yl]quinoline 743 mg of the title compound was obtained from 600 mg of 6-bromo-4-chloroquinoline and 670 mg of 4-[2-(methylsulfanyl)phenoxy]piperidine hydrochloride by the same method as in Production Example 82.

¹H-NMR (CDCl₃)

δ: 2.15–2.29(m, 4H), 2.44(s, 3H), 3.16–3.21(m, 2H), 3.48–3.54(m, 2H), 4.68–4.75(m, 1H), 6.91–6.93(m, 2H), 6.99 (td, J=7.6, 1.4 Hz, 1H), 7.11–7.17(m, 2H), 7.71(dd, J=9.2, 2.4 Hz, 1H), 7.91(d, J=9.2 Hz, 1H), 8.15(d, J=2.4 Hz, 1H), 8.72(d, J=4.4 Hz, 1H)

Production Example 222

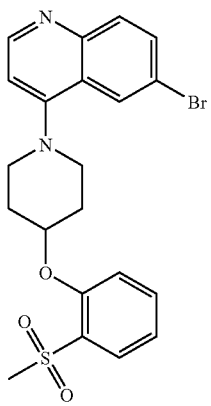

6-Bromo-4-[4-(2-methylsulfonylphenoxy)piperidin-1-yl]quinoline 351 mg of the title compound was obtained by the same method as in Production Example 43 from 743 mg of 6-bromo-4-[4-(2-methylsulfanylphenoxy)piperidin-1-yl]quinoline obtained in Production Example 221 and 2.1 g oxone.

¹H-NMR (CDCl₃)

δ: 2.22–2.39(m, 4H), 3.17–3.24(m, 2H), 3.27(s, 3H), 3.50–3.59(m, 2H), 4.86–4.91(m, 1H), 6.95(d, J=5.0 Hz, 1H), 7.10–7.15(m, 2H), 7.58–7.63(m, 1H), 7.73(dd, J=8.8, 2.4 Hz, 1H), 7.92(d, J=8.8 Hz, 1H), 8.03(dd, J=8.0, 1.6 Hz, 1H), 8.15(d, J=2.4 Hz, 1H), 8.74(d, J=5.0 Hz, 1H)

Production Example 223

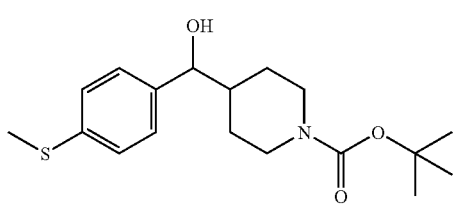

t-Butyl 4-[hydroxy-(4-methylsulfanylphenyl)-methyl]piperidine-1-carboxylate 380 mg of 1-bromo-4-methylsulfanyl benzene was dissolved in 10 mL anhydrous tetrahydrofuran, and 1.24 mL solution of 1.59 M n-butyl lithium in hexane was added dropwise thereto at –70° C. After the mixture was stirred for 1 hour, 3 mL solution of 400 mg t-butyl 4-formyl-piperidine-1-carboxylate in anhydrous tetrahydrofuran was added dropwise thereto, and the mixture was stirred at –70° C. for 2 hours. The temperature of the reaction mixture was increased gradually to 0° C., then water and an ammonium chloride solution were added thereto, and the reaction mixture was extracted with ethyl acetate. The extract was dried over magnesium sulfate and purified by silica gel column chromatography (ethyl acetate/hexane) to give 150 mg of the title compound as a colorless amorphous.

¹H-NMR (CDCl₃)

δ: 1.06–1.29(m, 3H), 1.44(s, 9H), 1.67–1.77(m, 1H), 1.93–1.97(m, 1H), 2.49(s, 3H), 2.52–2.66(m, 2H), 4.00–4.40(m, 2H), 4.45(dd, J=7.6, 2.0 Hz, 1H), 7.20–7.25 (m, 4H)

Production Example 224

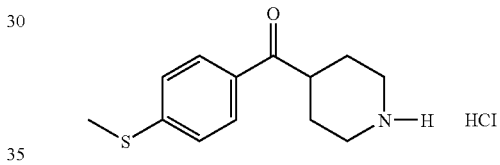

(4-Methylsulfanylphenyl)piperidin-4-yl-methanone hydrochloride 150 mg of t-butyl 4-[hydroxy-(4-methylsulfanylphenyl)-methyl]-piperidine-1-carboxylate (compound in Production Example 223) was dissolved in 4 mL dichloromethane, and 2 ml solution of 0.047 mL oxalyl chloride in dichloromethane was added dropwise thereto at –70° C. After the mixture was stirred for 1 hour, 2 mL of 0.079 mL dimethyl sulfoxide in dichloromethane was added dropwise thereto, and the mixture was stirred at –70° C. for 2 hours. 0.3 mL triethylamine was added thereto, then the temperature of the mixture was increased to room temperature, water was added thereto, and the reaction mixture was extracted with dichloromethane. The organic layer was dried over anhydrous sodium sulfate, the solvent was evaporated, and the residue was purified by silica gel column chromatography (hexane/ethyl acetate), to give 99 mg of t-butyl (4-methylsulfanylbenzoyl)piperidine-1-carboxylate as colorless oil. 5 mL solution of 4 N hydrogen chloride in ethyl acetate was added thereto and left for 1 hour. The solvent was removed, and the precipitated crystals were washed with ethyl acetate/ether, to give 74 mg of the title compound as colorless crystals.

¹H-NMR (DMSO-d₆)

δ: 1.69–1.80(m, 2H), 1.86–1.96(m, 2H), 2.55(s, 3H), 2.98–3.06(m, 2H), 3.26–3.38(m, 2H), 3.67–3.76(m, 1H), 7.37–7.42(m, 2H), 7.91–7.96(m, 2H), 8.79(brs, 2H)

Production Example 225

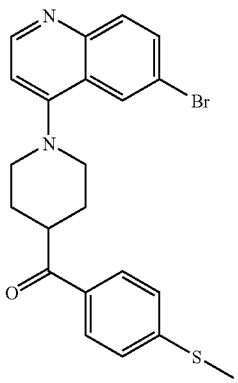

[1-(6-Bromoquinolin-4-yl)piperidin-4-yl]-(4-methyl-sulfanylphenyl)methanone 57 mg of the title compound was obtained from 70 mg of 6-bromo-4-chloroquinoline and 74 mg (4-methylsulfanylphenyl)piperidin-4-yl-methanone hydrochloride (compound in Production Example 224) by the same reaction as in Production Example 82.

$^1$H-NMR (CDCl$_3$)

δ: 2.05–2.24(m, 4H), 2.55(s, 3H), 2.97–3.05(m, 2H), 3.46–3.52(m, 1H), 3.62–3.68(m, 2H), 6.89(d, J=4.8 Hz, 1H), 7.29–7.33(m, 2H), 7.72(dd, J=9.2, 2.4 Hz, 1H), 7.90–7.94 (m, 3H), 8.15(d, J=2.4 Hz, 1H), 8.73(d, J=4.8 Hz, 1H)

Production Example 226

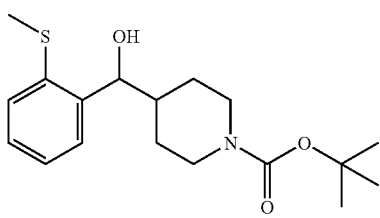

t-Butyl 4-[hydroxy-(2-methylsulfanylphenyl)-methyl]piperidine-1-carboxylate 150 mg of the title compound was obtained as a colorless amorphous from 570 mg of 1-bromo-2-methylsulfanyl benzene and 600 mg of t-butyl 4-formylpiperidine-1-carboxylate by the same method as in Production Example 223.

$^1$H-NMR (CDCl$_3$)

δ: 1.24–1.50(m, 3H), 1.41(s, 9H), 1.79–1.87(m, 2H), 2.48(s, 3H), 2.52–2.68(m, 2H), 4.00–4.40(m, 2H), 4.92(dd, J=6.2, 4.0 Hz, 1H), 7.17–7.30(m, 3H), 7.40–7.44(m, 1H)

Production Example 227

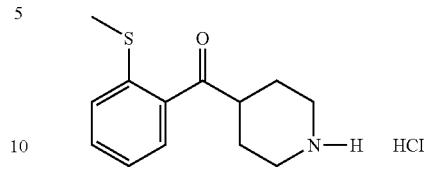

(2-Methylsulfanylphenyl)piperidin-4-yl-methanone hydrochloride 233 mg of the title compound was obtained as colorless crystals from 535 mg of t-butyl 4-[hydroxy-(2-methylsulfanylphenyl)-methyl]-piperidine-1-carboxylate (compound in Production Example 226) by the same reaction as in Production Example 224.

$^1$H-NMR (DMSO-d$_6$)

δ: 1.69–1.80(m, 2H), 1.84–1.96(m, 2H), 2.40(s, 3H), 2.94–3.06(m, 2H), 3.24–3.32(m, 2H), 3.64–3.73(m, 1H), 7.27–7.31(m, 1H), 7.43–7.47(m, 1H), 7.54–7.59(m, 1H), 7.94–7.97(m, 1H)

Production Example 228

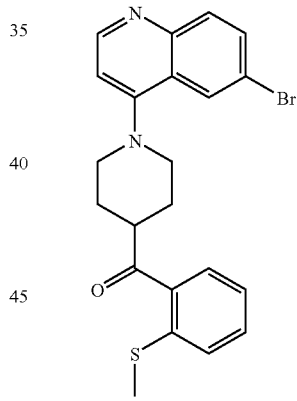

[1-(6-Bromoquinolin-4-yl)piperidin-4-yl]-(2-methyl-sulfanylphenyl)methanone 176 mg of the title compound was obtained as pale yellow crystals from 220 mg of 6-bromo-4-chloroquinoline and 233 mg of (2-methylsulfanylphenyl)piperidin-4-yl-methanone hydrochloride (compound in Production Example 227) by the same reaction as in Production Example 82.

$^1$H-NMR (CDCl$_3$)

δ: 2.05–2.24(m, 4H), 2.48(s, 3H), 2.94–3.01(m, 2H), 3.43–3.51(m, 1H), 3.60–3.66(m, 2H), 6.88(d, J=5.0 Hz, 1H), 7.22–7.26(m, 1H), 7.39(d, J=7.2 Hz, 1H), 7.47–7.51(m, 1H), 7.70–7.75(m, 2H), 7.91(d, J=8.8 Hz, 1H), 8.14(d, J=2.4 Hz, 1H), 8.72(d, J=5.0 Hz, 1H)

Production Example 229

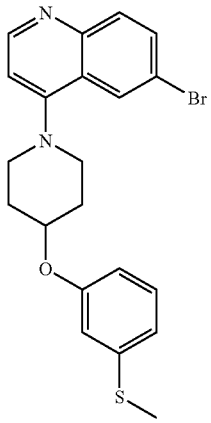

6-Bromo-4-[4-(3-methylsulfanylphenoxy)piperidin-1-yl]quinoline 96 mg of the title compound was obtained from 98 mg of 6-bromo-4-chloroquinoline and 100 mg of 4-(3-methylsulfanylphenoxy)piperidine hydrochloride by the same reaction as in Production Example 82.

$^1$H-NMR (CDCl$_3$)

δ: 2.09–2.17(m, 2H), 2.22–2.30(m, 2H), 2.50(s, 3H), 3.13–3.19(m, 2H), 3.43–3.50(m, 2H), 4.58–4.64(m, 1H), 6.73–6.76(m, 1H), 6.85–6.88(m, 2H), 6.90(d, J=4.8 Hz, 1H), 7.23(t, J=8.0 Hz, 1H), 7.72(dd, J=9.0, 2.2 Hz, 1H), 7.92(d, J=9.0 Hz, 1H), 8.15(d, J=2.2 Hz, 1H), 8.72(d, J=4.8 Hz, 1H)

Production Example 230

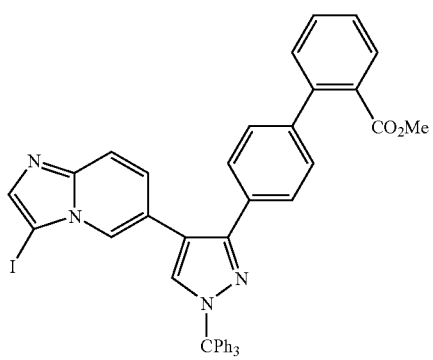

Methyl 4'-[4-(3-iodoimidazo[1,2-a]pyridin-6-yl)-1-trityl-1H-pyrazol-3-yl]biphenyl-2-carboxylate 134 mg of the title compound was obtained as a colorless amorphous from 142 mg of methyl 4'-(4-imidazo[1,2-a]pyridin-6-yl-1-trityl-1H-pyrazol-3-yl)biphenyl-2-carboxylate (compound in Production Example 219) by the same reaction as in Production Example 39.

$^1$H-NMR (CDCl$_3$)

δ: 3.66(s, 3H), 7.15(dd, J=9.2, 1.6 Hz, 1H), 7.27(m, 9H), 7.36(m, 11H), 7.48(s, 1H), 7.51(dd, J=9.2, 0.8 Hz, 1H), 7.54(d, J=8.4 Hz, 2H), 7.66(s, 1H), 7.80(dd, J=7.6, 0.8 Hz, 1H), 8.04(dd, J=1.6, 0.8 Hz, 1H)

Production Example 231

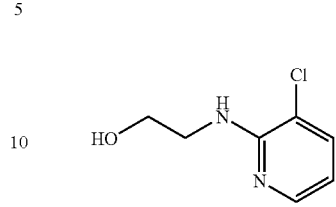

2-(3-Chloro-2-pyridinylamino)ethanol

After 11.46 g of 2,3-dichloropyridine and 9.8 mL 2-aminoethanol were heated at 100° C. for 24 hours, an aqueous saturated sodium bicarbonate solution was added thereto, and the reaction mixture was extracted with ethyl acetate. The extract was washed with brine, the organic layer was dried over anhydrous sodium sulfate, the solvent was removed, and the resulting crude product was purified by silica gel column chromatography (ethyl acetate/hexane) to give 2.1 g of the title compound (yellow oil).

$^1$H-NMR (CDCl$_3$)

δ: 3.63–3.68(m, 2H), 3.84(t, J=4.8 Hz, 2H), 4.48(brs, 1H), 5.45(brs, 1H), 6.57(dd, J=8.0, 5.2 Hz, 1H), 7.48(d, J=8.0 Hz, 1H), 7.97(d, J=5.2 Hz, 1H)

Production Example 232

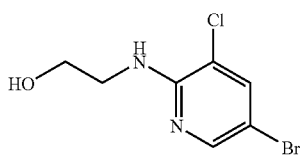

2-(5-Bromo-3-chloro-2-pyridinylamino)ethanol 2.1 g of 2-(3-chloro-2-pyridinylamino)ethanol was dissolved in 25 mL dichloromethane, and 2.3 g N-bromosuccinimide was added little by little thereto at 0° C. and stirred for 1.5 hours. The reaction mixture was diluted with ethyl acetate and then washed with an aqueous saturated sodium bicarbonate and brine, the organic layer was dried over anhydrous sodium sulfate, and the solvent was removed, whereby 3.17 g of the title compound (yellow oil) was obtained.

$^1$H-NMR (CDCl$_3$)

δ: 3.63–3.76(m, 2H), 3.86(t, J=4.8 Hz, 2H), 5.58(brs, 1H), 7.65(d, J=2.0 Hz, 1H), 8.05(d, J=2.0 Hz, 1H)

Production Example 233

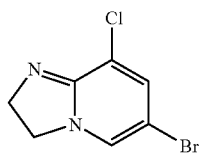

6-Bromo-8-chloro-2,3-dihydroimidazo[1,2-a]pyridine 3.17 g of 2-(5-bromo-3-chloro-2-pyridinylamino)ethanol was suspended in 25 mL xylene, and 4.5 mL thionyl chloride was added dropwise thereto at room temperature and stirred for 14 hours at 100° C. Formed solid was collected by filtration and washed with ethyl acetate to give 2.3 g hydrochloride of the title compound. This product was basified by adding an aqueous saturated sodium bicarbonate solution, and then extracted with ethyl acetate and dichloromethane. The organic layer was dried over anhydrous sodium sulfate, and the solvent was removed, whereby 2.08 g of the title compound (yellow solid) was obtained.
$^1$H-NMR (CDCl$_3$)
δ: 4.00–4.16(m, 4H), 7.00(d, J=2.0 Hz, 1H), 7.08(d, J=2.0 Hz, 1H)

Production Example 234

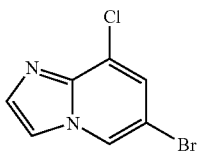

6-Bromo-8-chloroimidazo[1,2-a]pyridine 2.08 g of 6-bromo-8-chloro-2,3-dihydroimidazo[1,2-a]pyridine was dissolved in 36 mL acetone, and together with 9.1 g of manganese dioxide, the mixture was heated for 9 hours under reflux. The reaction solution was cooled to room temperature, filtered through Celite and washed with ethyl acetate. The solvent was removed, and the resulting crude product was purified by NH silica gel column chromatography (ethyl acetate/hexane) to give 1.27 g of the title compound (pale yellow crystals).
$^1$H-NMR (CDCl$_3$)
δ: 7.38(d, J=1.2 Hz, 1H), 7.63(s, 1H), 7.70(s, 1H), 8.25(d, J=1.2 Hz, 1H)

Production Example 235

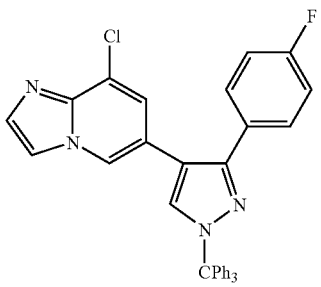

8-Chloro-6-[3-(4-fluorophenyl)-1-trityl-1H-4-pyrazolyl]imidazo[1,2-a]pyridine 929 mg of the title compound (pale yellow amorphous) was obtained from 400 mg of 6-bromo-8-chloroimidazo[1,2-a]pyridine and 853 mg of 3-(4-fluorophenyl)-1-trityl-1H-4-pyrazolylboronic acid (compound in Production Example 25) in the same manner as in Production Example 34.
$^1$H-NMR (CDCl$_3$)
δ: 6.95–7.02(m, 2H), 7.14(d, J=1.2 Hz, 1H), 7.21–7.29(m, 6H), 7.32–7.40(m, 9H), 7.42(s, 1H), 7.43–7.49(m, 2H), 7.54(d, J=1.2 Hz, 1H), 7.65(d, J=1.2 Hz, 1H), 7.93(d, J=1.2 Hz, 1H)

Production Example 236

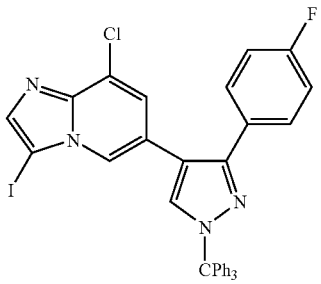

8-Chloro-6-[3-(4-fluorophenyl)-1-trityl-1H-4-pyrazolyl]-3-iodoimidazo[1,2-a]pyridine 1.01 g of the title compound was obtained as a pale brown amorphous from 929 mg of 8-chloro-6-[3-(4-fluorophenyl)-1-trityl-1H-4-pyrazolyl]imidazo[1,2-a]pyridine (compound in Production Example 235) and 395 mg of N-iodosuccinimide in the same manner as in Production Example 39.
$^1$H-NMR (CDCl$_3$)
δ: 6.98–7.05(m, 2H), 7.22(d, J=1.2 Hz, 1H), 7.23–7.30(m, 6H), 7.33–7.41(m, 9H), 7.43–7.48(m, 2H), 7.49(s, 1H), 7.71(s, 1H), 7.89(d, J=1.2 Hz, 1H)

Production Example 237

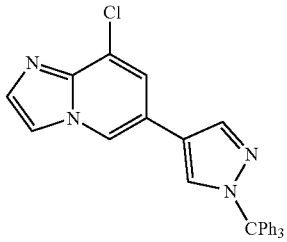

8-Chloro-6-(1-trityl-1H-4-pyrazolyl]imidazo[1,2-a]pyridine 820 mg of the title compound (white amorphous) was obtained from 400 mg of 6-bromo-8-chloroimidazo[1,2-a]pyridine (compound in Production Example 234) and 674 mg of 1-trityl-1H-4-pyrazolylboronic acid in the same manner as in Production Example 34.
$^1$H-NMR (CDCl$_3$)
δ: 7.16–7.22(m, 7H), 7.31–7.40(m, 10H), 7.62(s, 1H), 7.65–7.68(m, 1H), 7.90(s, 1H), 8.14–8.18(m, 1H)

Production Example 238

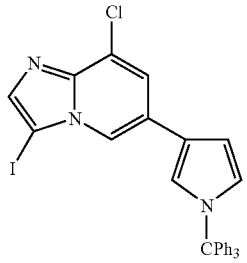

8-Chloro-3-iodo-6-(1-trityl-1H-4-pyrazolyl)imidazo[1,2-a]pyridine 0.86 g of the title compound was obtained as a pale brown amorphous from 820 mg of 8-chloro-6-(1-trityl-1H-4-pyrazolyl)imidazo[1,2-a]pyridine (compound in Production Example 237) in the same manner as in Production Example 39.

$^1$H-NMR (CDCl$_3$)

δ: 7.17–7.24(m, 6H), 7.33–7.40(m, 9H), 7.39(d, J=1.6 Hz, 1H), 7.67(s, 1H), 7.73(s, 1H), 7.95(s, 1H), 8.11(d, J=1.6 Hz, 1H)

Production Example 239

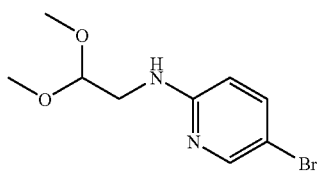

(5-Bromo-2-pyridinyl)-(2,2-dimethoxyethyl)amine

After 50 g of 2,5-dibromopyridine and 50 mL aminoacetaldehyde dimethyl acetal were heated at 130° C. for 8 hours, an aqueous saturated sodium bicarbonate solution was added thereto, and the reaction mixture was extracted with ethyl acetate. The extract was washed with brine, the organic layer was dried over anhydrous sodium sulfate, the solvent was removed, and the resulting crude product was purified by silica gel column chromatography (ethyl acetate/hexane), to give 23.53 g of the title compound (pale yellow oil).

$^1$H-NMR (CDCl$_3$)

δ: 3.42(s, 6H), 3.45(dd, J=5.6, 5.6 Hz, 2H), 4.53(t, J=5.6 Hz, 1H), 4.60–4.72(m, 1H), 6.34(d, J=8.8 Hz, 1H), 7.46(dd, J=8.8, 2.4 Hz, 1H), 8.11(d, J=2.4 Hz, 1H)

Production Example 240

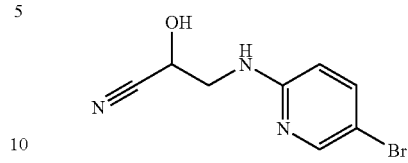

3-(5-Bromo-2-pyridinylamino)-2-hydroxypropionitrile 23.53 g of (5-bromo-2-pyridinyl)-(2,2-dimethoxyethyl)amine was dissolved in 180 mL tetrahydrofuran, then 180 mL of 1 N hydrochloric acid was added thereto and heated at 70° C. for 3.5 hours, and the reaction mixture was basified by adding an aqueous saturated sodium bicarbonate solution and extracted with ethylacetate. The extract was washed with brine, the organic layer was dried over anhydrous sodium sulfate, and the solvent was removed, whereby 11.8 g crude aldehyde was obtained. Subsequently, the crude aldehyde was dissolved in 110 mL toluene, and 83 mL of 1.0 M diethyl aluminum cyanide in toluene was slowly added dropwise thereto at 0° C. and stirred at room temperature for 18 hours. The reaction solution was poured into ice, and insolubles were separated by filtration through Celite and washed with ethyl acetate. The organic layer was washed with an aqueous saturated sodium bicarbonate solution and brine and dried over anhydrous sodium sulfate, the solvent was removed, and the resulting crude product was purified by silica gel column chromatography (ethyl acetate/hexane) to give 7.2 g of the title compound (yellow oil).

$^1$H-NMR (CDCl$_3$)

δ: 3.57–3.73(m, 1H), 3.81–3.92(m, 1H), 4.62–4.78(m, 1H), 5.00–5.14(m, 1H), 6.53(d, J=8.8 Hz, 1H), 7.57(dd, J=8.8, 2.4 Hz, 1H), 8.08(d, J=2.4 Hz, 1H)

Production Example 241

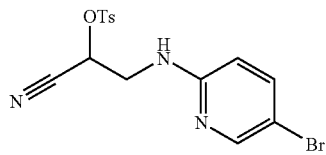

2-(5-Bromo-2-pyridinylamino)-1-cyanoethyl toluene-4-sulfonate 7.2 g of 3-(5-bromo-2-pyridinylamino)-2-hydroxypropionitrile was dissolved in 60 mL dichloromethane, and 7.8 mL diisopropyl ethylamine and 6.3 g of 4-toluenesulfonic acid chloride were added thereto, and while the temperature of the mixture was gradually increased to room temperature, the mixture was stirred for 2 hours. An aqueous saturated sodium bicarbonate solution was poured into the reaction mixture which was then extracted with ethyl acetate and washed with brine, then the organic layer was dried over anhydrous sodium sulfate, the solvent was removed, and the resulting crude product was purified by silica gel column chromatography (ethyl acetate/hexane) to give 7.64 g of the title compound (yellow oil).

¹H-NMR (CDCl₃)

δ: 2.44(s, 3H), 3.66–3.75(m, 1H), 3.91–3.98(m, 1H), 4.65–4.75(m, 1H), 5.39(dd, J=8.0, 3.2 Hz, 1H), 6.28(d, J=8.8 Hz, 1H), 7.30(d, J=8.0 Hz, 2H), 7.46(dd, J=8.8, 2.4 Hz, 1H), 7.76(d, J=8.0 Hz, 2H), 8.04(d, J=2.4 Hz, 1H)

Production Example 242

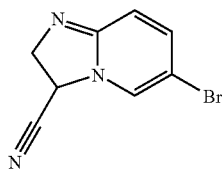

6-Bromo-2,3-dihydroimidazo[1,2-a]pyridine-3-carbonitrile 7.64 g of 2-(5-bromo-2-pyridinylamino)-1-cyanoethyl toluene-4-sulfonate was dissolved in 76 mL acetonitrile, and the mixture was heated for 15 hours under reflux. After the solvent was removed, an aqueous saturated sodium bicarbonate was poured into the reaction product which was then extracted with dichloromethane, and the organic layer was dried over anhydrous sodium sulfate and filtered through NH silica gel. The solvent was removed, whereby 3.83 g of the title compound (yellow solid) was obtained.

¹H-NMR (CDCl₃)

δ: 4.24(dd, J=14.8, 8.4 Hz, 1H), 4.33(dd, J=14.8, 12.0 Hz, 1H), 4.94(dd, J=12.0, 8.4 Hz, 1H), 6.33(d, J=10.0 Hz, 1H), 6.85(dd, J=10.0, 2.0 Hz, 1H), 7.16(d, J=2.0 Hz, 1H)

Production Example 243

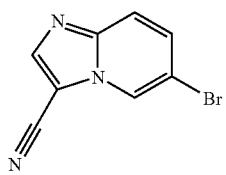

6-Bromoimidazo[1,2-a]pyridine-3-carbonitrile

Method 1) 3.83 g of 6-bromo-2,3-dihydroimidazo[1,2-a]pyridine-3-carbonitrile synthesized in Production Example 242 was dissolved in 34 mL 1,4-dioxane, and the solution together with 4.3 g of 2,3-dichloro-5,6-dicyano-1,4-benzoquinone was heated at 90° C. for 2 hours. The reaction solution was diluted with ethyl acetate, insolubles were filtered off with Celite, and the filtrate was washed with an aqueous saturated sodium bicarbonate solution and brine. The organic layer was dried over anhydrous sodium sulfate and filtered through NH silica gel. The solvent was removed, whereby 3.24 g of the title compound (brown solid) was obtained.

¹H-NMR (CDCl₃)

δ: 7.53(dd, J=9.2, 1.6 Hz, 1H), 7.68(dd, J=9.2, 0.4 Hz, 1H), 8.15(s, 1H), 8.51–8.54(m, 1H)

Method 2) 80 g of 6-bromo-3-iodoimidazo[1,2-a]pyridine (compound in Production Example 49) was dissolved in 500 mL tetrahydrofuran, and 273 mL of 1.0 M isopropyl magnesium bromide in tetrahydrofuran was slowly added dropwise thereto at 0° C. and stirred for 30 minutes, and 380 mL of 68 g 4-toluenesulfonyl cyanide in tetrahydrofuran was added dropwise slowly over 1 hour, and the mixture was stirred for additional 1.5 hours. The reaction solution was poured into iced water, diluted with ethyl acetate and filtered through Celite. The organic layer was separated, and the aqueous layer was extracted with ethyl acetate, and the collected organic layer was washed with brine. The organic layer was dried over anhydrous sodium sulfate and filtered through NH silica gel. Solid obtained by removing the solvent was triturated with diethyl ether, collected by filtration and washed with hexane to give 39.4 g of the title compound (brown solid).

Production Example 244

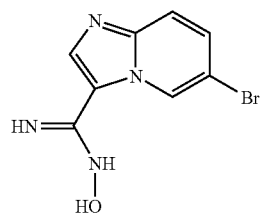

6-Bromo-N-hydroxyimidazo[1,2-a]pyridine-3-carboxyamidine 39.4 g of 6-bromoimidazo[1,2-a]pyridine-3-carbonitrile was suspended in a solvent mixture of 710 mL toluene and 90 mL methanol, and the solution together with 13.6 g hydroxylamine hydrochloride and 22 g potassium t-butyl oxide was heated for 2.5 hours under reflux. Solid obtained by removing the solvent was suspended in methanol, and water was added thereto. The resulting precipitates were collected by filtration, washed with water and dried, whereby 35.3 g of the title compound (dark brown solid) was obtained as a mixture with impurities.

¹H-NMR (DMSO-d₆)

δ: 6.12(brs, 2H), 7.49(dd, J=9.6, 2.0 Hz, 1H), 7.67(d, J=9.6 Hz, 1H), 8.15(s, 1H), 8.59(d, J=2.0 Hz, 1H), 9.95(s, 1H)

Production Example 245

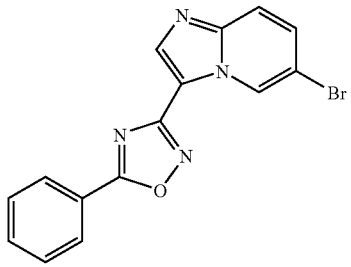

6-Bromo-3-(5-phenyl-[1,2,4]oxadiazol-3-yl)imidazo[1,2-a]pyridine 34 mg of 6-bromo-N-hydroxyimidazo[1,2-a]pyridine-3-carboxyamidine (compound in Production Example 244) was suspended in 1 mL dichloromethane, and 35 µL diisopropyl ethylamine and 17 µL benzoyl chloride were added thereto at 0° C. and stirred for 1 hour. An aqueous saturated sodium bicarbonate solution was added thereto, and the reaction mixture was extracted with a solvent mixture of ethyl acetate and tetrahydrofuran and washed with brine. The organic layer was dried over anhydrous sodium sulfate, and the solvent was removed, whereby 43 mg intermediate was obtained.

Subsequently, the resulting intermediate was dissolved in 4 mL tetrahydrofuran, and 0.12 mL of 1.0 M tetrabutyl ammonium fluoride in tetrahydrofuran was added dropwise thereto, and the mixture was stirred at room temperature for 3 hours. The reaction mixture was diluted with ethyl acetate, washed with water and brine and dried over anhydrous sodium sulfate, the solvent was removed, and the resulting crude product was purified by silica gel column chromatography (ethyl acetate/hexane) to give 13 mg of the title compound (yellow solid).

$^1$H-NMR (CDCl$_3$)

δ: 7.49(dd, J=9.6, 2.0 Hz, 1H), 7.56–7.68(m, 3H), 7.69 (dd, J=9.6, 0.8 Hz, 1H), 8.23–8.29(m, 2H), 8.47(s, 1H), 8.41–8.45(m, 1H)

Production Example 246

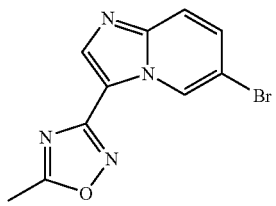

6-Bromo-3-(5-methyl-[1,2,4]oxadiazol-3-yl)imidazo[1,2-a]pyridine 33 mg of the title compound (pale yellow amorphous) was obtained from 120 mg of 6-bromo-N-hydroxyimidazo[1,2-a]pyridine-3-carboxyamidine (compound in Production Example 244) by using 53 µL acetic anhydride as an acylating agent in the same reaction as in Production Example 245.

$^1$H-NMR (CDCl$_3$)

δ: 2.71(s, 3H), 7.47(dd, J=9.6, 2.0 Hz, 1H), 7.67(dd, J=9.6, 0.8 Hz, 1H), 8.35(s, 1H), 9.34(dd, J=2.0, 0.8 Hz, 1H)

Production Example 247

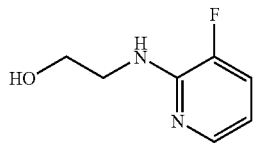

2-(3-Fluoro-2-pyridinylamino)ethanol 12.8 g of 2-chloro-3-aminopyridine was suspended in 120 mL of 60% aqueous hexafluorophosphoric acid, and 9.0 g sodium nitrite was added little by little thereto at 0° C. to precipitate crystals. The crystals were collected by filtration and washed with diethyl ether to give 15.75 g diazonium salt.

Subsequently, the diazonium salt was suspended in 100 mL xylene and heated at 85° C. for 3 hours, 28 mL triethylamine was added thereto, and the reaction mixture was diluted with an aqueous saturated sodium bicarbonate solution and then extracted with ethyl acetate. The extract was washed with brine, and the organic layer was dried over anhydrous sodium sulfate and then filtered through silica gel. The ethyl acetate was removed, and to the resulting xylene solution was added 6.0 mL 2-aminoethanol, and the mixture was heated at 130° C. for 10 hours. Then, the same procedure as in Production Example 231 was carried out, whereby 385 mg of the title compound (yellow oil) was obtained as a mixture.

$^1$H-NMR (CDCl$_3$)

δ: 3.60–3.68(m, 2H), 3.84(t, J=4.8 Hz, 2H), 6.52–6.60(m, 1H), 7.12–7.20(m, 1H), 7.80–7.85(m, 1H)

Production Example 248

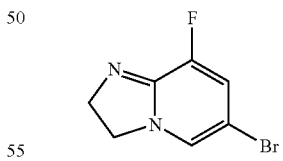

6-Bromo-8-fluoro-2,3-dihydroimidazo[1,2-a]pyridine 245 mg of 2-(5-bromo-3-fluoropyridin-2-ylamino) ethanol was obtained as a mixture in the same manner as in Production Example 232 from 385 mg of 2-(3-fluoro-2-pyridinylamino)ethanol obtained in Production Example 247. Subsequently, 87 mg of the title compound (yellow solid) was obtained in the same manner as in Production Example 233.

¹H-NMR (CDCl₃)

δ: 3.97–4.17(m, 4H), 6.63(dd, J=10.0, 2.0 Hz, 1H), 6.98 (d, J=2.0 Hz, 1H)

Production Example 249

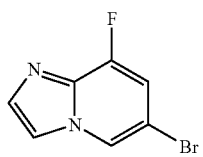

6-Bromo-8-fluoroimidazo[1,2-a]pyridine 46 mg of the title compound (pale yellow crystals) was obtained from 87 mg of 6-bromo-8-fluoro-2,3-dihydroimidazo[1,2-a]pyridine in the same manner as in Production Example 234.

¹H-NMR (CDCl₃)

δ: 7.03(dd, J=9.6, 1.6 Hz, 1H), 7.63(d, J=3.6 Hz, 1H), 7.67(s, 1H), 8.12–8.15(m, 1H)

Production Example 250

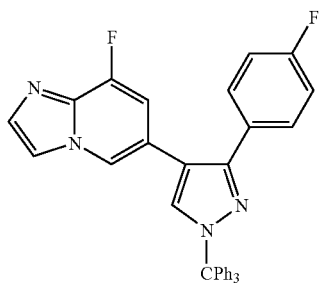

8-Fluoro-6-[3-(4-fluorophenyl)-1-trityl-1H-4-pyrazolyl]imidazo[1,2-a]pyridine 110 mg of the title compound (pale yellow amorphous) was obtained from 46 mg of 6-bromo-8-fluoroimidazo[1,2-a]pyridine and 115 mg of 3-(4-fluorophenyl)-1-trityl-1H-4-pyrazolylboronic acid (compound in Production Example 25) in the same manner as in Production Example 34.

¹H-NMR (CDCl₃)

δ: 6.75(dd, J=11.2, 1.6 Hz, 1H), 6.96–7.03(m, 2H), 7.21–7.29(m, 6H), 7.32–7.40(m, 9H), 7.42(s, 1H), 7.42–7.45(m, 2H), 7.55(dd, J=3.2, 1.2 Hz, 1H), 7.63(d, J=1.2 Hz, 1H), 7.84(d, J=1.6 Hz, 1H)

Production Example 251

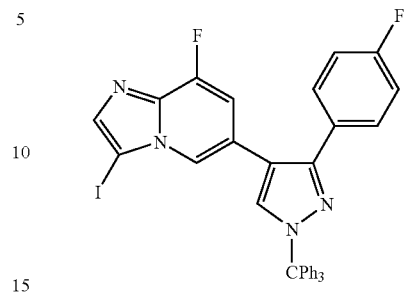

8-Fluoro-6-[3-(4-fluorophenyl)-1-trityl-1H-4-pyrazolyl]-3-iodoimidazo[1,2-a]pyridine 118 mg of the title compound was obtained as a white amorphous from 110 mg of 8-fluoro-6-[3-(4-fluorophenyl)-1-trityl-1H-4-pyrazolyl]imidazo[1,2-a]pyridine (compound in Production Example 250) in the same manner as in Production Example 39.

¹H-NMR (CDCl₃)

δ: 6.86(dd, J=10.8, 1.2 Hz, 1H), 6.98–7.05(m, 2H), 7.22–7.30(m, 6H), 7.32–7.42(m, 9H), 7.43–7.48(m, 2H), 7.48(s, 1H), 7.68(s, 1H), 7.80(d, J=1.2 Hz, 1H)

Production Example 252

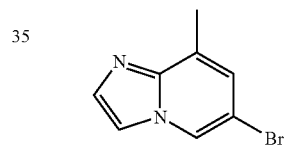

6-Bromo-8-methylimidazo[1,2-a]pyridine 6.17 g of the title compound (pale yellow crystals) was obtained from 5.0 g of 2-amino-3-methyl-5-bromopyridine by a method described in M. Yamanaka et al., Chem. Pharm. Bull., 39, 1556 (1991).

¹H-NMR (CDCl₃)

δ: 2.61(s, 3H), 7.06(s, 1H), 7.54(s, 1H), 7.61(s, 1H), 8.17(s, 1H)

Production Example 253

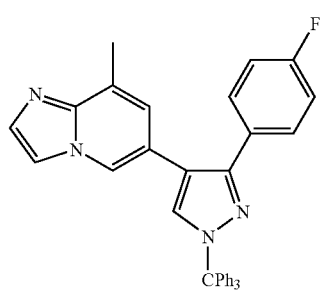

6-[3-(4-Fluorophenyl)-1-trityl-1H-4-pyrazolyl]-8-methyl-imidazo[1,2-a]pyridine 813 mg of the title compound (colorless crystals) was obtained from 396 mg of 6-bromo-8-methylimidazo[1,2-a]pyridine and 925 mg of 3-(4-fluorophenyl)-1-trityl-1H-4-pyrazolylboronic acid (compound in Production Example 25) in the same manner as in Production Example 34.

$^1$H-NMR (CDCl$_3$)

δ: 6.84(brs, 1H), 6.93–6.99(m, 2H), 7.21–7.28(m, 6H), 7.31–7.38(m, 9H), 7.39(s, 1H), 7.46–7.51(m, 3H), 7.59(d, J=1.6 Hz, 1H), 7.88(brs, 1H)

Production Example 254

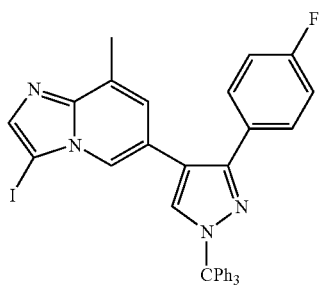

6-[3-(4-Fluorophenyl)-1-trityl-1H-4-pyrazolyl]-3-iodo-8-methylimidazo[1,2-a]pyridine 904 mg of the title compound was obtained as a colorless amorphous from 813 mg of 6-[3-(4-fluorophenyl)-1-trityl-1H-4-pyrazolyl]-8-methyl-imidazo[1,2-a]pyridine (compound in Production Example 253) in the same manner as in Production Example 39.

$^1$H-NMR (CDCl$_3$)

δ: 6.88–6.92(m, 1H), 6.94–7.02(m, 2H), 7.23–7.30(m, 6H), 7.32–7.40(m, 9H), 7.44–7.50(m, 3H), 7.65(d, J=1.6 Hz, 1H), 7.83–7.85(m, 1H)

Production Example 255

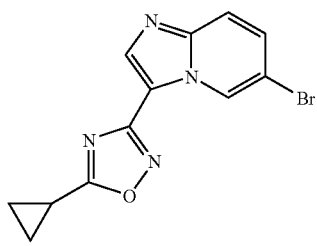

6-Bromo-3-(5-cyclopropyl-[1,2,4]oxadiazol-3-yl)imidazo[1,2-a]pyridine 170 mg of the title compound (pale yellow amorphous) was obtained from 295 mg of 6-bromo-N-hydroxyimidazo[1,2-a]-pyridine-3-carboxyamidine (compound in Production Example 244) by using 0.115 mL cyclopropane carbonyl chloride as an acylating agent in the same reaction as in Production Example 245.

$^1$H-NMR (CDCl$_3$)

δ: 1.27–1.42(m, 4H), 2.26–2.34(m, 1H), 7.44(dd, J=9.6, 2.0 Hz 1H), 7.65(dd, J=9.6, 0.8 Hz, 1H), 8.31(s, 1H), 9.31(dd, J=2.0, 0.8 Hz, 1H)

Production Example 256

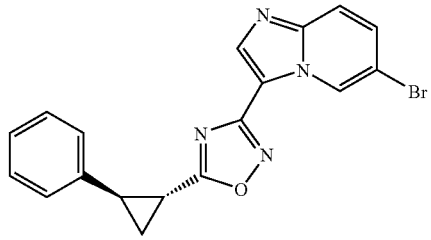

6-Bromo-3-[5-(2-phenylcyclopropyl)-[1,2,4]oxadiazol-3-yl]imidazo[1,2-a]pyridine 115 mg of the title compound (colorless crystals) was obtained from 202 mg of 6-bromo-N-hydroxyimidazo[1,2-a]pyridine-3-carboxyamidine (compound in Production Example 244) by using 0.14 mL trans-2-phenylcyclopropane carbonyl chloride as an acylating agent in the same reaction as in Production Example 245.

$^1$H-NMR (CDCl$_3$)

δ: 1.78(ddd, J=8.8, 6.8, 5.2 Hz, 1H), 1.97(ddd, J=8.8, 5.2, 5.2 Hz, 1H), 2.55(ddd, J=8.8, 5.2, 4.4 Hz, 1H), 2.85(ddd, J=8.8, 6.8, 4.4 Hz, 1H), 7.16–7.38(m, 5H), 7.45(dd, J=9.6, 2.0 Hz, 1H), 7.66(dd, J=9.6, 0.8 Hz, 1H), 8.34(s, 1H), 9.33(dd, J=2.0, 0.8 Hz, 1H)

Production Example 257

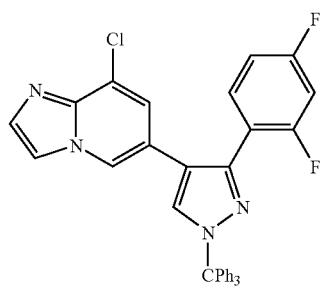

8-Chloro-6-[3-(2,4-difluorophenyl)-1-trityl-1H-4-pyrazolyl]imidazo[1,2-a]pyridine 301 mg of the title compound (pale yellow amorphous) was obtained from 200 mg of 6-bromo-8-chloroimidazo[1,2-a]pyridine (compound in Production Example 234) and 1.2 g of 3-(2,4-difluorophenyl)-1-trityl-1H-4-pyrazolylboronic acid (compound in Production Example 172) in the same manner as in Production Example 34.

$^1$H-NMR (CDCl$_3$)

δ: 6.76–6.83(m, 1H), 6.87–6.94(m, 1H), 7.08(d, J=1.2 Hz, 1H), 7.17–7.27(m, 6H), 7.30–7.47(m, 10H), 7.50(d, J=1.2 Hz, 1H), 7.51(s, 1H), 7.61–7.64(m, 1H), 7.82–7.85(m, 1H)

Production Example 258

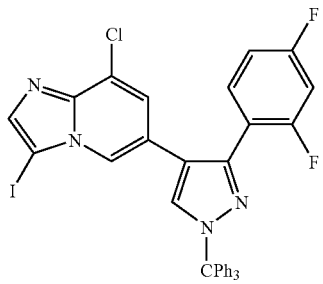

8-Chloro-6-[3-(2,4-difluorophenyl)-1-trityl-1H-4-pyrazolyl]-3-iodoimidazo[1,2-a]pyridine 337 mg of the title compound was obtained as a pale brown amorphous from 301 mg of 8-chloro-6-[3-(2,4-difluorophenyl)-1-trityl-1H-4-pyrazolyl]imidazo[1,2-a]pyridine (compound in Production Example 257) in the same manner as in Production Example 39.

$^1$H-NMR (CDCl$_3$)

δ: 6.79–6.86(m, 1H), 6.90–6.97(m, 1H), 7.19(d, J=1.2 Hz, 1H), 7.22–7.50(m, 16H), 7.59(s, 1H), 7.68(s, 1H), 7.78(d, J=1.2 Hz, 1H)

Production Example 259

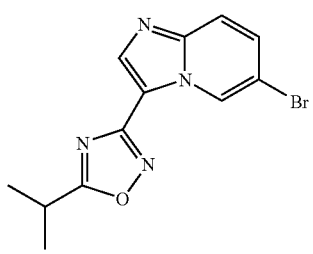

6-Bromo-3-(5-isopropyl-[1,2,4]oxadiazol-3-yl)imidazo[1,2-a]pyridine 238 mg of the title compound (colorless amorphous) was obtained from 510 mg of 6-bromo-N-hydroxyimidazo[1,2-a]-pyridine-3-carboxyamidine (compound in Production Example 244) by using 0.25 mL isobutyric acid chloride as an acylating agent in the same reaction as in Production Example 245.

$^1$H-NMR (CDCl$_3$)

δ: 1.49(d, J=6.8 Hz, 6H), 3.27–3.39(m, 1H), 7.45(dd, J=9.6, 2.0 Hz, 1H), 7.66(dd, J=9.6, 0.8 Hz, 1H), 8.37(s, 1H), 9.35(dd, J=2.0, 0.8 Hz, 1H)

Production Example 260

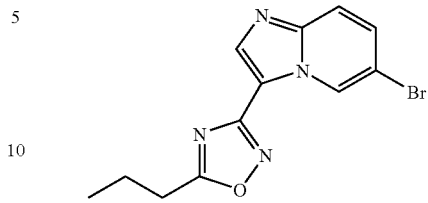

6-Bromo-3-(5-propyl-[1,2,4]oxadiazol-3-yl)imidazo[1,2-a]pyridine 167 mg of the title compound (colorless amorphous) was obtained from 510 mg of 6-bromo-N-hydroxyimidazo[1,2-a]pyridine-3-carboxyamidine (compound in Production Example 244) by using 0.25 mL butyric acid chloride as an acylating agent in the same reaction as in Production Example 245.

$^1$H-NMR (CDCl$_3$)

δ: 1.08(t, J=7.2 Hz, 3H), 1.89–1.99(m, 2H), 2.97(t, J=7.2 Hz, 2H), 7.46(dd, J=9.6, 2.0 Hz, 1H), 7.66(dd, J=9.6, 0.8 Hz, 1H), 8.36(s, 1H), 9.35(dd, J=2.0, 0.8 Hz, 1H)

Production Example 261

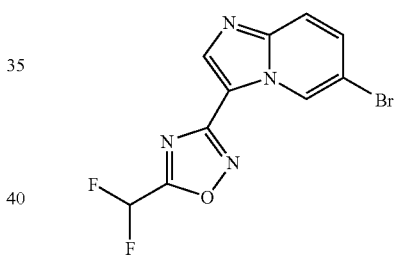

6-Bromo-3-(5-difluoromethyl-[1,2,4]oxadiazol-3-yl)imidazo[1,2-a]pyridine 2.0 mL N,N-diisopropylethylamine, 715 mg of 2-(1H-benzotriazol-1-yl)-1,1,3,3-tetramethyluronium tetrafluoroborate and 60 mg of 1-hydroxybenzotriazole were added in this order to a solution of 0.14 mL difluoroacetic acid in N,N-dimethylformamide (8 mL), and further 510 mg of 6-bromo-N-hydroxyimidazo[1,2-a]pyridine-3-carboxyamidine (compound in Production Example 244) was added thereto, and the mixture was stirred at room temperature for 1 hour and then at 100° C. for 5 hours. After addition of water, the reaction mixture was extracted with ethyl acetate, then the organic layer was washed with water and brine and dried over anhydrous sodium sulfate, the solvent was removed, and the resulting residue was purified by silica gel column chromatography (hexane/ethyl acetate) to give 258 mg of the title compound (colorless amorphous).

$^1$H-NMR (CDCl$_3$)

δ: 6.92(t, J=52.0 Hz, 1H), 7.52(dd, J=9.6, 2.0 Hz, 1H), 7.71(dd, J=9.6, 0.8 Hz, 1H), 8.43(s, 1H), 9.29(dd, J=2.0, 0.8 Hz, 1H)

Production Example 262

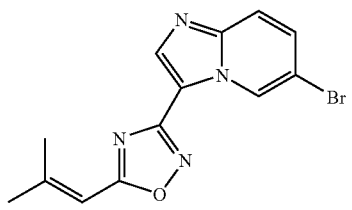

6-Bromo-3-[5-(2-methylpropenyl)-[1,2,4]oxadiazol-3-yl]imidazo[1,2-a]pyridine 91 mg of the title compound (colorless amorphous) was obtained from 300 mg of 6-bromo-N-hydroxyimidazo[1,2-a]pyridine-3-carboxyamidine (compound in Production Example 244) by using 0.16 mL 3,3-dimethylacrylic acid chloride as an acylating agent in the same reaction as in Production Example 245.

$^1$H-NMR (CDCl$_3$)

δ: 2.11(s, 3H), 2.39(s, 3H), 6.33–6.37(m, 1H), 7.45(dd, J=9.6, 2.4 Hz, 1H), 7.66(dd, J=9.6, 0.8 Hz, 1H), 8.37(s, 1H), 9.40(dd, J=2.4, 0.8 Hz, 1H)

Production Example 263

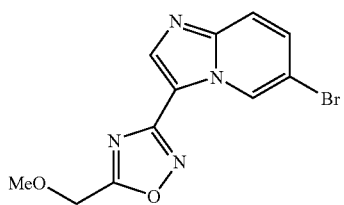

6-Bromo-3-(5-methoxymethyl-[1,2,4]oxadiazol-3-yl)imidazo-[1,2-a]pyridine

A suspension of 300 mg 6-bromo-N-hydroxyimidazo-[1,2-a]pyridine-3-carboxyamidine (compound in Production Example 244), 1.5 g of 4 Å molecular sieve powder and 60 mg of 60% sodium hydride in 5 mL tetrahydrofuran was stirred at 50° C. for 30 minutes, then 0.21 mL ethyl methoxyacetate was added thereto, and the mixture was heated for 2 hours under reflux. The reaction mixture was diluted with water and ethyl acetate and filtered through Celite, and the organic layer was washed with water and brine. The solution was dried over anhydrous sodium sulfate, the solvent was removed, and the resulting residue was purified by silica gel column chromatography (hexane/ethyl acetate) to give 135 mg of the title compound (colorless amorphous).

$^1$H-NMR (CDCl$_3$)

δ: 3.59(s, 3H), 4.80(s, 2H), 6.33–6.37(m, 1H), 7.48(dd, J=9.6, 2.0 Hz, 1H), 7.68(dd, J=9.6, 0.8 Hz, 1H), 8.41(s, 1H), 9.34(dd, J=2.0, 0.8 Hz, 1H)

Production Example 264

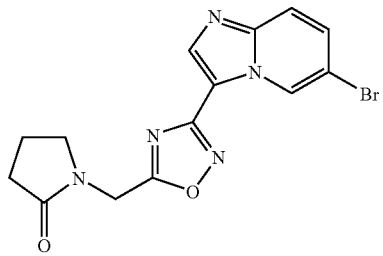

1-[3-(6-Bromoimidazo[1,2-a]pyridin-3-yl)-[1,2,4]oxadiazol-5-ylmethyl]-pyrrolidine-2-one 160 mg of the title compound (colorless amorphous) was obtained from 300 mg of 6-bromo-N-hydroxyimidazo[1,2-a]-pyridine-3-carboxyamidine (compound in Production Example 244) by using 0.24 mL methyl 2-oxo-1-pyrrolidine acetate as an acylating agent in the same reaction as in Production Example 263.

$^1$H-NMR (CDCl$_3$)

δ: 2.12–2.24(m, 2H), 2.47–2.56(m, 2H), 3.58–3.65(m, 2H), 4.84(s, 2H), 7.48(dd, J=9.6, 2.0 Hz, 1H), 7.67(dd, J=9.6, 0.8 Hz, 1H), 8.36(s, 1H), 9.30(dd, J=2.0, 0.8 Hz, 1H)

Production Example 265

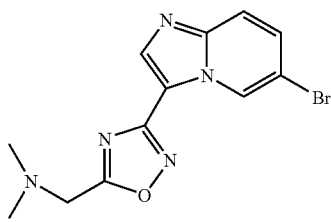

[3-(6-Bromoimidazo[1,2-a]pyridin-3-yl)-[1,2,4]oxadiazol-5-ylmethyl]-dimethylamine 159 mg of the title compound (colorless amorphous) was obtained from 310 mg of 6-bromo-N-hydroxyimidazo[1,2-a]pyridine-3-carboxyamidine (compound in Production Example 244) by using 0.26 mL N,N-dimethylglycine ethyl ester as an acylating agent in the same reaction as in Production Example 263.

¹H-NMR (CDCl₃)

δ: 2.45(s, 6H), 3.91(s, 2H), 7.47(dd, J=9.2, 2.0 Hz, 1H), 7.67(d, J=9.2 Hz, 1H), 8.41(s, 1H), 9.35(brs, 1H)

Production Example 266

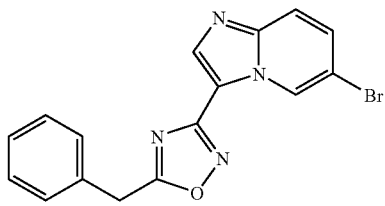

3-(5-Benzyl)-[1,2,4]oxadiazol-3-yl)-6-bromoimidazo[1,2-a]-pyridine 348 mg of the title compound (colorless crystals) was obtained from 690 mg of 6-bromo-N-hydroxyimidazo[1,2-a]pyridine-3-carboxyamidine (compound in Production Example 244) by using 0.66 mL methyl phenylacetate as an acylating agent in the same reaction as in Production Example 263.

¹H-NMR (CDCl₃)

δ: 4.34(s, 2H), 7.29–7.43(m, 5H), 7.45(dd, J=9.6, 2.0 Hz, 1H), 7.65(dd, J=9.6, 0.8 Hz, 1H), 8.36(s, 1H), 9.32(dd, J=2.0, 0.8 Hz, 1H)

Production Example 267

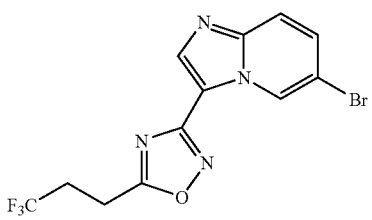

6-Bromo-3-[5-(3,3,3-trifluoropropyl)-[1,2,4]oxadiazol-3-yl]-imidazo[1,2-a]pyridine 423 mg of the title compound (colorless crystals) was obtained from 600 mg of 6-bromo-N-hydroxyimidazo[1,2-a]pyridine-3-carboxyamidine (compound in Production Example 244) by using 600 mg ethyl 4,4,4-trifluorobutyrate as an acylating agent in the same reaction as in Production Example 263.

¹H-NMR (CDCl₃)

δ: 2.72–2.87(m, 2H), 3.27(t, J=8.0 Hz, 2H), 7.48(dd, J=9.6, 2.0 Hz, 1H), 7.67(d, J=9.6 Hz, 1H), 8.36(s, 1H), 9.31(d, J=2.0 Hz, 1H)

Production Example 268

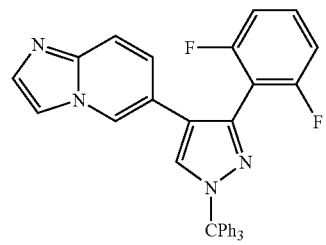

6-[3-(2,6-Difluorophenyl)-1-trityl-1H-4-pyrazolyl]imidazo[1,2-a]pyridine 2.89 g of the title compound (pale yellow amorphous) was obtained from 1.0 g of 6-bromoimidazo[1,2-a]pyridine and 4.0 g of 3-(2,6-difluorophenyl)-1-trityl-1H-4-pyrazolylboronic acid (compound in Production Example 211) in the same manner as in Production Example 34.

¹H-NMR (CDCl₃)

δ: 6.86–6.95(m, 2H), 6.97(dd, J=9.2, 2.4 Hz, 1H), 7.21–7.51(m, 19H), 7.56(s, 1H), 7.90–7.93(m, 1H)

Production Example 269

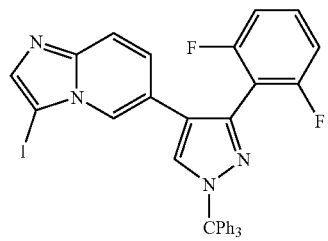

6-[3-(2,6-Difluorophenyl)-1-trityl-1H-4-pyrazolyl]-3-iodoimidazo[1,2-a]pyridine 3.08 g of the title compound was obtained as a pale brown amorphous was obtained from 2.89 g of 6-[3-(2,6-difluorophenyl)-1-trityl-1H-4-pyrazolyl]imidazo[1,2-a]pyridine (compound in Production Example 268) and 1.2 g of N-iodosuccinimide in the same manner as in Production Example 39.

¹H-NMR (CDCl₃)

δ: 6.90–7.00(m, 2H), 7.09(dd, J=9.2, 2.0 Hz, 1H), 7.22–7.42(m, 16H), 7.46(d, J=9.2 Hz, 1H), 7.61(s, 1H), 7.64(s, 1H), 7.85–7.88(m, 1H)

Production Example 270

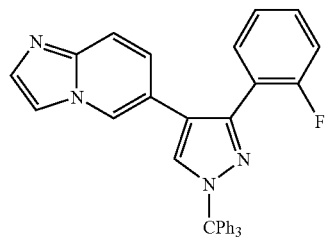

6-[3-(2-Fluorophenyl)-1-trityl-1H-4-pyrazolyl]imidazo[1,2-a]pyridine 2.49 g of the title compound (pale yellow amorphous) was obtained from 1.0 g of 6-bromoimidazo[1,2-a]pyridine and 4.0 g of 3-(2-fluorophenyl)-1-trityl-1H-4-pyrazolylboronic acid (compound in Production Example 197) in the same manner as in Production Example 34.

¹H-NMR (CDCl₃)

δ: 6.96(dd, J=9.2, 1.6 Hz, 1H), 6.98–7.04(m, 1H), 7.14 (ddd, J=8.0, 8.0, 1.2 Hz, 1H), 7.22–7.40(m, 17H), 7.41–7.47 (m, 2H), 7.50(s, 1H), 7.56(d, J=0.8 Hz, 1H), 7.90–7.93(m, 1H)

Production Example 271

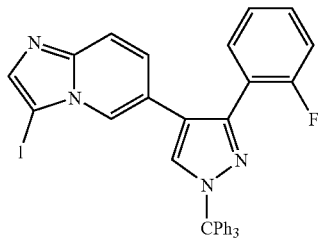

6-[3-(2-Fluorophenyl)-1-trityl-1H-4-pyrazolyl]-3-iodoimidazo[1,2-a]pyridine 2.73 g of the title compound was obtained as a pale brown amorphous from 2.49 g of 6-[3-(2-fluorophenyl)-1-trityl-1H-4-pyrazolyl]imidazo[1,2-a]pyridine (compound in Production Example 270) and 1.2 g of N-iodosuccinimide in the same manner as in Production Example 39.

¹H-NMR (CDCl₃)

δ: 6.92–7.10(m, 2H), 7.14–7.20(m, 1H), 7.24–7.43(m, 16H), 7.44–7.50(m, 2H), 7.58(s, 1H), 7.61(s, 1H), 7.85–7.89 (m, 1H)

Production Example 272

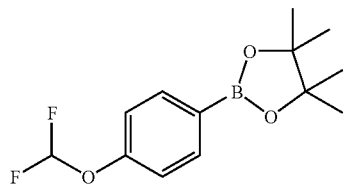

2-(4-Difluoromethoxyphenyl)-4,4,5,5-tetramethyl[1,3,2]-dioxaborolan 2.83 g of the title compound was obtained as a yellow oil from 3.0 g of 4-(difluoromethoxy) bromobenzene in the same manner as in Production Example 185.

¹H-NMR (CDCl₃)

δ: 1.35(s, 12H), 6.54(t, J=73.2 Hz, 1H), 7.09(d, J=8.4 Hz, 2H), 7.80(d, J=8.4 Hz, 2H)

Production Example 273

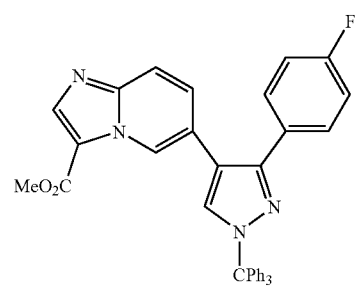

Methyl 6-[3-(4-fluorophenyl)-1-trityl-1H-pyrazol-4-yl]imidazo[1,2-a]pyridine-3-carboxylate 20 ml solution of 2.5 g 6-[3-(4-fluorophenyl)-1-trityl-1H-4-pyrazolyl]-3-iodoimidazo[1,2-a]pyridine (compound in Production Example 39) in anhydrous tetrahydrofuran was cooled to −70° C. or less in a dry ice/acetone bath in a stream of nitrogen, and 3 mL n-butyl lithium (1.57 M hexane solution) was added thereto little by little. The mixture was stirred for 50 minutes under the same conditions and then a suitable amount of dry ice was added thereto, and while the temperature of the mixture was increased gradually to room temperature, the mixture was stirred overnight. Diethyl ether, water, 1 N aqueous sodium hydroxide were added to the reaction solution, and the aqueous layer was separated. The organic layer was extracted with 1 N aqueous sodium hydroxide, and the combined aqueous layer was cooled and simultaneously neutralized with ammonium chloride.

This aqueous layer was extracted with ethyl acetate, and the organic layer was washed with brine and dried over anhydrous sodium sulfate. The drying agent was filtered off, and the filtrate was evaporated. 2.18 g crude product of 6-[3-(4-fluorophenyl)-1-trityl-1H-pyrazol-4-yl]imidazo[1,2a]pyridine-3-carboxylic acid was obtained as a pale brown amorphous. A mixture of this carboxylic acid, 0.38 mL dimethylsulfuric acid, 650 mg sodium bicarbonate and 30 mL acetone was heated for 4 hours under reflux. Ethyl acetate and water were added to the reaction solution, and then the organic layer was separated, washed with water and brine and dried over anhydrous sodium sulfate. The drying agent was filtered off, and the filtrate was evaporated. The resulting residue was purified by silica gel column chromatography (ethyl acetate/hexane) to give 742 mg of the title compound as a colorless amorphous.

¹H-NMR (CDCl₃)

δ: 3.89(s, 3H), 6.96(t, J=8.8 Hz, 2H), 7.25(m, 7H), 7.35(m, 9H), 7.43(m, 2H), 7.47(s, 1H), 7.62(dd, J=9.2, 1.2 Hz, 1H), 8.28(s, 1H), 9.20(dd, J=1.6, 1.2 Hz, 1H)

Production Example 274

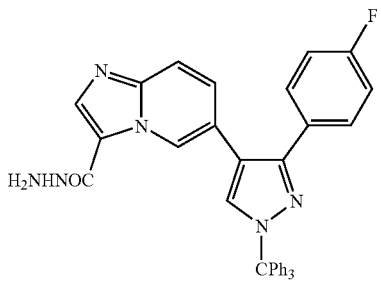

6-[3-(4-Fluorophenyl)-1-trityl-1H-pyrazol-4-yl]imidazo[1,2-a]pyridine-3-carboxylic acid hydrazide A mixture of 740 mg methyl 6-[3-(4-fluorophenyl)-1-trityl-1H-pyrazol-4-yl]imidazo[1,2-a]pyridine-3-carboxylate (compound in Production Example 273), 0.32 mL hydrazine monohydrate and 20 mL ethanol was heated for 6 hours under reflux. The reaction solution was evaporated, and the resulting residue was purified by NH silica gel column chromatography (ethyl acetate/hexane) to give 283 mg of the title compound as a color amorphous.
$^{1}$H-NMR (CDCl$_3$)
δ: 4.04(br, 2H), 6.95(t, J=8.8 Hz, 2H), 7.19(dd, J=9.2, 1.6 Hz, 1H), 7.25(m, 6H), 7.30(brs, 1H), 7.35(m, 9H), 7.43(m, 2H), 7.46(s, 1H), 7.59(dd, J=9.2, 1.2 Hz, 1H), 8.01(s, 1H), 9.31(dd, J=1.6, 1.2 Hz, 1H)

Production Example 275

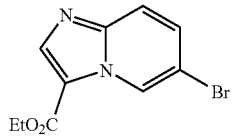

Ethyl 6-bromoimidazo[1,2-a]pyridine-3-carboxylate

A mixture of 9.69 g 6-bromo-3-iodoimidazo[1,2-a]pyridine (compound in Production Example 49) and 450 mL anhydrous tetrahydrofuran was added little by little to 4.5 mL isopropyl magnesium bromide (0.75 M tetrahydrofuran solution) under ice-cooling in a stream of nitrogen. Then, this reaction solution was returned to room temperature and stirred for 1.5 hours. The reaction solution was cooled to −60° C. or less in a dry ice/acetone bath, 50 mL solution of 4.5 mL ethyl chlorocarbonate in anhydrous tetrahydrofuran was added dropwise thereto over 30 minutes, and the temperature of the reaction solution was increased to 0° C. After saturated sodium bicarbonate was added to the reaction solution, ethyl acetate and water were added thereto, and the organic layer was separated. The aqueous layer was saturated with common salt and then extracted with ethyl acetate. The combined organic layer was washed with brine and then dried over anhydrous sodium sulfate. The drying agent was filtered off, and the filtrate was evaporated. The resulting residue was purified by NH silica gel column chromatography (ethyl acetate/hexane) to give 5.09 g of the title compound as white crystals.

$^{1}$H-NMR (CDCl$_3$)
δ: 1.43(t, J=7.2 Hz, 3H), 4.43 (q, J=7.2 Hz, 2H), 7.49(dd, J=9.2, 2.0 Hz, 1H), 7.63(dd, J=9.2, 0.8 Hz, 1H), 8.27(s, 1H), 9.49(dd, J=2.0, 0.8 Hz, 1H)

Production Example 276

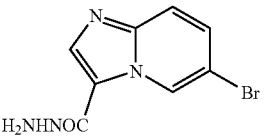

6-Bromoimidazo[1,2-a]pyridine-3-carboxylic acid hydrazide

A mixture of 1.94 g ethyl 6-bromoimidazo[1,2-a]pyridine-3-carboxylate, 6 mL hydrazine monohydrate and 20 mL ethanol was heated for 1 hour under reflux. The precipitated crystals were collected by filtration, washed with ethanol and dried under reduced pressure by a vacuum pump to give 1.71 g of the title compound as pale yellow crystals.
$^{1}$H-NMR (DMSO-d$_6$)
δ: 4.50(brs, 2H), 7.59(dd, J=9.6, 2.0 Hz, 1H), 7.72(dd, J=9.6, 0.8 Hz, 1H), 8.30(s, 1H), 9.62(dd, J=2.0, 0.8 Hz, 1H), 9.86(brs, 1H)

Production Example 277

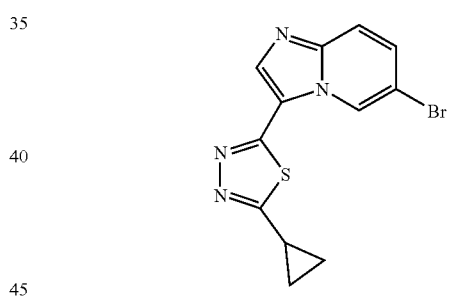

6-Bromo-3-(5-cyclopropyl[1,3,4]thiadiazol-2-yl)imidazo[1,2-a]pyridine 0.22 mL cyclopropane carbonyl chloride was added at room temperature to a mixture of 510 mg 6-bromoimidazo[1,2-a]pyridine-3-carboxylic acid hydrazide (compound in Production Example 276), 202 mg sodium bicarbonate, 15 mL tetrahydrofuran and 15 mL water, and the mixture was stirred overnight. The organic layer was separated by adding saturated sodium bicarbonate, common salt and tetrahydrofuran to the reaction solution. The aqueous layer was further extracted with tetrahydrofuran, and the combined organic layer was washed with brine and then dried over anhydrous sodium sulfate. The drying agent was filtered off, and the filtrate was evaporated. Diisopropyl ether was added to the resulting residues, and the formed crystals were collected by filtration and dried under reduced pressure by a vacuum pump. 606 mg crude product of cyclopropane carboxylic acid N'-(6-bromoimidazo[1,2-a]-pyridine-3-carbonyl)hydrazide was obtained as pale brown crystals. A mixture of 200 mg of this carboxylic acid hydrazide derivative, 250 mg Lawesson's reagent and 20 mL anhydrous toluene was heated for 1 hour under reflux. The reaction solution was evaporated, and the resulting residue was purified by NH silica gel column chromatography (ethyl acetate/hexane) to give 48 mg of the title compound as a white solid.

$^1$H-NMR (CDCl$_3$)

δ: 1.21–1.33(m, 4H), 2.45(m, 1H), 7.47(dd, J=9.2, 2.0 Hz, 1H), 7.63(dd, J=9.2, 0.8 Hz, 1H), 8.02(s, 1H), 9.89(dd, J=2.0, 0.8 Hz, 1H)

Production Example 278

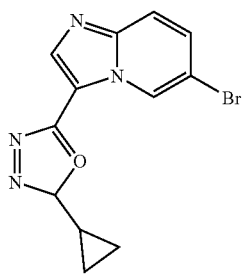

6-Bromo-3-(5-cyclopropyl[1,3,4]oxadiazol-2-yl)imidazo[1,2-a]pyridine

A mixture of 200 mg crude product of cyclopropane carboxylic acid N'-(6-bromoimidazo[1,2-a]pyridine-3-carbonyl)hydrazide obtained in the synthesis process in Production Example 277, 3 mL phosphorus oxychloride and 5 mL acetonitrile was heated for 2 hours under reflux. The reaction solution was evaporated, and ethyl acetate and water were added to the residues which were then poured into a mixture of iced water and saturated sodium bicarbonate. The organic layer was separated, washed with brine and dried over anhydrous sodium sulfate. The drying agent was filtered off, and the filtrate was evaporated. The resulting residue was purified by NH silica gel column chromatography (ethyl acetate/hexane) to give 50 mg of the title compound as a white solid.

$^1$H-NMR (CDCl$_3$)

δ: 1.25(m, 4H), 2.28(m, 1H), 7.50(dd, J=9.6, 1.6 Hz, 1H), 7.67(dd, J=9.6, 0.8 Hz, 1H), 8.19(s, 1H), 9.60(dd, J=2.0, 0.8 Hz, 1H)

Production Example 279

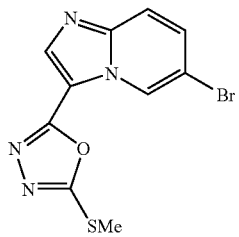

6-Bromo-3-(5-methylsulfanyl[1,3,4]oxadiazol-2-yl)imidazo[1,2-a]pyridine

A mixture of 1 g 6-bromoimidazo[1,2-a]pyridine-3-carboxylic acid hydrazide (compound in Production Example 276), 0.24 mL carbon disulfide, 157 mg sodium hydroxide, 15 mL ethanol and 15 mL water was heated for 5 hours under reflux. The reaction solution was poured into a mixture of iced water and an aqueous saturated ammonium chloride solution, and the precipitated crystals were collected by filtration. 1 N hydrochloric acid was added to the filtrate, and the resulting crystals were also collected by filtration. The combined crystals were dried under reduced pressure by a vacuum pump, to give 1.12 g crude product of 5-(6-bromoimidazo[1,2-a]pyridin-3-yl)[1,3,4]oxadiazole-2-thiol as pale brown crystals. 60 μL methyl iodide was added to a mixture of 258 mg of this thiol derivative, 242 mg potassium carbonate and 30 mL N,N-dimethylformamide under ice-coolingd water in a stream of nitrogen, and the mixture was stirred for 10 minutes. Ethyl acetate and water were added to the reaction solution, and the organic layer was separated. The aqueous layer was saturated with common salt and then extracted with ethyl acetate. The combined organic layer was washed twice with water and then with brine and dried over anhydrous sodium sulfate. The drying agent was filtered off, and the filtrate was evaporated. Hexane was added to the resulting residues, the crystals were collected by filtration and dried under reduced pressure with a vacuum pump. 245 mg of the title compound was obtained as pale brown crystals.

$^1$H-NMR (CDCl$_3$)

δ: 2.81(s, 3H), 7.52(dd, J=9.2, 2.0 Hz, 1H), 7.68(dd, J=9.6, 0.8 Hz, 1H), 8.22(s, 1H), 9.55(dd, J=2.0, 0.8 Hz, 1H)

Production Example 280

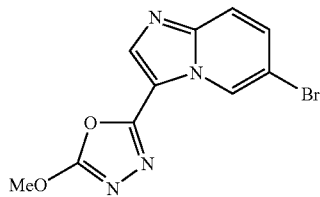

6-Bromo-3-(5-methoxy[1,3,4]oxadiazol-2-yl)imidazo[1,2-a]pyridine 1.16 g of m-chloroperbenzoic acid was added to a mixture of 981 mg 6-bromo-3-(5-methylsulfanyl[1,3,4]oxadiazol-2-yl)imidazo[1,2-a]pyridine (compound in Production Example 279) and 30 mL dichloromethane under ice-coolingd water, then retuned to room temperature and stirred overnight. Ethyl acetate and an aqueous saturated sodium thiosulfate solution were added to the reaction solution, and the mixture was stirred. The organic layer was separated, washed twice with an aqueous saturated sodium bicarbonate solution and then with brine and dried over anhydrous sodium sulfate. The drying agent was filtered off, and the filtrate was evaporated. 995 mg crude product of a mixture of 6-bromo-3-(5-methanesulfinyl[1,3,4]oxadiazol-2-yl)imidazo[1,2-a]pyridine and 6-bromo-3-(5-methylsulfonyl[1,3,4]oxadiazol-2-yl)imidazo[1,2-a]pyridine was obtained as pale brown crystals. A mixture of 150 mg of this mixture, 90 μL methylamine (30% methanol solution) and 10 mL methanol was stirred at room temperature for 10 minutes. Ethyl acetate, tetrahydrofuran and water were added to the reaction solution, and the organic layer was separated. The aqueous layer was saturated with common salt and then extracted with ethyl acetate. The combined organic layer was washed with brine and then dried over anhydrous sodium sulfate. The drying agent was filtered off, and the filtrate was evaporated. The resulting residue was purified by NH silica gel column chromatography (ethyl acetate/hexane) to give 121 mg of the title compound as a white solid.

$^1$H-NMR (CDCl$_3$)

δ: 4.28(s, 3H), 7.49(dd, J=9.6, 2.0 Hz, 1H), 7.66(dd, J=9.6, 0.8 Hz, 1H), 8.14(s, 1H), 9.50(dd, J=2.0, 0.8 Hz, 1H)

Production Example 281

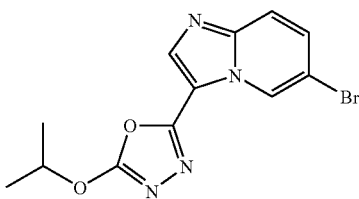

6-Bromo-3-(5-isopropoxy[1,3,4]oxadiazol-2-yl)imidazo[1,2-a]pyridine

A mixture consisting of 60 mg crude product of a mixture of 6-bromo-3-(5-methanesulfinyl[1,3,4]oxadiazol-2-yl)imidazo[1,2-a]pyridine and 6-bromo-3-(5-methylsulfonyl[1,3,4]oxadiazol-2-yl)imidazo[1,2-a]pyridine obtained in the synthesis process in Production Example 280, 2 mL isopropyl alcohol, 0.3 mL triethylamine and 3 mL anhydrous tetrahydrofuran was heated overnight under reflux. An aqueous saturated ammonium chloride solution, ethyl acetate and water were added to the reaction solution, and the organic layer was separated, washed with brine and dried over anhydrous sodium sulfate. The drying agent was filtered off, and the filtrate was evaporated. The resulting residue was purified by NH silica gel column chromatography (ethyl acetate/hexane) to give 33 mg of the title compound as a white solid.

$^1$H-NMR (CDCl$_3$)

δ: 1.54(d, J=6.4 Hz, 6H), 5.24(m, 1H), 7.48(dd, J=9.6, 2.0 Hz, 1H), 7.66(dd, J=9.6, 0.8 Hz, 1H), 8.13(s, 1H), 9.52(dd, J=2.0, 0.8 Hz, 1H)

Production Example 282

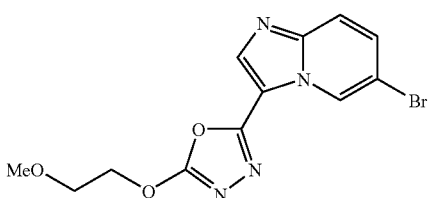

6-Bromo-3-[5-(2-methoxyethoxy)[1,3,4]oxadiazol-2-yl]imidazo[1,2-a]pyridine 56 mg of the title compound was obtained as a white solid by the same reaction as in Production Example 281 from 60 mg crude product of a mixture of 6-bromo-3-(5-methanesulfinyl[1,3,4]oxadiazol-2-yl)imidazo[1,2-a]pyridine and 6-bromo-3-(5-methylsulfonyl[1,3,4]oxadiazol-2-yl)imidazo[1,2-a]pyridine obtained in the synthesis process in Production Example 280 and 2 mL 2-methoxyethanol.

$^1$H-NMR (CDCl$_3$)

δ: 3.46(s, 3H), 3.84(m, 2H), 4.73(m, 2H), 7.49(dd, J=9.6, 2.0 Hz, 1H), 7.67(dd, J=9.6, 0.8 Hz, 1H), 8.13(s, 1H), 9.49(dd, J=2.0, 0.8 Hz, 1H)

Production Example 283

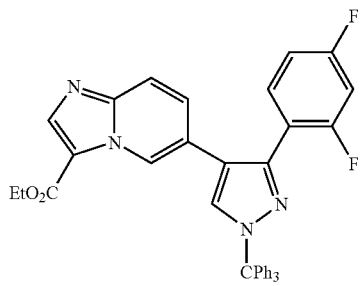

Ethyl 6-[3-(2,4-difluorophenyl)-1-trityl-1H-pyrazol-4-yl]imidazo[1,2-a]pyridine-3-carboxylate 665 mg of the title compound was obtained as a colorless amorphous from 286 mg of ethyl 6-bromoimidazo[1,2-a]pyridine-3-carboxylate (compound in Production Example 275) and 1.5 g of 3-(2,4-difluorophenyl)-1-trityl-1H-4-pyrazolylboronic acid (compound in Production Example 172) by the same reaction as in Production Example 34.

$^1$H-NMR (CDCl$_3$)

δ: 1.37(t, J=7.2 Hz, 3H), 4.35 (q, J=7.2 Hz, 2H), 6.76(m, 1H), 6.89(m, 1H), 7.18(dd, J=9.2, 1.6 Hz, 1H), 7.25(m, 6H), 7.35(m, 9H), 7.43(m, 1H), 7.56(s, 1H), 7.58(dd, J=9.2, 0.8 Hz, 1H), 8.25(s, 1H), 9.13(dd, J=1.6, 0.8 Hz, 1H)

Production Example 284

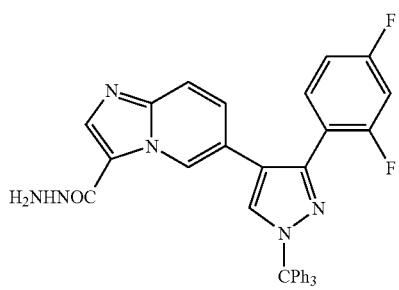

6-[3-(2,4-Difluorophenyl)-1-trityl-1H-pyrazol-4-yl]imidazo[1,2-a]pyridine-3-carboxylic acid hydrazide 195 mg of the title compound was obtained as pale brown crystals from 306 mg of ethyl 6-[3-(2,4-difluorophenyl)-1-trityl-1H-pyrazol-4yl]imidazo[1,2-a]pyridine-3-carboxylate (compound in Production Example 283) by the same reaction as in Production Example 274.

¹H-NMR (CDCl₃)

δ: 4.01(brs, 2H), 6.75(m, 1H), 6.89(m, 1H), 7.14(dd, J=9.2, 1.6 Hz, 1H), 7.25(m, 6H), 7.35(m, 9H), 7.43(m, 1H), 7.55(dd, J=9.2, 1.2 Hz, 1H), 7.56(s, 1H), 7.97(s, 1H), 9.24(dd, J=1.6, 1.2 Hz, 1H)

Production Example 285

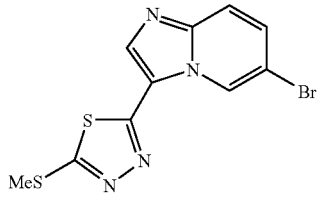

6-Bromo-3-(5-methylsulfanyl[1,3,4]thiadiazol-2-yl)imidazo[1,2-a]pyridine 66 mg potassium hydroxide (powder) was added to a mixture of 306 mg of 6-bromoimidazo[1,2-a]pyridine-3-carboxylic acid hydrazide (compound in Production Example 276), 195 mg carbon disulfide and 12 mL methanol under cooling with ice-water, and the mixture was stirred for 2.5 hours. Then, the reaction mixture was returned to room temperature, and 4 hours later, 75 μL methyl iodide was added thereto and stirred overnight. Ethyl acetate and water were added to the reaction solution, and the organic layer was separated, then washed with an aqueous saturated sodium bicarbonate solution and brine and dried over anhydrous sodium sulfate. The drying agent was filtered off, and the filtrate was evaporated. 243 mg crude product of methyl N'-(6-bromoimidazo[1,2-a]pyridine-3-carbonyl)hydrazine carbodithioate was obtained as pale yellow crystals. A mixture of this compound, 255 mg p-toluenesulfonic acid monohydrate and 15 mL toluene was heated for 1.5 hours under reflux. Ethyl acetate, tetrahydrofuran and water were added to the reaction solution which was then basified with sodium bicarbonate. The organic layer was separated, washed with brine and dried over anhydrous sodium sulfate. The drying agent was filtered off, and the filtrate was evaporated. The resulting residue was purified by NH silica gel column chromatography (ethyl acetate/hexane) to give 20 mg of the title compound as a white solid.

¹H-NMR (CDCl₃)

δ: 2.88(s, 3H), 7.49(dd, J=9.6, 2.0 Hz, 1H), 7.65(dd, J=9.6, 0.8 Hz, 1H), 8.02(s, 1H), 9.85(dd, J=2.0, 0.8 Hz, 1H)

Production Example 286

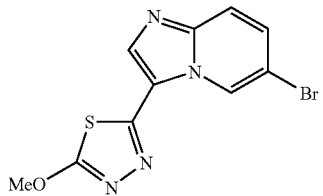

6-Bromo-3-(5-methoxy[1,3,4]thiadiazol-2-yl)imidazo[1,2-a]pyridine 9 mg of the title compound was obtained as a pale yellow amorphous from 18 mg of 6-bromo-3-(5-methylsulfanyl-[1,3,4]thiadiazol-2yl)imidazo[1,2-a]pyridine (compound in Production Example 285) by the same reaction as in Production Example 280.

¹H-NMR (CDCl₃)

δ: 4.28(s, 3H), 7.46(dd, J=9.6, 2.0 Hz, 1H), 7.65(dd, J=9.6, 0.8 Hz, 1H), 7.93(s, 1H), 9.80(dd, J=2.0, 0.8 Hz, 1H)

Production Example 287

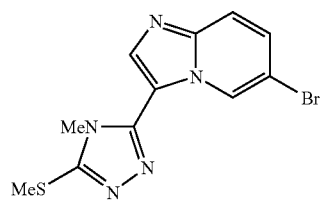

6-Bromo-3-(4-methyl-5-methylsulfanyl-4H-[1,2,4]triazol-3-yl)imidazo[1,2-a]pyridine 82 μL methyl isocyanate and 0.6 mL of 2 N aqueous sodium hydroxide were added in this order to a mixture of 306 mg 6-bromoimidazo[1,2-a]pyridine-3-carboxylic acid hydrazide (compound in Production Example 276) and 5 mL ethanol at room temperature, and then the mixture was stirred for 2 days. Saturated ammonium chloride and water were added to the reaction solution, and the resulting crystals were collected by filtration, washed water and dried overnight with hot air at 70° C. The crystals were triturated with ethylacetate and diisopropylether, collected by filtration and dried under reduced pressure with a vacuum pump. 283 mg crude product of 1-(6-bromoimidazo[1,2-a]pyridine-3-carboxyl)-4-methylthiose micarbazide was obtained as pale brown crystals. A mixture of this compound and 10 mL of 5% aqueous sodium carbonate was heated for 1.5 hours under reflux. Saturated ammonium chloride was added to the reaction solution, and the crystals were collected by filtration, washed with water, and dried under reduced pressure with a vacuum pump. 208 mg crude product of 5-(6-bromoimidazo[1,2-a]pyridin-3-yl)-4-methyl-2,4-dihydro[1, 2, 4]triazole-3-thione was obtained as pale yellow crystals. 50 μL methyl iodide was added to a mixture consisting of this compound, 187 mg potassium carbonate and 15 mL N,N-dimethylformamide under ice-coolingd water in a stream of nitrogen, and the mixture was stirred overnight. Ethyl acetate, tetrahydrofuran and water were added to the reaction solution, and the organic layer was separated. The aqueous layer was saturated with common salt and then extracted with ethyl acetate. The combined organic layer was washed twice with water and then with brine and dried over anhydrous sodium sulfate. The drying agent was filtered off, and the filtrate evaporated. The resulting residue was purified by NH silica gel column chromatography (ethyl acetate/hexane) to give 107 mg of the title compound as pale yellow crystals.

¹H-NMR (CDCl₃)

δ: 2.82(s, 3H), 3.77(s, 3H), 7.45(dd, J=9.6, 2.0 Hz, 1H), 7.63(dd, J=9.6, 0.8 Hz, 1H), 7.99(s, 1H), 9.75(dd, J=2.0, 0.8 Hz, 1H)

Production Example 288

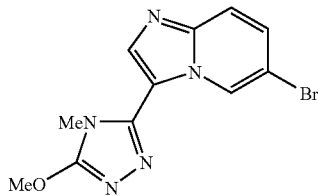

6-Bromo-3-(5-methoxy-4-methyl-4H-[1,2,4]triazol-3-yl)-imidazo[1,2-a]pyridine 35 mg of the title compound was obtained as a pale brown amorphous from 50 mg of 6-bromo-3-(4-methyl-5-methylsulfanyl-4H-[1,2,4]triazol-3-yl)imidazo[1,2-a]pyridine (compound in Production Example 287) by the same reaction as in Production Example 280.

$^1$H-NMR (CDCl$_3$)
$^1$H-NMR (CDCl$_3$)
δ: 3.64(s, 3H), 4.25(s, 3H), 7.44(dd, J=9.6, 1.6 Hz, 1H), 7.62(d, J=9.6 Hz, 1H), 7.95(s, 1H), 9.79(brs, 1H)

Production Example 289

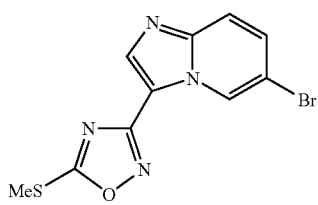

6-Bromo-3-(5-methylsulfanyl[1,2,4]oxadiazol-3-yl)imidazo[1,2-a]pyridine 77 mg of the title compound was obtained as a white solid from 1.02 g of 6-bromo-N-hydroxyimidazo[1,2-a]pyridine-3-carboxyamidine (compound in Production Example 244) by the same reaction as in Production Example 279.

$^1$H-NMR (CDCl$_3$)
δ: 2.85(s, 3H), 7.44(dd, J=9.6, 2.0 Hz, 1H), 7.65(dd, J=9.6, 0.8 Hz, 1H), 8.45(s, 1H), 9.84(dd, J=2.0, 0.8 Hz, 1H)

Production Example 290

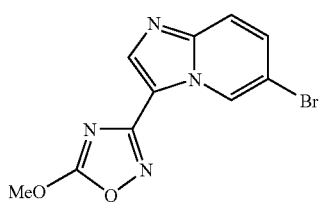

6-Bromo-3-(5-methoxy[1,2,4]oxadiazol-3-yl)imidazo[1,2-a]-pyridine 12 mg of the title compound was obtained as a colorless amorphous from 105 mg of 6-bromo-3-(5-methylsulfanyl-[1,2,4]oxadiazol-3-yl)imidazo[1,2-a]pyridine (compound in Production Example 289) by the same reaction as in Production Example 280.

$^1$H-NMR (CDCl$_3$)
δ: 4.28(s, 3H), 7.43(dd, J=9.6, 1.6 Hz, 1H), 7.63(dd, J=9.6, 0.8 Hz, 1H), 8.34(s, 1H), 9.85(dd, J=1.6, 0.8 Hz, 1H)

Production Example 291

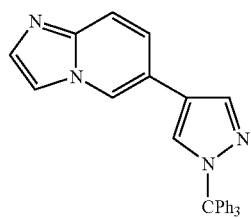

6-(1-Trityl-1H-4-pyrazolyl)imidazo[1,2-a]pyridine 8.9 g of the title compound was obtained from 4.6 g of 6-bromoimidazo[1,2-a]pyridine and 10 g of 1-trityl-1H-4-pyrazolylboronic acid by the same method as in Production Example 34.

$^1$H-NMR (DMSO-d$_6$)
δ: 7.18–7.22(m, 6H), 7.24(dd, J=9.6, 1.6 Hz, 1H), 7.32–7.37(m, 9H), 7.55–7.61(m, 3H), 7.62(d, J=0.8 Hz, 1H), 7.91(d, J=0.8 Hz, 1H), 8.22(dd, J=1.6, 0.8 Hz, 1H)

Production Example 292

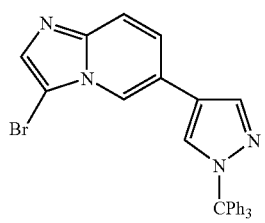

3-Bromo-6-(1-trityl-1H-4-pyrazolyl)imidazo[1,2-a]pyridine 6.2 g of the title compound (pale yellow crystals) was obtained from 6.4 g of 6-(1-trityl-1H-4-pyrazolyl)imidazo[1,2-a]pyridine (compound in Production Example 291) and 2.88 g N-bromosuccinimide in the same manner as in Production Example 39.

$^1$H-NMR (CDCl$_3$)
δ: 7.18–7.23(m, 6H), 7.29(dd, J=9.2, 1.8 Hz, 1H), 7.33–7.38(m, 9H), 7.58(dd, J=9.2, 0.8 Hz, 1H), 7.60(s, 1H), 7.66(d, J=1.0 Hz, 1H), 7.95(d, J=1.0 Hz, 1H), 8.15(dd, J=1.8, 0.8 Hz, 1H)

Production Example 293

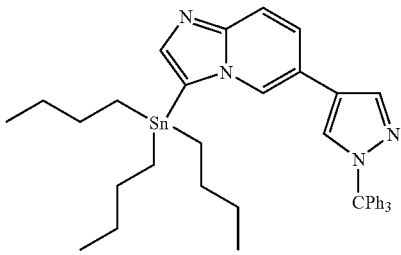

3-(1,1,1-Tributylstannyl)-6-(1-trityl-1H-4-pyrazolyl)imidazo[1,2-a]pyridine 6.7 g of the title compound was obtained as a pale brown viscous material by the same reaction as in Production Example 48 from 5.1 g of 3-bromo-6-(1-trityl-1H-4-pyrazolyl)imidazo[1,2-a]pyridine obtained in Production Example 292.

$^1$H-NMR (CDCl$_3$)

δ: 0.86(t, J=7.2 Hz, 9H), 1.16–1.21(m, 6H), 1.34(sext. J=7.2 Hz, 6H), 1.50–1.59(m, 6H), 7.18–7.24(m, 7H), 7.32–7.37(m, 9H), 7.56(s, 1H), 7.58(d, J=0.8 Hz, 1H), 7.60(dd, J=9.2, 0.8 Hz, 1H), 7.88(d, J=0.8 Hz, 1H), 8.13(dd, J=1.6, 0.8 Hz, 1H)

Production Example 294

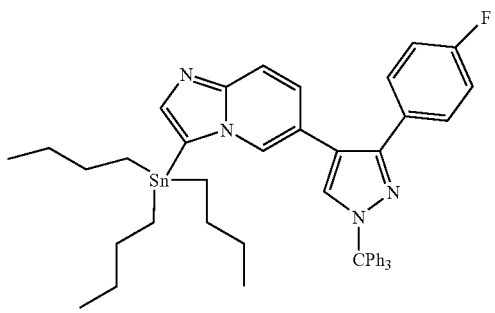

6-[3-(4-Fluorophenyl)-1-trityl-1H-4-pyrazolyl]-3-(1,1,1-tributylstannyl)imidazo[1,2-a]pyridine 1.78 g of the title compound was obtained as a pale yellow amorphous from 4 g of 6-[3-(4-fluorophenyl)-1-trityl-1H-4-pyrazolyl]-3-iodoimidazo[1,2-a]pyridine (compound in Production Example 39) in the same manner as in Production Example 48.

$^1$H-NMR (CDCl$_3$)

δ: 0.84(t, J=7.2 Hz, 9H), 1.00–1.05(m, 6H), 1.21–1.32(m, 6H), 1.41–1.51(m, 6H), 6.94–6.99(m, 2H), 7.04(dd, J=8.8, 2.4 Hz, 1H), 7.22–7.29(m, 6H), 7.31–7.37(m, 9H), 7.39(s, 1H), 7.45–7.49(m, 2H), 7.55(s, 1H), 7.57(dd, J=8.8, 0.8 Hz, 1H), 7.85–7.87(m, 1H)

Production Example 295

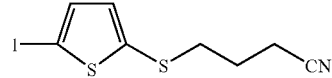

4-[(5-Iodo-2-thienyl)sulfanyl]butane nitrile 2.3 g of thiophen-2-thiol, 3.0 g of 4-bromobutyronitrile and 5.5 g of potassium carbonate were stirred in N,N-dimethylformamide at room temperature to give 3.4 g of 4-(2-thienylsulfanyl)butane nitrile. 3.4 g of 4-(2-thienylsulfanyl)butane nitrile was reacted with 5.4 g of N-iodosuccinimide in N,N-dimethylformamide, whereby 5.5 g of the title compound was obtained as a pale yellow oil.

$^1$H-NMR (CDCl$_3$)

δ: 1.95(quint., J=7.0 Hz, 2H), 2.52(t, J=7.0 Hz, 2H), 2.87(t, J=7.0 Hz, 2H), 6.83(dd, J=3.6, 0.8 Hz, 1H), 7.21(dd, J=3.6, 0.8 Hz, 1H)

Production Example 296

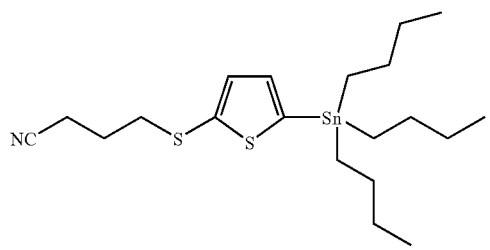

4-[5-(1,1,1-Tributylstannyl)-2-thienyl]sulfanyl]butane nitrile 5.0 mL isopropyl magnesium bromine (0.75 M tetrahydrofuran solution) was added dropwise to a solution of 1.0 g 4-[(5-iodo-2-thienyl)sulfanyl]butane nitrile obtained in Production Example 295 in dry tetrahydrofuran (20 mL), then the mixture was stirred for 1 hour, and 0.88 mL tributyltin chloride was added thereto and stirred at −40° C. for 3 hours. An aqueous saturated ammonium chloride solution was added to the reaction solution which was then extracted with ethyl acetate and purified by NH silica gel chromatography (hexane/ethyl acetate) to give 1.7 g of the title compound as a pale brown oil.

$^1$H-NMR (CDCl$_3$)

δ: 0.90(t, J=7.2 Hz, 9H), 1.08–1.13(m, 6H), 1.33(sext. J=7.2 Hz, 6H), 1.51–1.60(m, 6H), 1.94(quint., J=7.0 Hz, 2H), 2.53(t, J=7.0 Hz, 2H), 2.89(t, J=7.0 Hz, 2H), 7.04(d, J=3.6, 0.4 Hz, 1H), 7.21(d, J=3.6, 0.4 Hz, 1H)

Production Example 297

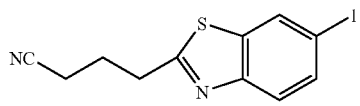

4-(6-Iodo-1,3-benzothiazol-2-yl)butane nitrile 1.1 g of 4-(6-amino-1,3-benzothiazol-2-yl)butane nitrile synthesized according to a method described in JP-A 5-194440, 2 mL isoamyl nitrite, 0.96 g of copper (I) iodide and 2 mL diiodomethane were heated in tetrahydrofuran at 80° C. for 1 hour. After the solvent was removed, the residue was purified by NH silica gel column to give 888 mg of the title compound as colorless crystals.

$^1$H-NMR (CDCl$_3$)

δ: 2.29(quint, J=7.2 Hz, 2H), 2.56(t, J=7.2 Hz, 2H), 3.26(t, J=7.2 Hz, 2H), 7:70(d, J=8.8 Hz, 1H), 7.76(dd, J=8.8, 1.6 Hz, 1H), 8.19(d, J=1.6 Hz, 1H)

Production Example 298

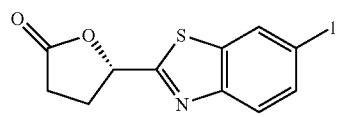

(5S)-5-(6-Iodo-1,3-benzothiazol-2-yl)tetrahydro-2-furanone 3.8 g of the title compound was obtained as pale reddish orange crystals by the same method as in Production Example 297 from 5.6 g of (5S)-5-(6-amino-1,3-benzothiazol-2-yl)tetrahydro-2-furanone synthesized according to a method described in JP-A 5-194440.

$^1$H-NMR (CDCl$_3$)

δ: 2.64–2.74(m, 3H), 2.82–2.90(m, 1H), 5.81–5.85(m, 1H), 7.75(dd, J=8.8, 0.4 Hz, 1H), 7.80(dd, J=8.8, 1.6 Hz, 1H), 8.27(dd, J=1.6, 0.4 Hz, 1H)

Production Example 299

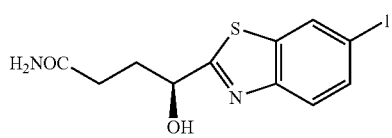

(4S)-4-Hydroxy-4-(6-iodo-1,3-benzothiazol-2-yl) butane amide 750 mg of (5S)-5-(6-iodo-1,3-benzothiazol-2-yl)tetrahydro-2-furanone obtained in Production Example 298 was dissolved in a solvent mixture of 2 mL acetonitrile and 2 mL tetrahydrofuran, then 2 mL of 28% ammonia water was added thereto, and the mixture was stirred at room temperature for 1 hour. Water was added thereto, and the reaction solution was extracted with ethyl acetate, and the organic layer was dried over magnesium sulfate. The solvent was removed, and the residue was recrystallized from ethanol/ethyl acetate/hexane, whereby 765 mg of the title compound was obtained as pale orange crystals.

$^1$H-NMR (CDCl$_3$)

δ: 2.26–2.36(m, 1H), 2.42–2.51(m, 1H), 2.56(t, J=6.0 Hz, 2H), 5.14–5.20(m, 1H), 5.51(brs, 1H), 5.65(brs, 1H), 5.79(d, 4.4 Hz, 1H), 7.69(d, J=8.8 Hz, 1H), 7.75(dd, J=8.8, 1.6 Hz, 1H), 8.25(d, J=1.6 Hz, 1H)

Production Example 300

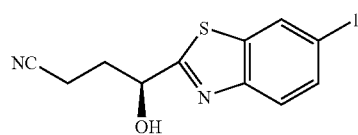

(4S)-4-Hydroxy-4-(6-iodo-1,3-benzothiazol-2-yl) butane nitrile 0.33 mL trifluoroacetic anhydride was added to a solution of 556 mg of (4S)-4-hydroxy-4-(6-iodo-1,3-benzothiazol-2-yl)butane amide obtained in Production Example 299 and 0.25 mL pyridine in tetrahydrofuran under ice-cooling, and the mixture was stirred for 2 hours. Water was added thereto, the reaction solution was then extracted with ethyl acetate, and the organic layer was dried over magnesium sulfate and purified by NH silica gel chromatography. The product was recrystallized from ethanol/ethyl acetate/hexane, to give 390 mg of the title compound as colorless crystals.

$^1$H-NMR (CDCl$_3$)

δ: 2.20–2.30(m, 1H), 2.37–2.47(m, 1H), 2.53–2.62(m, 1H), 2.64–2.74(m, 1H), 3.22(d, J=5.2 Hz, 1H), 5.19–5.25(m, 1H), 7.72(d, J=8.4 Hz, 1H), 7.79(dd, J=8.4, 1.6 Hz, 1H), 8.25(d, J=1.6 Hz, 1H)

Production Example 301

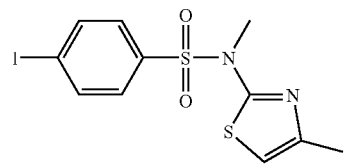

N1-Methyl-N1-(4-methyl-1,3-thiazol-2-yl)-4-iodo-1-benzene sulfonamide 760 mg of N1-(4-methyl-1,3-thiazol-2-yl)-4-iodo-1-benzene sulfonamide obtained by reacting 4-iodobenzenesulfonyl chloride with 2-amino-4-methylthiazole in pyridine was dissolved in a solvent mixture of 5 mL methanol and 3 mL tetrahydrofuran, then 1.1 mL (trimethylsilyl)diazomethane (2 M hexane solution) was added thereto, and the mixture was stirred for 1 hour. The solvent was evaporated and purified with an NH silica gel column, to give 335 mg of the title compound as a pale yellow solid.

$^1$H-NMR (CDCl$_3$)

δ: 2.28(d, J=1.2, 3H), 3.41(s, 3H), 6.53(d, J=1.2 Hz, 1H), 7.49–7.53(m, 2H), 7.82–7.87(m, 2H)

Production Example 302

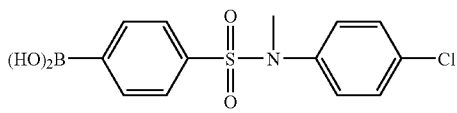

4-{[4-Chloro(methyl)anilino]sulfonyl}phenylboronic acid

From 407 mg N1-(4-chlorophenyl)-N-1-methyl-4-iodo-1-benzene sulfonamide obtained by reacting 4-iodobenzenesulfonyl chloride with 4-chloro-N-methyl aniline in the presence of triethylamine in N,N-dimethylformamide, 310 mg of the title compound was obtained as colorless crystals by the same method as in Production Example 25.

$^1$H-NMR (DMSO-$d_6$)

δ: 3.12(s, 3H), 7.09–7.15(m, 2H), 7.38–7.44(m, 2H), 7.47(d, J=8.0 Hz, 2H), 7.94(d, J=8.0 Hz, 2H), 8.39(s, 2H)

Production Example 303

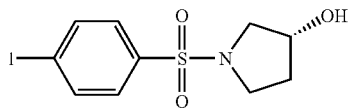

(3R)-1-[(4-Iodophenyl)sulfonyl]tetrahydro-1H-3-pyrrole 3.0 g of 4-iodobenzenesulfonyl chloride, 2.71 g (R)-(–)-3-pyrrolidinol hydrochloride and 4.2 g sodium bicarbonate were vigorously stirred overnight in a water/ethyl acetate solvent. The solvent in the organic layer was evaporated, and the product was crystallized from ethyl acetate/ether, to give 3.1 g of the title compound.

$^1$H-NMR (CDCl$_3$)

δ: 1.82–1.90(m, 1H), 1.92–2.02(m, 1H), 3.21–3.28(m, 1H), 3.32–3.46(m, 3H), 4.38–4.45(m, 1H), 7.54–7.57(m, 2H), 7.86–9.93(m, 2H)

Production Example 304

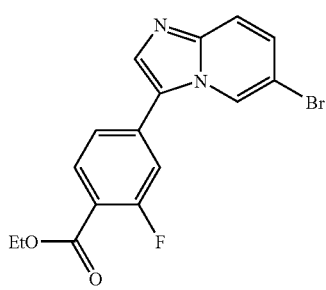

Ethyl 4-(6-bromoimidazo[1,2-a]pyridin-3-yl)-2-fluorobenzoate

From 4.4 g of ethyl 2-fluoro-4-(4,4,5,5-tetramethyl-1,3,2-dioxaborolan-2-yl)benzoate prepared from ethyl 4-bromo-2-fluorobenzoate by a method of T. Ishiyama et al., J. Org. Chem., 60, 7508 (1995) and 3.2 g of 6-bromo-3-iodoimidazo[1,2-a]pyridine (compound in Production Example 49), 1.6 g of the title compound (colorless crystals) was obtained by the same method as in Production Example 51.

$^1$H-NMR (CDCl$_3$)

δ: 1.44(t, J=7.2 Hz, 3H), 4.44 (q, J=7.2 Hz, 2H), 7.34(dd, J=9.6, 1.6 Hz, 1H), 7.35(dd, J=11.6, 1.6 Hz, 2H), 7.62(dd, J=9.6, 0.8 Hz, 1H), 7.80(s, 1H), 8.12(dd, J=8.0, 8.0 Hz, 1H), 8.50(dd, J=1.6, 0.8 Hz, 1H)

Production Example 305

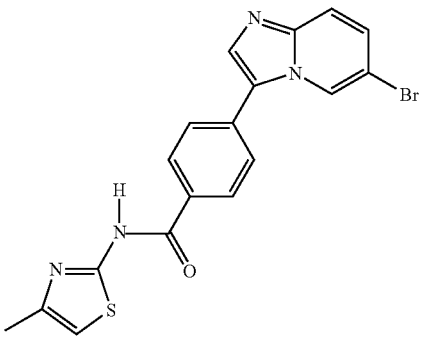

N1-(4-Methyl-1,3-thiazol-2-yl)-4-(6-bromoimidazo[1,2-a]-pyridin-3-yl)benzamide 159 mg of 4-(6-bromoimidazo[1,2-a]pyridin-3-yl)benzoic acid (compound in Production Example 54), 58 mg of 2-amino-4-methyl-1,3-thiazole, 243 mg benzotriazol-1-yloxy-tris(dimethylamino)phosphonium hexafluorophosphate and 83 μL triethylamine were reacted overnight in 4 mL dichloromethane. The reaction solution was purified by an NH silica gel column, to give 100 mg of the title compound (pale yellow crystals; recrystallization solvent, ethyl acetate-methanol).

$^1$H-NMR (CDCl$_3$)

δ: 2.34(d, J=0.8 Hz, 3H), 6.62(d, J=0.8 Hz, 1H), 7.33(dd, J=9.6, 1.6 Hz, 1H), 7.62(dd, J=9.6, 0.8 Hz, 1H), 7.70–7.75 (m, 2H), 7.81(s, 1H), 8.07–9.02(m, 2H), 8.51(dd, J=1.6, 0.8 Hz, 1H)

Production Example 306

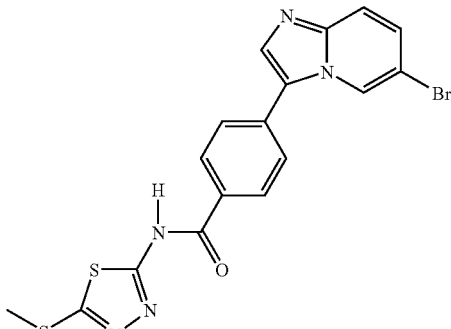

N1-[5-(Methylsulfanyl)-1,3,4-thiadiazol-2-yl]-4-(6-bromoimidazo[1,2-a]pyridin-3-yl)benzamide 178 mg of the title compound was obtained as a brown solid in the same manner as in Production Example 305 from 159 mg of 4-(6-bromoimidazo[1,2-a]pyridin-3-yl)benzoic acid (compound in Production Example 54) and 49 mg of 2-amino-5-(methylthio)-1,3,4-thiadiazole.

$^1$H-NMR (CDCl$_3$)

δ: 2.78(s, 3H), 7.44(dd, J=9.6, 2.0 Hz, 1H), 7.66(dd, J=9.6, 0.4 Hz, 1H), 7.74–7.79(m, 2H), 7.82(s, 1H), 8.23–8.28(m, 2H), 8.55(dd, J=2.0, 0.4 Hz, 1H)

Production Example 307

N1-[5-(Methylsulfonyl)-1,3,4-thiadiazol-2-yl]-4-(6-bromoimidazo[1,2-a]pyridin-3-yl)benzamide 74 mg of the title compound was obtained as a pale yellow solid in the same manner as in Production Example 59 from 150 mg of N1-[5-(methylsulfanyl)-1,3,4-thiadiazol-2-yl]-4-(6-bromoimidazo[1,2-a]pyridin-3-yl)benzamide (compound in Production Example 306) and 1.5 g oxone.

$^1$H-NMR (CDCl$_3$)

δ: 3.58(s, 3H), 7.50(dd, J=9.6, 2.0 Hz, 1H), 7.71(dd, J=9.6, 0.8 Hz, 1H), 7.94–7.99(m, 2H), 8.02(s, 1H), 8.31–8.36(m, 2H), 8.83(dd, J=2.0, 0.8 Hz, 1H)

Production Example 308

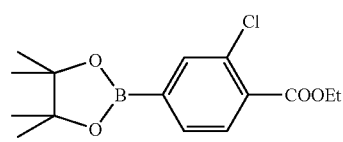

Ethyl 2-chloro-4-(4,4,5,5-tetramethyl-[1,3,2]dioxaborolan-2-yl)-benzoate 7.76 g of the title compound was obtained from 7.2 g of ethyl 4-bromo-2-chloro-benzoate prepared according to a method of T. Ishiyama et al., J. Org. Chem., 60, 7508 (1995).

$^1$H-NMR (CDCl$_3$)

δ: 1.35(s, 12H), 1.40(t, J=7.2 Hz, 3H), 4.40 (q, J=7.2 Hz, 2H), 7.69(dd, J=7.5, 0.9 Hz, 1H), 7.76(d, J=7.5 Hz, 1H), 7.86(d, J=0.9 Hz, 1H)

Production Example 309

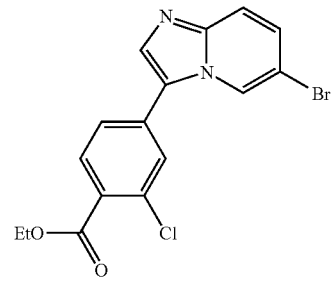

Ethyl 4-(6-bromo-imidazo[1,2-a]pyridin-3-yl)-2-chlorobenzoate 2.45 g of the title compound was obtained by the same method as in Production Example 304 from 3.0 g of 6-bromo-3-iodo-imidazo[1,2-a]pyridine (compound in Production Example 49) and 7.76 g of ethyl 2-chloro-4-(4,4,5,5-tetramethyl-[1,3,2]dioxaborolan-2-yl) benzoate (compound in Production Example 308).

$^1$H-NMR (CDCl$_3$)

δ: 1.43(t, J=7.0 Hz, 3H), 4.44 (q, J=7.0 Hz, 2H), 7.32(dd, J=9.5, 1.9 Hz, 1H), 7.51(dd, J=8.1, 1.7 Hz, 1H), 7.59(dd, J=9.5, 0.8 Hz, 1H), 7.64(d, J=1.7 Hz, 1H), 7.76(s, 1H), 8.00(d, J=8.1 Hz, 1H), 8.44(dd, J=1.9, 0.8 Hz, 1H)

Production Example 310

4-(6-Bromo-imidazo[1,2-a]pyridin-3-yl)-2-chlorobenzoic acid 2.45 g of ethyl 4-(6-bromo-imidazo[1,2-a]pyridin-3-yl)-2-chlorobenzoate obtained in Production Example 309 was dissolved in 60 mL solvent mixture of tetrahydrofuran and methanol (1:1), then 9.7 mL of 2 N sodium hydroxide was added thereto, and the mixture was left at room temperature for 24 hours. After half of the solvent was removed, the reaction solution was neutralized under ice-cooling. The precipitated crystals were collected by filtration, and after addition of ethanol, the crystals were heated in a water bath, cooled and collected by filtration, whereby 1.8 g of the title compound was obtained as colorless crystals.

$^1$H-NMR (DMSO-d$_6$)

δ: 7.48(dd, J=9.4, 2.0 Hz, 1H), 7.69(dd, J=9.4, 0.8 Hz, 1H), 7.78(dd, J=8.0, 1.6 Hz, 1H), 7.89(d, J=1.6 Hz, 1H), 7.95(d, J=8.0 Hz, 1H), 7.97(s, 1H), 8.80(dd, J=2.0, 0.8 Hz, 1H)

Production Example 311

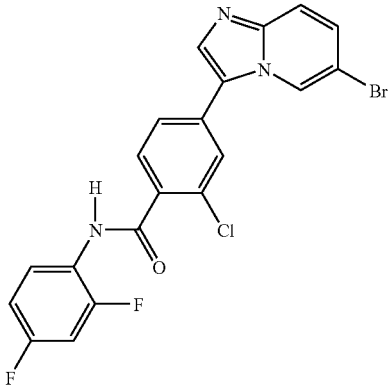

4-(6-Bromo-imidazo[1,2-a]pyridin-3-yl)-2-chloro!-
N-(2,4-difluoro-phenyl)benzamide 150 mg of 4-(6-bromo-imidazo[1,2-a]pyridin-3-yl)-2-chloro-benzoic acid obtained in Production Example 310 and 1.25 mL thionyl chloride were heated for 1 hour under reflux, and an excess of thionyl chloride was evaporated. The resulting acid chloride, together with 55 mg of 2,4-difluorophenylamine and 0.12 mL triethylamine, was stirred in a tetrahydrofuran solvent (6 mL) at room temperature for 5 hours. The reaction solution was purified by NH silica gel column chromatography (ethyl acetate/hexane) to give 42 mg of the title compound as colorless crystals.

$^1$H-NMR (CDCl$_3$)

δ: 6.90–7.01(m, 2H), 7.34(dd, J=9.5, 1.8 Hz, 1H), 7.61 (dd, J=8.1, 1.9 Hz, 1H), 7.62(dd, J=9.5, 0.8 Hz, 1H), 7.67(d, J=1.9 Hz, 1H), 7.78(s, 1H), 8.02(d, J=8.1 Hz, 1H), 8.28(brs, 1H), 8.42–8.49(m, 2H)

Production Example 312

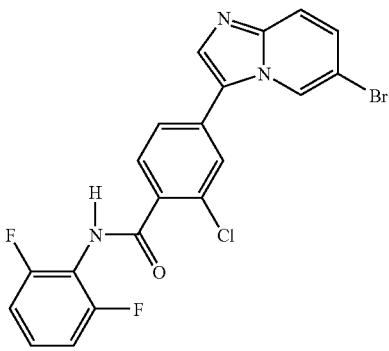

4-(6-Bromo-imidazo[1,2-a]pyridin-3-yl)-2-chloro!-
N-(2,6-difluorophenyl)benzamide An acid chloride of 4-(6-bromo-imidazo[1,2-a]pyridin-3-yl)-2-chloro-benzoic acid obtained in Production Example 310, prepared from 200 mg of the compound obtained in Production Example 310 and 1.7 mL thionyl chloride, and 80 mg of 2,6-difluorophenylamine, were stirred for 5 hours in a solution mixture (9 mL) of dichloromethane and water containing 0.14 g sodium bicarbonate (3:1). The reaction solution was purified by NH silica gel column chromatography (ethyl acetate), to give 48 mg of the title compound (colorless crystals; recrystallization solvent, diethyl ether/hexane).

$^1$H-NMR (CDCl$_3$)

δ: 7.04(dd, J=8.4, 8.4 Hz, 2H), 7.23–7.34(m, 1H), 7.34 (dd, J=9.3, 1.8 Hz, 1H), 7.59(brs, 1H), 7.62(d, J=9.3 Hz, 1H), 7.67(brs, 1H), 7.77(brs, 2H), 8.07(br, 1H), 8.46(brs, 1H)

Production Example 313

1-(2,4-Difluorophenyl)-cyclopropyl amine 1.14 g of the title compound was obtained as a colorless oil from 5 g of (2,4-difluorophenyl)-acetonitrile by a method described in U.S. Pat. No. 6,291,677.

$^1$H-NMR (CDCl$_3$)

δ: 0.84–0.87(m, 2H), 0.97–1.10(m, 2H), 1.82(brs, 2H), 6.75–6.82(m, 2H), 7.22–7.29(m, 1H)

Production Example 314

1-(3,4-Dichlorophenyl)-cyclopropyl amine 2.63 g of the title compound was obtained as a colorless oil from 5 g of (3,4-dichlorophenyl)-acetonitrile by a method described in U.S. Pat. No. 6,291,677.

$^1$H-NMR (CDCl$_3$)

δ: 0.95–0.99(m, 2H), 1.08–1.12(m, 2H), 1.79(brs, 2H), 7.08(dd, J=8.6, 2.2 Hz, 1H), 7.35(d, J=8.6 Hz, 1H), 7.40(d, J=2.2 Hz, 1H)

Production Example 315

1-(4-Fluorophenyl)-cyclopropyl amine 0.27 g of the title compound was obtained as a colorless oil from 5 g of (4-fluorophenyl)-acetonitrile by a method described in U.S. Pat. No. 6,291,677.

$^1$H-NMR (CDCl$_3$)

δ: 0.91–0.95(m, 2H), 1.02–1.06(m, 2H), 1.79(brs, 2H), 6.95–7.02(m, 2H), 7.24–7.30(m, 2H)

Production Example 316

1-(3-Chlorophenyl)-cyclopropyl amine 2.57 g of the title compound was obtained as a colorless oil from 5 g of (3-chlorophenyl)-acetonitrile by a method described in U.S. Pat. No. 6,291,677.

$^1$H-NMR (CDCl$_3$)

δ: 0.96–0.99(m, 2H), 1.07–1.11(m, 2H), 1.83(brs, 2H), 7.11–7.18(m, 2H), 7.22(d, J=7.6 Hz, 1H), 7.29(t, J=2.0 Hz, 1H)

Production Example 317

1-(3,4-Difluorophenyl)-cyclopropyl amine 1.73 g of the title compound was obtained as a pale yellow oil from 5 g of (3,4-difluorophenyl)-acetonitrile by a method described in U.S. Pat. No. 6,291,677.

¹H-NMR (CDCl₃)

δ: 0.92–0.96(m, 2H), 1.05–1.09(m, 2H), 1.80(brs, 2H), 6.96–7.14(m, 3H)

Production Example 318

1-(4-Trifluoromethylphenyl)-cyclopropyl amine 1.85 g of the title compound was obtained as a colorless oil from 4.83 g of (4-trifluoromethylphenyl)-acetonitrile by a method described in U.S. Pat. No. 6,291,677.

¹H-NMR (CDCl₃)

δ: 1.01–1.05(m, 2H), 1.13–1.17(m, 2H), 1.86(brs, 2H), 7.38(d, J=8.4 Hz, 2H), 7.55(d, J=8.4 Hz, 2H)

Production Example 319

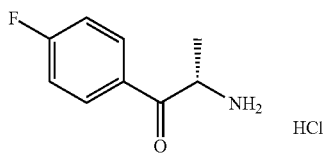

(2S)-2-Amino-1-(4-fluorophenyl)propan-1-one

A solution of 2.32 g t-butyl N-{(1S)-2-[methoxy(methyl) amino]-1-methyl-2-oxoethyl}carbamate in tetrahydrofuran was added dropwise under ice-cooling to a tetrahydrofuran solution of Grignard reagent prepared from 5.2 g of 1-bromo-4-fluorobenzene and 1 g magnesium. The mixture was stirred at 5° C. for 2 hours, then poured into an aqueous saturated ammonium chloride solution and extracted with ethyl acetate. The extract was purified by silica gel column, to give 2.6 g of t-butyl N-{(1S)-2-(4-fluorophenyl)-1-methyl-2-oxoethyl]carbamate as colorless oil. This product was treated with 4 N hydrochloric acid/ethyl acetate, to give 1.73 g of the title compound as colorless crystals.

¹H-NMR (DMSO-d₆)

δ: 1.43(d, J=7.2 Hz, 3H), 5.13 (q, J=7.2 Hz, 1H), 7.41–7.49(m, 2H), 8.13–8.21(m, 2H), 8.47(brs, 2H)

Production Example 320

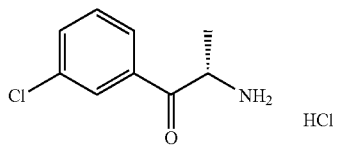

(2S)-2-Amino-1-(3-chlorophenyl)propan-1-one 1.64 g of the title compound was obtained as colorless crystals in the same manner as in Production Example 319 from 5.7 g Grignard reagent of 1-bromo-3-chlorobenzene and 2.32 g of t-butyl N-{(1S)-2-[methoxy(methyl)amino]-1-methyl-2-oxoethyl}carbamate.

¹H-NMR (DMSO-d₆)

δ: 1.41(d, J=7.2 Hz, 3H), 5.16 (q, J=7.2 Hz, 1H), 7.65(t, J=8.0 Hz, 1H), 7.83(ddd, J=8.0, 2.0, 1.2 Hz, 1H), 8.03(ddd, J=8.0, 1.2, 1.2 Hz, 1H), 8.10(dd, J=2.0, 2.0 Hz, 1H), 8.42(brs, 2H)

Production Example 321

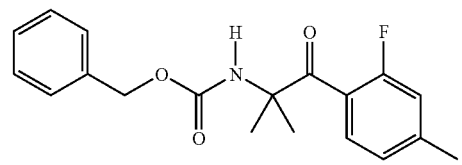

Benzyl N-[2-(2-fluoro-4-methylphenyl)-1,1-dimethyl-2-oxyethyl]carbamate 2.58 mL n-butyl lithium (1.59 M hexane solution) was added dropwise to a solution of 809 mg 4-bromo-3-fluorotoluene in tetrahydrofuran at −70° C. After the mixture was stirred for 30 minutes, a solution of benzyl N-{2-[methoxy (methyl)amino]-1,1-dimethyl-2-oxyethyl}carbamate in tetrahydrofuran was added dropwise thereto and stirred −40° C. for 1 hour. An aqueous saturated ammonium solution was added thereto, and the reaction solution was extracted with ethyl acetate and purified by silica gel chromatography, to give 253 mg of the title compound as an oil.

¹H-NMR (CDCl₃)

δ: 1.61(s, 6H), 2.36(s, 3H), 4.92(s, 2H), 5.49(brs, 1H), 6.84(d, J=11.6 Hz, 1H), 6.96(br.d, J=8.0 Hz, 1H), 7.15–7.20 (m, 2H), 7.26–7.32(m, 3H), 7.32–7.45(m, 1H)

Production Example 322

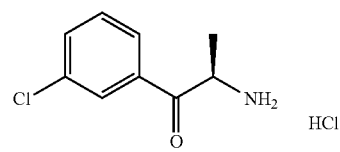

(2R)-2-Amino-1-(3-chlorophenyl)propan-1-one 1.1 g of the title compound was obtained as colorless crystals in the same manner as in Production Example 319 from 4.0 g Grignard reagent of 1-bromo-3-chlorobenzene and 1.6 g of t-butyl N-{(1R)-2-[methoxy(methyl)amino]-1-methyl-2-oxyethyl}carbamate.

¹H-NMR (DMSO-d₆)

δ: 1.41(d, J=7.2 Hz, 3H), 5.16 (q, J=7.2 Hz, 1H), 7.65(t, J=8.0 Hz, 1H), 7.83(ddd, J=8.0, 2.0, 1.2 Hz, 1H), 8.03(ddd, J=8.0, 1.2, 1.2 Hz, 1H), 8.10(dd, J=2.0, 2.0 Hz, 1H), 8.42(brs, 2H)

Production Example 323

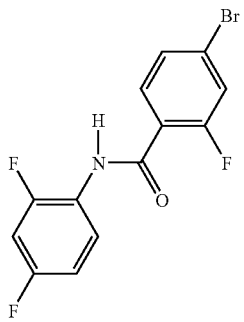

N1-(2,4-Difluorophenyl)-4-bromo-2-fluorobenzamide

284 µL oxalyl chloride was added to a suspension of 356 mg 4-bromo-2-fluorobenzoic acid in dichloromethane in the presence of a catalytic amount of N,N-dimethylformamide, and the mixture was stirred for 30 minutes. The reaction mixture was evaporated, and the resulting acid chloride was dissolved in 3 mL dichloromethane and then added dropwise to a solution mixture of 232 mg 2,4-difluoroaniline, 550 mg sodium bicarbonate, 5 mL water and 5 mL dichloromethane, and the mixture was vigorously stirred at room temperature for 1 hour. The organic layer was concentrated and purified by NH silica gel column, to give 400 mg of the title compound as colorless crystals.

$^1$H-NMR (CDCl$_3$)

δ: 6.79–6.97(m, 2H), 7.41(dd, J=11.6, 2.0 Hz, 1H), 7.49 (dd, J=8.4, 2.0 Hz, 1H), 8.06(dd, J=8.4, 8.4 Hz, 1H), 8.37–8.44(m, 1H), 8.57(br, 1H)

Production Example 324

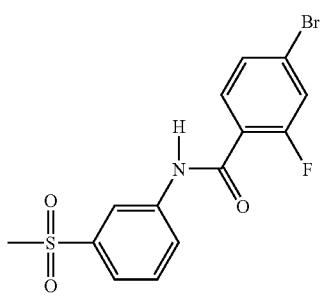

N1-[3-(Methylsulfonyl)phenyl]-4-bromo-2-fluorobenzamide 460 mg of N1-[3-(methylsulfanyl)phenyl]-4-bromo-2-fluorobenzamide obtained in the same manner as in Production Example 32 from 4-bromo-2-fluorobenzoic acid and 3-(methylthio)aniline was stirred for 1.5 hours together with 1.23 g oxone in 15 mL tetrahydrofuran, 10 mL methanol and 10 mL water. The reaction solution was extracted with ethylacetate and purified by NH silica gel column to give 500 mg of the title compound.

$^1$H-NMR (CDCl$_3$)

δ: 3.10(s, 3H), 7.44(dd, J=11.6, 1.6 Hz, 1H), 7.51(dd, J=8.4, 2.0 Hz, 1H), 7.60(dd, J=8.0, 8.0 Hz, 1H), 7.75(ddd, J=8.0, 2.0, 0.8 Hz, 1H), 8.05(ddd, J=8.0, 2.0, 0.8 Hz, 1H), 8.07(dd, J=8.4, 8.4 Hz, 1H), 8.19(dd, J=2.0, 2.0 Hz, 1H), 8.54(br. 1H)

Production Example 325

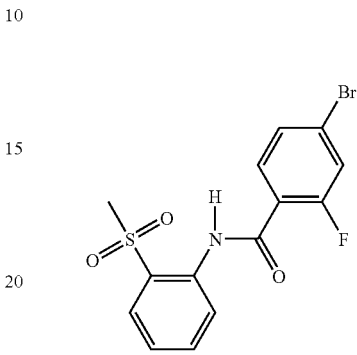

N1-[2-(Methylsulfonyl)phenyl]-4-bromo-2-fluorobenzamide 634 mg of the title compound was obtained as colorless crystals from 600 mg N1-[2-(methylsulfanyl)phenyl]-4-bromo-2-fluorobenzamide and 2.17 g oxone in the same manner as in Production Example 324.

$^1$H-NMR (CDCl$_3$)

δ: 3.10(s, 3H), 7.35(ddd, J=8.0, 8.0,1.2 Hz, 1H), 7.42(dd, J=10.8, 2.0 Hz, 1H), 7.49(ddd, J=8.4, 2.0, 0.4 Hz, 1H), 7.71(ddd, J=8.0, 8.0, 2.0 Hz, 1H), 7.97(d, J=8.0 Hz, 1H), 8.0(dd, J=8.0, 1.2 Hz, 1H), 8.60(dd, J=8.4, 0.4 Hz, 1H), 10.3(br, 1H)

Production Example 326

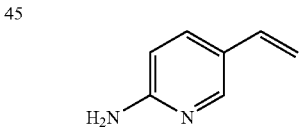

5-Vinylpyridin-2-yl amine 4.13 g 5-bromopyridin-2-yl amine, 7.95 g tributyl(vinyl) tin and 1.38 g tetrakis(triphenylphosphine)palladium were heated in 70 mL xylene at 120° C. for 3 hours under nitrogen atmosphere. The solvent was removed, and the residue was purified by silica gel column chromatography (hexane/ethyl acetate), to give 1.3 g of the title compound as pale yellow crystals.

$^1$H-NMR (CDCl$_3$)

δ: 4.50(brs, 2H), 5.11(dd, J=10.8 Hz, 0.8 Hz, 1H), 5.56 (dd, J=17.6, 0.8 Hz, 1H), 8.47(d, J=8.4 Hz, 1H), 6.58(dd, J=17.6, 10.8 Hz, 1H), 7.56(dd, J=8.4, 2.4 Hz, 1H), 8.05(d, J=2.4 Hz, 1H)

Production Example 327

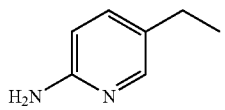

5-Ethylpyridin-2-yl amine 0.25 g 5-vinylpyridin-2-yl amine (compound in Production Example 326) and 0.1 g of 10% palladium-carbon were stirred in 5 mL ethyl acetate at room temperature for 2 hours under hydrogen atmosphere. The reaction solution was purified by NH silica gel column chromatography (ethyl acetate), to give 0.24 g of the title compound as a pale yellow oil.

$^1$H-NMR (CDCl$_3$)

δ: 1.18(t, J=7.2 Hz, 3H), 2.51 (q, J=7.2 Hz, 2H), 4.26(brs, 2H), 6.46(d, J=8.4 Hz, 1H), 7.29(dd, J=8.4 Hz, 1.8 Hz, 1H), 7.91(d, J=1.8 Hz, 1H)

Production Example 328

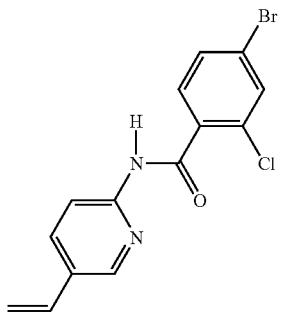

4-Bromo-2-fluoro-N-(5-vinylpyridin-2-yl)benzamide 108 mg of the title compound was obtained as colorless crystals from 250 mg 4-bromo-2-fluorobenzoic acid and 150 mg 5-vinylpyridin-2-yl amine (compound in Production Example 326) by the same method as in Production Example 323.

$^1$H-NMR (CDCl$_3$)

δ: 5.34(dd, J=11.1 Hz, 0.8 Hz, 1H), 5.78(dd, J=17.8 Hz, 0.8 Hz, 1H), 6.69(dd, J=17.8 Hz, 11.1 Hz, 1H), 7.42(dd, J=11.2 Hz, 1.6 Hz, 1H), 7.48(dd, J=8.6 Hz, 1.6 Hz, 1H), 7.83(dd, J=8.8 Hz, 2.1 Hz, 1H), 8.04(dd, J=8.6, 8.6 Hz, 1H), 8.33(d, J=2.1 Hz, 1H), 8.33(d, J=8.8 Hz, 1H), 8.98(br, 1H)

Production Example 329

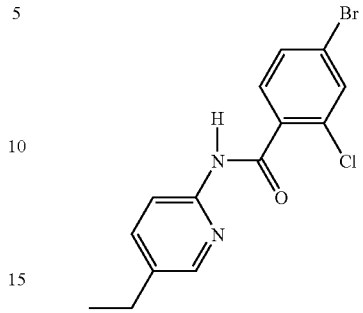

4-Bromo-N-(5-ethylpyridin-2-yl)-2-fluorobenzamide 102 mg of the title compound was obtained as colorless crystals from 250 mg 4-bromo-2-fluorobenzoic acid and 153 mg 5-ethylpyridin-2-yl amine (compound in Production Example 327) by the same method as in Production Example 323.

$^1$H-NMR (CDCl$_3$)

δ: 1.26(t, J=7.4 Hz, 3H), 2.51 (q, J=7.4 Hz, 2H), 7.41(dd, J=11.4 Hz, 1.9 Hz, 1H), 7.47(dd, J=8.4 Hz, 1.9 Hz, 1H), 7.60(dd, J=8.2 Hz, 2.4 Hz, 1H), 8.04(dd, J=8.4, 8.4 Hz, 1H), 8.17(d, J=2.4 Hz, 1H), 8.26(d, J=8.2 Hz, 1H), 8.91(br, 1H)

Production Example 330

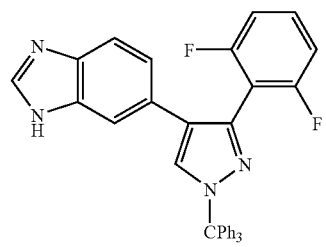

6-[3-(2,6-Difluorophenyl)-1-trityl-1H-4-pyrazolyl]-1-H-benzo[d]imidazole

From 2.0 g of the compound in Production Example 64 and 3.89 g 3-(2,6-difluorophenyl)-1-trityl-1H-pyrazolylboronic acid (compound in Production Example 211), 2.95 g of a 1:1 mixture of {6-[3-(2,6-difluorophenyl)-1-trityl-1H-4-pyrazolyl]-1H-benzo[d]imidazol-1-yl}methylpivalate and {5-[3-(2,6-difluorophenyl)-1-trityl-1H-4-pyrazolyl]-1H-benzo[d]imidazol-1-yl}methylpivalate was obtained as a colorless solid by the same method as in Production Example 34. This product was dissolved in 45 mL solvent mixture of methanol and dichloromethane (2:1), then 260 mg sodium hydride was added thereto, and the reaction mixture was stirred at room temperature for 3.0 hours. Water was added thereto, and the reaction mixture was extracted with ethyl acetate and purified by NH silica gel chromatography (ethyl acetate). By recrystallization from ethyl acetate/hexane, 2.63 g of the title compound was obtained as colorless crystals.

¹H-NMR (CDCl₃)

δ: 6.96–7.00(m, 1H), 7.14–7.24(m, 9H), 7.35–7.46(m, 10H), 7.49–7.58(m, 1H), 7.70(s, 1H), 8.14(s, 1H)

Production Example 331

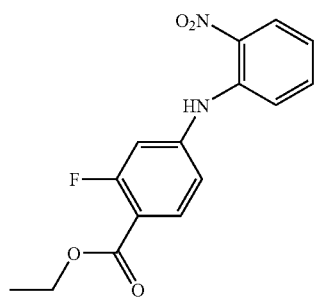

Ethyl 2-fluoro-4-(2-nitrophenylamino)benzoate 1.0 g ethyl 4-bromo-2-fluorobenzoate, 0.56 g 2-nitroaniline, 1.85 g cesium carbonate, 37 mg tris(dibenzylideneacetone)-dipalladium (0), 38 mg 2,2'-bis(diphenylphosphino)-1,1'-binaphthyl (racemic mixture) and 15 mL toluene were stirred at 100° C. for 24 hours under nitrogen atmosphere. Water was added thereto, then the reaction mixture was extracted with ether, and the organic layer was dried over sodium sulfate. After the solvent was evaporated, the residue was purified by NH silica gel chromatography (ethyl acetate/hexane). By recrystallization from ethyl acetate/hexane, 0.95 g of the title compound was obtained as yellow crystals.

¹H-NMR (CDCl₃)

δ: 1.40(t, J=7.0 Hz, 3H), 4.39 (q, J=7.0 Hz, 2H), 6.94–7.20(m, 3H), 7.47–7.55(m, 2H), 7.93–8.00(m, 1H), 8.21–8.25(m, 1H), 9.42(brs, 1H)

Production Example 332

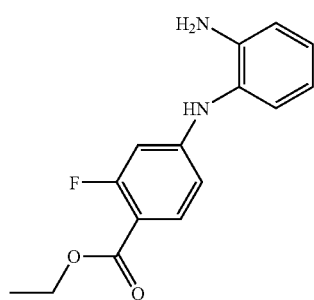

Ethyl 4-(2-amino-phenylamino)-2-fluoro-benzoate 200 mg ethyl 2-fluoro-4-(2-nitrophenylamino)benzoate (compound in Production Example 331), 180 mg iron powder, 350 mg ammonium chloride and 8 mL solution mixture of methanol and water (5:3) were stirred at 100° C. for 1 hour. Insolubles were filtered off with Celite, and water was added to the filtrate which was then extracted with dichloromethane. The extract was purified by NH silica gel chromatography (ethyl acetate), to give 179 mg of the title compound as pale brown crystals.

¹H-NMR (DMSO-d₆)

δ: 1.26(t, J=7.2 Hz, 3H), 4.22 (q, J=7.2 Hz, 2H), 4.89(brs, 2H), 6.27(dd, J=14.4, 2.1 Hz, 1H), 6.50(dd, J=8.8, 2.1 Hz, 1H), 6.58 (td, J=7.6, 1.6 Hz, 1H), 6.78(dd, J=8.0, 1.6 Hz, 1H), 6.90–7.03(m, 2H), 7.65(t, J=8.8 Hz, 1H), 8.18(brs, 1H)

Production Example 333

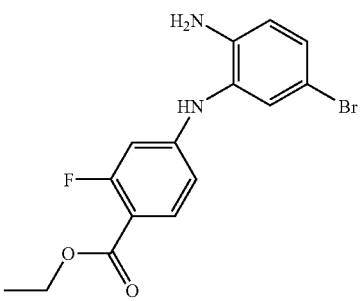

Ethyl 4-(2-amino-5-bromo-phenylamino)-2-fluoro-benzoate 179 mg ethyl 4-(2-amino-phenylamino)-2-fluoro-benzoate (compound in Production Example 332) was dissolved in 4 mL N,N-dimethylformamide, and 116 mg N-bromosuccinimide was added thereto under ice-cooling and stirred for 2 hours. An aqueous sodium thiosulfate solution and an aqueous sodium bicarbonate solution were added thereto and stirred for 1 hour, and the reaction mixture was extracted with ethyl acetate. The extract was purified by NH silica gel chromatography (ethyl acetate/hexane), to give 157 mg of the title compound as a red oil.

¹H-NMR (CDCl₃)

δ: 1.37(t, J=7.2 Hz, 3H), 4.34 (q, J=7.2 Hz, 2H), 3.78(brs, 2H), 5.55(brs, 1H), 6.35(dd, J=13.2, 2.6 Hz, 1H), 6.49(dd, J=8.4, 2.6 Hz, 1H), 6.71(d, J=8.4 Hz, 1H), 7.20(dd, J=8.4, 2.0 Hz, 1H), 7.26(brs, 1H), 7.81(t, J=8.4 Hz, 1H)

Production Example 334

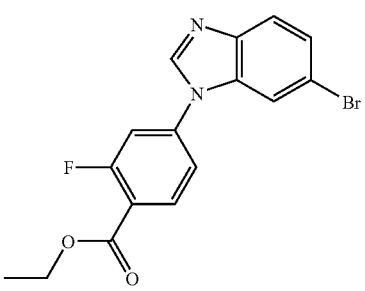

Ethyl 4-(6-bromo-1H-benzo[d]imidazol-1-yl)-2-fluoro-benzoate 917 mg ethyl 4-(2-amino-5-bromo-phenylamino)-2-fluoro-benzoate (compound in Production Example 333) and 7 mL triethoxymethane were stirred at 140° C. for 3 hours. The solvent was evaporated, and the residue was purified by NH silica gel chromatography (ethyl acetate/hexane). By recrystallization from ethyl acetate/hexane, 734 mg of the title compound was obtained as pale pink crystals.
¹H-NMR (CDCl₃)
δ: 1.44(t, J=7.0 Hz, 3H), 4.34 (q, J=7.0 Hz, 2H), 7.34(dd, J=10.8, 2.0 Hz, 1H), 7.39(ddd, J=8.2, 2.0, 0.4 Hz, 1H), 7.49(dd, J=8.6, 1.7 Hz, 1H), 7.40(d, J=1.7 Hz, 1H), 7.75(d, J=8.6 Hz, 1H), 8.12(s, 1H), 8.19(t, J=8.2 Hz, 1H)

Production Example 335

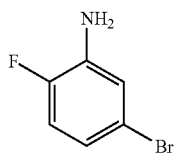

5-Bromo-2-fluorophenylamine 3.0 g of 5-bromo-2-fluoronitrobenzene, 3.8 g iron powder and 7.3 g ammonium chloride were heated at 80° C. for 2 hours in a solution mixture of 30 mL methanol and 30 mL water. The reaction mixture was filtered through Celite, the methanol was evaporated, and the reaction mixture was diluted with water and extracted with ethyl acetate. The extract was washed with brine, and the organic layer was dried over anhydrous sodium sulfate and filtered through a column with a small amount of silica gel. The solvent was evaporated to give 2.43 g of the title compound (yellow oil).
¹H-NMR (CDCl₃)
δ: 3.78(brs, 2H), 6.75–6.80(m, 1H), 6.84(dd, J=10.8, 8.4 Hz, 1H), 6.90(dd, J=8.4, 2.4 Hz, 1H)

Production Example 336

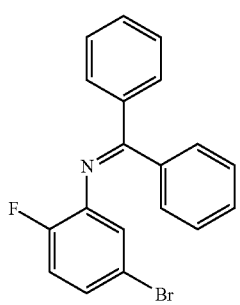

Benzhydrylidene-(5-bromo-2-fluorophenyl)-amine

While a solution of 2.43 g 5-bromo-2-fluorophenylamine (compound in Production Example 335), 2.6 g benzophenone and 122 mg 4-toluenesulfonic acid in 50 ml toluene was azeotropically dehydrated, the mixture was heated for 6 hours under reflux. The reaction mixture was diluted with ethyl acetate and washed with brine, the organic layer was dried over anhydrous sodium sulfate, the solvent was removed, and the resulting crude product was purified by silica gel column chromatography (ethyl acetate/hexane) to give 1.91 g of the title compound (colorless oil).
¹H-NMR (CDCl₃)
δ: 6.77(dd, J=10.6, 8.8 Hz, 1H), 6.92(dd, J=6.8, 2.4 Hz, 1H), 6.98(ddd, J=8.8,4.4,2.4 Hz, 1H), 7.1–7.19(m, 2H), 7.27–7.37(m, 3H), 7.38–7.54(m, 3H), 7.71–7.82(m, 2H)

Production Example 337

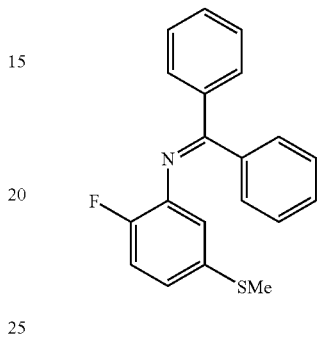

Benzhydrylidene-(2-fluoro-5-methylsulfanylphenyl)-amine 2.2 mL n-butyl lithium (2.66 M hexane solution) was added dropwise to a solution of 1.85 g benzhydrylidene-(5-bromo-2-fluorophenyl)-amine (compound in Production Example 336) in 10 mL tetrahydrofuran at −70° C., then the mixture was stirred for 15 minutes, a solution of 0.53 mL methyl sulfide in 5 mL tetrahydrofuran was added dropwise thereto, and the mixture was stirred at 0° C. for 2 hours. An aqueous saturated ammonium chloride solution was added thereto, and the reaction mixture was diluted with water, extracted with ethyl acetate and washed with brine. The organic layer was dried over anhydrous sodium sulfate, the solvent was removed, and the resulting crude product was purified by silica gel column chromatography (ethyl acetate/hexane) to give 1.24 g of the title compound (colorless oil).
¹H-NMR (CDCl₃)
δ: 2.31(s, 3H), 6.67–6.96(m, 3H), 7.13–7.19(m, 2H), 7.25–7.36(m, 3H), 7.38–7.54(m, 3H), 7.74–7.82(m, 2H)

Production Example 338

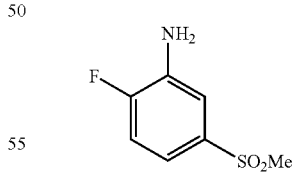

2-Fluoro-5-methylsulfonylphenylamine

A solution of 1.06 g benzhydrylidene-(2-fluoro-5-methylsulfanylphenyl)-amine (compound in Production Example 337), 116 mg tetra-n-propyl ammonium perruthenium, 1.5 g N-methylmorpholine-N-oxide and 2 g of 4 Å molecular sieve powder in 10 mL acetonitrile was stirred at room temperature for 19 hours, then 55 mg tetra-n-propyl ammonium perruthenate and 0.4 g N-methylmorpholine-N-oxide were added thereto, and the mixture was stirred for 3 hours. The reaction mixture was diluted with ethyl acetate and filtered through Celite, and the solvent was evaporated, whereby 1.8 g crude product was obtained. For hydrolysis, this product was then dissolved in a solvent mixture of 20 mL tetrahydrofuran and 5 mL of 1 N hydrochloric acid and stirred at room temperature for 1.5 hours. The reaction mixture was neutralized by adding an aqueous saturated sodium bicarbonate solution, then extracted with ethyl acetate and washed with brine. The organic layer was dried over anhydrous sodium sulfate, the solvent was removed and the resulting crude product was purified by silica gel column chromatography (ethyl acetate/hexane) to give 432 mg of the title compound (colorless oil).

$^1$H-NMR (CDCl$_3$)

3.02(s, 3H), 4.08(brs, 2H), 7.12(dd, J=10.8, 8.4 Hz, 1H), 7.23–7.30(m, 1H), 7.35(dd, J=8.4, 2.0 Hz, 1H)

Production Example 339

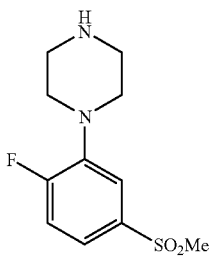

1-(2-Fluoro-5-methylsulfonylphenyl)piperazine 10 mL solution of 432 mg 2-fluoro-5-methylsulfonylphenylamine (compound in Production Example 338) and 490 mg bis(2-chloroethyl)amine hydrochloride in 1,2-dichlorobenzene was stirred at 200° C. for 9 hours. The reaction mixture was neutralized by adding an aqueous saturated sodium bicarbonate solution and then extracted with dichloromethane. The organic layer was dried over anhydrous sodium sulfate, the solvent was removed, and the resulting crude product was purified by NH silica gel column chromatography (ethyl acetate/hexane) to give 230 mg of the title compound (dark brown solid).

$^1$H-NMR (CDCl$_3$) 3.05(s, 3H), 3.03–3.08(m, 4H), 3.09–3.14(m, 4H), 7.17(dd, J=12.0, 8.4 Hz, 1H), 7.47(dd, J=8.4, 2.4 Hz, 1H), 7.51(ddd, J=8.4, 4.4, 2.4 Hz, 1H), Production Example 340

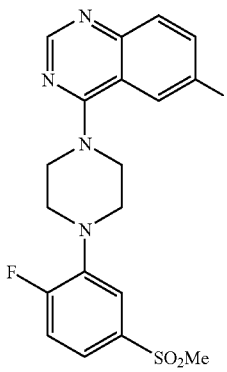

6-Bromo-4-[4-(2-fluoro-5-methylsulfonylphenyl)piperazin-1-yl]quinazoline

A mixture of 115 mg 6-bromo-4-quinazoline, 115 mg 1-(2-fluoro-5-methylsulfonylphenyl)piperazine (compound in Production Example 339), 123 mg potassium carbonate and 2 mL N,N-dimethylformamide was stirred at room temperature for 2 hours. Upon addition of water to the reaction solution, crystals were precipitated. The crystals were further washed with water and dried to give 165 mg of the title compound as pale yellow crystals.

$^1$H-NMR (CDCl$_3$)

δ: 3.06(s, 3H), 3.35–3.44(m, 4H), 3.92–3.99(m, 4H), 7.24(dd, J=12.0, 8.4 Hz, 1H), 7.51–7.60(m, 2H), 7.81(d, J=8.4 Hz, 1H), 7.85(dd, J=8.4, 2.0 Hz, 1H), 8.06(d, J=2.0 Hz, 1H), 8.78(s, 1H)

Production Example 341

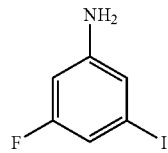

3-Fluoro-5-iodophenylamine 3.2 g crude title compound (yellow oil) was obtained from 3.0 g of 3-fluoro-5-iodonitrobenzene by the same reaction as in Production Example 335.

$^1$H-NMR (CDCl$_3$)

δ: 3.78(brs, 2H), 6.28–6.35(m, 1H), 6.75–6.84(m, 2H)

Production Example 342

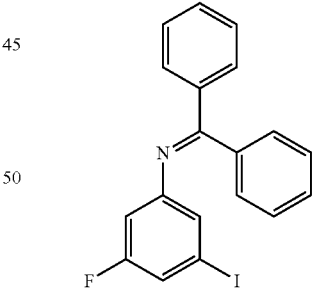

Benzhydrylidene-(3-fluoro-5-iodophenyl)-amine 0.75 g of the title compound (yellow oil) was obtained from 3.2 g of 3-fluoro-5-iodophenylamine (compound in Production Example 341) by the same reaction as in Production Example 336.

$^1$H-NMR (CDCl$_3$)

δ: 6.36–6.43(m, 1H), 6.86–6.92(m, 1H), 6.96–7.02(m, 1H), 7.08–7.16(m, 2H), 7.28–7.54(m, 6H), 7.68–7.76(m, 2H)

Production Example 343

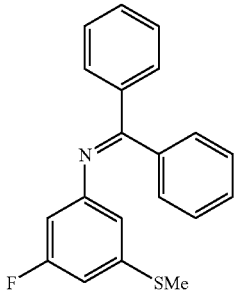

Benzhydrylidene-(3-fluoro-5-methylsulfanylphenyl)-amine 215 mg of the title compound (yellow oil) was obtained from 0.75 g of benzhydrylidene-(3-fluoro-5-iodophenyl)-amine (compound in Production Example 342) by the same reaction as in Production Example 337.

$^1$H-NMR (CDCl$_3$)

δ: 2.30(s, 3H), 6.18–6.24(m, 1H), 6.34–6.38(m, 1H), 6.50–6.55(m, 1H), 7.08–7.16(m, 2H), 7.24–7.35(m, 3H), 7.37–7.52(m, 3H), 7.68–7.77(m, 2H)

Production Example 344

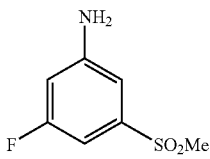

3-Fluoro-5-methylsulfonylphenylamine 81 mg of the title compound (yellow oil) was obtained from 215 g of benzhydrylidene-(3-fluoro-5-methylsulfanylphenyl)-amine (compound in Production Example 343) by the same reaction as in Production Example 338.

$^1$H-NMR (CDCl$_3$)

3.03(s, 3H), 4.11(brs, 2H), 6.52–6.63(m, 1H), 6.90–7.05 (m, 2H),

Production Example 345

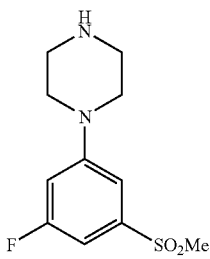

1-(3-Fluoro-5-methylsulfonylphenyl)piperazine 81 mg of the title compound (yellow oil) was obtained from 81 mg of 3-fluoro-5-methylsulfonylphenylamine (compound in Production Example 344) by the same reaction as in Production Example 339.

$^1$H-NMR (CDCl$_3$)

2.99–3.08(m, 4H), 3.04(s, 3H), 3.21–3.27(m, 4H), 6.67 (ddd, J=12.0, 2.0, 2.0 Hz, 1H), 7.01(ddd, J=7.6, 2.0, 2.0 Hz, 1H), 7.18–7.23(m, 1H),

Production Example 346

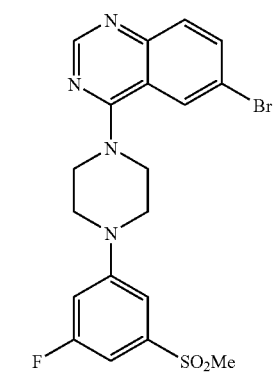

6-Bromo-4-[4-(3-fluoro-5-methylsulfonylphenyl)piperazin-1-yl]quinazoline 95 mg of the title compound (pale yellow crystals) was obtained from 60 mg of 6-bromo-4-chloroquinazoline and 58 mg of 1-(3-fluoro-5-methylsulfonylphenyl)piperazine (compound in Production Example 345) by the same reaction as in Production Example 340.

$^1$H-NMR (CDCl$_3$)

δ: 3.07(s, 3H), 3.50–3.58(m, 4H), 3.80–4.00(m, 4H), 6.80–6.87(m, 1H), 7.07–7.11(m, 1H), 7.24–7.29(m, 1H), 7.81(d, J=8.4 Hz, 1H), 7.85(dd, J=8.4, 1.6 Hz, 1H), 8.03–8.09(m, 1H), 8.78(s, 1H)

Production Example 347

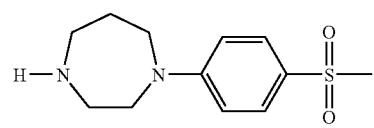

1-[4-(Methylsulfonyl)phenyl]-1,4-diazepam hydrobromide 1 g of 1-bromo-4-(methylsulfonyl)benzene obtained by oxidizing 1-bromo-4-(methylsulfanyl)benzene with oxone, and 2.13 g homopiperazine, were reacted at 150° C. for about 5 hours. An excess of homopiperazine in the reaction solution was evaporated, and the resulting residue was washed with ether to give 350 mg of the title compound.

¹H-NMR (DMSO-d₆)

δ: 1.99–2.07(m, 2H), 2.98–3.02(m, 2H), 3.08(s, 3H), 3.22(dd, J=5.2, 4.8 Hz, 2H), 3.59(dd, J=6.0, 6.0 Hz, 2H), 3.73–3.79(m, 2H), 6.97(d, J=9.2 Hz, 2H), 7.97(d, J=9.2 Hz, 2H)

Production Example 348

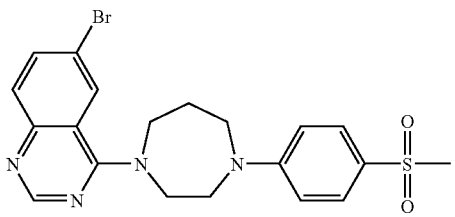

4-[4-(6-Bromo-4-quinazolinyl)-1,4-diazepam-1-yl]phenyl methylsulfone 203 mg of the title compound was obtained from 150 mg of 1-[4-(methylsulfonyl)phenyl]-1,4-diazepam hydrobromide (compound in Production Example 347) and 144 mg of 6-bromo-4-quinazoline by the same reaction as in Production Example 340.

¹H-NMR (DMSO-d₆)

δ: 2.22–2.28(m, 2H), 3.01(s, 3H), 3.72(dd, J=5.6, 5.6 Hz, 2H), 3.90(dd, J=5.6, 5.6 Hz, 2H), 3.93(dd, J=5.6, 5.6 Hz, 2H), 4.10–4.16(m, 2H), 6.79(d, J=9.0 Hz, 2H), 7.73(d, J=9.0 Hz, 2H), 7.74(d, J=9.2 Hz, 1H), 7.80(d, J=9.2, 2.0 Hz, 1H), 8.08(d, J=2.0 Hz, 1H), 8.63(s, 1H)

Production Example 349

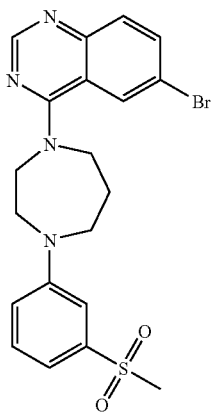

3-[4-(6-Bromo-4-quinazolinyl)-1,4-diazepam-1-yl]phenyl methylsulfone 220 mg tris(dibenzylideneacetone)dipalladium, 584 mg of 2,2'-bis(diphenylphosphino)-1,1'-binaphthyl, 1.46 g cesium carbonate and 13 mL toluene were added to 750 mg of 1-bromo-3-methylsulfonylbenzene obtained by oxidizing 1-bromo-3-methylsulfanylbenzene with oxone, and 2.0 g homopiperazine, and the mixture was heated at 100° C. for about 10 hours. The reaction solution was concentrated and purified by silica gel column chromatography to give 1-[3-(methylsulfonyl)nil]-1,4-diazepam. From 208 mg of this compound and 150 mg of 6-bromo-4-chloroquinazoline, 176 mg of the title compound was obtained by the same method as in Production Example 340.

¹H-NMR (CDCl₃)

δ: 2.27 (dddd, J=4.8, 4.8, 4.8, 4.8 Hz, 2H), 3.00(s, 3H), 3.70(dd, J=4.8, 4.8 Hz, 2H), 3.89(dd, J=4.8, 4.8 Hz, 2H), 3.90(dd, J=4.8, 4.8 Hz, 2H), 4.15(dd, J=4.8, 4.8 Hz, 2H), 6.96(dd, J=7.2, 2.8 Hz, 1H), 7.20(d, J=7.0 Hz, 1H), 7.38(dd, J=7.2, 7.2 Hz, 1H), 7.48(dd, J=7.2, 2.8 Hz, 1H), 7.71(d, J=9.6 Hz, 1H), 7.78(dd, J=9.6, 2.0 Hz, 1H), 8.08(d, J=2.0 Hz, 1H), 8.62(s, 1H), Production Example 350

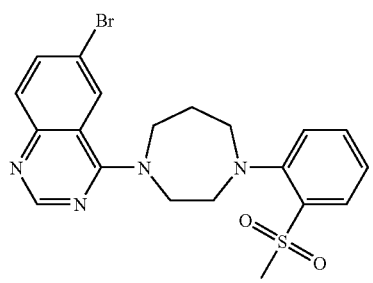

2-[4-(6-Bromo-4-quinazolinyl)-1,4-diazepam-1-ylphenyl]methylsulfone 191 mg of the title compound was obtained by the same method as in Production Example 340 from 150 mg of 1-[2-(methylsulfonyl)phenyl]-1,4-diazepam hydrochloride and 109 mg of 6-bromo-4-chloroquinazoline.

¹H-NMR (CDCl₃)

δ: 2.32–2.37(m, 2H), 3.23–3.27(m, 2H), 3.27(s, 3H), 3.48(dd, J=6.0, 6.0 Hz, 2H), 4.14(dd, J=6.0, 6.0 Hz, 2H), 4.21–4.22(m, 2H), 7.36(ddd, J=8.0, 8.0, 1.8 Hz, 1H), 7.40(dd, J=8.0, 1.6 Hz, 1H), 7.63(ddd, J=8.0, 8.0, 1.6 Hz, 1H), 7.76(d, J=9.0 Hz, 1H), 7.80(dd, J=9.0, 1.8 Hz, 1H), 8.09(dd, J=8.0, 1.6 Hz, 1H), 8.15(d, J=11.8 Hz, 1H), 8.65(s, 1H)

Production Example 351

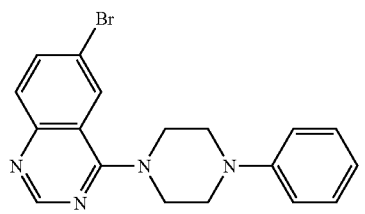

6-Bromo-4-(4-phenylpiperazin-1-yl)quinazoline 288 mg of the title compound was obtained by the same method as in Production Example 340 from 200 mg of 1-phenyl piperazine and 150 mg of 6-bromo-4-chloroquinazoline.

¹H-NMR (CDCl₃)

δ: 3.42(dd, J=5.2, 5.2 Hz, 2H), 3.42(dd, J=5.2, 5.2 Hz, 2H), 3.95(dd, J=5.2, 5.2 Hz, 2H), 3.95(dd, J=5.2, 5.2 Hz, 2H), 6.93–6.95(m, 2H), 7.29–7.43(m, 3H), 7.80(d, J=9.2, 1H), 7.83(dd, J=9.2, 2.0 Hz, 1H), 8.08(d, J=2.0 Hz, 1H), 8.76(s, 1H)

Production Example 352

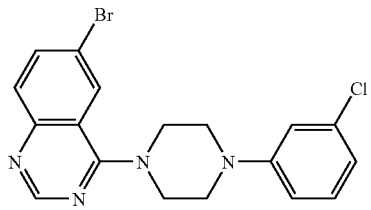

6-Bromo-4-[4-(3-chlorophenyl)piperazin-1-yl]quinazoline 491 mg of the title compound was obtained by the same method as in Production Example 340 from 958 mg of 1-(3-chlorophenyl)piperazine hydrochloride and 1.0 g of 6-bromo-4-chloroquinazoline.

¹H-NMR (CDCl₃)

δ: 3.43(dd, J=5.2, 5.2 Hz, 2H), 3.43(dd, J=5.2, 5.2 Hz, 2H), 3.93(dd, J=5.2, 5.2 Hz, 2H), 3.93(dd, J=5.2, 5.2 Hz, 2H), 6.85(ddd, J=8.4, 2.4,2.4 Hz, 1H), 6.88(ddd, J=8.4, 2.4,2.4 Hz, 1H), 6.95(dd, J=2.4, 2.4 Hz, 1H), 7.24(dd, J=8.4, 8.4 Hz, 1H), 7.81(d, J=8.8 Hz, 1H), 7.84(dd, J=8.8, 2.0 Hz, 1H), 8.07(d, J=2.0 Hz, 1H), 8.78(s, 1H)

Production Example 353

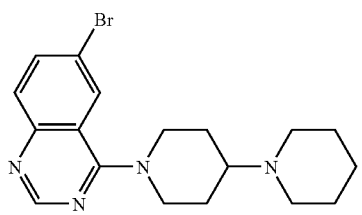

4-(1,4'-piperidinyl)-1'-yl-6-bromoquinazoline 424 mg of the title compound was obtained by the same method as in Production Example 340 from 414 mg of 1,4'-piperidinyl and 300 mg of 6-bromo-4-chloroquinazoline.

¹H-NMR (CDCl₃)

δ: 1.50–1.43(m, 2H), 1.66–1.58(m, 2H), 1.81–1.72(m, 2H), 2.01(d, J=5.2 Hz, 2H), 2.57(m, 6), 3.14(dd, J=12.4, 12.4 Hz, 2H), 4.38(d, J=12.4 Hz, 2H), 7.27(s, 1H), 7.75(d, J=8.8 Hz, 1H), 7.79(d, J=8.8 Hz, 1H), 8.00(s, 1H), 8.71(s, 1H)

Production Example 354

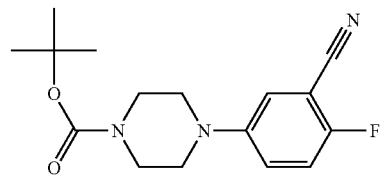

t-Butyl 4-(3-cyano-4-fluorophenyl)-1-piperazinecarboxylate 1.24 g of 2,2'-bis (diphenylphosphino)-1,1'-binaphthyl and 229 mg of tris (dibenzylideneacetone) dipalladium were dissolved in toluene and stirred at 80° C. for 10 minutes. The reaction mixture was returned to room temperature, and 2.28 g cesium carbonate, 1.0 g 5-bromo-2-fluorobenzonitrile and 1.09 g t-butyl 1-piperazine carboxylate were added thereto and stirred at 80° C. for 12 hours. The reaction solution was purified by silica gel column chromatography to give the title compound.

¹H-NMR (CDCl₃)

δ: 7.11–7.16(m, 2H), 7.03–7.08(m, 1H), 3.58–3.61(m, 4H), 3.08–3.10(m, 4H), 1.49(s, 9H)

Production Example 355

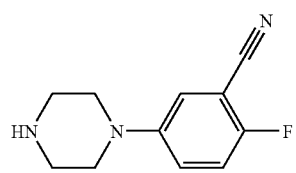

2-Fluoro-5-piperazin-1-yl-benzonitrile

Trifluoroacetic acid was added to 500 mg of t-butyl 4-(3-cyano-4-fluorophenyl)-1-piperazinecarboxylate (compound in Production Example 354) and stirred at room temperature for several hours. After the reaction solution was cooled on ice, ammonia water was added thereto and stirred, the aqueous layer was extracted with dichloromethane, and all the organic layer was combined, dried and concentrated to give 340 mg of the title compound.

¹H-NMR (CDCl₃)

δ: 3.04–3.15(m, 8H), 7.03–7.06(m, 1H), 7.08–7.16(m, 2H)

Production Example 356

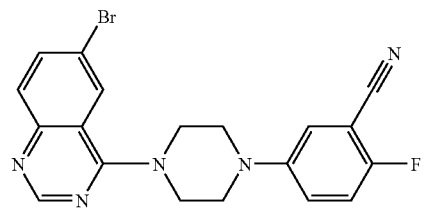

5-[4-(6-Bromo-4-quinazolinyl)piperazin-1-yl]-2-fluorobenzonitrile 200 mg of the title compound was obtained from 340 mg of 2-fluoro-5-piperazin-1-yl-benzonitrile (compound in Production Example 355) and 403 mg of 6-bromo-4-chloroquinazoline by the same method as in Production Example 340.

$^1$H-NMR (CDCl$_3$)

δ: 3.35–3.40(m, 4H), 3.85–3.88(m, 4H), 7.10–7.22(m, 3H), 7.82(d, J=8.8 Hz, 1H), 7.85(dd, J=8.8, 2.0 Hz, 1H), 8.06(d, J=2.0 Hz, 1H), 8.78(s, 1H)

Production Example 357 t-Butyl 4-(1,3-benzodioxol-5-yl)-1-piperazinecarboxylate 300 mg of the title compound was obtained from 1.0 g of 5-bromo-1,3-benzodioxol and 1.2 g t-butyl 1-piperazinecarboxylate by the same method as in Production Example 354.

$^1$H-NMR (CDCl$_3$)

δ: 1.50(s, 9H), 2.99–3.01(m, 4H), 3.56–3.59(m, 4H), 5.92(s, 2H), 6.38(dd, J=8.4, 2.4 Hz, 1H), 6.57(d, J=2.4 Hz, 1H), 6.74(d, J=8.4 Hz, 1H)

Production Example 358

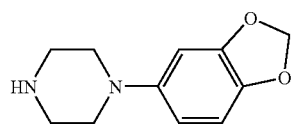

1-(1,3-Benzodioxol-5-yl)piperazine 204 mg of the title compound was obtained from 300 mg of t-butyl 4-(1,3-benzodioxol-5-yl)-1-piperazinecarboxylate (compound in Production Example 357) and trifluoroacetic acid by the same method as in Production Example 355.

$^1$H-NMR (CDCl$_3$)

δ: 3.02(bd, 8H), 5.90(s, 2H), 6.36(dd, J=8.4, 2.4 Hz, 1H), 6.56(d, J=2.4 Hz, 1H), 6.72(d, J=8.4 Hz, 1H)

Production Example 359

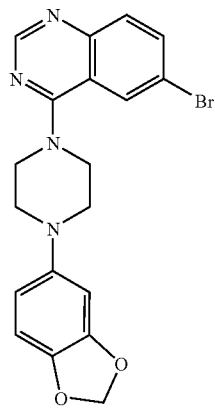

4-[4-(1,3-Benzodioxol-5-yl)piperazin-1-yl]-6-bromoquinazoline 250 mg of the title compound was obtained from 200 mg of 1-(1,3-benzodioxol-5-yl)piperazine (compound in Production Example 358) and 197 mg of 6-bromo-4-chloroquinazoline by the same method as in Production Example 340.

$^1$H-NMR (CDCl$_3$)

δ: 3.27(dd, J=4.8, 4.8 Hz, 2H), 3.27(dd, J=4.8, 4.8 Hz, 2H), 3.92(dd, J=4.8, 4.8 Hz, 2H), 3.92(dd, J=4.8, 4.8 Hz, 2H), 5.93(s, 2H), 6.43(dd, J=8.4, 2.4 Hz, 1H), 6.61(d, J=2.4 Hz, 1H), 6.75(d, J=8.4 Hz, 1H), 7.79(d, J=9.2 Hz, 1H), 7.82(dd, J=9.2, 1.6 Hz, 1H), 8.06(d, J=1.6 Hz, 1H), 8.76(s, 1H)

Production Example 360

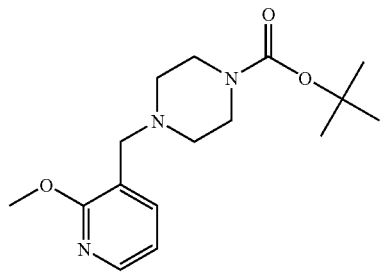

t-Butyl 4-[(2-methoxy-3-pyridyl)methyl]-1-piperazinecarboxylate 813 mg of the title compound was obtained from 400 mg of 3-(chloromethyl)-2-methoxy pyridine and 568 mg of t-butyl 1-piperazinecarboxylate by the same method as in Production Example 340.

¹H-NMR (CDCl₃)
δ: 1.45(s, 9H), 2.42–2.44(m, 4H), 3.43–3.45(m, 4H), 3.51(s, 2H), 3.94(s, 3H), 6.87(dd, J=7.2, 7.2 Hz, 1H), 7.63(dd, J=7.2, 2.0 Hz, 1H), 8.06(dd, J=7.2, 2.0 Hz, 1H)

Production Example 361

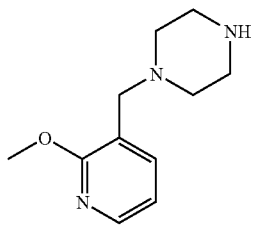

1-[(2-Methoxy-3-pyridyl)methyl]piperazine 572 mg of the title compound was obtained from –813 mg of t-butyl 4-[(2-methoxy-3-pyridyl)methyl]-1-piperazinecarboxylate (compound in Production Example 360) and trifluoroacetic acid by the same method as in Production Example 355.
¹H-NMR (CDCl₃)
δ: 2.40–2.50(bd, 4H), 2.89–2.91(m, 4H), 3.49(s, 2H), 3.94(s, 3H), 6.86(dd, J=7.2, 4.8 Hz, 1H), 7.65(d, J=7.2 Hz, 1H), 8.05(d, J=4.8 Hz, 1H)

Production Example 362

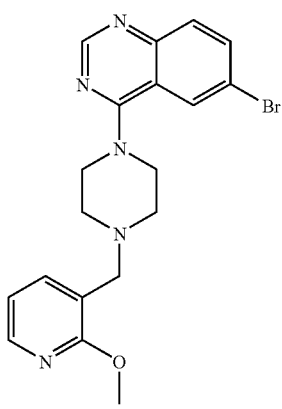

3-{[4-(6-Bromo-4-quinazolyl)piperazin-1-yl]methyl}-2-pyridyl methyl ether 373 mg of the title compound was obtained from 200 mg of 1-[(2-methoxy-3-pyridyl)methyl]piperazine (compound in Production Example 361) and 197 mg of 6-bromo-4-chloroquinazoline by the same method as in Production Example 340.

¹H-NMR (CD₃OD)
δ: 2.66–2.70(m, 4H), 3.61(bd, 2H), 3.85–3.90(m, 4H), 3.95(s, 3H), 6.95–6.98(m, 1H), 7.71(d, J=9.2 Hz, 1H), 7.75(d, J=9.2 Hz, 1H), 7.89–7.92(m, 1H), 8.05–8.06(m, 1H), 8.13(s, 1H), 8.58(s, 1H)

Production Example 363

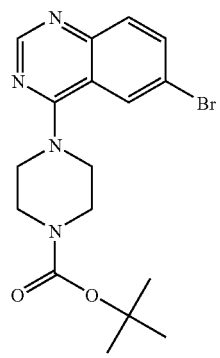

t-Butyl 4-(6-bromo-4-quinazolyl)-1-piperazinecarboxylate 2.8 g of the title compound was obtained from 1.67 g of t-butyl 1-piperazinecarboxylate and 2.0 g of 6-bromo-4-chloroquinazoline by the same method as in Production Example 340.
¹H-NMR (CDCl₃)
δ: 1.52(s, 9H), 3.64–3.75(m, 8H), 7.78(d, J=8.8 Hz, 1H), 7.81(dd, J=8.8, 2.0 Hz, 1H), 8.01(d, J=2.0 Hz, 1H), 8.74(s, 1H)

Production Example 364

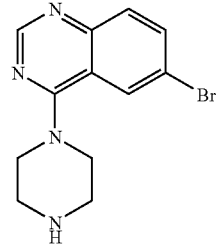

6-Bromo-4-piperazin-1-yl-quinazoline 2.0 g of the title compound was obtained from 2.80 g of t-butyl 4-(6-bromo-4-quinazolyl)-1-piperazinecarboxylate (compound in Production Example 363) by the same method as in Production Example 355.
¹H-NMR (CDCl₃)
δ: 3.00–3.10(m, 4H), 3.70–3.80(m, 4H), 7.75(dd, J=10, 2.0 Hz, 1H), 7.79(dd, J=10, 0.8 Hz, 1H), 8.00(dd, J=2.0, 0.8 Hz, 1H), 8.75(s, 1H)

Production Example 365

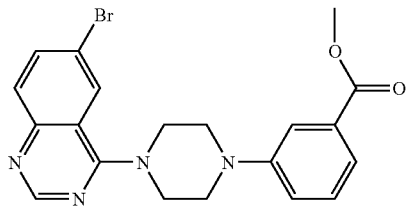

Methyl 3-[4-(6-bromo-4-quinazolinyl)piperidino]benzoate 2.89 g of the title compound was obtained from 1.41 g of methyl 3-piperazin-1-yl-benzoate and 1.56 g of 6-bromo-4-chloroquinazoline by the same method as in Production Example 340.

$^1$H-NMR (CDCl$_3$)

δ: 3.42–3.50(m, 4H), 3.86–3.98(m, 7H), 7.17(d, J=8.0 Hz, 1H), 7.37(dd, J=8.0, 8.0 Hz, 1H), 7.57(d, J=8.0 Hz, 1H), 7.65(bd, 1H), 7.79(d, J=9.2 Hz, 1H), 7.83(d, J=9.2 Hz, 1H), 8.07(s, 1H), 8.77(s, 1H)

Production Example 366

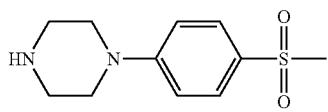

1-(4-Methylsulfonylphenyl)piperazine

A mixture of 3.0 g 1-bromo-4-methylsulfonyl benzene, 3.3 g piperazine and 470 mg tetrabutyl ammonium iodide was stirred at 120° C. to 140° C. for 5 hours. Water was added to the mixture, then insolubles were filtered off, the filtrate was extracted with dichloromethane. The organic layer was washed with brine and dried over anhydrous magnesium sulfate. The solvent was evaporated, and the residue was purified by NH silica gel column chromatography, to give 2.8 g of the title compound as a white solid.

$^1$H-NMR (CDCl$_3$)

δ: 3.00(s, 3H), 3.02(m, 4H), 3.31(m, 4H), 6.92(d, J=8.6 Hz, 2H), 7.98(d, J=8.6 Hz, 2H),

Production Example 367

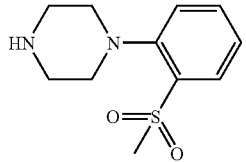

1-(2-Methylsulfonylphenyl)piperazine

A mixture of 2.0 g 1-(2-methane sulfanyl phenyl)piperazine, 11.8 g oxone and 200 mL methanol was stirred at room temperature for 14 hours. After the mixture was concentrated, an aqueous saturated sodium bicarbonate solution was added thereto, and the reaction mixture was extracted with dichloromethane. The organic layer was washed with brine and dried over anhydrous magnesium sulfate. The solvent was evaporated, and the residue was purified by NH silica gel column chromatography, to give 2.5 g of the title compound as a pale yellow solid.

$^1$H-NMR (CDCl$_3$)

δ: 3.00(s, 8H), 3.38(s, 3H), 7.32(t, J=8.0 Hz, 1H), 7.40(d, J=8.0 Hz, 1H), 7.62(t, J=8.0 Hz, 1H), 8.07(d, J=8.0 Hz, 1H), sProduction Example 368

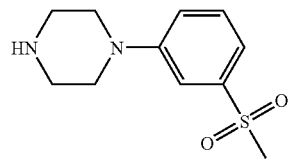

1-(3-Methylsulfonylphenyl)piperazine 120 mg of the title compound was obtained as a white solid from 1.0 g 1-bromo-3-methylsulfonyl benzene, 1.2 g piperazine and 150 mg tetrabutyl ammonium iodide in the same manner as in Production Example 366.

$^1$H-NMR (CDCl$_3$)

δ: 3.04(s, 3H), 3.04(m, 4H), 3.22(m, 4H), 7.12(m, 1H), 7.34(m, 1H), 7.39–7.44(m, 2H)

Production Example 369

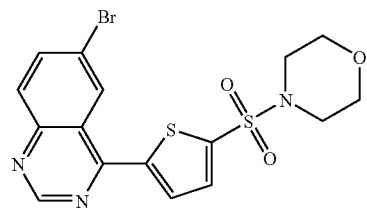

6-Bromo-4-[5-(morpholine-4-sulfonyl)-thiophen-2-yl]quinazoline 0.18 mL chlorosulfonic acid and 0.19 mL thionyl chloride were added to 0.1 g of 6-bromo-4-(2-thienyl)quinazoline (compound in Production Example 96) under ice-cooling in a stream of nitrogen, and the mixture was heated for 13 hours at 60° C., then neutralized by adding water and a sodium bicarbonate solution and extracted with dichloromethane. 5-(6-Bromoquinazolin-4-yl)-thiophen-2-sulfonyl chloride obtained by drying the organic layer over anhydrous sodium sulfate was dissolved in 3 mL tetrahydrofuran, then 0.3 mL morpholine was added thereto, and the mixture was stirred at room temperature for 1 hour. The solvent was removed, and the positional isomers were separated and purified by silica gel column chromatography (ethyl acetate/hexane) to give 57 mg of the title compound (colorless crystals).

¹H-NMR (CDCl₃)

δ: 3.15–3.25(m, 4H), 3.79–3.87(m, 4H), 7.67(d, J=4.0 Hz, 1H), 7.85(d, J=4.0 Hz, 1H), 8.03(d, J=8.6 Hz, 1H), 8.06(dd, J=8.6, 1.8 Hz, 1H), 8.57(d, J=1.8 Hz, 1H), 9.33(s, 1H)

Production Example 370

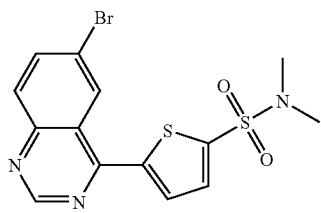

5-(6-Bromoquinazolin-4-yl)-thiophen-2-sulfonic acid dimethylamide 137 mg of the title compound was obtained as pale yellow crystals from 250 mg of 6-bromo-4-(2-thienyl)quinazoline (compound in Production Example 96) and 4.7 mL dimethylamine by the same reaction as in Production Example 369.

¹H-NMR (CDCl₃)

δ: 2.87(s, 6H), 7.68(d, J=4.0 Hz, 1H), 7.84(d, J=4.0 Hz, 1H), 8.03(dd, J=8.8, 0.6 Hz, 1H), 8.05(dd, J=8.8, 2.0 Hz, 1H), 8.58(dd, J=2.0, 0.6 Hz, 1H), 9.33(s, 1H)

Production Example 371

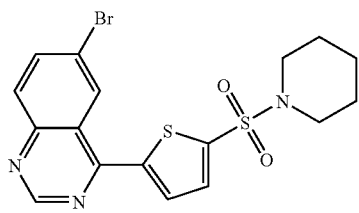

6-Bromo-4-[5-(piperidin-1-sulfonyl)-thiophen-2-yl]quinazoline 152 mg of the title compound was obtained as pale yellow crystals from 250 mg of 6-bromo-4-(2-thienyl)quinazoline (compound in Production Example 96) and 0.93 mL piperidine by the same reaction as in Production Example 369.

¹H-NMR (CDCl₃)

δ: 1.46–1.54(m, 2H), 1.68–1.78(m, 4H), 3.13–3.20(m, 4H), 7.64(d, J=4.0 Hz, 1H), 7.82(d, J=4.0 Hz, 1H), 8.02(dd, J=8.8, 0.7 Hz, 1H), 8.05(dd, J=8.8, 1.8 Hz, 1H), 8.58(dd, J=1.8, 0.7 Hz, 1H), 9.33(s, 1H)

Production Example 372

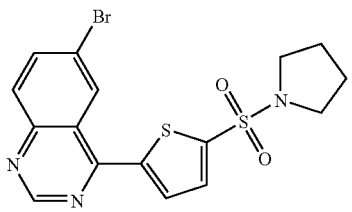

6-Bromo-4-[5-(pyrrolidine-1-sulfonyl)-thiophen-2-yl]quinazoline 127 mg of the title compound was obtained as pale orange crystals from 250 mg of 6-bromo-4-(2-thienyl)quinazoline (compound in Production Example 96) and 0.79 mL pyrrolidine by the same reaction as in Production Example 369.

¹H-NMR (CDCl₃)

δ: 1.80–1.90(m, 4H), 3.37–3.44(m, 4H), 7.71(d, J=4.0 Hz, 1H), 7.83(d, J=4.0 Hz, 1H), 8.02(d, J=8.8 Hz, 1H), 8.05(dd, J=8.8, 1.7 Hz, 1H), 8.58(d, J=1.7 Hz, 1H), 9.33(s, 1H)

Production Example 373

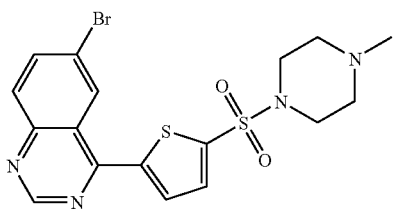

6-Bromo-4-[5-(4-methylpiperazine-1-sulfonyl)-thiophen-2-yl)quinazoline 149 mg of the title compound was obtained as colorless crystals from 250 mg of 6-bromo-4-(2-thienyl)quinazoline (compound in Production Example 96) and 1.05 mL 1-methyl piperazine by the same reaction as in Production Example 369.

¹H-NMR (CDCl₃)

δ: 2.32(s, 3H), 2.54–2.59(m, 4H), 3.18–3.27(m, 4H), 7.65(d, J=4.0 Hz, 1H), 7.82(d, J=4.0 Hz, 1H), 8.02(dd, J=9.0, 0.8 Hz, 1H), 8.06(dd, J=9.0, 1.7 Hz, 1H), 8.55(dd, J=1.7, 0.8 Hz, 1H), 9.32(s, 1H)

Production Example 374

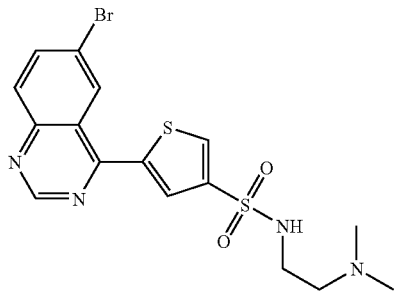

5-(6-Bromoquinazolin-4-yl)-thiophen-3-sulfonic acid (2-dimethylaminoethyl)amide 24 mg of the title compound was obtained as a yellow amorphous from 131 mg of 6-bromo-4-(2-thienyl)quinazoline (compound in Production Example 96) and 0.42 mL N,N-dimethylethylene diamine by the same reaction as in Production Example 369.

$^1$H-NMR(CDCl$_3$)

δ: 2.13(s, 6H), 2.38–2.43(m, 2H), 3.08–3.14(m, 2H), 7.98–8.08(m, 3H), 8.23–8.27(m, 1H), 8.55–8.58(m, 1H), 9.31(s, 1H)

Production Example 375

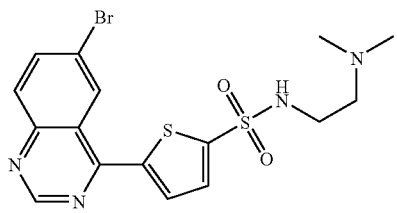

5-(6-Bromoquinazolin-4-yl)-thiophen-2-sulfonic acid (2-dimethylaminoethyl)amide 57 mg of the title compound was obtained as a pale brown amorphous from 131 mg of 6-bromo-4-(2-thienyl)quinazoline (compound in Production Example 96) and 0.42 mL N,N-dimethylethylene diamine by the same reaction as in Production Example 369.

$^1$H-NMR (CDCl$_3$)

δ: 2.16(s, 6H), 2.42–2.47(m, 2H), 3.16–3.20(m, 2H), 7.72–7.81(m, 2H), 7.95–8.07(m, 2H), 8.57(brs, 1H), 9.33(s, 1H)

Production Example 376

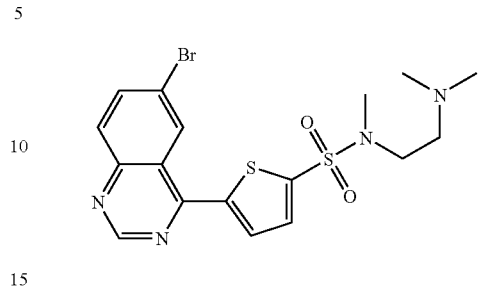

5-(6-Bromoquinazolin-4-yl)-thiophen-2-sulfonic acid (2-dimethylaminoethyl)-methyl-amide 131 mg of the title compound was obtained as a pale brown amorphous from 131 mg of 6-bromo-4-(2-thienyl)quinazoline (compound in Production Example 96) and 0.50 mL N,N,N'-trimethylethylene diamine by the same reaction as in Production Example 369.

$^1$H-NMR (CDCl$_3$)

δ: 2.29(s, 6H), 2.54–2.59(m, 2H), 2.95(s, 3H), 3.22–3.27 (m, 2H), 7.68(d, J=4.0 Hz, 1H), 7.81(d, J=4.0 Hz, 1H), 7.99–8.07(m, 2H), 8.57(d, J=1.6 Hz, 1H), 9.32(s, 1H)

Production Example 377

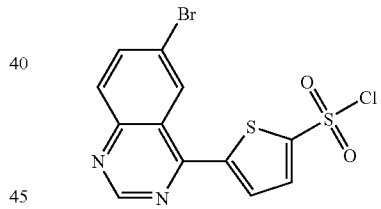

5-(6-Bromoquinazolin-4-yl)-thiophen-2-sulfonyl chloride 14.4 mL chlorosulfonic acid and 14.42 mL thionyl chloride were added to 7.78 g of 6-bromo-4-(2-thienyl)quinazoline (compound in Production Example 96) under ice-cooling in a stream of nitrogen, and the mixture was heated at 60° C. for 16 hours, then poured into iced water, neutralized by adding a sodium bicarbonate solution and extracted with dichloromethane. The organic layer was dried over anhydrous sodium sulfate. The residue was recrystallized from ether/hexane, to give 2.47 g of the title compound (pale skin-colored crystals).

$^1$H-NMR (CDCl$_3$)

δ: 7.84(d, J=4.0 Hz, 1H), 8.01(d, J=4.0 Hz, 1H), 8.04–8.09(m, 2H), 8.53–8.55(m, 1H), 9.37(s, 1H)

Production Example 378

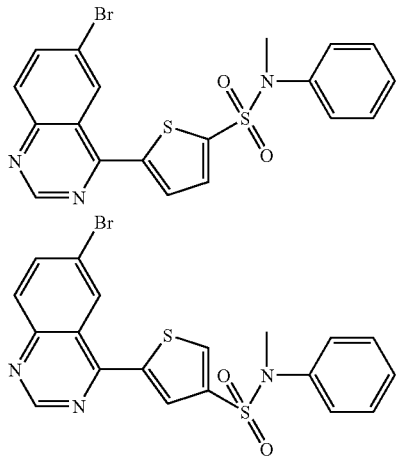

5-(6-Bromoquinazolin-4-yl)-thiophen-2-sulfonic acid methylphenylamide and 5-(6-bromoquinazolin-4-yl)-thiophen-3-sulfonic acid methylphenylamide 142 mg of the title compounds were obtained as a mixture of orange amorphous positional isomers from 131 mg of 6-bromo-4-(2-thienyl)quinazoline (compound in Production Example 96) and 0.42 mL N-methylaniline by the same reaction as in Production Example 369.

$^1$H-NMR (CDCl$_3$)

δ: 3.30(s, 1.05H), 3.36(s, 1.95H), 7.22–7.42(m, 6H), 7.67(d, J=1.6 Hz, 0.35H), 7.77(d, J=4.4 Hz, 0.65H), 7.98–8.06(m, 2H), 8.31(dd, J=2.0, 0.8 Hz, 0.35H), 8.54(dd, J=2.0, 0.8 Hz, 0.65H), 9.30(s, 0.35H), 9.32(s, 0.65H)

Production Example 379

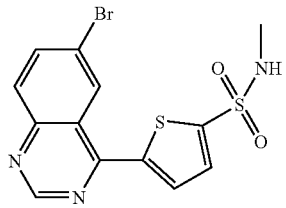

5-(6-Bromoquinazolin-4-yl)-thiophen-2-sulfonic acid methylamide 800 mg of 5-(6-bromoquinazolin-4-yl)-thiophen-2-sulfonyl chloride (compound in Production Example 377) was dissolved in 15 mL tetrahydrofuran, and 1.78 mL methylamine was added thereto and stirred at room temperature for 1 hour. The solvent was removed, and the residue was purified by silica gel column chromatography (ethyl acetate/hexane), to give 752 mg of the title compound (pale skin-colored crystals).

$^1$H-NMR (CDCl$_3$)

δ: 2.61(s, 3H), 7.74(d, J=4.0 Hz, 1H), 7.98(brs, 1H), 8.06(d, J=9.1 Hz, 1H), 8.16(d, J=4.0 Hz, 1H), 8.24(dd, J=2.1, 9.1 Hz, 1H), 8.66(d, J=2.1 Hz, 1H), 9.35(s, 1H)

Production Example 380

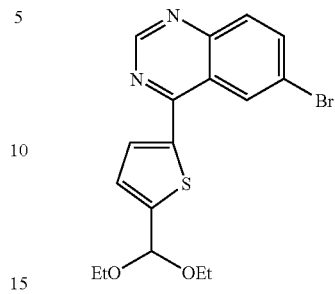

6-Bromo-4-(5-diethoxymethylthiophen-2-yl)quinazoline 2.73 g of the title compound was obtained as yellow oil from 3.5 g of 6-bromo-4-chloroquinazoline and 6.5 g of tributyl[5-(diethoxymethyl)-2-thienyl]stannane (compound in Production Example 47) by the same reaction as in Production Example 96.

$^1$H-NMR (CDCl$_3$)

δ: 1.29(t, J=6.8 Hz, 6H), 3.60–3.80(m, 4H), 5.83(s, 1H), 7.25(d, J=4.0 Hz, 1H), 7.40(d, J=4.0 Hz, 1H), 7.95(dd, J=8.8, 0.7 Hz, 1H), 7.98(dd, J=8.8, 2.0 Hz, 1H), 8.64(dd, J=2.0, 0.7 Hz, 1H), 9.26(s, 1H)

Production Example 381

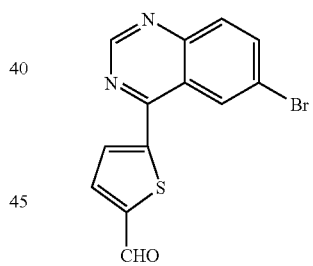

5-(6-Bromoquinazolin-4-yl)thiophen-2-carboaldehyde 2.6 g of 6-bromo-4-(5-diethoxymethylthiophen-2-yl)quinazoline (compound in Production Example 380) was dissolved in 10 mL dichloromethane, then 5 mL trifluoroacetic acid was added thereto, and the mixture was stirred at room temperature for 3 hours, neutralized by adding water and a sodium bicarbonate solution, and extracted with dichloromethane. The organic layer was dried over anhydrous sodium sulfate, and the solvent was evaporated, whereby 2.07 g of the title compound was obtained as pale yellow crystals.

$^1$H-NMR (CDCl$_3$)

δ: 7.89(d, J=4.0 Hz, 1H), 7.92(d, J=4.0 Hz, 1H), 8.00–8.11(m, 2H), 8.58(dd, J=1.6, 0.8 Hz, 1H), 9.36(s, 1H), 10.05(s, 1H)

Production Example 382

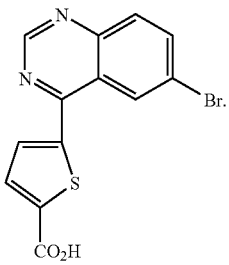

5-(6-Bromoquinazolin-4-yl)thiophen-2-carboxylic acid

A solution of 2.19 g silver nitrate in 40 mL water and a solution of 1.96 g 5-(6-bromoquinazolin-4-yl)thiophen-2-carboaldehyde (compound in Production Example 381) in 20 mL dimethyl sulfoxide were added little by little successively to a solution of 1.0 g sodium hydroxide in 40 mL water under ice-cooling, and the mixture was stirred at room temperature for 24 hours. The reaction solution was filtered through Celite and acidified with hydrochloric acid, and the precipitated crystals were filtered. This product was recrystallized from dichloromethane/methanol/ether, to give 1.7 g of the title compound as pale yellow crystals.

$^1$H-NMR (DMSO-$d_6$)

δ: 7.87(d, J=4.0 Hz, 1H), 8.06(d, J=8.8 Hz, 1H), 8.10(d, J=4.0 Hz, 1H), 8.23(dd, J=8.8, 2.0 Hz, 1H), 8.64(d, J=2.0 Hz, 1H), 9.35(s, 1H)

Production Example 383

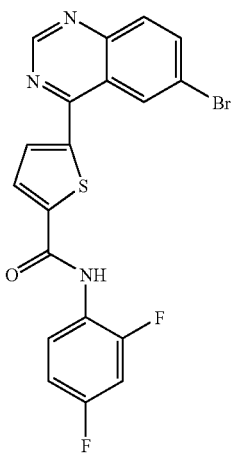

5-(6-Bromoquinazolin-4-yl)thiophen-2-carboxylic acid (2,4-difluorophenyl)amide 300 mg of 5-(6-bromoquinazolin-4-yl)thiophen-2-carboxylic acid (compound in Production Example 382) was dissolved in 4 mL tetrahydrofuran, then 0.37 mL triethylamine and 0.14 mL isobutyl chlorocarbonate were added thereto under ice-cooling, and the mixture was stirred for 1 hour under nitrogen atmosphere. This mixture was added to a solution of 1.15 g 2,4-difluorophenylamine in 10 mL tetrahydrofuran and stirred at room temperature for 1 hour. Further, the reaction mixture was stirred at 70° C. for 3 hours, then water was added thereto, the reaction mixture was extracted with ethyl acetate, and the solvent was evaporated. The residue was washed with ether to give 171 mg of the title compound as pale yellow crystals.

$^1$H-NMR (DMSO-$d_6$)

δ: 7.13–7.20(m, 1H), 7.38–7.46(m, 1H), 7.59–7.67(m, 1H), 8.07(d, J=8.8 Hz, 1H), 8.18(d, J=4.2 Hz, 1H), 8.19(d, J=4.2 Hz, 1H), 8.24(dd, J=8.8, 1.8 Hz, 1H), 8.64(d, J=1.8 Hz, 1H), 9.35(s, 1H), 10.45(s, 1H)

Production Example 384

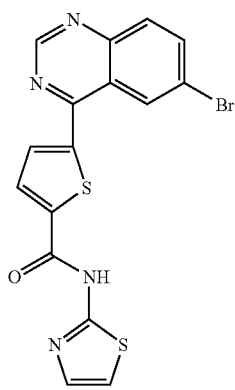

5-(6-Bromoquinazolin-4-yl)thiophen-2-carboxylic acid thiazol-2-yl amide 40 mg of the title compound was obtained as yellow crystals from 300 mg of 5-(6-bromoquinazolin-4-yl)thiophen-2-carboxylic acid (compound in Production Example 382) and 0.9 g of 2-aminothiazole by the same reaction as in Production Example 383.

$^1$H-NMR (DMSO-$d_6$)

δ: 7.27–7.33(m, 1H), 7.59(d, J=3.8 Hz, 1H), 8.07(d, J=8.8 Hz, 1H), 8.19(d, J=3.8 Hz, 1H), 8.24(dd, J=8.8, 2.2 Hz, 1H), 8.30–8.38(m, 1H), 8.68(d, J=2.2 Hz, 1H), 9.36(s, 1H)

Production Example 385

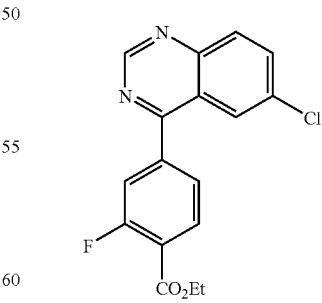

Ethyl 4-(6-chloroquinazolin-4-yl)-2-fluorobenzoate 0.74 g 4,6-dichloroquinazoline, 4.3 g ethyl 2-chloro-4-(4,4,5,5-tetramethyl-[1,3,2]dioxaborolan-2-yl)-benzoate prepared according to T. Ishiya et al., J. Org. Chem., 60, 7508 (1995), 1.2 g potassium phosphate, 210 mg tetrakistriphenyl phosphine palladium and 30 mL N,N-dimethylformamide were heated at 90° C. under nitrogen satmosphere. Water was added thereto, and the reaction mixture was extracted with ethyl acetate. The organic layer was washed with water and brine and dried over sodium sulfate. The solvent was evaporated, and the residue was purified by NH silica gel column chromatography (ethyl acetate) and further by silica gel column chromatography (hexane/ethyl acetate), to give 0.81 g of the title compound (colorless crystals).

¹H-NMR (CDCl₃)

δ: 1.45(t, J=7.0 Hz, 3H), 4.47 (q, J=7.0 Hz, 2H), 7.55–7.63(m, 2H), 7.89(dd, J=8.9, 2.2 Hz, 1H), 8.02(d, J=2.2 Hz, 1H), 8.11(d, J=8.9 Hz, 1H), 8.14–8.20(m, 1H), 9.40(s, 1H)

Production Example 386

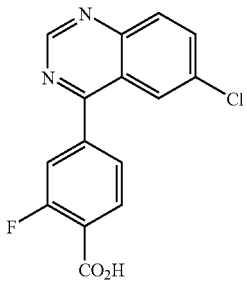

4-(6-Chloroquinazolin-4-yl)-2-fluorobenzoic acid 465 mg of the title compound was obtained as colorless crystals from 0.7 g of ethyl 4-(6-chloroquinazolin-4-yl)-2-fluorobenzoate (compound in Production Example 385) by the same reaction as in Production Example 310.

¹H-NMR (DMSO-d₆)

δ: 7.72(dd, J=8.0, 1.6 Hz, 1H), 7.77(dd, J=11.2, 1.6 Hz, 1H), 8.05–8.20(m, 4H), 9.44(s, 1H)

Production Example 387

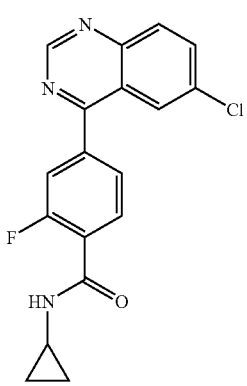

4-(6-Chloroquinazolin-4-yl) N-cyclopropyl-2-fluorobenzamide 0.2 g 4-(6-chloroquinazolin-4-yl)-2-fluorobenzoic acid (compound in Production Example 386), 41 mg cyclopropylamine and 0.12 mL triethylamine were dissolved in 6 mL dichloromethane, then 320 mg benzotriazol-1-yloxytris (dimethylamino)-phosphonium hexafluorophosphate was added thereto, and the mixture was stirred at room temperature for 3 hours. The reaction solution was purified by NH silica gel column chromatography (hexane/ethyl acetate) and then recrystallized from methanol/ethyl acetate/ether, to give 162 mg of the title compound as colorless crystals.

¹H-NMR (CDCl₃)

δ: 0.66–0.72(m, 2H), 0.91–0.97(m, 2H), 2.96–3.04(m, 1H), 6.87–6.93(m, 1H), 7.56(dd, J=12.0, 1.6 Hz, 1H), 7.66 (dd, J=8.0, 1.6 Hz, 1H), 7.88(dd, J=8.8, 1.8 Hz, 1H), 8.01(d, J=1.8 Hz, 1H), 8.10(d, J=8.8 Hz, 1H), 8.34(t, J=8.0 Hz, 1H), 9.40(s, 1H)

Production Example 388

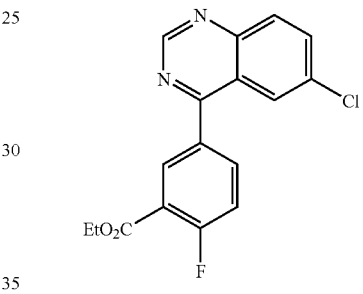

Ethyl 5-(6-chloroquinazolin-4-yl)-2-fluorobenzoate 1.84 g of the title compound was obtained as pale yellow crystals by the same reaction as in Production Example 385 from 5.9 g of ethyl 2-fluoro-5-(4,4,5,5-tetramethyl-[1,3,2] dioxaborolan-2-yl)-benzoate prepared according to T. Ishiya et al., J. Org. Chem., 60, 7508 (1995) and 0.9 g 4,6-dichloroquinazoline.

¹H-NMR (CDCl₃)

δ: 1.42(t, J=7.0 Hz, 3H), 4.45 (q, J=7.0 Hz, 2H), 7.39(dd, J=10.0, 8.4 Hz, 1H), 7.89(dd, J=9.1, 1.9 Hz, 1H), 7.92–7.97 (m, 1H), 8.02(d, J=1.9 Hz, 1H), 8.10(d, J=9.1 Hz, 1H), 8.37(dd, J=6.8, 2.4 Hz, 1H), 9.40(s, 1H)

Production Example 389

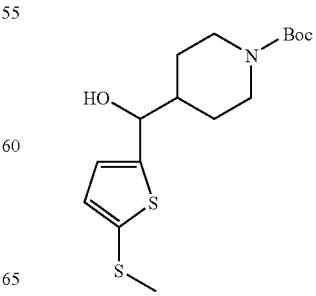

t-Butyl 4-[hydroxy-(5-methylsulfanylthiophen-2-yl)-methyl]-piperidine-1-carboxylate 1.2 g of 2-bromo-5-(methylsulfanyl)thiophen (compound in Production Example 45) was dissolved in 20 mL anhydrous tetrahydrofuran, and 3.72 mL solution of 1.59 M n-butyl lithium in hexane was added dropwise there to at −70° C. After the mixture was stirred for 1 hour, 6 ml solution of 1.2 g t-butyl 4-formyl-piperidine-1-carboxylate in anhydrous tetrahydrofuran was added dropwise thereto and stirred at −70° C. for 2 hours. The temperature of the reaction solution was gradually increased to 0° C., water and an ammonium chloride solution were added thereto, and the reaction solution was extracted with ethyl acetate. The extract was dried over magnesium sulfate and purified by silica gel column chromatography (ethyl acetate/hexane), to give 1.41 g of the title compound as pale pink crystals.

$^1$H-NMR (CDCl$_3$)

δ: 1.10–1.30(m, 2H), 1.35–1.42(m, 1H), 1.43(s, 9H), 1.69–1.80(m, 1H), 1.94–2.03(m, 1H), 2.47(s, 3H), 2.55–2.73(m, 2H), 4.00–4.23(m, 2H), 4.54(dd, J=7.6, 3.2 Hz, 1H), 6.77(d, J=3.4 Hz, 1H), 6.92(d, J=3.4 Hz, 1H)

Production Example 390

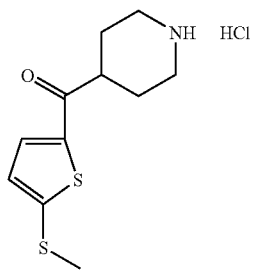

(5-Methylsulfanylthiophen-2-yl)piperidin-4-yl-methanone hydrochloride 1.41 g of t-butyl 4-[hydroxy-(5-methylsulfanylthiophen-2-yl)-methyl]-piperidine-1-carboxylate (compound in Production Example 389) was dissolved in 40 mL acetone, and 14 g manganese dioxide was added thereto and stirred at room temperature for 24 hours. The reaction mixture was filtered through Celite, then the solvent was removed to give 1.14 g t-butyl 4-(5-methylsulfanylthiophen-2-carbonyl)piperidine-1-carboxylate, 5 mL of 4 N hydrogen chloride in ethyl acetate was added thereto, and the mixture was left for 1 hour. The solvent was removed, and the precipitated crystals were washed with ethyl acetate/ether, to give 0.75 g of the title compound as colorless crystals.

$^1$H-NMR (DMSO-d$_6$)

δ: 1.73–1.96(m, 4H), 2.65(s, 3H), 2.94–3.04(m, 2H), 3.26–3.38(m, 2H), 3.54–3.64(m, 1H), 7.16(d, J=4.0 Hz, 1H), 8.00(d, J=4.0 Hz, 1H), 9.03(brs, 2H)

Production Example 391

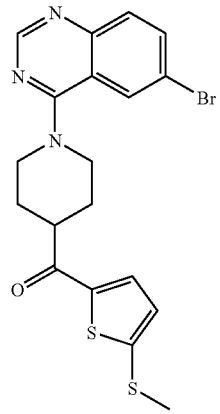

[1-(6-Bromoquinazolin-4-yl)piperidin-4-yl]-(5-methylsulfanylthiophen-2-yl)methanone A mixture of 220 mg 6-bromo-4-chloroquinazoline, 250 mg (5-methylsulfanylthiophen-2-yl)piperidin-4-yl-methanone hydrochloride (compound in Production Example 390), 0.31 mL triethylamine and 4 mL tetrahydrofuran was stirred at room temperature for 4 hours. Insolubles were filtered off, the solvent was evaporated, and the residue was purified by SiO$_2$ silica gel column chromatography (hexane/ethyl acetate), to give 304 mg pale yellow crystals as pale yellow crystals.

$^1$H-NMR (CDCl$_3$)

δ: 2.02–2.18(m, 4H), 2.62(s, 3H), 3.25–3.34(m, 2H), 3.35–3.44(m, 1H), 4.32–4.40(m, 2H), 6.96(d, J=3.8 Hz, 1H), 7.64(d, J=3.8 Hz, 1H), 7.77(d, J=8.8 Hz, 1H), 7.80(dd, J=8.8, 1.8 Hz, 1H), 8.02(d, J=1.8 Hz, 1H), 8.73(s, 1H)

Production Example 392

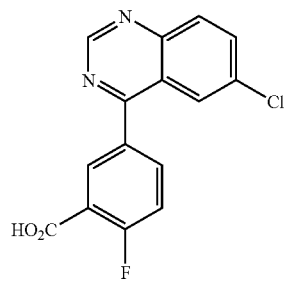

5-(6-Chloroquinazolin-4-yl)-2-fluoro-benzoic acid 694 mg of the title compound was obtained as colorless crystals from 940 mg of ethyl 5-(6-chloroquinazolin-4-yl)-2-fluorobenzoate (compound in Production Example 388) by the same reaction as in Production Example 310.

$^1$H-NMR (DMSO-d$_6$)

δ: 7.60(dd, J=10.6, 8.8 Hz, 1H), 8.06(d, J=2.0 Hz, 1H), 8.08–8.13(m, 2H), 8.1.6(d, J=8.8 Hz, 1H), 8.28(dd, J=6.8, 2.4 Hz, 1H), 9.41(s, 1H)

Production Example 393

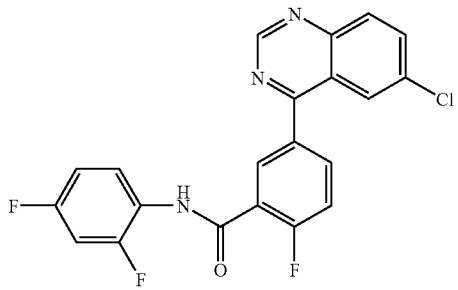

5-(6-Chloroquinazolin-4-yl)-N-(2,4-difluorophenyl)-2-fluoro-benzamide 72 mg of the title compound was obtained as colorless crystals from 100 mg of 2-fluoro-5-[6-(1-trityl-1H-pyrazol-4-yl)-quinazolin-4-yl]benzoic acid (compound in Production Example 392) and 43 mg of 2,4-difluorophenylamine by the same method as in Production Example 311.

$^1$H-NMR (CDCl$_3$)

δ: 6.84–6.92(m, 2H), 7.41(dd, J=11.6, 8.8 Hz, 1H), 7.83 (dd, J=9.0, 1.8 Hz, 1H), 7.90–7.96(m, 1H), 7.97(d, J=1.8 Hz, 1H), 8.05(d, J=9.0 Hz, 1H), 8.34–8.42(m, 1H), 8.53(dd, J=7.2, 2.4 Hz, 1H), 8.62–8.70(m, 1H), 9.33(s, 1H)

Production Example 394

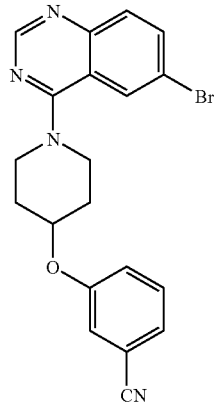

3-[1-(6-Bromoquinazolin-4-yl)piperidin-4-yloxy]-benzonitrile 81 mg of the title compound was obtained as a colorless amorphous from 100 mg of 6-bromo-4-chloroquinazoline and 88 mg of 3-(piperidin-4-yloxy)benzonitrile by the same reaction as in Production Example 391.

$^1$H-NMR (CDCl$_3$)

δ: 2.00–2.09(m, 2H), 2.15–2.24(m, 2H), 3.72–3.78(m, 2H), 3.97–4.05(m, 2H), 4.65–4.71(m, 1H), 7.17–7.22(m, 2H), 7.26–7.29(m, 1H), 7.38–7.43(m, 1H), 7.78(dd, J=8.6, 0.6 Hz, 1H), 7.82(dd, J=8.6, 1.9 Hz, 1H), 8.02(dd, J=1.9, 0.6 Hz, 1H), 8.75(s, 1H)

Production Example 395

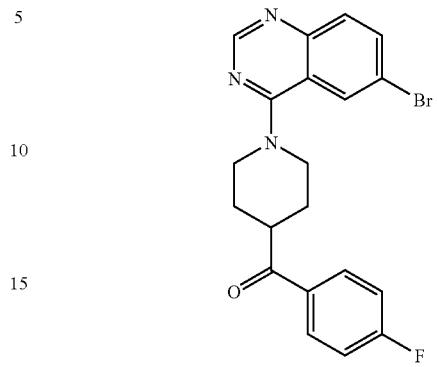

[1-(6-Bromoquinazolin-4-yl)piperidin-4-yl]-(4-fluorophenyl)methanone 53 mg of the title compound was obtained as a colorless amorphous from 100 mg of 6-bromo-4-chloroquinazoline and 100 mg of (4-fluorophenyl)-piperidin-4-yl-methanone hydrochloride by the same reaction as in Production Example 391.

$^1$H-NMR(CDCl$_3$)

δ: 2.04–2.12(m, 4H), 3.30–3.38(m, 2H), 3.55–3.64(m, 1H), 4.33–4.40(m, 2H), 7.17–7.22(m, 2H), 7.78(d, J=8.6 Hz, 1H), 7.81(dd, J=8.6, 2.0 Hz, 1H), 8.01–8.06(m, 3H), 8.75(s, 1H)

Production Example 396

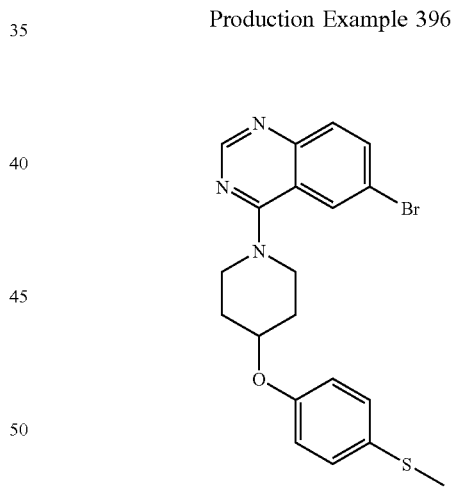

6-Bromo-4-[4-(4-methylsulfanylphenoxy)piperidin-1-yl]quinazoline 863 mg of the title compound was obtained as colorless crystals from 600 mg of 6-bromo-4-chloroquinazoline and 640 mg of 4-[4-(methylsulfanyl)phenoxy]piperidine hydrochloride by the same reaction as in Production Example 391.

$^1$H-NMR (CDCl$_3$)

δ: 1.99–2.07(m, 2H), 2.12–2.20(m, 2H), 2.46(s, 3H), 3.70–3.77(m, 2H), 3.96–4.03(m, 2H), 4.59–4.65(m, 1H), 6.89–6.93(m, 2H), 7.26–7.30(m, 2H), 7.77(d, J=9.0 Hz, 1H), 7.80(dd, J=9.0, 1.9 Hz, 1H), 8.02(dd, J=1.9, 0.8 Hz, 1H), 8.73(s, 1H)

Production Example 397

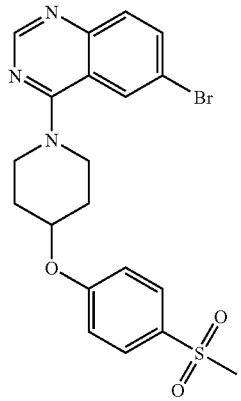

6-Bromo-4-[4-(4-methylsulfonylphenoxy)piperidin-1-yl]quinazoline 670 mg of the title compound was obtained as a colorless amorphous from 863 mg of 6-bromo-4-[4-(4-methylsulfanylphenoxy)piperidin-1-yl]quinazoline (compound in Production Example 396) and 2.47 g oxone by the same reaction as in Production Example 43.

$^1$H-NMR (CDCl$_3$)

δ: 2.01–2.11(m, 2H), 2.16–2.26(m, 2H), 3.05(s, 3H), 3.73–3.82(m, 2H), 3.96–4.03(m, 2H), 4.75–4.82(m, 1H), 7.05–7.10(m, 2H), 7.79(d, J=8.8 Hz, 1H), 7.82(dd, J=8.8, 1.8 Hz, 1H), 7.88–7.92(m, 2H), 8.02(d, J=1.8 Hz, 1H), 8.75(s, 1H)

Production Example 398

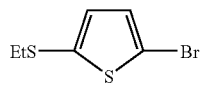

2-Bromo-5-(ethylsulfanyl)thiophen 4.05 g of the title compound was obtained as a pale yellow oil from 2.8 g 2-(ethylsulfanyl)thiophen by the same method as in Production Example 45.

$^1$H-NMR (CDCl$_3$)

δ: 1.26(t, J=7.2 Hz, 3H), 2.76 (q, J=7.2 Hz, 2H), 2.44(s, 3H), 6.88(d, J=4.0 Hz, 1H), 6.92(d, J=4.0 Hz, 1H)

Production Example 399

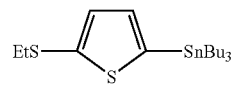

Tributyl[5-(ethylsulfanyl)-2-thienyl]stannane 8.45 g crude product of the title compound was obtained as a pale yellow oil from 4.04 g 2-bromo-5-(ethylsulfanyl)thiophen (compound in Production Example 398) by the same method as in Production Example 46. This product was used in the subsequent reaction without purification.

Production Example 400

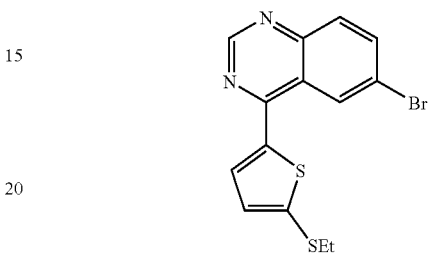

6-Bromo-4-(5-ethylsulfanylthiophen-2-yl)quinazoline 538 mg of the title compound was obtained as yellow crystals from 730 mg 6-bromo-4-chloroquinazoline and 1.3 g tributyl[5-(ethylsulfanyl)-2-thienyl]stannane (compound in Production Example 399) by the same method as in Production Example 96.

$^1$H-NMR (CDCl$_3$)

δ: 1.40(t, J=7.2 Hz, 3H), 3.03 (q, J=7.2 Hz, 2H), 7.20(t, J=4.0 Hz, 1H), 7.71(d, J=4.0 Hz, 1H), 7.94(dd, J=9.2, 0.8 Hz, 1H), 7.98(dd, J=9.2, 2.0 Hz, 1H), 8.61(dd, J=2.0, 0.8 Hz, 1H), 9.23(s, 1H)

Production Example 401

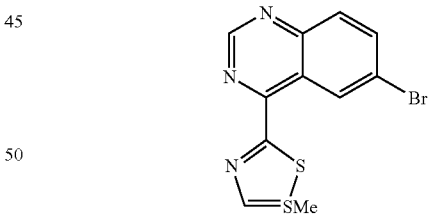

6-Bromo-4-(5-methylsulfanylthiazol-2-yl)quinazoline 64 mg of the title compound was obtained as yellow crystals from 77 mg 6-bromo-4-chloroquinazoline and 178 mg 5-methylsulfanyl-2-tributylstannyl thiazole (compound in Production Example 217) by the same method as in Production Example 96.

$^1$H-NMR (CDCl$_3$)

δ: 2.65(s, 3H), 7.92(s, 1H), 7.93(d, J=9.2 Hz, 1H), 8.01 (dd, J=9.2, 2.0 Hz, 1H), 9.28(s, 1H), 9.92(dd, J=2.0, 0.8 Hz, 1H)

Production Example 402

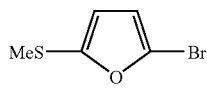

2-Bromo-5-(methylsulfanyl)furan 831 mg crude product of the title compound was obtained as a colorless oil from 2.69 g 2-(methylsulfanyl)furan by the same method as in Production Example 45.

$^1$H-NMR (CDCl$_3$)

δ: 2.40(s, 3H), 6.28(d, J=3.2 Hz, 1H), 6.43(d, J=3.2 Hz, 1H)

Production Example 403

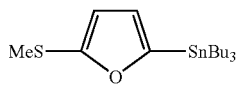

Tributyl[5-(methylsulfanyl)-2-furyl]stannane 1.42 g crude product of the title compound was obtained as a pale yellow oil from 830 mg 2-bromo-5-(methylsulfanyl)furan (compound in Production Example 402) by the same method as in Production Example 46. This product was used in the subsequent reaction without purification.

Production Example 404

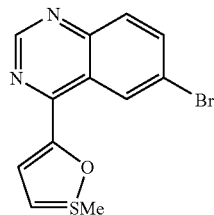

6-Bromo-4-(5-methylsulfanylfuran-2-yl)quinazoline 92 mg of the title compound was obtained as a yellow solid from 365 mg 6-bromo-4-chloroquinazoline and 665 mg tributyl[5-(methylsulfanyl)-2-furyl]stannane (compound in Production Example 403) by the same method as in Production Example 96.

$^1$H-NMR (CDCl$_3$)

δ: 2.65(s, 3H), 6.59(d, J=3.2 Hz, 1H), 7.59(d, J=3.2 Hz, 1H), 7.90(d, J=8.8 Hz, 1H), 7.96(dd, J=9.2, 2.0 Hz, 1H), 9.06(d, J=2.0 Hz, 1H), 9.23(s, 1H)

Production Example 405

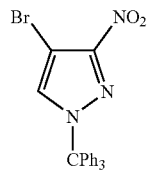

4-Bromo-3-nitro-1-trityl-1H-pyrazole 1.42 mL bromine was added at room temperature to a mixture of 3.13 g 3-nitro-1H-pyrazole (compound described in Janssen et al., J. Org. Chem., 36, 3081 (1971)) and 60 mL acetic acid, and the mixture was stirred for 6 hours. Iced water was added to the reaction solution which was then neutralized with 5 N aqueous sodium hydroxide and an aqueous saturated ammonium chloride solution. By adding ethyl acetate and water, the aqueous layer was separated. The aqueous layer was saturated with common salt and extracted with ethyl acetate. The combined organic layer was washed with an aqueous brine and then dried over anhydrous sodium sulfate. The drying agent was filtered off, and the filtrate was evaporated. 5.41 g crude product of 4-bromo-3-nitro-1H-pyrazole was obtained as pale brown crystals. From this compound, 11.05 g of the title compound was obtained as pale brown crystals by the same method as in Production Example 15.

$^1$H-NMR (CDCl$_3$)

δ: 7.10(m, 6H), 7.27–7.40(m, 9H), 7.46(s, 1H)

Production Example 406

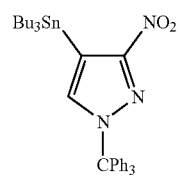

3-Nitro-4-tributylstannyl-1-trityl-1H-pyrazole 12 mg tetrakis(triphenylphosphine)palladium was added at room temperature to a mixture of 434 mg 4-bromo-3-nitro-1-trityl-1H-pyrazole (compound in Production Example 405), 1.26 mL 1,1, 1,2,2,2-hexabutyldistannane and 10 mL toluene in a stream of nitrogen, and the mixture was heated for 4 hours under reflux. Insolubles were filtered off, and the filtrate was evaporated. The resulting residue was purified by silica gel column chromatography (ethyl acetate/hexane) to give 130 mg of the title compound as a white product.

$^1$H-NMR (CDCl$_3$)

δ: 0.84(t, J=7.2 Hz, 9H), 1.03(m, 6H), 1.24(sext, J=7.2 Hz, 6H), 1.43(m, 6H), 7.14(m, 7H), 7.33(m, 9H)

Production Example 407

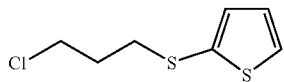

2-(3-Chloropropylsulfanyl)thiophene 2.7 mL 1-bromo-3-chloropropane was added to a mixture of 2 mL thiophen-2-thiol, 5.86 g potassium carbonate and 40 mL N,N-dimethylformamide under ice-cooling and then stirred at room temperature for 2 hours. Ethyl acetate and water were added to the reaction solution, and the organic layer was separated, washed with water plus brine (×2) and then with brine and dried over anhydrous sodium sulfate. The drying agent was filtered off, and the filtrate was evaporated. The resulting residue was purified by silica gel column chromatography (hexane) to give 4.19 g of the title compound as a pale yellow oil.

$^1$H-NMR (CDCl$_3$)

δ: 2.04(m, 2H), 2.93(t, J=6.8 Hz, 2H), 3.67(t, J=6.4 Hz, 2H), 6.98(dd, J=5.6, 3.6 Hz, 1H), 7.13(dd, J=3.6, 1.2 Hz, 1H), 7.36(dd, J=5.6, 1.2 Hz, 1H)

Production Example 408

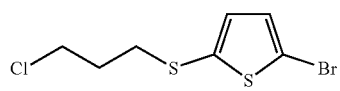

2-Bromo-5-(3-chloropropylsulfanyl)thiophene 1.91 g of the title compound was obtained as a pale yellow oil from 1.54 g 2-(3-chloropropylsulfanyl)thiophen (compound in Production Example 407) by the same method as in Production Example 45.

$^1$H-NMR (CDCl$_3$)

δ: 2.04(m, 2H), 2.90(t, J=6.8 Hz, 2H), 3.68(t, J=6.4 Hz, 2H), 6.93(m, 2H)

Production Example 409

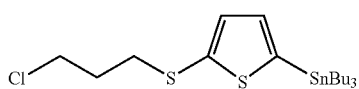

Tributyl[5-(3-chloropropylsulfanyl)-2-thienyl]stannane 1.37 g crude product of the title compound was obtained as a pale yellow oil from 815 mg 2-bromo-5-(3-chloropropylsulfanyl)thiophen (compound in Production Example 408) by the same method as in Production Example 46. This product was used in the subsequent reaction without purification.

Production Example 410

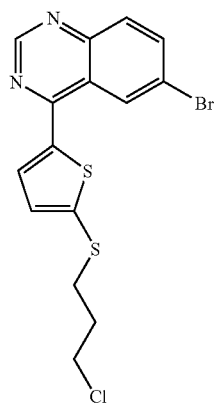

6-Bromo-4-[5-(3-chloropropylsulfanyl)thiophen-2-yl]quinazoline 217 mg of the title compound was obtained as a yellow oil from 487 mg 6-bromo-4-chloroquinazolin and 964 mg tributyl[5-(3-chloropropylsulfanyl)-2-thienyl]stannane (compound in Production Example 409) by the same method as in Production Example 96.

$^1$H-NMR (CDCl$_3$)

δ: 2.18(m, 2H), 3.15(t, J=6.8 Hz, 2H), 3.71(t, J=6.4 Hz, 2H), 7.24(d, J=4.0 Hz, 1H), 7.72(d, J=4.0 Hz, 1H), 7.97(dd, J=8.8, 0.4 Hz, 1H), 7.99(dd, J=8.8, 2.0 Hz, 1H), 8.61(dd, J=2.0, 0.4 Hz, 1H), 9.25(s, 1H)

Production Example 411

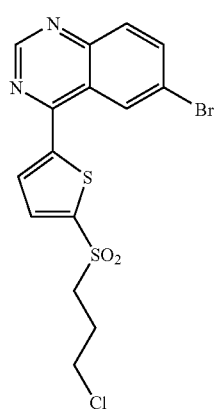

6-Bromo-4-[5-(3-chloropropane-1-sulfonyl)thiophen-2-yl]quinazoline 200 mg of the title compound was obtained as a pale yellow solid from 215 mg 6-bromo-4-[5-(3-chloropropylsulfanyl)-thiophen-2-yl]quinazoline (compound in Production Example 410) by the same method as in Production Example 59.

¹H-NMR (CDCl₃)

δ: 2.36(m, 2H), 3.48(t, J=6.8 Hz, 2H), 3.70(t, J=6.4 Hz, 2H), 7.84(d, J=4.0 Hz, 1H), 7.85(d, J=4.0 Hz, 1H), 8.05(m, 2H), 8.55(dd, J=2.0, 0.8 Hz, 1H), 9.35(s, 1H)

Production Example 412

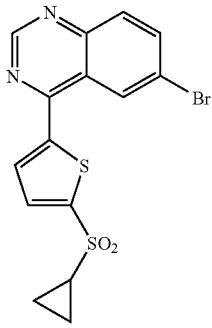

6-Bromo-4-(5-cyclopropanesulfonyl)thiophen-2-yl]quinazoline

A mixture of 198 mg 6-bromo-4-[5-(3-chloropropane-1-sulfonyl)thiophen-2-yl]quinazoline (compound in Production Example 411), 93 mg tetrabutyl ammonium iodide, 925 mg sodium hydroxide, 5 mL benzene, 5 mL acetone and 10 mL water was heated overnight under reflux. The reaction solution was poured into a mixture of iced water and ethyl acetate, the organic layer was separated and then washed with an aqueous saturated sodium thiosulfate solution, saturated sodium bicarbonate, and brine and dried over anhydrous sodium sulfate. The drying agent was filtered off, and the filtrate was evaporated. The resulting residue was purified by silica gel column chromatography (ethyl acetate/hexane) to give 148 mg of the title compound as pale yellow crystals.

¹H-NMR (CDCl₃)

δ: 1.18(m, 2H), 1.48(m, 2H), 2.70(m, 1H), 7.82(d, J=4.0 Hz, 1H), 7.83(d, J=4.0 Hz, 1H), 8.04(m, 2H), 8.57(dd, J=2.0, 0.8 Hz, 1H), 9.34(s, 1H)

Production Example 413

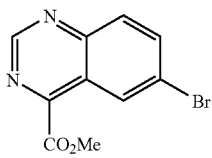

Methyl 6-bromoquinazolin-4-carboxylate

A mixture of 36.83 g 5-bromoisatin and 55 mL of 20% potassium hydroxide was stirred at 40° C. for 10 minutes. The reaction solution was evaporated at 40° C. or less, and ethanol was added to the residues which were then concentrated. Ethanol was added to the residues, and the crystals were collected by filtration and dried under reduced pressure with a vacuum pump. 39.25 g crude product of potassium 5-bromoisatate was obtained as yellowish brown crystals. To a mixture of 27.97 g of this potassium salt and 18.2 g sodium formate under ice-coolingd water in a stream of nitrogen was added 150 mL acetic formic anhydride (prepared from acetic anhydride and formic acid). While this reaction solution was gradually returned to room temperature, the solution was stirred for 2 days. The crystals were collected by filtration, washed with water and dried under reduced pressure with a vacuum pump. 22.01 g crude product of 5-bromo-N-formylisatin was obtained as yellow crystals. A mixture of 3.05 g of this compound and 13 mL of 1 N sodium hydroxide was stirred at 30° C. for 10 minutes. 26 mL water was added thereto, and while the reaction solution was stirred under ice-coolingd water, 8 mL of 2N hydrochloric acid was added thereto, and the precipitated crystals were collected by filtration. A mixture of the crystals and 20 mL ammonia (2 M ethanol solution) was stirred in a sealed tube at 100° C. for 2.5 hours. The reaction solution was evaporated, then diethyl ether was added to the residues, and the crystals were collected by filtration and dried under reduced pressure with a vacuum pump. 2.18 g crude product of ammonium 6-bromoquinazoline-4-carboxylate was obtained as brown crystals. A mixture of this salt, 0.67 mL conc. sulfuric acid and 50 mL methanol was heated for 4 hours under reflux. The reaction solution was basified with saturated sodium bicarbonate, and by adding ethyl acetate and water, the organic layer was separated. The aqueous layer was extracted with ethyl acetate, and the combined organic layer was washed with brine and dried over anhydrous sodium sulfate. The drying agent was filtered off, and the filtrate was evaporated. The resulting residue was purified by silica gel column chromatography (ethyl acetate/hexane) to give 983 mg of the title compound as pale brown crystals.

¹H-NMR (CDCl₃)

δ: 4.15(s, 3H), 8.02(d, J=9.2 Hz, 1H), 8.07(dd, J=8.8, 2.0 Hz, 1H), 8.97(dd, J=2.0, 0.8 Hz, 1H), 9.47(s, 1H)

Production Example 414

6-Bromoquinazoline-4-carboxylic acid hydrazide

A mixture of 961 mg methyl 6-bromoquinazoline-4-carboxylate (compound in Production Example 413), 0.9 mL hydrazine monohydrate and 70 mL methanol was stirred at room temperature for 30 minutes, and the precipitated crystals were collected by filtration. The filtrate was evaporated to give additional crystals. The title compound, 838 mg in total, was obtained as pale yellow crystals.

¹H-NMR (CDCl₃)

δ: 4.20(brs, 2H), 7.97(d, J=9.2 Hz, 1H), 8.04(dd, J=9.2, 2.4 Hz, 1H), 9.19(brs, 1H), 9.32(s, 1H), 9.65(dd, J=2.4, 0.8 Hz, 1H)

Production Example 415

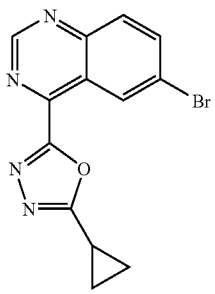

6-Bromo-4-(5-cyclopropyl[1,3,4]oxadiazol-2-yl) quinazoline 0.4 mL cyclopropane carbonyl chloride was added to a mixture of 796 mg of 6-bromoquinazoline-4-carboxylic acid hydrazide (compound in Production Example 414), 380 mg sodium bicarbonate, 15 mL tetrahydrofuran and 15 mL water, and the mixture was stirred at room temperature for 1 hour. 130 mg sodium bicarbonate and 0.13 mL cyclopropane carbonyl chloride were further added thereto, and the mixture was stirred overnight. An aqueous saturated sodium bicarbonate solution, common salt and tetrahydrofuran were added to the reaction solution, and the organic layer was separated, washed with brine and dried over anhydrous sodium sulfate. The drying agent was filtered off, and the filtrate was evaporated. Diisopropyl ether was added to the resulting residues, and the crystals were collected by filtration and dried under reduced pressure with a vacuum pump. 996 mg crude product of cyclopropane carboxylic acid N'-(6-bromoquinazoline-4-carbonyl) hydrazide was obtained as pale brown crystals. A mixture of 450 mg of this carboxylic acid hydrazide derivative, 0.24 mL pyridine and 20 mL anhydrous dichloromethane was cooled to −10° C. or less with ice/ethanol/dry ice in a stream of nitrogen, and 0.48 mL trifluoromethanesulfonic anhydride was added little by little to the reaction solution. The reaction solution was stirred at the same temperature for 30 minutes, then stirred at about 0° C. under ice-coolingd water for 40 minutes and then at room temperature for 1 hour. An aqueous saturated sodium bicarbonate solution, ethyl acetate and water were added to the reaction solution, and the organic layer was separated, washed with an aqueous saturated ammonium chloride solution and brine, and then dried over anhydrous sodium sulfate. The drying agent was filtered off, and the filtrate was evaporated. The resulting residue was purified by silica gel column chromatography (ethyl acetate/hexane) to give 282 mg of the title compound as a yellowish brown solid.

¹H-NMR (CDCl₃)

δ: 1.28–1.42(m, 4H), 2.37(m, 1H), 8.02(d, J=9.2 Hz, 1H), 8.08(dd, J=9.2, 2.4 Hz, 1H), 9.49(s, 1H), 9.68(dd, J=2.4, 0.4 Hz, 1H)

Production Example 416

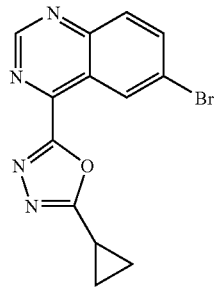

6-Bromo-4-(5-cyclopropyl[1,3,4]thiadiazol-2-yl) quinazoline 108 mg of the title compound was obtained as while crystals by the same method as in Production Example 277 from 182 mg cyclopropane carboxylic acid N'-(6-bromoquinazoline-4-carbonyl)hydrazide obtained in the synthesis process in Production Example 415.

¹H-NMR (CDCl₃)

δ: 1.33(m, 4H), 2.53(m, 1H), 7.98(d, J=9.2 Hz, 1H), 8.05(dd, J=9.2, 2.4 Hz, 1H), 9.34(s, 1H), 9.90(dd, J=2.4, 0.4 Hz, 1H)

Production Example 417

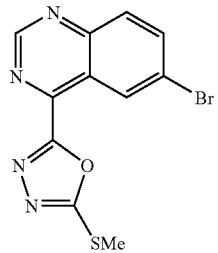

6-Bromo-4-(5-methylsulfanyl[1,3,4]oxadiazol-2-yl) quinazoline 1.32 g of the title compound was obtained as pale reddish brown crystals from 1.34 g 6-bromoquinazoline-4-carboxylic acid hydrazide (compound in Production Example 414) by the same method as in Production Example 279.

¹H-NMR (CDCl₃)

δ: 2.88(s, 3H), 8.03(d, J=8.8 Hz, 1H), 8.09(dd, J=8.8, 2.0 Hz, 1H), 9.49(s, 1H), 9.66(dd, J=2.0, 0.4 Hz, 1H)

Production Example 418

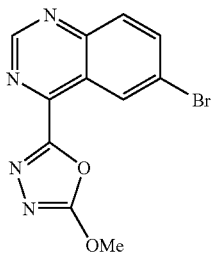

6-Bromo-4-(5-methoxy[1,3,4]oxadiazol-2-yl)quinazoline 71 mg of the title compound was obtained as a pale brown solid from 6-bromo-4-(5-methylsulfanyl[1,3,4]oxadiazol-2-yl)quinazoline (compound in Production Example 417) by the same method as in Production Example 280.

$^1$H-NMR (CDCl$_3$)

δ: 4.37(s, 3H), 8.01(d, J=8.8 Hz, 1H), 8.08(dd, J=9.2, 2.0 Hz, 1H), 9.46(s, 1H), 9.61(dd, J=2.0, 0.4 Hz, 1H)

Production Example 419

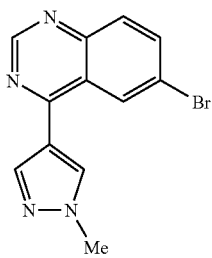

6-Bromo-4-(1-methyl-1H-pyrazol-4-yl)quinazoline 393 mg crude product of 6-bromo-4-(1-trityl-1H-pyrazol-4-yl)quinazoline was obtained as a pale yellow amorphous by the same method as in Production Example 96 from 365 mg 6-bromo-4-chloroquinazoline and 1.14 g 4-tributylstannyl-1-trityl-1H-pyrazole. A mixture of 391 mg of this compound, 7.2 mL of 5 N hydrochloric acid, 10 mL tetrahydrofuran and 10 mL methanol was stirred at room temperature for 2 hours. The reaction solution was cooled and basified with 5 N aqueous sodium hydroxide, then ethyl acetate and water were added thereto, and the organic layer was separated. The aqueous layer was saturated with common salt and then extracted with ethyl acetate. The combined organic layer was washed with brine and dried over anhydrous sodium sulfate. The drying agent was filtered off, the filtrate was evaporated, the resulting residue was triturated with ethyl acetate and diisopropylether, and the crystals were collected by filtration. The crystals were dried under vacuum to give 135 mg crude product of 6-bromo-4-(1H-pyrazol-4-yl)quinazoline as pale yellow crystals. 30 mg sodium hydride was suspended in 5 mL N,N-dimethylformamide, and while the suspension was stirred under ice-coolingd water in a stream of nitrogen, 5 mL of 130 mg of this compound in N,N-dimethylformamide was added thereto and stirred for 15 minutes, and 44 μl methyl iodide was added thereto and stirred overnight. Water and ethyl acetate were added to the reaction solution, and the organic layer was separated. The aqueous layer was saturated with common salt and then extracted with ethyl acetate. The combined organic layer was washed with water (×2) and brine and dried over anhydrous sodium sulfate. The drying agent was filtered off, and the filtrate was evaporated. The resulting residue was purified by NH silica gel column chromatography (ethyl acetate/hexane) to give 98 mg of the title compound as pale yellow crystals.

$^1$H-NMR (CDCl$_3$)

δ: 4.07(s, 3H), 7.94(dd, J=9.2, 0.4 Hz, 1H), 7.98(dd, J=9.2, 2.0 Hz, 1H), 8.12(s, 1H), 8.15(s, 1H), 8.49(dd, J=2.0, 0.8 Hz, 1H), 9.25(s, 1H)

Production Example 420

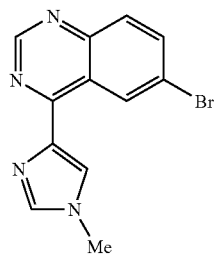

6-Bromo-4-(1-methyl-1H-imidazol-4-yl)quinazoline 143 mg of the title compound was obtained as a yellowish brown amorphous from 584 mg 6-bromo-4-chloroquinazoline and 1.13 g 4-tributylstannyl-1-methyl-1H-imidazole by the same method as in Production Example 96.

$^1$H-NMR (CDCl$_3$)

δ: 3.84(s, 3H), 7.64(d, J=1.2 Hz, 1H), 7.86(d, J=9.2 Hz, 1H), 7.93(dd, J=9.2, 2.0 Hz, 1H), 7.98(d, J=1.6 Hz, 1H), 9.19(s, 1H), 9.94(d, J=2.4 Hz, 1H)

Production Example 421

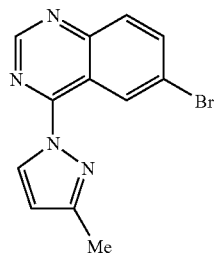

6-Bromo-4-(3-methylpyrazol-1-yl)quinazoline 60 mg of the title compound was obtained as a white solid from 73 mg 6-bromo-4-chloroquinazoline and 30 mg 3-methyl-1H-imidazole by the same method as in Production Example 96.

¹H-NMR (CDCl₃)

δ: 2.48(s, 3H), 6.38(dd, J=2.8, 0.4 Hz, 1H), 7.90(d, J=8.8 Hz, 1H), 7.97(dd, J=8.8, 2.4 Hz, 1H), 8.71(dd, J=2.8, 0.4 Hz, 1H), 9.05(s, 1H), 9.86(dd, J=2.4, 0.8 Hz, 1H)

Production Example 422

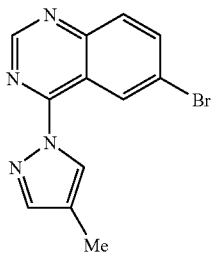

6-Bromo-4-(4-methylpyrazol-1-yl)quinazoline 63 mg of the title compound was obtained as a white solid from 100 mg 6-bromo-4-chloroquinazoline and 41 mg 4-methyl-1H-imidazole by the same method as in Production Example 96.

¹H-NMR (CDCl₃)

δ: 2.21(s, 3H), 7.77(s, 1H), 7.90(d, J=8.8 Hz, 1H), 7.97 (dd, J=8.8, 2.4 Hz, 1H), 8.55(s, 1H), 9.05(s, 1H), 9.81(d, J=2.4 Hz, 1H)

Production Example 423

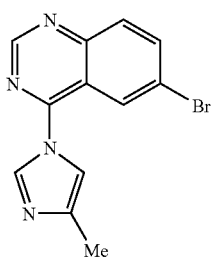

6-Bromo-4-(4-methylimidazol-1-yl)quinazoline 75 mg of the title compound was obtained as a pale yellow solid from 243 mg 6-bromo-4-chloroquinazoline and 148 mg 4-methyl-1H-imidazole by the same method as in Production Example 96.

¹H-NMR (CDCl₃)

δ: 2.38(s, 3H), 7.39(t, J=1.2 Hz, 1H), 8.03(dd, J=9.2, 0.8 Hz, 1H), 8.07(dd, J=9.2, 2.0 Hz, 1H), 8.19(d, J=12 Hz, 1H), 8.38(dd, J=2.0, 0.8 Hz, 1H), 9.10(s, 1H)

Production Example 424

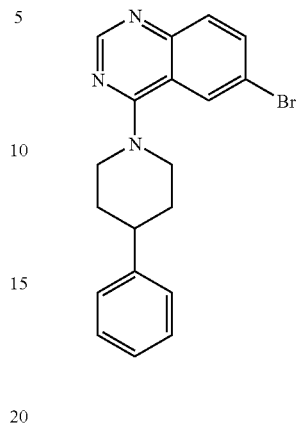

6-Bromo-4-(4-phenylpiperidin-1-yl)quinazoline 114 mg of the title compound was obtained as a colorless oil from 98 mg 6-bromo-4-chloroquinazoline and 78 mg 4-phenyl piperidine by the same method as in Production Example 96.

¹H-NMR (CDCl₃)

δ: 1.92–2.08(m, 4H), 2.88(m, 1H), 3.26(m, 2H), 4.48(m, 2H), 7.26(m, 3H), 7.35(m, 2H), 7.77(d, J=8.8 Hz, 1H), 7.81(dd, J=9.2, 2.0 Hz, 1H), 8.05(d, J=2.0 Hz, 1H), 8.74(s, 1H)

Production Example 425

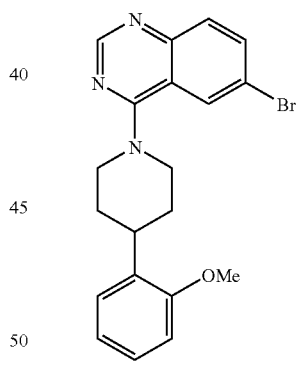

6-Bromo-4-[4-(2-methoxyphenyl)piperidin-1-yl]quinazoline 90 mg crude product of the title compound was obtained as pale yellow crystals from 50 mg 6-bromo-4-chloroquinazoline and 47 mg 4-(2-methoxyphenyl)piperidine by the same method as in Production Example 96.

¹H-NMR (CDCl₃)

δ: 1.88–1.98(m, 2H), 2.85(m, 2H), 3.85(s, 3H), 4.02(m, 2H), 4.46(m, 2H), 5.89(m, 1H), 6.91(dd, J=8.4, 1.2 Hz, 1H), 6.95(ddd, J=7.6, 7.2, 1.2 Hz, 1H), 7.19(dd, J=7.6, 2.0 Hz, 1H), 7.28(m, 1H), 7.76(d, J=8.8 Hz, 1H), 7.79(dd, J=8.8, 2.0 Hz, 1H), 8.08(d, J=2.0, 0.4 Hz, 1H), 8.70(s, 1H)

Production Example 426

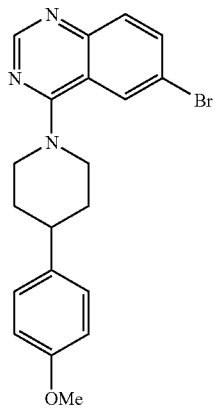

6-Bromo-4-[4-(4-methoxyphenyl)piperidin-1-yl]quinazoline 182 mg crude product of the title compound was obtained as a pale yellow oil from 100 mg 6-bromo-4-chloroquinazoline and 94 mg 4-(4-methoxyphenyl)piperidine by the same method as in Production Example 96.

$^1$H-NMR (CDCl$_3$)

δ: 1.88–2.08(m, 4H), 2.84(m, 1H), 3.26(m, 2H), 3.80(s, 3H), 4.46(m, 2H), 6.89(d, J=8.8 Hz, 2H), 7.20(d, J=8.8 Hz, 2H), 7.76(d, J=8.8 Hz, 1H), 7.80(dd, J=9.2, 2.0 Hz, 1H), 8.04(d, J=2.0 Hz, 1H), 8.74(s, 1H)

Production Example 427

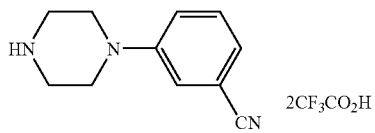

3-piperazin-1-yl-benzonitrile di-trifluoroacetate

A mixture of 2.0 g 3-bromo-benzonitrile, 2.5 g 1-Boc-piperazine, 1.5 g sodium t-butoxide, 50 mg (+)-BINAP, 30 mg trisdibenzylidene acetone dipalladium and 50 ml toluene was stirred at 80° C. for 3 hours. The mixture was cooled to room temperature, ethyl acetate was added thereto, and the organic layer was washed with brine. The organic layer was dried over magnesium sulfate, the solvent was evaporated, and the residue was stirred in 20 mL trifluoroacetic acid at room temperature for 20 minutes. The trifluoroacetic acid was evaporated, and the residue was purified by silica gel column chromatography to give 110 mg of the title compound as a dark brown solid.

$^1$H-NMR (CDCl$_3$)

δ: 3.38(m, 4H), 3.48(m, 4H), 7.12–7.16(m, 2H), 7.25(d, J=8.0, 1H), 7.41(t, J=8.0, 1H)

The compounds in Production Examples 428 to 433 were synthesized from a bromobenzene derivative and 1-Boc-piperazine by a similar procedure to that of Production Example 427.

Production Example 428

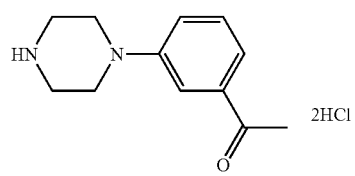

1-(3-piperazin-1-yl-phenyl)ethanone dihydrochloride $^1$H-NMR (DMSO-d$_6$)

δ: 2.56(s, 3H), 3.19(m, 4H), 3.43(m, 4H), 7.22–7.48(m, 4H)

Production Example 429

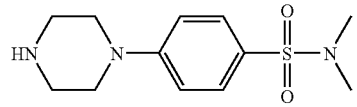

N,N-Dimethyl-4-piperazin-1-yl-benzene sulfonamide $^1$H-NMR (DMSO-d$_6$)

δ: 2.51(s, 6H), 2.81(m, 4H), 3.22(m, 4H), 7.04(d, J=8.4, 2H), 7.49(d, J=8.4, 2H)

Production Example 430

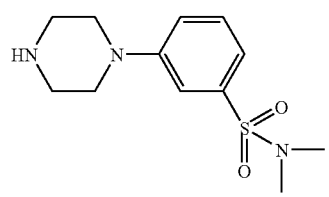

N,N-Dimethyl-3-piperazin-1-yl-benzene sulfonamide $^1$H-NMR (DMSO-d$_6$)

δ: 2.58(s, 6H), 3.04(m, 4H), 3.26(m, 4H), 7.10–7.16(m, 2H), 7.27(d, J=8.4, 1H), 7.47(t, J=8.4, 1H)

Production Example 431

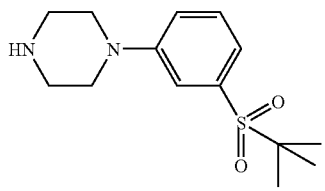

1-[3-(2-Methylpropane-2-sulfonyl)phenyl]piperazine

¹H-NMR (CDCl₃)
δ: 1.38(s, 9H), 3.01(m, 4H), 3.20(m, 4H), 7.12–7.42(m, 4H

Production Example 432

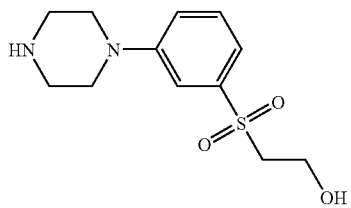

2-(3-piperazin-1-yl-benzenesulfonyl)ethanol

¹H-NMR (CDCl₃)
δ: 3.02(m, 4H), 3.22(m, 4H), 3.63(m, 2H), 4.00(m, 2H), 7.15(d, J=8.0 Hz, 1H), 7.33(d, J=8.0 Hz, 1H), 7.38(s, 1H), 7.44(t, J=8.0 Hz, 1H)

Production Example 433

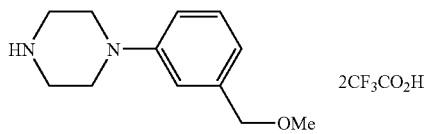

1-(3-Methoxymethylphenyl)piperazine di-trifluoroacetate

¹H-NMR (DMSO-d₆)
δ: 3.20(m, 4H), 3.25(s, 3H), 3.32(m, 4H), 4.34(s, 2H), 6.80(d, J=8.0 Hz, 1H), 6.86–6.92(m, 2H), 7.22(t, J=8.0 Hz, 1H)

Production Example 434

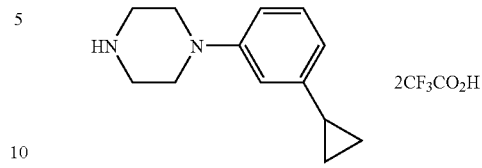

1-(3-Cyclopropylphenyl)piperazine di-trifluoroacetate 34 g of 3-cyclopropyl bromobenzene was synthesized from 50 g of 3-bromoacetophenone by a method described in J. Org. Chem., 41, 2263 (1976), and 2 g of this product was used to prepare 520 mg of the title compound as a white solid by the method described in Production Example 427.

¹H-NMR (DMSO-d₆)
δ: 0.63(m, 2H), 0.90(m, 2H), 1.83(m, 1H), 3.20(m, 4H), 3.30(m, 4H), 6.54(d, J=8.0 Hz, 1H), 6.68(s, 1H), 6.72(d, J=8.0 Hz, 1H), 7.10(t, J=8.0 Hz, 1H)

Production Example 435

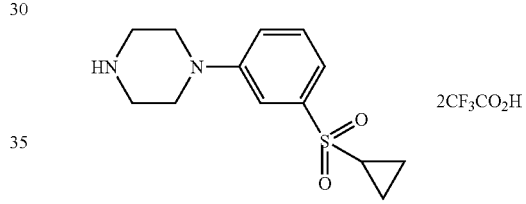

1-(3-Cyclopropylsulfonylphenyl)piperazine di-trifluoroacetate 2.1 g of 3-(cyclopropylsulfonyl)bromobenzene was synthesized from 10 g of 3-bromobenzenethiol by a method described in J. Org. Chem., 50, 1327 (1985), and this starting material was used to prepare 480 mg of the title compound as a dark brown oil by the method described in Production Example 427.

¹H-NMR (CDCl₃)
δ: 0.55–0.65(m, 4H), 2.24(m, 1H), 3.01(m, 4H), 3.20(m, 4H), 7.08(m, 1H), 7.30–7.40(m, 3H)

Production Example 436

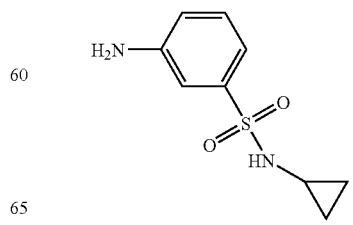

3-Amino-N-cyclopropyl-benzene sulfonamide

A mixture of 2.0 g 3-nitrobenzene sulfonyl chloride, 1.8 g cyclopropyl amine and 50 mL tetrahydrofuran was stirred for 30 minutes under ice-cooling. Water was added to the mixture which was then extracted with ethyl acetate. The organic layer was washed with brine and dried over anhydrous magnesium sulfate. The solvent was evaporated, then the residue was dissolved in 100 mL solvent mixture of tetrahydrofuran and methanol, 50 mg of 10% palladium-carbon was added thereto, and the mixture was hydrogenated at ordinary pressure for 12 hours. The reaction mixture was filtered through Celite, and the solvent was evaporated, whereby 1.5 g of the title compound was obtained as a pale yellow solid.

$^1$H-NMR (CDCl$_3$)
δ: 0.55–0.68(m, 4H), 2.22(m, 1H), 3.93(s, 2H), 4.93(s, 1H), 6.85(m, 1H), 7.18(t, J=1.6 Hz, 1H), 7.22–7.30(m, 2H)

Production Example 437

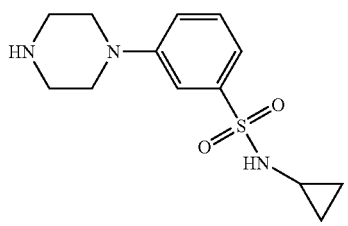

1-3-(Cyclopropylamino)sulfonyl phenyl piperazine

A mixture of 2.1 g 3-(cyclopropylamino)sulfonyl aniline, 2.0 g bis(2-chloroethyl)amine hydrochloride and 100 mL 1,2-dichlorobenzene was stirred at 190° C. to 200° C. for 3 hours. The mixture was cooled to room temperature, and an aqueous saturated sodium bicarbonate solution was added to the mixture which was then extracted with dichloromethane. The organic layer was washed with brine and then dried over anhydrous magnesium sulfate. The solvent was evaporated, and the residue was purified by NH silica gel column chromatography to give 60 mg of the title compound as a pale brown oil.

$^1$H-NMR (CDCl$_3$)
δ: 1.00(m, 2H), 1.34(m, 2H), 2.46(m, 1H), 3.02(m, 4H), 3.22(m, 4H), 7.12(m, 1H), 7.30(m, 1H), 7.36–7.42(m, 2H)

The compound in Production Example 438 was synthesized from an aniline derivative in the same manner as in Production Example 437.

Production Example 438

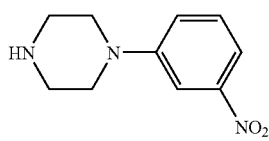

1-(3-Nitro)phenylpiperazine $^1$H-NMR (CDCl$_3$)
δ: 3.03(m, 4H), 3.23(m, 4H), 7.18(m, 1H), 7.36(t, J=8.0 Hz, 1H), 7.62–7.72(m, 2H)

Production Example 439

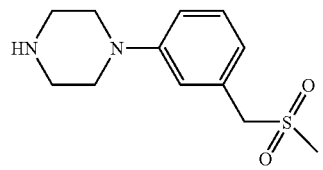

1-(3-Methylsulfonylmethylphenyl)piperazine 4.8 g of 1-methylsulfanylmethyl-3-nitrobenzene was synthesized from 5.0 g 3-bromomethylnitrobenzene and sodium thiomethoxide by a method known in the art, and this compound was oxidized by the method described in Production Example 367, to give 4.2 g of 1-methylsulfonylmethyl-3-nitrobenzene. This compound was catalytically reduced by the method described in Production Example 436, and the same procedure as in Production Example 437 was carried out to give 2.8 g of the title compound as a white solid.

$^1$H-NMR (CDCl$_3$)
δ: 2.74(s, 3H), 3.0(m, 4H), 3.18(m, 4H), 4.20(s, 2H), 6.83(d, J=8.0 Hz, 1H), 6.92–6.96 (mt, 2H), 7.8(t, J=8.0 Hz, 1H)

Production Example 440

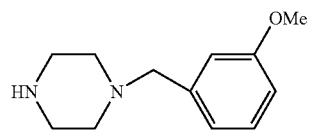

1-(3-Methoxybenzyl)piperazine

A mixture of 2.0 g 3-methoxy benzylchloride, 2.9 g 1-Boc piperazine, 5 mL triethylamine, and 20 mL tetrahydrofuran was stirred at room temperature for 20 minutes. The mixture was concentrated, and the residue was added to 20 mL trifluoroacetic acid and stirred at room temperature for 20 minutes. The trifluoroacetic acid was evaporated, and the residue was suspended in methanol and neutralized with an aqueous saturated sodium bicarbonate solution. The solvent was evaporated, and the residue was suspended in dichloromethane and purified by NH silica gel chromatography to give 2.4 g of the title compound as a white solid.

$^1$H-NMR (CDCl$_3$)
δ: 2.68(m, 4H), 3.15(m, 4H), 3.81(s, 3H), 4.20(s, 2H), 6.80–6.90 s(m, 3H), 7.24(t, J=8.0 Hz, 1H)

The compounds in Production Examples 441 to 443 were synthesized from a halogen derivative and 1-t-butoxycarbonyl piperazine by the same procedure as in Production Example 440.

Production Example 441

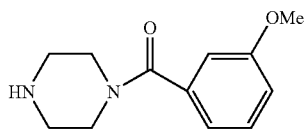

(3-Methoxyphenyl)piperazin-1-yl-methanone $^1$H-NMR (DMSO-$d_6$)
δ: 2.52–2.71(m, 4H), 3.15–3.52(m, 4H), 3.74(s, 3H), 4.20(s, 2H), 6.83–6.90(m, 2H), 6.97(dd, J=2.0, 8.0 Hz, 1H), 7.32(t, J=8.0 Hz, 1H)

Production Example 442

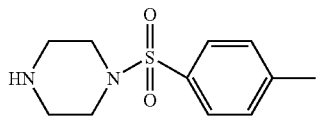

1-(Toluene-4-sulfonyl)piperazine $^1$H-NMR (DMSO-$d_6$)
δ: 2.42(s, 3H), 2.88–2.98(m, 8H), 7.32(d, J=8.4 Hz, 2H), 7.62(d, J=8.4 Hz, 1H)

Production Example 443

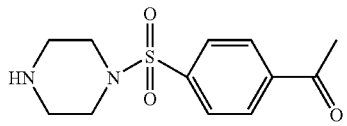

1-[4-(piperazin-1-sulfonyl)phenyl]ethanone $^1$H-NMR (CDCl$_3$)
δ: 2.66(s, 3H), 2.90–3.04(m, 8H), 7.84(d, J=8.0 Hz, 2H), 8.08(d, J=8.0 Hz, 1H)

Production Example 444

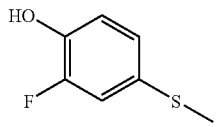

2-Fluoro-4-methylsulfanylphenol 5 g of 4-bromo-2-fluoro-1-methoxymethoxybenzene was dissolved in 50 mL anhydrous tetrahydrofuran, and 13.4 mL n-butyl lithium (1.59 M hexane solution) was added dropwise thereto at −70° C. After the mixture was stirred for 1 hour, 2.1 ml dimethyl sulfide was added dropwise thereto and stirred at −70° C. for 1 hour, and after the temperature of the reaction solution was raised to 0° C., the solution was stirred for 1 hour. An aqueous saturated ammonium chloride solution was added thereto, the mixture was stirred for 30 minutes, and water added to the mixture which was then extracted with ethyl acetate. The extract was dried over sodium sulfate and purified by silica gel chromatography (hexane/ethyl acetate) to give 3.67 g of 2-fluoro-1-methoxymethoxy-4-methylsulfanyl benzene. 4 mL solution of 4 N hydrogen chloride in ethyl acetate was added to this reaction product and left for 1 hour. Water was added to the product which was then extracted with ethyl acetate and purified by silica gel chromatography (hexane/ethyl acetate) to give 1.01 g of the title compound as a colorless oil.
$^1$H-NMR (CDCl$_3$)
δ: 2.45(s, 3H), 5.14(brs, 1H), 6.98(t, J=8.4 Hz, 1H), 6.99(ddd, J=8.4, 2.1, 0.8 Hz, 1H), 7.06(dd, J=11.2, 2.1 Hz, 1H)

Production Example 445

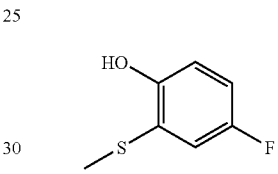

4-Fluoro-2-methylsulfanylphenol 1.10 g of the title compound was obtained as a pale yellow oil from 5.26 g of 2-bromo-4-fluoro-1-methoxymethoxybenzene by the same reaction as in Production Example 444.
$^1$H-NMR (CDCl$_3$)
δ: 2.36(s, 3H), 6.31(s, 1H), 6.89–6.97(m, 2H), 6.99(ddd, J=8.0, 2.8, 0.4 Hz, 1H)

Production Example 446

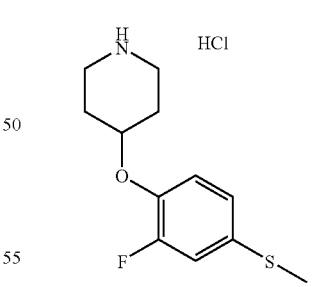

4-(2-Fluoro-4-methylsulfanylphenoxy)piperidine hydrochloride

A solution of 1.01 g 2-fluoro-4-methylsulfanyl phenol (compound in Production Example D088), 1.28 g t-butyl 4-hydroxy-1-piperidinecarboxylate, 2.5 g triphenylphosphine and 4.2 g diethyl azodicarboxylate (40% toluene solution) in anhydrous tetrahydrofuran (30 mL) was heated for 8 hours under reflux in a stream of nitrogen. Water was added thereto, the reaction mixture was extracted with ethyl acetate, and the extract was dried over sodium sulfate and purified by silica gel chromatography (hexane/ethyl acetate) to give 1.41 g t-butyl 4-(2-fluoro-4-methylsulfanylphenoxy)piperidine-1-carboxylate. 5 mL of 4 N hydrogen chloride in ethyl acetate was added to this product and left for 1 hour. The solvent was removed, and the precipitated crystals were washed with ethyl acetate-ether to give 780 mg of the title compound as colorless crystals.

$^1$H-NMR (DMSO-$d_6$)

δ: 1.81–1.91(m, 2H), 2.05–2.13(m, 2H), 2.28(s, 3H), 3.01–3.08(m, 2H), 3.17–3.23(m, 2H), 4.56–4.62(m, 1H), 7.05(ddd, J=8.8, 2.4, 1.2 Hz, 1H), 7.20–7.27(m, 2H), 9.02 (brs, 2H)

Production Example 447

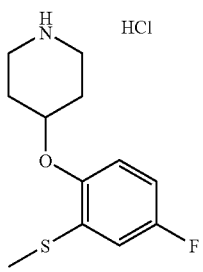

4-(4-Fluoro-2-methylsulfanylphenoxy)piperidine hydrochloride 726 mg of the title compound was obtained as colorless crystals from 1.1 g of 4-fluoro-2-methylsulfanylphenol (compound in Production Example 445) by the same method as in Production Example 446.

$^1$H-NMR (DMSO-$d_6$)

δ: 1.85–1.91(m, 2H), 2.03–2.10(m, 2H), 2.41(s, 3H), 3.06–3.10(m, 2H), 3.12–3.23(m, 2H), 4.66–4.72(m, 1H), 6.92 (td, J=8.4, 2.8 Hz, 1H), 7.01(dd, J=9.4, 2.8 Hz, 1H), 7.08(dd, J=9.4, 4.8 Hz, 1H), 9.02(brs, 1H), 9.13(brs, 1H)

Production Example 448

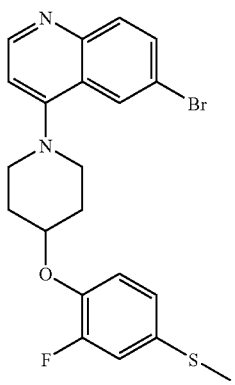

6-Bromo-4-[4-(2-fluoro-4-methylsulfanylphenoxy)piperidin-1-yl]quinoline 302 mg of the title compound was obtained as a pale yellow amorphous from 300 mg of 6-bromo-4-chloroquinoline and 330 mg of 4-(2-fluoro-4-methylsulfanylphenoxy)piperidine hydrochloride (compound in Production Example 446) by the same reaction as in Production Example 82.

$^1$H-NMR (CDCl$_3$)

δ: 2.11–2.27(m, 4H), 2.47(s, 3H), 3.10–3.18(m, 2H), 3.43–3.52(m, 2H), 4.50–4.59(m, 1H), 6.86–6.92(m, 2H), 6.97–7.02(m, 2H), 7.72(dt, J=6.8, 2.2 Hz, 1H), 7.92(dd, J=8.8, 2.2 Hz, 1H), 8.13(d, J=2.2 Hz, 1H), 8.71–8.73(m, 1H)

Production Example 449

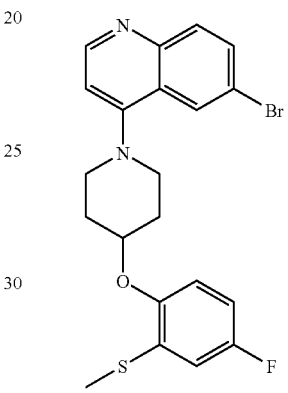

6-Bromo-4-[4-(4-fluoro-2-methylsulfanylphenoxy)piperidin-1-yl]quinoline 318 mg of the title compound was obtained as a colorless amorphous from 300 mg of 6-bromo-4-chloroquinoline and 330 mg of 4-(2-fluoro-4-methylsulfanylphenoxy)piperidine hydrochloride (compound in Production Example 447) by the same reaction as in Production Example 82.

$^1$H-NMR (CDCl$_3$)

δ: 2.11–2.27(m, 4H), 2.42(s, 3H), 3.14–3.21(m, 2H), 3.46–3.54(m, 2H), 4.59–4.63(m, 1H), 6.75–6.87(m, 3H), 6.91(d, J=5.2 Hz, 1H), 7.71(dd, J=8.8, 2.0 Hz, 1H), 7.91(d, J=8.8 Hz, 1H), 8.15(d, J=2.0 Hz, 1H), 8.72(d, J=5.2 Hz, 1H)

Production Example 450

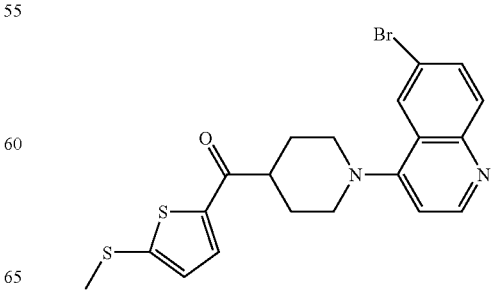

[1-(6-Bromo-quinolin-4-yl)-piperidin-4-yl]-(5-methylsulfanylthiophen-2-yl)methanone 206 mg of the title compound was obtained as a pale orange amorphous from 230 mg of 6-bromo-4-chloroquinoline and 250 mg of (5-methylsulfanylthiophen-2-yl)piperidin-4-yl-methane hydrochloride (compound in Production Example 390) by the same reaction as in Production Example 82.

$^1$H-NMR (CDCl$_3$)

δ: 2.05–2.11(m, 2H), 2.18–2.28(m, 2H), 2.63(s, 3H), 2.97 (td, J=12.2, 2.4 Hz, 2H), 3.25–3.33(m, 1H), 3.62–3.68(m, 2H), 6.88(d, J=5.0 Hz, 1H), 6.96(d, J=4.0 Hz, 1H), 7.63(d, J=4.0 Hz, 1H), 7.72(dd, J=8.8, 2.2 Hz, 1H), 7.91(d, J=8.8 Hz, 1H), 8.14(d, J=2.2 Hz, 1H), 8.72(d, J=5.0 Hz, 1H)

Production Example 451

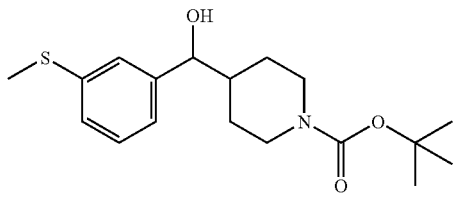

t-Butyl 4-[hydroxy-(3-methylsulfanylphenyl)-methyl]-piperidine-1-carboxylate 740 mg of the title compound was obtained as colorless oil from 950 mg of 1-bromo-3-methylsulfanylbenzene and 1.0 g of t-butyl 4-formyl-piperidine-1-carboxylate by the same method as in Production Example 223.

$^1$H-NMR (CDCl$_3$)

δ: 1.21–1.30(m, 2H), 1.44(s, 9H), 1.55–1.77(m, 2H), 1.90–1.97(m, 1H), 2.49(s, 3H), 2.50–2.77(m, 2H), 3.99–4.22(m, 2H), 4.35(d, J=7.2 Hz, 1H), 7.03–7.07(m, 1H), 7.15–7.22(m, 2H), 7.24–7.29(m, 1H)

Production Example 452

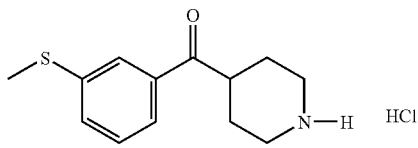

(3-Methylsulfanylphenyl)-piperidin-4-yl-methanone hydrochloride 66 mg of the title compound was obtained as colorless crystals from 689 mg of t-butyl 4-[4-hydroxy-(3-methylsulfanylphenyl)-methyl]-piperidine-1-carboxylate (compound in Production Example 451) by the same reaction as in Production Example 390.

$^1$H-NMR (DMSO-d$_6$)

δ: 1.66–1.79(m, 2H), 1.88–1.97(m, 2H), 2.54(s, 3H), 2.99–3.07(m, 2H), 3.29–3.37(m, 2H), 3.72–3.81(m, 1H), 7.48–7.57(m, 2H), 7.75–7.80(m, 2H)

Production Example 453

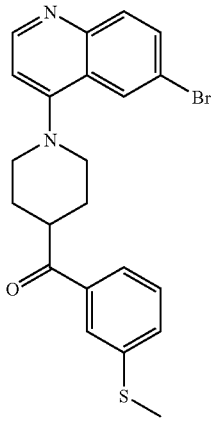

[1-(6-Bromoquinolin-4-yl)piperidin-4-yl]-(3-methylsulfanylphenyl)methanone 66 mg of the title compound was obtained as a colorless amorphous from 62 mg of 6-bromo-4-chloroquinoline and 66 mg of (3-methylsulfanylphenyl)-piperidin-4-yl-methanone hydrochloride (compound in Production Example 452) by the same reaction as in Production Example 82.

$^1$H-NMR (CDCl$_3$)

δ: 2.04–2.23(m, 4H), 2.55(s, 3H), 2.97–3.04(m, 2H), 3.46–3.54(m, 1H), 3.62–3.68(m, 2H), 6.89(d, J=5.0 Hz, 1H), 7.42(t, J=7.6 Hz, 1H), 7.45–7.49(m, 1H), 7.70–7.74(m, 2H), 7.86(t, J=1.8 Hz, 1H), 7.91(d, J=8.8 Hz, 1H), 8.14(d, J=2.4 Hz, 1H), 8.73(d, J=5.0 Hz, 1H)

Production Example 454

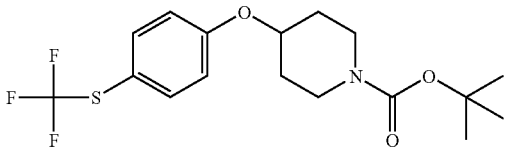

t-Butyl 4-(4-trifluoromethylsulfanyl-phenoxy)piperidine-1-carboxylate

A solution of 2 g 4-trifluoromethylsulfanyl-phenol, 2.07 g t-butyl 4-hydroxy-1-piperidinecarboxylate, 3.2 g triphenyl phosphine and 5.4 g diethyl azodicarboxylate (40% toluene solution) in anhydrous tetrahydrofuran (40 mL) was heated for 24 hours under reflux in a stream of nitrogen. Water was added thereto, and the reaction solution was extracted with ethyl acetate, dried over sodium sulfate, and purified by NH silica gel chromatography (hexane/ethyl acetate) to give 3.07 g of the title compound.

$^1$H-NMR (CDCl$_3$)

δ: 1.46(s, 9H), 1.71–1.80(m, 2H), 1.87–1.96(m, 2H), 3.32–3.40(m, 2H), 3.54–3.73(m, 2H), 4.48–4.52(m, 1H), 6.89–6.94(m, 2H), 7.53–7.58(m, 2H)

Production Example 455

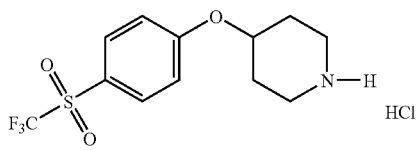

4-(4-Trifluoromethylsulfonylphenoxy)piperidine hydrochloride 2.55 g sodium periodate and 0.4 mg ruthenium (III) chloride hydrate were added to 60 mL solution mixture (carbon tetrachloride/acetonitrile/water=1:1:2) of 1.5 g t-butyl 4-(4-trifluoromethylsulfanyl-phenoxy)piperidine-1-carboxylate (compound in Production Example 454) with stirring under ice-cooling, and the mixture was stirred at room temperature for 1 hour. Water and a sodium bicarbonate solution were added thereto, and the reaction solution was extracted with ethyl acetate, dried over sodium sulfate and purified by silica gel chromatography (hexane/ethyl acetate) to give 1.3 g t-butyl 4-(4-trifluoromethylsulfonylphenoxy) piperidine-1-carboxylate. 2 mL solution of 4 N hydrogen chloride in ethyl acetate was added thereto and left for 1 hour. The solvent was removed, and the precipitated crystals were washed with ethyl acetate/ether to give 965 mg of the title compound as colorless crystals.

$^1$H-NMR (DMSO-$d_6$)
δ: 1.87–1.96(m, 2H), 2.14–2.20(m, 2H), 3.06–3.12(m, 2H), 3.21–3.27(m, 2H), 4.91–4.97(m, 1H), 7.40–7.43(m, 2H), 8.03–8.07(m, 2H), 9.11(brs, 2H)

Production Example 456

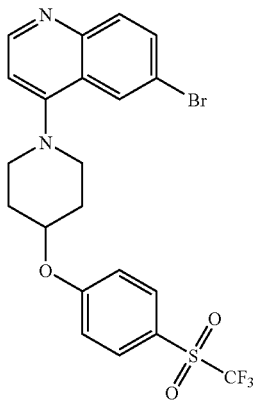

6-Bromo-4-[4-(4-trifluoromethylsulfonylphenoxy) piperidin-1-yl]quinoline 297 mg of the title compound was obtained as a colorless amorphous from 290 mg of 6-bromo-4-chloroquinoline and 400 mg of 4-(4-trifluoromethylsulfonylphenoxy)piperidin hydrochloride (compound in Production Example 455) by the same reaction as in Production Example 82.

$^1$H-NMR (CDCl$_3$)
δ: 2.14–2.23(m, 2H), 2.29–2.37(m, 2H), 3.17–3.24(m, 2H), 3.43–3.51(m, 2H), 4.77–4.81(m, 1H), 6.91(d, J=4.8 Hz, 1H), 7.14–7.17(m, 2H), 7.73(dd, J=8.8, 2.2 Hz, 1H), 7.93(d, J=8.8 Hz, 1H), 7.97–8.01(m, 2H), 8.14(d, J=2.2 Hz, 1H), 8.74(d, J=4.8 Hz, 1H)

Production Example 457

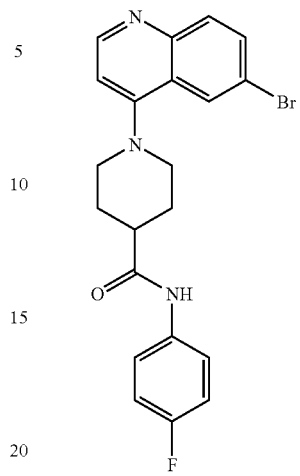

1-(6-Bromoquinolin-4-yl)piperidine-4-carboxylic acid (4-fluorophenyl)amide 0.34 mL triethylamine and 0.13 mL isobutyl chloroformate were added to a solution of 50 mg 1-(6-bromo-4-quinolyl)-4-piperidinecarboxylic acid in tetrahydrofuran (5 mL) with stirring under ice-cooling, and the mixture was stirred for 0.5 hour in a stream of nitrogen. To this solution was added a solution of 1.5 mL 4-fluoroaniline in tetrahydrofuran (8 mL), and the mixture was stirred at 60° C. for 2 hours. Water was added to the reaction mixture which was then extracted with ethyl acetate, and the organic layer was dried over anhydrous sodium sulfate and purified by NH silica gel column chromatography (ethyl acetate/hexane) to give 73 mg of the title compound as pale purple crystals.

$^1$H-NMR (CDCl$_3$)
δ: 1.94–2.05(m, 4H), 2.55–2.65(m, 1H), 2.84–2.95(m, 2H), 3.53–3.62(m, 2H), 7.09(d, J=5.2 Hz, 1H), 7.12–7.19(m, 2H), 7.63–7.69(m, 2H), 7.83(dd, J=9.2, 2.0 Hz, 1H), 7.91(d, J=9.2 Hz, 1H), 8.10(d, J=2.0 Hz, 1H), 8.73(d, J=5.2 Hz, 1H), 10.06(brs, 1H)

Production Example 458

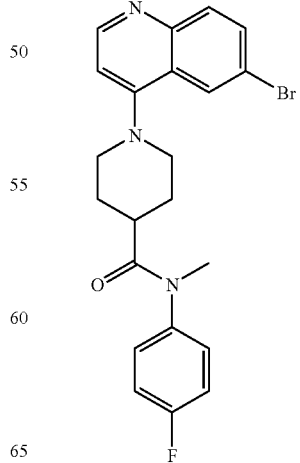

1-(6-Bromoquinolin-4-yl)piperidine-4-carboxylic acid (4-fluorophenyl)methylamide 10 mg sodium hydride was added to a solution of 100 mg 1-(6-bromoquinolin-4-yl)piperidine-4-carboxylic acid (4-fluorophenyl)amide (compound in Production Example 457) in 3 mL N,N-dimethylformamide, then the mixture was stirred for 15 minutes, 15 μL iodomethane was added thereto under ice-cooling, and the mixture was stirred for 3.5 hours. Water was added to the reaction solution which was then extracted with ethyl acetate, and the organic layer was dried over anhydrous sodium sulfate and purified by NH silica gel column chromatography (ethyl sacetate) to give 92 mg of the title compound.

$^1$H-NMR (CDCl$_3$)

δ: 1.74–1.83(m, 2H), 2.15–2.26(m, 2H), 2.38–2.46(m, 1H), 2.55–2.64(m, 2H), 3.28(s, 3H), 3.47–3.56(m, 2H), 6.74(d, J=5.0 Hz, 1H), 7.12–7.24(m, 4H), 7.69(dd, J=8.8, 2.4 Hz, 1H), 7.88(d, J=8.8 Hz, 1H), 8.12(d, J=2.4 Hz, 1H), 8.73(d, J=5.0 Hz, 1H)

Production Example 459

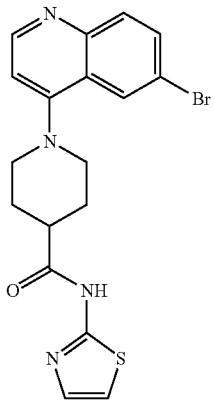

1-(6-Bromoquinolin-4-yl)piperidine-4-carboxylic acid thiazol-2-yl amide 208 mg of the title compound was obtained as pale skin-colored crystals from 400 mg of 1-(6-bromo-4-quinolyl)-4-piperidinecarboxylic acid and 2.1 g 2-aminothiazole by the same method as in Production Example 457.

$^1$H-NMR (CDCl$_3$)

δ: 1.94–2.08(m, 4H), 2.74–2.84(m, 1H), 2.85–2.95(m, 2H), 3.52–3.60(m, 2H), 7.09(d, J=5.2 Hz, 1H), 7.23(d, J=3.4 Hz, 1H), 7.49(d, J=3.4 Hz, 1H), 7.83(dd, J=9.2, 2.4 Hz, 1H), 7.91(d, J=9.2 Hz, 1H), 8.09(d, J=2.4 Hz, 1H), 8.73(d, J=5.2 Hz, 1H), 12.23(brs, 1H)

Production Example 460

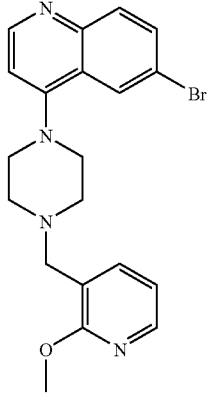

3-{[4-(6-Bromo-4-quinolyl)piperazin-1-yl]methyl}-2-pyridyl methyl ether 15 mg of the title compound was obtained from 200 mg of 1-[(2-methoxy-3-pyridyl)methyl]piperazine (Production Example 361) and 234 mg 6-bromo-4-chloroquinoline by the same method as in Production Example 82.

$^1$H-NMR (CD$_3$OD)

δ: 2.76–2.86(m, 4H), 3.22–3.30(m, 4H), 3.66(s, 2H), 3.99(s, 3H), 6.86(dd, J=4.8, 2.0 Hz, 1H), 6.90(dd, J=4.8, 4.8 Hz, 1H), 7.70(dd, J=9.2, 2.0 Hz, 1H), 7.91(d, J=9.2 Hz, 1H), 8.09(bd, 2H), 8.15(d, J=2.0 Hz, 1H), 8.71(d, J=4.8 Hz, 1H)

Production Example 461

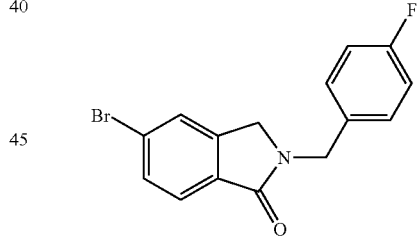

5-Bromo-2-(4-fluorobenzyl)-2,3-dihydroisoindol-1-one

A mixture of 458 mg methyl 4-bromo-2-methylbenzoate, 427 mg N-bromosuccinimide, 25 mg α,α'-azobisisobutyronitrile and 10 mL carbon tetrachloride was heated for 30 minutes under reflux. 50 mg N-bromosuccinimide was added thereto, and the mixture was further heated for 30 minutes under reflux. The reaction solution was cooled, insolubles were filtered off, and the filtrate was evaporated. 773 mg crude product of methyl 4-bromo-2-bromomethyl benzoate was obtained as a pale yellow oil. A mixture of this compound, 546 mg 4-fluorobenzyl amine, 0.34 mL triethylamine and 10 mL methanol was heated for 2 days under reflux. The reaction solution was cooled, and the precipitated crystals were collected by filtration and dried under reduced pressure with a vacuum pump, to give 219 mg of the title compound as pale brown crystals.

¹H-NMR (CDCl₃)

δ: 4.24(s, 2H), 4.75(s, 2H), 7.03(m, 2H), 7.27(m, 2H), 7.55(dd, J=1.6, 0.4 Hz, 1H), 7.62(dd, J=8.0, 1.6 Hz, 1H), 7.75(d, J=8.0 Hz, 1H)

Production Example 462

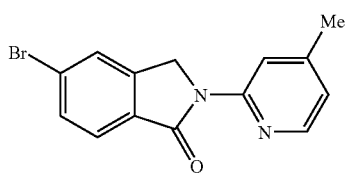

5-Bromo-2-(4-methylpyridin-2-yl)-2,3-dihydroisoindol-1-one 155 mg of the title compound was obtained as pale brown crystals by the same method as in Production Example 461 from 1.84 g of the crude product of methyl 4-bromo-2-bromomethylbenzoate obtained in the synthesis process in Production Example 461 and 811 mg 2-amino-4-picoline.

¹H-NMR(CDCl₃)

δ: 2.43(s, 3H), 5.08(s, 2H), 6.91(m, 1H), 7.64(dd, J=8.0, 1.6 Hz, 1H), 7.71(d, J=1.6 Hz, 1H), 7.79(d, J=8.0 Hz, 1H), 8.25(d, J=4.8 Hz, 1H), 8.47(d, J=1.2 Hz, 1H)

Production Example 463

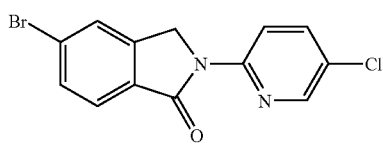

5-Bromo-2-(5-chloropyridin-2-yl)-2,3-dihydroisoindol-1-one 218 mg of the title compound was obtained as pale brown crystals by the same method as in Production Example 461 from 3.68 g of the crude product of methyl 4-bromo-2-bromo methylbenzoate obtained in the synthesis process in Production Example 461 and 1.93 g 2-amino-5-chloropyridine.

¹H-NMR (CDCl₃)

δ: 5.05(s, 2H), 7.65(dd, J=8.4, 1.2 Hz, 1H), 7.72(d, J=1.2 Hz, 1H), 7.73(dd, J=8.8, 2.4 Hz, 1H), 7.79(d, J=8.4 Hz, 1H), 8.34(dd, J=2.4, 0.4 Hz, 1H), 8.63(dd, J=8.8, 0.4 Hz, 1H)

Production Example 464

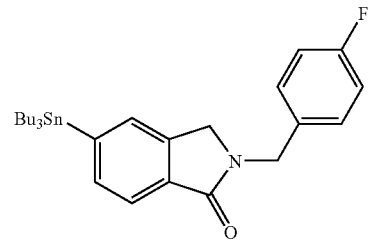

2-(4-Fluorobenzyl)-5-tributylstannyl-2,3-dihydroisoindol-1-one 102 mg of the title compound was obtained as a pale brown oil from 100 mg 5-bromo-2-(4-fluorobenzyl)-2,3-dihydroisoindol-1-one (compound in Production Example 461), 0.4 mL 1,1,1,2,2,2-hexabutyl distannane and 10 mg tetrakis (triphenylphosphine)palladium by the same method as in Production Example 406.

¹H-NMR(CDCl₃)

δ: 0.87(t, J=7.2 Hz, 9H), 1.07(m, 6H), 1.31(sext, J=7.2 Hz, 6H), 1.52(m, 6H), 4.25(s, 2H), 4.77(s, 2H), 7.01(t, J=8.8 Hz, 2H), 7.29(m, 2H), 7.49(d, J=0.8 Hz, 1H), 7.56(dd, J=7.6, 0.4 Hz, 1H), 7.82(dd, J=7.6, 0.8 Hz, 1H)

Production Example 465

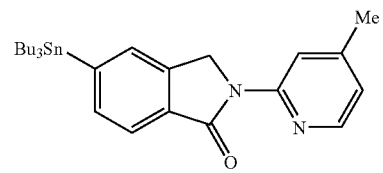

2-(4-Methylpyridin-2-yl)-5-tributylstannyl-2,3-dihydroisoindol-1-one 153 mg of the title compound was obtained as a colorless oil from 155 mg 5-bromo-2-(4-methylpyridin-2-yl)-2,3-dihydroisoindol-1-one (compound in Production Example 462), 0.65 mL 1,1,1,2,2,2-hexabutyl distannane and 14 mg tetrakis (triphenylphosphine)palladium by the same method as in Production Example 406.

¹H-NMR(CDCl₃)

δ: 0.90(t, J=7.2 Hz, 9H), 1.13(m, 6H), 1.36(sext, J=7.2 Hz, 6H), 1.55(m, 6H), 5.08(s, 2H), 6.90(d, J=5.2 Hz, 1H), 7.59(d, J=7.6 Hz, 1H), 7.63(s, 1H), 7.85(d, J=7.2 Hz, 1H), 8.25(d, J=5.2 Hz, 1H), 8.50(s, 1H)

Production Example 466

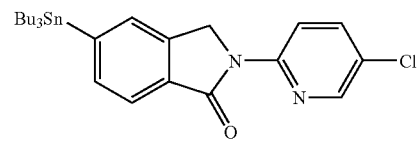

2-(5-Chloropyridin-2-yl)-5-tributylstannyl-2,3-dihydroisoindol-1-one 202 mg of the title compound was obtained as a colorless oil from 216 mg 5-bromo-2-(5-chloropyridin-2-yl)-2,3-dihydroisoindol-1-one (compound in Production Example 463), 0.85 mL 1,1,1,2,2,2-hexabutyl distannane and 17 mg tetrakis (triphenylphosphine)palladium by the same method as in Production Example 406.

$^1$H-NMR(CDCl$_3$)

δ: 0.88(t, J=7.2 Hz, 9H), 1.13(m, 6H), 1.35(sext, J=7.2 Hz, 6H), 1.57(m, 6H), 5.06(s, 2H), 7.61(d, J=7.2 Hz, 1H), 7.64(d, J=0.8 Hz, 1H), 7.72(dd, J=9.2, 2.4 Hz, 1H), 7.85(d, J=7.6 Hz, 1H), 8.34(dd, J=2.4, 0.8 Hz, 1H), 8.67(dd, J=9.2, 0.8 Hz, 1H)

Production Example 467

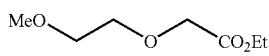

Ethyl (2-methoxyethoxy)acetate 150 mL solution of 10 g (2-methoxyethoxy)acetic acid and 1 mL conc. sulfuric acid in ethanol was heated for 3 hours under reflux, and then the solvent was removed. The resulting residue was diluted with ethyl acetate and washed with an aqueous saturated sodium bicarbonate solution and brine. The organic layer was dried over anhydrous sodium sulfate, and then the solvent was removed, whereby 9.5 g of the title compound (colorless oil) was obtained.

$^1$H-NMR (CDCl$_3$)

δ: 1.28(t, J=7.2 Hz, 3H), 3.89(s, 3H), 3.56–3.64(m, 2H), 3.70–3.78(m, 2H), 4.15(s, 2H), 4.22 (q, J=7.2 Hz, 2H), 7.48(d, J=8.0 Hz, 1H), 7.97(d, J=5.2 Hz, 1H)

Production Example 468

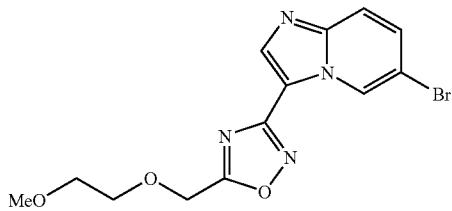

6-Bromo-3-[5-(2-methoxyethoxymethyl)-[1,2,4]oxadiazol-3-yl]-imidazo[1,2-a]pyridine 170 mg of the title compound (colorless crystals) was obtained from 300 mg of 6-bromo-N-hydroxyimidazo[1,2-a]pyridine-3-carboxyamidine (compound in Production Example 244) by using 290 mg ethyl (2-methoxyethoxy) acetate as an acylating agent in the same reaction as in Production Example 263.

$^1$H-NMR (CDCl$_3$)

δ: 3.41(s, 3H), 3.64–3.68(m, 2H), 3.85–3.90(m, 2H), 4.93(s, 2H), 7.47(dd, J=9.2, 1.6 Hz, 1H), 7.67(d, J=9.2 Hz, 1H), 8.39(s, 1H), 9.32–9.34(m, 1H)

Production Example 469

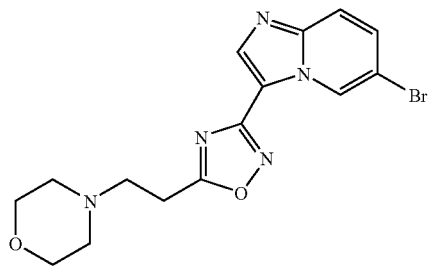

6-Bromo-3-[5-(2-morpholin-4-ylethyl)-[1,2,4]oxadiazol-3-yl]-imidazo[1,2-a]pyridine 158 mg of the title compound (pale yellow crystals) was obtained from 300 mg of 6-bromo-N-hydroxyimidazo[1,2-a]pyridine-3-carboxyamidine (compound in Production Example 244) by using 0.29 mL methyl 3-morpholin-4-ylpropionate as an acylating agent in the same reaction as in Production Example 263.

$^1$H-NMR (CDCl$_3$)

δ: 2.52–2.60(m, 4H), 2.94(t, J=7.2 Hz, 2H), 3.19(t, J=7.2 Hz, 2H), 3.66–3.74(m, 2H), 7.46(dd, J=9.2, 2.0 Hz, 1H), 7.66(dd, J=9.2, 0.8 Hz, 1H), 8.35(s, 1H), 9.34(dd, J=2.0, 0.8 Hz, 1H)

Production Example 470

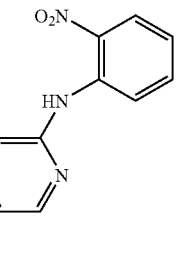

(5-Chloropyridin-2-yl)-(2-nitrophenyl)amine 9.9 g potassium hydroxide powder and 5.0 g 1-fluoro-2-nitrobenzene were added little by little in this order to a solution of 5.8 g 5-chloro-2-aminopyridine in dimethyl sulfoxide (100 mL), and the mixture was stirred at 20° C. for 4 hours under nitrogen atmosphere. The reaction solution was poured into iced water and extracted with ethyl acetate. The organic layer was washed with water and brine and dried over sodium sulfate. The solvent was evaporated, and the residue was purified by NH silica gel column chromatography (ethyl acetate/hexane) and recrystallized from ethyl acetate/hexane, to give 6.02 g of the title compound as orange crystals.

$^1$H-NMR (CDCl$_3$)

δ: 6.92(dd, J=8.7, 0.8 Hz, 1H), 6.97–7.01(m, 1H), 7.56–7.62(m, 2H), 8.24(dd, J=8.4, 1.6 Hz, 1H), 8.29(d, J=1.7 Hz, 1H), 8.70(dd, J=8.7, 1.7 Hz, 1H), 10.19(brs, 1H)

Production Example 471

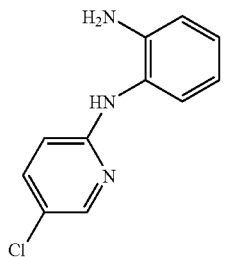

N-(5-Chloropyridin-2-yl)benzene-1,2-diamine 3.91 g of the title compound was obtained as colorless crystals from 6.02 g (5-chloropyridin-2-yl)-(2-nitrophenyl) amine (compound in Production Example 470) by the same procedure as in Production Example 332 and subsequent recrystallization from ethyl acetate/hexane.

$^1$H-NMR (DMSO-$d_6$)

δ: 3.83(brs, 2H), 6.18(brs, 1H), 6.36(dd, J=9.2, 0.8 Hz, 1H), 6.78 (td, J=7.6, 1.2 Hz, 1H), 6.82(dd, J=7.8, 1.4 Hz, 1H), 7.08–7.17(m, 2H), 7.38(dd, J=9.2, 2.5 Hz, 1H), 8.10 (dd, J=2.6, 0.6 Hz, 1H)

Production Example 472

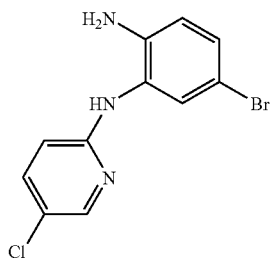

4-Bromo-N-2-(5-chloropyridin-2-yl)benzene-1,2-diamine 2 g of N-(5-chloropyridin-2-yl)benzene-1,2-diamine (compound in Production Example 471) was dissolved in 40 mL N,N-dimethylformamide, then 1.45 g of N-bromosuccinimide was added little by little to the solution under ice-cooling, and the mixture was stirred for 1 hour. An aqueous sodium thiosulfate solution and an aqueous sodium bicarbonate solution were added thereto, and the mixture was stirred for 1 hour and then extracted with ethyl acetate. The extract was purified by NH silica gel chromatography (ethyl acetate/hexane) to give 621 mg of the title compound as a dark red oil.

$^1$H-NMR (CDCl$_3$)

δ: 3.82(brs, 2H), 6.09(brs, 1H), 6.41(dd, J=8.9, 0.6 Hz, 1H), 6.70(d, J=8.6 Hz, 1H), 7.18(dd, J=8.6, 2.2 Hz, 1H), 7.33(d, J=2.2 Hz, 1H), 7.42(dd, J=8.9, 2.5 Hz, 1H), 8.12(dd, J=2.5, 0.6 Hz, 1H)

Production Example 473

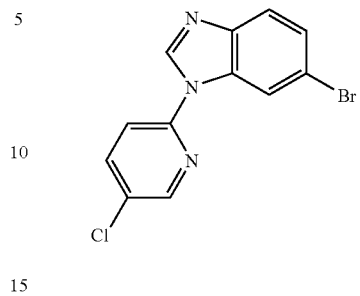

6-Bromo-1-(5-chloropyridin-2-yl)-1H-benzo[d]imidazole 367 mg of the title compound was obtained as dark purple crystals from 647 mg 4-bromo-N-2-(5-chloropyridin-2-yl) benzene-1,2-diamine (compound in Production Example 472) by the same procedure as in Production Example 334.

$^1$H-NMR (CDCl$_3$)

δ: 7.48(dd, J=8.6, 1.8 Hz, 1H), 7.51(d, J=8.7 Hz, 1H), 7.73(d, J=8.6 Hz, 1H), 7.90(dd, J=8.7, 2.5 Hz, 1H), 8.28(d, J=1.8 Hz, 1H), 8.47(s, 1H), 8.59(d, J=2.5 Hz, 1H)

Example 1

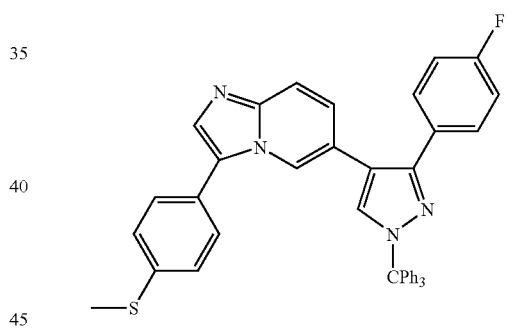

6-[3-(4-Fluorophenyl)-1-trityl-1H-4-pyrazolyl]-3-[4-(methylsulfanyl)phenyl] imidazo[1,2-a]pyridine 150 mg 6-[3-(4-fluorophenyl)-1-trityl-1H-4-pyrazolyl]-3-iodoimidazo[1,2-a]pyridine obtained in Production Example 39, 53 mg 4-methylthiophenylboronic acid, 13 mg tetrakis (triphenylphosphine)palladium and 96 mg potassium carbonate powder were heated at 80 to 90° C. for 4 hours in a solution mixture of 1 mL toluene, 1.5 mL ethanol and 0.3 mL water in a stream of nitrogen. The solvent was removed, and the residue was purified by an NH silica gel column (hexane/ethyl acetate) to give 138 mg of the title compound as a colorless solid.

$^1$H-NMR (CDCl$_3$)

δ: 2.45 (s, 3H), 7.02–7.04 (m, 2H), 7.12 (dd, J=9.2, 2.0 Hz, 1H), 7.19 (dt, J=8.0, 2.0 Hz, 2H), 7.21–7.26 (m, 8H), 7.31–7.36 (m, 9H), 7.44 (d, J=0.8 Hz, 1H), 7.44–7.49 (m, 2H), 7.63 (d, J=0.8 Hz, 1H), 7.64 (d, J=8.0 Hz, 1H), 8.02 (s, 1H)

Example 2

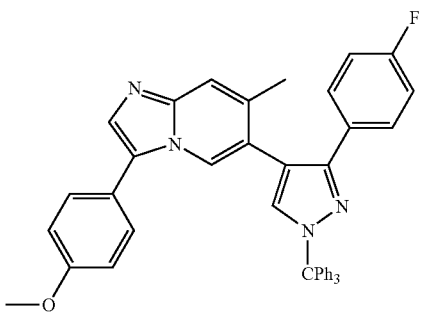

6-[3-(4-Fluorophenyl)-1-trityl-1H-4-pyrazolyl]-3-[4-(methoxyphenyl)-7-methylimidazo[1,2-a]pyridine 158 mg of the title compound was obtained as colorless crystals from 200 mg 3-bromo-6-[3-(4-fluorophenyl)-1-trityl-1H-4-pyrazolyl]-7-methylimidazo[1,2-a]pyridine and 62 mg 4-methoxyphenylboronic acid by the same method as in Example 1.

$^1$H-NMR (CDCl$_3$)

δ: 2.08(s, 3H), 3.86(s, 3H), 6.90–6.97(m, 2H), 6.97(dt, J=8.8, 2.0 Hz, 2H), 7.21–7.25(m, 6H), 7.28(s, 1H), 7.30–7.35(m, 11H), 7.41–7.48(m, 2H), 7.47(t, J=0.8 Hz, 1H), 7.56(s, 1H), 8.04 (s, 1H)

Example 3

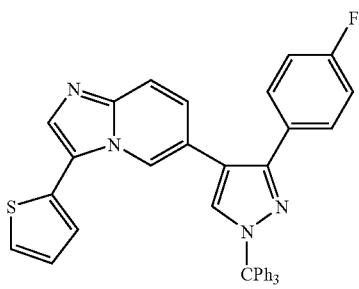

6-[3-(4-Fluorophenyl)-1-trityl-1H-4-pyrazolyl]-3-(2-thienyl)imidazo[1,2-a]pyridine 4.41 g 6-[3-(4-fluorophenyl)-1-trityl-1H-4-pyrazolyl]-3-iodoimidazo[1,2-a]pyridine obtained in Production Example 39, 1 g 2-thienyboronic acid and 340 mg tetrakis(triphenylphosphine)palladium were heated at 80° C. for 3 hours in a solution mixture of 10 mL of 2 N aqueous sodium carbonate, 15 mL ethanol and 15 mL toluene. The reaction solution was extracted with dichloromethane and dried over magnesium sulfate, the solvent was removed, and the residue was purified by NH silica gel column chromatography (dichloromethane/hexane/ethyl acetate) to give 3 g of the title compound as colorless crystals (recrystallization solvent: methanol/ethanol).

$^1$H-NMR (CDCl$_3$)

δ: 6.96(dd, J=3.6, 1.2 Hz, 1H), 6.97–7.04(m, 2H), 7.09 (dd, J=5.2, 3.6 Hz, 1H), 7.11(dd, J=9.2, 1.6 Hz, 1H), 7.21–7.27(m, 6H), 7.31–7.37(m, 9H), 7.36(dd, J=5.2, 1.2 Hz, 1H), 7.43–7.49(m, 2H), 7.45(s, 1H), 7.58(dd, J=9.2, 0.8 Hz, 1H), 7.71(s, 1H), 8.17(dd, J=1.6, 0.8 Hz, 1H)

Example 4

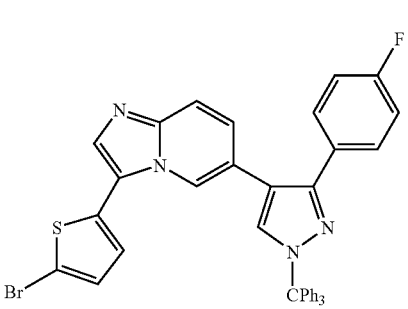

3-(5-Bromo-2-thienyl)-6-[3-(4-fluorophenyl)-1-trityl-1H-4-pyrazolyl]imidazo[1,2-a]pyridine 160 mg N-bromosuccinimide was added to 5 mL solution of 500 mg 6-[3-(4-fluorophenyl)-1-trityl-1H-4-pyrazolyl]-3-(2-thienyl)imidazo[1,2-a]pyridine obtained in Example 3 in N,N-dimethylformamide, and the mixture was stirred for 1 hour. An aqueous sodium thiosulfate solution was added thereto and stirred for 30 minutes, and the reaction solution was extracted with ethyl acetate and dried over magnesium sulfate. The residue was purified by NH silica gel column chromatography (hexane/dichloromethane/ethyl acetate) to give 612 mg of the title compound as pale yellow crystals.

$^1$H-NMR (CDCl$_3$)

δ: 6.70 (d, J=4.0 Hz, 1H), 7.02 (dt, J=8.8, 2.0 Hz, 2H), 7.04 (d, J=4.0 Hz, 1H), 7.13 (dd, 9.2, 1.6 Hz, 1H), 7.22–7.27 (m, 6H), 7.32–7.37 (m, 9H), 7.43–7.48 (m, 2H), 7.46 (s, 1H), 7.58 (dd, J=9.2, 0.8 Hz, 1H), 7.67 (s, 1H), 8.09 (dd, J=1.6, 0.8 Hz, 1H)

Example 5

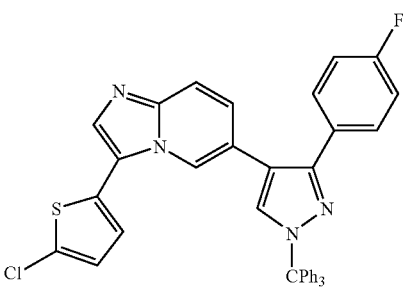

3-(5-Chloro-2-thienyl)-6-[3-(4-fluorophenyl)-1-trityl-1H-4-pyrazolyl]imidazo[1,2-a]pyridine 80 mg 6-[3-(4-fluorophenyl)-1-trityl-1H-4-pyrazolyl]-3-iodoimidazo[1,2-a]pyridine obtained in Production Example 39 and 27 mg 5-chloro-2-thienylboronic acid were reacted in the same manner as in Example 3, to give 70 mg of the title compound as a pale yellow amorphous.

¹H-NMR (CDCl₃)

δ: 6.71(d, J=4.0 Hz, 1H), 6.90(d, J=4.0 Hz, 1H), 7.02(m, 2H), 7.13(dd, J=9.2, 1.6 Hz, 1H), 7.24(m, 7H), 7.34(m, 8H), 7.44(m, 3H), 7.58(d, J=9.2 Hz, 1H), 7.66(s, 1H), 8.08(brs, 1H)

Example 6

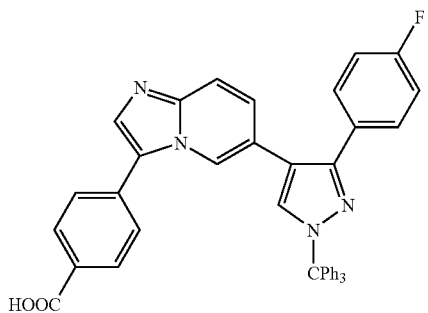

4-{6-[3-(4-Fluorophenyl)-1-trityl-1H-4-pyrazolyl]imidazo[1,2-a]pyridin-3-yl}benzoic acid 80 mg 6-[3-(4-fluorophenyl)-1-trityl-1H-4-pyrazolyl]-3-iodoimidazo[1,2-a]pyridine obtained in Production Example 39 and 27 mg 4-carboxyphenylboronic acid were reacted in the same manner as in Example 3, to give 28 mg of the title compound as a pale yellow solid.

¹H-NMR (CDCl₃)

δ: 7.14–7.26(m, 7H), 7.36(m, 1H), 7.48(m, 4H), 7.62(d, J=9.2 Hz, 1H), 7.76(s, 1H), 7.82(s, 1H), 7.91(d, J=8.4 Hz, 1H), 8.25(brs, 1H)

Example 7

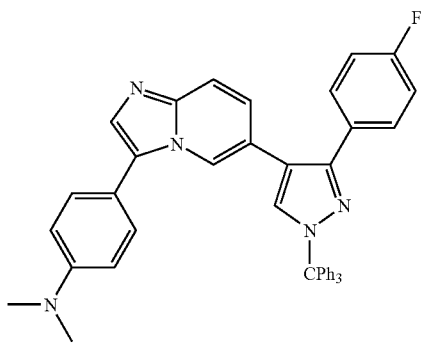

N,N-Dimethyl-4-{6-[3-(4-fluorophenyl)-1-trityl-1H-4-pyrazolyl]imidazo[1,2-a]pyridin-3-yl}aniline 129 mg 6-[3-(4-fluorophenyl)-1-trityl-1H-4-pyrazolyl]-3-iodoimidazo[1,2-a]pyridine obtained in Production Example 39 and 43 mg 4-(dimethylamino)phenylboronic acid were reacted in the same manner as in Example 3, to give 109 mg of the title compound as a pale yellow amorphous.

¹H-NMR (CDCl₃)

δ: 3.00(s, 6H), 6.70(d, J=8.8 Hz, 2H), 7.04(m, 3H), 7.14(d, J=8.8 Hz, 2H), 7.22(m, 7H), 7.32(m, 8H), 7.42(s, 1H), 7.47(m, 2H), 7.55(s, 1H), 7.56(dd, J=9.2, 0.4 Hz, 1H), 8.01(brs, 1H)

Example 8

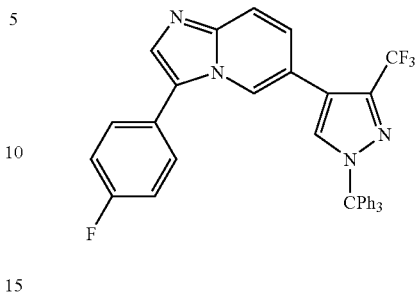

3-(4-Fluorophenyl)-6-(3-trifluoromethyl-1-trityl-1H-4-pyrazolyl)imidazo[1,2-a]pyridine 100 mg 3-iodo-6-(3-trifluoromethyl-1-trityl-1H-4-pyrazolyl)imidazo[1,2-a]pyridine obtained in Production Example 44 and 30 mg 4-fluorophenylboronic acid were reacted in the same manner as in Example 3, to give 88 mg of the title compound as a colorless amorphous.

¹H-NMR (CDCl₃)

δ: 7.15(m, 7H), 7.23(m, 2H), 7.34(m, 9H), 7.46(d, J=0.8 Hz, 1H), 7.53(m, 2H), 7.65(dd, J=9.2, 1.2 Hz, 1H), 7.67(s, 1H), 8.33(brs, 1H)

Example 9

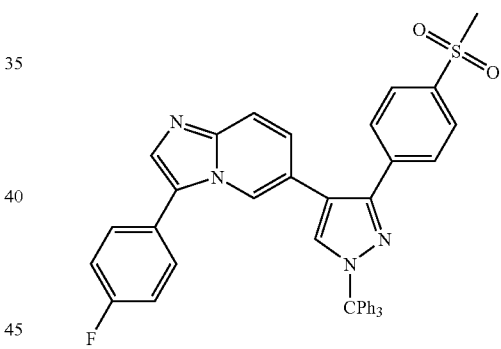

3-(4-Fluorophenyl)-6-{3-[4-(methylsulfonyl)phenyl]-1-trityl-1H-4-pyrazolyl}imidazo[1,2-a]pyridine 268 mg 3-iodo-6-{3-[4-(methylsulfonyl)phenyl]-1-trityl-1H-4-pyrazolyl}imidazo[1,2-a]pyridine obtained in Production Example 43, 64 mg 4-fluorophenylboronic acid and 22 mg tetrakis(triphenylphosphine)palladium were heated at 85° C. for 3 hours in a solution mixture of 1 mL toluene, 1.5 mL ethanol and 0.6 ml of 2 N aqueous sodium carbonate under nitrogen atmosphere. The reaction solution was dried over magnesium sulfate, the solvent was removed, and the residue was purified by NH silica gel column chromatography (hexane/ethyl acetate) to give 233 mg of the title compound as colorless crystals (recrystallization solvent: ethyl acetate).

¹H-NMR (CDCl₃)

δ: 3.04 (s, 3H) 7.09 (dd, J=9.2, 1.6 Hz, 1H) 7.13 (dt, J=8.4, 2.0 Hz, 2H) 7.19–7.25 (m, 6H) 7.27–7.32 (m, 2H) 7.32–7.37 (m, 9H) 7.46 (s, 1H) 7.63 (dd, J=9.2, 0.8 Hz) 7.64

(s, 1H) 7.72 (dt, J=8.8, 2.0 Hz, 2H) 7.88 (dt, J=8.8, 2.0 Hz, 2H) 8.01 (dd, J=1.6 Hz, 0.8 Hz, 1H)

Example 10

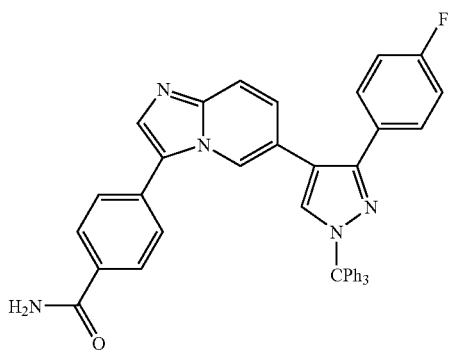

4-{6-[3-(4-Fluorophenyl)-1-trityl-1H-4-pyrazolyl]imidazo[1,2-a]pyridin-3-yl}benzamide 222 mg of 4-(4,4,5,5-tetramethyl-1,3,2-dioxaborolan-2-yl)benzamide prepared according to T. Ishiyama et al., J. Org. Chem., 60, 7508 (1995), 323 mg of 6-[3-(4-fluorophenyl)-1-trityl-1H-pyrazolyl]-3-iodoimidazo[1,2-a]pyridine (compound in Production Example 39), 200 mg tripotassium phosphate, 30 mg tetrakis(triphenylphosphine)palladium and 30 mL N,N-dimethylformamide were heated at 75° C. for 3 hours under nitrogen atmosphere. The solvent was removed, and the residue was purified by NH silica gel chromatography (hexane/ethyl acetate) to give 138 mg of the title compound (film).

$^1$H-NMR (CDCl$_3$)

δ: 7.02–7.09 (m, 2H), 7.18–7.25 (m, 7H), 7.31–7.36 (m, 9H), 7.37 (dt, J=8.4, 2.0 Hz, 2H), 7.44–7.50 (m, 2H), 7.47 (s, 1H), 7.67 (d, J=9.6 Hz, 1H), 7.73 (s, 1H), 7.81 (dt, J=8.4, 2.0 Hz, 2H), 8.08 (s, 1H)

Example 11

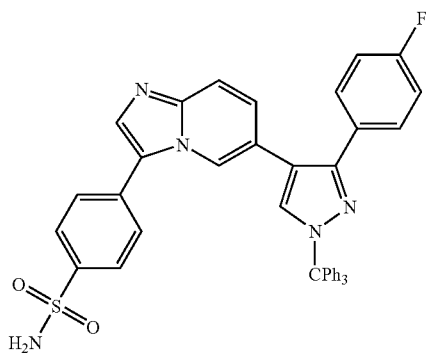

4-{6-[3-(4-Fluorophenyl)-1-trityl-1H-4-pyrazolyl]imidazo[1,2-a]pyridin-3-yl}-1-benzene sulfonamide 198 mg of the title compound (film) was obtained in the same manner as in Example 10 from 226 mg of 4-(4,4,5,5-tetramethyl-1,3,2-dioxaborolan-2-yl)benzene sulfonamide and 240 mg of 6-[3-(4-fluorophenyl)-1-trityl-1H-4-pyrazolyl]-3-iodoimidazo[1,2-a]pyridine (compound in Production Example 39).

$^1$H-NMR (CDCl$_3$)

δ: 4.96 (s, 2H), 7.01–7.08 (m, 2H), 7.19 (dd, J=9.2, 1.6 Hz, 1H), 7.20–7.26 (m, 6H), 7.30–7.37 (m, 9H), 7.42 (dt, J=8.8, 2.0 Hz, 2H), 7.44–7.49 (m, 2H), 7.47 (s, 1H), 7.65(dd, J=9.2, 0.8 Hz, 1H), 7.73 (s, 1H), 7.91 (dt, J=8.8, 2.0 Hz, 2H), 7.08 (dd, J=1.6 0.8 Hz, 1H)

Example 12

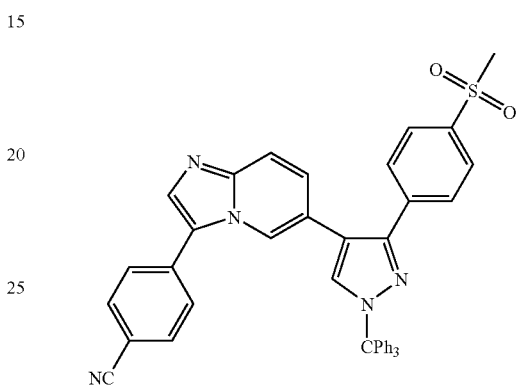

4-(6-{3-[4-(Methylsulfonyl)phenyl]-1-trityl-1H-4-pyrazolyl}imidazo[1,2-a]pyridin-3-yl)benzonitrile 213 mg of the title compound (film) was obtained in the same manner as in Example 10 from 137 mg of 4-(4,4,5,5-tetramethyl-1,3,2-dioxaborolan-2-yl)benzonitrile and 283 mg of 3-iodo-6-{3-[4-(methylsulfonyl)phenyl]-1-trityl-1H-4-pyrazolyl}imidazo[1,2-a]pyridine (compound in Production Example 43).

$^1$H-NMR (CDCl$_3$)

δ: 3.03 (s, 3H), 7.16 (dd, J=9.2, 1.6 Hz, 1H), 7.20–7.25 (m, 6H), 7.31–7.40 (m, 9H), 7.45 (dt, J=8.0, 2.0 Hz, 2H), 7.48 (s, 1H), 7.67 (d, J=9.2 Hz, 1H), 7.69–7.74 (m, 4H), 7.77 (s, 1H), 7.89 (dt, J=8.0, 2.0 Hz, 2H), 8.10–8.12 (m, 1H)

Example 13

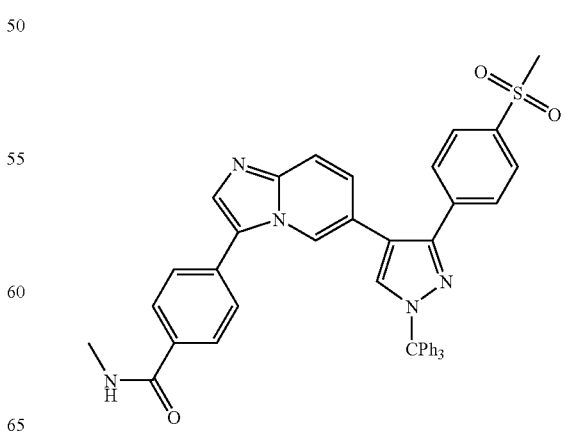

N1-Methyl-4-(6-{3-[4-(methylsulfonyl)phenyl]-1-trityl-1H-4-pyrazolyl}imidazo[1,2-a]pyridin-3-yl)benzamide 184 mg of the title compound (colorless crystals; recrystallization solvent, methanol) was obtained in the same manner as in Example 10 from 137 mg of N1-methyl-4-(4,4,5,5-tetramethyl-1,3,2-dioxaborolan-2-yl)benzamide and 283 mg of 3-iodo-6-{3-[4-(methylsulfonyl)phenyl]-1-trityl-1H-4-pyrazolyl}imidazo[1,2-a]pyridine (compound in Production Example 43).

$^1$H-NMR (CDCl$_3$)

δ: 3.03 (d, J=4.8 HZ, 3H), 3.14 (s, 3H), 6.93–6.99 (m, 1H), 7.18 (dt, J=8.4, 2.0 Hz, 2H), 7.18–7.25 (m, 7H), 7.31–7.39 (m, 9H), 7.58 (s, 1H), 7.65 (dd, J=9.2, 0.8 Hz, 1H), 7.67 (s, 1H), 7.77 (dt, J=8.4, 2.0 Hz, 2H), 7.81 (dt, J=8.4, 2.0 Hz, 2H), 7.92 (dd, J=1.6, 0.8 Hz, 1H), 8.01 (dt, J=8.4, 2.0 Hz, 2H)

Example 14

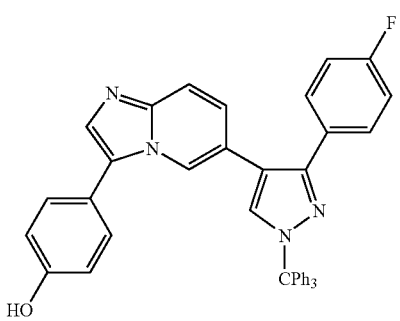

4-{6-[3-(4-Fluorophenyl)-1-trityl-1H-4-pyrazolyl]imidazo-[1,2-a]pyridin-3-yl}phenol While a mixture of 129 mg of 6-[3-(4-fluorophenyl)-1-trityl-1H-4-pyrazolyl]-3-iodoimidazo[1,2-a]pyridine obtained in Production Example 39, 53 mg of 4-(4, 4, 5, 5-tetramethyl-1,3,2-dioxaborolan-2-yl)phenol, 64 mg of tripotassium phosphate and 10 mL N,N-dimethylformamide was stirred in a stream of nitrogen, 10 mg of 1,1'-[bis(diphenylphosphino)-ferrocene]dichloropalladium (II) was added thereto, and the mixture was stirred at 80° C. for 3 hours. 20 mg of 4-(4,4, 5,5-tetramethyl-1,3,2-dioxaborolan-2-yl)phenol and 10 mg of 1,1'-[bis(diphenylphosphino)-ferrocene]-dichloropalladium (II) were added thereto, and the mixture was stirred for 3 hours. The reaction solution was cooled, water was added thereto, the solution was extracted with ethyl acetate, and the organic layer was dried over anhydrous sodium sulfate. The drying agent was filtered off, and the concentrated residue was purified by silica gel column chromatography (hexane/ethyl acetate) to give 86 mg of the title compound as a white solid.

$^1$H-NMR (CDCl$_3$)

δ: 6.73(s, 1H), 6.87(d, J=8.4 Hz, 2H), 7.01(m, 2H), 7.11(dd, J=9.2, 1.6 Hz, 1H), 7.13(d, J=8.4 Hz, 2H), 7.21(m, 7H), 7.32(m, 8H), 7.43(s, 1H), 7.45(m, 2H), 7.58(s, 1H), 7.59(dd, J=9.2, 0.8 Hz, 1H), 8.00(dd, J=1.6, 0.8 Hz, 1H)

Example 15

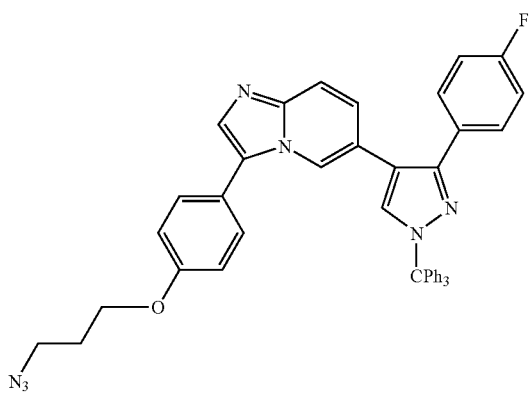

3-(4-{6-[3-(4-Fluorophenyl)-1-trityl-1H-4-pyrazolyl]imidazo[1,2-a]pyridin-3-yl}phenoxy)propyl azide A mixture of 184 mg 4-{6-[3-(4-fluorophenyl)-1-trityl-1H-4-pyrazolyl]imidazo[1,2-a]pyridin-3-yl}phenol obtained in Example 14, 0.3 mL 1-bromo-3-chloropropane, 250 mg potassium carbonate, and 10 mL acetone was heated for 1 hour under reflux. The reaction solution was diluted with ethyl acetate, then washed with water and brine and dried over anhydrous sodium sulfate. The drying agent was filtered off, and the filtrate was concentrated, and 195 mg sodium azide and 10 mL N,N-dimethylformamide were added to the resulting residue and heated at 80° C. for 4 hours. Ethyl acetate and water were added to the reaction solution, and the organic layer was separated, washed twice with water and then with brine, and dried over anhydrous sodium sulfate. The drying agent was filtered off, the filtrate was concentrated, and the residue was purified by silica gel column chromatography (hexane/ethyl acetate), to give 184 mg of the title compound as a pale brown amorphous.

$^1$H-NMR (CDCl$_3$)

δ: 2.10(m, 2H), 3.55(m, 2H), 4.09(m, 2H), 6.90(d, J=8.4 Hz, 2H), 7.03(m, 2H), 7.09(dd, J=9.2, 1.2 Hz, 1H), 7.22(m, 9H), 7.32(m, 8H), 7.43(s, 1H), 7.45(m, 2H), 7.58(s, 1H), 7.58(d, J=9.2 Hz, 1H), 7.99(brs, 1H)

Example 16

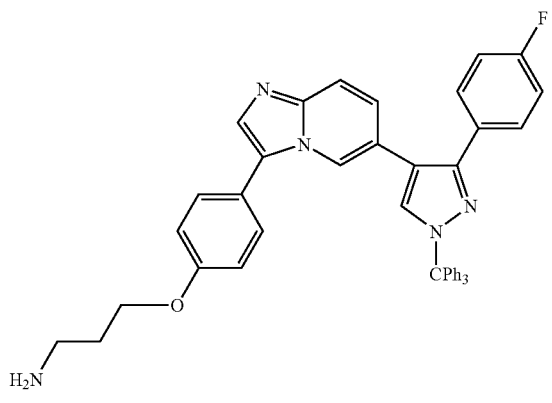

3-(4-{6-[3-(4-Fluorophenyl)-1-trityl-1H-4-pyrazolyl]
imidazo[1,2-a]pyridin-3-yl}phenoxy)propylamine A solution of 351 mg 3-(4-{6-[3-(4-fluorophenyl)-1-trityl-1H-4-pyrazolyl]imidazo[1,2-a]pyridin-3-yl}phenoxy)-propyl azide obtained in Example 15 in 10 mL tetrahydrofuran was stirred at room temperature in a stream of nitrogen, 0.15 mL n-butyl phosphine was added thereto and stirred for 2 hours. Then, 2 mL water was added thereto and further stirred for 4 hours. Ethyl acetate and anhydrous sodium sulfate were added to the reaction solution and stirred. The drying agent was filtered off, the filtrate was concentrated, and the residue was subjected to silica gel column chromatography. By gradual elution with an eluent from hexane:ethyl acetate=1:1 (v/v) to ethyl acetate:methanol 100:1 (v/v), 287 mg of the title compound was obtained as a pale brown amorphous.

$^1$H-NMR (CDCl$_3$)

δ: 1.97(m, 2H), 2.96(m, 2H), 4.09(m, 2H), 6.90(d, J=8.8 Hz, 2H), 7.03(m, 2H), 7.08(dd, J=9.6, 1.6 Hz, 1H), 7.19(d, J=8.8 Hz, 2H), 7.22(m, 7H), 7.33(m, 8H), 7.43(s, 1H), 7.45(m, 2H), 7.57(s, 1H), 7.58(dd, J=9.6, 0.8 Hz, 1H), 7.99(dd, J=1.6, 1.2 Hz, 1H)

Example 17

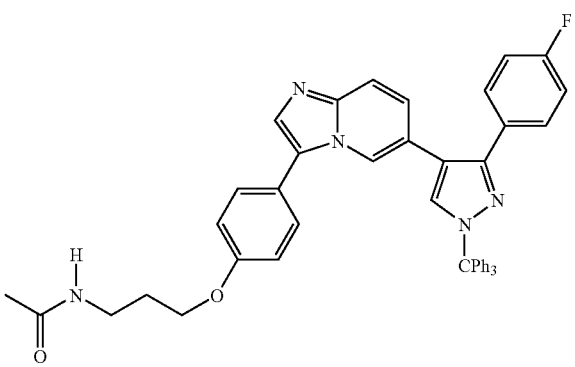

N-[3-(4-{6-[3-(4-Fluorophenyl)-1-trityl-1H-4-pyrazolyl]-imidazo[1,2-a]pyridin-3-yl}phenoxy)propyl]
acetamide While 5 mL solution of 37 mg 3-(4-{6-[3-(4-Fluorophenyl)-1-trityl-1H-4-pyrazolyl]imidazo[1,2-a]pyridin-3-yl}phenoxy)-propylamine obtained in Example 16 and 20 mg triethylamine in dichloromethane was stirred under ice-coolingd water in a stream of nitrogen, 9 μL acetic anhydride was added thereto and stirred for 1 hour. An aqueous saturated sodium bicarbonate solution and ethyl acetate were added to the reaction solution, the organic layer was separated, washed with brine and dried over anhydrous sodium sulfate. The drying agent was filtered off, the filtrate was concentrated, and the residue was purified by NH silica gel column chromatography (hexane/ethyl acetate) to give 30 mg of the title compound as a colorless oil.

$^1$H-NMR (CDCl$_3$)

δ: 2.00(s, 3H), 2.06(m, 2H), 3.49(m, 2H), 4.08(m, 2H), 5.80(brs, 1H), 6.88(d, J=8.4 Hz, 2H), 7.03(m, 2H), 7.10(dd, J=9.2, 1.2 Hz, 1H), 7.19(d, J=8.4 Hz, 2H), 7.22(m, 7H), 7.33(m, 8H), 7.44(s, 1H), 7.46(m, 2H), 7.58(s, 1H), 7.59(d, J=9.2 Hz, 1H), 7.98(brs, 1H)

Example 18

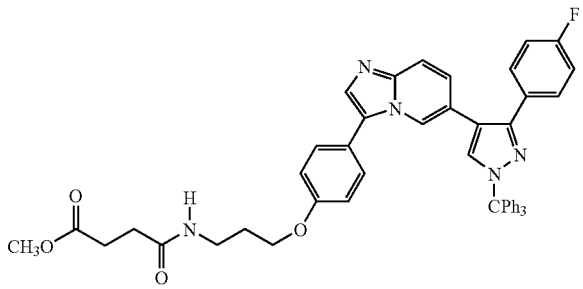

Methyl 4-{[3-(4-{6-[3-(4-Fluorophenyl)-1-trityl-1H-4-pyrazolyl]imidazo[1,2-a]pyridin-3-yl}phenoxy)
propyl]amino}-4-oxobutanoate 41 mg of 3-(4-{6-[3-(4-fluorophenyl)-1-trityl-1H-4-pyrazolyl]imidazo[1,2-a]pyridin-3-yl}phenoxy)propylamine obtained in Example 16 and 12 μL methyl 4-chloro-4-oxobutyrate were reacted in the same manner as in Example 17, to give 24 mg of the title compound as a colorless amorphous.

$^1$H-NMR (CDCl$_3$)

δ: 2.04(m, 2H), 2.51(m, 2H), 2.70(m, 2H), 3.50(m, 2H), 3.67(s, 3H), 4.07(m, 2H), 5.95(brs, 1H), 6.89(d, J=8.8 Hz, 2H), 7.03(t, J=8.8, 2H), 7.09(dd, J=9.2, 1.2 Hz, 1H), 7.19(d, J=8.8 Hz, 2H), 7.22(m, 7H), 7.33(m, 8H), 7.44(s, 1H), 7.46(m, 2H), 7.57(s, 1H), 7.58(d, J=9.2 Hz, 1H), 7.98(brs, 1H)

Example 19

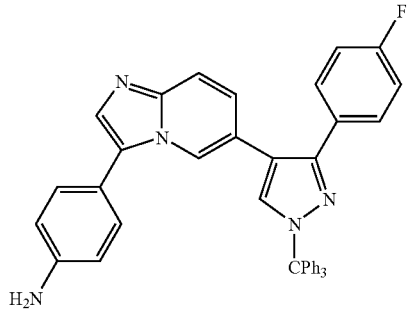

4-{6-[3-(4-Fluorophenyl)-1-trityl-1H-4-pyrazolyl]
imidazo-[1,2-a]pyridin-3-yl}aniline 150 mg of 6-[3-(4-fluorophenyl)-1-trityl-1H-4-pyrazolyl]-3-iodoimidazo[1,2-a]pyridine obtained in Production Example 39, 80 mg 4-(4,4,5,5-tetramethyl-1,3,2-dioxaborolan-2-yl)aniline, and 15 mg tetrakis (triphenylphosphine) palladium were reacted in the same manner as in Example 14, to give 108 mg of the title compound as a pale yellow amorphous.

$^1$H-NMR (CDCl$_3$)

δ: 6.67(d, J=8.4 Hz, 2H), 6.99–7.08 (m, 5H), 7.22 (m, 7H), 7.32 (m, 8H), 7.42 (s, 1H), 7.46 (m, 2H), 7.54 (s, 1H), 7.56 (dd, J=9.2, 1.2 Hz, 1H), 7.99 (dd, J=1.6, 1.2 Hz, 1H)

Example 20

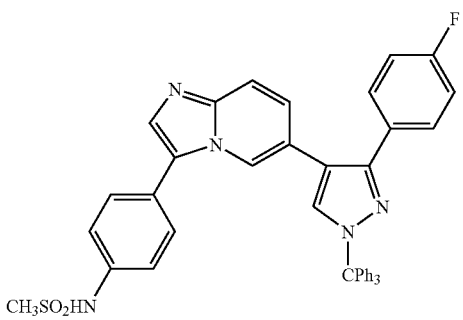

N-(4-{6-[3-(4-Fluorophenyl)-1-trityl-1H-4-pyrazolyl]-imidazo[1,2-a]pyridin-3-yl}phenyl)methane sulfonamide While 7 mL solution of 68 mg 4-{6-[3-(4-fluorophenyl)-1-trityl-1H-4-pyrazolyl]imidazo[1,2-a]pyridin-3-yl}aniline obtained in Example 19 and 34 mg triethylamine in dichloromethane was stirred in a stream of nitrogen, 20 μL methylsulfonyl chloride was added thereto. Then, the mixture was stirred at room temperature for 3 hours. Water was added to the reaction solution which was then extracted with ethyl acetate, and the organic layer was washed with brine and dried over anhydrous sodium sulfate. The drying agent was filtered off, and the concentrated residue was purified by silica gel column chromatography (hexane/ethyl acetate) to give 52 mg of the title compound as a pale yellow amorphous.

$^1$H-NMR (CDCl$_3$)

δ: 3.46 (s, 3H), 7.06 (m, 2H), 7.19 (dd, J=9.2, 1.6 Hz, 1H), 7.24 (m, 8H), 7.34 (m, 11H), 7.47 (m, 2H), 7.49 (s, 1H), 7.66 (d, J=9.2 Hz, 1H), 7.69 (s, 1H), 8.08 (brs, 1H)

Example 21

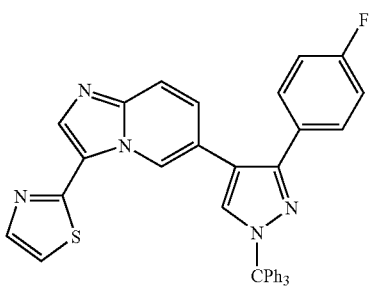

2-{6-[3-(4-Fluorophenyl)-1-trityl-1H-4-pyrazolyl]imidazo-[1,2-a]pyridin-3-yl}-1,3-thiazole 550 mg of 6-[3-(4-fluorophenyl)-1-trityl-1H-4-pyrazolyl]-3-iodoimidazo[1,2-a]pyridine obtained in Production Example 39, 382 mg of 2-(1,1,1-tributylstannyl)-1,3-thiazole and 50 mg tetrakis(triphenylphosphine)palladium were heated in 15 mL xylene at 120° C. for 2 hours under nitrogen atmosphere. The solvent was removed, and the residue was purified by NH silica gel column chromatography (hexane/ethyl acetate), to give 452 mg of the title compound (colorless crystals; recrystallization solvent, methanol).

$^1$H-NMR (CDCl$_3$)

δ: 6.97 (dt, J=8.8, 2.0 Hz, 2H), 7.22 (dd, J=9.2, 2.0 Hz, 1H), 7.24–9.29 (m, 7H), 7.32–7.38 (m, 9H), 7.45–7.50 (m, 2H), 7.52 (s,1H), 7.65 (d, J=9.2, 1H), 7.74 (d, J=3.2 Hz, 1H) 8.10 (s, 1H), 9.57 (dd, J=1.6, 0.8 Hz, 1H)

Example 22

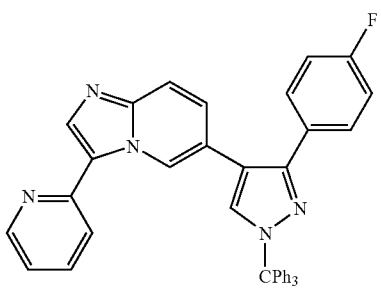

6-[3-(4-fluorophenyl)-1-trityl-1H-4-pyrazolyl]-3-(2-pyridyl) imidazo[1,2-a]pyridine 194 mg of 6-[3-(4-fluorophenyl)-1-trityl-1H-4-pyrazolyl]-3-iodoimidazo[1,2-a]pyridine obtained in Production Example 39 and 0.17 mL 2-(tri-n-butylstannyl)were pyridine were reacted in the same manner as in Example 21, to give 149 mg of the title compound as a colorless amorphous.

$^1$H-NMR (CDCl$_3$)

δ: 6.95(m, 2H), 7.13(m, 2H), 7.26(m, 7H), 7.33(m, 8H), 7.49(m, 3H), 7.59(dd, J=9.2, 1.2 Hz, 1H), 7.68(m, 2H), 8.10(s, 1H), 8.41(ddd, J=5.2, 1.2, 1.2 Hz, 1H), 9.80(dd, J=1.2, 0.8 Hz, 1H)

Example 23

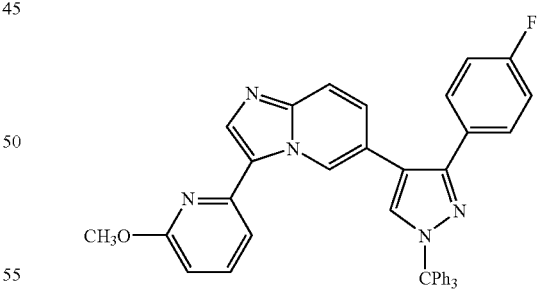

6-[3-(4-fluorophenyl)-1-trityl-1H-4-pyrazolyl]-3-(6-methoxy-2-pyridyl)imidazo[1,2-a]pyridine 162 mg of 6-[3-(4-fluorophenyl)-1-trityl-1H-4-pyrazolyl]-3-iodoimidazo[1,2-a]pyridine obtained in Production Example 39 and 300 mg of 2-methoxy-6-(tri-n-butylstannyl) pyridine were reacted in the same manner as in Example 21, to give 108 mg of the title compound as a colorless amorphous.

¹H-NMR (CDCl₃)

δ: 3.63(s, 3H), 6.59(d, J=8.0 Hz, 1H), 6.95(m, 2H), 7.11(dd, J=9.2, 1.6 Hz, 1H), 7.23(m, 7H), 7.32(d, J=8.0 Hz, 1H), 7.34(m, 8H), 7.42(s, 1H), 7.50(m, 2H), 7.59(dd, J=9.2, 0.4 Hz, 1H), 7.61(t, J=8.0 Hz, 1H), 8.11(s, 1H), 9.90(brs, 1H)

Example 24

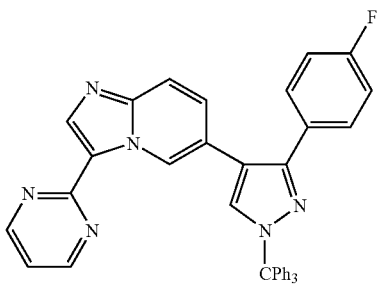

6-[3-(4-Fluorophenyl)-1-trityl-1H-4-pyrazolyl]-3-(2-pyrimidinyl)imidazo[1,2-a]pyridine 129 mg of 6-[3-(4-fluorophenyl)-1-trityl-1H-4-pyrazolyl]-3-iodoimidazo[1,2-a]pyridine obtained in Production Example 39 and 133 mg of 2-(tri-n-butylstannyl)-pyrimidine were reacted in the same manner as in Example 21, to give 96 mg of the title compound as a colorless amorphous.

¹H-NMR (CDCl₃)

δ: 6.98(m, 2H), 7.03(dd, J=9.2, 1.6 Hz, 1H), 7.26(m, 7H), 7.35(m, 9H), 7.42(s, 1H), 7.47(m, 2H), 7.50(t, J=0.8 Hz, 1H), 7.54(dd, J=9.2, 1.2 Hz, 1H), 7.62(d, J=1.2 Hz, 1H), 8.02(dd, J=1.6, 1.2 Hz, 1H), 8.54(d, J=5.2 Hz, 1H)

Example 25

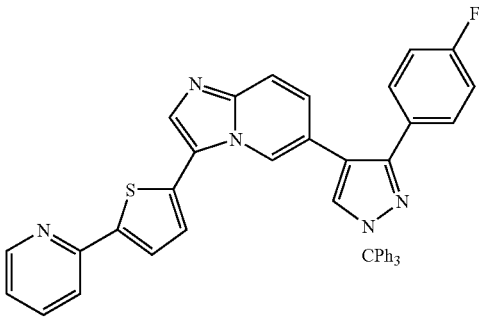

6-[3-(4-fluorophenyl)-1-trityl-1H-4-pyrazolyl]-3-[5-(2-pyridyl)-2-thienyl]imidazo[1,2-a]pyridine 150 mg of 3-(5-bromo-2-thienyl)-6-[3-(4-fluorophenyl)-1-trityl-1H-4-pyrazolyl]imidazo[1,2-a]pyridine obtained in Example 4 and 0.13 mL of 2-(tri-n-butylstannyl)pyridine were reacted in the same manner as in Example 21, to give 137 mg of the title compound as a yellow amorphous.

¹H-NMR (CDCl₃)

δ: 6.97(d, J=4.0 Hz, 1H), 7.01(m, 2H), 7.13(dd, J=9.2, 1.6 Hz, 1H, 7.24(m, 7H), 7.34(m, 8H), 7.47(m, 3H), 7.53(d, J=4.0 Hz, 1H), 7.60(d, J=9.2 Hz, 1H), 7.64–7.75(m, 3H), 7.79(s, 1H), 8.32(brs, 1H), 8.59(d, J=4.4 Hz, 1H)

Example 26

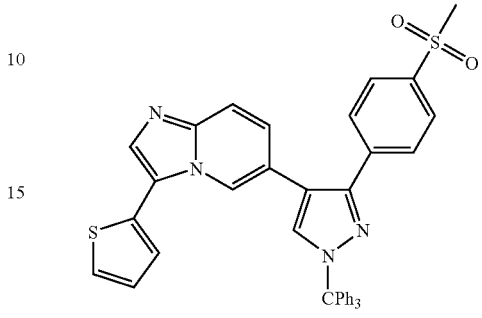

6-[3-(4-(Methylsulfonyl)phenyl]-1-trityl-1H-4-pyrazolyl]-3-(2-thienyl)imidazo[1,2-a]pyridine 155 mg of the title compound was obtained as a pale brown film in the same manner as in Example 21 from 160 mg of 3-iodo-6-{3-[4-(methylsulfonyl)phenyl]-1-trityl-1H-4-pyrazolyl}imidazo[1,2-a]pyridine obtained in Production Example 43 and 153 mg of 2-(tributylstannyl)thiophene.

¹H-NMR (CDCl₃)

δ: 3.10 (s, 3H) 7.01(dd, J=3.6, 0.8 Hz, 1H) 2.12 (dd, J=5.2, 3.6 Hz, 1H) 7.18–7.26 (m, 7H) 7.33–7.38 (m, 9H) 7.41(dd, J=5.2, 1.2 Hz, 1H) 7.51 (s, 1H) 7.71(dt, J=8.8, 2.0 Hz, 2H) 7.73 (d, J=9.2 Hz, 1H) 7.74 (s, 1H) 7.88 (dt, J=8.8, 2.0 Hz, 2H) 8.16–8.18 (m,1H)

Example 27

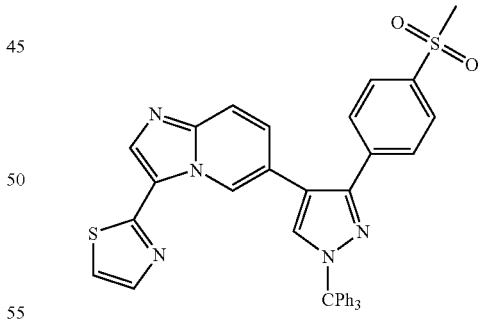

2-(6-{3-[4-(Methylsulfonyl)phenyl]-1-trityl-1H-4-pyrazolyl}imidazo[1,2-a]pyridin-6-yl)-1,3-thiazole 130 mg of the title compound was obtained as colorless crystals (recrystallization solvent: ethyl acetate) in the same manner as in Example 21 from 141 mg of 3-iodo-6-{3-[4-(methylsulfonyl)phenyl]-1-trityl-1H-4-pyrazolyl]imidazo[1,2-a]pyridine obtained in Production Example 43 and 86 mg of 2-(1,1,1-tributylstannyl)-1,3-thiazole.

¹H-NMR (CDCl₃)

δ: 3.00 (s, 3H) 7.20 (dd, J=9.6, 1.6 Hz, 1H) 7.23–7.40 (m, 7H) 7.33–7.41 (m, 9H) 7.56 (s, 1H) 7.67 (d, J=9.6 Hz, 1H) 7.72 (dt, J=8.0, 1.6 Hz, 2H) 7.74 (d, J=2.8 Hz 1H) 7.84 (dt, J=8.0, 1.6 Hz, 2H) 8.12 (s, 1H) 9.59 (dd, J=1.6, 0.4 Hz, 1H)

Example 28

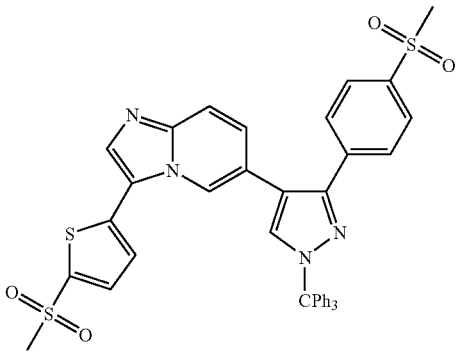

6-{3-[4-(Methylsulfonyl)phenyl]-1-trityl-1H-4-pyrazolyl]-3-[5-(methylsulfonyl)-2-thienyl]imidazo[1,2-a]pyridine 113 mg of 3-[5-(methylsulfanyl)-2-thienyl]-6-{3-[4-(methylsulfonyl)phenyl]-1-trityl-1H-4-pyrazolyl}imidazo-[1,2-a]pyridine was obtained as a pale yellow film by the same reaction as in Example 21 from 177 mg of 3-iodo-6-{3-[4-(methylsulfonyl)phenyl]-1-trityl-1H-4-pyrazolyl}imidazo-[1,2-a]pyridine obtained in Production Example 43 and 126 mg of tributyl[5-(methylsulfanyl)-2-thienyl]stannane (compound in Production Example 46). The product was dissolved in 2 mL solvent mixture of tetrahydrofuran and methanol (1/1), then 0.5 mL water containing 197 mg oxone was added thereto, and the mixture was stirred for 2 hours. The reaction mixture was extracted with ethyl acetate and purified by NH silica gel (hexane/ethyl acetate) to give 98 mg of the title compound as film.

¹H-NMR (CDCl₃)

δ: 3.04 (s, 3H) 3.23 (s, 3H) 7.02 (dd, J=4.0, 0.8 Hz, 1H) 7.21–7.30 (m, 7H) 7.33–7.39 (m, 9H) 7.53 (s, 1H) 7.68–7.73 (m, 4H) 7.85 (s, 1H) 7.88 (dt, J=8.0, 2.0 Hz, 2H) 8.19 (t, J=0.8 Hz, 1H)

Example 29

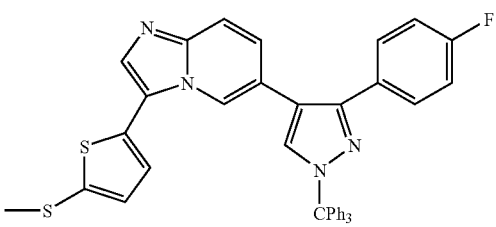

6-[3-(4-Fluorophenyl)-1-trityl-1H-4-pyrazolyl]-3-[5-(methylsulfanyl)-2-thienyl]imidazo[1,2-a]pyridine 736 mg 3-(4-fluorophenyl)-1-trityl-1H-4-pyrazolylboronic acid (compound in Production Example 25), 550 mg 6-bromo-3-[5-(methylsulfanyl)-2-thienyl]imidazo[1,2-a]-pyridine (compound in Production Example 58) and 100 mg tetrakis (triphenylphosphine)palladium were stirred at 80° C. for 3 hours in a solution mixture of 5 mL toluene, 5 mL ethanol and 2.5 mL of 2 N aqueous sodium carbonate under nitrogen atmosphere. The reaction solution was extracted with ethyl acetate, the organic layer was dried over magnesium sulfate, the solvent was removed, and the resulting residue was purified by NH silica gel column chromatography (hexane/ethyl acetate) to give 685 mg of the title compound (pale greenish yellow crystals; recrystallization solvent, ethyl acetate/methanol).

¹H-NMR (CDCl₃)

δ: 2.52 (s, 3H) 6.79 (d, J=3.6 Hz, 1H) 7.01 (tt, J=8.8, 2.0 Hz, 2H) 7.02 (d, J=3.6 Hz, 1H) 7.13 (dd, 9.2, 1.6 Hz, 1H) 7.22–7.28 (m, 6H) 7.31–7.38 (m, 9H) 7.44–7.49 (m, 2H) 7.46 (s, 1H) 7.58 (dd, J=9.2, 0.8 Hz, 1H) 7.68 (s, 1H) 8.16 (dd, J=1.6, 0.8 Hz, 1H)

Example 30

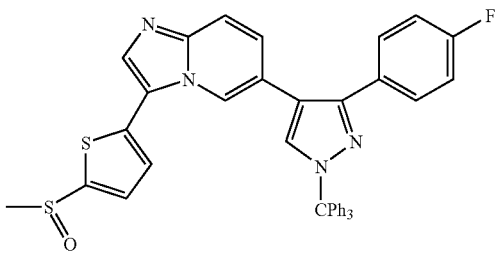

6-[3-[4-(Fluorophenyl)-1-trityl-1H-4-pyrazolyl]-3-[5-(methylsulfinyl)-2-thienyl]imidazo[1,2-a]pyridine 2 mL aqueous solution of 142 mg oxone was added to a solution mixture of 150 mg 6-[3-(4-fluorophenyl)-1-trityl-1H-4-pyrazolyl]-3-[5-(methylsulfanyl)-2-thienyl]imidazo[1,2-a]-pyridine obtained in Example 29, 3 mL tetrahydrofuran and 3 mL methanol, and the mixture was stirred for 30 minutes. The reaction mixture was treated with an aqueous sodium thiosulfate solution, extracted with ethyl acetate, and purified by NH silica gel column chromatography (hexane/ethyl acetate), to give 173 mg of the title compound as a colorless solid.

¹H-NMR (CDCl₃)

δ: 2.96 (s, 3H) 6.91 (d, J=3.6 Hz, 1H) 6.99–7.07 (m, 2H) 7.19 (dd, J=9.2, 1.2 Hz, 1H) 7.22–7.28 (m, 6H) 7.32–7.39 (m, 9H) 7.43–7.50 (m, 2H) 7.44 (d, J=3.6 Hz, 1H) 7.48 (s, 1H) 7.63 (dd, J=9.2, 0.4 Hz, 1H) 7.78 (s, 1H) 8.16 (dd, J=1.2, 0.4 Hz, 1H)

Example 31

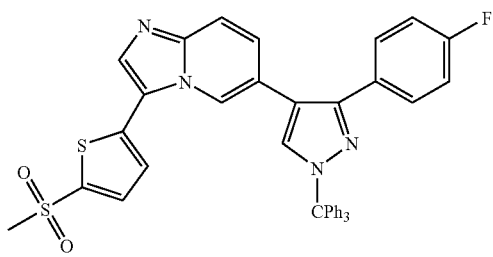

6-[3-[4-(Fluorophenyl)-1-trityl-1H-4-pyrazolyl]-3-[5-(methylsulfonyl)-2-thienyl]imidazo[1,2-a]pyridine 490 mg of the title compound (colorless crystals; recrystallization solvent, ethyl acetate/methanol) was obtained by the same reaction as in Example 30 from 518 mg 6-[3-(4-fluorophenyl)-1-trityl-1H-4-pyrazolyl]-3-[5-(methylsulfanyl)-2-thienyl]imidazo[1,2-a]pyridine obtained in Example 29 and 1.0 g oxone.

$^1$H-NMR (CDCl$_3$)

δ: 3.22 (s, 3H) 6.93 (d, J=4.0 Hz, 1H) 7.00–7.07 (m, 2H) 7.21 7.27 (m, 7H) 7.30–7.38 (m, 9H) 7.43–7.48 (m, 2H) 7.50 (s, 1H) 7.65 (d, J=4.0 Hz, 1H) 7.67 (dd, J=9.2, 0.8 Hz, 1H) 7.82 (s, 1H) 8.17 (dd, J=1.6, 0.8 Hz, 1H)

Example 32

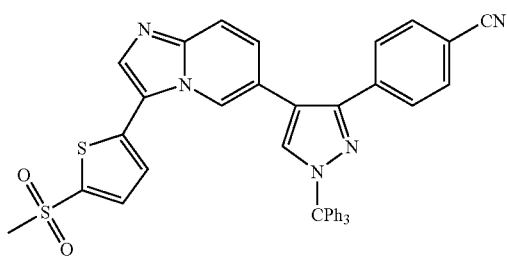

4-(4-{3-[5-(Methylsulfonyl)-2-thienyl]imidazo[1,2-a]-pyridin-6-yl}-1-trityl-1H-3-pyrazolyl)benzonitrile 110 mg of the title compound (film) was obtained in the same manner as in Example 29 from 85 mg of 3-(4-cyanophenyl)-1-trityl-1H-4-pyrazolylboronic acid (compound in Production Example 32) and 53.6 mg of 6-bromo-3-[5-(methylsulfonyl)-2-thienyl]imidazo[1,2-a]pyridine (compound in Production Example 59).

$^1$H-NMR (CDCl$_3$)

δ: 3.24 (s, 3H) 7.09 (d, J=3.6 Hz, 1H) 7.20–7.26 (m, 7H) 7.33–7.39 (m, 9H) 7.50 (s, 1H) 7.61 (s, 4H) 7.70 (d, J=3.2 Hz, 1H) 7.71 (d, J=9.2 Hz, 1H) 7.86 (s, 1H) 8.20 (s, 1H)

Example 33

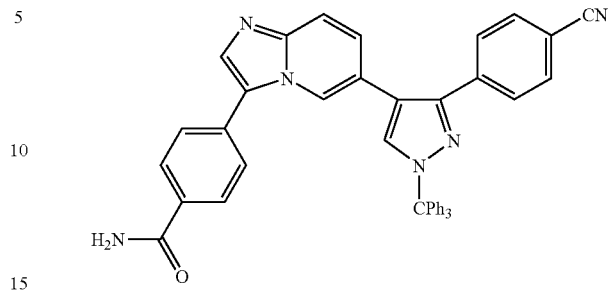

4-{6-[3-(4-Cyanophenyl)-1-trityl-1H-4-pyrazolyl]imidazo-[1,2-a]pyridin-3-yl)benzamide 103 mg of the title compound (film) was obtained in the same manner as in Example 29 from 95 mg of 3-(4-cyanophenyl)-1-trityl-1H-4-pyrazolylboronic acid (compound in Production Example 32) and 48 mg of 4-(6-bromoimidazo[1,2-a]-pyridin-3-yl)benzamide (compound in Production Example 52).

$^1$H-NMR (CDCl$_3$)

δ: 7.14 (dd, J=9.2, 1.6 Hz, 1H) 7.18–7.24 (m, 6H) 7.31–7.38 (m, 9H) 7.44 (dt, J=8.4, 2.0 Hz, 2H) 7.48 (s, 1H) 7.59–7.66 (m, 4H) 7.67 (dd, J=9.2, 0.8 Hz, 1H) 7.86 (dt, J=8.4, 2.0 Hz, 2H) 8.08 (dd, 1.6, 0.8 Hz, 1H)

Example 34

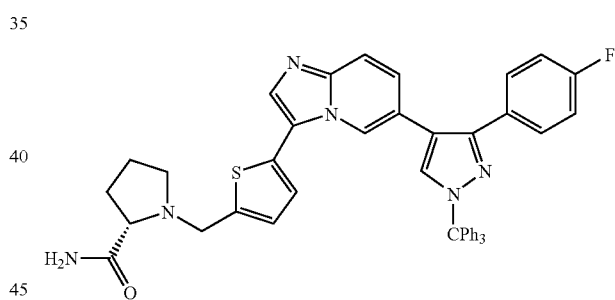

(2S)-1-[(5-{6-[3-(4-Fluorophenyl)-1-trityl-1H-4-pyrazolyl]imidazo[1,2-a]pyridin-3-yl}-2-thienyl)methyl]-tetrahydro-1H-2-pyrrole carboxyamide 132 mg of the title compound (film) was obtained in the same manner as in Example 29 from 81 mg of 3-(4-fluorophenyl)-1-trityl-1H-4-pyrazolylboronic acid (compound in Production Example 25) and 61 mg of (2S)-1-{[5-(6-bromoimidazo[1,2-a]pyridin-3-yl)-2-thienyl]methyl}-tetrahydro-1H-2-pyrrole carboxyamide (compound in Production Example 61).

$^1$H-NMR (CDCl$_3$)

δ: 1.78–1.89 (m, 2H) 1.92–2.01(m, 1H) 2.18–2.31 (m, 1H) 2.42–2.50 (m, 1H) 3.15–3.20 (m, 1H) 3.24 (dd, J=10.0, 5.2 Hz, 1H) 3.77 (d, J=14.4 Hz, 1H) 4.04 (d, J=14.4 Hz, 1H) 5.32 (d, J=5.2 Hz, 1H) 6.75 (d, J=3.2 Hz, 1H) 6.87 (d, J=3.2 Hz, 1H) 6.97–7.04 (m, 2H) 7.14 (d, J=9.2 Hz, 1H) 7.14–7.20 (m, 1H) 7.20–7.27 (m, 6H) 7.31–7.38 (m, 9H) 7.44–7.49 (m, 2H) 7.47 (s, 1H) 7.61 (d, J=9.2 Hz, 1H) 7.68 (s, 1H) 8.15 (s, 1H)

Example 35

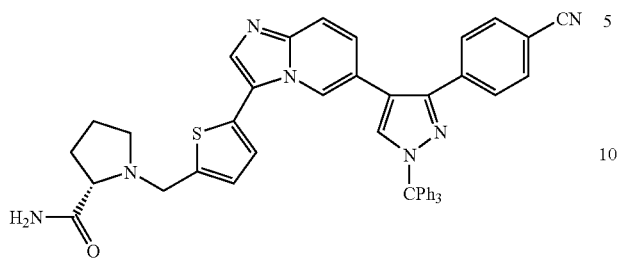

(2S)-1-[(5-{6-[3-(4-Cyanophenyl)-1-trityl-1H-4-pyrazolyl]-imidazo[1,2-a]pyridin-3-yl}-2-thienyl)methyl]tetrahydro-1H-2-pyrrole carboxyamide 254 mg of the title compound (film) was obtained in the same manner as in Example 29 from 186 mg of 3-(4-cyanophenyl)-1-trityl-1H-4-pyrazolylboronic acid (compound in Production Example 32) and 128 mg of (2S)-1-{[5-(6-bromoimidazo-[1,2-a]pyridin-3-yl)-2-thienyl]methyl}tetrahydro-1H-2-pyrrole carboxyamide (compound in Production Example 61).

$^1$H-NMR (CDCl$_3$)

δ: 1.77–1.88 (m, 2H) 1.92–1.21 (m, 1H) 2.20–2.31 (m, 1H) 2.43–2.52 (m, 1H) 3.16–3.22 (m, 1H) 3.25 (dd, J=9.6, 5.2 Hz, 1H) 3.81 (d, J=14.0 Hz, 1H) 4.06 (d, J=14.0 Hz, 1H) 5.31 (d, J=5.2 Hz, 1H) 6.82 (d, J=3.6 Hz, 1H) 6.91 (d, J=3.6 Hz, 1H) 7.11 (dd, J=9.2, 1.6 Hz, 1H) 7.14–7.26 (m, 7H) 7.32–7.48 (m, 9H) 7.49 (s, 1H) 7.56–7.66 (m, 5H) 7.71 (s, 1H) 8.17 (dd, J=1.6, 1.2 Hz, 1H)

Example 36

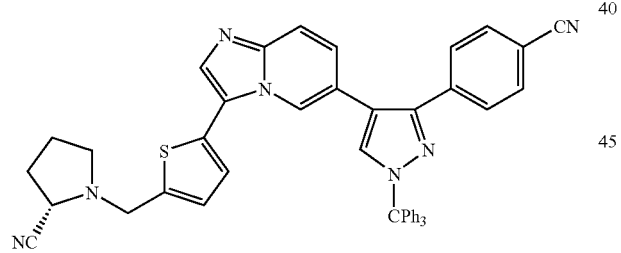

(2S)-1-[(5-{6-[3-(4-Cyanophenyl)-1-trityl-1H-4-pyrazolyl]imidazo[1,2-a]pyridin-3-yl}-2-thienyl)methyl]-tetrahydro-1H-2-pyrrole carbonitrile While 144 mg of (2S)-1-[(5-{6-[3-(4-cyanophenyl)-1-trityl-1H-4-pyrazolyl]imidazo[1,2-a]pyridin-3-yl}-2-thienyl)methyl]tetrahydro-1H-2-pyrrole carboxyamide obtained in Example 35 was cooled in 1 mL tetrahydrofuran under ice-cooling, 0.05 mL pyridine and 0.57 mL trifluoroacetic anhydride were added thereto, and the mixture was stirred for 30 minutes. The solvent was removed, and the residue was purified with an NH silica gel column (hexane/ethyl acetate) to give 116 mg of the title compound (film)

$^1$H-NMR (CDCl$_3$)

δ: 1.88–2.10 (m, 2H) 2.10–2.28 (m, 2H) 2.60–2.70 (m, 1H) 3.01–3.08 (m, 1H) 3.83 (dd, J=7.2, 2.8 Hz, 1H) 3.95 (d, J=14.0 Hz, 1H) 4.07 (d, J=14.0 Hz, 1H) 6.88 (d, J=3.6, 1H) 7.00 (d, J=3.6, 1H) 7.10 (dd, J=9.2, 0.8 Hz, 1H) 7.20–7.27 (m, 6H) 7.31–7.40 (m, 9H) 7.48 (s, 1H) 7.57 (d, J=8.0 Hz, 2H) 7.60–7.65 (m, 3H) 7.71 (s, 1H) 7.80 (t, J=0.8 Hz, 1H)

Example 37

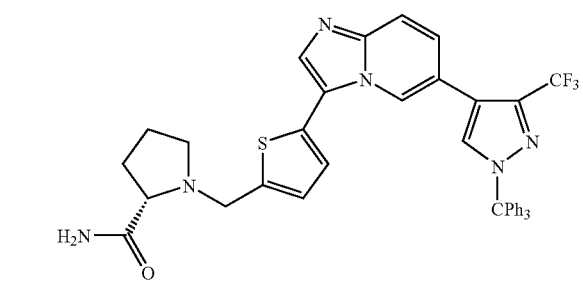

(2S)-1-({5-[6-(3-Trifluoromethyl-1-trityl-1H-4-pyrazolyl)-imidazo[1,2-a]pyridin-3-yl]-2-thienyl}methyl)tetrahydro-1H-2-pyrrole carboxyamide 130 mg of the title compound (film) was obtained in the same manner as in Example 29 from 101 mg of 3-trifluoromethyl-1-trityl-1H-4-pyrazolylboronic acid (compound in Production Example 31) and 82 mg of (2S)-1-({5-(6-bromoimidazo[1,2-a]-pyridin-3-yl)-2-thienyl}methyl)tetrahydro-1H-2-pyrrole carboxyamide (compound in Production Example 61).

$^1$H-NMR (CDCl$_3$)

δ: 1.78–1.90 (m, 2H) 1.93–2.03 (m, 1H) 2.21–2.33 (m, 1H) 2.44–2.54 (m, 1H) 3.20–3.32 (m, 2H) 3.84 (d, J=14.0 Hz, 1H) 4.12 (d, J=14.0 Hz, 1H) 5.36 (d, J=5.2 Hz, 1H) 7.00 (d, J=3.2 Hz, 1H) 7.12 (d, J=3.2 Hz, 1H) 7.13–7.40 (m, 17H) 7.50 (s, 1H) 7.65 (d, J=9.2 Hz, 1H) 7.74 (s, 1H) 8.51 (s, 1H)

Example 38

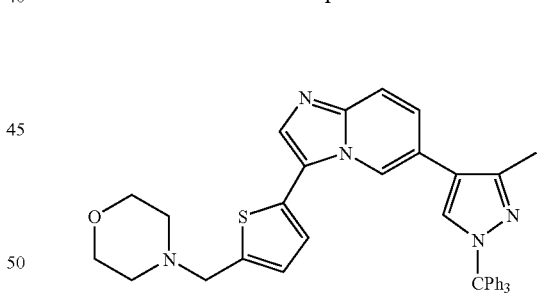

4-({5-[6-(3-Methyl-1-trityl-1H-4-pyrazolyl)imidazo[1,2-a]pyridin-3-yl]-2-thienyl}methyl)morpholine 190 mg of the title compound (film) was obtained in the same manner as in Example 29 from 150 mg of 3-methyl-1-trityl-1H-4-pyrazolylboronic acid (compound in Production Example 30) and 113 mg of 4-{[5-(6-bromoimidazo[1,2-a]pyridin-3-yl)-2-thienyl]methyl}morpholine (compound in Production Example 62).

$^1$H-NMR (CDCl$_3$)

δ: 2.42 (s, 3H) 2.59 (br. s, 4H) 3.72–3.82 (m, 6H) 7.20–7.40 (m, 1H) 7.13 (d, J=3.6 Hz, 1H) 7.17–7.37 (m, 16H) 7.35 (br. s, 1H) 7.63 (dd, J=9.2 0.8 Hz, 1H) 7.73 (s, 1H) 7.83 (dd, J=1.6, 0.8 Hz, 1H)

Example 39

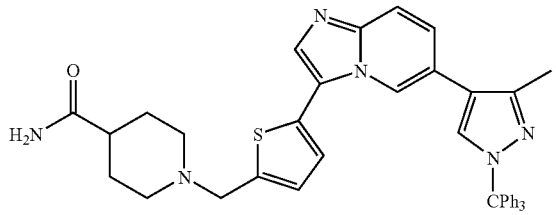

1-({5-[6-(3-Methyl-1-trityl-1H-4-pyrazolyl)imidazo[1,2-a]-pyridin-3-yl]-2-thienyl}methyl)-4-piperidine carboxyamide 225 mg of the title compound (film) was obtained in the same manner as in Example 29 from 184 mg of 4-{[5-(6-bromoimidazo[1,2-a]pyridin-3-yl)-2-thienyl]methyl}-morpholine (compound in Production Example 62) and 161 mg of 1-{[5-(6-bromoimidazo[1,2-a]pyridin-3-yl)-2-thienyl]-methyl}-4-piperidine carboxyamide obtained by the same reaction as in Production Example 61 from 5-(6-bromoimidazo[1,2-a]-pyridin-3-yl)-2-thiophene carboxy aldehyde and isonipecotic acid amide.

$^1$H-NMR (CDCl$_3$)

δ: 1.73–1.86 (m, 2H) 1.86–1.97 (m, 2H) 2.06–2.24 (m, 3H) 2.42 (s, 3H) 3.02–3.10 (m, 2H) 3.78 (s, 2H) 5.27 (br.s, 1H) 5.48 (br. s, 1H) 6.96–7.02 (m, 1H) 7.10 (d, J=3.6 Hz, 1H) 7.17 (dd, J=8.8, 2.0 Hz, 1H) 7.17–7.24 (m, 6H) 7.30–7.35 (m, 9H) 7.44 (s, 1H) 7.61 (dd, J=8.8, 0.8 Hz, 1H) 7.72 (s, 1H) 8.42 (dd, J=1.6, 0.8 Hz, 1H)

Example 40

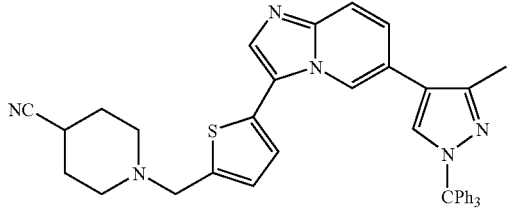

1-({5-[6-(3-Methyl-1-trityl-1H-4-pyrazolyl)imidazo[1,2-a]-pyridin-3-yl]-2-thienyl}methyl)-4-piperidine carbonitrile 100 mg of the title compound (colorless crystals; recrystallization solvent, ethyl acetate-diethyl ether) was obtained by the same reaction as in Example 36 from 125 mg of 1-({5-[6-(3-methyl-1-trityl-1H-4-pyrazolyl)imidazo[1,2-a]-pyridin-3-yl]-2-thienyl}methyl)-4-piperidine carboxyamide obtained in Example 39.

$^1$H-NMR (CDCl$_3$)

δ: 1.84–2.06 (m, 4H) 2.35–2.60 (m, 2H) 2.42 (s, 3H) 2.64–2.80 (m, 3H) 3.78 (s, 2H) 6.96–7.03 (m, 1H) 7.12 (d, J=3.6 Hz, 1H) 7.18 (dd, J=9.2, 1.6 Hz, 1H) 7.18–7.23 (m, 6H) 7.30–7.38 (m, 9H) 7.44 (s, 1H) 7.63 (d, J=9.2 Hz, 1H) 7.72 (s, 1H) 8.42 (dd, J=1.6, 0.4 Hz, 1H)

Example 41

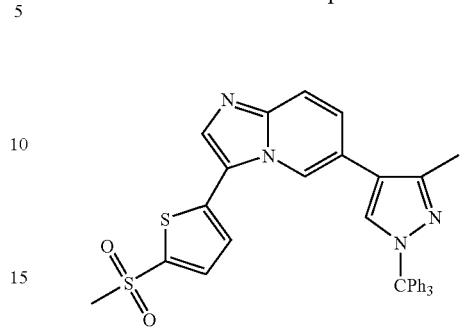

6-(3-Methyl-1-trityl-1H-4-pyrazolyl)-3-[5-(methylsulfonyl)-2-thienyl]imidazo[1,2-a]pyridine 86 mg of the title compound (film) was obtained in the same manner as in Example 29 from 69 mg of 3-methyl-1-trityl-1H-4-pyrazolylboronic acid (compound in Production Example 30) and 54 mg of 6-bromo-3-[5-(methylsulfonyl)-2-thienyl]imidazo-[1,2-a]pyridine (compound in Production Example 59).

$^1$H-NMR (CDCl$_3$)

δ: 2.43 (s, 3H) 3.26 (s, 3H) 6.80–7.40 (m, 17H) 7.45 (s, 1H) 7.73 (d, J=9.2 Hz, 1H) 7.79 (d, J=3.6 Hz, 1H) 7.87 (s, 1H) 8.38 (t, J=0.8 Hz, 1H)

Example 42

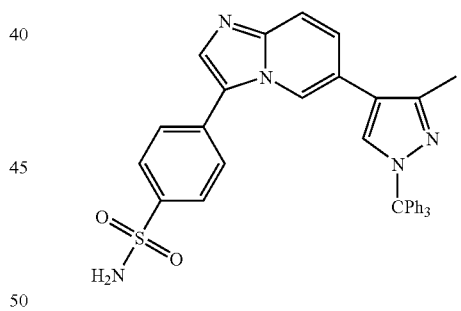

4-[6-(3-Methyl-1-trityl-1H-4-pyrazolyl)imidazo[1,2-a]-pyridin-3-yl]-1-benzene sulfonamide 86 mg of the title compound (film) was obtained in the same manner as in Example 29 from 69 mg of 3-methyl-1-trityl-1H-4-pyrazolylboronic acid (compound in Production Example 30) and 52.8 mg of 4-(6-bromoimidazo[1,2-a]pyridin-3-yl)-1-benzene sulfonamide (compound in Production Example 53).

$^1$H-NMR (DMSO-d$_6$)

δ: 2.35 (s, 3H) 7.12–7.16 (m, 6H) 7.32–7.41 (m, 9H) 7.43 (dd, J=9.2, 1.6 Hz, 1H) 7.46 (s, 2H) 7.67 (dd, J=9.2, 0.8 Hz, 1H) 7.74 (s, 1H) 7.89 (s, 1H) 7.92–7.98 (m, 4H) 8.57 (dd, J=1.6, 0.8 Hz, 1H)

Example 43

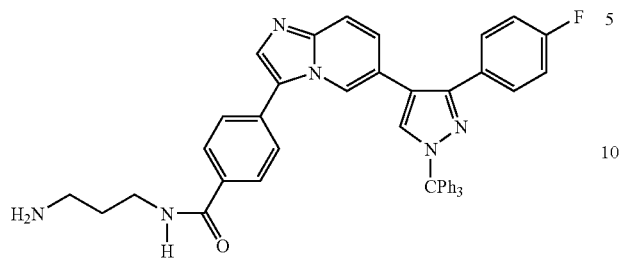

N1-(3-Aminopropyl)-4-{6-[3-(4-fluorophenyl)-1-trityl-1H-4-pyrazolyl]imidazo[1,2-a]pyridin-3-yl}benzamide 400 mg of the title compound (film) was obtained in the same manner as in Example 29 from 302 mg of 3-(4-fluorophenyl)-1-trityl-1H-4-pyrazolylboronic acid (compound in Production Example 25) and 210 mg of N-1-(3-aminopropyl)-4-(6-bromoimidazo[1,2-a]pyridin-3-yl) benzamide (compound in Production Example 55).

$^1$H-NMR (CDCl$_3$)

δ: 1.79 (quint, J=6.0 Hz, 2H) 2.99 (t, J=6.0 Hz, 2H) 3.64 (q, J=6.0 Hz, 2H) 7.01–7.08 (m, 2H) 7.14 (dd, J=9.2, 1.6 Hz, 1H) 7.20–7.25 (m, 6H) 7.31–7.36 (m, 11H) 7.44 (s, 1H) 7.45–7.50 (m, 2H) 7.61 (dd, J=9.2, 0.8 Hz, 1H) 7.70 (s, 1H) 7.80 (d, J=8.4 Hz, 2H) 8.05 (t, J=6.0 Hz, 1H) 8.09(t, J=1.6 Hz, 1H)

Example 44

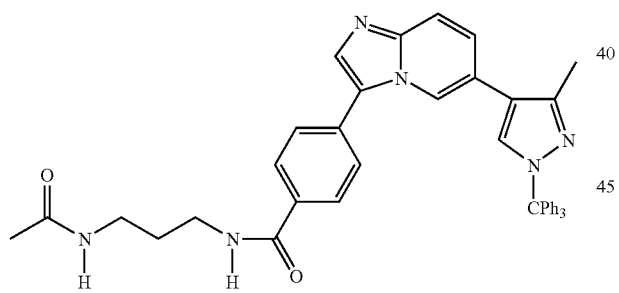

N1-[3-(Acetylamino)propyl]-4-[6-(3-methyl-1-trityl-1H-4-pyrazolyl)imidazo[1,2-a]pyridin-3-yl]benzamide 65 mg of the title compound (film) was obtained by the same reaction as in Example 29 from 43.8 mg of 3-methyl-1-trityl-1H-4-pyrazolylboronic acid (compound in Production Example 30) and 38 mg of N1-[3-(acetylamino)propyl]-4-(6-imidazo[1,2-a]pyridin-3-yl)benzamide (compound in Production Example 56).

$^1$H-NMR (CDCl$_3$)

δ: 1.72–1.79 (m, 2H) 2.07 (s, 3H) 2.38 (s, 3H) 3.41 (q, J=6.0 Hz, 2H) 3.53(q, J=6.0 Hz, 2H) 6.05 (t, J=6.0 Hz, 1H) 7.16–7.23 (m, 6H) 7.29–7.35 (m, 10H) 7.40 (s, 1H) 7.56 (t, J=6.0 Hz, 1H) 7.65 (d, J=9.6 Hz, 1H) 7.67 (dt, J=8.4, 2.0 Hz, 2H) 7.74 (s, 1H) 8.40 (dd, J=8.4, 2.0 Hz, 2H) 8.34 (s, 1H)

Example 45

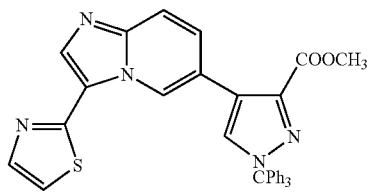

Methyl 4-[3-(1,3-thiazol-2-yl)imidazo[1,2-a]pyridin-6-yl]-1-trityl-1H-3-pyrazole carboxylate A solution of 223 mg methyl 4-bromo-1-trityl-1H-3-pyrazole carboxylate obtained in Production Example 24, 147 mg potassium acetate, 140 mg bis(pinacolate)diboron, and 20 mg 1,1'-[bis(diphenylphosphino)-ferrocene]dichloropalladium (II) in 3 mL dimethyl sulfoxide was heated at 80° C. for 12 hours under nitrogen atmosphere. Water was added to the reaction solution which was then extracted with diethyl ether, and the solvent was removed, whereby 250 mg residue containing methyl 4-(4,4,5,5-tetramethyl-1,3,2-dioxaborolan-2-yl)-1-trityl-1H-pyrazole carboxylate were obtained. This product, together with 110 mg 2-(6-bromoimidazo[1,2-a]pyridin-3-yl)-1,3-thiazole obtained in Production Example 57, 160 mg tripotassium phosphate, and 23 mg tetrakis(triphenylphosphine)palladium, was stirred in 6 mL N,N-dimethylformamide at 90° C. for 2 hours under nitrogen atmosphere. The solvent was removed, and the residue was purified by NH silica gel column chromatography (hexane/ethyl acetate) and recrystallized from ethyl acetate/diethyl ether to give 118 mg of the title compound (pale yellow crystals).

$^1$H-NMR (CDCl$_3$)

δ: 3.81 (s, 1H), 7.18–7.25 (m, 6H), 7.26 (d, J=3.2 Hz, 1H), 7.33–7.39 (m, 9H), 7.41 (dd, J=9.2, 1.2 Hz, 1H), 7.49 (s, 1H), 7.68 (d, J=9.2, 1H), 7.84 (d, J=3.2 Hz, 1H), 8.13 (s, 1H), 9.74–9.76 (m, 1H)

Example 46

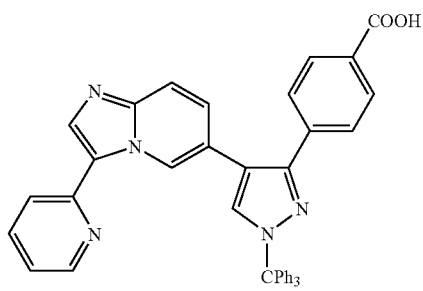

4-{4-[3-(2-Pyridyl)imidazo[1,2-a]pyridin-6-yl]-1-trityl-1H-3-pyrazolyl} benzoic acid 430 mg 6-bromo-3-(2-pyridyl)imidazo[1,2-a]pyridine obtained in Production Example 63, 1.07 g of the mixture of methyl 4-[4-(4,4,5,5-trimethyl-1,3,2-dioxaborolan-2-yl)-1-trityl-1H-3-pyrazolyl] benzoate and ethyl 4-[4-(4,4,5,5-trimethyl-1,3,2-dioxaborolan-2-yl)-1-trityl-1H-3-pyrazolyl] benzoate, and 91 mg tetrakis(triphenylphosphine)palladium were reacted in the same manner as in Example 10, and to the resulting ester were added 2.2 mL of 1 N aqueous sodium hydroxide and ethanol, and the mixture was stirred overnight at room temperature. Ethyl acetate, an aqueous saturated ammonium chloride solution, and water were added to the reaction solution, and the organic layer was separated, washed with brine and dried over anhydrous sodium sulfate. The drying agent was filtered off, the filtrate was evaporated, and the residue was recrystallized from methanol/dichloromethane/diisopropyl ether, to give 219 mg of the title compound as white crystals.

$^1$H-NMR (DMSO-$d_6$)

δ: 7.20(m, 7H), 7.37(m, 10H), 7.56(d, J=8.0 Hz, 2H), 7.65(d, J=9.6 Hz, 1H), 7.75(s, 1H), 7.80 (td, J=8.0, 2.0 Hz, 1H), 7.88(d, J=8.0 Hz, 2H), 7.92(d, J=8.0 Hz, 1H), 8.23(m, 1H), 8.35(s, 1H), 9.79(brs, 1H)

Example 47

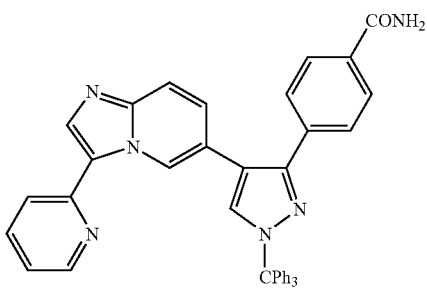

4-{4-[3-(2-Pyridyl)imidazo[1,2-a]pyridin-6-yl]-1-trityl-1H-3-pyrazolyl} benzamide 125 mg benzotriazol-1-yloxytripyrrolidinophosphonium hexafluorophosphate, 1-hydroxy-1H-benzotriazole monohydrate, 83 mg diisopropylethylamine, and 18 mg ammonium chloride were added in this order to a mixture of 100 mg 4-{4-[3-(2-pyridyl)imidazo[1,2-a]pyridin-6-yl]-1-trityl-1H-3-pyrazolyl} benzoic acid obtained in Example 46 and 3 mL N,N-dimethylformamide, and the mixture was stirred at room temperature for 2 hour. Ethyl acetate and water were added to the reaction solution, the organic layer was separated, the solvent was evaporated, and the residue was purified by NH silica gel column chromatography (hexane/ethyl acetate) to give 114 mg of the title compound as a colorless amorphous.

$^1$H-NMR (CDCl$_3$)

δ: 7.10(ddd, J=4.8, 2.0, 2.0 Hz, 1H), 7.15(dd, J=9.6, 1.6 Hz, 1H), 7.27(m, 7H), 7.35(m, 8H), 7.52(s, 1H), 7.61(m, 3H), 7.68(m, 4H), 8.10(s, 1H), 8.38(m, 1H), 9.82(dd, J=1.6, 0.8 Hz, 1H)

Example 48

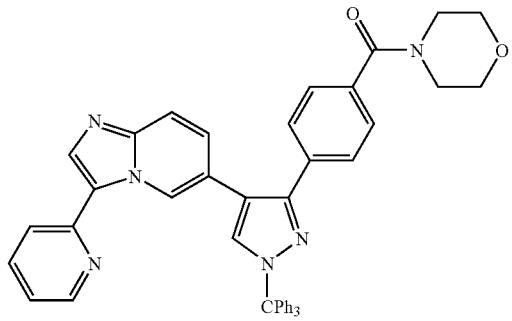

Morpholino(4-{4-[3-(2-pyridyl)imidazo[1,2-a]pyridin-6-yl]-1-trityl-1H-3-pyrazolyl}phenyl)methanone 17 mg N-methyl morpholine and 13 mg 1-hydroxy-1H-benzotriazole monohydrate were added in this order at room temperature to a mixture of 50 mg 4-{4-[3-(2-pyridyl)imidazo[1,2-a]pyridin-6-yl]-1-trityl-1H-3-pyrazolyl} benzoic acid obtained in Example 46, 7.7 mg morpholine, 17 mg 1-ethyl-3-(3-dimethylaminopropyl)-carbodiimide hydrochloride and 8 mL N,N-dimethylformamide. Ethyl acetate and water were added to the reaction solution, and the organic layer was separated, washed twice with water and then with brine and dried over anhydrous sodium sulfate. The drying agent was filtered off, the filtrate was evaporated, and the residue was purified by NH silica gel column chromatography (hexane/ethyl acetate) to give 52 mg of the title compound as a colorless amorphous.

$^1$H-NMR (CDCl$_3$)

δ: 3.63(br, 8H), 7.13(ddd, J=4.8, 1.2,1.2 Hz, 1H), 7.17(dd, J=9.6, 1.6 Hz, 1H), 7.27(m, 7H), 7.32(d, J=8.0 Hz, 2H), 7.35(m, 8H), 7.51(s, 1H), 7.59(d, J=8.0 Hz, 2H), 7.60(d, J=9.6 Hz, 1H), 7.69(m, 2H), 8.10(s, 1H), 8.46(d, J=5.2 Hz, 1H), 9.83(brs, 1H)

Example 49

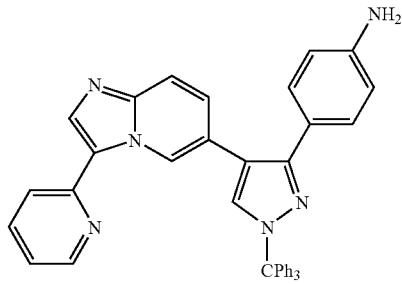

4-{4-[3-(2-Pyridyl)imidazo[1,2-a]pyridin-6-yl]-1-trityl-1H-3-pyrazolyl}aniline

A mixture of 100 mg 4-{4-[3-(2-pyridyl)imidazo[1,2-a]pyridin-6-yl]-1-trityl-1H-3-pyrazolyl}benzoic acid obtained in Example 48, 44 mg diphenyl phosphoryl azide, 23 mg potassium carbonate, and 4 mL N,N-dimethylformamide was stirred at 80° C. for 6 hours. Ethyl acetate and water were added to the reaction solution, and the organic layer was separated, washed twice with water and then with brine, and dried over anhydrous sodium sulfate. The drying agent was filtered off, the filtrate was evaporated, and the residue was purified by NH silica gel column chromatography (ethyl acetate/methanol), to give 30 mg of the title compound as a pale yellow amorphous.

$^1$H-NMR (CDCl$_3$)

δ: 6.59(d, J=8.0 Hz, 2H), 7.12(m, 1H), 7.19(dd, J=9.6, 1.2 Hz, 1H), 7.22~7.38(m, 17H), 7.44(s, 1H), 7.57(d, J=9.2 Hz, 1H), 7.69(m, 2H), 8.09(s, 1H), 8.49(d, J=4.8 Hz, 1H), 9.81(brs, 1H)

Example 50

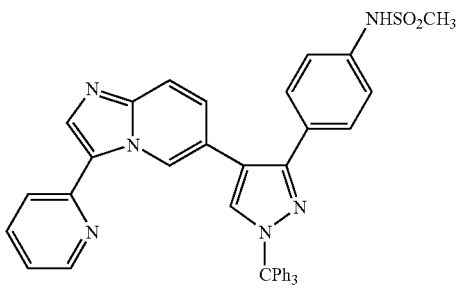

N-(4-{4-[3-(2-Pyridyl)imidazo[1,2-a]pyridin-6-yl]-1-trityl-1H-3-pyrazolyl}phenyl)methane sulfonamide 26 mg 4-{4-[3-(2-pyridyl)imidazo[1,2-a]pyridin-6-yl]-1-trityl-1H-3-pyrazolyl}aniline obtained in Example 49 and 9 µL methyl sulfonyl chloride were reacted in the same manner as in Example 20, to give 14 mg of the title compound as a colorless amorphous.

$^1$H-NMR (CDCl$_3$)

δ: 3.33(s, 3H), 7.12(ddd, J=4.8, 2.0, 2.0 Hz, 1H), 7.24(m, 11H), 7.35(m, 8H), 7.49(s, 1H), 7.64(d, J=9.2 Hz, 1H), 7.69(m, 3H), 8.13(s, 1H), 8.50(m, 1H), 9.80(brs, 1H)

Example 51

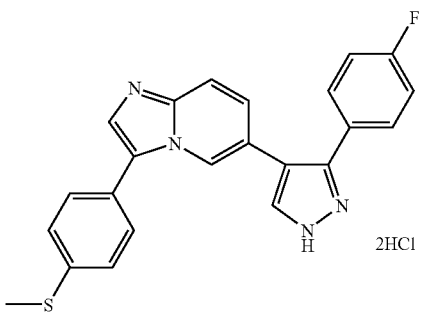

6-[3-(4-Fluorophenyl)-1H-4-pyrazolyl]-3-[4-(methylsulfanyl)phenyl]imidazo[1,2-a]pyridine dihydrochloride A mixture of 136 mg 6-[3-(4-fluorophenyl)-1-trityl-1H-4-pyrazolyl]-3-[4-(methylsulfanyl)phenyl]imidazo[1,2-a]pyridine obtained in Example 1, 3 mL tetrahydrofuran, 3 mL methanol and 4 mL of 5 N hydrochloric acid was left at room temperature for 3 hours. The mixture was washed with 4 mL diethyl ether, and then the aqueous layer was neutralized with 5 N sodium hydroxide, and solid formed by adding water was collected by filtration. The solid were washed with water, dried and suspended in methanol, and 5 N hydrochloric acid/methanol was added thereto to give a transparent solution (pH 1). Colorless crystals formed by adding ether were collected to give 83 mg of the title compound.

$^1$H-NMR (DMSO-d$_6$)

δ: 2.56 (s, 3H) 7.23–7.31 (m, 2H) 7.37 (dt, J=8.4, 2.0 Hz, 2H) 7.50 (dt, 8.0, 2.0 Hz, 2H) 7.49–7.55(m, 2H) 7.92 (dd, J=9.2, 1.6 Hz, 1H) 7.92 (dd, J=9.2, 0.8 Hz, 1H) 8.21 (s, 1H) 8.30 (s, 1H) 8.38 (s, 1H)

MS m/e (ESI) 401 (MH$^+$)

Example 52

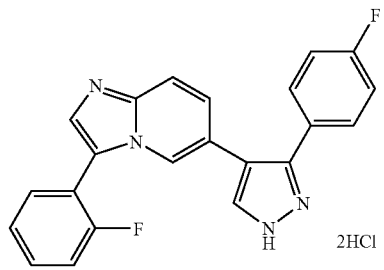

3-(2-Fluorophenyl)-6-[3-(4-fluorophenyl)-1H-4-pyrazolyl]imidazo[1,2-a]pyridine dihydrochloride A mixture of 20 mg 2-fluorophenylboronic acid, 40 mg 6-[3-(4-fluorophenyl)-1-trityl-1H-4-pyrazolyl]-3-iodoimidazo[1,2-a]pyridine (compound in Production Example 39), 2 mg tetrakis(triphenylphosphine)palladium, 1 mL of 2 N aqueous sodium carbonate, 1 mL ethanol and 1 mL toluene was heated at 90° C. for 5 hours. The reaction solution was extracted with 2 mL ethyl acetate, and the solvent was removed in a stream of nitrogen. 1.2 mL tetrahydrofuran, 1.25 mL methanol, and 2 mL of 5 N hydrochloric acid were added to the residue and left at room temperature for 2 hours. The mixture was washed with 4 mL diethyl ether, and the aqueous layer was neutralized with 5 N sodium hydroxide and extracted with ethyl acetate. The solvent was removed, and the residue was dissolved in dimethyl sulfoxide and purified by high performance liquid chromatography (WAKO PAK ODS column; solvent, water/acetonitrile/0.1% trifluoroacetic acid). The product was converted into its corresponding hydrochloride by adding aqueous hydrochloric acid and drying it under reduced pressure, to give 8 mg of the title compound as a colorless solid.

MS m/e (ESI) 373 (MH$^+$)

Example 53

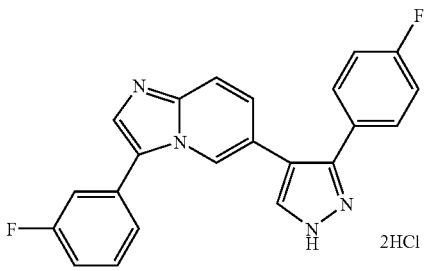

3-(3-Fluorophenyl)-6-[3-(4-fluorophenyl)-1H-4-pyrazolyl]imidazo[1,2-a]pyridine dihydrochloride The title compound (colorless solid, 7 mg) was obtained from 40 mg of the compound in Production Example 39 and 20 mg 2-fluorophenylboronic acid in the same manner as in Example 52.
MS m/e (ESI) 373 (MH$^+$)

Example 54

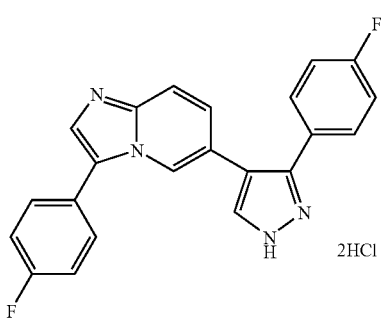

3-(4-Fluorophenyl)-6-[3-(4-fluorophenyl)-1H-4-pyrazolyl]imidazo[1,2-a]pyridine dihydrochloride The title compound (colorless solid, 18 mg) was obtained from 40 mg of the compound in Production Example 39 and 20 mg 4-fluorophenylboronic acid in the same manner as in Example 52.
MS m/e (ESI) 373 (MH$^+$)

Example 55

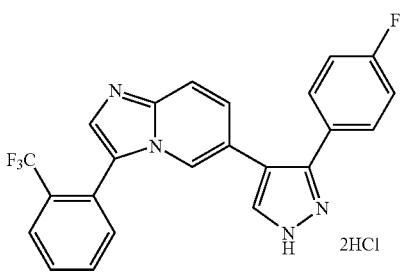

6-[3-(4-Fluorophenyl)-1H-4-pyrazolyl]-3-[2-(trifluoromethyl)phenyl]imidazo[1,2-a]pyridine dihydrochloride The title compound (colorless solid, 12 mg) was obtained from 40 mg of the compound in Production Example 39 and 20 mg 2-(trifluoromethyl)phenylboronic acid in the same manner as in Example 52.
MS m/e (ESI) 423 (MH$^+$)

Example 56

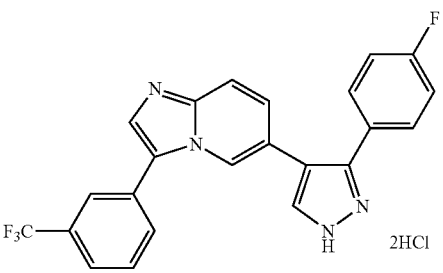

6-[3-(4-Fluorophenyl)-1H-4-pyrazolyl]-3-[3(trifluoromethyl)phenyl]imidazo[1,2-a]pyridine dihydrochloride The title compound (colorless solid, 13 mg) was obtained from 40 mg of the compound in Production Example 39 and 20 mg 3-(trifluoromethyl)phenylboronic acid in the same manner as in Example 52.
MS m/e (ESI) 423 (MH$^+$)

Example 57

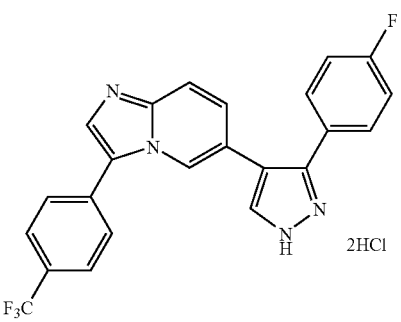

6-[3-(4-Fluorophenyl)-1H-4-pyrazolyl]-3-[4-(trifluoromethyl)phenyl]imidazo[1,2-a]pyridine dihydrochloride The title compound (colorless solid, 13 mg) was obtained from 40 mg of the compound in Production Example 39 and 20 mg 4-(trifluoromethyl) phenylboronic acid in the same manner as in Example 52.
MS m/e (ESI) 423 (MH$^+$)

Example 58

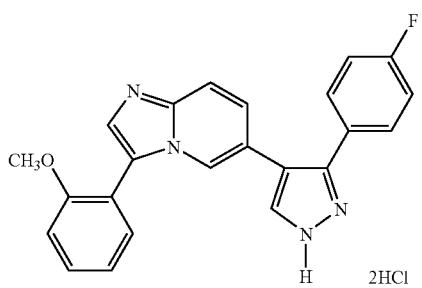

6-[3-(4-Fluorophenyl)-1H-4-pyrazolyl]-3-(2-methoxyphenyl)imidazo[1,2-a]pyridine dihydrochloride The title compound (colorless solid, 13 mg) was obtained from 40 mg of the compound in Production Example 39 and 20 mg 2-methoxyphenylboronic acid in the same manner as in Example 52.

MS m/e (ESI) 385 (MH$^+$)

Example 59

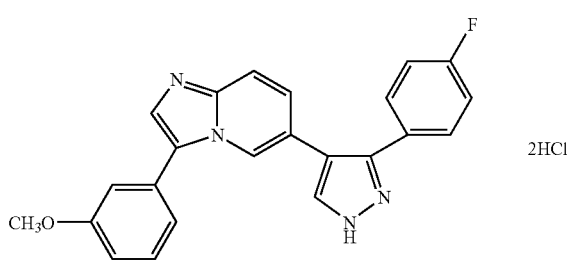

6-[3-(4-Fluorophenyl)-1H-4-pyrazolyl]-3-(3-methoxyphenyl)-imidazo[1,2-a]pyridine dihydrochloride The title compound (colorless solid, 13 mg) was obtained from 40 mg of the compound in Production Example 39 and 20 mg 3-methoxyphenylboronic acid in the same manner as in Example 52.

MS m/e (ESI) 385 (MH$^+$)

Example 60

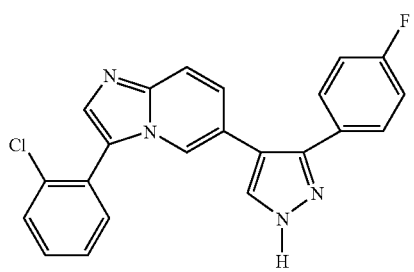

3-(2-Chlorophenyl)-6-[3-(4-fluorophenyl)-1H-4-pyrazolyl]-imidazo[1,2-a]pyridine dihydrochloride The title compound (colorless solid, 14 mg) was obtained from 40 mg of the compound in Production Example 39 and 20 mg 2-chlorophenylboronic acid in the same manner as in Example 52.

MS m/e (ESI) 389 (MH$^+$)

Example 61

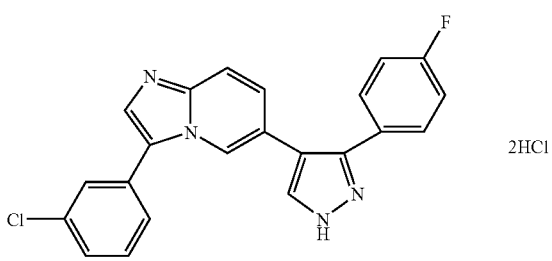

3-(3-Chlorophenyl)-6-[3-(4-fluorophenyl)-1H-4-pyrazolyl]-imidazo[1,2-a]pyridine dihydrochloride The title compound (colorless solid, 16 mg) was obtained from 40 mg of the compound in Production Example 39 and 20 mg 3-chlorophenylboronic acid in the same manner as in Example 52.

MS m/e (ESI) 389 (MH$^+$)

Example 62

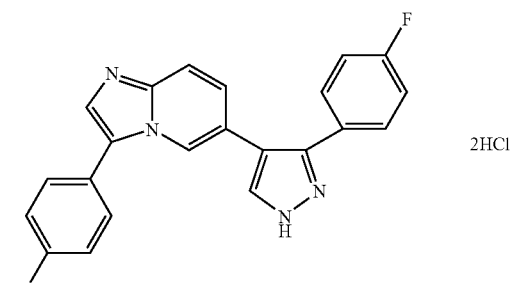

3-(4-Chlorophenyl)-6-[3-(4-fluorophenyl)-1H-4-pyrazolyl]-imidazo[1,2-a]pyridine dihydrochloride The title compound (colorless solid, 15 mg) was obtained from 40 mg of the compound in Production Example 39 and 20 mg 4-chlorophenylboronic acid in the same manner as in Example 52.

MS m/e (ESI) 389 (MH$^+$)

Example 63

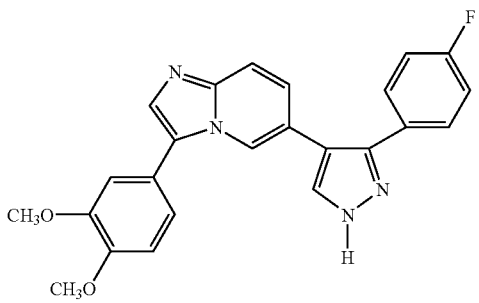

3-(3,4-Dimethoxyphenyl)-6-[3-(4-fluorophenyl)-1H-4-pyrazolyl]imidazo[1,2-a]pyridine dihydrochloride The title compound (colorless solid, 11 mg) was obtained from 40 mg of the compound in Production Example 39 and 20 mg 3,4-dimethoxyphenylboronic acid in the same manner as in Example 52.
MS m/e (ESI) 415 (MH+)

Example 64

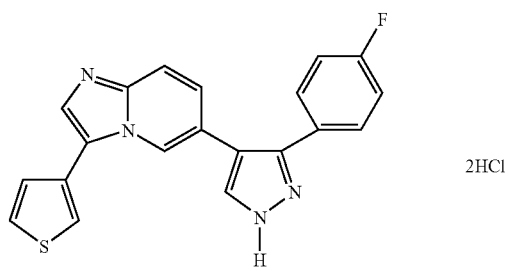

6-[3-(4-Fluorophenyl)-1H-4-pyrazolyl]-3-(3-thienyl)-imidazo[1,2-a]pyridine

The title compound (pale yellow solid, 4 mg) was obtained from 40 mg of the compound in Production Example 39 and 20 mg 3-thienyboronic acid in the same manner as in Example 52.
MS m/e (ESI) 361 (MH+)

Example 65

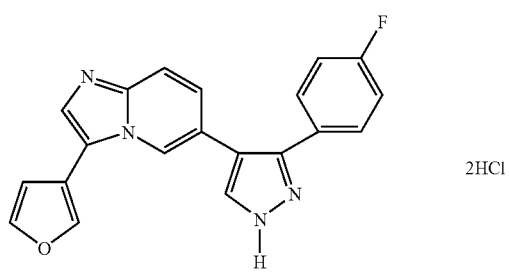

6-[3-(4-Fluorophenyl)-1H-4-pyrazolyl]-3-(3-furyl)imidazo-[1,2-a]pyridine

The title compound (colorless solid, 16 mg) was obtained from 40 mg of the compound in Production Example 39 and 20 mg 3-furylboronic acid in the same manner as in Example 52.
MS m/e (ESI) 361 (MH+)

Example 66

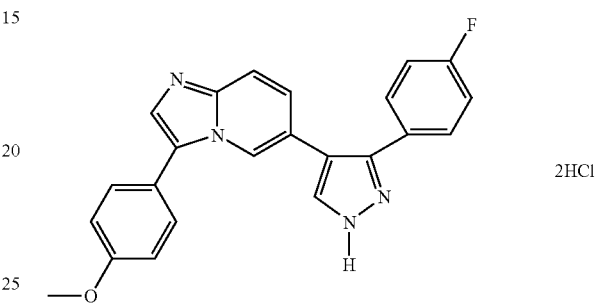

6-[3-(4-Fluorophenyl)-1H-4-pyrazolyl]-3-(4-methoxyphenyl)-imidazo[1,2-a]pyridine dihydrochloride 1.21 g of 6-[3-(4-fluorophenyl)-1-trityl-1H-4-pyrazolyl]-3-(4-methoxyphenyl)imidazo[1,2-a]pyridine was obtained as colorless crystals in the same manner as in Example 29 from 0.8 g of 6-bromo-3-(4-methoxyphenyl)imidazo[1,2-a]pyridine (compound in Production Example 50) and 1.42 g of the compound in Production Example 39. The product was subjected to deprotection of the trityl group and converted into the corresponding hydrochloride by the same method as in Example 51 to give 835 mg of the title compound as colorless crystals.
$^1$H-NMR (DMSO-d$_6$)
δ: 3.83 (s, 3H), 7.04 (dt, J=8.8, 2.4 Hz, 2H), 7.21–7.28 (m, 2H), 7.43–7.51 (m, 4H), 7.91 (dd, J=9.2, 1.6 Hz, 1H), 8.01 (dd, J=9.2, 1.2 Hz, 1H), 8.19 (s, 1H), 8.21 (dd, J=1.6, 1.2 Hz, 1H), 8.29 (s, 1H)
MS m/e (ESI) 385 (MH+)

Example 67

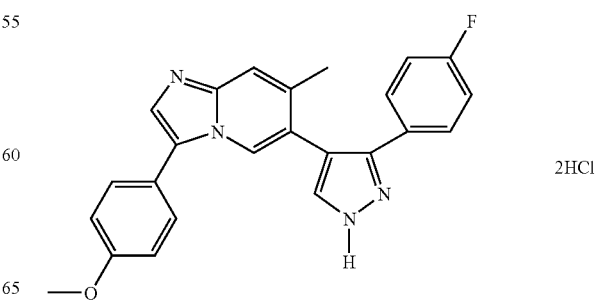

6-[3-(4-Fluorophenyl)-1H-4-pyrazolyl]-3-(4-methoxyphenyl)-7-methylimidazo[1,2-a]pyridine dihydrochloride 150 mg of 6-[3-(4-fluorophenyl)-1-trityl-1H-pyrazolyl]-3-[(4-methoxyphenyl)-7-methylimidazo[1,2-a]-pyridine obtained in Example 2 was dissolved in 1 mL dichloromethane, then 3 mL trifluoroacetic acid was added thereto, and the mixture was left at room temperature for 2 hours. The solvent was concentrated to 1 mL, then the concentrate was neutralized by adding an aqueous sodium carbonate solution, ethyl acetate was added thereto, and the organic layer was dried over magnesium sulfate. solid obtained by removing the solvent was washed with diethyl ether and suspended in methanol. The solution was acidified by adding 4 N hydrochloric acid/ethyl acetate, diethyl ether was added thereto, and the formed colorless crystals were collected to give 88 mg of the title compound.

$^1$H-NMR (DMSO-$d_6$)

δ: 2.16 (s, 3H), 3.84 (s, 3H), 7.11 (dt, J=8.8, 2.4 Hz, 2H), 7.14–7.21 (m, 2H), 7.43–7.50 (m, 2H), 7.56 (dt, J=8.8, 2.4 Hz, 2H), 7.93 (s, 1H), 7.94 (s, 1H), 8.30 (s, 1H), 8.32 (s, 1H)

Example 68

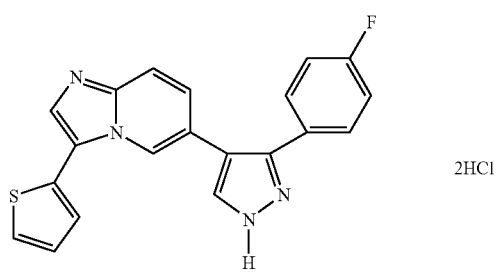

6-[3-(4-Fluorophenyl)-1H-4-pyrazolyl]-3-(2-thienyl)imidazo-[1,2-a]pyridine dihydrochloride 1.62 g of 6-[3-(4-fluorophenyl)-1-trityl-1H-4-pyrazolyl]-3-(2-thienyl)imidazo[1,2-a]pyridine obtained in Example 3 was dissolved in 20 mL tetrahydrofuran and 10 mL methanol, then 18 mL of 5 N hydrochloric acid was added thereto, and the mixture was left at room temperature for 3 hours. The reaction solution was washed with diethyl ether, and the aqueous layer was adjusted to pH 12 by adding 18 mL of 5 N sodium hydroxide and an aqueous sodium carbonate solution. The solution was extracted twice with ethyl acetate, and the organic layer was dried over magnesium sulfate. The drying agent was removed, the solvent was removed, and the residue was recrystallized from methanol/diethyl ether to give 926 mg colorless crystals. The crystals were dissolved in a solution mixture of methanol and tetrahydrofuran (1:1) and acidified by adding 10N hydrochloric acid/methanol. The solvent was removed, and the residue was recrystallized from methanol and diethyl ether to give 1.0 g of the title compound as colorless crystals.

$^1$H-NMR (DMSO-$d_6$)

δ: 8.20–8.28(m, 3H), 7.44(dd, J=3.6, 1.2 Hz, 1H), 7.47–7.54(m, 2H), 7.79(dd, J=9.2, 1.2 Hz, 1H), 7.85(dd, J=5.2 Hz, 0.8 Hz, 1H), 7.96(dd, J=9.2 Hz, 0.8 Hz, 1H), 8.21(s, 1H), 8.36(s, 1H), 8.39(t, J=1.2 Hz, 1H)

Example 69

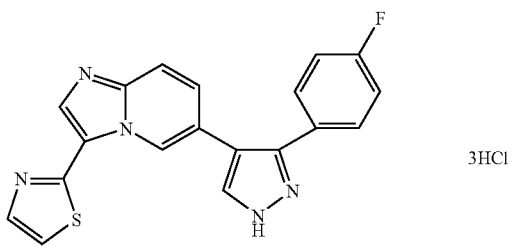

2-{6-[3-(4-Fluorophenyl)-1H-4-pyrazolyl]imidazo[1,2-a]-pyridin-3-yl}-1,3-thiazole trihydrochloride 265 mg of the title compound (colorless solid) was obtained in the same manner as in Example 68 from 250 mg 2-{6-[3-(4-fluorophenyl)-1-trityl-1H-4-pyrazolyl]imidazo[1,2-a]pyridin-3-yl)-1,3-thiazole obtained in Example 21.

$^1$H-NMR (DMSO-$d_6$)

δ: 7.20–7.28(m, 2H), 7.49–7.55(m, 2H), 7.78(d, J=9.6 Hz, 1H), 7.86(d, J=3.2 Hz, 1H), 7.89(d, J=3.2 Hz, 1H), 7.96(d, J=9.6 Hz, 1H), 8.18(s, 1H), 8.78(s, 1H), 9.67(s, 1H)

MS m/e (ESI) 362 (MH$^+$)

Example 70

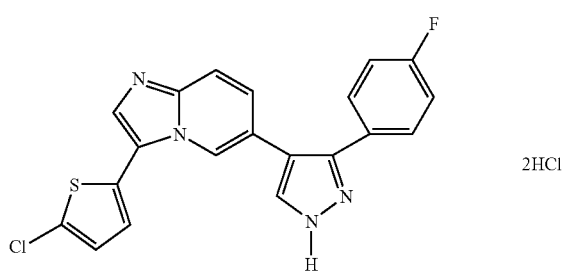

3-(5-Chloro-2-thienyl)-6-[3-(4-fluorophenyl)-1H-4-pyrazolyl]imidazo[1,2-a]pyridine dihydrochloride 22 mg of the title compound was obtained as colorless crystals in the same manner as in Example 68 from 68 mg 3-(5-chloro-2-thienyl)-6-[3-(4-fluorophenyl)-1-trityl-1H-4-pyrazolyl]imidazo[1,2-a]pyridine obtained in Example 5.

$^1$H-NMR (DMSO-$d_6$)

δ: 7.22(m, 2H), 7.29(dd, J=4.0, 1.2 Hz, 1H), 7.37(dd, J=4.0, 1.2 Hz, 1H), 7.47(m, 2H), 7.92(dd, J=9.2, 1.2 Hz, 1H), 8.02(d, J=9.6 Hz, 1H), 8.22(s, 1H), 8.36(d, J=1.2 Hz, 1H), 8.48(s, 1H)

Example 71

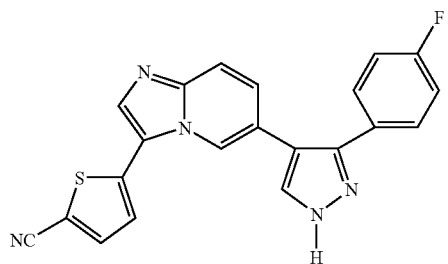

5-{6-[3-(4-Fluorophenyl)-1H-4-pyrazolyl]imidazo[1,2-a]-pyridin-3-yl}-2-thiophene carboxynitrile dihydrochloride 276 mg 3-(5-bromo-2-thienyl)-6-[3-(4-fluorophenyl)-1-trityl-1H-4-pyrazolyl]imidazo[1,2-a]pyridine obtained in Example 4, 118 mg zinc cyanide and 93 mg tetrakis (triphenylphosphine) palladium were stirred at 100° C. for 1.5 hours in xylene. Ethyl acetate was added thereto, insolubles were filtered off, and the solvent was removed. The residue was purified by NH silica gel column chromatography (hexane/ethyl acetate), to give 290 mg 5-(6-[3-(4-fluorophenyl)-1-trityl-1H-4-pyrazolyl]imidazo[1,2-a]pyridin-3-yl}-2-thiophene carboxynitrile (film). This product was subjected to deprotection of the trityl group and converted into the corresponding hydrochloride by the same method as in Example 68, to give 121 mg of the title compound (colorless crystals; recrystallization solvent, methanol).

$^1$H-NMR (DMSO-$d_6$)

δ: 7.21–7.28 (m, 2H), 7.47–7.54 (m, 2H), 7.64 (d, J=4.0 Hz, 1H), 7.70 (d, J=9.2 Hz, 1H), 7.92 (d, J=9.2 Hz, 1H) 8.10 (d, J=4.0 Hz, 1H), 8.19 (s, 1H), 8.41 (s, 1H), 8.44–8.47 (m, 1H)

Example 72

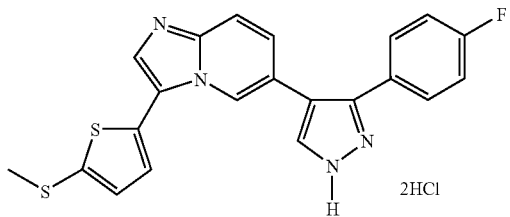

6-[3-(4-Fluorophenyl)-1H-4-pyrazolyl]-3-[5-(methylsulfanyl)-2-thienyl)]imidazo[1,2-a]pyridine dihydrochloride 87 mg of the title compound was obtained as pale greenish yellow crystals in the same manner as in Example 68 from 167 mg 6-[3-(4-fluorophenyl)-1-trityl-1H-4-pyrazolyl]-3-[5-(methylsulfanyl)-2-thienyl)]imidazo[1,2-a]pyridine obtained in Example 29.

$^1$H-NMR (DMSO-$d_6$)

δ: 2.59 (s, 3H), 7.21 (d, 4.0 Hz, 1H), 7.21–7.28 (m, 2H), 7.37 (d, J=4.0 Hz, 1H), 7.47–7.54 (m, 2H), 7.84 (dd, J=9.2, 1.2,Hz, 1H), 7.98 (d, J=9.2 Hz, 1H), 8.22 (s, 1H), 8.39 (s, 1H), 8.40 (s, 1H)

MS m/e (ESI) 407 (MH$^+$)

Example 73

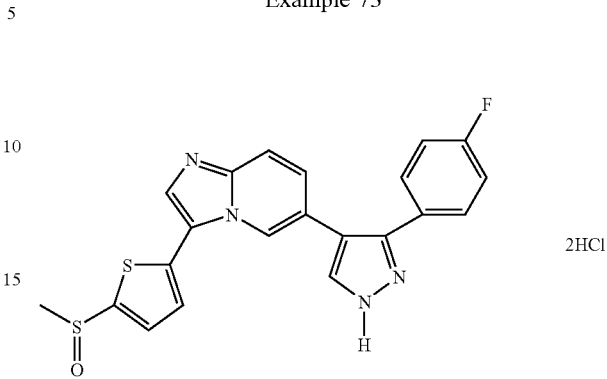

6-[3-(4-Fluorophenyl)-1H-4-pyrazolyl]-3-[5-(methylsulfinyl)-2-thienyl)]imidazo[1,2-a]pyridine dihydrochloride 77 mg of the title compound was obtained as pale brown crystals in the same manner as in Example 68 from 170 mg 6-[3-[4-(fluorophenyl)-1-trityl-1H-4-pyrazolyl]-3-[5-(methylsulfinyl)-2-thienyl)]imidazo[1,2-a]pyridine obtained in Example 30.

$^1$H-NMR (DMSO-$d_6$)

δ: 2.98 (s, 3H), 7.18–7.27 (m, 2H), 7.46–7.53 (m, 2H), 7.51(d, J=3.6 Hz, 1H), 7.65 (d, J=3.6 Hz, 1H), 7.70 (d, J=9.6 Hz, 1H), 7.92 (d, J=9.6 Hz, 1H), 8.17 (s, 1H), 8.38 (s, 1H), 8.44 (s, 1H)

Example 74

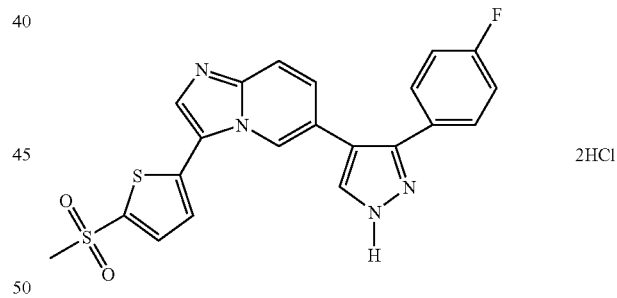

6-[3-(4-Fluorophenyl)-1H-4-pyrazolyl]-3-[5-(methylsulfonyl)-2-thienyl)]imidazo[1,2-a]pyridine dihydrochloride 208 mg of the title compound was obtained as colorless crystals (recrystallization solvent: acetonitrile/diethyl ether) in the same manner as in Example 68 from 490 mg 6-[3-[4-(fluorophenyl)-1-trityl-1H-4-pyrazolyl]-3-[5-(methylsulfonyl)-2-thienyl)]imidazo[1,2-a]pyridine obtained in Example 31.

$^1$H-NMR (DMSO-$d_6$)

δ: 3.43 (s, 3H), 7.21–7.28 (m, 2H), 7.48–7.54 (m, 2H), 7.60 (d, J=3.6 Hz, 1H), 7.63 (dd, J=8.8, 1.6 Hz, 1H), 7.90 (d, J=3.6 Hz, 1H), 7.90 (dd, J=8.8, 0.8 Hz, 1H), 8.17 (s, 1H), 8.38 (s, 1H), 8.50 (dd, J=1.6, 0.8 Hz, 1H)

MS m/e (ESI) 439 (MH$^+$)

Example 75

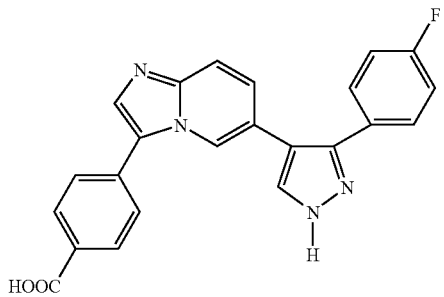

4-{6-[3-(4-Fluorophenyl)-1H-4-pyrazolyl]imidazo[1,2-a]-pyridin-3-yl}benzoate dihydrochloride 5 mg of the title compound was obtained as pale green scrystals in the same manner as in Example 68 from 25 mg 4-{6-[3-(4-fluorophenyl)-1-trityl-1H-4-pyrazolyl]imidazo-[1,2-a]-pyridin-3-yl}benzoic acid obtained in Example 6.

¹H-NMR (DMSO-d₆)

δ: 7.23(d, J=8.4 Hz, 2H), 7.49(m, 2H), 7.69(d, J=7.6 Hz, 2H), 7.89(d, J=9.6 Hz, 1H), 8.03(m, 3H), 8.19(s, 1H), 8.40(s, 1H), 8.47(s, 1H)

Example 76

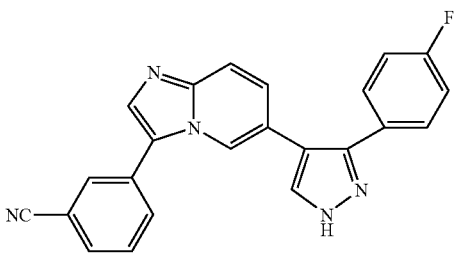

3-{6-[3-(4-Fluorophenyl)-1H-4-pyrazolyl]imidazo[1,2-a]-pyridin-3-yl}benzonitrile dihydrochloride 46 mg 3-cyanophenylboronic acid and 161 mg 6-[3-(4-fluorophenyl)-1-trityl-1H-4-pyrazolyl]-3-iodoimidazo[1,2-a]pyridine (compound in Production Example 39) were reacted in the same manner as in Example 3, to give 136 mg 3-{6-[3-(4-fluorophenyl)-1-trityl-1H-4-pyrazolyl]imidazo[1,2-a]pyridin-3-yl} benzonitrile as colorless crystals. This product was subjected to deprotection of the trityl group and converted into the corresponding hydrochloride by the same method as in Example 68, to give 90 mg of the title compound as colorless crystals.

¹H-NMR (DMSO-d₆)

δ: 7.18–7.26 (m, 2H), 7.48–7.54 (m, 2H), 7.74 (t, 8.0 Hz, 1H), 7.85 (dd, J=9.2, 1.6 Hz, 1H), 7.95 (dt, J=8.0, 1.6 Hz, 1H), 8.04 (dd, J=9.2, 1.2 Hz, 1H), 8.06 (dt, J=8.0, 1.6 Hz, 1H), 8.17 (s, 1H), 8.20 (t, J=1.6 Hz, 1H), 8.47 (s, 1H), 8.49 (dd, J=1.6, 1.2 Hz, 1H)

MS m/e (ESI) 380 (MH⁺)

Example 77

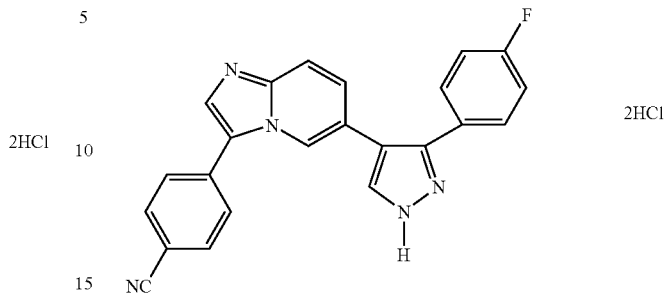

4-{6-[3-(4-Fluorophenyl)-1H-4-pyrazolyl]imidazo[1,2-a]-pyridin-3-yl}benzonitrile dihydrochloride 76 mg 4-{6-[3-(4-fluorophenyl)-1-trityl-1H-4-pyrazolyl] imidazo[1,2-a]pyridin-3-yl}benzonitrile (colorless crystals) was obtained by the same reaction as in Example 10 from 54 mg 4-(4,4,5,5-tetramethyl-1,3,2-dioxaborolan-2-yl)benzonitrile and 130 mg 6-[3-(4-fluorophenyl)-1-trityl-1H-4-pyrazolyl]-3-iodoimidazo[1,2-a]pyridine (compound in Production Example 39). The product was subjected to deprotection of the trityl group and converted into the corresponding hydrochloride by the same method as in Example 68, to give 37 mg of the title compound as colorless crystals.

¹H-NMR (DMSO-d₆)

δ: 7.21–7.29 (m, 2H), 7.47–7.54 (m, 2H), 7.79 (dd, J=9.2, 1.2 Hz, 1H) 7.83 (dt, J=8.4, 1.6 Hz, 2H), 7.99 (dd, J=9.2, 0.4 Hz, 1H), 8.00 (dt, J=8.4, 1.6 Hz, 2H), 8.18 (s, 1H), 8.44 (s, 2H)

MS m/e (ESI) 380 (MH⁺)

Example 78

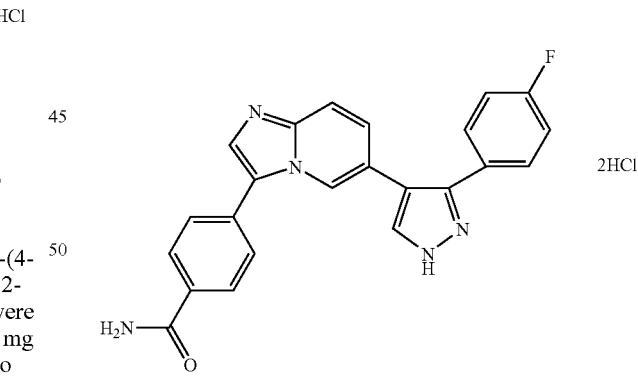

4-{6-[3-(4-Fluorophenyl)-1H-4-pyrazolyl]imidazo[1,2-a]-pyridin-3-yl}benzamide dihydrochloride 60 mg of the title compound was obtained as colorless crystals in the same manner as in Example 68 from 138 mg 4-{6-[3-(4-fluorophenyl)-1-trityl-1H-4-pyrazolyl]imidazo-[1,2-a]-pyridin-3-yl}benzamide (compound in Example 10).

¹H-NMR (DMSO-d₆)

δ: 7.21–7.28 (m, 2H), 7.49–7.55 (m, 2H), 7.56 (brs, 1H), 7.71 (d, J=8.4 Hz, 2H), 7.87 (dd, J=9.2, 1.2 Hz, 1H), 8.03 (d, J=8.4 Hz, 2H), 8.05 (d, J=9.2 Hz, 1H), 8.17 (brs, 1H), 8.19 (s, 1H), 8.46 (s, 1H), 8.48 (s, 1H)
MS m/e (ESI) 398 (MH+)

Example 79

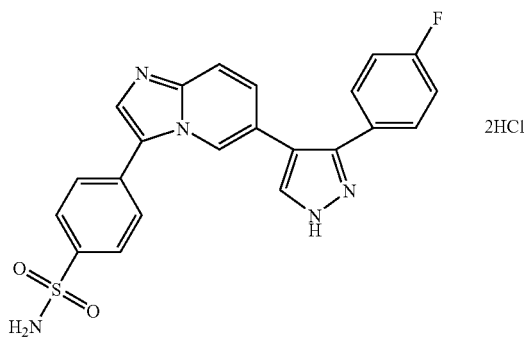

4-{6-[3-(4-Fluorophenyl)-1H-4-pyrazolyl]imidazo[1,2-a]-pyridin-3-yl}-1-benzenesulfonamide dihydrochloride 185 mg 4-{6-[3-(4-fluorophenyl)-1-trityl-1H-4-pyrazolyl]imidazo[1,2-a]pyridin-3-yl}-1-benzene sulfonamide obtained in Example 11 was dissolved in 3.5 mL solvent mixture of tetrahydrofuran and methanol (1:1), then 3.5 mL of 5 N hydrochloric acid was added thereto, and the mixture was stirred at room temperature for 3 hours. The reaction solution was washed with 4 mL diethyl ether, and the aqueous layer was evaporated into dryness under reduced pressure (azeotropic evaporation with ethanol). The residue was recrystallized from ethanol and diethyl ether to give 123 mg of the title compound as colorless crystals.
$^1$H-NMR (DMSO-$d_6$)
δ: 7.23–7.30 (m, 2H), 7.50–7.57 (m, 2H), 7.57 (s, 2H), 7.82 (dd, J=9.2, 1.2 Hz, 1H), 7.83 (dt, J=8.4, 2.0 Hz, 2H), 7.96 (dt, J=8.4, 2.0 Hz, 2H), 8.03 (d, J=9.2 Hz, 1H), 8.17 (s, 1H), 8.49 (s, 1H), 8.53 (t, J=1.2 Hz, 1H)

Example 80

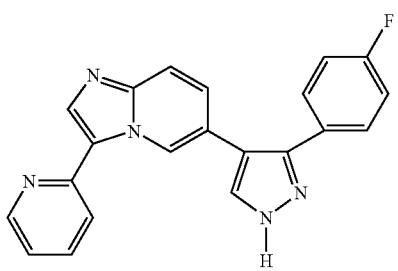

6-[3-(4-Fluorophenyl)-1H-4-pyrazolyl]-3-(2-pyridyl)imidazo-[1,2-a]pyridine 147 mg 6-[3-(4-fluorophenyl)-1-trityl-1H-4-pyrazolyl]-3-(2-pyridyl)imidazo[1,2-a]pyridine obtained in Example 22, 1.8 mL of 5 N hydrochloric acid, 4 ml tetrahydrofuran and 4 mL methanol were stirred overnight at room temperature. The reaction solution was cooled and then basified with 5 N aqueous sodium hydroxide, followed by adding ethyl acetate and water to separate an organic layer. The organic layer was washed with water and brine and dried over anhydrous sodium sulfate. The drying agent was filtered off, the filtrate was evaporated, the residue was triturated with dichloromethane, and the crystals were separated by filtration. This product was dried under vacuum to give 39 mg of the title compound as colorless crystals.
$^1$H-NMR (DMSO-$d_6$)
δ: 7.11–7.36(m, 4H), 7.50(m, 2H), 7.68(d, J=9.2 Hz, 1H), 7.83(m, 2H), 7.95(dd, J=8.0, 0.8 Hz, 1H), 8.15(s, 1H), 8.38(m, 1H), 9.84(brs, 1H), 13.20(brs, 1H)

Example 81

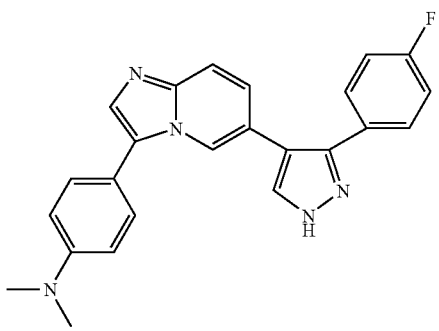

N,N-Dimethyl-4-(6-[3-(4-fluorophenyl)-1H-4-pyrazolyl]-imidazo[1,2-a]pyridin-3-yl}aniline 47 mg of the title compound was obtained as white crystals by the same method as in Example 80 from 107 mg N,N-dimethyl-4-{6-[3-(4-fluorophenyl)-1-trityl-1H-4-pyrazolyl]imidazo-[1,2-a]pyridin-3-yl}aniline obtained in Example 7.
$^1$H-NMR (CDCl$_3$)
δ: 3.01(s, 6H), 6.73(d, J=8.8 Hz, 2H), 7.12(m, 3H), 7.19(d, J=8.8 Hz, 2H), 7.47(m, 2H), 7.58(s, 1H), 7.60(dd, J=9.2, 0.4 Hz, 1H), 7.73(s, 1H), 8.11(brs, 1H)

Example 82

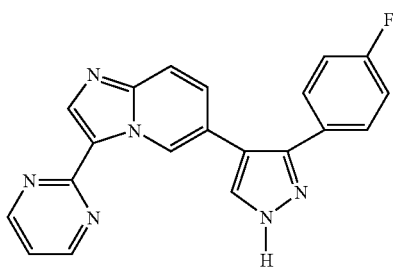

6-[3-(4-Fluorophenyl)-1H-4-pyrazolyl]-3-(2-pyrimidinyl)-imidazo[1,2-a]pyridine 18 mg of the title compound was obtained as white crystals by the same method as in Example 80 from 93 mg 6-[3-(4-fluorophenyl)-1-trityl-1H-4-pyrazolyl]-3-(2-pyrimidinyl)-imidazo[1,2-a]pyridine obtained in Example 24.

$^1$H-NMR (CDCl$_3$)

δ: 7.07(m, 3H), 7.46(m, 2H), 7.54(s, 1H), 7.58(d, J=9.6 Hz, 1H), 7.64(d, J=1.2 Hz, 1H), 7.73(s, 1H), 8.07(dd, J=1.6, 1.2 Hz, 1H)

Example 83

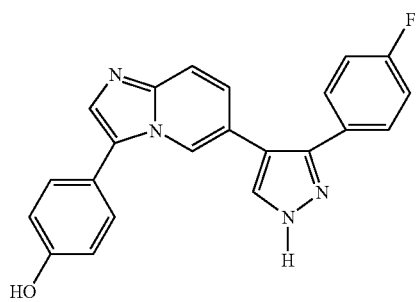

4-{6-[3-(4-Fluorophenyl)-1H-4-pyrazolyl]imidazo[1,2-a]-pyridin-3-yl}phenol 36 mg of the title compound was obtained as pale gray crystals by the same method as in Example 80 from 84 mg 4-{6-[3-(4-fluorophenyl)-1-trityl-1H-4-pyrazolyl]imidazo-[1,2-a]-pyridin-3-yl}phenol obtained in Example 14.

$^1$H-NMR (DMSO-d$_6$)

δ: 6.79(d, J=8.0 Hz, 2H), 7.14–7.37(m, 5H), 7.49(m, 2H), 7.57(s, 1H), 7.59(d, J=9.2 Hz, 1H), 8.06(s, 1H), 8.13(brs, 1H), 9.73(brs, 1H)

Example 84

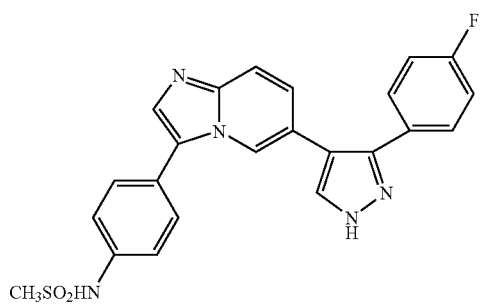

N-(4-{6-[3-(4-Fluorophenyl)-1H-4-pyrazolyl]imidazo[1,2-a]-pyridin-3-yl}phenyl)methane sulfonamide A mixture of 71 mg N-(4-{6-[3-(4-fluorophenyl)-1-trityl-1H-4-pyrazolyl]imidazo[1,2-a]-pyridin-3-yl}phenyl)-methane sulfonamide obtained in Example 20, 0.36 mL trifluoroacetic acid and 5 mL dichloromethane was stirred overnight at room temperature. The reaction solution was cooled and made weakly alkaline with 5 N aqueous sodium hydroxide, followed by adding ethyl acetate and water to separate an organic layer. The organic layer was washed with brine and dried over anhydrous sodium sulfate. The drying agent was filtered off, the filtrate was evaporated, the residue was triturated with diethyl ether, and the crystals were separated by filtration. This product was dried under vacuum to give 33 mg of the title compound as a white solid.

$^1$H-NMR (DMSO-d$_6$)

δ: 3.55(s, 3H), 7.20(m, 3H), 7.28~7.40(m, 2H), 7.53(m, 4H), 7.65(m, 2H), 7.86(s, 1H), 8.16(brs, 1H), 8.34(s, 1H), 13.18(brs, 1H)

Example 85

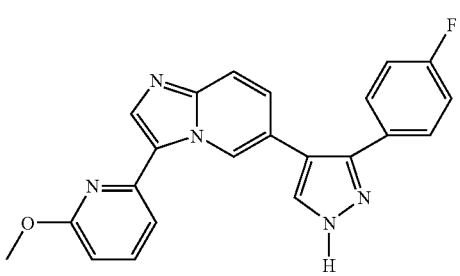

6-[3-(4-Fluorophenyl)-1H-4-pyrazolyl]-3-(6-methoxy-2-pyridyl)imidazo[1,2-a]pyridine 22 mg of the title compound was obtained as a white solid in the same method as in Example 84 by treating, with trifluoroacetic acid, 54 mg 6-[3-(4-fluorophenyl)-1-trityl-1H-4-pyrazolyl]-3-(6-methoxy-2-pyridyl)imidazo[1,2-a]pyridine obtained in Example 23.

$^1$H-NMR (CDCl$_3$)

δ: 3.80(s, 3H), 6.62(d, J=8.4 Hz, 1H), 7.05(m, 2H), 7.13(dd, J=9.2, 1.6 Hz, 1H), 7.33(d, J=7.6 Hz, 1H), 7.48(m, 2H), 7.63(m, 2H), 7.74(s, 1H), 8.13(s, 1H), 9.90(brs, 1H)

Example 86

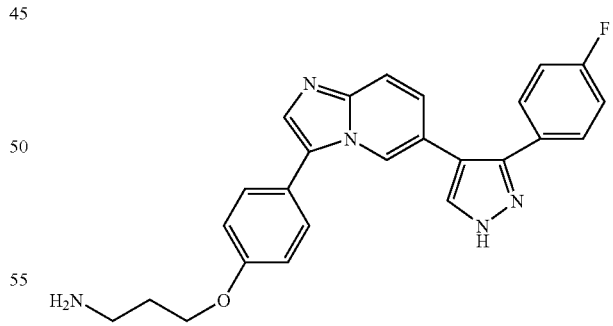

3-(4-{6-[3-(4-Fluorophenyl)-1H-4-pyrazolyl]imidazo[1,2-a]-pyridin-3-yl}phenoxy)propylamine 157 mg of the title compound was obtained as white crystals by the same method as in Example 80 from 287 mg 3-(4-{6-[3-(4-fluorophenyl)-1-trityl-1H-4-pyrazolyl]imidazo[1,2-a]-pyridin-3-yl}phenoxy)propylamine obtained in Example 16.

¹H-NMR (DMSO-d₆)

δ: 1.80(m, 2H), 2.70(m, 2H), 4.06(m, 2H), 6.95(d, J=8.8 Hz, 2H), 7.16–7.30(m, 3H), 7.33(d, J=8.8 Hz, 2H), 7.49(m, 2H), 7.60(dd, J=9.6, 0.4 Hz, 1H), 7.62(s, 1H), 8.04(s, 1H), 8.08(s, 1H)

Example 87

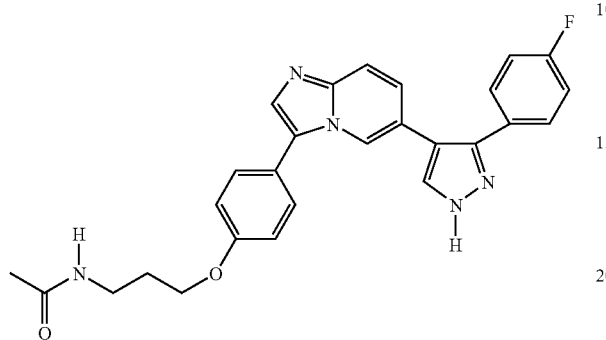

N-[3-(4-{6-[3-(4-Fluorophenyl)-1H-4-pyrazolyl]imidazo-[1,2-a]pyridin-3-yl}phenoxy)propyl]acetamide 11 mg of the title compound was obtained as gray crystals by the same method as in Example 84 from 29 mg N-[3-(4-{6-[3-(4-fluorophenyl)-1-trityl-1H-4-pyrazolyl]imidazo[1,2-a]-pyridin-3-yl}phenoxy)propyl]acetamide obtained in Example 18.

¹H-NMR (CDCl₃)

δ: 2.01(s, 3H), 2.06(t, J=6.4 Hz, 2H), 3.50(m, 2H), 4.09(t, J=6.4 Hz, 2H), 5.81(brs, 1H), 6.92(d, J=8.4 Hz, 2H), 7.12(t, J=8.4 Hz, 2H), 7.16(dd, J=9.2, 1.2 Hz, 1H), 7.24(d, J=8.4 Hz, 2H), 7.28(m, 1H), 7.46(m, 2H), 7.64(d, J=9.2 Hz, 1H), 7.74(s, 1H), 8.06(brs, 1H)

Example 88

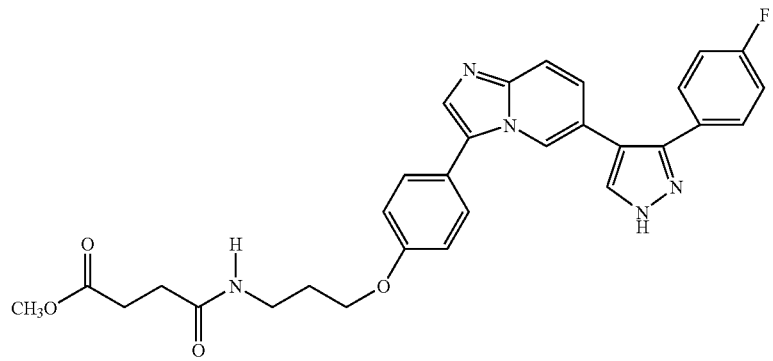

Methyl 4-{[3-(4-{6-[3-(4-Fluorophenyl)-1H-4-pyrazolyl]-imidazo[1,2-a]pyridin-3-yl}phenoxy)propyl]amino}-4-oxobutanoate 9 mg of the title compound was obtained as white solid by the same method as in Example 84 from 24 mg methyl 4-{[3-(4-{6-[3-(4-fluorophenyl)-1-trityl-1H-4-pyrazolyl]imidazo[1,2-a]pyridin-3-yl}phenoxy)propyl]amino}-4-oxobutanoate obtained in Example 18.

¹H-NMR (CDCl₃)

δ: 2.06(m, 2H), 2.50(m, 2H), 2.70(m, 2H), 3.50(m, 2H), 3.68(s, 3H), 4.08(m, 2H), 5.96(brs, 1H), 6.93(d, J=8.8 Hz, 2H), 7.13(m, 3H), 7.25(m, 2H), 7.46(m, 2H), 7.61(s, 1H), 7.63(d, J=9.2 Hz, 1H), 7.74(s, 1H), 8.06(brs, 1H)

Example 89

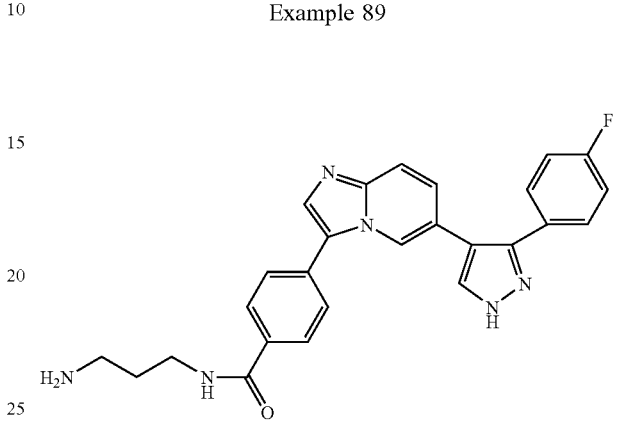

N1-(3-Aminopropyl)-4-{6-[3-(4-fluorophenyl)-1H-4-pyrazolyl]imidazo[1,2-a]pyridin-3-yl}benzamide A solution of 50 mg N1-(3-aminopropyl)-4-{6-[3-(4-fluorophenyl)-1-trityl-1H-4-pyrazolyl]imidazo[1,2-a]pyridin-3-yl}benzamide obtained in Example 43 in a solvent mixture of 1.5 mL tetrahydrofuran, 1.5 mL methanol and 1.5 mL of 5 N hydrochloric acid was left at room temperature for 1 hour. The mixture was washed with ethyl acetate, and the aqueous layer was basified with 5N aqueous sodium hydroxide. Water was added thereto, and the formed solid was collected and recrystallized from ethanol/diethyl ether to give 15 mg of the title compound as colorless crystals.

¹H-NMR (DMSO-d₆)

δ: 1.60(quint, J=6.8 Hz, 2H), 2.60(t, J=6.8 Hz, 2H), 3.32(t, J=6.8 Hz, 2H), 7.21(dd, J=9.2, 1.6 Hz, 1H), 7.22–7.30(m, 2H), 7.48–7.54(m, 2H), 7.58(d, J=8.4 Hz, 2H), 7.64(d, J=9.2 Hz, 1H), 7.83(s, 1H), 7.88(d, J=8.4 Hz, 2H), 8.06(s, 1H), 8.30(s, 1H), 8.62(t, J=6.0 Hz, 1H)

MS m/e (ESI) 455 (MH⁺)

Example 90

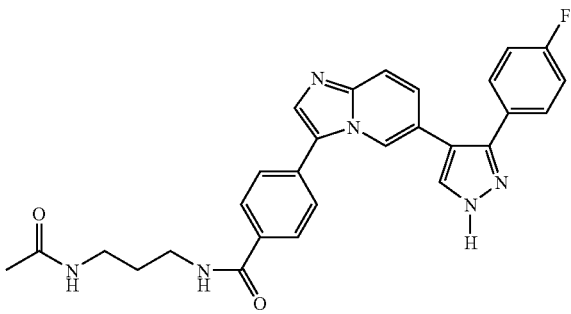

N1-[3-(Acetylamino)propyl]-4-{6-[3-(4-fluorophenyl)-1H-4-pyrazolyl]imidazo[1,2-a]pyridin-3-yl}benzamide 0.014 mL acetic anhydride was added to a solution mixture of 50 mg N1-(3-aminopropyl)-4-{6-[3-(4-fluorophenyl)-1-trityl-1H-4-pyrazolyl]imidazo[1,2-a]pyridin-3-yl}benzamide obtained in Example 43, 0.4 mL tetrahydrofuran and 0.2 mL pyridine under ice-cooling. The mixture was stirred at room temperature for 1 hour, water was added thereto, and the mixture was stirred for 30 minutes. The solvent was evaporated, and the residue was purified by NH silica gel column chromatography (acetic acid/methanol) to give 53 mg N1-[3-(acetylamino)propyl]-4-(6-[3-(4-fluorophenyl)-1-trityl-1H-4-pyrazolyl]imidazo[1,2-a]pyridin-3-yl}benzamide. This product was subjected to deprotection of the trityl group in the same manner as in Example 89, to give 27 mg of the title compound (colorless crystals; recrystallization solvent, methanol/diethyl ether).

$^1$H-NMR (DMSO-$d_6$)

δ: 1.65(quint, J=6.8 Hz, 2H), 1.80(s, 3H), 3.09 (q, J=6.8 Hz, 2H), 3.27 (q, J=6.8 Hz, 2H), 7.17–7.26(m, 2H), 7.32(t, J=5.6 Hz, 1H), 7.47–7.54(m, 2H), 7.59(d, J=8.0, 2H), 7.64 (d, J=8.8 Hz, 1H), 7.83(s, 1H), 7.84–7.91(m, 3H), 8.16(s, 1H), 8.30(s, 1H), 8.52(t, J=5.6 Hz, 1H)

MS m/e (ESI) 497 (MH$^+$)

Example 91

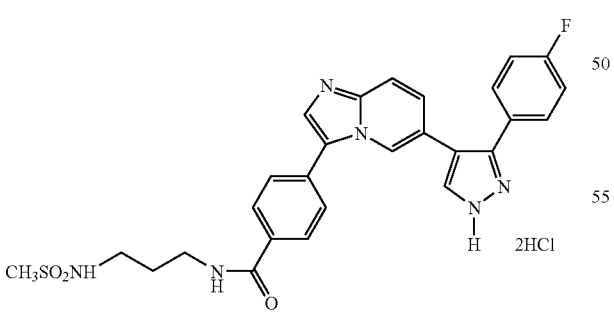

N1-{3-[(Methylsulfonyl)amino]propyl}-4-{6-[3-(4-fluorophenyl)-1H-4-pyrazolyl]imidazo[1,2-a)pyridin-3-yl}benzamide 0.009 mL methyl sulfonyl chloride was added to a solution mixture of 67 mg of N1-(3-aminopropyl)-4-{6-[3-(4-fluorophenyl)-1-trityl-1H-4-pyrazolyl]imidazo[1,2-a]-pyridin-3-yl}benzamide obtained in Example 43, 0.4 mL tetrahydrofuran and 0.017 mL triethylamine under ice-cooling. The mixture was stirred at room temperature for 30 minutes, the solvent was evaporated, and the residue was purified by NH silica gel column chromatography (acetic acid/methanol) to give 51 mg N4-{6-[3-(4-fluorophenyl)-1-trityl-1H-4-pyrazolyl]imidazo-[1,2-a]pyridin-3-yl}-1-[3-(methylsulfonylamino)propyl]-1-[3-(methylsulfonylamino)propyl]benzamide. This product was subjected to deprotection of the trityl group and converted into the corresponding hydrochloride by the same method as in Example 68, to give 30 mg of the title compound as an amorphous.

$^1$H-NMR (DMSO-$d_6$)

δ: 1.74(quint, J=7.6 Hz, 2H), 2.89(s, 3H), 2.97–3.03(m, 2H), 3.30–3.36(m, 2H), 7.03 (t, J=5.6 Hz, 1H), 7.19–7.26 (m, 2H), 7.46–7.53 (m, 2H), 7.69 (d, J=8.4 Hz, 2H), 7.81(d, J=9.6 Hz, 1H), 7.97(d, J=8.4 Hz, 2H), 7.99(d, J=9.6 Hz, 1H), 8.17(s, 1H), 8.42(s, 1H), 8.43(s, 1H), 8.65(t, J=5.6 Hz, 1H)

MS m/e (ESI) 533 (MH$^+$)

Example 92

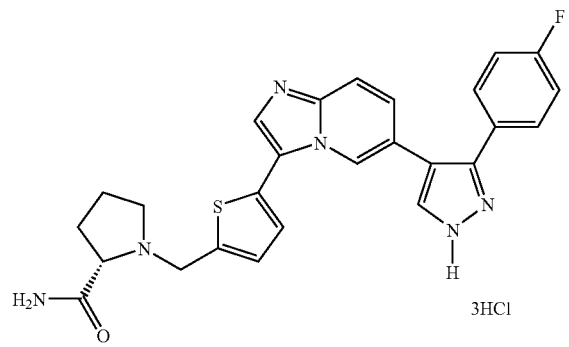

(2S)-1-[(5-{6-[3-(4-Fluorophenyl)-1H-4-pyrazolyl]-imidazo-[1,2-a]pyridin-3-yl}-2-thienyl)methyl]tetrahydro-1H-2-pyrrole carboxyamide trihydrochloride 75 mg of the title compound was obtained as pale brown solid by the same method as in Example 79 from 130 mg (2S)-1-[(5-{6-[3-(4-fluorophenyl)-1-trityl-1H-4-pyrazolyl]-imidazo[1,2-a]pyridin-3-yl}-2-thienyl)methyl]tetrahydro-1H-2-pyrrole carboxyamide obtained in Example 34.

$^1$H-NMR (DMSO-$d_6$)

δ: 1.80–1.88(m, 2H), 2.00–2.15(m, 1H), 2.45–2.56(m, 1H), 3.27–3.38(m, 1H), 3.50–3.60(m, 1H), 4.28(t, J=8.0 Hz, 1H), 4.65 (d, J=16.0 Hz, 1H), 4.75(d, J=16.0 Hz, 1H), 7.27–7.36(m, 2H), 7.40(d, J=3.6 Hz, 1H), 7.44(d, J=3.6 Hz, 1H), 7.45–7.55(m, 2H), 7.70(s, 1H), 7.81(d, J=9.6 Hz, 1H), 8.01(d, J=9.6 Hz, 1H), 8.19(s, 1H), 8.20(s, 1H), 8.41(s, 1H), 8.48(s, 1H)

MS m/e (ESI) 487 (MH$^+$)

Example 93

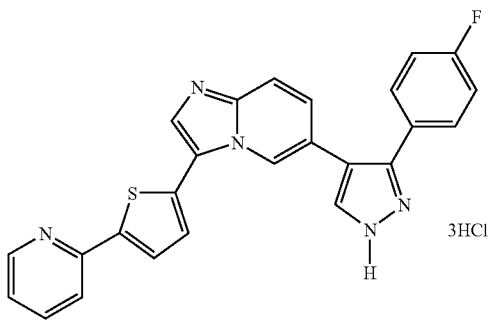

6-[3-(4-Fluorophenyl)-1H-4-pyrazolyl]-3-[5-(2-pyridyl)-2-thienyl]imidazo[1,2-a]pyridine trihydrochloride 66 mg of the title compound was obtained as yellow crystals by the same method as in Example 68 from 135 mg 6-[3-(4-fluorophenyl)-1-trityl-1H-4-pyrazolyl]-3-(5-(2-pyridyl)-2-thienyl]imidazo[1,2-a]pyridine obtained in Example 25.

$^1$H-NMR (DMSO-$d_6$)

δ: 7.19(t, J=8.8 Hz, 2H), 7.37(m, 1H), 7.49(m, 2H), 7.55(d, J=4.0 Hz, 1H), 7.92(m, 2H), 7.94(d, J=4.0 Hz, 1H), 8.04(m, 2H), 8.23(s, 1H), 8.56(m, 3H)

Example 94

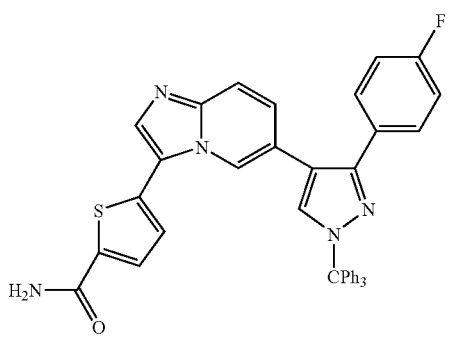

5-{6-[3-(4-Fluorophenyl)-1-trityl-1H-4-pyrazolyl]imidazo-[1,2-a]pyridin-3-yl}-2-thiophene carboxamide A mixture of 200 mg 6-[3-(4-fluorophenyl)-1-trityl-1H-4-pyrazolyl]-3-(1,1,1-tributylstannyl)imidazo[1,2-a]-pyridine prepared from 6-[3-(4-fluorophenyl)-1-trityl-1H-4-pyrazolyl]-3-iodoimidazo[1,2-a]pyridine (compound in Production Example 39) and tributyltin chloride by the same method as in Production Example 48, 51 mg 5-bromo-2-thiophene carboxamide, 14 mg tetrakis (triphenylphosphine) palladium and 3 mL xylene was stirred at 120° C. for 2 hours under nitrogen atmosphere. The solvent was evaporated, and the residue was purified by silica gel chromatography (ethyl acetate/methanol) to give 37 mg of the title compound as a colorless amorphous.

$^1$H-NMR (CDCl$_3$)

δ: 6.92 (d, J=3.6 Hz, 1H), 7.00–7.06 (m, 2H), 7.18 (dd, J=9.3, 1.6 Hz, 1H), 7.20–7.50 (m, 20H), 7.60–7.64 (m, 1H), 8.22 (brs, 1H)

MS m/e (ESI) 646 (MH$^+$)

Example 95

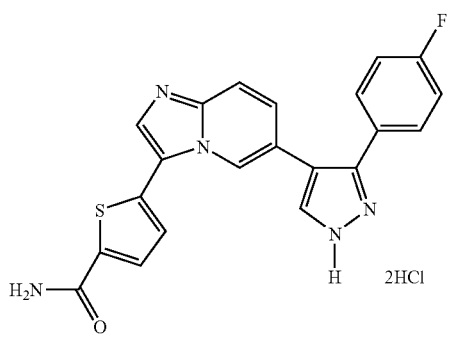

5-{6-[3-(4-Fluorophenyl)-1H-4-pyrazolyl]imidazo[1,2-a]pyridin-3-yl}-2-thiophene carboxamide dihydrochloride 18 mg of the title compound was obtained as colorless crystals by the same method as in Example 67 from 37 mg 5-{6-[3-(4-fluorophenyl)-1-trityl-1H-4-pyrazolyl]imidazo-[1,2-a]pyridin-3-yl}-2-thiophene carboxamide obtained in Example 94.

$^1$H-NMR (DMSO-$d_6$)

δ: 7.16–7.24 (m, 2H), 7.45 (d, J=3.8 Hz, 1H), 7.46–7.52 (m, 2H), 7.72–7.88 (m, 1H), 7.84 (d, J=3.8 Hz, 1H), 7.91–8.00 (m, 1H), 8.19 (brs, 2H), 8.51 (s, 1H)

MS m/e (ESI) 404 (MH$^+$)

Example 96

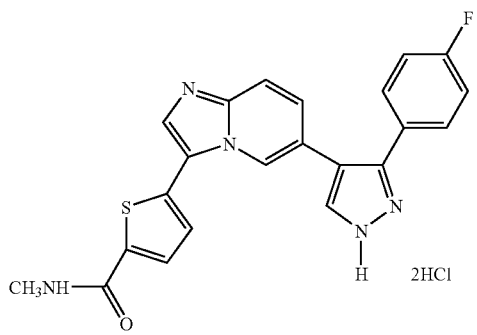

N2-Methyl-5-{6-[3-(4-fluorophenyl)-1H-4-pyrazolyl]imidazo-[1,2-a]pyridin-3-yl)-2-thiophene carboxamide dihydrochloride 23 mg of N2-methyl-5-{6-[3-(4-fluorophenyl)-1-trityl-1H-4-pyrazolyl]imidazo[1,2-a]pyridin-3-yl}-2-thiophene carboxamide was obtained as a colorless amorphous in the same manner as in Production Example 94 from 370 mg 6-[3-(4-fluorophenyl)-1-trityl-1H-4-pyrazolyl]-3-(1,1,1-tributylstannyl)imidazo[1,2-a]pyridine and 110 mg N2-methyl-5-bromo-2-thiophene carboxamide. The product was subjected to deprotection of the trityl group and converted into the corresponding hydrochloride by the same method as in Example 67 to give 14 mg of the title compound as colorless crystals.

$^1$H-NMR (DMSO-$d_6$)

δ: 2.78 (s, 3H), 7.17–7.25 (m, 2H), 7.44(d, J=3.8 Hz, 1H), 7.45–7.52 (m, 2H), 7.76(d, J=8.8 Hz, 1H), 7.82(d, J=3.8 Hz, 1H), 7.96(d, J=8.8 Hz, 1H), 8.18(br, 1H,), 8.46(brs, 1H), 8.48(s, 1H), 8.74 (d, J=4.4 Hz, 1H)

MS m/e (ESI) 418 (MH$^+$)

Example 97

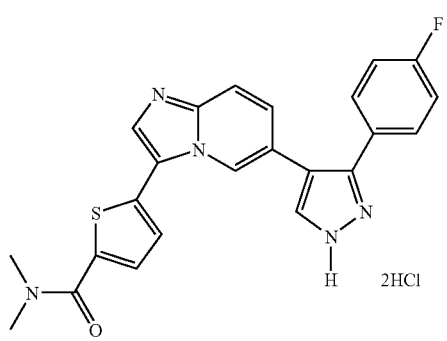

N2,N2-Dimethyl-5-{6-[3-(4-fluorophenyl)-1H-4-pyrazolyl]-imidazo[1,2-a]pyridin-3-yl}-2-thiophene carboxamide dihydrochloride 23 mg of N2,N2-dimethyl-5-{6-[3-(4-fluorophenyl)-1-trityl-1H-4-pyrazolyl]imidazo[1,2-a]pyridin-3-yl}-2-thiophene carboxamide was obtained as a colorless amorphous in the same manner as in Production Example 94 from 370 mg 6-[3-(4-fluorophenyl)-1-trityl-1H-4-pyrazolyl]-3-(1,1,1-tributylstannyl)imidazo[1,2-a]pyridine and 120 mg N2,N2-dimethyl-5-bromo-2-thiophene carboxamide. The product swas subjected to deprotection of the trityl group and converted into the corresponding hydrochloride by the same method as in Example 67 to give 15 mg of the title compound as colorless crystals.

$^1$H-NMR (DMSO-$d_6$)

δ: 3.00–3.30(br, 6H), 7.21(t, J=8.4 Hz, 2H), 7.47(d, J=3.6 Hz, 1H), 7.44–7.52(m, 2H), 7.56(d, J=3.6 Hz, 1H), 7.81(dd, J=11.6 Hz, J=9.2 Hz, 1H), 7.97(d, J=9.2 Hz, 1H), 8.20(s, 1H), 8.46(s, 1H), 8.47(s, 1H)

MS m/e (ESI) 432 (MH$^+$)

Example 98

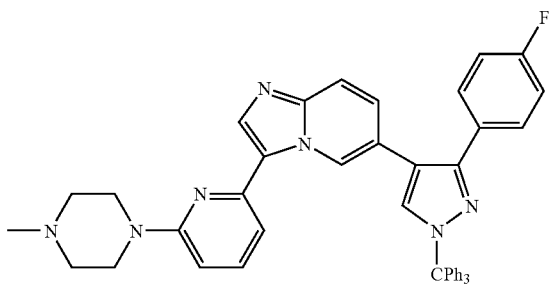

6-[3-(4-Fluorophenyl)-1-trityl-1H-4-pyrazolyl]-3-[6-(4-methylpiperazin-1-yl)-2-pyridyl]imidazo[1,2-a]pyridine 190 mg 1-methyl-4-(6-tributylstannyl-2-pyridyl)-piperazine obtained from 1-(6-bromo-2-pyridyl)-4-methyl piperazine and tributyltin chloride by the same method as in Production Method 46 was reacted in the same manner as in Example 21 with 129 mg 6-[3-(4-fluorophenyl)-1-trityl-1H-4-pyrazolyl]-3-iodoimidazo[1,2-a]pyridine obtained in Production Example 39, to give 91 mg of the title compound as a colorless amorphous.

$^1$H-NMR (CDCl$_3$)δ: 2.20(s, 3H), 2.33(m, 4H), 3.45(m, 4H), 6.59(d, J=8.4 Hz, 1H), 6.93(t, J=8.8 Hz, 2H), 7.06(m, 2H), 7.24(m, 7H), 7.35(m, 8H), 7.41(s, 1H), 7.46–7.59(m, 3H), 7.66(m, 1H), 8.08(s, 1H), 9.78(brs, 1H)

Example 99

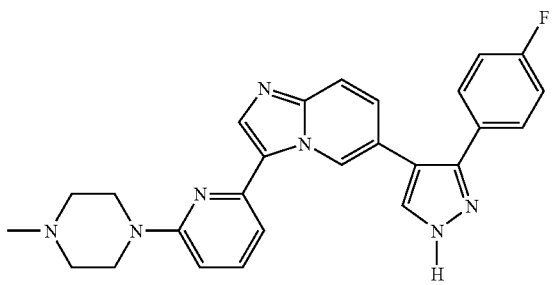

6-[3-(4-Fluorophenyl)-1H-4-pyrazolyl]-3-[6-(4-methylpiperazin-1-yl)-2-pyridyl]imidazo[1,2-a]pyridine 39 mg of the title compound was obtained as white crystals by the same method as in Example 80 from 89 mg 6-[3-(4-fluorophenyl)-1-trityl-1H-4-pyrazolyl]-3-[6-(4-methylpiperazin-1-yl)-2-pyridyl]imidazo[1,2-a]pyridine obtained in Example 98.

$^1$H-NMR (CDCl$_3$)

δ: 2.35(s, 3H), 2.54(m, 4H), 3.60(m, 4H), 6.56(d, J=8.8 Hz, 1H), 7.05(m, 3H), 7.10(d, J=7.6 Hz, 1H), 7.48(m, 2H), 7.57(m, 2H), 7.71(s, 1H), 8.09(s, 1H), 9.91(brs, 1H)

Example 100

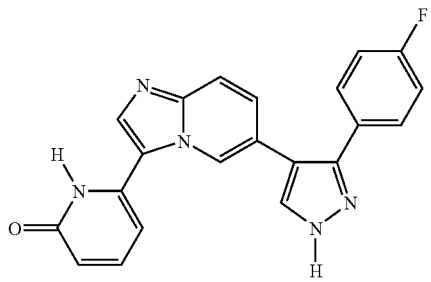

6-{6-[3-(4-Fluorophenyl)-1H-4-pyrazolyl] imidazo[1,2-a]-pyridin-3-yl}-1,2-dihydro-2-pyridinone A mixture of 54 mg 6-[3-(4-fluorophenyl)-1-trityl-1H-4-pyrazolyl]-3-(6-methoxy-2-pyridyl)imidazo[1,2-a]pyridine obtained in Example 23, 2 mL of 48% hydrobromic acid and 2 mL acetic acid was stirred at room temperature for 4 hours and then heated for 10 minutes under reflux. The reaction solution was cooled and neutralized with 5 N aqueous sodium hydroxide, and the precipitated solid was collected by filtration, washed with water and air-dried. Then, the solid was triturated with diethyl ether, collected by filtration and dried in vacuo to give 5.4 mg of the title compound as white crystals.

MS m/e (ESI) 372 (MH$^+$)

Example 101

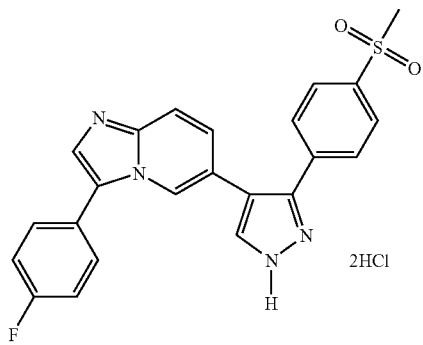

3-(4-Fluorophenyl)-6-{3-[4-(methylsulfonyl)phenyl]-1H-4-pyrazolyl}imidazo[1,2-a]pyridine dihydrochloride 156 mg of the title compound was obtained as colorless crystals by the same method as in Example 68 from 228 mg 3-(4-fluorophenyl)-6-{3-[4-(methylsulfonyl)phenyl]-1-trityl-1H-4-pyrazolyl}imidazo[1,2-a]pyridine obtained in Example 9.

$^1$H-NMR (DMSO-d$_6$)

δ: 3.28(s, 3H), 7.3–7.42(m, 2H), 7.62–7.68(m, 2H), 7.67 (dt, J=8.4, 2.0 Hz, 2H), 7.85(dd, J=9.2, 1.6 Hz, 1H), 7.96(dt, J=8.4, 2.0 Hz, 2H), 8.05(dd, J=9.2, 0.8 Hz, 1H), 8.25(s, 1H), 8.37(s, 2H)

MS m/e (ESI) 439 (MH$^+$)

Example 102

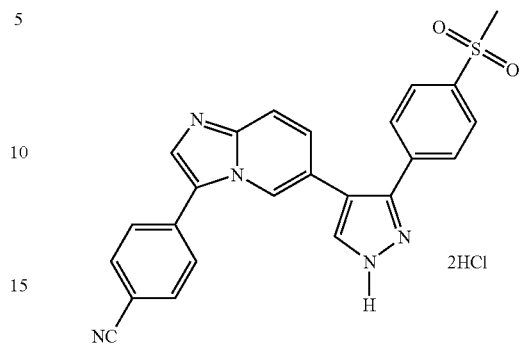

4–6-(3-[4-(Methylsulfonyl)phenyl]-1H-4-pyrazolyl}imidazo-[1,2-a]pyridin-3-yl)benzonitrile dihydrochloride 123 mg of the title compound was obtained as colorless crystals by the same method as in Example 79 from 212 mg 4-(6-{3-[4-(methylsulfonyl)phenyl]-1-trityl-1H-4-pyrazolyl}imidazo[1,2-a]pyridin-3-yl)benzonitrile obtained in Example 12.

$^1$H-NMR (DMSO-d$_6$)

δ: 3.28(s, 3H), 7.75–7.81(m, 3H), 7.84(dt, J=8.4, 2.0 Hz, 2H), 7.96(dt, J=8.4, 2.0 Hz, 2H), 8.00(dt, J=8.4, 2.0 Hz, 2H), 8.01(dd, J=9.2, 0.8 Hz, 1H) 8.23(s, 1H), 8.46(s, 1H), 8.55 (dd, J=1.6, 0.8 Hz, 1H)

MS m/e (ESI) 440 (MH$^+$)

Example 103

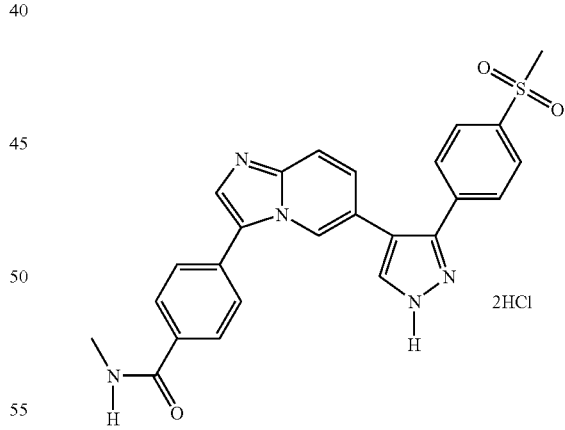

N1-Methyl-4-(6-{3-[4-(methylsulfonyl)phenyl]-1H-4-pyrazolyl}Illimidazo[1,2-a]pyridin-3-yl)benzonitrile dihydrochloride 102 mg of the title compound was obtained as colorless crystals by the same method as in Example 79 from 184 mg N1-methyl-4-(6-{3-[4-(methylsulfonyl)phenyl]-1-trityl-1H-4-pyrazolyl}imidazo[1,2-a]pyridin-3-yl)benzamide obtained in Example 13.

¹H-NMR (DMSO-d₆)
δ: 2.82(d, J=4.8 Hz, 3H), 3.27(s, 3H), 7,71(d, J=9.2 Hz, 1H), 7.75–7.81(m, 4H), 7.92–8.20(m, 5H), 8.23(s, 1H), 8.41(s, 1H), 5.56 (q, J=4.8 Hz, 1H), 8.59(s, 1H)
MS m/e (ESI) 472 (MH⁺)

Example 104

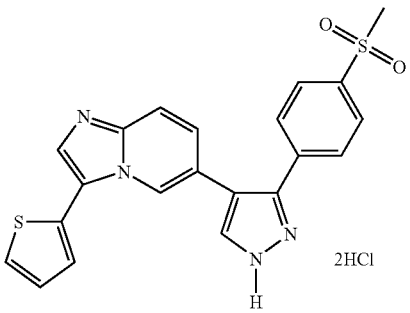

6-{3-[4-(Methylsulfonyl)phenyl]-1H-4-pyrazolyl}-3-(2-thienyl)imidazo[1,2-a]pyridine dihydrochloride 66 mg of the title compound was obtained as colorless crystals by the same method as in Example 79 from 150 mg 6-{3-[4-(methylsulfonyl)phenyl]-1-trityl-1H-4-pyrazolyl]-3-(2-thienyl)imidazo[1,2-a]pyridine obtained in Example 26.
¹H-NMR (DMSO-d₆)
δ: 3.27(s, 3H), 7.26(dd, J=5.2, 4.0 Hz, 1H), 7.47(d, J=4.0 Hz, 1H), 7.76(d, J=8.0 Hz, 2H), 7.83(d, J=5.2 Hz, 1H), 7.85(d, J=9.2 Hz, 1H), 7.94(d, J=8.0 Hz, 2H), 8.02(d, J=9.2 Hz, 1H), 8.29(s, 1H), 8.45(s, 2H)

Example 105

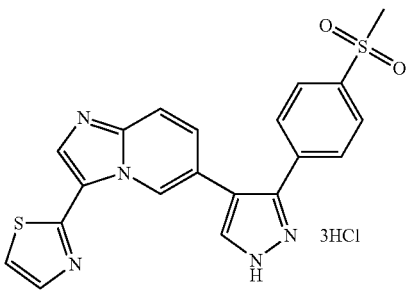

2-(6-{3-[4-(Methylsulfonyl)phenyl]-1H-4-pyrazolyl}-imidazo-[1,2-a]pyridin-3-yl)-1,3-thiazole trihydrochloride 82 mg of the title compound was obtained as colorless crystals by the same method as in Example 79 from 125 mg 2-(6-{3-[4-(methylsulfonyl)phenyl]-1-trityl-1H-4-pyrazolyl}imidazo[1,2-a]pyridin-6-yl)-1,3-thiazole obtained in Example 27.
¹H-NMR (DMSO-d₆)
δ: 3.21(s, 3H), 7.73–7.78(m, 2H), 7.85–7.96(m, 5H), 8.03(d, J=9.6 Hz, 1H), 8.28(s, 1H), 8.93(s, 1H), 8.72(s, 1H)
MS m/e (ESI) 422 (MH⁺)

Example 106

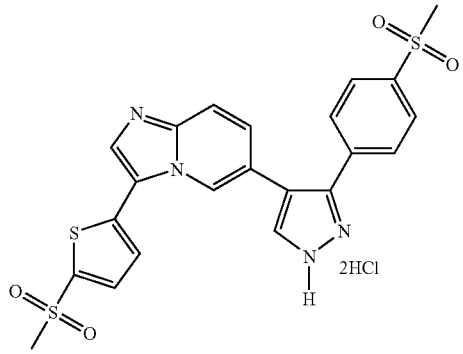

6-{3-[4-(Methylsulfonyl)phenyl]-1H-4-pyrazolyl}-3-[5-(methylsulfonyl)-2-thienyl}imidazo[1,2-a]pyridine dihydrochloride 56 mg of the title compound was obtained as pale yellow crystals by the same method as in Example 79 from 95 mg 6-{3-[4-(methylsulfonyl)phenyl]-1-trityl-1H-4-pyrazolyl}-3-[5-(methylsulfonyl)-2-thienyl)imidazo[1,2-a]pyridine obtained in Example 28.
¹H-NMR DMSO-d₆)
δ: 3.24(s, 3H), 3.41(s, 3H), 7.61(d, J=9.6 Hz, 1H), 7.62(d, J=4.0 Hz, 1H), 7.73(dt, J=8.4, 2.0 Hz, 2H), 7.88–7.94(m, 4H), 8.21(s, 1H), 8.43(s, 1H), 8.60(t, J=1.6 Hz, 1H)
MS m/e (ESI) 499 (MH⁺)

Example 107

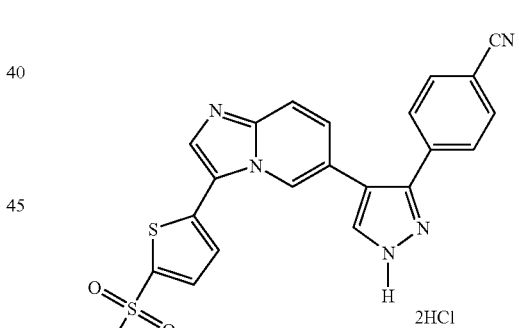

4-(4-{3-[5-(Methylsulfonyl)2-thienyl]imidazo[1,2-a]pyridin-3-yl}-1H-3-pyrazolyl)benzonitrile dihydrochloride 63 mg of the title compound was obtained as pale yellow crystals in the same manner as in Example 79 from 110 mg 4-(4-{3-[5-(methylsulfonyl)-2-thienyl]imidazo[1,2-a]-pyridin-3-yl}-1-trityl-1H-3-pyrazolyl)benzonitrile obtained in Example 32.
¹H-NMR (DMSO-d₆)
δ: 3.43(s, 3H), 7.66(dt, J=8.0, 2.0 Hz, 2H), 7.70(d, J=4.0 Hz, 1H), 7.73(dd, J=9.2, 1.6 Hz, 1H), 7.83(dt, J=8.0, 2.0 Hz, 2H), 7.93(d, J=4.0 Hz, 1H), 7.99(dd, J=9.2, 0.8 Hz, 1H), 8.22(s, 1H), 8.57(s, 1H), 8.62(dd, J=1.6, 0.8 Hz, 1H)
MS m/e (ESI) 446 (MH⁺)

Example 108

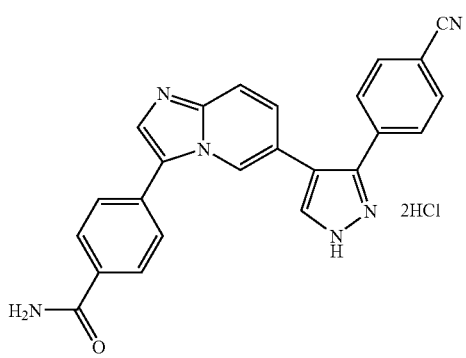

4-{6-[3-(4-Cyanophenyl)-1H-4-pyrazolyl]imidazo[1,2-a]-pyridin-3-yl}benzamide dihydrochloride 61 mg of the title compound was obtained as colorless crystals in the same manner as in Example 79 from 103 mg 4-{6-[3-(4-cyanophenyl)-1-trityl-1H-4-pyrazolyl]imidazo-[1,2-a]pyridin-3-yl}benzamide obtained in Example 33.

$^1$H-NMR (DMSO-$d_6$)

δ: 7.55(s, 1H), 7.67(dt, J=8.4, 1.6 Hz, 2H), 7.72–7.78(m, 3H), 7.84(d, J=8.4 Hz, 2H), 8.10(d, J=9.2 Hz, 1H), 8.02(dt, J=8.4, 1.6 Hz, 2H), 8.14(s, 1H), 8.21(s, 1H), 8.47(s, 1H), 8.57(s, 1H)

MS m/e (ESI) 405 (MH$^+$)

Example 109

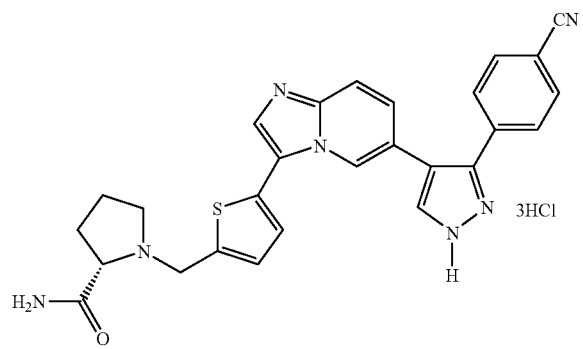

(2S)-1-{[(5-{6-[3-(4-Cyanophenyl)-1H-4-pyrazolyl]imidazo-[1,2-a]pyridin-3-yl}-2-thienyl)methyl]tetrahydro-1H-2-pyrrole carboxyamide trihydrochloride 68 mg of the title compound was obtained as colorless crystals in the same manner as in Example 79 from 100 mg (2S)-1-{[(5-{6-[3-(4-cyanophenyl)-1-trityl-1H-4-pyrazolyl]-imidazo[1,2-a]pyridin-3-yl}-2-thienyl)methyl]tetrahydro-1H-2-pyrrole carboxyamide obtained in Example 35.

$^1$H-NMR (DMSO-$d_6$)

δ: 1.77–1.94(m, 2H), 2.00–2.12(m, 1H), 2.40–2.55(m, 1H), 3.25–3.45(m, 1H), 3.48–3.60(m, 1H), 4.25(t, J=8.0 Hz, 1H), 4.63(d, J=13.6 Hz, 1H), 4.74(d, J=13.6 Hz, 1H), 7.43(d, J=3.2 Hz, 1H), 7.47(d, J=3.2 Hz, 1H), 7.64–7.74(m, 2H), 7.66(d, J=8.0 Hz, 2H), 7.83(d, J=8.0 Hz, 2H), 7.97(d, J=9.2 Hz, 1H), 8.14(s, 1H), 8.23(s, 1H), 8.42(s, 1H), 8.47(s, 1H)

MS m/e (ESI) 494 (MH$^+$)

Example 110

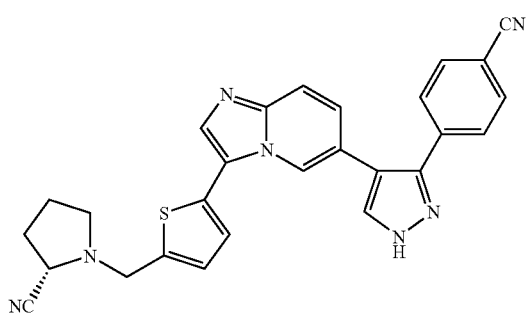

(2S)-1-{[(5-{6-[3-(4-Cyanophenyl)-1H-4-pyrazolyl]imidazo-[1,2-a]pyridin-3-yl}-2-thienyl)methyl]tetrahydro-1H-2-pyrrole carbonitrile 35 mg of the title compound was obtained as colorless crystals by the same method as in Example 84 from 110 mg (2S)-1-{[(5-{6-[3-(4-cyanophenyl)-1-trityl-1H-4-pyrazolyl]-imidazo[1,2-a]pyridin-3-yl}-2-thienyl)methyl]tetrahydro-1H-2-pyrrole carbonitrile obtained in Example 36.

$^1$H-NMR (CDCl$_3$)

δ: 1.90–2.05(m, 2H), 2.10–2.26(m, 2H), 2.63–2.71(m, 1H), 3.00–3.08(m, 1H), 3.83(dd, J=7.6, 2.8 Hz, 1H), 3.97(d, J=14.0 Hz, 1H), 4.08(d, J=14.0 Hz, 1H), 6.96(d, J=3.6 Hz, 1H), 7.03(d, J=3.6 Hz, 1H), 7.16(dd, J=9.2, 1.6 Hz, 1H), 7.62–7.68(m, 4H), 7.71(d, 9.2 Hz, 1H), 7.76(s, 1H), 7.79(s, 1H), 8.30(dd, J=1.6, 0.8 Hz, 1H)

MS m/e (ESI) 476 (MH$^+$), 449(M−26)

Example 111

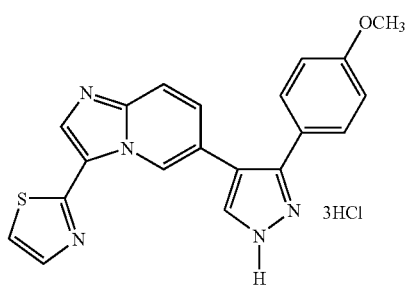

2-{6-[3-(4-Methoxyphenylphenyl)-1H-4-pyrazolyl]imidazo-[1,2-a]pyridin-6-yl}-1,3-thiazole trihydrochloride 120 mg 2-{6-[3-(4-methoxyphenylphenyl)-1-trityl-1H-4-pyrazolyl]imidazo[1,2-a]pyridin-3-yl}-1,3-thiazole was obtained as a colorless amorphous by the same reaction as in Example 29 from 50 mg of 2-(6-bromoimidazo[1,2-a]pyridin-3-yl)-1,3-thiazole (compound in Production Example 57) and 110 mg of 3-(4-methoxyphenyl)-1-trityl-1H-4-pyrazolylboronic acid (compound in Production Example 27). The product was subjected to deprotection of the trityl group and converted into the corresponding hydrochloride by the same method as in Example 79, to give 37 mg of the title compound as colorless crystals.

$^1$H-NMR (DMSO-$d_6$)

δ: 3.75(s, 3H), 6.95(d, J=8.6 Hz, 2H), 7.39(d, J=8.6 Hz, 2H), 7.85(d, J=3.2 Hz, 1H), 7.86(d, J=9.2 Hz, 1H), 7.90(d, J=3.2 Hz, 1H), 7.98(d, J=9.2 Hz, 1H), 8.09(s, 1H), 8.89(s, 1H), 9.72(s, 1H)

MS m/e(ESI)374(MH$^+$)

Example 112

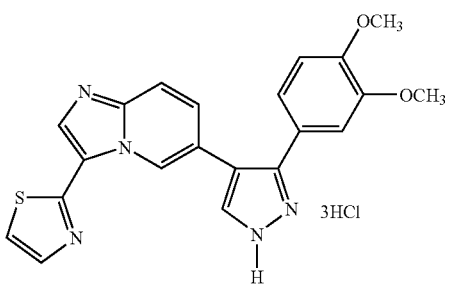

2-{6-[3-(3,4-Dimethoxyphenylphenyl)-1H-4-pyrazolyl]imidazo-[1,2-a]pyridin-3-yl}-1,3-thiazole trihydrochloride 50 mg of 2-(6-bromoimidazo[1,2-a]pyridin-3-yl)-1,3-thiazole (compound in Production Example 57) and 110 mg of 3-(3,4-dimethoxyphenyl)-1-trityl-1H-4-pyrazolylboronic acid (compound in Production Example 29) were reacted in the same manner as in Example 29, to give 85 mg 2-{6-[3-(3,4-dimethoxyphenylphenyl)-1-trityl-1H-4-pyrazolyl]imidazo-[1,2-a]pyridin-3-yl}-1,3-thiazole as a colorless amorphous. This product was subjected to deprotection of the trityl group and converted into the corresponding hydrochloride by the same method as in Example 79, to give 32 mg of the title compound as colorless crystals.

$^1$H-NMR (DMSO-$d_6$)

δ: 3.62(s, 3H), 3.76(s, 3H), 6.95(s, 2H), 7.07(s, 1H), 7.83(d, J=3.2 Hz, 1H), 7.90(d, J=3.2 Hz, 1H), 7.91(dd, J=1.6, 9.2 Hz, 1H), 7.98(d, J=9.2 Hz, 1H), 8.11(s, 1H), 8.88(s, 1H), 9.73(s, 1H)

MS m/e(ESI)404(MH$^+$)

Example 113

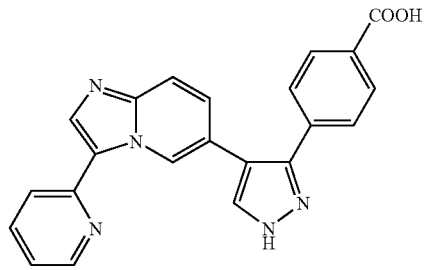

4-{4-[3-(2-Pyridyl)imidazo[1,2-a]pyridin-6-yl]-1H-3-pyrazolyl} benzoic acid 20 mg of the title compound was obtained as colorless crystals in the same manner as in Example 84 from 40 mg 4-{4-[3-(2-pyridyl)imidazo[1,2-a]pyridin-6-yl]-1-trityl-1H-3-pyrazolyl} benzoic acid obtained in Example 46.

$^1$H-NMR (DMSO-$d_6$)

δ: 7.18(dd, J=6.0, 5.2 Hz, 1H), 7.28(brd, J=8.4 Hz, 1H), 7.37(d, J=8.0 Hz, 2H), 7.65(d, J=9.6 Hz, 1H), 7.82(m, 4H), 7.93(d, J=8.0 Hz, 1H), 8.35(s, 1H), 8.42(d, J=4.4 Hz, 1H), 9.88(brs, 1H)

Example 114

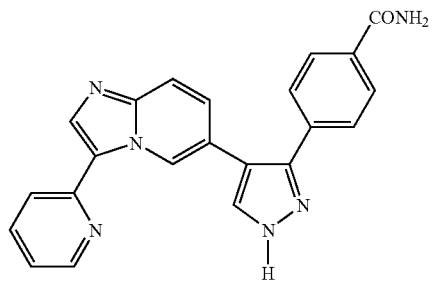

4-{4-[3-(2-Pyridyl)imidazo[1,2-a]pyridin-6-yl]-1H-3-pyrazolyl} benzamide 19 mg of the title compound was obtained as white solid in the same manner as in Example 84 from 112 mg 4-{4-[3-(2-pyridyl)imidazo[1,2-a]pyridin-6-yl]-1-trityl-1H-3-pyrazolyl) benzamide obtained in Example 47.

$^1$H-NMR (DMSO-$d_6$)

δ: 7.10(ddd, J=5.2, 0.8,0.8 Hz, 1H), 7.33(m, 2H), 7.55(d, J=8.4 Hz, 2H), 7.68(dd, J=9.6, 0.8 Hz, 1H), 7.83(m, 3H), 7.95(d, J=8.4 Hz, 2H), 8.35(d, J=4.4 Hz, 1H), 8.37(s, 1H), 9.87(brs, 1H)

Example 115

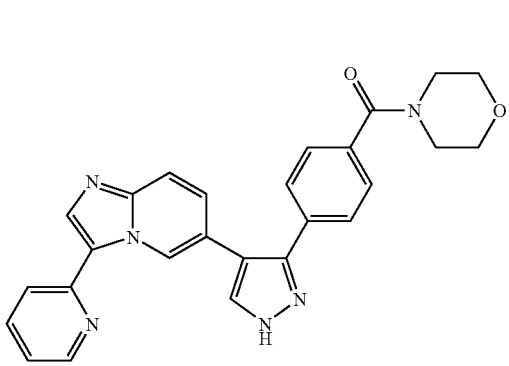

Morpholino(4-{4-[3-(2-pyridyl)imidazo[1,2-a]pyridin-6-yl]-1H-3-pyrazolyl}phenyl)methanone 21 mg of the title compound was obtained as a white solid from 50 mg morpholino(4-{4-[3-(2-pyridyl)imidazo[1,2-a]-pyridin-6-yl]-1-trityl-1H-3-pyrazolyl}phenyl)methanone obtained in Example 48.

$^1$H-NMR (CDCl$_3$)

δ: 7.10(ddd, J=5.2, 0.8,0.8 Hz, 1H), 7.33(m, 2H), 7.55(d, J=8.4 Hz, 2H), 7.68(dd, J=9.6, 0.8 Hz, 1H), 7.83(m, 3H), 7.95(d, J=8.4 Hz, 2H), 8.35(d, J=4.4 Hz, 1H), 8.37(s, 1H), 9.87(brs, 1H)

Example 116

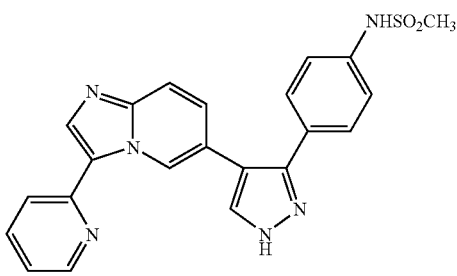

N-(4-{4-[3-(2-Pyridyl)imidazo[1,2-a]pyridin-6-yl]-1H-3-pyrazolyl}phenyl) methane sulfonamide 5.2 mg of the title compound was obtained as a white solid in the same manner as in Example 84 from 14 mg N-(4-{4-[3-(2-pyridyl)imidazo[1,2-a]pyridin-6-yl]-1-trityl-1H-3-pyrazolyl}phenyl)methane sulfonamide obtained in Example 48.

$^1$H-NMR (CDCl$_3$)

δ: 3.30(s, 3H), 7.08 (q, J=4.4 Hz, 1H), 7.13(dd, J=9.2, 1.2 Hz, 1H), 7.26(d, J=8.0 Hz, 2H), 7.61(d, J=8.0 Hz, 2H), 7.67(m, 2H), 7.75(s, 1H), 8.10(s, 1H), 8.48(d, J=4.8 Hz, 1H), 9.98(brs, 1H)

Example 117

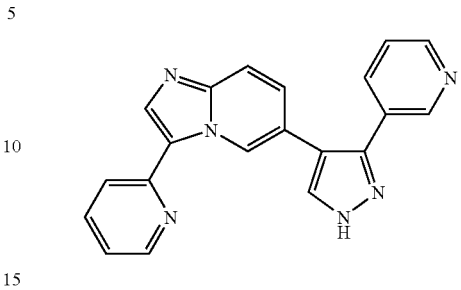

3-(2-Pyridyl)-6-[3-(3-pyridyl)-1H-4-pyrazolyl]imidazo-[1,2-a]pyridine 3-(2-Pyridyl)-6-[3-(3-pyridyl)-1-trityl-1H-4-pyrazolyl] imidazo[1,2-a]pyridine, obtained in the same manner as in Example 29 by reacting 55 mg 6-bromo-3-(2-pyridyl)imidazo[1,2-a]pyridine obtained in Production Example 63 with 173 mg 3-(3-pyridyl)-1-trityl-1H-4-pyrazolylboronic acid, was subjected to deprotection of the trityl group in the same manner as in Example 84, to give 36 mg of the title compound as colorless crystals.

$^1$H-NMR (CDCl$_3$)

δ: 7.13(m, 1H), 7.20(dd, J=9.2, 1.6 Hz, 1H), 7.27(m, 1H), 7.67(d, J=9.2, 0.8 Hz, 1H), 7.71(m, 2H), 7.84(dt, J=8.0, 2.0 Hz, 1H), 7.86(s, 1H), 8.15(s, 1H), 8.45(m, 1H), 8.59(dd, J=4.8, 1.6 Hz, 1H), 8.87(d, J=1.6 Hz, 1H), 9.98(s, 1H)

Example 118

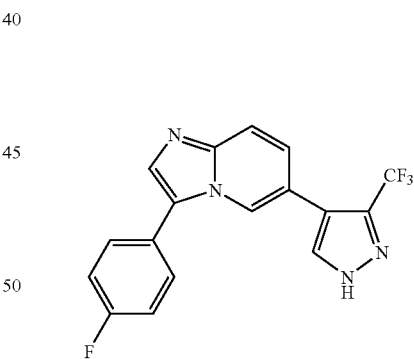

3-(4-Fluorophenyl)-6-(3-trifluoromethyl-1H-4-pyrazolyl)-imidazo[1,2-a]pyridine 30 mg of the title compound was obtained as colorless crystals in the same manner as in Example 84 from 86 mg 3-(4-fluorophenyl)-6-(3-trifluoromethyl-1-trityl-1H-4-pyrazolyl)imidazo[1,2-a]pyridine obtained in Example 8.

$^1$H-NMR (DMSO-d$_6$)

δ: 7.37(m, 3H), 7.73(m, 4H), 8.33(s, 1H), 8.43(s, 1H), 13.85(brs, 1H)

Example 119

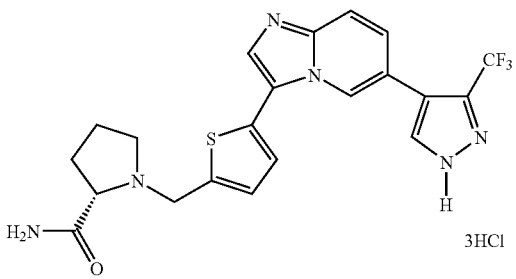

3HCl (2S)-1-({5-[6-(3-Trifluoromethyl-1H-4-pyrazolyl)imidazo-[1,2-a]pyridin-3-yl]-2-thienyl}methyl)tetrahydro-1H-2-pyrrole carboxyamide trihydrochloride 77 mg of the title compound was obtained as colorless crystals by the same method as in Example 67 from 130 mg (2S)-1-({5-[6-(3-trifluoromethyl-1-trityl-1H-4-pyrazolyl)-imidazo[1,2-a]pyridin-3-yl]-2-thienyl}methyl)tetrahydro-1H-2-pyrrole carboxyamide obtained in Example 37.

$^1$H-NMR (DMSO-$d_6$)

δ: 1.80–1.97(m, 2H), 2.00–2.14(m, 1H), 2.40–2.50(m, 1H), 3.23–3.62 (m, 2H), 4.16–4.24(m, 1H), 4.63(d, J=13.6 Hz, 1H), 4.73(d, J=13.6 Hz, 1H), 7.46(d, J=3.6 Hz, 1H), 7.58(d, J=3.6 Hz, 1H), 7.65–7.76(m, 2H), 7.96(d, J=9.2 Hz, 1H), 8.02(s, 1H), 8.21(s, 1H), 8.406(s, 1H), 8.60(s, 1H)

MS m/e (ESI) 461 (MH$^+$)

Example 120

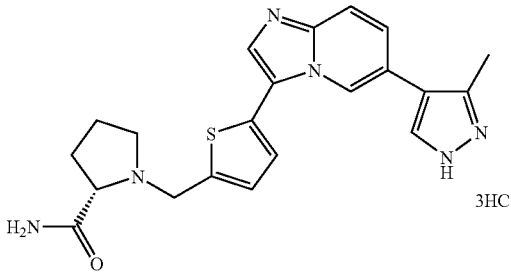

3HCl (2S)-1-({5-[6-(3-Methyl-1H-4-pyrazolyl)imidazo[1,2-a]-pyridin-3-yl]-2-thienyl}methyl)tetrahydro-1H-2-pyrrole carboxyamide trihydrochloride 146 mg (2S)-1-({5-[6-(3-methyl-1-trityl-1H-4-pyrazolyl) imidazo[1,2-a]pyridin-3-yl]-2-thienyl}methyl)-tetrahydro-1H-2-pyrrole carboxyamide (film) was obtained in the same manner as in Example 29 from 110 mg 3-methyl-1-trityl-1H-4-pyrazolylboronic acid (compound in Production Example 30) and 82 mg (2S)-1-{[5-(6-bromoimidazo[1,2-a]pyridin-3-yl)-2-thienyl]methyl}-tetrahydro-1H-2-pyrrole carboxyamide (compound in Production Example 61). The product was subjected to deprotection of the trityl group in the same manner as in Example 79, to give 74 mg of the title compound as colorless crystals.

$^1$H-NMR (DMSO-$d_6$)

δ: 1.0–1.98(m, 2H), 2.02–2.17(m, 1H), 2.42(s, 3H), 3.03–3.70(m, 3H), 4.26(t, J=8.0 Hz, 1H), 4.67(d, J=13.6 Hz, 1H), 4.78(d, J=13.6 Hz, 1H), 7.51(d, J=3.6 Hz, 1H), 7.66–7.72(m, 2H), 8.00–8.12(m, 4H), 8.40(s, 1H), 8.58(s, 1H)

MS m/e (ESI) 407 (MH$^+$)

Example 121

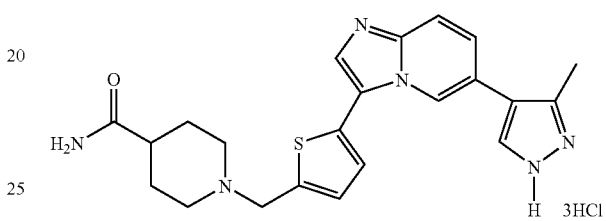

3HCl 1-({5-[6-(3-Methyl-1H-4-pyrazolyl)imidazo[1,2-a]pyridin-3-yl]-2-thienyl}methyl)-4-piperidine carboxyamide trihydrochloride 33 mg of the title compound was obtained as colorless crystals in the same manner as in Example 79 from 125 mg 1-({5-[6-(3-methyl-1-trityl-1H-4-pyrazolyl)imidazo[1,2-a]-pyridin-3-yl]-2-thienyl}methyl)-4-piperidine carboxyamide obtained in Example 39.

MS m/e (ESI) 421 (MH$^+$)

Example 122

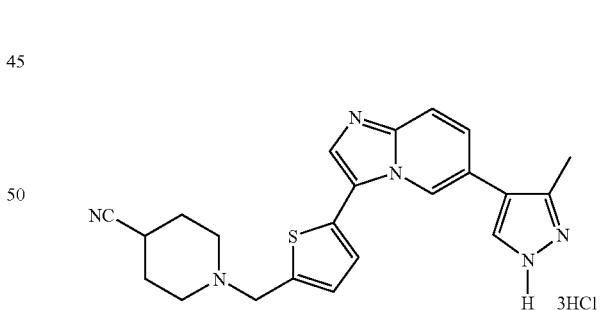

3HCl 1-({5-[6-(3-Methyl-1H-4-pyrazolyl)imidazo[1,2-a]pyridin-3-yl]-2-thienyl}methyl)-4-piperidine carbonitrile trihydrochloride 35 mg of the title compound was obtained as colorless crystals in the same manner as in Example 79 from 100 mg 1-({5-[6-(3-methyl-1-trityl-1H-4-pyrazolyl)imidazo[1,2-a]-pyridin-3-yl}-2-thienyl}methyl)-4-piperidine carbonitrile obtained in Example 40.

MS m/e (ESI) 403 (MH$^+$)

Example 123

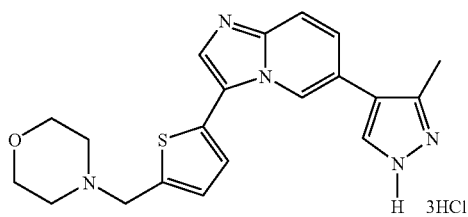

4-({5-[6-(3-Methyl-1H-4-pyrazolyl)imidazo[1,2-a]pyridin-3-yl]-2-thienyl}methyl)morpholine trihydrochloride 112 mg of the title compound was obtained as colorless crystals in the same manner as in Example 79 from 190 mg 4-({5-[6-(3-methyl-1-trityl-1H-4-pyrazolyl)imidazo[1,2-a]pyridin-3-yl]-2-thienyl}methyl)morpholine obtained in Example 38.

$^1$H-NMR (DMSO-$d_6$)

δ: 2.43(s, 3H), 3.05–3.20(m, 2H), 3.30–3.40(m, 2H), 3.80–4.05(m, 4H), 4.68(s, 2H), 7.64(d, J=3.6 Hz, 1H), 7.74(d, J=3.6 Hz, 1H), 8.06–8.12(m, 2H), 8.19(d, J=9.6 Hz, 1H), 8.54(s, 1H), 8.67(s, 1H)

Example 124

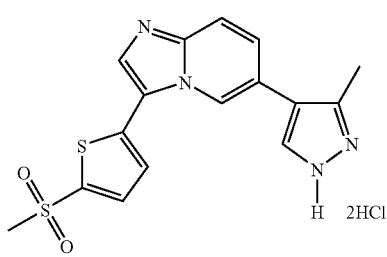

6-(3-Methyl-1H-4-pyrazolyl)-3-[5-(methylsulfonyl)-2-thienyl]imidazo[1,2-a]pyridine dihydrochloride 38 mg of the title compound was obtained as colorless crystals in the same manner as in Example 79 from 85 mg 6-(3-methyl-1-trityl-1H-4-pyrazolyl)-3-[5-(methylsulfonyl)-2-thienyl]imidazo[1,2-a]pyridine obtained in Example 41.

$^1$H-NMR (DMSO-$d_6$)

δ: 2.42(s, 3H), 3.46(s, 3H), 7.86(d, J=4.0 Hz, 1H), 8.00(d, J=4.0 Hz, 1H), 8.00–8.07(m, 3H), 8.49(s, 1H), 8.67(t, J=0.8 Hz, 1H)

MS m/e (ESI) 359 (MH$^+$)

Example 125

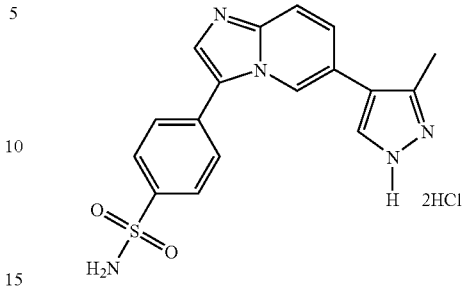

4-[6-(3-Methyl-1H-4-pyrazolyl)imidazo[1,2-a]pyridin-3-yl]-1-benzene sulfonamide dihydrochloride 40 mg of the title compound was obtained as colorless crystals in the same manner as in Example 79 from 68 mg 4-[6-(3-methyl-1-trityl-1H-4-pyrazolyl)imidazo[1,2-a]pyridin-3-yl]-1-benzene sulfonamide obtained in Example 42.

$^1$H-NMR (DMSO-$d_6$)

δ: 2.40(s, 3H), 7.58(s, 2H), 8.01–8.08(m, 5H), 8.11(d, J=9.2 Hz, 1H), 8.19(dd, J=9(dd, J=9.2, 1.6 Hz, 1H), 8.55(s, 1H), 8.69(s, 1H)

MS m/e (ESI) 354 (MH$^+$)

Example 126

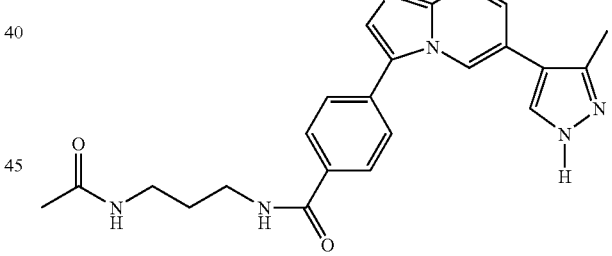

N1-[3-(Acetylamino)propyl]-4-[6-(3-methyl-1H-4-pyrazolyl)-imidazo[1,2-a]pyridin-3-yl]benzamide 12 mg of the title compound was obtained as colorless crystals in the same manner as in Example 89 from 65 mg N1-[3-(acetylamino)propyl]-4-[6-(3-methyl-1-trityl-1H-4-pyrazolyl)imidazo[1,2-a]pyridin-3-yl]benzamide obtained in Example 44.

$^1$H-NMR (DMSO-$d_6$)

δ: 1.64(quint, J=6.8 Hz, 2H), 1.79(s, 3H), 2.37(brs, 3H), 3.05–3.12(m, 2H), 3.24–3.32(m, 2H), 7.49(dd, J=9.2, 1.6 Hz, 1H), 7.70(d, J=9.2 Hz, 1H), 7.76(brs, 1H), 7.82(d, J=8.0 Hz, 2H), 7.85(s, 1H), 7.87(t, J=5.2 Hz, 1H), 7.99(d, J=8.0 Hz, 2H), 8.50(s, 1H), 8.55(t, J=5.6 Hz, 1H)

MS m/e (ESI) 417 (MH$^+$)

Example 127

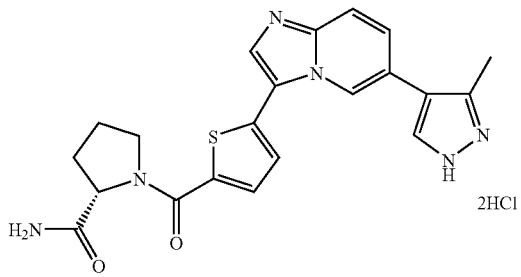

(2S)-1-({5-[6-(3-Methyl-1H-4-pyrazolyl)imidazo[1,2-a]-pyridin-3-yl}-2-thienyl}carbonyl)tetrahydro-1H-2-pyrrole carboxyamide trihydrochloride 140 mg of 6-(3-methyl-1-trityl-1H-4-pyrazolyl)-3-(1,1,1-tributylstannyl)imidazo[1,2-a]pyridine obtained in Production Example 48 and 45 mg of (2S)-1-{[5-(6-bromoimidazo-[1,2-a]pyridin-3-yl)-2-thienyl]carbonyl}tetrahydro-1H-2-pyrrole carboxyamide were reacted in the same manner as in Example 96, whereby 95 mg of (2S)-1-({5-[6-(3-methyl-1-trityl-1H-4-pyrazolyl)imidazo[1,2-a]pyridin-3-yl]-2-thienyl}carbonyl)-tetrahydro-1H-2-pyrrole carboxyamide was obtained as film. This product was subjected to deprotection of the trityl group in the same manner as in Example 79, to give 48 mg of the title compound as colorless crystals.

MS m/e (ESI) 421 (MH⁺)

Example 128

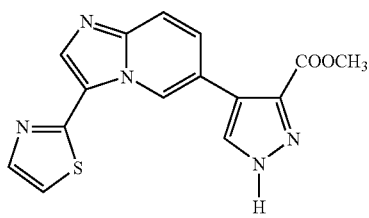

Methyl 4-[3-(1,3-thiazol-2-yl)imidazo[1,2-a]pyridin-6-yl]-1H-3-pyrazole carboxylate 18 mg of the title compound was obtained as a colorless solid in the same manner as in Example 84 from 50 mg methyl 4-[3-(1,3-thiazol-2-yl)imidazo[1,2-a]pyridin-6-yl]-1-trityl-1H-3-pyrazole carboxylate obtained in Example 45.

¹H-NMR (DMSO-d₆)

δ: 3.76(s, 3H), 7.53–7.70(m, 1H), 7.76(d, J=3.6 Hz, 1H), 7.79(s, 1H), 7.97(d, J=3.6 Hz, 1H), 8.18–8.28((m, 1H), 8.35(s, 1H), 9.73(s, 1H)

MS m/e (ESI) 326 (MH⁺)

Example 129

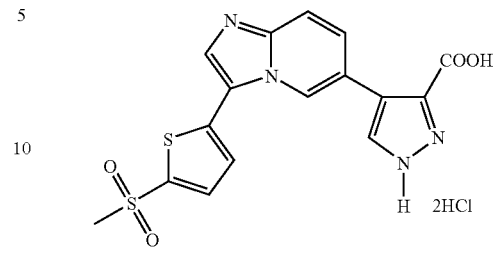

4-{3-(5-(Methylsulfonyl)-2-thienyl]imidazo[1,2-a]pyridin-6-yl}-1H-3-pyrazole carboxylate dihydrochloride 360 mg of methyl 4-{3-(5-(methylsulfonyl)-2-thienyl)-imidazo[1,2-a]pyridin-6-yl}-1-trityl-1H-3-pyrazole carboxylate was obtained as a colorless solid in the same manner as in Example 45 from 600 mg methyl 4-(4,4,5,5-tetramethyl-1,3,2-dioxaborolan-2-yl)-1-trityl 1H-pyrazole carboxylate and 214 mg 6-bromo-3-[5-(methylsulfonyl)-2-thienyl]imidazo[1,2-a]pyridine obtained in Production Example 59. The product was dissolved in 2 mL tetrahydrofuran and 1 mL methanol, 0.75 mL of 2 N sodium hydroxide was added thereto, and the mixture was stirred at room temperature for 1 hour. The reaction solution was neutralized with 0.75 mL of 2 N hydrochloric acid and extracted with ethyl acetate, and the solvent was evaporated, whereby 320 mg 4-{3-(5-(methylsulfonyl)-2-thienyl)imidazo[1,2-a)pyridin-6-yl}-1-trityl-1H-3-pyrazole carboxylic acid was obtained as colorless crystals. 34 mg 4-{3-[5-(methylsulfonyl)-2-thienyl]imidazo[1,2-a]pyridin-6-yl}-1-trityl-1H-3-pyrazole carboxylic acid was subjected to deprotection of the trityl group in the same manner as in Example 79, to give 15 mg of the title compound as colorless crystals.

¹H-NMR (DMSO-d₆)

δ: 3.46(s, 3H), 7.81(d, J=4.4 Hz, 1H), 7.96(d, J=9.2 Hz, 1H), 7.97(d, J=4.4 Hz, 1H), 8.03(d, 9.2 Hz, 1H), 8.22(s, 1H), 8.44(s, 1H), 9.18(s, 1H)

MS m/e (ESI) 389 (MH⁺)

Example 130

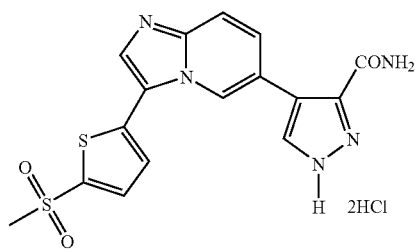

4-{3-[5-(Methylsulfonyl)-2-thienyl]imidazo[1,2-a]pyridin-6-yl}-1H-3-pyrazole carboxamide dihydrochloride A mixture of 40 mg 4-{3-[5-(methylsulfonyl)-2-thienyl]imidazo[1,2-a]pyridin-6-yl}-1-trityl-1H-3-pyrazole carboxylic acid, 37 mg 1-ethyl-3-(3-dimethylaminopropyl)-carbodiimide hydrochloride, 26 mg 1-oxybenzotriazole, 17 mg ammonium chloride, 0.077 mL triethylamine and 3 mL N,N-dimethylformamide was left overnight at room temperature. The solvent was evaporated, and the residue was purified by NH silica gel column chromatography (ethyl acetate/methanol) to give 22 mg 4-{3-[5-(methylsulfonyl)-2-thienyl]imidazo[1,2-a]-pyridin-6-yl}-1-trityl-1H-3-pyrazole carboxamide as colorless crystals. This product was subjected to deprotection of the trityl group in the same manner as in Example 79, to give 14 mg of the title compound as colorless crystals.

$^1$H-NMR (DMSO-$d_6$)

δ: 3.48(s, 3H), 7.51(s, 1H), 7.78(s, 1H), 7.88(d, J=4.0 Hz, 1H), 7.99(d, J=9.2 Hz, 1H), 8.00(d, J=4.0 Hz, 1H), 8.17(d, J=9.2 Hz, 1H), 8.44(s, 1H), 8.52(s, 1H), 9.60(s, 1H)

MS m/e (ESI) 388 (MH$^+$)

Example 131

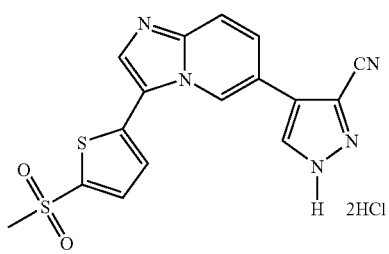

4-{3-[5-(Methylsulfonyl)-2-thienyl]imidazo[1,2-a]pyridin-6-yl}-1H-3-pyrazole carbonitrile dihydrochloride 78 mg 4-{3-[5-(methylsulfonyl)-2-thienyl]imidazo-[1,2-a]pyridin-6-yl}-1-trityl-1H-3-pyrazole carboxamide obtained in the process of synthesizing the compound in Example 130, 0.044 mL trifluoroacetic anhydride and 0.035 mL pyridine were reacted in the same manner as in Example 36, to give 72 mg 4-{3-[5-(methylsulfonyl)-2-thienyl]imidazo[1,2-a]-pyridin-6-yl}-1-trityl-1H-3-pyrazole carbonitrile as pale yellow crystals. This product was subjected to deprotection of the trityl group in the same manner as in Example 84, to give 22 mg of the title compound as pale yellow crystals.

$^1$H-NMR (DMSO-$d_6$)

δ: 3.41(s, 3H), 7.69(dd, J=9.2, 1.6 Hz, 1H), 7.74(d, J=4.0 Hz, 1H), 7.87(d, J=9.2 Hz, 1H), 7.92(d, 4.0 Hz, 1H), 8.07(s, 1H), 8.62(s, 1H), 8.92(s, 1H)

MS m/e (ESI) 370 (MH$^+$)

Example 132

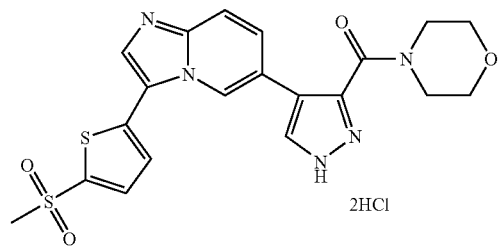

(4-{3-[5-(Methylsulfonyl)-2-thienyl]imidazo[1,2-a]pyridin-6-yl}-1H-3-pyrazole) (morpholino)methanone dihydrochloride 40 mg 4-{3-[5-(methylsulfonyl)-2-thienyl]imidazo-[1,2-a]pyridin-6-yl}-1-trityl-1H-3-pyrazole carboxylic acid obtained in the process of synthesizing the compound in Example 129, 6 µL morpholine, 13.4 mg 1-ethyl-3-(3-dimethylaminopropyl)carbodiimide hydrochloride, and 9.4 mg 1-oxybenzotriazole were stirred for 5 hours in 3 mL N,N-dimethylformamide. The solvent was evaporated, and the residue was purified by NH silica gel column chromatography (ethyl acetate/methanol) to give 30 mg (4-{3-[5-(methylsulfonyl)-2-thienyl]imidazo[1,2-a]pyridin-6-yl}-1-trityl-1H-3-pyrazole) (morpholino)methanone as pale brown crystals. This product was subjected to deprotection of the trityl group in the same manner as in Example 79, to give 18 mg of the title compound as colorless crystals.

$^1$H-NMR (DMSO-$d_6$)

δ: 3.40–3.80(m, 8H), 3.46(s, 3H), 7.76(d, J=3.6 Hz, 1H), 7.97(s, 2H), 8.03(d, J=3.6 Hz, 1H), 8.40(s, 1H), 8.48(s, 1H), 8.90(s, 1H)

MS m/e (ESI) 458 (MH$^+$)

Example 133

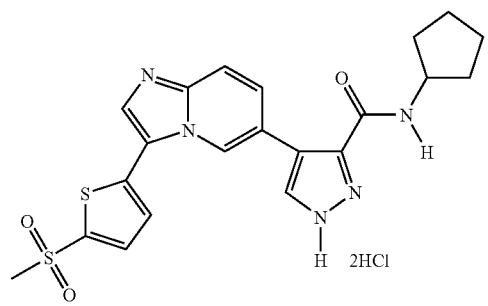

N3-Cyclopentyl-4-{3-[5-(methylsulfonyl)-2-thienyl]imidazo-[1,2-a]pyridin-6-yl}-1H-3-pyrazole carboxyamide dihydrochloride 40 mg N3-cyclopentyl-4-{3-[5-(methylsulfonyl)-2-thienyl]imidazo[1,2-a]pyridin-6-yl}-1-trityl-1H-3-pyrazole carboxyamide was obtained as a pale brown film by the same method as in Example 132 from 40 mg 4-{3-[5-(methylsulfonyl)-2-thienyl]imidazo[1,2-a]pyridin-6-yl}-1-trityl-1H-3-pyrazole carboxylic acid and 5.9 mg cyclopentylamine. The product was subjected to deprotection of the trityl group in the same manner as in Example 79, to give 22 mg of the title compound as colorless crystals.

$^1$H-NMR (DMSO-d$_6$)

δ: 1.44–1.60(m, 4H), 1.60–1.74(m, 2H), 1.78–1.92(m, 2H), 3.46(s, 3H), 4.14–4.24(m, 1H), 7.86(d, 4.0 Hz, 1H), 7.98(d, J=9.6 Hz, 1H), 8.01(d, J=4.0 Hz, 1H), 8.14(d, J=9.6 Hz, 1H), 8.25(d, J=7.6 Hz, 1H), 8.42(s, 1H), 8.50(s, 1H), 9.40(s, 1H)

MS m/e (ESI) 456 (MH$^+$)

Example 134

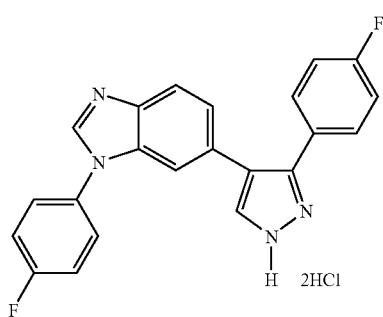

1-(4-Fluorophenyl)-6-[3-(4-fluorophenyl)-1H-4-pyrazolyl]-1H-benzo[d]imidazol dihydrochloride A solution mixture of 0.3 g 6-[3-(4-fluorophenyl)-1-trityl-1H-4-pyrazolyl]-1H-benzo[d]imidazole obtained in Production Example 65, 0.16 g 4-fluorophenylboronic acid, 0.16 g copper (II) acetate, 0.093 mL pyridine, 0.21 g of 4 Å molecular sieves and 6 mL dichloromethane were stirred at room temperature for 96 hours. The reaction mixture was filtered through Celite, the solvent was evaporated, and the residue was purified by silica gel chromatography (hexane/ethyl acetate) to give 33 mg 1-(4-fluorophenyl)-6-[3-(4-fluorophenyl)-1-trityl-1H-4-pyrazolyl]-1H-benzo[d]imidazol as colorless oil. This product was subjected to deprotection of the trityl group in the same manner as in Example 84 and then purified by NAM silica gel chromatography (NAM 200H silica gel, manufactured by NAM Kenkyusho Co., Ltd.) (ethyl acetate/methanol). The residue was dissolved in methanol, then 4 N hydrochloric acid/ethyl acetate was added thereto, and the solvent was evaporated, whereby 19 mg of the title compound was obtained as colorless crystals.

$^1$H-NMR (CD$_3$OD)

δ: 7.18–7.25(m, 2H), 7.40–7.53(m, 5H), 7.68–7.73(m, 3H), 7.78(dd, J=8.6, 1.4 Hz, 1H), 7.95(d, J=8.6 Hz, 1H), 8.17(s, 1H)

Example 135

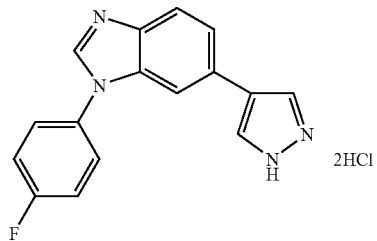

1-(4-Fluorophenyl)-6-(1H-4-pyrazolyl)-1H-benzo[d]imidazol dihydrochloride 1-(4-Fluorophenyl)-6-(1-trityl-1H-4-pyrazolyl)-1H-benzo[d]imidazole, 40 mg, was obtained by the same method as in Example 29 from 30 mg 1-(4-fluorophenyl)-6-iodo-1H-benzo[d]imidazole obtained in Production Example 70 and 47 mg 1-trityl-1H-4-pyrazolylboronic acid. The product was subjected to deprotection of the trityl group in the same manner as in Example 84 and then purified by NAM silica gel chromatography (ethyl acetate/methanol). The residue was dissolved in methanol, then 2 mL of 4 N hydrochloric acid/ethyl acetate was added thereto, and the solvent was evaporated, whereby 17 mg of the title compound was obtained as colorless crystals.

$^1$H-NMR (DMSO-d$_6$)

δ: 7.43–7.58(m, 4H), 7.67–7.78(m, 5H), 8.44(s, 1H)

MS m/e (ESI) 279 (MH$^+$)

Example 136

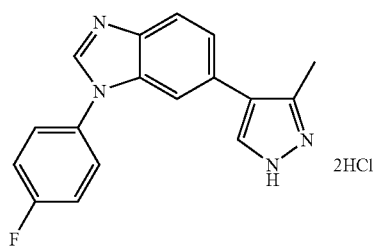

1-(4-Fluorophenyl)-6-(3-methyl-1H-4-pyrazolyl)-1H-benzo[d]-imidazole dihydrochloride 21 mg of the title compound was obtained as colorless scrystals by the same method as in Example 135 from 30 mg 1-(4-fluorophenyl)-6-iodo-1H-benzo[d]imidazole obtained in Production Example 70 and 49 mg 3-methyl-1-trityl-1H-4-pyrazolylboronic acid (compound in Production Example 30).

$^1$H-NMR (DMSO-d$_6$)

δ: 2.36(s, 3H), 7.52–7.60(m, 2H), 7.63(s, 1H), 7.70(dd, J=9.2, 1.2 Hz, 1H), 7.87–7.92(m, 2H), 7.94(d, J=9.2 Hz, 1H), 7.97(s, 1H), 9.65(s, 1H)

Example 137

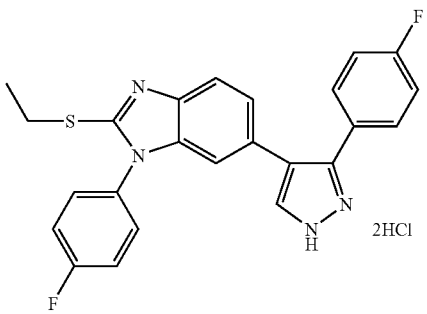

2-(Ethylsulfanyl)-1-(4-fluorophenyl)-6-[3-(4-fluorophenyl)-1H-4-pyrazolyl]-1H-benzo[d]imidazole dihydrochloride A solution mixture of 7.2 g 2-(ethylsulfanyl)-6-[3-(4-fluorophenyl)-1-trityl-1H-4-pyrazolyl]-1H-benzo[d]imidazole obtained in Production Example 73, 3.5 g 4-fluorophenylboronic acid, 3.4 g copper (II) acetate, 2.0 mL pyridine, 4.6 g of 4 Å molecular sieves and 140 mL dichloromethane was stirred at room temperature for 96 hours. The reaction mixture was filtered through Celite, the solvent was evaporated, and the residue was purified by silica gel chromatography (hexane/ethyl acetate) to give 1.06 g 2-(ethylsulfanyl)-1-(4-fluorophenyl)-6-[3-(4-fluorophenyl)-1-trityl-1H-4-pyrazolyl]-1H-benzo[d]imidazole as colorless crystals. 30 mg of 2-(ethylsulfanyl)-1-(4-fluorophenyl)-6-[3-(4-fluorophenyl)-1-trityl-1H-4-pyrazolyl]-1H-benzo[d]imidazole was subjected to deprotection of the trityl group and converted into the corresponding hydrochloride by the same method as in Example 67, to give 13 mg of the title compound as colorless crystals.

$^1$H-NMR (DMSO-d$_6$)

δ: 1.35(t, J=7.6 Hz, 3H), 3.28 (q, J=7.6 Hz, 2H), 6.83(s, 1H), 7.14–7.21(m, 3H), 733–7.42(m, 4H), 7.46–7.52(m, 2H), 7.57(d, J=8.4 Hz, 1H), 7.89(s, 1H)

MS m/e (ESI) 433 (MH$^+$)

Example 138

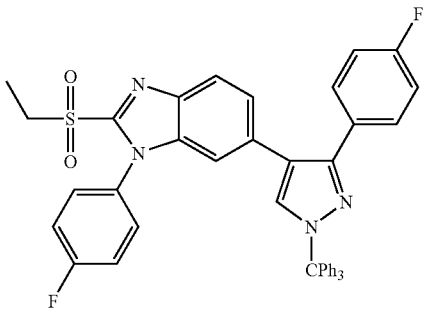

2-(Ethylsulfonyl)-1-(4-fluorophenyl)-6-[3-(4-fluorophenyl)-1-trityl-1H-4-pyrazolyl]-1H-benzo[d]imidazole 1.03 g 2-(ethylsulfanyl)-1-(4-fluorophenyl)-6-[3-(4-fluorophenyl)-1-trityl-1H-4-pyrazolyl]-1H-benzo[d]imidazole synthesized in the method described in Example 136 was dissolved in 17 mL dichloromethane, then 1.2 g 3-chloroperbenzoacetic acid was added thereto under ice-cooling, and the mixture was stirred at room temperature for 2 hours. An aqueous saturated sodium bicarbonate solution was added to the reaction solution which was then extracted with dichloromethane, and the organic layer was dried over sodium sulfate. The solvent was evaporated, and the residue was purified by silica gel chromatography (hexane/ethyl acetate) to give 1.05 g of the title compound as a pale brown amorphous.

$^1$H-NMR (DMSO-d$_6$)

δ: 1.23(t, J=7.6 Hz, 3H), 3.56 (q, J=7.6 Hz, 2H), 6.83(br, 1H), 7.08–7.18(m, 8H), 7.26–7.40(m, 11H), 7.50–7.56(m, 3H), 7.60–7.63(m, 1H), 7.66–7.71(m, 1H), 7.81–7.85(m, 1H), 7.86–7.90(m, 1H)

Example 139

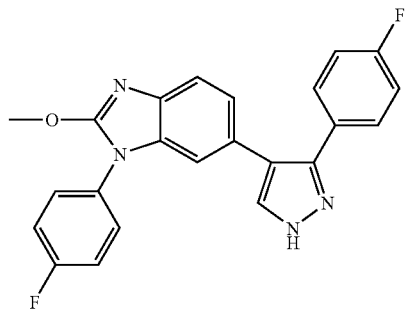

1-(4-Fluorophenyl)-6-[3-(4-fluorophenyl)-1H-4-pyrazolyl]-2-methoxy-1H-benzo[d]imidazole 50 mg 2-(ethylsulfonyl)-1-(4-fluorophenyl)-6-[3-(4-fluorophenyl)-1-trityl-1H-4-pyrazolyl]-1H-benzo[d]imidazole obtained in Example 138 was dissolved in 0.5 mL tetrahydrofuran and 3 mL methanol, then 28 mg sodium hydride was added thereto, and the mixture was heated for 3 hours under reflux under nitrogen atmosphere. After the reaction mixture was cooled, water and ethyl acetate were added thereto, and the organic layer was washed with brine and dried over sodium sulfate. The solvent was evaporated, and the residue was purified by silica gel chromatography (hexane/ethyl acetate) to give 1-(4-fluorophenyl)-6-[3-(4-fluorophenyl)-1-trityl-1H-4-pyrazolyl]-2-methoxy-1H-benzo[d]imidazole. This product was subjected to deprotection of the trityl group in the same manner as in Example 84 and then purified by NAM silica gel chromatography (ethyl acetate/methanol), to give 18 mg of the title compound as colorless crystals.

$^1$H-NMR (DMSO-d$_6$)

δ: 4.08(s, 3H), 6.84–6.88(m, 1H), 7.06–7.18(m, 2H), 7.20–7.52(m, 8H), 7.95(br, 1H)

MS m/e(ESI) 403(MH$^+$)

Example 140

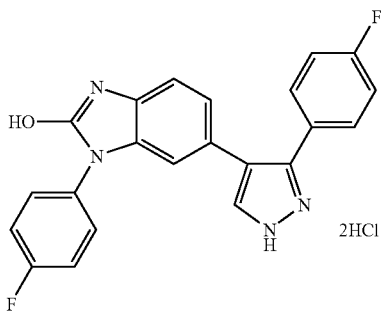

1-(4-Fluorophenyl)-6-[3-(4-fluorophenyl)-1H-4-pyrazolyl]-1H-benzo[d]imidazol-2-ol dihydrochloride 15 mg 1-(4-fluorophenyl)-6-[3-(4-fluorophenyl)-1H-4-pyrazolyl]-2-methoxy-1H-benzo [d] imidazole obtained in Example 139 was dissolved in methanol, then 2 mL of 4 N hydrochloric acid/ethyl acetate was added thereto, and the solvent was evaporated. The residue was crystallized from methanol/ether and then washed with ethyl acetate to give 12 mg of the title compound as colorless crystals.

$^1$H-NMR (DMSO-$d_6$)

δ: 6.70(s, 1H), 6.97–7.04(m, 2H), 7.16–7.29(m, 4H), 7.36–7.46(m, 4H), 7.84(s, 1H), 11.15(s, 1H)

MS m/e (ESI) 389 (MH$^+$)

Example 141

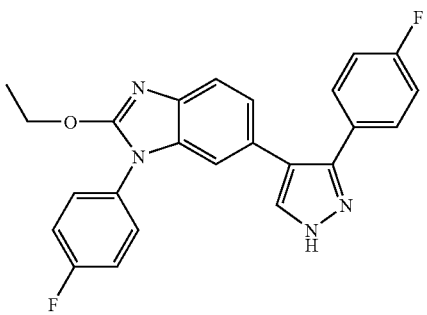

2-Ethoxy-1-(4-fluorophenyl)-6-[3-(4-fluorophenyl)-1H-4-pyrazolyl]-1H-benzo[d]imidazole 20 mg of the title compound was obtained as colorless crystals by the same method as in Example 139 from 50 mg 2-(ethylsulfonyl)-1-(4-fluorophenyl)-6-[3-(4-fluorophenyl)-1-trityl-1H-4-pyrazolyl]-1H-benzo[d]imidazole obtained in Example 138, 0.5 mL tetrahydrofuran, 3 mL ethanol and 28 mg sodium hydride.

$^1$H-NMR (DMSO-$d_6$)

δ: 1.34(t, J=7.2 Hz, 3H), 4.52 (q, J=7.2 Hz, 2H), 6.85–6.89(m, 1H), 7.06–7.18(m, 2H), 7.20–7.52(m, 8H), 7.95(br, 1H)

MS m/e(ESI) 417(MH$^+$)

Example 142

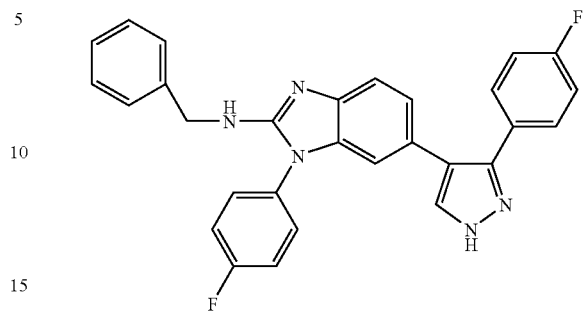

N2-Benzyl-1-(4-fluorophenyl)-6-[3-(4-fluorophenyl)-1H-4-pyrazolyl]-1H-benzo[d]imidazol-2-amine 1 mL benzyl amine was added to 40 mg 2-(ethylsulfonyl)-1-(4-fluorophenyl)-6-[3-(4-fluorophenyl)-1-trityl-1H-4-pyrazolyl]-1H-benzo[d]imidazole obtained in Example 138, and then stirred at 150° C. for 24 hours. The reaction product was purified by silica gel chromatography (hexane/ethyl acetate) to give 26 mg N2-benzyl-1-(4-fluorophenyl)-6-[3-(4-fluorophenyl)-1-trityl-1H-4-pyrazolyl]-1H-benzo[d]imidazol-2-amine. This product was subjected to deprotection of the trityl group in the same manner as in Example 84 and then purified by NAM silica gel chromatography (ethyl acetate/hexane), to give 18 mg of the title compound as colorless crystals.

$^1$H-NMR (DMSO-$d_6$)

δ: 4.49–4.53(m, 2H), 6.54–6.58(m, 1H), 6.90–7.02(m, 2H), 7.08–7.50(m, 14H)

MS m/e(ESI) 478 (MH$^+$)

Example 143

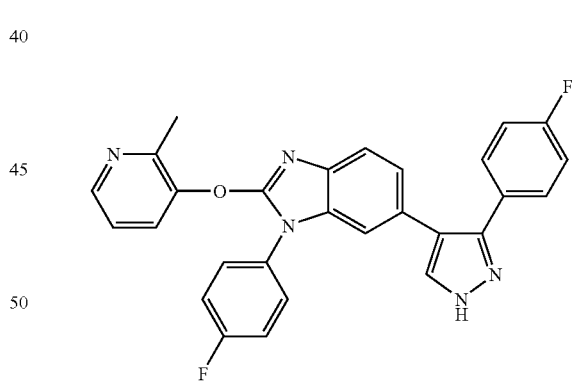

1-(4-Fluorophenyl)-6-[3-(4-fluorophenyl)-1H-4-pyrazolyl]-2-[(2-methyl-3-pyridyl)oxy]-1H-benzo[d]imidazole 40 mg 2-(ethylsulfonyl)-1-(4-fluorophenyl)-6-[3-(4-fluorophenyl)-1-trityl-1H-4-pyrazolyl]-1H-benzo[d]imidazole obtained in Example 138 was dissolved in 2 mL N,N-dimethylformamide, then 6.8 mg sodium hydride was added thereto and stirred for 20 minutes, and 3 mL 2-methyl-3-pyridinol was added thereto and stirred at 80° C. for 3 hours. Water was added thereto, and the reaction solution was extracted with ethyl acetate, and the organic layer was washed with water and brine and dried over sodium sulfate.

The solvent was evaporated, and the residue was purified by silica gel chromatography (hexane/ethyl acetate) to give 1-(4-fluorophenyl)-6-[3-(4-fluorophenyl)-1-trityl-1H-4-pyrazolyl]-2-[(2-methyl-3-pyridyl)oxy]-1H-benzo[d] imidazole. This product was subjected to deprotection of the trityl group by the same method as in Example 84 and then purified by NAM silica gel chromatography (ethyl acetate/methanol), to give 6 mg of the title compound as colorless crystals.

MS m/e (ESI) 480 (MH⁺)

Example 144

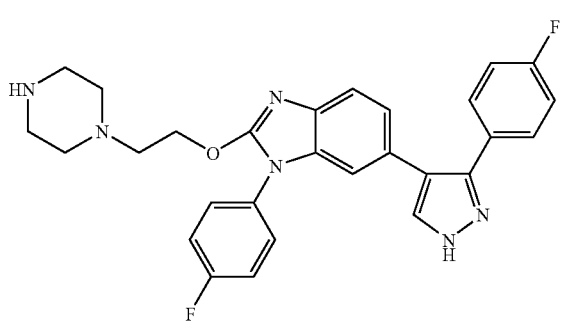

1-(4-Fluorophenyl)-6-[3-(4-fluorophenyl)-1H-4-pyrazolyl]-2-(2-piperazin-1-yl-ethoxy)-1H-benzo[d]imidazole 13 mg of the title compound was obtained as colorless crystals by the same procedure as in Example 143 from 50 mg 2-(ethylsulfonyl)-1-(4-fluorophenyl)-6-[3-(4-fluorophenyl)-1-trityl-1H-4-pyrazolyl]-1H-benzo[d]imidazole obtained in Example 138, 2 mL N,N-dimethylformamide, 8.5 mg sodium hydroxide and 28 mg 2-piperazin-1-yl-1-ethanol.

¹H-NMR (DMSO-d₆)
δ: 2.26–2.36(br, 4H), 2.57–2.68(m, 6H), 4.55–4.60(m, 2H), 6.88–6.91(m, 1H), 7.07–7.24(m, 3H), 7.27–7.52(m, 8H)

MS m/e(ESI) 501(MH⁺)

Example 145

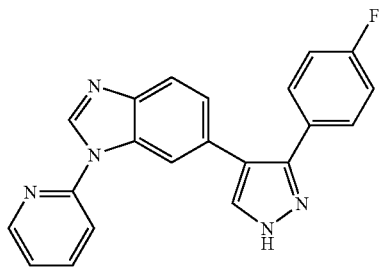

6-[3-(4-Fluorophenyl)-1H-4-pyrazolyl]-1-(2-pyridyl)-1H-benzo[d]imidazole 0.32 g 6-[3-(4-fluorophenyl)-1-trityl-1H-4-pyrazolyl]-1H-benzo[d]imidazole obtained in Production Example 65, 0.42 g potassium carbonate, and 1.73 mL 2-bromopyridine were stirred at 30° C. for 30 hours in 6 mL N,N-dimethylformamide. Water, an aqueous ammonium chloride solution, and ethyl acetate were added thereto, and the organic layer was washed with water and brine. The solvent was evaporated, and then the residue was purified by silica gel chromatography (hexane/ethyl acetate) to give 0.3 g 6-[3-(4-fluorophenyl)-1-trityl-1H-4-pyrazolyl]-1-(2-pyridyl)-1H-benzo[d]imidazole. This product was subjected to deprotection of the trityl group by the same method as in Example 84, and the resulting solid was purified by NAM silica gel chromatography (ethyl acetate/methanol), to give 51 mg of the title compound as colorless crystals.

¹H-NMR (DMSO-d₆)
δ: 7.10–7.30(m, 3H), 7.38–7.50(m, 4H), 7.71(d, J=8.0 Hz, 1H), 7.85(d, J=8.0 Hz, 1H), 7.98–8.05(m, 1H), 8.16(s, 1H), 8.46–8.52(m, 1H), 8.93(s, 1H)

MS m/e(ESI)356(MH⁺)

Example 146

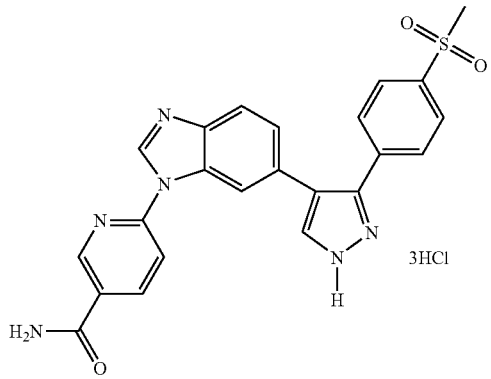

6-(6-{3-[4-(Methylsulfonyl)phenyl]-1H-4-pyrazolyl}-1H-benzo[d]imidazol-1-yl)nicotinamide trihydrochloride 0.2 g of the mixture of 6-(6-bromo-1H-benzo[d]imidazol-1-yl)nicotinic acid amide and 6-(5-bromo-1H-benzo[d]imidazol-1-yl)nicotinic acid amide as positional isomers in a ratio of 1:1, prepared from 5-bromo-1H-benzo[d]imidazole and 6-chloronicotinic acid amide by the same method as in Production Example 105, and 0.36 g 3-[4-(methylsulfanyl)phenyl]-1-trityl-1H-4-pyrazolylboronic acid (compound in Production Example 26), were reacted in the same manner as in Example 29, to give 0.39 g brown amorphous as a mixture of 6-(6-{3-[4-(methylsulfanyl)phenyl]-1-trityl-1H-4-pyrazolyl}-1H-benzo[d]imidazol-1-yl)nicotinamide and 6-(5-{3-[4-(methylsulfanyl)phenyl]-1-trityl-1H-4-pyrazolyl}-1H-benzo [d]imidazol-1-yl)nicotinamide. This product was dissolved in 10 mL tetrahydrofuran and 5 mL methanol, then a solution of 0.17 g oxone in 3 mL water was added thereto, and the mixture was stirred at room temperature for 2 hours. Water and an aqueous sodium thiosulfate solution were added thereto, the reaction solution was stirred for 0.5 hour and extracted with ethyl acetate, and the organic layer was washed with brine and dried over sodium sulfate. The solvent was evaporated, and then the residue was purified by NAM silica gel chromatography (dichloromethane/methanol) to separate the positional isomer to give 0.14 g 6-(6-{3-[4-(methylsulfinyl)phenyl]-1-trityl-1H-4-pyrazolyl}-1H-benzo[d]imidazol-1-yl)nicotinamide as a colorless amorphous. This product was dissolved in 6 mL tetrahydrofuran and 3 mL methanol, then a solution of 0.13 g oxone in 2 mL water was added thereto, and the mixture was stirred at room temperature for 2 hours. Water and an aqueous sodium thiosulfate solution were added thereto, the reaction solution was stirred for 0.5 hour and extracted with ethyl acetate, and the organic layer was washed with brine and dried over sodium sulfate. The solvent was removed, whereby 0.15 g 6-(6-{3-[4-(methylsulfonyl)phenyl]-1-trityl-1H-4-pyrazolyl}-1H-benzo-[d]imidazol-1-yl)nicotinamide was obtained as a colorless amorphous. This product was subjected to deprotection of the trityl group and converted into the corresponding hydrochloride by the same method as in Example 67, to give 62 mg of the title compound as colorless crystals.

¹H-NMR (DMSO-d$_6$)

δ: 3.23(s, 3H), 7.30–7.34(m, 1H), 7.64–7.70(m, 4H), 7.84–7.90(m, 2H), 8.04(s, 1H), 8.09(d, J=8.4 Hz, 1H), 8.34–8.38(m, 1H), 8.45–8.49(m, 1H), 9.05–9.07(m, 1H)

MS m/e (ESI) 459 (MH⁺)

Example 147

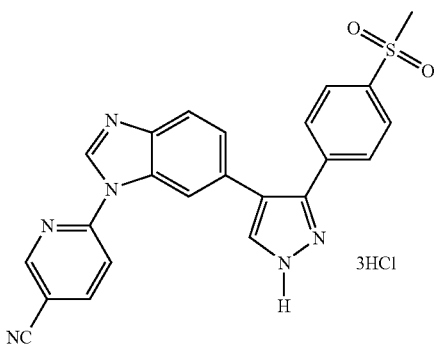

6-(6-{3-[4-(Methylsulfonyl)phenyl]-1H-4-pyrazolyl}-1H-benzo[d]imidazol-1-yl)-3-pyridyl cyanide trihydrochloride 0.2 g of the mixture of 6-(6-bromo-1H-benzo[d]imidazol-1-yl)-3-pyridyl cyanide and 6-(5-bromo-1H-benzo[d]imidazol-1-yl)-3-pyridyl cyanide as positional isomers in a ratio of 1:1, obtained in Production Example 105, and 0.38 g 3-[4-(methylsulfanyl)phenyl]-1-trityl-1H-4-pyrazolylboronic acid (compound in Production Example 26), were reacted in the same manner as in Example 29, and the isomers were separated by silica gel chromatography (ethyl acetate/methanol) to give 0.17 g 6-(6-{3-[4-(methylsulfanyl)phenyl]-1-trityl-1H-4-pyrazolyl-1H-benzo[d]imidazol-1-yl}-3-pyridyl cyanide as a colorless amorphous. This product was oxidized with oxone by the same manner as in Example 29, to give 0.17 g of 6-(6-{3-[4-(methylsulfonyl)phenyl]-1-trityl-1H-4-pyrazolyl}-1H-benzo[d]imidazol-1-yl)-3-pyridyl cyanide as a pale brown amorphous. This product was subjected to deprotection of the trityl group and converted into the corresponding hydrochloride by the same method as in Example 67, to give 42 mg of the title compound as colorless crystals.

¹H-NMR (DMSO-d$_6$)

δ: 3.21(s, 3H), 7.32(dd, J=8.4, 1.6 Hz, 1H), 7.64–7.70(m, 2H), 7.76(d, J=8.4 Hz, 1H), 7.86–7.89(m, 2H), 8.05(s, 1H), 8.16(dd, J=8.8, 0.8 Hz, 1H), 8.32(d, J=1.6 Hz, 1H), 8.53(dd, J=8.8, 2.2 Hz, 1H), 8.88(dd, J=2.2, 0.8 Hz, 1H), 9.25(s, 1H)

MS m/e (ESI) 441 (MH⁺)

Example 148

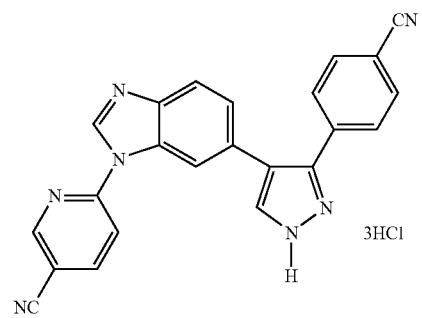

6-{6-[3-(4-Cyanophenyl)-1H-4-pyrazolyl]-1H-benzo[d]-imidazol-1-yl}nicotinonitrile trihydrochloride The mixture of 6-(6-bromo-1H-benzo[d]imidazol-1-yl)-3-pyridyl cyanide and 6-(5-bromo-1H-benzo[d]imidazol-1-yl)-3-pyridyl cyanide as positional isomers in a ratio of 1:1, obtained in Production Example 105, and 0.32 g 3-(4-cyanophenyl)-1-trityl-1H-4-pyrazolylboronic acid (compound in Production Example 32), were reacted in the same manner as in Example 29, and the isomers were separated by silica gel chromatography (hexane/ethyl acetate) to give 6-{6-[3-(4-cyanophenyl)-1-trityl-1H-4-pyrazolyl]-1H-benzo[d]imidazol-1-yl}nicotinonitrile as a colorless amorphous. This product was subjected to deprotection of the trityl group and converted into the corresponding hydrochloride by the same method as in Example 67, to give 52 mg of the title compound as colorless crystals.

¹H-NMR (DMSO-d$_6$)

δ: 7.27(dd, J=8.0, 1.4 Hz, 1H), 7.59(d, J=8.6 Hz, 2H), 7.75(d, J=8.0 Hz, 1H), 7.79(d, J=8.6 Hz, 2H), 8.03(s, 1H), 8.18(d, J=8.6 Hz, 1H), 8.34(d, J=1.4 Hz, 1H), 8.55(dd, J=8.6, 2.4 Hz, 1H), 8.91(d, J=2.4 Hz, 1H), 9.26(s, 1H)

MS m/e(ESI)388(MH⁺)

Example 149

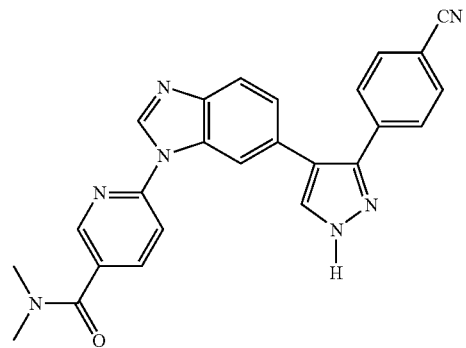

N3,N3-Dimethyl-6-{6-[3-(4-cyanophenyl)-1H-4-pyrazolyl]-1H-benzo[d]imidazol-1-yl}nicotinamide trihydrochloride A mixture of N3,N3-dimethyl-6-(6-bromo-1H-benzo[d]-imidazol-1-yl)nicotinamide and N3,N3-dimethyl-6-(5-bromo-1H-benzo[d]imidazol-1-yl)|nicotinamide as positional isomers in a ratio of 1:1, synthesized in the same manner as in Production Example 105 from N3,N3-dimethyl-6-chloronictinamide and 5-bromo-1H-benzo[d]imidazole, and 0.24 g 3-(4-cyanophenyl)-1-trityl-1H-4-pyrazolylboronic acid (compound in Production Example 32), were reacted in the same manner as in Example 29, to give a mixture of N3,N3-dimethyl-6-{6-[3-(4-cyanophenyl)-1H-4-pyrazolyl]-1-trityl-1H-benzo[d]imidazol-1-yl}-nicotinamide and N3,N3-dimethyl-6-{5-[3-(4-cyanophenyl)-1H-4-pyrazolyl]-1-trityl-1H-benzo[d]imidazol-1-yl}-nicotinamide as a colorless amorphous. This product was subjected to deprotection of the trityl group in the same manner as in Example 84, and then the isomers were separated by reverse phase liquid chromatography (WAKO PAK ODS column; eluent, water/acetonitrile/0.1% trifluoroacetic acid). 4 N hydrochloric acid/ethyl acetate was added to a methanol solution of the product and then the solvent was evaporated, to give the product as hydrochloride, whereby 42 mg of the title compound was obtained as colorless crystals.

$^1$H-NMR (DMSO-$d_6$)

δ: 2.98(s, 3H), 3.02(s, 3H), 7.33(d, J=8.8 Hz, 1H), 7.61(d, J=8.4 Hz, 0.2H), 7.76–7.83(m, 3H), 8.02(d, J=8.4 Hz, 1H), 8.07(s, 1H), 8.14(dd, J=8.4, 2.2 Hz, 1H), 8.28(s, 1H,), 8.53(d, J=2.2 Hz, 1H), 9.44(s, 1H)

MS m/e(ESI) 434 (MH$^+$)

Example 150

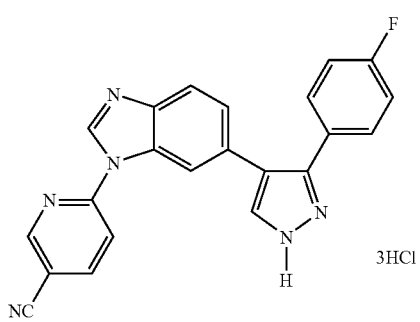

6-{6-[3-(4-Fluorophenyl)-1H-4-pyrazolyl]-1H-benzo[d]-imidazol-1-yl}-3-pyridylcyanide trihydrochloride The mixture (1.97 g) of 6-(6-bromo-1H-benzo[d]imidazol-1-yl)-3-pyridyl cyanide and 6-(5-bromo-1H-benzo[d]imidazol-1-yl)-3-pyridyl cyanide as positional isomers in a ratio of 1:1, obtained in Production Example 105, and 3.54 g 3-(4-fluorophenyl)-1-trityl-1H-4-pyrazolylboronic acid (compound in Example 25), were reacted in the same manner as in Example 29, and the isomers were separated by silica gel chromatography (hexane/ethyl acetate) to give 1.94 g 6-{6-[3-(4-fluorophenyl)-1-trityl-1H-4-pyrazolyl]-1H-benzo[d]imidazol-1-yl}-3-pyridyl cyanide as a pale brown amorphous. This product was subjected to deprotection of the trityl group and converted into the corresponding hydrochloride by the same method as in Example 67, to give 0.95 g of the title compound as colorless crystals.

$^1$H-NMR (DMSO-$d_6$)

δ: 7.16–7.24(m, 2H), 7.33(dd, J=1.6 Hz, J=8.2 Hz, 1H), 7.40–7.46(m, 2H), 7.75(d, J=8.2 Hz, 1H), 8.00(s, 1H), 8.19(d, J=8.6 Hz, 1H), 8.33(d, J=1.6 Hz, 1H), 8.58(dd, J=8.6, 2.2 Hz, 1H), 8.92(d, J=2.2 Hz, 1H), 9.47(s, 1H)

MS m/e(ESI)381(MH$^+$)

Example 151

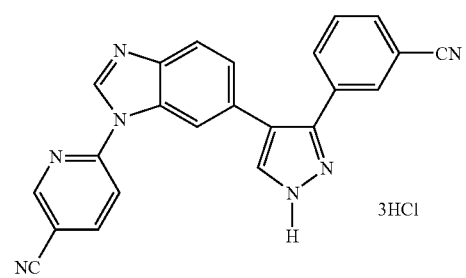

6-{6-[3-(3-Cyanophenyl)-1H-4-pyrazolyl]-1H-benzo[d]imidazol-1-yl}nicotinonitrile trihydrochloride 34 mg of the title compound was obtained as colorless crystals by the same procedure as in Example 150 from 0.15 g sof the mixture of 6-(6-bromo-1H-benzo[d]imidazol-1-yl)-3-pyridyl cyanide and 6-(5-bromo-1H-benzo[d]imidazol-1-yl)-3-pyridyl cyanide as positional isomers in a ratio of 1:1, obtained in Production Example 105, and 0.27 g 3-(3-cyanophenyl)-1-trityl-1H-4-pyrazolylboronic acid (compound in Production Example 33).

$^1$H-NMR (DMSO-$d_6$)

δ: 7.20–7.30(m, 1H), 7.50–7.58(m, 1H), 7.67–7.88(m, 4H), 8.03(s, 1H), 8.16(d, J=8.8 Hz, 1H), 8.32(s, 1H), 8.50–8.59(m, 1H), 8.89(s, 1H), 9.19(s, 1H)

Example 152

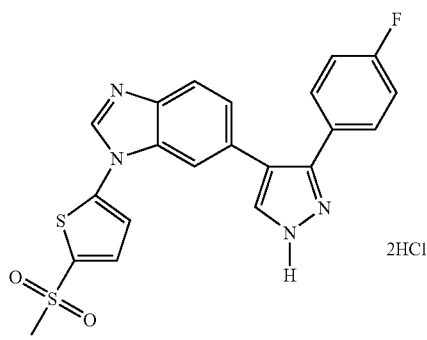

5-{6-[3-(4-Fluorophenyl)-1H-4-pyrazolyl]-1H-benzo[d]-imidazol-1-yl}-2-thienylmethylsulfone dihydrochloride 24.5 mg of the title compound was obtained as colorless crystals by the same procedure as in Example 150 from 0.14 g mixture of 5-(6-bromo-1H-benzo[d]imidazol-1-yl)-2-thienyl methyl sulfone and 5-(5-bromo-1H-benzo[d]imidazol-1-yl)₂-thienyl methyl sulfone as positional isomers in a ratio of 1:1 and 0.23 g 3-(4-fluorophenyl)-1-trityl-1H-4-pyrazolylboronic acid (compound in Production Example 25).

¹H-NMR (DMSO-d₆)

δ: 3.42(s, 3H), 7.16–7.23(m, 2H), 7.32(dd, J=1.2 Hz, J=8.4 Hz, 1H), 7.40–7.46(m, 2H), 7.57(d, J=4.0 Hz, 1H), 7.58(s, 1H), 7.77(d, J=8.4 Hz, 1H), 7.87(d, J=4.0 Hz, 1H), 8.03(s, 1H), 9.00(s, 1H)

MS m/e(ESI) 439 (MH⁺)

Example 153

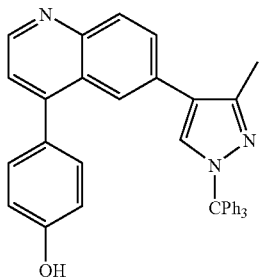

4-[6-(3-Methyl-1-trityl-1H-4-pyrazolyl)-4-quinolyl]phenol

A mixture of 180 mg 6-(3-methyl-1-trityl-1H-pyrazolyl)-4-quinolyl trifluoromethane sulfonate obtained in Production Example 91, 80 mg 4-(4,4,5,5-tetramethyl-1,3,2-dioxaborolan-2-yl)phenol, 83 mg potassium carbonate, 18 mg tetrakis(triphenylphosphine)palladium and 15 mL 1,2-dimethoxyethane was heated overnight under reflux in a stream of nitrogen. The reaction solution was cooled, then ethyl acetate and water were added thereto, and the organic layer was separated, washed with brine and dried over anhydrous sodium sulfate. The drying agent was filtered off, the filtrate was evaporated, and the residue was purified by silica gel column chromatography (hexane/ethyl acetate), to give 9.6 g of the title compound as a colorless amorphous.

¹H-NMR (CDCl₃)

δ: 2.35(s, 3H), 7.20(m, 7H), 7.31(m, 9H), 7.46(m, 3H), 7.61(m, 2H), 7.72(dd, J=8.8, 2.0 Hz, 1H), 7.75(d, J=2.0 Hz, 1H), 8.13(D, J=8.8 Hz, 1H), 8.90(d, J=4.4 Hz, 1H)

Example 154

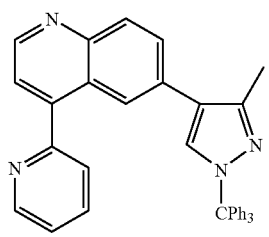

6-(3-Methyl-1-trityl-1H-pyrazolyl)-4-(2-pyridyl)quinoline

While a mixture of 67 mg 6-(3-methyl-1-trityl-1H-4-pyrazolyl)-4-quinolyl trifluoromethane sulfonate obtained in Production Example 91, 74 mg 2-(tri-n-butylstannyl)pyridine and 10 mL xylene was stirred in a stream of nitrogen, 10 mg tetrakis(triphenylphosphine)palladium was added thereto, and then the mixture was stirred at 120° C. for 5 hours. Further, 30 mg 2-(tri-n-butylstannyl)pyridine and 5 mg tetrakis (triphenylphosphine)palladium were added thereto, and the reaction mixture was stirred for 3 hours under the same conditions. The reaction solution was cooled, then ethyl acetate and anhydrous sodium sulfate were added thereto, and the mixture was stirred. The drying agent was filtered off, the filtrate was evaporated, and the residue was purified by silica gel column chromatography (hexane/ethyl acetate) to give 35 mg of the title compound as a colorless amorphous.

¹H-NMR (CDCl₃)

δ: 2.40(s, 3H), 7.20(m, 7H), 7.30(m, 8H), 7.43(ddd, J=7.6, 7.6, 1.2 Hz, 1H), 7.49(s, 1H), 7.51(d, J=4.4 Hz, 1H), 7.65(m, 1H), 7.71(dd, J=8.8, 2.0 Hz, 1H), 7.89 (td, J=7.6, 1.6 Hz, 1H), 8.12(d, J=8.8 Hz, 1H), 8.16(d, J=2.0 Hz, 1H), 8.82(m, 1H), 8.93(d, J=4.4 Hz, 1H)

Example 155

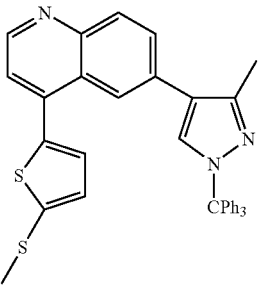

4-[5-(Methylsulfanyl)-2-thienyl]-6-(3-methyl-1-trityl-1H-4-pyrazolyl)quinoline 240 mg 6-(3-methyl-1-trityl-1H-4-pyrazolyl)-4-quinolyl trifluoromethane sulfonate obtained in Production Example 91 and 300 mg tributyl(5-methylsulfanyl)-2-thienyl]stannane (compound in Production Example 46) were reacted in the same manner as in Example 154, to give 69 mg of the title compound as a pale yellow amorphous.

¹H-NMR (CDCl₃)

δ: 2.49(s, 3H), 2.60(s, 3H), 7.16(d, J=3.6 Hz, 1H), 7.22(m, 8H), 7.32(m, 8H), 7.39(d, J=4.4 Hz, 1H), 7.52(s, 1H), 7.71(dd, J=8.8, 2.0 Hz, 1H), 8.09(d, J=8.8 Hz, 1H), 8.29(d, J=2.0 Hz, 1H), 8.83(d, J=4.4 Hz, 1H)

Example 156

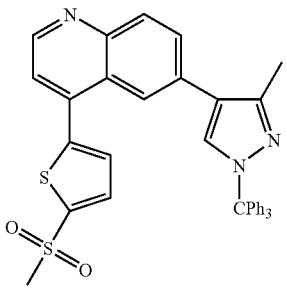

4-[5-(Methylsulfonyl)-2-thienyl]-6-(3-methyl-1-trityl-1H-4-pyrazolyl)quinoline 1 mL aqueous solution of 86 mg oxone was added at room temperature to a solution of 67 mg 4-[5-(methylsulfanyl)-2-thienyl]-6-(3-methyl-1-trityl-1H-4-pyrazolyl)quinoline obtained in Example 155 in tetrahydrofuran, and the mixture was stirred for 1 hour. Further, 60 mg oxone was added thereto and stirred overnight. An aqueous saturated sodium thiosulfate solution was added to the reaction solution, and the mixture was stirred. Then, ethyl acetate, an aqueous saturated sodium bicarbonate solution and water were added thereto, and the organic layer was separated, washed with brine and dried over anhydrous sodium sulfate. The drying agent was filtered off, the filtrate was evaporated, and the residue was purified by silica gel column chromatography (hexane/ethyl acetate), to give 35 mg of the title compound as a pale yellow amorphous.

$^1$H-NMR (CDCl$_3$)
δ: 2.46(s, 3H), 3.28(s, 3H), 7.20(m, 7H), 7.33(m, 8H), 7.39(d, J=3.6 Hz, 1H), 7.43(d, J=4.4 Hz, 1H), 7.52(s, 1H), 7.76(dd, J=8.8, 2.0 Hz, 1H), 7.82(d, J=3.6 Hz, 1H), 8.09(d, J=2.0 Hz, 1H), 8.14(d, J=8.8 Hz, 1H), 8.91(d, J=4.4 Hz, 1H)

Example 157

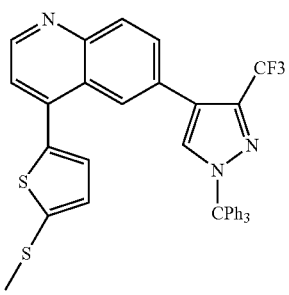

4-(5-Methylsulfanyl-2-thienyl)-6-(3-trifluoromethyl-1-trityl-1H-4-pyrazolyl)quinoline 261 mg 6-(3-trifluoromethyl-1-trityl-1H-pyrazolyl)-4-quinolyl trifluoromethane sulfonate obtained in Production Example 93 and 300 mg tributyl(5-methylsulfanyl-2-thienyl)stannane were reacted in the same manner as in Example 154, to give 106 mg of the title compound as a pale yellow amorphous.

$^1$H-NMR (CDCl$_3$)
δ: 2.60(s, 3H), 7.18(m, 7H), 7.34(m, 9H), 7.41(d, J=4.4 Hz, 1H), 7.51(d, J=1.2 Hz, 1H), 7.70(dd, J=8.8, 2.0 Hz, 1H), 8.12(d, J=8.8 Hz, 1H), 8.36(d, J=2.0 Hz, 1H), 8.87(d, J=4.4 Hz, 1H)

Example 158

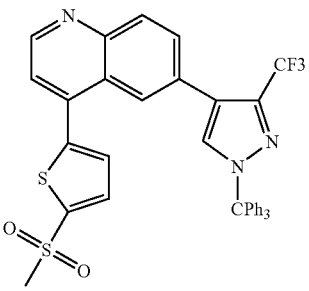

4-(5-methylsulfonyl-2-thienyl)-6-(3-trifluoromethyl-1-trityl-1H-4-pyrazolyl)quinoline 104 mg 4-(5-methylsulfanyl-2-thienyl)-6-(3-trifluoromethyl-1-trityl-1-1H-4-pyrazolyl)quinoline obtained in Example 157 and 253 mg oxone were reacted in the same manner as in Example 156, to give 60 mg of the title compound as a pale yellow amorphous.

$^1$H-NMR (CDCl$_3$)
δ: 3.28(s, 3H), 7.17(m, 7H), 7.35(m, 8H), 7.38(d, J=3.6 Hz, 1H), 7.46(d, J=4.4 Hz, 1H), 7.53(s, 1H), 7.73(dd, J=8.8, 2.0 Hz, 1H), 7.82(d, J=3.6 Hz, 1H), 8.17(d, J=8.8 Hz, 1H), 8.20(d, J=2.0 Hz, 1H), 8.95(d, J=4.4 Hz, 1H)

Example 159

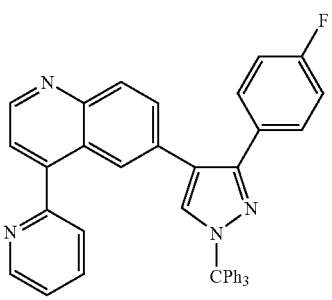

6-[3-(4-fluorophenyl)-1-trityl-1H-4-pyrazolyl]-4-(2-pyridyl)quinoline 100 mg 6-[3-(4-fluorophenyl)-1-trityl-1H-4-pyrazolyl]-4-quinolyl trifluoromethane sulfonate obtained in Production Example 95 and 109 mg 2-(tri-n-butylstannyl)pyridine were reacted in the same manner as in Example 154, to give 65 mg of the title compound as a colorless amorphous.

$^1$H-NMR (CDCl$_3$)
δ: 6.93(m, 2H), 7.24(m, 7H), 7.31(m, 10H), 7.40(m, 2H), 7.46(d, J=4.4 Hz, 1H), 7.50(s, 1H), 7.65(m, 2H), 7.85(d, J=1.6 Hz, 1H), 8.09(d, J=8.8 Hz, 1H), 8.63(m, 1H), 8.92(d, J=4.4 Hz, 1H)

Example 160

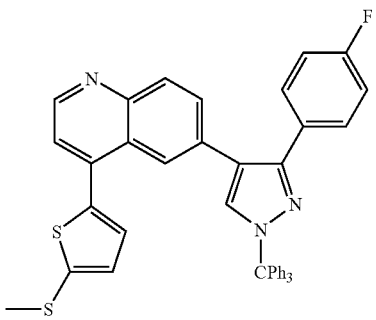

6-[3-(4-Fluorophenyl)-1-trityl-1H-4-pyrazolyl]-4-(5-methylsulfanyl-2-thienyl)quinoline 272 mg 6-[3-(4-fluorophenyl)-1-trityl-1H-4-pyrazolyl]-4-quinolyl trifluoromethane sulfonate obtained in Production Example 104 and 335 mg tributyl (5-methylsulfanyl-2-thienyl)stannane (compound in Production Example 46) were reacted in the same manner as in Example 154, to give 84 mg of the title compound as a pale yellow amorphous.

$^1$H-NMR (CDCl$_3$)

δ: 2.55(s, 3H), 6.72(d, J=3.6 Hz, 1H), 6.94(d, J=3.6 Hz, 1H), 7.00(m, 2H), 7.25(m, 8H), 7.33(m, 8H), 7.44(m, 2H), 7.51(s, 1H), 7.66(dd, J=8.8, 2.0 Hz, 1H), 8.06(d, J=2.0 Hz, 1H), 8.07(d, J=8.8 Hz, 1H), 8.81(d, J=4.8 Hz, 1H)

Example 161

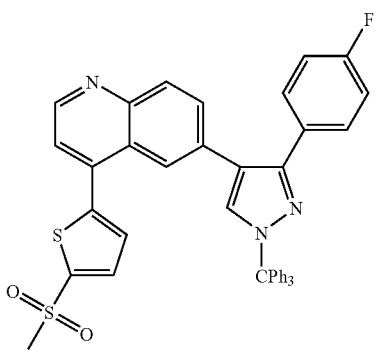

6-[3-(4-Fluorophenyl)-1-trityl-1H-4-pyrazolyl]-4-(5-methylsulfonyl-2-thienyl)quinoline 82 mg 6-[3-(4-fluorophenyl)-1-trityl-1H-4-pyrazolyl]-4-(5-methylsulfanyl-2-thienyl)quinoline obtained in Example 160 and 230 mg oxone were reacted in the same manner as in Example 156, to give 39 mg of the title compound as a pale yellow amorphous.

$^1$H-NMR (CDCl$_3$)

δ: 3.23(s, 3H), 6.83(d, J=3.6 Hz, 1H), 7.02(m, 2H), 7.25(m, 7H), 7.34(m, 8H), 7.37(d, J=4.4 Hz, 1H), 7.42(m, 2H), 7.53(s, 1H), 7.57(d, J=3.6 Hz, 1H), 7.72(dd, J=8.8, 2.0 Hz, 1H), 7.87(d, J=2.0 Hz, 1H), 8.12(d, J=8.8 Hz, 1H), 8.88(d, J=4.4 Hz, 1H)

Example 162

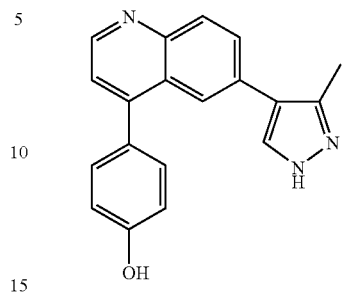

4-[6-(3-Methyl-1H-4-pyrazolyl)-4-quinolyl]phenol

A mixture of 9.5 mg 4-[6-(3-methyl-1-trityl-1H-4-pyrazolyl)-4-quinolyl]phenol obtained in Example 153, 0.13 mL of 5 N hydrochloric acid, 1 mL tetrahydrofuran, and 1 mL methanol was stirred overnight at room temperature. The reaction solution was cooled and then neutralized with 2 N aqueous sodium hydroxide and an aqueous saturated sodium bicarbonate solution. Then, ethyl acetate and water were added thereto, the organic layer was separated, the solvent was evaporated, and the residue was purified by silica gel column chromatography (hexane/ethyl acetate) to give 4 mg of the title compound as a colorless amorphous.

$^1$H-NMR (CDCl$_3$)

δ: 2.39(s, 3H), 7.27(d, J=4.4 Hz, 1H), 7.41(m, 2H), 7.56(m, 2H), 7.66(s, 1H), 7.68(d, J=2.0 Hz, 1H), 7.78(dd, J=8.8, 2.0 Hz, 1H), 8.15(d, J=8.8 Hz, 1H), 8.87(d, J=4.4 Hz, 1H)

Example 163

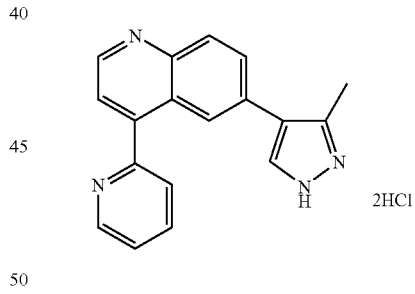

6-(3-Methyl-1H-4-pyrazolyl)-4-(2-pyridyl)quinoline dihydrochloride

A mixture of 33 mg 6-(3-methyl-1-trityl-1H-pyrazolyl)-4-(2-pyridyl)quinoline obtained in Example 154, 0.48 mL of 5 N hydrochloric acid, 3 mL tetrahydrofuran, and 3 mL methanol was stirred overnight at room temperature. The reaction solution was cooled with iced water and basified with 5N aqueous sodium hydroxide, then ethyl acetate and water were added thereto, and the organic layer was separated. The organic layer was washed with brine and dried over anhydrous sodium sulfate. The drying agent was filtered off, and the filtrate was evaporated. The residue was dissolved in ethyl acetate, and 0.15 mL of 4 N hydrochloric acid/ethyl acetate was added thereto. The reaction solution was evaporated, then ethyl acetate was added to the residue, and the formed crystals were separated by filtration to give 19 mg of the title compound as yellow crystals.

$^1$H-NMR (DMSO-d$_6$)

δ: 2.40(s, 3H), 7.71(m, 1H), 8.05(d, J=7.6 Hz, 1H), 8.16(m, 3H), 8.35(d, J=8.8 Hz, 1H), 8.46(s, 1H), 8.48(dd, J=8.8, 1.2 Hz, 1H), 8.92(dd, J=4.8, 0.8 Hz, 1H), 9.29(dd, J=5.6, 1.6 Hz, 1H)

Example 164

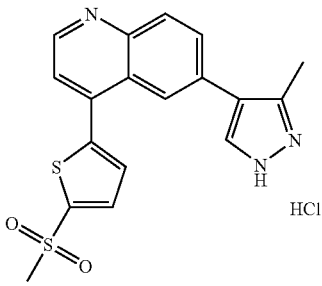

6-(3-Methyl-1H-4-pyrazolyl)-4-(5-methylsulfonyl-2-thienyl)quinoline hydrochloride A mixture of 33 mg 4-[5-(methylsulfonyl)-2-thienyl]-6-(3-methyl-1-trityl-1H-4-pyrazolyl)quinoline obtained in Example 156, 0.5 mL trifluoroacetic acid and 2 mL dichloromethane was stirred overnight at room temperature. The reaction solution was cooled with iced water and basified with 5 N aqueous sodium hydroxide, then ethyl acetate and water were added thereto, and the organic layer was separated. The aqueous layer was saturated with common salt and then extracted with ethyl acetate, and the combined organic layer was dried over anhydrous sodium sulfate. The drying agent was filtered off, and the filtrate was evaporated. The residue was dissolved in methanol, and 0.15 mL of 4 N hydrochloric acid/ethyl acetate was added thereto. The reaction solution was evaporated, then ethyl acetate was added to the residue, and the formed crystals were separated by filtration to give 13 mg of the title compound as a pale yellow solid.

$^1$H-NMR (DMSO-d$_6$)

δ: 2.40(s, 3H), 3.45(s, 3H), 7.79(d, J=4.8 Hz, 1H), 7.79(d, J=4.0 Hz, 1H), 7.98(d, J=4.0 Hz, 1H), 8.02(s, 1H), 8.12(dd, J=8.8, 2.0 Hz, 1H), 8.19(s, 1H), 8.20(d, J=8.8 Hz, 1H), 8.99(d, J=4.8 Hz, 1H)

Example 165

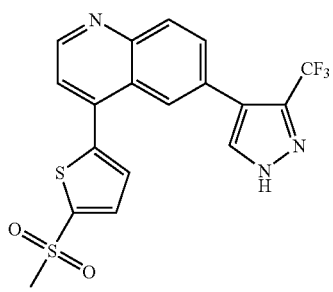

4-(5-Methylsulfonyl 2-thienyl)-6-(3-trifluoromethyl-1H-4-pyrazolyl)quinoline

A mixture of 58 mg 4-(5-methylsulfonyl 2-thienyl)-6-(3-trifluoromethyl-1-trityl-1H-4-pyrazolyl)quinoline obtained in Example 158, 1 mL trifluoroacetic acid and 3 mL dichloromethane was stirred overnight at room temperature. The reaction solution was cooled with iced water and basified with 5 N aqueous sodium hydroxide, then ethyl acetate and water were added thereto, and the organic layer was separated. The aqueous layer was then extracted with ethyl acetate, and the combined organic layer was washed with water and an aqueous brine and dried over anhydrous sodium sulfate. The drying agent was filtered off, and the filtrate was evaporated. The residue was triturated with diethyl ether, and the crystals were separated by filtration to give 18 mg of the title compound as pale yellow crystals.

$^1$H-NMR (CDCl$_3$)

δ: 3.29(s, 3H), 7.40(d, J=3.6 Hz, 1H), 7.49(d, J=4.4 Hz, 1H), 7.84(m, 3H), 8.21(d, J=2.0 Hz, 1H), 8.25(d, J=8.8 Hz, 1H), 8.99(d, J=4.4 Hz, 1H)

Example 166

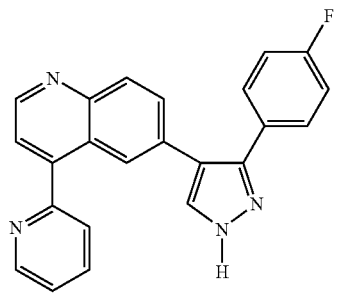

6-[3-(4-Fluorophenyl)-1H-4-pyrazolyl]-4-(2-pyridyl)quinoline 63 mg 6-[3-(4-fluorophenyl)-1-trityl-1H-4-pyrazolyl]-4-(2-pyridyl)quinoline obtained in Example 159 and 0.82 mL of 5 N hydrochloric acid were reacted in the same manner as in Example 162, to give 20 mg of the title compound as a colorless amorphous.

$^1$H-NMR (CDCl$_3$)

δ: 7.01(m, 2H), 7.37(m, 4H), 7.49(d, J=4.4 Hz, 1H), 7.72(m, 2H), 7.78(s, 1H), 7.92(d, J=1.6 Hz, 1H), 8.14(d, J=8.8 Hz, 1H), 8.69(d, J=4.8 Hz, 1H), 8.96(d, J=4.4 Hz, 1H)

Example 167

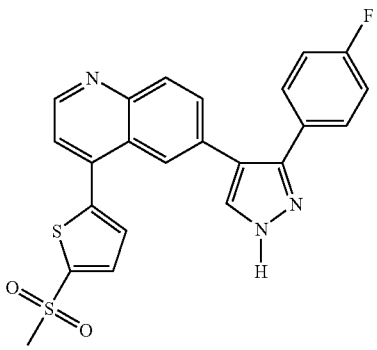

6-[3-(4-Fluorophenyl)-1H-4-pyrazolyl]-4-(5-methyl-sulfonyl-2-thienyl)quinoline 39 mg 6-[3-(4-fluorophenyl)-1-trityl-1H-4-pyrazolyl]-4-(5-methylsulfonyl 2-thienyl)quinoline obtained in Example 167 and 0.5 mL trifluoroacetic acid were reacted in the same manner as in Example 165, to give 14 mg of the title compound as pale yellow crystals.

$^1$H-NMR (CDCl$_3$)

δ: 3.25(s, 3H), 6.93(d, J=4.0 Hz, 1H), 7.09(m, 2H), 7.42(m, 3H), 7.63(d, J=4.0 Hz, 1H), 7.79(dd, J=8.8, 1.6 Hz, 1H), 7.83(s, 1H), 7.94(d, J=1.6 Hz, 1H), 8.17(d, J=8.8 Hz, 1H), 8.92(d, J=4.4 Hz, 1H)

Example 168

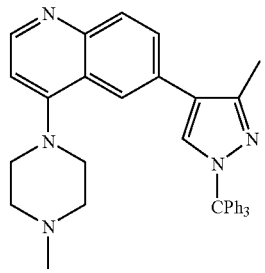

4-(4-Methylpiperazin-1-yl)-6-(3-methyl-1-trityl-1H-4-pyrazolyl)quinoline

A mixture of 153 mg 6-bromo-4-(4-methylpiperazin-lyl)quinoline obtained in Production Example 74, 239 mg 3-methyl-1-trityl-1H-4-pyrazolylboronic acid (compound in Production Example 30), 152 mg sodium carbonate, 5 mL toluene, 10 mL ethanol and 15 mg tetrakis(triphenylphosphine)palladium was heated for 3 hours under reflux in a stream of nitrogen. Ethyl acetate and anhydrous magnesium sulfate were added to the reaction solution, and the mixture was stirred. The drying agent was filtered off, the filtrate was evaporated, and the residue was purified by silica gel column chromatography (hexane/ethyl acetate) to give 248 mg of the title compound as a colorless amorphous.

$^1$H-NMR (CDCl$_3$)

δ: 2.45(s, 3H), 2.55(s, 3H), 2.70(m, 4H), 3.39(m, 4H), 6.84(d, J=5.2 Hz, 1H), 7.23(m, 7H), 7.34(m, 8H), 7.52(s, 1H), 7.64(dd, J=8.8, 2.0 Hz, 1H), 7.99(d, J=8.8 Hz, 1H), 8.00(d, J=2.0 Hz, 1H), 8.67(d, J=5.2 Hz, 1H)

Example 169

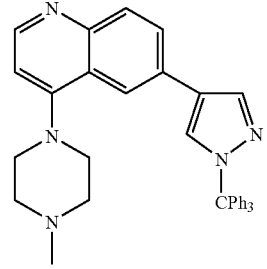

4-(4-Methylpiperazin-1-yl)-6-(1-trityl-1H-4-pyrazolyl)quinoline 153 mg 6-bromo-4-(4-methylpiperazin-1-yl)quinoline obtained in Production Example 74 and 230 mg 1-trityl-1H-4-pyrazolylboronic acid were reacted in the same manner as in Example 168, to give 187 mg of the title compound as a pale yellow amorphous.

$^1$H-NMR (CDCl$_3$)

δ: 2.44(s, 3H), 2.69(m, 4H), 3.26(m, 4H), 6.82(d, J=5.2 Hz, 1H), 7.23(m, 7H), 7.34(m, 8H), 7.71(dd, J=8.8, 2.0 Hz, 1H), 7.72(s, 1H), 7.99(d, J=8.8 Hz, 1H), 8.02(d, J=2.0 Hz, 1H), 8.07(s, 1H), 8.65(d, J=5.2 Hz, 1H)

Example 170

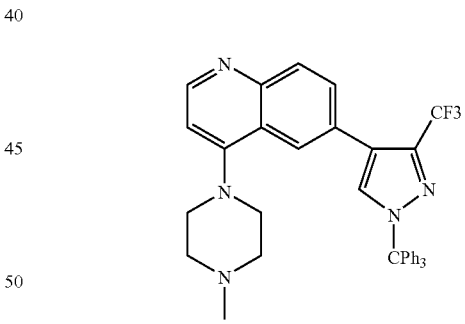

4-(4-Methylpiperazin-1-yl)-6-(3-trifluoromethyl-1-trityl-1H-4-pyrazolyl)quinoline 62 mg 6-bromo-4-(4-methylpiperazin-1-yl)quinoline obtained in Production Example 74 and 425 mg 3-trifluoromethyl-1-trityl-1H-4-pyrazolylboronic acid were reacted in the same manner as in Example 168, to give 126 mg of the title compound as a pale yellow amorphous.

$^1$H-NMR (CDCl$_3$)

δ: 2.42(s, 3H), 2.70(m, 4H), 3.27(m, 4H), 6.86(d, J=5.2 Hz, 1H), 7.20(m, 7H), 7.35(m, 8H), 7.52(s, 1H), 7.58(dd, J=8.8, 2.0 Hz, 1H), 8.01(d, J=8.8 Hz, 1H), 8.12(d, J=2.0 Hz, 1H), 8.70(d, J=5.2 Hz, 1H)

Example 171

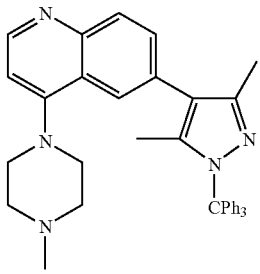

6-(3,5-Dimethyl-1-trityl-1H-pyrazolyl)-4-(4-methylpiperazin-1-yl)quinoline 46 mg 6-bromo-4-(4-methylpiperazin-1-yl)quinoline obtained in Production Example 74 and 97 mg 3,5-dimethyl-1-trityl-1H-4-pyrazolylboronic acid were reacted in the same manner as in Example 168, to give 77 mg of the title compound as a white solid.

$^1$H-NMR (CDCl$_3$)

δ: 2.31(s, 3H), 2.42(s, 3H), 2.68(m, 4H), 3.28(m, 4H), 6.84(d, J=4.8 Hz, 1H), 7.21(m, 7H), 7.30(m, 8H), 7.55(dd, J=8.8, 1.6 Hz, 1H), 7.83(d, J=1.6 Hz, 1H), 8.03(d, J=8.8 Hz, 1H), 8.70(d, J=4.8 Hz, 1H)

Example 172

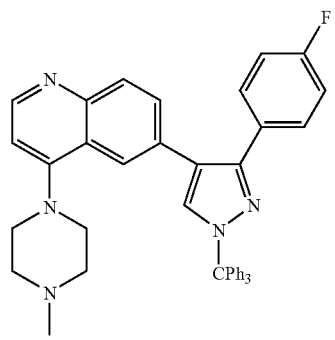

6-[3-(4-Fluorophenyl)-1-trityl-1H-pyrazolyl]-4-(4-methylpiperazin-1-yl)quinoline 189 mg 6-bromo-4-(4-methylpiperazin-1-yl)quinoline obtained in Production Example 74 and 360 mg 3-(4-fluorophenyl)-1-trityl-1H-4-pyrazolylboronic acid (compound in Production Example 25) were reacted in the same manner as in Example 168, to give 373 mg of the title compound as a colorless amorphous.

$^1$H-NMR (CDCl$_3$)

δ: 2.34(s, 3H), 2.38(m, 4H), 3.05(m, 4H), 6.78(d, J=5.2 Hz, 1H), 6.97(m, 2H), 7.27(m, 7H), 7.35(m, 8H), 7.49(s, 1H), 7.50(m, 2H), 7.58(dd, J=8.8, 2.0 Hz, 1H), 7.77(d, J=2.0 Hz, 1H), 7.97(d, J=8.8 Hz, 1H), 8.65(d, J=5.2 Hz, 1H)

Example 173

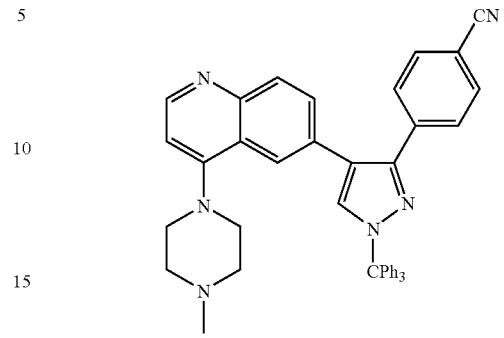

4-{4-[4-(4-Methylpiperazin-1-yl)-6-quinolyl]-1-trityl-1H-3-pyrazolyl}benzonitrile 46 mg 6-bromo-4-(4-methylpiperazin-1-yl)quinoline obtained in Production Example 74 and 72 mg 3-(4-cyanophenyl)-1-trityl-1H-4-pyrazolylboronic acid (compound in Production Example 32) were reacted in the same manner as in Example 168, to give 44 mg of the title compound as a colorless amorphous.

$^1$H-NMR (CDCl$_3$)

δ: 2.34(s, 3H), 2.39(m, 4H), 3.08(m, 4H), 6.81(d, J=5.2 Hz, 1H), 7.27(m, 7H), 7.36(m, 8H), 7.51(s, 1H), 7.55(d, J=8.4 Hz, 2H), 7.56(dd, J=8.8, 2.0 Hz, 1H), 7.66(d, J=8.4 Hz, 2H), 7.77(d, J=2.0 Hz, 1H), 7.99(d, J=8.8 Hz, 1H), 8.68(d, J=5.2 Hz, 1H)

Example 174

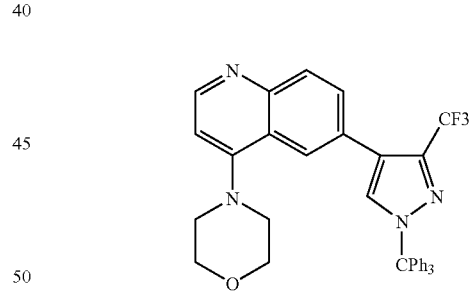

4-[6-(3-Trifluoromethyl-1-trityl-1H-4-pyrazolyl)-4-quinolyl]morpholine 66 mg 4-(6-bromo-4-quinolyl)morpholine obtained in Production Example 75 and 125 mg 3-trifluoromethyl-1-trityl-1H-4-pyrazolylboronic acid (compound in Production Example 31) were reacted in the same manner as in Example 168, to give 124 mg of the title compound as a white solid.

$^1$H-NMR (CDCl$_3$)

δ: 3.23(m, 4H), 3.96(m, 4H), 6.87(d, J=5.2 Hz, 1H), 7.19(m, 7H), 7.36(m, 8H), 7.53(s, 1H), 7.59(dd, J=8.8, 2.0 Hz, 1H), 8.02(d, J=8.8 Hz, 1H), 8.15(d, J=2.0 Hz, 1H), 8.73(d, J=5.2 Hz, 1H)

Example 175

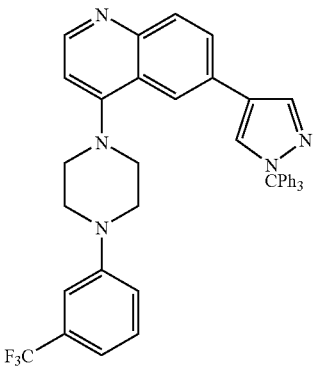

4-[4-(3-Trifluoromethylphenyl)piperazin-1-yl]-6-(1-trityl-1H-4-pyrazolyl)quinoline 100 mg 6-bromo-4-{4-[3-(trifluoromethyl)phenyl]-piperazin-1-yl}quinoline obtained in Production Example 76 and 244 mg 1-trityl-1H-4-pyrazolylboronic acid were reacted in the same manner as in Example 168, to give 106 mg of the title compound as a pale yellow amorphous.

$^1$H-NMR (CDCl$_3$)

δ: 3.40(m, 4H), 3.46(m, 4H), 6.89(d, J=5.2 Hz, 1H), 7.18(m, 2H), 7.22(m, 7H), 7.33(m, 8H), 7.44(m, 2H), 7.73(s, 1H), 7.76(dd, J=8.8, 1.6 Hz, 1H), 8.03(d, J=8.8 Hz, 1H), 8.06(d, J=1.6 Hz, 1H), 8.07(s, 1H), 8.70(d, J=5.2 Hz, 1H)

Example 176

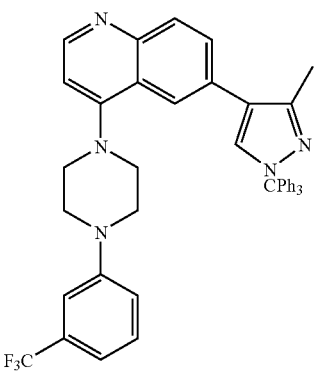

6-(3-Methyl-1-trityl-1H-4-pyrazolyl)-4-[4-(3-trifluoromethylphenyl)piperazin-1-yl]quinoline 72 mg 6-bromo-4-[4-(3-trifluoromethylphenyl)-piperazin-1-yl]quinoline obtained in Production Example 76 and 79 mg 3-methyl-1-trityl-1H-4-pyrazolylboronic acid were reacted in the same manner as in Example 168, to give 117 mg of the title compound as a pale yellow amorphous.

$^1$H-NMR (CDCl$_3$)

δ: 2.55(s, 3H), 3.40(m, 4H), 3.49(m, 4H), 6.90(d, J=4.8 Hz, 1H), 7.17(m, 2H), 7.23(m, 7H), 7.31(m, 8H), 7.43(m, 2H), 7.53(s, 1H), 7.68(dd, J=8.8, 1.6 Hz, 1H), 8.03(d, J=8.8 Hz, 1H), 8.04(d, J=1.6 Hz, 1H), 8.71(d, J=4.8 Hz, 1H)

Example 177

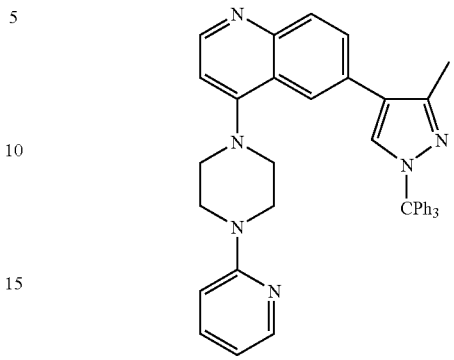

6-(3-Methyl-1-trityl-1H-4-pyrazolyl-4-[4-(2-pyridyl)piperazin-1-yl]quinoline 92 mg 6-bromo-4-[4-(2-pyridyl)piperazin-1-yl]quinoline obtained in Production Example 77 and 138 mg 3-methyl-1-trityl-1H-4-pyrazolylboronic acid were reacted in the same manner as in Example 168, to give 150 mg of the title compound as a pale yellow amorphous.

$^1$H-NMR (CDCl$_3$)

δ: 2.56(s, 3H), 3.36(m, 4H), 3.80(m, 4H), 6.71(m, 1H), 6.74(d, J=8.4 Hz, 1H), 6.88(d, J=5.2 Hz, 1H), 7.24(m, 7H), 7.32(m, 8H), 7.53(s, 1H), 7.55(m, 1H), 7.66(dd, J=8.8, 2.0 Hz, 1H), 8.02(d, J=8.8 Hz, 1H), 8.08(d, J=2.0 Hz, 1H), 8.26(m, 1H), 8.69(d, J=5.2 Hz, 1H)

Example 178

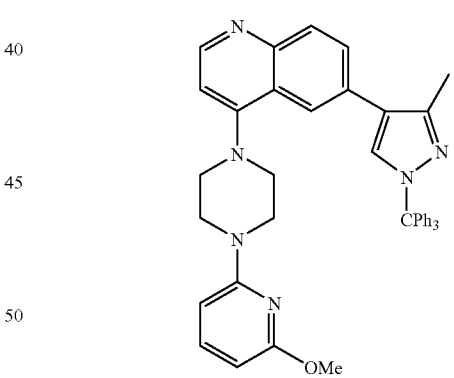

4-[4-(6-Methoxy-2-pyridyl)piperazin-1-yl]-6-(3-methyl-1-trityl-1H-4-pyrazolyl)quinoline A mixture of 250 mg 6-(3-methyl-1-trityl-1H-pyrazolyl)-4-quinolyl trifluoromethane sulfonate obtained in Production Example 91, 230 mg 4-(6-methoxy-2-pyridyl)piperazine trihydrochloride, 170 mg triethylamine and 10 mL dimethylformamide was stirred at 80° C. overnight. The reaction solution was cooled to room temperature, then ethyl acetate and water were added thereto, and the organic layer was separated, washed with water and brine, and dried over anhydrous magnesium sulfate. The drying agent was filtered off, the filtrate was evaporated, and the residue was purified by silica gel column chromatography (hexane/ethylacetate) to give 232 mg of the title compound as white crystals.

¹H-NMR (CDCl₃)

δ: 2.55(s, 3H), 3.35(m, 4H), 3.78(m, 4H), 3.91(s, 3H), 6.16(d, J=8.0 Hz, 1H), 6.27(d, J=8.0 Hz, 1H), 6.89(d, J=4.8 Hz, 1H), 7.24(m, 7H), 7.32(m, 8H), 7.48(t, J=8.0 Hz, 1H), 7.54(s, 1H), 7.66(dd, J=8.8, 1.6 Hz, 1H), 8.02(d, J=8.8 Hz, 1H), 8.08(d, J=1.6 Hz, 1H), 8.70(d, J=4.8 Hz, 1H)

Example 179

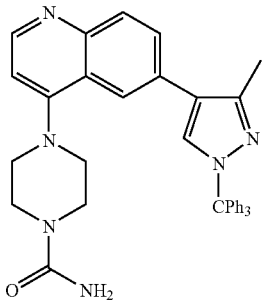

4-[6-(3-Methyl-1-trityl-1H-4-pyrazolyl)-4-quinolyl]-1-piperazine carboxamide

A mixture of 150 mg 6-(3-methyl-1-trityl-1H-pyrazolyl)-4-quinolyl trifluoromethane sulfonate obtained in Production Example 91, 83 mg 1-piperazinecarboxamide hydrochloride, 105 mg triethylamine and 10 mL anhydrous tetrahydrofuran was heated overnight under reflux. Then, 5 mL dimethyl sulfoxide was added to the reaction solution, and the solution was stirred at 80° C. for 2 days. The reaction solution was cooled to room temperature, then ethyl acetate, water and brine were added thereto, and the organic layer was separated, washed twice with water and then with brine, and dried over anhydrous magnesium sulfate. The drying agent was evaporated, and the residue was purified by silica gel column chromatography (hexane/ethyl acetate), to give 96 mg of the title compound as a pale yellow amorphous.

¹H-NMR (CDCl₃)

δ: 2.55(s, 3H), 3.24(m, 4H), 3.68(m, 4H), 4.60(brs, 2H), 6.85(d, J=5.2 Hz, 1H), 7.24(m, 7H), 7.33(m, 8H), 7.53(s, 1H), 7.65(dd, J=8.8, 1.6 Hz, 1H), 8.00(d, J=1.6 Hz, 1H), 8.01(d, J=8.8 Hz, 1H), 8.70(d, J=5.2 Hz, 1H)

Example 180

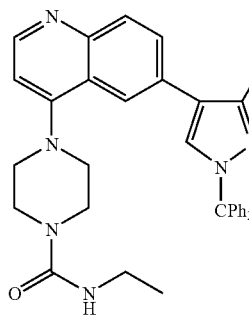

N-Ethyl-4-[6-(3-methyl-1-trityl-1H-pyrazolyl)-4-quinolyl]-1-piperazine carboxamide 200 mg 6-(3-methyl-1-trityl-1H-pyrazolyl)-4-quinolyl trifluoromethane sulfonate obtained in Production Example 91 and 129 mg N1-ethyl-1-piperazine carboxamide hydrochloride were reacted in the same manner as in Example 179, to give 120 mg of the title compound as a colorless amorphous.

¹H-NMR (CDCl₃)

δ: 1.20(t, J=7.2 Hz, 3H), 2.53(s, 3H), 3.23(m, 4H), 3.34(m, 2H), 3.63(m, 4H), 4.50(m, 1H), 6.84(d, J=5.2 Hz, 1H), 7.24(m, 7H), 7.33(m, 8H), 7.52(s, 1H), 7.65(dd, J=8.8, 2.0 Hz, 1H), 8.00(d, J=8.8 Hz, 1H), 8.01(d, J=2.0 Hz, 1H), 8.68(d, J=5.2 Hz, 1H)

Example 181

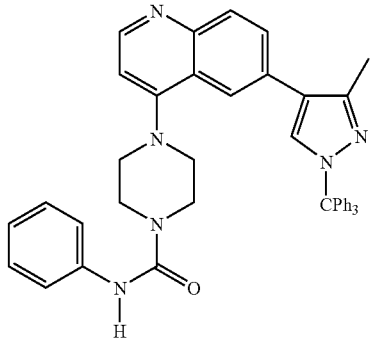

N-Phenyl-4-[6-(3-methyl-1-trityl-1H-pyrazolyl)-4-quinolyl]-1-piperazine carboxamide 150 mg 6-(3-methyl-1-trityl-1H-pyrazolyl)-4-quinolyl trifluoromethane sulfonate obtained in Production Example 91 and 121 mg N1-phenyl-1-piperazine carboxamide hydrochloride were reacted in the same manner as in Example 179, to give 120 mg of the title compound as a pale yellow solid.

¹H-NMR (CDCl₃)

δ: 2.55(s, 3H), 3.29(m, 4H), 3.76(m, 4H), 6.43(brs, 1H), 6.87(d, J=5.2 Hz, 1H), 7.08(m, 1H), 7.22–7.40(m, 19H), 7.53(s, 1H), 7.66(dd, J=8.8, 2.0 Hz, 1H), 8.02(d, J=8.8 Hz, 1H), 8.03(d, J=2.0 Hz, 1H), 8.71(d, J=5.2 Hz, 1H)

Example 182

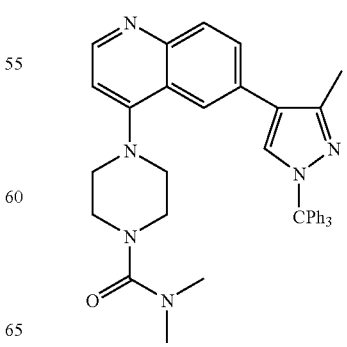

N,N-Dimethyl-4-[6-(3-methyl-1-trityl-1H-pyrazolyl)-4-quinolyl]-1-piperazine carboxamide 180 mg 6-(3-methyl-1-trityl-1H-pyrazolyl)-4-quinolyl trifluoromethane sulfonate obtained in Production Example 91 and 116 mg N1,N1-dimethyl-1-piperazine carboxamide hydrochloride were reacted in the same manner as in Example 179, to give 38 mg of the title compound as a colorless amorphous.

$^1$H-NMR (CDCl$_3$)

δ: 2.54(s, 3H), 2.92(s, 6H), 3.25(m, 4H), 3.50(m, 4H), 6.84(d, J=5.2 Hz, 1H), 7.24(m, 7H), 7.33(m, 8H), 7.52(s, 1H), 7.65(dd, J=8.8, 2.0 Hz, 1H), 8.01(d, J=8.8 Hz, 1H), 8.02(d, J=2.0 Hz, 1H), 8.68(d, J=5.2 Hz, 1H)

Example 183

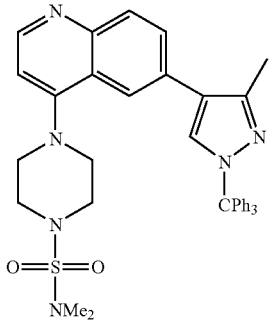

N,N-Dimethyl-4-[6-(3-methyl-1-trityl-1H-pyrazolyl)-4-quinolyl]-1-piperazine sulfonamide 180 mg 6-(3-methyl-1-trityl-1H-pyrazolyl)-4-quinolyl trifluoromethane sulfonate obtained in Production Example 91 and 116 mg N1,N1-dimethyl-1-piperazine sulfonamide hydrochloride were reacted in the same manner as in Example 179, to give 40 mg of the title compound as a pale yellow amorphous.

$^1$H-NMR (CDCl$_3$)

δ: 0.54(s, 3H), 2.91(s, 6H), 3.29(m, 4H), 3.51(m, 4H), 6.85(d, J=5.2 Hz, 1H), 7.24(m, 7H), 7.33(m, 8H), 7.50(s, 1H), 7.68(dd, J=8.8, 2.0 Hz, 1H), 7.95(d, J=2.0 Hz, 1H), 8.02(d, J=8.8 Hz, 1H), 8.69(d, J=5.2 Hz, 1H)

Example 184

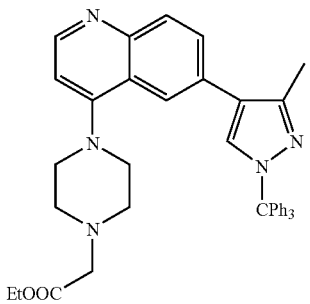

Ethyl 2-4-(6-(3-methyl-1-trityl-1H-4-pyrazolyl)-4-quinolyl]piperazin-1-ylacetate 300 mg 6-(3-methyl-1-trityl-1H-pyrazolyl)-4-quinolyl trifluoromethane sulfonate obtained in Production Example 91 and 130 mg ethyl 2-piperazin-1-ylacetate were reacted in the same manner as Example 179, to give 259 mg of the title compound as a colorless amorphous.

$^1$H-NMR (CDCl$_3$)

δ: 1.31(t, J=7.2 Hz, 3H), 2.53(s, 3H), 2.87(m, 4H), 3.32(m, 4H), 3.36(s, 2H), 4.23 (q, J=7.2 Hz, 2H), 6.84(d, J=5.2 Hz, 1H), 7.25(m, 7H), 7.33(m, 8H), 7.51(s, 1H), 7.64(dd, J=8.8, 2.4 Hz, 1H), 7.99(d, J=8.8 Hz, 1H), 8.00(d, J=2.4 Hz, 1H), 8.67(d, J=5.2 Hz, 1H)

Example 185

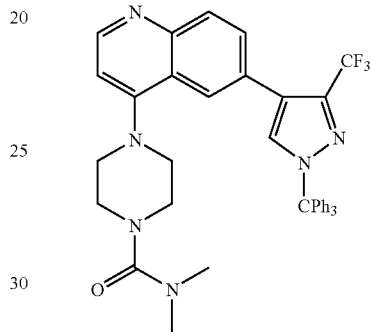

N,N-Dimethyl-4-[6-(3-trifluoromethyl-1-trityl-1H-4-pyrazolyl)-4-quinolyl]-1-piperazine carboxamide 68 mg N,N-dimethyl-4-(6-bromo-4-quinolyl)-1-piperazine carboxamide obtained in Production Example 80 and 103 mg 3-trifluoromethyl-1-trityl-1H-4-pyrazolylboronic acid (compound in Production Example 31) were reacted in the same manner as in Example 168, to give 116 mg of the title compound as a colorless amorphous.

$^1$H-NMR (CDCl$_3$)

δ: 2.90(s, 6H), 3.22(m, 4H), 3.52(m, 4H), 6.86(d, J=4.8 Hz, 1H), 7.19(m, 7H), 7.36(m, 8H), 7.53(s, 1H), 7.59(dd, J=8.8, 2.0 Hz, 1H), 8.02(d, J=8.8 Hz, 1H), 8.14(d, J=2.0 Hz, 1H), 8.72(d, J=4.8 Hz, 1H)

Example 186

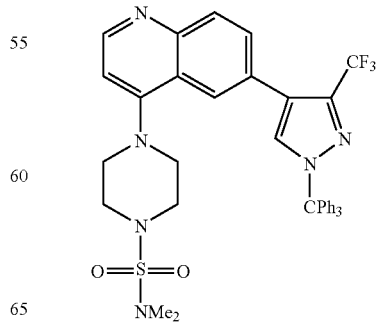

N,N-Dimethyl-4-[6-(3-trifluoromethyl-1-trityl-1H-4-pyrazolyl)-4-quinolyl]-1-piperazine sulfonamide 69 mg N,N-dimethyl-4-(6-bromo-4-quinolyl)-1-piperazine sulfonamide obtained in Production Example 81 and 95 mg 3-trifluoromethyl-1-trityl-1H-4-pyrazolylboronic acid (compound in Production Example 31) were reacted in the same manner as in Example 168, to give 109-mg of the title compound as a colorless amorphous.

$^1$H-NMR (CDCl$_3$)

δ: 2.92(s, 6H), 3.28(m, 4H), 3.53(m, 4H), 6.87(d, J=4.8 Hz, 1H), 7.19(m, 7H), 7.36(m, 8H), 7.53(s, 1H), 7.60(dd, J=8.8, 2.0 Hz, 1H), 8.03(d, J=8.8 Hz, 1H), 8.10(d, J=2.0 Hz, 1H), 8.73(d, J=4.8 Hz, 1H)

Example 187

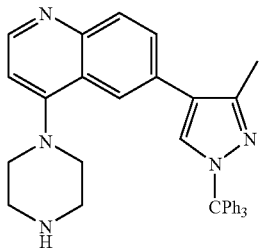

6-(3-Methyl-1-trityl-1H-4-pyrazolyl)-4-piperazin-1-yl-quinoline 275 mg 6-bromo-4-piperazin-1-yl-quinoline obtained in Production Example 79 and 344 mg 3-methyl-1-trityl-1H-4-pyrazolylboronic acid (compound in Production Example 30) were reacted in the same manner as in Example 168, to give 323 mg of the title compound as a white solid.

$^1$H-NMR (CDCl$_3$)

δ: 2.54(s, 3H), 3.12–3.26(m, 8H), 6.84(d, J=5.2 Hz, 1H), 7.24(m, 7H), 7.33(m, 8H), 7.52(s, 1H), 7.63(dd, J=8.8, 2.0 Hz, 1H), 7.99(d, J=8.8 Hz, 1H), 8.03(d, J=2.0 Hz, 1H), 8.67(d, J=5.2 Hz, 1H)

Example 188

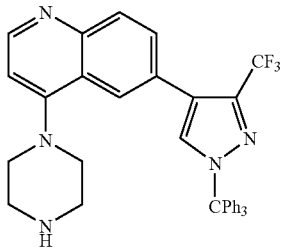

4-piperazin-1-yl-6-(3-trifluoromethyl-1-trityl-1H-4-pyrazolyl)quinoline 2.08 g crude 6-bromo-4-piperazin-1-yl-quinoline obtained in Production Example 79 and 1.76 g 3-trifluoromethyl-1-trityl-1H-4-pyrazolylboronic acid (compound in Production Example 31) were reacted in the same manner as in Example 168, to give 1.22 g of the title compound as a pale yellow solid.

$^1$H-NMR (CDCl$_3$)

δ: 3.12–3.26(m, 8H), 6.85(d, J=5.2 Hz, 1H), 7.20(m, 7H), 7.36(m, 8H), 7.53(s, 1H), 7.58(dd, J=8.8, 1.6 Hz, 1H), 8.01(d, J=8.8 Hz, 1H), 8.15(d, J=1.6 Hz, 1H), 8.70(d, J=5.2 Hz, 1H)

Example 189

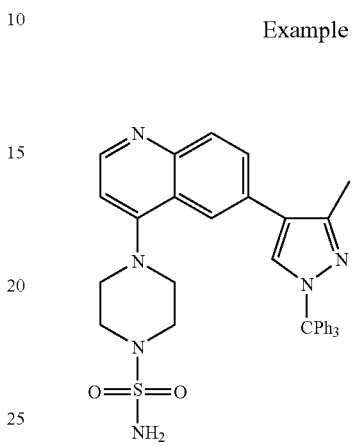

4-[6-(3-Methyl-1-trityl-1H-4-pyrazolyl)-4-quinolyl]-1-pyrazine sulfonamide

A mixture of 54 mg 6-(3-methyl-1-trityl-1H-4-pyrazolyl)-4-piperazin-1-yl-quinoline obtained in Example 187, 96 mg sulfamide, and 5 mL dioxane was heated for 4 hours under reflux. The reaction solution was evaporated, then ethyl acetate and water were added to the residue, and the organic layer was separated, then washed with brine and dried over anhydrous magnesium sulfate. The solvent was evaporated, and the residue was purified by silica gel column chromatography (hexane/ethyl acetate) to give 45 mg of the title compound as a white solid.

$^1$H-NMR (CDCl$_3$)

δ: 2.54(s, 3H), 3.20–3.38(m, 8H), 6.95(s, 2H), 7.00(d, J=4.8 Hz, 1H), 7.15(m, 7H), 7.37(m, 8H), 7.67(s, 1H), 7.72(dd, J=8.8, 1.6 Hz, 1H), 7.90(d, J=8.8 Hz, 1H), 7.91(d, J=1.6 Hz, 1H), 8.65(d, J=4.8 Hz, 1H)

Example 190

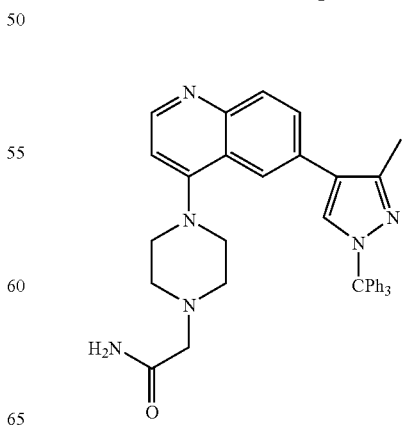

2-{4-[6-(3-Methyl-1-trityl-1H-4-pyrazolyl)-4-quinolyl]piperazin-1-yl}acetamide A mixture of 54 mg 6-(3-methyl-1-trityl-1H-4-pyrazolyl)-4-piperazin-1-yl-quinoline obtained in Example 187, 9.4 mg 2-chloroacetamide, 16 mg potassium carbonate and 3 mL dimethylformamide was stirred at 115° C. for 5 hours. 3 mg of 2-chloroacetamide was added thereto, and the mixture was stirred at the same temperature for 3 hours. Ethyl acetate and water were added to the reaction solution, and the organic layer was separated, then washed twice with water and then with brine and dried over anhydrous magnesium sulfate. The solvent was evaporated, and the residue was purified by silica gel column chromatography (hexane/ethyl acetate) to give 41 mg of the title compound as a colorless amorphous.

$^1$H-NMR (CDCl$_3$)

δ: 2.45(s, 3H), 2.75(m, 4H), 3.09(s, 2H), 3.20(m, 4H), 5.49(br, 1H), 6.76(d, J=4.8 Hz, 1H), 6.94(br, 1H), 7.16(m, 7H), 7.25(m, 8H), 7.44(s, 1H), 7.59(dd, J=8.8, 2.0 Hz, 1H), 7.89(d, J=2.0 Hz, 1H), 7.93(d, J=8.8 Hz, 1H), 8.60(d, J=4.8 Hz, 1H)

Example 191

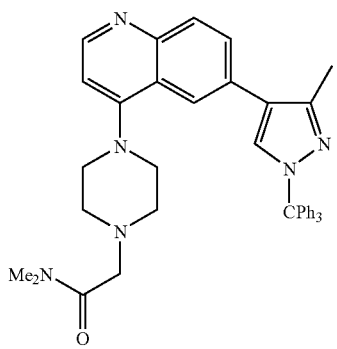

N,N-Dimethyl-2-{4-[6-(3-methyl-1-trityl-1H-4-pyrazolyl)-4-quinolyl]piperazin-1-yl}acetamide 80 mg 6-(3-methyl-1-trityl-1H-4-pyrazolyl)-4-piperazin-1-yl-quinoline obtained in Example 187 and 27 mg N,N-dimethyl-2-chloroacetamide were reacted in the same manner as in Example 190, to give 84 mg of the title compound as a pale yellow amorphous.

$^1$H-NMR (CDCl$_3$)

δ: 2.53(s, 3H), 2.84(m, 4H), 2.99(s, 3H), 3.12(s, 3H), 3.30(m, 4H), 3.33(s, 2H), 6.84(d, J=5.2 Hz, 1H), 7.25(m, 7H), 7.34(m, 8H), 7.51(s, 1H), 7.63(dd, J=8.8, 2.0 Hz, 1H), 7.99(d, J=8.8 Hz, 1H), 8.00(d, J=2.0 Hz, 1H), 8.66(d, J=5.2 Hz, 1H)

Example 192

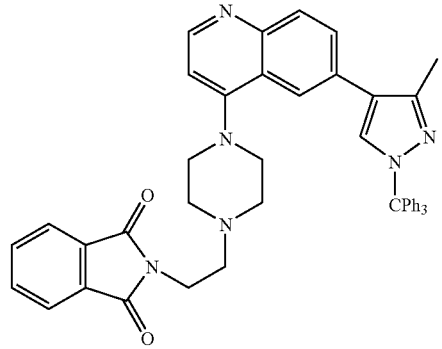

N-(2-{4-[6-(3-Methyl-1-trityl-1H-4-pyrazolyl)-4-quinolyl]piperazin-1-yl}ethyl)phthalimide A mixture of 80 mg 6-(3-methyl-1-trityl-1H-4-pyrazolyl)-4-piperazin-1-yl-quinoline obtained in Example 187, 46 mg N-(2-bromoethyl)phthalimide, 19 mg sodium carbonate, and 8 mL acetonitrile was heated overnight under reflux. Ethyl acetate and water were added to the reaction solution, and the organic layer was separated, washed with brine and dried over anhydrous sodium sulfate. The solvent was evaporated, and the residue was purified by silica gel column chromatography (hexane/ethyl acetate) to give 61 mg of the title compound as a colorless amorphous.

$^1$H-NMR (CDCl$_3$)

δ: 2.53(s, 3H), 2.78(m, 6H), 3.20(m, 4H), 3.90(m, 2H), 6.79(d, J=4.8 Hz, 1H), 6.94(br, 1H), 7.24(m, 7H), 7.33(m, 8H), 7.51(s, 1H), 7.63(dd, J=8.8, 2.0 Hz, 1H), 7.73(m, 2H), 7.87(m, 2H), 7.98(d, J=2.0 Hz, 1H), 7.98(d, J=8.8 Hz, 1H), 8.64(d, J=4.8 Hz, 1H)

Example 193

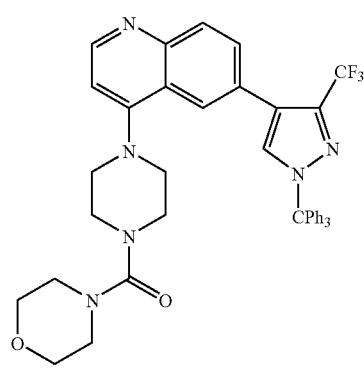

Morpholino{4-[6-(3-trifluoromethyl-1-trityl-1H-pyrazolyl)-4-quinolyl]piperazin-1-yl}methanone While a solution of 118 mg 4-piperazin-1-yl-6-[3-(trifluoromethyl)-1-trityl-1H-4-pyrazolyl]quinoline obtained in Example 188 and 61 mg triethylamine in dichloromethane was stirred under ice-cooling in a stream of nitrogen, 35 μL 4-morpholine carbonyl chloride was added thereto, and the mixture was stirred overnight at room temperature. Ethyl acetate and water were added to the reaction solution, and the organic layer was separated, washed with brine and dried over anhydrous sodium sulfate. The solvent was evaporated, and the residue was purified by silica gel column chromatography (hexane/ethyl acetate) to give 125 mg of the title compound as a colorless amorphous.

$^1$H-NMR (CDCl$_3$)

δ: 3.22(m, 4H), 3.35(m, 4H), 3.56(m, 4H), 3.73(m, 4H), 6.85(d, J=5.2 Hz, 1H), 7.19(m, 7H), 7.36(m, 8H), 7.54(d, J=0.8 Hz, 1H), 7.59(dd, J=8.8, 2.0 Hz, 1H), 8.02(d, J=8.8 Hz, 1H), 8.15(d, J=2.0 Hz, 1H), 8.72(d, J=5.2 Hz, 1H)

Example 194

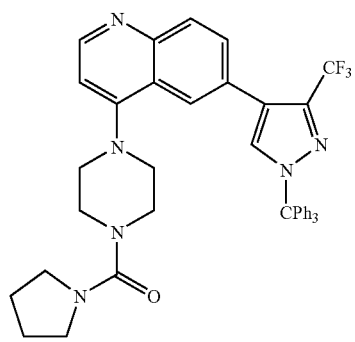

Tetrahydro-1H-1-pyrrolyl{4-[6-(3-trifluoromethyl-1-trityl-1H-pyrazolyl)-4-quinolyl]piperazin-1-yl}methanone 118 mg 4-piperazin-1-yl-6-(3-trifluoromethyl-1-trityl-1H-4-pyrazolyl)quinoline obtained in Example 188 and 33 μL 1-pyrrolidine carbonyl chloride were reacted in the same manner as in Example 193, to give 126 mg of the title compound as a colorless amorphous.

$^1$H-NMR (CDCl$_3$)

δ: 1.86(m, 4H), 3.22(m, 4H), 3.43(m, 4H), 3.56(m, 4H), 6.85(d, J=5.2 Hz, 1H), 7.19(m, 7H), 7.36(m, 8H), 7.53(s, 1H), 7.59(dd, J=8.8, 2.0 Hz, 1H), 8.02(d, J=8.8 Hz, 1H), 8.15(d, J=2.0 Hz, 1H), 8.72(d, J=5.2 Hz, 1H)

Example 195

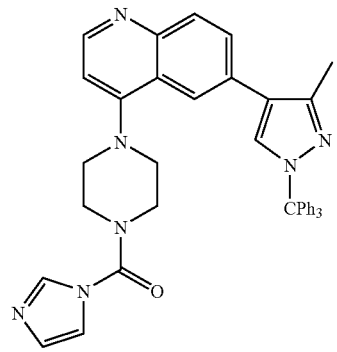

1H-1-Imidazolyl{4-[6-(3-methyl-1-trityl-1H-pyrazolyl)-4-quinolyl]piperazin-1-yl}methanone While 8 mL aqueous solution of 110 mg N,N-carbonyl diimidazole and 0.24 mL N-methyl morpholine in anhydrous tetrahydrofuran was stirred at room temperature in a stream of nitrogen, an anhydrous tetrahydrofuran solution of 321 mg 6-(3-methyl-1-trityl-1H-4-pyrazolyl)-4-piperazin-1-yl-quinoline obtained in Example 187 was added thereto little by little, and the mixture was stirred for 4 hours under the same conditions. Ethyl acetate and water were added to the reaction solution, and the organic layer was separated, washed with brine and dried over anhydrous sodium sulfate. The drying agent was filtered off, the filtrate was evaporated, and the residue was triturated with diethyl ether to give 353 mg of the title compound as white crystals.

$^1$H-NMR (CDCl$_3$)

δ: 2.53(s, 3H), 3.32(m, 4H), 3.90(m, 4H), 6.87(d, J=4.8 Hz, 1H), 7.16(d, J=1.2 Hz, 1H), 7.24(m, 8H), 7.33(m, 8H), 7.52(s, 1H), 7.67(dd, J=8.8, 2.0 Hz, 1H), 7.95(d, J=1.2 Hz, 1H), 7.98(d, J=2.0 Hz, 1H), 8.03(d, J=8.8 Hz, 1H), 8.72(d, J=4.8 Hz, 1H)

Example 196

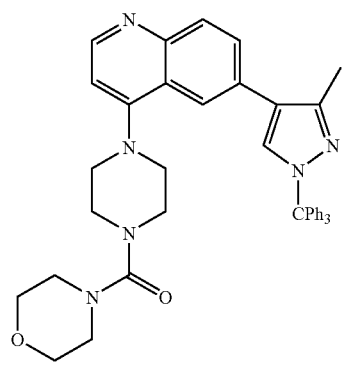

{4-[6-(3-Methyl-1-trityl-1H-4-pyrazolyl)-4-quinolyl]-piperazin-1-yl}morpholinomethanone A mixture of 100 mg 1H-1-imidazolyl{4-[6-(3-methyl-1-trityl-1H-pyrazolyl)-4-quinolyl]piperazin-1-yl}methanone obtained in Example 195 and 1 mL morpholine was stirred overnight at 140° C. Ethyl acetate and water were added to the reaction solution, and the organic layer was separated, washed with brine and dried over anhydrous sodium sulfate. The solvent was evaporated, and the residue was purified by silica gel column chromatography (hexane/ethyl acetate) to give 96 mg of the title compound as a pale yellow solid.

$^1$H-NMR (CDCl$_3$)

δ: 2.53(s, 3H), 3.23(m, 4H), 3.35(m, 4H), 3.55(m, 4H), 3.73(m, 4H), 6.84(d, J=5.2 Hz, 1H), 7.24(m, 7H), 7.33(m, 8H), 7.52(s, 1H), 7.65(dd, J=8.8, 2.0 Hz, 1H), 8.01(d, J=2.0 Hz, 1H), 8.01(d, J=8.8 Hz, 1H), 8.68(d, J=5.2 Hz, 1H)

Example 197

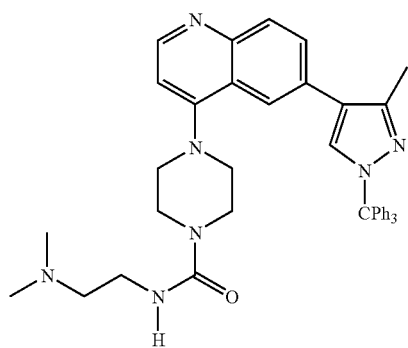

N-[2-(Dimethylamino)ethyl]-4-[6-(3-methyl-1-trityl-1H-4-pyrazolyl)-4-quinolyl]-1-piperazine carboxamide 60 mg 1H-1-imidazolyl{4-[6-(3-methyl-1-trityl-1H-pyrazolyl)-4-quinolyl]piperazin-1-yl}methanone obtained in Example 195 and 1 mL N,N-dimethylethylene diamine were reacted in the same manner as in Example 196, to give 29 mg of the title compound as a pale yellow oil.

$^1$H-NMR (CDCl$_3$)

δ: 2.29(s, 6H), 2.51(m, 2H), 2.65(s, 3H), 3.23(m, 4H), 3.38(m, 2H), 3.65(m, 4H), 5.45(brs, 1H), 6.84(d, J=5.2 Hz, 1H), 7.24(m, 7H), 7.33(m, 8H), 7.51(s, 1H), 7.65(dd, J=8.8, 2.0 Hz, 1H), 8.01(d, J=2.0 Hz, 1H), 8.01(d, J=8.8 Hz, 1H), 8.69(d, J=5.2 Hz, 1H)

Example 198

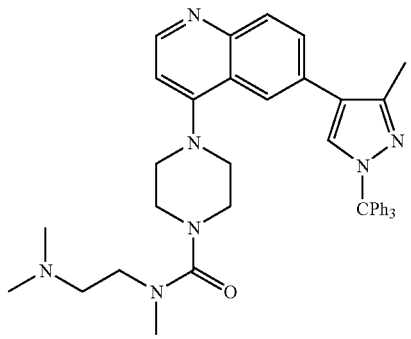

N-[2-(Dimethylamino)ethyl]-N1-methyl-4-[6-(3-methyl-1-trityl-1H-4-pyrazolyl)-4-quinolyl]-1-piperazine carboxamide 100 mg 1H-1-imidazolyl{4-[6-(3-methyl-1-trityl-1H-pyrazolyl)-4-quinolyl]piperazin-1-yl}methanone obtained in Example 195 and 1 mL N,N,N'-trimethylethylene diamine were reacted in the same manner as in Example 196, to give 69 mg of the title compound as a pale brown amorphous.

$^1$H-NMR (CDCl$_3$)

δ: 2.28(s, 6H), 2.53(m, 2H), 2.53(s, 3H), 2.95(s, 3H), 3.25(m, 4H), 3.37(m, 2H), 3.50(m, 4H), 5.45(brs, 1H), 6.84(d, J=5.2 Hz, 1H), 7.24(m, 7H), 7.33(m, 8H), 7.52(s, 1H), 7.64(dd, J=8.8, 2.0 Hz, 1H), 8.00(d, J=8.8 Hz, 1H), 8.02(d, J=2.0 Hz, 1H), 8.69(d, J=5.2 Hz, 1H)

Example 199

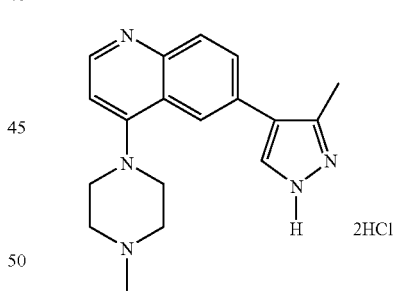

4-(4-Methylpiperazin-1-yl)-6-(3-methyl-1H-4-pyrazolyl)quinoline dihydrochloride 247 mg 4-(4-methylpiperazin-1-yl)-6-(3-methyl-1-trityl-1H-4-pyrazolyl)quinoline obtained in Example 168 and 3.4 mL of 5 N hydrochloric acid were reacted in the same manner as in Example 163, to give 147 mg of the title compound as yellow crystals.

$^1$H-NMR (DMSO-d$_6$)

δ: 2.86(s, 3H), 3.37–3.65(m, 6H), 4.30(m, 2H), 7.40(d, J=6.4 Hz, 1H), 8.02(d, J=1.6 Hz, 1H), 8.14(s, 1H), 8.21(dd, J=8.8, 1.6 Hz, 1H), 8.26(d, J=8.8 Hz, 1H), 8.84(d, J=6.4 Hz, 1H), 11.75(brs, 1H)

Example 200

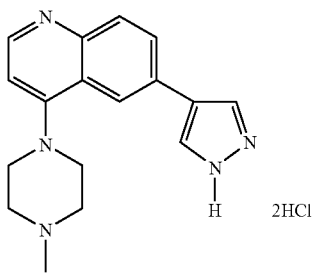

4-(4-Methylpiperazin-1-yl)-6-(1H-4-pyrazolyl)quinoline dihydrochloride 186 mg 4-(4-methylpiperazin-1-yl)-6-(1-trityl-1H-4-pyrazolyl)quinoline obtained in Example 169 and 2.6 mL of 5 N hydrochloric acid were reacted in the same manner as in Example 163, to give 127 mg of the title compound as yellow crystals.

$^1$H-NMR (D$_2$O)

δ: 2.89(s, 3H), 3.38(m, 2H), 3.59(m, 4H), 4.10(m, 2H), 7.08(d, J=7.2 Hz, 1H), 7.71(d, J=8.8 Hz, 1H), 7.77(d, J=2.0 Hz, 1H), 7.83(dd, J=8.8, 2.0 Hz, 1H), 8.03(s, 1H), 8.39(d, J=7.2 Hz, 1H)

Example 201

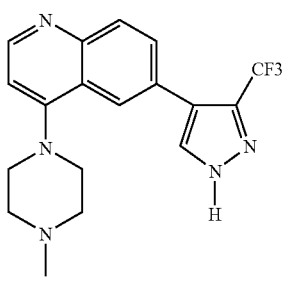

4-(4-Methylpiperazin-1-yl)-6-(3-fluoromethyl-1H-4-pyrazolyl)quinoline 123 mg 4-(4-methylpiperazin-1-yl)-6-(3-trifluoromethyl-1-trityl-1H-4-pyrazolyl)quinoline obtained in Example 170 and 0.7 mL trifluoroacetic acid were reacted in the same manner as in Example 165, to give 35 mg of the title compound as pale yellow crystals.

$^1$H-NMR (CDCl$_3$)

δ: 2.44(s, 3H), 2.75(m, 4H), 3.35(m, 4H), 6.90(d, J=4.8 Hz, 1H), 7.70(dd, J=8.8, 2.0 Hz, 1H), 7.85(s, 1H), 8.10(d, J=8.8 Hz, 1H), 8.17(d, J=2.0 Hz, 1H), 8.74(d, J=4.8 Hz, 1H)

Example 202

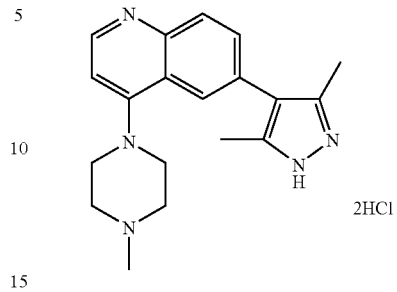

6-(3,5-Dimethyl-1H-4-pyrazolyl)-4-(4-methylpiperazin-1-yl)quinoline dihydrochloride 75 mg 6-(3,5-dimethyl-1-trityl-1H-pyrazolyl)-4-(4-methylpiperazin-1-yl)quinoline obtained in Example 171 and 1 mL of 5 N hydrochloric acid were reacted in the same manner as in Example 163, to give 147 mg of the title compound as pale yellow crystals.

$^1$H-NMR(DMSO-d$_6$)

δ: 2.31(s, 6H), 2.81(s, 3H), 3.40(m, 2H), 3.58(m, 2H), 3.85(m, 2H), 4.21(m, 2H), 7.40(d, J=6.8 Hz, 1H), 7.92(d, J=1.6 Hz, 1H), 8.04(dd, J=8.8, 1.6 Hz, 1H), 8.27(d, J=8.8 Hz, 1H), 8.86(d, J=6.8 Hz, 1H), 11.75(brs, 1H)

Example 203

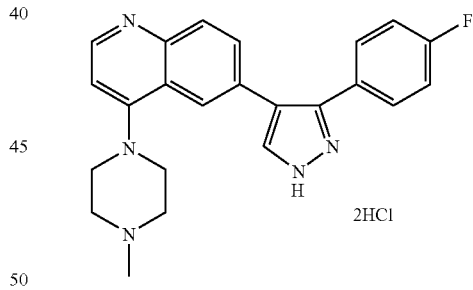

6-[3-(4-Fluorophenyl)-1H-4-pyrazolyl]-4-(4-methylpiperazin-1-yl)quinoline dihydrochloride 371 mg 6-[3-(4-fluorophenyl)-1-trityl-1H-pyrazolyl]-4-(4-methylpiperazin-1-yl)quinoline obtained in Example 172 and 4.5 mL of 5 N hydrochloric acid were reacted in the same manner as in Example 163, to give 201 mg of the title compound as pale yellow crystals.

$^1$H-NMR(DMSO-d$_6$)

δ: 2.75(s, 3H), 3.18(m, 2H), 3.39(m, 2H), 3.72(m, 2H), 4.05(m, 2H), 7.24(t, J=8.0 Hz, 2H), 7.34(d, J=6.4 Hz, 1H), 7.45(m, 2H), 7.85(d, J=8.8 Hz, 1H), 7.89(s, 1H), 8.18(m, 2H), 8.81(d, J=6.4 Hz, 1H), 11.85(brs, 1H)

Example 204

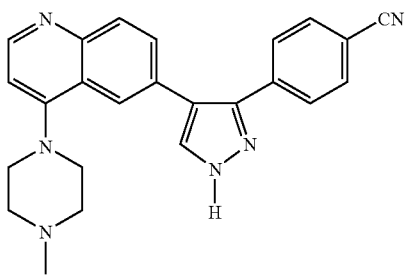

4-14-[4-(4-Methylpiperazin-1-yl)-6-quinolyl]-1H-3-pyrazolyl}benzonitrile 42 mg 4-{4-[4-(4-methylpiperazin-1-yl)-6-quinolyl]-1-trityl-1H-3-pyrazolyl}benzonitrile obtained in Example 173 and 0.21 mL trifluoroacetic acid were reacted in the same manner as in Example 165, to give 17 mg of the title compound as white crystals.

$^1$H-NMR (CDCl$_3$)

δ: 2.35(s, 3H), 2.43(m, 4H), 3.11(m, 4H), 6.84(d, J=5.2 Hz, 1H), 7.66(m, 5H), 7.83(d, J=2.0 Hz, 1H), 7.83(s, 1H), 8.06(d, J=8.4 Hz, 1H), 8.71(d, J=5.2 Hz, 1H)

Example 205

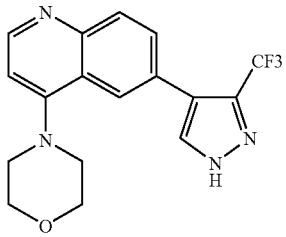

4-[6-(3-Trifluoromethyl-1H-4-pyrazolyl)-4-quinolyl morpholine 122 mg 4-[6-(3-trifluoromethyl-1-trityl-1H-4-pyrazolyl)-4-quinolyl]morpholine obtained in Example 174 and 1.5 mL trifluoroacetic acid were reacted in the same manner as in Example 165, to give 57 mg of the title compound as pale yellow crystals.

$^1$H-NMR (DMSO-d$_6$)

δ: 3.12(m, 4H), 3.84(m, 4H), 7.02(d, J=5.2 Hz, 1H), 7.79(dd, J=8.8, 2.0 Hz, 1H), 7.99(d, J=8.8 Hz, 1H), 8.07(d, J=2.0 Hz, 1H), 8.40(s, 1H), 8.70(d, J=5.2 Hz, 1H)

Example 206

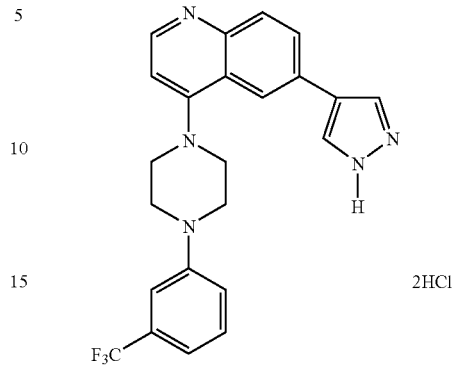

6-(1H-4-Pyrazolyl)-4-[4-(3-trifluoromethylphenyl)piperazin-1-yl]quinoline dihydrochloride 104 mg 4-[4-(3-trifluoromethylphenyl)piperazin-1-yl]-6-(1-trityl-1H-4-pyrazolyl) quinoline obtained in Example 175 and 1.2 mL of 5 N hydrochloric acid were reacted in the same manner as in Example 163, to give 74 mg of the title compound as yellowish orange crystals.

$^1$H-NMR (DMSO-d$_6$)

δ: 3.60(m, 4H), 4.05(m, 4H), 7.10(d, J=8.0 Hz, 1H), 7.22(m, 3H), 7.47(t, J=8.0 Hz, 1H), 8.11(d, J=8.8 Hz, 1H), 8.28(m, 4H), 8.64(d, J=6.8 Hz, 1H)

Example 207

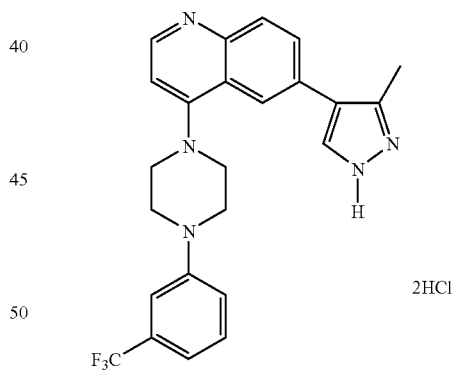

6-(3-Methyl-1H-4-pyrazolyl)-4-[4-(3-trifluoromethylphenyl)-piperazin-1-yl]quinoline dihydrochloride 115 mg 6-(3-methyl-1-trityl-1H-4-pyrazolyl)-4-[4-(3-trifluoromethylphenyl)piperazin-1-yl]quinoline obtained in Example 176 and 1.3 mL of 5 N hydrochloric acid were reacted in the same manner as in Example 163, to give 68 mg of the title compound as yellowish orange crystals.

$^1$H-NMR (DMSO-d$_6$)

δ: 2.52(s, 3H), 3.59(m, 4H), 4.03(m, 4H), 7.10(d, J=8.0 Hz, 1H), 7.22(m, 3H), 7.47(t, J=8.0 Hz, 1H), 8.14(m, 4H), 8.67(d, J=7.2 Hz, 1H)

Example 208

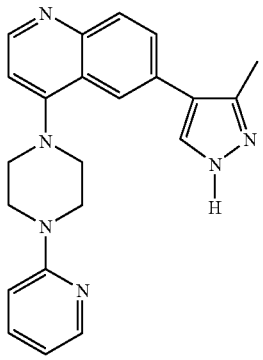

6-(3-Methyl-1H-4-pyrazolyl)-4-[4-(2-pyridyl)piper-azin-1-yl]quinoline 148 mg 6-(3-methyl-1-trityl-1H-4-pyrazolyl-4-[4-(2-pyridyl)piperazin-1-yl]quinoline obtained in Example 177 and 1.9 mL of 5 N hydrochloric acid were reacted in the same manner as in Example 162, to give 60 mg of the title compound as pale yellow crystals.

$^1$H-NMR (CDCl$_3$)

δ: 2.60(s, 3H), 3.39(m, 4H), 3.83(m, 4H), 6.71(dd, J=7.6, 5.2 Hz, 1H), 6.75(d, J=8.8 Hz, 1H), 6.92(d, J=5.2 Hz, 1H), 7.55(m, 1H), 7.77(dd, J=8.8, 2.0 Hz, 1H), 7.82(s, 1H), 8.10(m, 2H), 8.24(m, 1H), 8.74(d, J=5.2 Hz, 1H)

Example 209

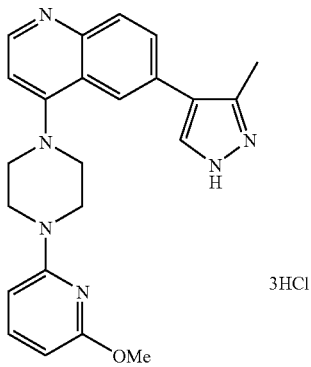

4-[4-(6-Methoxy-2-pyridyl)piperazin-1-yl]-6-(3-methyl-1H-4-pyrazolyl)quinoline trihydrochloride 120 mg 4-[4-(6-methoxy-2-pyridyl)piperazin-1-yl]-6-(3-methyl-1-trityl-1H-4-pyrazolyl)quinoline obtained in Example 178 and 1.4 mL of 5 N— hydrochloric acid were reacted in the same manner as in Example 163, to give 87 mg of the title compound as pale yellow crystals.

$^1$H-NMR (DMSO-d$_6$)

δ: 2.48(s, 3H), 3.77(s, 3H), 3.81(m, 4H), 4.03(m, 4H), 6.09(d, J=8.0 Hz, 1H), 6.34(d, J=8.0 Hz, 1H), 7.21(d, J=7.2 Hz, 1H), 7.50(t, J=8.0 Hz, 1H), 8.06(d, J=2.0 Hz, 1H), 8.09(s, 1H), 8.14(m, 2H), 8.66(d, J=7.2 Hz, 1H)

Example 210

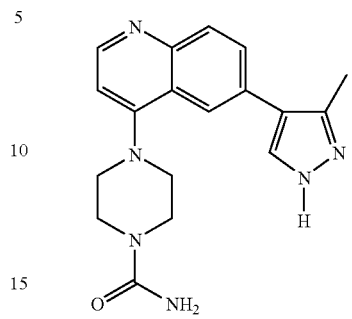

4-[6-(3-Methyl-1H-4-pyrazolyl)-4-quinolyl]-1-piperazine carboxamide 94 mg 4-[6-(3-methyl-1-trityl-1H-4-pyrazolyl)-4-quinolyl]-1-piperazine carboxamide obtained in Example 179 and 1.3 mL of 5 N hydrochloric acid were reacted in the same manner as in Example 162, to give 23 mg of the title compound as a pale yellow solid.

$^1$H-NMR (DMSO-d$_6$)

δ: 2.47(s, 3H), 3.11(m, 4H), 3.58(m, 4H), 6.10(brs, 2H), 6.98(d, J=5.2 Hz, 1H), 7.86(dd, J=8.8, 2.0 Hz, 1H), 7.94(m, 3H), 8.62(d, J=5.2 Hz, 1H)

Example 211

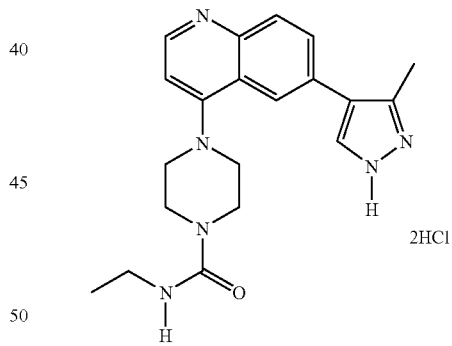

N-Ethyl-4-[6-(3-methyl-1H-4-pyrazolyl)-4-quinolyl]-1-piperazine carboxamide dihydrochloride 118 mg N-ethyl-4-[6-(3-methyl-1-trityl-1H-4-pyrazolyl)-4-quinolyl]-1-piperazine carboxamide obtained in Example 180 and 1.5 mL of 5 N hydrochloric acid were reacted in the same manner as in Example 163, to give 72 mg of the title compound as a pale yellow solid.

$^1$H-NMR (DMSO-d$_6$)

δ: 1.00(t, J=7.2 Hz, 3H), 2.51(s, 3H), 3.06(m, 2H), 3.58(m, 4H), 3.87(m, 4H), 7.16(m, 1H), 8.07(s, 1H), 8.11(m, 3H), 8.64(d, J=6.8 Hz, 1H)

Example 212

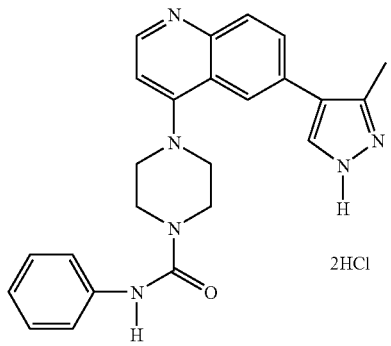

N-Phenyl-4-[6-(3-methyl-1H-4-pyrazolyl)-4-quinolyl]-1-piperazine carboxamide dihydrochloride 63 mg N1-phenyl-4-[6-(3-methyl-1-trityl-1H-pyrazolyl)-4-quinolyl]-1-piperazine carboxamide obtained in Example 181 and 0.7 mL of 5 N hydrochloric acid were reacted in the same manner as in Example 163, to give 30 mg of the title compound as pale yellow crystals.

$^1$H-NMR (DMSO-d$_6$)

δ: 2.50(s, 3H), 3.80(m, 4H), 3.98(m, 4H), 6.94(t, J=7.2 Hz, 1H), 7.22(m, 3H), 7.48(d, J=7.6 Hz, 1H), 8.10(m, 4H), 8.66(d, J=6.8 Hz, 1H), 8.70(s, 1H)

Example 213

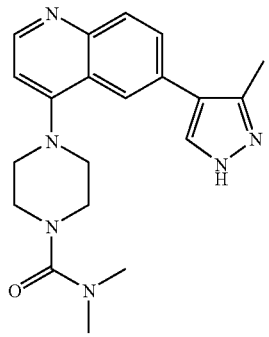

N,N-Dimethyl-4-[6-(3-methyl-1H-4-pyrazolyl)-4-quinolyl]-1-piperazine carboxamide 38 mg N,N-dimethyl 4-[6-(3-methyl-1-trityl-1H-pyrazolyl)-4-quinolyl]-1-piperazine carboxamide obtained in Example 182 and 0.2 mL trifluoroacetic acid were reacted in the same manner as in Example 165, to give 16 mg of the title compound as pale yellow crystals.

$^1$H-NMR (CDCl$_3$)

δ: 2.55(s, 3H), 2.91(s, 6H), 3.28(m, 4H), 3.53(m, 4H), 6.88(d, J=5.2 Hz, 1H), 7.77(dd, J=8.8, 2.0 Hz, 1H), 7.80(s, 1H), 8.04(d, J=2.0 Hz, 1H), 8.10(d, J=8.8 Hz, 1H), 8.73(d, J=5.2 Hz, 1H)

Example 214

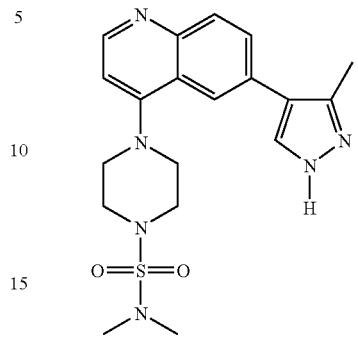

N,N-Dimethyl-4-[6-(3-methyl-1H-4-pyrazolyl)-4-quinolyl]-1-piperazine sulfonamide 37 mg N,N-dimethyl-4-[6-(3-methyl-1-trityl-1H-pyrazolyl)-4-quinolyl]-1-piperazine sulfonamide obtained in Example 183 and 0.2 mL trifluoroacetic acid were reacted in the same manner as in Example 165, to give 16 mg of the title compound as pale yellow crystals.

$^1$H-NMR (CDCl$_3$)

δ: 2.54(s, 3H), 2.91(s, 6H), 3.31(m, 4H), 3.55(m, 4H), 6.90(d, J=5.2 Hz, 1H), 7.77(dd, J=8.8, 2.0 Hz, 1H), 7.79(s, 1H), 7.98(d, J=2.0 Hz, 1H), 8.11(d, J=8.8 Hz, 1H), 8.74(d, J=5.2 Hz, 1H)

Example 215

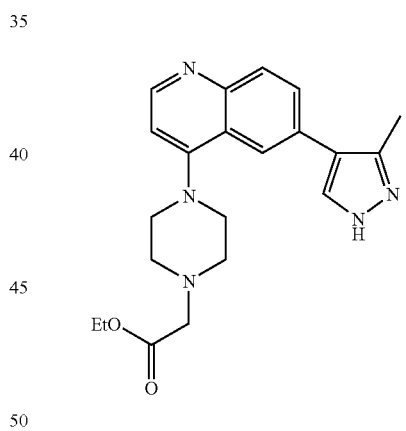

Ethyl 2-{4-[6-(3-methyl-1H-4-pyrazolyl)-4-quinolyl]-piperazin-1-yl}acetate

A mixture of 257 mg ethyl 2-4-[6-(3-methyl-1-trityl-1H-4-pyrazolyl)-4-quinolyl]piperazin-1-ylacetate obtained in Example 184, 1.5 mL trifluoro acetic acid and 5 mL dichloromethane was stirred overnight at room temperature. The reaction solution was cooled with iced water and basified with 5 N aqueous sodium hydroxide, then ethyl acetate and water were added thereto, and the organic layer was separated. The solvent was evaporated, and the residue was purified by silica gel column chromatography (hexane/ethyl acetate) to give 61 mg of the title compound as a colorless amorphous.

$^1$H-NMR (CDCl$_3$)

δ: 1.30(t, J=7.2 Hz, 3H), 2.55(s, 3H), 2.90(m, 4H), 3.34(m, 6H), 4.23 (q, J=7.2 Hz, 2H), 6.88(d, J=5.2 Hz, 1H), 7.74(dd, J=8.8, 2.0 Hz, 1H), 7.80(s, 1H), 8.02(d, J=2.0 Hz, 1H), 8.08(d, J=8.8 Hz, 1H), 8.71(d, J=5.2 Hz, 1H)

Example 216

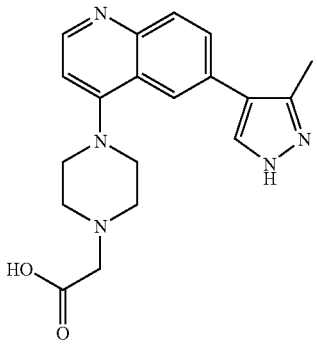

2-{4-[6-(3-Methyl-1H-4-pyrazolyl)-4-quinolyl]piperazin-1-yl}acetic acid

In the procedure in Example 215, the compound in Example 215 was extracted, and the aqueous layer was adjusted to about pH 7 with 2 N aqueous sodium hydroxide and 2 N hydrochloric acid and left at room temperature for 4 days. The precipitated crystals were collected by filtration and washed with water, to give 63 mg of the title compound as pale yellow crystals.

$^1$H-NMR (DMSO-$d_6$)

δ: 2.48(s, 3H), 3.07(m, 4H), 3.60(s, 2H), 3.73(m, 4H), 7.18(d, J=6.4 Hz, 1H), 7.96(s, 1H), 8.03(m, 3H), 8.67(d, J=6.4 Hz, 1H)

Example 217

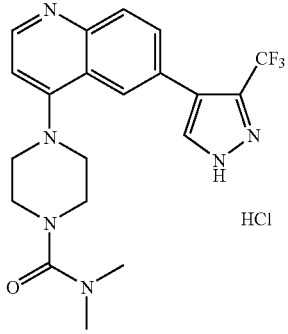

N,N-Dimethyl-4-[6-(3-trifluoromethyl-1H-4-pyrazolyl)-4-quinolyl]-1-piperazine carboxamide hydrochloride 114 mg N,N-dimethyl-4-[6-(3-trifluoromethyl-1-trityl-1H-4-pyrazolyl)-4-quinolyl]-1-piperazine carboxamide obtained in Example 185 and 1 mL trifluoroacetic acid were reacted in the same manner as in Example 164, to give 51 mg of the title compound as pale yellow crystals.

$^1$H-NMR (DMSO-$d_6$)

δ: 2.77(s, 6H), 3.40(m, 4H), 3.86(m, 4H), 7.18(d, J=7.2 Hz, 1H), 8.02(d, J=9.2 Hz, 1H), 8.12(s, 1H), 8.13(d, J=9.2 Hz, 1H), 8.45(s, 1H), 8.70(d, J=7.2 Hz, 1H)

Example 218

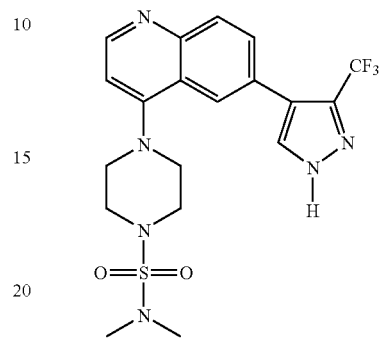

N,N-Dimethyl-4-[6-(3-trifluoromethyl-1H-4-pyrazolyl)-4-quinolyl]-1-piperazine sulfonamide 107 mg N1,N1-dimethyl-4-[6-(3-trifluoromethyl-1-trityl-1H-4-pyrazolyl)-4-quinolyl]-1-piperazine sulfonamide obtained in Example 186 and 1 mL trifluoroacetic acid were reacted in the same manner as in Example 165, to give 46 mg of the title compound as pale yellow crystals.

$^1$H-NMR (CDCl$_3$)

δ: 2.90(s, 6H), 3.31(m, 4H), 3.55(m, 4H), 6.91(d, J=4.8 Hz, 1H), 7.73(dd, J=8.8, 2.0 Hz, 1H), 7.87(s, 1H), 8.13(d, J=8.8 Hz, 1H), 8.14(s, 1H), 8.78(d, J=4.8 Hz, 1H)

Example 219

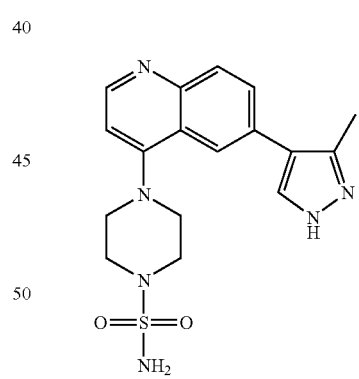

4-[6-(3-Methyl-1H-4-pyrazolyl)-4-quinolyl]-1-pyrazine sulfonamide 40 mg 4-[6-(3-methyl-1-trityl-1H-4-pyrazolyl)-4-quinolyl]-1-pyrazine sulfonamide obtained in Example 189 and 0.5 mL of 5 N hydrochloric acid were reacted in the same manner as in Example 162, to give 14 mg of the title compound as white crystals.

$^1$H-NMR (DMSO-$d_6$)

δ: 2.48(s, 3H), 3.39(m, 8H), 6.93(s, 1H), 7.01(d, J=4.8 Hz, 1H), 7.86(dd, J=8.8, 1.2 Hz, 1H), 7.93(m, 2H), 8.65(d, J=4.8 Hz, 1H)

Example 220

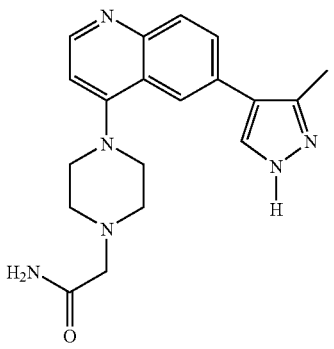

2-{4-[6-(3-Methyl-1H-4-pyrazolyl)-4-quinolyl]piperazin-1-yl}acetamide 39 mg 2-{4-[6-(3-methyl-1-trityl-1H-4-pyrazolyl)-4-quinolyl]piperazin-1-yl}acetamide obtained in Example 190 and 1 mL trifluoroacetic acid were reacted in the same manner as in Example 165, to give 8 mg of the title compound as a pale yellow solid.

$^1$H-NMR (DMSO-d$_6$)

δ: 2.48(s, 3H), 2.71(m, 4H), 2.98(s, 2H), 3.23(m, 4H), 6.97(d, J=4.8 Hz, 1H), 7.17(s, 1H), 7.26(s, 1H), 7.84(dd, J=8.8, 2.0 Hz, 1H), 7.93(m, 2H), 8.62(d, J=4.8 Hz, 1H)

Example 221

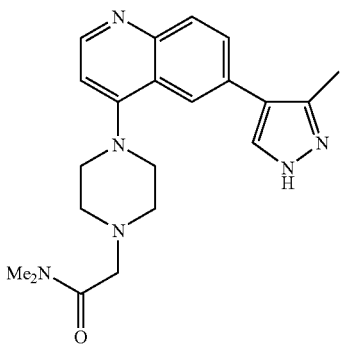

N,N-Dimethyl-2-{4-[6-(3-methyl-1H-4-pyrazolyl)-4-quinolyl]piperazin-1-yl}acetamide 82 mg N,N-dimethyl-2-{4-[6-(3-methyl-1-trityl-1H-4-pyrazolyl)-4-quinolyl]piperazin-1-yl}acetamide obtained in Example 191 and 1 mL trifluoroacetic acid were reacted in the same manner as in Example 165, to give 8 mg of the title compound as pale yellow crystals.

$^1$H-NMR (CDCl$_3$)

δ: 2.53(s, 3H), 2.86(m, 4H), 2.99(s, 3H), 3.12(s, 3H), 3.33(m, 6H), 6.87(d, J=4.8 Hz, 1H), 7.74(dd, J=8.8, 2.0 Hz, 1H), 7.79(s, 1H), 8.02(d, J=2.0 Hz, 1H), 8.08(d, J=8.8 Hz, 1H), 8.70(d, J=4.8 Hz, 1H)

Example 222

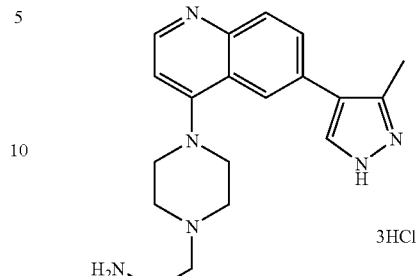

2-{4-[6-(3-Methyl-1H-4-pyrazolyl)-4-quinolyl]pyrazin-1-yl}ethylamine trihydrochloride A mixture of 59 mg N-(2-{4-[6-(3-methyl-1-trityl-1H-4-pyrazolyl)-4-quinolyl]1-pyrazin-1-yl}ethyl)phthalimide obtained in Example 192, 8 μL hydrazine monohydrate and 3 mL ethanol was heated for 3 hours under reflux. Insolubles were filtered off, and the filtrate was evaporated, and the resulting crude amine derivative was reacted with 0.64 mL of 5 N hydrochloric acid in the same method as in Example 163, to give 32 mg of the title compound as pale yellow crystals.

$^1$H-NMR (DMSO-d$_6$)

δ: 2.51(s, 3H), 3.38(m, 2H), 3.48(m, 2H), 7.38(d, J=6.8 Hz, 1H), 8.01(s, 1H), 8.09(s, 1H), 8.21(m, 2H), 8.48(m, 2H), 8.83(d, J=6.8 Hz, 1H)

Example 223

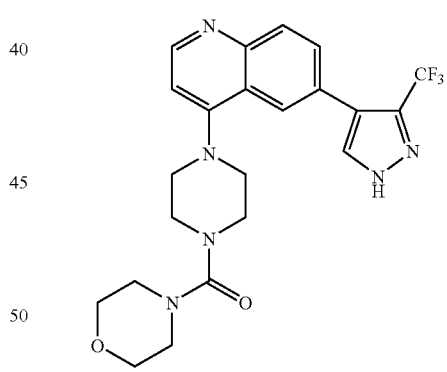

Morpholino{4-[6-(3-trifluoromethyl-1H-4-pyrazolyl)-4-quinolyl]piperazin-1-yl}methanone 123 mg morpholino{4-[6-(3-trifluoromethyl-1-trityl-1H-pyrazolyl)-4-quinolyl]piperazin-1-yl}methanone obtained in Example 193 and 1.5 mL trifluoroacetic acid were reacted in the same manner as in Example 165, to give 66 mg of the title compound as a pale yellow amorphous.

$^1$H-NMR (CDCl$_3$)

δ: 3.25(m, 4H), 3.36(m, 4H), 3.57(m, 4H), 3.72(m, 4H), 6.90(d, J=4.8 Hz, 1H), 7.72(dd, J=8.8, 2.0 Hz, 1H), 7.86(d, J=0.8 Hz, 1H), 8.12(d, J=8.8 Hz, 1H), 8.18(d, J=2.0 Hz, 1H), 8.77(d, J=4.8 Hz, 1H)

Example 224

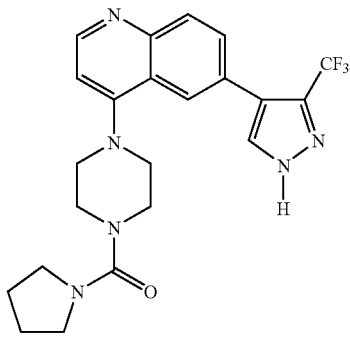

Tetrahydro-1H-1-pyrrolyl{4-[6-(3-trifluoromethyl-1H-pyrazolyl)-4-quinolyl]piperazin-1-yl}methanone 124 mg tetrahydro-1H-1-pyrrolyl{4-[6-(3-trifluoromethyl-1-trityl-1H-pyrazolyl)-4-quinolyl]piperazin-1-yl}methanone obtained in Example 194 and 1.5 mL trifluoroacetic acid were reacted in the same manner as in Example 165, to give 58 mg of the title compound as a pale colorless amorphous.

¹H-NMR (CDCl₃)

δ: 1.88(m, 4H), 3.27(m, 4H), 3.45(m, 4H), 3.59(m, 4H), 6.89(d, J=5.2 Hz, 1H), 7.72(dd, J=8.8, 2.0 Hz, 1H), 7.84(s, 1H), 8.10(d, J=8.8 Hz, 1H), 8.18(d, J=2.0 Hz, 1H), 8.76(d, J=5.2 Hz, 1H)

Example 225

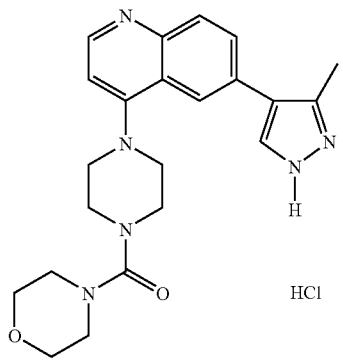

4-[6-(3-Methyl-1H-4-pyrazolyl)-4-quinolyl]piperazin-1-yl-(morpholino)methanone hydrochloride 90 mg 4-[6-(3-methyl-1-trityl-1H-4-pyrazolyl)-4-quinolyl]piperazin-1-yl-(morpholino)methanone obtained in Example 196 and 1 mL of 5 N hydrochloric acid were reacted in the same manner as in Example 163, to give 36 mg of the title compound as a yellow solid.

¹H-NMR (CDCl₃)

δ2.48(s, 3H), 3.19(m, 4H), 3.50(m, 4H), 3.58(m, 4H), 3.88(m, 4H), 7.16(d, 6(d, J=6.8 Hz, 1H), 8.09(m, 4H), 8.66(d, J=6.8 Hz, 1H)

Example 226

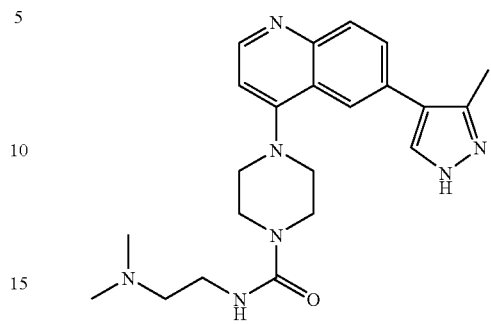

N-[2-(Dimethylamino)ethyl]-4-[6-(3-methyl-1H-4-pyrazolyl)-4-quinolyl]-1-piperazine carboxamide 27 mg N-[2-(dimethylamino)ethyl]-4-[6-(3-methyl-1-trityl-1H-4-pyrazolyl)-4-quinolyl]-1-piperazine carboxamide obtained in Example 197 and 0.32 mL of 5 N hydrochloric acid were reacted in the same manner as in Example 162, to give 1.6 mg of the title compound as a pale yellow solid.

MS m/e (ESI) 408 (MH⁺)

Example 227

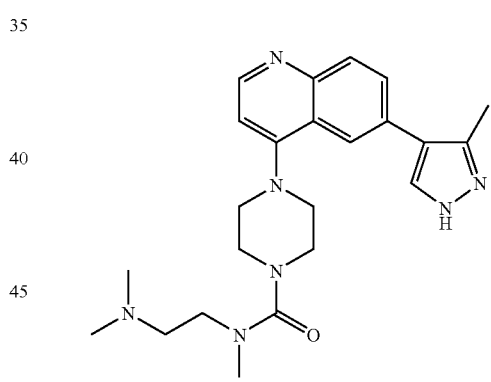

N-[2-(Dimethylamino)ethyl]-N-methyl-4-[6-(3-methyl-1H-4-pyrazolyl)-4-quinolyl]-1-piperazine carboxamide dihydrochloride 67 mg N-[2-(dimethylamino)ethyl]-N-methyl-4-[6-(3-methyl-1-trityl-1H-4-pyrazolyl)-4-quinolyl]-1-piperazine carboxamide obtained in Example 198 and 0.72 mL of 5 N hydrochloric acid were reacted in the same manner as in Example 163, to give 37 mg of the title compound as pale yellow crystals.

¹H-NMR (DMSO-d₆)

δ: 2.48(s, 3H), 2.74(s, 3H), 2.75(s, 3H), 2.89(s, 3H), 3.25(m, 2H), 3.53(m, 6H), 3.90(m, 4H), 7.17(d, J=6.8 Hz, 1H), 8.10(m, 4H), 8.66(d, J=6.8 Hz, 1H)

Example 228

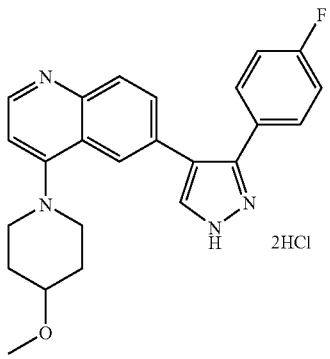

6-[3-(4-Fluorophenyl)-1H-4-pyrazolyl]-4-(4-methoxypiperidino)quinoline dihydrochloride 15 mg of 1-(6-bromo-4-quinolyl)-4-piperidyl methyl ether obtained in Production Example 82 and 31 mg 3-(4-fluorophenyl)-1-trityl-1H-4-pyrazolylboronic acid (compound in Production Example 25) were reacted in the same manner as in Example 168, to give 6-[3-(4-fluorophenyl)-1-trityl-1H-4-pyrazolyl]-4-(4-methoxy piperidino)quinoline. This product was reacted with 1.5 mL of N hydrochloric acid in the same manner as in Example 163, to give 12 mg of the title compound as pale yellow crystals.

$^1$H-NMR (DMSO-$d_6$)

δ: 1.37–1.50(br, 2H), 1.70–1.80(br, 2H), 3.10–3.70 (m, 8H), 7.11(d, J=6.6 Hz, 1H), 7.14–7.28(m, 2H), 7.36–7.50(m, 2H), 7.73(s, 1H), 7.90–8.14(m, 3H), 8.58(d, J=6.6 Hz, 1H)

Example 229

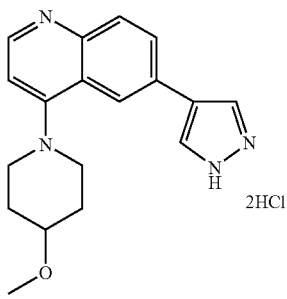

4-(4-Methoxypiperidino)-6-(1H-4-pyrazolyl)quinoline dihydrochloride 15 mg of 1-(6-bromo-4-quinolyl)-4-piperidyl methyl ether obtained in Production Example 82 and 25 mg 1-trityl-1H-4-pyrazolylboronic acid were reacted in the same manner as in Example 168, to give 4-(4-methoxypiperidino)-6-(1-trityl-1H-4-pyrazolyl)quinoline. Then, this product was subjected to deprotection of the trityl group and converted into the corresponding hydrochloride in the same manner as in Example 163, to give 9 mg of the title compound as pale yellow crystals.

$^1$H-NMR (DMSO-$d_6$)

δ: 1.68–1.84(br, 2H), 2.00–2.16(br, 2H), 3.00–4.06(m, 8H), 7.10–7.22(m, 1H), 7.96–8.36(m, 5H), 8.52–8.64(m, 1H)

Example 230


4-(4-Methoxypiperidino)-6-(3-methyl-1H-4-pyrazolyl)quinoline dihydrochloride 105 mg of 1-(6-bromo-4-quinolyl)-4-piperidyl methyl ether obtained in Production Example 82 and 180 mg 3-methyl-1-trityl-1H-4-pyrazolylboronic acid (compound in Production Example 30) were reacted in the same manner as in Example 168, to give 4-(4-methoxypiperidino)-6-(3-methyl-1-trityl-1H-4-pyrazolyl)quinoline. This product was subjected to deprotection of the trityl group in the same manner as in Example 162, and the resulting solid was purified by NAM silica gel chromatography (methanol/ethyl acetate). The residue was dissolved in methanol, then 2 mL of 4 N hydrochloric acid/ethyl acetate was added thereto, and the solvent was evaporated, whereby 88 mg of the title compound was obtained as pale yellow crystals.

$^1$H-NMR (DMSO-$d_6$)

δ: 1.67–1.80(br, 2H), 2.02–2.13(br, 2H), 2.40–2.52(br, 3H), 2.93–3.01(m, 2H), 3.25–3.47(m, 6H), 6.94(d, J=4.6 Hz, 1H), 7.78–7.98(m, 4H), 8.59(d, J=4.6 Hz, 1H)

MS m/e(ESI) 323(MH$^+$)

Example 231

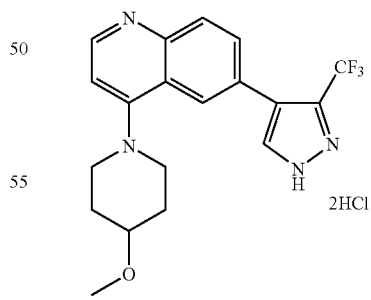

4-(4-Methoxypiperidino)-6-[3-(trifluoromethyl)-1H-4-pyrazolyl]quinoline dihydrochloride 120 mg of 1-(6-bromo-4-quinolyl)-4-piperidyl methyl ether obtained in Production Example 82 and 190 mg- 3-trifluoromethyl-1-trityl-1H-4-pyrazolylboronic acid (compound in Production Example 31) were reacted in the same manner as in Example 168, to give 4-(4-methoxypiperidino)-6-[3-(trifluoromethyl)-1-trityl-1H-4-pyrazolyl]quinoline. This product was subjected to deprotection of the trityl group and converted into the corresponding hydrochloride in the same manner as in Example 164, to give 76 mg of the title compound as colorless crystals.

$^1$H-NMR (DMSO-$d_6$)

δ: 1.67–1.77(br, 2H), 2.02–2.20(br, 2H), 3.30(s, 3H), 3.54–3.65(m, 3H), 3.87–3.95(m, 2H), 7.22(d, J=7.0 Hz, 1H), 7.98–8.06(m, 2H), 8.13(d, J=8.8 Hz, 1H), 8.44(s,1H), 8.65 (d, J=7.0 Hz, 1H)

MS m/e(ESI) 377 (MH$^+$)

Example 232

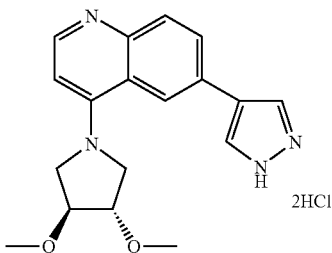

4-[(3S,4S)-3,4-dimethoxytetrahydro-1H-1-pyrrolyl]-6-(3-methyl-1H-4-pyrazolyl)quinoline dihydrochloride 4-[(3S,4S)-3,4-Dimethoxytetrahydro-1H-1-pyrrolyl]-6-(3-methyl-1-trityl-1H-4-pyrazolyl)quinoline was obtained by the same method as in Example 168 from 110 mg of 6-bromo-4-[(3S,4S)-3,4-dimethoxytetrahydro-1H-1-pyrrolyl]quinoline obtained in Production Example 83 and 180 mg 3-methyl-1-trityl-1H-4-pyrazolylboronic acid (compound in Production Example 30). Then, the product was subjected to deprotection of the trityl group and converted into the corresponding hydrochloride in the same manner as in Example 164, to give 90 mg of the title compound as colorless crystals.

$^1$H-NMR (DMSO-$d_6$)

δ: 2.50(s, 3H), 3.35(s, 6H), 3.90–4.15(m, 6H), 6.79(d, J=7.0 Hz, 1H), 8.05–8.14(m, 2H), 8.24(s, 1H), 8.41(s, 1H), 8.45(d, J=7.0 Hz, 1H)

MS m/e(ESI) 339(MH$^+$)

Example 233

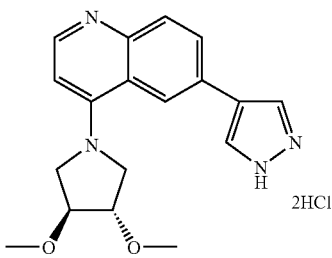

4-[(3S,4S)-3,4-Dimethoxytetrahydro-1H-1-pyrrolyl]-6-(1H-4-pyrazolyl)quinoline dihydrochloride 4-[(3S,4S)-3,4-Dimethoxytetrahydro-1H-1-pyrrolyl]-6-(1-trityl-1H-4-pyrazolyl)quinoline was obtained by the same method as in Example 168 from 120 mg of 6-bromo-4-[(3S,4S)-3,4-dimethoxytetrahydro-1H-1-pyrrolyl]quinoline obtained in Production Example 83 and 190 mg 1-trityl-1H-4-pyrazolylboronic acid. Then, the product was subjected to deprotection of the trityl group and converted into the corresponding hydrochloride in the same manner as in Example 164, to give 103 mg of the title compound as colorless crystals.

$^1$H-NMR (CD$_3$OD)

δ: 3.46(s, 6H), 3.90–4.10(m, 4H), 4.16–4.21(m, 2H), 6.84(d, J=7.4 Hz, 1H), 7.89(d, J=8.8 Hz, 1H), 8.23(dd, J=2.0 Hz, J=8.8 Hz, 1H), 8.29(d, J=7.4 Hz, 1H), 8.54(s, 2H), 8.68(d, J=2.0 Hz, 1H

MS m/e(ESI) 325(MH$^+$)

Example 234

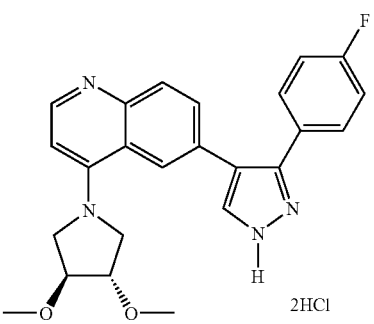

4-[(3S,4S)-3,4-Dimethoxytetrahydro-1H-1-pyrrolyl]-6-[3-(4-fluorophenyl)-1H-4-pyrazolyl]quinoline dihydrochloride 4-[(3S,4S)-3,4-Dimethoxytetrahydro-1H-1-pyrrolyl]-6-[3-(4-fluorophenyl)-1-trityl-1H-4-pyrazolyl]quinoline was obtained in the same manner as in Example 168 from 106 mg of 6-bromo-4-[(3S,4S)-3,4-dimethoxytetrahydro-1H-1-pyrrolyl]quinoline obtained in Production Example 8 and 211 mg 3-(4-fluorophenyl)-1-trityl-1H-4-pyrazolylboronic acid. Then, the product was subjected to deprotection of the trityl group and converted into the corresponding hydrochloride in the same manner as in Example 164, to give 90 mg of the title compound as colorless crystals.

$^1$H-NMR (DMSO-$d_6$)

δ: 3.40(s, 6H), 3.42–3.54(m, 2H), 3.67–3.73(m, 2H), 3.94(br, 2H), 6.73(d, J=7.2 Hz, 1H), 7.18–7.30(m, 2H), 7.47–7.55(m, 2H), 7.85(d, J=8.8 Hz, 1H), 8.02–8.16(m, 3H), 8.24(d, J=7.2 Hz, 1H)

MS m/e(ESI) 419(MH$^+$)

Example 235

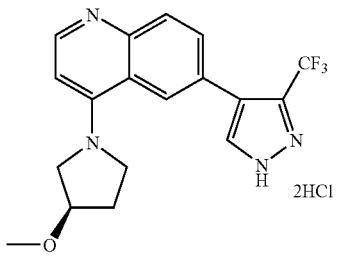

4-[(3R)-3-Methoxytetrahydro-1H-1-pyrrolyl]-6-[3-(trifluoromethyl)-1H-4-pyrazolyl]quinoline dihydrochloride 4-[(3R)-3-Methoxytetrahydro-1H-1-pyrrolyl]-6-[3-(trifluoromethyl)-1-trityl-1H-4-pyrazolyl]quinoline was obtained in the same manner as in Example 168 from 100 mg 6-bromo-4-[(3R)-3-methoxytetrahydro-1H-1-pyrrolyl] quinoline obtained in Production Example 84 and 165 mg 3-trifluoromethyl-1-trityl-1H-4-pyrazolylboronic acid. Then, the product was subjected to deprotection of the trityl group and converted into the corresponding hydrochloride in the same manner as in Example 164, to give 68 mg of the title compound as pale yellow crystals.

$^1$H-NMR (DMSO-$d_6$)

δ: 2.02–2.14(m, 1H), 2.20–2.34(m, 1H), 3.28(s, 3H), 3.80–4.26(m, 5H), 6.80(d, J=7.2 Hz, 1H), 7.97(d, J=9.0 Hz, 1H), 8.07(d, J=9.0 Hz, 1H), 8.40–8.44(s, 2H), 8.46(d, J=7.2 Hz, 1H)

MS m/e(ESI) 363 (MH$^+$)

Example 236

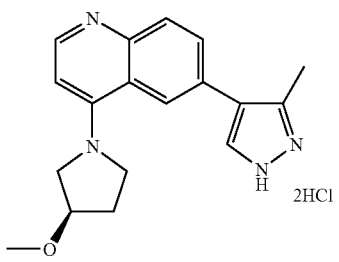

4-[(3R)-3-Methoxytetrahydro-1H-1-pyrrolyl]-6-(3-methyl-1H-4-pyrazolyl)quinoline dihydrochloride 4-[(3R)-3-Methoxytetrahydro-1H-1-pyrrolyl]-6-(3-methyl-1-trityl-1H-4-pyrazolyl)quinoline was obtained in the same manner as in Example 168 from 100 mg 6-bromo-4-[(3R)-3-methoxytetrahydro-1H-1-pyrrolyl]quinoline obtained in Production Example 84 and 144 mg 3-methyl-1-trityl-1H-4-pyrazolylboronic acid (compound in Production Example 30). Then, the product was subjected to deprotection of the trityl group and converted into the corresponding hydrochloride in the same manner as in Example 164, to give 58 mg of the title compound as pale yellow crystals.

$^1$H-NMR (DMSO-$d_6$)

δ: 2.02–2.14(m, 1H), 2.20–2.34(m, 1H), 2.47(s, 3H), 3.28(s, 3H), 3.90–4.30(m, 5H), 6.76(d, J=7.2 Hz, 1H), 7.98–8.10(m, 3H), 8.38–8.46(m, 2H)

MS m/e(ESI) 309(MH$^+$)

Example 237

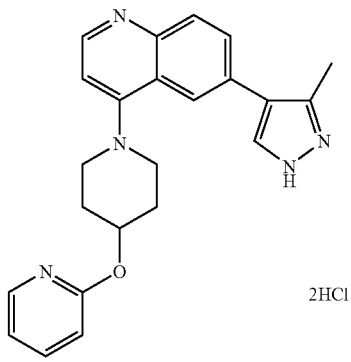

6-(3-Methyl-1H-4-pyrazolyl)-4-[4-(2-pyridyloxy)piperidino]quinoline dihydrochloride 6-(3-Methyl-1-trityl-1H-4-pyrazolyl)-4-[4-(2-pyridyloxy)piperidino]quinoline was obtained in the same manner as in Example 168 from 120 mg 6-bromo-4-[4-(2-pyridyloxy)piperidino] quinoline obtained in Production Example 85 and 140 mg 3-methyl-1-trityl-1H-4-pyrazolylboronic acid. Then, the product was subjected to deprotection of the trityl group and converted into the corresponding hydrochloride in the same manner as in Example 164, to give 91 mg of the title compound as colorless crystals.

$^1$H-NMR (DMSO-$d_6$)

δ: 1.90–2.02(m, 2H), 2.21–2.32(m, 2H), 2.50(s, 3H), 3.72–3.83(m, 2H), 3.95–4.10(m, 2H), 5.34–5.42(m, 1H), 6.88(d, J=8.4 Hz, 1H), 6.99–7.02(m, 1H), 7.24(d, J=6.8 Hz, 1H), 7.72–7.79(m,1H), 8.04(s, 1H), 8.12–8.21(m, 4H), 8.65 (d, J=6.8 Hz, 1H)

Example 238

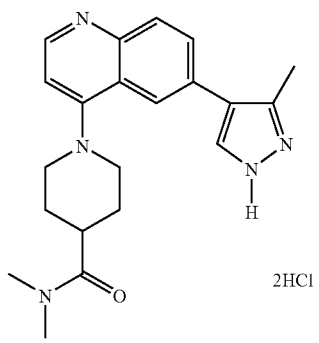

N4,N4-Dimethyl-1-[6-(3-methyl-1H-4-pyrazolyl)-4-quinolyl]-4-piperidine carboxamide dihydrochloride N4,N4-Dimethyl-1-[6-(3-methyl-1-trityl-1H-4-pyrazolyl)-4-quinolyl]-4-piperidine carboxamide was obtained in the same manner as in Example 168 from 81 mg N4,N4-dimethyl-1-(6-bromo-4-quinolyl)-4-piperidine carboxamide obtained in Production Example 87 and 99 mg 3-methyl-1-trityl-1H-4-pyrazolylboronic acid. Then, the product was subjected to deprotection of the trityl group and converted into the corresponding hydrochloride in the same manner as in Example 164, to give 62 mg of the title compound as pale yellow crystals.

$^1$H-NMR (DMSO-$d_6$)

δ: 1.76–1.90(m, 4H), 2.48(s, 3H), 2.82(s, 3H), 3.07(s, 3H), 3.00–3.14(m, 1H), 3.50–3.60(m, 2H), 4.13–4.25(m, 2H), 7.14–7.20(m, 1H), 7.96–8.14(m, 4H), 8.56–8.63(m, 1H)

MS m/e(ESI) 364(MH$^+$)

Example 239

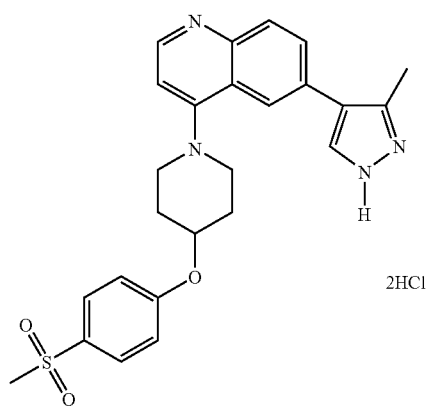

6-(3-Methyl-1H-4-pyrazolyl)-4-{4-[4-(methylsulfonyl)-phenoxy]piperidino}quinoline dihydrochloride 6-(3-Methyl-1-trityl-1H-4-pyrazolyl)-4-{4-[4-(methylsulfonyl)phenoxy]piperidino}quinoline was obtained in the same manner as in Example 168 from 50 mg 6-bromo-4-{4-[4-(methylsulfonyl)phenoxy]piperidino}quinoline obtained in Production Example 89 and 52 mg 3-methyl-1-trityl-1H-4-pyrazolylboronic acid (compound in Production Example 30). Then, the product was subjected to deprotection of the trityl group and converted into the corresponding hydrochloride in the same manner as in Example 164, to give 32 mg of the title compound as pale yellow crystals.

$^1$H-NMR (DMSO-$d_6$)

δ: 1.92–2.20(m, 2H), 2.22–2.31(m, 2H), 2.49(s, 3H), 3.16(s, 3H), 3.75–3.84(m, 2H), 3.98–4.06(m, 2H), 4.95–5.02(m, 1H), 7.22–7.28(m, 3H), 7.82–7.88(m, 2H), 8.04(s, 1H), 8.10(s, 1H), 8.13–8.17(m, 2H), 8.64(d, J=6.8 Hz, 1H)

MS m/e(ESI) 463(MH$^+$)

Example 240

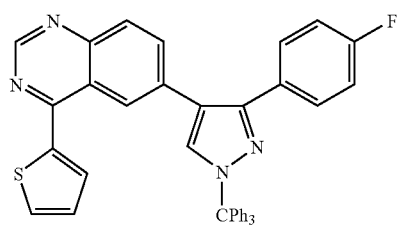

6-[3-(4-Fluorophenyl)-1-trityl-1H-4-pyrazolyl]-4-(2-thienyl)quinazoline 0.2 g of the title compound was obtained as yellow crystals in the same manner as in Example 168 from 0.1 g 6-bromo-4-(2-thienyl)quinazoline obtained in Production Example 96 and 0.2 g 3-(4-fluorophenyl)-1-trityl-1H-4-pyrazolylboronic acid (compound in Production Example 25).

$^1$H-NMR (CDCl$_3$)

δ: 7.08–7.00(m, 4H), 7.30–7.22(m, 6H), 7.38–7.30(m, 9H), 7.49–7.44(m, 2H), 7.85–7.54(m, 2H), 7.85(dd, J=8.4, 1.6 Hz, 1H), 8.02(d, J=8.4 Hz, 1H), 8.23(d, J=1.6 Hz, 1H), 9.19(s, 1H)

Example 241

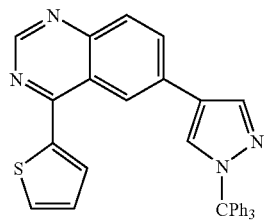

4-(2-Thienyl)-6-(1-trityl-1H-4-pyrazolyl)quinazoline 89 mg of the title compound was obtained as colorless crystals in the same manner as in Example 168 from 50 mg 6-bromo-4-(2-thienyl)quinazoline obtained in Production Example 96 and 80 mg 1-trityl-1H-4-pyrazolylboronic acid.

$^1$H-NMR (CDCl$_3$)

δ: 7.19–7.28(m, 7H), 7.33–7.38(m, 9H), 7.68(d, J=5.2 Hz, 1H), 7.77(s, 1H), 7.84–7.87(m, 1H), 7.96(dd, J=2.0, J=8.6 Hz, 1H), 8.04(d, J=8.6 Hz, 1H), 8.07(s, 1H), 8.53(d, J=2.0 Hz, 1H), 9.21(s, 1H)

Example 242

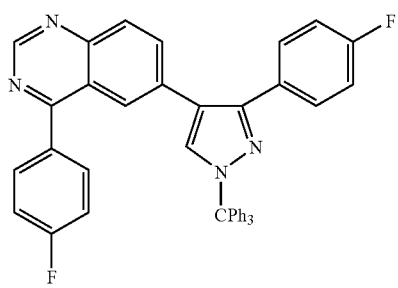

4-(4-Fluorophenyl)-6-[3-(4-fluorophenyl)-1-trityl-1H-4-pyrazolyl]quinazoline 150 mg of the title compound was obtained as a pale yellow amorphous in the same manner as in Example 168 from 96 mg 6-bromo-4-(4-fluorophenyl)quinazoline obtained in Production Example 97 and 210 mg 3-(4-fluorophenyl)-1-trityl-1H-4-pyrazolylboronic acid (compound in Production Example 25).

$^1$H-NMR (CDCl$_3$)

δ: 7.14–7.42(m, 21H), 7.50–7.54(m, 2H), 7.66–7.67(m, 1H), 7.82(s, 1H), 7.82–7.85(m, 2H), 9.23(s, 1H)

Example 243

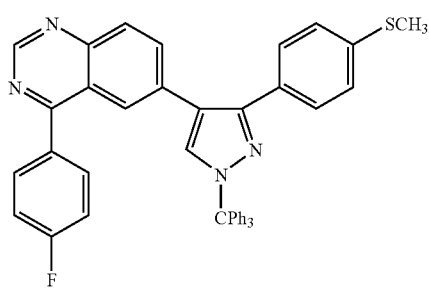

4-(4-Fluorophenyl)-6-{3-[4-(methylsulfanyl)phenyl]-1-trityl-1H-4-pyrazolyl}quinazoline 230 mg of the title compound was obtained as a yellow amorphous in the same manner as in Example 168 from 100 mg 6-bromo-4-(4-fluorophenyl)quinazoline obtained in Production Example 97 and 240 mg 3-[4-(methylsulfanyl)phenyl]-1-trityl-1H-4-pyrazolylboronic acid (compound in Production Example 26).

$^1$H-NMR (DMSO-d$_6$)

δ: 2.50(s, 3H), 7.07–7.18(m, 8H), 7.29(s, 3H), 7.32–7.40 (m, 10H), 7.47–7.52(m, 2H), 7.69(br, 1H), 7.78(s, 1H), 8.00–8.08(m, 2H), 9.25(s, 1H)

Example 244

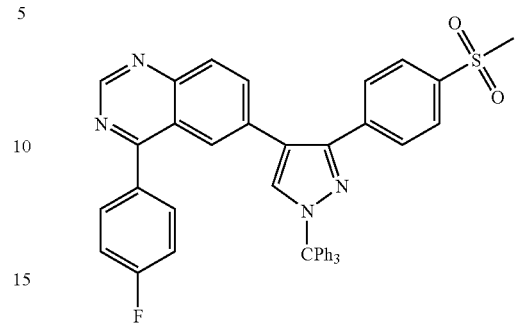

4-(4-Fluorophenyl)-6-{3-[4-(methylsulfonyl)phenyl]-1-trityl-1H-4-pyrazolyl}quinazoline 200 mg of 4-(4-fluorophenyl)-6-{3-[4-(methylsulfanyl)phenyl]-1-trityl-1H-4-pyrazolyl}quinazoline obtained in Example 243 was oxidized by the same method as in Example 156, to give 160 mg of the title compound as pale brown crystals.

$^1$H-NMR (CDCl$_3$)

δ: 3.05(s, 3H), 7.08–7.15(m, 2H), 7.20–7.25(m, 6H), 7.32–7.38(m, 9H), 7.50–7.55(m, 3H), 7.66–7.69(m, 2H), 7.84–7.92(m, 4H), 8.12–8.17(m, 1H), 9.33(s, 1H)

Example 245

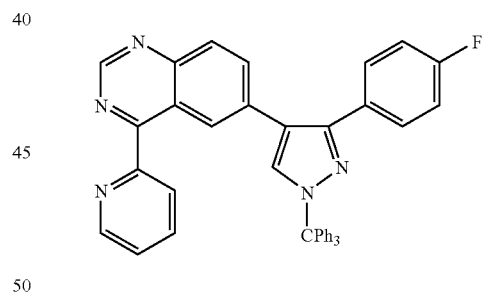

6-[3-(4-Fluorophenyl)-1-trityl-1H-4-pyrazolyl]-4-(2-pyridyl)quinazoline 13 mg of the title compound was obtained as a pale yellow amorphous by the same method as in Example 154 from 100 mg 6-[3-(4-fluorophenyl)-1-trityl-1H-4-pyrazolyl]-4-quinolyl trifluoromethane sulfonate obtained in Production Example 95 and 85 mg tri-n-butyl(2-pyridyl)stannane.

$^1$H-NMR (CDCl$_3$)

δ: 6.90–6.96(m, 2H), 7.23–7.45(m, 18H), 7.57(s, 1H), 7.78–7.88(m, 2H), 7.97–8.01(m, 2H), 8.52–8.55(m, 1H), 8.59–8.60(m, 1H), 9.34(s, 1H)

MS m/e(ESI) 610(MH$^+$)

Example 246

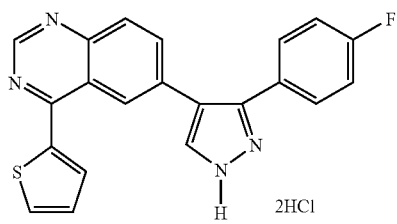

6-[3-(4-Fluorophenyl)-1H-4-pyrazolyl]-4-(2-pyridyl)-quinazoline dihydrochloride 72 mg of the title compound was obtained as orange crystals (recrystallization solvent: methanol/ether) by the same method as in Example 163 from 100 mg 6-[3-(4-fluorophenyl)-1-trityl-1H-4-pyrazolyl]-4-(2-thienyl)quinazoline and 2.2 mL of 5 N hydrochloric acid.

$^1$H-NMR (DMSO-$d_6$)

δ: 7.09(t, J=4.2 Hz, 1H), 7.24–7.32(m, 3H), 7.48–7.51(m, 2H), 7.92(d, J=4.2 Hz, 1H), 8.02(d, J=8.8 Hz, 1H), 8.08(dd, J=8.8, 1.6 Hz, 1H), 8.20(d, J=1.6 Hz, 1H), 8.23(s, 1H), 9.16(s, 1H)

Example 247

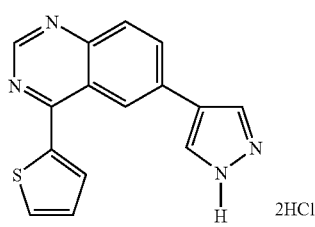

6-(1H-4-Pyrazolyl)-4-(2-thienyl)quinazoline dihydrochloride 38 mg of the title compound was obtained as yellow crystals by the same method as in Example 163 from 89 mg 4-(2-thienyl)-6-(1-trityl-1H-4-pyrazolyl)quinazoline obtained in Example 241.

$^1$H-NMR (DMSO-$d_6$)

δ: 7.36–7.38(m, 1H), 7.99(d, J=5.6 Hz, 1H), 8.04(d, J=9.2 Hz, 1H), 8.21(d, J=4.0 Hz, 1H), 8.34–8.36(m, 3H), 8.60–8.63(m, 1H), 9.16(s, 1H)

Example 248

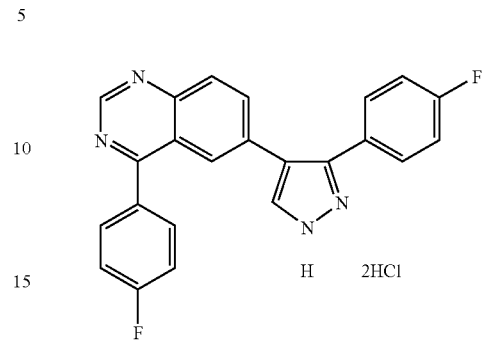

4-(4-Fluorophenyl)-6-[3-(4-fluorophenyl)-1H-4-pyrazolyl]-quinazoline dihydrochloride 95 mg of the title compound was obtained as yellow crystals by the same method as in Example 163 from 150 mg 4-(4-fluorophenyl)-6-[3-(4-fluorophenyl)-1-trityl-1H-4-pyrazolyl]quinazoline obtained in Example 242.

$^1$H-NMR (DMSO-$d_6$)

δ: 7.17–7.24(m, 4H), 7.38–7.42(m, 2H), 7.56–7.60(m, 2H), 7.72–7.73(m, 1H), 8.06–8.09(m, 2H), 8.15(s, 1H), 9.27(s, 1H)

Example 249

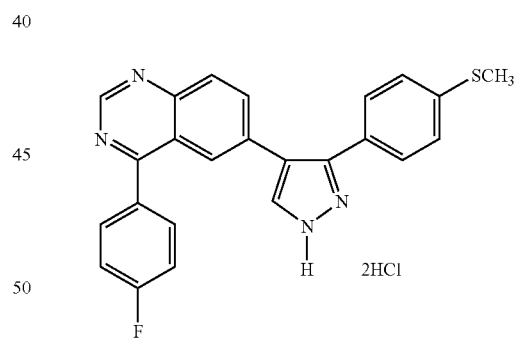

4-(4-Fluorophenyl)-6-{3-[4-(methylsulfanyl)phenyl]-1H-4-pyrazolyl}quinazoline dihydrochloride 11 mg of the title compound was obtained as yellow crystals by the same procedure as in Example 163 from 25 mg 4-(4-fluorophenyl)-6-{3-[4-(methylsulfanyl)phenyl]-1-trityl-1H-4-pyrazolyl)quinazoline obtained in Example 243.

$^1$H-NMR (DMSO-$d_6$)

δ: 2.51(s, 3H), 7.14–7.37(m, 6H), 7.53–7.62(m, 2H), 7.68–7.77(m, 1H), 8.04–8.10(m, 3H), 9.26(s, 1H)

Example 250

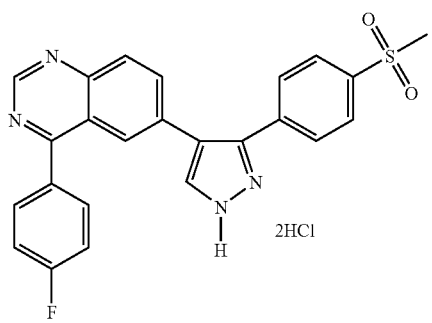

4-(4-Fluorophenyl)-6-{3-[4-(methylsulfonyl)phenyl]-1H-4-pyrazolyl}quinazoline dihydrochloride 68 mg of the title compound was obtained as yellow crystals by the same method as in Example 163 from 160 mg 4-(4-fluorophenyl)-6-{3-[4-(methylsulfonyl)phenyl]-1-trityl-1H-4-pyrazolyl}quinazoline obtained in Example 244.

$^1$H-NMR (DMSO-d$_6$)

δ: 3.26(s, 3H), 7.18–7.25(m, 2H), 7.55–7.61(m, 2H), 7.68–7.72(m, 2H), 7.73(d, J=1.6 Hz, 1H), 7.94–7.97(m, 2H), 8.05–8.12(m, 2H), 8.19(s, 1H), 9.29(s, 1H)

Example 251

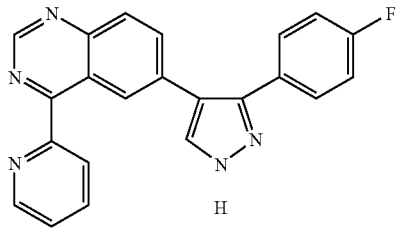

6-[3-(4-Fluorophenyl)-1H-4-pyrazolyl]-4-(2-pyridyl)-quinazoline 13 mg 6-[3-(4-fluorophenyl)-1-trityl-1H-4-pyrazolyl]-4-(2-pyridyl)quinazoline obtained in Example 245 was subjected to deprotection of the trityl group in the same manner as in Example 165 and further purified by NAM silica gel chromatography (ethyl acetate/methanol) to give 5 mg of the title compound as pale yellow crystals.

$^1$H-NMR (CDCl$_3$)

δ: 7.01–7.07(m, 2H), 7.40–7.48(m, 3H), 7.83–7.93(m, 3H), 8.02–8.09(m, 2H), 8.61–8.64(m, 1H), 8.74(d, J=2.0 Hz, 1H), 9.37(s, 1H)

MS m/e(ESI) 368 (MH$^+$)

Example 252

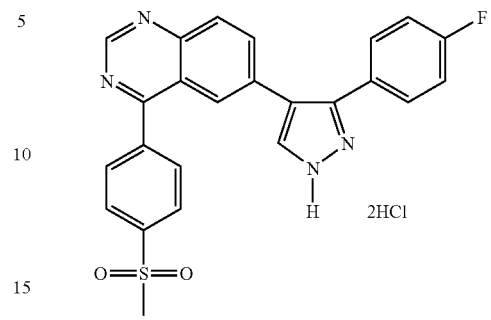

6-[3-(4-Fluorophenyl)-1H-4-pyrazolyl]-4-[4-(methylsulfonyl)phenyl]-quinazoline dihydrochloride 60 mg 6-bromo-4-[4-(methylsulfonyl)phenyl]quinazoline obtained in Production Example 98 and 90 mg 3-(4-fluorophenyl)-1-trityl-1H-4-pyrazolylboronic acid (compound in Production Example 25) were reacted in the same manner as in Example 168, to give 130 mg 6-[3-(4-fluorophenyl)-1-trityl-1H-4-pyrazolyl]-4-[4-(methylsulfonyl)phenyl]quinazoline as pale orange oil. This product was subjected to deprotection of the trityl group and converted into the corresponding hydrochloride in the same manner as in Example 164, to give 69 mg of the title compound as yellow crystals.

$^1$H-NMR (DMSO-d$_6$)

δ: 3.28(s, 3H), 7.18–7.24(m, 2H), 7.39–7.43(m, 2H), 7.69(s, 1H), 7.78–7.83(m, 2H), 7.90–7.97(m, 3H), 8.09(s, 2H), 9.33(s, 1H)

MS m/e(ESI) 477 (MH$^+$ MeOH adduct)

Example 253

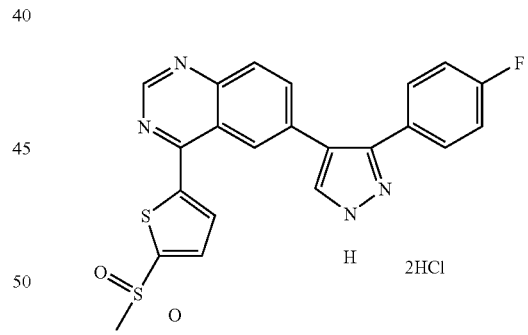

6-[3-(4-Fluorophenyl)-1H-4-pyrazolyl]-4-[5-(methylsulfonyl)-2-thienyl]quinazoline dihydrochloride 6-[3-(4-Fluorophenyl)-1-trityl-1H-4-pyrazolyl]-4-[5-(methylsulfonyl)-2-thienyl]quinazoline was obtained by the same method as in Example 168 from 60 mg 6-bromo-4-[5-(methylsulfonyl)-2-thienyl]quinazoline obtained in Production Example 101 and 87 mg 3-(4-fluorophenyl)-1-trityl-1H-4-pyrazolylboronic acid (compound in Production Example 25). The product was subjected to deprotection of the trityl group and converted into the corresponding hydrochloride in the same manner as in Example 164, to give 39 mg of the title compound as orange crystals.

$^1$H-NMR (DMSO-d$_6$)

δ: 3.45(s, 3H), 7.23–7.32(m, 2H), 7.44(d, J=4.0 Hz, 1H), 7.45–7.52(m, 2H), 7.73(d, J=4.0 Hz, 1H), 8.06(s, 2H), 8.18(s, 1H), 8.25(s, 1H), 9.24(s, 1H)
MS m/e(ESI) 483(MH⁺ MeOH adduct)

Example 254

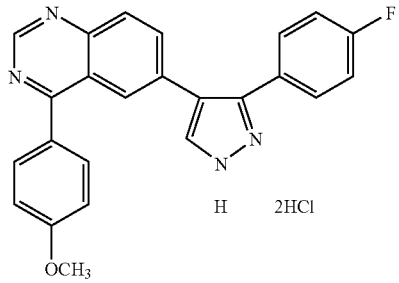

6-[3-(4-Fluorophenyl)-1H-4-pyrazolyl]-4-[4-(methoxyphenyl)-quinazoline dihydrochloride 6-[3-(4-Fluorophenyl)-1-trityl-1H-4-pyrazolyl]-4-(4-methoxyphenyl)quinazoline was obtained by the same method as in Example 168 from 25 mg 6-bromo-4-(4-methoxyphenyl)-quinazoline obtained in Production Example 102 and 43 mg 3-(4-fluorophenyl)-1-trityl-1H-4-pyrazolylboronic acid (compound in Production Example 25). The product was subjected to deprotection of the trityl group and converted into the corresponding hydrochloride in the same manner as in Example 164, to give 15 mg of the title compound as yellow crystals.
¹H-NMR (DMSO-d₆)
δ: 3.83(s, 3H), 6.89–6.94(m, 2H), 7.22–7.28(m, 2H), 7.40–7.52(m, 4H), 7.78–7.81(m, 1H), 8.02–8.14(m, 3H), 9.22(s, 1H)
MS m/e (ESI) 397 (MH⁺), 429 (MH⁺ MeOH adduct)

Example 255

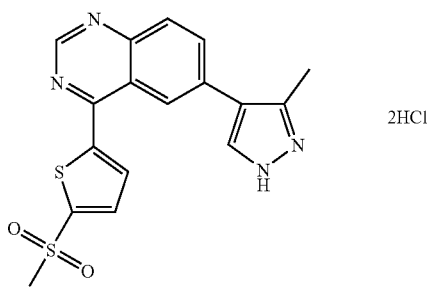

6-(3-Methyl-1H-4-pyrazolyl)-4-[5-(methylsulfonyl)-2-thienyl]quinazoline dihydrochloride 6-(3-Methyl-1-trityl-1H-4-pyrazolyl)-4-[5-(methylsulfonyl)-2-thienyl]quinazoline was obtained by the same method as in Example 168 from 110 mg 6-bromo-4-[5-(methylsulfonyl)-2-thienyl]quinazoline obtained in Production Example 101 and 130 mg 3-methyl-1-trityl-1H-4-pyrazolylboronic acid (compound in Production Example 30). The product was subjected to deprotection of the trityl group and converted into the corresponding hydrochloride in the same manner as in Example 164, to give 42 mg of the title compound as orange crystals.
¹H-NMR (DMSO-d₆)
δ: 2.50(s, 3H), 3.47(s, 3H), 7.94–7.98(m, 1H), 8.10–8.16(m, 2H), 8.21–8.23(m, 1H), 8.26–8.30(m, 1H), 8.41–8.44(m, 1H), 9.26(s, 1H)

Example 256

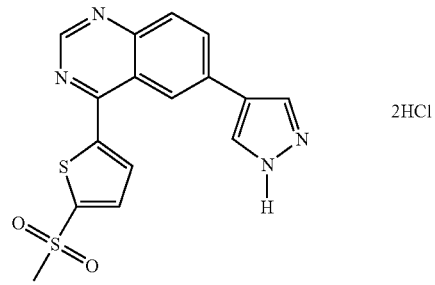

4-[5-(Methylsulfonyl)-2-thienyl]-6-(1H-4-pyrazolyl)-quinazoline dihydrochloride

4-[5-(Methylsulfonyl)-2-thienyl]-6-(1-trityl-1H-4-pyrazolyl)quinazoline was obtained by the same method as in Example 168 from 110 mg 6-bromo-4-[5-(methylsulfonyl)-2-thienyl]quinazoline obtained in Production Example 101 and 130 mg 1-trityl-1H-4-pyrazolylboronic acid. The product was subjected to deprotection of the trityl group and converted into the corresponding hydrochloride in the same manner as in Example 164, to give 78 mg of the title compound as orange crystals.
¹H-NMR (DMSO-d₆)
δ: 3.48(s, 3H), 7.95(d, J=4.2 Hz, 1H), 8.07–8.11(m, 1H), 8.29(d, J=4.2 Hz, 1H), 8.39(s, 2H), 8.40–8.42(m, 1H), 8.55(d, J=2.0 Hz, 1H), 9.23(s, 1H)

Example 257

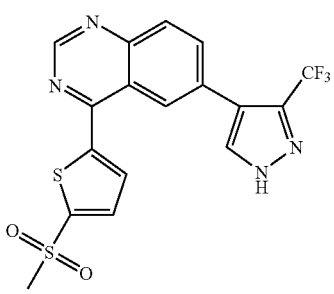

4-[5-(Methylsulfonyl)-2-thienyl]-6-[3-(trifluoromethyl)-1H-4-pyrazolyl]quinazoline dihydrochloride 4-[5-(Methylsulfonyl)-2-thienyl]-6-[3-(trifluoromethyl)-1-trityl-1H-4-pyrazolyl]quinazoline was obtained by the same method as in Example 168 from 100 mg 6-bromo-4-[5-(methylsulfonyl)-2-thienyl]quinazoline obtained in Production Example 101 and 140 mg 3-trifluoromethyl-1-trityl-1H-4-pyrazolylboronic acid (compound in Production Example 31). The product was subjected to deprotection of the trityl group and converted into the corresponding hydrochloride in the same manner as in Example 164, to give 42 mg of the title compound as orange crystals.

¹H-NMR (DMSO-$d_6$)

δ: 3.47(s, 3H), 7.97(d, J=3.8 Hz, 1H), 8.14(d, J=3.8 Hz, 1H), 8.15–8.21(m, 2H), 8.49(s, 1H), 8.53(s, 1H), 9.32(s, 1H)

MS m/e (ESI) 457 (MH⁺ MeOH adduct)

Example 258

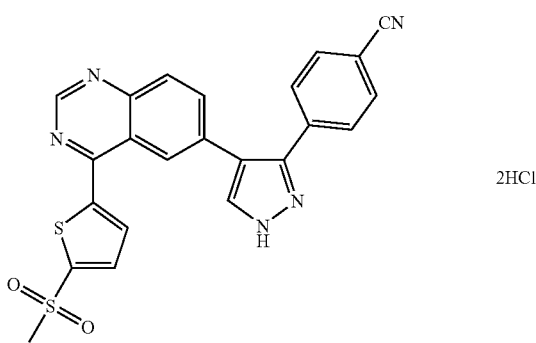

4-(4-{4-[5-(Methylsulfonyl)-2-thienyl]-6-quinazolinyl}-1H-3-pyrazolyl)benzonitrile dihydrochloride 4-(4-{4-[5-(Methylsulfonyl)-2-thienyl]-6-quinazolinyl}-1-trityl-1H-3-pyrazolyl) benzonitrile was obtained by the same method as in Example 168 from 100 mg 6-bromo-4-[5-(methylsulfonyl)-2-thienyl]quinazoline obtained in Production Example 101 and 150 mg 3-(4-cyanophenyl)-1-trityl-1H-4-pyrazolylboronic acid (compound in Production Example 32). The product was subjected to deprotection of the trityl group and converted into the corresponding hydrochloride in the same manner as in Example 164, to give 67 mg of the title compound as yellow crystals.

¹H-NMR (DMSO-$d_6$)

δ: 3.44(s, 3H), 7.58–7.66(m, 3H), 7.78(d, J=4.0 Hz, 1H), 7.87(d, J=8.0 Hz, 2H), 7.99(dd, J=8.8 Hz, 1.6 Hz, 1H), 8.07(d, J=8.8 Hz, 1H), 8.23(d, J=1.6 Hz, 1H), 8.31(s, 1H), 9.27(s, 1H)

Example 259

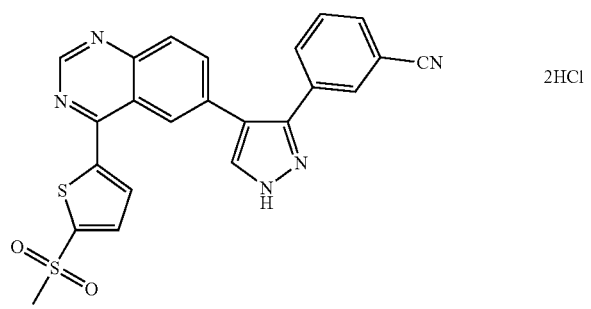

3-(4-{4-[5-(Methylsulfonyl)-2-thienyl]-6-quinazolinyl}-1H-3-pyrazolyl)benzonitrile dihydrochloride 3-(4-{4-[5-(Methylsulfonyl)-2-thienyl]-6-quinazolinyl}-1-trityl-1H-3-pyrazolyl)benzonitrile was obtained by the same method as in Example 168 from 120 mg 6-bromo-4-[5-(methylsulfonyl)-2-thienyl]quinazoline obtained in Production Example 101 and 180 mg 3-(3-cyanophenyl)-1-trityl-1H-4-pyrazolylboronic acid (compound in Production Example 33). Then, the product was subjected to deprotection of the trityl group and converted into the corresponding hydrochloride in the same manner as in Example 164, to give 84 mg of the title compound as yellow crystals.

¹H-NMR (DMSO-$d_6$)

δ: 3.46(s, 3H), 7.52(d, J=3.6 Hz, 1H), 7.58–7.64(m, 1H), 7.72–7.79(m, 2H), 7.86–7.94(m, 2H), 8.01–8.09(m, 2H), 8.18–8.22(m, 1H), 8.33(s, 1H), 9.26(s, 1H)

Example 260

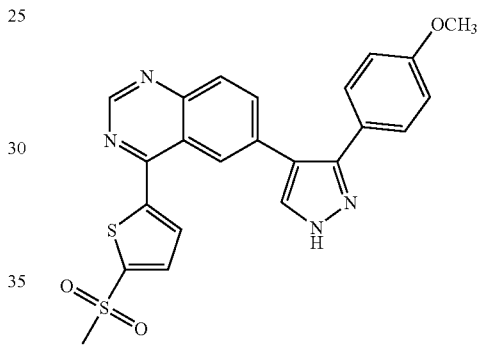

6-[3-(4-Methoxyphenyl)-1H-4-pyrazolyl]-4-[5-(methylsulfonyl)-2-thienyl]quinazoline dihydrochloride 94 mg 6-[3-(4-methoxyphenyl)-1-trityl-1H-4-pyrazolyl]-4-[5-(methylsulfanyl)-2-thienyl]quinazoline was obtained by the same method as in Example 168 from 60 mg 6-bromo-4-[5-(methylsulfanyl)-2-thienyl]quinazoline obtained in Production Example 100 and 110 mg 3-(4-methoxyphenyl)-1-trityl-1H-4-pyrazolylboronic acid (compound in Production Example 27). The product was oxidized by the same method as in Example 156, to give 82 mg 6-[3-(4-methoxyphenyl)-1-trityl-1H-4-pyrazolyl]-4-[5-(methylsulfonyl)-2-thienyl]quinazoline. Then, this product was subjected to deprotection of the trityl group and converted into the corresponding hydrochloride in the same manner as in Example 164, to give 31 mg of the title compound as yellow crystals.

¹H-NMR (DMSO-$d_6$)

δ: 3.44(s, 3H), 3.79(s, 3H), 7.03(d, J=8.4 Hz, 2H), 7.33(d, J=4.0 Hz, 1H), 7.37(d, J=8.4 Hz, 2H), 7.64(d, J=4.0 Hz, 1H), 8.05(d, J=8.8 Hz, 1H), 8.11(dd, J=8.8 Hz, 1.8 Hz, 1H), 8.18(d, J=1.8 Hz, 2H), 9.22(s, 1H)

MS m/e(ESI) 463 (MH⁺)

Example 261

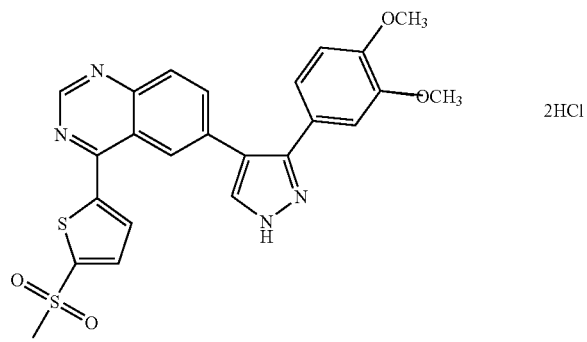

6-[3-(3,4-Dimethoxyphenyl)-1H-4-pyrazolyl]-4-[5-(methylsulfonyl)-2-thienyl]quinazoline dihydrochloride The title compound was synthesized according to the synthesis process in Example 261. 6-[3-(3,4-Dimethoxyphenyl)-1-trityl-1H-4-pyrazolyl]-4-[5(methylsulfanyl)-2-thienyl]quinazoline was obtained by the same method as in Example 168 from 60 mg 6-bromo-4-[5-(methylsulfanyl)-2-thienyl]quinazoline obtained in Production Example 100 and 110 mg 3-(3,4-dimethoxyphenyl)-1-trityl-1H-4-pyrazolylboronic acid (compound in Production Example 29). The product was oxidized by the same method as in Example 156, and the resulting 6-[3-(3,4-dimethoxyphenyl)-1-trityl-1H-4-pyrazolyl]-4-[5-(methylsulfonyl)-2-thienyl]quinazoline was subjected to deprotection of the trityl group and converted into the corresponding hydrochloride in the same manner as in Example 164, to give 31 mg of the title compound as orange crystals.

$^1$H-NMR (DMSO-$d_6$)

δ: 3.45(s, 3H), 3.61(s, 3H), 3.79(s, 3H), 6.94(dd, J=8.4, 1.6 Hz, 1H), 7.00–7.05(m, 2H), 7.36(d, J=3.8 Hz, 1H), 7.62(d, J=3.8 Hz, 1H), 8.06(d, J=9.0 Hz, 1H), 8.15(dd, J=9.0, 1.8 Hz, 1H), 8.22(s, 1H), 8.24(d, J=1.8 Hz, 1H), 9.22(s, 1H)

MS m/e(ESI) 525 (MH$^+$ MeOH adduct)

Example 262

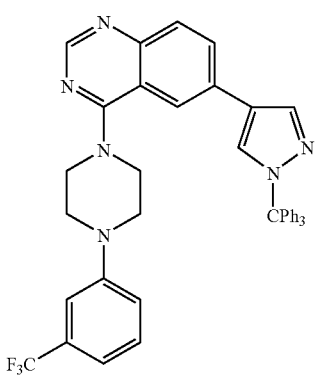

4-{4-[3-(Trifluoromethyl)phenyl]piperazin-1-yl}}-6-(1-trityl-1H-4-pyrazolyl)quinazoline 174 mg of the title compound was obtained as colorless crystals by the same method as in Example 168 from 110 mg 6-bromo-4-{4-[3-(trifluoromethyl)phenyl]piperazin-1-yl}quinazoline obtained in Production Example 106 and 120 mg 1-trityl-1H-4-pyrazolylboronic acid.

$^1$H-NMR (DMSO-$d_6$)

δ: 3.40–3.48(m, 4H), 3.92–4.05(m, 4H), 7.10–7.25(m, 9H), 7.30–7.38(m, 9H), 7.43(t, J=8.0 Hz, 1H), 7.71(d, J=0.8 Hz, 1H), 7.85(dd, J=8.8, 1.6 Hz, 1H), 7.92(d, J=1.6 Hz, 1H), 7.95–8.04(br, 1H), 8.02(d, J=0.8 Hz, 1H), 8.72(s, 1H)

Example 263

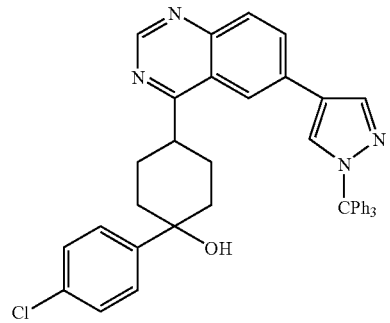

4-(4-Chlorophenyl)-1-[6-(1-trityl-1H-4-pyrazolyl)-4-quinazolyl]-4-piperidinol 185 mg of the title compound was obtained as a pale yellow solid by the same method as in Example 168 from 100 mg 1-(6-bromo-4-quinazolinyl)-4-(4-chlorophenyl)-4-piperidinol obtained in Example 107 and 110 mg 1-trityl-1H-4-pyrazolyl-boronic acid.

$^1$H-NMR (DMSO-$d_6$)

δ: 1.85–1.93(m, 2H), 2.19–2.29(m, 2H), 3.63–3.75(m, 2H), 4.26–4.37(m, 2H), 7.16–7.25(m, 6H), 7.26–7.35(m, 9H), 7.39(dt, J=8.8, 2.0 Hz, 2H), 7.48(dt, J=8.8, 2.0 Hz, 2H), 7.68(d, J=0.8 Hz, 1H), 7.82(dd, J=8.4, 2.0 Hz, 1H), 7.87–7.95(m, 1H), 7.79(d, J=2.0 Hz, 1H), 8.01(d, J=0.8 Hz, 1H), 8.68(s, 1H)

Example 264

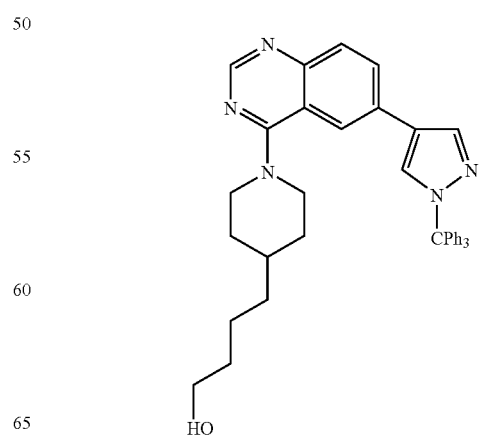

4-{1-[6-(1-Trityl-1H-4-pyrazolyl)-4-quinazolyl]-4-piperidyl}-1-butanol 165 mg of the title compound was obtained as an oil by the same method as in Example 168 from 100 mg 4-[1-(6-bromo-4-quinazolinyl)-4-piperidyl]-1-butanol obtained in Production Example 108 and 114 mg 1-trityl-1H-4-pyrazolylboronic acid.

$^1$H-NMR (DMSO-d$_6$)

δ: 1.32–1.70(m, 9H), 1.83–1.91(m, 2H), 3.09(t, J=14.0 Hz, 2H), 3.66–3.73(m, 2H), 4.60–4.72(m, 2H), 7.19–7.25 (m, 6H), 7.32–7.38(m, 9H), 7.69(d, J=0.8 Hz, 1H), 7.78(dd, J=8.8, 2.0 Hz, 1H), 7.82–7.90(br 1H), 7.86(d, J=2.0 Hz, 1H), 8.02(d, J=0.8 Hz, 1H), 8.64(s, 1H)

Example 265

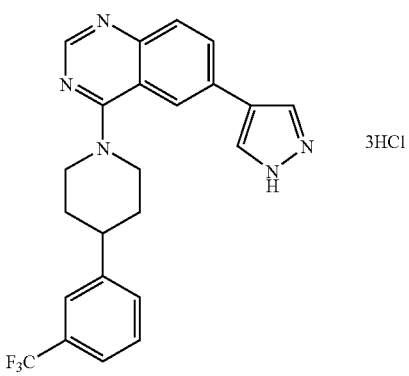

6-(1H-4-Pyrazolyl)-4-{4-[3-(trifluoromethyl)phenyl]-piperazin-1-yl}quinazoline trihydrochloride From 160 mg 4-{4-[3-(trifluoromethyl)phenyl]piperazin-1-yl)-6-(1-trityl-1H-4-pyrazolyl)quinazoline obtained in Example 262 and 2 mL of 5 N hydrochloric acid, 98 mg of the title compound was obtained as pale yellow crystals by deprotection of the trityl group and conversion into the corresponding hydrochloride in the same manner as in Example 163.

$^1$H-NMR (DMSO-d$_6$)

δ: 3.62–3.68(m, 4H), 4.40–4.46(m, 4H), 7.09(d, J=8.0 Hz, 1H), 7.163(s, 1H), 7.21(dd, J=8.0, 0.8 Hz, 1H), 7.48(t, J=8.0 Hz, 1H), 7.90(d, J=8.8 Hz, 1H), 8.30–8.35(m, 3H), 8.88(s, 1H)

Example 266

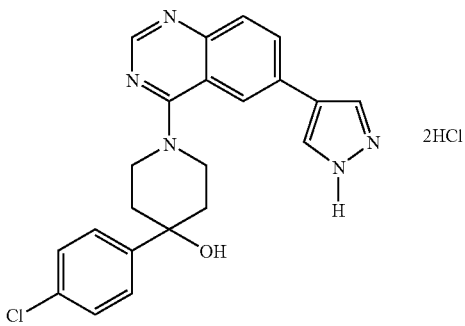

4-(4-Chlorophenyl)-1-[6-(1H-4-pyrazolyl)-4-quinazolyl]-4-piperidinol dihydrochloride From 180 mg 4-(4-chlorophenyl)-1-[6-(1-trityl-1H-4-pyrazolyl)-4-quinazolyl]-4-piperidinol obtained in Example 263 and 2 mL of 5 N hydrochloric acid, 77 mg of the title compound was obtained as pale yellow crystals by deprotection of the trityl group and conversion into the corresponding hydrochloride in the same manner as in Example 163.

$^1$H-NMR (DMSO-d$_6$)

δ: 1.82–1.89(m, 4H), 2.15–2.30(m, 4H), 7.41(dt, J=8.8, 2.0 Hz, 2H), 7.57(dt, J=8.8, 2.0 Hz, 2H), 7.86(d, J=9.2 Hz, 1H), 8.26–8.32(m, 4H), 8.81(s, 1H)

Example 267

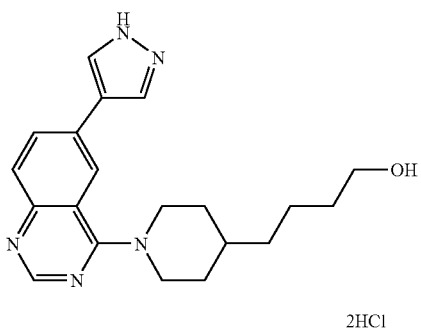

4-{1-[6-(1H-4-pyrazolyl)-4-quinazolyl]-4-piperidyl}-1-butanol dihydrochloride

From 160 mg 4-{1-[6-(1-trityl-1H-4-pyrazolyl)-4-quinazolyl]-4-piperidyl}-1-butanol obtained in Example 264 and 2 mL of 5 N hydrochloric acid, 98 mg of the title compound was obtained as pale yellow crystals by deprotection of the trityl group and conversion into the corresponding hydrochloride in the same manner as in Example 163.

$^1$H-NMR (DMSO-$d_6$)

δ: 1.23–1.48(m, 8H), 1.68–1.81(m, 1H), 1.90–1.99(m, 2H), 3.40(t, J=6.4 Hz, 2H), 3.59(brs, 2H), 7.77(brs, 2H), 7.87(d, J=8.8 Hz, 1H), 8.18(d, J=1.6 Hz, 1H), 8.27(s, 2H), 8.29(dd, J=8.8, 1.6 Hz, 1H), 8.78(s, 1H)

Example 268

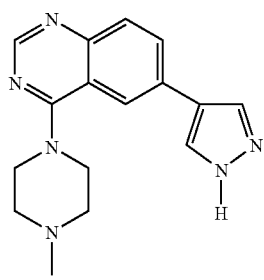

4-(4-Methylpiperazin-1-yl)-6-(1H-4-pyrazolyl)quinazoline

A mixture of 20 mg 6-bromo-4-chloroquinazoline, 10 mg 1-methylpiperazine, 15 μL triethylamine and 1 mL tetrahydrofuran was stirred for 1 hour. The solvent was removed in a stream of nitrogen, and 40 mg 1-trityl-1H-4-pyrazolylboronic acid, 2 mg tetrakis(triphenylphoshine)palladium, 1 mL of 2 N aqueous sodium carbonate, 1 mL ethanol and 1 mL toluene was added thereto, and the mixture was stirred overnight at 85° C. The solvent was removed, and 0.5 mL dichloromethane and 0.5 mL trifluoroacetic acid were added to the residue and left for 2 hours. The solvent was evaporated, 0.5 mL dimethyl sulfoxide was added thereto, insolubles were filtered off, and the filtrate was purified by high performance liquid chromatography (WAKO PAK ODS column; solvent, water/acetonitrile/0.1% trifluoroacetic acid) to give 16.3 mg of the title compound.

MS m/e(ESI) 295 (MH$^+$)

The compounds in Examples 269 to 292 were synthesized from 20 mg 6-bromo-4-chloroquinazoline and 10 mg amine as the starting materials by the same method as in Example 268.

Example 269

6-(1H-4-Pyrazolyl)-4-(1,2,3,4-tetrahydro-2-isoquinolyl)-quinazoline

Yield: 9.0 mg

Example 270

4-(4-Benzylpiperazin-1-yl)-6-(1H-4-pyrazolyl)-quinazoline

Yield: 1.4 mg

Example 271

1-[6-(1H-4-Pyrazolyl)-4-quinazolinyl]-4-piperinone

Yield: 3.0 mg

Example 272

1-[6-(1H-4-Pyrazolyl)-4-quinazolinyl]-3-piperidinol

Yield: 7.1 mg

Example 273

4-(2-Methyl-1-aziranyl)-6-(1H-4-pyrazolyl)quinazoline

Yield: 7.8 mg

Example 274

4-[4-(1,3-Benzodioxol-5-ylmethyl)piperazin-1-yl]-6-(1H-4-pyrazolyl)quinazoline

Yield: 6.7 mg

Example 275

4-[4-(2,4-Difluorobenzyl)piperazin-1-yl]-6-(1H-4-pyrazolyl)quinazoline

Yield: 6.0 mg

Example 276

4-[4-(4-Methoxybenzyl)piperazin-1-yl]-6-(1H-4-pyrazolyl)quinazoline

Yield: 6.1 mg

Example 277

4-[4-(4-Fluorophenethyl)piperazin-1-yl]-6-(1H-4-pyrazolyl)-quinazoline

Yield: 3.8 mg

Example 278

2-{4-[6-(1H-4-Pyrazolyl)-4-quinazolinyl]piperidino}aniline

Yield: 10.2 mg

Example 279

(4-Chlorophenyl){4-[6-(1H-4-pyrazolyl)-4-quinazolinyl]-piperazin-1-yl}methanone

Yield: 0.41 mg

Example 280

1-[6-(1H-4-Pyrazolyl)-4-quinazolinyl]-piperidylamine

Yield: 1.76 mg

Example 281

N1-{1-[6-(1H-4-Pyrazolyl)-4-quinazolinyl]-4-piperidyl}-benzamide

Yield: 4.2 mg

Example 282

N-(4-Fluorophenyl)-N{1-[6-(1H-4-pyrazolyl)-4-quinazolinyl]-4-piperidyl}amine

Yield: 2.59 mg

Example 283

N,N-Dimethyl-N'-1-[6-(1H-4-pyrazolyl)-4-quinazolinyl]-4-piperidyl}sulfamide

Yield: 0.89 mg

Example 284

4-(4-Benzyl-2-methylpiperazin-1-yl)-6-(1H-4-pyrazolyl)-quinazoline

Yield: 5.1 mg

Example 285

4-(4-Phenethylpiperazin-1-yl)-6-(1H-4-pyrazolyl)-quinazoline

Yield: 6.0 mg

Example 286

4-{4-[6-(1H-4-Pyrazolyl)-4-quinazolinyl]piperidino}phenol

Yield: 1.62 mg

Example 287

4-[4-(2-Chlorophenyl)piperazin-1-yl]-6-(1H-4-pyrazolyl)-quinazoline

Yield: 3.2 mg

Example 288

N1,N1-Dimethyl-4-[6-(1H-4-pyrazolyl)-4-quinazolinyl]-1-piperazine sulfonamide

Yield: 4.2 mg

Example 289

N-[4-({4-[6-(1H-4-Pyrazolyl)-4-quinazolinyl]piperazin-1-yl}methyl)phenyl]methane sulfonamide Yield: 8.2 mg

Example 290

N-[4-({4-[6-(1H-4-Pyrazolyl)-4-quinazolinyl]piperazin-1-yl}carbonyl)phenyl]methane sulfonamide Yield: 2.33 mg

Example 291

7-({4-[6-(1H-4-Pyrazolyl)-4-quinazolinyl]piperazin-1-yl}-carbonyl)-1,2,3,4,-tetrahydro-2$\lambda^6$, 1-benzothiazine-2,2-dione Yield: 4.1 mg

Example 292

N-[4-({1-[6-(1H-4-Pyrazolyl)-4-quinazolinyl]-4-piperidyl)-sulfonyl)phenyl]methane sulfonamide Yield: 6.5 mg

Example 293

4-(4-Methylpiperazin-1-yl)-6-(3-methyl-1H-4-pyrazolyl)-quinazoline

A mixture of 20 mg 6-bromo-4-chloroquinazoline, 10 mg 1-methyl piperazine, 15 µL triethylamine, and 1 mL tetrahydrofuran was stirred for 1 hour. The solvent was removed in a stream of nitrogen, and 40 mg 3-methyl-1-trityl-1H-4-pyrazolylboronic acid (compound in Production Example 30), 2 mg tetrakis(triphenylphosphine)palladium, 1 mL of 2 N aqueous sodium carbonate, 1 mL ethanol and 1 mL toluene were added to the residue, and the mixture was stirred overnight at 85° C. The solvent was removed, and 0.5 mL dichloromethane and 0.5 mL trifluoroacetic acid were added to the residue and left for 2 hours. The solvent was evaporated, 0.5 mL dimethyl sulfoxide was added thereto, insolubles were removed by filtration, and the filtrate was purified by high performance liquid chromatography (WAKO PAK ODS column; solvent, water/acetonitrile/0.1% trifluoroacetic acid), to give 16.5 mg of the title compound.

MS m/e(ESI) 309 (MH⁺)

The compounds in Examples 294 to 313 were synthesized from 20 mg 6-bromo-4-chloroquinazoline and 10 mg amine as the starting materials by the same method as in Example 293.

Example 294

6-(3-Methyl-1H-4-pyrazolyl)-4-(1,2,3,4-tetrahydro-2-isoquinolyl)quinazoline

Yield: 5.8 mg

Example 295

4-(4-Benzylpiperazin-1-yl)-6-(3-methyl-1H-4-pyrazolyl)-quinazoline

Yield: 24.1 mg

Example 296

1-[6-(3-Methyl-1H-4-pyrazolyl)-4-quinazolinyl]-4-piperinone

Yield: 10.1 mg

Example 297

1-[6-(3-Methyl-1H-4-pyrazolyl)-4-quinazolinyl]-3-piperidinol

Yield: 9.6 mg

Example 298

6-(3-Methyl-1H-4-pyrazolyl)-4-{4-[3-(trifluoromethyl)-phenyl]piperazin-1-yl}quinazoline Yield: 21.9 mg

Example 299

4-(2-Methyl-1-aziranyl)-6-(3-methyl-1H-4-pyrazolyl)-quinazoline

Yield: 16.3 mg

Example 300

4-[4-(1,3-Benzodioxol-5-ylmethyl)piperazin-1-yl]-6-(3-methyl-1H-4-pyrazolyl)quinazoline Yield: 2.94 mg

Example 301

4-[4-(2,4-Difluorobenzyl)piperazin-1-yl]-6-(3-methyl-1H-4-pyrazolyl)quinazoline

Yield: 7.5 mg

Example 302

4-[4-(4-Methoxybenzyl)piperazin-1-yl]-6-(3-methyl-1H-4-pyrazolyl)quinazoline

Yield: 7.1 mg

Example 303

4-[4-(4-Fluorophenethyl)piperazin-1-yl]-6-(3-methyl-1H-4-pyrazolyl)quinazoline

Yield: 8.8 mg

Example 304

2-{4-[6-(3-Methyl-1H-4-pyrazolyl)-4-quinazolinyl]-piperazin-1-yl}aniline

Yield: 1.30 mg

Example 305

Benzo[b]furan-2-yl{4-[6-(3-methyl-1H-4-pyrazolyl)-4-quinazolinyl]piperazin-1-yl}methanone Yield: 3.7 mg

Example 306

(4-Chlorophenyl){4-[6-(3-methyl-1H-4-pyrazolyl)-4-quinazolinyl]piperazin-1-yl}methanone Yield: 0.61 mg

Example 307

1-[6-(3-Methyl-1H-4-pyrazolyl)-4-quinazolinyl]-piperidylamine

Yield: 7.8 mg

Example 308

N,N-Dimethyl-N'-1-[6-(3-methyl-1H-4-pyrazolyl)-4-quinazolinyl]-4-piperidyl}sulfamide Yield: 5.4 mg

Example 309

4-[4-(1H-3-Indolyl)piperazino]-6-(3-methyl-1H-4-pyrazolyl)quinazoline

Yield: 0.91 mg

Example 310

4-(4-Benzyl-2-methylpiperazin-1-yl)-6-(3-methyl-1H-4-pyrazolyl)quinazoline

Yield: 3.68 mg

Example 311

6-(3-Methyl-1H-4-pyrazolyl)-4-(4-phenethylpiperazin-1-yl)-quinazoline

Yield: 2.14 mg

Example 312

4-[4-(2-Chlorophenyl)piperazin-1-yl]-6-(3-methyl-1H-4-pyrazolyl)quinazoline

Yield: 0.49 mg

Example 313

N-[4-({4-[6-(3-Methyl-1H-4-pyrazolyl)-4-quinazolinyl]-piperidyl}methyl)phenyl]methane sulfonamide Yield: 5.8 mg

Example 314

4-(4-Methylpiperazin-1-yl)-6-[3-(4-fluorophenyl)-1H-4-pyrazolyl]quinazoline

A mixture of 20 mg 6-bromo-4-chloroquinazoline, 10 mg 1-methyl piperazine, 15 µL triethylamine, and 1 mL tetrahydro furan was stirred for 1 hour. The solvent was removed in a stream of nitrogen, then 45 mg 3-(4-fluorophenyl)-1-trityl-1H-4-pyrazolylboronic acid (compound in Production Example 25), 2 mg tetrakis(triphenylphosphine)palladium, 1 mL of 2 N aqueous sodium carbonate, 1 mL ethanol and 1 mL toluene were added to the residue, and the mixture was stirred at 85° C. overnight. The solvent was removed, and 0.5 mL dichloromethane and 0.5 mL trifluoroacetic acid were added to the residue and left for 2 hours. The solvent was evaporated, 0.6 mL dimethyl sulfoxide was added thereto, insolubles were removed with a filter, and the filtrate was purified by high performance liquid chromatography (WAKO PAK ODS column; solvent, water/acetonitrile/0.1% trifluoroacetic acid) to give 15.5 mg of the title compound.

MS m/e(ESI) 389 (MH$^+$)

Example 315

6-[3-(4-Fluorophenyl)-1H-4-pyrazolyl]-4-(1,2,3,4-tetrahydro-2-isoquinolinyl)quinazoline Yield: 11.5 mg The compounds in Examples 315 to 345 were synthesized from 20 mg 6-bromo-4-chloroquinazoline and 10 mg amine as the starting materials by the same method as in Example 314.

Example 316

4-(4-Benzylpiperazin-1-yl)-6-[3-(4-fluorophenyl)-1H-4-pyrazolyl]quinazoline

Yield: 19.0 mg

Example 317

1-{6-[3-(4-Fluorophenyl)-1H-4-pyrazolyl]-4-quinazolinyl}-4-piperidinone

Yield: 3.6 mg

Example 318

1-{6-[3-(4-Fluorophenyl)-1H-4-pyrazolyl]-4-quinazolinyl}-3-piperidinol

Yield: 14.6 mg

Example 319

(1-{6-[3-(4-Fluorophenyl)-1H-4-pyrazolyl]-4-quinazolinyl}-2-piperidyl)methanol

Yield: 11.2 mg

Example 320

6-[3-(4-Fluorophenyl)-1H-4-pyrazolyl]-4-[4-(3-trifluoromethylphenyl)piperazin-1-yl]quinazoline Yield: 22.9 mg

Example 321

6-[3-(4-Fluorophenyl)-1H-4-pyrazolyl]-4-(2-methyl-1-aziranyl)quinazoline

Yield: 21.1 mg

Example 322

4-[4-(1,3-Benzodioxol-5-ylmethyl)piperazin-1-yl]-6-[3-(4-fluorophenyl)-1H-4-pyrazolyl]quinazoline Yield: 6.3 mg

Example 323

4-[4-(2,4-Difluorobenzylpiperazin-1-yl)-6-[3-(4-fluorophenyl)-1H-4-pyrazolyl]quinazoline Yield: 11.3 mg

Example 324

6-[3-(4-Fluorophenyl)-1H-4-pyrazolyl]-4-[4-(4-methoxybenzylpiperazin-1-yl]quinazoline Yield: 9.5 mg

Example 325

4-[4-(4-Fluorophenethylpiperazin-1-yl)-6-[3-(4-fluorophenyl)-1H-4-pyrazolyl]quinazoline Yield: 9.1 mg

Example 326

2-(4-{6-[3-(4-Fluorophenyl)-1H-4-pyrazolyl]-4-quinazolinyl}piperazin-1-yl)aniline Yield: 8.4 mg

Example 327

Benzo[b]furan-2-yl(4-{6-[3-(4-fluorophenyl)-1H-4-pyrazolyl]-4-quinazolinyl}piperazin-1-yl)methanone Yield: 7.4 mg

Example 328

(4-Chlorophenyl)(4-{6-[3-(4-fluorophenyl)-1H-4-pyrazolyl]-4-quinazolinyl}piperazin-1-yl)methanone Yield: 5.5 mg

Example 329

3-(Diethylamino)-1-(4-{6-[3-(4-fluorophenyl)-1H-4-pyrazolyl]-4-quinazolinyl}piperazin-1-yl)-1-propane Yield: 5.9 mg

Example 330

1-{6-[3-(4-fluorophenyl)-1H-4-pyrazolyl]-4-quinazolinyl}-4-piperidylamine

Yield: 8.2 mg

Example 331

N-(1-{6-[3-(4-Fluorophenyl)-1H-4-pyrazolyl]-4-quinazolinyl}-4-piperidyl)benzamide Yield: 7.0 mg

Example 332

N-(4-Fluorophenyl)-N-(1-{6-[3-(4-fluorophenyl)-1H-4-pyrazolyl]-4-quinazolinyl}-4-piperidyl)amine Yield: 9.4 mg

Example 333

N,N-Dimethyl-N'-(1-{6-[3-(4-fluorophenyl)-1H-4-pyrazolyl]-4-quinazolinyl}-4-piperidyl)sulfamide Yield: 6.6 mg

Example 334

4-[4-(1H-3-Indolyl)piperidino]-6-[3-(4-fluorophenyl)-1H-4-pyrazolyl]quinazoline

Yield: 11.8 mg

Example 335

4-(4-Benzyl-2-methylpiperazin-1-yl)-6-[3-(4-fluorophenyl)-1H-4-pyrazolyl]quinazoline Yield: 11.6 mg

Example 336

6-[3-(4-Fluorophenyl)-1H-4-pyrazolyl]-4-(4-phenylpiperazin-1-yl)quinazoline

Yield: 13.7 mg

Example 337

4-(4-{6-[3-(4-Fluorophenyl)-1H-4-pyrazolyl]-4-quinazolinyl}piperazin-1-yl)benzonitrile Yield: 8.3 mg

Example 338

4-(4-{6-[3-(4-Fluorophenyl)-1H-4-pyrazolyl]-4-quinazolinyl}piperazin-1-yl)phenol Yield: 9.1 mg

Example 339

4-[4-(2-Chlorophenyl)piperazin-1-yl]-6-[3-(4-fluorophenyl)-1H-4-pyrazolyl]quinazoline Yield: 6.3 mg

Example 340

4-(1-{6-[3-(4-Fluorophenyl)-1H-4-pyrazolyl]-4-quinazolinyl}-4-piperidyl)-1-butanol Yield: 3.8 mg

Example 341

N,N-Dimethyl-4-{6-[3-(4-fluorophenyl)-1H-4-pyrazolyl]-4-quinazolinyl}-1-piperazine sulfonamide Yield: 2.7 mg

Example 342

N-{4-[(1-{6-[3-(4-Fluorophenyl)-1H-4-pyrazolyl]-4-quinazolinyl}-4-piperidyl)methyl]phenyl}methane sulfonamide Yield: 14.5 mg

Example 343

N-{4-[(1-{6-[3-(4-Fluorophenyl)-1H-4-pyrazolyl]-4-quinazolinyl}-4-piperidyl)carbonyl]phenyl}methane sulfonamide Yield: 13.8 mg

Example 344

6-[(1-{6-[3-(4-Fluorophenyl)-1H-4-pyrazolyl]-4-quinazolinyl}-4-piperidyl)carbonyl]-1,2,3,4-tetrahydro-2$\lambda^6$,1-benzothiadine-2,2-dione Yield: 11.9 mg

Example 345

N-{4-[(1-{6-[3-(4-Fluorophenyl)-1H-4-pyrazolyl]-4-quinazolinyl}-4-piperidyl)sulfonyl]phenyl}methane sulfonamide Yield: 8.4 mg The structures and MS spectrum data of the compounds in Examples 269 to 345 are shown in Tables 2 to 8.

TABLE 2
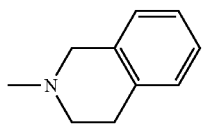
| Ex. No. | —R¹ | —Q | MSm/e(ESI) (MH⁺) |
|---|---|---|---|
| 269 | H | 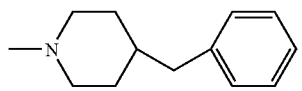 | 328 |
| 270 | H | 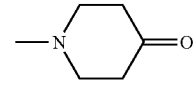 | 371 |
| 271 | H | 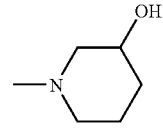 | 294 |
| 272 | H | 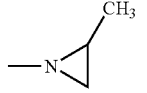 | 296 |
| 273 | H | 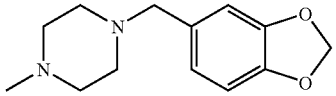 | 252 |
| 274 | H | 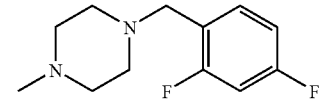 | 415 |
| 275 | H | 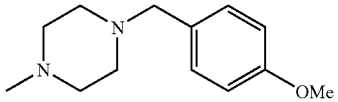 | 407 |
| 276 | H | 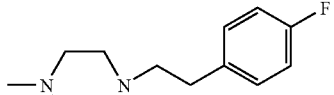 | 401 |
| 277 | H | 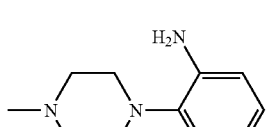 | 403 |
| 278 | H | 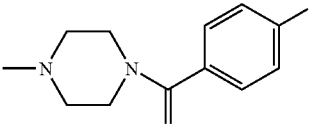 | 372 |
TABLE 3
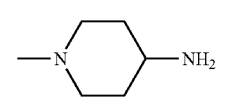
| Ex. No. | R¹ | —Q | MSm/e(ESI) (MH⁺) |
|---|---|---|---|
| 279 | H | 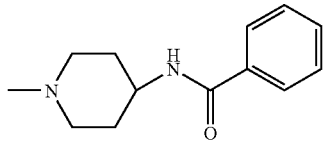 | 419 |
| 280 | H | 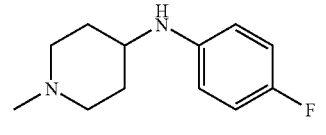 | 295 |
| 281 | H | 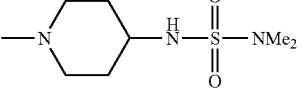 | 399 |
| 282 | H | 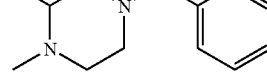 | 389 |
| 283 | H | 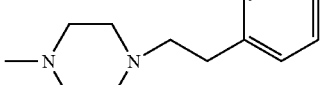 | 402 |
| 284 | H | 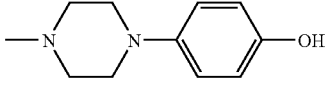 | 385 |
| 285 | H | 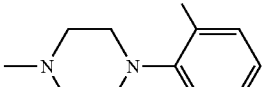 | 385 |
| 286 | H | 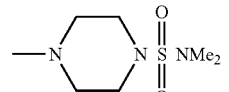 | 373 |
| 287 | H | | 391 |
| 288 | H | | 388 |

TABLE 3-continued

[Structure: quinazoline-pyrazole core with R¹ and Q substituents]

| Ex. No. | R¹ | —Q | MSm/e(ESI) (MH⁺) |
|---|---|---|---|
| 289 | H | 1-methylpiperidin-4-ylmethyl-(4-methanesulfonamido)phenyl | 463 |
| 290 | H | 1-methylpiperidin-4-yl-carbonyl-(4-methanesulfonamido)phenyl | 477 |

TABLE 4

[Structure: quinazoline-pyrazole core with R¹ and Q substituents]

| Ex. No. | R¹ | —Q | MSm/e(ESI) (MH⁺) |
|---|---|---|---|
| 291 | H | 1-methylpiperidin-4-yl-carbonyl-benzothiadiazine dioxide | 489 |
| 292 | H | 1-methylpiperidin-4-ylsulfonyl-(4-methanesulfonamido)phenyl | 513 |
| 293 | Me | 1,4-dimethylpiperazine | 309 |
| 294 | Me | 2-methyl-1,2,3,4-tetrahydroisoquinoline | 342 |
| 295 | Me | 1-methyl-4-benzylpiperidine | 385 |
| 296 | Me | 1-methylpiperidin-4-one | 308 |
| 297 | Me | 1-methyl-3-hydroxypiperidine | 266 |
| 298 | Me | 4-methyl-1-(3-trifluoromethylphenyl)piperazine | 439 |
| 299 | Me | 1,2-dimethylaziridine | 266 |
| 300 | Me | 4-methyl-1-(1,3-benzodioxol-5-ylmethyl)piperazine | 429 |
| 301 | Me | 4-methyl-1-(3,4-difluorobenzyl)piperazine | 421 |
| 302 | Me | 4-methyl-1-(4-methoxybenzyl)piperazine | 415 |
| 303 | Me | 4-methyl-1-[2-(4-fluorophenyl)ethyl]piperazine | 417 |

TABLE 5
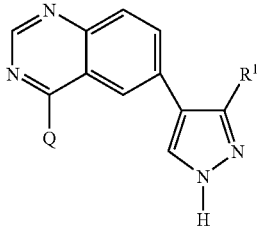
| Ex. No. | R¹ | —Q | MSm/e(ESI) (MH⁺) |
|---|---|---|---|
| 304 | Me | 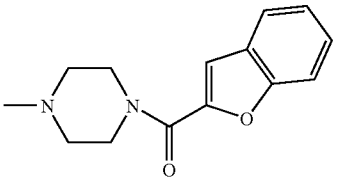 | 386 |
| 305 | Me | 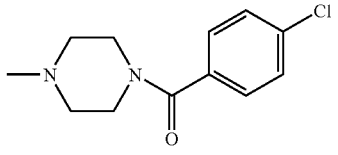 | 439 |
| 306 | Me | 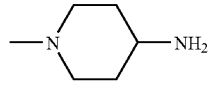 | 433 |
| 307 | Me | 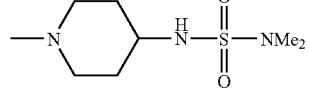 | 309 |
| 308 | Me | 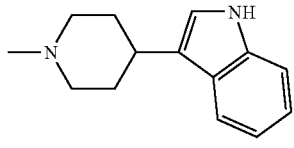 | 416 |
| 309 | Me | 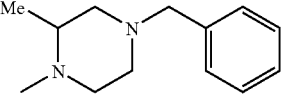 | 409 |
| 310 | Me | 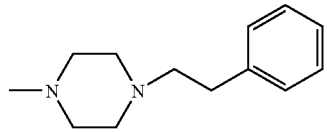 | 399 |
| 311 | Me | 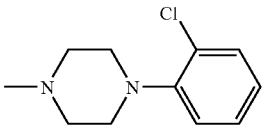 | 399 |
| 312 | Me |  | 405 |

TABLE 5-continued
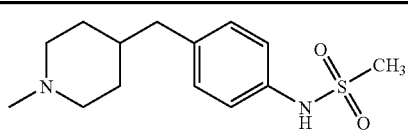
| Ex. No. | R¹ | —Q | MSm/e(ESI) (MH⁺) |
|---|---|---|---|
| 313 | Me |  | 477 |
| 314 | 4-F—Ph | 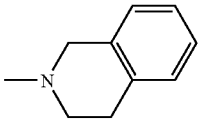 | 389 |
| 315 | 4-F—Ph | 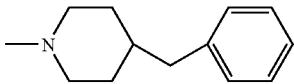 | 422 |
| 316 | 4-F—Ph | 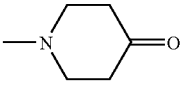 | 465 |
TABLE 6
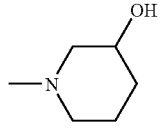
| Ex. No. | R¹ | —Q | MSm/e(ESI) (MH⁺) |
|---|---|---|---|
| 317 | 4-F—Ph | 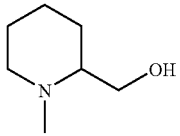 | 388 |
| 318 | 4-F—Ph | | 390 |
| 319 | 4-F—Ph | | 404 |

TABLE 6-continued
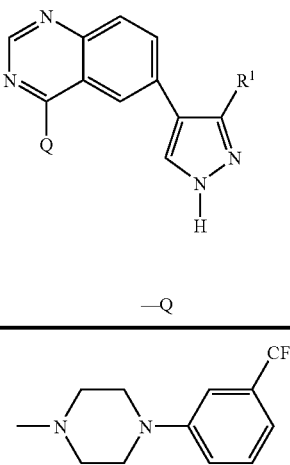
| Ex. No. | R¹ | —Q | MSm/e(ESI) (MH⁺) |
|---|---|---|---|
| 320 | 4-F—Ph | 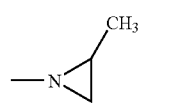 | 519 |
| 321 | 4-F—Ph | 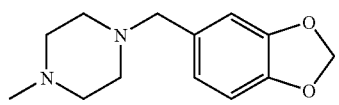 | 346 |
| 322 | 4-F—Ph | 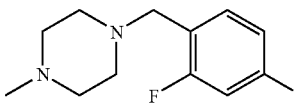 | 509 |
| 323 | 4-F—Ph | 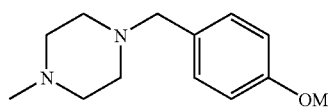 | 501 |
| 324 | 4-F—Ph | 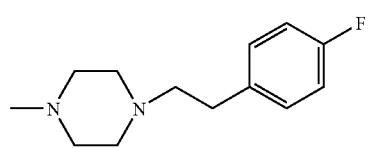 | 495 |
| 325 | 4-F—Ph | 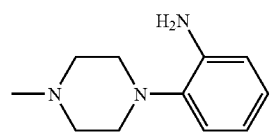 | 497 |
| 326 | 4-F—Ph | 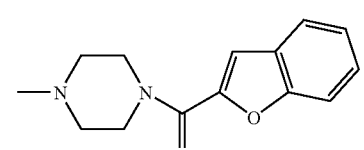 | 466 |
| 327 | 4-F—Ph | 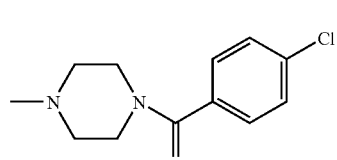 | 519 |
| 328 | 4-F—Ph | | 513 |

TABLE 6-continued
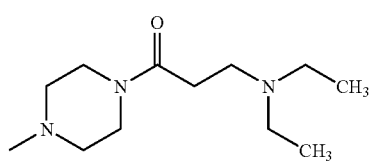
| Ex. No. | R¹ | —Q | MSm/e(ESI) (MH⁺) |
|---|---|---|---|
| 329 | 4-F—Ph | (4-methylpiperazin-1-yl)-C(O)-CH₂CH₂-N(CH₂CH₃)₂ | 502 |
TABLE 7
| Ex. No. | R¹ | —Q | MSm/e(ESI) (MH⁺) |
|---|---|---|---|
| 330 | 4-F—Ph | 1-methylpiperidin-4-yl, 4-NH₂ | 389 |
| 331 | 4-F—Ph | 1-methylpiperidin-4-yl-NH-C(O)-Ph | 493 |
| 332 | 4-F—Ph | 1-methylpiperidin-4-yl-NH-(4-F-phenyl) | 483 |
| 333 | 4-F—Ph | 1-methylpiperidin-4-yl-NH-S(O)₂-NMe₂ | 496 |
| 334 | 4-F—Ph | 1-methylpiperidin-4-yl-(1H-indol-3-yl) | 489 |

TABLE 7-continued
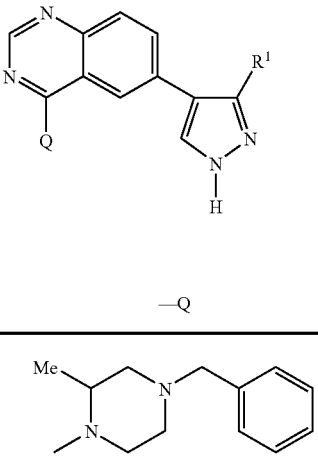
| Ex. No. | R¹ | —Q | MS m/e(ESI) (MH⁺) |
|---|---|---|---|
| 335 | 4-F—Ph | 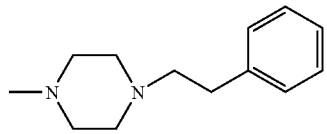 | 479 |
| 336 | 4-F—Ph | 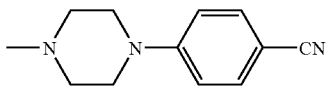 | 479 |
| 337 | 4-F—Ph | 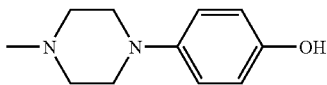 | 476 |
| 338 | 4-F—Ph | 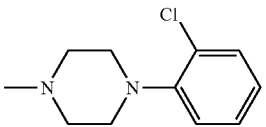 | 467 |
| 339 | 4-F—Ph | 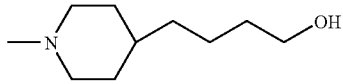 | 485 |
| 340 | 4-F—Ph | 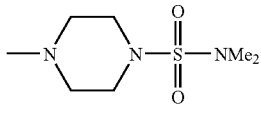 | 446 |
| 341 | 4-F—Ph | 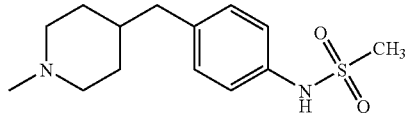 | 482 |
| 342 | 4-F—Ph |  | 557 |

TABLE 8

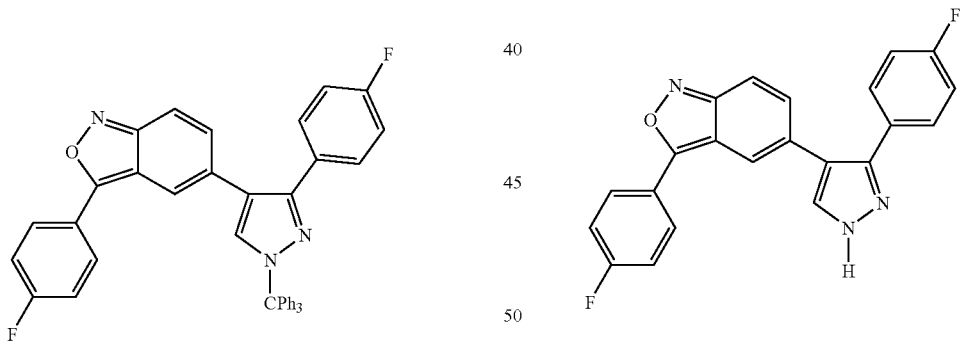

| Ex. No. | R¹ | —Q | MSm/e(ESI) (MH⁺) |
|---|---|---|---|
| 343 | 4-F—Ph | (1-methylpiperidin-4-yl)-C(O)-(4-methanesulfonamidophenyl) | 571 |
| 344 | 4-F—Ph | (1-methylpiperidin-4-yl)-C(O)-(3,4-dihydro-2H-benzo[1,2,6]thiadiazin-7-yl 1,1-dioxide) | 583 |
| 345 | 4-F—Ph | (1-methylpiperidin-4-yl)-SO₂-(4-methanesulfonamidophenyl) | 607 |

Example 346

3(4-Fluorophenyl)-5-[3-(4-fluorophenyl)-1-trityl-1H-4-pyrazoyl]benzo[c]isoxazole 131 mg of the title compound was obtained as pale yellow crystals by the same method as in Example 21 from 100 mg 5-bromo-3-(4-fluorophenyl)benzo[c]isoxazole obtained in Production Example 109 and 230 mg 3-(4-fluorophenyl)-1-trityl-1H-4-pyrazolylboronic acid (compound in Production Example 25).

¹H-NMR (DMSO-d₆)
δ: 7.16–7.24(m, 8H), 7.32–7.45(m, 14H), 7.58(d, J=9.6 Hz, 1H), 7.78(s, 1H), 7.82(s, 1H), 7.98–8.04(m, 2H)

Example 347

3-(4-Fluorophenyl)-5-[3-(4-fluorophenyl)-1H-4-pyrazolyl]-benzo[c]isoxazole 28 mg of the title compound was obtained as pale yellow crystals by deprotection of the trityl group in the same method as in Example 84 from 58 mg 3-(4-fluorophenyl)-5-[3-(4-fluorophenyl)-1-trityl-1H-4-pyrazolyl]benzo[c] isoxazole obtained in Example 346 and 1 mL trifluoroacetic acid.

¹H-NMR (DMSO-d₆)
δ: 7.25(dd, J=9.2, 1.2 Hz, 1H), 7.20–7.32(m, 2H), 7.38–7.52(m, 4H), 7.60(dd, J=9.2, 0.8 Hz, 1H), 7.85(br, 1H), 8.05–8.08(m, 2H), 8.12–8.26(br, 1H)
MS m/e(ESI) 374(MH⁺)

Example 348

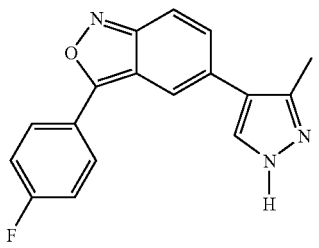

3-(4-Fluorophenyl)-5-(3-methyl-1H-4-pyrazolyl)benzo[c]-isoxazole 3-(4-Fluorophenyl)-5-(3-methyl-1-trityl-1H-4-pyrazolyl)benzo[c]isoxazole was obtained as pale yellow crystals by the same method as in Example 21 from 100 mg 5-bromo-3-(4-fluorophenyl)benzo[c]isoxazole obtained in Production Example 109 and 94 mg 3-methyl-1-trityl-1H-4-pyrazolylboronic acid (compound in Production Example 30). Then, the product was subjected to deprotection of the trityl group with 1 mL trifluoroacetic acid by the same method as in Example 84, to give 24 mg of the title compound as pale yellow crystals.

$^1$H-NMR (DMSO-$d_6$)
δ: 2.44(s, 3H), 7.46(m, 2H), 7.64(d, J=9.2 Hz, 1H), 7.70(d, J=9.2 Hz, 1H), 7.89(s, 2H), 8.14–8.22(m, 2H)
MS m/e(ESI) 294(MH$^+$)

Example 349

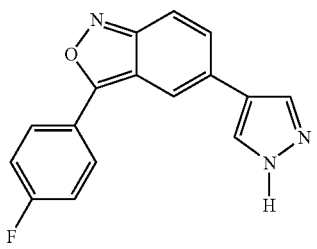

3-(4-Fluorophenyl)-5-(1H-4-pyrazolyl)benzo[c]isoxazole 75 mg of 3-(4-fluorophenyl)-5-(1-trityl-1H-4-pyrazolyl)-benzo[c]isoxazole was obtained as yellow crystals by the same method as in Example 21 from 50 mg 5-bromo-3-(4-fluorophenyl)-benzo[c]isoxazole obtained in Production Example 109 and 90 mg 1-trityl-1H-4-pyrazolylboronic acid. The product was subjected to deprotection of the trityl group with 1 mL trifluoroacetic acid by the same method as in Example 84, to give 29 mg of the title compound as pale yellow crystals.

$^1$H-NMR (DMSO-$d_6$)
δ: 7.42–7.50(m, 2H), 7.68(d, J=9.5 Hz, 1H), 7.80(dd, J=1.6 Hz, J=9.5 Hz, 1H), 8.15(s, 1H), 8.18–8.26(m, 4H)
MS m/e(ESI) 280(MH$^+$)

Example 350

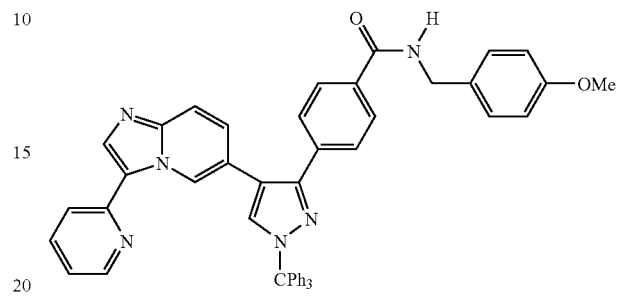

N-(4-Methoxybenzyl)-4-[4-(3-pyridin-2-yl)imidazo[1,2-a]-pyridin-6-yl)-1-trityl-1H-pyrazol-3-yl]benzamide 139 mg of the title compound was obtained as a colorless amorphous by the same reaction as in Example 48 from 120 mg 4-{4-[3-(2-pyridyl)imidazo[1,2-a]pyridin-6-yl]-1-trityl-1H-3-pyrazolyl}benzoic acid (compound in Example 46) and 30 mg p-methoxybenzylamine.

$^1$H-NMR (CDCl$_3$)
δ: 3.79(s, 3H), 4.55(d, J=4.8 Hz, 2H), 6.27(t, J=4.8 Hz, 1H), 6.86(d, J=8.8 Hz, 2H), 7.07(m, 1H), 7.14(dd, J=9.2, 1.6 Hz, 1H), 7.26(m, 8H), 7.35(m, 9H), 7.50(s, 1H), 7.60(m, 3H), 7.68(m, 4H), 8.09(s, 1H), 8.38(d, J=6.4 Hz, 1H), 9.81(dd, J=1.6, 0.8 Hz, 1H)

Example 351

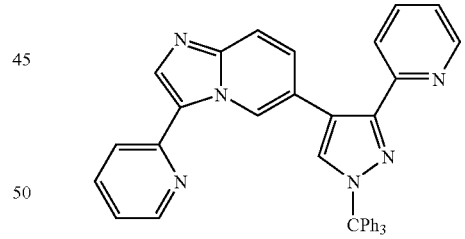

3-Pyridin-2-yl-6-(3-pyridin-2-yl-1-trityl-1H-pyrazol-4-yl)-imidazo[1,2-a]pyridine 142 mg of the title compound was obtained as a colorless amorphous by the same reaction as in Example 29 from 55 mg 6-bromo-3-(2-pyridyl)imidazo[1,2-a]pyridine (compound in Production Example 63) and 173 mg 3-(2-pyridyl)-1-trityl-1H-4-pyrazolylboronic acid (compound in Production Example 166).

$^1$H-NMR (CDCl$_3$)
δ: 7.10(m, 1H), 7.16(m, 2H), 7.25–7.40(m, 15H), 7.48(m, 1H), 7.56(m, 2H), 7.68(m, 3H), 7.77(d, J=7.6 Hz, 1H), 8.08(s, 1H), 8.42(m, 1H), 10.00(brs, 1H)

Example 352

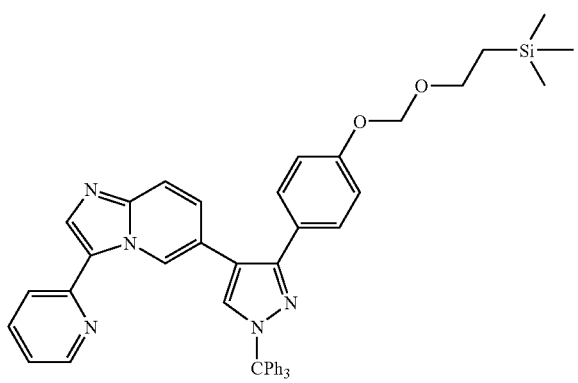

3-(Pyridin-2-yl)-6-{3-[4-(2-trimethylsila-
nylethoxymethoxy)-phenyl]-1-trityl-1H-pyrazol-4-
yl}imidazo[1,2-a]pyridine 1.24 g of the title compound was obtained as a colorless amorphous by the same reaction as in Example 29 from 548 mg 6-bromo-3-(2-pyridyl)imidazo[1,2-a]pyridine (compound in Production Example 63) and 2.3 g 3-[4-(2-trimethylsilanylethoxymethoxy)phenyl]-1-trityl-1H-4-pyrazolylboronic acid (compound in Production Example 165).

$^1$H-NMR (CDCl$_3$)
δ: 0.05(s, 9H), 0.95(m, 2H), 3.74(m, 2H), 5.19(s, 2H), 6.96(d, J=8.8 Hz, 2H), 7.12(ddd, J=6.8, 6.8, 2.0 Hz, 1H), 7.20(dd, J=9.2, 1.6 Hz, 1H), 7.23–7.39(m, 15H), 7.48(m, 3H), 7.59(dd, J=9.2, 0.8 Hz, 1H), 7.71(m, 2H), 8.11(s, 1H), 8.48(m, 1H), 9.83(dd, J=1.6, 0.8 Hz, 1H)

Example 353

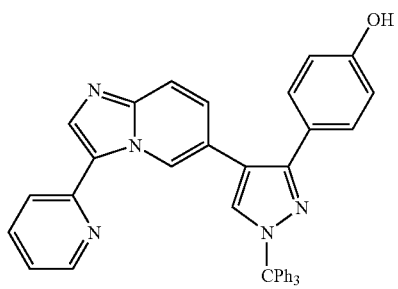

4-{4-[3-(Pyridin-2-yl)imidazo[1,2-a]pyridin-6-yl]-1-
trityl-1H-pyrazol-3-yl}phenol A mixture of 1.23 g 3-(pyridin-2-yl)-6-{3-[4-(2-trimethylsilanylethoxymethoxy)phenyl]-1-trityl-1H-pyrazol-4-yl}imidazo[1,2-a]pyridin (compound in Example 352), 8.5 mL tetrabutylammoniumchloride (1 M tetrahydrofuran solution) and 10 mL hexamethyl phosphorous acid triamide was stirred at 80° C. for 2 hours. Ethyl acetate, an aqueous saturated ammonium chloride solution and water were added to the reaction solution, and the organic layer was separated. The organic layer was dried over anhydrous sodium sulfate, the solvent was evaporated, the resulting residue was triturated with diisopropyl ether, and the crystals were collected by filtration to give 1.01 g of the title compound as white crystals.

$^1$H-NMR (CDCl$_3$)
δ: 6.80(d, J=8.4 Hz, 2H), 7.15(t, J=6.8 Hz, 1H), 7.21(dd, J=9.2, 1.2 Hz, 1H), 7.23–7.40(m, 17H), 7.44(s, 1H), 7.53(d, J=9.2 Hz, 1H), 7.69(m, 2H), 8.07(s, 1H), 8.54(d, J=4.8 Hz, 1H), 9.82(brs, 1H)

Example 354

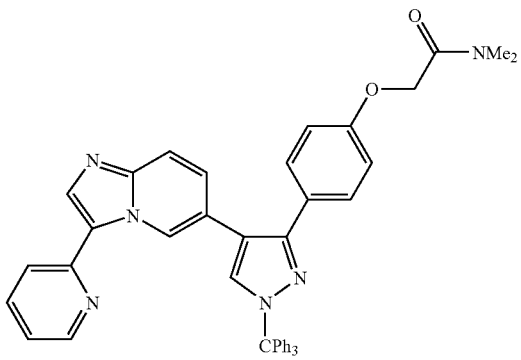

N,N-Dimethyl-2-(4-[4-(3-pyridin-2-ylimidazo[1,2-a]
pyridin-6-yl)-1-trityl-1H-pyrazol-3-yl]
phenoxy}acetamide 90 mg 4-{4-[3-(pyridin-2-yl)imidazo[1,2-a]pyridin-6-yl]-1-trityl-1H-pyrazol-3-yl}phenol (compound in Example 353) and 28 mg 2-chloro-N,N-dimethylacetamide were reacted under the same conditions as in Example 190, to give 80 mg of the title compound as a pale yellow amorphous matter.

$^1$H-NMR (CDCl$_3$)
δ: 2.93(s, 3H), 3.03(s, 3H), 4.60(s, 2H), 6.84(d, J=8.0 Hz, 2H), 7.11(t, J=6.4 Hz, 1H), 7.17(dd, J=9.2, 2.0 Hz, 1H), 7.20–7.38(m, 16H), 7.45(m, 2H), 7.57(d, J=9.2 Hz, 1H), 7.68(m, 2H), 8.08(s, 1H), 8.44(d, J=4.8 Hz, 1H), 9.80(brs, 1H)

Example 355

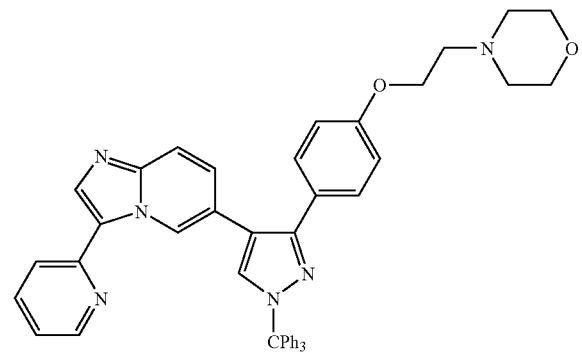

6-{3-[4-(2-Morpholine-4-ylethoxy)phenyl]-1-trityl-
1H-pyrazol-4-yl}-3-(pyridin-2-yl)imidazo[1,2-a]
pyridine 90 mg 4-{4-[3-(pyridin-2-yl)imidazo[1,2-a]pyridin-6-yl]-1-trityl-1H-pyrazol-3-yl}phenol (compound in Example 353) and 42 mg N-(2-chloroethyl)morpholine hydrochloride were reacted under the same conditions as in Example 190, to give 63 mg of the title compound as a colorless amorphous matter.

$^1$H-NMR (CDCl$_3$)

δ: 2.55(t, J=4.4 Hz, 4H), 2.77(t, J=5.6 Hz, 2H), 3.72(t, J=4.4 Hz, 4H), 4.06(t, J=5.6 Hz, 2H), 6.81(d, J=8.8 Hz, 2H), 7.11(ddd, J=6.4, 6.4, 1.6 Hz, 1H), 7.17(dd, J=9.2, 1.6 Hz, 1H), 7.23–7.38(m, 15H), 7.44(m, 3H), 7.57(d, J=9.2 Hz, 1H), 7.68(m, 2H), 8.09(s, 1H), 8.44(m, 1H), 9.81(dd, J=1.6, 0.8 Hz, 1H)

Example 356

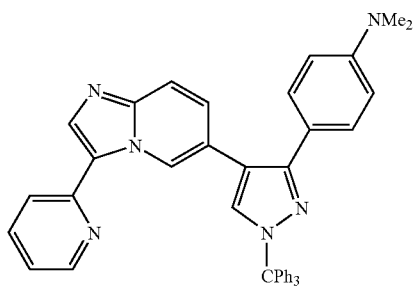

Dimethyl{4-[4-(3-pyridin-2-ylimidazo[1,2-a]pyridin-6-yl)-1-trityl-1H-pyrazol-3-yl]phenyl}amine 89 mg of the title compound was obtained as a pale yellow amorphous by the same reaction as in Example 153 from 100 mg 4-[4-[3-(2-pyridyl)imidazo[1,2-a]pyridin-6-yl]-1-trityl-1H-3-pyrazolyl]aniline (compound in Example 49).

$^1$H-NMR (CDCl$_3$)

δ: 2.91(s, 6H), 6.62(d, J=8.8 Hz, 2H), 7.11(m, 1H), 7.21(dd, J=9.2, 1.6 Hz, 1H), 7.22–7.38(m, 16H), 7.40(m, 2H), 7.56(d, J=9.2 Hz, 1H), 7.69(m, 2H), 8.08(s, 1H), 8.46(m, 1H), 9.80(brs, 1H)

Example 357

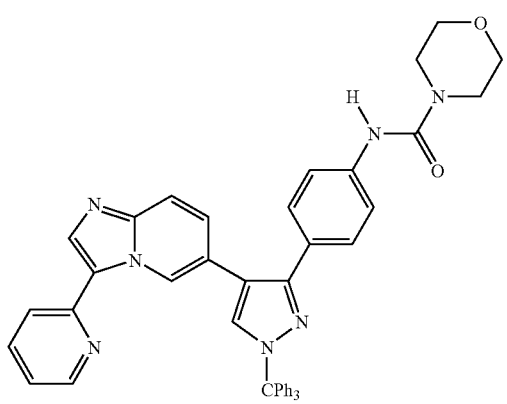

Morpholine-4-carboxylic acid {4-[4-(3-pyridin-2-ylimidazo-[1,2-a]pyridin-6-yl)-1-trityl-1H-pyrazol-3-yl]phenyl}amide 147 mg of the title compound was obtained as a pale brown amorphous under the same conditions as in Example 193 from 220 mg 4-{4-[3-(2-pyridyl)imidazo[1,2-a]pyridin-6-yl]-1-trityl-1H-3-pyrazolyl}aniline (compound in Example 49) and 47 µL 4-morpholine carbonyl chloride.

$^1$H-NMR (CDCl$_3$)

δ: 3.46(t, J=4.4 Hz, 4H), 3.71(t, J=4.4 Hz, 4H), 6.38(s, 1H), 7.11(ddd, J=6.4, 6.4, 1.6 Hz, 1H), 7.16(dd, J=9.2, 1.6 Hz, 1H), 7.23–7.38(m, 17H), 7.46(m, 3H), 7.57(d, J=9.2 Hz, 1H), 7.68(m, 2H), 8.09(s, 1H), 8.49(m, 1H), 9.82(dd, J=1.6, 0.8 Hz, 1H)

Example 358

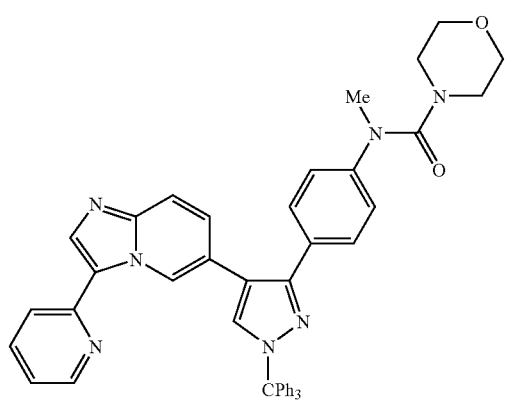

Morpholine-4-carboxylic acid methyl{4-[4-(3-pyridin-2-ylimidazo[1,2-a]pyridin-6-yl)-1-trityl-1H-pyrazol-3-yl]phenyl}amide 6 mg sodium hydride was suspended in 2 mL N,N-dimethylformamide, then 3 mL of 64 mg morpholine-4-carboxylic acid {4-[4-(3-pyridin-2-ylimidazo[1,2-a]-pyridin-6-yl)-1-trityl-1H-pyrazol-3-yl]phenyl}amide (compound in Example 357) in N,N-dimethylformamide was added thereto under ice-coolingd water in a stream of nitrogen, and the reaction solution was returned to room temperature and stirred for 20 minutes. 7 µL methyl iodide was added thereto under ice-cooling and stirred for 20 minutes. Water and ethyl acetate were added to the reaction solution, and the organic layer was separated and dried over anhydrous sodium sulfate. The solvent was evaporated, and the resulting residue was purified by NH silica gel column chromatography (ethyl acetate/hexane) to give 55 mg of the title compound as a colorless amorphous.

$^1$H-NMR (CDCl$_3$)

δ: 3.14(t, J=4.4 Hz, 4H), 3.18(s, 3H), 3.43(t, J=4.4 Hz, 4H), 6.97(d, J=8.4 Hz, 2H), 7.13(m, 1H), 7.17(dd, J=9.2, 1.6 Hz, 1H), 7.28(m, 6H), 7.35(m, 9H), 7.48(s, 1H), 7.50(d, J=8.4 Hz, 2H), 7.60(d, J=9.2 Hz, 1H), 7.71(m, 2H), 8.12(s, 1H), 8.47(m, 1H), 9.84(dd, J=1.6, 0.8 Hz, 1H)

Example 359

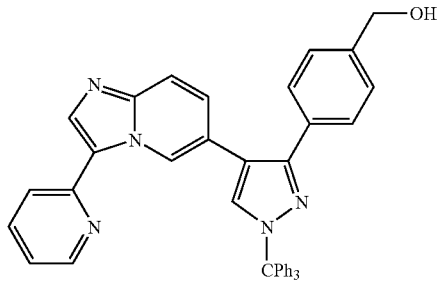

{4-[4-(3-Pyridin-2-ylimidazo[1,2-a]pyridin-6-yl)-1-trityl-1H-pyrazol-3-yl]phenyl}methanol 2 g 6-bromo-3-(2-pyridyl)imidazo[1,2-a]pyridine (compound in Production Example 63) and 5 g mixture of methyl 4-[4-(4,4,5,5-tetramethyl-1,3,2-dioxaborolan-2-yl)-1-trityl-1H-3-pyrazolyl]benzoate and ethyl 4-[4-(4,4,5,5-tetramethyl-1,3,2-dioxaborolan-2-yl)-1-trityl-1H-3-pyrazolyl]benzoate were reacted in the same manner as in Example 10, whereby 4.54 g mixture of methyl 4-[4-(3-pyridin-2-ylimidazo[1,2-a]pyridin-6-yl)-1-trityl-1H-pyrazol-3-yl]-benzoate and ethyl 4-[4-(3-pyridin-2-ylimidazo[1,2-a]-pyridin-6-yl)-1-trityl-1H-pyrazol-3-yl]benzoate was obtained as a pale yellow amorphous. 638 mg of this ester mixture was added to 10 mL suspension of 50 mg lithium aluminum hydride in tetrahydrofuran, and the mixture was stirred at 50° C. for 2 hours. The reaction solution was cooled on iced water, then 220 mg sodium fluoride and 80 μL water were added thereto, and the reaction solution was returned to room temperature and stirred for 40 minutes. Insolubles were filtered off, and the filtrate was evaporated. The residue was purified by NH silica gel column chromatography (ethyl acetate/hexane) to give 298 mg of the title compound as white crystals.

$^1$H-NMR (CDCl$_3$)

δ: 4.65(s, 2H), 7.11(m, 1H), 7.17(dd, J=9.2, 1.2 Hz, 1H), 7.23–7.38(m, 15H), 7.49(s, 1H), 7.53(d, J=8.0 Hz, 2H), 7.56(d, J=9.2 Hz, 1H), 7.68(m, 2H), 8.09(s, 1H), 8.44(m, 1H), 9.82(dd, J=1.6, 0.8 Hz, 1H)

Example 360

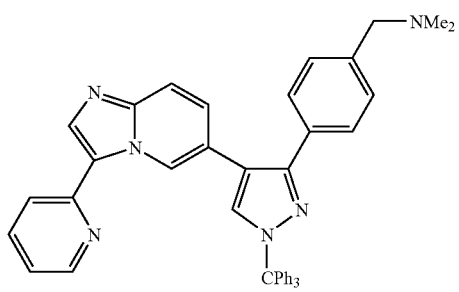

Dimethyl{4-[4-(3-pyridin-2-ylimidazo[1,2-a]pyridin-6-yl)-1-trityl-1H-pyrazol-3-yl]benzyl}amine A mixture of 296 mg {4-[4-(3-pyridin-2-ylimidazo[1,2-a]pyridin-6-yl)-1-trityl-1H-pyrazol-3-yl]phenyl}methanol (compound in Example 359), 844 mg manganese (IV) oxide and 20 mL chloroform was heated for 1 hour under reflux. The reaction solution was cooled to remove insolubles, and the filtrate was evaporated. 264 mg crude product of 4-[4-(3-pyridin-2-ylimidazo[1,2-a]pyridin-6-yl)-1-trityl-1H-pyrazol-3-yl]benzaldehyde was obtained as a pale brown amorphous. From 100 mg of this aldehyde derivative and 35 μL dimethylamine (50% aqueous solution), 81 mg of the title compound was obtained as a colorless amorphous under the same conditions as in Production Example 153.

$^1$H-NMR (CDCl$_3$)

δ: 2.18(s, 6H), 3.38(s, 2H), 7.11(m, 1H), 7.17(dd, J=9.2, 1.6 Hz, 1H), 7.19(d, J=8.0 Hz, 2H), 7.23–7.38(m, 15H), 7.48(m, 3H), 7.57(d, J=9.2 Hz, 1H), 7.67(m, 2H), 8.09(s, 1H), 8.44(m, 1H), 9.82(dd, J=1.6, 0.8 Hz, 1H)

Example 361

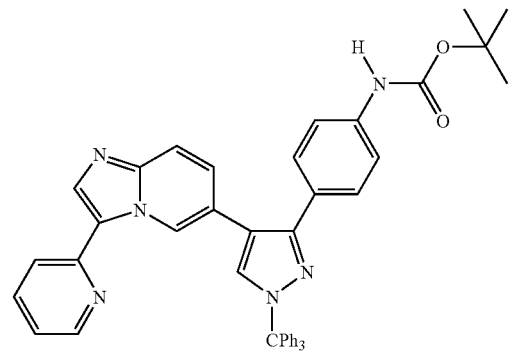

t-Butyl {4-[4-(3-pyridin-2-ylimidazo[1,2-a]pyridin-6-yl)-1-trityl-1H-pyrazol-3-yl]phenyl}carbaminate A mixture of 200 mg 4-{4-[3-(2-pyridyl)imidazo[1,2-a]-pyridin-6-yl]-1-trityl-1H-3-pyrazolyl} benzoic acid (compound in Example 46), 70 μL diphenylphosphonic acid azide, 33 mg triethylamine, 2.4 mL t-butyl alcohol, 12 mL toluene, and 3 mL N,N-dimethylformamide was stirred at 80° C. for 4 hours. An aqueous saturated sodium bicarbonate solution, ethyl acetate and water were added to the reaction solution, and the organic layer was separated, washed with brine and dried over anhydrous sodium sulfate. The drying agent was filtered off, and the filtrate was evaporated. The resulting residue was purified by NH silica gel column chromatography (ethyl acetate/hexane) to give 95 mg of the title compound as a colorless amorphous.

$^1$H-NMR (CDCl$_3$)

δ: 1.50(s, 9H), 6.46(brs, 1H), 7.09(m, 1H), 7.17(dd, J=9.2, 2.0 Hz, 1H), 7.23–7.38(m, 17H), 7.45(m, 3H), 7.57(d, J=9.2 Hz, 1H), 7.68(m, 2H), 8.09(s, 1H), 8.45(m, 1H), 9.81(dd, J=1.6, 0.8 Hz, 1H)

Example 362

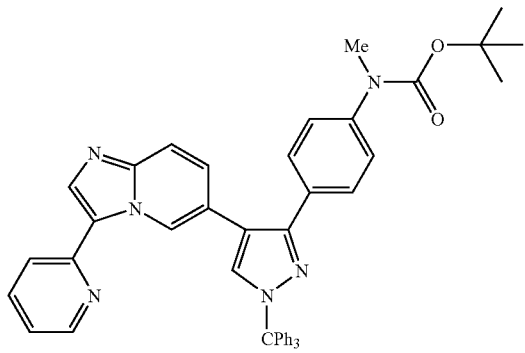

t-Butyl methyl {4-[4-(3-pyridin-2-ylimidazo[1,2-a]pyridin-6-yl)-1-trityl-1H-pyrazol-3-yl]phenyl}carbaminate 71 mg of the title compound was obtained as a colorless amorphous under the same conditions as in Example 358 from 93 mg t-butyl {4-[4-(3-pyridin-2-ylimidazo[1,2-a]pyridin-6-yl)-1-trityl-1H-pyrazol-3-yl]phenyl}carbaminate (compound in Example 361).

$^1$H-NMR (CDCl$_3$)

δ: 1.40(s, 9H), 3.20(s, 3H), 7.12(m, 3H), 7.18(dd, J=9.2, 2.0 Hz, 1H), 7.23–7.38(m, 15H), 7.47(s, 1H), 7.49(d, J=8 Hz, 2H), 7.58(d, J=9.2 Hz, 1H), 7.69(m, 2H), 8.10(s, 1H), 8.47(m, 1H), 9.85(dd, J=1.6, 0.8 Hz, 1H)

Example 363

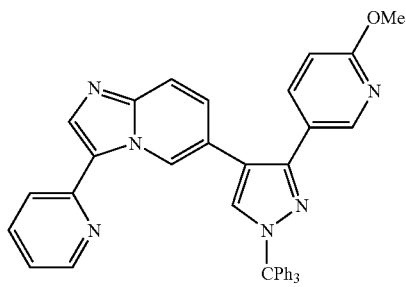

6-[3-(6-Methoxypyridin-3-yl)-1-trityl-1H-pyrazol-4-yl]-3-(pyridin-2-yl)imidazo[1,2-a]pyridine 254 mg of the title compound was obtained as a colorless amorphous by the same reaction as in Example 29 from 137 mg 6-bromo-3-(2-pyridyl)imidazo[1,2-a]pyridine (compound in Example 63) and 408 mg 3-(2-methoxypyridin-5-yl)-1-trityl-1H-4-pyrazolylboronic acid (compound in Production Example 167).

$^1$H-NMR (CDCl$_3$)

δ: 3.86(s, 3H), 6.67(d, J=8.8 Hz, 1H), 7.11(m, 1H), 7.18(dd, J=9.2, 2.0 Hz, 1H), 7.23–7.38(m, 15H), 7.51(s, 1H), 7.61(d, J=9.2 Hz, 1H), 7.70(m, 4H), 8.10(s, 1H), 8.41(m, 1H), 9.83(dd, J=1.6, 0.8 Hz, 1H)

Example 364

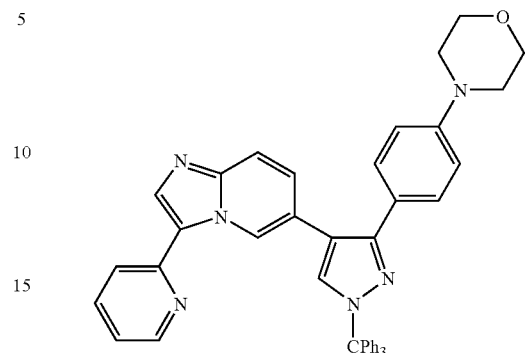

6-[3-(4-Morpholine-4-ylphenyl)-1-trityl-1H-pyrazol-4-yl]-3-(pyridin-2-yl)imidazo[1,2-a]pyridine 156 mg of the title compound was obtained as a pale brown amorphous by the same reaction as in Example 29 from 83 mg 6-bromo-3-(2-pyridyl)imidazo[1,2-a]pyridine (compound in Example 63) and 312 mg 3-[4-(morpholine-4-yl)phenyl]-1-trityl-1H-4-pyrazolylboronic acid (compound in Production Example 170).

$^1$H-NMR (CDCl$_3$)

δ: 3.11(t, J=4.4 Hz, 4H), 3.84(t, J=4.4 Hz, 4H), 6.80(d, J=9.2 Hz, 2H), 7.11(m, 1H), 7.20(m, 1H), 7.23–7.38(m, 15H), 7.45(m, 3H), 7.57(d, J=9.2 Hz, 1H), 7.68(m, 2H), 8.09(s, 1H), 8.46(d, J=4.8 Hz, 1H), 9.82(dd, J=1.6, 0.8 Hz, 1H)

Example 365

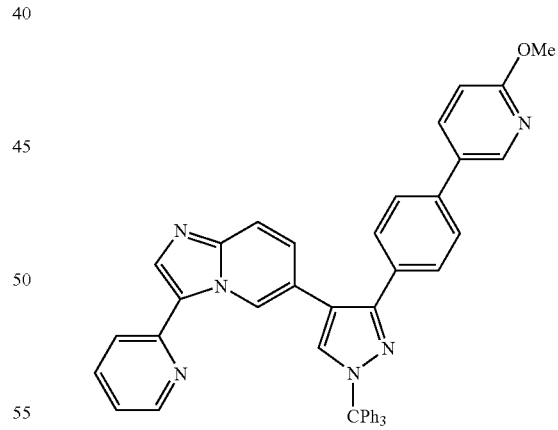

6-Methoxypyridin-3-yl)phenyl]-1-trityl-1H-pyrazol-4-yl}-3-(pyridin-2-yl)imidazo[1,2-a]pyridine 219 mg of the title compound was obtained as a colorless amorphous by the same reaction as in Example 29 from 83 mg 6-bromo-3-(2-pyridyl)imidazo[1,2-a]pyridine (compound in Example 63) and 326 mg 3-[4-(6-methoxypyridin-3-yl)phenyl]-1-trityl-1H-4-pyrazolylboronic acid (compound in Production Example 73).

¹H-NMR (CDCl₃)

δ: 3.96(s, 3H), 6.79(dd, J=8.8, 0.8 Hz, 1H), 7.10(m, 1H), 7.23(dd, J=90.2, 1.6 Hz, 1H), 7.24–7.38(m, 15H), 7.43(m, 2H), 7.52(s, 1H), 7.61–7.70(m, 5H), 7.73(dd, J=8.8, 2.4 Hz, 1H), 8.10(s, 1H), 8.35(m, 2H), 9.87(dd, J=1.6, 0.8 Hz, 1H)

Example 366

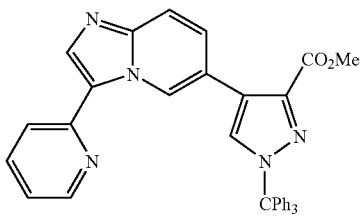

Methyl 4-[3-(pyridin-2-yl)imidazo[1,2-a]pyridin-6-yl]-1-trityl-1H-pyrazole-3-carboxylate 274 mg 6-bromo-3-(2-pyridyl)imidazo[1,2-a]pyridine (compound in Production Example 63) and 625 mg methyl 4-(4,4,5,5-tetramethyl-1,3,2-dioxaborolan-2-yl)-1-trityl-1H-pyrazolecarboxylate obtained in the synthesis process in Example 45 were reacted in the same manner as in Example 10, to give 230 mg of the title compound as a pale yellow amorphous.

¹H-NMR (CDCl₃)

δ: 3.80(s, 3H), 7.16(m, 1H), 7.22(m, 6H), 7.35(m, 9H), 7.47(m, 2H), 7.66(m, 2H), 7.73(m, 1H), 8.12(s, 1H), 8.60(m, 1H), 10.01(dd, J=1.6, 0.8 Hz, 1H)

Example 367

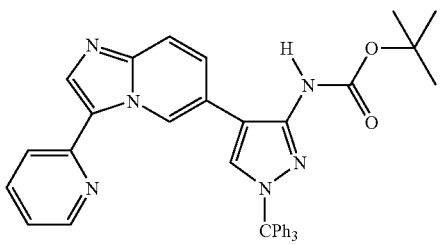

t-Butyl {4-[3-(pyridin-2-yl)imidazo[1,2-a]pyridin-6-yl]-1-trityl-1H-pyrazol-3-yl}carbaminate A mixture of 228 mg methyl 4-[3-(pyridin-2-yl)imidazo-[1,2-a]pyridin-6-yl]-1-trityl-1H-pyrazole-3-carboxylate (compound in Example 366), 0.8 mL of 1 N aqueous sodium hydroxide, 5 mL methanol and 3 mL tetrahydrofuran was stirred at 50° C. for 4 hours. Saturated ammonium chloride, ethyl acetate and water were added to the reaction solution, and then the organic layer was separated, washed with brine and dried over anhydrous sodium sulfate. The drying agent was filtered off, and the filtrate was evaporated. The resulting residue was crystallized from diisopropyl ether, triturated and dried under reduced pressure with a vacuum pump, to give 172 mg 4-[3-(pyridin-2-yl)imidazo-[1,2-a]pyridin-6-yl]-1-trityl-1H-pyrazole-3-carboxylic acid as pale brown crystals. From this carboxylic acid derivative, 78 mg of the title compound was obtained as a pale yellow amorphous under the same conditions as in Example 361.

¹H-NMR (CDCl₃)

δ: 1.20(s, 9H), 7.14(m, 1H), 7.21(m, 6H), 7.34(m, 10H), 7.54(s, 1H), 7.62(d, J=9.2 Hz, 1H), 7.71(m, 2H), 8.10(s, 1H), 8.64(d, J=4.4 Hz, 1H), 10.16(brs, 1H)

Example 368

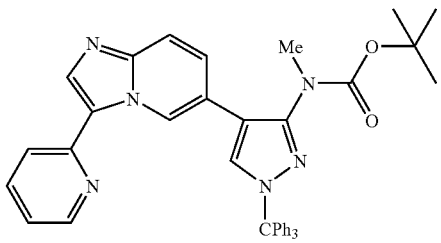

t-Butyl methyl{4-[3-(pyridin-2-yl)imidazo[1,2-a]pyridin-6-yl]-1-trityl-1H-pyrazol-3-yl}carbaminate 42 mg of the title compound was obtained as a colorless amorphous under the same conditions as in Example 358 from 76 mg t-butyl {4-[3-(pyridin-2-yl)imidazo[1,2-a]pyridin-6-yl]1-trityl-1H-pyrazol-3-yl}carbaminate.

¹H-NMR (CDCl₃)

δ: 1.16(s, 9H), 3.29(s, 3H), 7.15(m, 1H), 7.21(m, 6H), 7.33(m, 10H), 7.54(s, 1H), 7.62(d, J=9.2 Hz, 1H), 7.71(m, 2H), 8.11(s, 1H), 8.74(m, 1H), 10.25(brs, 1H)

Example 369

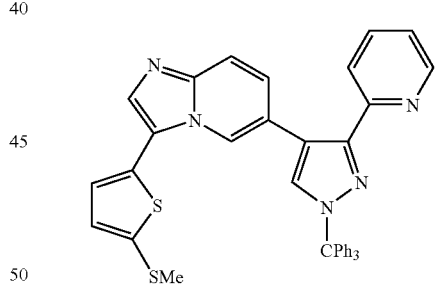

3-(5-Methylsulfanylthiophen-2-yl)-6-[3-(pyridin-2-yl)-1-trityl-1H-pyrazol-4-yl]imidazo[1,2-a]pyridine 171 mg of the title compound was obtained as a pale yellow amorphous by the same reaction as in Example 21 from 216 mg 3-iodo-6-[3-(pyridin-2-yl)-1-trityl-1H-pyrazol-4-yl]-imidazo[1,2-a]pyridine (compound in Production Example 216) and 260 mg tributyl[5-(methylsulfanyl)-2-thienyl]stannane (compound in Production Example 46).

¹H-NMR (CDCl₃)

δ: 2.53(s, 3H), 7.05(d, J=4.0 Hz, 1H), 7.07(d, J=4.0 Hz, 1H), 7.20(m, 1H), 7.22–7.38(m, 15H), 7.46(m, 1H), 7.54(m, 2H), 7.67(m, 2H), 7.76(d, J=7.6 Hz, 1H), 8.47(m, 1H), 8.84(dd, J=2.0, 0.8 Hz, 1H)

Example 370

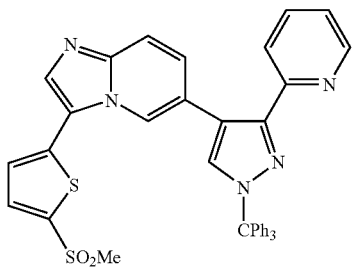

3-(5-Methylsulfonylthiophen-2-yl)-6-[3-(pyridin-2-yl)-1-trityl-1H-pyrazol-4-yl]imidazo[1,2-a]pyridine 111 mg of the title compound was obtained as a pale yellow amorphous by the same method as in Production Example 59 from 169 mg 3-(5-methylsulfanylthiophen-2-yl)-6-[3-(pyridin-2-yl)-1-trityl-1H-pyrazol-4-yl]imidazo[1,2-a]pyridine (compound in Example 369).

$^1$H-NMR (CDCl$_3$)

δ: 3.23(s, 3H), 7.21–7.38(m, 18H), 7.55(s, 1H), 7.60(dd, J=9.2, 0.8 Hz, 1H), 7.69(ddd, J=8.0, 8.0, 1.6 Hz, 1H), 7.72(d, J=4.4 Hz, 1H), 7.80(d, J=8.0 Hz, 1H), 7.83(s, 1H), 8.48(m, 1H), 8.95(brs, 1H)

Example 371

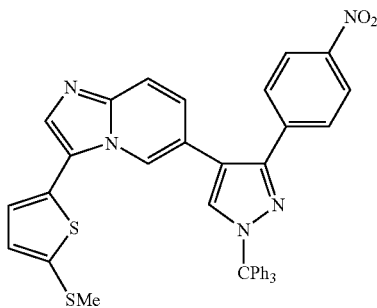

3-(5-Methylsulfanylthiophen-2-yl)-6-[3-(4-nitrophenyl)-1-trityl-1H-pyrazol-4-yl]imidazo[1,2-a]pyridine 246 mg of the title compound was obtained as a pale yellow amorphous by the same reaction as in Example 10 from 260 mg 6-bromo-3-[5-(methylsulfanyl)-2-thienyl]imidazo[1,2-a]-pyridine (compound in Production Example 58) and 535 mg 3-(4-nitrophenyl)-4-(4,4,5,5-tetramethyl-1,3,2-dioxaborolan-2-yl)-1-trityl-1H-pyrazole (compound in Production Example 168).

$^1$H-NMR (CDCl$_3$)

δ: 2.49(s, 3H), 6.91(d, J=3.6 Hz, 1H), 7.01(d, J=3.6 Hz, 1H), 7.11(dd, J=9.2, 1.6 Hz, 1H), 7.24(m, 6H), 7.35(m, 9H), 7.49(s, 1H), 7.62(d, J=9.6 Hz, 1H), 7.69(d, J=8.8 Hz, 2H), 7.72(s, 1H), 8.15(d, J=8.8 Hz, 2H), 8.21(d, J=0.8 Hz, 1H)

Example 372

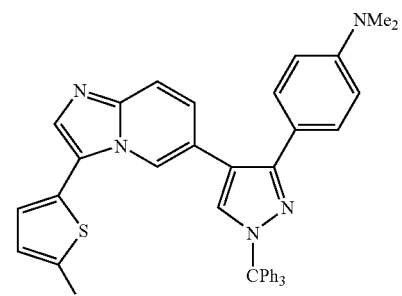

4-{4-[3-(5-Methylsulfanylthiophen-2-yl)imidazo[1,2-a]-pyridin-6-yl]-1-trityl-1H-pyrazol-3-yl}phenylamine 160 mg of the title compound was obtained as a pale yellow amorphous by the same reaction as in Production Example 152 from 244 mg 3-(5-methylsulfanylthiophen-2-yl)-6-[3-(4-nitrophenyl)-1-trityl-1H-pyrazol-4-yl]imidazo[1,2-a]-pyridine (compound in Example 371).

$^1$H-NMR (CDCl$_3$)

δ: 2.47(br, 2H), 2.52(s, 3H), 6.63(d, J=8.4 Hz, 2H), 6.79(d, J=3.6 Hz, 1H), 7.04(d, J=3.6 Hz, 1H), 7.16(dd, J=9.2, 1.2 Hz, 1H), 7.22–7.38(m, 15H), 7.41(s, 1H), 7.46(m, 1H), 7.54(m, 1H), 7.58(d, J=9.2 Hz, 1H), 7.67(s, 1H), 8.22(brs, 1H)

Example 373

Dimethyl(4-{4-[3-(5-methylsulfanylthiophen-2-yl)imidazo-[1,2-a]pyridin-6-yl]-1-trityl-1H-pyrazol-3-yl}phenyl)amine 97 mg of the title compound was obtained as a pale yellow solid by the same reaction as in Production Example 153 from 158 mg 4-{4-[3-(5-methylsulfanylthiophen-2-yl)imidazo-[1,2-a]pyridin-6-yl]-1-trityl-1H-pyrazol-3-yl}phenylamine (compound in Example 372).

$^1$H-NMR (CDCl$_3$)

δ: 2.50(s, 3H), 2.95(8, 6H), 6.67(d, J=9.2 Hz, 2H), 6.76(d, J=3.6 Hz, 1H), 6.95(d, J=3.6 Hz, 1H), 7.17(dd, J=9.2, 1.6 Hz, 1H), 7.25(m, 6H), 7.32(m, 9H), 7.36(d, J=8.8 Hz, 2H), 7.47(m, 1H), 7.56(dd, J=9.2, 0.8 Hz, 1H), 7.65(s, 1H), 8.24(dd, J=1.6, 0.8 Hz, 1H)

Example 374

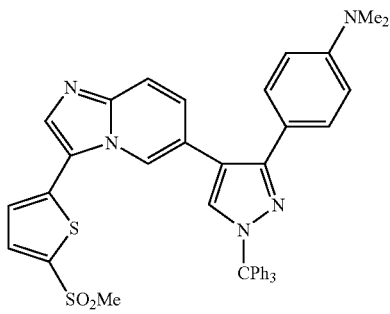

(4-{4-[3-(5-Methylsulfonylthiophen-2-yl)imidazo[1,2-a]-pyridin-6-yl]-1-trityl-1H-pyrazol-3-yl}phenyl)dimethylamine 88 mg of the title compound was obtained as a pale yellow amorphous by the same method as in Production Example 59 from 95 mg dimethyl(4-{4-[3-(5-methylsulfanylthiophen-2-yl)imidazo[1,2-a]pyridin-6-yl]-1-trityl-1H-pyrazol-3-yl}-phenyl)amine (compound in Example 373).

$^1$H-NMR (CDCl$_3$)

δ: 2.96(s, 6H), 3.20(s, 3H), 6.69(d, J=9.2 Hz, 2H), 6.85(d, J=4.0 Hz, 1H), 7.22–7.38(m, 18H), 7.45(s, 1H), 7.57(d, J=4.0 Hz, 1H), 7.62(dd, J=9.2, 0.8 Hz, 1H), 7.79(s, 1H), 8.24(brs, 1H)

Example 375

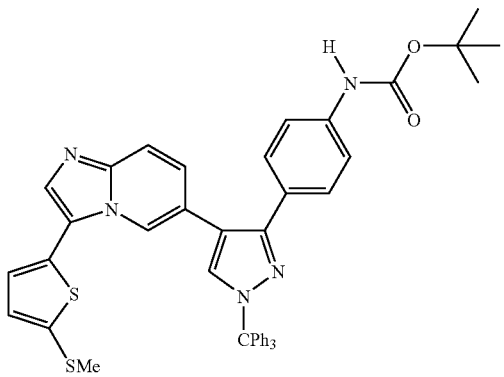

t-Butyl (4-{4-[3-(5-methylsulfanylthiophen-2-yl)imidazo-[1,2-a]pyridin-6-yl]-1-trityl-1H-pyrazol-3-yl}phenyl)-carbaminate 260 mg 6-bromo-3-[5-(methylsulfanyl)-2-thienyl]imidazo[1,2-a]pyridine (compound in Production Example 58) and 1 g mixture of methyl 4-[4-(4,4,5,5-tetramethyl-1,3,2-dioxaborolan-2-yl)-1-trityl-1H-3-pyrazolyl]benzoate and methyl 4-[4-(4,4,5,5-tetramethyl-1,3,2-dioxaborolan-2-yl)-1-trityl-1H-3-pyrazolyl]benzoate were reacted in the same manner as in Example 10, whereby 515 mg mixture of methyl 4-{4-[3-(5-methylsulfanylthiophen-2-yl)imidazo[1,2-a]-pyridin-6-yl]-1-trityl-1H-pyrazol-3-yl}benzoate and ethyl 4-{4-[3-(5-methylsulfanylthiophen-2-yl)imidazo[1,2-a]-pyridin-6-yl]-1-trityl-1H-pyrazol-3-yl}benzoate was obtained as a pale yellow amorphous. A mixture of 300 mg of this ester derivative, 1.3 mL of 1 N aqueous sodium hydroxide and 7 mL ethanol was stirred at 50° C. for 5 hours. An aqueous saturated ammonium chloride solution, ethylacetate, tetrahydrofuran and water were added to the reaction solution, and the organic layer was separated. To dissolve insolubles, dichloromethane and methanol were added to this organic layer which was then dried over anhydrous sodium sulfate. The drying agent was filtered off, and the filtrate was evaporated. The resulting residue was subjected to azeotropic distillation with toluene to give 416 mg crude product of 4-{4-[3-(5-methylsulfanylthiophen-2-yl)imidazo[1,2-a]pyridin-6-yl]-1-trityl-1H-pyrazol-3-yl}-benzoic acid as white crystals. From 414 mg of this carboxylic acid, 62 mg of the title compound was obtained as a pale yellow amorphous by the same reaction as in Example 361.

$^1$H-NMR (CDCl$_3$)

δ: 1.50(s, 9H), 2.51(s, 3H), 6.53(brs, 1H), 6.78(d, J=3.6 Hz, 1H), 7.01(d, J=3.6 Hz, 1H), 7.13(dd, J=9.2, 1.6 Hz, 1H), 7.22–7.38(m, 17H), 7.42(m, 3H), 7.56(dd, J=9.2, 0.8 Hz, 1H), 7.67(s, 1H), 8.19(dd, J=1.6, 0.8 Hz, 1H)

Example 376

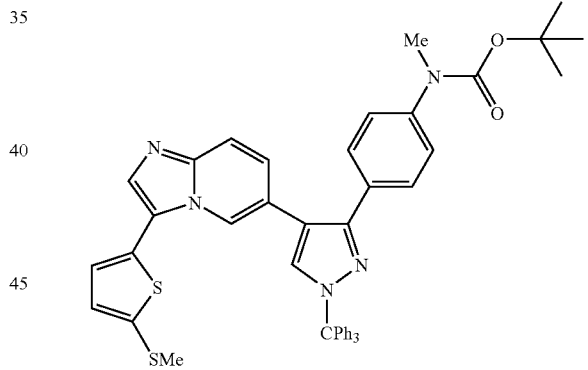

t-Butyl methyl(4-{4-[3-(5-methylsulfanylthiophen-2-yl)-imidazo[1,2-a]pyridin-6-yl]-1-trityl-1H-pyrazol-3-yl}-phenyl)carbaminate 59 mg of the title compound was obtained as a pale brown amorphous by the same method as in Example 358 from 60 mg t-butyl (4-{4-[3-(5-methylsulfanylthiophen-2-yl)imidazo[1,2-a]-pyridin-6-yl]-1-trityl-1H-pyrazol-3-yl}phenyl)carbaminate (compound in Example 375).

$^1$H-NMR (CDCl$_3$)

δ: 1.43(s, 9H), 2.52(s, 3H), 3.25(s, 3H), 6.81(d, J=4.0 Hz, 1H), 7.03(d, J=4.0 Hz, 1H), 7.14(dd, J=9.2, 1.6 Hz, 1H), 7.18(d, J=8.4 Hz, 2H), 7.25(m, 6H), 7.33(m, 9H), 7.42(s, 1H), 7.45(d, J=8.4 Hz, 2H), 7.57(dd, J=9.2, 0.8 Hz, 1H), 7.68(s, 1H), 8.22(d, J=0.8 Hz, 1H)

Example 377

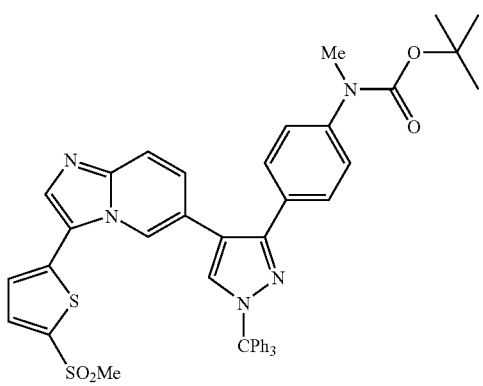

t-Butyl methyl(4-{4-[3-(5-methylsulfonylthiophen-2-yl)-imidazo[1,2-a]pyridin-6-yl]-1-trityl-1H-pyrazol-3-yl}-phenyl)carbaminate 49 mg of the title compound was obtained as a pale brown amorphous by the same method as in Production Example 59 from 57 mg t-butyl methyl(4-{4-[3-(5-methylsulfanylthiophen-2-yl)-imidazo[1,2-a]pyridin-6-yl]-1-trityl-1H-pyrazol-3-yl}-phenyl)carbaminate (compound in Example 376).

$^1$H-NMR (CDCl$_3$)
δ: 1.45(s, 9H), 3.20(s, 3H), 3.25(s, 3H), 6.91(d, J=4.0 Hz, 1H), 7.24(m, 9H), 7.34(m, 9H), 7.45(m, 3H), 7.63(dd, J=9.2, 0.8 Hz, 1H), 7.67(d, J=4.0 Hz, 1H), 7.81(s, 1H), 8.22(dd, J=1.6, 0.8 Hz, 1H)

Example 378

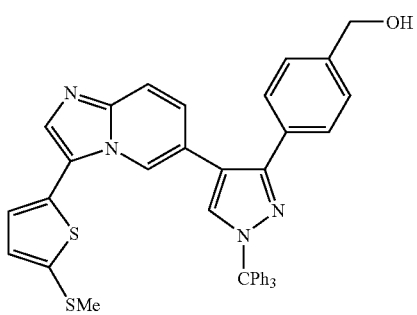

(4-{4-[3-(5-Methylsulfanylthiophen-2-yl)imidazo[1,2-a]-pyridin-6-yl]-1-trityl-1H-pyrazol-3-yl}phenyl)methanol 124 mg of the title compound was obtained as a pale yellow solid by the same method as in Example 359 from 196 mg of the mixture of methyl 4-{4-[3-(5-methylsulfanylthiophen-2-yl)-imidazo[1,2-a]pyridin-6-yl]-1-trityl-1H-pyrazol-3-yl}benzoate and ethyl 4-{4-[3-(5-methylsulfanylthiophen-2-yl)imidazo[1,2-a]pyridin-6-yl]-1-trityl-1H-pyrazol-3-yl]benzoate obtained in the synthesis process in Example 375.

$^1$H-NMR (CDCl$_3$)
δ: 2.51(s, 3H), 4.71(s, 2H), 6.79(d, J=3.6 Hz, 1H), 7.01(d, J=3.6 Hz, 1H), 7.15(dd, J=9.2, 1.6 Hz, 1H), 7.25(m, 8H), 7.34(m, 9H), 7.46(s, 1H), 7.50(d, J=8.4 Hz, 2H), 7.57(dd, J=9.2, 0.8 Hz, 1H), 7.67(s, 1H), 8.20(dd, J=1.6, 0.8 Hz, 1H)

Example 379

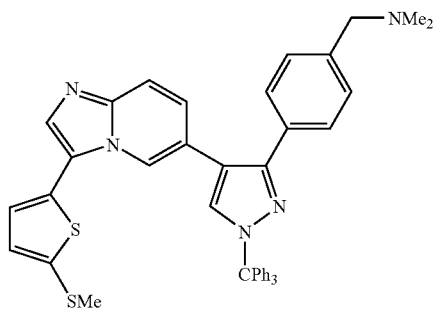

Dimethyl(4-{4-[3-(5-methylsulfanylthiophen-2-yl)imidazo-[1,2-a]pyridin-6-yl]-1-trityl-1H-pyrazol-3-yl}benzyl)amine 82 mg of the title compound was obtained as a colorless amorphous by the same method as in Example 360 from 122 mg (4-{4-[3-(5-methylsulfanylthiophen-2-yl)imidazo[1,2-a]-pyridin-6-yl]-1-trityl-1H-pyrazol-3-yl}phenyl)methanol (compound in Example 378).

$^1$H-NMR (CDCl$_3$)
δ: 2.24(s, 6H), 2.50(s, 3H), 3.44(s, 2H), 6.75(d, J=3.6 Hz, 1H), 6.97(d, J=3.6 Hz, 1H), 7.14(dd, J=9.2, 1.6 Hz, 1H), 7.25(m, 8H), 7.34(m, 9H), 7.44(s, 1H), 7.45(d, J=8.8 Hz, 2H), 7.57(dd, J=9.2, 0.8 Hz, 1H), 7.67(s, 1H), 8.19(dd, J=1.6, 0.8 Hz, 1H)

Example 380

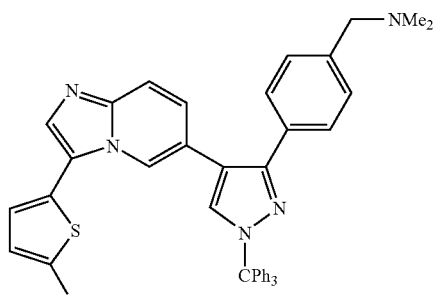

Dimethyl(4-{4-[3-(5-methylsulfonylthiophen-2-yl)imidazo-[1,2-a]pyridin-6-yl]-1-trityl-1H-pyrazol-3-yl}benzyl)amine 62 mg of the title compound was obtained as a pale yellow amorphous by the same method as in Production Example 59 from 80 mg dimethyl(4-{4-[3-(5-methylsulfanylthiophen-2-yl)-imidazo[1,2-a]pyridin-6-yl]-1-trityl-1H-pyrazol-3-yl}-benzyl)amine (compound in Example 379).

¹H-NMR (CDCl₃)

δ: 2.22(s, 6H), 3.20(s, 3H), 3.44(s, 2H), 6.86(d, J=4.0 Hz, 1H), 7.25(m, 9H), 7.34(m, 9H), 7.45(d, J=8.4 Hz, 2H), 7.47(s, 1H), 7.61(d, J=4.0 Hz, 1H), 7.63(dd, J=9.2, 0.8 Hz, 1H), 7.81(s, 1H), 8.20(dd, J=1.6, 0.8 Hz, 1H)

Example 381

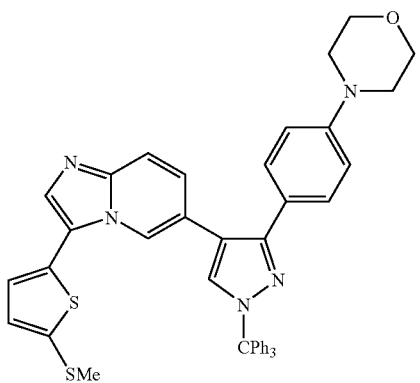

3-(5-Methylsulfanylthiophen-2-yl)-6-[3-(4-Morpholine-4-ylphenyl)-1-trityl-1H-pyrazol-4-yl]imidazo[1,2-a]pyridine 178 mg of the title compound was obtained as a pale brown amorphous by the same reaction as in Example 29 from 98 mg 6-bromo-3-[5-(methylsulfanyl)-2-thienyl]imidazo[1,2-a]-pyridine (compound in Example 58) and 3-[4-(morpholine-4-yl)phenyl]-1-trityl-1H-4-pyrazolylboronic acid (compound in Production Example 170).

¹H-NMR (CDCl₃)

δ: 2.52(s, 3H), 3.15(t, J=4.4 Hz, 4H), 3.85(t, J=4.4 Hz, 4H), 6.77(d, J=4.0 Hz, 1H), 6.85(d, J=9.2 Hz, 2H), 7.00(d, J=4.0 Hz, 1H), 7.16(dd, J=9.2, 1.6 Hz, 1H), 7.23–7.38(m, 15H), 7.40(d, J=9.2 Hz, 2H), 7.42(s, 1H), 7.56(dd, J=9.2, 1.2 Hz, 1H), 7.67(s, 1H), 8.22(dd, J=1.6, 0.8 Hz, 1H)

Example 382

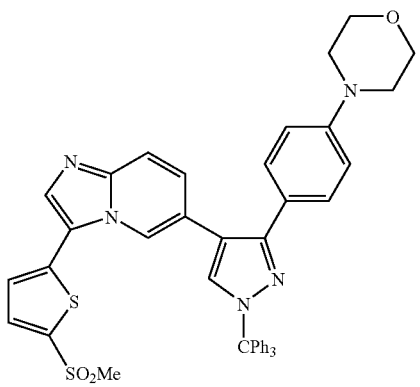

3-(5-Methylsulfonylthiophen-2-yl)-6-[3-(4-Morpholine-4-ylphenyl)-1-trityl-1H-pyrazol-4-yl]imidazo[1,2-a]pyridine 149 mg of the title compound was obtained as a pale brown amorphous by the same method as in Production Example 59 from 176 mg 3-(5-methylsulfanylthiophen-2-yl)-6-[3-(4-morpholine-4-ylphenyl)-1-trityl-1H-pyrazol-4-yl]imidazo[1,2-a]pyridine (compound in Example 381).

¹H-NMR (CDCl₃)

δ: 3.16(t, J=4.8 Hz, 4H), 3.21(s, 3H), 3.86(t, J=4.8 Hz, 4H), 6.87(d, J=9.2 Hz, 2H), 6.88(d, J=4.0 Hz, 1H), 7.24(m, 7H), 7.33(m, 9H), 7.40(d, J=8.8 Hz, 2H), 7.45(s, 1H), 7.62(dd, J=9.2, 0.8 Hz, 1H), 7.63(d, J=4.0 Hz, 1H), 7.80(s, 1H), 8.23(dd, J=1.6, 0.8 Hz, 1H)

Example 383

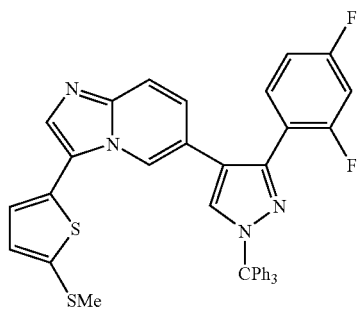

6-(3-(2,4-Difluorophenyl)-1-trityl-1H-pyrazol-4-yl)-3-(5-methylsulfanylthiophen-2-yl)imidazo[1,2-a]pyridine 128 mg of the title compound was obtained as a white solid by the same reaction as in Example 29 from 130 mg 6-bromo-3-[5-(methylsulfanyl)-2-thienyl]imidazo[1,2-a]-pyridine (compound in Production Example 58) and 467 mg 3-(2,4-difluorophenyl)-1-trityl-1H-4-pyrazolylboronic acid (compound in Production Example 172).

¹H-NMR (CDCl₃)

δ: 2.53(s, 3H), 6.72(d, J=4.0 Hz, 1H), 6.82(m, 1H), 6.93(m, 1H), 7.01(d, J=4.0 Hz, 1H), 7.11(dd, J=9.2, 1.6 Hz, 1H), 7.23(m, 6H), 7.34(m, 9H), 7.42(m, 1H), 7.55(dd, J=9.2, 0.8 Hz, 1H), 7.56(s, 1H), 7.66(s, 1H), 8.09(dd, J=1.6, 0.8 Hz, 1H)

Example 384

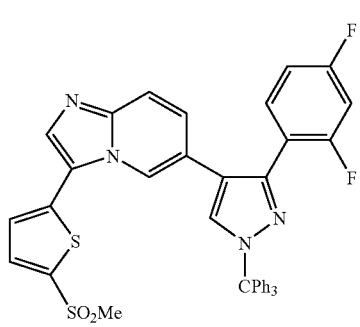

6-[3-(2,4-Difluorophenyl)-1-trityl-1H-pyrazol-4-yl]-3-(5-methylsulfonylthiophen-2-yl)imidazo[1,2-a]pyridine 120 mg of the title compound was obtained as a colorless amorphous by the same method as in Production Example 59 from 126 mg 6-[3-(2,4-difluorophenyl)-1-trityl-1H-pyrazol-4-yl]-3-(5-methylsulfanylthiophen-2-yl)imidazo[1,2-a]pyridine (compound in Example 383).

¹H-NMR (CDCl₃)
δ: 3.23(s, 3H), 6.83(ddd, J=9.2, 9.2,2.4 Hz, 1H), 6.90(d, J=4.0 Hz, 1H), 6.98(m, 1H), 7.20(dd, J=9.2, 1.6 Hz, 1H), 7.24(m, 6H), 7.34(m, 9H), 7.46(m, 1H), 7.58(s, 1H), 7.62(dd, J=9.2, 0.8 Hz, 1H), 7.65(d, J=4.0 Hz, 1H), 7.81(s, 1H), 8.12(dd, J=1.6, 0.8 Hz, 1H)

Example 385

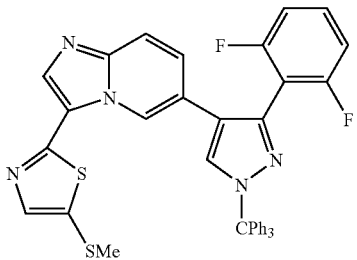

6-[3-(2,6-Difluorophenyl)-1-trityl-1H-pyrazol-4-yl]-3-(5-methylsulfanylthiazol-2-yl)imidazo[1,2-a]pyridine 152 mg of the title compound was obtained as a colorless amorphous by the same reaction as in Example 29 from 98 mg 6-bromo-3-(5-methylsulfanylthiazol-2-yl)imidazo[1,2-a]-pyridine (compound in Production Example 218) and 280 mg 3-(2,6-difluorophenyl)-1-trityl-1H-4-pyrazolylboronic acid (compound in Production Example 211).

¹H-NMR (CDCl₃)
δ: 2.51(s, 3H), 6.93(dd, J=8.8, 8.4 Hz, 1H), 7.22(dd, J=9.2, 2.0 Hz, 1H), 7.24–7.38(m, 17H), 7.50(s, 1H), 7.57(dd, J=9.2, 0.8 Hz, 1H), 7.67(s, 1H), 7.99(s, 1H), 9.43(dd, J=2.0, 0.8 Hz, 1H)

Example 386

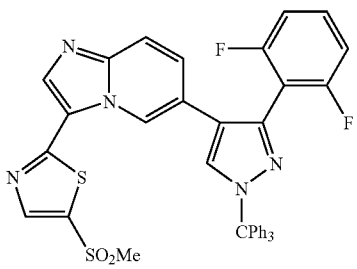

6-[3-(2,6-Difluorophenyl)-1-trityl-1H-pyrazol-4-yl]-3-(5-methylsulfonylthiazol-2-yl)imidazo[1,2-a]pyridine 152 mg of the title compound was obtained as a colorless amorphous by the same method as in Production Example 59 from 150 mg 6-[3-(2,6-difluorophenyl)-1-trityl-1H-pyrazol-4-yl]-3-(5-methylsulfanylthiazol-2-yl)imidazo[1,2-a]pyridine (compound in Example 385).

¹H-NMR (CDCl₃)
δ: 3.26(s, 3H), 6.95(dd, J=8.4, 8.4 Hz, 1H), 7.24–7.40(m, 18H), 7.64(dd, J=9.2, 0.8 Hz, 1H), 7.69(s, 1H), 8.05(s, 1H), 8.16(s, 1H), 9.42(dd, J=2.0, 0.8 Hz, 1H)

Example 387

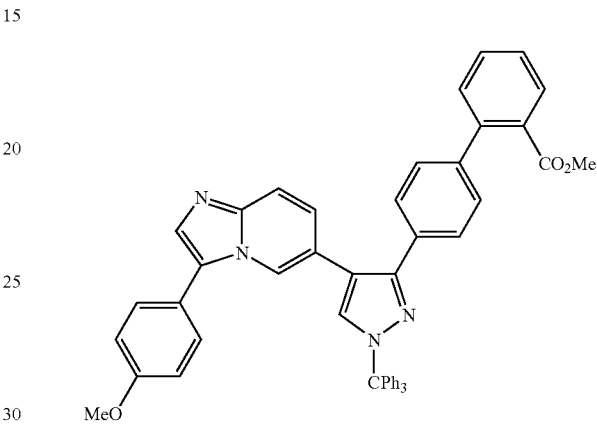

Methyl 4'-{4-[3-(4-methoxyphenyl)imidazo[1,2-a]pyridin-6-yl]-1-trityl-1H-pyrazol-3-yl}biphenyl-2-carboxylate 121 mg of the title compound was obtained as a colorless amorphous by the same reaction as in Example 29 from 132 mg methyl 4'-[4-(3-iodoimidazo[1,2-a]pyridin-6-yl)-1-trityl-1H-pyrazol-3-yl]biphenyl-2-carboxylate (compound in Production Example 230) and 40 mg 4-methoxyphenylboronic acid.

¹H-NMR (CDCl₃)
δ: 3.62(s, 3H), 3.77(s, 3H), 6.89(d, J=8.8 Hz, 2H), 7.13(dd, J=9.6, 1.6 Hz, 1H), 7.22–7.39(m, 19H), 7.40(m, 3H), 7.52(ddd, J=7.6, 7.6,1.6 Hz, 1H), 7.58(m, 4H), 7.80(dd, J=7.6, 1.6 Hz, 1H), 8.14(t, J=1.2 Hz, 1H)

Example 388

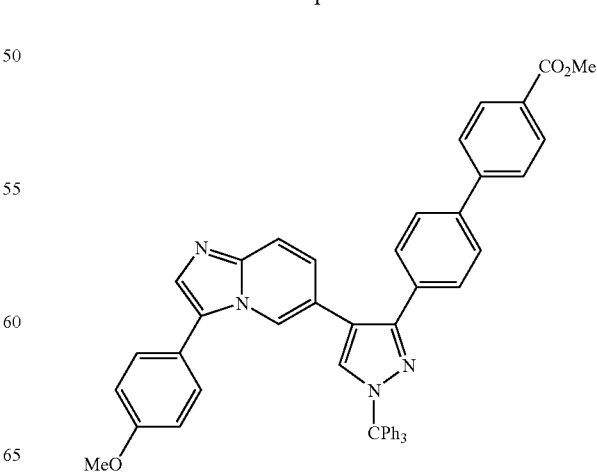

Methyl 4'-{4-[3-(4-methoxyphenyl)imidazo[1,2-a]pyridin-6-yl]-1-trityl-1H-pyrazol-3-yl}biphenyl-4-carboxylate 149 mg of the title compound was obtained as a colorless amorphous by the same reaction as in Example 10 from 123 mg 6-bromo-3-(4-methoxyphenyl)imidazo[1,2-a]pyridine (compound in Production Example 50) and 238 mg methyl 4'-[4-(4,4,5,5-tetramethyl-1,3,2-dioxaborolan-2-yl)-1-trityl-1H-pyrazol-3-yl]biphenyl-4-carboxylate (compound in Production Example 175).

$^1$H-NMR (CDCl$_3$)

δ: 3.67(s, 3H), 3.93(s, 3H), 6.76(d, J=8.8 Hz, 2H), 7.14 (dd, J=9.6, 1.6 Hz, 1H), 7.19(d, J=8.8 Hz, 2H), 7.24(m, 7H), 7.33(m, 9H), 7.46(s, 1H), 7.62(m, 5H), 7.69(d, J=8.4 Hz, 2H), 8.07(brs, 1H), 8.11(d, J=8.4 Hz, 2H)

Example 389

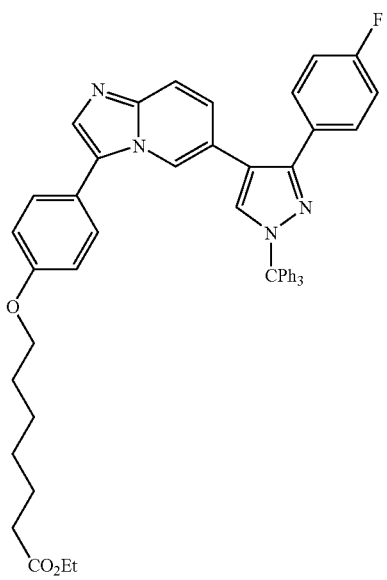

Ethyl 7-(4-{6-[3-(4-fluorophenyl)-1-trityl-1H-pyrazol-4-yl]imidazo[1,2-a]pyridin-3-yl}phenoxy)heptanoate A mixture of 200 mg 4-{6-[3-(4-fluorophenyl)-1-trityl-1H-4-pyrazolyl]imidazo[1,2-a]pyridin-3-yl}phenol (compound in Example 14), 232 mg ethyl 7-bromoheptanoate, 6 mg sodium iodate, 68 mg potassium carbonate, and 15 mL N,N-dimethylformamide was stirred overnight at 80° C. Ethyl acetate and water were added to the reaction solution, and the organic layer was separated, then washed with water, an aqueous saturated sodium thiosulfate, an aqueous solution of sodium chloride (×2) and brine, and dried over anhydrous sodium sulfate. The drying agent was filtered off, and the filtrate was evaporated. The resulting residue was purified by NH silica gel column chromatography (ethyl acetate/hexane) to give 157 mg of the title compound as a pale brown amorphous.

$^1$H-NMR (CDCl$_3$)

δ: 1.26(t, J=7.2 Hz, 3H), 1.43(m, 2H), 1.52(m, 2H), 1.67(m, 2H), 1.82(m, 2H), 2.33(t, J=7.6 Hz, 2H), 3.99(t, J=6.4 Hz, 2H), 4.14 (q, J=7.2 Hz, 2H), 6.88(d, J=8.8 Hz, 2H), 7.03(t, J=8.8 Hz, 2H), 7.08(dd, J=9.2, 1.6 Hz, 1H), 7.18(d, J=8.8 Hz, 2H), 7.21(m, 8H), 7.32(m, 8H), 7.43(s, 1H), 7.47(dd, J=8.8, 5.2 Hz, 1H), 7.57(s, 1H), 7.58(dd, J=9.2, 0.8 Hz, 1H), 7.99(dd, J=1.6, 0.8 Hz, 1H)

Example 390

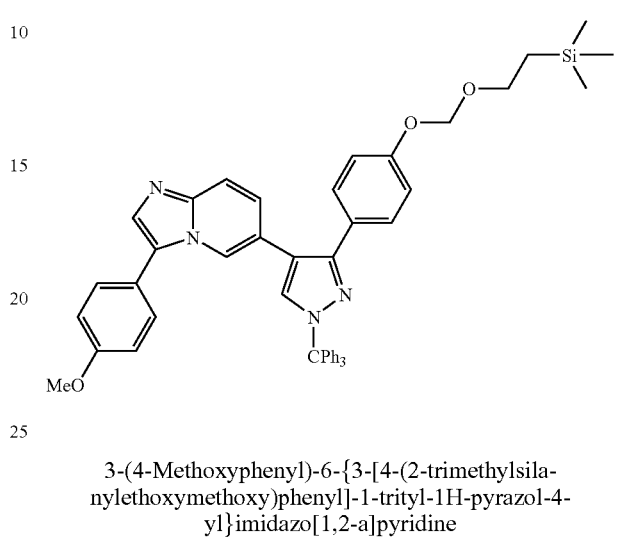

3-(4-Methoxyphenyl)-6-{3-[4-(2-trimethylsilanylethoxymethoxy)phenyl]-1-trityl-1H-pyrazol-4-yl}imidazo[1,2-a]pyridine 698 mg of the title compound was obtained as a colorless amorphous by the same reaction as in Example 29 from 364 mg 6-bromo-3-(4-methoxyphenyl)imidazo[1,2-a]pyridine (compound in Production Example 50) and 1.35 g 3-[4-(2-trimethylsilanylethoxymethoxy)phenyl]-1-trityl-1H-4-pyrazolylboronic acid (compound in Production Example 165).

$^1$H-NMR (CDCl$_3$)

δ: 0.05(s, 9H), 0.96(t, J=7.2 Hz, 2H), 3.77(t, J=7.2 Hz, 2H), 3.87(s, 3H), 5.25(s, 2H), 6.93(d, J=8.8 Hz, 2H), 7.04(d, J=9.2 Hz, 2H), 7.13(dd, J=9.2, 1.6 Hz, 1H), 7.24(m, 8H), 7.34(m, 9H), 7.43(m, 3H), 7.59(dd, J=9.2, 0.8 Hz, 1H), 7.60(s, 1H), 8.07(dd, J=1.6, 1.2 Hz, 1H)

Example 391

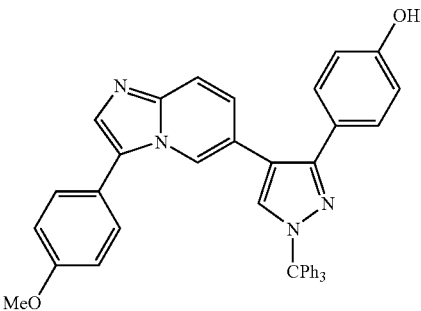

4-{4-[3-(4-Methoxyphenyl)imidazo[1,2-a]pyridin-6-yl]-1-trityl-1H-pyrazol-3-yl}phenol 696 mg 3-(4-methoxyphenyl)-6-{3-[4-(2-trimethylsilanylethoxymethoxy)phenyl]-1-trityl-1H-pyrazol-4-yl}imidazo[1,2-a]pyridine (compound in Example 390) was reacted in the same manner as in Example 353, to give 553 mg of the title compound as pale brown crystals.

¹H-NMR (CDCl₃)

δ: 3.85(s, 3H), 6.85(d, J=8.4 Hz, 2H), 6.97(d, J=8.8 Hz, 2H), 7.11(dd, J=9.2, 1.6 Hz, 1H), 7.20–7.36(m, 19H), 7.52 (d, J=9.2 Hz, 1H), 7.56(s, 1H), 8.07(brs, 1H)

Example 392

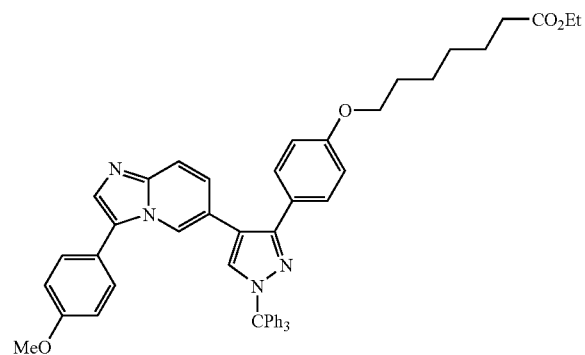

Ethyl 7-(4-{4-[3-(4-methoxyphenyl)imidazo[1,2-a]-6-yl]-1-trityl-1H-pyrazol-3-yl)phenoxy)heptanoate 187 mg 4-{4-[3-(4-methoxyphenyl)imidazo[1,2-a]-pyridin-6-yl]-1-trityl-1H-pyrazol-3-yl}phenol (compound in Example 391) and 214 mg ethyl 7-bromoheptanoate were reacted in the same manner as in Example 389, to give 162 mg of the title compound as a colorless amorphous.

¹H-NMR (CDCl₃)

δ: 1.25(t, J=7.2 Hz, 3H), 1.40(m, 2H), 1.48(m, 2H), 1.66(m, 2H), 1.80(m, 2H), 2.30(t, J=7.2 Hz, 2H), 3.84(s, 3H), 3.96(t, J=6.4 Hz, 2H), 4.12 (q, J=7.2 Hz, 2H), 6.87(d, J=9.2 Hz, 2H), 6.88(d, J=8.8 Hz, 2H), 7.11(dd, J=9.6, 1.6 Hz, 1H), 7.19(d, J=8.8 Hz, 2H), 7.23(m, 6H), 7.32(m, 9H), 7.40(d, J=8.8 Hz, 2H), 7.40(s, 1H), 7.56(dd, J=9.2, 0.8 Hz, 1H), 7.57(s, 1H), 8.03(dd, J=1.6, 0.8 Hz, 1H)

Example 393

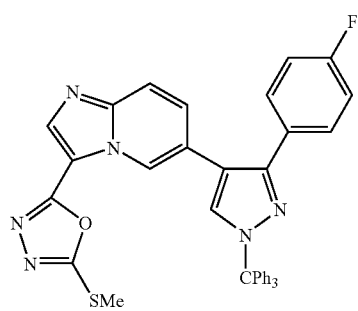

6-[3-(4-Fluorophenyl)-1-trityl-1H-pyrazol-4-yl]-3-(5-methylsulfanyl[1,3,4]oxadiazol-2-yl)imidazo[1,2-a]pyridine A mixture of 283 mg 6-[3-(4-fluorophenyl)-1-trityl-1H-pyrazol-4-yl]imidazo[1,2-a]pyridine-3-carboxylic acid hydrazide (compound in Production Example 274), 38 mg carbon disulfide, 20 mg sodium hydroxide, 5 mL ethanol and 5 mL water was heated for 4 hours under reflux. Ethyl acetate, tetrahydrofuran and an aqueous saturated ammonium chloride solution were added to the reaction solution, and the organic layer was separated, washed with brine and dried over anhydrous sodium sulfate. The drying agent was filtered off, and the filtrate was evaporated. 285 mg crude product of 5-{6-[3-(4-fluorophenyl)-1-trityl-1H-pyrazol-4-yl]imidazo[1,2-a]pyridin-3-yl}[1,3,4]oxadiazol-2-thiol was obtained as pale yellow crystals. To a mixture of this thiol derivative, 128 mg potassium carbonate and 10 mL N,N-dimethylformamide under ice-coolingd water in a stream of nitrogen was added 32 μL methyl iodide, and the mixture was stirred for 10 minutes. Ethyl acetate and water were added to the reaction solution, and the organic layer was separated, washed twice with water and then with brine and dried over anhydrous sodium sulfate. The drying agent was filtered off, and the filtrate was evaporated. The resulting residue was purified by NH silica gel column chromatography (ethyl acetate/hexane) to give 148 mg of the title compound as a colorless amorphous.

¹H-NMR (CDCl₃)

δ: 2.80(s, 3H), 6.95(t, J=8.8 Hz, 2H), 7.23(dd, J=9.2, 1.6 Hz, 1H), 7.26(m, 6H), 7.35(m, 9H), 7.43(d, J=8.8 Hz, 1H), 7.44(d, J=8.8 Hz, 1H), 7.49(s, 1H), 7.66(dd, J=9.2, 0.8 Hz, 1H), 8.22(s, 1H), 9.25(dd, J=1.6, 0.8 Hz, 1H)

Example 394

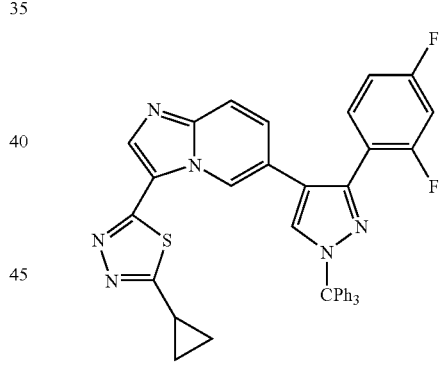

3-(5-Cyclopropyl[1,3,4]thiadiazol-2-yl)₆-[3-(2,4-difluorophenyl)-1-trityl-1H-pyrazol-4-yl]imidazo[1,2-a]-pyridine 67 mg of the title compound was obtained as a colorless amorphous by the same reaction as in Example 29 from 46 mg 6-bromo-3-(5-cyclopropyl[1,3,4]thiadiazol-2-yl)imidazo-[1,2-a]pyridine (compound in Production Example 277) and 200 mg 3-(2,4-difluorophenyl)-1-trityl-1H-4-pyrazolylboronic acid (compound in Production Example 172).

¹H-NMR (CDCl₃)

δ: 1.17–1.32(m, 4H), 2.41(m, 1H), 6.73(m, 1H), 6.88(m, 1H), 7.15(dd, J=9.2, 2.0 Hz, 1H), 7.25(m, 6H), 7.35(m, 9H), 7.46(m, 1H), 7.57(dd, J=9.2, 0.8 Hz, 1H), 7.58(s, 1H), 7.97(s, 1H), 9.48(dd, J=2.0, 0.8 Hz, 1H)

Example 395

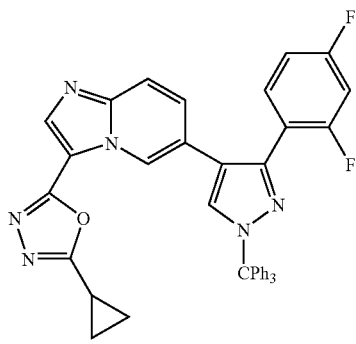

3-(5-Cyclopropyl[1,3,4]oxadiazol-2-yl)₆-[3-(2,4-difluorophenyl)-1-trityl-1H-pyrazol-4-yl]imidazo[1,2-a]-pyridine 61 mg of the title compound was obtained as a colorless amorphous by the same reaction as in Example 29 from 48 mg 6-bromo-3-(5-cyclopropyl[1,3,4]oxadiazol-2-yl)imidazo[1,2-a]pyridine (compound in Production Example 278) and 220 mg 3-(2,4-difluorophenyl)-1-trityl-1H-4-pyrazolylboronic acid (compound in Production Example 172).

¹H-NMR (CDCl₃)
δ: 1.20(m, 4H), 2.23(m, 1H), 6.74(m, 1H), 6.89(m, 1H), 7.18(dd, J=9.2, 2.0 Hz, 1H), 7.25(m, 6H), 7.33(m, 9H), 7.45(m, 1H), 7.59(s, 1H), 7.61(dd, J=9.2, 0.8 Hz, 1H), 8.14(s, 1H), –9.21(dd, J=2.0, 0.8 Hz, 1H)

Example 396

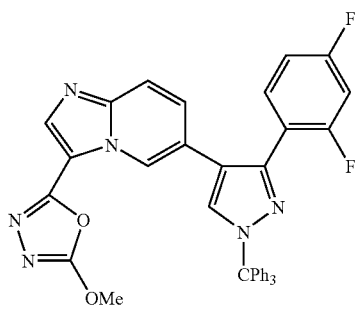

6-[3-(2,4-Difluorophenyl)-1-trityl-1H-pyrazol-4-yl]-3-(5-methoxy[1,3,4]oxadiazol-2-yl)imidazo[1,2-a]pyridine 50 mg of the title compound was obtained as a colorless amorphous by the same reaction as in Example 29 from 32 mg 6-bromo-3-(5-methoxy[1,3,4]oxadiazol-2-yl)imidazo[1,2-a]-pyridine (compound in Production Example 280) and 152 mg 3-(2,4-difluorophenyl)-1-trityl-1H-4-pyrazolylboronic acid (compound in Production Example 172).

¹H-NMR (CDCl₃)
δ: 4.25(s, 3H), 6.74(m, 1H), 6.89(m, 1H), 7.18(dd, J=9.2, 1.6 Hz, 1H), 7.25(m, 6H), 7.33(m, 9H), 7.45(m, 1H), 7.59(s, 1H), 7.61(dd, J=9.2, 0.8 Hz, 1H), 8.10(s, 1H), 9.11(dd, J=1.6, 0.8 Hz, 1H)

Example 397

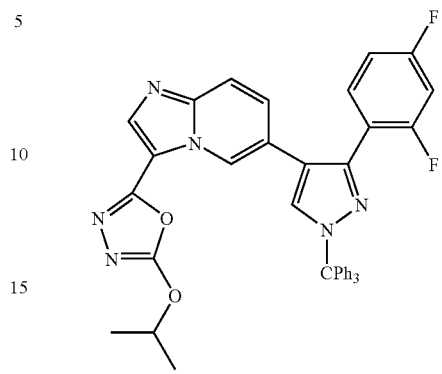

6-[3-(2,4-Difluorophenyl)-1-trityl-1H-pyrazol-4-yl]-3-(5-isopropoxy[1,3,4]oxadiazol-2-yl)imidazo[1,2-a]pyridine 48 mg of the title compound was obtained as a colorless amorphous by the same reaction as in Example 29 from 31 mg 6-bromo-3-(5-isopropoxy[1,3,4]oxadiazol-2-yl)imidazo[1,2-a]pyridine (compound in Production Example 281) and 160 mg 3-(2,4-difluorophenyl)-1-trityl-1H-4-pyrazolylboronic acid (compound in Production Example 172).

¹H-NMR (CDCl₃)
δ: 1.51(d, J=6.4 Hz, 6H), 5.20(m, 1H), 6.74(m, 1H), 6.89(m, 1H), 7.16(dd, J=9.2, 1.6 Hz, 1H), 7.25-(m, 6H), 7.35(m, 9H), 7.45(m, 1H), 7.58(s, 1H), 7.60(dd, J=9.2, 0.8 Hz, 1H), 8.09(s, 1H), 9.13(dd, J=1.6, 0.8 Hz, 1H)

Example 398

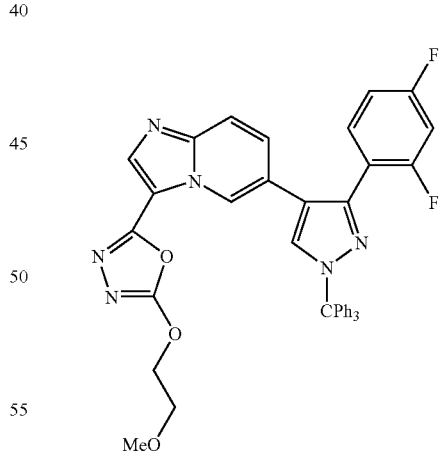

6-[3-(2,4-Difluorophenyl)-1-trityl-1H-pyrazol-4-yl]-3-[5-(2-methoxyethoxy)[1,3,4]oxadiazol-2-yl]imidazo[1,2-a]-pyridine 109 mg of the title compound was obtained as a colorless amorphous by the same reaction as in Example 29 from 54 mg 6-bromo-3-[5-(2-methoxyethoxy)[1,3,4]oxadiazol-2-yl]imidazo[1,2-a]pyridine (compound in Production Example 282) and 300 mg 3-(2,4-difluorophenyl)-1-trityl-1H-pyrazolylboronic acid (compound in Production Example 172).

¹H-NMR (CDCl₃)

δ: 3.25(s, 3H), 3.41(m, 2H), 4.68(m, 2H), 6.75(m, 1H), 6.89(m, 1H), 7.18(dd, J=9.2, 1.6 Hz, 1H), 7.25(m, 6H), 7.35(m, 9H), 7.46(m, 1H), 7.58(s, 1H), 7.60(dd, J=9.2, 0.8 Hz, 1H), 8.09(s, 1H), 9.10(dd, J=1.6, 0.8 Hz, 1H)

Example 399

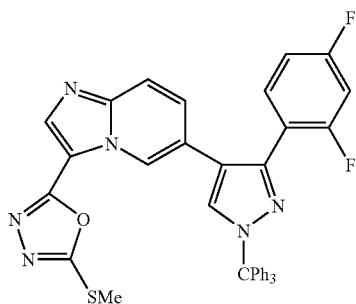

6-[3-(2,4-Fluorophenyl)-1-trityl-1H-pyrazol-4-yl]-3-(5-methylsulfanyl[1,3,4]oxadiazol-2-yl)imidazo[1,2-a]pyridine 213 mg of the title compound was obtained as a pale brown amorphous by the same reaction as in Example 393 from 193 mg 6-[3-(2,4-difluorophenyl)-1-trityl-1H-pyrazol-4-yl]imidazo-[1,2-a]pyridine-3-carboxylic acid hydrazide (compound in Production Example 284).

¹H-NMR (CDCl₃)

δ: 2.78(s, 3H), 6.74(m, 1H), 6.89(m, 1H), 7.20(dd, J=9.2, 1.6 Hz, 1H), 7.25(m, 6H), 7.33(m, 9H), 7.45(m, 1H), 7.59(s, 1H), 7.62(d, J=9.2 Hz, 1H), 8.18(s, 1H), 9.17(brs, 1H)

Example 400

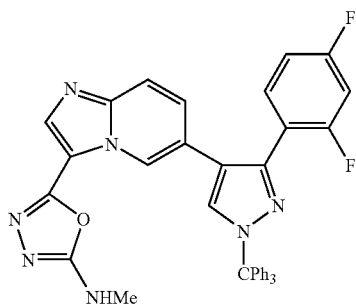

(5-{6-[3-(2,4-Fluorophenyl)-1-trityl-1H-pyrazol-4-yl]imidazo[1,2-a]pyridin-3-yl}[1,3,4]oxadiazol-2-yl)methylamine 140 mg m-chloroperbenzoic acid was added to a mixture of 211 mg 6-[3-(2,4-fluorophenyl)-1-trityl-1H-pyrazol-4-yl]-3-(5-methylsulfanyl[1,3,4]oxadiazol-2-yl)imidazo[1,2-a]-pyridine (compound in Example 399) and 10 mL dichloromethane under ice-coolingd water, and then the mixture was retuned to room temperature and stirred overnight. Ethyl acetate and an aqueous saturated sodium thiosulfate solution were added to the reaction solution and stirred. The organic layer was separated, washed with an aqueous saturated sodium bicarbonate solution and brine and dried over anhydrous sodium sulfate. The drying agent was filtered off, and the filtrate was evaporated. 211 mg crude product of a mixture of 6-[3-(2,4-fluorophenyl)-1-trityl-1H-pyrazol-4-yl]-3-(5-methylsulfinyl[1,3,4]-oxadiazol-2-yl)imidazo[1,2-a]pyridine and 6-[3-(2,4-fluorophenyl)-1-trityl-1H-pyrazol-4-yl]-3-(5-methylsulfonyl[1,3,4]oxadiazol-2-yl)imidazo[1,2-a]pyridine was obtained as a greenish brown amorphous. A mixture of 110 mg of this mixture, 4 mL methylamine (2 M tetrahydrofuran solution), and 6 mL anhydrous tetrahydrofuran was stirred in a sealed tube at 80° C. for 6 hours. The reaction solution was evaporated, and the residue was purified by NH silica gel column chromatography (ethyl acetate/hexane) to give 81 mg of the title compound as a colorless amorphous.

¹H-NMR (CDCl₃)

δ: 3.10(d, J=4.0 Hz, 3H), 4.78(brd, J=4.0 Hz, 1H), 6.74 (m, 1H), 6.88(m, 1H), 7.13(dd, J=9.6, 1.6 Hz, 1H), 7.25(m, 6H), 7.35(m, 9H), 7.43(m, 1H), 7.58(s, 1H), 7.58(dd, J=9.6, 0.8 Hz, 1H), 8.02(s, 1H), 9.17(dd, J=1.6, 0.8 Hz, 1H)

Example 401

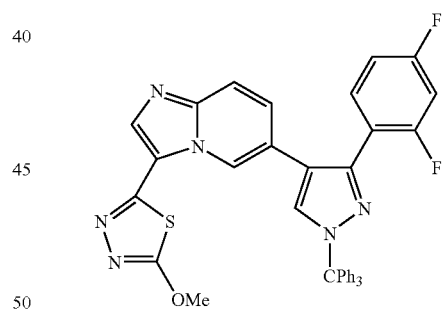

6-[3-(2,4-Fluorophenyl)-1-trityl-1H-pyrazol-4-yl]-3-(5-methoxy[1,3,4]thiadiazol-2-yl)imidazo[1,2-a]pyridine 11 mg of the title compound was obtained as a colorless amorphous by the same reaction as in Example 29 from 8 mg 6-bromo-3-(5-methoxy[1,3,4]thiadiazol-2-yl)imidazo[1,2-a]-pyridine (compound in Production Example 286) and 42 mg 3-(2,4-difluorophenyl)-1-trityl-1H-4-pyrazolylboronic acid (compound in Production Example 172).

¹H-NMR (CDCl₃)

δ: 4.24(s, 3H), 6.74(m, 1H), 6.89(m, 1H), 7.16(dd, J=9.2, 2.0 Hz, 1H), 7.23–7.38(m, 15H), 7.46(m, 1H), 7.54(m, 1H), 7.58(s, 1H), 7.89(s, 1H), 9.39(dd, J=2.0, 0.8 Hz, 1H)

Example 402

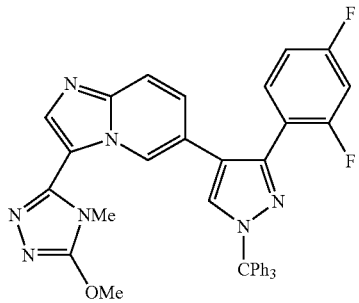

6-[3-(2,4-Fluorophenyl)-1-trityl-1H-pyrazol-4-yl]-3-(5-methoxy-4-methyl-4H-[1,2,4]triazol-3-yl)imidazo[1,2-a]-pyridine 26 mg of the title compound was obtained as a colorless amorphous by the same reaction as in Example 29 from 35 mg 6-bromo-3-(5-methoxy-5-methyl-4H-[1,2,4]triazol-3-yl)imidazo[1,2-a]pyridine (compound in Production Example 288) and 168 mg 3-(2,4-difluorophenyl)-1-trityl-1H-4-pyrazolylboronic acid (compound in Production Example 172).

$^1$H-NMR (CDCl$_3$)

δ: 3.60(s, 3H), 4.23(s, 3H), 6.72(m, 1H), 6.85(m, 1H), 7.09(dd, J=9.2, 2.0 Hz, 1H), 7.24(m, 6H), 7.33(m, 9H), 7.42(m, 1H), 7.55(dd, J=9.2, 0.8 Hz, 1H), 7.57(s, 1H), 7.90(s, 1H), 9.33(dd, J=2.0, 0.8 Hz, 1H)

Example 403

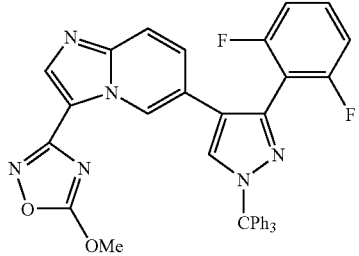

6-[3-(2,6-Difluorophenyl)-1-trityl-1H-pyrazol-4-yl]-3-(5-methoxy-[1,2,4]oxadiazol-3-yl)imidazo[1,2-a]pyridine 35 mg of the title compound was obtained as a colorless amorphous by the same reaction as in Example 29 from 11 mg 6-bromo-3-(5-methoxy[1,2,4]oxadiazol-3-yl)imidazo[1,2-a]-pyridine (compound in Production Example 290) and 35 mg 3-(2,6-difluorophenyl)-1-trityl-1H-4-pyrazolylboronic acid (compound in Production Example 211).

$^1$H-NMR (CDCl$_3$)

δ: 4.03(s, 3H), 6.93(t, J=8.0 Hz, 2H), 7.22(dd, J=9.2, 2.0 Hz, 1H), 7.23–7.38(m, 17H), 7.58(m, 1H), 7.70(s, 1H), 8.25(s, 1H), 9.50(brs, 1H)

Example 404

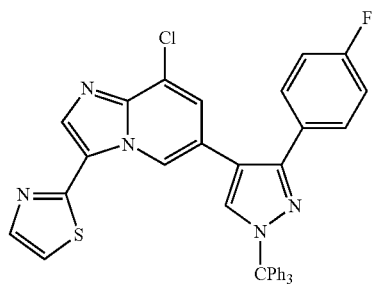

2-{8-Chloro-6-[3-(4-fluorophenyl)-1-trityl-1H-4-pyrazolyl]-imidazo[1,2-a]pyridin-3-yl}-1,3-thiazole 137 mg of the title compound was obtained as a yellow amorphous by reacting 300 mg 8-chloro-6-[3-(4-fluorophenyl)-1-trityl-1H-4-pyrazolyl]-3-iodoimidazo[1,2-a]pyridine obtained in Production Example 236, with 182 mg 2-(1,1,1-tributylstannyl)-1,3-thiazole in the same manner as in Example 21.

$^1$H-NMR (CDCl$_3$)

δ: 6.95–7.03(m, 2H), 7.21–7.42(m, 17H), 7.43–7.51(m, 2H), 7.52(s, 1H), 7.73(d, J=3.2 Hz, 1H), 8.12(s, 1H), 9.51(d, J=1.6 Hz, 1H)

Example 405

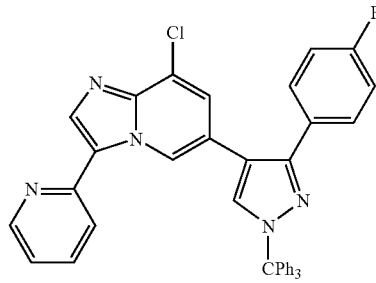

8-Chloro-6-[3-(4-fluorophenyl)-1-trityl-1H-4-pyrazolyl]-3-(2-pyridinyl)imidazo[1,2-a]pyridine 235 mg of the title compound was obtained as a yellow amorphous by reacting 300 mg 8-chloro-6-[3-(4-fluorophenyl)-1-trityl-1H-4-pyrazolyl]-3-iodoimidazo[1,2-a]pyridine obtained in Production Example 236, with 179 mg 2-(tri-n-butylstannyl)pyridine in the same manner as in Example 21.

$^1$H-NMR (CDCl$_3$)

δ: 6.95–7.03(m, 2H), 7.13–7.78(m, 22H), 8.13(s, 1H), 8.39(d, J=4.0 Hz, 1H), 9.76(d, J=1.6 Hz, 1H)

Example 406

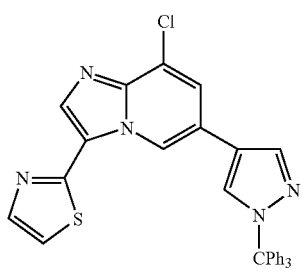

2-[8-Chloro-6-(1-trityl-1H-4-pyrazolyl)imidazo[1,2-a]-pyridin-3-yl]-1,3-thiazole 171 mg of the title compound was obtained as a pale yellow amorphous by reacting 250 mg 8-chloro-3-iodo-6-(1-trityl-1H-4-pyrazolyl)imidazo[1,2-a]pyridine obtained in Production Example 238, with 192 mg 2-(1,1,1-tributylstannyl)-1,3-thiazole in the same manner as in Example 21.

$^1$H-NMR (CDCl$_3$)

δ: 7.18–7.25(m, 6H), 7.32(d, J=3.2 Hz, 1H), 7.33–7.45(m, 9H), 7.48(d, J=1.2 Hz, 1H), 7.69(s, 1H), 7.89(d, J=3.2 Hz, 1H), 8.00(s, 1H), 8.14(s, 1H), 9.77(d, J=1.2 Hz, 1H)

Example 407

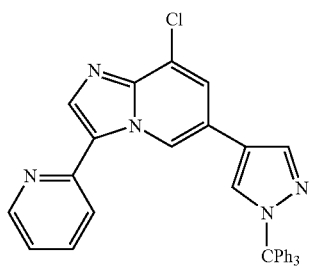

8-Chloro-6-(1-trityl-1H-4-pyrazolyl)-3-(2-pyridinyl)-imidazo[1,2-a]pyridine 87 mg of the title compound was obtained as a yellow amorphous by reacting 250 mg 8-chloro-3-iodo-6-(1-trityl-1H-4-pyrazolyl)imidazo[1,2-a]pyridine obtained in Production Example 238, with 189 mg 2-(tri-n-butylstannyl)pyridine in the same manner as in Example 21.

$^1$H-NMR (CDCl$_3$)

δ: 7.13–7.43(m, 16H), 7.45(d, J=1.2 Hz, 1H), 7.68(s, 1H), 7.73–7.81(m, 2H), 7.99(s, 1H), 8.15(s, 1H), 8.64(d, J=4.8 Hz, 1H), 10.05(d, J=1.2 Hz, 1H)

Example 408

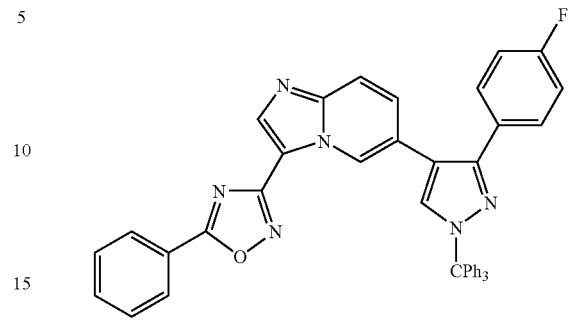

6-[3-(4-Fluorophenyl)-1-trityl-1H-4-pyrazolyl]-3-(5-phenyl-[1,2,4]oxadiazol-3-yl)-imidazo[1,2-a]pyridine 18 mg of the title compound (colorless crystals) was obtained from 19 mg 3-(4-fluorophenyl)-1-trityl-1H-4-pyrazolylboronic acid (compound in Production Example 25) and 13 mg 6-bromo-3-(5-phenyl-[1,2,4]oxadiazol-3-yl)imidazo[1,2-a]pyridine (compound in Production Example 245) by the same reaction as in Example 29 with 1,2-dimethoxyethane as the solvent.

$^1$H-NMR (CDCl$_3$)

δ: 6.94–7.02(m, 2H), 7.22–7.44(m, 16H), 7.45–7.51(m, 2H), 7.52(s, 1H), 7.56–7.71(m, 4H), 8.20(d, J=8.4 Hz, 2H), 8.45(s, 1H), 9.13–9.16(m, 1H)

Example 409

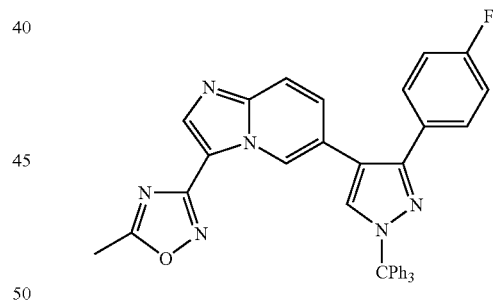

6-[3-(4-Fluorophenyl)-1-trityl-1H-4-pyrazolyl]-3-(5-methyl-[1,2,4]oxadiazol-3-yl)-imidazo[1,2-a]pyridine 78 mg of the title compound (white amorphous) was obtained from 64 mg 3-(4-fluorophenyl)-1-trityl-1H-4-pyrazolylboronic acid (compound in Production Example 25) and 33 mg 6-bromo-3-(5-methyl-[1,2,4]oxadiazol-3-yl)imidazo[1,2-a]pyridine (compound in Production Example 246) by the same reaction as in Example 29 with 1,2-dimethoxyethane as the solvent.

$^1$H-NMR (CDCl$_3$)

δ: 2.66(s, 3H), 6.92–7.00(m, 2H), 7.17–7.42(m, 16H), 7.44–7.49(m, 2H), 7.50(s, 1H), 7.65(d, J=9.6 Hz, 1H), 8.33(s, 1H), 9.02–9.06(m, 1H)

Example 410

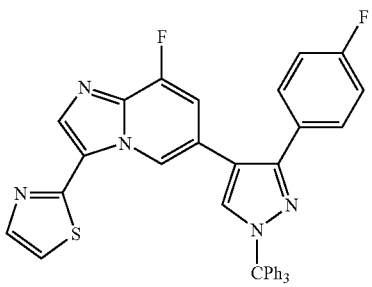

2-{8-Fluoro-6-[3-(4-fluorophenyl)-1-trityl-1H-4-pyrazolyl]-imidazo[1,2-a]pyridin-3-yl}-1,3-thiazole 91 mg of the title compound was obtained as a yellow amorphous by reacting 118 mg 8-fluoro-6-[3-(4-fluorophenyl)-1-trityl-1H-4-pyrazolyl]-3-iodoimidazo[1,2-a]pyridine obtained in Production Example 251, with 80 mg 2-(1,1,1-tributylstannyl)-1,3-thiazole in the same manner as in Example 21.

$^1$H-NMR (CDCl$_3$)
δ: 6.92(dd, J=10.8, 1.2 Hz, 1H), 6.95–7.02(m, 2H), 7.21–7.43(m, 16H), 7.44–7.51(m, 2H), 7.51(s, 1H), 7.74(d, J=3.2 Hz, 1H), 8.09(s, 1H), 9.39(d, J=1.2 Hz, 1H)

Example 411

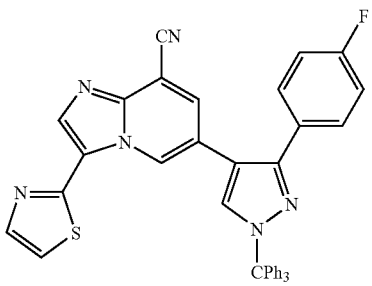

6-[3-(4-Fluorophenyl)-1-trityl-1H-4-pyrazolyl]-3-(2-thiazolyl)imidazo[1,2-a]pyridin-8-carbonitrile A solution of 213 mg 2-{8-chloro-6-[3-(4-fluorophenyl)-1-trityl-1H-4-pyrazolyl]imidazo[1,2-a]pyridin-3-yl}-1,3-thiazole obtained in Example 404 in 2 mL N,N-dimethylacetamide, together with 24 mg zinc cyanide, 6 mg zinc powder, 12 mg tris(dibenzylidene acetone)dipalladium (0) and 15 mg diphenylphosphinoferrocene, was heated at 150° C. for 5 hours, and the reagents were added in the same amounts as described above, and the mixture was heated at 150° C. for 10 hours. The reaction solution was diluted with water and ethyl acetate and filtered through Celite, and the organic layer was washed with brine. The solution was dried over anhydrous sodium sulfate, the solvent was removed, and the resulting crude product was purified by silica gel column chromatography (ethyl acetate/hexane) and then recrystallized to give 68 mg of the title compound (yellow solid).

$^1$H-NMR (CDCl$_3$)
δ: 6.90–7.03(m, 2H), 7.16–7.42(m, 15H), 7.43–7.50(m, 2H), 7.60(s, 1H), 7.68(d, J=3.2 Hz, 1H), 8.06(s, 1H), 8.27(d, J=1.2 Hz, 1H), 9.68(d, J=1.2 Hz, 1H), 9.88–9-93(m, 1H)

Example 412

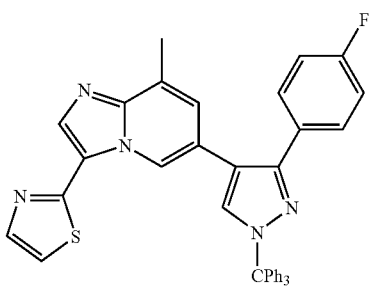

2-{6-[3-(4-Fluorophenyl)-1-trityl-1H-4-pyrazolyl]-8-methylimidazo[1,2-a]pyridin-3-yl}-1,3-thiazole 118 mg of the title compound was obtained as a pale yellow amorphous by reacting 195 mg 6-[3-(4-fluorophenyl)-1-trityl-1H-4-pyrazolyl]-3-iodo-8-methylimidazo[1,2-a]pyridine obtained in Production Example 254, with 132 mg 2-(1,1,1-tributylstannyl)-1,3-thiazole in the same manner as in Example 21.

$^1$H-NMR (CDCl$_3$)
δ: 2.59(s, 3H), 6.92–6.99(m, 2H), 7.01(brs, 1H), 7.23(d, J=3.6 Hz, 1H), 7.23–7.42(m, 15H), 7.44–7.53(m, 3H), 7.73(d, J=3.6 Hz, 1H), 8.07(s, 1H), 9.41(brs, 1H)

Example 413

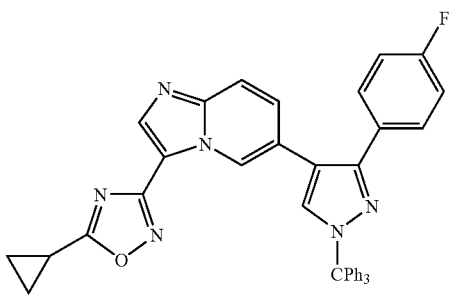

3-(5-Cyclopropyl-[1,2,4]oxadiazol-3-yl)-6-[3-(4-fluorophenyl)-1-trityl-1H-4-pyrazolyl]-imidazo[1,2-a]-pyridine 138 mg of the title compound (pale yellow amorphous) was obtained from 157 mg 3-(4-fluorophenyl)-1-trityl-1H-4-pyrazolylboronic acid (compound in Production Example 25) and 89 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

¹H-NMR (CDCl₃)

δ: 1.20–1.39(m, 4H), 2.22–2.30(m, 1H), 6.92–7.02(m, 2H), 7.21(dd, J=9.6, 2.0 Hz, 1H), 7.23–7.43(m, 15H), 7.43–7.48(m, 2H), 7.49(s, 1H), 7.64(d, J=9.6 Hz, 1H), 8.30(s, 1H), 9.01–9.05(m, 1H)

Example 414

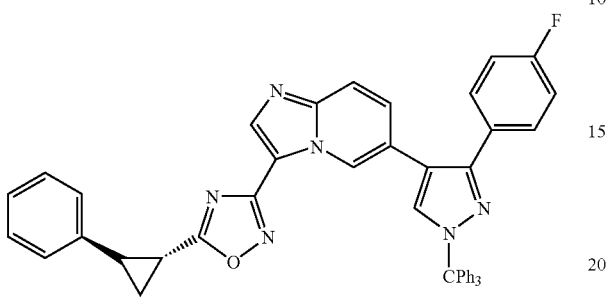

6-[3-(4-Fluorophenyl)-1-trityl-1H-4-pyrazolyl]-3-[5-(2-phenylcyclopropyl)-[1,2,4]oxadiazol-3-yl]-imidazo[1,2-a]-pyridine 107 mg of the title compound (colorless crystals) was obtained from 105 mg 3-(4-fluorophenyl)-1-trityl-1H-4-pyrazolylboronic acid (compound in Production Example 25) and 74 mg 6-bromo-3-[5-(2-phenylcyclopropyl)-[1,2,4]oxadiazol-3-yl]imidazo[1,2-a]pyridine (compound in Production Example 256) by the same reaction as in Example 29 with 1,2-dimethoxyethane as the solvent.

¹H-NMR (CDCl₃)

δ: 1.75(ddd, J=8.8, 6.8,5.2 Hz, 1H), 1.91(ddd, J=8.8, 5.2,5.2 Hz, 1H), 2.50(ddd, J=8.8, 5.2, 4.4 Hz, 1H), 2.80(ddd, J=8.8, 6.8, 4.4 Hz, 1H), 6.92–7.00(m, 2H), 7.16–7.41(m, 21H), 7.43–7.48(m, 2H), 7.49(s, 1H), 7.65(dd, J=9.2, 0.8 Hz, 1H), 8.32(s, 1H), 9.02–9.05(m, 1H)

Example 415

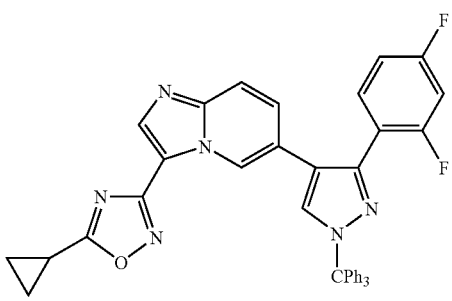

3-(5-Cyclopropyl-[1,2,4]oxadiazol-3-yl)-6-[3-(2,4-difluorophenyl)-1-trityl-1H-4-pyrazolyl]-imidazo[1,2-a]-pyridine 207 mg of the title compound (colorless amorphous) was obtained from 628 mg 3-(2,4-difluorophenyl)-1-trityl-1H-4-pyrazolylboronic acid (compound in Production Example 172) and 137 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

¹H-NMR (CDCl₃)

δ: 1.20–1.38(m, 4H), 2.20–2.30(m, 1H), 6.72–6.80(m, 1H), 6.86–6.95(m, 1H), 7.18(dd, J=9.6, 2.0 Hz, 1H), 7.22–7.48(m, 16H), 7.48–7.64(m, 2H), 8.26(s, 1H), 8.94 (brs, 1H)

Example 416

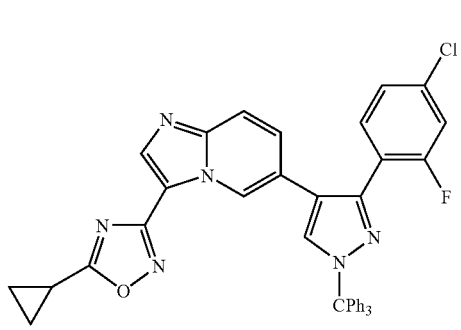

6-[3-(4-Chloro-2-fluorophenyl)-1-trityl-1H-4-pyrazolyl]-3-(5-cyclopropyl-[1,2,4]oxadiazol-3-yl)-imidazo[1,2-a]-pyridine 317 mg of the title compound (pale yellow amorphous) was obtained from 807 mg 3-(4-chloro-2-fluorophenyl)-1-trityl-1H-4-pyrazolylboronic acid (compound in Production Example 180) and 170 mg 6-bromo-3-(5-cyclopropyl-[1,2,4]oxadiazol-3-yl)imidazo[1,2-a]pyridine (compound in Production Example 255) by the same reaction as in Example 29 with 1,2-dimethoxyethane as the solvent.

¹H-NMR (CDCl₃)

δ: 1.23–1.35(m, 4H), 2.21–2.29(m, 1H), 7.04(dd, J=9.6, 2.0 Hz, 1H), 7.13–7.21(m, 2H), 7.22–7.39(m, 15H), 7.41 (dd, J=8.4, 8.4 Hz, 1H), 7.59(s, 1H), 7.61(dd, J=9.2, 0.8 Hz, 1H), 8.26(s, 1H), 8.92–8.96(m, 1H)

Example 417

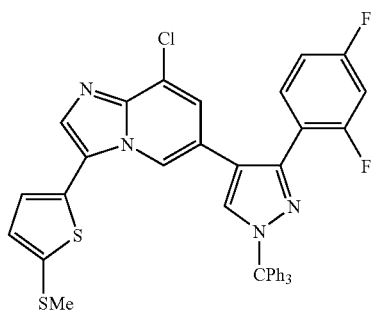

8-Chloro-6-[3-(2,4-difluorophenyl)-1-trityl-1H-4-pyrazolyl]-3-[5-(methylsulfanyl)-2-thienyl]imidazo[1,2-a]-pyridine 206 mg of the title compound (yellow solid) was obtained in the same manner as in Production Example 57 from 223 mg tributyl[5-(methylsulfanyl)-2-thienyl]stannane (compound in Production Example 46) and 337 mg 8-chloro-6-[3-(2,4-difluorophenyl)-1-trityl-1H-4-pyrazolyl]-3-iodoimidazo[1,2-a]pyridine (compound in Production Example 258).

¹H-NMR (CDCl₃)

δ: 2.53(s, 3H), 6.71(d, J=3.6 Hz, 1H), 6.79–6.86(m, 1H), 6.90–6.98(m, 1H), 7.00(d, J=3.6 Hz, 1H), 7.19–7.46(m, 17H), 7.57(s, 1H), 7.69(s, 1H), 8.00(d, J=1.6 Hz, 1H)

Example 418

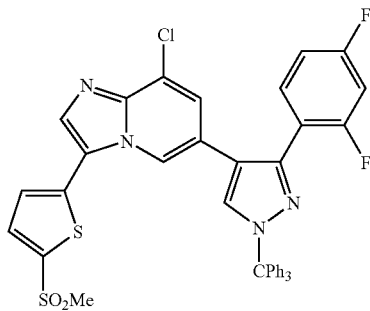

8-Chloro-6-[3-(2,4-difluorophenyl)-1-trityl-1H-4-pyrazolyl]-3-[5-(methylsulfonyl)-2-thienyl]imidazo[1,2-a]-pyridine 178 mg of the title compound (pale yellow amorphous) was obtained in the same manner as in Example 31 from 206 mg 8-chloro-6-[3-(2,4-difluorophenyl)-1-trityl-1H-4-pyrazolyl]-3-[5-(methylsulfanyl)-2-thienyl]imidazo[1,2-a]-pyridine obtained in Example 417.

¹H-NMR (CDCl₃)

δ: 3.22(s, 3H), 6.80–6.87(m, 1H), 6.89(d, J=4.0 Hz, 1H), 6.96–6.72(m, 1H), 7.19–7.27(m, 6H), 7.30(d, J=1.2 Hz, 1H), 7.32–7.49(m, 9H), 7.42–7.50(m, 1H), 7.59(s, 1H), 7.65(d, J=4.0 Hz, 1H), 7.84(s, 1H), 8.01(d, J=1.2 Hz, 1H)

Example 419

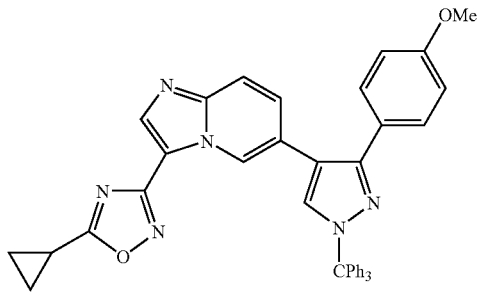

3-(5-Cyclopropyl-[1,2,4]oxadiazol-3-yl)-6-[3-(4-methoxyphenyl)-1-trityl-1H-4-pyrazolyl]-imidazo[1,2-a]-pyridine 140 mg of the title compound (colorless amorphous) was obtained from 215 mg 3-(4-methoxyphenyl)-1-trityl-1H-4-pyrazolylboronic acid (compound in Production Example 27) and 95 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

¹H-NMR (CDCl₃)

δ: 1.22–1.38(m, 4H), 2.21–2.32(m, 1H), 3.78(s, 3H), 6.80(d, J=8.8 Hz, 2H), 7.22(dd, J=9.2, 1.6 Hz, 1H), 7.24–7.39(m, 15H), 7.41(d, J=8.8 Hz, 2H), 7.45(s, 1H), 7.62(d, J=9.2 Hz, 1H), 8.29(s, 1H), 9.03(brs, 1H)

Example 420

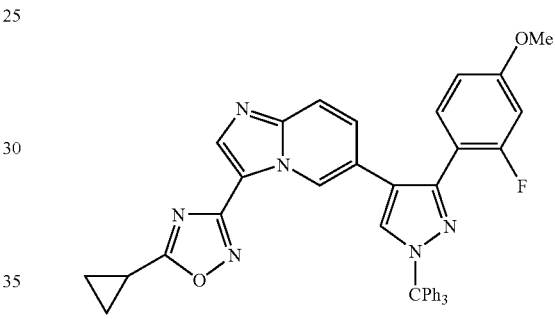

3-(5-Cyclopropyl-[1,2,4]oxadiazol-3-yl)-6-[3-(2-fluoro-4-methoxyphenyl)-1-trityl-1H-4-pyrazolyl]-imidazo[1,2-a]-pyridine 82 mg 6-bromo-3-(5-cyclopropyl-[1,2,4]oxadiazol-3-yl)-imidazo[1,2-a]pyridine (compound in Production Example 255), 227 mg 3-(2-fluoro-4-methoxyphenyl)-4-(4,4,5,5-tetramethyl-[1,3,2]dioxaborolan-2-yl)-1-trityl-1H-pyrazole (compound in Production Example 185), 86 mg tripotassium phosphate hydrate and 31 mg tetrakis(triphenylphosphine)palladium were stirred at 80° C. for 14 hours in 3 mL N,N-dimethylformamide under nitrogen atmosphere. Water and ethyl acetate were added thereto, then the reaction solution was filtered through Celite, and the organic layer was washed with brine. The solution was dried over anhydrous sodium sulfate, the solvent was removed, and the resulting residue was purified by NH silica gel column chromatography (hexane/ethyl acetate) to give 130 mg of the title compound (colorless oil).

¹H-NMR (CDCl₃)

δ: 1.20–1.37(m, 4H), 2.20–2.29(m, 1H), 3.78(s, 3H), 6.56(dd, J=11.6, 2.4 Hz, 1H), 6.71(dd, J=8.4, 2.4 Hz, 1H), 7.19(dd, J=9.2, 1.6 Hz, 1H), 7.23–7.50(m, 16H), 7.56(s, 1H), 7.58(d, J=9.2 Hz, 1H), 8.25(s, 1H), 8.96(brs, 1H)

Example 421

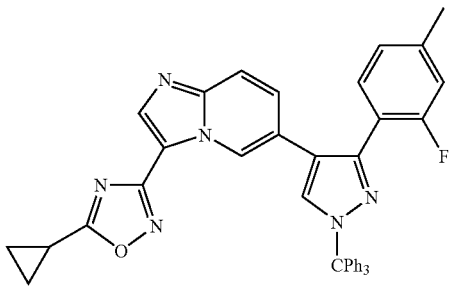

3-(5-Cyclopropyl-[1,2,4]oxadiazol-3-yl)-6-[3-(2-fluoro-4-methylphenyl)-1-trityl-1H-4-pyrazolyl]-imidazo[1,2-a]-pyridine

From 1.0 g 4-bromo-3-(2-fluoro-4-methoxyphenyl)-1-trityl-1H-pyrazole (compound in Production Example 187), 0.97 g crude 3-(2-fluoro-4-methylphenyl)-1-trityl-1H-4-pyrazolyl]boronic acid was obtained as a colorless amorphous.

Subsequently, 364 mg crude 3-(2-fluoro-4-methylphenyl)-1-trityl-1H-4-pyrazolyl]boronic acid and 80 mg 6-bromo-3-(5-cyclopropyl-[1,2,4]oxadiazol-3-yl)imidazo[1,2-a]pyridine (compound in Production Example 255) was reacted in the same manner as in Example 29 by using 1,2-dimethoxyethane as the solvent, to give 139 mg of the title compound (colorless amorphous).

$^1$H-NMR (CDCl$_3$)
δ: 1.22–1.33(m, 4H), 2.18(d, J=2.0 Hz, 3H), 2.22–2.30(m, 1H), 6.87(dd, J=8.8, 8.8 Hz, 1H), 7.19(dd, J=9.2, 1.6 Hz, 1H), 7.22–7.44(m, 17H), 7.47(s, 1H), 7.62(dd, J=9.2, 0.8 Hz, 1H), 8.29(s, 1H), 9.00–9.05(m, 1H)

Example 422

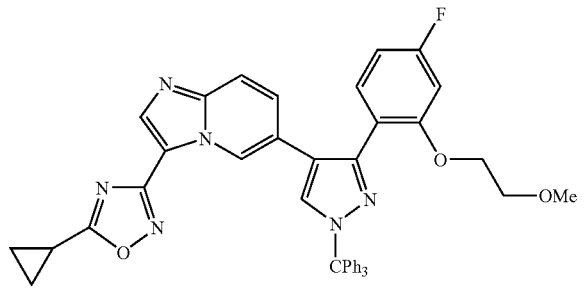

3-(5-Cyclopropyl-[1,2,4]oxadiazol-3-yl)-6-{3-[4-fluoro-2-(2-methylethoxy)phenyl]-1-trityl-1H-4-pyrazolyl}-imidazo-[1,2-a]pyridine

95 mg of the title compound (colorless amorphous) was obtained in the same manner as in Example 420 from 70 mg 6-bromo-3-(5-cyclopropyl-[1,2,4]oxadiazol-3-yl)imidazo[1,2-a]pyridine (compound in Production Example 255) and 400 mg 3-[4-fluoro-2-(2-methoxyethoxy)phenyl]-4-(4,4,5,5-tetramethyl-[1,3,2]dioxaborolan-2-yl)-1-trityl-1H-pyrazole (compound in Production Example 193).

$^1$H-NMR (CDCl$_3$)
δ: 1.20–1.38(m, 4H), 2.21–2.30(m, 1H), 3.05(s, 3H), 3.20(t, J=5.2 Hz, 2H), 3.82(t, J=5.2 Hz, 2H), 6.61(dd, J=10.8, 2.4 Hz, 1H), 6.70(ddd, J=8.4, 8.4, 2.4 Hz, 1H), 7.20(dd, J=9.2, 1.6 Hz, 1H), 7.23–7.43(m, 16H), 7.56(d, J=9.2 Hz, 1H), 7.58(s, 1H), 8.23(s, 1H), 8.85–8.87(m, 1H)

Example 423

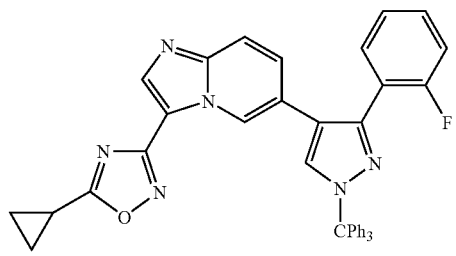

3-(5-Cyclopropyl-[1,2,4]oxadiazol-3-yl)-6-[3-(2-fluorophenyl)-1-trityl-1H-4-pyrazolyl]-imidazo[1,2-a]-pyridine

248 mg of the title compound (colorless amorphous) was obtained from 265 mg 3-(2-fluorophenyl)-1-trityl-1H-4-pyrazolylboronic acid (compound in Production Example 197) and 120 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

$^1$H-NMR (CDCl$_3$)
δ: 1.23–1.33(m, 4H), 2.20–2.28(m, 1H), 6.96–7.03(m, 1H), 7.12–7.17(m, 1H), 7.17(dd, J=9.2, 2.0 Hz, 1H), 7.23–7.40(m, 16H), 7.47(ddd, J=7.2, 7.2, 1.6 Hz, 1H), 7.57(d, J=9.2 Hz, 1H), 7.58(s, 1H), 8.25(s, 1H), 8.94–8.98(m, 1H)

Example 424

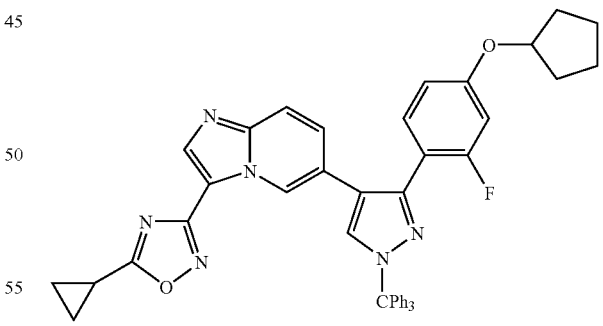

6-[3-(4-Cyclopentyloxy-2-fluorophenyl)-1-trityl-1H-4-pyrazolyl]-3-(5-cyclopropyl-[1,2,4]oxadiazol-3-yl)-imidazo[1,2-a]pyridine

86 mg of the title compound (colorless amorphous) was obtained from 118 mg 3-(4-cyclopentyloxy-2-fluorophenyl)-1-trityl-1H-4-pyrazolylboronic acid (compound in Production Example 206) and 56 mg 6-bromo-3-(5-cyclopropyl-[1,2,4]-oxadiazol-3-yl)imidazo[1,2-a]pyridine (compound in Production Example 255) by the same reaction as in Example 29 with 1,2-dimethoxyethane as the solvent.

¹H-NMR (CDCl₃)

δ: 1.20–1.36(m, 4H), 1.52–1.93(m, 8H), 2.20–2.28(m, 1H), 4.67–4.74(m, 1H), 6.52(dd, J=12.0, 2.4 Hz, 1H), 6.57 (dd, J=8.4, 2.4 Hz, 1H), 7.19(dd, J=9.2, 2.0 Hz, 1H), 7.23–7.44(m, 16H), 7.56(s, 1H), 7.58(dd, J=9.2, 0.8 Hz, 1H), 8.25(s, 1H), 8.94–8.99(m, 1H)

Example 425

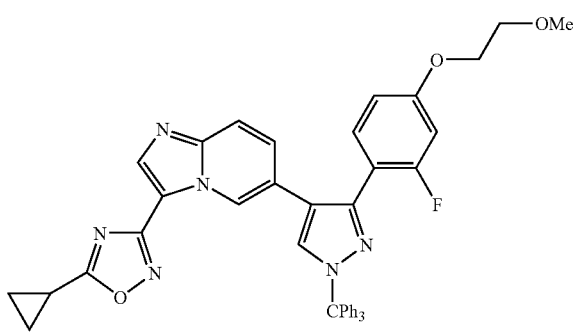

3-(5-Cyclopropyl-[1,2,4]oxadiazol-3-yl)-6-{3-[2-fluoro-4-(2-methoxyethoxy)phenyl]-1-trityl-1H-4-pyrazolyl}-imidazo-[1,2-a]pyridine 73 mg of the title compound (colorless amorphous) was obtained from 147 mg 3-[2-fluoro-4-(2-methoxyethoxy)phenyl]-1-trityl-1H-4-pyrazolylboronic acid (compound in Production Example 207) and 71 mg 6-bromo-3-(5-cyclopropyl-[1,2,4]-oxadiazol-3-yl)imidazo[1,2-a]pyridine (compound in Production Example 255) by the same reaction as in Example 29 with 1,2-dimethoxyethane as the solvent.

¹H-NMR (CDCl₃)

δ: 1.20–1.35(m, 4H), 2.20–2.29(m, 1H), 3.44(s, 3H), 3.71–3.80(m, 2H), 4.06–4.15(m, 2H), 6.58(dd, J=11.6, 2.4 Hz, 1H), 6.73(dd, J=8.4, 2.4 Hz, 1H), 7.17(dd, J=9.2, 2.4 Hz, 1H), 7.23–7.42(m, 16H), 7.56(s, 1H), 7.57(d, J=9.2 Hz, 1H), 8.25(s, 1H), 8.96(brs, 1H)

Example 426

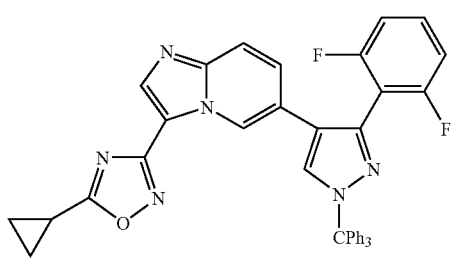

3-(5-Cyclopropyl-[1,2,4]oxadiazol-3-yl)-6-[3-(2,6-difluorophenyl)-1-trityl-1H-4-pyrazolyl]-imidazo[1,2-a]-pyridine 211 mg of the title compound (colorless amorphous) was obtained from 275 mg 3-(2,6-difluorophenyl)-1-trityl-1H-4-pyrazolylboronic acid (compound in Production Example 211) and 120 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

¹H-NMR (CDCl₃)

δ: 1.23–1.34(m, 4H), 2.21–2.29(m, 1H), 6.87–6.96(m, 2H), 7.20(dd, J=9.2, 1.6 Hz, 1H), 7.24–7.43(m, 16H), 7.59 (dd, J=9.2, 0.8 Hz, 1H), 7.65(s, 1H), 8.24(s, 1H), 8.93–8.98 (m, 1H)

Example 427

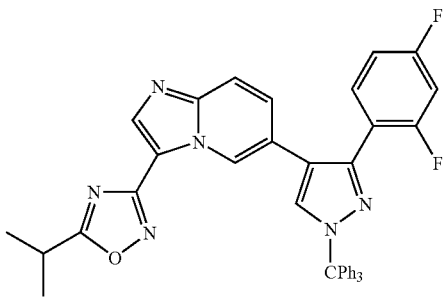

6-[3-(2,4-Difluorophenyl)-1-trityl-1H-4-pyrazolyl]-3-(5-isopropyl-[1,2,4]oxadiazol-3-yl)-imidazo[1,2-a]pyridine 128 mg of the title compound (colorless amorphous) was obtained from 363 mg 3-(2,4-difluorophenyl)-1-trityl-1H-4-pyrazolylboronic acid (compound in Production Example 172) and 80 mg 6-bromo-3-(5-isopropyl-[1,2,4]oxadiazol-3-yl)imidazo-[1,2-a]pyridine (compound in Production Example 259) by the same reaction as in Example 29 with 1,2-dimethoxyethane as the solvent.

¹H-NMR (CDCl₃)

δ: 1.45(d, J=6.8 Hz, 3H), 3.23–3.35(m, 1H), 6.76(ddd, J=9.2, 9.2, 2.4 Hz, 1H), 6.90(ddd, J=8.8, 8.8, 2.4 Hz, 1H), 7.18(dd, J=9.2, 2.0 Hz, 1H), 7.22–7.48(m, 16H), 7.58–7.65 (m, 2H), 8.31(s, 1H), 8.98(brs, 1H)

Example 428

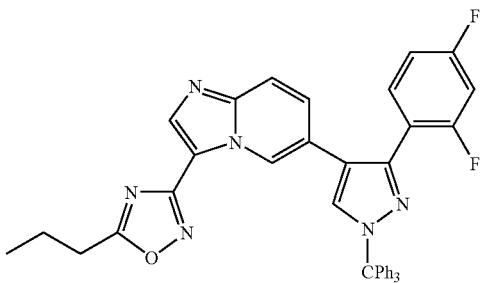

501

6-[3-(2,4-Difluorophenyl)-1-trityl-1H-4-pyrazolyl]-3-(5-propyl-[1,2,4]oxadiazol-3-yl)-imidazo[1,2-a]pyridine 128 mg of the title compound (colorless amorphous) was obtained from 330 mg 3-(2,4-difluorophenyl)-1-trityl-1H-4-pyrazolylboronic acid (compound in Production Example 172) and 80 mg 6-bromo-3-(5-propyl-[1,2,4]oxadiazol-3-yl)imidazo[1,2-a]pyridine (compound in Production Example 260) by the same reaction as in Example 29 with 1,2-dimethoxyethane as the solvent.

¹H-NMR (CDCl₃)

δ: 1.06(t, J=7.2 Hz, 3H), 1.85–1.95(m, 2H), 2.91(t, J=7.2 Hz, 2H), 6.77(ddd, J=9.6, 9.6, 2.4 Hz, 1H), 6.91(ddd, J=8.8, 8.8, 2.4 Hz, 1H), 7.19(dd, J=9.2, 2.0 Hz, 1H), 7.23–7.48(m, 16H), 7.59–7.64(m, 2H), 8.30(s, 1H), 8.97(brs, 1H)

Example 429

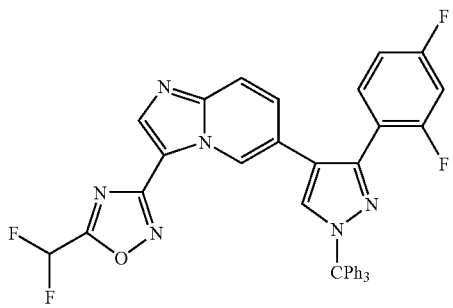

6-[3-(2,4-Difluorophenyl)-1-trityl-1H-4-pyrazolyl]-3-(5-difluoromethyl-[1,2,4]oxadiazol-3-yl)-imidazo[1,2-a]-pyridine 105 mg of the title compound (yellow solid) was obtained from 444 mg 3-(2,4-difluorophenyl)-1-trityl-1H-4-pyrazolylboronic acid (compound in Production Example 172) and 100 mg 6-bromo-3-(5-difluoromethyl-[1,2,4]oxadiazol-3-yl)-imidazo[1,2-a]pyridine (compound in Production Example 261) by the same reaction as in Example 29 with 1,2-dimethoxyethane as the solvent.

¹H-NMR (CDCl₃)

δ: 6.78(ddd, J=9.6, 9.6, 2.4 Hz, 1H), 6.86(t, J=52.0 Hz, 1H), 6.92(ddd, J=8.4, 8.4, 2.4 Hz, 1H), 7.14–7.50(m, 17H), 7.62(s, 1H), 7.66(d, J=9.6 Hz, 1H), 8.37(s, 1H), 8.90(brs, 1H)

Example 430

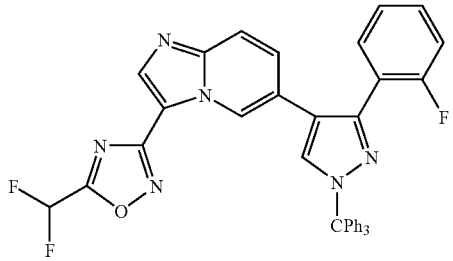

502

3-(5-Difluoromethyl-[1,2,4]oxadiazol-3-yl)-6-[3-(2-fluorophenyl)-1-trityl-1H-4-pyrazolyl]-imidazo[1,2-a]pyridine 132 mg of the title compound (yellow solid) was obtained from 544 mg 3-(2-fluorophenyl)-1-trityl-1H-4-pyrazolylboronic acid (compound in Production Example 197) and 156 mg 6-bromo-3-(5-difluoromethyl-[1,2,4]oxadiazol-3-yl)imidazo-[1,2-a]pyridine (compound in Production Example 261) by the same reaction as in Example 29 with 1,2-dimethoxyethane as the solvent.

¹H-NMR (CDCl₃)

δ: 6.85(t, J=52.0 Hz, 1H), 6.98–7.05(m, 1H), 7.15–7.22 (m, 1H), 7.23–7.44(m, 17H), 7.49(ddd, J=7.2, 7.2, 1.6 Hz, 1H), 7.61(s, 1H), 7.64(d, J=9.2 Hz, 1H), 8.36(s, 1H), 8.92 (brs, 1H)

Example 431

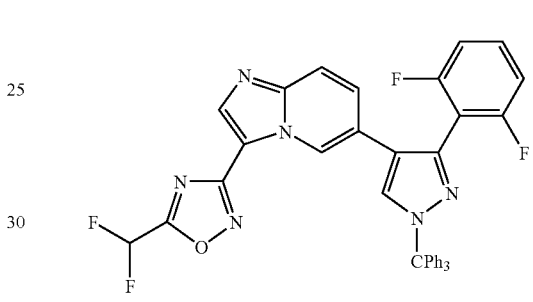

6-[3-(2,6-Difluorophenyl)-1-trityl-1H-4-pyrazolyl]-3-(5-difluoromethyl-[1,2,4]oxadiazol-3-yl)-imidazo[1,2-a]-pyridine 105 mg of the title compound (colorless solid) was obtained from 440 mg 3-(2,6-difluorophenyl)-1-trityl-1H-4-pyrazolylboronic acid (compound in Production Example 211) and 119 mg 6-bromo-3-(5-difluoromethyl-[1,2,4]oxadiazol-3-yl)imidazo[1,2-a]pyridine (compound in Production Example 261) by the same reaction as in Example 29 with 1,2-dimethoxyethane as the solvent.

¹H-NMR (CDCl₃)

δ: 6.86(t, J=52.0 Hz, 1H), 6.90–7.00(m, 2H), 7.21–7.46 (m, 17H), 7.65(d, J=9.2 Hz, 1H), 7.68(s, 1H), 8.34(s, 1H), 8.92(brs, 1H)

Example 432

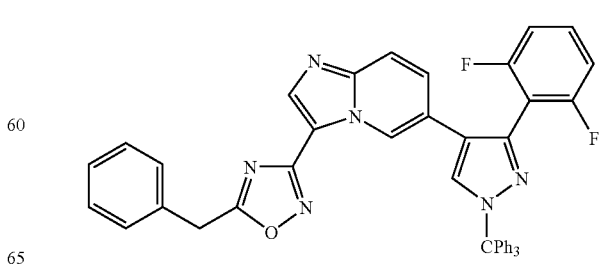

3-(5-Benzyl-[1,2,4]oxadiazol-3-yl)-6-[3-(2,6-difluorophenyl)-1-trityl-1H-4-pyrazolyl]-imidazo[1,2-a]pyridine 65 mg of the title compound (colorless amorphous) was obtained from 164 mg 3-(2,6-difluorophenyl)-1-trityl-1H-4-pyrazolylboronic acid (compound in Production Example 211) and 55 mg 6-bromo-3-(5-benzyl-[1,2,4]oxadiazol-3-yl)imidazo[1,2-a]pyridine (compound in Production Example 266) by the same reaction as in Example 29 with 1,2-dimethoxyethane as the solvent.

$^1$H-NMR (CDCl$_3$)

δ: 4.28(s, 2H), 6.85–6.95(m, 2H), 7.19–7.45(m, 22H), 7.59(d, J=9.2 Hz, 1H), 7.65(s, 1H), 8.28(d, J=1.2 Hz, 1H), 8.96(brs, 1H)

Example 433

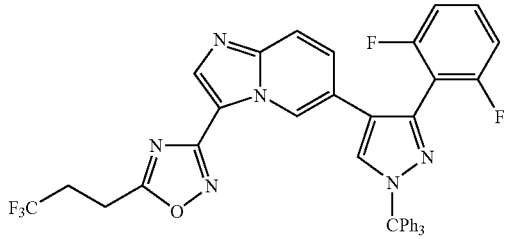

3-[5-(3,3,3-Trifluoropropyl)-[1,2,4]oxadiazol-3-yl]-6-[3-(2,6-difluorophenyl)-1-trityl-1H-4-pyrazolyl]-imidazo[1,2-a]pyridine 83 mg of the title compound (colorless amorphous) was obtained from 260 mg 3-(2,6-difluorophenyl)-1-trityl-1H-4-pyrazolylboronic acid (compound in Production Example 211) and 80 mg 6-bromo-3-[5-(3,3,3-trifluoropropyl)-[1,2,4]oxadiazol-3-yl]-imidazo[1,2-a]pyridine (compound in Production Example 267) by the same reaction as in Example 29 with 1,2-dimethoxyethane as the solvent.

$^1$H-NMR (CDCl$_3$)

δ: 2.68–2.82(m, 2H), 3.16–3.27(m, 2H), 6.88–6.97(m, 2H), 7.21–7.43(m, 17H), 7.62(dd, J=9.2, 0.8 Hz, 1H), 7.66(s, 1H), 8.27(d, J=1.2 Hz, 1H), 8.92–8.95(m, 1H)

Example 434

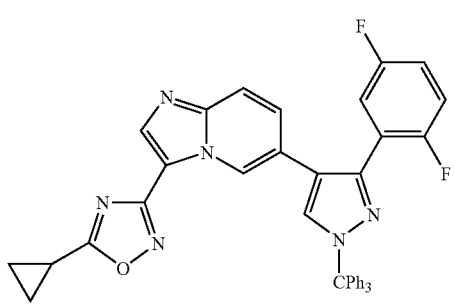

3-(5-Cyclopropyl)-[1,2,4]oxadiazol-3-yl)-6-[3-(2,5-difluorophenyl)-1-trityl-1H-4-pyrazolyl]-imidazo[1,2-a]pyridine 92 mg of the title compound (colorless amorphous) was obtained from 153 mg 3-(2,5-difluorophenyl)-1-trityl-1H-4-pyrazolylboronic acid (compound in Production Example 215) and 50 mg 6-bromo-3-(5-cyclopropyl-[1,2,4]oxadiazol-3-yl)-imidazo[1,2-a]pyridine (compound in Production Example 255) by the same reaction as in Example 29 with 1,2-dimethoxyethane as the solvent.

$^1$H-NMR (CDCl$_3$)

δ: 1.22–1.34(m, 4H), 2.20–2.28(m, 1H), 6.90–7.04(m, 2H), 7.12–7.50(m, 17H), 7.59(s, 1H), 7.61(d, J=9.2 Hz, 1H), 8.26(s, 1H), 8.96(brs, 1H)

Example 435

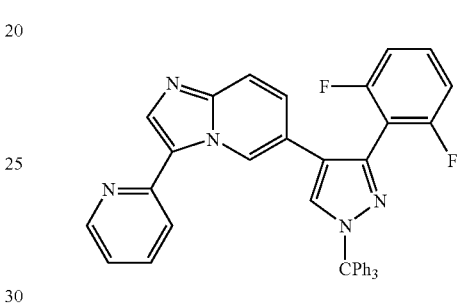

6-[3-(2,6-Difluorophenyl)-1-trityl-1H-4-pyrazolyl]-3-(2-pyridinyl)imidazo[1,2-a]pyridine 238 mg of the title compound was obtained as a colorless amorphous by reacting 183 mg 6-[3-(2,6-difluorophenyl)-1-trityl-1H-4-pyrazolyl]-3-iodoimidazo[1,2-a]pyridine obtained in Production Example 269, with 183 mg 2-(tri-n-butylstannyl)pyridine in the same manner as in Example 21.

$^1$H-NMR (CDCl$_3$)

δ: 6.85–6.95(m, 2H), 6.97(dd, J=9.2, 1.6 Hz, 1H), 7.05–7.12(m, 1H), 7.16(dd, J=9.2, 1.6 Hz, 1H), 7.19–7.80 (m, 18H), 7.91(s, 1H), 8.06(s, 1H), 8.39(d, J=4.4 Hz, 1H), 9.78(brs, 1H)

Example 436

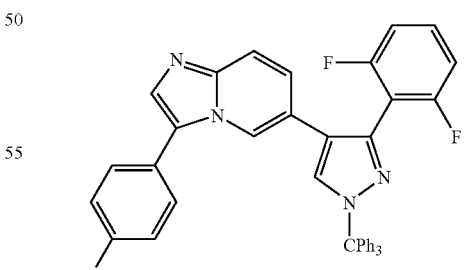

6-[3-(2,6-Difluorophenyl)-1-trityl-1H-4-pyrazolyl]-3-(4-fluorophenyl)imidazo[1,2-a]pyridine 250 mg of the title compound was obtained as colorless crystals by reacting 300 mg 6-[3-(2,6-difluorophenyl)-1- trityl-1H-4-pyrazolyl]-3-iodoimidazo[1,2-a]pyridine obtained in Production Example 269, with 76 mg 4-fluorophenylboronic acid in the same manner as in Example 9 with 1,2-dimethoxyethane as the solvent.

$^1$H-NMR (CDCl$_3$)

δ: 6.86–6.96(m, 2H), 7.02–7.20(m, 5H), 7.20–7.44(m, 16H), 7.50–7.64(m, 3H), 7.93(brs, 1H)

Example 437

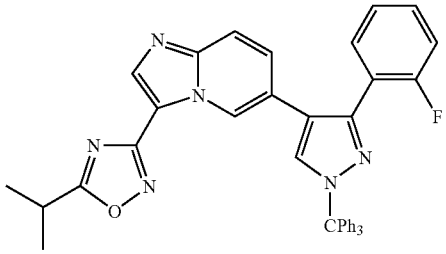

6-[3-(2-Fluorophenyl)-1-trityl-1H-4-pyrazolyl]-3-(5-isopropyl-[1,2,4]oxadiazol-3-yl)-imidazo[1,2-a]pyridine 203 mg of the title compound (colorless amorphous) was obtained from 348 mg 3-(2-fluorophenyl)-1-trityl-1H-4-pyrazolylboronic acid (compound in Production Example 197) and 119 mg 6-bromo-3-(5-isopropyl-[1,2,4]oxadiazol-3-yl)imidazo[1,2-a]pyridine (compound in Production Example 259) by the same reaction as in Example 29 with 1,2-dimethoxyethane as the solvent.

$^1$H-NMR (CDCl$_3$)

δ: 1.45(d, J=6.8 Hz, 3H), 3.23–3.32(m, 1H), 6.96–7.03(m, 1H), 7.11–7.20(m, 1H), 7.24–7.42(m, 16H), 7.47(ddd, J=7.2,7.2, 1.6 Hz, 1H), 7.56–7.63(m, 2H), 8.30(s, 1H), 9.00(brs, 1H)

Example 438

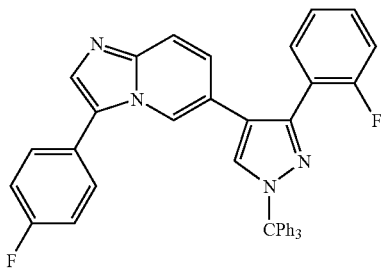

3-(4-Fluorophenyl)-6-[3-(2-fluorophenyl)-1-trityl-1H-4-pyrazolyl]imidazo[1,2-a]pyridine 150 mg of the title compound was obtained as colorless crystals by reacting 200 mg 6-[3-(2-fluorophenyl)-1-trityl-1H-4-pyrazolyl]-3-iodoimidazo[1,2-a]pyridine obtained in Production Example 271, with 261 mg 4-fluorophenylboronic acid in the same manner as in Example 9 with 1,2-dimethoxyethane as the solvent.

$^1$H-NMR (CDCl$_3$)

δ: 6.97–7.16(m, 6H), 7.17–7.48(m, 18H), 7.56–7.62(m, 3H), 7.91(brs, 1H)

Example 439

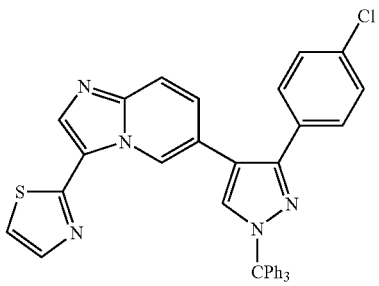

6-[3-(4-Chlorophenyl)-1-trityl-1H-pyrazol-4-yl]-3-thiazol-2-yl-imidazo[1,2-a]pyridine 111 mg of the title compound was obtained as colorless crystals from 50 mg 2-(6-bromoimidazo[1,2-a]pyridin-3-yl)-1,3-thiazole (compound in Production Example 57) and 148 mg 3-(4-chlorophenyl)-1-trityl-1H-4-pyrazolylboronic acid (compound in Production Example 28) by the same reaction as in Example 29.

$^1$H-NMR (CDCl$_3$)

δ: 7.19(dd, J=9.2, 1.4 Hz, 1H), 7.22–7.28(m, 10H), 7.33–7.38(m, 8H), 7.42–7.47(m, 2H), 7.51(s, 1H), 7.60–7.64(m, 1H), 7.75(d, J=3.2 Hz, 1H), 8.11(s, 1H), 9.57(br, 1H)

Example 440

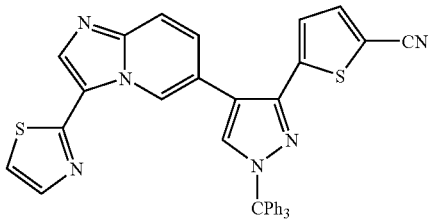

5-[4-(3-Thiazol-2-yl-imidazo[1,2-a]pyridin-6-yl)-1-trityl-1H-pyrazol-3-yl]-thiophen-2-carbonitrile 101 mg of the title compound was obtained as colorless crystals from 50 mg 2-(6-bromoimidazo[1,2-a]pyridin-3-yl)-1,3-thiazole (compound in Production Example 57) and 107 mg 3-(5-cyano-2-thienyl)-1-trityl-1H-4-pyrazolylboronic acid (compound in Production Example 116) by the same reaction as in Example 29.

$^1$H-NMR (CDCl$_3$)

δ: 7.03(d, J=4.0 Hz, 1H), 7.20–7.27(m, 6H), 7.28(d, J=3.2 Hz, 1H), 7.33–7.38(m, 10H), 7.40(d, J=4.0 Hz, 1H), 7.48(s, 1H), 7.72(d, J=8.8 Hz, 1H), 7.80(d, J=3.2 Hz, 1H), 8.16(brs, 1H), 9.70(brs, 1H)

Example 441

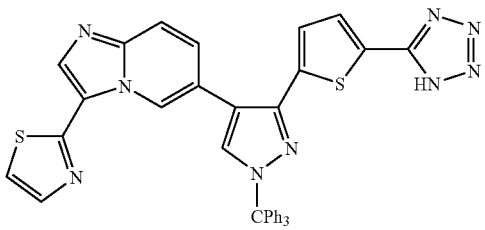

6-{3-[5-(1H-Tetrazol-5-yl)-thiophen-2-yl]-1-trityl-1H-pyrazol-4-yl}-3-thiazol-2-yl-imidazo[1,2-a]pyridine 100 mg 5-[4-(3-thiazol-2-yl-imidazo[1,2-a]pyridin-6-yl)-1-trityl-1H-pyrazol-3-yl]-thiophen-2-carbonitrile (compound in Example 440) was dissolved in 3 mL N,N-dimethylformamide, and 12 mg sodium azide and 9.5 mg ammonium chloride were added thereto and stirred at 100° C. for 18 hours in a stream of nitrogen. 24 mg sodium azide and 19 mg ammonium chloride were further added thereto and stirred for additional 24 hours. Water was added to the reaction solution which was then extracted with ethyl acetate and purified by silica gel column chromatography (ethyl acetate/hexane), to give 60 mg of the title compound (pale pink solid).

$^1$H-NMR (CDCl$_3$)
δ: 7.05(d, J=3.6 Hz, 1H), 7.13–7.24(m, 6H), 7.34–7.44(m, 10H), 7.48(dd, J=9.2, 1.8 Hz, 1H), 7.66–7.70(m, 2H), 7.76 (dd, J=9.2, 0.8 Hz, 1H), 7.81(d, J=3.6 Hz, 1H), 8.32(s, 1H), 9.64(dd, J=1.8, 0.8 Hz, 1H)

Example 442

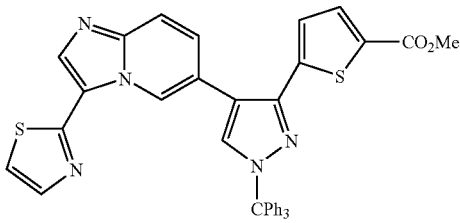

Methyl 5-{4-[3-(1,3-thiazol-2-yl)imidazo[1,2-a]pyridin-6-yl]-1-trityl-1H-3-pyrazolyl}-2-thiophene carboxylate 1.6 g methyl 5-[4-(4,4,5,5-tetramethyl-1,3,2-dioxaborolan-2-yl)-1-trityl-1H-3-pyrazolyl]-2-thiophene carboxylate (compound in Production Example 117), 0.6 g 2-(6-bromoimidazo[1,2-a]pyridin-3-yl)-1,3-thiazole (compound in Production Example 57), 0.68 g tripotassium phosphate, 0.12 g tetrakis (triphenylphosphine)palladium and 30 mL N,N-dimethylformamide were heated at 85° C. for 2.5 hours under nitrogen atmosphere. After the solvent was removed, the residue was purified by silica gel chromatography (hexane/ethyl acetate) to give 1.2 g of the title compound.

$^1$H-NMR (CDCl$_3$)
δ: 3.83(s, 3H), 7.05(d, J=3.6 Hz, 1H), 7.22–7.28(m, 7H), 7.31(dd, J=9.1, 1.7 Hz, 1H), 7.33–7.40(m, 9H), 7.45(s, 1H), 7.59(d, J=4.0 Hz, 1H), 7.69(dd, J=9.1, 1.0 Hz, 1H), 7.79(d, J=3.6 Hz, 1H), 8.15(s, 1H), 9.67(dd, J=1.7, 1.0 Hz, 1H)

Example 443

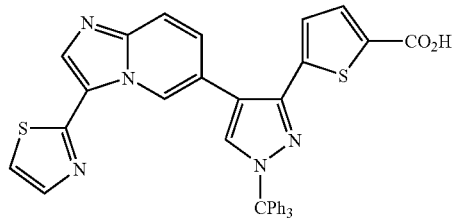

5-(4-[3-(1,3-Thiazol-2-yl)imidazo[1,2-a]pyridin-6-yl]-1-trityl-1H-3-pyrazolyl}-2-thiophene carboxylic acid 1.20 g methyl 5-{4-[3-(1,3-thiazol-2-yl)imidazo-[1,2-a)pyridin-6-yl]-1-trityl-1H-3-pyrazolyl}-2-thiophene carboxylate obtained in Example 442, 0.16 g lithium hydroxide, 30 mL ethanol and 15 mL water were heated at 85° C. for 5 hours. Under ice-cooling, the reaction solution was neutralized by adding water and 1 N aqueous hydrochloric acid and then extracted with ethyl acetate, and the organic layer was dried over anhydrous sodium sulfate. The drying agent was removed, and the solvent was concentrated, whereby 1.08 g of the title compound was obtained as a white solid.

$^1$H-NMR (DMSO-d$_6$)
δ: 7.05(d, J=4.0 Hz, 1H), 7.15–7.20(m, 6H), 7.34–7.43(m, 9H), 7.45(dd, J=9.2, 1.7 Hz, 1H), 7.51(d, J=4.0 Hz, 1H), 7.70(d, J=3.4 Hz, 1H), 7.72(s, 1H), 7.76(d, J=9.2 Hz, 1H), 7.82(d, J=3.4 Hz, 1H), 8.31(s, 1H), 9.60(dd, J=1.7, 1.0 Hz, 1H)

Example 444

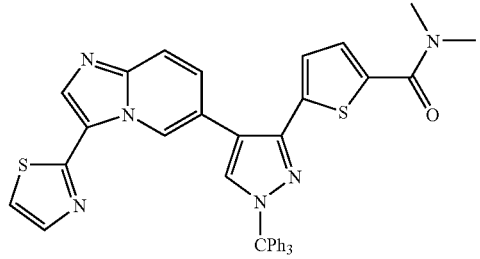

5-[4-(3-Thiazol-2-yl-imidazo[1,2-a]pyridin-6-yl)-1-trityl-1H-pyrazol-3-yl]-thiophene-2-carboxylic acid dimethylamide 100 mg 5-{4-[3-(1,3-thiazol-2-yl)imidazo[1,2-a]pyridin-6-yl]-1-trityl-1H-3-pyrazolyl}-2-thiophene carboxylic acid (compound in Example 443), together with 66 μL triethylamine and 25 μL isobutyl chloroformate, was stirred for 30 minutes in 4 mL tetrahydrofuran under ice-cooling in a stream of nitrogen, and then 0.79 mL dimethylamine was added thereto and stirred at room temperature for 3 hours. Water was added to the reaction solution which was then extracted with ethyl acetate, and the organic layer was dried over anhydrous sodium sulfate and purified by NH silica gel column chromatography (ethyl acetate/hexane) to give 29 mg of the title compound (colorless solid).

$^1$H-NMR (CDCl$_3$)

δ: 3.12(s, 6H), 6.98(d, J=4.0 Hz, 1H), 7.16(d, J=4.0 Hz, 1H), 7.22–7.27(m, 7H), 7.33–7.37(m, 10H), 7.44(s, 1H), 7.71(d, J=9.6 Hz, 1H), 7.83(d, J=3.2 Hz, 1H), 8.14(s, 1H), 9.68(brs, 1H)

Example 445

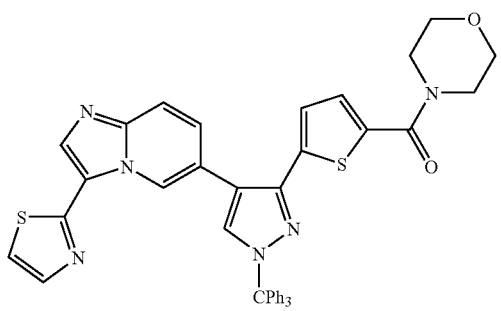

Morpholine-4-yl-{5-[4-(3-thiazol-2-yl-imidazo[1,2-a]-pyridin-6-yl)-1-trityl-1H-pyrazol-3-yl]-thiophen-2-yl}methanone 47 mg of the title compound was obtained in the same manner as in Example 444 from 100 mg 5-{4-[3-(1,3-thiazol-2-yl)-imidazo[1,2-a]pyridin-6-yl]-1-trityl-1H-3-pyrazolyl}-2-thio phene carboxylic acid (compound in Example 443) and 0.14 mL morpholine.

$^1$H-NMR (CDCl$_3$)

δ: 3.63–3.73(m, 8H), 6.98(d, J=3.8 Hz, 1H), 7.10(d, J=3.8 Hz, 1H), 7.22–7.27(m, 7H), 7.30–7.37(m, 10H), 7.44(s, 1H), 7.66–7.70(m, 1H), 7.82(d, J=3.2 Hz, 1H), 8.14(s, 1H), 9.67(dd, J=1.8, 1.0 Hz, 1H)

Example 446

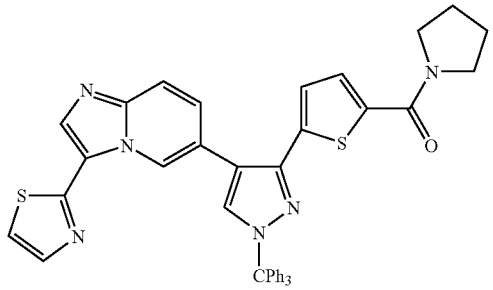

Pyrrolidine-1-yl-{5-[4-(3-thiazol-2-yl-imidazo[1,2-a]-pyridin-6-yl)-1-trityl-1H-pyrazol-3-yl]-thiophen-2-yl}methanone 46 mg of the title compound was obtained in the same manner as in Example 444 from 100 mg 5-{4-[3-(1,3-thiazol-2-yl)imidazo[1,2-a]pyridin-6-yl]-1-trityl-1H-3-pyrazolyl}-2-thiophene carboxylic acid (compound in Example 443) and 0.66 mL pyrrolidine.

$^1$H-NMR (CDCl$_3$)

δ: 1.83–2.00(m, 4H), 3.59–3.70(m, 4H), 7.01(d, J=4.0 Hz, 1H), 7.23–7.28(m, 8H), 7.30–7.38(m, 10H), 7.44(s, 1H), 7.67(dd, J=8.8, 0.9 Hz, 1H), 7.81(d, J=3.2 Hz, 1H), 8.14(s, 1H), 9.66(dd, J=2.0, 0.9 Hz, 1H)

Example 447

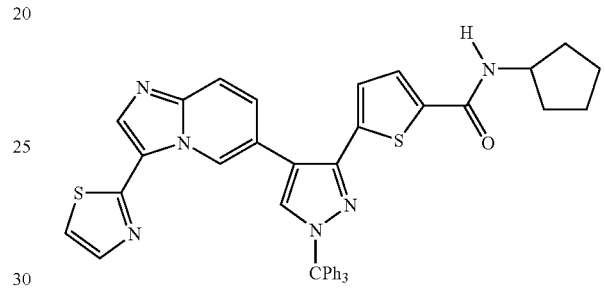

5-[4-(3-Thiazol-2-yl-imidazo[1,2-a]pyridin-6-yl)-1-trityl-1H-pyrazol-3-yl]-thiophen-2-carboxylic acid cyclopentylamide 70 mg of the title compound was obtained in the same manner as in Example 444 from 100 mg 5-{4-[3-(1,3-thiazol-2-yl)imidazo[1,2-a]pyridin-6-yl]-1-trityl-1H-3-pyrazolyl}-2-thiophene carboxylic acid (compound in Example 443) and 0.78 mL cyclopentylamine.

$^1$H-NMR (CDCl$_3$)

δ: 1.37–1.48(m, 2H), 1.59–1.72(m, 4H), 2.00–2.09(m, 2H), 4.25–4.38(m, 1H), 6.98(d, J=4.0 Hz, 1H), 7.24–7.28(m, 7H), 7.30(d, J=4.0 Hz, 1H), 7.33–7.38(m, 10H), 7.45(s, 1H), 7.68(dd, J=9.2, 1.1 Hz, 1H), 7.81(d, J=3.6 Hz, 1H), 8.14(s, 1H), 9.67(dd, J=1.8, 1.1 Hz, 1H)

Example 448

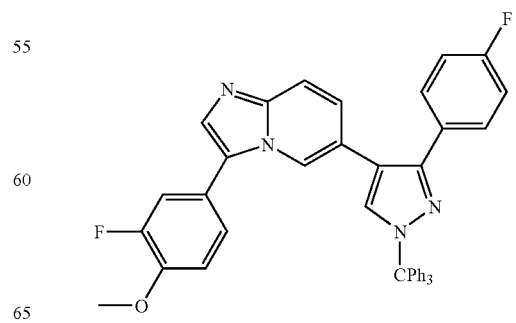

3-(3-Fluoro-4-methoxyphenyl)-6-[3-(4-fluorophenyl)-1-trityl-1H-4-pyrazolyl]imidazo[1,2-a]pyridine 180 mg of the title compound was obtained as colorless crystals in the same manner as in Example 3 from 161 mg 6-[3-(4-fluorophenyl)-1-trityl-1H-4-pyrazolyl]-3-iodoimidazo[1,2-a]pyridine (compound in Production Example 39) and 53 mg 3-fluoro-4-methoxyphenylboronic acid.

$^1$H-NMR (CDCl$_3$)

δ: 3.95 (s, 3H), 6.92–7.06 (m, 5H), 7.11 (dd, J=9.2, 1.6 Hz, 1H), 7.21–7.26 (m, 6H), 7.31–7.35 (m, 9H), 7.44 (s, 1H), 7.44–7.48 (m, 2H), 7.58 (dd, J=9.2, 0.8 Hz, 1H), 7.59 (s, 1H), 7.99 (d, J=1.6, 0.8 Hz, 1H)

Example 449

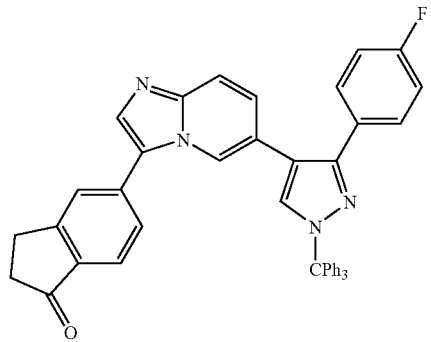

5-{6-[3-(4-Fluorophenyl)-1-trityl-1H-4-pyrazolyl]imidazo-[1,2-a]pyridin-3-yl}-1-indanone 111 mg of the title compound was obtained as film in the same manner as in Example 10 from 84 mg 4-(4,4,5,5-tetramethyl-1,3,2-dioxaborolan-2-yl)-1-indanone prepared from 5-bromo-1-indanone by a method of T. Ishiyama et al., J. Org. Chem., 60, 7508 (1995) and 6-[3-(4-fluorophenyl)-1-trityl-1H-4-pyrazolyl]-3-iodoimidazo[1,2-a]pyridine (compound in Production Example 39).

$^1$H-NMR (CDCl$_3$)

δ: 2.72–2.76(m, 2H), 3.06–3.11 (m, 2H), 7.03–7.08 (m, 2H), 7.19 (dd, J=9.2, 1.6 Hz, 1H), 7.21–7.25 (m, 6H), 7.31–7.36 (m, 11H), 7.45(s, 1H), 7.48–7.53 (m, 2H), 7.65 (dd, J=9.2, 1.2 Hz, 1H), 7.75 (d, J=7.2 Hz, 1H), 7.77(s, 1H), 8.17 (dd, J=1.6, 1.2 Hz, 1H)

Example 450

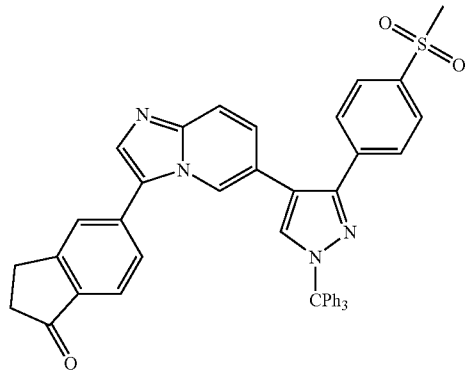

5-(6-{3-[4-(Methylsulfonyl)phenyl]-1-trityl-1H-4-pyrazolyl}imidazo[1,2-a]pyridin-3-yl)-1-indanone 45 mg of the title compound was obtained as colorless crystals in the same manner as in Example 10 from 68 mg 4-(4,4,5,5-tetramethyl-1,3,2-dioxaborolan-2-yl)-1-indanone and 141 mg 3-iodo-6-{3-[4-(methylsulfonyl)phenyl]-1-trityl-1H-4-pyrazolyl}imidazo[1,2-a]pyridine (compound in Production Example 43).

$^1$H-NMR (CDCl$_3$)

δ: 2.72–2.77(m, 2H), 3.03(s, 3H), 3.08–3.13 (m, 2H), 7.15 (dd, J=9.2, 1.6 Hz, 1H), 7.20–7.25 (m, 6H), 7.33–7.38 (m, 9H), 7.41–7.45(m, 2H), 7.47(s, 1H), 7.67(dd, J=9.2, 1.2 Hz, 1H), 7.73–7.77(m, 2H), 7.80(s, 1H), 7.80(d, J=8.4 Hz, 1H), 7.86–7.90(m, 2H), 8.23 (dd, J=1.6, 1.2 Hz, 1H)

Example 451

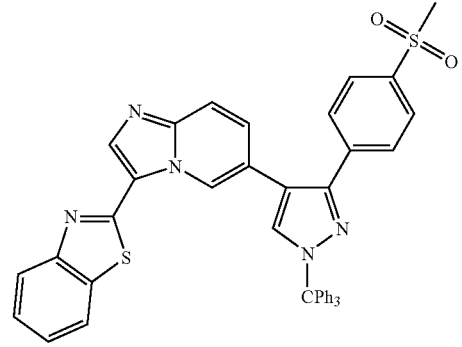

2-(6-{3-[4-(Methylsulfonyl)phenyl]-1-trityl-1H-4-pyrazolyl}imidazo[1,2-a]pyridin-3-yl)-1,3-benzothiazole 61 mg of the title compound was obtained as colorless crystals by the same reaction as in Example 21 from 141 mg 3-iodo-6-{3-[4-(methylsulfonyl)phenyl]-1-trityl-1H-4-pyrazolyl}imidazo[1,2-a]pyridine (compound in Production Example 43) and 106 mg 2-(1,1,1-tributylstannyl)-1,3-benzothiazole.

$^1$H-NMR (CDCl$_3$)

δ: 2.85(s, 3H), 7.25–7.42(m, 17H), 7.46–7.51(m, 1H), 7.60(s, 1H), 7.70(dd, J=9.2, 0.8 Hz, 1H), 7.75–7.79(m, 3H), 7.83–7.89(m, 3H), 8.24(s, 1H), 9.87(dd, J=1.6, 1.2 Hz, 1H)

Example 452

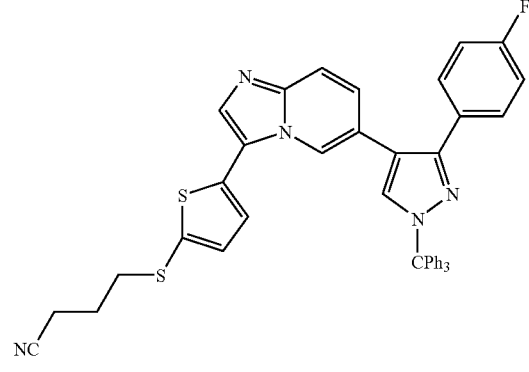

4-[(5-{6-[3-(4-Fluorophenyl)-1-trityl-1H-4-pyrazolyl]-imidazo[1,2-a]pyridin-3-yl}-2-thienyl)sulfanyl]butane nitrile 312 mg of the title compound was obtained as a brown viscous material by the same reaction as in Example 21 from 161 mg 6-[3-(4-fluorophenyl)-1-trityl-1H-4-pyrazolyl]-3-iodoimidazo[1,2-a]pyridine (compound in Production Example 39) and 292 mg 4-[5-(1,1,1-tributylstannyl)-2-thienyl]-sulfanyl]butane nitrile (compound in Production Example 296).

$^1$H-NMR (CDCl$_3$)

δ: 1.99(quint, J=7.2 Hz, 2H), 2.55(t, J=7.2 Hz, 2H), 2.93(t, J=7.2 Hz, 2H), 6.81(d, J=3.6 Hz, 1H), 6.99–7.06(m, 2H), 7.09(d, J=3.6 Hz, 1H), 7.15(dd, J=9.2, 1.6 Hz, 1H), 7.22–7.26(m, 6H), 7.32–7.37(m, 9H), 7.45–7.50(m, 3H), 7.59(dd, J=9.2, 1.2 Hz, 1H), 7.71(s, 1H), 8.17(dd, J=1.6, 1.2 Hz, 1H)

Example 453

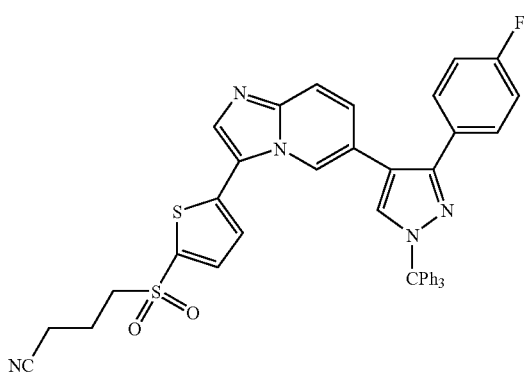

4-[(5-{6-[3-(4-Fluorophenyl)-1-trityl-1H-4-pyrazolyl]-imidazo[1,2-a]pyridin-3-yl}-2-thienyl)sulfonyl]butane nitrile 287 mg of the title compound was obtained as film in the same method as in Example 31 by oxidizing, with 558 mg oxone, 310 mg 4-[(5-{6-[3-(4-fluorophenyl)-1-trityl-1H-4-pyrazolyl]imidazo[1,2-a]pyridin-3-yl}-2-thienyl)sulfanyl]-butane nitrile obtained in Example 452.

$^1$H-NMR (CDCl$_3$)

δ: 2.24(quint, J=7.2 Hz, 2H), 2.65(t, J=7.2 Hz, 2H), 3.35–3.40(m, 2H), 6.96(d, J=4.0 Hz, 1H), 7.03–7.09(m, 2H), 7.22–7.28(m, 7H), 7.33–7.38(m, 9H), 7.45–7.50(m, 2H), 7.51(s, 1H), 7.65(d, J=4.0 Hz, 1H), 7.65(dd, J=9.2, 1.2 Hz, 1H), 7.85(s, 1H), 8.17(dd, J=1.6, 1.2 Hz, 1H)

Example 454

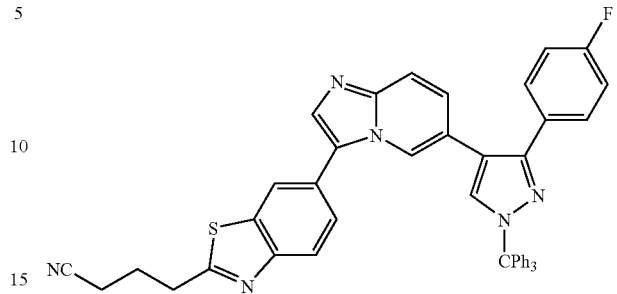

4-(6-{6-[3-(4-Fluorophenyl)-1-trityl-1H-4-pyrazolyl]-imidazo[1,2-a]pyridin-3-yl}-1,3-benzothiazol-2-yl)butane nitrile 109 mg of the title compound was obtained as pale yellow crystals by the same method as in Example 94 from 150 mg 6-[3-(4-fluorophenyl)-1-trityl-1H-4-pyrazolyl]-3-(1,1,1-tributylstannyl)imidazo[1,2-a]pyridine (compound in Production Example 294) and 64 mg 4-(6-iodo-1,3-benzothiazol-2-yl)butane nitrile (compound in Production Example 297).

$^1$H-NMR (CDCl$_3$)

δ: 2.32(quint, J=7.2 Hz, 2H), 2.59(t, J=7.2 Hz, 2H), 3.31(t, J=7.2 Hz, 2H), 7.02–7.09(m, 2H), 7.16(dd, J=9.2, 1.6 Hz, 1H), 7.20–7.24(m, 6H), 7.30–7.35(m, 9H), 7.38(dd, J=8.4, 2.0 Hz, 1H), 7.44(s, 1H), 7.46–7.52(m, 2H), 7.63(dd, J=9.2, 1.2 Hz, 1H), 7.71(s, 1H), 7.73(d, J=2.0 Hz, 1H), 7.95(d, J=8.4 Hz, 1H), 8.10(dd, J=1.6, 0.8 Hz, 1H)

Example 455

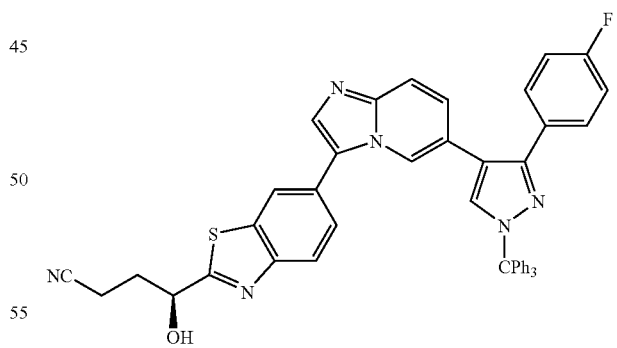

(4S)-4-(6-{6-[3-(4-Fluorophenyl)-1-trityl-1H-4-pyrazolyl]-imidazo[1,2-a]pyridin-3-yl}-1,3-benzothiazol-2-yl)-4-hydroxy butane nitrile 65 mg of the title compound was obtained as a colorless film by the same method as in Example 94 from 121 mg 6-[3-(4-fluorophenyl)-1-trityl-1H-4-pyrazolyl]-3-(1,1,1-tributylstannyl)imidazo[1,2-a]pyridine (compound in Production Example 294) and 45 mg (4S)-4-hydroxy-4-(6-iodo-1,3-benzothiazol-2-yl)butane nitrile (compound in Production Example 300).

¹H-NMR (CDCl₃)

δ: 2.24–2.32(m, 1H), 2.41–2.50(m, 1H), 2.56–2.65(m, 1H), 2.68–2.77(m, 1H), 3.77–3.85(m, 1H), 5.24–5.30(m, 1H), 7.02–7.08(m, 2H), 7.17(dd, J=9.2, 1.6 Hz, 1H), 7.19–7.24(m, 6H), 7.30–7.35(m, 9H), 7.39(dd, J=8.8, 1.6 Hz, 1H), 7.45(s, 1H), 7.46–7.51(m, 2H), 7.64(dd, J=9.2, 0.8 Hz, 1H), 7.70(s, 1H), 7.78(d, J=1.2 Hz, 1H), 7.96(d, J=8.8 Hz, 1H), 8.09(dd, J=1.6, 0.8 Hz, 1H)

Example 456

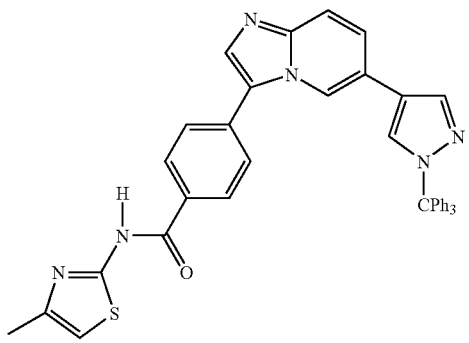

N1-(4-Methyl-1,3-thiazol-2-yl)-4-[6-(1-trityl-1H-4-pyrazolyl)imidazo[1,2-a]pyridin-3-yl]benzamide 45 mg of the title compound was obtained as pale yellow crystals by the same reaction as in Example 29 from 38 mg N1-(4-methyl-1,3-thiazol-2-yl)-4-(6-bromoimidazo[1,2-a]-pyridin-3-yl)benzamide (compound in Production Example 305) and 71 mg 1-trityl-1H-4-pyrazolylboronic acid.

¹H-NMR (CDCl₃)

δ: 2.38(d, J=0.8 Hz, 3H), 6.61(d, J=0.8 Hz, 1H), 7.17–7.22(m, 6H), 7.29–7.37(m, 10H), 7.62(d, J=0.8 Hz, 1H), 7.67(dd, J=9.6, 1.2 Hz, 1H), 7.73–7.77(m, 2H), 7.78(s, 1H), 7.88(d, J=0.8 Hz, 1H), 8.07–8.11(m, 2H), 8.43(m, 1H)

Example 457

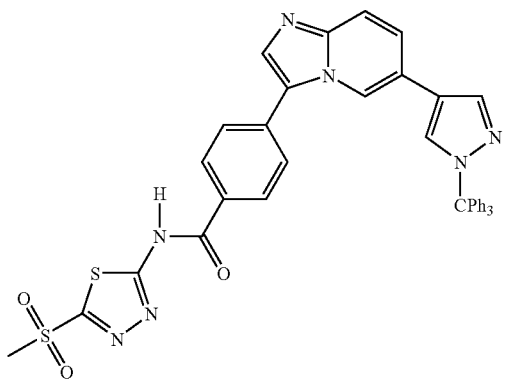

N1-[5-(methylsulfonyl)-1,3,4-thiadiazol-2-yl]-4-[6-(1-trityl-1H-4-pyrazolyl)imidazo[1,2-a]pyridin-3-yl]benzamide 50 mg of the title compound was obtained as pale greenish yellow crystals by the same reaction as in Example 29 from 72 mg N1-[5-(methylsulfonyl)-1,3,4-thiadiazol-2-yl]-4-(6-bromoimidazo[1,2-a]pyridin-3-yl)benzamide (compound in Production Example 307) and 74 mg 1-trityl-1H-4-pyrazolylboronic acid.

¹H-NMR (CDCl₃)

δ: 3.43(s, 3H), 7.17–7.22(m, 6H), 7.32–7.37(m, 10H), 7.65(d, J=0.4 Hz, 1H), 7.67(dd, J=9.2, 0.8 Hz, 1H), 7.77–7.82(m, 3H), 7.88(d, J=0.8 Hz, 1H), 8.24–8.28(m, 2H), 8.47(m, 1H)

Example 458

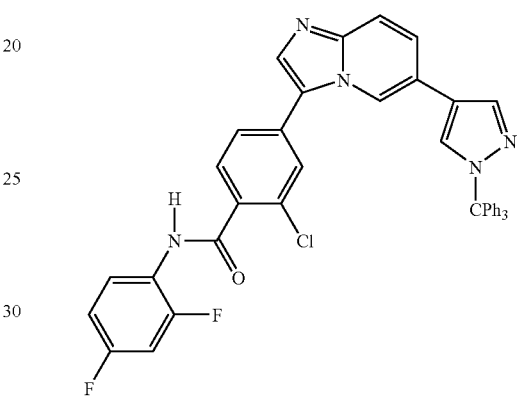

N1-(2,4-Difluorophenyl)-2-chloro-4-[6-(1-trityl-1H-4-pyrazolyl)imidazo[1,2-a]pyridin-3-yl]benzamide 65 mg of the title compound was obtained by the same reaction as in Example 29 from 42 mg 4-(6-bromo-imidazo[1,2-a]pyridin-3-yl)-2-chloro-N-(2,4-difluorophenyl)benzamide (compound in Production Example 311) and 42 mg 1-trityl-1H-4-pyrazolylboronic acid.

¹H-NMR (CDCl₃)

δ: 6.92–7.00(m, 2H), 7.17–7.23(m, 6H), 7.31–7.37(m, 10H), 7.60–7.71(m, 4H), 7.76(s, 1H), 7.89(d, J=0.8 Hz, 1H), 8.00(d, J=8.0 Hz, 1H), 8.26–8.30(m, 1H), 8.38(brs, 1H), 8.43–8.51(m, 1H)

Example 459

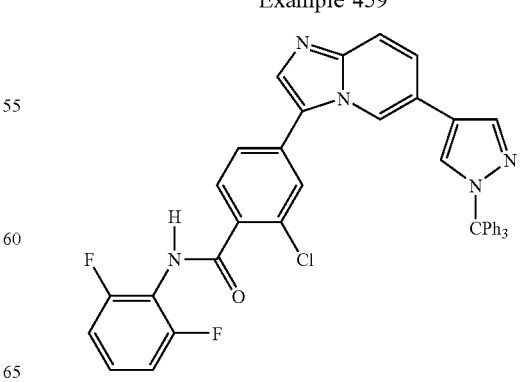

517

N1-(2,6-Difluorophenyl)-2-chloro-4-[6-(1-trityl-1H-4-pyrazolyl)imidazo[1,2-a]pyridin-3-yl]benzamide 52 mg of the title compound was obtained by the same reaction as in Example 29 from 48 mg 4-(6-bromo-imidazo[1,2-a]pyridin-3-yl)-2-chloro-N-(2,6-difluorophenyl)benzamide (compound in Production Example 312) and 48 mg 1-trityl-1H-4-pyrazolylboronic acid.

$^1$H-NMR (CDCl$_3$)

δ: 6.90–7.07(m, 2H), 7.17–7.23(m, 6H), 7.29–7.37(m, 10H), 7.58–7.70(m, 5H), 7.74–7.78(m, 2H), 7.89(d, J=0.8 Hz, 1H), 8.02–8.07(m, 1H), 8.37(brs, 1H)

Example 460

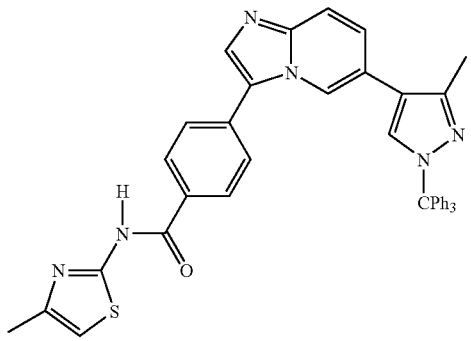

N1-(4-Methyl-1,3-thiazol-2-yl)-4-[6-(3-methyl-1-trityl-1H-4-pyrazolyl)imidazo[1,2-a]pyridin-3-yl]benzamide 41 mg of the title compound was obtained as colorless crystals by the same reaction as in Example 29 from 38 mg N1-(4-methyl-1,3-thiazol-2-yl)-4-(6-bromoimidazo[1,2-a]pyridin-3-yl)benzamide (compound in Production Example 305) and 74 mg 3-methyl-1-trityl-1H-4-pyrazolylboronic acid (compound in Production Example 30).

$^1$H-NMR (CDCl$_3$)

δ: 2.37(d, J=0.8 Hz, 3H), 2.40(s, 3H), 6.61(d, J=0.8 Hz, 1H), 7.17–7.25(m, 7H), 7.30–7.35(m, 9H), 7.42(s, 1H), 7.67(dd, J=9.2, 0.8 Hz, 1H), 7.73–7.78(m, 2H), 7.80(s, 1H), 8.05–9.00(m, 2H), 8.37(m, 1H)

Example 461

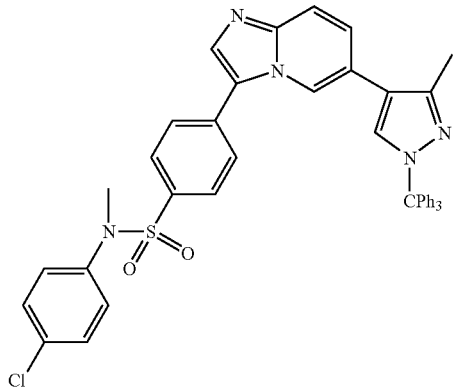

518

N1-(4-Chlorophenyl)-N-1-methyl-4-[6-(3-methyl-1-trityl-1H-4-pyrazolyl)imidazo[1,2-a]pyridin-3-yl]-1-benzene sulfonamide 45 mg of the title compound was obtained as colorless crystals by the same reaction as in Example 3 from 113 mg 3-iodo-6-(3-methyl-1-trityl-1H-4-pyrazolyl)imidazo[1,2-a]-pyridine obtained in Production Example 41 and 100 mg 4-{[4-chloro(methyl)anilino]sulfonyl}phenylboronic acid (compound in Production Example 302).

$^1$H-NMR (CDCl$_3$)

δ: 2.40(s, 3H), 3.22(s, 3H), 7.09–7.13(m, 2H), 7.18–7.22(m, 6H), 7.24(dd, J=9.2, 1.6 Hz, 1H), 7.28–7.35(m, 11H), 7.42(s, 1H), 7.67(dd, J=9.2, 1.2 Hz, 1H), 7.68(s, 4H), 7.79(s, 1H), 8.32(dd, J=1.6, 1.2 Hz, 1H)

Example 462

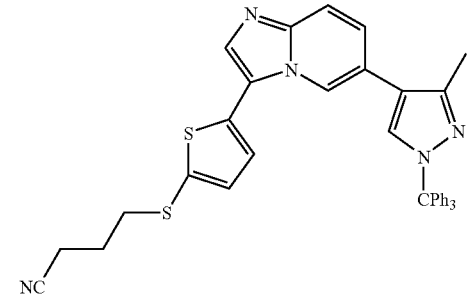

4-({5-[6-(3-Methyl-1-trityl-1H-4-pyrazolyl)imidazo[1,2-a]-pyridin-3-yl]-2-thienyl}sulfanyl)butane nitrile 20 mg of the title compound was obtained as yellow crystals (recrystallization solvent: ethyl acetate/diethyl ether) by the same reaction as in Example 21 from 250 mg 3-iodo-6-(3-methyl-1-trityl-1H-4-pyrazolyl)imidazo[1,2-a]pyridine (compound in Production Example 41) and 320 mg 4-[5-(1,1,1-tributylstannyl)-2-thienyl]sulfanyl]butane nitrile (compound in Production Example 296).

$^1$H-NMR (CDCl$_3$)

δ: 2.02(quint, J=6.8 Hz, 2H), 2.44(s, 3H), 2.56(t, J=6.8 Hz, 2H), 2.94(t, J=6.8 Hz, 2H), 7.16(d, J=4.0 Hz, 1H), 7.18–7.24(m, 8H), 7.31–7.35(m, 9H), 7.44(s, 1H), 7.63(dd, J=9.2, 0.8 Hz, 1H), 7.75(s, 1H), 8.40(m, 1H)

Example 463

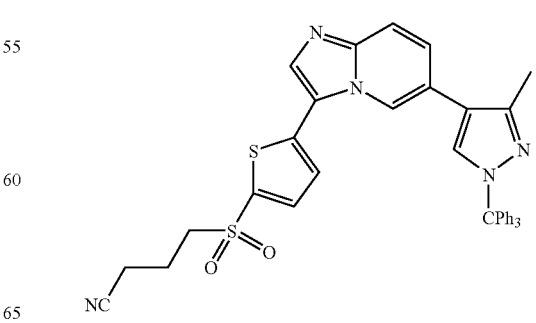

519

4-({5-[6-(3-Methyl-1-trityl-1H-4-pyrazolyl)imidazo[1,2-a]-pyridin-3-yl]-2-thienyl}sulfonyl)butane nitrile 140 mg of the title compound was obtained as a colorless film in the same method as in Example 31 by oxidizing, with 424 mg oxone, 200 mg 4-({5-[6-(3-methyl-1-trityl-1H-4-pyrazolyl)imidazo[1,2-a]pyridin-3-yl]-2-thienyl}sulfanyl)-butane nitrile obtained in Production Example 462.

$^1$H-NMR (CDCl$_3$)

δ: 2.24(quint, J=7.2 Hz, 2H), 2.44(s, 3H), 2.65(t, J=7.2 Hz, 2H), 3.35–3.40(m, 2H), 6.96(d, J=4.0 Hz, 1H), 7.03–7.09(m, 2H), 7.22–7.28(m, 7H), 7.33–7.38(m, 9H), 7.45–7.50(m, 2H), 7.51(s, 1H), 7.65(d, J=4.0 Hz, 1H), 7.65(dd, J=9.2, 1.2 Hz, 1H), 7.85(s, 1H), 8.17(dd, J=1.6, 1.2 Hz, 1H)

Example 464

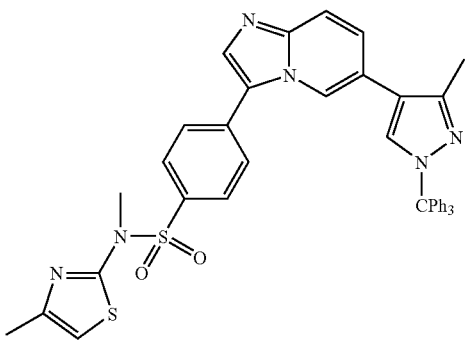

N1-Methyl-N1-(4-methyl-1,3-thiazol-2-yl)-4-[6-(3-methyl-1-trityl-1H-4-pyrazolyl)imidazo[1,2-a]pyridin-3-yl]-1-benzene sulfonamide 110 mg 6-(3-methyl-1-trityl-1H-4-pyrazolyl)-3-(1,1,1-tributylstannyl)imidazo[1,2-a]pyridine obtained in Production Example 48, 60 mg N1-methyl-N1-(4-methyl-1,3-thiazol-2-yl)-4-iodo-1-benzene sulfonamide (compound in Production Example 301) and 8.7 mg tetrakis (trisphenylphosphine) palladium were heated in xylene at 110° C. for 1 hour. The solvent was filtered off, and the residue was purified with an NH silica gel column to give 110 mg of the title compound as film.

$^1$H-NMR (CDCl$_3$)

δ: 2.28(d, J=1.2 Hz, 3H), 2.38(s, 3H), 3.48(s, 3H), 6.55(d, 1.2 Hz, 1H), 7.17–7.23(m, 6H), 7.23(dd, J=9.2, 1.6 Hz, 1H), 7.29–7.36(m, 9H), 7.41(s, 1H), 7.66(dd, J=9.2, 1.2 Hz, 1H), 7.68–7.72(m, 2H), 7.77(s, 1H), 7.93–7.97(m, 2H), 8.31(dd, J=1.6, 1.2 Hz, 1H)

520

Example 465

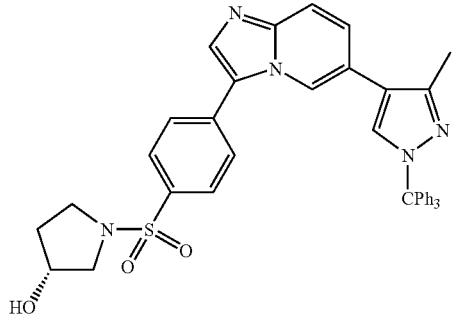

(3R)-1-(14-[6-(3-Methyl-1-trityl-1H-4-pyrazolyl)imidazo-[1,2-a]pyridin-3-yl]phenyl}sulfonyl)tetrahydro-1H-3-pyrrole 71 mg of the title compound was obtained as film in the same manner as in Example 464 from 110 mg 6-(3-methyl-1-trityl-1H-4-pyrazolyl)-3-(1,1,1-tributylstannyl)imidazo-[1,2-a]pyridine (compound in Production Example 48) and 40 mg (3R)-1-[(4-iodophenyl)sulfonyl]tetrahydro-1H-3-pyrrole (compound in Production Example 303).

$^1$H-NMR (CDCl$_3$)

δ: 1.85–1.94(m, 1H), 1.97–2.07(m, 1H), 2.39(s, 3H), 3.30–3.35(m, 1H), 3.40–3.54(m, 3H), 4.42–4.48(m, 1H), 7.17–7.22(m, 6H), 7.23(dd, J=9.6, 1.6 Hz, 1H), 7.30–7.35 (m, 9H), 7.42(s, 1H), 7.66(dd, J=9.6, 1.2 Hz, 1H), 7.72–7.76 (m, 2H), 7.77(s, 1H), 7.97–8.01(m, 2H), 8.33(dd, J=1.6, 1.2 Hz, 1H)

Example 466

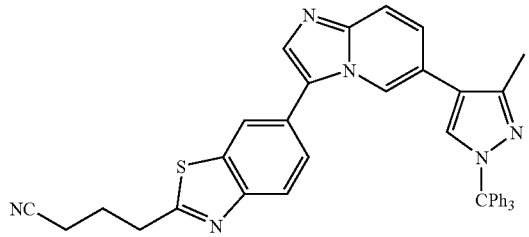

4-{6-{6-[3-Methyl-1-trityl-1H-4-pyrazolyl]imidazo[1,2-a]-pyridin-3-yl}-1,3-benzothiazol-2-yl)butane nitrile 77 mg of the title compound was obtained as colorless crystals in the same manner as in Example 464 from 110 mg 6-(3-methyl-1-trityl-1H-4-pyrazolyl)-3-(1,1,1-tributylstannyl)imidazo[1,2-a]pyridine (compound in Production Example 48) and 49 mg 4-(6-iodo-1,3-benzothiazol-2-yl) butane nitrile (compound in Production Example 297).

$^1$H-NMR (CDCl$_3$)

δ: 2.34(quint. J=7.2 Hz, 2H), 2.37(s, 3H), 2.60(t, J=7.2 Hz, 2H), 3.33(t, J=7.2 Hz, 2H), 7.17–7.22(m, 7H), 7.29–7.34(m, 9H), 7.40(s, 1H), 7.65(dd, J=9.2, 0.8 Hz, 1H), 7.68(dd, J=8.4, 2.0 Hz, 1H), 7.74(s, 1H), 8.04(dd, J=2.0, 0.4 Hz, 1H), 8.11(dd, J=8.4, 0.4 Hz, 1H), 8.32(dd, J=1.6, 0.8 Hz, 1H)

Example 467

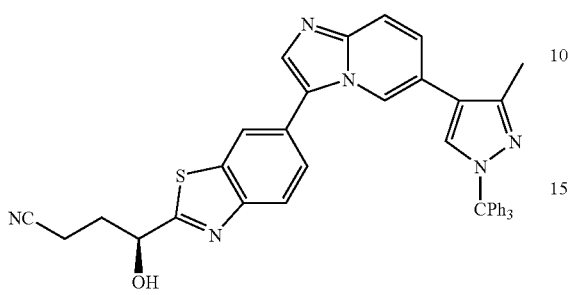

(4S)-4-Hydroxy-4-{6-[6-(3-methyl-1-trityl-1H-4-pyrazolyl)-imidazo[1,2-a]pyridin-3-yl]-1,3-benzothiazol-2-yl}butane nitrile 65 mg of the title compound was obtained as film in the same manner as in Example 464 from 121 mg 6-(3-methyl-1-trityl-1H-4-pyrazolyl)-3-(1,1,1-tributylstannyl)imidazo-[1,2-a]pyridine (compound in Production Example 48) and 45 mg (4S)-4-hydroxy-4-(6-iodo-1,3-benzothiazol-2-yl)butane nitrile (compound in Production Example 300).
¹H-NMR (CDCl₃)
δ: 2.24–2.35(m, 1H), 2.37(s, 3H), 2.40–2.52(m, 1H), 2.56–2.66(m, 1H), 2.67–2.78(m, 1H), 3.88–3.98(m, 1H), 5.23–5.30(m, 1H), 7.16–7.24(m, 7H), 7.28–7.35(m, 9H), 7.40(s, 1H), 7.64–7.67(m, 1H), 7.69(dd, J=8.4, 2.0 Hz, 1H), 7.72(s, 1H), 8.08(d, J=2.0 Hz, 1H), 8.12(d, J=8.4 Hz, 1H), 8.31(m, 1H)

Example 468

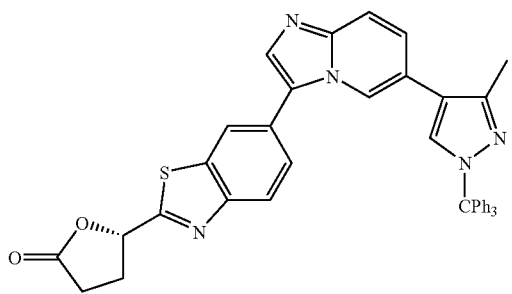

(5S)-5-{6-[6-(3-Methyl-1-trityl-1H-4-pyrazolyl)imidazo[1,2-a]pyridin-3-yl]-1,3-benzothiazol-2-yl}tetrahydro-2-furanone 100 mg of the title compound was obtained as a pale yellow solid in the same manner as in Example 464 from 110 mg 6-(3-methyl-1-trityl-1H-4-pyrazolyl)-3-(1,1,1-tributylstannyl)-imidazo[1,2-a]pyridine (compound in Production Example 48) and 55 mg (5S)-5-(6-iodo-1,3-benzothiazol-2-yl)tetrahydro-2-furanone (compound in Production Example 298).

¹H-NMR (CDCl₃)
δ: 2.37(s, 3H), 2.68–2.80(m, 3H), 2.84–2.95(m, 1H), 5.88–5.93(m, 1H), 7.15–7.24(m, 7H), 7.28–7.35(m, 9H), 7.41(s, 1H), 7.66(dd, J=9.2, 1.2 Hz, 1H), 7.72(dd, J=8.4, 2.0 Hz, 1H), 7.75(s, 1H), 8.11(dd, J=2.0, 0.4 Hz, 1H), 8.16(dd, J=8.4, 0.4 Hz, 1H), 8.31(dd, J=1.6, 1.2 Hz, 1H)

Example 469

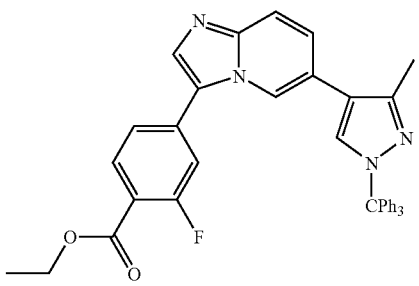

Ethyl 2-fluoro-4-[6-(3-methyl-1-trityl-1H-4-pyrazolyl)-imidazo[1,2-a]pyridin-3-yl] benzoate 1.21 g of the title compound was obtained as colorless crystals by the same method as in Example 29 from 726 mg ethyl 4-(6-bromoimidazo[1,2-a]pyridin-3-yl)-2-fluorobenzoate (compound in Production Example 304) and 921 mg 3-methyl-1-trityl-1H-4-pyrazolylboronic acid (compound in Production Example 30).
¹H-NMR (CDCl₃)
δ: 1.44(t, J=7.2 Hz, 3H), 2.41(s, 3H), 4.44 (q, J=7.2 Hz, 2H), 7.18–7.23(m, 6H), 7.24(dd, J=9.6, 1.6 Hz, 1H), 7.30–7.35(m, 9H), 7.37(dd, J=11.2, 1.2 Hz, 1H), 7.42(s, 1H), 7.44(dd, J=8.0, 1.2 HZ, 1H), 7.66(dd, J=9.6, 1.2 Hz, 1H), 7.79(s, 1H), 8.09(dd, J=8.0, 8.0 Hz, 1H), 8.36(dd, J=1.6, 1.2 Hz, 1H)

Example 470

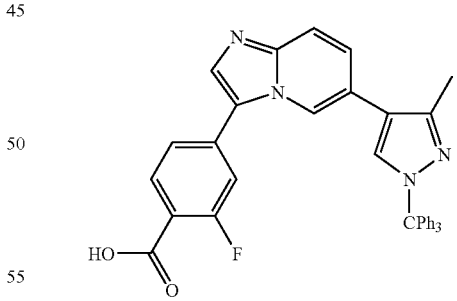

2-Fluoro-4-[6-(3-methyl-1-trityl-1H-4-pyrazolyl)imidazo-[1,2-a]pyridin-3-yl] benzoic acid 1.2 g ethyl 2-fluoro-4-[6-(3-methyl-1-trityl-1H-4-pyrazolyl)imidazo[1,2-a]pyridin-3-yl] benzoate obtained in Example 469 was dissolved in a solvent mixture of tetrahydrofuran and methanol, and 4.5 mL of 2 N aqueous sodium hydroxide was added thereto and stirred for 5 hours. The reaction solution was neutralized with 2 N hydrochloric

Example 471

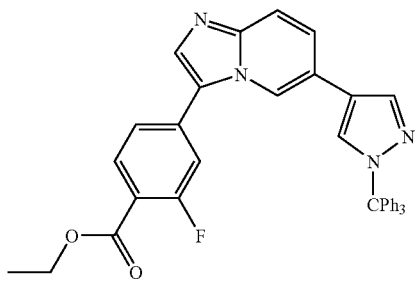

Ethyl 2-fluoro-4-[6-(1-trityl-1H-4-pyrazolyl)imi-dazo-[1,2-a]pyridin-3-yl] benzoate 1.21 g of the title compound was obtained as colorless crystals by the same method as in Example 29 from 726 mg ethyl 4-(6-bromoimidazo[1,2-a]pyridin-3-yl)-2-fluorobenzoate (compound in Production Example 304) and 921 mg 1-trityl-1H-4-pyrazolylboronic acid.

$^1$H-NMR (CDCl$_3$)
δ: 1.44(t, J=7.4 Hz, 3H), 4.44 (q, J=7.4 Hz, 2H), 7.17–7.23(m, 6H), 7.29–7.39(m, 11H), 7.44(dd, J=8.0, 1.6 Hz, 1H), 7.62(d, J=1.2 Hz, 1H), 7.67(dd, J=9.6, 0.8 Hz, 1H), 7.77(s, 1H), 7.88(d, J=1.2 Hz, 1H), 8.09(dd, J=8.0, 8.0 Hz, 1H), 8.41(dd, J=1.6, 0.8 Hz, 1H)

Example 472

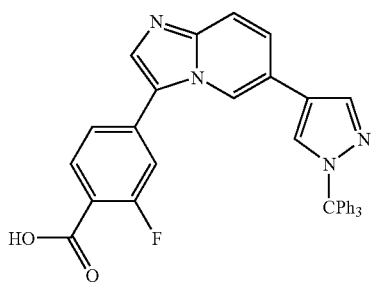

2-Fluoro-4-[6-(1-trityl-1H-4-pyrazolyl)imidazo[1,2-a]-pyridin-3-yl] benzoic acid 1.1 g of the title compound was obtained as a colorless solid in the same manner as in Example 470 from 1.2 g ethyl 2-fluoro-4-[6-(1-trityl-1H-4-pyrazolyl)imidazo[1,2-a]-pyridin-3-yl] benzoate (compound in Example 471).

$^1$H-NMR (CDCl$_3$—CD$_3$OD)
δ: 7.15–7.25(m, 6H), 7.32–7.40(m, 11H), 7.45(dd, J=8.0, 1.6 Hz, 1H), 7.66(d, J=9.2 Hz, 1H), 7.66(s, 1H), 7.74(s, 1H), 7.89(s, 1H), 8.14(dd, J=8.0, 8.0 Hz, 1H), 8.44(m, 1H)

Example 473

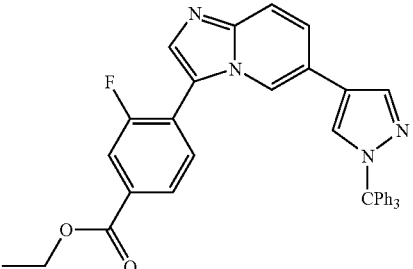

Ethyl 3-fluoro-4-[6-(1-trityl-1H-4-pyrazolyl)imidazo[1,2-a]pyridin-3-yl] benzoate 400 mg 3-(1,1,1-tributylstannyl)-6-(1-trityl-1H-4-pyrazolyl)imidazo[1,2-a]pyridine (compound in Production Example 293), 180 mg ethyl 3-fluoro-4-{[(trifluoromethyl)-sulfonyl]oxy}benzoate, 32 mg tetrakistriphenyl phosphine palladium, 71 mg lithium chloride and 110 mg cuprous chloride were stirred in 10 mL N,N-dimethylformamide at 80° C. for 5 hours. The solvent was removed, and the residue was purified by an NH silica gel column, to give 114 mg of the title compound as a colorless solid.

$^1$H-NMR (CDCl$_3$)
δ: 1.44(t, J=7.2 Hz, 3H), 4.44 (q, J=7.2 Hz, 2H), 7.15–7.22(m, 6H), 7.31(dd, J=9.2, 1.6 Hz, 1H), 7.31–7.36 (m, 9H), 7.60(s, 1H), 7.62(dd, J=7.6, 7.6 Hz, 1H), 7.67(dd, J=9.2, 0.8 Hz, 1H), 7.78(s, 1H), 7.85(d, J=0.4 Hz, 1H), 7.92(dd, J=10.8, 1.6 Hz, 1H), 7.98(dd, J=7.6, 1.6 Hz, 1H), 8.07–8.09(m, 1H)

Example 474

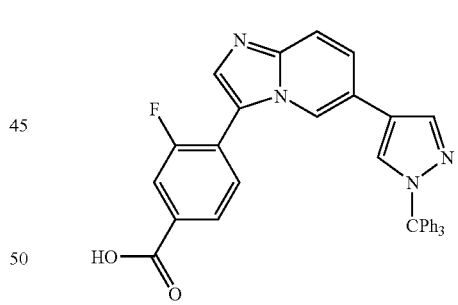

3-Fluoro-4-[6-(1-trityl-1H-4-pyrazolyl)imidazo[1,2-a]-pyridin-3-yl]}benzoic acid 100 mg of the title compound was obtained as colorless crystals in the same manner as in Example 470 from 113 mg ethyl 3-fluoro-4-[6-(1-trityl-1H-4-pyrazolyl)imidazo[1,2-a]-pyridin-3-yl]} benzoate (compound in Production Example 473).

$^1$H-NMR (CDCl$_3$—CD$_3$OD)
δ: 7.15–7.24(m, 6H), 7.32–7.40(m, 9H), 7.54(d, J=8.8 Hz, 1H), 7.65(dd, J=7.6, 7.6 Hz, 1H), 7.68(s, 1H), 7.83–7.90(m, 3H), 7.97(dd, J=10.4, 1.6 Hz, 1H), 8.04(dd, J=7.6, 1.6 Hz, 1H), 8.11–8.14(m, 1H)

Example 475

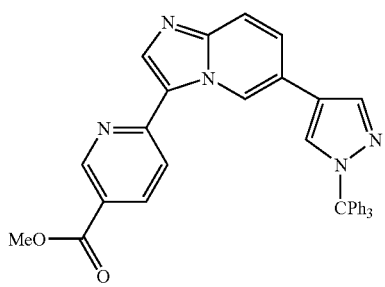

Methyl 6-[6-(1-trityl-1H-4-pyrazolyl)imidazo[1,2-a]pyridin-3-yl] nicotinate 219 mg of the title compound was obtained as colorless crystals in the same manner as in Example 464 from 370 mg 3-(1,1,1-tributylstannyl)-6-(1-trityl-1H-4-pyrazolyl)-imidazo[1,2-a]pyridine (compound in Production Example 293) and 89 mg methyl 6-chloronicotinate.

$^1$H-NMR (CDCl$_3$)

δ: 3.99(d, J=0.4 Hz, 3H), 7.20–7.30(m, 6H), 7.33–7.40(m, 9H), 7.42(dd, J=9.2, 1.6 HZ, 1H), 7.69(s, 1H), 7.69(d, J=9.2 Hz, 1H), 7.80(d, J=8.4 Hz, 1H), 8.01(s, 1H), 8.25(d, J=0.8 Hz, 1H), 8.30(ddd, J=8.4, 2.0, 0.4 Hz, 1H), 9.22(d, J=2.0 Hz, 1H), 10.2(m, 1H)

Example 476

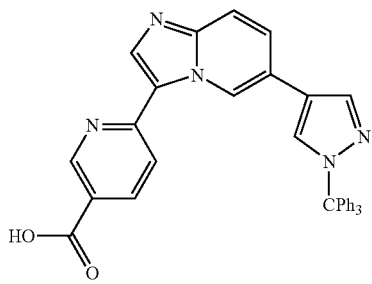

6-[6-(1-Trityl-1H-4-pyrazolyl)imidazo[1,2-a]pyridin-3-yl]nicotinic acid 209 mg of the title compound was obtained as colorless crystals in the same manner as in Example 470 from 217 mg methyl 6-[6-(1-trityl-1H-4-pyrazolyl)imidazo[1,2-a]pyridin-3-yl]nicotinate (compound in Example 475).

$^1$H-NMR (CDCl$_3$—CD$_3$OD)

δ: 7.20–7.27(m, 6H), 7.33–7.39(m, 9H), 7.44(dd, J=9.6, 0.8 Hz, 1H), 7.68(d, J=9.6 Hz, 1H), 7.70(s, 1H), 7.80(d, J=8.0 Hz, 1H), 8.01(s, 1H), 8.23(s, 1H), 8.33(dd, J=8.0, 2.0 Hz, 1H), 9.24(d, J=2.0 Hz, 1H), 10.2(m, 1H)

Example 477

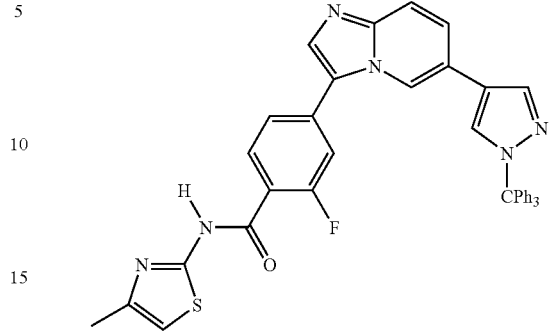

N1-(4-Methyl-1,3-thiazol-2-yl)-2-fluoro-4-[6-(1-trityl-1H-4-pyrazolyl)imidazo[1,2-a]pyridin-3-yl] benzamide 170 mg 2-fluoro-4-[6-(1-trityl-1H-4-pyrazolyl)imidazo-[1,2-a]pyridin-3-yl]benzoic acid (compound in Example 472) and 34.4 mg 2-amino-4-methyl-1,3-thiazole were allowed to react overnight with 146 mg benzotriazol-1-yloxy-tris-(dimethylamino)phosphonium hexafluorophosphate and 50 µL triethylamine in 6 mL dichloromethane. The reaction solution was purified by an NH silica gel column, to give 169 mg of the title compound as colorless crystals (recrystallization solvent: ethyl acetate).

$^1$H-NMR (CDCl$_3$)

δ: 2.41(d, J=1.2 Hz, 3H), 6.63(d, J=1.2 Hz, 1H), 7.17–7.24(m, 6H), 7.32–7.38(m, OH), 7.45(dd, J=12.8, 1.6 Hz, 1H), 7.59(dd, J=8.4, 1.6 Hz, 1H), 7.63(d, J=0.8 Hz, 1H), 7.69(dd, J=9.6, 0.4 Hz, 1H), 7.82(s, 1H), 7.90(s, 1H), 8.37(dd, J=8.4, 8.4 Hz, 1H), 8.44(m, 1H)

Example 478

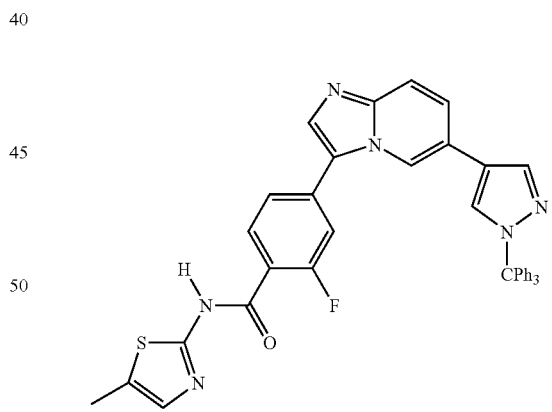

N1-(5-Methyl-1,3-thiazol-2-yl)-2-fluoro-4-[6-(1-trityl-1H-4-pyrazolyl)imidazo[1,2-a]pyridin-3-yl] benzamide 123 mg of the title compound was obtained as colorless crystals in the same manner as in Example 477 from 110 mg of the compound in Example 472 and 23 mg 2-amino-5-methyl-1,3-thiazole.

$^1$H-NMR (CDCl$_3$)

δ: 2.46(d, J=1.2 Hz, 3H), 7.15–7.22(m, 7H), 7.32–7.40(m, 10H), 7.46(dd, J=12.4, 1.6 Hz, 1H), 7.58(dd, J=8.0, 1.6 Hz,

1H), 7.66(d, J=0.8 Hz, 1H), 7.67(dd, J=9.6, 0.8 Hz, 1H), 7.78(s, 1H), 7.90(d, J=0.8 Hz, 1H), 8.28(dd, J=8.0, 8.0 Hz, 1H), 8.42(m, 1H)

Example 479

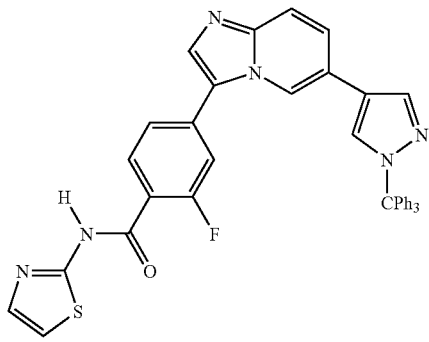

N1-(1,3-Thiazol-2-yl)-2-fluoro-4-[6-(1-trityl-1H-4-pyrazolyl)imidazo[1,2-a]pyridin-3-yl] benzamide 152 mg of the title compound was obtained as colorless crystals in the same manner as in Example 477 from 150 mg of the compound in Example 472 and 27 mg 2-amino-1,3-thiazole.

$^1$H-NMR (CDCl$_3$)

δ: 7.08(d, J=3.6 Hz, 1H), 7.17–7.23(m, 6H), 7.32–7.38(m, 10H), 7.46(dd, J=13.2, 1.6 Hz, 1H), 7.55(d, J=3.6 Hz, 1H), 7.60(dd, J=8.0, 1.6 Hz, 1H), 7.63(d, J=0.8 Hz, 1H), 7.69(dd, J=9.2, 0.8 Hz, 1H), 7.83(s, 1H), 7.90(d, J=1.2 Hz, 1H), 8.38(dd, J=8.0, 8.0 Hz, 1H), 8.44(dd, J=1.6, 0.8 Hz, 1H)

Example 480

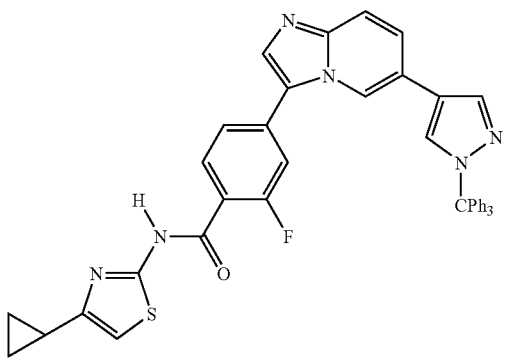

N1-(4-Cyclopropyl-1,3-thiazol-2-yl)-2-fluoro-4-[6-(1-trityl-1H-4-pyrazolyl)imidazo[1,2-a]pyridin-3-yl] benzamide 100 mg of the title compound was obtained as colorless crystals in the same manner as in Example 477 from 150 mg of the compound in Example 472 and 25 mg 2-amino-4-cyclopropyl-1,3-thiazole.

$^1$H-NMR (CDCl$_3$)

δ: 0.82–0.89(m, 2H), 0.8.9–0.97(m, 2H), 1.96–2.05(m, 1H), 6.59(d, J=0.4 Hz, 1H), 7.17–7.23(m, 6H), 7.32–7.38(m, 10H), 7.45(dd, J=13.2, 1.6 Hz, 1H), 7.59(dd, J=8.0, 1.6 Hz, 1H), 7.63(d, J=0.8 Hz, 1H), 7.69(dd, J=9.2, 1.2 Hz, 1H), 7.82(s, 1H), 7.90(d, J=0.8 Hz, 1H), 8.36(dd, J=8.0, 8.0 Hz, 1H), 8.43(dd, J=1.6, 1.2 Hz, 1H)

Example 481

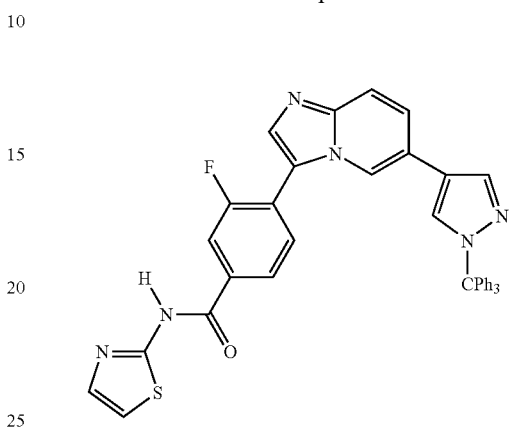

N1-(1,3-Thiazol-2-yl)-3-fluoro-4-[6-(1-trityl-1H-4-pyrazolyl)imidazo[1,2-a]pyridin-3-yl] benzamide 20 mg of the title compound was obtained as yellow crystals by the same reaction as in Example 477 from 40 mg 3-fluoro-4-[6-(1-trityl-1H-4-pyrazolyl)imidazo[1,2-a]pyridin-3-yl]}-benzoic acid (compound in Example 474) and 7.8 mg 2-amino-1,3-thiazole.

$^1$H-NMR (CDCl$_3$)

δ: 7.06(d, J=3.6 Hz, 1H), 7.16–7.22(m, 6H), 7.31–7.36(m, 10H), 7.46(d, J=3.6 Hz, 1H), 7.62(d, J=0.8 Hz, 1H), 7.69(dd, J=9.2, 0.8 Hz, 1H), 7.72(dd, J=8.0, 8.0 Hz, 1H), 7.82(d, J=0.4 Hz, 1H), 7.87(d, J=0.8 Hz, 1H), 8.89(dd, J=8.0, 1.6 Hz, 1H), 7.93(dd, J=10.4, 1.6 Hz, 1H), 8.09–8.12(m, 1H)

Example 482

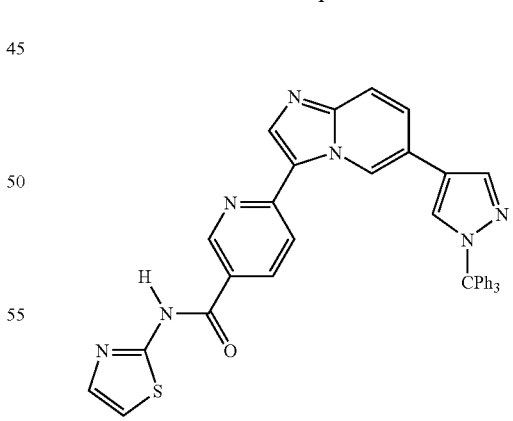

N3-(1,3-Thiazol-2-yl)-6-[6-(1-trityl-1H-4-pyrazolyl)-imidazo[1,2-a]pyridin-3-yl] nicotinic acid amide 66 mg of the title compound was obtained as yellow crystals by the same reaction as in Example 477 from 100 mg 6-[6-(1-trityl-1H-4-pyrazolyl)imidazo[1,2-a]pyridin-3-yl] nicotinic acid (compound in Example 476) and 18.3 mg 2-amino-1,3-thiazole.

$^1$H-NMR (CDCl$_3$)

δ: 7.13–7.19(m, 6H), 7.35–7.45(m, 10H), 7.51–7.58(m, 1H), 7.70(dd, J=9.6, 1.6 Hz, 1H), 7.75(dd, J=9.6, 0.8 Hz, 1H), 7.91(s, 1H), 8.16(d, J=8.4 Hz, 1H), 8.17(s, 1H), 8.50 (dd, J=8.4, 2.0 Hz, 1H), 8.55(s, 1H), 9.29(d, J=2.0 Hz, 1H), 10.2(m, 1H)

Example 483

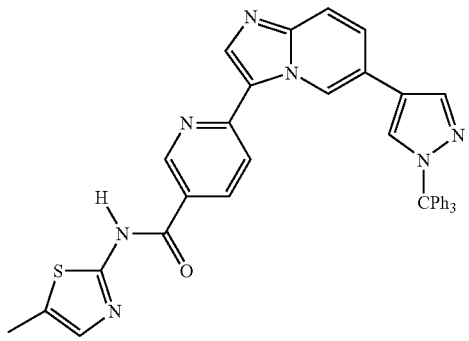

N3-(5-Methyl-1,3-thiazol-2-yl)-6-[6-(1-trityl-1H-4-pyrazolyl)imidazo[1,2-a]pyridin-3-yl] nicotinic acid amide 29 mg of the title compound was obtained as colorless crystals by the same reaction as in Example 477 from 55 mg 6-[6-(1-trityl-1H-4-pyrazolyl)imidazo[1,2-a]pyridin-3-yl] nicotinic acid (compound in Example 476) and 12 mg 2-amino-5-methyl-1,3-thiazole.

$^1$H-NMR (CDCl$_3$)

δ: 2.44(d, J=0.8 Hz, 3H), 7.10(d, J=0.8 Hz, 1H), 7.20–7.27(m, 6H), 7.34–7.40(m, 9H), 7.44(dd, J=9.6, 1.6 Hz, 1H), 7.70(s, 1H), 7.71(d, J=9.6 Hz, 1H), 7.87(d, J=8.8 Hz, 1H), 8.02(d, 0.8 Hz, 1H), 8.27(dd, J=8.8, 2.0 Hz, 1H), 8.28(s, 1H), 9.20(d, J=2.0 Hz, 1H), 10.2(m, 1H)

Example 484

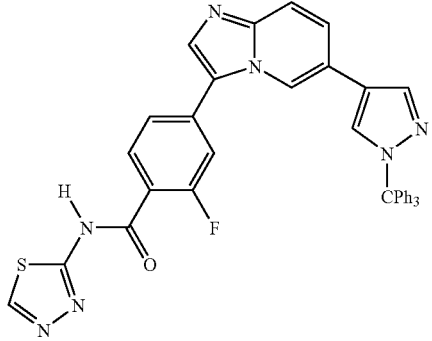

N1-(1,3,4-Thiadiazol-2-yl)-2-fluoro-4-[6-(1-trityl-1H-4-pyrazolyl)imidazo[1,2-a]pyridin-3-yl] benzamide 40 mg of the title compound was obtained as colorless crystals in the same manner as in Example 477 from 60 mg of the compound in Example 472 and 10 mg 2-amino-1,3,4-thiadiazole.

$^1$H-NMR (CDCl$_3$)

δ: 7.16–7.23(m, 6H), 7.32–7.39(m, 9H), 7.40(dd, J=9.2, 1.6 Hz, 1H), 7.51(dd, J=12.0, 1.2 Hz, 1H), 7.61(dd, J=8.0, 1.2 Hz, 1H), 7.68(dd, J=9.2, 0.8 Hz, 1H), 7.68(d, J=0.4 Hz, 1H), 7.80(s, 1H), 7.91(d, J=0.4 Hz, 1H), 8.22(dd, J=8.0, 8.0 Hz, 1H), 8.48(dd, J=1.6, 0.8 Hz, 1H), 8.95(s, 1H)

Example 485

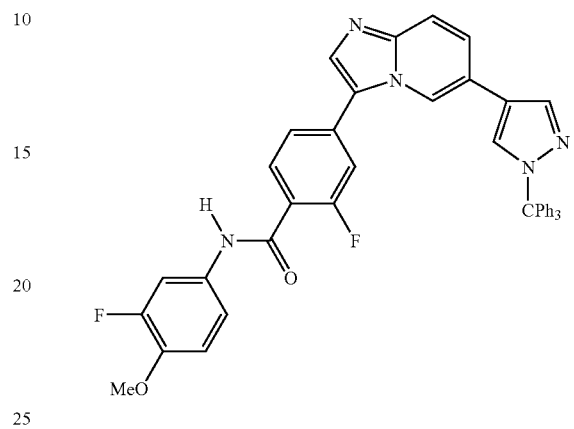

N1-(3-Fluoro-4-methoxyphenyl)-2-fluoro-4-[6-(1-trityl-1H-4-pyrazolyl)imidazo[1,2-a]pyridin-3-yl] benzamide 27 mg of the title compound was obtained as colorless crystals in the same manner as in Example 477 from 56 mg of the compound in Example 472 and 16 mg 3-fluoro-4-methoxyaniline.

$^1$H-NMR (CDCl$_3$)

δ: 3.19(s, 3H), 6.98(dd, J=9.2, 9.2 Hz, 1H), 7.17–7.23(m, 6H), 7.28–7.32(m, 2H), 7.32–7.37(m, 9H), 7.41(dd, J=13.2, 2.0 Hz, 1H), 7.56(dd, J=8.4, 2.0 Hz, 1H), 7.63(s, 1H), 7.64(dd, J=12.8, 2.0 Hz, 1H), 7.68(dd, J=9.2, 0.8 Hz, 1H), 7.79(s, 1H), 7.88(d, J=1.6 Hz, 1H), 8.32(dd, J=8.4, 8.4 Hz, 1H), 8.36–8.44(m, 2H)

Example 486

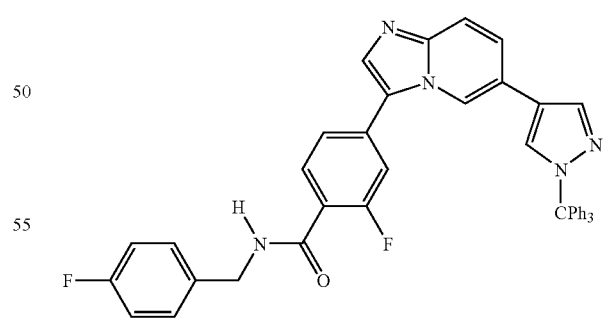

N1-(4-Fluorobenzyl)-2-fluoro-4-[6-(1-trityl-1H-4-pyrazolyl) imidazo[1,2-a]pyridin-3-yl] benzamide 55 mg of the title compound was obtained in the same manner as in Example 477 from 57 mg of the compound in Example 472 and 14 mg 4-fluorobenzylamine.

¹H-NMR (CDCl₃)

δ: 4.69(d, J=5.6 Hz, 2H), 7.03–7.08(m, 2H), 7.16–7.22(m, 6H), 7.29–7.39(m, 13H), 7.52(dd, J=8.4, 1.8 Hz, 1H), 7.61 (d, J=1.0 Hz, 1H), 7.66(dd, J=9.2, 1.0 Hz, 1H), 7.76(s, 1H), 7.87(d, J=1.0 Hz, 1H), 8.29(t, J=8.4 Hz, 1H), 8.39(dd, J=1.6, 1.0 Hz, 1H)

Example 487

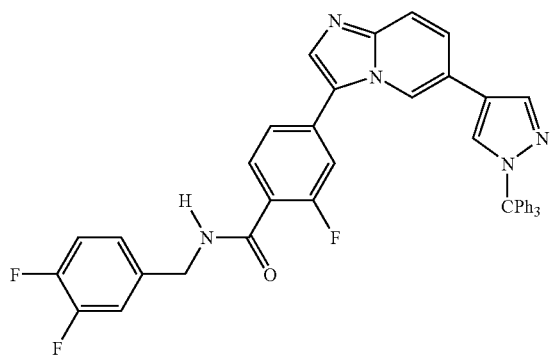

N1-(3,4-Difluorobenzyl)-2-fluoro-4-[6-(1-trityl-1H-4-pyrazolyl)imidazo[1,2-a]pyridin-3-yl] benzamide 58 mg of the title compound was obtained in the same manner as in Example 477 from 57 mg of the compound in Example 472 and 16 mg 3,4-difluorobenzylamine.

¹H-NMR (CDCl₃)

δ: 4.67(d, J=5.6 Hz, 2H), 7.08–7.22(m, 9H), 7.29–7.38(m, 11H), 7.52(dd, J=8.4, 1.4 Hz, 1H), 7.61(d, J=0.8 Hz, 1H), 7.66(dd, J=9.2, 0.8 Hz, 1H), 7.77(s, 1H), 7.87(d, J=0.4 Hz, 1H), 8.29(t, J=8.0 Hz, 1H), 8.38–8.41(m, 1H)

Example 488

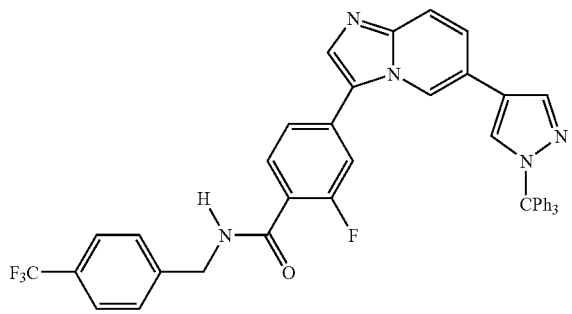

N1-(4-Trifluoromethylbenzyl)-2-fluoro-4-[6-(1-trityl-1H-4-pyrazolyl)imidazo[1,2-a]pyridin-3-yl] benzamide 58 mg of the title compound was obtained in the same manner as in Example 477 from 57 mg of the compound in Example 472 and 19 mg 4-trifluoromethyl benzylamine.

¹H-NMR (CDCl₃)

δ: 4.78(d, J=5.6 Hz, 2H), 7.16–7.22(m, 6H), 7.29–7.38(m, 11H), 7.49–7.55(m, 3H), 7.61–7.65(m, 3H), 7.67(dd, J=9.6, 0.9 Hz, 1H), 7.77(s, 1H), 7.87(d, J=0.4 Hz, 1H), 8.29(t, J=8.0 Hz, 1H), 8.40(dd, J=1.6, 0.9 Hz, 1H)

Example 489

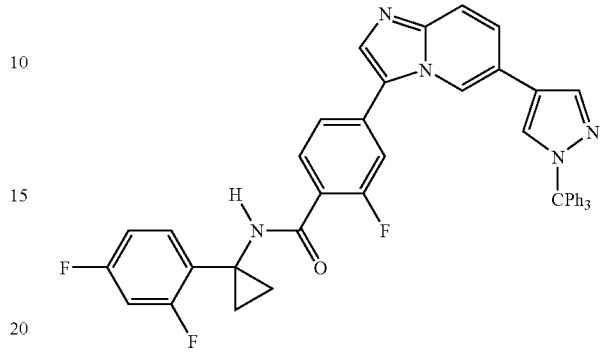

N1-[1-(2,4-Difluorophenyl)cyclopropyl]-2-fluoro-4-[6-(1-trityl-1H-4-pyrazolyl)imidazo[1,2-a]pyridin-3-yl] benzamide 212 mg of the title compound was obtained in the same manner as in Example 477 from 250 mg of the compound in Example 472 and 82 mg 1-(2,4-difluorophenyl)-cyclopropyl amine (compound in Production Example 313).

¹H-NMR (CDCl₃)

δ: 1.27–1.34(m, 4H), 6.75–6.88(m, 2H), 7.16–7.22(m, 6H), 7.28–7.37(m, 11H), 7.45(dd, J=8.0, 1.8 Hz, 1H), 7.52 (d, J=13.6 Hz, 1H), 7.60(s, 1H), 7.65(dd, J=9.6, 0.8 Hz, 1H), 7.67–7.74(m, 2H), 7.85(d, J=0.8 Hz, 1H), 8.16(t, J=8.4 Hz, 1H), 8.35(brs, 1H)

Example 490

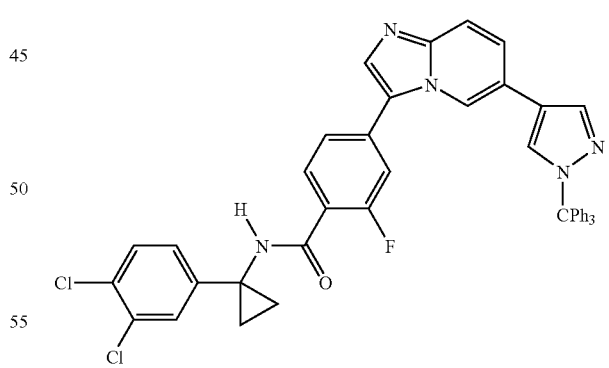

N1-[1-(3,4-Difluorophenyl)cyclopropyl]-2-fluoro-4-[6-(1-trityl-1H-4-pyrazolyl)imidazo[1,2-a)pyridin-3-yl] benzamide 275 mg of the title compound was obtained in the same manner as in Example 477 from 220 mg of the compound in Example 472 and 87 mg 1-(3,4-dichlorophenyl)-cyclopropyl amine (compound in Production Example 314).

¹H-NMR (CDCl₃)
δ: 1.37–1.45(m, 4H), 7.16–7.22(m, 7H), 7.28–7.40(m, 12H), 7.42(d, J=2.4 Hz, 1H), 7.51(dd, J=8.0, 1.6 Hz, 1H), 7.61(s, 1H), 7.66(d, J=9.2 Hz, 1H), 7.76(d, J=0.8 Hz, 1H), 7.87(d, J=0.4 Hz, 1H), 8.23(t, J=8.4 Hz, 1H), 8.39(brs, 1H)

Example 491

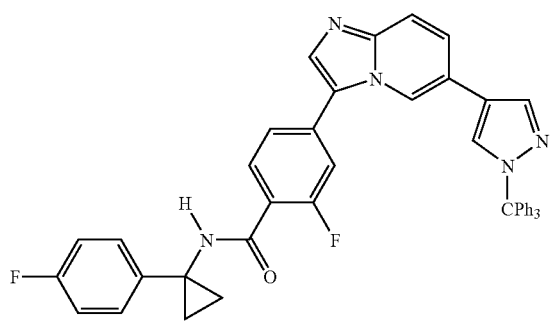

N1-[1-(4-Fluorophenyl)-cyclopropyl]-2-fluoro-4-[6-(1-trityl-1H-4-pyrazolyl)imidazo[1,2-a]pyridin-3-yl] benzamide 255 mg of the title compound was obtained in the same manner as in Example 477 from 220 mg of the compound in Example 472 and 65 mg 1-(4-fluorophenyl)-cyclopropyl amine (compound in Production Example 315).
¹H-NMR (CDCl₃)
δ: 1.37–1.40(m, 4H), 6.97–7.03(m, 2H), 7.16–7.22(m, 6H), 7.30(dd, J=9.2, 1.6 Hz, 1H), 7.31–7.44(m, 12H), 7.49 (dd, J=8.0, 1.6 Hz, 1H), 7.61(d, J=0.6 Hz, 1H), 7.66(dd, J=9.2, 0.8 Hz, 1H), 7.75(s, 1H), 7.86(d, J=0.6 Hz, 1H), 8.23(t, J=8.4 Hz, 1H), 8.37–8.38(m, 1H)

Example 492

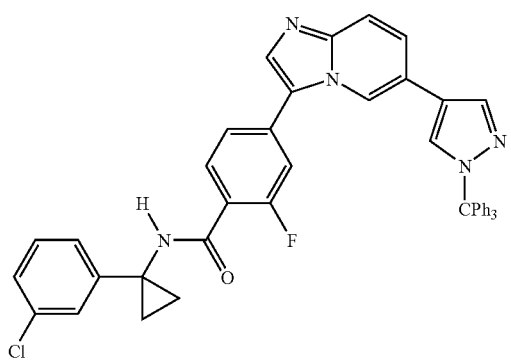

N1-[1-(3-Chlorophenyl)cyclopropyl]-2-fluoro-4-[6-(1-trityl-1H-4-pyrazolyl)imidazo[1,2-a]pyridin-3-yl] benzamide 278 mg of the title compound was obtained in the same manner as in Example 477 from 220 mg of the compound in Example 472 and 72 mg 1-(3-chlorophenyl)-cyclopropyl amine (compound in Production Example 316).

¹H-NMR(CDCl₃)
δ: 1.41–1.45(m, 4H), 7.16–7.44(m, 21H), 7.51(dd, J=8.0, 1.6 Hz, 1H), 7.61(d, J=0.8 Hz, 1H), 7.65–7.68(m, 1H), 7.76(s, 1H), 7.87(d, J=0.8 Hz, 1H), 8.25(t, J=8.4 Hz, 1H), 8.37–8.39(m, 1H)

Example 493

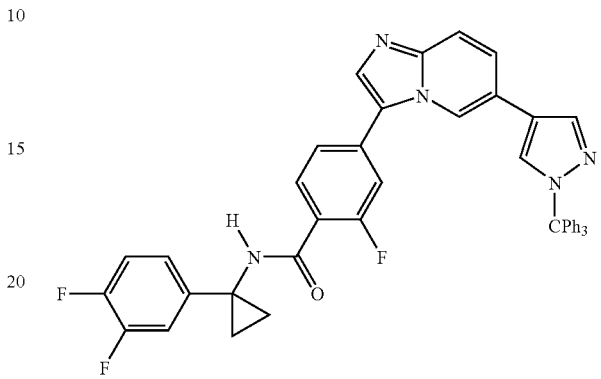

N1-[1-(3,4-Difluorophenyl)-cyclopropyl]-2-fluoro-4-[6-(1-trityl-1H-4-pyrazolyl)imidazo[1,2-a]pyridin-3-yl] benzamide 306 mg of the title compound was obtained in the same manner as in Example 477 from 220 mg of the compound in Example 472 and 73 mg 1-(3,4-difluorophenyl)-cyclopropyl amine (compound in Production Example 317).
¹H-NMR (CDCl₃)
δ: 1.34–1.44(m, 4H), 7.06–7.12(m, 2H), 7.16–7.24(m, 6H), 7.29–7.44(m, 12H), 7.50(dd, J=8.4, 1.6 Hz, 1H), 7.61 (d, J=0.8 Hz, 1H), 7.66(dd, J=9.2, 0.8 Hz, 1H), 7.76(s, 1H), 7.86(d, J=0.8 Hz, 1H), 8.23(t, J=8.4 Hz, 1H), 8.38(dd, J=1.6, 1.2 Hz, 1H)

Example 494

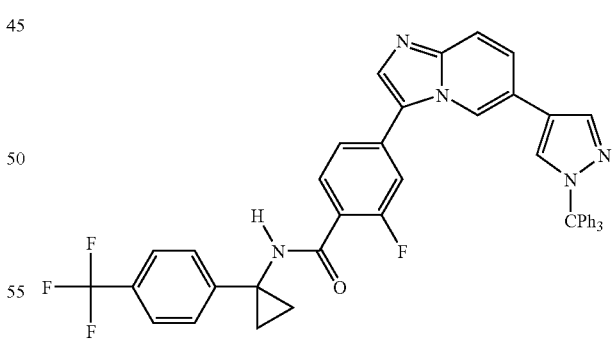

N1-[1-(4-Trifluoromethylphenyl)cyclopropyl]-2-fluoro-4-[6-(1-trityl-1H-4-pyrazolyl)imidazo[1,2-a] pyridin-3-yl] benzamide 284 mg of the title compound was obtained in the same manner as in Example 477 from 220 mg of the compound in Example 472 and 86 mg 1-(4-trifluoromethylphenyl)-cyclopropyl amine (compound in Production Example 318).

¹H-NMR (CDCl₃)
δ: 1.44–1.50(m, 4H), 7.16–7.23(m, 6H), 7.29–7.37(m, 11H), 7.38–7.48(m, 3H), 7.52(dd, J=8.4, 1.4 Hz, 1H), 7.57 (d, J=8.4 Hz, 1H), 7.62(d, J=0.8 Hz, 1H), 7.67(dd, J=9.6, 1.0 Hz, 1H), 7.77(s, 1H), 7.87(d, J=0.8 Hz, 1H), 8.25(t, J=8.4 Hz, 1H), 8.38–8.40(m, 1H)

Example 495

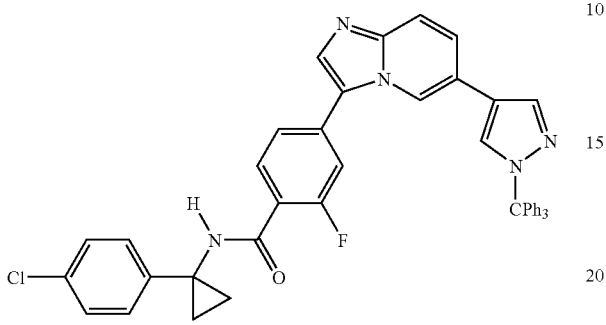

N1-[1-(4-Chlorophenyl)cyclopropyl]-2-fluoro-4-[6-(1-trityl-1H-4-pyrazolyl)imidazo[1,2-a]pyridin-3-yl] benzamide 35 mg of the title compound was obtained in the same manner as in Example 477 from 150 mg of the compound in Example 472 and 51 mg 1-(4-chlorophenyl)-1-cyclopropanamine.
¹H-NMR (CDCl₃)
δ: 2.65(d, J=8.0 Hz, 4H), 7.18–7.21(m, 7H), 7.28–7.37(m, 13H), 7.39–7.43(d, J=14 Hz, 1H), 7.50(dd, J=8.4, 1.6 Hz, 1H), 7.61(d, J=0.8 Hz, 1H), 7.66(dd, J=9.2 Hz, 1H), 7.76(s, 1H), 7.86(d, J=0.8 Hz, 1H), 8.24(dd, J=8.4, 8.4 Hz, 1H), 8.34(m, 1H)

Example 496

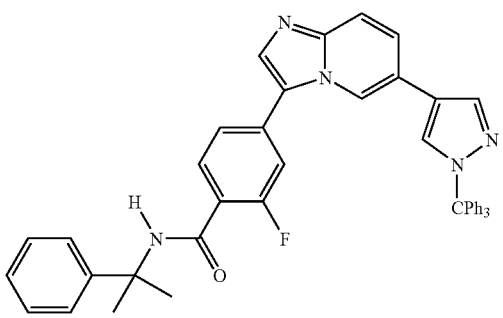

N1-(1-Methyl-1-phenylethyl)-2-fluoro-4-[6-(1-trityl-1H-4-pyrazolyl)imidazo[1,2-a]pyridin-3-yl] benzamide 35 mg of the title compound was obtained in the same manner as in Example 477 from 150 mg of the compound in Example 472 and 41 mg 1-methyl-1-phenylethylamine.
¹H-NMR (CDCl₃)
δ: 1.83(s, 6H), 7.18–7.22(m, 7H), 7.28–7.39(m, 14H), 7.46–7.50(m, 3H), 7.61(d, J=0.8 Hz, 1H), 7.66(d, J=9.2 Hz, 1H), 7.75(s, 1H), 7.87(d, J=0.8 Hz, 1H), 8.17(dd, J=8.4, 8.4 Hz, 1H), 8.38–8.38(m, 1H)

Example 497

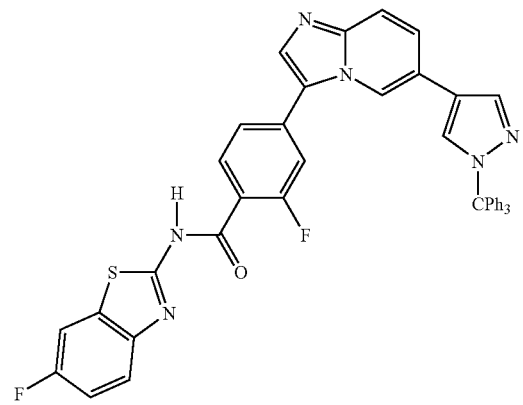

N1-(6-Fluoro-1,3-benzothiazol-2-yl)-2-fluoro-4-[6-(1-trityl-1H-4-pyrazolyl)imidazo[1,2-a]pyridin-3-yl] benzamide 57 mg of the compound in Example 472 and 20 mg 2-amino-6-fluoro-1,3-benzothiazole were allowed to react with 78 mg benzotriazol-1-yloxy-tris(dimethylamino)phosphonium hexafluorophosphate and 35 μL N,N-diisopropylethylamine in 6 mL N,N-dimethylformamide at 60° C. for 6 hours. The reaction solution was purified by an NH silica gel column to give 49 mg of the title compound as colorless crystals (recrystallization solvent: methanol/diethyl ether).
¹H-NMR (CDCl₃)
δ: 7.17–7.26(m, 7H), 7.31–7.41(m, 10H), 7.49(dd, J=12.8, 1.6 Hz, 1H), 7.57(dd, J=8.4, 2.4 Hz, 1H), 7.63(dd, J=8.4, 1.6 Hz, 1H), 7.64(s, 1H), 7.72(br.d, J=9.2 Hz, 1H), 7.79(dd, J=9.2, 4.4 Hz, 1H), 7.85(s, 1H), 7.90(s, 1H), 8.41(dd, J=8.4, 8.4 Hz, 1H), 8.45(m, 1H)

Example 498

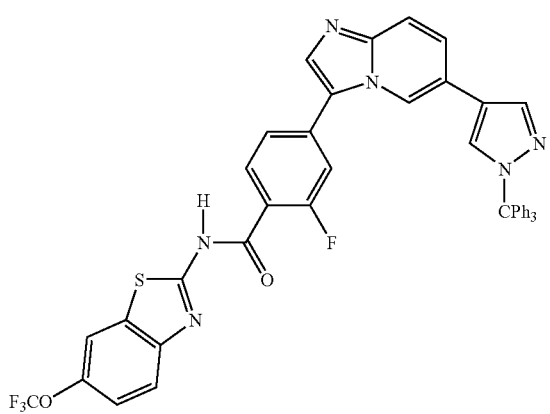

N1-[6-(Trifluoromethoxy)-1,3-benzothiazol-2-yl]-2-fluoro-4-[6-(1-trityl-1H-4-pyrazolyl)imidazo[1,2-a]pyridin-3-yl] benzamide 63 mg of the title compound was obtained as colorless crystals in the same manner as in Example 497 from 57 mg of the compound in Example 472 and 35 mg 2-amino-6-(trifluoromethoxy)-1,3-benzothiazole.

¹H-NMR (CDCl₃)
δ: 7.17–7.23(m, 6H), 7.32–7.41(m, 11H), 7.50(dd, J=12.8, 1.2 Hz, 1H), 7.63(dd, J=8.4, 1.2 Hz, 1H), 7.65(s, 1H), 7.70–7.76(m, 2H), 7.84(d, J=8.4 Hz, 1H), 7.85(s, 1H), 7.90(d, J=0.4 Hz, 1H), 8.41(dd, J=8.4, 8.4 Hz, 1H), 8.45(m, 1H)

Example 499

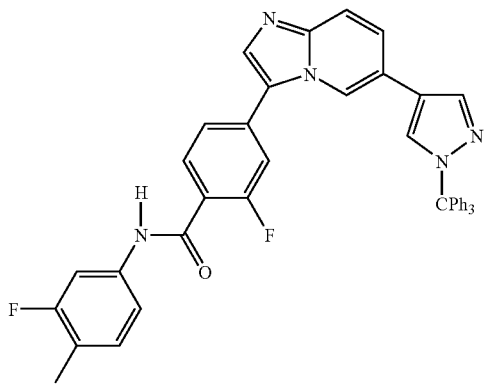

N1-(3-Fluoro-4-methylphenyl)-2-fluoro-4-[6-(1-trityl-1H-4-pyrazolyl)imidazo[1,2-a]pyridin-3-yl] benzamide 50 mg of the title compound was obtained as colorless crystals in the same manner as in Example 497 from 56 mg of the compound in Example 472 and 18 mg 3-fluoro-4-methylaniline.

¹H-NMR (CDCl₃)
δ: 2.28(d, J=1.6 Hz, 3H), 7.15–7.24(m, 8H), 7.31–7.38(m, 10H), 7.42(dd, J=13.2, 1.6 Hz, 1H), 7.57(dd, J=8.0, 1.6 Hz, 1H), 7.63(dd, J=11.2, 1.6 HZ, 1H), 7.63(s, 1H), 7.69(d, J=9.2 Hz, 1H), 7.80(s, 1H), 7.89(s, 1H), 8.33(dd, J=8.0, 8.0 Hz, 1H), 8.43(m, 1H), 8.46(br.d, J=16 Hz, 1H)

Example 500

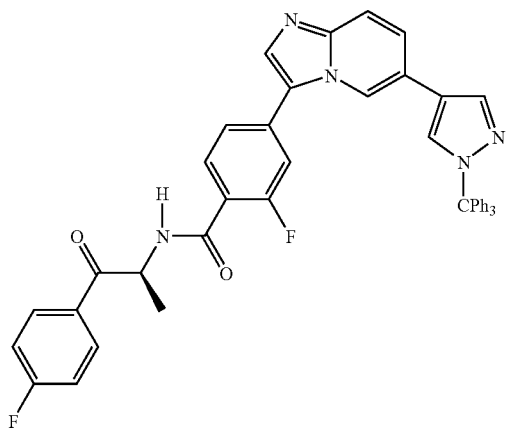

N1-[(1S)-2-(4-Fluorophenyl)-1-methyl-2-oxoethyl]-2-fluoro-4-[6-(1-trityl-1H-4-pyrazolyl)imidazo[1,2-a]pyridin-3-yl] benzamide 200 mg of the compound in Example 472 and 76 mg (2S)-2-amino-1-(4-fluorophenyl)propan-1-one hydrochloride (compound in Production Example 319) were allowed to react with 164 mg benzotriazol-1-yloxy-tris(dimethylamino)phosphonium hexafluorophosphate and 130 µL N,N-diisopropylethylamine in 10 mL dichloromethane for 3 hours. The reaction solution was purified by a silica gel column to give 277 mg of the title compound as a colorless film.

¹H-NMR (CDCl₃)
δ: 1.59(d, J=6.8 Hz, 3H), 5.74–5.83(m, 1H), 7.16–7.25(m, 8H), 7.30–7.38(m, 11H), 7.39(dd, J=12.4, 1.6 Hz, 1H), 7.51(dd, J=8.0, 1.6 Hz, 1H), 7.62(s, 1H), 7.87–7.95(m, 2H), 8.08–8.14(m, 2H), 8.25(dd, J=0.8 Hz, 1H), 8.41(s, 1H)

Example 501

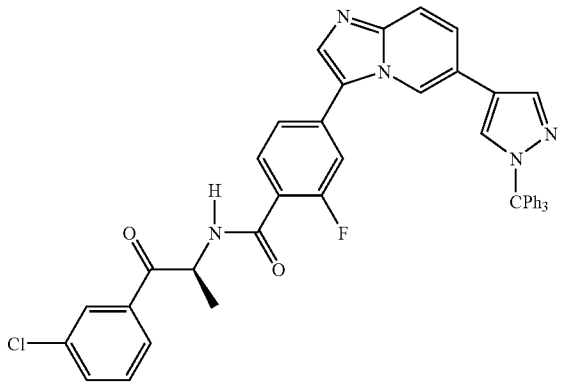

N1-[(1S)-2-(3-Chlorophenyl)-1-methyl-2-oxoethyl]-2-fluoro-4-[6-(1-trityl-1H-4-pyrazolyl)imidazo[1,2-a]pyridin-3-yl] benzamide 200 mg of the title compound was obtained as a colorless film in the same manner as in Example 500 from 150 mg of the compound in Example 472 and 62 mg (2S)-2-amino-1-(3-chlorophenyl)propan-1-one hydrochloride (compound in Production Example 320).

¹H-NMR (CDCl₃)
δ: 1.59(d, J=7.2 Hz, 3H), 5.72–5.81(m, 1H), 7.16–7.23(m, 6H), 7.31–7.37(m, 10H), 7.39(dd, J=12.4, 1.6 Hz, 1H), 7.46–7.53(m, 2H), 7.60–7.64(m, 2H), 7.68(dd, J=9.2, 0.8 Hz, 1H), 7.77(s, 1H), 7.82–7.90(m, 2H), 7.94(ddd, J=7.6, 1.2, 1.2 Hz, 1H), 8.04(dd, J=1.6, 1.6 Hz, 1H), 8.25(dd, J=8.0, 8.0 Hz, 1H), 8.40(m, 1H)

Example 502

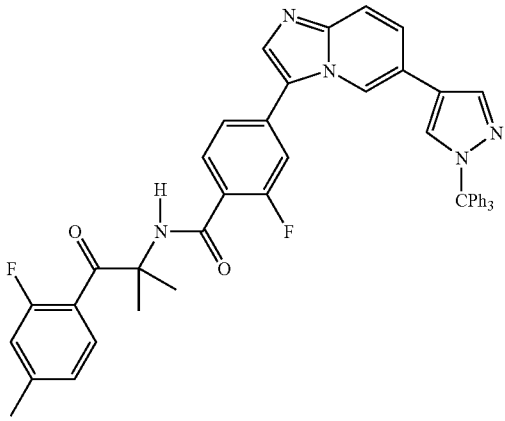

N1-[2-(2-Fluoro-4-methylphenyl)-1,1-dimethyl-2-oxoethyl]-2-fluoro-4-[6-(1-trityl-1H-4-pyrazolyl)imidazo[1,2-a]pyridin-3-yl] benzamide 367 mg of the title compound was obtained as colorless crystals in the same manner as in Example 500 from 338 mg of the compound in Example 472 and 127 mg 2-amino-1-(2-fluoro-4-methylphenyl)-2-methyl-1-propanone obtained by catalytically reducing the compound in Production Example 321, with hydrogen/Pd-C.

$^1$H-NMR (CDCl$_3$)

δ: 1.76(d, J=0.4 Hz, 6H), 2.34(s, 3H), 6.85(d, J=12.4 Hz, 1H), 6.99–7.04(m, 1H), 7.16–7.23(m, 6H), 7.29–7.40(m, 11H), 7.43(dd, J=8.4, 1.6 Hz, 1H), 7.55(dd, J=7.2, 7.2 Hz, 1H), 7.62(d, J=0.8 Hz, 1H), 7.68(d, J=9.6 Hz, 1H), 7.75(s, 1H), 7.87(d, J=1.2 Hz, 1H), 8.04(dd, J=8.0, 8.0 Hz, 1H), 8.38(m, 1H)

Example 503

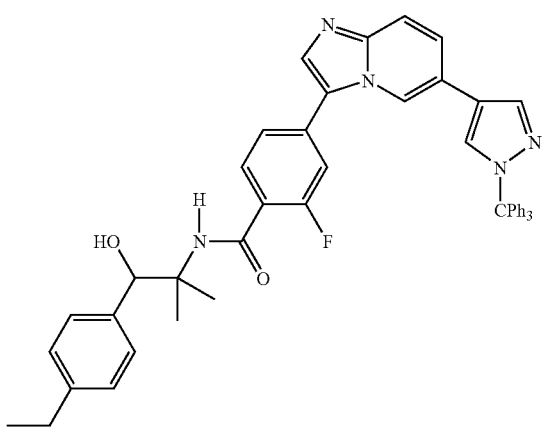

N1-[2-(4-Ethylphenyl)-2-hydroxy-1,1-dimethyl-ethyl]-2-fluoro-4-[6-(1-trityl-1H-4-pyrazolyl)imidazo[1,2-a]pyridin-3-yl] benzamide 348 mg of the title compound was obtained as colorless crystals by the same reaction as in Example 500 from 300 mg of the compound in Example 472 and 150 mg 2-amino-1-(4-ethylphenyl)-2-methyl-1-propanol obtained by catalytically reducing, with hydrogen/Pd-C, benzyl N-[2-(4-ethylphenyl)-1,1-dimethyl-2-oxyethyl] carbamate synthesized in the same manner as in Production Example 321.

$^1$H-NMR (CDCl$_3$)

δ: 1.22(t, J=8.0 Hz, 3H), 1.41(s, 3H), 1.59(s, 3H), 2.63 (q, J=8.0 Hz, 2H), 4.83(d, J=5.2 Hz, 1H), 5.12(d, J=5.2 Hz, 1H), 6.78(d, J=13.2 Hz, 1H), 7.13–7.18(m, 2H), 7.18–7.23(m, 6H), 7.26–7.38(m, 13H), 7.52(dd, J=8.0, 1.2 Hz, 1H), 7.62 (d, J=0.8 Hz, 1H), 7.67(dd, J=9.2, 0.8 Hz, 1H), 7.76(s, 1H), 7.88(d, J=0.4 Hz, 1H), 8.24(dd, J=8.0, 8.0 Hz, 1H), 8.40(m, 1H)

Example 504

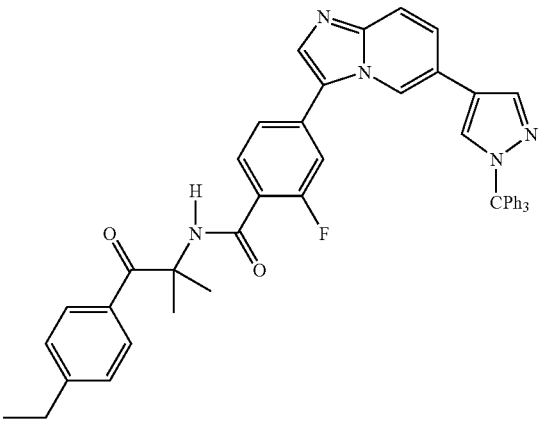

N1-[2-(4-Ethylphenyl)-1,1-dimethyl-2-oxoethyl]-2-fluoro-4-[6-(1-trityl-1H-4-pyrazolyl)imidazo[1,2-a]pyridin-3-yl] benzamide 100 mg N1-[2-(4-ethylphenyl)-2-hydroxy-1,1-dimethyl-ethyl]-2-fluoro-4-[6-(1-trityl-1H-4-pyrazolyl)-imidazo[1,2-a]pyridin-3-yl] benzamide obtained in Example 503 and 288 mg Dess-Martin reagent were stirred for 15 hours in dichloromethane. After an aqueous sodium bicarbonate solution and an aqueous sodium thiosulfate solution were added thereto, and the reaction solution was extracted with ethyl acetate and purified by NH silica gel chromatography, to give 92 mg of the title compound as colorless crystals.

$^1$H-NMR (CDCl$_3$)

δ: 1.23(t, J=7.6 Hz, 3H), 1.85(s, 6H), 2.66 (q, J=7.6 Hz, 2H), 7.16–7.25(m, 8H), 7.30–7.40(m, 11H), 7.45(dd, J=8.4, 1.6 Hz, 1H), 7.61(d, J=0.4 Hz, 1H), 7.65–7.72(m, 2H), 7.76(s, 1H), 7.87(d, J=0.4 Hz, 1H), 7.98–8.03(m, 2H), 8.09(dd, J=8.4, 8.4 Hz, 1H), 8.38(m, 1H)

Example 505

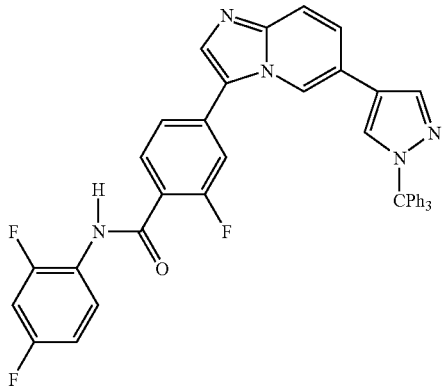

N1-(2,4-Difluorophenyl)-2-fluoro-4-[6-(1-trityl-1H-4-pyrazolyl)imidazo[1,2-a]pyridin-3-yl] benzamide 215 mg 3-(1,1,1-tributylstannyl)-6-(1-trityl-1H-4-pyrazolyl)imidazo[1,2-a]pyridine (compound in Production Example 293), 99 mg N1-(2,4-difluorophenyl)-4-bromo-2-fluorobenzamide (compound in Production Example 323) and 15 mg tetrakis (triphenylphosphine) palladium were heated in xylene at 70° C. for 3 hours. The solvent was evaporated, and the residue was purified by an NH silica gel column, to give 80 mg of the title compound as colorless crystals.

$^1$H-NMR (CDCl$_3$)

δ: 6.92–7.00(m, 2H), 7.17–7.23(m, 6H), 7.31–7.38(m, 10H), 7.43(dd, J=13.2, 1.6 Hz, 1H), 7.57(dd, J=8.0, 1.6 Hz, 1H), 7.63(d, 0.8 Hz, 1H), 7.69(dd, 9.2,1.6 Hz, 1H), 7.81(s, 1H), 7.89(d, 0.8 Hz, 1H), 8.33(dd, J=8.8, 8.0 Hz, 1H), 8.41–8.51(m, 2H), 8.71(br.d, J=16.4 Hz, 1H)

Example 506

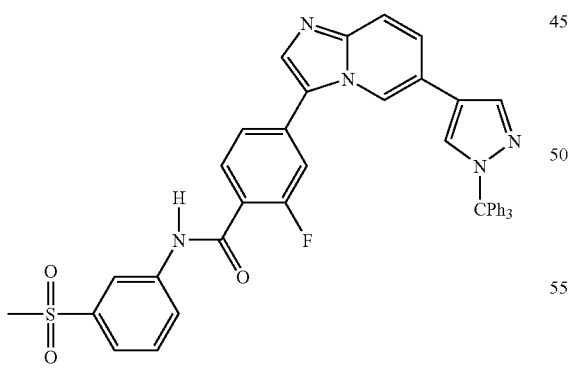

N1-[3-(Methylsulfonyl)phenyl]-2-fluoro-4-[6-(1-trityl-1H-4-pyrazolyl)imidazo[1,2-a]pyridin-3-yl] benzamide 135 mg of the title compound was obtained as colorless crystals in the same manner as in Example 505 from 150 mg of the compound in Production Example 293 and 74 mg N1-[3-(methylsulfonyl)phenyl]-4-bromo-2-fluorobenzamide (compound in Production Example 324).

$^1$H-NMR (CDCl$_3$)

δ: 3.12(s, 3H), 7.17–7.23(m 6H), 7.30–7.38(m, 10H), 7.45(dd, J=13.2, 1.2 Hz, 1H), 7.59(dd, J=8.0, 1.2 Hz, 1H), 7.63(dd, J=8.0, 8.0 Hz, 1H), 7.64(d, J=0.8 Hz, 1H), 7.69(dd, J=9.6, 0.8 Hz, 1H), 7.75–7.79(m, 1H), 7.82(s, 1H), 7.90(d, J=0.4 Hz, 1H), 8.10(ddd, J=8.4, 2.0, 0.4 Hz, 1H), 8.24(dd, J=1.6 Hz, 1H), 8.34(dd, J=8.4, 8.4 Hz, 1H), 8.44(m, 1H), 8.67(brd, J=16.4 Hz, 1H)

Example 507

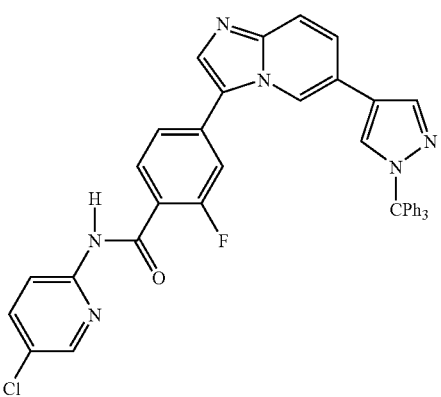

N1-(5-Chloro-2-pyridyl)-2-fluoro-4-[6-(1-trityl-1H-4-pyrazolyl)imidazo[1,2-a]pyridin-3-yl] benzamide 130 mg of the title compound was obtained as colorless crystals in the same manner as in Example 505 from 200 mg of the compound in Production Example 293 and 130 mg N1-(5-chloro-2-pyridyl)-4-bromo-2-fluorobenzamide synthesized in the same manner as in Production Example 323.

$^1$H-NMR (CDCl$_3$)

δ: 7.17–7.23(m, 6H), 7.31–7.38(m, 10H), 7.44(dd, J=12.8, 1.6 Hz, 1H), 7.57(dd, J=8.0, 1.6 Hz, 1H), 7.63(s, 1H), 7.69(d, J=9.2 Hz, 1H), 7.75(dd, J=8.8, 2.4 Hz, 1H), 7.81(s, 1H), 7.89(s, 1H), 8.31(dd, J=8.0, 8.0 Hz, 1H), 8.32(d, J=2.4 HZ, 1H), 8.41(d, J=8.8 Hz, 1H), 8.43(s, 1H), 9.12(brd, J=14.8 Hz, 1H)

Example 508

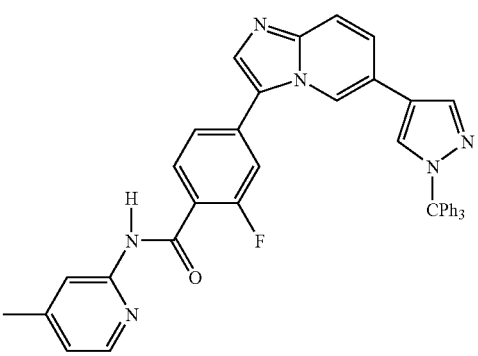

543

N1-(4-Methyl-2-pyridyl)-2-fluoro-4-[6-(1-trityl-1H-4-pyrazolyl)imidazo[1,2-a]pyridin-3-yl] benzamide 78 mg of the title compound was obtained as colorless crystals in the same manner as in Example 505 from 195 mg of the compound in Production Example 293 and 80 mg N1-(4-methyl-2-pyridyl)-4-bromo-2-fluorobenzamide synthesized in the same manner as in Production Example 323.

¹H-NMR (CDCl₃)

δ: 2.43(s, 3H), 6.95(dd, J=4.8, 0.8 Hz, 1H), 7.16–7.24(m, 6H), 7.30–7.40(m, 10H), 7.43(dd, J=12.8, 1.6 Hz, 1H), 7.57(dd, J=8.0, 1.6 Hz, 1H), 7.63(d, J=0.8 Hz, 1H), 7.69(dd, J=9.2, 0.8 Hz, 1H), 7.80(s, 1H), 7.89(d, J=1.6 Hz, 1H), 8.22(d, J=4.8 Hz, 1H), 8.27(s, 1H), 8.31(dd, J=8.0, 8.0 Hz, 1H), 8.44(dd, J=1.6, 0.8 Hz, 1H), 9.06(brd, J=13.6 Hz, 1H)

Example 509

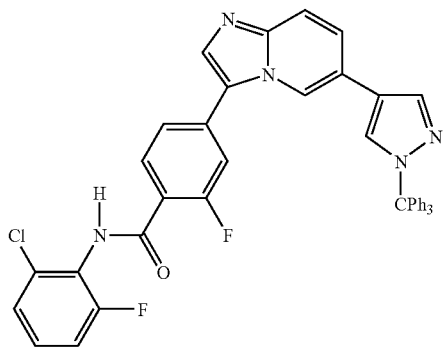

N1-(2-Chloro-6-fluorophenyl)-2-fluoro-4-[6-(1-trityl-1H-4-pyrazolyl)imidazo[1,2-a]pyridin-3-yl] benzamide 17 mg of the title compound was obtained in the same manner as in Example 505 from 100 mg of the compound in Production Example 293 and 53 mg 4-bromo-N-(2-chloro-6-fluorophenyl)-2-fluorobenzamide synthesized in the same method as in Production Example 323.

¹H-NMR (CDCl₃)

δ: 7.16–7.23(m, 6H), 7.29–7.37(m, 9H), 7.42–7.48(m, 3H), 7.55–7.58(m, 1H), 7.62(d, J=0.8 Hz, 1H), 7.64–7.72(m, 2H), 7.81(s, 1H), 7.89(d, J=0.8 Hz, 1H), 8.18(d, J=15.2 Hz, 1H), 8.36(t, J=8.4 Hz, 1H), 8.42–8.43(m, 1H)

Example 510

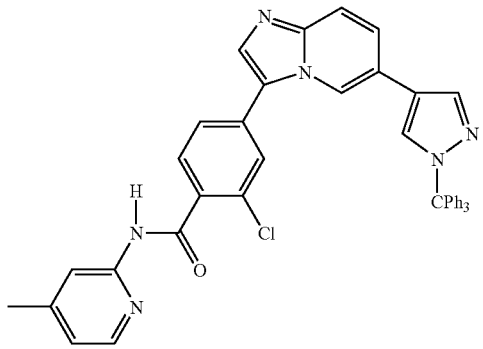

544

N1-(4-Methyl-2-pyridyl)-2-chloro-4-[6-(1-trityl-1H-4-pyrazolyl)imidazo[1,2-a]pyridin-3-yl] benzamide 44 mg of the title compound was obtained by the same reaction as in Example 505 from 150 mg of the compound in Production Example 293 and 68 mg 4-bromo-2-chloro-N-(4-methylpyridin-2-yl)benzamide synthesized in the same method as in Production Example 323.

¹H-NMR (CDCl₃)

δ: 2.36(s, 3H), 6.88(d, J=5.2 Hz, 1H), 7.10–7.17(m, 6H), 7.24–7.31(m, 10H), 7.53(dd, J=8.1, 1.7 Hz, 1H), 7.55(d, J=0.4 Hz, 1H), 7.62(d, J=1.7 Hz, 1H), 7.65(d, J=9.2 Hz, 1H), 7.69(s, 1H), 7.83(d, J=0.4 Hz, 1H), 7.85(d, J=8.1 Hz, 1H), 8.09(d, J=5.2 Hz, 1H), 8.18(brs, 1H), 8.32(brs, 1H), 8.66(brs, 1H)

Example 511

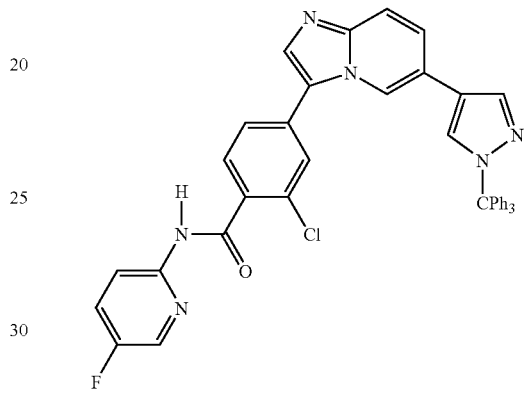

N1-(5-Fluoro-2-pyridyl)-2-chloro-4-[6-(1-trityl-1H-4-pyrazolyl)imidazo[1,2-a]pyridin-3-yl] benzamide 36 mg of the title compound was obtained by the same reaction as in Example 505 from 140 mg of the compound in Production Example 293 and 64 mg 4-bromo-2-chloro-N-(5-fluoropyridin-2-yl)benzamide synthesized in the same method as in Production Example 323.

¹H-NMR (CDCl₃)

δ: 7.10–7.17(m, 6H), 7.32–7.44(m, 9H), 7.58(dd, J=11.4, 2.2 Hz, 1H), 7.68(dd, J=9.4, 0.6 Hz, 1H), 7.72(d, J=8.0 Hz, 1H), 7.80–7.85(m, 2H), 7.89(s, 1H), 7.90(d, J=1.6 Hz, 1H), 7.99(d, J=0.8 Hz, 1H), 8.15(d, J=0.8 Hz, 1H), 8.24–8.29(m, 1H), 8.40(d, J=3.2 Hz, 1H), 8.70(brs, 1H)

Example 512

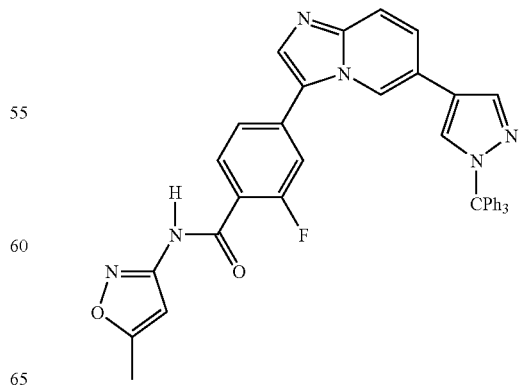

545

N1-(5-Methylisoxazol-3-yl)-2-fluoro-4-[6-(1-trityl-1H-4-pyrazolyl)imidazo[1,2-a]pyridin-3-yl] benzamide 52 mg of the title compound was obtained in the same manner as in Example 505 from 150 mg of the compound in Production Example 293 and 4-bromo-2-fluoro-N-(5-methylisoxazol-3-yl)benzamide synthesized in the same method as in Production Example 323.

$^1$H-NMR (DMSO-d$_6$)

δ: 2.43(d, J=0.8 Hz, 3H), 6.76(s, 1H), 7.10–7.17(m, 6H), 7.32–7.44(m, 9H), 7.58(dd, J=9.6, 1.6 Hz, 1H), 7.66–7.72 (m, 2H), 7.77(dd, J=11.6, 1.4 Hz, 1H), 7.82(t, J=8.0 Hz, 1H), 7.92(s, 1H), 8.00(d, J=0.4 Hz, 1H), 8.17(d, J=0.4 Hz, 1H), 8.75–8.76(m, 1H)

Example 513

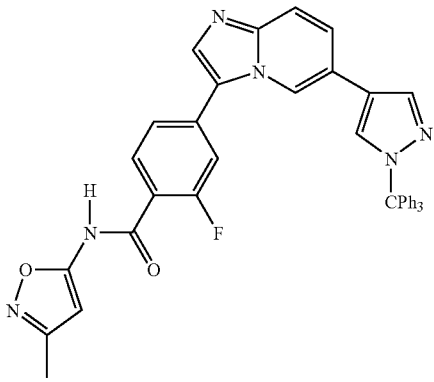

N1-(3-Methylisoxazol-5-yl)-2-fluoro-4-[6-(1-trityl-1H-4pyrazolyl)imidazo[1,2-a]pyridin-3-yl] benzamide 42 mg of the title compound was obtained in the same manner as in Example 505 from 150 mg of the compound in Production Example 293 and 63 mg 4-bromo-2-fluoro-N-(3-methylisoxazol-5-yl)benzamide synthesized in the same method as in Production Example 323.

$^1$H-NMR (DMSO-d$_6$)

δ: 2.24(s, 3H), 6.34(s, 1H), 7.10–7.17(m, 6H), 7.32–7.44 (m, 9H), 7.59(dd, J=9.4, 1.6 Hz, 1H), 7.68(dd, J=9.4, 0.8 Hz, 1H), 7.73(dd, J=8.0, 1.5 Hz, 1H), 7.80(dd, J=11.4, 1.5 Hz, 1H), 7.85(t, J=8.0 Hz, 1H), 7.93(s, 1H), 8.00(d, J=0.8 Hz, 1H), 8.18(d, J=0.8 Hz, 1H), 8.77(brs, 1H)

Example 514

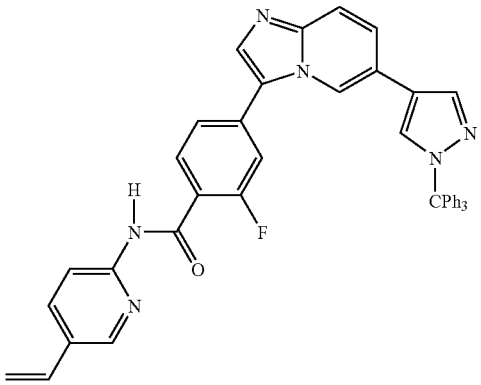

546

N1-(5-Vinyl-2-pyridyl)-2-fluoro-4-[6-(1-trityl-1H-4-pyrazolyl)imidazo[1,2-a]pyridin-3-yl] benzamide 106 mg of the title compound was obtained in the same manner as in Example 505 from 240 mg of the compound in Production Example 293 and 108 mg 4-bromo-2-fluoro-N-(5-vinylpyridin-2-yl)benzamide (compound in Production Example 328).

$^1$H-NMR (CDCl$_3$)

δ: 5.34(d, J=11.0 Hz, 1H), 5.80(d, J=17.6 Hz, 1H), 6.70(dd, J=17.6, 11.0 Hz, 1H), 7.17–7.24(m, 6H), 7.32–7.40 (m, 10H), 7.43(dd, J=12.8, 1.6 Hz, 1H), 7.57(dd, J=8.4, 1.6 Hz, 1H), 7.62(s, 1H), 7.68(dd, J=8.6, 0.8 Hz, 1H), 7.81(s, 1H), 7.86(dd, J=8.8, 2.4 Hz, 1H), 7.89(s, 1H), 8.32(t, J=8.4 Hz, 1H), 8.36(d, J=2.4 Hz, 1H), 8.39(d, J=8.8 Hz, 1H), 8.43(s, 1H), 9.12(d, J=14.0 Hz, 1H)

Example 515

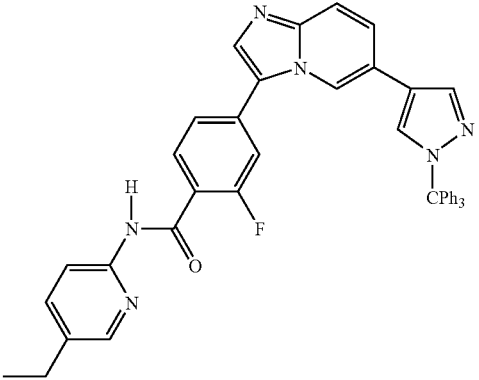

N1-(5-Ethyl-2-pyridyl)-2-fluoro-4-[6-(1-trityl-1H-4-pyrazolyl)imidazo[1,2-a]pyridin-3-yl] benzamide 99 mg of the title compound was obtained in the same manner as in Example 505 from 230 mg of the compound in Production Example 293 and 102 mg 4-bromo-N-(5-ethylpyridin-2-yl)-2-fluorobenzamide (compound in Production Example 329).

$^1$H-NMR(CDCl$_3$)

δ: 1.27(t, J=7.6 Hz, 3H), 2.66 (q, J=7.6 Hz, 2H), 7.17–7.24(m, 6H), 7.32–7.38(m, 10H), 7.42(dd, J=13.0, 1.4 Hz, 1H), 7.56(dd, J=8.0, 1.6 Hz, 1H), 7.62(s, 1H), 7.62(dd, J=8.5, 2.4 Hz, 1H), 7.68(d, J=9.2 Hz, 1H), 7.80(d, J=0.8 Hz, 1H), 7.89(s, 1H), 8.20(d, J=2.4 Hz, 1H), 8.31(t, J=8.0 Hz, 1H), 8.32(d, J=8.5 Hz, 1H), 8.43(s, 1H), 9.05(d, J=13.6 Hz, 1H)

Example 516

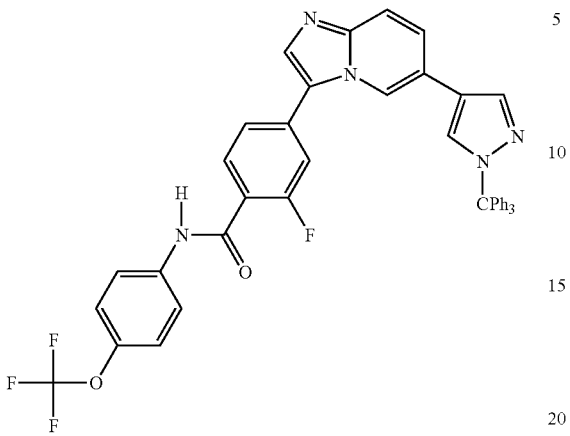

N1-[4-(Trifluoromethoxy)phenyl]-2-fluoro-4-[6-(1-trityl-1H-4-pyrazolyl)imidazo[1,2-a]pyridin-3-yl] benzamide 55 mg of the title compound was obtained in the same manner as in Example 505 from 300 mg of the compound in Production Example 293 and 158 mg N1-[4-(trifluoromethoxy)phenyl]-4-bromo-2-fluorobenzamide synthesized in the same method as in Production Example 323.

$^1$H-NMR (CDCl$_3$)
δ: 7.12–7.15(m, 7H), 7.20(d, J=9.2 Hz, 2H), 7.25–7.30(m, 9H), 7.36(dd, J=13.2, 1.6 Hz, 1H), 7.51(dd, J=8.4, 1.6 Hz, 1H), 7.56(d, J=0.8 Hz, 1H), 7.61(dd, J=9.2, 0.8 Hz, 1H), 7.66(d, J=9.2 Hz, 1H), 7.73(s, 1H), 7.82(d, J=0.8 Hz, 1H), 8.27(dd, J=8.4, 8.4 Hz, 1H), 8.34–8.36(m, 1H), 8.45(d, J=15.6 Hz, 1H)

Example 517

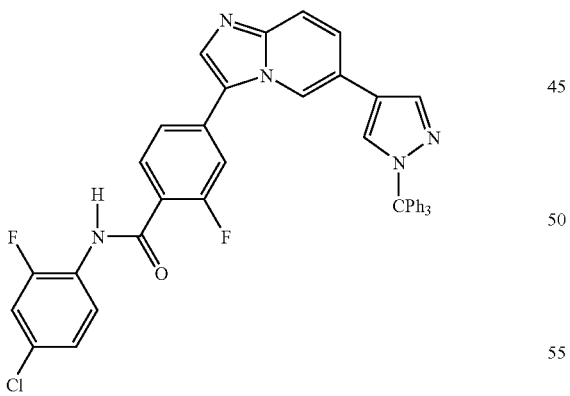

N1-(4-Chloro-2-fluorophenyl)-2-fluoro-4-[6-(1-trityl-1H-4-pyrazolyl)imidazo[1,2-a]pyridin-3-yl] benzamide 40 mg of the title compound was obtained in the same manner as in Example 505 from 300 mg of the compound in Production Example 293 and 145 mg N1-(4-chloro-2-fluorophenyl)-4-bromo-2-fluorobenzamide synthesized in the same method as in Production Example 323.

$^1$H-NMR (CDCl$_3$)
δ: 7.17–7.22(m, 7H), 7.31–7.36(m, 10H), 7.43(dd, J=13.2, 1.6 Hz, 1H), 7.57(dd, J=8.4, 1.6 Hz, 1H), 7.63(d, J=0.8 Hz, 1H), 7.68(d, J=9.2 Hz, 1H), 7.80(s, 1H), 7.89(d, J=0.8 Hz, 1H), 8.33(dd, J=8.4, 8.4 Hz, 1H), 8.43(m, 1H), 8.50(dd, J=8.4, 8.4 Hz, 1H), 8.79(dd, J=16.8, 3.2 Hz, 1H)

Example 518

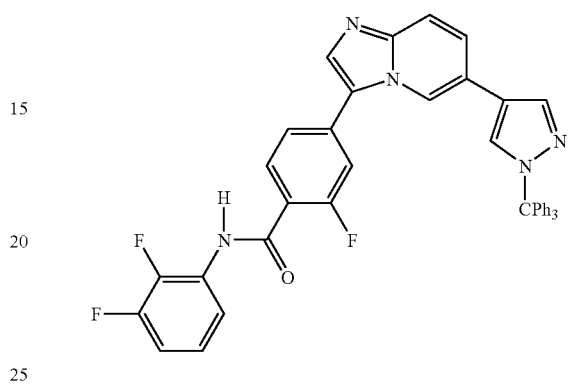

N1-(2,3-Difluorophenyl)-2-fluoro-4-[6-(1-trityl-1H-4-pyrazolyl)imidazo[1,2-a]pyridin-3-yl] benzamide 42 mg of the title compound was obtained in the same manner as in Example 505 from 300 mg of the compound in Production Example 293 and 100 mg N1-(2,3-difluorophenyl)-4-bromo-2-fluorobenzamide synthesized in the same method as in Production Example 323.

$^1$H-NMR (CDCl$_3$)
δ: 6.95–7.02(m, 1H), 7.12–7.22(m, 8H), 7.31–7.36(m, 9H), 7.44(dd, J=13.2, 1.6 Hz, 1H), 7.58(dd, J=8.4, 1.6 Hz, 1H), 7.63(d, J=0.8 Hz, 1H), 7.68(d, J=9.2 Hz, 1H), 7.81(s, 1H), 7.89(d, J=0.8 Hz, 1H), 8.27–8.30(m, 1H), 8.33(dd, J=8.4, 8.4 Hz, 1H), 8.43(m, 1H), 8.80–8.84(m, 1H)

Example 519

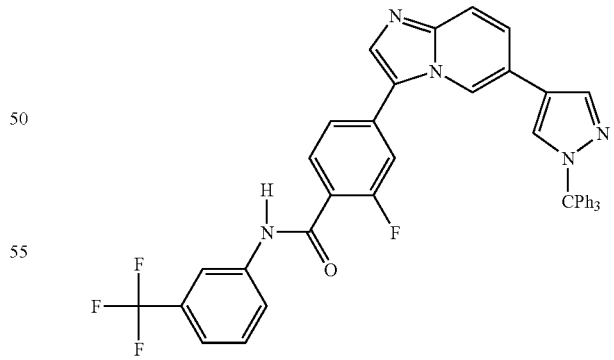

N1-[4-(Trifluoromethyl)phenyl]-2-fluoro-4-[6-(1-trityl-1H-4-pyrazolyl)imidazo[1,2-a]pyridin-3-yl] benzamide 50 mg of the title compound was obtained in the same manner as in Example 505 from 300 mg of the compound in Production Example 293 and 152 mg N1-[4-(trifluoromethyl)phenyl]-4-bromo-2-fluorobenzamide synthesized in the same method as in Production Example 323.

¹H-NMR (CDCl₃)

δ: 7.18–7.22(m, 7H), 7.31–7.36(m, 10H), 7.44(dd, J=13.2, 1.6 Hz, 1H), 7.58(dd, J=8.4, 1.6 Hz, 1H), 7.63(d, J=0.8 Hz, 1H), 7.65(d, J=8.4 Hz, 1H), 7.69(s, 1H), 7.81(s, 1H), 7.84(d, J=8.4 Hz, 1H), 8.89(d, J=0.8 Hz, 1H), 8.34(dd, J=8.4, 8.4 Hz, 1H), 8.43(m, 1H), 8.61–8.65(m, 1H)

Example 520

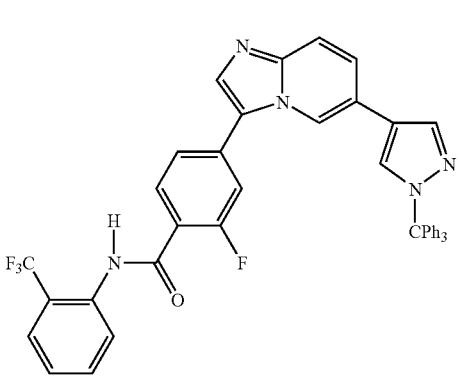

N1-[2-(Trifluoromethyl)phenyl]-2-fluoro-4-[6-(1-trityl-1H-4-pyrazolyl)imidazo[1,2-a]pyridin-3-yl] benzamide 50 mg of the title compound was obtained in the same manner as in Example 505 from 300 mg of the compound in Production Example 293 and 152 mg N1-[2-(trifluoromethyl)phenyl]-4-bromo-2-fluorobenzamide synthesized in the same method as in Production Example 323.

¹H-NMR (CDCl₃)

δ: 7.18–7.21(m, 7H), 7.28–7.35(m, 10H), 7.43(dd, J=13.2, 1.6 Hz, 1H), 7.57(dd, J=8.4, 1.6 Hz, 1H), 7.62–7.70 (m, 4H), 7.81(s, 1H), 7.90(s, 1H), 8.35(dd, J=8.4, 8.4 Hz, 1H), 8.43–8.46(m, 2H), 8.98–9.02(m, 1H)

Example 521

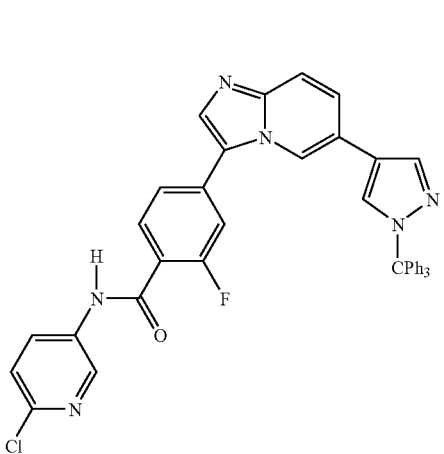

N1-(6-Chloro-3-pyridyl)-2-fluoro-4-[6-(1-trityl-1H-4-pyrazolyl)imidazo[1,2-a]pyridin-3-yl] benzamide 56 mg of the title compound was obtained in the same manner as in Example 505 from 300 mg of the compound in Production Example 293 and 152 mg N1-(6-chloro-3-pyridyl)-4-bromo-2-fluorobenzamide synthesized in the same method as in Production Example 323.

Example 522

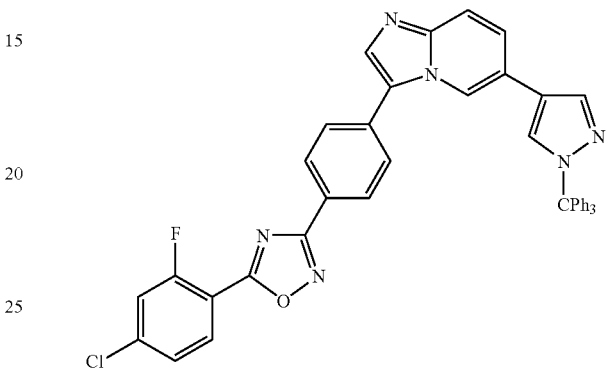

5-(4-Chloro-2-fluorophenyl)-3-{4-[6-(1-trityl-1H-4-pyrazolyl)imidazo[1,2-a]pyridin-3-yl]-1,2,4-oxadiazole 56 mg of the title compound was obtained in the same manner as in Example 505 from 300 mg of the compound in Production Example 293 and 152 mg 3-(4-bromophenyl)-5-(4-chloro-2-fluorophenyl)-1,2,4-oxadiazole.

¹H-NMR (DMSO-d₆)

δ: 7.18–7.24(m, 7H), 7.30–7.39(m, 10H), 7.61(s, 1H), 7.67(d, J=9.2 Hz, 1H), 7.74(d, J=8.4 Hz, 2H), 7.78(s, 1H), 7.88(s, 1H), 8.21(dd, J=8.8, 8.0 Hz, 1H), 8.33(d, J=8.4 Hz, 2H), 8.45(s, 1H)

Example 523

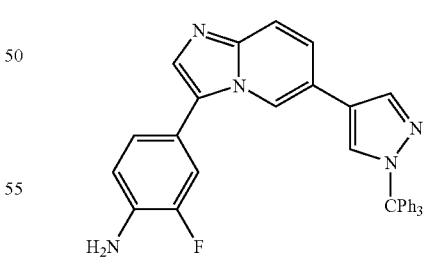

2-Fluoro-4-[6-(1-trityl-1H-4-pyrazolyl)imidazo[1,2-a]-pyridin-3-yl] aniline 56 mg of the title compound was obtained in the same manner as in Example 505 from 300 mg of the compound in Production Example 293 and 152 mg 4-bromo-2-fluoroaniline.

¹H-NMR (CDCl₃)

δ: 6.91 (dd, J=8.8, 8.4 Hz, 1H), 7.13(dd, J=8.8, 2.4 Hz, 1H), 7.17–7.24(m, 7H), 7.30–7.38(m, 10H), 7.57–7.62(m, 3H), 7.85(s, 1H), 8.28(s, 1H)

Example 524

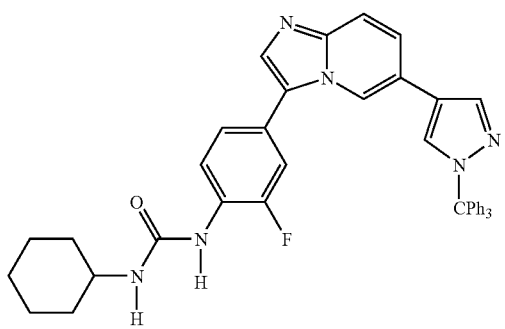

N-Cyclohexyl-N'-{2-fluoro-4-[6-(1-trityl-1H-4-pyrazolyl)imidazo[1,2-a]pyridin-3-yl] phenyl} urea 300 mg 2-fluoro-4-[6-(1-trityl-1H-4-pyrazolyl)imidazo[1,2-a]pyridin-3-yl] aniline (compound in Example 523) and 1-isocyanate cyclohexane were stirred in toluene at 80° C. for 12 hours, and the reaction solution was purified by silica gel column chromatography to give the title compound.

MS m/e(ESI)661(MH⁺)

Example 525

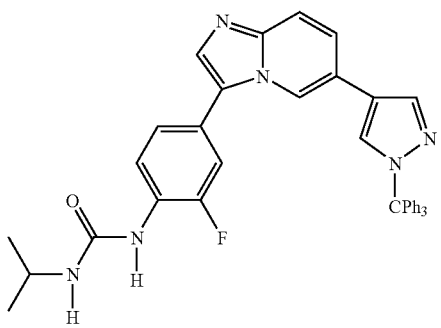

N-{2-Fluoro-4-[6-(1-trityl-1H-4-pyrazolyl)imidazo[1,2-a]pyridin-3-yl] phenyl}-N'-isopropyl urea 300 mg 2-fluoro-4-[6-(1-trityl-1H-4-pyrazolyl)imidazo[1,2-a]pyridin-3-yl] aniline (compound in Example 523) and 2-isocyanate propane were stirred in toluene at 80° C. for 12 hours, and the reaction solution was purified by silica gel column chromatography to give the title compound.

MS m/e(ESI)621(MH⁺)

Example 526

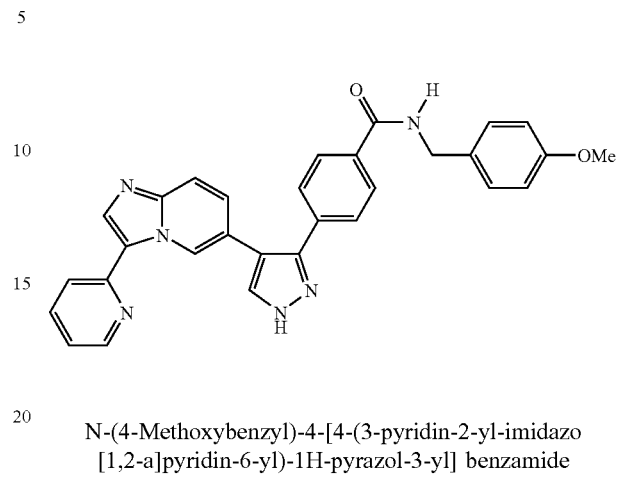

N-(4-Methoxybenzyl)-4-[4-(3-pyridin-2-yl-imidazo[1,2-a]pyridin-6-yl)-1H-pyrazol-3-yl] benzamide 12 mg of the title compound was obtained as white crystals in the same method as in Example 84 from 25 mg N-(4-methoxybenzyl)-4-[4-(3-pyridin-2-yl-imidazo[1,2-a]pyridin-6-yl)-1-trityl-1H-pyrazol-3-yl] benzamide (compound in Example 350).

¹H-NMR (CDCl₃)

δ: 3.80(s, 3H), 4.57(d, J=5.2 Hz, 2H), 6.33(brs, 1H), 6.87(d, J=8.8 Hz, 2H), 7.09(dd, J=8.8, 4.4 Hz, 1H), 7.15(dd, J=9.2, 1.6 Hz, 1H), 7.60(m, 2H), 7.70–7.80(m, 4H), 7.83(s, 1H), 8.13(s, 1H), 8.45(d, J=4.8 Hz, 1H), 9.96(brs, 1H)

Example 527

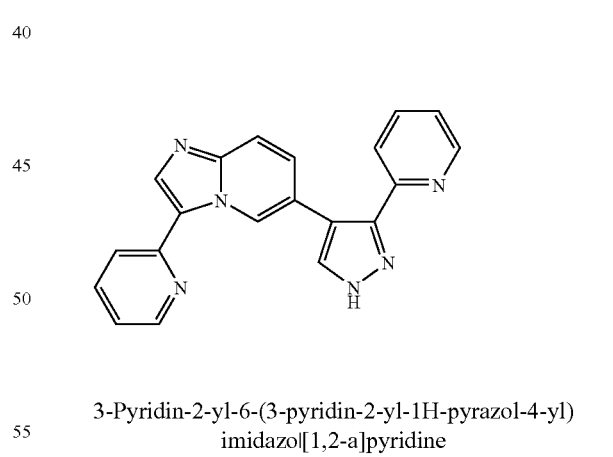

3-Pyridin-2-yl-6-(3-pyridin-2-yl-1H-pyrazol-4-yl)imidazo[1,2-a]pyridine 46 mg of the title compound was obtained as grayish white crystals in the same method as in Example 84 from 140 mg 3-pyridin-2-yl-6-(3-pyridin-2-yl-1-trityl-1H-pyrazol-4-yl)imidazo[1,2-a] pyridine (compound in Example 351).

¹H-NMR (DMSO-d₆)

δ: 7.22(m, 1H), 7.26–7.45(m, 2H), 7.48–7.74(m, 2H), 7.84(m, 3H), 7.96(m, 1H), 8.30–8.46(m, 2H), 10.00(brs, 1H)

Example 528

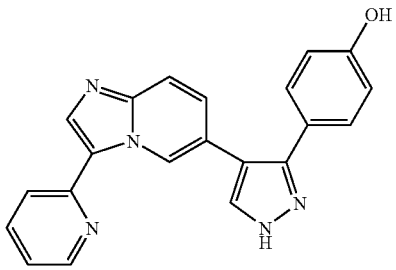

4-{4-[3-(Pyridin-2-yl)imidazo[1,2-a]pyridin-6-yl]-1H-pyrazol-3-yl} phenol 20 mg of the title compound was obtained as grayish white crystals in the same method as in Example 84 from 80 mg 4-{4-[3-(pyridin-2-yl)imidazo[1,2-a]pyridin-6-yl]-1-trityl-1H-pyrazol-3-yl} phenol (compound in Example 353).

$^1$H-NMR (DMSO-$d_6$)

δ: 6.75(m, 2H), 7.26(m, 4H), 7.65(d, J=8.8 Hz, 1H), 7.82(m, 2H), 7.94(d, J=8.0 Hz, 1H), 8.35(s, 1H), 8.44(brs, 1H), 9.87(brs, 1H), 13.20(br, 1H)

Example 529

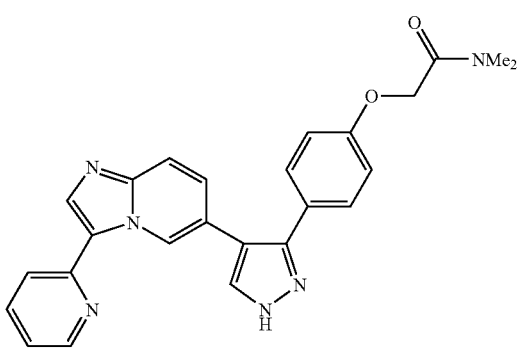

N,N-Dimethyl-2-{4-[4-(3-pyridin-2-ylimidazo[1,2-a]pyridin-6-yl)-1H-pyrazol-3-yl] phenoxy} acetamide 22 mg of the title compound was obtained as white crystals in the same method as in Example 84 from 78 mg N,N-dimethyl-2-{4-[4-(3-pyridin-2-ylimidazo[1,2-a]pyridin-6-yl)-1-trityl-1H-pyrazol-3-yl]phenoxy}acetamide (compound in Example 354).

$^1$H-NMR (CDCl$_3$)

δ: 2.98(s, 3H), 3.08(s, 3H), 4.69(s, 2H), 6.94(d, J=8.4 Hz, 2H), 7.14(m, 1H), 7.19(dd, J=8.8, 1.6 Hz, 1H), 7.42(d, J=8.4 Hz, 2H), 7.62(d, J=8.8 Hz, 1H), 7.72(m, 2H), 7.81(s, 1H), 8.13(s, 1H), 8.52(d, J=4.8 Hz, 1H), 9.98(dd, J=2.0, 0.8 Hz, 1H)

Example 530

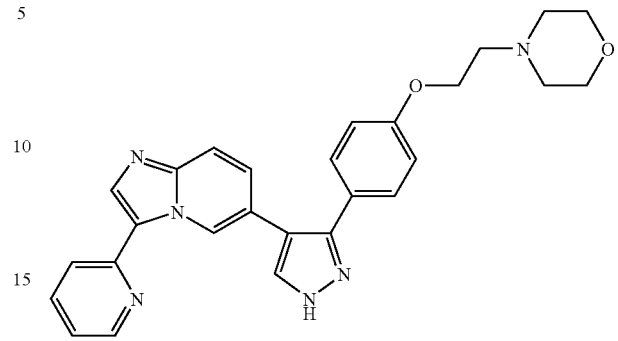

6-{3-[4-(2-Morpholine-4-ylethoxy)phenyl]-1H-pyrazol-4-yl}-3-(pyridin-2-yl)imidazo[1,2-a] pyridine 23 mg of the title compound was obtained as white crystals in the same method as in Example 84 from 61 mg 6-{3-[4-(2-Morpholine-4-ylethoxy)phenyl]-1-trityl-1H-pyrazol-4-yl}-3-(pyridin-2-yl)imidazo[1,2-a] pyridine (compound in Example 355).

$^1$H-NMR (CDCl$_3$)

δ: 2.58(t, J=4.4 Hz, 4H), 2.81(t, J=5.6 Hz, 2H), 3.73(t, J=4.4 Hz, 4H), 4.11(t, J=5.6 Hz, 2H), 6.90(d, J=8.8 Hz, 2H), 7.11(m, 1H), 7.17(dd, J=9.2, 1.6 Hz, 1H), 7.41(d, J=8.8 Hz, 2H), 7.61(dd, J=9.2, 0.8 Hz, 1H), 7.72(m, 2H), 7.81(s, 1H), 8.13(s, 1H), 8.51(m, 1H), 9.98(dd, J=1.6, 0.8 Hz, 1H)

Example 531

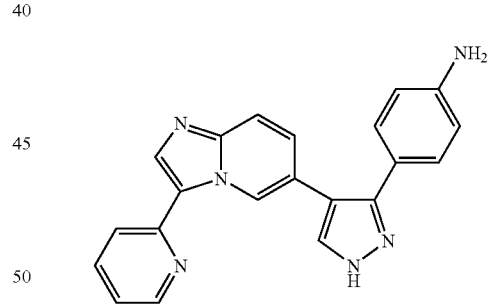

4-{4-[3-(2-Pyridyl)imidazo[1,2-a]pyridin-6-yl]-1H-3-pyrazolyl} aniline 18 mg of the title compound was obtained as pale brown crystals in the same method as in Example 84 from 60 mg 4-{4-[3-(2-pyridyl)imidazo[1,2-a]pyridin-6-yl]-1-trityl-1H-3-pyrazolyl} aniline (compound in Example 49).

$^1$H-NMR (CDCl$_3$)

δ: 6.68(d, J=8.4 Hz, 2H), 7.14(m, 1H), 7.19(dd, J=9.6, 2.0 Hz, 1H), 7.27(d, J=8.4 Hz, 2H), 7.60(d, J=9.6 Hz, 1H), 7.72(m, 2H), 7.80(s, 1H), 8.12(s, 1H), 8.54(d, J=4.8 Hz, 1H), 9.99(brs, 1H)

Example 532

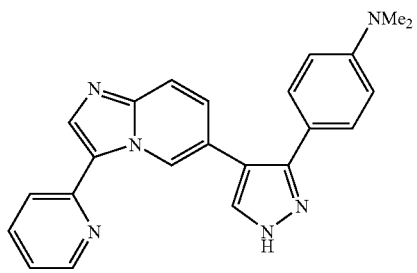

Dimethyl{4-[4-(3-pyridin-2-yl-imidazo[1,2-a]pyridin-6-yl)-1H-pyrazol-3-yl] phenyl} amine 54 mg of the title compound was obtained as white crystals in the same method as in Example 84 from 87 mg dimethyl{4-[4-(3-pyridin-2-yl-imidazo[1,2-a]pyridin-6-yl)-1-trityl-1H-pyrazol-3-yl]phenyl} amine (compound in Example 356).

$^1$H-NMR (CDCl$_3$)

δ: 2.98(s, 6H), 6.69(d, J=9.2 Hz, 2H), 7.12(m, 1H), 7.23(dd, J=9.2, 1.6 Hz, 1H), 7.33(d, J=9.2 Hz, 2H), 7.60(d, J=9.2 Hz, 1H), 7.70(m, 2H), 7.80(s, 1H), 8.12(m, 1H), 8.53(d, J=4.8 Hz, 1H), 10.00(brs, 1H)

Example 533

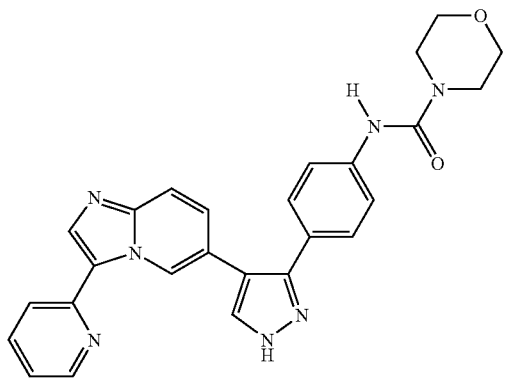

Morpholine-4-carboxylic acid {4-[4-(3-pyridin-2-ylimidazo[1,2-a]pyridin-6-yl)-1H-pyrazol-3-yl] phenyl} amide 37 mg of the title compound was obtained as pale brown crystals in the same method as in Example 84 from 72 mg morpholine-4-carboxylic acid {4-[4-(3-pyridin-2-ylimidazo[1,2-a]pyridin-6-yl)-1-trityl-1H-pyrazol-3-yl]phenyl}amide (compound in Example 357).

$^1$H-NMR (DMSO-d$_6$)

δ: 3.40(brs, 4H), 3.60(brs, 4H), 6.38(s, 1H), 7.19(m, 1H), 7.23–7.37(m, 3H), 7.38–7.55(m, 2H), 7.65(d, J=9.6 Hz, 1H), 7.83(m, 1H), 7.95(d, J=8.0 Hz, 1H), 8.36(s, 1H), 8.45(m, 1H), 9.89(m, 1H), 13.30(br, 1H)

Example 534

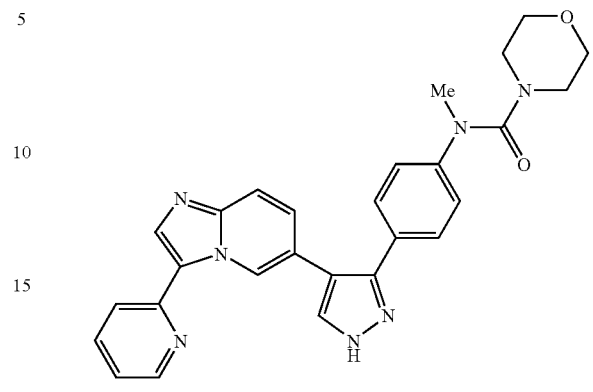

Morpholine-4-carboxylic acid methyl(4-[4-(3-pyridin-2-ylimidazo[1,2-a]pyridin-6-yl)-1H-pyrazol-3-yl] phenyl} amide 23 mg of the title compound was obtained as a colorless amorphous in the same method as in Example 84 from 53 mg morpholine-4-carboxylic acid methyl{4-[4-(3-pyridin-2-ylimidazo[1,2-a]pyridin-6-yl)-1-trityl-1H-pyrazol-3-yl]phenyl}amide (compound in Example 358).

$^1$H-NMR (CDCl$_3$)

δ: 3.17(m, 4H), 3.22(s, 3H), 3.45(m, 4H), 7.09(d, J=8.4 Hz, 2H), 7.14(m, 1H), 7.19(dd, J=9.2, 1.6 Hz, 1H), 7.50(d, J=8.4 Hz, 2H), 7.64(d, J=9.2 Hz, 1H), 7.73(m, 2H), 7.82(s, 1H), 8.16(s, 1H), 8.52(d, J=5.2 Hz, 1H), 10.00(brs, 1H)

Example 535

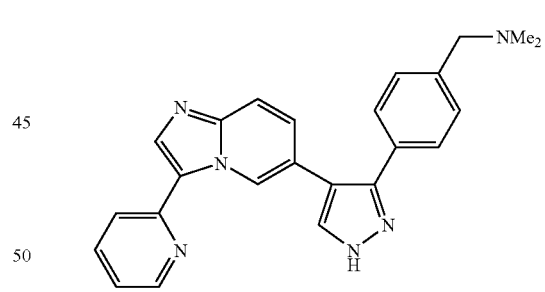

Dimethyl{4-[4-(3-pyridin-2-ylimidazo[1,2-a]pyridin-6-yl)-1H-pyrazol-3-yl] benzyl} amine 28 mg of the title compound was obtained as white crystals in the same method as in Example 84 from 78 mg dimethyl{4-[4-(3-pyridin-2-ylimidazo[1,2-a]pyridin-6-yl)-1-trityl-1H-pyrazol-3-yl]benzyl} amine (compound in Example 360).

$^1$H-NMR (CDCl$_3$)

δ: 2.25(s, 6H), 3.46(s, 2H), 7.10(m, 1H), 7.19(dd, J=9.2, 1.6 Hz, 1H), 7.31(d, J=8.0 Hz, 2H), 7.46(d, J=8.0 Hz, 2H), 7.61(dd, J=9.2, 0.8 Hz, 1H), 7.72(m, 2H), 7.82(s, 1H), 8.13(s, 1H), 8.49(m, 1H), 9.99(dd, J=1.6, 0.8 Hz, 1H)

Example 536

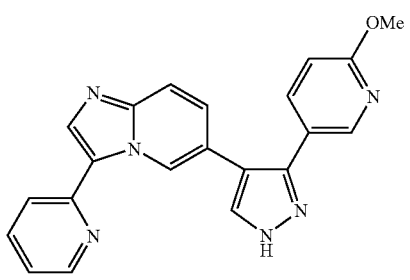

Methyl{4-[4-(3-pyridin-2-ylimidazo[1,2-a]pyridin-6-yl)-1H-pyrazol-3-yl] phenyl} amine 25 mg of the title compound was obtained as white crystals in the same method as in Example 84 from 69 mg t-butyl methyl {4-[4-(3-pyridin-2-ylimidazo[1,2-a]pyridin-6-yl)-1-trityl-1H-pyrazol-3-yl]phenyl} carbaminate (compound in Example 362).

$^1$H-NMR (CDCl$_3$)

δ: 2.85(s, 3H), 6.59(d, J=8.4 Hz, 2H), 7.13(m, 1H), 7.23(dd, J=9.2, 2.0 Hz, 1H), 7.28(m, 3H), 7.59(d, J=9.2 Hz, 1H), 7.72(m, 2H), 7.80(s, 1H), 8.12(s, 1H), 8.54(d, J=5.2 Hz, 1H), 9.99(brs, 1H)

Example 537

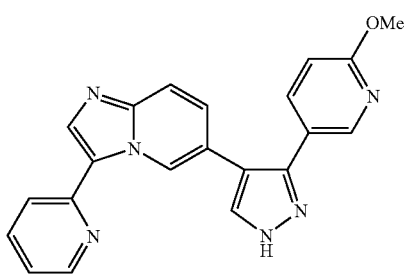

6-[3-(6-Methoxypyridin-3-yl)-1H-pyrazol-4-yl]-3-(pyridin-2-yl)imidazo[1,2-a]pyridine 42 mg of the title compound was obtained as white crystals in the same method as in Example 84 from 126 mg 6-[3-(6-methoxypyridin-3-yl)-1-trityl-1H-pyrazol-4-yl]-3-(pyridin-2-yl)imidazo[1,2-a]pyridine (compound in Example 363).

$^1$H-NMR (CDCl$_3$)

δ: 3.93(s, 3H), 6.74(d, J=8.8 Hz, 1H), 7.13(m, 1H), 7.21(dd, J=9.2, 1.6 Hz, 1H), 7.66(d, J=9.2 Hz, 1H), 7.72(m, 3H), 7.84(s, 1H), 8.14(s, 1H), 8.34(d, J=2.8 Hz, 1H), 8.48(d, J=5.2 Hz, 1H), 9.97(dd, J=1.6, 0.8 Hz, 1H)

Example 538

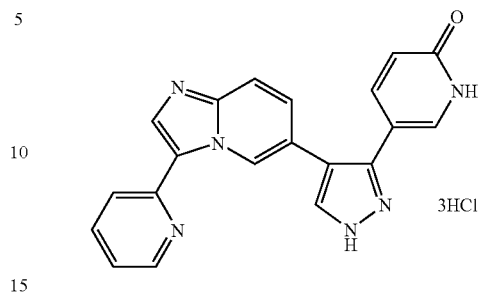

5-[4-(3-Pyridin-2-ylimidazo[1,2-a]pyridin-6-yl)-1H-pyrazol-3-yl]-1H-pyridin-2-one trihydrochloride A mixture of 126 mg 6-[3-(6-methoxypyridin-3-yl)-1-trityl-1H-pyrazol-4-yl]-3-(pyridin-2-yl)imidazo[1,2-a]pyridine (compound in Example 363), 5 mL of 5 N hydrochloric acid and 5 mL ethanol was heated overnight under reflux. The reaction solution was evaporated, and the residue was subjected to azeotropic distillation with toluene. The residue was triturated with methanol and ethyl acetate. The crystals were collected by filtration and then dried under reduced pressure with a vacuum pump, to give 66 mg of the title compound as white crystals.

$^1$H-NMR (DMSO-d$_6$)

δ: 6.38(d, J=9.6 Hz, 1H), 7.46(m, 1H), 7.51(dd, J=9.2, 2.4 Hz, 1H), 7.57(d, J=2.4 Hz, 1H), 8.02(dd, J=7.6, 2.0 Hz, 1H), 8.10(m, 3H), 8.19(s, 1H), 8.54(d, J=4.0 Hz, 1H), 9.03(s, 1H), 10.11(brs, 1H)

Example 539

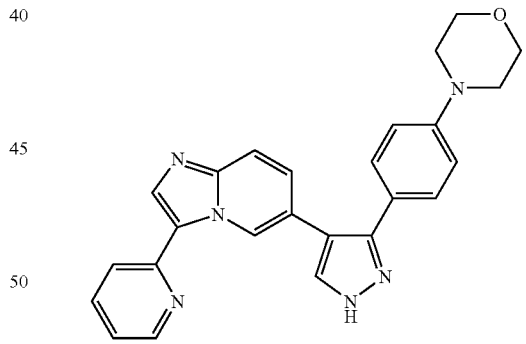

6-[3-(4-Morpholine-4-ylphenyl)-1H-pyrazol-4-yl]-3-(pyridin-2-yl)imidazo[1,2-a]pyridine 62 mg of the title compound was obtained as pale yellowish brown crystals in the same method as in Example 84 from 154 mg 6-[3-(4-Morpholine-4-ylphenyl)-1-trityl-1H-pyrazol-4-yl]-3-(pyridin-2-yl)imidazo[1,2-a]pyridine (compound in Example 364).

$^1$H-NMR (CDCl$_3$)

δ: 3.18(t, J=4.4 Hz, 4H), 3.85(t, J=4.4 Hz, 4H), 6.89(d, J=8.8 Hz, 2H), 7.13(m, 1H), 7.22(dd, J=9.2, 1.6 Hz, 1H), 7.39(d, J=8.8 Hz, 2H), 7.61(d, J=9.2 Hz, 1H), 7.72(m, 2H), 7.81(s, 1H), 8.13(s, 1H), 8.52(m, 1H), 10.00(brs, 1H)

Example 540

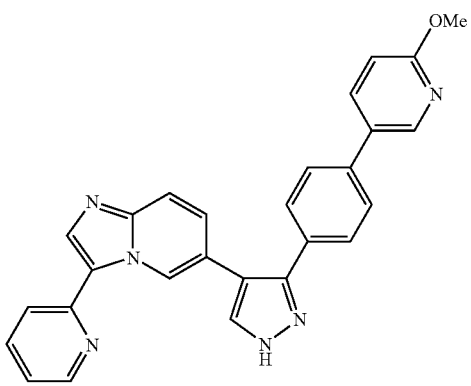

6-{3-[4-(6-Methoxypyridin-3-yl)phenyl]-1H-pyrazol-4-yl}-3-(pyridin-2-yl)imidazo[1,2-a]pyridine 32 mg of the title compound was obtained as white crystals in the same method as in Example 84 from 100 mg 6-{3-[4-(6-methoxypyridin-3-yl)phenyl]-1-trityl-1H-pyrazol-4-yl}-3-(pyridin-2-yl)imidazo[1,2-a]pyridine (compound in Example 365).

$^1$H-NMR (CDCl$_3$)

δ: 3.98(s, 3H), 6.82(dd, J=8.8, 0.8 Hz, 1H), 7.09(m, 1H), 7.26(dd, J=9.2, 1.6 Hz, 1H), 7.53(d, J=8.4 Hz, 2H), 7.60(d, J=8.4 Hz, 2H), 7.66(dd, J=9.2, 0.8 Hz, 1H), 7.70(m, 2H), 7.77(dd, J=4.4, 2.4 Hz, 1H), 7.86(s, 1H), 8.14(s, 1H), 8.38(dd, J=2.4, 0.8 Hz, 1H), 8.43(d, J=4.4 Hz, 1H), 10.02 (dd, J=1.6, 0.8 Hz, 1H)

Example 541

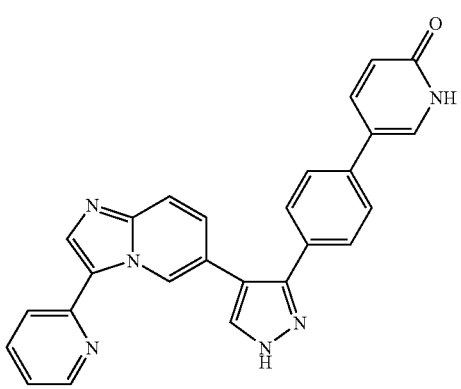

5-{4-[4-(3-Pyridin-2-ylimidazo[1,2-a]pyridin-6-yl)-1H-pyrazol-3-yl]phenyl}-1H-pyridin-2-one A mixture of 114 mg 6-{3-[4-(6-methoxypyridin-3-yl)phenyl]-1-trityl-1H-pyrazol-4-yl}-3-(pyridin-2-yl)imidazo[1,2-a]pyridine (compound in Example 365), 4 mL of 5 N hydrochloric acid and 4 mL ethanol was heated overnight under reflux. The reaction solution was basified with 5 N sodium hydroxide under ice-coolingd water, and the precipitated crystals were collected by filtration. The crystals were dried over hot air at 70° C., then dissolved in a mixture of methanol and dichloromethane and filtered. The filtrate was evaporated, then ethyl acetate was added to the residue which was then triturated, and the crystals were collected by filtration and dried under reduced pressure with a vacuum pump, to give 36 mg of the title compound as white crystals.

$^1$H-NMR (DMSO-d$_6$)

δ: 6.18(d, J=9.2 Hz, 1H), 7.12(m, 1H), 7.34(dd, J=9.2, 1.6 Hz, 1H), 7.45(d, J=8.4 Hz, 2H), 7.51(d, J=8.4 Hz, 2H), 7.60(m, 1H), 7.67(d, J=9.2, 1H), 7.80(m, 2H), 7.94(d, J=8.0 Hz, 1H), 7.97(s, 1H), 8.36(brs, 2H), 9.91(brs, 1H)

Example 542

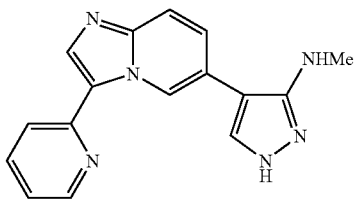

Methyl {4-[3-(pyridin-2-yl)imidazo[1,2-a]pyridin-6-yl]-1H-pyrazol-3-yl}amine 8 mg of the title compound was obtained as white crystals in the same method as in Example 84 from 40 mg t-butyl methyl{4-[3-(pyridin-2-yl)imidazo[1,2-a]pyridin-6-yl]-1-trityl-1H-pyrazol-3-yl}carbaminate (compound in Example 368).

$^1$H-NMR (CDCl$_3$)

δ: 3.00(s, 3H), 7.17(m, 1H), 7.39(dd, J=9.2, 2.0 Hz, 1H), 7.59(s, 1H), 7.72(d, J=9.6 Hz, 1H), 7.75(m, 2H), 8.14(s, 1H), 8.66(m, 1H), 10.06(brs, 1H)

Example 543

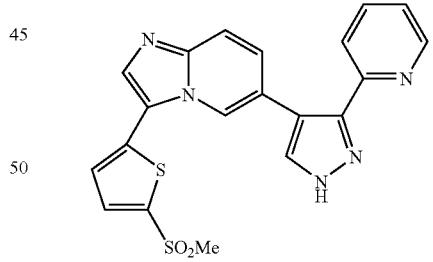

3-(5-Methylsulfonylthiophen-2-yl)-6-[3-(pyridin-2-yl)-1H-pyrazol-4-yl]imidazo[1,2-a]pyridine 27 mg of the title compound was obtained as pale yellow crystals in the same method as in Example 84 from 109 mg 3-(5-methylsulfonylthiophen-2-yl)-6-[3-(pyridin-2-yl)-1-trityl-1H-pyrazol-4-yl]imidazo[1,2-a]pyridine (compound in Example 370).

$^1$H-NMR (CDCl$_3$)

δ: 3.23(s, 3H), 7.28(d, J=3.6 Hz, 1H), 7.28(m, 1H), 7.37(dd, J=9.2, 2.0 Hz, 1H), 7.45(d, J=8.0 Hz, 1H), 7.65

(ddd, J=8.0, 8.0, 2.0 Hz, 1H), 7.74(m, 3H), 7.91(s, 1H), 8.57(d, J=1.2 Hz, 1H), 8.63(dd, J=4.8, 0.8 Hz, 1H)

Example 544

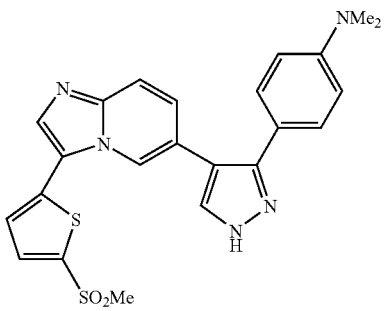

(4-{4-[3-(5-Methylsulfonylthiophen-2-yl)imidazo[1,2-a]pyridin-6-yl]-1H-pyrazol-3-yl}phenyl)dimethylamine 74 mg of the title compound was obtained as pale yellow crystals in the same method as in Example 84 from 86 mg (4-{4-[3-(5-methylsulfonylthiophen-2-yl)imidazo[1,2-a]-pyridin-6-yl]-1-trityl-1H-pyrazol-3-yl}phenyl)dimethylamine (compound in Example 374).

$^1$H-NMR (CDCl$_3$)

δ: 3.00(s, 6H), 3.21(s, 3H), 6.73(d, J=8.8 Hz, 2H), 6.93(d, J=4.0 Hz, 1H), 7.30(d, J=8.8 Hz, 2H), 7.37(dd, J=9.2, 2.0 Hz, 1H), 7.59(d, J=4.0 Hz, 1H), 7.68(d, J=9.2 Hz, 1H), 7.78(s, 1H), 7.82(s, 1H), 8.32(brs, 1H)

Example 545

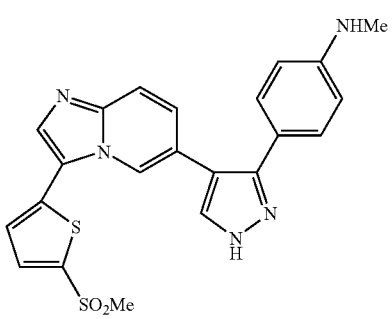

(4-{4-[3-(5-Methylsulfonylthiophen-2-yl)imidazo[1,2-a]-pyridin-6-yl]-1H-pyrazol-3-yl}phenyl)methylamine 21 mg of the title compound was obtained as pale yellow crystals in the same method as in Example 84 from 48 mg t-butyl methyl(4-{4-[3-(5-methylsulfonylthiophen-2-yl)imidazo[1,2-a]pyridin-6-yl]-1-trityl-1H-pyrazol-3-yl}phenyl)carbaminate (compound in Example 377).

$^1$H-NMR (CDCl$_3$)

δ: 2.87(s, 3H), 3.20(s, 3H), 6.65(d, J=8.8 Hz, 2H), 6.94(d, J=4.0 Hz, 1H), 7.25(d, J=8.8 Hz, 2H), 7.38(dd, J=9.2, 2.0 Hz, 1H), 7.63(d, J=4.0 Hz, 1H), 7.68(dd, J=9.2, 0.8 Hz, 1H), 7.79(s, 1H), 7.82(s, 1H), 8.29(dd, J=2.0, 0.8 Hz, 1H)

Example 546

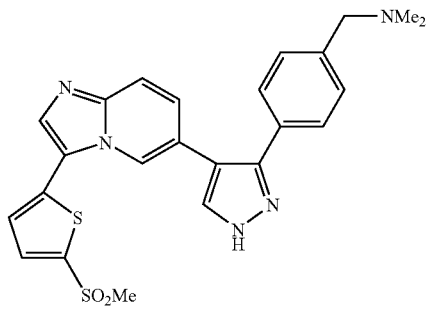

Dimethyl(4-{4-[3-(5-methylsulfonylthiophen-2-yl)imidazo[1,2-a]pyridin-6-yl]-1H-pyrazol-3-yl}benzyl)amine 28 mg of the title compound was obtained as pale yellow crystals in the same method as in Example 84 from 60 mg dimethyl(4-{4-[3-(5-methylsulfonylthiophen-2-yl)imidazo-[1,2-a]pyridin-6-yl]-1-trityl-1H-pyrazol-3-yl}benzyl)amine (compound in Example 380).

$^1$H-NMR (CDCl$_3$)

δ: 2.28(s, 6H), 3.22(s, 3H), 3.50(s, 2H), 6.97(d, J=4.0 Hz, 1H), 7.30(dd, J=9.6, 1.6 Hz, 1H), 7.37(d, J=8.4 Hz, 2H), 7.42(d, J=8.4 Hz, 2H), 7.65(d, J=4.0 Hz, 1H), 7.68(dd, J=9.6, 0.8 Hz, 1H), 7.79(s, 1H), 7.84(s, 1H), 8.29(dd, J=1.6, 0.8 Hz, 1H)

Example 547

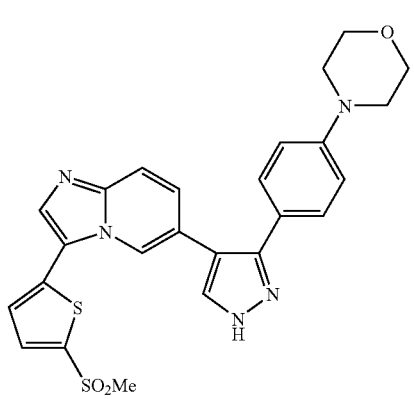

3-(5-Methylsulfonylthiophen-2-yl)-6-[3-(4-Morpholine-4-ylphenyl)-1H-pyrazol-4-yl]imidazo[1,2-a]pyridine 25 mg of the title compound was obtained as pale yellow crystals in the same method as in Example 84 from 147 mg 3-(5-methylsulfonylthiophen-2-yl)-6-[3-(4-Morpholine-4-ylphenyl)-1-trityl-1H-pyrazol-4-yl]imidazo[1,2-a]pyridine (compound in Example 382).

¹H-NMR (DMSO-d₆)

δ: 3.31(brs, 4H), 3.38(s, 3H), 3.73(m, 4H), 6.96(br, 3H), 7.28–7.42(m, 4H), 7.68(d, J=9.2 Hz, 1H), 7.79(d, J=4.0 Hz, 1H), 7.98(s, 1H), 8.42(brs, 1H)

Example 548

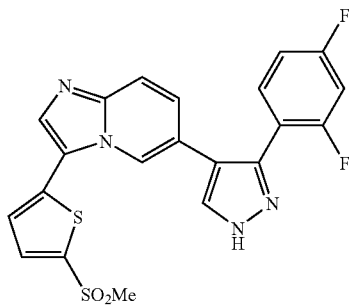

6-[3-(2,4-Difluorophenyl)-1H-pyrazol-4-yl]-3-(5-methylsulfonylthiophen-2-yl)imidazo[1,2-a]pyridine 52 mg of the title compound was obtained as grayish white crystals in the same method as in Example 84 from 118 mg 6-[3-(2,4-difluorophenyl)-1-trityl-1H-pyrazol-4-yl]-3-(5-methylsulfonylthiophen-2-yl)imidazo[1,2-a]pyridine (compound in Example 384).

¹H-NMR (DMSO-d₆)

δ: 3.40(s, 3H), 7.18–7.26(m, 3H), 7.37(dd, J=9.6, 1.6 Hz, 1H), 7.56(m, 1H), 7.72(dd, J=9.6, 0.8 Hz, 1H), 8.01(s, 1H), 8.25(brs, 1H), 8.36(brs, 1H), 13.40(brs, 1H)

MS m/e (ESI) 457 (MH⁺)

Example 549

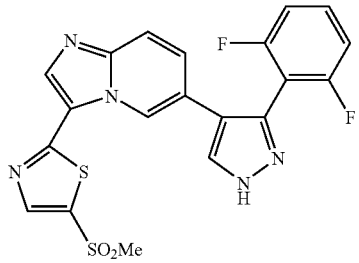

6-[3-(2,6-Difluorophenyl)-1H-pyrazol-4-yl]-3-(5-methylsulfonylthiazol-2-yl)imidazo[1,2-a]pyridine 78 mg of the title compound was obtained as pale yellow crystals in the same method as in Example 80 from 146 mg 6-[3-(2,6-difluorophenyl)-1-trityl-1H-pyrazol-4-yl]-3-(5-methylsulfonylthiazol-2-yl)imidazo[1,2-a]pyridine (compound in Example 386).

¹H-NMR (DMSO-d₆)

δ: 3.26(s, 3H), 7.24–7.36(br, 2H), 7.58–7.68(br, 1H), 7.72(dd, J=9.6, 2.0 Hz, 1H), 7.84(dd, J=9.6, 0.8 Hz, 1H), 8.18(s, 1H), 8.40–8.54(br, 1H), 8.51(s, 1H), 9.30(brs, 1H), 13.58(brs, 1H)

Example 550

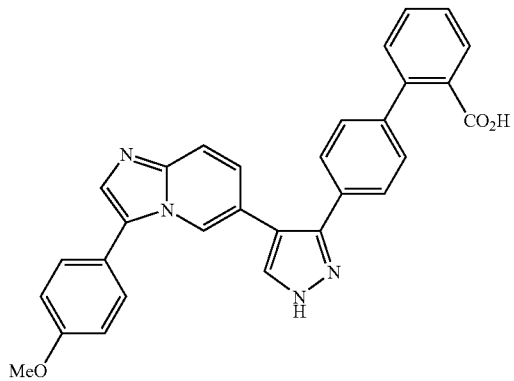

4'-{4-[3-(4-Methoxyphenyl)imidazo[1,2-a]pyridin-6-yl]-1H-pyrazol-3-yl}biphenyl-2-carboxylic acid A mixture of 119 mg methyl 4'-{4-[3-(4-methoxyphenyl)-imidazo[1,2-a]pyridin-6-yl]-1-trityl-1H-pyrazol-3-yl}biphenyl-2-carboxylate (compound in Example 387), 0.5 mL of 1 N aqueous sodium hydroxide and 3 mL methanol was heated at 60° C. overnight under reflux. An aqueous saturated ammonium chloride solution, ethyl acetate, tetrahydrofuran and water were added to the reaction solution, and the organic layer was separated, washed with brine and dried over anhydrous sodium sulfate. The drying agent was filtered off, and the filtrate was evaporated. 134 mg crude product of 4'-{4-[3-(4-methoxyphenyl)imidazo[1,2-a]pyridin-6-yl]-1-trityl-1H-pyrazol-3-yl}biphenyl-2-carboxylic acid was obtained as a colorless amorphous. From this compound, 30 mg of the title compound was obtained as white crystals by the same method as in Example 84.

¹H-NMR (DMSO-d₆)

δ: 3.69(s, 3H), 6.91(d, J=8.8 Hz, 2H), 7.18(m, 1H), 7.24(dd, J=9.2, 1.6 Hz, 1H), 7.32–7.52(m, 9H), 7.56–7.64 (m, 3H), 8.21(brs, 1H)

Example 551

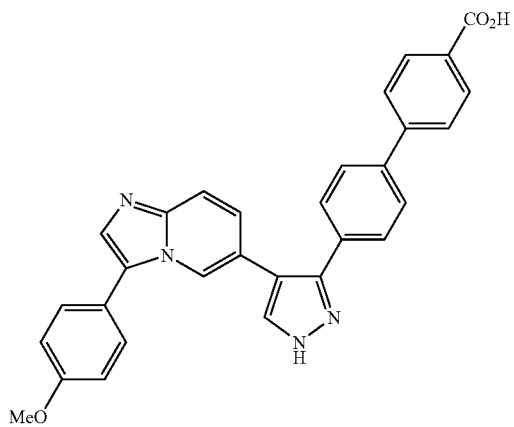

4'-{4-[3-(4-Methoxyphenyl)imidazo[1,2-a]pyridin-6-yl]-1H-pyrazol-3-yl}biphenyl-4-carboxylic acid 65 mg of the title compound was obtained as pale white crystals in the same method as in Example 550 from methyl 4'-{4-[3-(4-methoxyphenyl)imidazo[1,2-a]pyridin-6-yl]-1-trityl-1H-pyrazol-3-yl}biphenyl-4-carboxylate (compound in Example 388).

$^1$H-NMR (DMSO-$d_6$)

δ: 3.58(s, 3H), 6.80(d, J=8.4 Hz, 2H), 7.30(m, 3H), 7.61(m, 5H), 7.85(m, 4H), 8.02(d, J=8.0 Hz, 2H), 8.13(s, 1H)

Example 552

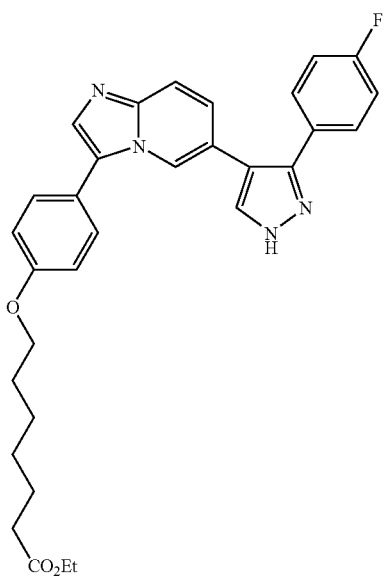

Ethyl 7-(4-{6-[3-(4-fluorophenyl)-1H-pyrazol-4-yl]imidazo[1,2-a]pyridin-3-yl}phenoxy)heptanoate 16 mg of the title compound was obtained as white crystals in the same method as in Example 84 from 40 mg ethyl 7-(4-{6-[3-(4-fluorophenyl)-1-trityl-1H-pyrazol-4-yl]imidazo[1,2-a]pyridin-3-yl}phenoxy)heptanoate (compound in Example 389).

$^1$H-NMR (CDCl$_3$)

δ: 1.26(t, J=7.2 Hz, 3H), 1.43(m, 2H), 1.52(m, 2H), 1.68(m, 2H), 1.82(m, 2H), 2.33(t, J=7.2 Hz, 2H), 4.00(t, J=6.4 Hz, 2H), 4.14 (q, J=7.2 Hz, 2H), 6.92(d, J=8.8 Hz, 2H), 7.12(m, 3H), 7.23(d, J=8.8 Hz, 2H), 7.47(m, 2H), 7.61(s, 1H), 7.62(dd, J=9.2, 0.8 Hz, 1H), 7.74(s, 1H), 8.08(s, 1H)

Example 553

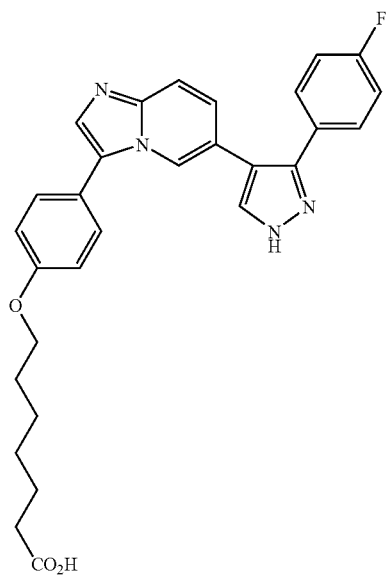

7-(4-{6-[3-(4-Fluorophenyl)-1H-pyrazol-4-yl]imidazo[1,2-a]-pyridin-3-yl}phenoxy)heptanoic acid 48 mg of the title compound was obtained as white crystals in the same method as in Example 550 from 115 mg ethyl 7-(4-{6-[3-(4-fluorophenyl)-1-trityl-1H-pyrazol-4-yl]imidazo[1,2-a]pyridin-3-yl}phenoxy)heptanoate (compound in Example 389).

$^1$H-NMR (DMSO-$d_6$)

δ: 1.36(m, 2H), 1.45(m, 2H), 1.54(m, 2H), 1.75(m, 2H), 2.23(t, J=7.2 Hz, 2H), 4.01(t, J=6.4 Hz, 2H), 6.97(d, J=8.8 Hz, 2H), 7.20–7.32(m, 4H), 7.34(d, J=8.8 Hz, 2H), 7.51(m, 2H), 7.62(dd, J=9.2, 0.8 Hz, 1H), 7.63(s, 1H), 8.10(s, 1H)

Example 554

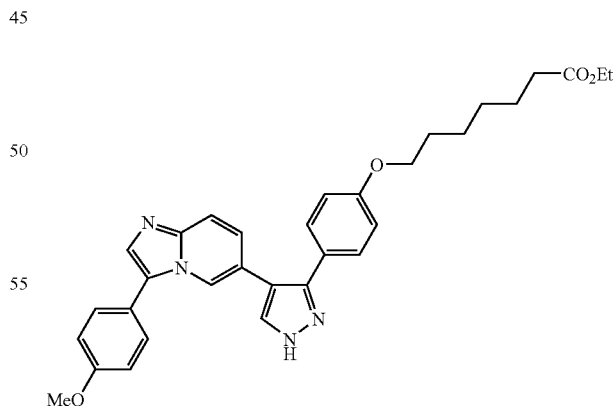

Ethyl 7-(4-{4-[3-(4-methoxyphenyl)imidazo[1,2-a]-6-yl]-1H-pyrazol-3-yl}phenoxy)heptanoate 15 mg of the title compound was obtained as white crystals in the same method as in Example 84 from 40 mg ethyl 7-(4-{4-[3-(4-methoxyphenyl)imidazo[1,2-a]-6-yl]-1-trityl-1H-pyrazol-3-yl}phenoxy)heptanoate (compound in Example 392).

¹H-NMR (CDCl₃)

δ: 1.25(t, J=7.2 Hz, 3H), 1.42(m, 2H), 1.46(m, 2H), 1.66(m, 2H), 1.80(m, 2H), 2.31(t, J=7.6 Hz, 2H), 3.86(s, 3H), 3.96(t, J=6.4 Hz, 2H), 4.13 (q, J=7.2 Hz, 2H), 6.92(d, J=8.8 Hz, 2H), 6.94(d, J=9.2 Hz, 2H), 7.18(dd, J=9.2, 1.2 Hz, 1H), 7.25(m, 2H), 7.37(d, J=8.8 Hz, 2H), 7.61(m, 2H), 7.73(s, 1H), 8.12(s, 1H)

Example 555

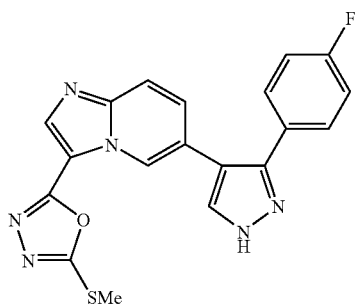

6-[3-(4-Fluorophenyl)-1H-pyrazol-4-yl]-3-(5-methylsulfanyl[1,3,4]oxadiazol-2-yl)imidazo[1,2-a]pyridine 13 mg of the title compound was obtained as white crystals in the same method as in Example 84 from 30 mg 6-[3-(4-fluorophenyl)-1-trityl-1H-pyrazol-4-yl]-3-(5-methylsulfanyl[1,3,4]oxadiazol-2-yl)imidazo[1,2-a]pyridine (compound in Example 393).

¹H-NMR (DMSO-d₆)

δ: 2.78(s, 3H), 7.20–7.32(br, 3H), 7.40(d, J=9.6 Hz, 1H), 7.51(m, 2H), 7.83(d, J=9.6 Hz, 1H), 8.37(s, 1H), 9.12(s, 1H)

MS m/e (ESI) 392 (MH⁺)

Example 556

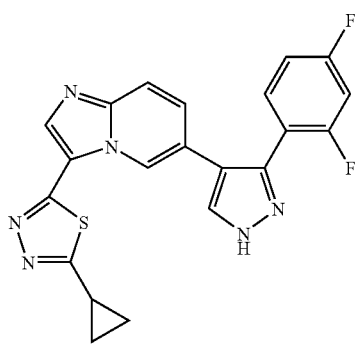

3-(5-Cyclopropyl[1,3,4]thiadiazol-2-yl)₆-[3-(2,4-difluorophenyl)-1H-pyrazol-4-yl]imidazo[1,2-a]pyridine 24 mg of the title compound was obtained as white crystals in the same method as in Example 84 from 65 mg 3-(5-cyclopropyl[1,3,4]thiadiazol-2-yl)₆-[3-(2,4-difluorophenyl)-1-trityl-1H-pyrazol-4-yl]imidazo[1,2-a]-pyridine (compound in Example 394).

¹H-NMR (DMSO-d₆)

δ: 1.07(m, 2H), 1.25(m, 2H), 2.56(m, 1H), 7.18(m, 2H), 7.40–7.58(m, 2H), 7.75(d, J=9.2 Hz, 1H), 8.23(s, 1H), 8.33(s, 1H), 9.32(s, 1H), 13.40(brs, 1H)

MS m/e (ESI) 421 (MH⁺)

Example 557

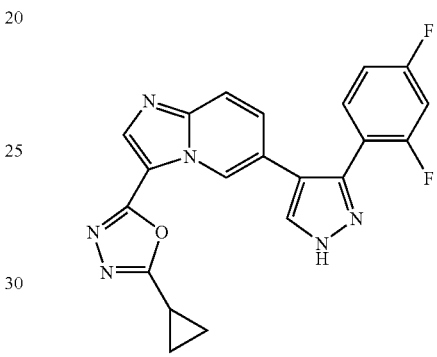

3-(5-Cyclopropyl[1,3,4]oxadiazol-2-yl)6-[3-(2,4-difluorophenyl)-1H-pyrazol-4-yl]imidazo[1,2-a] pyridine 22 mg of the title compound was obtained as white crystals in the same method as in Example 84 from 59 mg 3-(5-cyclopropyl[1,3,4]oxadiazol-2-yl)₆-[3-(2,4-difluorophenyl)-1-trityl-1H-pyrazol-4-yl]imidazo[1,2-a]pyridine (compound in Example 395).

¹H-NMR (CDCl₃)

δ: 1.23(m, 4H), 2.26(m, 1H), 6.91(m, 2H), 7.24(dd, J=9.2, 2.0 Hz, 1H), 7.42(m, 1H), 7.68(dd, J=9.2, 0.8 Hz, 1H), 7.89(s, 1H), 8.19(s, 1H), 9.40(dd, J=2.0, 0.8 Hz, 1H)

Example 558

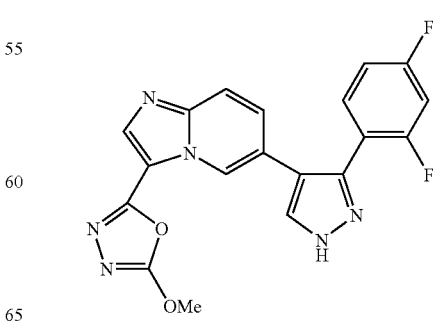

6-[3-(2,4-Difluorophenyl)-1H-pyrazol-4-yl]-3-(5-methoxy[1,3,4]oxadiazol-2-yl)imidazo[1,2-a]pyridine 17 mg of the title compound was obtained as white crystals in the same method as in Example 84 from 48 mg 6-[3-(2,4-difluorophenyl)-1-trityl-1H-pyrazol-4-yl]-3-(5-methoxy[1,3,4]oxadiazol-2-yl)imidazo[1,2-a]pyridine (compound in Example 396).
$^1$H-NMR (CDCl$_3$)
δ: 4.28(s, 3H), 6.92(m, 2H), 7.23(dd, J=9.2, 1.6 Hz, 1H), 7.41(m, 1H), 7.68(dd, J=9.2, 0.8 Hz, 1H), 7.89(s, 1H), 8.15(s, 1H), 9.30(dd, J=1.6, 0.8 Hz, 1H)
MS m/e (ESI) 395 (MH$^+$)

Example 559

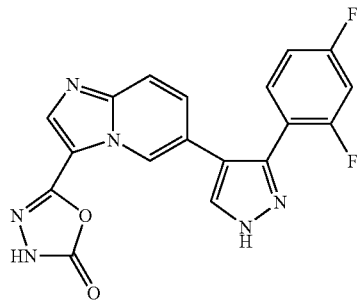

5-{6-[3-(2,4-Difluorophenyl)-1H-pyrazol-4-yl]imidazo[1,2-a]pyridin-3-yl}-3H-[1,3,4]oxadiazol-2-one 18 mg of the title compound was obtained as white crystals in the same method as in Example 84 from 46 mg 6-[3-(2,4-difluorophenyl)-1-trityl-1H-pyrazol-4-yl]-3-(5-isopropoxy[1,3,4]oxadiazol-2-yl)imidazo[1,2-a]pyridine (compound in Example 397).
$^1$H-NMR (DMSO-d$_6$)
δ: 7.14–7.32(m, 2H), 7.48(dd, J=9.2, 2.0 Hz, 1H), 7.55(m, 1H), 7.81(dd, J=9.2, 1.2 Hz, 1H), 8.17(s, 1H), 8.33(s, 1H), 8.71(s, 1H), 12.65(brs, 1H), 13.44(brs, 1H)

Example 560

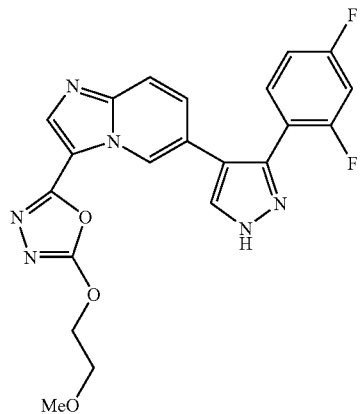

6-[3-(2,4-Difluorophenyl)-1H-pyrazol-4-yl]-3-[5-(2-methoxyethoxy)[1,3,4]oxadiazol-2-yl]imidazo[1,2-a]pyridine 17 mg of the title compound was obtained as white crystals in the same method as in Example 84 from 107 mg 6-[3-(2,4-difluorophenyl)-1-trityl-1H-pyrazol-4-yl]-3-[5-(2-methoxyethoxy)[1,3,4]oxadiazol-2-yl]imidazo[1,2-a]pyridine (compound in Example 398).
$^1$H-NMR (CDCl$_3$)
δ: 3.46(s, 3H), 3.83(m, 2H), 4.70(m, 2H), 6.91(m, 2H), 7.23(dd, J=9.2, 1.6 Hz, 1H), 7.43(m, 1H), 7.67(m, 1H), 7.88(s, 1H), 8.14(s, 1H), 9.29(brs, 1H)

Example 561

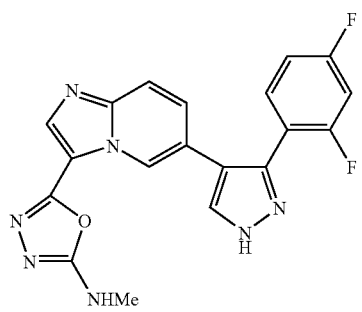

(5-{6-[3-(2,4-Fluorophenyl)-1H-pyrazol-4-yl]imidazo[1,2-a]-pyridin-3-yl}[1,3,4]oxadiazol-2-yl)methylamine 30 mg of the title compound was obtained as white crystals in the same method as in Example 84 from 79 mg (5-{6-[3-(2,4-fluorophenyl)-1-trityl-1H-pyrazol-4-yl]imidazo[1,2-a]-pyridin-3-yl}[1,3,4]oxadiazol-2-yl)methylamine (compound in Example 400).
$^1$H-NMR (DMSO-d$_6$)
δ: 2.88(d, J=4.8 Hz, 3H), 7.14–7.34(m, 2H), 7.37(dd, J=9.2, 1.6 Hz, 1H), 7.57(m, 1H), 7.73 (q, J=4.8 Hz, 1H), 7.76(dd, J=9.2, 0.8 Hz, 1H), 8.07(s, 1H), 8.14–8.26(br, 1H), 8.05(s, 1H), 13.44(brs, 1H)

Example 562

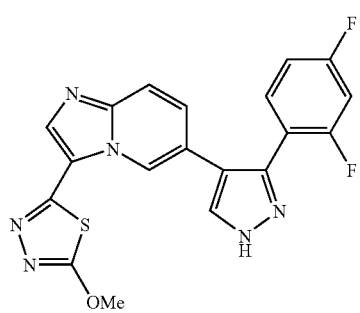

6-[3-(2,4-Fluorophenyl)-1H-pyrazol-4-yl]-3-(5-methoxy[1,3,4]thiadiazol-2-yl)imidazo[1,2-a]pyridine 3 mg of the title compound was obtained as white crystals in the same method as in Example 84 from 11 mg 6-[3-(2,4-fluorophenyl)-1-trityl-1H-pyrazol-4-yl]-3-(5-methoxy[1,3,4]thiadiazol-2-yl)imidazo[1,2-a]pyridine (compound in Example 401).

MS m/e (ESI) 410 (MH+)

Example 563

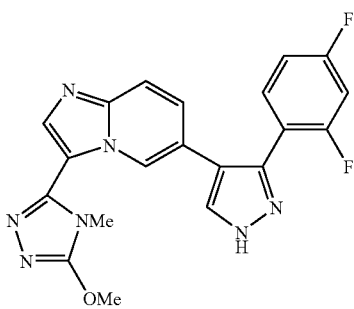

6-[3-(2,4-Fluorophenyl)-1H-pyrazol-4-yl]-3-(5-methoxy-4-methyl-4H-[1,2,4]triazol-3-yl)imidazo[1,2-a]pyridine 10 mg of the title compound was obtained as white crystals in the same method as in Example 84 from 24 mg 6-[3-(2,4-fluorophenyl)-1-trityl-1H-pyrazol-4-yl]-3-(5-methoxy-4-methyl-4H-[1,2,4]triazol-3-yl)imidazo[1,2-a]pyridine (compound in Example 402).

¹H-NMR (DMSO-d₆)

δ: 3.56(s, 3H), 4.11(s, 3H), 7.12–7.32(m, 2H), 7.28(dd, J=9.2, 1.6 Hz, 1H), 7.54(m, 1H), 7.70(d, J=9.2, 1H), 8.05–8.28(br, 1H), 8.15(s, 1H), 9.24(brs, 1H), 13.40(brs, 1H)

MS m/e (ESI) 430 (MH+ Na adduct)

Example 564

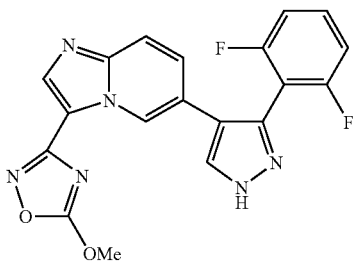

6-[3-(2,6-Difluorophenyl)-1H-pyrazol-4-yl]-3-(5-methoxy-[1,2,4]oxadiazol-3-yl)imidazo[1,2-a]pyridine 9.3 mg of the title compound was obtained as a white solid in the same method as in Example 84 from 34 mg 6-[3-(2,6-difluorophenyl)-1-trityl-1H-pyrazol-4-yl]-3-(5-methoxy-[1,2,4]oxadiazol-3-yl)imidazo[1,2-a]pyridine (compound in Example 403).

¹H-NMR (CDCl₃)

δ: 4.25(s, 3H), 7.00(m, 2H), 7.32(dd, J=9.2, 2.0 Hz, 1H), 7.41(m, 1H), 7.66(dd, J=9.2, 0.4 Hz, 1H), 7.98(s, 1H), 8.31(s, 1H), 9.62(brs, 1H)

Example 565

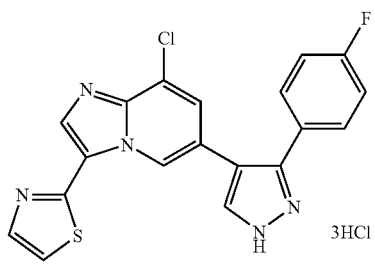

2-{8-Chloro-6-[3-(4-fluorophenyl)-1H-4-pyrazolyl]imidazo-[1,2-a]pyridin-3-yl}-1,3-thiazole trihydrochloride 60 mg of the title compound (colorless crystals) was obtained in the same manner as in Example 68 from 137 mg 2-{8-chloro-6-[3-(4-fluorophenyl)-1-trityl-1H-4-pyrazolyl]imidazo[1,2-a]pyridin-3-yl}-1,3-thiazole obtained in Example 404.

¹H-NMR (DMSO-d₆)

δ: 7.21–7.29(m, 2H), 7.48–7.57(m, 2H), 7.71–7.83(m, 3H), 8.16–8.22(m, 1H), 8.40–8.49(m, 1H), 9.47–9.52(m, 1H)

MS m/e (ESI) 396 (MH+)

Example 566

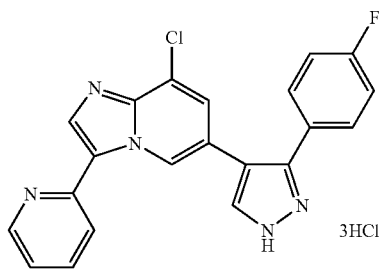

8-Chloro-6-[3-(4-fluorophenyl)-1H-4-pyrazolyl]-3-(2-pyridyl)imidazo[1,2-a]pyridine trihydrochloride 27 mg of the title compound (colorless crystals) was obtained in the same manner as in Example 68 from 235 mg 8-chloro-6-[3-(4-fluorophenyl)-1-trityl-1H-4-pyrazolyl]-3-(2-pyridinyl)imidazo[1,2-a]pyridine obtained in Example 405.

¹H-NMR (DMSO-d₆)
δ: 7.18–7.28(m, 2H), 7.33–7.43(m, 1H), 7.49–7.59(m, 2H), 7.89–8.14(m, 3H), 8.20–8.28(m, 1H), 8.31–8.36(m, 1H), 8.70–8.85(m, 1H), 9.86–9.93(m, 1H)
MS m/e (ESI) 390 (MH⁺)

Example 567

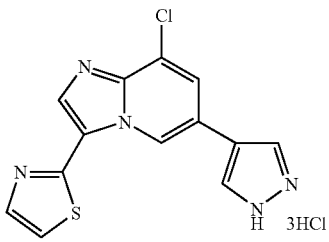

2-[8-Chloro-6-(1H-4-pyrazolyl)imidazo[1,2-a]pyridin-3-yl]-1,3-thiazole trihydrochloride 75 mg of the title compound (pale yellow amorphous) was obtained in the same manner as in Example 68 from 171 mg 2-[8-chloro-6-(1-trityl-1H-4-pyrazolyl)imidazo[1,2-a]pyridin-3-yl]-1,3-thiazole obtained in Example 406.
¹H-NMR (DMSO-d₆)
δ: 7.87–7.92(m, 1H), 8.05–8.12(m, 1H), 8.17–8.31(m, 3H), 8.56–8.64(m, 1H), 9.83(s, 1H).
MS m/e (ESI) 302 (MH⁺)

Example 568

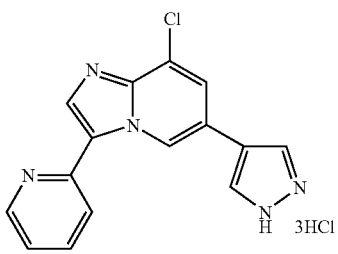

8-[8-Chloro-6-(1H-4-pyrazolyl)-3-(2-pyridinyl)imidazo[1,2-a]pyridine trihydrochloride 30 mg of the title compound (colorless crystals) was obtained in the same manner as in Example 68 from 87 mg 8-chloro-6-(1-trityl-1H-4-pyrazolyl)-3-(2-pyridinyl)imidazo[1,2-a]-pyridine obtained in Example 407.
¹H-NMR (DMSO-d₆)
δ: 7.44–7.51(m, 1H), 7.99–8.08(m, 1H), 8.15(d, J=8.0 Hz, 1H), 8.24–8.32(m, 2H), 8.38(s, 1H), 8.79–8.90(m, 2H), 10.26(s, 1H)
MS m/e (ESI) 296 (MH⁺)

Example 569

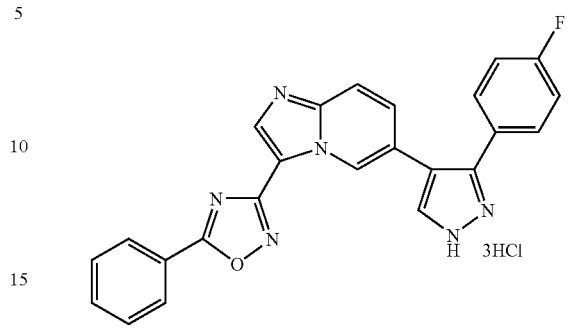

6-[3-(4-Fluorophenyl)-1H-4-pyrazolyl]-3-(5-phenyl-[1,2,4]oxadiazol-3-yl)-imidazo[1,2-a]pyridine trihydrochloride 1.2 mg of the title compound (colorless crystals) was obtained in the same manner as in Example 67 from 18 mg 6-[3-(4-fluorophenyl)-1-trityl-1H-4-pyrazolyl]-3-(5-phenyl-[1,2,4]oxadiazol-3-yl)-imidazo[1,2-a]pyridine obtained in Example 408.
¹H-NMR (DMSO-d₆)
δ: 7.20–7.28(m, 2H), 7.52–7.59(m, 2H), 7.62(d, J=9.6 Hz, 1H), 7.52(s, 1H), 7.67–7.80(m, 3H), 7.93(d, J=9.6 Hz, 1H), 8.11–8.20(m, 3H), 8.61(s, 1H), 9.15(m, 1H)

Example 570

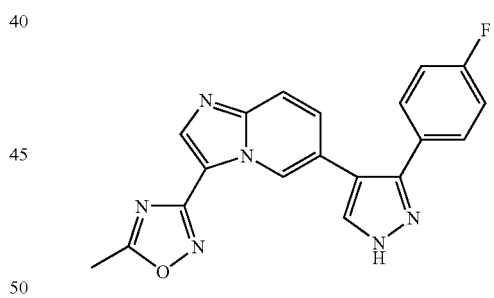

6-[3-(4-Fluorophenyl)-1H-4-pyrazolyl]-3-(5-methyl-[1,2,4]oxadiazol-3-yl)-imidazo[1,2-a]pyridine 23 mg of the title compound (colorless crystals) was obtained in the same manner as in Example 80 from 18 mg 6-[3-(4-fluorophenyl)-1-trityl-1H-4-pyrazolyl]-3-(5-methyl-[1,3,4]oxadiazol-3-yl)-imidazo[1,2-a]pyridine obtained in Example 409.
¹H-NMR (DMSO-d₆)
δ: 2.67(s, 3H), 7.14–7.32(m, 2H), 7.42(dd, J=9.2, 2.0 Hz, 1H), 7.47–7.57(m, 2H), 7.81(dd, J=9.2, 1.2 Hz, 1H), 8.11–8.23(m, 1H), 8.29(s, 1H), 8.98(dd, J=2.0, 1.2 Hz, 1H)
MS m/e (ESI) 361 (MH⁺)

Example 571

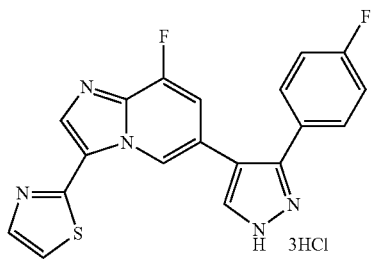

2-{8-Fluoro-6-[3-(4-fluorophenyl)-1H-4-pyrazolyl]imidazo-[1,2-a]pyridin-3-yl}-1,3-thiazole trihydrochloride 40 mg of the title compound (slightly brown crystals) was obtained in the same manner as in Example 68 from 91 mg 2-{8-fluoro-6-[3-(4-fluorophenyl)-1-trityl-1H-4-pyrazolyl]-imidazo[1,2-a]pyridin-3-yl}-1,3-thiazole obtained in Example 410.

$^1$H-NMR (DMSO-$d_6$)

δ: 7.21–7.32(m, 2H), 7.45(brd, J=12.0 Hz, 1H), 7.50–7.59 (m, 2H), 7.74–7.84(m, 2H), 8.11–8.19(m, 1H), 8.36(s, 1H), 9.36(d, J=1.6 Hz, 1H)

MS m/e (ESI) 380 (MH$^+$)

Example 572

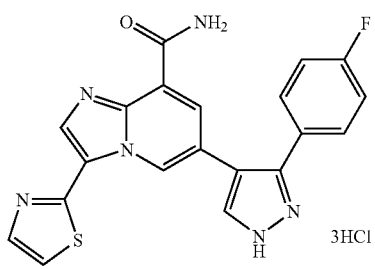

6-[3-(4-Fluorophenyl)-1H-4-pyrazolyl]-3-(2-thiazolyl)imidazo[1,2-a]pyridin-8-carboxyamide From 68 mg 6-[3-(4-fluorophenyl)-1-trityl-1H-4-pyrazolyl]-3-(2-thiazolyl)imidazo[1,2-a]pyridin-8-carbonitrile obtained in Example 411, 30 mg of the title compound (pale yellow crystals) was obtained in the same manner as in Example 68, under the conditions of which the hydrolysis of the cyano group simultaneously proceeded.

$^1$H-NMR (DMSO-$d_6$)

δ: 7.19–7.30(m, 2H), 7.50–7.60(m, 2H), 7.78–7.90(m, 2H), 8.11–8.30(m, 3H), 8.56(brs, 1H), 8.24(brs, 1H), 9.75(d, J=1.6 Hz, 1H)

MS m/e (ESI) 405 (MH$^+$)

Example 573

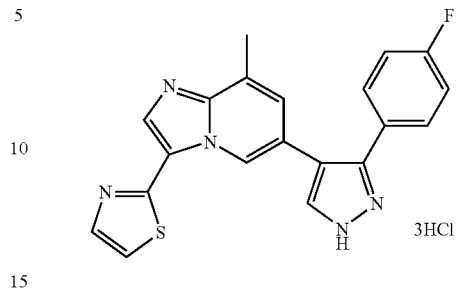

2-{6-[3-(4-Fluorophenyl)-1H-4-pyrazolyl]-8-methylimidazo-[1,2-a]pyridin-3-yl}-1,3-thiazole trihydrochloride 30 mg of the title compound (colorless crystals) was obtained in the same manner as in Example 68 from 118 mg 2-{6-[3-(4-fluorophenyl)-1-trityl-1H-4-pyrazolyl]-8-methylimidazo[1,2-a]pyridin-3-yl}-1,3-thiazole obtained in Example 412.

$^1$H-NMR (DMSO-$d_6$)

δ: 2.61(s, 3H), 7.20–7.31(m, 2H), 7.45–7.60(m, 2H), 7.70–7.93(m, 3H), 8.12–8.24(m, 1H), 8.80–8.98(m, 1H), 9.49–9.57(m, 1H)

MS m/e (ESI) 376 (MH$^+$)

Example 574

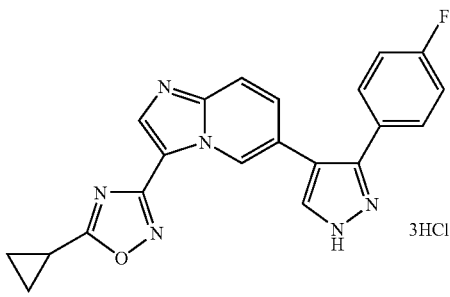

3-(5-Cyclopropyl-[1,2,4]oxadiazol-3-yl)-6-[3-(4-fluorophenyl)-1H-4-pyrazolyl]-imidazo[1,2-a]pyridine trihydrochloride 51 mg of the title compound (colorless crystals) was obtained in the same manner as in Example 68 from 138 mg 3-(5-cyclopropyl-[1,2,4]oxadiazol-3-yl)-6-[3-(4-fluorophenyl)-1-trityl-1H-4-pyrazolyl]-imidazo[1,2-a]-pyridine obtained in Example 413.

$^1$H-NMR (DMSO-$d_6$)

δ: 1.14–1.24(m, 2H), 1.28–1.42(m, 2H), 2.40–2.64(m, 1H), 7.16–7.28(m, 2H), 7.44–7.56(m, 2H), 7.60–7.70(m, 1H), 7.88–7.96(m, 1H), 8.13(s, 1H), 8.48–8.59(m, 1H), 9.03(s, 1H)

MS m/e (ESI) 387 (MH$^+$)

Example 575

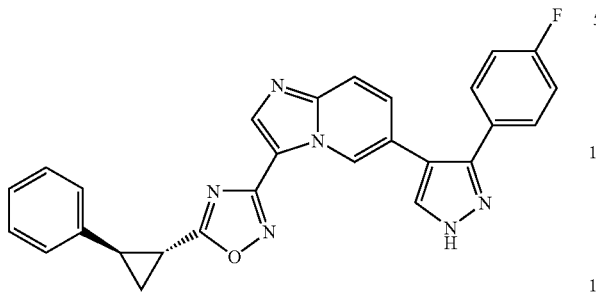

6-[3-(4-Fluorophenyl)-1H-4-pyrazolyl]-3-[5-(2-phenylcyclopropyl)-[1,2,4]oxadiazol-3-yl]-imidazo[1,2-a]-pyridine 45 mg of the title compound (colorless crystals) was obtained in the same manner as in Example 80 from 107 mg 6-[3-(4-fluorophenyl)-1-trityl-1H-4-pyrazolyl]-3-[5-(2-phenylcyclopropyl)-[1,2,4]oxadiazol-3-yl]-imidazo[1,2-a]pyridine obtained in Example 414.

$^1$H-NMR (CDCl$_3$)

δ: 1.71–1.79(m, 1H), 1.90–1.97(m, 1H), 2.50–2.56(m, 1H), 2.78–2.86(m, 1H), 7.02–7.11(m, 2H), 7.15–7.37(m, 6H), 7.42–7.50(m, 2H), 7.68(d, J=9.2 Hz, 1H), 7.83(s, 1H), 8.35(s, 1H), 9.13–9.17(m, 1H)

Example 576

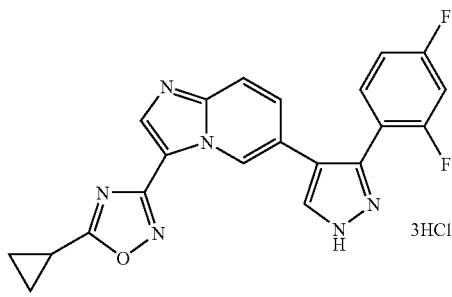

3-(5-Cyclopropyl-[1,2,4]oxadiazol-3-yl)-6-[3-(2,4-difluorophenyl)-1H-4-pyrazolyl]-imidazo[1,2-a]pyridine trihydrochloride 90 mg of the title compound (colorless crystals) was obtained in the same manner as in Example 68 from 207 mg 3-(5-cyclopropyl-[1,2,4]oxadiazol-3-yl)-6-[3-(2,4-difluorophenyl)-1-trityl-1H-4-pyrazolyl]-imidazo[1,2-a]-pyridine obtained in Example 415.

$^1$H-NMR (DMSO-d$_6$)

δ: 1.14–1.22(m, 2H), 1.30–1.38(m, 2H), 2.40–2.49(m, 1H), 7.23(ddd, J=8.4, 8.4, 2.4 Hz, 1H), 7.34(ddd, J=10.0, 10.0,2.4 Hz, 1H), 7.60(ddd, J=8.4, 6.4, 6.4 Hz, 1H), 7.81(brd, J=9.6 Hz, 1H), 7.94(d, J=9.6 Hz, 1H), 8.34(s, 1H), 8.54(s, 1H), 8.92(s, 1H)

MS m/e (ESI) 405 (MH$^+$)

Example 577

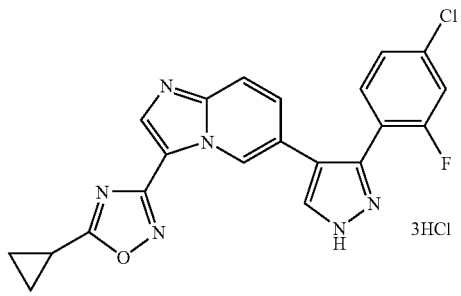

6-[3-(4-Chloro-2-fluorophenyl)-1H-4-pyrazolyl]-3-(5-cyclopropyl-[1,2,4]oxadiazol-3-yl)-imidazo[1,2-a]pyridine trihydrochloride 115 mg of the title compound (colorless amorphous) was obtained in the same manner as in Example 68 from 317 mg 6-[3-(4-chloro-2-fluorophenyl)-1-trityl-1H-4-pyrazolyl]-3-(5-cyclopropyl-[1,2,4]oxadiazol-3-yl)-imidazo[1,2-a]-pyridine obtained in Example 416.

$^1$H-NMR (DMSO-d$_6$)

δ: 1.12–1.46(m, 4H), 2.38–2.62(m, 1H), 7.43(dd, J=8.0, 2.0 Hz, 1H), 7.52(dd, J=10.4, 2.0 Hz, 1H), 7.57(dd, J=8.0, 8.0 Hz, 1H), 7.75–7.90(m, 1H), 7.95(brd, J=9.2 Hz, 1H), 8.36(s, 1H), 8.51–8.64(m, 1H), 8.93(brs, 1H)

MS m/e (ESI) 421 (MH$^+$)

Example 578

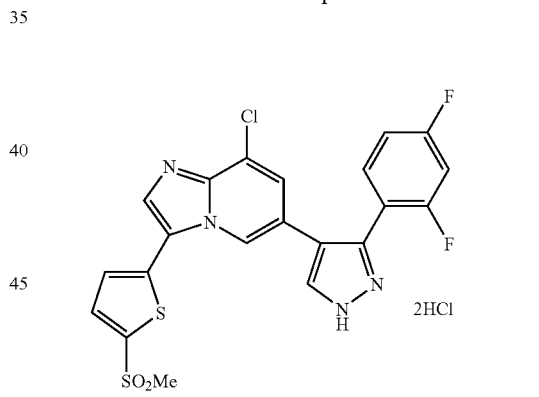

8-Chloro-6-[3-(2,4-difluorophenyl)-1H-4-pyrazolyl]-3-[5-(methylsulfonyl)-2-thienyl]imidazo[1,2-a]pyridine dihydrochloride 82 mg of the title compound (colorless crystals) was obtained in the same manner as in Example 68 from 178 mg 8-chloro-6-[3-(2,4-difluorophenyl)-1-trityl-1H-4-pyrazolyl]-3-[5-(methylsulfonyl)-2-thienyl]imidazo[1,2-a]pyridine obtained in Example 418. $^1$H-NMR data are those of the salt in a free form.

$^1$H-NMR (CDCl$_3$)

δ: 3.24(s, 3H), 6.92–6.99(m, 1H), 7.00–7.07(m, 2H), 7.38(d, J=1.2 Hz, 1H), 7.46(ddd, J=8.4, 6.4, 6.4 Hz, 1H), 7.70(d, J=4.0 Hz, 1H), 7.85(s, 1H), 7.88(s, 1H), 8.13(d, J=1.2 Hz, 1H)

MS m/e (ESI) 491 (MH$^+$)

Example 579

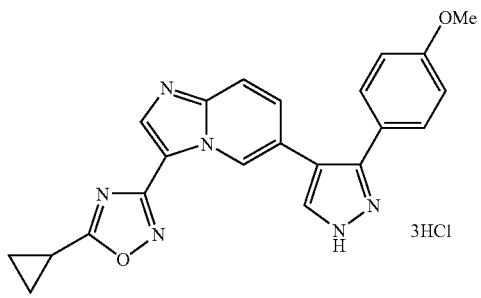

3-(5-Cyclopropyl-[1,2,4]oxadiazol-3-yl)-6-[3-(4-methoxyphenyl)-1H-4-pyrazolyl]-imidazo[1,2-a]pyridine trihydrochloride 80 mg of the title compound (colorless crystals) was obtained in the same manner as in Example 68 from 140 mg 3-(5-cyclopropyl-[1,2,4]oxadiazol-3-yl)-6-[3-(4-methoxyphenyl)-1-trityl-1H-4-pyrazolyl]-imidazo[1,2-a]pyridine obtained in Example 419. $^1$H-NMR data are those of the salt in a free form.

$^1$H-NMR (CDCl$_3$)

δ: 1.22–1.38(m, 4H), 2.23–2.32(m, 1H), 3.83(s, 3H), 6.88–6.95(m, 2H), 7.24(dd, J=9.2, 1.6 Hz, 1H), 7.35–7.41 (m, 2H), 7.65(dd, J=9.2, 0.8 Hz, 1H), 7.81(s, 1H), 8.32(s, 1H), 9.16–9.22(m, 1H)

MS m/e (ESI) 399 (MH$^+$)

Example 580

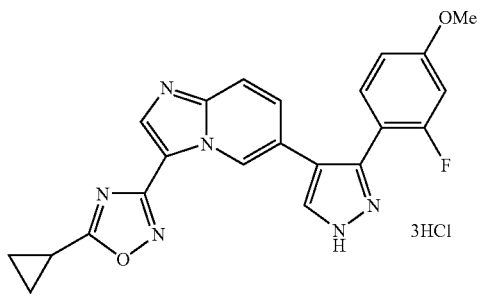

3-(5-Cyclopropyl-[1,2,4]oxadiazol-3-yl)-6-[3-(2-fluoro-4-methoxyphenyl)-1H-4-pyrazolyl]-imidazo[1,2-a]pyridine trihydrochloride 25 mg of the title compound (colorless crystals) was obtained in the same manner as in Example 68 from 130 mg 3-(5-cyclopropyl-[1,2,4]oxadiazol-3-yl)-6-[3-(2-fluoro-4-methoxyphenyl)-1-trityl-1H-4-pyrazolyl]-imidazo[1,2-a]-pyridine obtained in Example 420.

$^1$H-NMR (DMSO-d$_6$)

δ: 1.12–1.23(m, 2H), 1.30–1.40(m, 2H), 2.48–2.63(m, 1H), 3.83(s, 3H), 6.88–6.96(m, 2H), 7.42(dd, J=8.4, 8.4 Hz, 1H), 7.78–7.83(m, 2H), 8.24–8.32(m, 1H), 8.54–8.72(m, 1H), 8.98–9.04(m, 1H)

MS m/e (ESI) 417 (MH$^+$)

Example 581

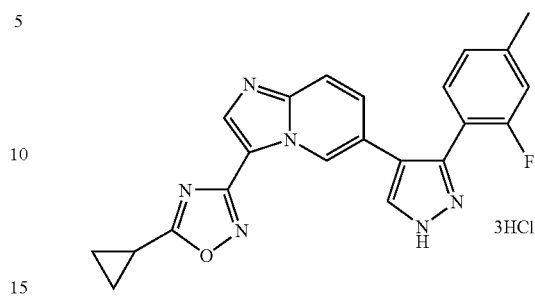

3-(5-Cyclopropyl-[1,2,4]oxadiazol-3-yl)-6-[3-(2-fluoro-4-methylphenyl)-1H-4-pyrazolyl]-imidazo[1,2-a]pyridine trihydrochloride 60 mg of the title compound (colorless crystals) was obtained in the same manner as in Example 68 from 139 mg 3-(5-cyclopropyl-[1,2,4]oxadiazol-3-yl)-6-[3-(2-fluoro-4-methylphenyl)-1-trityl-1H-4-pyrazolyl]-imidazo[1,2-a]-pyridine obtained in Example 421.

$^1$H-NMR (DMSO-d$_6$)

δ: 1.12–1.23(m, 2H), 1.27–1.40(m, 2H), 2.23(s, 3H), 2.35–2.55(m, 1H), 7.15(dd, J=8.4, 8.4 Hz, 1H), 7.24–7.32 (m, 1H), 7.44–7.54(m, 1H), 7.64–7.75(m, 1H), 7.92(d, J=9.6 Hz, 1H), 8.14(s, 1H), 8.55(s, 1H), 9.06(s, 1H)

MS m/e (ESI) 401 (MH$^+$)

Example 582

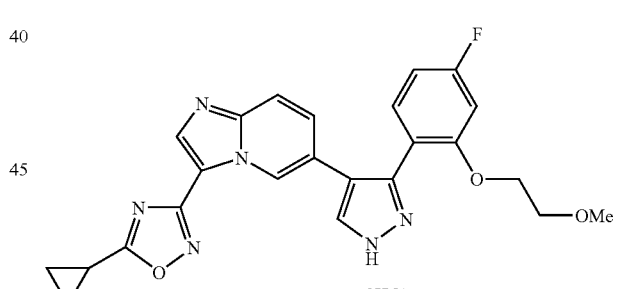

3-(5-Cyclopropyl-[1,2,4]oxadiazol-3-yl)-6-{3-[4-fluoro-2-(2-methylethoxy)phenyl]-1H-4-pyrazolyl}-imidazo[1,2-a]-pyridine trihydrochloride 15 mg of the title compound (colorless crystals) was obtained in the same manner as in Example 68 from 95 mg 3-(5-cyclopropyl-[1,2,4]oxadiazol-3-yl)-6-{3-[4-fluoro-2-(2-methylethoxy)phenyl]-1-trityl-1H-4-pyrazolyl}-imidazo[1,2-a]pyridine obtained in Example 422. $^1$H-NMR data are those of the salt in a free form.

$^1$H-NMR (CDCl$_3$)

δ: 1.21–1.38(m, 4H), 2.21–2.32(m, 1H), 3.55(s, 3H), 3.76–3.81(m, 2H), 4.25–4.30(m, 2H), 6.58(ddd, J=8.4, 8.4, 2.4 Hz, 1H), 6.76(dd, J=10.4, 2.4 Hz, 1H), 7.17(dd, J=8.4, 6.4 Hz, 1H), 7.27(dd, J=9.2, 2.0 Hz, 1H), 7.67(d, J=9.2 Hz, 1H), 7.75(s, 1H), 8.33(s, 1H), 9.18(brs, 1H)

MS m/e (ESI) 461 (MH⁺)

Example 583

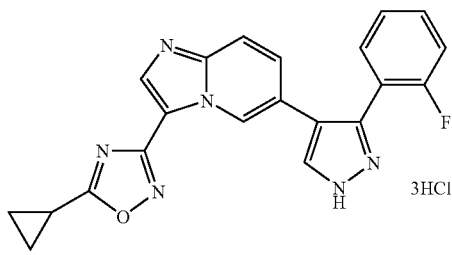

3-(5-Cyclopropyl-[1,2,4]oxadiazol-3-yl)-6-[3-(2-fluorophenyl)-1H-4-pyrazolyl]-imidazo[1,2-a]pyridine trihydrochloride 120 mg of the title compound (colorless crystals) was obtained in the same manner as in Example 68 from 248 mg 3-(5-cyclopropyl-[1,2,4]oxadiazol-3-yl)-6-[3-(2-fluorophenyl)-1-trityl-1H-4-pyrazolyl]-imidazo[1,2-a]-pyridine obtained in Example 423.

¹H-NMR (DMSO-d₆)

δ: 1.10–1.22(m, 2H), 1.25–1.38(m, 2H), 2.27–2.45(m, 1H), 7.21–7.28(m, 1H), 7.30(ddd, J=7.2, 7.2,1.2 Hz, 1H), 7.44–7.58(m, 2H), 7.75(dd, J=9.6, 0.8 Hz, 1H), 7.92(d, J=9.6 Hz, 1H), 8.27(s, 1H), 8.54(s, 1H), 8.93(d, J=0.8 Hz, 1H)

MS m/e (ESI) 387 (MH⁺)

Example 584

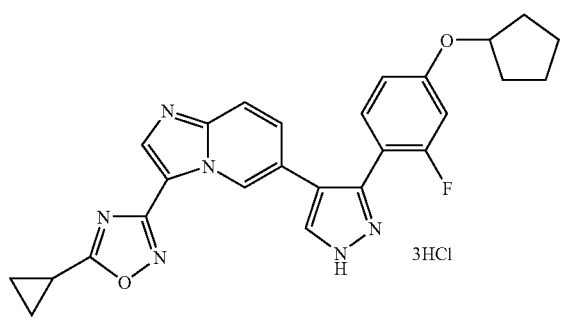

6-[3-(4-Cyclopentyloxy-2-fluorophenyl)-1H-4-pyrazolyl]-3-(5-cyclopropyl-[1,2,4]oxadiazol-3-yl)-imidazo[1,2-a]-pyridine trihydrochloride 35 mg of the title compound (colorless crystals) was obtained in the same manner as in Example 68 from 86 mg 6-[3-(4-cyclopentyloxy-2-fluorophenyl)-1-trityl-1H-4-pyrazolyl]-3-(5-cyclopropyl-[1,2,4]oxadiazol-3-yl)-imidazo[1,2-a]-pyridine obtained in Example 424. ¹H-NMR data are those of the salt in a free form.

¹H-NMR (CDCl₃)

δ: 1.20–1.37(m, 4H), 1.40–1.98(m, 8H), 2.23–2.32(m, 1H), 4.70–4.80(m, 1H), 6.61–6.72(m, 2H), 7.19–7.32(m, 2H), 7.66(d, J=9.2 Hz, 1H), 7.84(s, 1H), 8.31(s, 1H), 9.13–9.16(m, 1H)

MS m/e (ESI) 471 (MH⁺)

Example 585

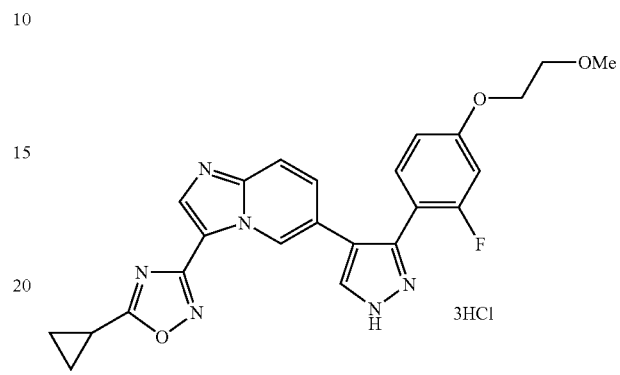

3-(5-Cyclopropyl-[1,2,4]oxadiazol-3-yl)-6-{3-[2-fluoro-4-(2-methoxyethoxy)phenyl]-1H-4-pyrazolyl}-imidazo[1,2-a]-pyridine trihydrochloride 38 mg of the title compound (colorless crystals) was obtained in the same manner as in Example 68 from 73 mg 3-(5-cyclopropyl-[1,2,4]oxadiazol-3-yl)-6-{3-[2-fluoro-4-(2-methoxyethoxy)phenyl]-1-trityl-1H-4-pyrazolyl}-imidazo[1,2-a]pyridine obtained in Example 425. ¹H-NMR data are those of the salt in a free form.

¹H-NMR (CDCl₃)

δ: 1.22–1.37(m, 4H), 2.23–2.42(m, 1H), 3.45(s, 3H), 3.72–3.81(m, 2H), 4.08–4.17(m, 2H), 6.69–6.80(m, 2H), 7.24(dd, J=9.2, 1.2 Hz, 1H), 7.27(d, J=8.4 Hz, 1H), 7.65(dd, J=9.2, 0.8 Hz, 1H), 7.84(s, 1H), 8.31(s, 1H), 9.13–9.18(m, 1H)

MS m/e (ESI) 461 (MH⁺)

Example 586

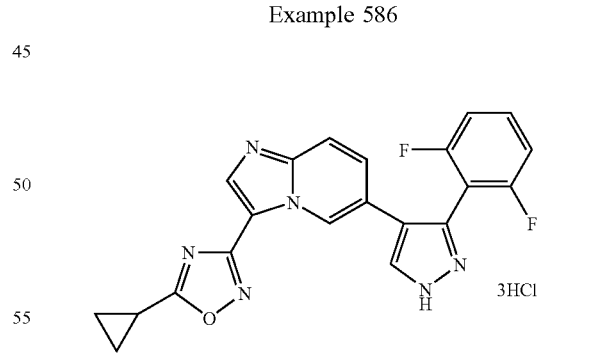

3-(5-Cyclopropyl-[1,2,4]oxadiazol-3-yl)-6-[3-(2,6-difluorophenyl)-1H-4-pyrazolyl]-imidazo[1,2-a]pyridine trihydrochloride 105 mg of the title compound (colorless crystals) was obtained in the same manner as in Example 68 from 211 mg 3-(5-cyclopropyl-[1,2,4]oxadiazol-3-yl)-6-[3-(2,6-difluorophenyl)-1-trityl-1H-4-pyrazolyl]-imidazo[1,2-a]pyridine obtained in Example 426.

¹H-NMR (DMSO-d₆)

δ: 1.17–1.23(m, 2H), 1.30–1.37(m, 2H), 2.38–2.48(m, 1H), 7.18–7.29(m, 2H), 7.54–7.64(m, 1H), 7.71–7.79(m, 1H), 7.89(d, J=9.2, 1H), 8.35–8.46(m, 2H), 8.89(s, 1H)

MS m/e (ESI) 405 (MH⁺)

Example 587

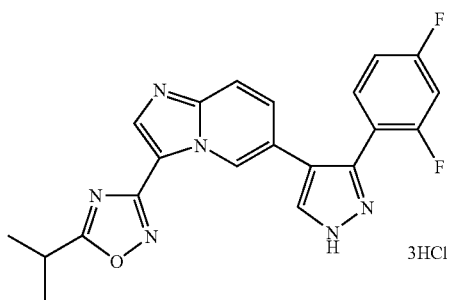

6-[3-(2,4-Difluorophenyl)-1H-4-pyrazolyl]-3-(5-isopropyl-[1,2,4]oxadiazol-3-yl)-imidazo[1,2-a]pyridine trihydrochloride 60 mg of the title compound (colorless crystals) was obtained in the same manner as in Example 68 from 128 mg 6-[3-(2,4-difluorophenyl)-1-trityl-1H-4-pyrazolyl]-3-(5-isopropyl-[1,2,4]oxadiazol-3-yl)-imidazo[1,2-a]pyridine obtained in Example 427.

¹H-NMR (DMSO-d₆)

δ: 1.39(d, J=6.8 Hz, 6H), 3.37–3.43(m, 1H), 7.18–7.27(m, 1H), 7.30–7.38(m, 1H), 7.55–7.64(m, 1H), 7.74–7.88(m, 1H), 7.91–8.00(m, 1H), 8.29–8.38(m, 1H), 8.53–8.66(m, 1H), 8.93–8.99(m, 1H)

MS m/e (ESI) 407 (MH⁺)

Example 588

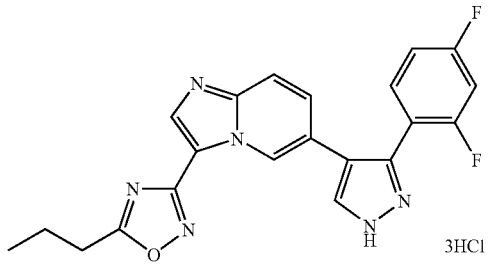

6-[3-(2,4-Difluorophenyl)-1H-4-pyrazolyl]-3-(5-propyl-[1,2,4]oxadiazol-3-yl)-imidazo[1,2-a]pyridine trihydrochloride 54 mg of the title compound (colorless crystals) was obtained in the same manner as in Example 68 from 128 mg 6-[3-(2,4-difluorophenyl)-1-trityl-1H-4-pyrazolyl]-3-(5-propyl-[1,2,4]oxadiazol-3-yl)-imidazo[1,2-a]pyridine obtained in Example 428.

¹H-NMR (DMSO-d₆)

δ: 1.00(t, J=7.2 Hz, 3H), 1.75–1.87(m, 2H), 3.00(t, J=7.2 Hz, 2H), 7.19–7.28(m, 1H), 7.29–7.40(m, 1H), 7.55–7.65(m, 1H), 7.82(d, J=9.2 Hz, 1H), 7.95(d, J=9.2 Hz, 1H), 8.35(s, 1H), 8.58(s, 1H), 8.95(s, 1H)

MS m/e (ESI) 407 (MH⁺)

Example 589

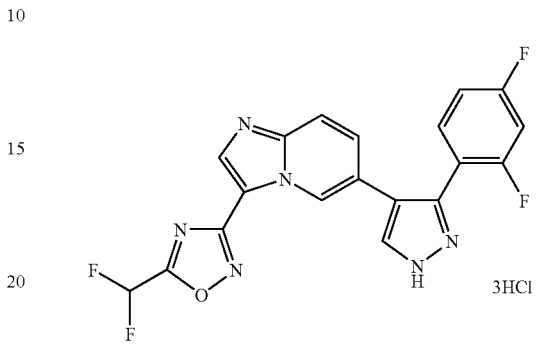

6-[3-(2,4-Difluorophenyl)-1H-4-pyrazolyl]-3-(5-difluoromethyl-[1,2,4]oxadiazol-3-yl)-imidazo[1,2-a]-pyridine trihydrochloride 50 mg of the title compound (colorless amorphous) was obtained in the same manner as in Example 68 from 105 mg 6-[3-(2,4-difluorophenyl)-1-trityl-1H-4-pyrazolyl]-3-(5-difluoromethyl-[1,2,4]oxadiazol-3-yl)-imidazo[1,2-a]-pyridine obtained in Example 429.

¹H-NMR (DMSO-d₆)

δ: 7.17–7.28(m, 1H), 7.28–7.38(m, 1H), 7.57(t, J=51.6 Hz, 1H), 7.54–7.64(m, 1H), 7.70–7.78(m, 1H), 7.93(d, J=9.2 Hz, 1H), 8.34(s, 1H), 8.49–8.55(m, 1H), 8.85(s, 1H)

MS m/e (ESI) 415 (MH⁺)

Example 590

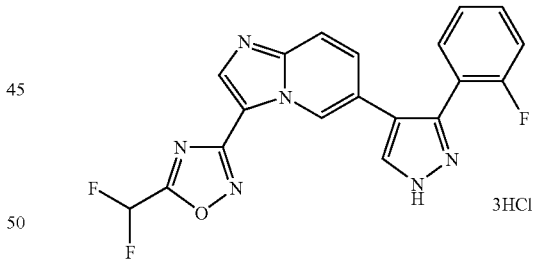

3-(5-Difluoromethyl-[1,2,4]oxadiazol-3-yl)-6-[3-(2-fluorophenyl)-1H-4-pyrazolyl]-imidazo[1,2-a]pyridine trihydrochloride 69 mg of the title compound (colorless amorphous) was obtained in the same manner as in Example 68 from 132 mg 3-(5-difluoromethyl-[1,2,4]oxadiazol-3-yl)-6-[3-(2-fluorophenyl)-1-trityl-1H-4-pyrazolyl]-imidazo[1,2-a]-pyridine obtained in Example 430.

¹H-NMR (DMSO-d₆)

δ: 7.22–7.38(m, 2H), 7.48–7.60(m, 2H), 7.57(t, J=52.4 Hz, 1H), 7.78(d, J=9.2 Hz, 1H), 7.96(d, J=9.2 Hz, 1H), 8.32(s, 1H), 8.66(m, 1H), 8.91(s, 1H)

MS m/e (ESI) 397 (MH⁺)

Example 591

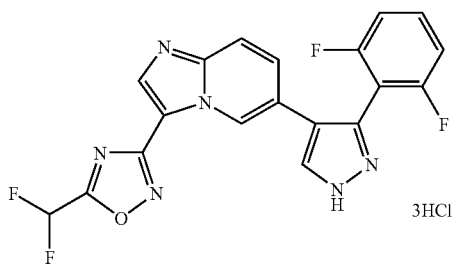

6-[3-(2,4-Difluorophenyl)-1H-4-pyrazolyl]-3-(5-difluoromethyl-[1,2,4]oxadiazol-3-yl)-imidazo[1,2-a]-pyridine trihydrochloride When 105 mg 6-[3-(2,4-difluorophenyl)-1-trityl-1H-4-pyrazolyl]-3-(5-difluoromethyl-[1,2,4]oxadiazol-3-yl)-imidazo[1,2-a]pyridine obtained in Example 431 was reacted in the same manner as in Example 68, crystals of the salt in a free form were formed upon alkalifying the reaction solution, thus making an extraction procedure unnecessary. The crystals were converted into the corresponding salt in the same manner as in Example 68, to give 33 mg of the title compound (colorless amorphous).

$^1$H-NMR (DMSO-$d_6$)

δ: 7.20–7.32(m, 2H), 7.56(t, J=51.6 Hz, 1H), 7.56–7.65 (m, 1H), 7.70–7.82(m, 1H), 7.88–7.96(m, 1H), 8.43(s, 1H), 8.44–8.53(m, 1H), 8.84(s, 1H)

MS m/e (ESI) 415 (MH$^+$)

Example 592

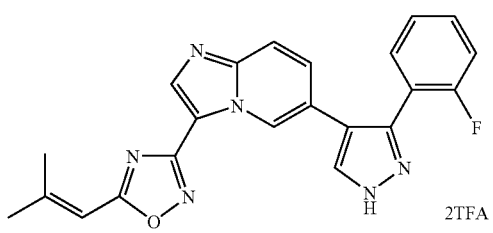

6-[3-(2,4-Fluorophenyl)-1H-4-pyrazolyl]-3-[5-(2-methylpropenyl)-[1,2,4]oxadiazol-3-yl]-imidazo[1,2-a]-pyridine di-trihydroacetate A solution of 32 mg (0.10 mmol) of 6-bromo-3-[5-(2-methylpropenyl)-[1,2,4]oxadiazol-3-yl]imidazo[1,2-a]-pyridine (compound in Production Example 262), 135 mg (0.30 mmol) of 3-(2-fluorophenyl)-1-trityl-1H-4-pyrazolylboronic acid (compound in Production Example 197) and 0.45 mL of 12 mg tetrakis(triphenylphosphine)palladium in 2 N aqueous sodium carbonate and 2.2 mL 1,2-dimethoxyethane was heated at 80° C. for 5 hours. 2 mL aqueous saturated sodium bicarbonate solution was added thereto, the reaction solution was extracted with ethyl acetate, the organic layer was filtered through a membrane filter, and the solvent was removed. 1 mL tetrahydrofuran, 1 mL methanol and 1 mL of 5 N hydrochloric acid were added to the residue and left overnight at room temperature. The reaction solution was basified with 5 N aqueous sodium hydroxide and then extracted with ethyl acetate, the organic layer was filtered through a membrane filter, and the solvent was removed. The residue was dissolved by adding 2.1 mL dimethyl sulfoxide and 2 drops of trifluoroacetic acid and then purified by high performance liquid chromatography (WAKO PAK ODS column; solvent, water/acetonitrile/ 0.1% trifluoroacetic acid) to give 12 mg of the title compound.

MS m/e(ESI) 401 (MH$^+$)

Example 593

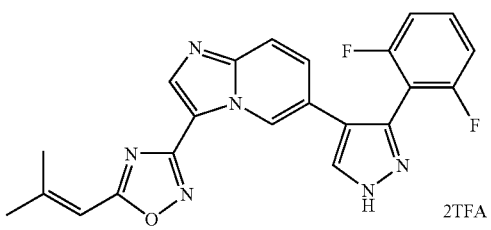

6-[3-(2,6-Difluorophenyl)-1H-4-pyrazolyl]-3-[5-(2-methylpropenyl)-[1,2,4]oxadiazol-3-yl]-imidazo[1,2-a]-pyridine di-trifluoroacetate 13 mg of the title compound was obtained in the same manner as in Example 592 from 32 mg 6-bromo-3-[5-(2-methylpropenyl)-[1,2,4]oxadiazol-3-yl]imidazo[1,2-a]pyridine (compound in Production Example 262) and 140 mg 3-(2,6-difluorophenyl)-1-trityl-1H-4-pyrazolylboronic acid (compound in Production Example 211).

MS m/e(ESI) 419 (MH$^+$)

Example 594

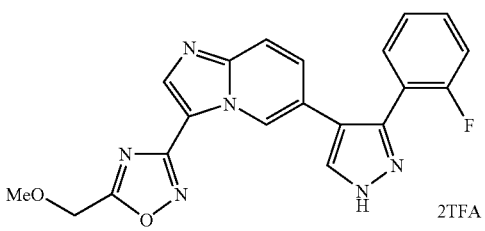

6-[3-(2-Fluorophenyl)-1H-4-pyrazolyl]-3-(5-methoxymethyl-[1,2,4]oxadiazol-3-yl)-imidazo[1,2-a] pyridine di-trifluoroacetate 7 mg of the title compound was obtained in the same manner as in Example 128 from 31 mg 6-bromo-3-(5-methoxymethyl-[1,2,4]oxadiazol-3-yl)imidazo[1,2-a]pyridine (compound in Production Example 263) and 135 mg 3-(2-fluorophenyl)-1-trityl-1H-4-pyrazolylboronic acid (compound in Production Example 197).

MS m/e(ESI) 391 (MH$^+$)

Example 595

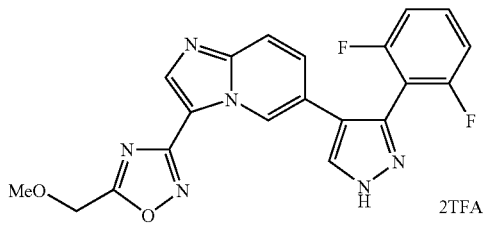

6-[3-(2,6-Difluorophenyl)-1H-4-pyrazolyl]-3-(5-methoxymethyl-[1,2,4]oxadiazol-3-yl)-imidazo[1,2-a]pyridine di-trifluoroacetate 9 mg of the title compound was obtained in the same manner as in Example 128 from 31 mg 6-bromo-3-(5-methoxymethyl-[1,2,4]oxadiazol-3-yl)imidazo[1,2-a]pyridine (compound in Production Example 263) and 140 mg 3-(2,6-difluorophenyl)-1-trityl-1H-4-pyrazolylboronic acid (compound in Production Example 211).

MS m/e(ESI) 409 (MH+)

Example 596

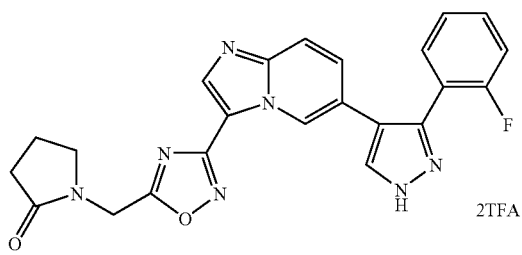

1-(3-{6-[3-(2-Fluorophenyl)-1H-4-pyrazolyl]-imidazo[1,2-a]-pyridin-3-yl}-[1,2,4]oxadiazol-5-ylmethyl)-pyrrolidin-2-one di-trifluoroacetate 3 mg of the title compound was obtained in the same manner as in Example 128 from 36 mg 1-[3-(6-bromoimidazo[1,2-a]pyridin-3-yl)-[1,2,4]oxadiazol-5-ylmethyl]-pyrrolidin-2-one (compound in Production Example 264) and 135 mg 3-(2-fluorophenyl)-1-trityl-1H-4-pyrazolylboronic acid (compound in Production Example 197).

MS m/e(ESI) 444 (MH+)

Example 597

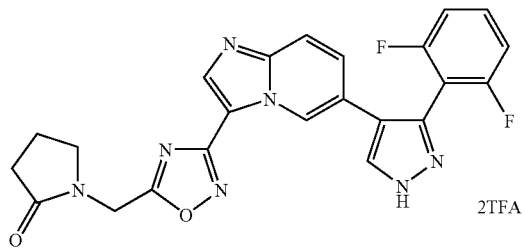

1-(3-{6-[3-(2,6-Difluorophenyl)-1H-4-pyrazolyl]-imidazo[1,2-a]pyridin-3-yl}-[1,2,4]oxadiazol-5-ylmethyl)-Pyrrolidine-2-one di-trifluoroacetate 9 mg of the title compound was obtained in the same manner as in Example 128 from 36 mg 1-[3-(6-bromoimidazo[1,2-a]pyridin-3-yl)-[1,2,4]oxadiazol-5-ylmethyl]-pyrrolidin-2-one (compound in Production Example 264) and 140 mg 3-(2,6-difluorophenyl)-1-trityl-1H-4-pyrazolylboronic acid (compound in Production Example 211).

MS m/e(ESI) 462 (MH+)

Example 598

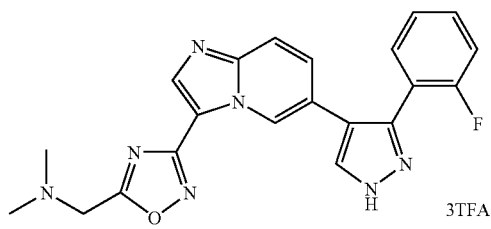

(3-{6-[3-(2-Fluorophenyl)-1H-4-pyrazolyl]-imidazo[1,2-a]-pyridin-3-yl}-[1,2,4]oxadiazol-5-ylmethyl) dimethylamine tri-trifluoroacetate 7 mg of the title compound was obtained in the same manner as in Example 128 from 32 mg [3-(6-bromoimidazo[1,2-a]pyridin-3-yl)-[1,2,4]oxadiazol-5-ylmethyl]-dimethylamine (compound in Production Example 265) and 135 mg 3-(2-fluorophenyl)-1-trityl-1H-4-pyrazolylboronic acid (compound in Production Example 197).

MS m/e(ESI) 404 (MH+)

Example 599

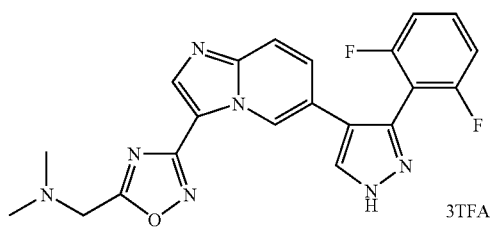

(3-{6-[3-(2,6-Difluorophenyl)-1H-4-pyrazolyl]-imidazo[1,2-a]pyridin-3-yl}-[1,2,4]oxadiazol-5-ylmethyl)dimethylamine tri-trifluoroacetate 14 mg of the title compound was obtained in the same manner as in Example 128 from 32 mg [3-(6-bromoimidazo[1,2-a]pyridin-3-yl)-[1,2,4]oxadiazol-5-ylmethyl]-dimethylamine (compound in Production Example 265) and 140 mg 3-(2,6-difluorophenyl)-1-trityl-1H-4-pyrazolylboronic acid (compound in Production Example 211).
MS m/e(ESI) 422 (MH+)

Example 600

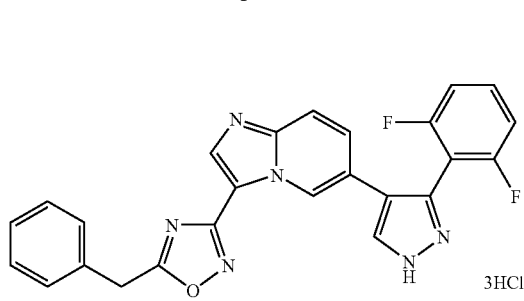

3-(5-Benzyl-[1,2,4]oxadiazol-3-yl)-6-[3-(2,6-difluorophenyl)-1H-4-pyrazolyl]-imidazo[1,2-a]pyridine trihydrochloride 30 mg of the title compound (colorless crystals) was obtained in the same manner as in Example 68 from 65 mg 3-(5-benzyl-[1,2,4]oxadiazol-3-yl)-6-[3-(2,6-difluorophenyl)-1-trityl-1H-4-pyrazolyl]-imidazo[1,2-a]pyridine obtained in Example 432. $^1$H-NMR data are those of the salt in a free form.
$^1$H-NMR (CDCl$_3$)
δ: 4.30(s, 2H), 6.94–7.03(m, 2H), 7.23–7.43(m, 7H), 7.66(dd, J=9.2, 0.8 Hz, 1H), 7.95(s, 1H), 8.33(s, 1H), 9.08–9.12(m, 1H)
MS m/e (ESI) 455 (MH+)

Example 601

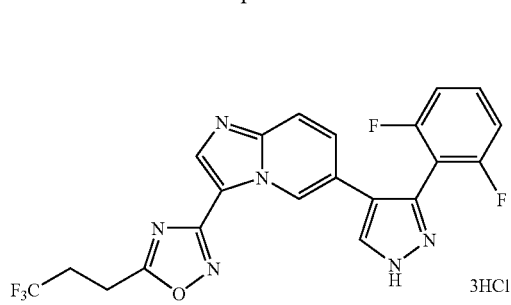

3-[5-(3,3,3-Trifluoropropyl)-[1,2,4]oxadiazol-3-yl]-6-[3-(2,6-difluorophenyl)-1H-4-pyrazolyl]-imidazo[1,2-a]pyridine 19 mg of the title compound (colorless crystals) was obtained in the same manner as in Example 68 from 83 mg 3-[5-(3,3,3-trifluoropropyl)-[1,2,4]oxadiazol-3-yl]-6-[3-(2,6-difluorophenyl)-1-trityl-1H-4-pyrazolyl]-imidazo[1,2-a]-pyridine obtained in Example 433. $^1$H-NMR data are those of the salt in a free form.

$^1$H-NMR (CDCl$_3$)
δ: 2.70–2.83(m, 2H), 3.17–3.30(m, 2H), 6.95–7.06(m, 2H), 7.31(dd, J=9.2, 1.6 Hz, 1H), 7.35–7.45(m, 1H), 7.68(d, J=9.2 Hz, 1H), 7.97(s, 1H), 8.33(s, 1H), 9.02–9.11(m, 1H)
MS m/e (ESI) 461 (MH+)

Example 602

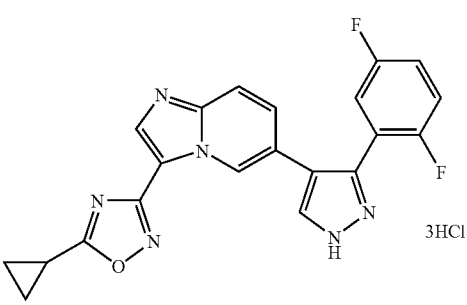

3-(5-Cyclopropyl)-[1,2,4]oxadiazol-3-yl)-6-[3-(2,5-difluorophenyl)-1H-4-pyrazolyl]-imidazo[1,2-a]pyridine trihydrochloride 40 mg of the title compound (colorless crystals) was obtained in the same manner as in Example 68 from 92 mg 3-(5-cyclopropyl)-[1,2,4]oxadiazol-3-yl)-6-[3-(2,5-difluorophenyl)-1-trityl-1H-4-pyrazolyl]-imidazo[1,2-a]-pyridine obtained in Example 434.
$^1$H-NMR (DMSO-d$_6$)
δ: 1.10–1.23(m, 2H), 1.26–1.38(m, 2H), 2.35–2.48(m, 1H), 7.24–7.48(m, 3H), 7.64–7.80(m, 1H), 7.84–7.96(m, 1H), 8.26–8.54(m, 2H), 8.91(brs, 1H)
MS m/e (ESI) 405 (MH+)

Example 603

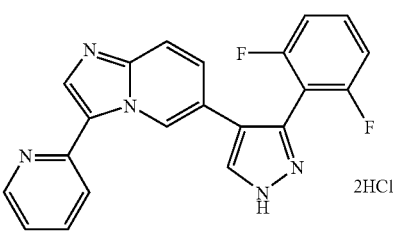

6-[3-(2,6-Difluorophenyl)-1H-4-pyrazolyl]-3-(2-pyridinyl)-imidazo[1,2-a]pyridine dihydrochloride 40 mg of the title compound (colorless crystals) was obtained in the same manner as in Example 68 from 238 mg 6-[3-(2,6-difluorophenyl)-1-trityl-1H-4-pyrazolyl]-3-(2-pyridinyl)-imidazo[1,2-a]pyridine obtained in Example 435.
$^1$H-NMR (DMSO-d$_6$)
δ: 7.14–7.21(m, 2H), 7.22–7.42(m, 1H), 7.50–7.62(m, 1H), 7.83–8.12(m, 4H), 8.32–8.50(m, 2H), 8.80–8.90(m, 1H), 9.83–9.90(m, 1H)
MS m/e (ESI) 374 (MH+)

Example 604

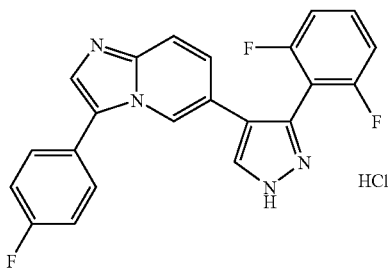

6-[3-(2,6-Difluorophenyl)-1H-4-pyrazolyl]-3-(4-fluorophenyl)imidazo[1,2-a]pyridine hydrochloride 86 mg of the title compound (colorless crystals) was obtained in the same manner as in Example 68 from 250 mg 6-[3-(2,6-difluorophenyl)-1-trityl-1H-4-pyrazolyl]-3-(4-fluorophenyl)imidazo[1,2-a]pyridine obtained in Example 436.

¹H-NMR (DMSO-$d_6$)

δ: 7.14–7.24(m, 2H), 7.35–7.42(m, 2H), 7.43–7.52(m, 2H), 7.53–7.63(m, 1H), 7.87–8.11(m, 3H), 8.33(d, J=3.2 Hz, 1H), 8.47(d, J=2.4 Hz, 1H)

MS m/e (ESI) 391 (MH⁺)

Example 605

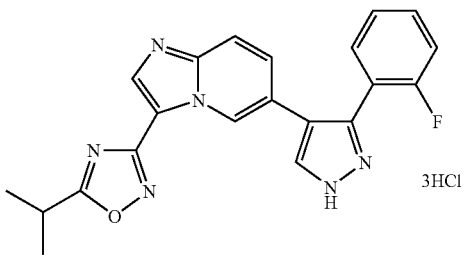

6-[3-(2-Fluorophenyl)-1H-4-pyrazolyl]-3-(5-isopropyl-[1,2,4]oxadiazol-3-yl)-imidazo[1,2-a]pyridine trihydrochloride 115 mg of the title compound (colorless crystals) was obtained in the same manner as in Example 68 from 203 mg 6-[3-(2-fluorophenyl)-1-trityl-1H-4-pyrazolyl]-3-(5-isopropyl-[1,2,4]oxadiazol-3-yl)-imidazo[1,2-a]pyridine obtained in Example 437.

¹H-NMR (DMSO-$d_6$)

δ: 1.39(d, J=7.2 Hz, 6H), 3.36–3.45(m, 1H), 7.22–7.37(m, 2H), 7.46–7.62(m, 2H), 7.81–7.92(m, 1H), 7.96–8.04(m, 1H), 8.31(brs, 1H), 8.68–8.77(m, 1H), 9.04(brs, 1H)

MS m/e (ESI) 389 (MH⁺)

Example 606

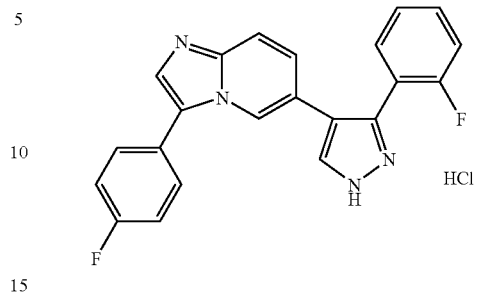

3-(4-Fluorophenyl)-6-[3-(2-fluorophenyl)-1H-4-pyrazolyl]imidazo[1,2-a]pyridine hydrochloride 71 mg of the title compound (slightly yellow crystals) was obtained in the same manner as in Example 68 from 150 mg 3-(4-fluorophenyl)-6-[3-(2-fluorophenyl)-1-trityl-1H-4-pyrazolyl]imidazo[1,2-a]pyridine obtained in Example 438.

¹H-NMR (DMSO-$d_6$)

δ: 7.22–7.40(m, 4H), 7.42–7.58(m, 4H), 7.94–8.06(m, 2H), 8.10(brs, 1H), 8.32–8.40 (m, -2H)

MS m/e (ESI) 373 (MH⁺)

Example 607

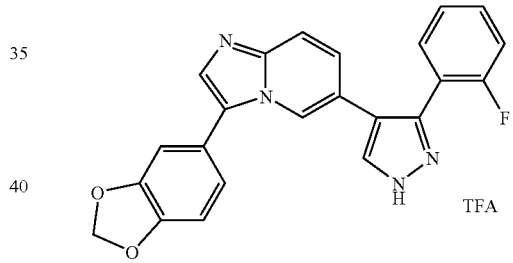

3-Benzo[1,3]dioxol-5-yl-6-[3-(2-fluorophenyl)-1H-4-pyrazolyl]imidazo[1,2-a]pyridine trifluoroacetate A solution of 65 mg (0.10 mmol) of 6-[3-(2-fluorophenyl)-1-trityl-1H-4-pyrazolyl]-3-iodoimidazo[1,2-a]pyridine (compound in Production Example 271), 34 mg (0.20 mmol) of 3,4-methylene dioxyphenylboronic acid, 0.2 mL of 6 mg tetrakis(triphenylphosphine)palladium in 2 N aqueous sodium carbonate, and 2 mL 1,2-dimethoxyethane was heated at 85° C. for 5 hours. An aqueous saturated sodium bicarbonate solution was added thereto, the reaction solution was extracted with ethyl acetate, the organic layer was filtered through a membrane filter, and the solvent was removed. 1 mL dichloromethane and 2 mL trifluoroacetic acid were added to the residue and left overnight at 40° C. The solvent was removed until the trifluoroacetic acid was reduced to a small volume, then 2 mL dimethyl sulfoxide was added thereto, and the reaction solution was filtered through a membrane filter. The filtrate was purified by high performance liquid chromatography (WAKO PAK ODS column; solvent, water/acetonitrile/0.1% trifluoroacetic acid) to give 26 mg of the title compound.

¹H-NMR (DMSO-d₆)

δ: 6.14(s, 2H), 6.79(brd, J=8.4 Hz, 1H), 6.98(d, J=8.4 Hz, 1H), 7.00(brs, 1H), 7.17–7.34(m, 2H), 7.41–7.56(m, 2H), 7.79(brd, J=9.2 Hz, 1H), 7.89(d, J=9.2 Hx, 1H), 8.00–8.14 (m, 2H)

MS m/e(ESI) 399 (MH⁺)

Example 608

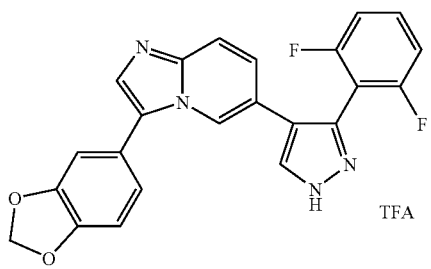

3-Benzo[1,3]dioxol-5-yl-6-[3-(2,6-difluorophenyl)-1H-4-pyrazolyl]imidazo[1,2-a]pyridine trifluoroacetate 3 mg of the title compound was obtained in the same manner as in Example 607 from 67 mg 6-[3-(2,6-difluorophenyl)-1-trityl-1H-4-pyrazolyl]-3-iodoimidazo[1,2-a]pyridine (compound in Production Example 269) and 34 mg 3,4-methylene dioxyphenylboronic acid.

MS m/e(ESI) 417 (MH⁺)

Example 609

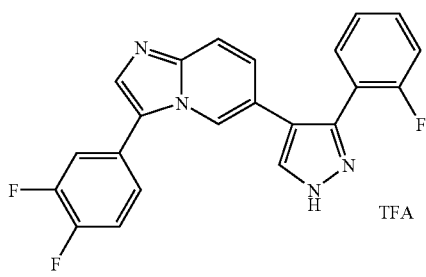

3-(3,4-Difluorophenyl)-6-[3-(2-fluorophenyl)-1H-4-pyrazolyl]imidazo[1,2-a]pyridine trifluoroacetate 7 mg of the title compound was obtained in the same manner as in Example 607 from 65 mg 6-[3-(2-fluorophenyl)-1-trityl-1H-4-pyrazolyl]-3-iodoimidazo[1,2-a]pyridine (compound in Production Example 271) and 32 mg 3,4-difluorophenylboronic acid.

MS m/e(ESI) 391 (MH⁺)

Example 610

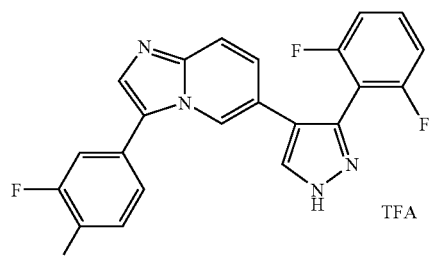

3-(3,4-Difluorophenyl)-6-[3-(2,6-difluorophenyl)-1H-4-pyrazolyl]imidazo[1,2-a]pyridine trifluoroacetate 5 mg of the title compound was obtained in the same manner as in Example 607 from 67 mg 6-[3-(2,6-difluorophenyl)-1-trityl-1H-4-pyrazolyl]-3-iodoimidazo[1,2-a]pyridine (compound in Production Example 269) and 32 mg 3,4-difluorophenylboronic acid.

MS m/e(ESI) 409 (MH⁺)

Example 611

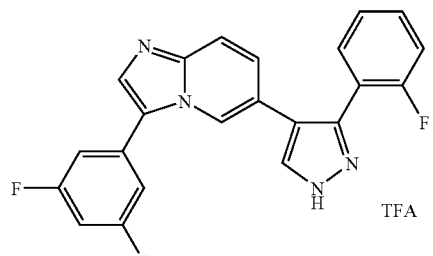

3-(3,5-Difluorophenyl)-6-[3-(2-fluorophenyl)-1H-4-pyrazolyl]imidazo[1,2-a]pyridine trifluoroacetate 11 mg of the title compound was obtained in the same manner as in Example 607 from 65 mg 6-[3-(2-fluorophenyl)-1-trityl-1H-4-pyrazolyl]-3-iodoimidazo[1,2-a]pyridine (compound in Production Example 271) and 32 mg 3,5-difluorophenylboronic acid.

MS m/e(ESI) 391 (MH⁺)

Example 612

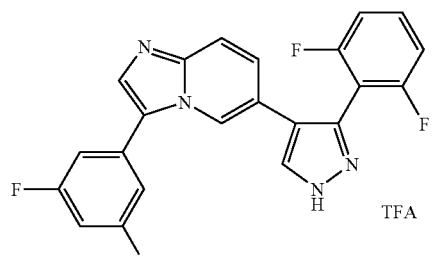

3-(3,5-Difluorophenyl)-6-[3-(2,6-difluorophenyl)-1H-4-pyrazolyl]imidazo[1,2-a]pyridine trifluoroacetate 3 mg of the title compound was obtained in the same manner as in Example 607 from 67 mg 6-[3-(2,6-difluorophenyl)-1-trityl-1H-4-pyrazolyl]-3-iodoimidazo[1,2-a]pyridine (compound in Production Example 269) and 32 mg 3,5-difluorophenylboronic acid.

MS m/e(ESI) 409 (MH$^+$)

Example 613

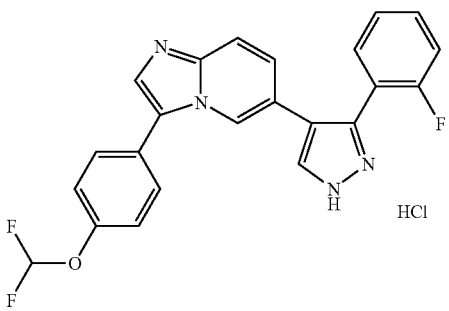

3-[4-(Difluoromethoxy)phenyl]-6-[3-(2-fluorophenyl)-1H-4-pyrazolyl-]imidazo[1,2-a]pyridine hydrochloride 200 mg 6-[3-(2-fluorophenyl)-1-trityl-1H-4-pyrazolyl]-3-iodoimidazo[1,2-a]pyridine obtained in Production Example 271 and 126 mg 2-(4-difluoromethoxyphenyl)-4,4,5,5-tetramethyl[1,3,2]dioxaborolan obtained in Production Example 272 were subjected to coupling reaction in the same manner as in Example 420 and then to deprotection of the trityl group in the same manner as in Example 68, to give 95 mg of the title compound (colorless crystals).

$^1$H-NMR (DMSO-d$_6$)

δ: 7.18–7.60(m, 9H), 7.96–8.08(m, 2H), 8.13(brs, 1H), 8.30–8.40(m, 2H)

MS m/e (ESI) 421 (MH$^+$)

Example 614

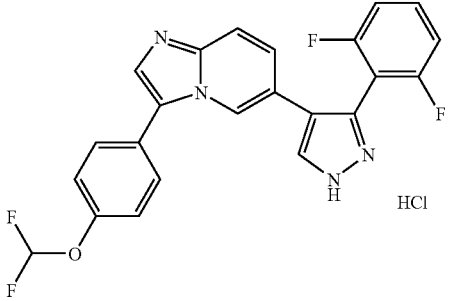

3-[4-(Difluoromethoxy)phenyl]-6-[3-(2,6-difluorophenyl)-1H-4-pyrazolyl]imidazo[1,2-a]pyridine hydrochloride 200 mg 6-[3-(2,6-difluorophenyl)-1-trityl-1H-4-pyrazolyl]-3-iodoimidazo[1,2-a]pyridine obtained in Production Example 269 and 122 mg 2-(4-difluoromethoxyphenyl)-4,4,5,5-tetramethyl [1,3,2]dioxaborolan obtained in Production Example 272 were subjected to coupling reaction in the same manner as in Example 420 and then to deprotection of the trityl group in the same manner as in Example 68, to give 55 mg of the title compound (colorless crystals).

$^1$H-NMR (DMSO-d$_6$)

δ: 7.11–7.22(m, 2H), 7.32(d, J=8.4 Hz, 2H), 7.42(t, J=73.6 Hz, 1H), 7.47(d, J=8.4 Hz, 2H), 7.50–7.62(m, 1H), 7.98–8.12(m, 3H), 8.31(s, 1H), 8.47(brs, 1H)

MS m/e (ESI) 439 (MH$^+$)

Example 615

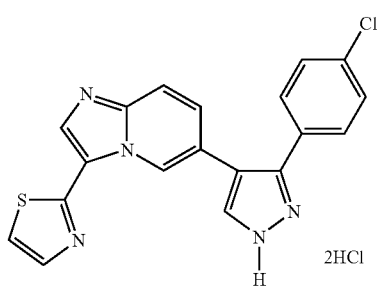

6-[3-(4-Chlorophenyl)-1H-pyrazol-4-yl]-3-thiazol-2-yl-imidazo[1,2-a]pyridine dihydrochloride 46 mg of the title compound was obtained as colorless crystals in the same manner as in Example 67 from 111 mg 6-[3-(4-chlorophenyl)-1-trityl-1H-pyrazol-4-yl]-3-thiazol-2-yl-imidazo[1,2-a]pyridine (compound in Example 439).

$^1$H-NMR (DMSO-d$_6$)

δ: 7.41–7.51(m, 4H), 7.82–7.92(m, 1H), 7.85(d, J=3.0 Hz, 1H), 7.91(d, J=3.0 Hz, 1H), 7.99(d, J=9.2 Hz, 1H), 8.19(s, 1H), 8.88(s, 1H), 9.68(s, 1H)

MS m/e (ESI) 378 (MH$^+$)

Example 616

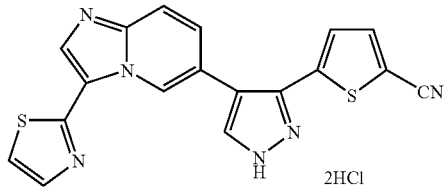

5-[4-(3-Thiazol-2-yl-imidazo[1,2-a]pyridin-6-yl)-1H-pyrazol-3-yl]-thiophen-2-carbonitrile dihydrochloride 37 mg of the title compound was obtained as colorless crystals in the same manner as in Example 68 from 101 mg 5-[4-(3-thiazol-2-yl-imidazo[1,2-a]pyridin-6-yl)-1-trityl-1H-pyrazol-3-yl]-thiophen-2-carbonitrile (compound in Example 440).

$^1$H-NMR (DMSO-d$_6$)

δ: 7.16(d, J=3.8 Hz, 1H), 7.84(d, J=3.8 Hz, 1H), 7.88(dd, J=9.1, 1.2 Hz, 1H), 7.90(d, J=3.4 Hz, 1H), 7.96(d, J=3.4 Hz, 1H), 8.03(d, J=9.1 Hz, 1H), 8.26(s, 1H), 8.87(s, 1H), 9.79(s, 1H)

MS m/e (ESI) 375 (MH$^+$)

Example 617

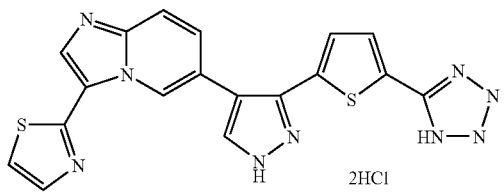

6-{3-[5-(1H-Tetrazol-5-yl)-thiophen-2-yl]-1H-pyrazol-4-yl}-3-thiazol-2-yl-imidazo[1,2-a]pyridine dihydrochloride 60 mg 6-{3-[5-(1H-tetrazol-5-yl)-thiophen-2-yl]-1-trityl-1H-pyrazol-4-yl}-3-thiazol-2-yl-imidazo[1,2-a]-pyridine obtained in Example 441 was dissolved in 8.0 mL solvent mixture of tetrahydrofuran and methanol (1:1), then 3.0 mL of 5 N hydrochloric acid was added thereto, and the mixture was left at room temperature for 3 hours. Water was poured into the reaction solution, and the precipitated crystals were collected by filtration and washed with diethyl ether, to give 14.5 mg of the title compound as pale pink crystals.

$^1$H-NMR (DMSO-d$_6$)

δ: 7.19(brs, 1H), 7.66(dd, J=9.2, 1.6 Hz, 1H), 7.68(d, J=3.6 Hz, 1H), 7.77(d, J=3.2 Hz, 1H), 7.85(d, J=3.2 Hz, 1H), 7.90(d, J=9.2 Hz, 1H), 8.18(brs, 1H), 8.55(s, 1H), 9.74(s, 1H)

MS m/e (ESI) 418 (MH$^+$)

Example 618

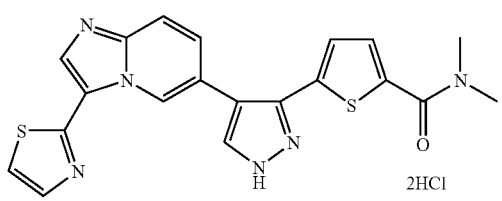

5-[4-(3-Thiazol-2-yl-imidazo[1,2-a]pyridin-6-yl)-1H-pyrazol-3-yl]-thiophen-2-carboxylic acid dimethylamide dihydrochloride 29 mg 5-[4-(3-thiazol-2-yl-imidazo[1,2-a]pyridin-6-yl)-1-trityl-1H-pyrazol-3-yl]-thiophen-2-carboxylic acid dimethylamide obtained in Example 444 was dissolved in 8.0 mL solvent mixture of tetrahydrofuran and methanol (1:1), then 3.0 mL of 5 N hydrochloric acid was added thereto, and the mixture was left at room temperature for 3 hours. The reaction solution was neutralized, then extracted with ethyl acetate and purified by NH silica gel column chromatography (ethyl acetate/hexane) The product was converted into the corresponding hydrochloride by 4 N hydrogen chloride in ethyl acetate and recrystallized from methanol/ethyl acetate to give 20 mg of the title compound as colorless crystals.

$^1$H-NMR (DMSO-d$_6$)

δ: 3.05(brs, 6H), 7.06(d, J=3.8 Hz, 1H), 7.34(d, J=3.8 Hz, 1H), 7.84(dd, J=9.4, 0.8 Hz, 1H), 7.87(d, J=3.2 Hz, 1H), 7.95(d, J=3.2 Hz, 1H), 7.99(d, J=9.4 Hz, 1H), 8.18(s, 1H), 8.78(s, 1H), 9.78–9.79(m, 1H)

MS m/e (ESI) 421 (MH$^+$)

Example 619

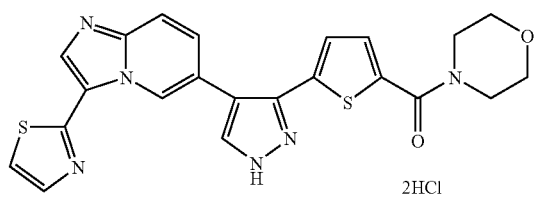

Morpholine-4-yl-{5-[4-(3-thiazol-2-yl-imidazo[1,2-a]-pyridin-6-yl)-1H-pyrazol-3-yl]-thiophen-2-yl}methanone dihydrochloride 27 mg of the title compound was obtained as colorless crystals in the same manner as in Example 67 from 47 mg morpholine-4-yl-{5-[4-(3-thiazol-2-yl-imidazo[1,2-a]-pyridin-6-yl)-1-trityl-1H-pyrazol-3-yl]-thiophen-2-yl}methanone (compound in Example 445).

$^1$H-NMR (DMSO-d$_6$)

δ: 3.58(brs, 8H), 7.06(d, J=4.0 Hz, 1H), 7.29(d, J=4.0 Hz, 1H), 7.80(d, J=9.0 Hz, 1H), 7.86(d, J=3.4 Hz, 1H), 7.94(d, J=3.4 Hz, 1H), 7.97(d, J=9.0 Hz, 1H), 8.18(s, 1H), 8.74(s, 1H), 9.78(s, 1H)

MS m/e (ESI) 463 (MH$^+$)

Example 620

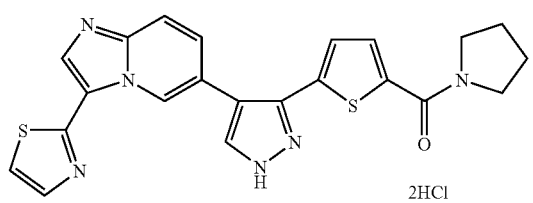

Pyrrolidine-1-yl-{5-[4-(3-thiazol-2-yl-imidazo[1,2-a]pyridin-6-yl)-1H-pyrazol-3-yl]-thiophen-2-yl}methanone dihydrochloride 10 mg of the title compound was obtained as pale yellow crystals in the same manner as in Example 68 from 46 mg pyrrolidin-1-yl-{5-[4-(3-thiazol-2-yl-imidazo[1,2-a]pyridin-6-yl)-1-trityl-1H-pyrazol-3-yl]-thiophen-2-yl}methanone (compound in Example 446).

¹H-NMR (DMSO-d₆)

δ: 1.75–1.95(m, 4H), 3.35–3.70(m, 4H), 7.11(d, J=4.0 Hz, 1H), 7.46(d, J=4.0 Hz, 1H), 7.85–7.94(m, 2H), 7.97(d, J=3.4 Hz, 1H), 8.05(d, J=9.2 Hz, 1H), 8.21(s, 1H), 8.89(s, 1H), 9.82(s, 1H)

MS m/e (ESI) 447 (MH⁺)

Example 621

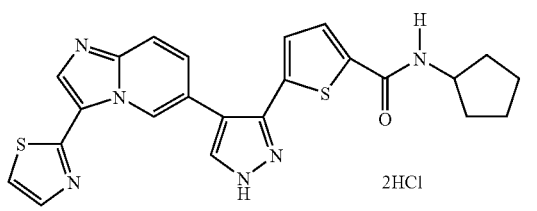

5-[4-(3-Thiazol-2-yl-imidazo[1,2-a]pyridin-6-yl)-1H-pyrazol-3-yl]-thiophen-2-carboxylic acid cyclopentylamide dihydrochloride 43 mg of the title compound was obtained as colorless crystals in the same manner as in Example 68 from 70 mg 5-[4-(3-thiazol-2-yl-imidazo[1,2-a]pyridin-6-yl)-1-trityl-1H-pyrazol-3-yl]-thiophen-2-carboxylic acid cyclopentylamide (compound in Example 447).

¹H-NMR (DMSO-d₆)

δ: 1.45–1.60(m, 4H), 1.61–1.77(m, 2H), 1.80–1.93(m, 2H), 4.10–4.21(m, 1H), 7.10(d, J=3.8 Hz, 1H), 7.72(d, J=3.8 Hz, 1H), 7.88(dd, J=9.3, 1.5 Hz, 1H), 7.91(d, J=3.2 Hz, 1H), 7.96(d, J=3.2 Hz, 1H), 8.03(dd, J=9.3, 0.8 Hz, 1H), 8.21(s, 1H), 8.36(d, J=7.2 Hz, 1H), 8.86(s, 1H), 9.80(dd, J=1.5, 0.8 Hz, 1H)

MS m/e (ESI) 461 (MH⁺)

Example 622

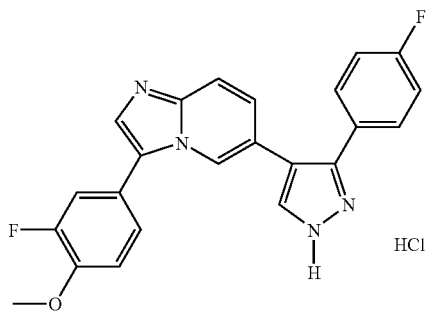

3-(3-Fluoro-4-methoxyphenyl)-6-[3-(4-fluorophenyl)-1H-4-pyrazolyl]imidazo[1,2-a]pyridine hydrochloride 89 mg of the title compound was obtained as colorless crystals by the same method as in Example 79 from 142 mg 3-(3-fluoro-4-methoxyphenyl)-6-[3-(4-fluorophenyl)-1-trityl-1H-4-pyrazolyl]imidazo[1,2-a]pyridine (compound in Example 448).

¹H-NMR (DMSO-d₆)

δ: 3.92(s, 3H), 7.18–7.25(m, 2H), 7.31(dd, J=8.4, 8.4 Hz, 1H), 7.33–7.37(m, 1H), 7.45–7.51(m, 3H), 7.89(dd, J=9.2, 1.6 Hz, 1H), 8.01(dd, J=9.2, 0.8 Hz, 1H), 8.19(brs, 1H), 8.29(dd, J=1.6, 0.8 Hz, 1H), 8.31(s, 1H)

MS m/e(ESI)403 (MH⁺)

Example 623

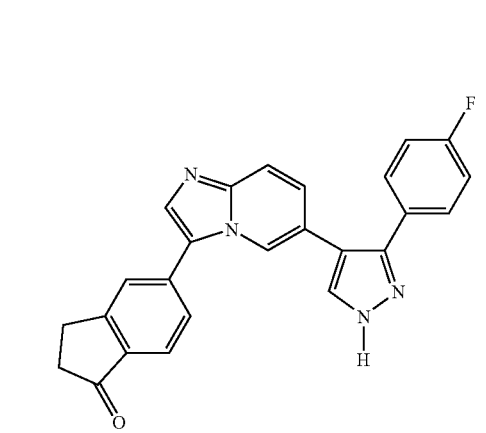

5-{6-[3-(4-Fluorophenyl)-1H-4-pyrazolyl]imidazo[1,2-a]pyridin-3-yl}-1-indanone 27 mg of the title compound was obtained (pale yellow crystals; recrystallization solvent, methanol/diethyl ether) in the same manner as in Example 80 from 110 mg 5-{6-[3-(4-fluorophenyl)-1-trityl-1H-pyrazolyl]imidazo[1,2-a]pyridin-3-yl}-1-indanone (compound in Example 449).

¹H-NMR (CDCl₃)

δ: 2.73–2.78(m, 2H), 3.13(dd, J=6.0, 6.0 Hz, 2H), 7.11–7.17(m, 2H), 7.25(dd, J=9.2, 1.6 Hz, 1H), 7.33–7.37(m, 1H), 7.41–7.43(m, 1H), 7.48–7.53(m, 2H), 7.70(dd, J=9.2, 1.2 Hz, 1H), 7.77(s, 1H), 7.78(d, J=8.0 Hz, 1H), 7.80(s, 1H), 8.23(dd, J=1.6, 1.2 Hz, 1H)

MS m/e(ESI)409(MH⁺)

Example 624

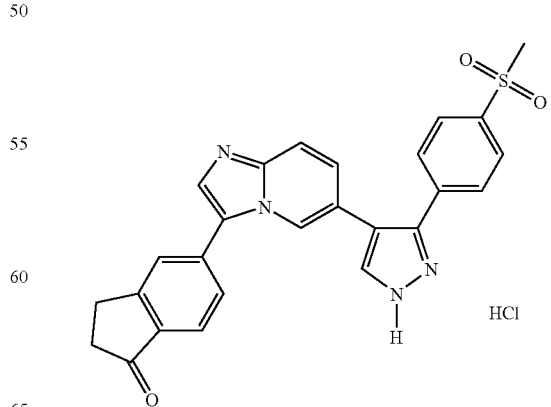

5-(6-{3-[4-(Methylsulfonyl)phenyl]-1H-4-pyrazolyl}imidazo-[1,2-a]pyridin-3-yl)-1-indanone hydrochloride 27 mg of the title compound was obtained as pale yellow crystals by the same method as in Example 79 from 44 mg 5-(6-{3-[4-(methylsulfonyl)phenyl]-1-trityl-1H-4-pyrazolyl}imidazo[1,2-a]pyridin-3-yl)-1-indanone (compound in Example 450).

$^1$H-NMR (DMSO-$d_6$)

δ: 2.66–2.71(m, 2H), 3.10–3.15(m, 2H), 3.22(s, 3H), 7.63(dd, J=8.0, 1.2 Hz, 1H), 7.70–7.78(m, 4H), 7.7.84(s, 1H), 7.88–7.93(m, 2H), 7.99(d, J=9.2 Hz, 1H), 8.20(brs, 1H), 8.42(s, 1H), 8.59(m, 1H)

MS m/e (ESI)469(MH$^+$)

Example 625

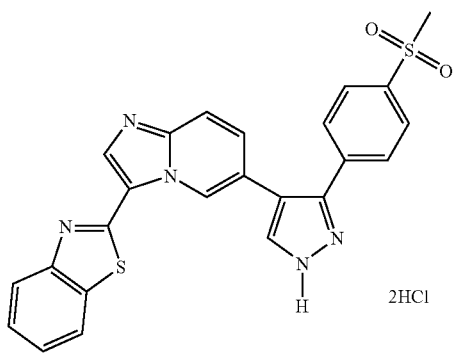

2-(6-{3-[4-(Methylsulfonyl)phenyl]-1H-4-pyrazolyl}imidazo-[1,2-a]pyridin-3-yl)-1,3-benzothiazole dihydrochloride 33 mg of the title compound was obtained as colorless crystals by the same method as in Example 79 from 61 mg 2-(6-{3-[4-(methylsulfonyl)phenyl]-1-trityl-1H-4-pyrazolyl}imidazo[1,2-a]pyridin-3-yl)-1,3-benzothiazole (compound in Example 451).

$^1$H-NMR (DMSO-$d_6$)

δ: 3.00(s, 3H), 7.44 (td, J=7.2, 1.2 Hz, 1H), 7.50 (td, J=7.2, 1.2 Hz, 1H), 7.66(dd, J=9.2, 1.2 Hz, 1H), 7.77–7.82 (m, 3H), 7.87–7.92(m, 2H), 7.93(d, J=9.2 Hz, 1H), 8.13(dd, J=7.2, 0.8 Hz, 1H), 8.25(s, 1H), 8.73(s, 1H), 9.86(dd, J=1.6, 0.8 Hz, 1H)

MS m/e(ESI)472(MH$^+$)

Example 626

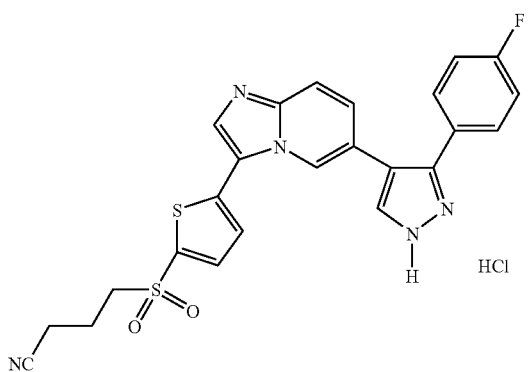

4-[(5-{6-[3-(4-Fluorophenyl)-1H-4-pyrazolyl]imidazo[1,2-a]pyridin-3-yl}-2-thienyl)sulfonyl]butane nitrile hydrochloride 60 mg of the title compound was obtained as colorless crystals by the same method as in Example 68 from 180 mg 4-[(5-{6-[3-(4-fluorophenyl)-1-trityl-1H-4-pyrazolyl]-imidazo[1,2-a]pyridin-3-yl}-2-thienyl)sulfonyl]butane nitrile (compound in Example 453).

$^1$H-NMR (DMSO-$d_6$)

δ: 1.92–2.01(m, 2H), 2.66(t, J=7.2 Hz, 2H), 3.52–3.58(m, 2H), 7.19–7.26(m, 2H), 7.46–7.52(m, 2H), 7.63(d, J=8.8 Hz, 1H), 7.63(d, J=3.6 Hz, 1H), 7.89(d, J=8.8 Hz, 1H), 7.91(d, J=3.6 Hz, 1H), 8.14(brs, 1H), 8.40(s, 1H), 8.50(s, 1H)

MS m/e(ESI)492(MH$^+$)

Example 627

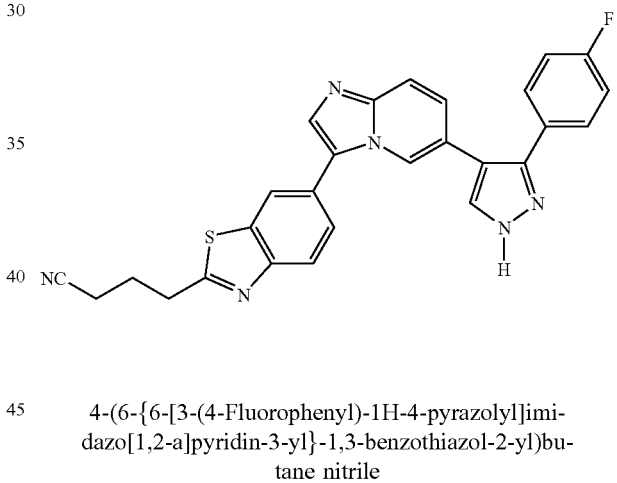

4-(6-{6-[3-(4-Fluorophenyl)-1H-4-pyrazolyl]imidazo[1,2-a]pyridin-3-yl}-1,3-benzothiazol-2-yl)butane nitrile 65 mg of the title compound was obtained (colorless crystals; recrystallization solvent, ethyl acetate) in the same manner as in Example 80 from 108 mg 4-(6-{6-[3-(4-fluorophenyl)-1-trityl-1H-4-pyrazolyl]imidazo[1,2-a]pyridin-3-yl}-1,3-benzothiazol-2-yl)butane nitrile (compound in Example 454).

$^1$H-NMR (CDCl$_3$)

δ: 2.33(tt, J=7.2, 7.2 Hz, 2H), 2.59(t, J=7.2 Hz, 2H), 3.32(t, J=7.2 Hz, 2H), 7.11–7.18(m, 2H), 7.22(dd, J=9.2, 1.6 Hz, 1H), 7.41(dd, J=8.8, 1.6 Hz, 1H), 7.46–7.51(m, 2H), 7.69(dd, J=9.2, 0.8 Hz, 1H), 7.74(s, 1H), 7.50(s, 1H), 7.79(d, J=1.6 Hz, 1H), 7.97(d, J=8.8 Hz, 1H), 8.17(dd, J=1.6, 0.8 Hz, 1H)

MS m/e(ESI)479(MH$^+$)

603

Example 628

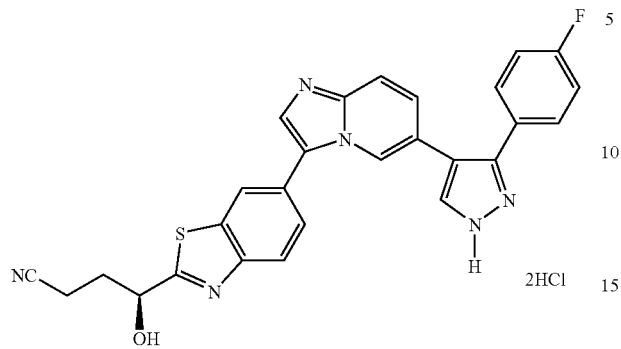

(4S)-4-(6-{6-[3-(4-Fluorophenyl)-1H-4-pyrazolyl]
imidazo-[1,2-a]pyridin-3-yl)-1,3-benzothiazol-2-yl)-
4-hydroxybutane nitrile dihydrochloride 27 mg of the title compound was obtained as colorless crystals by the same method as in Example 68 from 65 mg (4S)-4-(6-{6-[3-(4-fluorophenyl)-1-trityl-1H-4-pyrazolyl]-imidazo[1,2-a]pyridin-3-yl}-1,3-benzothiazol-2-yl)-4-hydroxybutane nitrile (compound in Example 455).
$^1$H-NMR (DMSO-$d_6$)
δ: 2.04–2.14(m, 1H), 2.25–2.35(m, 1H), 2.63–2.77(m, 2H), 5.03–5.09(m, 1H), 7.17–7.26(m, 2H), 7.48–7.55(m, 2H), 7.67(dd, J=8.4, 2.0 Hz, 1H), 7.81–7.88(m, 1H), 8.00–8.04(m, 1H), 8.07(d, 8.4 Hz), 8.18(brs, 1H), 8.38(d, J=2.0 Hz, 1H), 8.41(s, 1H), 8.46(m, 1H)
MS m/e(ESI)495(MH$^+$)

Example 629

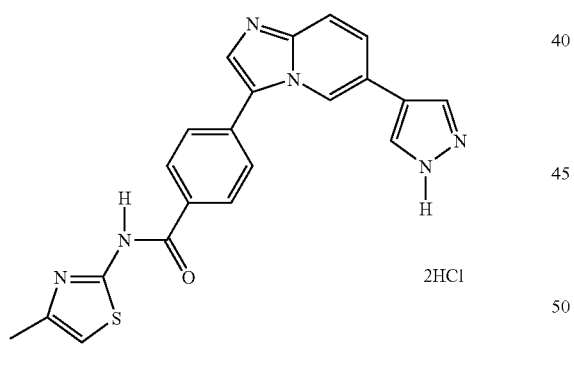

N1-(4-Methyl-1,3-thiazol-2-yl)-4-[6-(1H-4-pyra-
zolyl)-imidazo[1,2-a]pyridin-3-yl]benzamide dihy-
drochloride 31 mg of the title compound was obtained as pale yellow crystals by the same method as in Example 68 from 43 mg N1-(4-methyl-1,3-thiazol-2-yl)-4-[6-(1-trityl-1H-4-pyrazolyl)imidazo[1,2-a]pyridin-3-yl]benzamide (compound in Example 456).
$^1$H-NMR (DMSO-$d_6$)
δ: 2.34(d, J=1.2 Hz, 3H), 6.88(m, 1H), 7.96–8.00(m, 2H), 8.09(dd, J=9.2, 0.8 Hz, 1H), 8.28–8.37(m, 5H), 8.50(s, 1H), 8.90(m, 1H)
MS m/e(ESI)401(MH$^+$)

604

Example 630

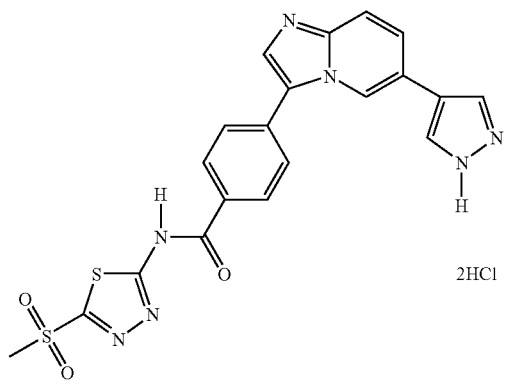

N1-[5-(Methylsulfonyl)-1,3,4-thiadiazol-2-yl]-4-[6-
(1H-4-pyrazolyl)imidazo[1,2-a]pyridin-3-yl]benza-
mide dihydrochloride 25 mg of the title compound was obtained as colorless crystal by the same method as in Example 68 from 50 mg N1-[5-(methylsulfonyl)-1,3,4-thiadiazol-2-yl]-4-[6-(1-trityl-1H-4-pyrazolyl)imidazo[1,2-a]pyridin-3-yl]benzamide (compound in Example 457).
$^1$H-NMR (DMSO-$d_6$)
δ: 3.61(s, 3H), 7.99–8.07(m, 3H), 8.14–8.20(m, 1H), 8.35–8.35(m, 2H), 8.38–8.43(m, 3H), 8.89(m, 1H)
MS m/e(ESI)466(MH$^+$)

Example 631

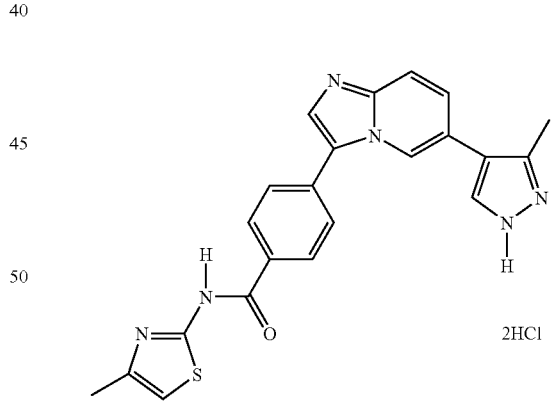

N1-(4-Methyl-1,3-thiazol-2-yl)-4-[6-(3-methyl-1H-
4-pyrazolyl)imidazo[1,2-a]pyridin-3-yl]benzamide
dihydrochloride 24 mg of the title compound was obtained as colorless crystal by the same method as in Example 68 from 40 mg N1-(4-methyl-1,3-thiazol-2-yl)-4-[6-(3-methyl-1-trityl-1H-4-pyrazolyl)imidazo[1,2-a]pyridin-3-yl]benzamide (compound in Example 460).

¹H-NMR (DMSO-d₆)

δ: 2.31(d, J=1.2 Hz, 3H), 2.39(s, 3H), 6.85(s, 1H), 7.96–8.05(m, 2H), 8.05(s, 1H), 8.10(dd, J=9.6, 1.2 Hz, 1H), 8.19(dd, J=9.6, 1.6 Hz, 1H), 8.29–8.34(m, 2H), 8.54(s, 1H), 8.67(dd, J=1.6, 0.8 Hz, 1H)

MS m/e(ESI)415(MH⁺)

Example 632

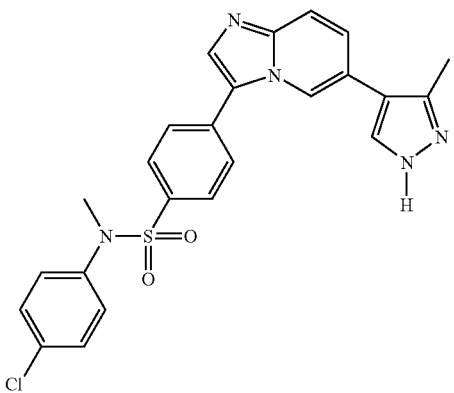

N1-(4-Chlorophenyl)-N1-methyl-4-[6-(3-methyl-1H-4-pyrazolyl)imidazo[1,2-a]pyridin-3-yl]-1-benzene sulfonamide 20 mg of the title compound was obtained as colorless crystals (recrystallization solvent, ethyl acetate) by the same method as in Example 80 from 43 mg N1-(4-chlorophenyl)-N1-methyl-4-[6-(3-methyl-1-trityl-1H-4-pyrazolyl)imidazo[1,2-a]pyridin-3-yl]-1-benzene sulfonamide (compound in Example 461).

¹H-NMR (CDCl₃)

δ: 2.43(s, 3H), 3.23(s, 3H), 7.09–7.14(m, 2H), 7.28–7.33(m, 2H), 7.35(dd, J=9.2, 2.0 Hz, 1H), 7.67(s, 1H), 7.69–7.72(m, 4H), 7.75(dd, J=9.2, 0.8 Hz, 1H), 7.83(s, 1H), 8.33(dd, J=2.0, 0.8 Hz, 1H)

MS m/e(ESI)478(MH⁺)

Example 633

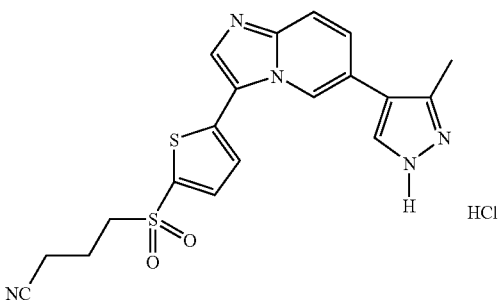

4-({5-[6-(3-Methyl-1H-4-pyrazolyl)imidazo[1,2-a]pyridin-3-yl]-2-thienyl}sulfonyl)butane nitrile hydrochloride 51 mg of the title compound was obtained as colorless crystal by the same method as in Example 68 from 140 mg 4-({5-[6-(3-methyl-1-trityl-1H-4-pyrazolyl)imidazo[1,2-a]pyridin-3-yl]-2-thienyl)sulfonyl)butane nitrile (compound in Example 463).

¹H-NMR (DMSO-d₆)

δ: 1.95–2.02(m, 2H), 2.40(s, 3H), 2.66(t, J=7.2 Hz, 2H), 3.57–3.63(m, 2H), 7.89(d, J=4.0 Hz, 1H), 8.02(d, J=4.0 Hz, 1H), 8.04(s, 1H), 8.05(d, J=10 Hz, 1H), 8.09–8.14(m, 1H), 8.57(s, 1H), 8.68(m, 1H)

MS m/e(ESI)412(MH⁺)

Example 634

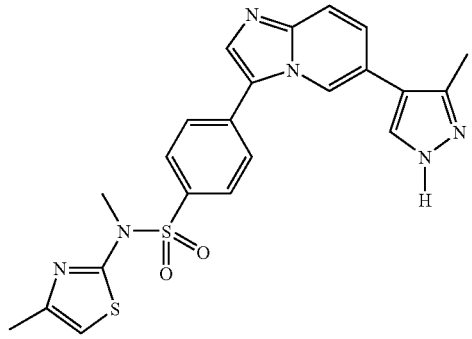

N1-Methyl-N1-(4-methyl-1,3-thiazol-2-yl)-4-[6-(3-methyl-1H-4-pyrazolyl)imidazo[1,2-a]pyridin-3-yl]-1-benzene sulfonamide 39 mg of the title compound was obtained as colorless crystals (recrystallization solvent, ethyl acetate) by the same method as in Example 80 from 110 mg N1-methyl-N1-(4-methyl-1,3-thiazol-2-yl)-4-[6-(3-methyl-1-trityl-1H-4-pyrazolyl)-imidazo[1,2-a]pyridin-3-yl]-1-benzene sulfonamide (compound in Example 464).

¹H-NMR (CDCl₃)

δ: 2.29(d, J=1.2 Hz, 3H), 2.42(s, 3H), 3.48(s, 3H), 6.56(d, J=1.2 Hz, 1H), 7.34(dd, J=9.2, 1.6 Hz, 1H), 7.66(s, 1H), 7.69–7.77(m, 3H), 7.80(s, 1H), 7.95–7.98(m, 2H), 8.33(dd, J=1.6, 1.2 Hz, 1H)

MS m/e(ESI)465(MH⁺)

Example 635

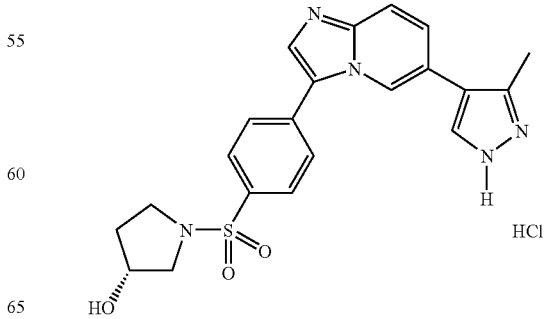

607

(3R)-1-(14-[6-(3-Methyl-1H-4-pyrazolyl)imidazo[1,2-a]-pyridin-3-yl]phenyl}sulfonyl)tetrahydro-1H-3-pyrrole hydrochloride 38 mg of the title compound was obtained as a colorless solid by the same method as in Example 68 from 70 mg (3R)-1-(4-[6-(3-methyl-1-trityl-1H-4-pyrazolyl)imidazo-[1,2-a]pyridin-3-yl]phenyl}sulfonyl)tetrahydro-1H-3-pyrrole (compound in Example 465).

¹H-NMR (DMSO-d₆)

δ: 1.61–1.71(m, 1H), 1.71–1.83(m, 1H), 2.36(s, 3H), 3.06–3.12 (m, 1H), 3.22–3.40(m, 3H), 4.15–4.21(m, 1H), 7.99–8.40(m, 5H), 8.07(dd, J=9.2, 0.8 Hz, 1H), 8.13(dd, J=9.2, 1.6 Hz, 1H), 8.50(s, 1H), 8.63(dd, J=1.6, 0.8 Hz, 1H)

MS m/e(ESI)424(MH⁺)

Example 636

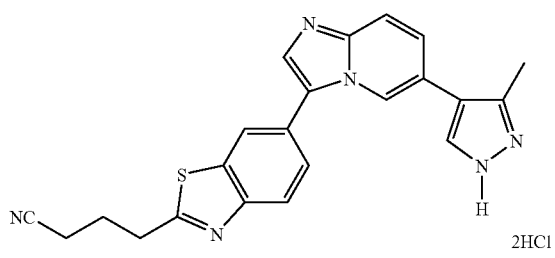

4-{6-{6-[3-Methyl-1H-4-pyrazolyl]imidazo[1,2-a]pyridin-3-yl}-1,3-benzothiazol-2-yl}butane nitrile 43 mg of the title compound was obtained as colorless crystals (recrystallization solvent, methanol/diethyl ether) by the same method as in Example 68 from 70 mg 4-{6-{6-[3-methyl-1-trityl-1H-4-pyrazolyl]imidazo[1,2-a]pyridin-3-yl}-1,3-benzothiazol-2-yl}butane nitrile (compound in Example 466).

¹H-NMR (DMSO-d₆)

δ: 2.151(tt. J=7.2, 7.2 Hz, 2H), 2.35(s, 3H), 2.68(t, J=7.2 Hz, 2H), 3.28(t, J=7.2 Hz, 2H), 7.88(dd, J=8.4, 1.6 Hz, 1H), 7.99–8.05(m, 1H), 8.08(dd, J=9.6, 1.2 Hz, 1H), 8.16(dd, J=9.6, 1.6 Hz, 1H), 8.19(d, J=8.4 Hz, 1H), 8.46(s, 1H), 8.56(d, J=1.6 Hz, 1H), 8.66(dd, J=1.6, 1.2 Hz, 1H)

MS m/e(ESI)399(MH⁺)

Example 637

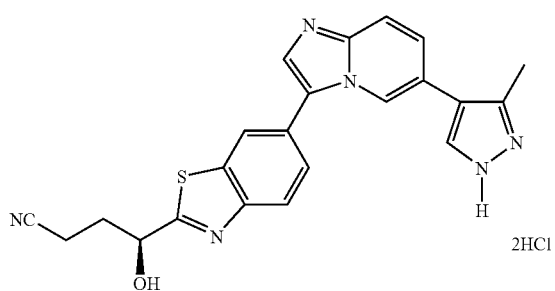

608

(4S)-4-Hydroxy-4-{6-[6-(3-methyl-1H-4-pyrazolyl)imidazo-[1,2-a]pyridin-3-yl]-1,3-benzothiazol-2-yl}butane nitrile 52 mg of the title compound was obtained as a colorless solid by the same method as in Example 51 from 80 mg (4S)-4-{6-[6-(3-methyl-1-trityl-1H-4-pyrazolyl)imidazo[1,2-a]pyridin-3-yl]-1,3-benzothiazol-2-yl}4-hydroxybutane nitrile (compound in Example 467).

¹H-NMR (DMSO-d₆)

δ: 2.03–2.14(m, 1H), 2.25–2.35(m, 1H), 2.37(s, 3H), 2.65–2.76(m, 2H), 5.06(dd, J=8.4, 4.8 Hz, 1H), 7.91(dd, J=8.4, 1.6 Hz, 1H), 8.04(brs, 1H), 8.11(dd, J=9.6, 0.4 Hz, 1H), 8.19(dd, J=9.6, 1.6 Hz, 1H), 8.21(d, J=8.4 Hz, 1H), 8.49(s, 1H), 8.61(d, J=1.6 Hz, 1H), 8.69(dd, J=1.6, 0.4 Hz, 1H)

MS m/e(ESI)415(MH⁺)

Example 638

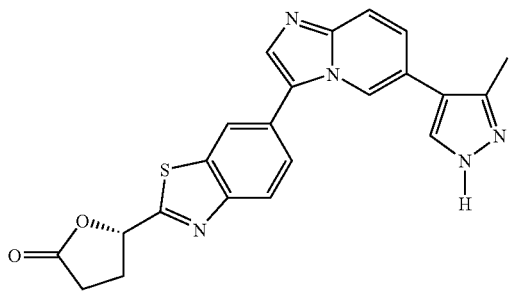

(5S)-5-{6-[6-(3-Methyl-1H-4-pyrazolyl)imidazo[1,2-a]-pyridin-3-yl]-1,3-benzothiazol-2-yl}tetrahydro-2-furanone 8 mg of the title compound was obtained as a colorless solid by the same method as in Example 80 from 30 mg (5S)-5-{6-[6-(3-methyl-1-trityl-1H-4-pyrazolyl)imidazo[1,2-a]pyridin-3-yl]-1,3-benzothiazol-2-yl}tetrahydro-2-furanone (compound in Example 468).

¹H-NMR (DMSO-d₆)

δ: 2.39(s, 3H), 2.64–2.85(m, 4H), 6.01–6.08(m, 1H), 7.48–7.54(m, 1H), 7.73(d, J=9.6 Hz, 1H), 7.67(s, 1H), 7.90(dd, J=8.4, 1.2 Hz, 1H), 8.09(m, 1H), 8.18(d, J=8.4 Hz, 1H), 8.51–8.60(m, 2H)

MS m/e(ESI)416(MH⁺)

Example 639

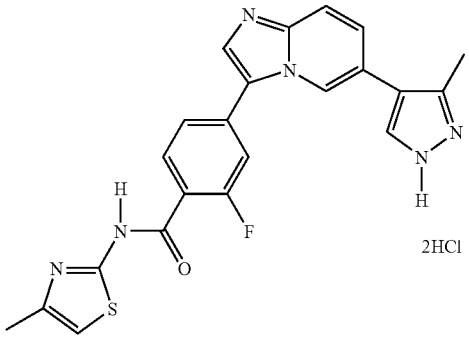

N1-(4-Methyl-1,3-thiazol-2-yl)-2-fluoro-4-[6-(3-methyl-1H-4-pyrazolyl)imidazo[1,2-a]pyridin-3-yl] benzamide dihydrochloride 58 mg 2-fluoro-4-[6-(3-methyl-1-trityl-1H-4-pyrazolyl) imidazo[1,2-a]pyridin-3-yl] benzoic acid (compound in Example 470) and 13 mg 2-amino-4-methyl-1,3-thiazole were allowed to react for 12 hours with 49 mg benzotriazol-1-yloxy-tris(dimethylamino)phosphonium hexafluorophosphate and 17 μL triethylamine in 2 mL dichloromethane. The reaction solution was purified by an NH silica gel column to give 59 mg N1-(4-methyl-1,3-thiazol-2-yl)-2-fluoro-4-[6-(3-methyl-trityl-1H-4-pyrazolyl)imidazo[1,2-a]pyridin-3-yl] benzamide as colorless crystals. This product was subjected to deprotection of the trityl group by the same method as in Example 68, to give 42 mg of the title compound as pale yellow crystals.

$^1$H-NMR (DMSO-$d_6$)

δ: 2.32(d, J=1.2 Hz, 3H), 2.43(s, 3H), 6.89(d, J=1.2 Hz, 1H), 7.81(dd, J=8.0, 1.2 Hz, 1H), 7.92(dd, J=11.2, 1.2 Hz, 1H), 7.99(dd, J=8.0, 8.0 Hz, 1H), 8.09(s, 1H), 8.13(dd, J=9.6, 1.2 Hz, 1H), 8.21(dd, J=9.6, 1.6 Hz, 1H), 8.60(s, 1H), 8.72(dd, J=1.6, 1.2 Hz, 1H)

MS m/e(ESI)433(MH$^+$)

Example 640

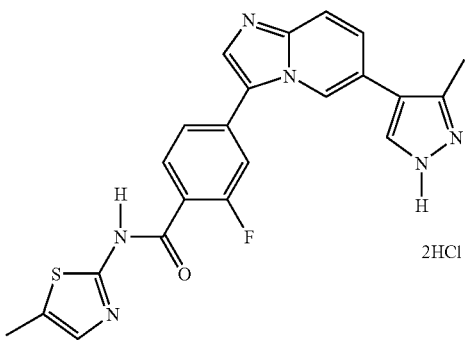

N1-(5-Methyl-1,3-thiazol-2-yl)-2-fluoro-4-[6-(3-methyl-1H-4-pyrazolyl)imidazo[1,2-a]pyridin-3-yl] benzamide dihydrochloride 31 mg of the title compound was obtained as pale yellow crystals in the same manner as in Example 639 from 58 mg of the compound in Example 470 and 13 mg 2-amino-5-methyl-1,3-thiazole.

$^1$H-NMR (DMSO-$d_6$)

δ: 2.40(d, J=1.2 Hz, 3H), 2.42(s, 3H), 7.25(d, J=1.2 HZ, 1H), 7.80(d, J=8.0, 1,6 Hz, 1H), 7.91(dd, J=11.2, 1.6 Hz, 1H), 7.98(dd, J=8.0, 8.0 Hz, 1H), 8.07(s, 1H), 8.12(dd, J=9.2, 0.8 Hz, 1H), 8.20(dd, J=9.2, 1.6 Hz, 1H), 8.58(s, 1H), 8.70(m, 1H)

MS m/e(ESI)433(MH$^+$)

Example 641

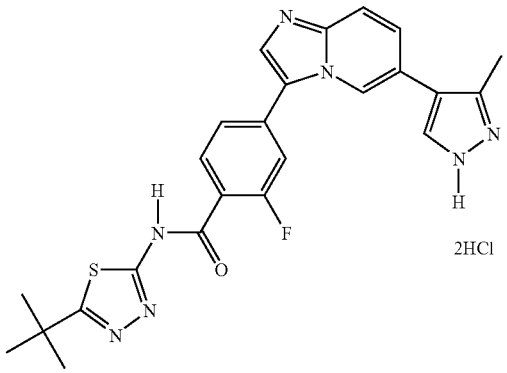

N1-[5-(t-Butyl)-1;3,4-thiadiazol-2-yl]-2-fluoro-4-[6-(3-methyl-1H-4-pyrazolyl)imidazo[1,2-a]pyridin-3-yl] benzamide dihydrochloride 43 mg of the title compound was obtained as colorless crystals in the same manner as in Example 639 from 58 mg of the compound in Example 470 and 18 mg 2-amino-5-t-butyl-1,3,4-thiadiazole.

$^1$H-NMR (DMSO-$d_6$)

δ: 1.45(s, 9H), 2.42(s, 3H), 7.82(dd, J=8.0, 1.6 Hz, 1H), 7.93(dd, J=11.2, 1.6 Hz, 1H), 8.01(dd, J=8.0, 8.0 Hz, 1H), 8.063(s, 1H), 8.11(dd, J=9.2, 0.8 Hz, 1H), 8.19(dd, J=9.2, 1.6 Hz, 1H), 8.57(s, 1H), 8.72(dd, J=1.6, 0.8 Hz, 1H)

MS m/e(ESI)476(MH$^+$)

Example 642

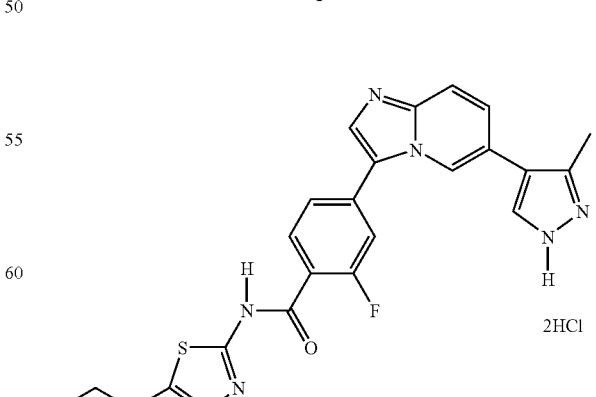

611

N1-[5-(Ethylsulfanyl)-1,3,4-thiadiazol-2-yl]-2-fluoro-4-[6-(3-methyl-1H-4-pyrazolyl)imidazo[1,2-a]pyridin-3-yl]benzamide dihydrochloride 16 mg of the title compound was obtained as colorless crystals in the same manner as in Example 639 from 28 mg of the compound in Example 470 and 8.2 mg 2-amino-5-(ethylsulfanyl)-1,3,4-thiadiazole.

$^1$H-NMR (DMSO-$d_6$)

δ: 1.81(t, J=7.2 Hz, 3H), 2.42(s, 3H), 3.28 (q, J=7.2 Hz, 2H), 7.82(dd, J=8.0, 1.6 Hz, 1H), 7.94(dd, J=11.2, 1.6 Hz, 1H), 8.03(dd, J=8.0, 8.0 Hz, 1H), 8.05(brs, 1H), 8.08(dd, J=9.2, 1.2 Hz, 1H), 8.13(dd, J=9.2, 1.2 Hz, 1H), 8.52(s, 1H), 8.71(dd, J=1.2, 1.2 Hz, 1H)

MS m/e(ESI)480(MH$^+$)

Example 643

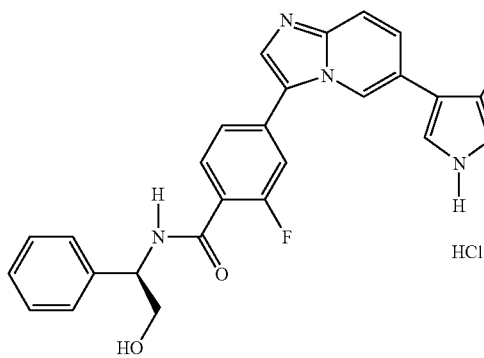

N1-[(1R)-2-hydroxy-1-phenylethyl]-2-fluoro-4-[6-(3-methyl-1H-4-pyrazolyl)imidazo[1,2-a]pyridin-3-yl] benzamide hydrochloride 40 mg of the title compound was obtained as a colorless solid in the same manner as in Example 639 from 58 mg of the compound in Example 470 and 15 mg (R)-(–)-2-phenyl glycinol.

MS m/e(ESI)456(MH$^+$)

Example 644

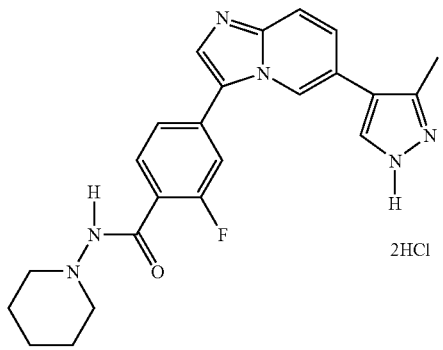

N1-Piperidino-2-fluoro-4-[6-(3-methyl-1H-4-pyrazolyl)-imidazo[1,2-a]pyridin-3-yl] benzamide dihydrochloride 20 mg of the title compound was obtained as colorless crystals in the same manner as in Example 639 from 58 mg of the compound in Example 470 and 11 mg 1-aminopiperidine.

612

$^1$H-NMR (DMSO-$d_6$)

δ: 1.36–1.47(m, 2H), 1.63–1.71(m, 4H), 2.41(s, 3H), 2.95–3.03(m, 4H), 7.75(dd, J=8.0, 1.6 Hz, 1H), 7.82(dd, 8.0, 8.0 Hz, 1H), 7.84(dd, J=10.8, 1.6 Hz, 1H), 8.05(s, 1H), 8.10(d, J=9.2 Hz, 1H), 8.18(dd, J=9.2, 1.6 Hz, 1H), 8.52(s, 1H), 8.67(s, 1H), 10.09(brs, 1H)

MS m/e(ESI)419(MH$^+$)

Example 645

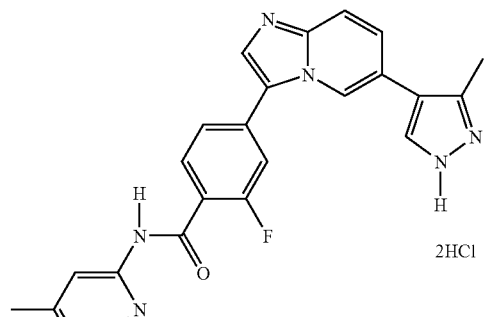

N1-(4-Methyl-2-pyridyl)-2-fluoro-4-[6-(3-methyl-1H-4-pyrazolyl)imidazo[1,2-a]pyridin-3-yl] benzamide dihydrochloride 16 mg of the title compound was obtained as colorless crystals in the same manner as in Example 639 from 58 mg of the compound in Example 470 and 12 mg 2-amino-4-methylpiperidine. In this process, the amide-forming reaction was conducted at 60° C. for 5 hours.

$^1$H-NMR (DMSO-$d_6$)

δ: 2.40(s, 3H), 2.42(s, 3H), 7.10(d, J=4.8 Hz, 1H), 7.79 (dd, J=7.6, 1.2 HZ, 1H), 7.89(dd, J=10.8, 1.2 Hz, 1H), 7.95(dd, J=7.6, 7.6 Hz, 1H), 8.03–8.08(m, 2H), 8.11(d, J=9.2 Hz, 1H), 8.18(d, J=9.2 Hz, 1H), 8.27(d, J=4.8 Hz, 1H), 8.56(s, 1H), 8.69(m, 1H), 11.1(brs, 1H)

MS m/e(ESI)427(MH$^+$)

Example 646

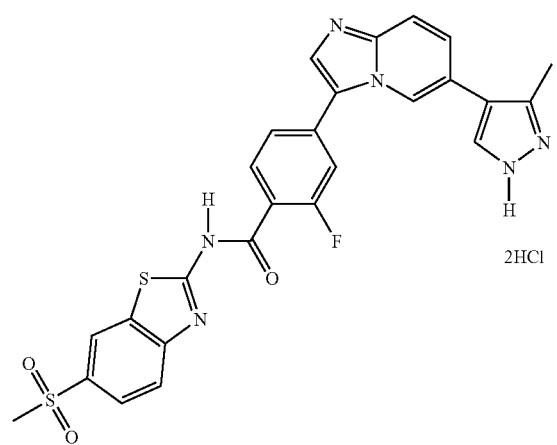

N1-[6-(Methylsulfonyl)-1,3-benzothiazol-2-yl]-2-fluoro-4-[6-(3-methyl-1H-4-pyrazolyl)imidazo[1,2-a]pyridin-3-yl] benzamide dihydrochloride 39 mg of the title compound was obtained as colorless crystals in the same manner as in Example 639 from 58 mg of the compound in Example 470 and 23 mg 2-amino-6-(methylsulfonyl)-1,3-benzothiazole. In this process, the amide-forming reaction was conducted at 60° C. for 5 hours.

$^1$H-NMR (DMSO-$d_6$)

δ: 2.43(s, 3H), 3.29(s, 3H), 7.85(dd, J=8.0, 1.6 Hz, 1H), 7.97(dd, J=11.2, 1.6 Hz, 1H), 8.00–8.03(m, 2H), 8.07(brs, 1H), 8.08(dd, J=8.0, 8.0 Hz, 1H), 8.11(dd, J=9.2, 0.8 Hz, 1H), 8.18(dd, J=9.2, 1.2 Hz, 1H), 8.58(s, 1H), 8.73(dd, J=1.2, 0.8 Hz, 1H), 8.74(dd, J=1.2, 1.2 Hz, 1H)

MS m/e(ESI)547(MH$^+$)

Example 647

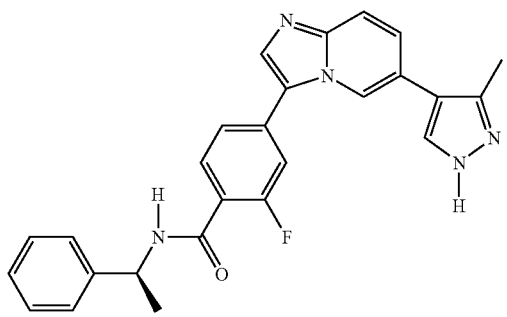

N1-[(1S)-1-Phenylethyl]-2-fluoro-4-[6-(3-methyl-1H-4-pyrazolyl)imidazo[1,2-a]pyridin-3-yl] benzamide 28 mg of the title compound was obtained as colorless crystals in the same manner as in Example 639 from 58 mg of the compound in Example 470 and 12 mg (S)-(–)-1-phenylethylamine. The product was subjected to deprotection of the trityl group in the same manner as in Example 68, but the procedure of converting it into its hydrochloride was not conducted.

$^1$H-NMR (CDCl$_3$)

δ: 1.64(d, J=6.8 Hz, 3H), 2.44(s, 3H), 5.34–5.43(m, 1H), 6.98–7.08(m, 1H), 7.25–7.44(m, 7H), 7.51(dd, J=8.8, 1.6 Hz, 1H), 7.67(s, 1H), 7.74(dd, J=8.8, 1.2 Hz, 1H), 7.81(s, 1H), 8.26(dd, J=8.0, 8.0 Hz, 1H), 8.35(dd, J=1.6, 1.2 Hz, 1H)

MS m/e(ESI)440(MH$^+$)

Example 648

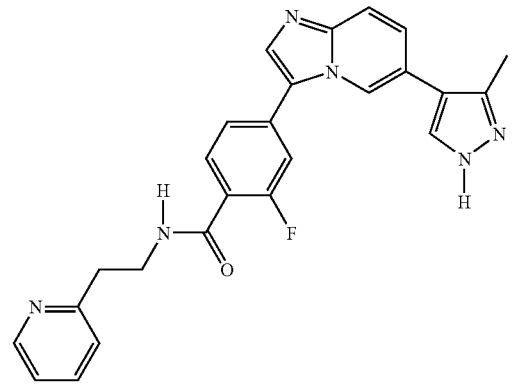

N1-[2-(2-Pyridyl)ethyl]-2-fluoro-4-[6-(3-methyl-1H-4-pyrazolyl)imidazo[1,2-a]pyridin-3-yl] benzamide 28 mg of the title compound was obtained as colorless crystals in the same manner as in Example 639 from 58 mg of the compound in Example 470 and 13.5 mg 2-(2-aminoethyl)pyridine. The product was subjected to deprotection of the trityl group in the same manner as in Example 68, but the procedure of converting it into its hydrochloride was not conducted.

$^1$H-NMR (CDCl$_3$)

δ: 2.44(s, 3H), 3.14(t, J=6.4 Hz, 2H), 3.91–3.98(m, 2H), 7.19(ddd, J=7.6, 4.8,1.2 Hz, 1H), 7.21–7.24(m, 1H), 7.33 (dd, J=12.8, 1.6 Hz, 1H), 7.34(dd, J=9.2, 1.6 Hz, 1H), 7.50(dd, J=8.0, 1.6 Hz, 1H), 7.65(ddd, J=8.0, 8.0, 1.6 Hz, 1H), 7.67(s, 1H), 7.74(dd, J=9.2, 0.8 Hz, 1H), 7.80(s, 1H), 7.78–7.88(m, 1H), 8.25(dd, J=8.0, 8.0 Hz, 1H), 8.35(dd, J=1.6, 0.8 Hz, 1H), 8.57–8.60(m, 1H)

MS m/e(ESI)441(MH$^+$)

Example 649

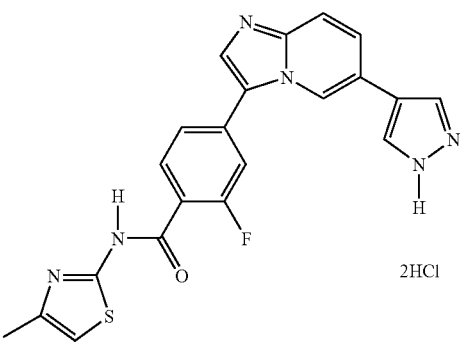

N1-(4-Methyl-1,3-thiazol-2-yl)-2-fluoro-4-[6-(1H-4-pyrazolyl)imidazo[1,2-a]pyridin-3-yl]benzamide dihydrochloride 122 mg of the title compound was obtained as pale yellow crystals in the same manner as in Example 79 from 165 mg N1-(4-methyl-1,3-thiazol-2-yl)-2-fluoro-4-[6-(1-trityl-1H-4-pyrazolyl)imidazo[1,2-a]pyridin-3-yl] benzamide (compound in Example 477).

$^1$H-NMR (DMSO-$d_6$)

δ: 2.32(d, J=1.2 Hz, 3H), 6.90(d, J=1.2 Hz, 1H), 7.78(dd, J=8.0, 1.6 Hz, 1H), 7.88(dd, J=10.8, 1.6 Hz, 1H), 8.00(dd, J=8.0, 8.0 Hz, 1H), 8.08(d, J=9.6 Hz, 1H), 8.28(dd, J=9.6, 0.8 Hz, 1H), 8.33(brs, 2H), 8.50(s, 1H), 8.92(s, 1H)

MS m/e(ESI)419(MH$^+$)

Example 650

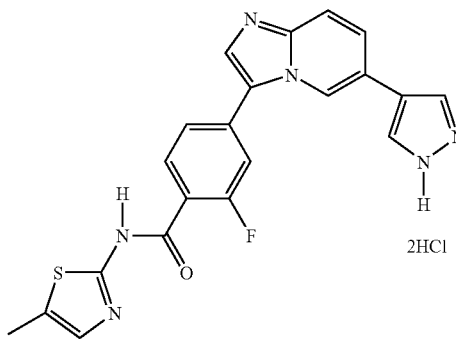

N1-(5-Methyl-1,3-thiazol-2-yl)-2-fluoro-4-[6-(1H-4-pyrazolyl)imidazo[1,2-a]pyridin-3-yl]benzamide dihydrochloride 113 mg of the title compound was obtained as colorless crystals in the same manner as in Example 79 from 152 mg N1-(5-methyl-1,3-thiazol-2-yl)-2-fluoro-4-[6-(1-trityl-1H-4-pyrazolyl)imidazo[1,2-a]pyridin-3-yl]benzamide (compound in Example 478).

$^1$H-NMR (DMSO-$d_6$)

δ: 2.40(d, J=1.2 Hz, 3H), 7.25(d, J=1.2 Hz, 1H), 7.78(dd, J=8.0, 1.6 Hz, 1H), 8.89(dd, J=10.8, 1.6 Hz, 1H), 7.99(dd, J=8.0, 8.0 Hz, 1H), 8.10(dd, J=9.2, 0.8 Hz, 1H), 8.31(dd, J=9.2, 1.2 Hz, 1H), 8.33(brs, 2H), 8.52(s, 1H), 8.91(dd, J=1.2, 0.8 Hz, 1H)

MS m/e(ESI)419(MH$^+$)

Example 651

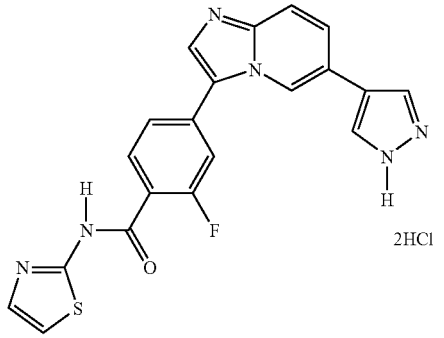

N1-(1,3-Thiazol-2-yl)-2-fluoro-4-[6-(1H-4-pyrazolyl)-imidazo[1,2-a]pyridin-3-yl]benzamide dihydrochloride 98 mg of the title compound was obtained as pale yellow crystals in the same manner as in Example 79 from 150 mg N1-(1,3-thiazol-2-yl)-2-fluoro-4-[6-(1-trityl-1H-4-pyrazolyl)imidazo[1,2-a]pyridin-3-yl]benzamide (compound in Example 479).

$^1$H-NMR (DMSO-$d_6$)

δ: 7.36(d, J=3.6 Hz, 1H), 7.59(d, J=3.6 Hz, 1H), 7.79(dd, J=8.0, 1.6 Hz, 1H), 7.90(dd, J=11.2, 1.6 Hz, 1H), 8.00(dd, J=8.0, 8.0 Hz, 1H), 8.08(d, J=9.2 Hz, 1H), 8.25–8.36(m, 3H), 8.51(s, 1H), 8.92(m, 1H)

MS m/e(ESI)405(MH$^+$)

Example 652

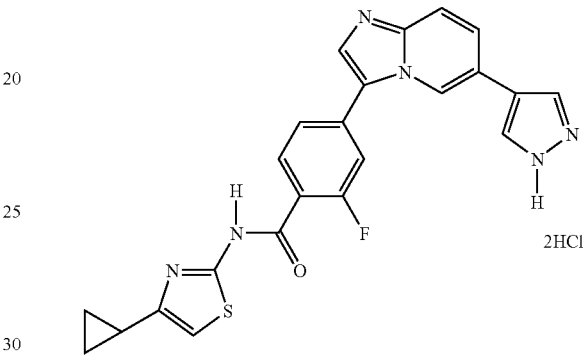

N1-(4-Cyclopropyl-1,3-thiazol-2-yl)-2-fluoro-4-[6-(1H-4-pyrazolyl)imidazo[1,2-a]pyridin-3-yl]benzamide dihydrochloride 61 mg of the title compound was obtained as yellow crystals in the same manner as in Example 79 from 100 mg N1-(4-cyclopropyl-1,3-thiazol-2-yl)-2-fluoro-4-[6-(1-trityl-1H-4-pyrazolyl)imidazo[1,2-a]pyridin-3-yl]benzamide (compound in Example 480).

$^1$H-NMR (DMSO-$d_6$)

δ: 0.77–0.83(m, 2H), 0.86–0.93(m, 2H), 2.00–2.08(m, 1H), 6.92(s, 1H), 7.77(dd, J=8.0, 1.6 Hz, 1H), 7.88(dd, J=10.8, 1.6 Hz, 1H), 7.97(dd, J=8.0, 8.0 Hz, 1H), 8.08(d, J=9.6 Hz, 1H), 8.29(dd, J=9.6, 1.2 Hz, 1H), 8.33(brs, 2H), 8.51(s, 1H), 8.92(s, 1H), 12.7(brs, 1H)

MS m/e(ESI)445(MH$^+$)

Example 653

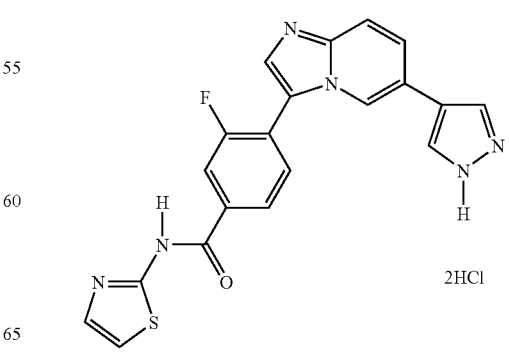

N1-(1,3-Thiazol-2-yl)-3-fluoro-4-[6-(1H-4-pyrazolyl)-imidazo[1,2-a]pyridin-3-yl]benzamide dihydrochloride 15 mg of the title compound was obtained as colorless crystals in the same manner as in Example 79 from 20 mg N1-(1,3-thiazol-2-yl)-3-fluoro-4-[6-(1-trityl-1H-4-pyrazolyl)imidazo[1,2-a]pyridin-3-yl]benzamide (compound in Example 481).
$^1$H-NMR (DMSO-$d_6$)
δ: 7.36(d, J=3.6 Hz, 1H), 7.62(d, J=3.6 Hz, 1H), 7.97(dd, J=8.0, 8.0 Hz, 1H), 8.10(dd, J=9.2, 0.8 Hz, 1H), 8.22(dd, J=8.0, 2.0 Hz, 1H), 8.25(dd, J=10.8, 2.0 Hz, 1H), 8.30–8.37 (m, 3H), 8.53(s, 1H), 8.78(m, 1H)
MS m/e(ESI)405(MH$^+$)

Example 654

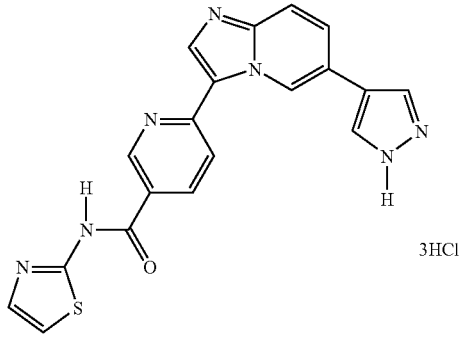

3HCl

N3-(1,3-Thiazol-2-yl)-6-[6-(1H-4-pyrazolyl)imidazo[1,2-a]-pyridin-3-yl] nicotinic acid amide trihydrochloride 41 mg of the title compound was obtained as colorless crystals in the same manner as in Example 79 from 65 mg N3-(1,3-thiazol-2-yl)-6-[6-(1-trityl-1H-4-pyrazolyl)-imidazo[1,2-a]pyridin-3-yl] nicotinic acid amide (compound in Example 482).
$^1$H-NMR (DMSO-$d_6$)
δ: 7.35(d, J=1.6 Hz, 1H), 7.62(d, J=1.6 Hz, 1H), 8.08(d, J=9.6 Hz, 1H), 8.21–8.35(m, 4H), 8.65(dd, J=8.8, 2.0 Hz, 1H), 9.03(s, 1H), 9.48(d, J=2.0 Hz, 1H), 10.4(s, 1H)
MS m/e(ESI)388(MH$^+$)

Example 655

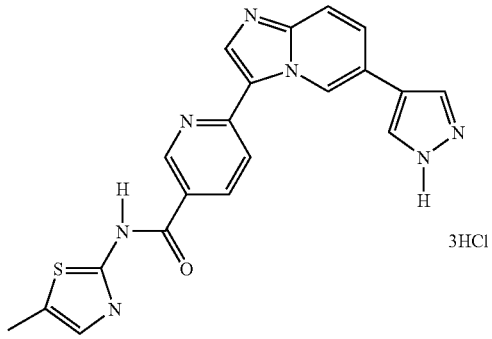

3HCl

N3-(5-Methyl-1,3-thiazol-2-yl)-6-[6-(1H-4-pyrazolyl)-imidazo[1,2-a]pyridin-3-yl]nicotinic acid amide trihydrochloride 23 mg of the title compound was obtained as colorless crystals in the same manner as in Example 79 from 40 mg N3-(5-methyl-1,3-thiazol-2-yl)-6-[6-(1-trityl-1H-4-pyrazolyl)imidazo[1,2-a]pyridin-3-yl] nicotinic acid amide (compound in Example 483).
$^1$H-NMR (DMSO-$d_6$)
δ: 2.40(d, J=0.8 Hz, 3H), 7.28(d, J=1.6 Hz, 1H), 8.09(d, J=9.2 Hz, 1H), 8.25–8.36(m, 4H), 8.63(dd, J=8.4, 2.0 Hz, 1H), 9.05(s, 1H), 9.47(d, J=2.0 Hz, 1H), 10.4(s, 1H)
MS m/e(ESI)402(MH$^+$)

Example 656

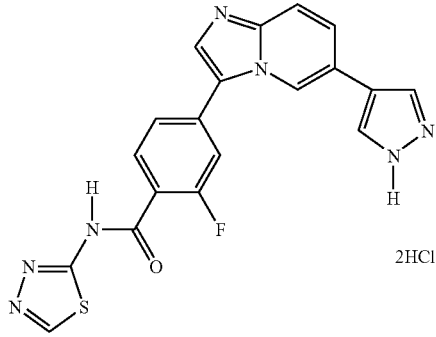

2HCl

N1-(1,3,4-Thiadiazol-2-yl)-2-fluoro-4-[6-(1H-4-pyrazolyl)-imidazo[1,2-a]pyridin-3-yl]benzamide dihydrochloride 29 mg of the title compound was obtained as colorless crystals in the same manner as in Example 79 from 40 mg N1-(1,3,4-thiadiazol-2-yl)-2-fluoro-4-[6-(1-trityl-1H-4-pyrazolyl)imidazo[1,2-a]pyridin-3-yl] benzamide (compound in Example 484).
$^1$H-NMR (DMSO-$d_6$)
δ: 7.81(dd, J=8.0, 1.6 Hz, 1H), 7.92(dd, J=11.2, 1.6 Hz, 1H), 8.04(dd, J=8.0, 8.0 Hz, 1H), 8.06(d, J=9.6 Hz, 1H), 8.24(d, J=9.6 Hz, 1H), 8.32(brs, 2H), 8.48(s, 1H), 8.92(s, 1H), 9.30(s, 1H), 13.3(brs, 1H)
MS m/e(ESI)406(MH$^+$)

Example 657

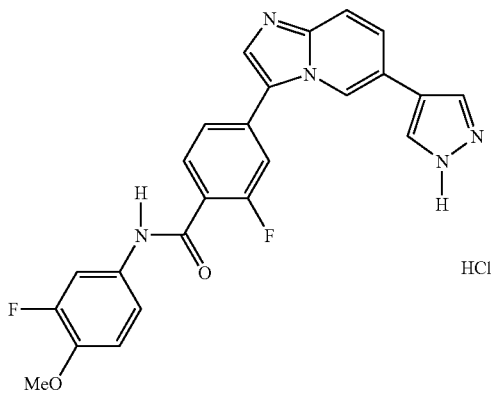

HCl

619

N1-(3-Fluoro-4-methoxyphenyl)-2-fluoro-4-[6-(1H-4-pyrazolyl)imidazo[1,2-a]pyridin-3-yl]benzamide hydrochloride 12 mg of the title compound was obtained as colorless crystals in the same manner as in Example 79 from 25 mg N1-(3-fluoro-4-methoxyphenyl)-2-fluoro-4-[6-(1-trityl-1H-4-pyrazolyl)imidazo[1,2-a]pyridin-3-yl]benzamide (compound in Example 485).

$^1$H-NMR (DMSO-$d_6$)

δ: 3.84(s, 3H), 7.20(dd, J=9.6, 9.6 Hz, 1H), 7.46(d, J=9.6 Hz, 1H), 7.73(dd, J=13.6, 1.6 Hz, 1H), 7.77(dd, J=8.0, 1.6 Hz, 1H), 7.88(dd, J=10.8, 1.6 Hz, 1H), 7.93(dd, J=8.0, 8.0 Hz, 1H), 8.07(d, J=9.6 Hz, 1H), 8.26(d, J=9.6 Hz, 1H), 8.32(brs, 2H), 8.46(s, 1H), 8.89(d, J=0.4 Hz, 1H), 10.6(s, 1H)

MS m/e(ESI)446(MH$^+$)

Example 658

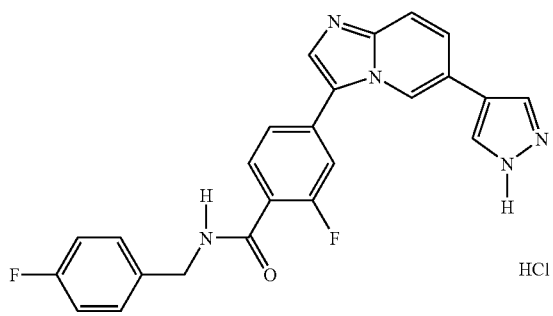

N1-(4-Fluorobenzyl)-2-fluoro-4-[6-(1H-4-pyrazolyl)imidazo-[1,2-a]pyridin-3-yl]benzamide hydrochloride 29 mg of the title compound was obtained as colorless crystals in the same manner as in Example 68 from 55 mg N1-(4-fluorobenzyl)-2-fluoro-4-[6-(1-trityl-1H-4-pyrazolyl)imidazo[1,2-a]pyridin-3-yl]benzamide (compound in Example 486).

$^1$H-NMR (DMSO-$d_6$)

δ: 4.50(d, J=6.0 Hz, 2H), 7.17–7.23(m, 2H), 7.39–7.44(m, 2H), 7.72(dd, J=8.0, 1.6 Hz, 1H), 7.83(dd, J=11.0, 1.8 Hz, 1H), 7.90(t, J=8.0 Hz, 1H), 8.08(dd, J=9.6, 0.8 Hz, 1H), 8.30(dd, J=9.6, 1.6 Hz, 1H), 8.32(brs, 2H), 8.48(s, 1H), 8.88–8.89(m, 1H), 9.04–9.09(m, 1H)

MS m/e (ESI) 430 (MH$^+$)

Example 659

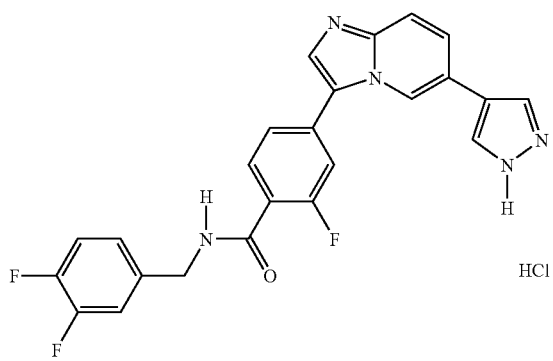

620

N1-(3,4-Difluorobenzyl)-2-fluoro-4-[6-(1H-4-pyrazolyl)-imidazo[1,2-a]pyridin-3-yl]benzamide hydrochloride 25 mg of the title compound was obtained as colorless crystals in the same manner as in Example 68 from 58 mg N1-(3,4-difluorobenzyl)-2-fluoro-4-[6-(1-trityl-1H-4-pyrazolyl)imidazo[1,2-a]pyridin-3-yl]benzamide (compound in Example 487).

$^1$H-NMR (DMSO-$d_6$)

δ: 4.67(d, J=5.6 Hz, 2H), 7.19–7.25(m, 1H), 7.37–7.48(m, 2H), 7.73(dd, J=7.8, 0.8 Hz, 1H), 7.84(dd, J=10.8, 1.6 Hz, 1H), 7.92(t, J=7.8 Hz, 1H), 8.07(d, J=9.6 Hz, 1H), 8.29(dd, J=9.6, 1.2 Hz, 1H), 8.32(s, 2H), 8.47(s, 1H), 8.82(d, J=1.2 Hz, 1H), 9.07–9.14(m, 1H)

MS m/e (ESI) 448 (MH$^+$)

Example 660

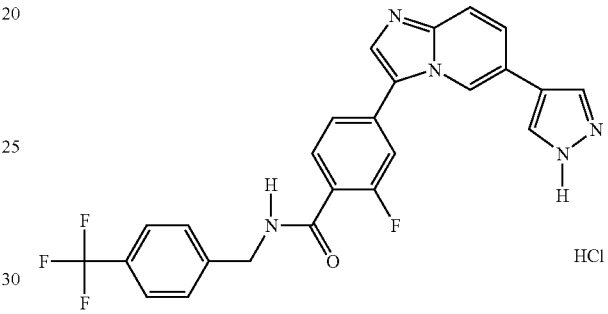

N1-(4-Trifluoromethylbenzyl)-2-fluoro-4-[6-(1H-4-pyrazolyl)imidazo[1,2-a]pyridin-3-yl]benzamide hydrochloride 24 mg of the title compound was obtained as colorless crystals in the same manner as in Example 68 from 58 mg N1-(4-trifluoromethylbenzyl)-2-fluoro-4-[6-(1-trityl-1H-4-pyrazolyl)imidazo[1,2-a]pyridin-3-yl]benzamide (compound in Example 488).

$^1$H-NMR (DMSO-$d_6$)

δ: 4.61(d, J=6.0 Hz, 2H), 7.59(d, J=7.6 Hz, 2H), 7.71–7.77(m, 3H), 7.84(dd, J=11.2, 1.6 Hz, 1H), 7.92(t, J=8.0 Hz, 1H), 8.06(d, J=9.6 Hz, 1H), 8.23–8.28(m, 1H), 8.32(brs, 2H), 8.44(s, 1H), 8.88(s, 1H), 9.13–9.19(m, 1H)

MS m/e (ESI) 480 (MH$^+$)

Example 661

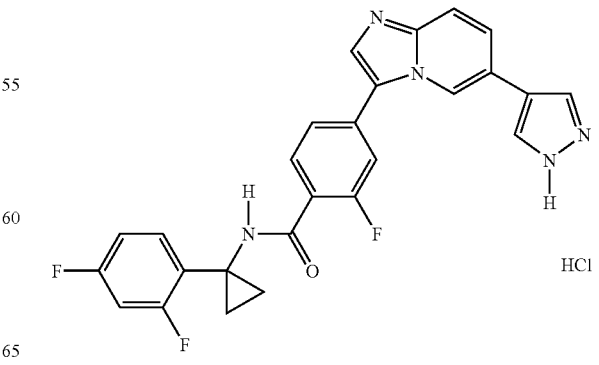

621

N1-[1-(2,4-Difluorophenyl)cyclopropyl]-2-fluoro-4-[6-(1H-4-pyrazolyl)imidazo[1,2-a]pyridin-3-yl]benzamide hydrochloride 128 mg of the title compound was obtained as colorless crystals in the same manner as in Example 79 from 212 mg N1-[1-(2,4-difluorophenyl)cyclopropyl]-2-fluoro-4-[6-(1-trityl-1H-4-pyrazolyl)imidazo[1,2-a]pyridin-3-yl] benzamide (compound in Example 489).

$^1$H-NMR (DMSO-d$_6$)

δ: 1.22(brs, 4H), 7.02–7.08(m, 1H), 7.16–7.24(m, 1H), 7.64–7.78(m, 4H), 8.08(dd, J=9.2, 0.8 Hz, 1H), 8.28–8.34 (m, 3H), 8.47(s, 1H), 8.82–8.83(m, 1H), 9.23(s, 1H)

MS m/e (ESI) 474 (MH$^+$)

Example 662

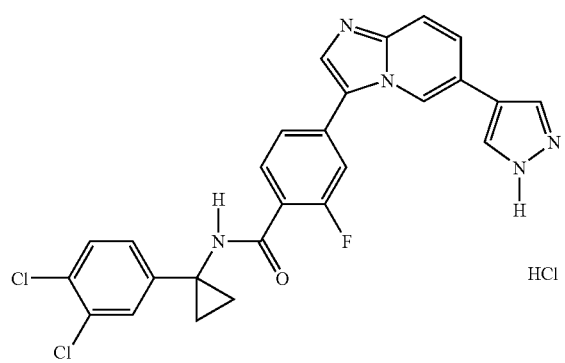

N1-[1-(3,4-Difluorophenyl)cyclopropyl]-2-fluoro-4-[6-(1H-4-pyrazolyl)imidazo[1,2-a]pyridin-3-yl]benzamide hydrochloride 147 mg of the title compound was obtained as colorless crystals in the same manner as in Example 79 from 275 mg N1-[1-(3,4-difluorophenyl)cyclopropyl]-2-fluoro-4-[6-(1-trityl-1H-4-pyrazolyl)imidazo[1,2-a]pyridin-3-yl] benzamide (compound in Example 490).

$^1$H-NMR (DMSO-d$_6$)

δ: 1.31–1.41(m, 4H), 7.23(dd, J=8.4, 2.4 Hz, 1H), 7.49(d, J=2.4 Hz, 1H), 7.58(d, J=8.4 Hz, 1H), 7.73(dd, J=8.0, 1.6 Hz, 1H), 7.82–7.89(m, 2H), 8.11(dd, J=9.3, 1.0 Hz, 1H), 8.33(dd, J=9.3, 1.6 Hz, 1H), 8.34(s, 2H), 8.51(s, 1H), 8.87–8.89(m, 1H), 9.37(s, 1H)

MS m/e (ESI) 507 (MH$^+$)

Example 663

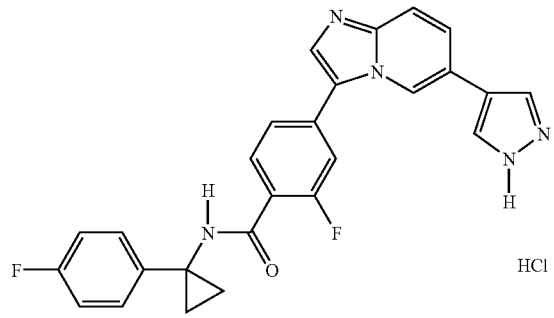

622

N1-[1-(4-Fluorophenyl)cyclopropyl]-2-fluoro-4-[6-(1H-4-pyrazolyl)imidazo[1,2-a]pyridin-3-yl]benzamide hydrochloride 135 mg of the title compound was obtained as colorless crystals in the same manner as in Example 79 from 255 mg N1-[1-(4-fluorophenyl)cyclopropyl]-2-fluoro-4-[6-(1-trityl-1H-4-pyrazolyl)imidazo[1,2-a]pyridin-3-yl] benzamide (compound in Example 491).

$^1$H-NMR (DMSO-d$_6$)

δ: 1.29(brs, 4H), 7.12–7.18(m, 2H), 7.28–7.36(m, 2H), 7.72(dd, J=8.0, 1.6 Hz, 1H), 7.80–7.88(m, 2H), 8.10(dd, J=9.5, 0.6 Hz, 1H), 8.33(dd, J=9.5, 1.6 Hz, 1H), 8.34(s, 2H), 8.51(s, 1H), 8.87–8.89(m, 1H), 9.29(s, 1H)

MS m/e (ESI) 472 (MH$^+$)

Example 664

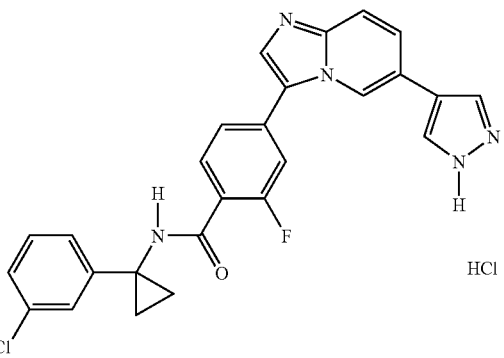

N1-[1-(3-Chlorophenyl)-cyclopropyl]-2-fluoro-4-[6-(1H-4-pyrazolyl)imidazo[1,2-a]pyridin-3-yl]benzamide hydrochloride 120 mg of the title compound was obtained as colorless crystals in the same manner as in Example 79 from 278 mg N1-[1-(3-chlorophenyl)cyclopropyl]-2-fluoro-4-[6-(1-trityl-1H-4-pyrazolyl)imidazo[1,2-a]pyridin-3-yl] benzamide (compound in Example 492).

$^1$H-NMR (DMSO-d$_6$)

δ: 1.32–1.38(m, 4H), 7.18–7.22(m, 1H), 7.25–7.28(m, 1H), 7.30–7.33(m, 1H), 7.36(t, J=8.0 Hz, 1H), 7.73(dd, J=8.0, 1.6 Hz, 1H), 7.81–7.89(m, 2H), 8.10(dd, J=9.4, 1.0 Hz, 1H), 8.32(dd, J=9.4, 1.6 Hz, 1H), 8.33(s, 2H), 8.50(s, 1H), 8.87–8.89(m, 1H), 9.33(s, 1H)

MS m/e (ESI) 456 (MH$^+$)

Example 665

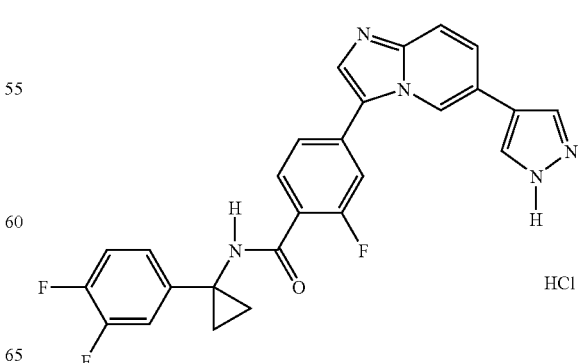

623

N1-[1-(3,4-Difluorophenyl)cyclopropyl]-2-fluoro-4-[6-(1H-4-pyrazolyl)imidazo[1,2-a]pyridin-3-yl]benzamide hydrochloride

144 mg of the title compound was obtained as colorless crystals in the same manner as in Example 79 from 306 mg N1-[1-(3,4-difluorophenyl)-cyclopropyl]-2-fluoro-4-[6-(1-trityl-1H-4-pyrazolyl)imidazo[1,2-a]pyridin-3-yl] benzamide (compound in Example 493).

$^1$H-NMR (DMSO-$d_6$)

δ: 1.29–1.38(m, 4H), 7.10–7.15(m, 1H), 7.25–7.31(m, 1H), 7.35–7.42(m, 1H), 7.73(dd, J=7.6, 1.6 Hz, 1H), 7.81–7.89(m, 2H), 8.11(dd, J=9.2, 0.9 Hz, 1H), 8.33(dd, J=9.2, 1.5 Hz, 1H), 8.34(s, 2H), 8.52(s, 1H), 8.88(dd, J=1.5, 0.9 Hz, 1H), 9.34(s, 1H)

MS m/e (ESI) 474 (MH$^+$)

Example 666

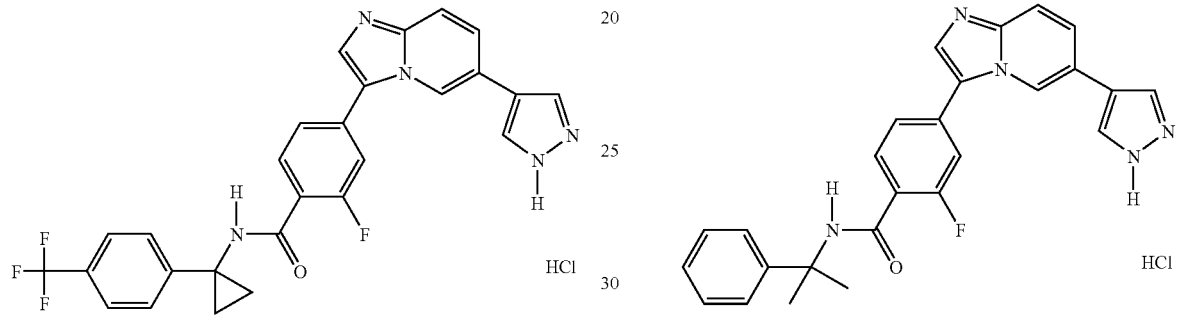

N1-[1-(4-Trifluoromethylphenyl)cyclopropyl]-2-fluoro-4-[6-(1H-4-pyrazolyl)imidazo[1,2-a]pyridin-3-yl]benzamide hydrochloride

151 mg of the title compound was obtained as colorless crystals in the same manner as in Example 79 from 284 mg N1-[1-(4-trifluoromethylphenyl)cyclopropyl]-2-fluoro-4-[6-(1-trityl-1H-4-pyrazolyl)imidazo[1,2-a]pyridin-3-yl] benzamide (compound in Example 494).

$^1$H-NMR (DMSO-$d_6$)

δ: 1.37–1.46(m, 4H), 7.45(d, J=8.2 Hz, 2H), 7.69(d, J=8.2 Hz, 2H), 7.74(dd, J=7.8, 1.5 Hz, 1H), 7.85(dd, J=10.8, 1.5 Hz, 1H), 7.89(t, J=7.8 Hz, 1H), 8.10(dd, J=9.2, 0.8 Hz, 1H), 8.31(dd, J=9.2, 2.0 Hz, 1H), 8.33(s, 2H), 8.50(s, 1H), 8.88–8.89(m, 1H), 9.38(s, 1H)

MS m/e (ESI) 506 (MH$^+$)

Example 667

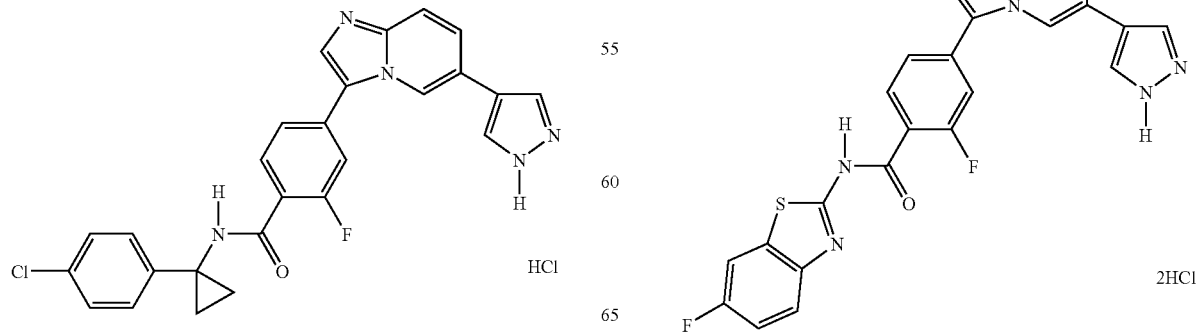

624

N1-[1-(4-Chlorophenyl)cyclopropyl]-2-fluoro-4-[6-(1H-4-pyrazolyl)imidazo[1,2-a]pyridin-3-yl]benzamide hydrochloride

9 mg of the title compound was obtained in the same manner as in Example 79 from 35 mg N1-[1-(4-chlorophenyl)cyclopropyl]-2-fluoro-4-[6-(1-trityl-1H-4-pyrazolyl)imidazo[1,2-a]pyridin-3-yl] benzamide (compound in Example 495).

$^1$H-NMR (DMSO-$d_6$)

δ: 3.40–4.00(bd, 4H), 7.28(d, J=8.8 Hz, 2H), 7.38(d, J=8.8 Hz, 2H), 7.72(dd, J=8.0, 1.6 Hz, 1H), 7.83(dd, J=8.0, 1.6 Hz, 1H), 7.86(dd, J=8.0, 8.0 Hz, 1H), 8.09(dd, J=9.2, 1.2 Hz, 1H), 8.31(d, J=9.2 Hz, 1H), 8.32(s, 1H), 8.33(s, 1H), 8.45(s, 1H), 8.88(m, 1H), 9.30(s, 1H)

Example 668

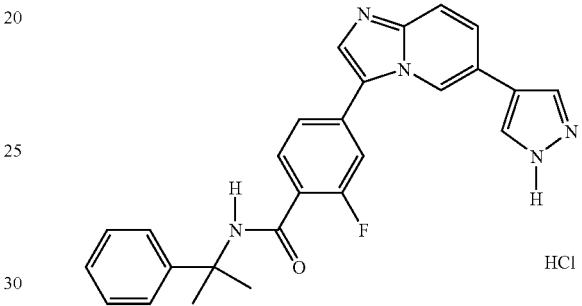

N1-(1-Methyl-1-phenylethyl)-2-fluoro-4-[6-(1H-4-pyrazolyl)-imidazo[1,2-a]pyridin-3-yl]benzamide hydrochloride

9 mg of the title compound was obtained in the same manner as in Example 79 from 35 mg N1-(1-methyl-1-phenylethyl)-2-fluoro-4-[6-(1-trityl-1H-4-pyrazolyl)imidazo[1,2-a]pyridin-3-yl] benzamide (compound in Example 496).

$^1$H-NMR (DMSO-$d_6$)

δ: 1.64(s, 6H), 7.22(dd, J=7.2, 7.2 Hz, 1H), 7.34(dd, J=7.2, 7.2 Hz, 2H), 7.46(dd, J=7.2, 7.2 Hz, 2H), 7.70(dd, J=9.2, 0.8 Hz, 1H), 7.77–7.81(m, 2H), 8.07(d, J=13.2 Hz, 1H), 8.26–8.32(m, 3H), 8.44(s, 1H), 8.69(s, 1H), 8.85(s, 1H)

Example 669

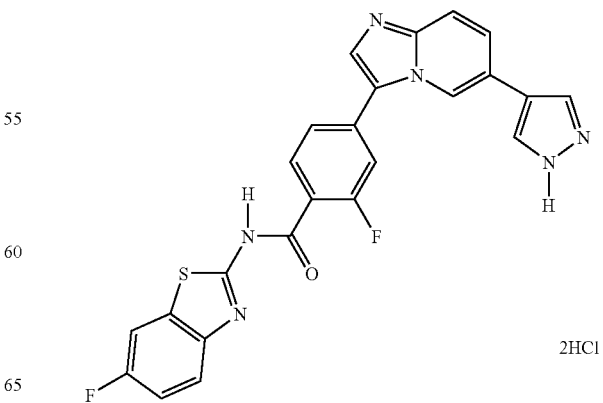

N1-(6-Fluoro-1,3-benzothiazol-2-yl)-2-fluoro-4-[6-(1H-4-pyrazolyl)imidazo[1,2-a]pyridin-3-yl]benzamide dihydrochloride 31 mg of the title compound was obtained as pale yellow crystals in the same manner as in Example 79 from 48 mg N1-(6-fluoro-1,3-benzothiazol-2-yl)-2-fluoro-4-[6-(1-trityl-1H-4-pyrazolyl)imidazo[1,2-a]pyridin-3-yl] benzamide (compound in Example 497).

$^1$H-NMR (DMSO-$d_6$)

δ: 7.36(ddd, J=8.8, 8.8, 2.4 Hz, 1H), 7.79–7.87(m, 2H), 7.93(dd, J=11.2, 1.2 Hz, 1H), 7.99(dd, J=8.4, 2.4 Hz, 1H), 8.02–8.09(m, 2H), 8.25(d, J=9.2 Hz, 1H), 8.28–8.37 (br. 2H), 8.48(s, 1H), 8.92(m, 1H), 13.1(brs, 1H)

MS m/e(ESI)473(MH$^+$)

Example 670

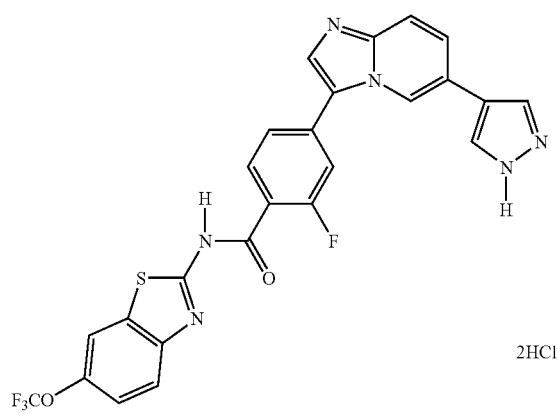

2HCl

N1-[6-(Trifluoromethoxy)-1,3-benzothiazol-2-yl]-2-fluoro-4-[6-(1H-4-pyrazolyl)imidazo[1,2-a]pyridin-3-yl]benzamide dihydrochloride 37 mg of the title compound was obtained as colorless crystals in the same manner as in Example 79 from 57 mg N1-[6-(trifluoromethoxy)-1,3-benzothiazol-2-yl]-2-fluoro-4-[6-(1-trityl-1H-4-pyrazolyl)imidazo[1,2-a]pyridin-3-yl] benzamide (compound in Example 498).

$^1$H-NMR (DMSO-$d_6$)

δ: 7.49(ddd, J=8.8, 2.8, 0.8 Hz, 1H), 7.83(dd, J=8.0, 1.6 Hz, 1H), 7.88–7.97(m, 2H), 8.04–8.11(m, 2H), 8.22(d, J=1.6 Hz, 1H), 8.29(dd, J=9.2, 1.6 Hz, 1H), 8.33(brs, 2H), 8.53(s, 1H), 8.93(dd, J=1.2, 0.8 Hz, 1H), 13.2(brs, 1H)

MS m/e(ESI)539(MH$^+$)

Example 671

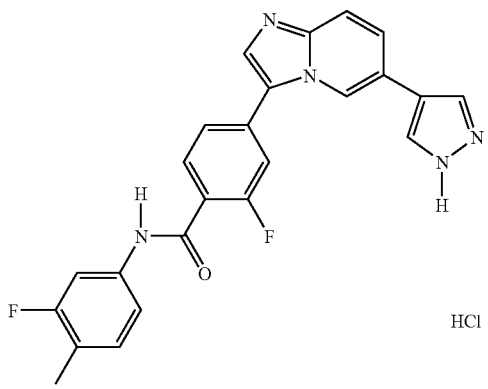

HCl

N1-(3-Fluoro-4-methylphenyl)-2-fluoro-4-[6-(1H-4-pyrazolyl)imidazo[1,2-a]pyridin-3-yl]benzamide hydrochloride 45 mg of the title compound was obtained as colorless crystals in the same manner as in Example 79 from 65 mg N1-(3-fluoro-4-methylphenyl)-2-fluoro-4-[6-(1-trityl-1H-4-pyrazolyl)imidazo[1,2-a]pyridin-3-yl] benzamide (compound in Example 499).

$^1$H-NMR (DMSO-$d_6$)

δ: 2.22(d, J=1.2 Hz, 3H), 7.27(dd, J=8.4, 8.4 Hz, 1H), 7.41(dd, J=8.4, 2.0 Hz, 1H), 7.68(dd, J=12.0, 1.6 Hz, 1H), 7.78(dd, J=7.6, 1.6 Hz, 1H), 7.88(dd, J=12.0, 1.2 Hz, 1H), 7.93(dd, J=7.6, 7.6 Hz, 1H), 8.08(d, J=8.8 Hz, 1H), 8.25–8.38(m, 3H), 8.482(s, 1H), 8.89(s, 1H), 10.7(m, 1H)

MS m/e(ESI)430(MH$^+$)

Example 672

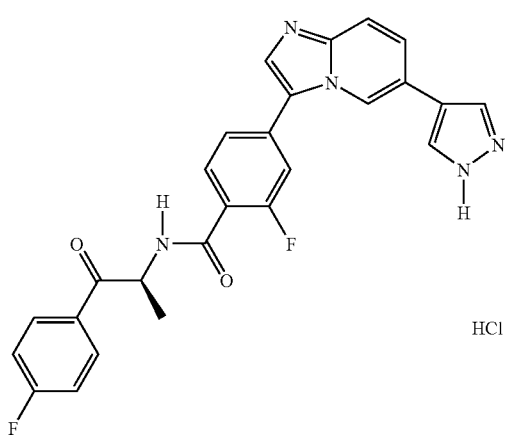

HCl

N1-[(1S)-2-(4-Fluorophenyl)-1-methyl-2-oxoethyl]-2-fluoro-4-[6-(1H-4-pyrazolyl)imidazo[1,2-a]pyridin-3-yl]benzamide hydrochloride 270 mg N1-[(1S)-2-(4-fluorophenyl)-1-methyl-2-oxoethyl]-2-fluoro-4-[6-(1-trityl-1H-4-pyrazolyl)imidazo-[1,2-a]pyridin-3-yl] benzamide (compound in Example 500) was suspended in 5 mL 1,4-dioxane, and a solution of 4 N hydrogen hydride in 1,4-dioxane was added thereto. After the mixture was left for 1 hour, hexane and diethyl ether were added thereto, and the precipitated solid was collected and dried under reduced pressure. The product was crystallized from ethanol, to give 110 mg of the title compound as pale brown crystals (optical purity: 74% ee).

$^1$H-NMR (DMSO-d$_6$)

δ: 1.41(d, J=7.2 Hz, 3H), 5.49–5.58(m, 1H), 7.37–7.44(m, 2H), 7.71(dd, J=7.6, 1.6 Hz, 1H), 7.76–7.84(m, 2H), 8.00(d, J=8.8 Hz, 1H), 8.08–8.18(m, 3H), 8.29(brs, 2H), 8.34(s, 1H), 8.84(s, 1H), 8.93–8.98(m, 1H)

MS m/e(ESI)472(MH$^+$)

Example 673

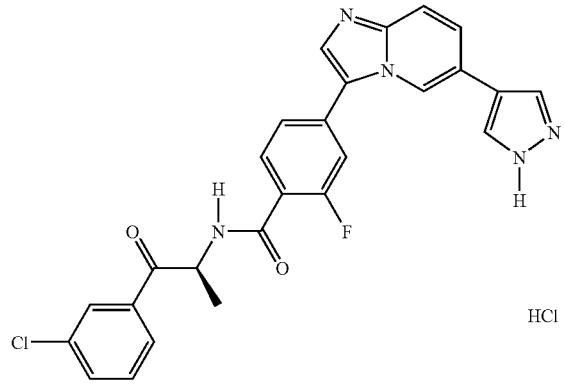

N1-[(1S)-2-(3-Chlorophenyl)-1-methyl-2-oxoethyl]-2-fluoro-4-[6-(1H-4-pyrazolyl)imidazo[1,2-a]pyridin-3-yl]benzamide hydrochloride 35 mg of the title compound was obtained as colorless crystals in the same manner as in Example 672 from 100 mg N1-[(1S)-2-(3-chlorophenyl)-1-methyl-2-oxoethyl]-2-fluoro-4-[6-(1-trityl-1H-4-pyrazolyl)imidazo[1,2-a]pyridin-3-yl] benzamide (compound in Example 501) (optical purity: 96% ee).

$^1$H-NMR (DMSO-d$_6$)

δ: 1.42(d, J=7.2 Hz, 3H), 5.45–5.55(m, 1H), 7.61(dd, J=8.0, 8.0 Hz, 1H), 7.72(ddd, J=8.0, 8.0, 1.6 Hz, 1H), 7.45–7.65(m, 3H), 7.97–8.05(m, 2H), 8.07(d, J=9.2 Hz, 1H), 8.25–8.35(m, 3H), 8.46(s, 1H), 8.88(m, 1H), 9.05(d, J=6.8 Hz, 1H)

MS m/e(ESI)488(MH$^+$)

Example 674

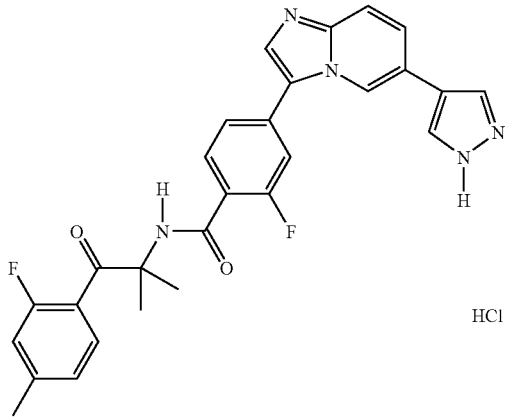

N1-[2-(2-Fluoro-4-methylphenyl)-1,1-dimethyl-2-oxoethyl]-2-fluoro-4-[6-(1-trityl-1H-4-pyrazolyl)imidazo[1,2-a]pyridin-3-yl]benzamide hydrochloride 151 mg of the title compound was obtained as colorless crystals in the same manner as in Example 79 from 250 mg N1-[2-(2-fluoro-4-methylphenyl)-1,1-dimethyl-2-oxoethyl]-2-fluoro-4-[6-(1-trityl-1H-4-pyrazolyl)imidazo[1,2-a]pyridin-3-yl] benzamide (compound in Example 502).

$^1$H-NMR (DMSO-d$_6$)

δ: 1.59(s, 6H), 2.34(s, 3H), 7.06(d, J=8.0 Hz, 1H), 7.11(d, J=11.6 Hz, 1H), 7.52(dd, J=8.0, 8.0 Hz, 1H), 7.60(dd, J=8.0, 8.0 Hz, 1H), 7.66(dd, J=8.0, 1.6 Hz, 1H), 7.76(dd, J=10.8, 1.6 Hz, 1H), 8.07(d, J=9.6 Hz, 1H), 8.25–8.35(m, 3H), 8.45(s, 1H), 8.83(s, 1H), 9.15(s, 1H)

MS m/e(ESI)500(MH$^+$)

Example 675

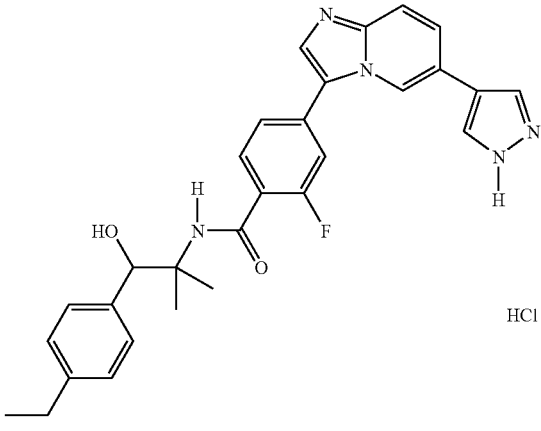

N1-[2-(4-Ethylphenyl)-2-hydroxy-1,1-dimethylethyl]-2-fluoro-4-[6-(1H-4-pyrazolyl)imidazo[1,2-a]pyridin-3-yl]benzamide hydrochloride 31 mg of the title compound was obtained as colorless crystals in the same manner as in Example 79 from 61 mg N1-[2-(4-ethylphenyl)-2-hydroxy-1,1-dimethylethyl]-2-fluoro-4-[6-(1-trityl-1H-4-pyrazolyl)imidazo[1,2-a]pyridin-3-yl] benzamide (compound in Example 503).

¹H-NMR (DMSO-d₆)

δ: 1.18(t, J=7.6 Hz, 3H), 1.27(s, 3H), 1.41(s, 3H), 2.59 (q, J=7.6 Hz, 2H), 5.03(s, 1H), 7.15–7.20(m, 2H), 7.28–7.34(m, 2H), 7.70(dd, J=8.0, 1.2 Hz, 1H), 7.76–7.87(m, 3H), 8.09(d, J=9.2 Hz, 1H), 8.28–8.37(m, 3H), 8.47(s, 1H), 8.86(s, 1H)

MS m/e(ESI)498(MH⁺)

Example 676

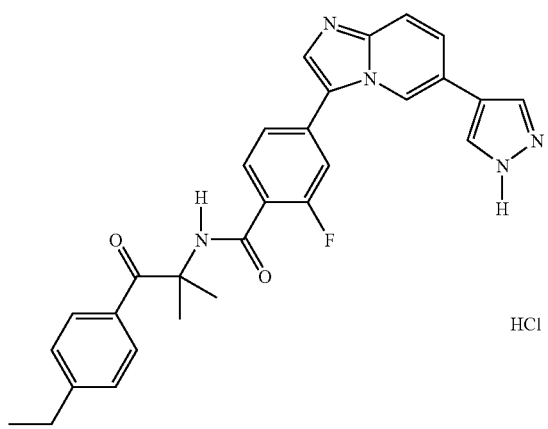

N1-[2-(4-Ethylphenyl)-1,1-dimethyl-2-oxyethyl]-2-fluoro-4-[6-(1H-4-pyrazolyl)imidazo[1,2-a]pyridin-3-yl]benzamide hydrochloride 78 mg of the title compound was obtained as colorless crystals in the same manner as in Example 79 from 120 mg N1-[2-(4-ethylphenyl)-1,1-dimethyl-2-oxyethyl]-2-fluoro-4-[6-(1-trityl-1H-4-pyrazolyl)imidazo[1,2-a]pyridin-3-yl] benzamide (compound in Example 504).

¹H-NMR (DMSO-d₆)

δ: 1.19(t, J=7.6 Hz, 3H), 1.60(s, 6H), 2.65 (q, J=7.6 Hz, 2H), 7.27–7.32(m, 2H), 7.55(dd, J=8.0, 8.0 Hz, 1H), 7.66 (dd, J=8.0, 1.6 Hz, 1H), 7.79(dd, J=10.8, 1.6 HZ, 1H), 8.00–8.05(m, 2H), 8.08(dd, J=9.2, 0.8 Hz, 1H), 8.27–8.34 (m, 3H), 8.46(s, 1H), 8.83(m, 1H), 9.37(s, 1H)

MS m/e(ESI)497(MH⁺)

Example 677

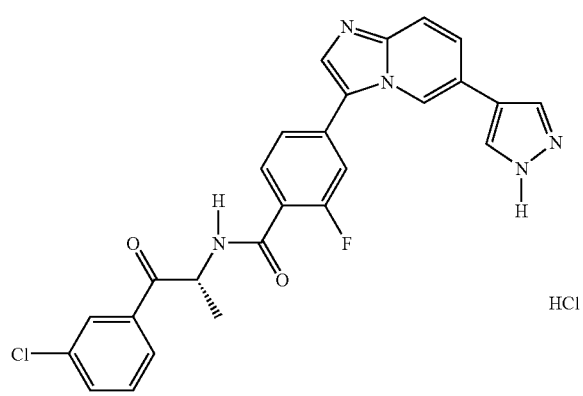

N1-[(1R)-2-(3-Chlorophenyl)-1-methyl-2-oxoethyl]-2-fluoro-4-[6-(1H-4-pyrazolyl)imidazo[1,2-a]pyridin-3-yl]benzamide hydrochloride 132 mg of the compound in Example 472 and 51 mg (2R)-2-amino-1-(3-chlorophenyl)propan-1-one (compound in Example 322) were reacted in the same manner as in Example 500, and then subjected to deprotection of the trityl group in the same method as in Example 672, to give 90 mg of the title compound as colorless crystals (optical purity: 95% ee).

¹H-NMR (DMSO-d₆)

δ: 1.42(d, J=7.2 Hz, 3H), 5.45–5.55(m, 1H), 7.61(dd, J=8.0, 8.0 Hz, 1H), 7.72(ddd, J=8.0, 8.0, 1.6 Hz, 1H), 7.45–7.65(m, 3H), 7.97–8.05(m, 2H), 8.07(d, J=9.2 Hz, 1H), 8.25–8.35(m, 3H), 8.46(s, 1H), 8.88(m, 1H), 9.05(d, J=6.8 Hz, 1H)

Example 678

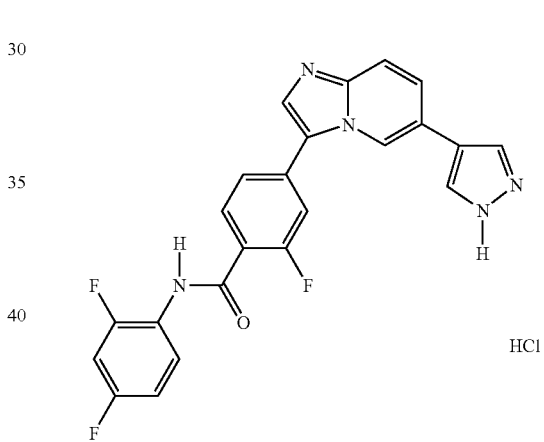

N1-(2,4-Difluorophenyl)-2-fluoro-4-[6-(1H-4-pyrazolyl)-imidazo[1,2-a]pyridin-3-yl]benzamide hydrochloride 55 mg of the title compound was obtained as colorless crystals in the same manner as in Example 79 from 79 mg N1-(2,4-difluorophenyl)-2-fluoro-4-[6-(1-trityl-1H-4-pyrazolyl)imidazo[1,2-a]pyridin-3-yl] benzamide (compound in Example 505).

¹H-NMR (DMSO-d₆)

δ: 7.12–7.21(m, 1H), 7.37–7.46(m, 1H), 7.73–7.84(m, 2H), 7.89(d, J=11.2 Hz, 1H), 7.99(dd, J=7.6, 7.6 Hz, 1H), 8.09(d, J=9.2 Hz, 1H), 8.30(d, J=9.2 Hz, 1H), 8.33(s, 2H), 8.50(s, 1H), 8.90(s, 1H), 10.3(s, 1H)

MS m/e(ESI)434(MH⁺)

Example 679

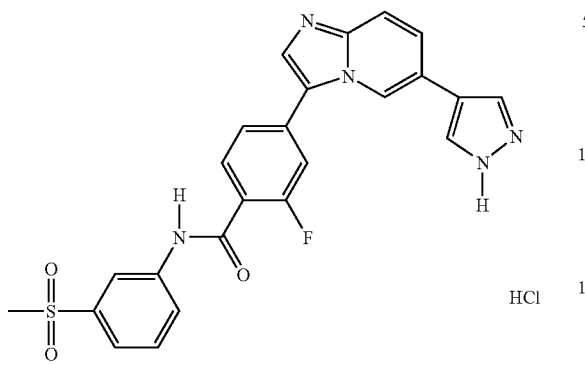

N1-[3-(Methylsulfonyl)phenyl]-2-fluoro-4-[6-(1H-4-pyrazolyl)imidazo[1,2-a]pyridin-3-yl]benzamide hydrochloride 80 mg of the title compound was obtained as colorless crystals in the same manner as in Example 79 from 133 mg N1-[3-(methylsulfonyl)phenyl]-2-fluoro-4-[6-(1-trityl-1H-4-pyrazolyl)imidazo[1,2-a]pyridin-3-yl] benzamide (compound in Example 506).

$^1$H-NMR (DMSO-$d_6$)

δ: 3.24(s, 3H), 7.66–7.74(m, 2H), 7.80(dd, J=7.6, 1.6 Hz, 1H), 7.91(dd, J=10.8, 1.6 Hz, 1H), 7.98(dd, J=7.6, 7.6 Hz, 1H), 8.02–8.07(m, 1H), 8.10(d, J=9.2 Hz, 1H), 8.31(dd, J=9.2, 1.6 Hz, 1H), 8.34(brs, 2H), 8.44(s, 1H), 8.51(s, 1H), 8.92(s, 1H), 11.0(s, 1H)

MS m/e(ESI)476(MH$^+$)

Example 680

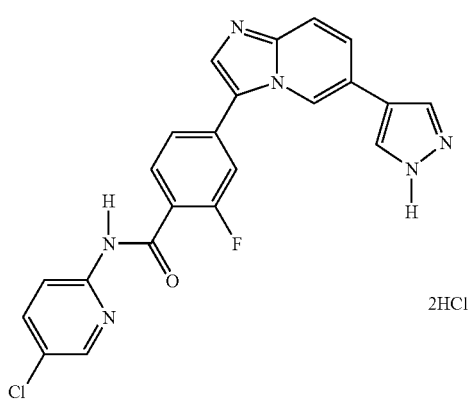

N1-(5-Chloro-2-pyridyl)-2-fluoro-4-[6-(1H-4-pyrazolyl)-imidazo[1,2-a]pyridin-3-yl]benzamide dihydrochloride 93 mg of the title compound was obtained as colorless crystals in the same manner as in Example 79 from 128 mg N1-(5-chloro-2-pyridyl)-2-fluoro-4-[6-(1-trityl-1H-4-pyrazolyl)imidazo[1,2-a]pyridin-3-yl] benzamide (compound in Example 507).

$^1$H-NMR (DMSO-$d_6$)

δ: 7.77(dd, J=8.0, 1.2 Hz, 1H), 7.87(dd, J=10.8, 1.2 Hz, 1H), 7.95(dd, J=8.0, 8.0 Hz, 1H), 8.02(dd, J=8.8, 2.8 Hz, 1H), 8.10(dd, J=9.2, 0.8 Hz, 1H), 8.24–8.36(m, 4H), 8.47(d, J=2.8 Hz, 1H), 8.53(s, 1H), 8.90(s, 1H), 11.2(s, 1H)

MS m/e(ESI)433(MH$^+$)

Example 681

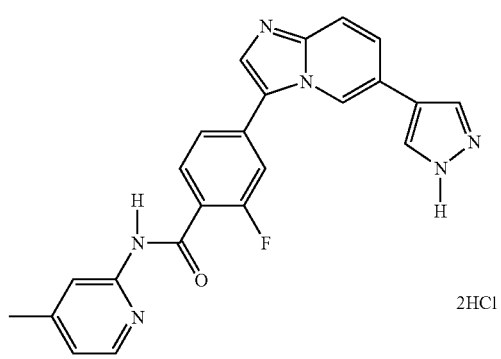

N1-(4-Methyl-2-pyridyl)-2-fluoro-4-[6-(1H-4-pyrazolyl)-imidazo[1,2-a]pyridin-3-yl]benzamide dihydrochloride 55 mg of the title compound was obtained as colorless crystals in the same manner as in Example 79 from 76 mg N1-(4-methyl-2-pyridyl)-2-fluoro-4-[6-(1-trityl-1H-4-pyrazolyl)imidazo[1,2-a]pyridin-3-yl] benzamide (compound in Example 508).

$^1$H-NMR (DMSO-$d_6$)

δ: 2.40(s, 3H), 7.09(dd, J=5.2, 0.4 Hz, 1H), 7.77(dd, J=8.0, 1.6 Hz, 1H), 7.86(dd, J=11.2, 1.6 Hz, 1H), 7.95(dd, J=8.0, 8.0 Hz, 1H), 8.07(s, 1H), 8.09(d, J=10.0 Hz, 1H), 8.26(d, J=5.2 Hz, 1H), 8.29(dd, J=10.0, 1.2 Hz, 1H), 8.33(brs, 2H), 8.50(s, 1H), 8.90(s, 1H), 11.0(s, 1H)

MS m/e(ESI)413(MH$^+$)

Example 682

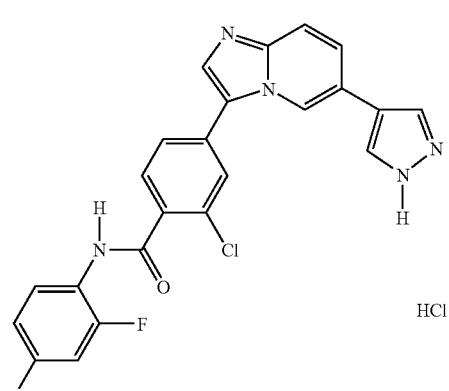

N1-(2,4-Difluorophenyl)-2-chloro-4-[6-(1H-4-pyrazolyl)-imidazo[1,2-a]pyridin-3-yl]benzamide hydrochloride 26 mg of the title compound was obtained as colorless crystals in the same manner as in Example 79 from 65 mg N1-(2,4-difluorophenyl)-2-chloro-4-[6-(1-trityl-1H-4-pyrazolyl)imidazo[1,2-a]pyridin-3-yl] benzamide (compound in Example 458).

$^1$H-NMR (DMSO-$d_6$)

δ: 7.13–7.21(m, 1H), 7.36–7.44(m, 1H), 7.78–7.84(m, 1H), 7.86(d, J=8.0 Hz, 1H), 7.92(dd, J=8.0, 1.6 Hz, 1H), 8.01(d, J=1.6 Hz, 1H), 8.10(d, J=8.4 Hz, 1H), 8.31(dd, J=8.4, 1.2 Hz, 1H), 8.32(s, 2H), 8.50(s, 1H), 8.87(s, 1H), 10.5(s, 1H)

MS m/e (ESI) 450 (MH$^+$)

Example 683

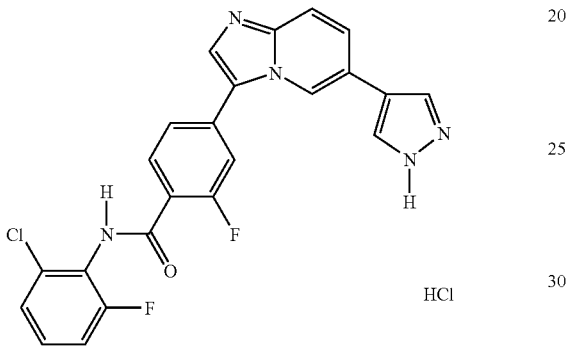

N1-(2-Chloro-6-fluorophenyl)-2-fluoro-4-[6-(1H-4-pyrazolyl)imidazo[1,2-a]pyridin-3-yl]benzamide hydrochloride 8 mg of the title compound was obtained as colorless crystals in the same manner as in Example 79 from 17 mg N1-(2-chloro-6-fluorophenyl)-2-fluoro-4-[6-(1-trityl-1H-4-pyrazolyl)-imidazo[1,2-a]pyridin-3-yl] benzamide (compound in Example 509).

$^1$H-NMR (DMSO-$d_6$)

δ: 7.36–7.51(m, 3H), 7.76–7.82(m, 1H), 7.90(d, J=11.2 Hz, 1H), 7.86–8.02(m, 1H), 8.08(d, J=9.2 Hz, 1H), 8.27–7.37(m, 3H), 8.50(s, 1H), 8.93(s, 1H), 10.32(s, 1H)

MS m/e (ESI) 450 (MH$^+$)

Example 684

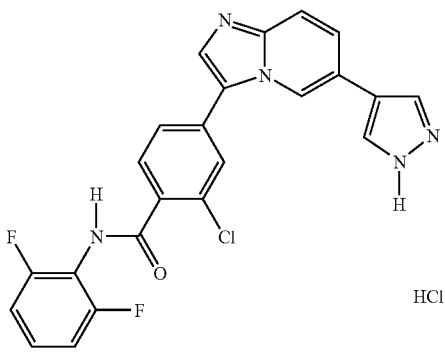

N1-(2,6-Difluorophenyl)-2-chloro-4-[6-(1H-4-pyrazolyl)-imidazo[1,2-a]pyridin-3-yl]benzamide hydrochloride 24 mg of the title compound was obtained as colorless crystals in the same manner as in Example 79 from 52 mg N1-(2,6-difluorophenyl)-2-chloro-4-[6-(1-trityl-1H-4-pyrazolyl)imidazo[1,2-a]pyridin-3-yl] benzamide (compound in Example 459).

$^1$H-NMR (DMSO-$d_6$)

δ: 7.26(t, J=8.0 Hz, 2H), 7.40–7.50(m, 1H), 7.85(d, J=8.0 Hz, 1H), 7.94(dd, J=8.0, 1.2 Hz, 1H), 8.03(d, J=1.2 Hz, 1H), 8.10(dd, J=9.4, 0.6 Hz, 1H), 8.30–8.36(m, 3H), 8.52(s, 1H), 8.88(s, 1H), 10.45(s, 1H)

MS m/e (ESI) 450 (MH$^+$)

Example 685

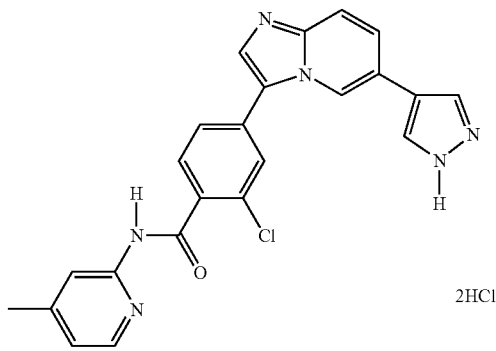

N1-(4-Methyl-2-pyridyl)-2-chloro-4-[6-(1H-4-pyrazolyl)-imidazo[1,2-a]pyridin-3-yl]benzamide dihydrochloride 34 mg of the title compound was obtained as colorless crystals in the same manner as in Example 79 from 44 mg N1-(4-methyl-2-pyridyl)-2-chloro-4-[6-(1-trityl-1H-4-pyrazolyl)imidazo[1,2-a]pyridin-3-yl] benzamide (compound in Example 510).

$^1$H-NMR (DMSO-$d_6$)

δ: 2.43(s, 3H), 7.15(d, J=5.0 Hz, 1H), 7.87(d, J=8.0 Hz, 1H), 7.92(dd, J=8.0, 1.4 Hz, 1H), 8.01(d, J=1.4 Hz, 1H), 8.03(brs, 1H), 8.11(d, J=9.2 Hz, 1H), 8.28(d, J=5.0 Hz, 1H), 8.33(dd, J=9.2, 1.2 Hz, 1H), 8.33(s, 2H), 8.53(s, 1H), 8.87(s, 1H)

MS m/e (ESI) 429 (MH$^+$)

Example 686

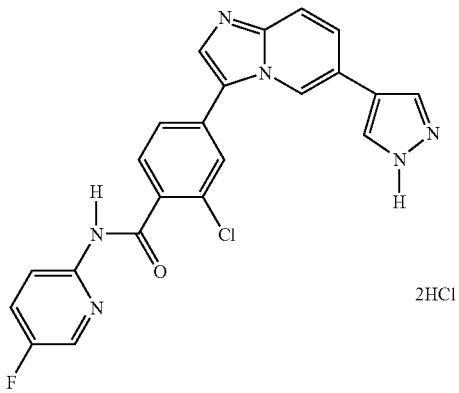

N1-(5-Fluoro-2-pyridyl)-2-chloro-4-[6-(1H-4-pyrazolyl)-imidazo[1,2-a]pyridin-3-yl]benzamide dihydrochloride 30 mg of the title compound was obtained as colorless crystals in the same-manner as in Example 79 from 36 mg N1-(5-fluoro-2-pyridyl)-2-chloro-4-[6-(1-trityl-1H-4-pyrazolyl)imidazo[1,2-a]pyridin-3-yl] benzamide (compound in Example 511).

$^1$H-NMR (DMSO-$d_6$)

δ: 7.82–7.88(m, 2H), 7.91(dd, J=8.0, 1.4 Hz, 1H), 8.00(d, J=1.4 Hz, 1H), 8.11(dd, J=9.4, 1.0 Hz, 1H), 8.25–8.35(m, 4H), 8.41(d, J=3.2 Hz, 1H), 8.53(s, 1H), 8.85–8.86(m, 1H), 11.32(s, 1H)

MS m/e (ESI) 433 (MH$^+$)

Example 687

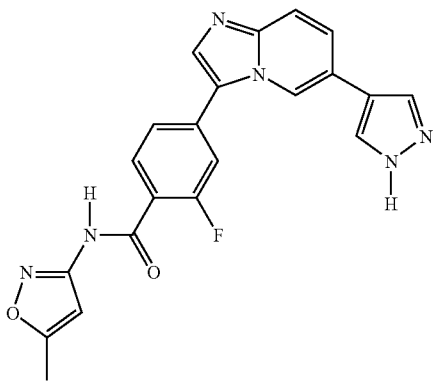

N1-(5-Methylisoxazol-3-yl)-2-fluoro-4-[6-(1H-4-pyrazolyl)-imidazo[1,2-a]pyridin-3-yl]benzamide dihydrochloride 36 mg of the title compound was obtained as colorless crystals in the same manner as in Example 79 from 52 mg N1-(5-methylisoxazol-3-yl)-2-fluoro-4-[6-(1-trityl-1H-4-pyrazolyl)imidazo[1,2-a]pyridin-3-yl] benzamide (compound in Example 512).

$^1$H-NMR (DMSO-$d_6$)

δ: 2.44(d, J=1.2 Hz, 3H), 6.77(s, 1H), 7.77(dd, J=8.0, 1.6 Hz, 1H), 7.86(dd, J=10.8, 1.6 Hz, 1H), 7.94(t, J=8.0 Hz, 1H), 8.10(dd, J=9.4, 0.8 Hz, 1H), 8.32(dd, J=9.4, 1.6 Hz, 1H), 8.33(s, 2H), 8.53(s, 1H), 8.89–8.91(m, 1H), 11.57(s, 1H)

MS m/e (ESI) 403 (MH$^+$)

Example 688

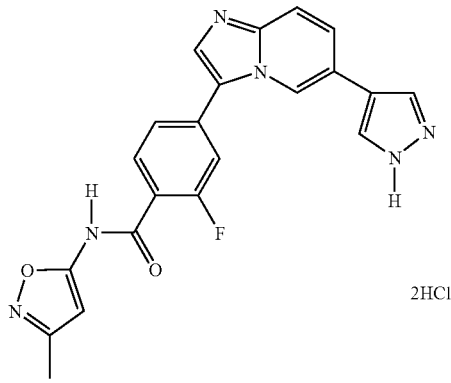

N1-(3-Methylisoxazol-5-yl)-2-fluoro-4-[6-(1H-4-pyrazolyl)-imidazo[1,2-a]pyridin-3-yl]benzamide dihydrochloride 33 mg of the title compound was obtained as colorless crystals in the same manner as in Example 79 from 42 mg N1-(3-methylisoxazol-5-yl)-2-fluoro-4-[6-(1-trityl-1H-4-pyrazolyl)imidazo[1,2-a]pyridin-3-yl] benzamide (compound in Example 513).

$^1$H-NMR (DMSO-$d_6$)

δ: 2.25(s, 3H), 6.37(s, 1H), 7.79(dd, J=7.9, 1.3 Hz, 1H), 7.91(dd, J=10.8, 1.3 Hz, 1H), 7.98(t, J=7.9 Hz, 1H), 8.09(d, J=9.4 Hz, 1H), 8.30(dd, J=9.4, 1.2 Hz, 1H), 8.33(s, 2H), 8.51(s, 1H), 8.91(s, 1H), 12.23(s, 1H)

MS m/e (ESI) 403 (MH$^+$)

Example 689

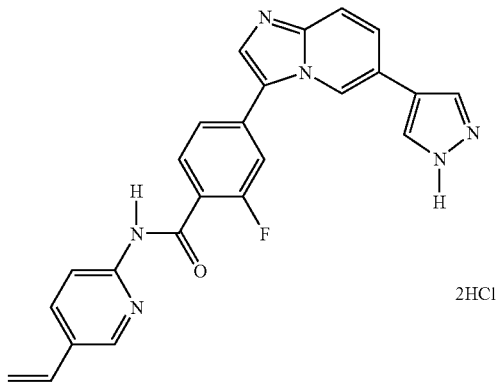

N1-(5-Vinyl-2-pyridyl)-2-fluoro-4-[6-(1H-4-pyrazolyl)-imidazo[1,2-a]pyridin-3-yl]benzamide dihydrochloride 81 mg of the title compound was obtained as colorless crystals in the same manner as in Example 79 from 106 mg N1-(5-vinyl-2-pyridyl)-2-fluoro-4-[6-(1-trityl-1H-4-pyrazolyl)imidazo[1,2-a]pyridin-3-yl] benzamide (compound in Example 514).

$^1$H-NMR (DMSO-d$_6$)

δ: 5.37(d, J=11.4 Hz, 1H), 5.80(d, J=17.6 Hz, 1H), 6.70(dd, J=17.6, 11.4 Hz, 1H), 7.78(dd, J=8.0, 1.6 Hz, 1H), 7.87(dd, J=10.8, 1.6 Hz, 1H), 7.97(t, J=8.0 Hz, 1H), 8.09(dd, J=8.8, 1.6 Hz, 1H), 8.12(dd, J=8.8, 0.8 Hz, 1H), 8.22(d, J=9.0 Hz, 1H), 8.34(s, 2H), 8.35(dd, J=9.0, 2.0 Hz, 1H), 8.48(d, J=2.0 Hz, 1H), 8.55(s, 1H), 8.90–8.92(m, 1H), 11.16(s, 1H)

MS m/e (ESI) 425 (MH$^+$)

Example 690

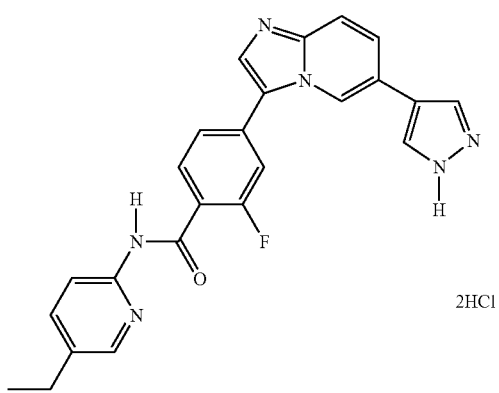

N1-(5-Ethyl-2-pyridyl)-2-fluoro-4-[6-(1H-4-pyrazolyl)-imidazo[1,2-a]pyridin-3-yl]benzamide dihydrochloride 60 mg of the title compound was obtained as colorless crystals in the same manner as in Example 79 from 99 mg N1-(5-ethyl-2-pyridyl)-2-fluoro-4-[6-(1-trityl-1H-4-pyrazolyl)imidazo[1,2-a]pyridin-3-yl] benzamide (compound in Example 515).

$^1$H-NMR (DMSO-d$_6$)

δ: 1.22(t, J=7.6 Hz, 3H), 2.65 (q, J=7.6 Hz, 2H), 7.78(dd, J=8.0, 1.6 Hz, 1H), 7.85(dd, J=8.6, 2.4 Hz, 1H), 7.87(dd, J=10.8, 1.6 Hz, 1H), 7.98(t, J=8.0 Hz, 1H), 8.12(d, J=9.3 Hz, 1H), 8.14(d, J=8.6 Hz, 1H), 8.29(d, J=2.4 Hz, 1H), 8.34(s, 2H), 8.34(dd, J=9.3, 1.4 Hz, 1H), 8.55(s, 1H), 8.90–8.92(m, 1H), 11.16(s, 1H)

MS m/e (ESI) 407 (MH$^+$)

Example 691

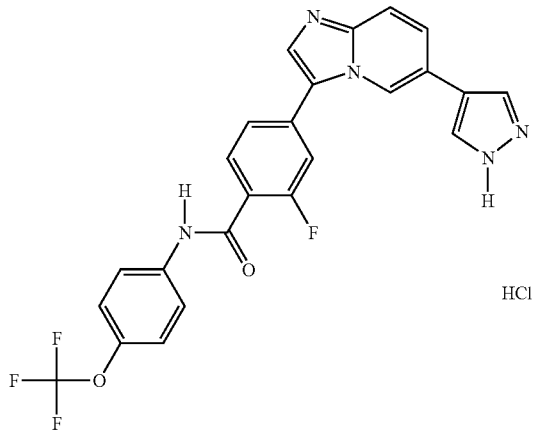

N1-[4-(Trifluoromethoxy)phenyl]-2-fluoro-4-[6-(1H-4-pyrazolyl)imidazo[1,2-a]pyridin-3-yl]benzamide hydrochloride 10 mg of the title compound was obtained in the same manner as in Example 79 from 58 mg N1-[4-(trifluoromethoxy)phenyl]-2-fluoro-4-[6-(1-trityl-1H-4-pyrazolyl)imidazo[1,2-a]pyridin-3-yl] benzamide (compound in Example 516).

MS m/e(ESI)482(MH$^+$)

Example 692

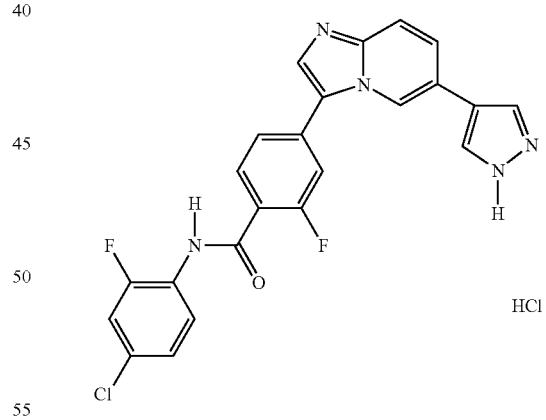

N1-(4-Chloro-2-fluorophenyl)-2-fluoro-4-[6-(1H-4-pyrazolyl)imidazo[1,2-a]pyridin-3-yl)benzamide hydrochloride 30 mg of the title compound was obtained in the same manner as in Example 79 from 30 mg N1-(4-chloro-2-fluorophenyl)-2-fluoro-4-[6-(1-trityl-1H-4-pyrazolyl)imidazo[1,2-a]pyridin-3-yl] benzamide (compound in Example 517).

¹H-NMR (CDCl₃)
δ: 7.37(d, J=8.4 Hz, 1H), 7.59(dd, J=13.2, 1.6 Hz, 1H), 7.78(dd, J=8.4, 1.6 Hz, 1H), 7.85–7.90(m, 2H), 7.98(dd, J=8.4, 8.4 Hz, 1H), 8.08(d, J=9.2 Hz, 1H), 8.30(dd, J=9.2, 0.8 Hz, 1H), 8.33(bd, 2H), 8.50(s, 1H), 8.90(s, 1H), 10.4(s, 1H)

Example 693

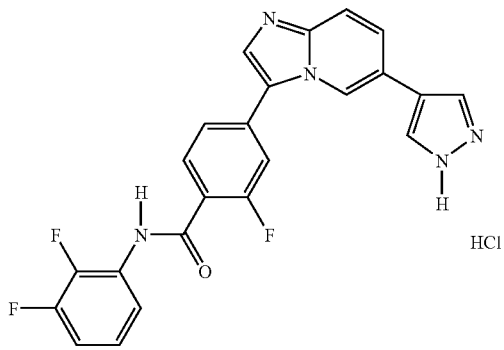

N1-(2,3-Difluorophenyl)-2-fluoro-4-[6-(1H-4-pyrazolyl)-imidazo[1,2-a]pyridin-3-yl]benzamide hydrochloride 12 mg of the title compound was obtained in the same manner as in Example 79 from 35 mg N1-(2,3-difluorophenyl)-2-fluoro-4-[6-(1-trityl-1H-4-pyrazolyl)imidazo[1,2-a]pyridin-3-yl] benzamide (compound in Example 518).
MS m/e(ESI)434(MH⁺)

Example 694

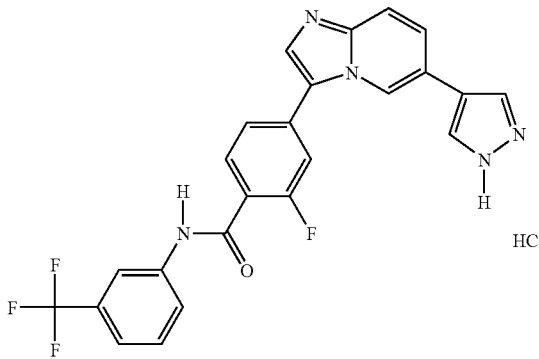

N1-[4-(Trifluoromethyl)phenyl]-2-fluoro-4-[6-(1H-4-pyrazolyl)imidazo[1,2-a]pyridin-3-yl]benzamide hydrochloride 15 mg of the title compound was obtained in the same manner as in Example 79 from 41 mg N1-[4-(trifluoromethyl)phenyl]-2-fluoro-4-[6-(1-trityl-1H-4-pyrazolyl)imidazo[1,2-a]pyridin-3-yl] benzamide (compound in Example 519).
MS m/e(ESI)466(MH⁺)

Example 695

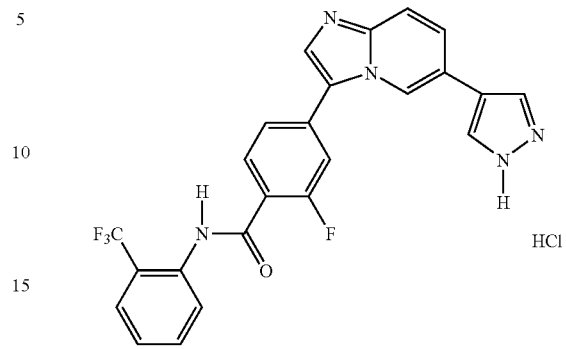

N1-[2-(Trifluoromethyl)phenyl]-2-fluoro-4-[6-(1H-4-pyrazolyl)imidazo[1,2-a]pyridin-3-yl]benzamide hydrochloride 9 mg of the title compound was obtained in the same manner as in Example 79 from 35 mg N1-[2-(trifluoromethyl)phenyl]-2-fluoro-4-[6-(1-trityl-1H-4-pyrazolyl)imidazo[1,2-a]pyridin-3-yl] benzamide (compound in Example 520).
MS m/e(ESI)466(MH⁺)

Example 696

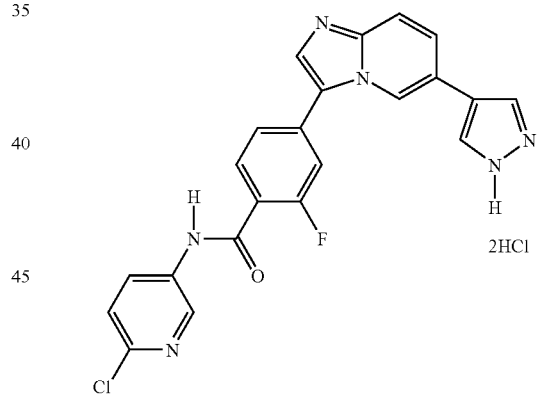

N1-(6-Chloro-3-pyridyl)-2-fluoro-4-[6-(1H-4-pyrazolyl)-imidazo[1,2-a]pyridin-3-yl]benzamide hydrochloride 9 mg of the title compound was obtained in the same manner as in Example 79 from 35 mg N1-(6-chloro-3-pyridyl)-2-fluoro-4-[6-(1-trityl-1H-4-pyrazolyl)imidazo[1,2-a]pyridin-3-yl] benzamide (compound in Example 521).
¹H-NMR (DMSO-d₆)
δ: 7.55(d, J=8.8 Hz, 1H), 7.78(dd, J=8.0, 1.2 Hz, 1H), 7.90(d, J=10.8 Hz, 1H), 7.97(dd, J=8.0, 7.2 Hz, 1H), 8.08(d, J=9.6 Hz, 1H), 8.24(dd, J=8.8, 2.4 Hz, 1H), 8.29–8.32(m, 2H), 8.51(s, 1H), 8.78(d, J=2.8 Hz, 1H), 8.89(d, J=2.4 Hz, 1H), 11.0(s, 1H)
MS m/e(ESI)433(MH⁺)

Example 697

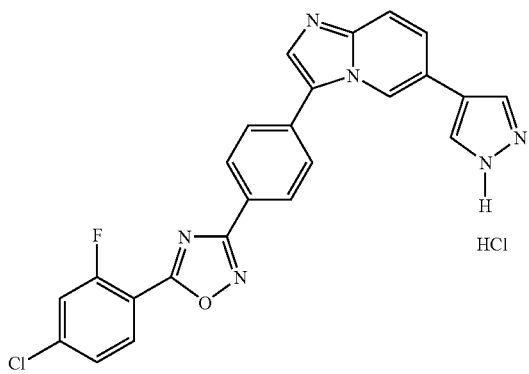

5-(4-Chloro-2-fluorophenyl)-3-{4-[6-(1H-4-pyrazolyl)-imidazo[1,2-a]pyridin-3-yl]-1,2,4-oxadiazole hydrochloride 9 mg of the title compound was obtained in the same manner as in Example 79 from 35 mg 5-(4-chloro-2-fluorophenyl)-3-{4-[6-(1-trityl-1H-4-pyrazolyl)imidazo[1,2-a]pyridin-3-yl]-1,2,4-oxadiazole (compound in Example 522).

$^1$H-NMR (CD$_3$OD)

δ: 7.47–7.51(m, 2H), 7.63–7.75(m, 3H), 7.81(br, 1H), 7.87(d, J=8.4 Hz, 2H), 7.99(br, 2H), 8.28(dd, J=8.4, 8.0 Hz, 1H), 8.39(d, J=8.4 Hz, 2H), 8.67(br, 1H)

MS m/e(ESI)457(MH$^+$)

Example 698

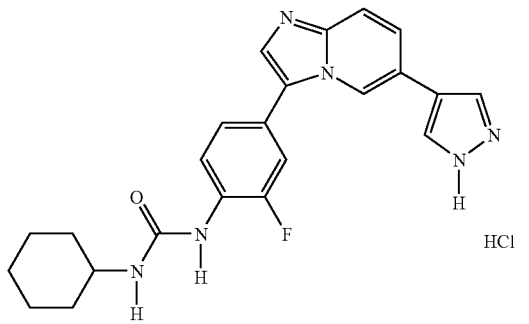

N-Cyclohexyl-N'-(2-fluoro-4-[6-(1H-4-pyrazolyl)imidazo[1,2-a]pyridin-3-yl] phenyl}urea hydrochloride The title compound was obtained in the same manner as in Example 79 from N-cyclohexyl-N'-{2-fluoro-4-[6-(1-trityl-1H-4-pyrazolyl)imidazo[1,2-a]pyridin-3-yl] phenyl}urea (compound in Example 524).

$^1$H-NMR (DMSO-d$_6$)

δ: 1.14–1.24(m, 4H), 1.26–1.36(m, 2H), 1.48–1.58(m, 1H), 1.60–1.70(m, 1H), 1.76–1.84(m, 2H), 6.76–6.78(m, 1H), 7.46–7.48(m, 1H), 7.63–7.66(m, 1H), 8.01–8.03(m, 1H), 8.22–8.28(m, 4H), 8.44(dd, J=8.4, 8.4 Hz, 1H), 8.52(m, 1H), 8.76(s, 1H)

Example 699

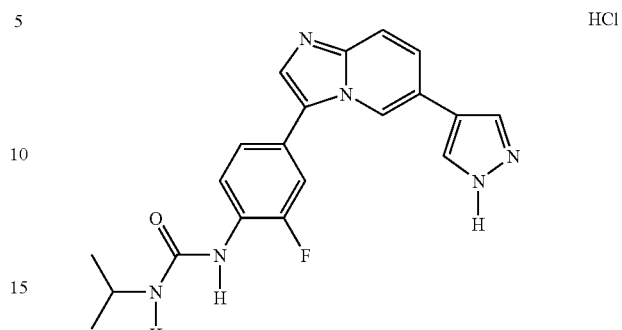

N-12-Fluoro-4-[6-(1H-4-pyrazolyl)imidazo[1,2-a]pyridin-3-yl] phenyl}-N'-isopropylurea hydrochloride The title compound was obtained in the same manner as in Example 79 from N-{2-fluoro-4-[6-(1-trityl-1H-4-pyrazolyl)imidazo[1,2-a]pyridin-3-yl] phenyl}-N'-isopropylurea (compound in Example 525).

$^1$H-NMR (DMSO)

δ: 1.10(d, J=6.8 Hz, 6H), 3.77(m, 1H), 6.61(d, J=7.6 Hz, 1H), 7.42(d, J=10 Hz, 1H), 7.53(dd, J=12.4, 2.0 Hz, 1H), 7.56(dd, J=9.2, 1.6 Hz, 1H), 7.65(dd, J=9.2, 1.6 hz, 1H), 7.68(s, 1H), 8.31–8.35(m, 2H), 8.58(bd, 1H)

MS m/e(ESI)378(MH$^+$)

Example 700

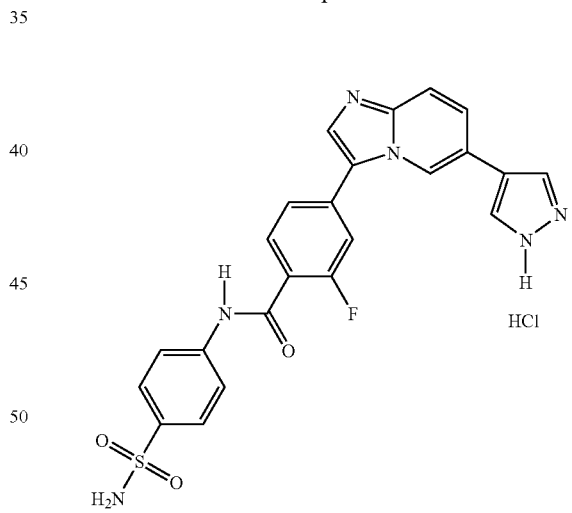

N1-[4-(Aminosulfonyl)phenyl]-2-fluoro-4-[6-(1H-4-pyrazolyl)imidazo[1,2-a]pyridin-3-yl]benzamide hydrochloride 165 mg 3-(1,1,1-tributylstannyl)-6-(1-trityl-1H-4-pyrazolyl)imidazo[1,2-a]pyridine (compound in Production Example 293), 85 mg N1-[4-(aminosulfonyl)phenyl]-4-bromo-2-fluorobenzamide synthesized in the same method as in Production Example 323 and 13 mg tetrakistriphenyl phosphine palladium were heated in xylene at 70° C. for 3 hours. The solvent was evaporated, and the residue was purified by an NH silica gel column, to give 115 mg N1-[4-(aminosulfonyl)phenyl]-2-fluoro-4-[6-(1-trityl-1H-4-pyrazolyl)imidazo[1,2-a]pyridin-3-yl] benzamide as colorless crystals. This product was subjected to deprotection of the trityl group in the same method as in Example 79, to give 82 mg of the title compound.

$^1$H-NMR (DMSO-$d_6$)

δ: 7.33(brs, 2H), 7.79(dd, J=8.0, 1.6 Hz, 1H), 7.81–8.00 (m, 6H), 8.09(dd, J=9.6, 0.8 Hz, 1H), 8.30(dd, J=9.6, 1.6 Hz, 1H), 8.33(brs, 2H), 8.50(s, 1H), 8.90(s, 1H), 10.9(s, 1H)

MS m/e(ESI)477(MH$^+$)

Example 701

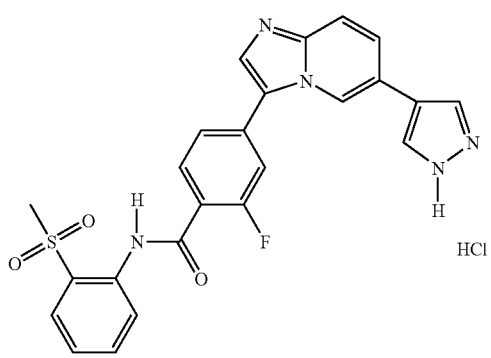

N1-[2-(Methylsulfonyl)phenyl]-2-fluoro-4-[6-(1H-4-pyrazolyl)imidazo[1,2-a]pyridin-3-yl]benzamide hydrochloride 14 mg of the title compound was obtained as colorless crystals in the same manner as in Example 700 from 150 mg of the compound in Production Example 293 and 74 mg N1-[2-(methylsulfonyl)phenyl]-4-bromo-2-fluorobenzamide (compound in Production Example 325).

$^1$H-NMR (DMSO-$d_6$)

δ: 3.36(s, 3H), 7.52(ddd, J=8.0, 8.0, 1.2 Hz, 1H), 7.81–7.87(m, 2H), 7.95(dd, J=8.0, 1.2 Hz, 1H), 8.00(dd, J=8.0, 1.6 Hz, 1H), 8.07(d, J=9.2 Hz, 1H), 8.17(dd, J=8.0, 8.0 Hz, 1H), 8.27(d, J=10.7 Hz, 1H), 8.30–8.40(m, 3H), 8.48(s, 1H), 8.95(s, 1H), 10.5(d, J=5.6 Hz, 1H)

MS m/e(ESI)476(MH$^+$)

Example 702

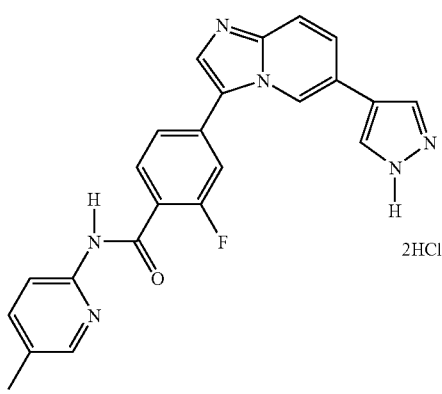

N1-(5-Methyl-2-pyridyl)-2-fluoro-4-[6-(1H-4-pyrazolyl)-imidazo[1,2-a]pyridin-3-yl]benzamide dihydrochloride 41 mg of the title compound was obtained as colorless crystals in the same manner as in Example 700 from 358 mg of the compound in Production Example 293 and 154 mg N1-(5-methyl-2-pyridyl)-4-bromo-2-fluorobenzamide synthesized in the same method as in Production Example 323. The Stille reaction in this process was carried out in the presence of 2 mg copper (I) iodide.

$^1$H-NMR (DMSO-$d_6$)

δ: 2.40(s, 3H), 7.09(dd, J=5.2, 0.4 Hz, 1H), 7.77(dd, J=8.0, 1.6 Hz, 1H), 7.86(dd, J=10.8, 1.6 Hz, 1H), 7.95(dd, J=8.0, 8.0 Hz, 1H), 8.07(s, 1H), 8.08(d, J=9.2 Hz, 1H), 8.26(d, J=5.2 Hz, 1H), 8.29(dd, J=9.2, 1.6 Hz, 1H), 8.33(brs, 2H), 8.50(s, 1H), 8.90(s, 1H), 11.0(s, 1H)

MS m/e(ESI)413(MH$^+$)

Example 703

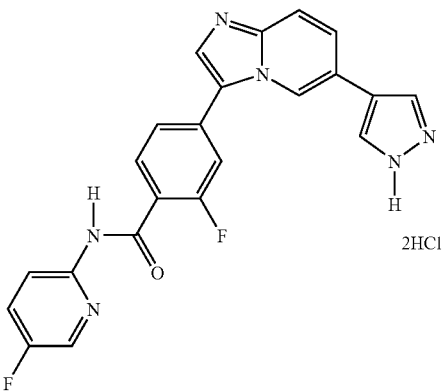

N1-(5-Fluoro-2-pyridyl)-2-fluoro-4-[6-(1H-4-pyrazolyl)-imidazo[1,2-a]pyridin-3-yl]benzamide dihydrochloride 100 mg of the title compound was obtained as colorless crystals in the same manner as in Example 700 from 200 mg of the compound in Production Example 293 and 88 mg N1-(5-fluoro-2-pyridyl)-4-bromo-2-fluorobenzamide synthesized in the same method as in Production Example 323.

$^1$H-NMR (DMSO-$d_6$)

δ: 7.77(dd, J=8.0, 1.2 Hz, 1H), 7.82–7.9(m, 2H), 7.95(dd, J=8.0, 8.0 Hz, 1H), 8.01(dd, J=9.6, 0.8 Hz, 1H), 8.27(dd, J=9.2, 4.0 Hz, 1H), 8.31–8.36(m, 3H), 8.42(d, J=3.2 Hz, 1H), 8.54(s, 1H), 8.90(m, 1H), 11.2(s, 1H)

MS m/e(ESI)417(MH$^+$)

Example 704

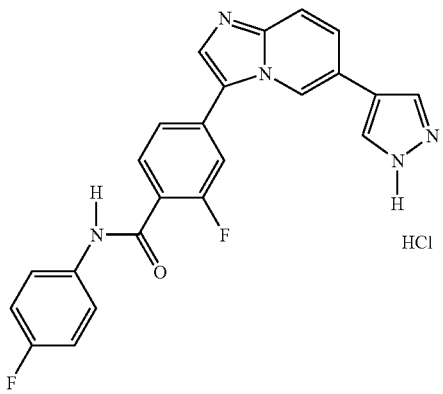

N1-(4-Fluorophenyl)-2-fluoro-4-[6-(1H-4-pyrazolyl)imidazo-[1,2-a]pyridin-3-yl]benzamide hydrochloride 92 mg of the title compound was obtained as colorless crystals in the same manner as in Example 700 from 200 mg of the compound in Production Example 293 and 87 mg N1-(4-fluorophenyl)-4-bromo-2-fluorobenzamide synthesized in the same method as in Production Example 323.

$^1$H-NMR (DMSO-$d_6$)
δ: 7.20–7.28(m, 2H), 7.75–7.83(m, 3H), 7.88(d, J=10.8 Hz, 1H), 7.94(dd, J=7.6, 7.6 Hz, 1H), 8.08(d, J=9.6 Hz, 1H), 8.29(d, =9.6 Hz, 1H), 8.33(br, 2H), 8.49(s, 1H), 8.90(s, 1H), 10.6(s, 1H)
MS m/e(ESI)416(MH$^+$)

Example 705

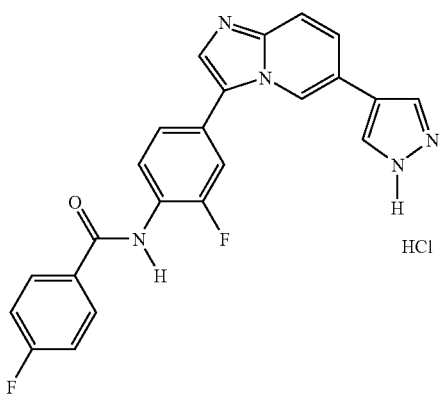

N1-{2-Fluoro-4-[6-(1H-4-pyrazolyl)imidazo[1,2-a]pyridin-3-yl]phenyl}-4-fluorobenzamide hydrochloride 13 mg of the title compound was obtained as colorless crystals in the same manner as in Example 700 from 143 mg of the compound in Production Example 293 and 62 mg N1-(4-bromo-2-fluorophenyl)-4-fluorobenzamide synthesized from 4-fluorobenzoyl chloride and 4-bromo-2-fluoroaniline. The Stille reaction in this process was carried out in the presence of 3 mg copper (I) iodide.

$^1$H-NMR (DMSO-$d_6$)
δ: 7.38–7.46(m, 2H), 7.67(dd, J=8.4, 1.6 Hz, 1H), 7.82 (dd, J=10.8, 1.6 Hz, 1H), 7.95(dd, KJ=8.4, 8.4 Hz, 1H), 8.07–8.215(m, 3H), 8.30(dd, J=9.2, 1.2 Hz, 1H), 8.34(brs, 2H), 8.44(s, 1H), 8.89(s, 1H), 10.4(s, 1H)
MS m/e(ESI)416(MH$^+$)

Example 706

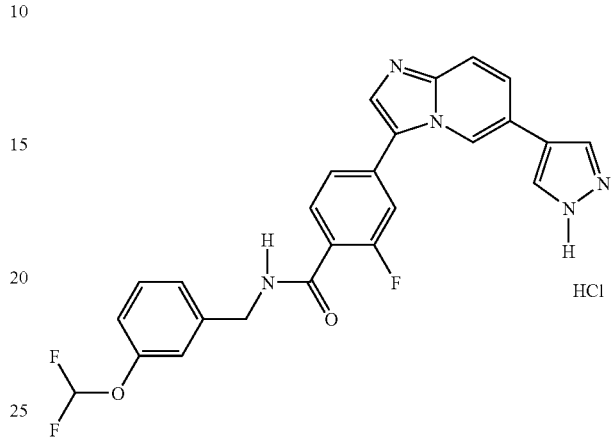

N1-[3-(Difluoromethoxy)benzyl]-2-fluoro-4-[6-(1H-4-pyrazolyl)imidazo[1,2-a]pyridin-3-yl]benzamide hydrochloride 90 mg N1-[3-(difluoromethoxy)benzyl]-2-fluoro-4-[6-(1-trityl-1H-4-pyrazolyl)imidazo[1,2-a]pyridin-3-yl] benzamide was obtained in the same manner as in Example 477 from 65 mg of the compound in Example 472 and 21 mg 3-(difluoromethoxy)benzylamine. Subsequently, the product was subjected to deprotection of the trityl group in the same manner as in Example 79, to give 40 mg of the title compound as colorless crystals.

$^1$H-NMR (DMSO-$d_6$)
δ: 4.55(d, J=6.0 Hz, 2H), 7.10(dd, J=8.4, 1.6 Hz, 1H), 7.18(s, 1H), 7.24(t, J=74 Hz, 1H), 7.25(d, J=8.4,Hz, 1H), 7.43(dd, J=8.4, 8.4 Hz, 1H), 7.74(dd, J=8.4, 1.2 Hz, 1H), 7.85(dd, J=10.8, 1.6 Hz, 1H), 7.91(dd, J=8.0, 8.0, 1H), 8.09(d, J=9.6 Hz, 1H), 8.28–8.36 m, 3H), 8.49(s, 1H), 8.90(s, 1H), 9.08–9.15(m, 1H)
MS m/e(ESI)478(MH$^+$)

Example 707

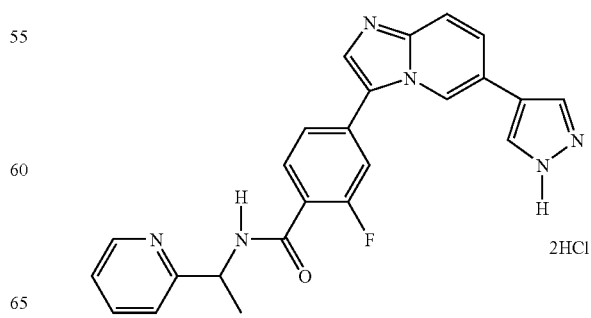

N1-[1-(2-Pyridyl)ethyl]-2-fluoro-4-[6-(1H-4-pyrazolyl)-imidazo[1,2-a]pyridin-3-yl]benzamide dihydrochloride 70 mg N1-[1-(2-pyridyl)ethyl]-2-fluoro-4-[6-(1-trityl-1H-4-pyrazolyl)imidazo[1,2-a]pyridin-3-yl] benzamide was obtained in the same manner as in Example 477 from 60 mg of the compound in Example 472 and 14 mg 1-(2-pyridyl)ethylamine. The product was subjected to deprotection of the trityl group in the same manner as in Example 68, to give 35 mg of the title compound as colorless crystals.

$^1$H-NMR (DMSO-$d_6$)

δ: 1.54(d, J=6.8 Hz, 3H), 5.24–5.32(m, 1H), 7.42–7.50(br, 1H), 7.58–7.65(m, 1H), 7.74(dd, J=8.0, 1.6 Hz, 1H), 7.84 (dd, J=11.2, 1.2 Hz, 1H), 7.93(dd, J=8.0, 8.0 Hz, 1H), 7.95–8.04(br, 1H), 8.07(d, J=9.6 Hz, 1H), 8.24–8.37(m, 3H), 8.46(s, 1H), 8.62–8.66(m, 1H), 8.88(m, 1H), 9.02–9.08(m, 1H)

MS m/e(ESI)427(MH$^+$)

Example 708

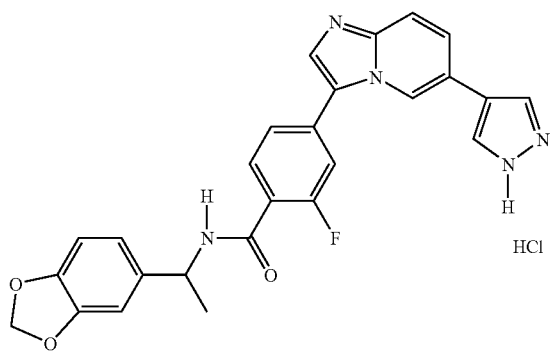

N1-[1-(1,3-Benzodioxol-5-yl)ethyl]-2-fluoro-4-[6-(1H-4-pyrazolyl)imidazo[1,2-a]pyridin-3-yl]benzamide hydrochloride 74 mg N1-[1-(1,3-benzodioxol-5-yl)ethyl]-2-fluoro-4-[6-(1-trityl-1H-4-pyrazolyl)imidazo[1,2-a]pyridin-3-yl] benzamide was obtained in the same manner as in Example 477 from 57 mg of the compound in Example 472 and 14 mg 1-(1,3-benzodioxol-5-yl)ethylamine. The product was subjected to deprotection of the trityl group in the same manner as in Example 79, to give 26 mg of the title compound as colorless crystals.

$^1$H-NMR (DMSO-$d_6$)

δ: 1.44(d, J=7.2 Hz, 3H), 5.05–5.15(m, 1H), 6.00(s, 2H), 6.88(s, 2H), 7.02(s, 1H), 7.70(dd, J=8.0, 1.6 Hz, 1H), 7.76–7.83(m, 2H), 8.00–8.05(m, 1H), 8.17–8.36(m, 3H), 8.39(s, 1H), 8.82–8.89(m, 2H)

MS m/e(ESI)470(MH$^+$)

Example 709

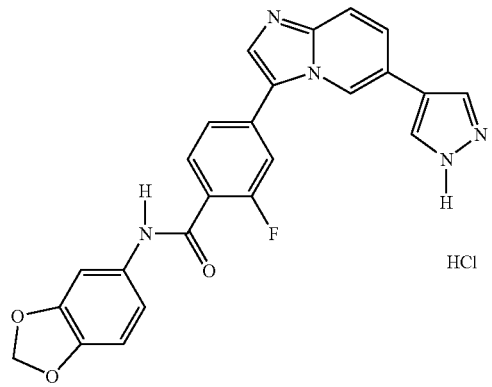

N1-(1,3-Benzodioxol-5-yl)-2-fluoro-4-[6-(1H-4-pyrazolyl)-imidazo[1,2-a]pyridin-3-yl]benzamide hydrochloride 45 mg N1-(1,3-benzodioxol-5-yl)-2-fluoro-4-[6-(1-trityl-1H-4-pyrazolyl)imidazo[1,2-a]pyridin-3-yl] benzamide was obtained in the same manner as in Example 477 from 57 mg of the compound in Example 472 and 14 mg 3,4-(methylenedioxy) aniline. Subsequently, the product was subjected to deprotection of the trityl group in the same manner as in Example 79, to give 22 mg of the title compound as colorless crystals.

$^1$H-NMR (DMSO-$d_6$)

δ: 6.03(s, 2H), 6.93(d, J=8.4 Hz, 1H), 7.18(dd, J=8.4, 2.0 Hz, 1H), 7.44(d, J=2.0 Hz, 1H), 7.77(dd, J=7.6, 1.6 Hz, 1H), 7.87(dd, J=10.8, 1.6 Hz, 1H), 7.92(dd, J=7.6, 7.6 Hz, 1H), 8.09(dd, J=9.6, 0.8 Hz, 1H), 8.28–8.38(m, 3H), 8.50(s, 1H), 8.90(s, 1H), 10.5(s, 1H)

MS m/e(ESI)442(MH$^+$)

Example 710

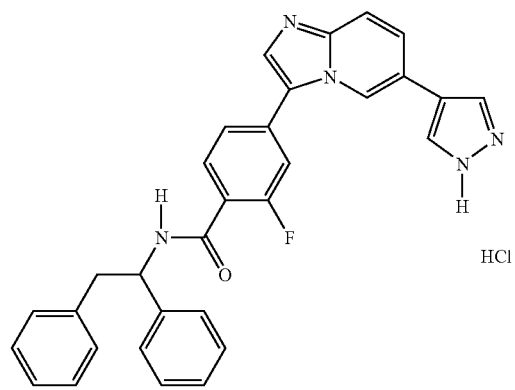

N1-(1,2-Diphenylethyl)-2-fluoro-4-[6-(1H-4-pyrazolyl)-imidazo[1,2-a]pyridin-3-yl]benzamide hydrochloride 77 mg N1-(1,2-diphenylethyl)-2-fluoro-4-[6-(1-trityl-1H-4-pyrazolyl)imidazo[1,2-a]pyridin-3-yl] benzamide was obtained in the same manner as in Example 477 from 57 mg of the compound in Example 472 and 20 mg 1,2-diphenyl ethylamine. Subsequently, the product was subjected to deprotection of the trityl group in the same manner as in Example 68, to give 35 mg of the title compound as colorless crystals.

$^1$H-NMR (CDCl$_3$—CD$_3$OD)
δ: 3.18–3.31(m, 2H), 5.46–5.54(m, 1H), 7.12–7.16(m, 2H), 7.20–7.39(m, 9H), 7.42(dd, J=11.2, 1.2 Hz, 1H), 7.51 (dd, J=8.0, 1.2 Hz, 1H), 7.91(brs, 2H), 7.99(s, 1H), 8.04(dd, J=9.2, 1.2 Hz, 1H), 8.25(ddd, J=8.0, 8.0, 1.2 Hz, 1H), 8.39–8.44(m, 2H)
MS m/e(ESI)502(MH$^+$)

Example 711

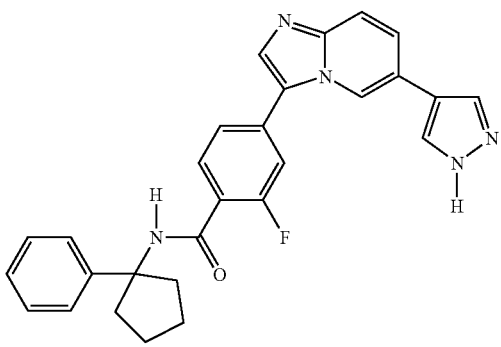

N1-(1-Phenylcyclopentyl)-2-fluoro-4-[6-(1H-4-pyrazolyl)imidazo[1,2-a]pyridin-3-yl] benzamide 48 mg N1-(1-phenylcyclopentyl)-2-fluoro-4-[6-(1-trityl-1H-4-pyrazolyl)imidazo[1,2-a]pyridin-3-yl] benzamide was obtained in the same manner as in Example 477 from 57 mg of the compound in Example 472 and 16 mg 1-phenylcyclopentylamine. Subsequently, the product was subjected to deprotection of the trityl group in the same manner as in Example 89, to give 26 mg of the title compound as colorless crystals.

$^1$H-NMR (CDCl$_3$)
δ: 1.86–1.98(m, 4H), 2.17–2.28(m, 2H), 2.46–2.55(m, 2H), 7.07(br.d, J=14 Hz, 1H), 7.21–7.26(m, 1H), 7.32–7.40 (m, 3H), 7.44(dd, J=9.2, 1.6 Hz, 1H), 7.47–7.53(m, 3H), 7.74–7.81(m, 2H), 7.84(brs, 2H), 8.18(dd, 8.4, 8.4 Hz, 1H), 8.45(m, 1H)
MS m/e(ESI)466(MH$^+$)

Example 712

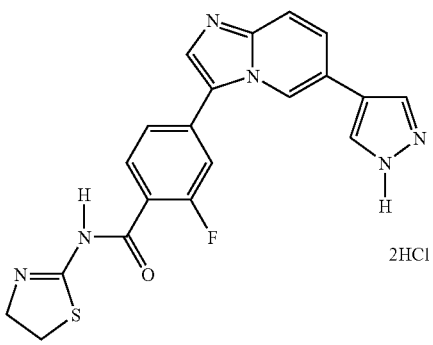

N1-(4,5-Dihydro-1,3-thiazol-2-yl)-2-fluoro-4-[6-(1H-4-pyrazolyl)imidazo[1,2-a]pyridin-3-yl]benzamide dihydrochloride 83 mg N1-(4,5-dihydro-1,3-thiazol-2-yl)-2-fluoro-4-[6-(1-trityl-1H-4-pyrazolyl)imidazo[1,2-a]pyridin-3-yl] benzamide was obtained in the same manner as in Example 477 from 100 mg of the compound in Example 472 and 18 mg 2-amino-4,5-dihydro-1,3-thiazole. Subsequently, the product was subjected to deprotection of the trityl group in the same manner as in Example 89, to give 48 mg of the title compound as colorless crystals.

$^1$H-NMR (DMSO-d$_6$)
δ: 3.32(dd, J=8.0, 8.0 Hz, 2H), 3.69(dd, J=8.0, 8.0 Hz, 2H), 7.69(dd, J=8.0, 1.6 Hz, 1H), 7.75(dd, J=11.2, 1.6 Hz, 1H), 8.05–8.13(m, 2H), 8.26–8.36(m, 3H), 8.47(s, 1H), 8.92(m, 1H)
MS m/e(ESI)407(MH$^+$)

Example 713

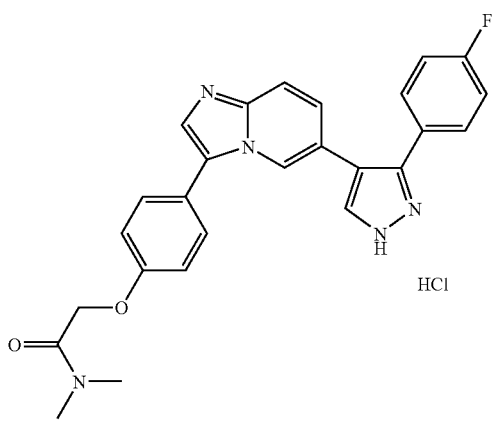

N1,N1-Dimethyl-2-(4-{6-[3-(4-fluorophenyl)-1H-4-pyrazolyl]-imidazo[1,2-a]pyridin-3-yl}phenoxy) acetamide hydrochloride 58 mg N1,N1-dimethyl-2-(4-{6-[3-(4-fluorophenyl)-1-trityl-1H-4-pyrazolyl]imidazo[1,2-a]pyridin-3-yl}phenoxy) acetamide was obtained in the same manner as in Example 94 from 100 mg of 6-[3-(4-fluorophenyl)-1-trityl-1H-4-pyrazolyl]-3-(1,1,1-tributylstannyl)imidazo[1,2-a]pyridine (compound in Production Example 294) and 57 mg N1,N1-dimethyl-2-(4-iodophenoxy)acetamide. Subsequently, the product was subjected to deprotection of the trityl group in the same manner as in Example 67, to give 10 mg of the title compound as colorless crystals.
MS m/e(ESI)456(MH$^+$)

Example 714

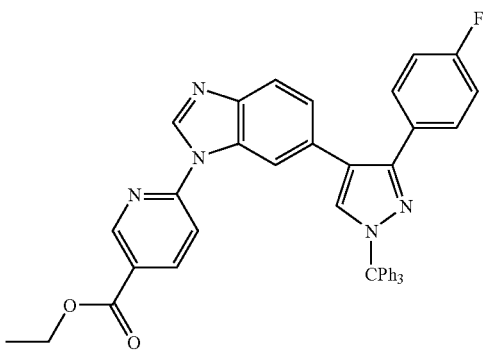

Ethyl 6-{6-[3-(4-fluorophenyl)-1-trityl-1H-4-pyrazolyl]-1H-benzo[d]imidazol-1-yl}nicotinate 1.0 g mixture of methyl 6-(6-bromo-1H-benzo[d]imidazol-1-yl)nicotinate and methyl 6-(5-bromo-1H-benzo[d]imidazol-1-yl)nicotinate as positional isomers in a ratio of 1:1 was obtained in the same manner as in Production Example 105 from methyl 6-chloronicotinate and 5-bromo-1H-benzo[d]imidazole. 1.0 g of this mixture and 1.75 g 3-(4-fluorophenyl)-1-trityl-1H-4-pyrazolylboronic acid (compound in Production Example 25) were reacted in the same manner as in Example 29, and the positional isomers were separated by silica gel column chromatography (ethyl acetate/hexane) to give 734 mg of the title compound.
$^1$H-NMR (CDCl$_3$)
δ: 1.44(t, J=7.0 Hz, 3H), 4.44 (q, J=7.0 Hz, 2H), 6.94–7.00(m, 2H), 7.24–7.38(m, 8H), 7.32–7.40(m, 9H), 7.47–7.51(m, 3H), 7.77(d, J=8.4 Hz, 1H), 7.90(d, J=1.2 Hz, 1H), 8.38(dd, J=8.4, 2.2 Hz, 1H), 8.63(s, 1H), 9.10(dd, J=2.2, 0.8 Hz, 1H)

Example 715

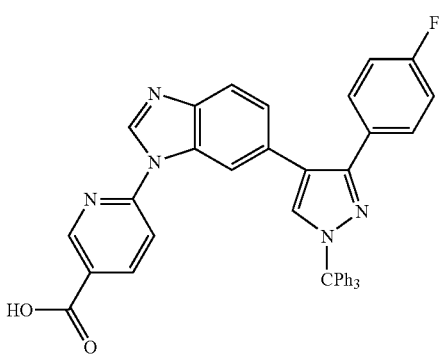

6-{6-[3-(4-Fluorophenyl)-1-trityl-1H-4-pyrazolyl]-1H-benzo[d]imidazol-1-yl}nicotinic acid 659 mg of the title compound was obtained as pale brown crystals by the same reaction as in Example 443 from 743 mg ethyl 6-{6-[3-(4-fluorophenyl)-1-trityl-1H-4-pyrazolyl]-1H-benzo[d]imidazol-1-yl}nicotinate (compound in Example 714).

$^1$H-NMR (DMSO-d$_6$)
δ: 7.11–7.24(m, 9H), 7.32–7.44(m, 11H), 7.58(s, 1H), 7.68(d, J=8.0 Hz, 1H), 7.95(d, J=8.4 Hz, 1H), 8.20(d, J=1.2 Hz, 1H), 8.38(dd, J=8.4, 1.9 Hz, 1H), 8.85(d, J=1.9 Hz, 1H), 8.63(s, 1H)

Example 716

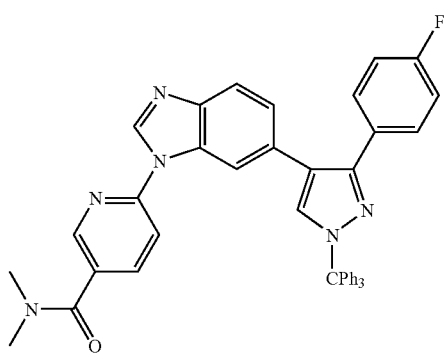

6-{6-[3-(4-Fluorophenyl)-1-trityl-1H-4-pyrazolyl]-1H-benzo[d]imidazol-1-yl}-N,N-dimethyl-nicotinamide 43 mg of the title compound was obtained by the same method as in Example 444 from 100 mg 6-{6-[3-(4-fluorophenyl)-1-trityl-1H-4-pyrazolyl]-1H-benzo[d]imidazol-1-yl}nicotinic acid (compound in Example 715) and 2.5 mL dimethylamine.
$^1$H-NMR (CDCl$_3$)
δ: 3.09(brs, 3H), 3.17(brs, 3H), 6.94–7.00(m, 2H), 7.25–7.30(m, 8H), 7.32–7.36(m, 9H), 7.47–7.52(m, 3H), 7.77(d, J=8.4 Hz, 1H), 7.82(d, J=0.8 Hz, 1H), 7.89(d, J=8.4, 2.4 Hz, 1H), 8.55–8.58(m, 2H)

Example 717

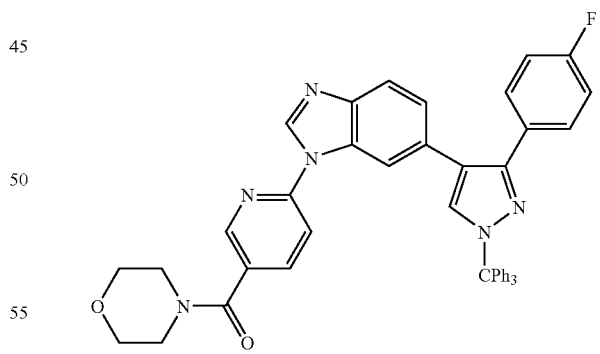

6-{6-[3-(4-Fluorophenyl)-1-trityl-1H-4-pyrazolyl]-1H-benzo-[d]imidazol-1-yl}-pyridin-3-yl)-morpholin-4-yl-methanone 36 mg of the title compound was obtained by the same method as in Example 444 from 100 mg 6-{6-[3-(4-fluorophenyl)-1-trityl-1H-4-pyrazolyl]-1H-benzo[d]imidazol-1-yl)nicotinic acid (compound in Example 715) and 0.136 mL morpholine.

¹H-NMR (CDCl₃)

δ: 3.44–4.00(m, 8H), 6.94–7.00(m, 2H), 7.25–7.32(m, 8H), 7.32–7.36(m, 9H), 7.47–7.52(m, 3H), 7.78(d, J=8.2 Hz, 1H), 7.82(d, J=1.2 Hz, 1H), 7.88(dd, J=8.2, 2.2 Hz, 1H), 8.54(dd, J=2.2, 0.4 Hz, 1H), 8.58(s, 1H)

Example 718

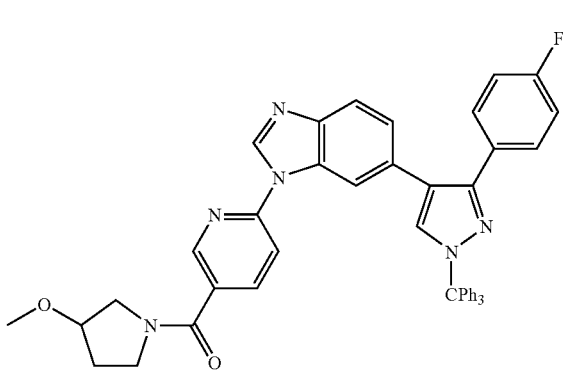

6-{6-[3-(4-Fluorophenyl)-1-trityl-1H-4-pyrazolyl]-1H-benzo[d]imidazol-1-yl}-pyridin-3-yl)-(3-methoxypyrrolidin-1-yl) methanone 44 mg of the title compound was obtained by the same method as in Example 444 from 100 mg 6-{6-[3-(4-fluorophenyl)-1-trityl-1H-4-pyrazolyl]-1H-benzo[d]imidazol-1-yl}nicotinic acid (compound in Example 715) and 0.21 g of 3-methoxypyrrolidine hydrochloride.

¹H-NMR (CDCl₃)

δ: 1.70–2.24(m, 2H), 3.41(s, 3H), 3.52–3.84(m, 4H), 3.78–4.12 (m, 1H), 6.90–7.00(m, 2H), 7.25–7.32(m, 7H), 7.32–7.36(m, 10H), 7.47–7.52(m, 3H), 7.77(d, J=8.4 Hz, 1H), 7.84(d, J=1.2 Hz, 1H), 7.87–8.02(m, 1H), 8.58(s, 1H), 8.67(dd, J=14.8, 1.6 Hz, 1H)

Example 719

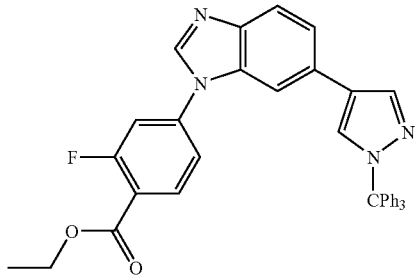

Ethyl 2-fluoro-4-[6-(1-trityl-1H-4-pyrazolyl)-1H-benzo[d]imidazol-1-yl}benzoate 534 mg of the title compound was obtained as pale pink crystals by the same reaction as in Example 29 from 385 mg ethyl 4-(6-bromo-1H-benzo[d]imidazol-1-yl)-2-fluoro-benzoate (compound in Production Example 334) and 488 mg 1-trityl-1H-4-pyrazolylboronic acid.

¹H-NMR (CDCl₃)

δ: 1.44(t, J=7.0 Hz, 3H), 4.46 (q, J=7.0 Hz, 2H), 7.18–7.23(m, 6H), 7.30–7.38(m, 10H), 7.39–7.44(m, 2H), 7.59(d, J=1.2 Hz, 1H), 7.66(s, 1H), 7.81(d, J=8.8 Hz, 1H), 7.94(s, 1H), 8.09(s, 1H), 8.18(t, J=8.4 Hz, 1H)

Example 720

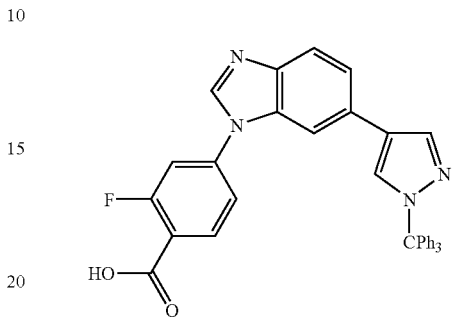

2-Fluoro-4-[6-(1-trityl-1H-4-pyrazolyl)-1H-benzo[d]imidazol-1-yl]benzoic acid 443 mg of the title compound was obtained as pink crystals by the same reaction as in Production Example 310 from 534 mg ethyl 2-fluoro-4-[6-(1-trityl-1H-4-pyrazolyl)-1H-benzo[d]imidazol-1-yl}benzoate (compound in Example 719).

¹H-NMR (DMSO-d₆)

δ: 7.12–7.18(m, 6H), 7.34–7.42(m, 9H), 7.49(dd, J=8.4, 1.8 Hz, 1H), 7.70–7.74(m, 2H), 7.81(dd, J=11.6, 1.8 Hz, 1H), 7.87(d, J=1.2 Hz, 1H), 7.88(s, 1H), 8.08(t, J=8.4 Hz, 1H), 7.17(s, 1H), 7.61(s, 1H)

Example 721

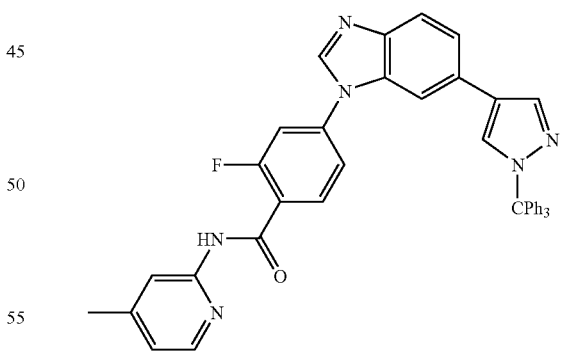

N1-(4-Methyl-2-pyridyl)-2-fluoro-4-[6-(1-trityl-1H-4-pyrazolyl)-1H-benzo[d]imidazol-1-yl] benzamide 8 mg of the title compound was obtained by the same reaction as in Example 497 from 100 mg 2-fluoro-4-[6-(1-trityl-1H-4-pyrazolyl)-1H-benzo[d]imidazol-1-yl]benzoic acid (compound in Example 720) and 21 mg 2-amino-4-methylpyridine.

¹H-NMR (CDCl₃)

δ: 2.44(s, 3H), 6.94–6.97(m, 1H), 7.18–7.24(m, 6H), 7.31–7.36(m, 9H), 7.41–7.46(m, 2H), 7.54(dd, J=8.8, 2.0 Hz, 1H), 7.61(d, J=1.6 Hz, 1H), 7.67(s, 1H), 7.83(d, J=8.4 Hz, 1H), 7.96(s, 1H), 8.12(d, J=0.8 Hz, 1H), 8.22(d, J=5.2 Hz, 1H), 8.25(brs, 1H), 8.40(t, J=8.4 Hz, 1H), 8.90–9.04(m, 1H)

Example 722

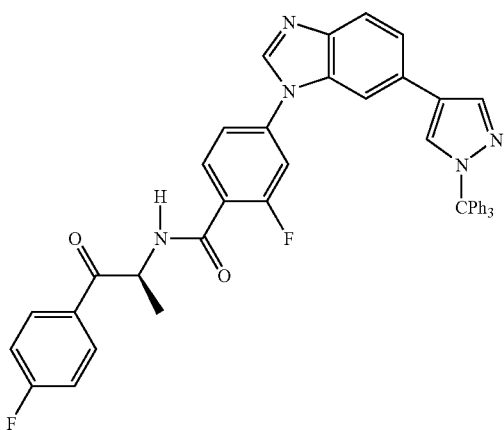

N1-[(1S)-2-(4-Fluorophenyl-1-methyl-2-oxoethyl)-2-fluoro-4-[6-(1-trityl-1H-4-pyrazolyl)-1H-benzo[d]imidazol-1-yl] benzamide 40 mg of the title compound was obtained by the same reaction as in Example 497 from 50 mg 2-fluoro-4-[6-(1-trityl-1H-4-pyrazolyl)-1H-benzo [d] imidazol-1-yl]benzoic acid (compound in Example 720) and 20 mg (2S)-2-amino-1-(4-fluorophenyl)propane-1-one hydrochloride (compound in Production Example 319).

¹H-NMR (CDCl₃)

δ: 1.59(d, J=6.8 Hz, 3H), 5.73–5.82(m, 1H), 7.19–7.25(m, 8H), 7.30–7.36(m, 9H), 7.39(dd, J=10.2, 2.0 Hz, 1H), 7.43 (dd, J=8.3, 1.6 Hz, 1H), 7.48(dd, J=8.4, 2.0 Hz, 1H), 7.59(d, J=1.6 Hz, 1H), 7.66(d, J=0.6 Hz, 1H), 7.82(d, J=8.3 Hz, 1H), 7.94(d, J=0.6 Hz, 1H), 8.07–8.13(m, 3H), 8.34(t, J=8.4 Hz, 1H)

Example 723

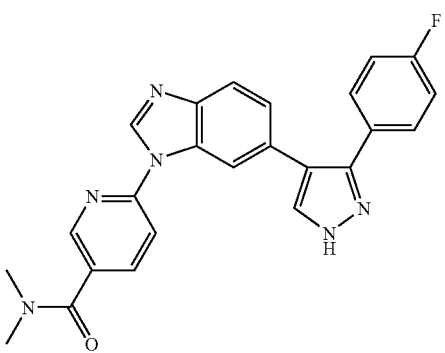

6-{6-[3-(4-Fluorophenyl)-1H-4-pyrazolyl]-1H-benzo[d]imidazol-1-yl}-N,N-dimethyl-nicotinamide 43 mg 6-{6-[3-(4-fluorophenyl)-1-trityl-1H-4-pyrazolyl]-1H-benzo[d]imidazol-1-yl}-N,N-dimethyl-nicotinamide (compound in Example 716) was dissolved in 8.0 mL solvent mixture of tetrahydrofuran and methanol (1:1), 3.0 mL of 5 N hydrochloric acid was added thereto, and the mixture was left at room temperature for 3 hours. The reaction solution was neutralized and then extracted with ethyl acetate. The extract was purified by silica gel column chromatography (ethyl acetate/methanol) and recrystallized from methanol/diethyl ether, to give 24 mg of the title compound as colorless crystals.

¹H-NMR (CDCl₃)

δ: 3.11(brs, 3H), 3.18(brs, 3H), 7.03–7.09(m, 2H), 7.32–7.35(m, 1H), 7.40(d, J=8.4 Hz, 1H), 7.45–7.51(m, 2H), 7.77–7.83(m, 2H), 7.91–7.96(m, 2H), 8.58–8.60(m, 2H)

MS m/e (ESI) 427 (MH⁺)

Example 724

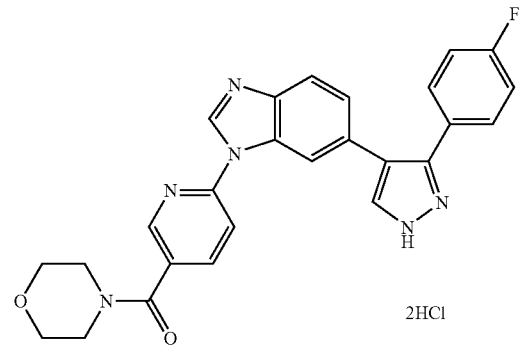

6-{6-[3-(4-Fluorophenyl)-1H-4-pyrazolyl]-1H-benzo[d]-imidazol-1-yl}-pyridin-3-yl)-morpholin-4-yl-methanone dihydrochloride 36 mg 6-{6-[3-(4-fluorophenyl)-1-trityl-1H-4-pyrazolyl]-1H-benzo[d]imidazol-1-yl}-pyridin-3-yl)-morpholin-4-yl-methanone (compound in Example 717) was subjected to deprotection of the trityl group and converted into the corresponding hydrochloride by the same method as in Example 68 to give 16 mg of the title compound as colorless crystals.

¹H-NMR (DMSO-d₆)

δ: 3.35–3.75(m, 8H), 7.17–7.24(m, 2H), 7.31(dd, J=8.4, 1.4 Hz, 1H), 7.42–7.47(m, 2H), 7.74(d, J=8.4 Hz, 1H), 7.98(s, 1H), 7.99(dd, J=8.0, 0.8 Hz, 1H), 8.11(dd, J=8.0, 2.2 Hz, 1H), 8.25(d, J=1.4 Hz, 1H), 8.53(dd, J=2.2, 0.8 Hz, 1H), 9.29(s, 1H)

MS m/e (ESI) 469 (MH⁺)

Example 725

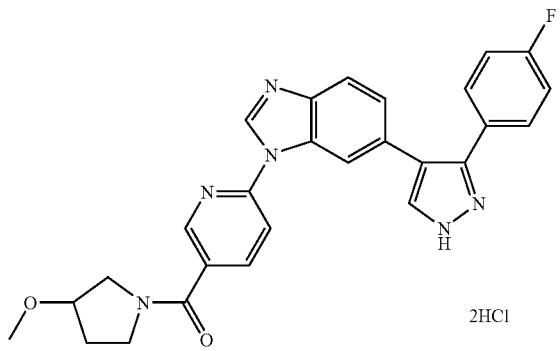

6-{6-[3-(4-Fluorophenyl)-1H-4-pyrazolyl]-1H-benzo[d]imidazol-1-yl}-pyridin-3-yl)-(3-methoxypyrrolidin-1-yl)methanone dihydrochloride 24 mg of the title compound was obtained as colorless crystals by the same method as in Example 68 from 44 mg 6-{6-[3-(4-fluorophenyl)-1-trityl-1H-4-pyrazolyl]-1H-benzo[d]imidazol-1-yl}-pyridin-3-yl)-(3-methoxypyrrolidin-1-yl) methanone (compound in Example 718).

¹H-NMR (DMSO-d₆)
δ: 1.92–2.60(m, 2H), 3.27(s, 3H), 3.40–3.74(m, 4H), 3.94–4.06 (m, 1H), 7.17–7.24(m, 2H), 7.28–7.34(m, 1H), 7.41–7.49(m, 2H), 7.74(dd, J=8.4, 0.4 Hz, 1H), 7.94–8.00 (m, 2H), 8.18–8.23(m, 1H), 8.25(dd, J=8.8, 1.0 Hz, 1H), 8.62–8.64(m, 1H), 9.30(s, 1H)
MS m/e (ESI) 483 (MH⁺)

Example 726

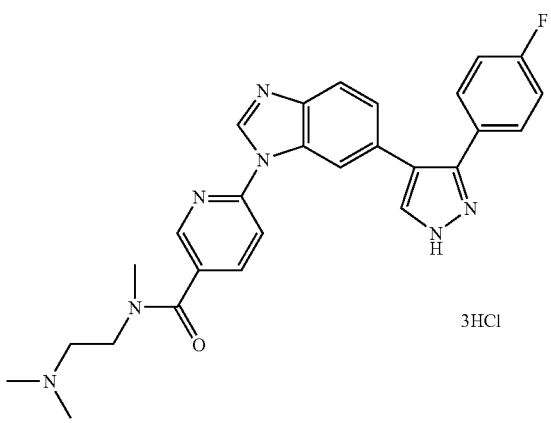

N-(2-Dimethylaminoethyl)-6-{6-[3-(4-fluorophenyl)-1H-4-pyrazolyl]-1H-benzo[d]imidazol-1-yl}-N-methyl-nicotinamide trihydrochloride 32 mg N-(2-dimethylaminoethyl)-6-{6-[3-(4-fluorophenyl)-1-trityl-1H-4-pyrazolyl]-1H-benzo[d]imidazol-1-yl}-N-methyl-nicotinamide was obtained by the same method as in Example 444 from 100 mg 6-{6-[3-(4-fluorophenyl)-1-trityl-1H-4-pyrazolyl]-1H-benzo[d]imidazol-1-yl}nicotinic acid (compound in Example 715) and 0.2 mL N,N,N'-trimethyl ethylene diamine. The product was subjected to deprotection of the trityl group and converted into the corresponding hydrochloride by the same method as in Example 68 to give 23 mg of the title compound as colorless crystals.

¹H-NMR (DMSO-d₆)
δ: 2.86(br, 6H), 3.05(s, 3H), 3.35–3.42(m, 2H), 3.84–3.91 (m, 2H), 7.17–7.24(m, 2H), 7.25–7.32(m, 1H), 7.43–7.49 (m, 2H), 7.74(d, J=8.4 Hz, 1H), 7.98(s, 1H), 8.00(dd, J=8.4, 0.8 Hz, 1H), 8.24–8.32(m, 2H), 8.65(brs, 1H), 9.16(s, 1H)
MS m/e (ESI) 484 (MH⁺)

Example 727

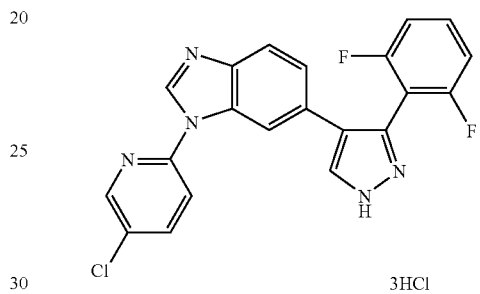

1-(5-Chloropyridin-2-yl)-6-[3-(2,6-difluorophenyl)-1H-4-pyrazolyl]-1H-benzo[d]imidazole trihydrochloride 300 mg 6-[3-(2,6-difluorophenyl)-1-trityl-1H-4-pyrazolyl]-1H-benzo[d]imidazole (compound in Production Example 330) and 91 mg 2,5-dichloropyridine were reacted by the same method as in Example 145 to give 159 mg mixture of 1-(5-chloropyridin-2-yl)-6-[3-(2,6-difluorophenyl)-1-trityl-1H-4-pyrazolyl]-1H-benzo[d]imidazole and 1-(5-chloropyridin-2-yl)-5-[3-(2,6-difluorophenyl)-1-trityl-1H-4-pyrazolyl]-1H-benzo[d]imidazole as positional isomers. The product was dissolved in 8.0 mL solvent mixture of tetrahydrofuran and methanol (1:1), then 2.0 mL of 5 N hydrochloric acid was added thereto, and the solution was left at room temperature for 3 hours. The reaction solution was neutralized and then extracted with ethyl acetate. Crystals precipitated by adding dichloromethane were diluted with ether and then concentrated to separate the positional isomers. 4 N hydrogen chloride solution in ethyl acetate was added thereto, the solution was concentrated to form the corresponding hydrochloride which was then dissolved in dichloromethane/methanol and recrystallized from ethanol/ether, to give 25 mg of the title compound as colorless crystals.

¹H-NMR (DMSO-d₆)
δ: 7.22–7.30(m, 2H), 7.45(dd, J=8.6, 1.4 Hz, 1H), 7.57–7.65(m, 1H), 7.75(dd, J=8.8, 0.6 Hz, 1H), 7.91(dd, J=8.6, 0.4 Hz, 1H), 8.08(d, J=1.4 Hz, 1H), 8.24(dd, J=8.8, 2.7 Hz, 1H), 8.28(s, 1H), 8.47(dd, J=2.7, 0.6 Hz, 1H), 9.33(s, 1H)
MS m/e (ESI) 408 (MH⁺)

Example 728

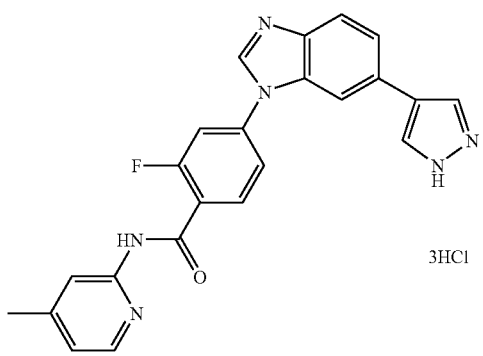

N1-(4-Methyl-2-pyridyl)-2-fluoro-4-[6-(1H-4-pyrazolyl)-1H-benzo[d]imidazol-1-yl]benzamide trihydrochloride 5 mg of the title compound was obtained as colorless crystals in the same manner as in Example 79 from 8 mg N1-(4-methyl-2-pyridyl)-2-fluoro-4-[6-(1-trityl-1H-4-pyrazolyl)-1H-benzo[d]imidazol-1-yl] benzamide (compound in Example 721).

$^1$H-NMR (DMSO-$d_6$)

δ: 2.42(s, 3H), 7.14(d, J=5.2 Hz, 1H), 7.75(dd, J=8.6, 1.6 Hz, 1H), 7.82(dd, J=8.0, 1.6 Hz, 1H), 7.85(d, J=8.6 Hz, 1H), 7.91–7.96(m, 2H), 8.01(t, J=8.0 Hz, 1H), 8.03(brs, 1H), 8.20(s, 2H), 8.29(d, J=5.2 Hz, 1H), 9.14(brs, 1H)

MS m/e (ESI) 413 (MH$^+$)

Example 729

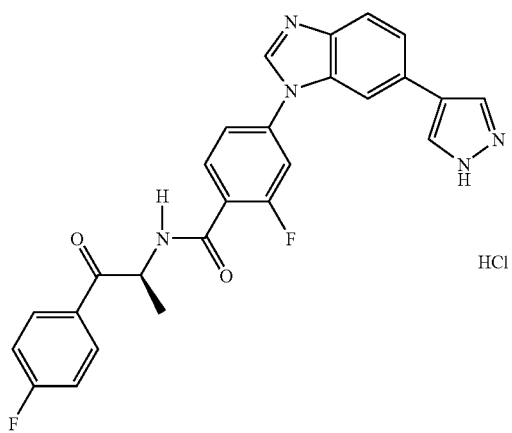

N1-[(1S)-2-(4-Fluorophenyl-1-methyl-2-oxoethyl)-2-fluoro-4-[6-(1H-4-pyrazolyl)-1H-benzo[d]imidazol-1-yl]benzamide hydrochloride 40 mg N1-[(1S)-2-(4-fluorophenyl-1-methyl-2-oxoethyl)-2-fluoro-4-[6-(1-trityl-1H-4-pyrazolyl)-1H-benzo[d]imidazol-1-yl} benzamide (compound in Example 722) was subjected to deprotection of the trityl group and converted into the corresponding hydrochloride by the same method as in Example 79 to give 12 mg of the title compound as colorless crystals.

$^1$H-NMR (DMSO-$d_6$)

δ: 1.42(d, J=6.8 Hz, 3H), 5.50–5.58(m, 1H), 7.37–7.46(m, 2H), 7.76–7.96(m, 6H), 8.13–8.25(m, 4H), 9.05(d, J=6.8 Hz, 1H), 9.31(brs, 1H)

MS m/e (ESI) 472 (MH$^+$)

Example 730

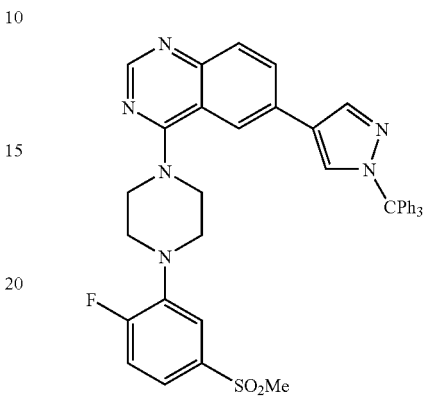

4-[4-(2-Fluoro-5-methylsulfonylphenyl)piperazin-1-yl]-6-(1-trityl-1H-4-pyrazolyl) quinazoline 211 mg of the title compound was obtained as a colorless amorphous by reacting 165 mg 6-bromo-4-[4-(2-fluoro-5-methylsulfonylphenyl)piperazin-1-yl] quinazoline obtained in Production Example 340, with 138 mg 1-trityl-1H-4-pyrazolylboronic acid in the same manner as in Example 168.

$^1$H-NMR (CDCl$_3$)

δ: 3.07(s, 3H), 3.32–3.42(m, 4H), 3.90–3.99(m, 4H), 7.18–7.68(m, 18H), 7.70(s, 1H), 7.82(dd, J=8.8, 2.0 Hz, 1H), 7.88(d, J=8.8 Hz, 1H), 7.91(d, J=2.0 Hz, 1H), 8.02(s, 1H), 8.73(s, 1H)

Example 731

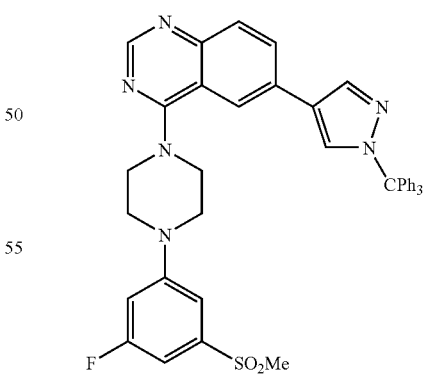

4-[4-(3-Fluoro-5-methylsulfonylphenyl)piperazin-1-yl]-6-(1-trityl-1H-4-pyrazolyl) quinazoline 130 mg of the title compound was obtained as a pale yellow amorphous by reacting 95 mg 6-bromo-4-[4-(3- fluoro-5-methylsulfonylphenyl)piperazin-1-yl] quinazoline obtained in Production Example 346, with 94 mg 1-trityl-1H-4-pyrazolylboronic acid in the same manner as in Example 168.

¹H-NMR (CDCl₃)

δ: 3.08(s, 3H), 3.45–3.56(m, 4H), 3.84–3.98(m, 4H), 6.80–6.88(m, 1H), 7.07–7.13(m, 1H), 7.15–7.43(m, 16H), 7.71(s, 1H), 7.83(dd, J=8.8, 2.0 Hz, 1H), 7.87–7.95(m, 2H), 8.02(s, 1H), 8.74(s, 1H)

Example 732

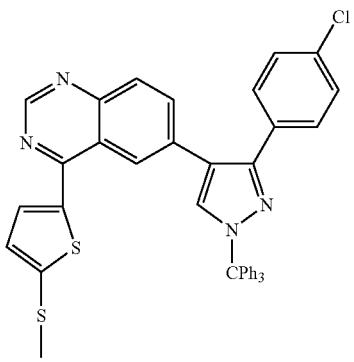

6-[3-(4-Chlorophenyl)-1-trityl-1H-pyrazol-4-yl]-4-(5-methylsulfanylthiophen-2-yl) quinazoline 106 mg of the title compound was obtained as colorless crystals by the same reaction as in Example 9 from 60 mg 6-bromo-4-[5-(methylsulfanyl)-2-thienyl] quinazoline (compound in Production Example 100) and 148 mg 3-(4-chlorophenyl)-1-trityl-1H-4-pyrazolylboronic acid (compound in Production Example 28).

¹H-NMR (CDCl₃)

δ: 2.61(s, 3H), 6.83(d, J=4.0 Hz, 1H), 6.89(d, J=4.0 Hz, 1H), 7.22–7.28(m, 6H), 7.32–7.40(m, 11H), 7.43–7.47(m, 2H), 7.56(s, 1H), 7.83(dd, J=8.6, 1.8 Hz, 1H), 7.98(d, J=8.6 Hz, 1H), 8.16(d, J=1.8 Hz, 1H), 9.13(s, 1H)

Example 733

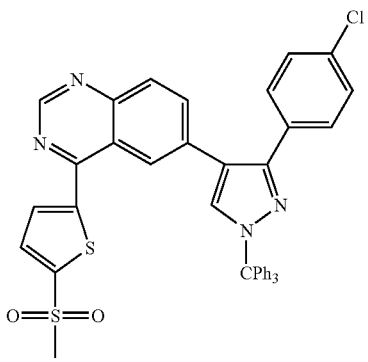

6-[3-(4-Chlorophenyl)-1-trityl-1H-pyrazol-4-yl]-4-(5-methylsulfonylthiophen-2-yl) quinazoline 78 mg of the title compound was obtained as colorless crystals by the same reaction as in Production Example 43 from 106 mg 6-[3-(4-chlorophenyl)-1-trityl-1H-pyrazol-4-yl]-4-(5-methylsulfanylthiophen-2-yl) quinazoline (compound in Example 732).

¹H-NMR (CDCl₃)

δ: 3.25(s, 3H), 6.90(d, J=4.0 Hz, 1H), 7.22–7.28(m, 6H), 7.32–7.40(m, 11H), 7.42–7.46(m, 2H), 7.58(d, J=4.0 Hz, 1H), 7.58(s, 1H), 7.91(dd, J=8.8, 1.8 Hz, 1H), 8.07(d, J=8.8 Hz, 1H), 8.08(d, J=1.8 Hz, 1H), 9.24(s, 1H)

Example 734

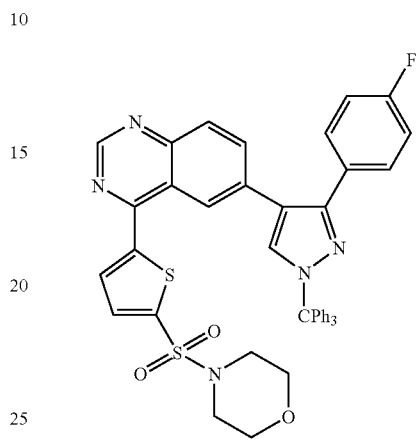

6-[3-(4-Fluorophenyl)-1-trityl-1H-pyrazol-4-yl]-4-[5-(morpholine-4-sulfonyl)thiophen-2-yl] quinazoline 86 mg of the title compound was obtained as yellow crystals by the same reaction as in Example 9 from 56 mg 6-bromo-4-[5-(morpholine-4-sulfonyl)-thiophen-2-yl] quinazoline (compound in Production Example 369) and 74 mg 3-(4-fluorophenyl)-1-trityl-1H-4-pyrazolylboronic acid (compound in Production Example 25).

¹H-NMR (CDCl₃)

δ: 3.12–3.16(m, 4H), 3.79–3.83(m, 4H), 6.94(d, J=4.0 Hz, 1H), 7.05–7.12(m, 2H), 7.22–7.30(m, 7H), 7.32–7.38(m, 9H), 7.46–7.53(m, 2H), 7.59(s, 1H), 7.90(dd, J=8.8, 0.8 Hz, 1H), 8.05(d, J=8.8 Hz, 1H), 8.11(d, J=0.8 Hz, 1H), 9.23(s, 1H)

Example 735

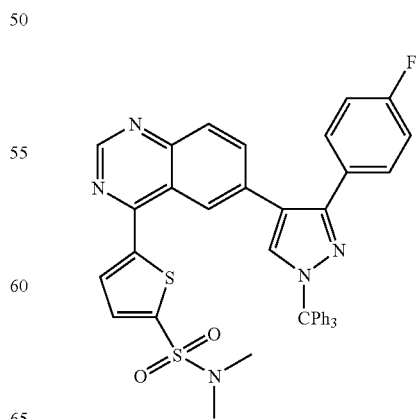

5-{6-[3-(4-Fluorophenyl)-1-trityl-1H-pyrazol-4-yl]-quinazolin-4-yl}thiophen-2-sulfonic acid dimethylamide 74 mg of the title compound was obtained as yellow crystals by the same reaction as in Example 9 from 50 mg 5-(6-bromoquinazolin-4-yl)-thiophen-2-sulfonic acid dimethylamide (compound in Production Example 370) and 73 mg 3-(4-fluorophenyl)-1-trityl-1H-4-pyrazolylboronic acid (compound in Production Example 25).

$^1$H-NMR (CDCl$_3$)

δ: 2.83(s, 6H), 6.96(d, J=4.0 Hz, 1H), 7.40–7.11(m, 2H), 7.23–7.28(m, 6H), 7.34–7.38(m, 10H), 7.45–7.50(m, 2H), 7.58(s, 1H), 7.90(dd, J=8.8, 1.8 Hz, 1H), 8.05(d, J=8.8 Hz, 1H), 8.12(d, J=1.8 Hz, 1H), 9.23(s, 1H)

Example 736

6-[3-(4-Fluorophenyl)-1-trityl-1H-pyrazol-4-yl]-4-[5-(piperidin-1-sulfonyl)thiophen-2-yl] quinazoline 79 mg of the title compound was obtained as yellow crystals by the same reaction as in Example 9 from 50 mg 6-bromo-4-[5-(piperidin-1-sulfonyl)-thiophen-2-yl] quinazoline (compound in Production Example 371) and 66 mg 3-(4-fluorophenyl)-1-trityl-1H-4-pyrazolylboronic acid (compound in Production Example 25).

$^1$H-NMR (CDCl$_3$)

δ: 1.46–1.54(m, 2H), 1.68–1.78(m, 4H), 3.08–3.15(m, 4H), 6.94(d, J=4.4 Hz, 1H), 7.05–7.11(m, 2H), 7.23–7.28(m, 6H), 7.34–7.38(m, 10H), 7.45–7.50(m, 2H), 7.58(s, 1H), 7.99(dd, J=8.6, 1.8 Hz, 1H), 8.05(d, J=8.6 Hz, 1H), 8.12(d, J=1.8 Hz, 1H), 9.23(s, 1H)

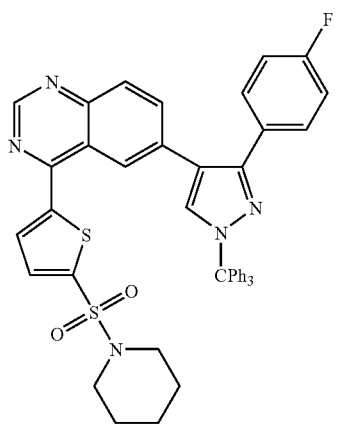

Example 737

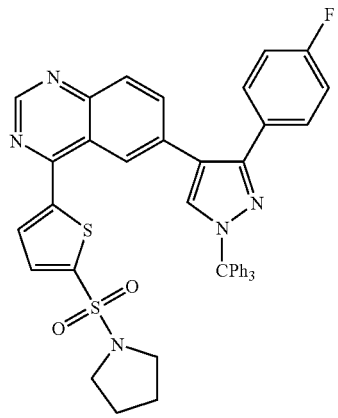

6-[3-(4-Fluorophenyl)-1-trityl-1H-pyrazol-4-yl]-4-[5-(pyrrolidine-1-sulfonyl)thiophen-2-yl] quinazoline 95 mg of the title compound was obtained as yellow crystals by the same reaction as in Example 9 from 50 mg 6-bromo-4-[5-(pyrrolidine-1-sulfonyl)-thiophen-2-yl] quinazoline (compound in Production Example 372) and 69 mg 3-(4-fluorophenyl)-1-trityl-1H-4-pyrazolylboronic acid (compound in Production Example 25).

$^1$H-NMR (CDCl$_3$)

δ: 1.82–1.90(m, 4H), 3.34–3.41(m, 4H), 6.94(d, J=4.0 Hz, 1H), 7.05–7.11(m, 2H), 7.23–7.30(m, 6H), 7.34–7.39(m, 9H), 7.41(d, J=4.0 Hz, 1H), 7.45–7.50(m, 2H), 7.58(s, 1H), 7.89(dd, J=8.8, 1.8 Hz, 1H), 8.05(d, J=8.8 Hz, 1H), 8.13(d, J=1.8 Hz, 1H), 9.23(s, 1H)

Example 738

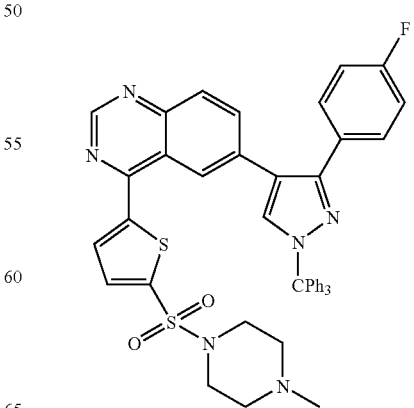

6-[3-(4-Fluorophenyl)-1-trityl-1H-pyrazol-4-yl]-4-[5-(4-methylpiperazine-1-sulfonyl)thiophen-2-yl]quinazoline 87 mg of the title compound was obtained as yellow crystals by the same reaction as in Example 9 from 50 mg 6-bromo-4-[5-(4-methylpiperazine-1-sulfonyl)-thiophen-2-yl]quinazoline (compound in Production Example 373) and 64 mg 3-(4-fluorophenyl)-1-trityl-1H-4-pyrazolylboronic acid (compound in Production Example 25).

$^1$H-NMR (CDCl$_3$)

δ: 2.31(s, 3H), 2.51–2.60(m, 4H), 3.13–3.24(m, 4H), 6.91(d, J=4.0 Hz, 1H), 7.06–7.12(m, 2H), 7.23–7.29(m, 6H), 7.34–7.39(m, 9H), 7.45–7.50(m, 2H), 7.58(s, 1H), 7.89(dd, J=8.7, 1.7 Hz, 1H), 8.05(d, J=8.7 Hz, 1H), 8.10(d, J=1.7 Hz, 1H), 9.22(s, 1H)

Example 739

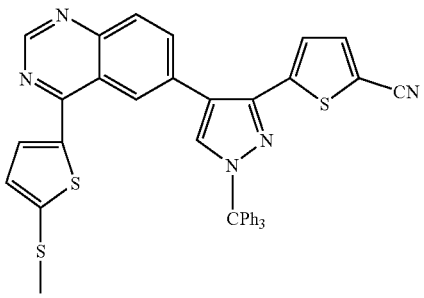

5-{4-[4-(5-Methylsulfanylthiophen-2-yl)quinazolin-6-yl]-1-trityl-1H-pyrazol-3-yl}thiophen-2-carbonitrile 202 mg of the title compound was obtained as yellow crystals by the same reaction as in Example 9 from 120 mg 6-bromo-4-[5-(methylsulfanyl)-2-thienyl] quinazoline (compound in Production Example 100) and 210 mg 3-(5-cyano-2-thienyl)-1-trityl-1H-4-pyrazolylboronic acid (compound in Production Example 116).

$^1$H-NMR (CDCl$_3$)

δ: 2.63(s, 3H), 7.01(d, J=3.8 Hz, 1H), 7.02(d, J=3.8 Hz, 1H), 7.20–7.26(m, 6H), 7.35–7.38(m, 9H), 7.39(d, J=3.8 Hz, 1H), 7.45(d, J=3.8 Hz, 1H), 7.49(s, 1H), 7.87(dd, J=8.6, 1.8 Hz, 1H), 8.05(d, J=8.6 Hz, 1H), 8.38(d, J=1.8 Hz, 1H), 9.20(s, 1H)

Example 740

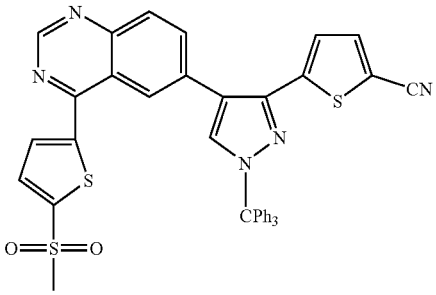

5-{4-[4-(5-Methylsulfonylthiophen-2-yl)quinazolin-6-yl]-1-trityl-1H-pyrazol-3-yl}thiophen-2-carbonitrile 180 mg of the title compound was obtained by the same reaction as in Production Example 43 from 202 mg 5-{4-[4-(5-methylsulfanylthiophen-2-yl)quinazolin-6-yl]-1-trityl-1H-pyrazol-3-yl}thiophen-2-carbonitrile (compound in Production Example 739).

$^1$H-NMR (CDCl$_3$)

δ: 3.27(s, 3H), 7.02(d, J=4.0 Hz, 1H), 7.20–7.26(m, 6H), 7.35–7.39(m, 9H), 7.46(d, J=4.0 Hz, 1H), 7.51(s, 1H), 7.52(d, J=4.0 Hz, 1H), 7.74(d, J=4.0 Hz, 1H), 7.94(dd, J=8.8, 1.8 Hz, 1H), 8.14(d, J=8.8 Hz, 1H), 8.30(d, J=1.8 Hz, 1H), 9.32(s, 1H)

Example 741

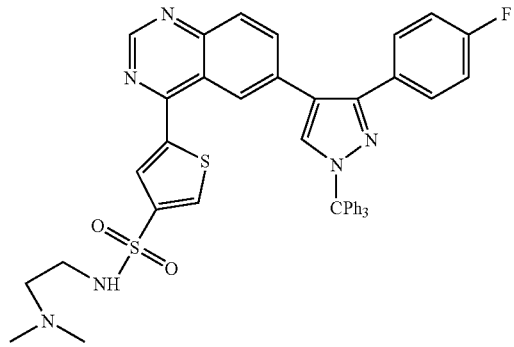

5-{6-[3-(4-Fluorophenyl)-1-trityl-1H-pyrazol-4-yl]quinazolin-4-yl}thiophen-3-sulfonic acid (2-dimethylaminoethyl)amide 30 mg of the title compound was obtained as yellow crystals by the same reaction as in Example 9 from 24 mg 5-(6-bromoquinazolin-4-yl)-thiophen-3-sulfonic acid (2-dimethylaminoethyl)amide (compound in Production Example 374) and 32 mg 3-(4-fluorophenyl)-1-trityl-1H-4-pyrazolylboronic acid (compound in Production Example 25).

$^1$H-NMR (CDCl$_3$)

δ: 2.04(s, 6H), 2.31–2.36(m, 2H), 2.98–3.02(m, 2H), 6.98–7.03(m, 2H), 7.24–7.30(m, 6H), 7.32–7.38(m, 9H), 7.43–7.49(m, 2H), 7.56(s, 1H), 7.60(d, J=1.4 Hz, 1H), 7.85(dd, J=8.6, 1.8 Hz, 1H), 8.03(d, J=8.6 Hz, 1H), 8.14(d, J=1.4 Hz, 1H), 8.24(d, J=1.8 Hz, 1H), 9.24(br, 1H)

Example 742

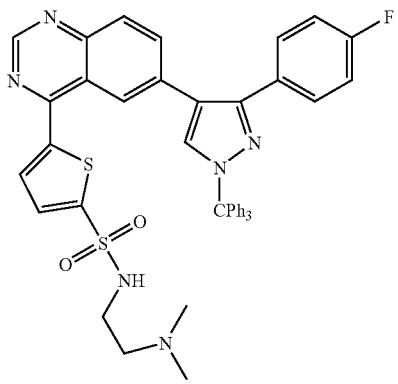

5-{6-[3-(4-Fluorophenyl)-1-trityl-1H-pyrazol-4-yl]
quinazolin-4-yl}thiophen-2-sulfonic acid (2-dim-
ethylaminoethyl)amide 83 mg of the title compound was obtained as yellow crystals by the same reaction as in Example 9 from 57 mg 5-(6-bromoquinazolin-4-yl)-thiophen-2-sulfonic acid (2-dimethylaminoethyl)amide (compound in Production Example 375) and 75 mg 3-(4-fluorophenyl)-1-trityl-1H-4-pyrazolylboronic acid (compound in Production Example 25).
$^{1}$H-NMR (CDCl$_{3}$)
δ: 2.15(s, 6H), 2.40–2.45(m, 2H), 3.12–3.16(m, 2H), 6.90(d, J=4.0 Hz, 1H), 7.05–7.11(m, 2H), 7.24–7.30(m, 6H), 7.32–7.38(m, 9H), 7.44(d, J=4.0 Hz, 1H), 7.45–7.49(m, 2H), 7.57(s, 1H), 7.89(dd, J=8.8, 1.8 Hz, 1H), 8.04(d, J=8.8 Hz, 1H), 8.12(d, J=1.8 Hz, 1H), 9.22(s, 1H)

Example 743

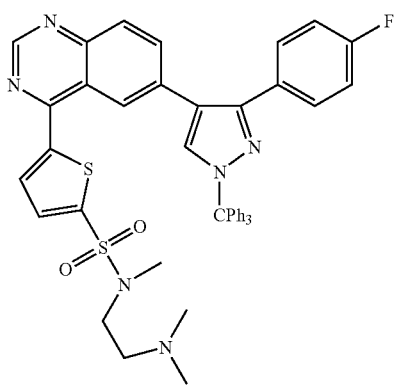

5-{6-[3-(4-Fluorophenyl)-1-trityl-1H-pyrazol-4-yl]
quinazolin-4-yl}thiophen-2-sulfonic acid (2-dim-
ethylaminoethyl)methylamide 131 mg 5-(6-bromoquinazolin-4-yl)-thiophen-2-sulfonic acid (2-dimethylaminoethyl)-methyl-amide (compound in Production Example 376) and 168 mg 3-(4-fluorophenyl)-1-trityl-1H-4-pyrazolylboronic acid (compound in Production Example 25) were subjected to the same reaction as in Example 9, and the isomer was separated and purified by a column to give 66 mg of the title compound as yellow crystals.
$^{1}$H-NMR (CDCl$_{3}$)
δ: 2.28(s, 6H), 2.55(t, J=6.8 Hz, 2H), 2.91(s, 3H), 3.21(t, J=6.8 Hz, 2H), 6.92(d, J=4.0 Hz, 1H), 7.04–7.11(m, 2H), 7.23–7.29(m, 6H), 7.33–7.38(m, 9H), 7.39(d, J=4.0 Hz, 1H), 7.45–7.50(m, 2H), 7.58(s, 1H), 7.89(dd, J=8.8, 1.8 Hz, 1H), 8.04(d, J=8.8 Hz, 1H), 8.12(d, J=1.8 Hz, 1H), 9.22(s, 1H)

Example 744

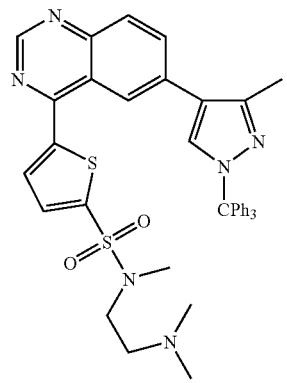

5-{6-[3-Methyl-1-trityl-1H-pyrazol-4-yl]quinazolin-
4-yl}-thiophen-2-sulfonic acid (2-dimethylaminoet-
hyl)methylamide 75 mg of the title compound was obtained by the same reaction as in Example 9 from 50 mg 5-(6-bromoquinazolin-4-yl)-thiophen-2-sulfonic acid (2-dimethylaminoethyl)-methyl-amide (compound in Production Example 376) and 53 mg 3-methyl-1-trityl-1H-4-pyrazolylboronic acid (compound in Production Example 30).
$^{1}$H-NMR (CDCl$_{3}$)
δ: 2.28(s, 6H), 2.54(s, 3H), 2.53–2.59(m, 2H), 2.94(s, 3H), 3.22–3.27(m, 2H), 7.21–7.26(m, 6H), 7.33–7.38(m, 9H), 7.57(s, 1H), 7.67(d, J=4.0 Hz, 1H), 7.80(d, J=4.0 Hz, 1H), 7.93(dd, J=8.6, 2.0 Hz, 1H), 8.07(d, J=8.6 Hz, 1H), 8.37(d, J=2.0 Hz, 1H), 9.26(s, 1H)

Example 745

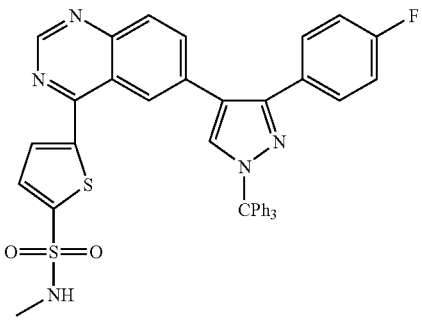

669

5-{6-[3-(4-Fluorophenyl)-1-trityl-1H-pyrazol-4-yl]quinazolin-4-yl}thiophen-2-sulfonic acid methylamide 356 mg of the title compound was obtained as a yellow amorphous by the same reaction as in Example 9 from 200 mg 5-(6-bromoquinazolin-4-yl)-thiophen-2-sulfonic acid methylamide (compound in Production Example 379) and 303 mg 3-(4-fluorophenyl)-1-trityl-1H-4-pyrazolylboronic acid (compound in Production Example 25).

$^1$H-NMR (CDCl$_3$)
δ: 2.82(d, J=5.2 Hz, 3H), 6.92(d, J=4.0 Hz, 1H), 7.05–7.11(m, 2H), 7.23–7.29(m, 6H), 7.33–7.38(m, 9H), 7.44(d, J=4.0 Hz, 1H), 7.45–7.50(m, 2H), 7.58(s, 1H), 7.89(dd, J=8.6, 1.8 Hz, 1H), 8.05(d, J=8.6 Hz, 1H), 8.11(d, J=1.8 Hz, 1H), 9.22(s, 1H)

Example 746

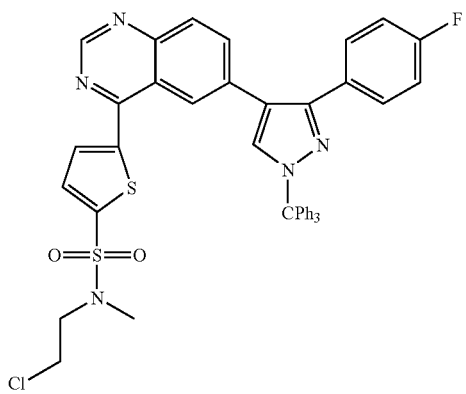

5-{6-[3-(4-Fluorophenyl)-1-trityl-1H-pyrazol-4-yl]quinazolin-4-yl}thiophen-2-sulfonic acid (2-chloroethyl)methylamide 314 mg 5-{6-[3-(4-fluorophenyl)-1-trityl-1H-pyrazol-4-yl]quinazolin-4-yl}thiophen-2-sulfonic acid methylamide (compound in Example 745) was dissolved in 8 mL N,N-dimethylformamide, then 21 mg sodium hydride was added thereto and stirred for 20 minutes, and 0.35 mL 1,2-dichloroethane was added thereto and stirred at room temperature for 2 hours. Further, 0.35 mL 1,2-dichloroethane was added thereto and stirred at 60° C. for 24 hours. Water was added to the reaction solution which was then extracted with ethyl acetate. The organic layer was washed with water and brine and dried over sodium sulfate. The solvent was evaporated, and then the residue was purified by silica gel chromatography (hexane/ethyl acetate) to give 325 mg of the title compound as a colorless amorphous.

670

$^1$H-NMR (CDCl$_3$)
δ: 2.98(s, 3H), 3.41–3.46(m, 2H), 3.69–3.73(m, 2H), 6.93(d, J=4.0 Hz, 1H), 7.03–7.11(m, 2H), 7.23–7.29(m, 6H), 7.34–7.38(m, 9H), 7.40(d, J=4.0 Hz, 1H), 7.45–7.50(m, 2H), 7.58(s, 1H), 7.90(dd, J=9.0, 1.8 Hz, 1H), 8.05(d, J=9.0 Hz, 1H), 8.11(d, J=1.8 Hz, 1H), 9.23(s, 1H)

Example 747

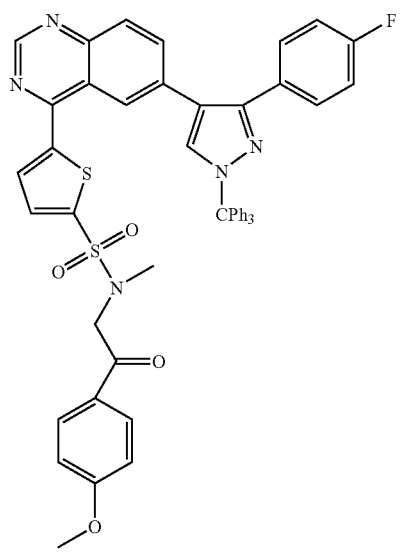

5-{6-[3-(4-Fluorophenyl)-1-trityl-1H-pyrazol-4-yl]quinazolin-4-yl}thiophen-2-sulfonic acid [2-(4-methoxyphenyl) 2-oxoethyl]methylamide 50 mg 5-{6-[3-(4-fluorophenyl)-1-trityl-1H-pyrazol-4-yl]quinazolin-4-yl}thiophen-2-sulfonic acid methylamide (compound in Example 745) was dissolved in 3 mL N,N-dimethylformamide, then 3.1 mg sodium hydride was added thereto and stirred at room temperature for 0.5 hour. Under ice-cooling, a solution of 18 mg 4-methoxyphenacyl bromide in 2 mL N,N-dimethylformamide was added thereto and stirred for 1.0 hour under ice-cooling. Water was added to the reaction solution which was then extracted with ethyl acetate, and the organic layer was washed with brine and dried over sodium sulfate. The solvent was evaporated, and the residue was purified by silica gel column chromatography (ethyl acetate/hexane) to give 47 mg of the title compound.

$^1$H-NMR (CDCl$_3$)
δ: 2.96(s, 3H), 3.89(s, 3H), 4.59(s, 2H), 6.94(d, J=4.0 Hz, 1H), 6.94–6.99(m, 2H), 7.04–7.10(m, 2H), 7.24–7.30(m, 6H), 7.32–7.38(m, 9H), 7.43(d, J=4.0 Hz, 1H), 7.45–7.49(m, 2H), 7.58(s, 1H), 7.89(dd, J=8.8, 1.8 Hz, 1H), 7.96–8.00(m, 2H), 8.05(d, J=8.8 Hz, 1H), 8.15(d, J=1.8 Hz, 1H), 9.23(s, 1H)

Example 748

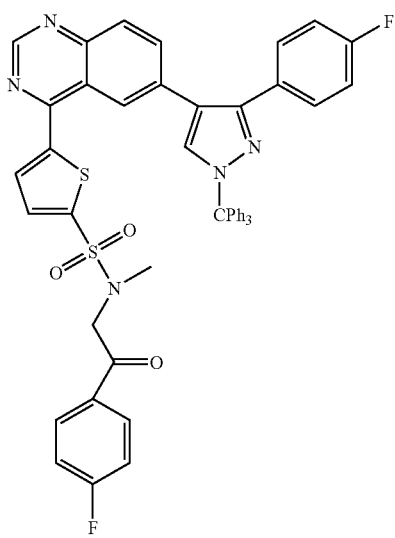

5-{6-[3-(4-Fluorophenyl)-1-trityl-1H-pyrazol-4-yl]-quinazolin-4-yl}thiophen-2-sulfonic acid [2-(4-fluorophenyl) 2-oxoethyl] methylamide 9 mg of the title compound was obtained by the same reaction as in Example 747 from 50 mg 5-{6-[3-(4-fluorophenyl)-1-trityl-1H-pyrazol-4-yl]quinazolin-4-yl}thiophen-2-sulfonic acid methylamide (compound in Production Example 745) and 13 mg 4-fluorophenacyl chloride.

$^1$H-NMR (CDCl$_3$)

δ: 2.96(s, 3H), 4.60(s, 2H), 6.93(d, J=4.0 Hz, 1H), 7.04–7.12(m, 2H), 7.14–7.21(m, 2H), 7.24–7.30(m, 6H), 7.32–7.38(m, 9H), 7.43(d, J=4.0 Hz, 1H), 7.45–7.49(m, 2H), 7.59(s, 1H), 7.90(dd, J=8.8, 1.6 Hz, 1H), 8.01–8.07(m, 3H), 8.14(d, J=1.6 Hz, 1H), 9.23(s, 1H)

Example 749

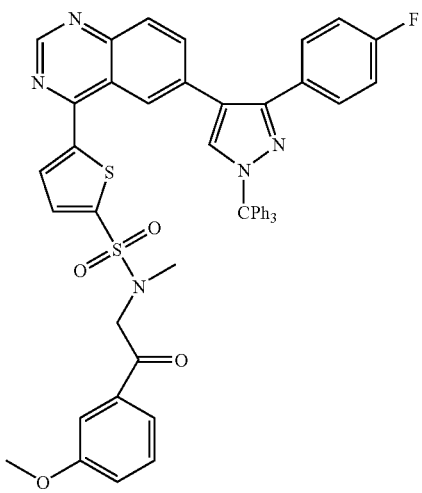

5-{6-[3-(4-Fluorophenyl)-1-trityl-1H-pyrazol-4-yl]-quinazolin-4-yl}thiophen-2-sulfonic acid [2-(3-methoxyphenyl) 2-oxoethyl]methylamide 50 mg 5-{6-[3-(4-fluorophenyl)-1-trityl-1H-pyrazol-4-yl]quinazolin-4-yl}thiophen-2-sulfonic acid methylamide (compound in Example 745) was dissolved in 5 mL tetrahydrofuran, then 0.07 mL of 1.0 M lithium bistrimethyl silyl amide was added thereto under ice-cooling, and the mixture was stirred for 0.5 hour. Under ice-cooling, a solution of 80 mg 3-methoxyphenacyl bromide in 2 mL tetrahydrofuran was added thereto and stirred for 1.5 hour. Water was added to the reaction solution which was then extracted with ethyl acetate, and the organic layer was washed with brine and dried over sodium sulfate. The solvent was evaporated, and the residue was purified by silica gel column chromatography (ethyl acetate/hexane) to give 17 mg of the title compound.

$^1$H-NMR (CDCl$_3$)

δ: 2.98(s, 3H), 3.86(s, 3H), 4.65(s, 2H), 6.94(d, J=4.0 Hz, 1H), 7.04–7.10(m, 2H), 7.14–7.18(m, 1H), 7.24–7.30(m, 6H), 7.32–7.38(m, 9H), 7.39–7.57(m, 6H), 7.59(s, 1H), 7.89(dd, J=8.8, 1.8 Hz, 1H), 8.05(d, J=8.8 Hz, 1H), 8.15(d, J=1.8 Hz, 1H), 9.23(s, 1H)

Example 750

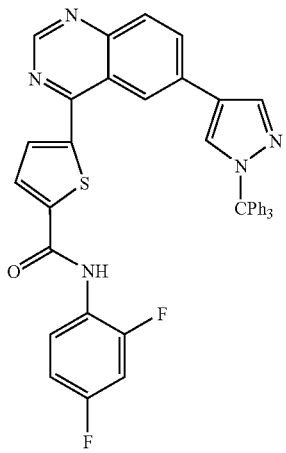

5-[6-(1-Trityl-1H-pyrazol-4-yl)quinazolin-4-yl]-thiophen-2-carboxylic acid (2,4-difluorophenyl) amide 122 mg of the title compound was obtained by reacting 100 mg 5-(6-bromoquinazolin-4-yl)thiophen-2-carboxylic acid (2,4-difluorophenyl) amide (compound in Production Example 383) with 100 mg 1-trityl-1H-4-pyrazolylboronic acid in the same manner as in Example 9 (with 3 mL dimethyl sulfoxide and 1 mL water as the reaction solvent).

$^1$H-NMR (CDCl$_3$)

δ: 6.92–6.99(m, 2H), 7.20–7.28(m, 6H), 7.32–7.38(m, 9H), 7.77–7.80(m, 2H), 7.84(d, J=4.0 Hz, 1H), 7.86–7.89(m, 1H), 7.99(dd, J=8.8, 1.8 Hz, 1H), 8.07(d, J=11.2 Hz, 1H), 8.07(d, J=8.8 Hz, 1H), 8.35–8.43(m, 1H), 8.46(d, J=1.2 Hz, 1H), 9.25(s, 1H)

Example 751

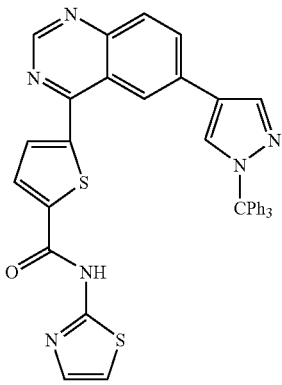

5-[6-(1-Trityl-1H-pyrazol-4-yl)quinazolin-4-yl]thiophene-2-carboxylic acid thiazol-2-ylamide 38 mg of the title compound was obtained by reacting 39 mg 5-(6-bromoquinazolin-4-yl)thiophene-2-carboxylic acid thiazol-2-ylamide (compound in Production Example 384) with 43 mg 1-trityl-1H-4-pyrazolylboronic acid in the same manner as in Example 9 (with 3 mL dimethyl sulfoxide and 1 mL water as the reaction solvent).

$^1$H-NMR (CDCl$_3$)

δ: 7.14–7.19(m, 7H), 7.34–7.45(m, 10H), 7.54–7.58(m, 1H), 8.04 (d, J=8.8 Hz, 1H), 8.12(d, J=0.6 Hz, 1H), 8.20(d, J=4.0 Hz, 1H), 8.31(dd, J=8.8, 1.8 Hz, 1H), 8.37(d, J=0.6 Hz, 1H), 8.57(d, J=1.8 Hz, 1H), 9.23(s, 1H)

Example 752

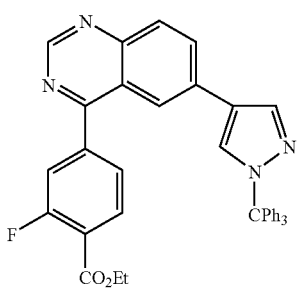

Ethyl 2-fluoro-4-[6-(1-trityl-1H-pyrazol-4-yl)-quinazolin-4-yl]benzoate 0.64 g ethyl 4-(6-chloroquinazolin-4-yl)-2-fluorobenzoate (compound in Production Example 385), 1.02 g 1-trityl-1H-4-pyrazolylboronic acid, 0.34 g potassium fluoride, 43 mg palladium (II) acetate, 0.11 g 2-(di-t-butylphosphino)biphenyl, 20 mL N,N-dimethylformamide and 2 mL water were heated at 70° C. for 24 hours under nitrogen atmosphere. Water was added thereto, the reaction solution was filtered, and crystals collected by filtration were washed with water. The crystals were dissolved in dichloromethane, washed with water and dried over sodium sulfate. The solvent was evaporated, and the residue was purified by NH silica gel column chromatography (hexane/ethyl acetate), to give 0.82 g of the title compound (pale yellow crystals).

$^1$H-NMR (CDCl$_3$)

δ: 1.47(t, J=7.2 Hz, 3H), 4.48 (q, J=7.2 Hz, 2H), 7.14–7.24(m, 6H), 7.29–7.37(m, 9H), 7.56–7.64(m, 2H), 7.70(s, 1H), 7.96–8.02(m, 3H), 8.07–8.15(m, 2H), 9.33(s, 1H)

Example 753

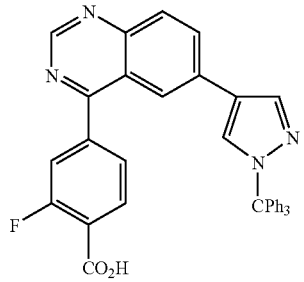

2-Fluoro-4-[6-(1-trityl-1H-pyrazol-4-yl)-quinazolin-4-yl]benzoic acid 0.82 g ethyl 2-fluoro-4-[6-(1-trityl-1H-pyrazol-4-yl)-quinazolin-4-yl]benzoate (compound in Example 752) was dissolved in 30 mL solvent mixture of ethanol and water (2:1), then 0.11 g lithium hydroxide was added thereto, and the mixture was heated for 5 hours under reflux. The reaction solution was neutralized under ice-cooling. The solution was extracted with dichloromethane and recrystallized from ethanol/ether, to give 570 mg of the title compound as pale yellow crystals.

$^1$H-NMR (DMSO-d$_6$)

δ: 7.11–7.17(m, 6H), 7.33–7.42(m, 9H), 7.62–7.66(m, 2H), 7.88–7.95(m, 1H), 7.96(s, 1H), 8.05(d, J=8.8 Hz, 1H), 8.09(d, J=1.8 Hz, 1H), 9.20(s, 1H), 8.29(dd, J=8.8, 1.8 Hz, 1H), 9.30(s, 1H)

Example 754

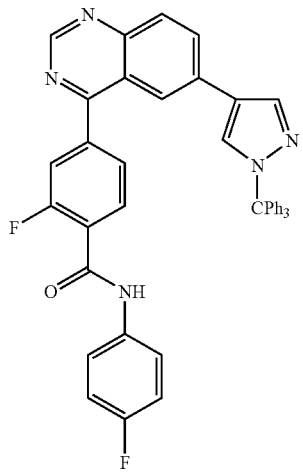

2-Fluoro-N-(4-fluorophenyl)-4-[6-(1-trityl-1H-pyrazol-4-yl)quinazolin-4-yl]benzamide 62 mg of the title compound was obtained by the same method as in Production Example 387 from 100 mg 2-fluoro-4-[6-(1-trityl-1H-pyrazol-4-yl)-quinazolin-4-yl]benzoic acid (compound in Example 753) and 19 mg 4-fluorophenylamine.

$^1$H-NMR (CDCl$_3$)

δ: 7.08–7.15(m, 2H), 7.15–7.23(m, 6H), 7.32–7.38(m, 9H), 7.65–7.72(m, 4H), 7.74(dd, J=8.0, 1.6 Hz, 1H), 7.97(d, J=0.8 Hz, 1H), 8.00(dd, J=8.8, 2.0 Hz, 1H), 8.01–8.05(m, 1H), 8.10(d, J=8.8 Hz, 1H), 8.37(t, J=8.0 Hz, 1H), 8.46–8.54 (m, 1H), 9.34(s, 1H)

Example 755

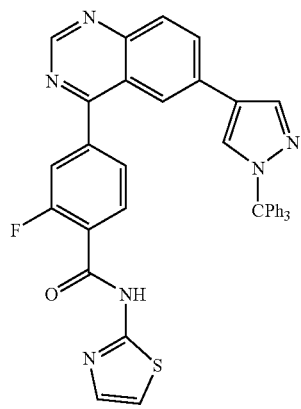

2-Fluoro-N-thiazol-2-yl-4-[6-(1-trityl-1H-pyrazol-4-yl)quinazolin-4-yl] benzamide 42 mg of the title compound was obtained by the same method as in Production Example 387 from 100 mg 2-fluoro-4-[6-(1-trityl-1H-pyrazol-4-yl)-quinazolin-4-yl]benzoic acid (compound in Example 753) and 17.4 mg 2-aminothiazole (in post-treatment, the reaction solution was diluted with ethyl acetate, and precipitated crystals were filtered.).

$^1$H-NMR (DMSO-d$_6$)

δ: 7.10–7.17(m, 6H), 7.31–7.42(m, 10H), 7.58(d, J=4.0 Hz, 1H), 7.76–7.86(m, 2H), 7.96(t, J=7.6 Hz, 1H), 8.00(s, 1H), 8.08(d, J=9.0 Hz, 1H), 8.10(d, J=2.0 Hz, 1H), 8.18(s, 1H), 8.31(dd, J=9.0, 2.0 Hz, 1H), 9.34(s, 1H)

Example 756

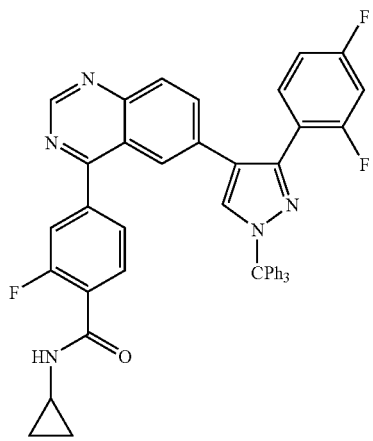

N-Cyclopropyl-4-{6-[3-(2,4-difluorophenyl)-1-trityl-1H-pyrazol-4-yl]quinazolin-4-yl}-2-fluorobenzamide 19 mg of the title compound was obtained by the same reaction as in Example 752 from 0.1 g 4-(6-chloroquinazolin-4-yl) N-cyclopropyl-2-fluorobenzamide (compound in Production Example 387) and 0.36 g 3-(2,4-difluorophenyl)-1-trityl-1H-4-pyrazolylboronic acid (compound in Production Example 172).

$^1$H-NMR (CDCl$_3$)

δ: 1.20–1.30(m, 4H), 2.97–3.05(m, 1H), 6.66–6.74(m, 1H), 6.84–6.93(m, 2H), 7.19–7.28(m, 6H), 7.30–7.40(m, 11H), 7.62(s, 1H), 7.67(d, J=2.0 Hz, 1H), 7.83(d, J=8.8, 2.0 Hz, 1H), 8.03(d, J=8.8 Hz, 1H), 8.12(t, J=8.0 Hz, 1H), 9.30(s, 1H)

Example 757

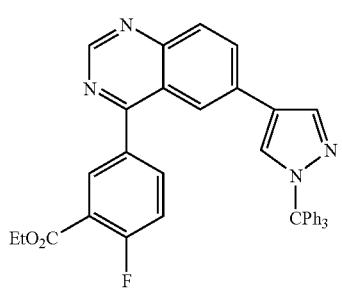

Ethyl 2-fluoro-5-[6-(1-trityl-1H-pyrazol-4-yl)-quinazolin-4-yl]benzoate 1.02 g of the title compound was obtained as a colorless amorphous by the same reaction as in Example 752 from 0.9 g ethyl 5-(6-chloroquinazolin-4-yl)-2-fluorobenzoate (compound in Production Example 388) and 1.45 g 1-trityl-1H-4-pyrazolylboronic acid.

$^1$H-NMR (CDCl$_3$)

δ: 1.47(t, J=7.2 Hz, 3H), 4.48 (q, J=7.2 Hz, 2H), 7.16–7.24(m, 6H), 7.30–7.38(m, 10H), 7.72(d, J=0.8 Hz, 1H), 7.95–7.80(m, 3H), 8.05 (d, J=1.6 Hz, 1H), 8.07(d, J=8.8 Hz, 1H), 8.42(dd, J=6.8, 1.6 Hz, 1H), 9.31(s, 1H)

Example 758

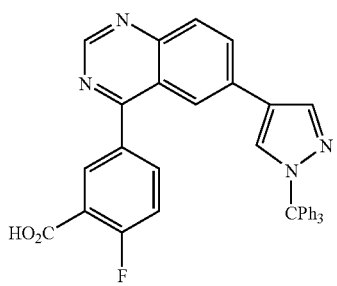

2-Fluoro-5-[6-(1-trityl-1H-pyrazol-4-yl)-quinazolin-4-yl]benzoic acid 0.69 g of the title compound was obtained as colorless crystals by the same reaction as in Production Example 310 from 0.94 g ethyl 2-fluoro-5-[6-(1-trityl-1H-pyrazol-4-yl)-quinazolin-4-yl]benzoate (compound in Production Example 757)

$^1$H-NMR (DMSO-d$_6$)

δ: 7.10–7.16(m, 6H), 7.33–7.42(m, 9H), 7.51–7.58(m, 1H), 7.99(s, 1H), 8.06(d, J=8.8 Hz, 1H), 8.11(d, J=2.0 Hz, 1H), 8.09–8.15(m, 1H), 8.19(s, 1H), 8.28–8.33(m, 2H), 9.29(s, 1H)

Example 759

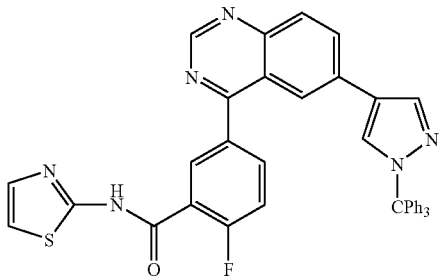

2-Fluoro-N-thiazol-2-yl-5-[6-(1-trityl-1H-pyrazol-4-yl)quinazolin-4-yl] benzamide 48 mg of the title compound was obtained by the same method as in Production Example 387 from 100 mg 2-fluoro-5-[6-(1-trityl-1H-pyrazol-4-yl)-quinazolin-4-yl]benzoic acid (compound in Production Example 758) and 17.4 mg 2-aminothiazole.

$^1$H-NMR (CDCl$_3$)

δ: 7.08(d, J=3.6 Hz, 1H), 7.16–7.22(m, 6H), 7.28–7.34(m, 9H), 7.47(dd, J=11.4, 8.6 Hz, 1H), 7.56(d, J=3.6 Hz, 1H), 7.72(d, J=0.8 Hz, 1H), 7.99(d, J=0.8 Hz, 1H), 7.98–8.11(m, 4H), 8.68(dd, J=7.2, 2.4 Hz, 1H), 9.32(s, 1H)

Example 760

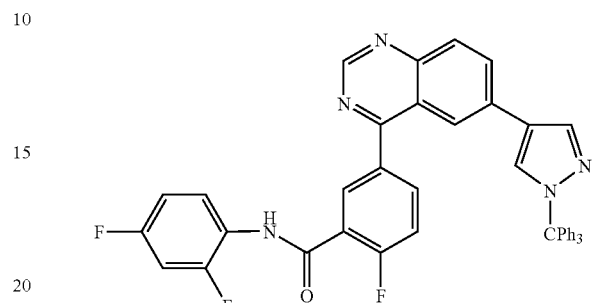

N-(2,4-Difluorophenyl)-2-fluoro-5-[6-(1-trityl-1H-pyrazol-4-yl)quinazolin-4-yl] benzamide 68 mg of the title compound was obtained by the same reaction as in Example 752 from 72 mg 5-(6-chloroquinazolin-4-yl)-N-(2,4-difluorophenyl)-2-fluoro-benzamide (compound in Production Example 393) and 93 mg 1-trityl-1H-4-pyrazolylboronic acid.

$^1$H-NMR (CDCl$_3$)

δ: 6.92–7.00(m, 2H), 7.16–7.22(m, 6H), 7.28–7.34(m, 9H), 7.44 (dd, J=11.6, 8.4 Hz, 1H), 7.73(d, J=0.8 Hz, 1H), 7.99(dd, J=8.6, 2.0 Hz, 1H), 7.99(d, J=0.8 Hz, 1H), 8.01–8.06(m, 1H), 8.07(d, J=2.0 Hz, 1H), 8.08(d, J=8.6 Hz, 1H), 8.42–8.50(m, 1H), 8.65(dd, J=7.4, 2.2 Hz, 1H), 8.70–8.78(m, 1H), 9.32(s, 1H)

Example 761

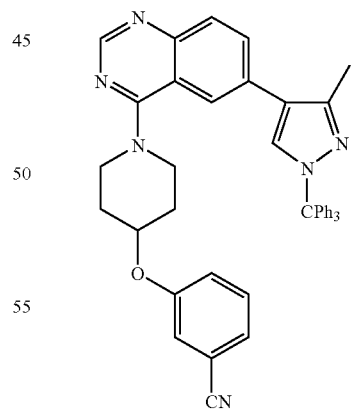

3-{1-[6-(3-Methyl-1-trityl-1H-pyrazol-4-yl)quinazolin-4-yl]piperazine-4-yloxy} benzonitrile 93 mg of the title compound was obtained by the same reaction as in Example 9 from 81 mg 3-[1-(6-bromoquinazolin-4-yl)piperidin-4-yloxy]benzonitrile (compound in Production Example 394) and 92 mg 3-methyl-1-trityl-1H-4-pyrazolylboronic acid (compound in Production Example 30).

¹H-NMR (CDCl₃)

δ: 1.90–2.07(m, 2H), 2.15–2.24(m. 2H), 2.52(s, 3H), 3.65–3.72(m, 2H), 3.97–4.03(m, 2H), 4.64–4.69(m, 1H), 7.18–7.36(m, 18H), 7.39–7.43(m, 1H), 7.49(s, 1H), 7.73(dd, J=8.8, 2.1 Hz, 1H), 7.85 (d, J=2.1 Hz, 1H), 7.86(d, J=8.8 Hz, 1H), 8.72(s, 1H)

Example 762

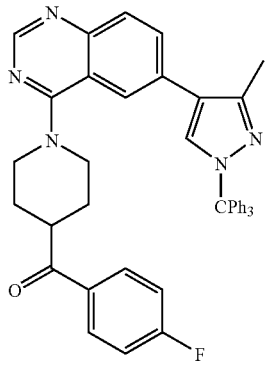

(4-Fluorophenyl)-{1-[6-(3-methyl-1-trityl-1H-pyrazol-4-yl)quinazolin-4-yl]piperidin-4-yl}methanone 74 mg of the title compound was obtained by the same reaction as in Example 9 from 53 mg [1-(6-bromoquinazolin-4-yl)piperidin-4-yl]-(4-fluorophenyl) methanone (compound in Production Example 395) and 61 mg 3-methyl-1-trityl-1H-4-pyrazolylboronic acid (compound in Production Example 30).

¹H-NMR (CDCl₃)

δ: 2.02–2.11(m, 4H), 2.51(s, 3H), 3.23–3.31(m, 2H), 3.55–3.63(m, 1H), 4.35–4.40(m, 2H), 7.18–7.25(m, 8H), 7.29–7.36(m, 9H), 7.48 (s, 1H), 7.73(dd, J=8.8, 2.0 Hz, 1H), 7.83–7.87(m, 2H) 8.03–8.08(m, 2H), 8.72(s, 1H)

Example 763

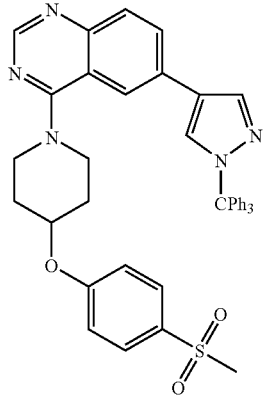

4-[4-(4-Methylsulfonylphenoxy)piperidin-1-yl]-6-(1-trityl-1H-pyrazol-4-yl) quinazoline 102 mg of the title compound was obtained by the same reaction as in Example 9 from 80 mg 6-bromo-4-[4-(4-methylsulfonylphenoxy)piperidin-1-yl] quinazoline (compound in Production Example 397) and 80 mg 1-trityl-1H-4-pyrazolylboronic acid.

¹H-NMR (CDCl₃)

δ: 1.98–2.07(m, 2H), 2.16–2.26(m, 2H), 3.06(s, 3H), 3.65–3.74(m, 2H), 3.97–4.06(m, 2H), 4.74–4.80(m, 1H), 7.07–7.11(m, 2H), 7.19–7.24(m, 6H), 7.31–7.37(m, 9H), 7.70(d, J=1.0 Hz, 1H), 7.79 (dd, J=8.8, 1.7 Hz, 1H), 7.86(d, J=8.8 Hz, 1H), 7.88(d, J=1.7 Hz, 1H), 7.89–7.93(m, 2H), 8.01(d, J=1.0 Hz, 1H), 8.71(s, 1H)

Example 764

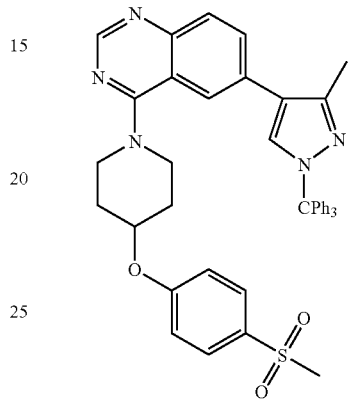

4-[4-(4-Methylsulfonylphenoxy)piperidin-1-yl]-6-(3-methyl-1-trityl-1H-pyrazol-4-yl) quinazoline 126 mg of the title compound was obtained by the same reaction as in Example 9 from 80 mg 6-bromo-4-[4-(4-methylsulfonylphenoxy)piperidin-1-yl] quinazoline (compound in Production Example 397) and 83 mg 3-methyl-1-trityl-1H-4-pyrazolylboronic acid (compound in Production Example 30).

¹H-NMR (CDCl₃)

δ: 1.98–2.10(m, 2H), 2.18–2.27(m, 2H), 2.52(s, 3H), 3.05(s, 3H), 3.66–3.74(m, 2H), 3.97–4.04(m, 2H), 4.74–4.80(m, 1H), 7.07–7.11(m, 2H), 7.20–7.25(m, 6H), 7.31–7.36(m, 9H), 7.49(s, 1H), 7.73(dd, J=8.6, 2.2 Hz, 1H), 7.85(d, J=2.2 Hz, 1H), 7.87(d, J=8.6 Hz, 1H), 7.89–7.93(m, 2H), 8.73(s, 1H)

Example 765

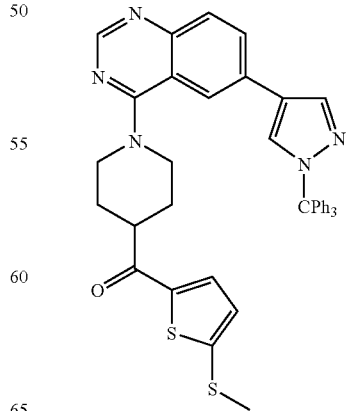

681

(5-Methylsulfanylthiophen-2-yl)-{1-[6-(1-trityl-1H-pyrazol-4-yl)quinazolin-4-yl]piperidin-4-yl} methanone 159 mg of the title compound was obtained as a colorless amorphous by the same reaction as in Example 9 from 100 mg [1-(6-bromoquinazolin-4-yl)piperidin-4-yl]-(5-methylsulfanylthiophen-2-yl)methanone (compound in Production Example 391) and 103 mg 1-trityl-1H-4-pyrazolylboronic acid.

¹H-NMR (CDCl₃)

δ: 1.97–2.13(m, 4H), 2.63(s, 3H), 3.19–3.27(m, 2H), 3.34–3.42(m, 1H), 4.32–4.40(m, 2H), 6.98(d, J=4.0 Hz, 1H), 7.19–7.24(m, 6H), 7.32–7.38(m, 9H), 7.65(d, J=4.0 Hz, 1H), 7.68(s, 1H), 7.81(dd, J=8.8, 1.8 Hz, 1H), 7.85(d, J=1.8 Hz, 1H), 7.85(d, J=8.8 Hz, 1H), 8.01(d, J=0.8 Hz, 1H), 8.69(s, 1H)

Example 766

(5-Methylsulfonylthiophen-2-yl)-{1-[6-(1-trityl-1H-pyrazol-4-yl)quinazolin-4-yl]piperidin-4-yl} methanone 87 mg of the title compound was obtained by the same reaction as in Production Example 43 from 159 mg (5-methylsulfanylthiophen-2-yl)-{1-[6-(1-trityl-1H-pyrazol-4-yl)quinazolin-4-yl]piperidin-4-yl} methanone (compound in Example 765) and 288 mg oxone.

¹H-NMR (CDCl₃)

δ: 2.03–2.13(m, 4H), 3.24(s, 3H), 3.23–3.30(m, 2H), 3.39–3.47(m, 1H), 4.32–4.40(m, 2H), 7.19–7.24(m, 6H), 7.32–7.38(m, 9H), 7.69 (d, J=0.6 Hz, 1H), 7.76(s, 2H), 7.81(dd, J=8.8, 1.6 Hz, 1H), 7.84–7.88(m, 2H), 8.01(d, J=0.6 Hz, 1H), 8.70(s, 1H)

682

Example 767

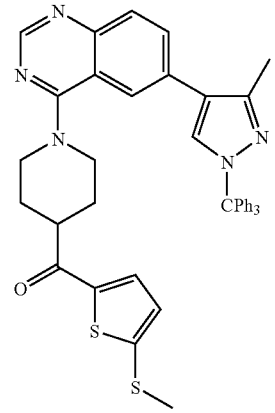

(5-Methylsulfanylthiophen-2-yl)-{1-[6-(3-methyl-1-trityl-1H-pyrazol-4-yl)quinazolin-4-yl]piperidin-4-yl} methanone 154 mg of the title compound was obtained as a colorless amorphous by the same reaction as in Example 9 from 100 mg [1-(6-bromoquinazolin-4-yl)piperidin-4-yl]-(5-methylsulfanylthiophen-2-yl) methanone (compound in Production Example 391) and 110 mg 3-methyl-1H-4-pyrazolylboronic acid (compound in Production Example 30).

¹H-NMR (CDCl₃)

δ: 1.97–2.15(m, 4H), 2.50(s, 3H), 2.63(s, 3H), 3.18–3.28 (m, 2H), 3.33–3.42(m, 1H), 4.34–4.41(m, 2H), 6.97(d, J=4.0 Hz, 1H), 7.19–7.24(m, 6H), 7.30–7.36(m, 9H), 7.47(s, 1H), 7.65(d, J=4.0 Hz, 1H), 7.73(dd, J=8.6, 1.8 Hz, 1H), 7.83(d, J=1.8 Hz, 1H), 7.85(d, J=8.6 Hz, 1H), 8.71(s, 1H)

Example 768

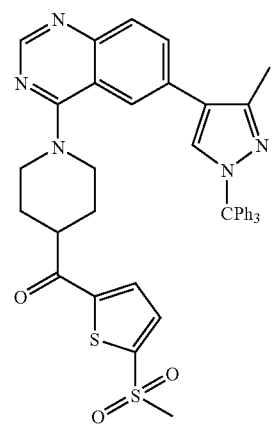

(5-Methylsulfonylthiophen-2-yl)-{1-[6-(3-methyl-1-trityl-1H-pyrazol-4-yl)quinazolin-4-yl]piperidin-4-yl} methanone 59 mg of the title compound was obtained by the same reaction as in Production Example 43 from 154 mg (5-methylsulfanylthiophen-2-yl)-{1-[6-(3-methyl-1-trityl-1H-pyrazol-4-yl)quinazolin-4-yl]piperidin-4-yl} methanone (compound in Example 767) and 270 mg oxone.

¹H-NMR (CDCl₃)

δ: 2.04–2.15(m, 4H), 2.51(s, 3H), 3.24(s, 3H), 3.24–3.30 (m, 2H), 3.38–3.47(m, 1H), 4.34–4.41(m, 2H), 7.20–7.24 (m, 6H), 7.30–7.36(m, 9H), 7.49(s, 1H), 7.73(dd, J=8.8, 1.9 Hz, 1H), 7.76(brs, 2H), 7.83(d, J=1.9 Hz, 1H), 7.86(d, J=8.8 Hz, 1H), 8.72(s, 1H)

Example 769

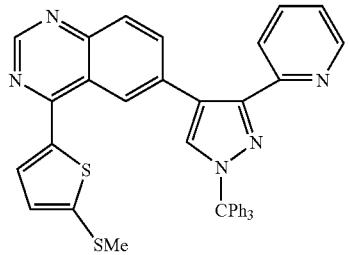

4-(5-Methylsulfanylthiophen-2-yl)-6-[3-(pyridin-2-yl)-1-trityl-1H-pyrazol-4-yl] quinazoline 224 mg of the title compound was obtained as a yellow amorphous by the same reaction as in Example 29 from 135 mg 6-bromo-4-(5-(methylsulfanyl)-2-thienyl] quinazoline (compound in Production Example 100) and 345 mg 3-(2-pyridyl)-1-trityl-1H-4-pyrazolylboronic acid (compound in Production Example 166).

¹H-NMR (CDCl₃)

δ: 2.60(s, 3H), 6.92(d, J=4.0 Hz, 1H), 7.20–7.40(m, 17H), 7.38(s, 1H), 7.23(ddd, J=7.6, 7.6, 1.6 Hz, 1H), 7.79(m, 1H), 7.89(dd, J=8.4, 2.0 Hz, 1H), 7.95(d, J=8.8 Hz, 1H), 8.49 (ddd, J=4.8, 1.6, 0.8 Hz, 1H), 8.53(d, J=5.6 Hz, 1H), 9.13(s, 1H)

Example 770

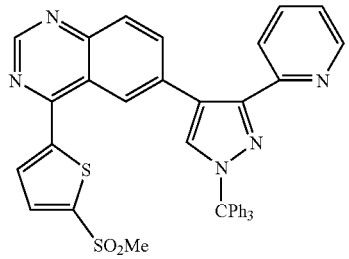

4-(5-Methylsulfonylthiophen-2-yl)-6-[3-(pyridin-2-yl)-1-trityl-1H-pyrazol-4-yl] quinazoline 204 mg of the title compound was obtained as a pale yellow amorphous by the same method as in Production Example 59 from 222 mg 4-(5-methylsulfanylthiophen-2-yl)-6-[3-(pyridin-2-yl)-1-trityl-1H-pyrazol-4-yl] quinazoline (compound in Example 769).

¹H-NMR (CDCl₃)

δ: 3.25(s, 3H), 7.25(m, 7H), 7.35(m, 9H), 7.48(d, J=4.0 Hz, 1H), 7.61(s, 1H), 7.62(d, J=4.0 Hz, 1H), 7.74(ddd, J=8.0, 7.6, 1.6 Hz, 1H), 7.81(m, 1H), 7.96(dd, J=8.8, 2.0 Hz, 1H), 8.03(d, J=8.8 Hz, 1H), 8.46(m, 2H), 9.23(s, 1H)

Example 771

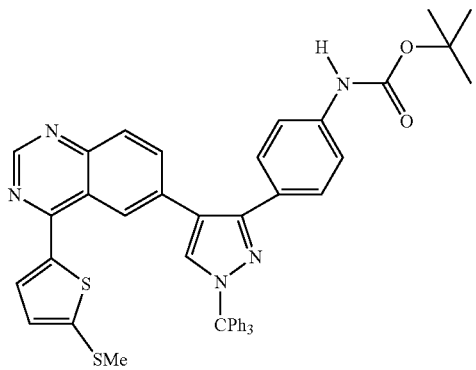

t-Butyl (4-{4-[4-(5-methylsulfanylthiophen-2-yl) quinazolin-6-yl]-1-trityl-1H-pyrazol-3-yl}phenyl) carbaminate 215 mg of the title compound was obtained as a yellow amorphous by the same reaction process as in Example 375 from 270 mg 6-bromo-4-[5-(methylsulfanyl)-2-thienyl] quinazoline (compound in Production Example 100) and 1.1 g mixture of methyl 4-[4-(4,4,5,5-tetramethyl-1,3,2-dioxaborolan-2-yl)-1-trityl-1H-3-pyrazolyl]benzoate and ethyl 4-[4-(4,4,5,5-tetramethyl-1,3,2-dioxaborolan-2-yl)-1-trityl-1H-3-pyrazolyl]benzoate.

¹H-NMR (CDCl₃)

δ: 1.52(s, 9H), 2.58(s, 3H), 6.54(brs, 1H), 6.79(d, J=4.0 Hz, 1H), 6.86(d, J=4.0 Hz, 1H), 7.22–7.40(m, 15H), 7.42(d, J=8.8 Hz, 2H), 7.53(s, 1H), 7.83(dd, J=8.8, 2.0 Hz, 1H), 7.96(d, J=8.8 Hz, 1H), 8.19(d, J=1.2 Hz, 1H), 9.11(s, 1H)

Example 772

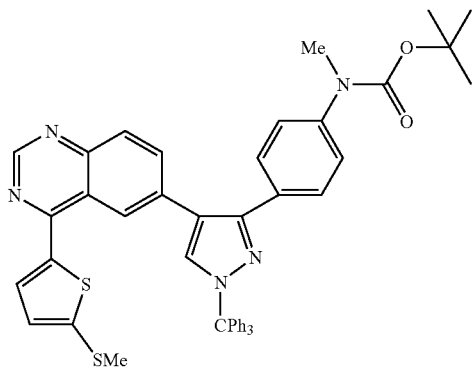

t-Butyl methyl(4-{4-[4-(5-methylsulfanylthiophen-2-yl)quinazolin-6-yl]-1-trityl-1H-pyrazol-3-yl}phenyl)-carbaminate 209 mg of the title compound was obtained as a pale brown amorphous by the same method as in Example 358 from 213 mg t-butyl (4-{4-[4-(5-methylsulfanylthiophen-2-yl)quinazolin-6-yl]-1-trityl-1H-pyrazol-3-yl}phenyl)carbaminate (compound in Example 771).

¹H-NMR (CDCl₃)

δ: 1.22(s, 9H), 2.60(s, 3H), 3.26(s, 3H), 6.90(m, 2H), 7.20–7.40(m, 17H), 7.46(d, J=8.4 Hz, 2H), 7.52(s, 1H), 7.84(dd, J=8.8, 2.0 Hz, 1H), 7.97(d, J=8.8 Hz, 1H), 8.24(d, J=2.0 Hz, 1H), 9.13(s, 1H)

Example 773

(4-{4-[4-(5-Methylsulfanylthiophen-2-yl)quinazolin-6-yl]-1-trityl-1H-pyrazol-3-yl}phenyl)methanol 126 mg of the title compound was obtained as a yellow solid by the same method as in Example 359 from 238 mg mixture of methyl 4-{4-[4-(5-methylsulfanylthiophen-2-yl)quinazolin-6-yl]-1-trityl-1H-pyrazol-3-yl}benzoate and ethyl 4-{4-[4-(5-methylsulfanylthiophen-2-yl)quinazolin-6-yl]-1-trityl-1H-pyrazol-3-yl}benzoate obtained in the synthesis process in Example 771.

¹H-NMR (CDCl₃)

δ: 2.60(s, 3H), 4.72(s, 2H), 6.81(d, J=4.0 Hz, 1H), 6.83(d, J=4.0 Hz, 1H), 7.25(m, 6H), 7.34(m, 11H), 7.50(d, J=8.0 Hz, 2H), 7.55(s, 1H), 7.84(dd, J=8.8, 2.0 Hz, 1H), 7.97(d, J=8.8 Hz, 1H), 8.20(d, J=1.6 Hz, 1H), 9.12(s, 1H)

Example 775

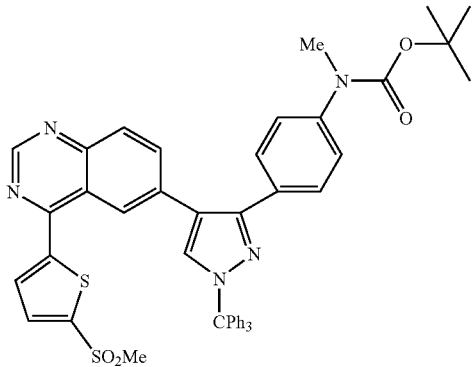

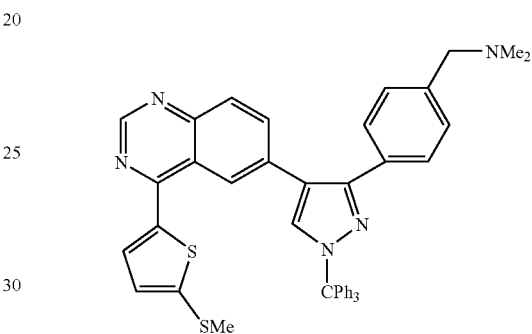

t-Butyl methyl(4-{4-[4-(5-methylsulfonylthiophen-2-yl)quinazolin-6-yl]-1-trityl-1H-pyrazol-3-yl}phenyl)-carbaminate 170 mg of the title compound was obtained as a yellow amorphous by the same method as in Production Example 59 from 207 mg t-butyl methyl(4-{4-[3-(5-methylsulfanylthiophen-2-yl)quinazolin-6-yl]-1-trityl-1H-pyrazol-3-yl}phenyl)-carbaminate (compound in Example 772).

¹H-NMR (CDCl₃)

δ: 1.45(s, 9H), 3.20(s, 3H), 3.27(s, 3H), 6.93(d, J=4.0 Hz, 1H), 7.22–7.40(m, 17H), 7.46(d, J=8.4 Hz, 2H), 7.54(s, 1H), 7.61(d, J=4.0 Hz, 1H), 7.92(dd, J=8.8, 2.0 Hz, 1H), 8.05(d, J=8.8 Hz, 1H), 8.15(d, J=1.2 Hz, 1H), 9.23(s, 1H)

Example 774

Dimethyl(4-{4-[4-(5-methylsulfanylthiophen-2-yl)quinazolin-6-yl]-1-trityl-1H-pyrazol-3-yl}benzyl)amine 94 mg of the title compound was obtained as a yellow amorphous by the same method as in Example 360 from 124 mg (4-{4-[4-(5-methylsulfanylthiophen-2-yl)quinazolin-6-yl]-1-trityl-1H-pyrazol-3-yl}phenyl)methanol (compound in Example 774).

¹H-NMR (CDCl₃)

δ: 2.24(s, 6H), 2.60(s, 3H), 3.25(s, 2H), 6.78(d, J=4.0 Hz, 1H), 6.81(d, J=4.0 Hz, 1H), 7.25(m, 8H), 7.34(m, 9H), 7.45(d, J=8.4 Hz, 2H), 7.53(s, 1H), 7.84(dd, J=8.4, 1.6 Hz, 1H), 7.97(s, 1H), 8.20(d, J=1.6 Hz, 1H), 9.12(s, 1H)

Example 776

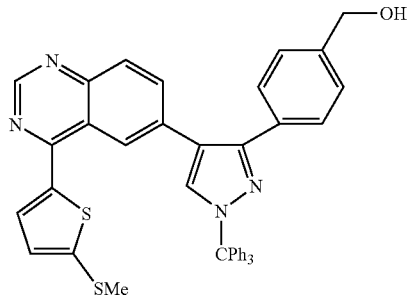

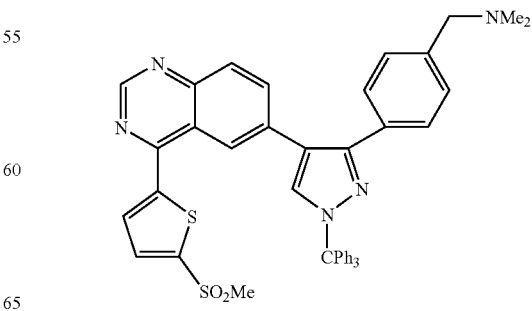

Dimethyl(4-{4-[4-(5-methylsulfonylthiophen-2-yl)quinazolin-6-yl]-1-trityl-1H-pyrazol-3-yl}benzyl)amine 77 mg of the title compound was obtained as a yellow amorphous by the same method as in Production Example 59 from 92 mg dimethyl(4-{4-[4-(5-methylsulfanylthiophen-2-yl)quinazolin-6-yl]-1-trityl-1H-pyrazol-3-yl)benzyl)amine (compound in Example 775).

$^1$H-NMR (CDCl$_3$)

δ: 2.23(s, 6H), 3.22(s, 3H), 3.45(s, 2H), 6.85(d, J=4.0 Hz, 1H), 7.26(m, 6H), 7.31(d, J=8.4 Hz, 2H), 7.34(m, 9H), 7.44(d, J=8.0 Hz, 2H), 7.49(d, J=4.0 Hz, 1H), 7.57(s, 1H), 7.92(dd, J=8.8, 1.6 Hz, 1H), 8.05(d, J=8.4 Hz, 1H), 8.13(d, J=2.0 Hz, 1H), 9.22(s, 1H)

Example 777

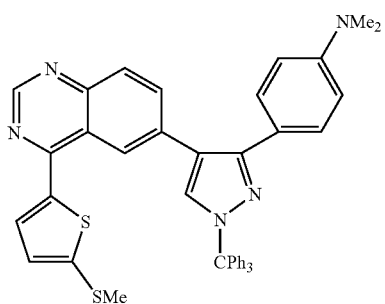

Dimethyl(4-{4-[4-(5-methylsulfanylthiophen-2-yl)quinazolin-6-yl]-1-trityl-1H-pyrazol-3-yl}phenyl)amine 147 mg of the title compound was obtained as a yellow solid by the same reaction as in Example 29 from 135 mg 6-bromo-4-[5-(methylsulfanyl)-2-thienyl] quinazoline (compound in Production Example 100) and 379 mg 3-(4-dimethylaminophenyl)-1-trityl-1H-4-pyrazolylboronic acid (compound in Production Example 169).

$^1$H-NMR (CDCl$_3$)

δ: 2.60(s, 3H), 2.96(s, 6H), 6.71(d, J=8.8 Hz, 2H), 6.74(d, J=4.0 Hz, 1H), 6.85(d, J=4.0 Hz, 1H), 7.25(m, 6H), 7.33(m, 9H), 7.36(d, J=8.8 Hz, 2H), 7.51(s, 1H), 7.86(dd, J=8.8, 2.0 Hz, 1H), 7.95(d, J=8.8 Hz, 1H), 8.26(d, J=1.6 Hz, 1H), 9.11(s, 1H)

Example 778

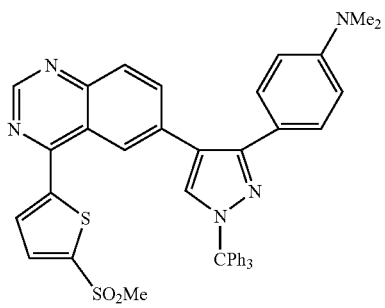

Dimethyl(4-{4-[4-(5-methylsulfonylthiophen-2-yl)quinazolin-6-yl]-1-trityl-1H-pyrazol-3-yl}phenyl)amine 113 mg of the title compound was obtained as a yellowish brown amorphous by the same method as in Production Example 59 from 145 mg dimethyl(4-{4-[4-(5-methylsulfanylthiophen-2-yl)quinazolin-6-yl]-1-trityl-1H-pyrazol-3-yl}phenyl)amine (compound in Example 777).

$^1$H-NMR (CDCl$_3$)

δ: 2.98(s, 6H), 3.22(s, 3H), 6.72(d, J=8.8 Hz, 2H), 6.87(d, J=4.0 Hz, 1H), 7.25(m, 6H), 7.34(m, 11H), 7.42(d, J=4.0 Hz, 1H), 7.55(s, 1H), 7.93(dd, J=8.4, 2.0 Hz, 1H), 8.03(d, J=8.8 Hz, 1H), 8.20(d, J=1.6 Hz, 1H), 9.20(s, 1H)

Example 779

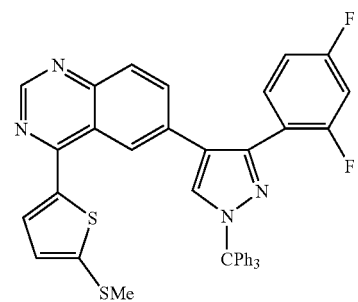

6-[3-(2,4-Difluorophenyl)-1-trityl-1H-pyrazol-4-yl]-4-(5-methylsulfanylthiophen-2-yl)quinazoline 196 mg of the title compound was obtained as yellow crystals by the same reaction as in Example 29 from 169 mg 6-bromo-4-[5-(methylsulfanyl)-2-thienyl] quinazoline (compound in Production Example 100) and 580 mg 3-(2,4-difluorophenyl)-1-trityl-1H-4-pyrazolylboronic acid (compound in Production Example 172).

$^1$H-NMR (CDCl$_3$)

δ: 2.62(s, 3H), 6.82(d, J=4.0 Hz, 1H), 6.83(m, 1H), 6.87(d, J=4.0 Hz, 1H), 6.98(m, 1H), 7.23(m, 6H), 7.35(m, 9H), 7.49(m, 1H), 7.65(s, 1H), 7.80(dd, J=8.8, 2.0 Hz, 1H), 7.96(d, J=8.8 Hz, 1H), 8.12(d, J=1.6 Hz, 1H), 9.12(s, 1H)

Example 780

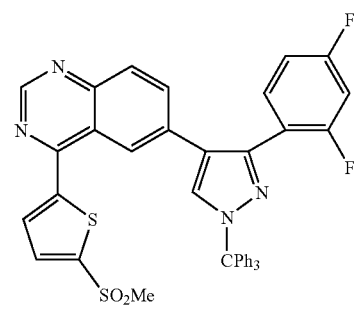

6-[3-(2,4-Difluorophenyl)-1-trityl-1H-pyrazol-4-yl]-4-(5-methylsulfonylthiophen-2-yl) quinazoline 203 mg of the title compound was obtained as a pale yellow amorphous by the same method as in Production Example 59 from 194 mg 6-[3-(2,4-difluorophenyl)-1-trityl-1H-pyrazol-4-yl]-4-(5-methylsulfanylthiophen-2-yl) quinazoline (compound in Example 779).

$^1$H-NMR (CDCl$_3$)

δ: 3.25(s, 3H), 6.83(m, 1H), 6.93(d, J=4.0 Hz, 1H), 7.02(m, 1H), 7.24(m, 6H), 7.35(m, 9H), 7.50(m, 1H), 7.57(d, J=4.0 Hz, 1H), 7.67(s, 1H), 7.88(dd, J=8.8, 1.6 Hz, 1H), 8.04(m, 2H), 9.23(s, 1H)

Example 781

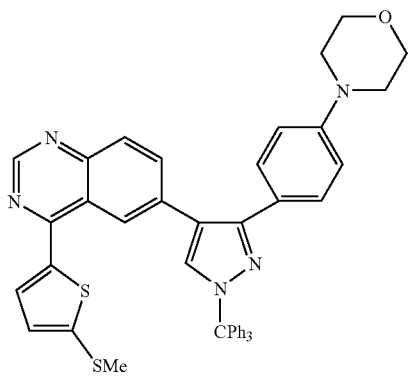

4-(5-Methylsulfanylthiophen-2-yl)-6-[3-(4-morpholin-4-ylphenyl)-1-trityl-1H-pyrazol-4-yl] quinazoline 160 mg of the title compound was obtained as a pale yellow amorphous by the same reaction as in Example 29 from 101 mg 6-bromo-4-[5-(methylsulfanyl)-2-thienyl] quinazoline (compound in Production Example 100) and 312 mg 3-[4-(morpholin-4-yl)phenyl]-1-trityl-1H-4-pyrazolylboronic acid (compound in Production Example 170).

$^1$H-NMR (CDCl$_3$)

δ: 2.60(s, 3H), 3.16(t, J=4.4 Hz, 4H), 3.87(t, J=4.4 Hz, 4H), 6.83(d, J=4.0 Hz, 1H), 6.84(d, J=4.0 Hz, 1H), 6.89(d, J=8.8 Hz, 2H), 7.26(m, 6H), 7.32(m, 9H), 7.41(d, J=8.8 Hz, 2H), 7.52(s, 1H), 7.85(dd, J=8.8, 1.6 Hz, 1H), 7.96(d, J=8.8 Hz, 1H), 8.24(d, J=1.6 Hz, 1H), 9.11(s, 1H)

Example 782

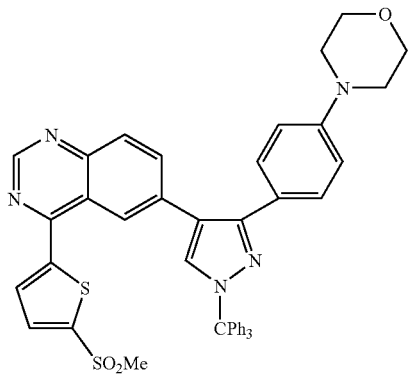

4-(5-Methylsulfonylthiophen-2-yl)-6-[3-(4-morpholin-4-ylphenyl)-1-trityl-1H-pyrazol-4-yl] quinazoline 133 mg of the title compound was obtained as yellow crystals by the same method as in Production Example 59 from 158 mg 4-(5-methylsulfanylthiophen-2-yl)-6-[3-(4-morpholin-4-ylphenyl)-1-trityl-1H-pyrazol-4-yl] quinazoline (compound in Example 781).

$^1$H-NMR (CDCl$_3$)

δ: 3.18(t, J=4.4 Hz, 4H), 3.23(s, 3H), 3.88(t, J=4.4 Hz, 4H), 6.88(d, J=4.0 Hz, 1H), 6.91(d, J=8.8 Hz, 2H), 7.26(m, 6H), 7.34(m, 9H), 7.39(d, J=8.8 Hz, 2H), 7.55(d, J=4.0 Hz, 1H), 7.56(s, 1H), 7.92(dd, J=8.8, 2.0 Hz, 1H), 8.03(d, J=8.8 Hz, 1H), 8.16(d, J=2.0 Hz, 1H), 9.21(s, 1H)

Example 783

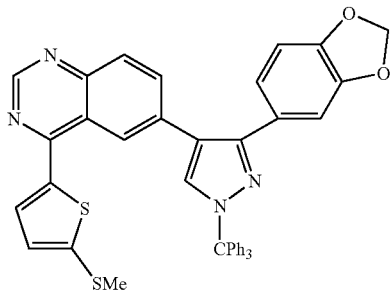

6-(3-Benzo[1,3]dioxol-5-yl-1-trityl-1H-pyrazol-4-yl)-4-(5-methylsulfanylthiophen-2-yl) quinazoline 70 mg of the title compound was obtained as a pale yellow amorphous by the same reaction as in Example 29 from 135 mg 6-bromo-4-[5-(methylsulfanyl)-2-thienyl] quinazoline (compound in Production Example 100) and 474 mg 3-benzo[1,3]-dioxol-5-yl-1-trityl-1H-4-pyrazolylboronic acid.

$^1$H-NMR (CDCl$_3$)

δ: 2.61(s, 3H), 5.95(s, 2H), 6.81(d, J=8.4 Hz, 1H), 6.89(d, J=4.0 Hz, 1H), 6.98(m, 2H), 7.25(m, 6H), 7.34(m, 9H), 7.54(s, 1H), 7.83(dd, J=8.8, 2.0 Hz, 1H), 7.97(d, J=8.8 Hz, 2H), 8.25(d, J=1.6 Hz, 1H), 9.13(s, 1H)

Example 784

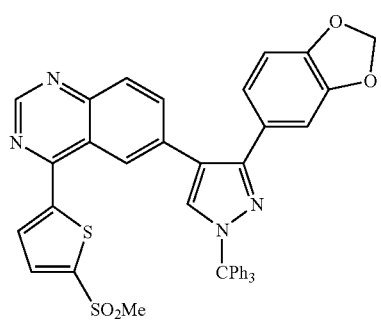

6-(3-Benzo[1,3]dioxol-5-yl-1-trityl-1H-pyrazol-4-yl)-4-(5-methylsulfonylthiophen-2-yl) quinazoline 48 mg of the title compound was obtained as yellow crystals by the same method as in Production Example 59 from 68 mg 6-(3-benzo[1,3]dioxol-5-yl-1-trityl-1H-pyrazol-4-yl)-4-(5-methylsulfanylthiophen-2-yl) quinazoline (compound in Example 783).

$^1$H-NMR (CDCl$_3$)

δ: 3.25(s, 3H), 5.98(s, 2H), 6.81(d, J=8.4 Hz, 1H), 6.98(m, 2H), 7.07(d, J=4.0 Hz, 1H), 7.25(m, 6H), 7.35(m, 9H), 7.57(s, 1H), 7.60(d, J=4.0 Hz, 1H), 7.91(dd, J=8.8, 2.0 Hz, 1H), 8.04(d, J=8.8 Hz, 1H), 8.17(d, J=1.6 Hz, 1H), 9.23(s, 1H)

Example 785

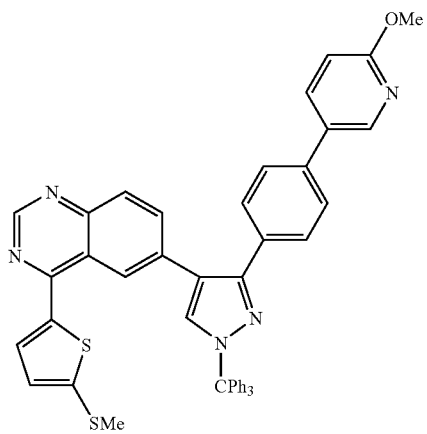

6-{3-[4-(6-Methoxypyridin-3-yl)phenyl]-1-trityl-1H-pyrazol-4-yl}-4-(5-methylsulfanylthiophen-2-yl) quinazoline 175 mg of the title compound was obtained as a pale yellow amorphous by the same reaction as in Example 29 from 101 mg 6-bromo-4-[5-(methylsulfanyl)-2-thienyl] quinazoline (compound in Production Example 100) and 326 mg 3-[4-(6-methoxypyridin-3-yl)phenyl]-1-trityl-1H-4-pyrazolylboronic acid (compound in Production Example 173).

$^1$H-NMR (CDCl$_3$)

δ: 2.52(s, 3H), 3.98(s, 3H), 6.61(d, J=4.0 Hz, 1H), 6.82 (dd, J=8.8, 0.8 Hz, 1H), 6.86(d, J=4.0 Hz, 1H), 7.27(m, 6H), 7.35(m, 9H), 7.53(d, J=8.4 Hz, 2H), 7.57(s, 1H), 7.60(d, J=8.4 Hz, 2H), 7.77(dd, J=8.8, 2.4 Hz, 1H), 7.88(dd, J=8.8, 2.0 Hz, 1H), 7.99(d, J=8.4 Hz, 1H), 8.25(d, J=1.6 Hz, 1H), 8.39(dd, J=2.4, 0.8 Hz, 1H), 9.13(s, 1H)

Example 786

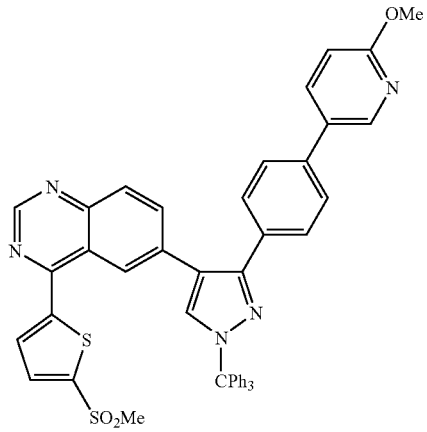

6-{3-[4-(6-Methoxypyridin-3-yl)phenyl]-1-trityl-1H-pyrazol-4-yl}-4-(5-methylsulfonylthiophen-2-yl) quinazoline 159 mg of the title compound was obtained as a pale yellow amorphous by the same method as in Production Example 59 from 173 mg 6-[3-[4-(6-methoxypyridin-3-yl)phenyl]-1-trityl-1H-pyrazol-4-yl}-4-(5-methylsulfanylthiophen-2-yl) quinazoline (compound in Example 785).

$^1$H-NMR (CDCl$_3$)

δ: 3.15(s, 3H), 3.97(s, 3H), 6.84(dd, J=8.8, 0.8 Hz, 1H), 6.92(d, J=4.0 Hz, 1H), 7.27(m, 6H), 7.34(d, J=4.0 Hz, 1H), 7.36(m, 9H), 7.57(m, 5H), 7.79(dd, J=8.8, 2.8 Hz, 1H), 7.95(dd, J=8.8, 2.0 Hz, 1H), 8.08(d, J=8.8 Hz, 1H), 8.17(d, J=1.6 Hz, 1H), 8.37(dd, J=2.8, 0.8 Hz, 1H), 9.24(s, 1H)

Example 787

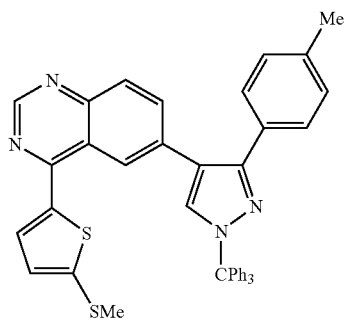

4-(5-Methylsulfanylthiophen-2-yl)-6-(3-p-tolyl-1-trityl-1H-pyrazol-4-yl) quinazoline 260 mg of the title compound was obtained as a yellow amorphous by the same reaction as in Example 29 from 169 mg 6-bromo-4-[5-(methylsulfanyl)-2-thienyl]quinazoline (compound in Production Example 100) and 555 mg 3-p-tolyl-1-trityl-1H-4-pyrazolylboronic acid (compound in Production Example 176).

¹H-NMR (CDCl₃)

δ: 2.38(s, 3H), 2.60(s, 3H), 6.71(d, J=4.0 Hz, 1H), 6.75(d, J=4.0 Hz, 1H), 7.18(dd, J=8.4, 0.4 Hz, 2H), 7.26(m, 6H), 7.35(m, 9H), 7.39(d, J=8.0 Hz, 2H), 7.54(s, 1H), 7.85(dd, J=8.8, 2.0 Hz, 1H), 7.96(d, J=8.8 Hz, 1H), 8.18(d, J=1.6 Hz, 1H), 9.12(s, 1H)

Example 788

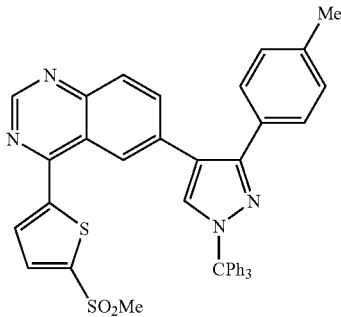

4-(5-Methylsulfonylthiophen-2-yl)-6-(3-p-tolyl-1-trityl-1H-pyrazol-4-yl) quinazoline 250 mg of the title compound was obtained as a pale yellow amorphous by the same method as in Production Example 59 from 258 mg 4-(5-methylsulfanylthiophen-2-yl)-6-(3-p-tolyl-1-trityl-1H-pyrazol-4-yl) quinazoline (compound in Example 787).

¹H-NMR (CDCl₃)

δ: 2.40(s, 3H), 3.20(s, 3H), 6.75(d, J=4.0 Hz, 1H), 7.20(d, J=8.0 Hz, 2H), 7.26(m, 6H), 7.35(m, 9H), 7.38(d, J=8.0 Hz, 2H), 7.44(d, J=4.0 Hz, 1H), 7.57(s, 1H), 7.92(dd, J=8.8, 2.0 Hz, 1H), 8.05(d, J=8.8 Hz, 1H), 8.11(d, J=1.6 Hz, 1H), 9.22(s, 1H)

Example 789

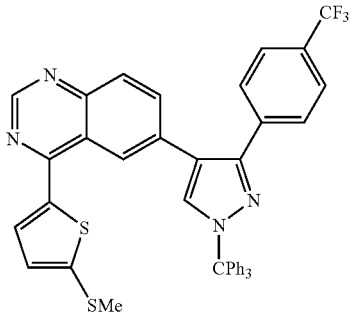

4-(5-Methylsulfanylthiophen-2-yl)-6-[3-(4-trifluoromethylphenyl)-1-trityl-1H-pyrazol-4-yl] quinazoline 287 mg of the title compound was obtained as a yellow amorphous by the same reaction as in Example 29 from 169 mg 6-bromo-4-[5-(methylsulfanyl)-2-thienyl]quinazoline (compound in Production Example 100) and 747 mg 3-(4-trifluoromethylphenyl)-1-trityl-1H-4-pyrazolylboronic acid (compound in Production Example 177).

¹H-NMR (CDCl₃)

δ: 2.58(s, 3H), 6.77(d, J=3.6 Hz, 1H), 6.79(d, J=4.0 Hz, 1H), 7.26(m, 6H), 7.35(m, 9H), 7.57(s, 1H), 7.64(m, 4H), 7.84(dd, J=8.8, 2.0 Hz, 1H), 8.00(d, J=8.8 Hz, 1H), 8.16(d, J=1.6 Hz, 1H), 9.14(s, 1H)

Example 790

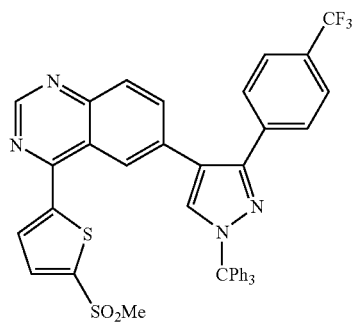

4-(5-Methylsulfonylthiophen-2-yl)-6-[3-(4-trifluoromethylphenyl)-1-trityl-1H-pyrazol-4-yl] quinazoline 262 mg of the title compound was obtained as a pale yellow solid by the same method as in Production Example 59 from 285 mg 4-(5-methylsulfanylthiophen-2-yl)-6-[3-(4-trifluoromethoxyphenyl)-1-trityl-1H-pyrazol-4-yl] quinazoline (compound in Example 789).

¹H-NMR (CDCl₃)

δ: 3.23(s, 3H), 6.87(d, J=4.0 Hz, 1H), 7.25(m, 6H), 7.36(m, 9H), 7.48(d, J=4.0 Hz, 1H), 7.59(s, 1H), 7.64(m, 4H), 7.92(dd, J=8.8, 2.0 Hz, 1H), 8.09(m, 2H), 9.25(s, 1H)

Example 791

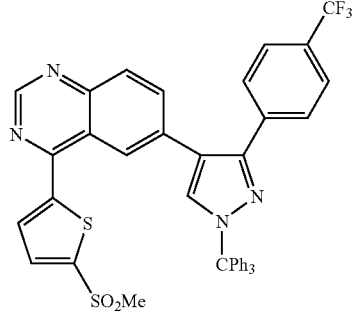

4-(5-Methylsulfanylthiophen-2-yl)-6-[3-(4-trifluoromethoxyphenyl)-1-trityl-1H-pyrazol-4-yl] quinazoline 280 mg of the title compound was obtained as a yellow amorphous by the same reaction as in Example 29 from 169 mg 6-bromo-4-[5-(methylsulfanyl)-2-thienyl]quinazoline (compound in Production Example 100) and 643 mg 3-(4- trifluoromethoxylphenyl)-1-trityl-1H-4-pyrazolylboronic acid (compound in Production Example 178).

¹H-NMR (CDCl₃)
δ: 2.60(s, 3H), 6.83(d, J=4.0 Hz, 1H), 6.87(d, J=4.0 Hz, 1H), 7.20(dd, J=8.8, 0.8 Hz, 2H), 7.23–7.38(m, 15H), 7.55 (m, 3H), 7.84(dd, J=8.4, 2.0 Hz, 1H), 7.99(d, J=8.8 Hz, 1H), 8.19(d, J=2.0 Hz, 1H), 9.15(s, 1H)

Example 792

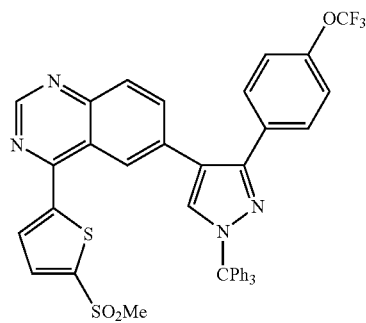

4-(5-Methylsulfonylthiophen-2-yl)-6-[3-(4-trifluoromethoxyphenyl)-1-trityl-1H-pyrazol-4-yl] quinazoline 257 mg of the title compound was obtained as a pale yellow amorphous by the same method as in Production Example 59 from 278 mg 4-(5-methylsulfanylthiophen-2-yl)-6-[3-(4-trifluoromethoxyphenyl)-1-trityl-1H-pyrazol-4-yl] quinazoline (compound in Example 791).

¹H-NMR (CDCl₃)
δ: 3.24(s, 3H), 6.94(d, J=4.4 Hz, 1H), 7.22(d, J=8.0 Hz, 1H), 7.25(m, 7H), 7.36(m, 9H), 7.54(m, 4H), 7.91(dd, J=8.8, 1.6 Hz, 1H), 8.08(d, J=8.8 Hz, 1H), 8.11(d, J=1.6 Hz, 1H), 9.25(s, 1H)

Example 793

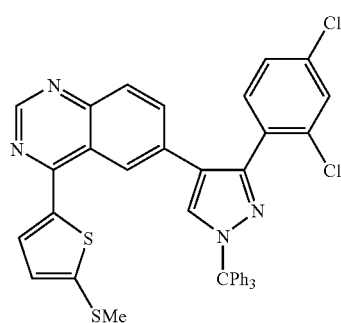

6-[3-(2,4-Dichlorophenyl)-1-trityl-1H-pyrazol-4-yl]-4-(5-methylsulfanylthiophen-2-yl) quinazoline 156 mg of the title compound was obtained as a yellow amorphous by the same reaction as in Example 29 from 135 mg 6-bromo-4-[5-(methylsulfanyl)-2-thienyl]quinazoline (compound in Production Example 100) and 653 mg 3-(2, 4-dichlorophenyl)-1-trityl-1H-4-pyrazolylboronic acid (compound in Production Example 179).

¹H-NMR (CDCl₃)
δ: 2.64(s, 3H), 6.65(d, J=4.0 Hz, 1H), 6.93(d, J=4.0 Hz, 1H), 7.22–7.38(m, 16H), 7.41(d, J=8.0 Hz, 1H), 7.47(d, J=2.0 Hz, 1H), 7.71(s, 1H), 7.80(dd, J=8.8, 2.0 Hz, 1H), 7.95(d, J=8.8 Hz, 1H), 7.99(d, J=2.4 Hz, 1H), 9.10(s, 1H)

Example 794

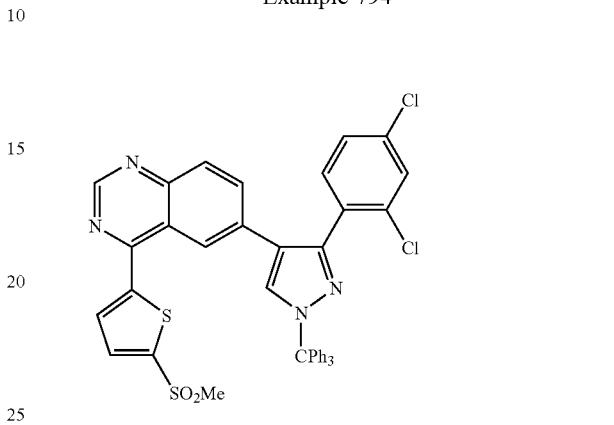

6-[3-(2,4-Dichlorophenyl)-1-trityl-1H-pyrazol-4-yl]-4-(5-methylsulfonylthiophen-2-yl) quinazoline 148 mg of the title compound was obtained as a yellow amorphous by the same method as in Production Example 59 from 154 mg 6-[3-(2,4-dichlorophenyl)-1-trityl-1H-pyrazol-4-yl]-4-(5-methylsulfanylthiophen-2-yl) quinazoline (compound in Example 793).

¹H-NMR (CDCl₃)
δ: 3.26(s, 3H), 6.77(d, J=4.0 Hz, 1H), 7.22–7.38(m, 16H), 7.42(d, J=8.0 Hz, 1H), 7.48(d, J=2.0 Hz, 1H), 7.63(d, J=4.0 Hz, 1H), 7.74(s, 1H), 7.87(dd, J=8.8, 2.0 Hz, 1H), 7.91(d, J=1.2 Hz, 1H), 8.03(d, J=8.4 Hz, 1H), 9.21(s, 1H)

Example 795

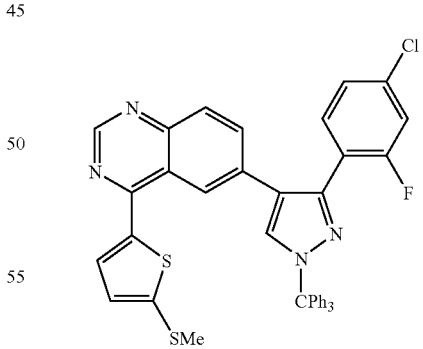

6-[3-(4-Chloro-2-fluorophenyl)-1-trityl-1H-pyrazol-4-yl]-4-(5-methylsulfanylthiophen-2-yl) quinazoline 234 mg of the title compound was obtained as a yellow amorphous by the same reaction as in Example 29 from 169 mg 6-bromo-4-[5-(methylsulfanyl)-2-thienyl]quinazoline (compound in Production Example 100) and 724 mg 3-(4- chloro-2-fluorophenyl)-1-trityl-1H-4-pyrazolylboronic acid (compound in Production Example 180).

$^1$H-NMR (CDCl$_3$)

δ: 2.63(s, 3H), 6.75(d, J=4.0 Hz, 1H), 6.90(d, J=4.0 Hz, 1H), 7.12(dd, J=9.6, 2.0 Hz, 1H), 7.22–7.38(m, 16H), 7.45 (dd, J=8.4, 7.6 Hz, 1H), 7.65(s, 1H), 7.81(dd, J=8.8, 2.0 Hz, 1H), 7.97(d, J=8.8 Hz, 1H), 8.10(d, J=1, 6 Hz, 1H), 9.12(s, 1H)

Example 796

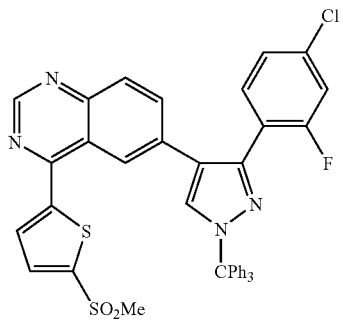

6-[3-(4-Chloro-2-fluorophenyl)-1-trityl-1H-pyrazol-4-yl]-4-(5-methylsulfonylthiophen-2-yl) quinazoline 222 mg of the title compound was obtained as a yellow amorphous by the same method as in Production Example 59 from 232 mg 6-[3-(4-chloro-2-fluorophenyl)-1-trityl-1H-pyrazol-4-yl]-4-(5-methylsulfanylthiophen-2-yl) quinazoline (compound in Example 795).

$^1$H-NMR (CDCl$_3$)

δ: 3.25(s, 3H), 6.88(d, J=4.0 Hz, 1H), 7.11(dd, J=9.6, 2.0 Hz, 1H), 7.22–7.38(m, 16H), 7.48(dd, J=8.0, 7.6 Hz, 1H), 7.61(d, J=4.0 Hz, 1H), 7.67(s, 1H), 7.88(dd, J=8.8, 2.0 Hz, 1H), 8.02(d, J=2.0 Hz, 1H), 8.05(d, J=8.8 Hz, 1H), 9.23(s, 1H)

Example 797

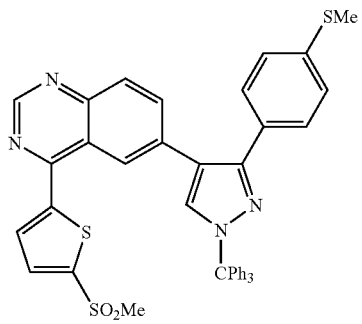

6-[3-(4-Methylsulfanylphenyl)-1-trityl-1H-pyrazol-4-yl]-4-(5-methylsulfonylthiophen-2-yl) quinazoline 300 mg of the title compound was obtained as yellow crystals by the same reaction as in Example 29 from 140 mg 6-bromo-4-[5-(methylsulfonyl)-2-thienyl]quinazoline (compound in Production Example 101) and 253 mg 3-[4-(methylsulfanyl)phenyl]-1-trityl-1H-4-pyrazolylboronic acid (compound in Production Example 26).

$^1$H-NMR (CDCl$_3$)

δ: 2.50(s, 3H), 3.24(s, 3H), 6.84(d, J=4.0 Hz, 1H), 7.22–7.38(m, 15H), 7.42(d, J=8.0 Hz, 2H), 7.48(m, 2H), 7.58(s, 1H), 7.67(m, 1H), 7.92(dd, J=8.8, 2.0 Hz, 1H), 8.05(d, J=8.4 Hz, 1H), 8.10(d, J=2.0 Hz, 1H), 9.22(s, 1H)

Example 798

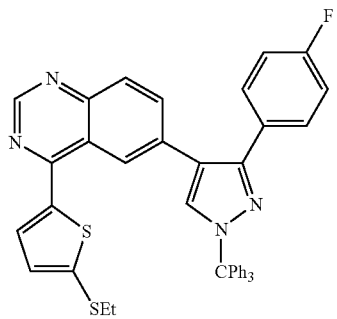

4-(5-Ethylsulfanylthiophen-2-yl)-6-[3-(4-fluorophenyl)-1-trityl-1H-pyrazol-4-yl] quinazoline 270 mg of the title compound was obtained as a yellow amorphous by the same reaction as in Example 29 from 176 mg 6-bromo-4-(5-ethylsulfanylthiophen-2-yl)quinazoline (compound in Production Example 400) and 291 mg 3-(4-fluorophenyl)-1-trityl-1H-4-pyrazolylboronic acid (compound in Production Example 25).

$^1$H-NMR (CDCl$_3$)

δ: 1.38(t, J=7.2 Hz, 3H), 2.97 (q, J=7.2 Hz, 2H), 6.88(d, J=4.0 Hz, 1H), 6.93(d, J=4.0 Hz, 1H), 7.06(t, J=8.8 Hz, 2H), 7.26(m, 6H), 7.35(m, 9H), 7.47(d, J=8.8 Hz, 1H), 7.48(d, J=8.8 Hz, 1H), 7.55(s, 1H), 7.83(dd, J=8.8, 2.0 Hz, 1H), 7.98(d, J=8.8 Hz, 1H), 8.18(d, J=2.0 Hz, 1H), 9.15(s, 1H)

Example 799

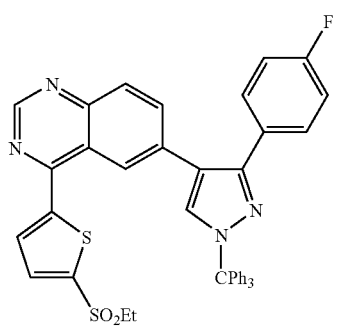

4-(5-Ethanesulfonylthiophen-2-yl)-6-[3-(4-fluorophenyl)-1-trityl-1H-pyrazol-4-yl] quinazoline 260 mg of the title compound was obtained as a pale yellow amorphous by the same method as in Production Example 59 from 268 mg 4-(5-ethylsulfanylthiophen-2-yl)-6-[3-(4-fluorophenyl)-1-trityl-1H-pyrazol-4-yl] quinazoline (compound in Example 798).

¹H-NMR (CDCl₃)

δ: 1.40(t, J=7.2 Hz, 3H), 3.28 (q, J=7.2 Hz, 2H), 6.96(d, J=4.0 Hz, 1H), 7.07(t, J=8.8 Hz, 2H), 7.26(m, 6H), 7.35(m, 9H), 7.46(d, J=8.8 Hz, 1H), 7.47(d, J=8.8 Hz, 1H), 7.52(d, J=4.0 Hz, 1H), 7.58(s, 1H), 7.90(dd, J=8.8, 2.0 Hz, 1H), 8.05(d, J=8.8 Hz, 1H), 8.10(d, J=2.0 Hz, 1H), 9.23(s, 1H)

Example 800

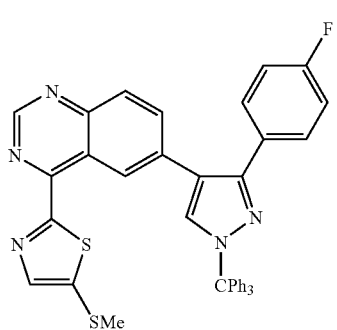

6-[3-(4-Fluorophenyl)-1-trityl-1H-pyrazol-4-yl]-4-(5-methylsulfanylthiazol-2-yl) quinazoline 65 mg of the title compound was obtained as a yellow amorphous by the same reaction as in Example 29 from 62 mg 6-bromo-4-(5-methylsulfanylthiazol-2-yl)quinazoline (compound in Production Example 401) and 124 mg 3-(4-fluorophenyl)-1-trityl-1H-4-pyrazolylboronic acid (compound in Production Example 25).

¹H-NMR (CDCl₃)

δ: 2.64(s, 3H), 6.97(t, J=8.8 Hz, 2H), 7.27(m, 6H), 7.35(m, 9H), 7.47(d, J=8.8 Hz, 1H), 7.48(d, J=8.8 Hz, 1H), 7.61(s, 1H), 7.65(s, 1H), 7.79(dd, J=8.8, 2.0 Hz, 1H), 7.93(d, J=8.8 Hz, 1H), 9.20(s, 1H), 9.52(dd, J=2.0, 0.4 Hz, 1H)

Example 801

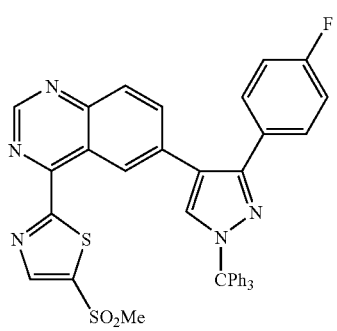

6-[3-(4-Fluorophenyl)-1-trityl-1H-pyrazol-4-yl]-4-(5-methylsulfonylthiazol-2-yl) quinazoline 59 mg of the title compound was obtained as a pale yellow amorphous by the same method as in Production Example 59 from 63 mg 6-[3-(4-fluorophenyl)-1-trityl-1H-pyrazol-4-yl]-4-(5-methylsulfanylthiazol-2-yl) quinazoline (compound in Example 800).

¹H-NMR (CDCl₃)

δ: 3.30(s, 3H), 6.98(t, J=8.8 Hz, 2H), 7.27(m, 6H), 7.35(m, 9H), 7.46(d, J=8.8 Hz, 1H), 7.47(d, J=8.8 Hz, 1H), 7.63(s, 1H), 7.86(dd, J=8.8, 2.0 Hz, 1H), 8.00(d, J=8.8 Hz, 1H), 8.29(s, 1H), 9.28(s, 1H), 9.42(dd, J=1.6, 0.4 Hz, 1H)

Example 802

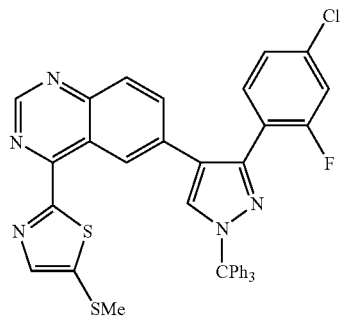

6-[3-(4-Chloro-2-fluorophenyl)-1-trityl-1H-pyrazol-4-yl]-4-(5-methylsulfanylthiazol-2-yl) quinazoline 262 mg of the title compound was obtained as a yellow solid by the same reaction as in Example 29 from 169 mg 6-bromo-4-(5-methylsulfanylthiazol-2-yl)quinazoline (compound in Production Example 401) and 724 mg 3-(4-fluoro-2-fluorophenyl)-1-trityl-1H-4-pyrazolylboronic acid (compound in Production Example 180).

¹H-NMR (CDCl₃)

δ: 2.64(s, 3H), 7.03(dd, J=9.6, 2.0 Hz, 1H), 7.22(ddd, J=8.8, 2.0, 0.8 Hz, 1H), 7.27(m, 6H), 7.36(m, 9H), 7.48(dd, J=8.4, 7.6 Hz, 1H), 7.56(s, 1H), 7.73(s, 1H), 7.82(dd, J=8.8, 2.0 Hz, 1H), 7.94(d, J=8.8 Hz, 1H), 9.18(s, 1H), 9.43(d, J=2.0 Hz, 1H)

Example 803

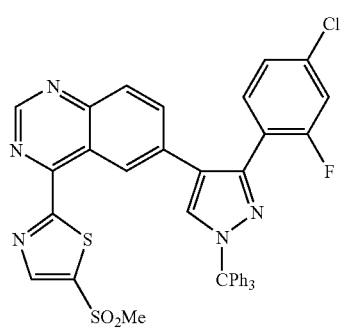

6-[3-(4-Chloro-2-fluorophenyl)-1-trityl-1H-pyrazol-4-yl]-4-(5-methylsulfonylthiazol-2-yl) quinazoline 159 mg of the title compound was obtained as a yellow solid by the same method as in Production Example 59 from 260 mg 6-[3-(4-chloro-2-fluorophenyl)-1-trityl-1H-pyrazol-4-yl]-4-(5-methylsulfanylthiazol-2-yl) quinazoline (compound in Example 802).

¹H-NMR (CDCl₃)

δ: 3.30(s, 3H), 7.02(dd, J=9.6, 2.0 Hz, 1H), 7.26(m, 7H), 7.36(m, 9H), 7.49(dd, J=8.0, 7.6 Hz, 1H), 7.74(s, 1H), 7.87(dd, J=9.2, 2.0 Hz, 1H), 8.00(d, J=8.8 Hz, 1H), 8.22(s, 1H), 9.26(s, 1H), 9.34(d, J=2.0 Hz, 1H)

Example 804

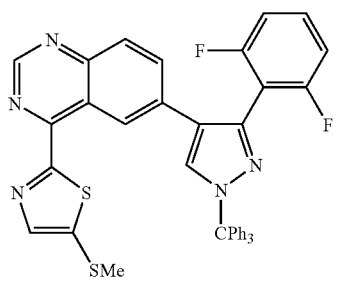

6-[3-(2,6-Difluorophenyl)-1-trityl-1H-pyrazol-4-yl]-4-(5-methylsulfanylthiazol-2-yl) quinazoline 111 mg of the title compound was obtained as a yellow solid by the same reaction as in Example 29 from 104 mg 6-bromo-4-(5-methylsulfanylthiazol-2-yl)quinazoline (compound in Production Example 401) and 287 mg 3-(2,6-difluorophenyl)-1-trityl-1H-4-pyrazolylboronic acid (compound in Production Example 211).

¹H-NMR (CDCl₃)

δ: 2.63(s, 3H), 6.92(d, J=8.4 Hz, 1H), 6.94(d, J=8.4 Hz, 1H), 7.27(m, 7H), 7.36(m, 9H), 7.62(s, 1H), 7.78(s, 1H), 7.79(dd, J=8.8, 2.0 Hz, 1H), 7.91(dd, J=8.8, 0.4 Hz, 1H), 9.17(s, 1H), 9.46(d, J=2.0 Hz, 1H)

Example 805

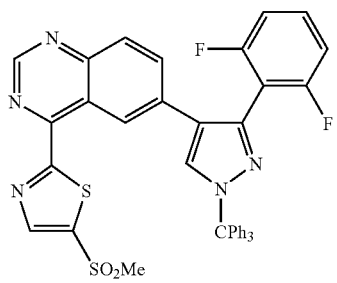

6-[3-(2,6-Difluorophenyl)-1-trityl-1H-pyrazol-4-yl]-4-(5-methylsulfonylthiazol-2-yl) quinazoline 88 mg of the title compound was obtained as a yellow amorphous by the same method as in Production Example 59 from 109 mg 6-[3-(2,6-difluorophenyl)-1-trityl-1H-pyrazol-4-yl]-4-(5-methylsulfanylthiazol-2-yl) quinazoline (compound in Example 804).

¹H-NMR (CDCl₃)

δ: 3.29(s, 3H), 6.94(d, J=8.4 Hz, 1H), 6.96(d, J=8.4 Hz, 1H), 7.28(m, 7H), 7.36(m, 9H), 7.80(s, 1H), 7.87(dd, J=9.2, 2.0 Hz, 1H), 7.99(d, J=8.8 Hz, 1H), 8.23(s, 1H), 9.25(s, 1H), 9.36(d, J=2.0 Hz, 1H)

Example 806

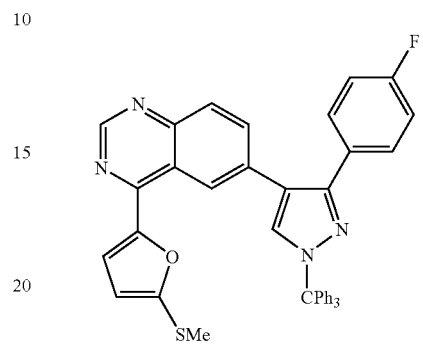

6-[3-(4-Fluorophenyl)-1-trityl-1H-pyrazol-4-yl]-4-(5-methylsulfanylfuran-2-yl) quinazoline 103 mg of the title compound was obtained as a yellowish brown amorphous by the same reaction as in Example 29 from 92 mg 6-bromo-4-(5-methylsulfanylfuran-2-yl) quinazoline (compound in Production Example 404) and 194 mg 3-(4-fluorophenyl)-1-trityl-1H-4-pyrazolylboronic acid (compound in Production Example 25).

¹H-NMR (CDCl₃)

δ: 2.40(s, 3H), 6.49(d, J=3.6 Hz, 1H), 6.97(t, J=8.8 Hz, 2H), 7.27(m, 7H), 7.35(m, 9H), 7.47(d, J=8.8 Hz, 1H), 7.48(d, J=8.8 Hz, 1H), 7.57(s, 1H), 7.74(dd, J=8.8, 2.0 Hz, 1H), 7.92(d, J=8.8 Hz, 1H), 8.69(d, J=2.0 Hz, 1H), 9.19(s, 1H)

Example 807

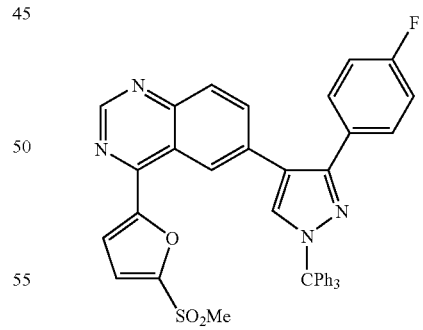

6-[3-(4-Fluorophenyl)-1-trityl-1H-pyrazol-4-yl]-4-(5-methylsulfonylfuran-2-yl) quinazoline 73 mg of the title compound was obtained as a pale yellow amorphous by the same method as in Production Example 59 from 101 mg 6-[3-(4-fluorophenyl)-1-trityl-1H-pyrazol-4-yl]-4-(5-methylsulfanylfuran-2-yl) quinazoline (compound in Example 806).

¹H-NMR (CDCl₃)
δ: 3.08(s, 3H), 6.98(t, J=8.8 Hz, 2H), 7.27(m, 8H), 7.35(m, 9H), 7.45(d, J=8.8 Hz, 1H), 7.46(d, J=8.8 Hz, 1H), 7.64(s, 1H), 7.80(dd, J=8.8, 2.0 Hz, 1H), 7.99(d, J=8.8 Hz, 1H), 8.60(dd, J=2.0, 0.8 Hz, 1H), 9.30(s, 1H)

Example 808

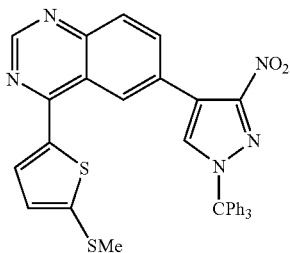

4-(5-Methylsulfanylthiophen-2-yl)-6-(3-nitro-1-tri-tyl-1H-pyrazol-4-yl) quinazoline 14 mg of the title compound was obtained as a yellow oil by the same reaction as in Example 96 from 56 mg 6-bromo-4-(5-methylsulfanylthiophen-2-yl]quinazoline (compound in Production Example 100) and 128 mg 3-nitro-4-tributyl-stannyl-1-trityl-1H-pyrazole (compound in Production Example 406).

¹H-NMR (CDCl₃)
δ: 2.65(s, 3H), 7.13(d, J=4.0 Hz, 1H), 7.20(m, 6H), 7.38(m, 9H), 7.54(s, 1H), 7.76(d, J=4.0 Hz, 1H), 7.85(dd, J=8.8, 2.0 Hz, 1H), 8.05(d, J=8.8 Hz, 1H), 8.59(d, J=1.6 Hz, 1H), 9.21(s, 1H)

Example 809

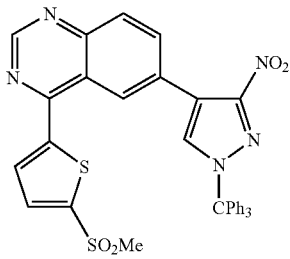

4-(5-Methylsulfonylthiophen-2-yl)-6-(3-nitro-1-tri-tyl-1H-pyrazol-4-yl) quinazoline 8 mg of the title compound was obtained as a pale yellow solid by the same method as in Production Example 59 from 13 mg 4-(5-methylsulfanylthiophen)-6-(3-nitro-1-trityl-1H-pyrazol-4-yl) quinazoline (compound in Example 808).

¹H-NMR (CDCl₃)
δ: 3.27(s, 3H), 7.20(m, 6H), 7.38(m, 9H), 7.56(s, 1H), 7.84(d, J=4.0 Hz, 1H), 7.86(d, J=4.0 Hz, 1H), 7.91(dd, J=8.8, 2.0 Hz, 1H), 8.13(d, J=8.8 Hz, 1H), 8.54(d, J=1.6 Hz, 1H), 9.32(s, 1H)

Example 810

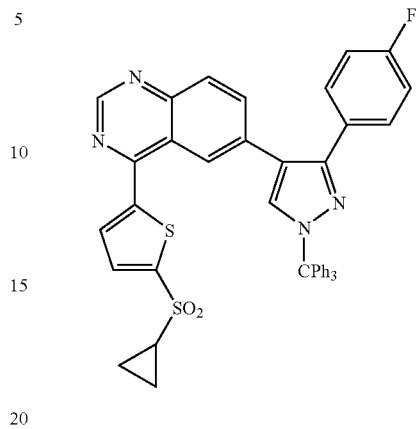

4-(5-Cyclopropanesulfonylthiophen-2-yl)-6-[3-(4-fluorophenyl)-1-trityl-1H-pyrazol-4-yl] quinazoline 271 mg of the title compound was obtained as a yellow amorphous by the same reaction as in Example 29 from 146 mg 6-bromo-4-(5-cyclopropanesulfonyl)thiophen-2-yl] quinazoline (compound in Production Example 412) and 232 mg 3-(4-fluorophenyl)-1-trityl-1H-4-pyrazolylboronic acid (compound in Production Example 25).

¹H-NMR (CDCl₃)
δ: 1.15(m, 2H), 1.45(m, 2H), 2.64(m, 1H), 6.93(d, J=4.0 Hz, 1H), 7.08(t, J=8.8 Hz, 2H), 7.26(m, 6H), 7.35(m, 9H), 7.46(d, J=8.8 Hz, 1H), 7.48(d, J=8.8 Hz, 1H), 7.52(d, J=4.0 Hz, 1H), 7.58(s, 1H), 7.90(dd, J=8.8, 2.0 Hz, 1H), 8.05(d, J=8.8 Hz, 1H), 8.10(d, J=1.6 Hz, 1H), 9.23(s, 1H)

Example 811

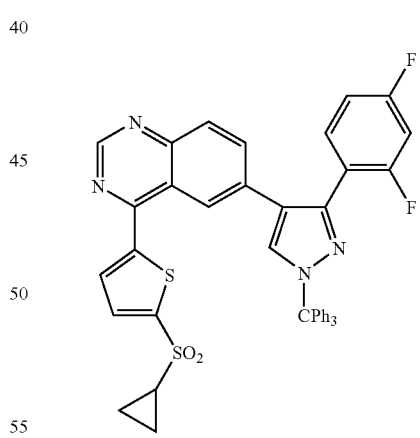

4-(5-Cyclopropanesulfonylthiophen-2-yl)-6-[3-(2,4-difluorophenyl)-1-trityl-1H-pyrazol-4-yl] quinazo-line 304 mg of the title compound was obtained as a pale yellow amorphous by the same reaction as in Example 29 from 158 mg 6-bromo-4-(5-cyclopropanesulfonyl)thiophen-2-yl] quinazoline (compound in Production Example 412) and 653 mg 3-(2,4-difluorophenyl)-1-trityl-1H-4-pyrazolylboronic acid (compound in Production Example 172).

¹H-NMR (CDCl₃)

δ: 1.16(m, 2H), 1.45(m, 2H), 2.66(m, 1H), 6.82(m, 1H), 6.93(d, J=4.0 Hz, 1H), 7.01(m, 1H), 7.22–7.38(m, 15H), 7.51(m, 1H), 7.54(d, J=4.0 Hz, 1H), 7.67(s, 1H), 7.87(dd, J=8.8, 2.0 Hz, 1H), 8.03(d, J=8.8 Hz, 1H), 8.05(d, J=2.0 Hz, 1H), 9.22(s, 1H)

Example 812

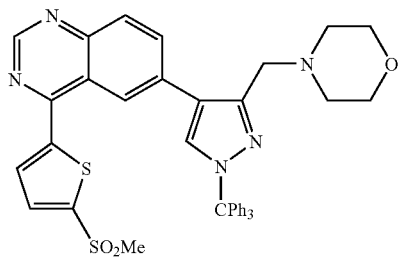

4-(5-Methylsulfonylthiophen-2-yl)-6-(3-morpholin-4-ylmethyl-1-trityl-1H-pyrazol-4-yl) quinazoline A mixture of 62 mg 6-(3-methyl-1-trityl-1H-4-pyrazolyl)-4-[5-(methylsulfonyl)-2-thienyl] quinazoline obtained in the synthesis process in Example 255, 22 mg N-bromosuccinimide, 1 mg α,α'-azobisisobutyronitrile and 5 mL carbon tetrachloride was heated for 2 hours under reflux. The reaction solution was cooled, insolubles were filtered off, and the filtrate was concentrated under reflux. 83 mg crude product of 6-(3-bromomethy-1-trityl-1H-pyrazol-4-yl)-(5-methylsulfonylthiophen-2-yl) quinazoline was obtained as a pale yellow oil. A mixture of this compound, 44 μl morpholine, 30 mg potassium carbonate and 5 mL N,N-dimethylformamide was stirred at 80° C. for 2.5 hours. Ethyl acetate and water were added to the reaction solution, and the organic layer was separated, washed with water (2×) and brine and dried over anhydrous sodium sulfate. The drying agent was filtered off, and the filtrate was evaporated. The resulting residue was purified by silica gel column chromatography (ethyl acetate/hexane) to give 36 mg of the title compound as a yellow oil.

¹H-NMR (CDCl₃)

δ: 2.36(m, 4H), 3.29(s, 3H), 3.55(m, 4H), 3.65(s, 2H), 7.22(m, 6H), 7.34(m, 9H), 7.63(s, 1H), 7.80(d, J=4.0 Hz, 1H), 7.83(d, J=4.0 Hz, 1H), 8.07(d, J=8.4 Hz, 1H), 8.20(dd, J=8.8, 1.6 Hz, 1H), 8.58(d, J=1.6 Hz, 1H), 9.27(s, 1H)

Example 813

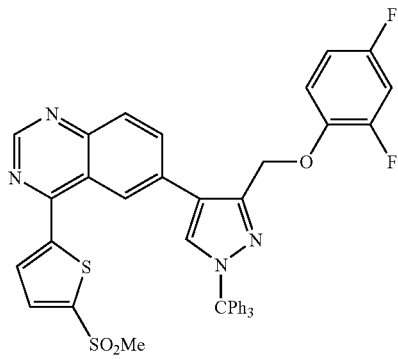

6-[3-(2,4-Difluorophenoxymethyl)-1-trityl-1H-pyrazol-4-yl]-4-(5-methylsulfonylthiophen-2-yl) quinazoline 53 mg of the title compound was obtained as a pale yellow amorphous by reacting 107 mg 6-(3-bromomethyl-1-trityl-1H-pyrazol-4-yl)-4-(5-methylsulfonylthiophen-2-yl) quinazoline obtained in the synthesis process in Example 812, with 23 mg 2,4-difluorophenol obtained in the synthesis process in Example 812.

¹H-NMR (CDCl₃)

δ: 3.24(s, 3H), 5.30(s, 2H), 6.62(m, 1H), 6.80(m, 2H), 7.16(m, 6H), 7.33(m, 9H), 7.69(d, J=4.0 Hz, 1H), 7.70(s, 1H), 7.96(dd, J=8.8, 2.0 Hz, 1H), 8.07(d, J=4.0 Hz, 1H), 8.08(d, J=8.8 Hz, 1H), 8.81(d, J=2.0 Hz, 1H), 9.27(s, 1H)

Example 814

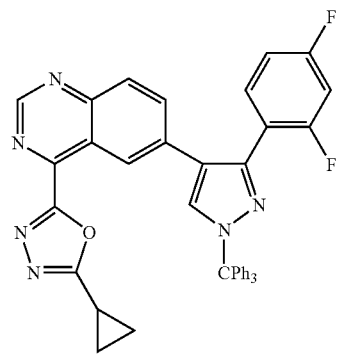

4-(5-Cyclopropyl[1,3,4]oxadiazol-2-yl)-6-[3-(2,4-difluorophenyl)-1-trityl-1H-pyrazol-4-yl] quinazoline 476 mg of the title compound was obtained as a pale yellow amorphous by the same reaction as in Example 29 from 282 mg 6-bromo-4-(5-cyclopropyl[1,3,4]oxadiazol-2-yl) quinazoline (compound in Production Example 415) and 1.24 g 3-(2,4-difluorophenyl)-1-trityl-1H-4-pyrazolylboronic acid (compound in Production Example 172).

¹H-NMR (CDCl₃)

δ: 1.24–1.37(m, 4H), 2.31(m, 1H), 6.72(m, 1H), 6.93(m, 1H), 7.27(m, 6H), 7.37(m, 9H), 7.49(m, 1H), 7.72(s, 1H), 7.80(dd, J=8.8, 2.0 Hz, 1H), 7.99(d, J=8.8 Hz, 1H), 9.17(d, J=2.0 Hz, 1H), 9.38(s, 1H)

Example 815

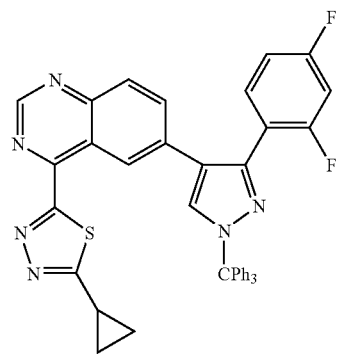

4-(5-Cyclopropyl[1,3,4]thiadiazol-2-yl)-6-[3-(2,4-difluorophenyl)-1-trityl-1H-pyrazol-4-yl] quinazoline 195 mg of the title compound was obtained as yellow crystals by the same reaction as in Example 29 from 106 mg 6-bromo-4-(5-cyclopropyl[1,3,4]thiadiazol-2-yl)quinazoline (compound in Production Example 416) and 445 mg 3-(2,4-difluorophenyl)-1-trityl-1H-4-pyrazolylboronic acid (compound in Production Example 172).

$^1$H-NMR (CDCl$_3$)

δ: 1.22–1.36(m, 4H), 2.50(m, 1H), 6.70(m, 1H), 6.92(m, 1H), 7.27(m, 6H), 7.35(m, 9H), 7.48(m, 1H), 7.71(s, 1H), 7.78(dd, J=8.8, 2.0 Hz, 1H), 7.95(d, J=8.8 Hz, 1H), 9.24(s, 1H), 9.40(d, J=1.6 Hz, 1H)

Example 816

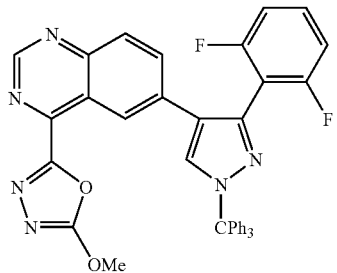

6-[3-(2,6-Difluorophenyl)-1-trityl-1H-pyrazol-4-yl]-4-(5-methoxy[1,3,4]oxadiazol-2-yl) quinazoline 143 mg of the title compound was obtained as a yellow amorphous by the same reaction as in Example 29 from 69 mg 6-bromo-4-(5-methoxy[1,3,4]oxadiazol-2-yl)quinazoline (compound in Production Example 418) and 210 mg 3-(2,6-difluorophenyl)-1-trityl-1H-4-pyrazolylboronic acid (compound in Production Example 211).

$^1$H-NMR (CDCl$_3$)

δ: 4.33(s, 3H), 6.92(d, J=8.4 Hz, 1H), 6.94(d, J=8.4 Hz, 1H), 7.26–7.38(m, 16H), 7.78(s, 1H), 7.81(dd, J=8.8, 2.0 Hz, 1H), 7.97(d, J=8.8 Hz, 1H), 9.10(d, J=1.6 Hz, 1H), 9.34(s, 1H)

Example 817

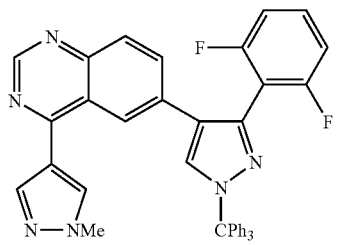

6-[3-(2,6-Difluorophenyl)-1-trityl-1H-pyrazol-4-yl]-4-(1-methyl-1H-pyrazol-4-yl) quinazoline 126 mg of the title compound was obtained as a pale yellow solid by the same reaction as in Example 29 from 58 mg 6-bromo-4-(1-methyl-1H-pyrazol-4-yl)quinazoline (compound in Production Example 419) and 186 mg 3-(2,6-difluorophenyl)-1-trityl-1H-4-pyrazolylboronic acid (compound in Production Example 211).

$^1$H-NMR (CDCl$_3$)

δ: 3.98(s, 3H), 6.95(d, J=8.4 Hz, 1H), 6.97(d, J=8.4 Hz, 1H), 7.28(m, 6H), 7.35(m, 9H), 7.47(m, 1H), 7.53(s, 1H), 7.68(s, 1H), 7.73(s, 1H), 7.79(dd, J=8.8, 2.0 Hz, 1H), 7.94(d, J=8.8 Hz, 1H), 8.02(d, J=2.0 Hz, 1H), 9.13(s, 1H)

Example 818

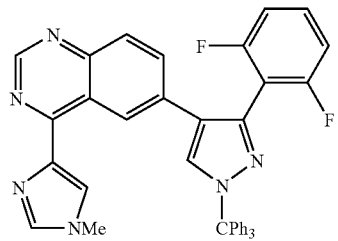

6-[3-(2,6-Difluorophenyl)-1-trityl-1H-pyrazol-4-yl]-4-(1-methyl-1H-imidazol-4-yl) quinazoline 216 mg of the title compound was obtained as a pale yellow solid by the same reaction as in Example 29 from 141 mg 6-bromo-4-(1-methyl-1H-imidazol-4-yl)quinazoline (compound in Production Example 420) and 409 mg 3-(2,6-difluorophenyl)-1-trityl-1H-4-pyrazolylboronic acid (compound in Production Example 211).

$^1$H-NMR (CDCl$_3$)

δ: 3.77(s, 3H), 6.88(d, J=8.4 Hz, 1H), 6.90(d, J=8.4 Hz, 1H), 7.24–7.38(m, 16H), 7.40(d, J=1.6 Hz, 1H), 7.69(dd, J=8.8, 2.0 Hz, 1H), 7.75(d, J=1.6 Hz, 1H), 7.76(s, 1H), 7.84(d, J=8.4 Hz, 1H), 9.10(s, 1H), 9.40(d, J=2.0 Hz, 1H)

Example 819

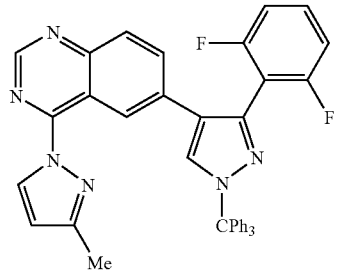

6-[3-(2,6-Difluorophenyl)-1-trityl-1H-pyrazol-4-yl]-4-(3-methylpyrazol-1-yl) quinazoline 74 mg of the title compound was obtained as a colorless amorphous by the same reaction as in Example 29 from 58 mg 6-bromo-4-(3-methylpyrazol-1-yl)quinazoline (compound in Production Example 421) and 187 mg 3-(2,6-- difluorophenyl)-1-trityl-1H-4-pyrazolylboronic acid (compound in Production Example 211).

¹H-NMR (CDCl₃)

δ: 2.33(s, 3H), 6.29(d, J=2.8 Hz, 1H), 6.86(d, J=8.0 Hz, 1H), 6.88(d, J=8.0 Hz, 1H), 7.24–7.38(m, 16H), 7.69(dd, J=8.8, 2.0 Hz, 1H), 7.77(s, 1H), 7.86(d, J=8.8 Hz, 1H), 8.57(dd, J=2.8, 0.4 Hz, 1H), 8.96(s, 1H), 9.39(dd, J=2.0, 0.8 Hz, 1H)

Example 820

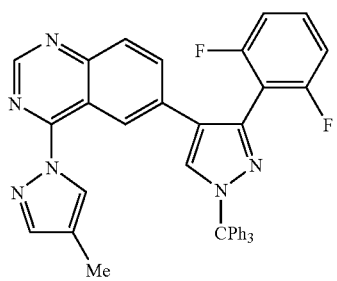

6-[3-(2,6-Difluorophenyl)-1-trityl-1H-pyrazol-4-yl]-4-(4-methylpyrazol-1-yl) quinazoline 33 mg of the title compound was obtained as a colorless amorphous by the same reaction as in Example 29 from 61 mg 6-bromo-4-(4-methylpyrazol-1-yl)quinazoline (compound in Production Example 422) and 197 mg 3-(2,6-difluorophenyl)-1-trityl-1H-4-pyrazolylboronic acid (compound in Production Example 211).

¹H-NMR (CDCl₃)

δ: 2.17(s, 3H), 6.91(d, J=8.4 Hz, 1H), 6.93(d, J=8.4 Hz, 1H), 7.24–7.38(m, 16H), 7.45(s, 1H), 7.74(dd, J=8.8, 2.4 Hz, 1H), 7.75(s, 1H), 7.88(d, J=8.4 Hz, 1H), 8.43(s, 1H), 8.95(s, 1H), 9.33(d, J=2.0 Hz, 1H)

Example 821

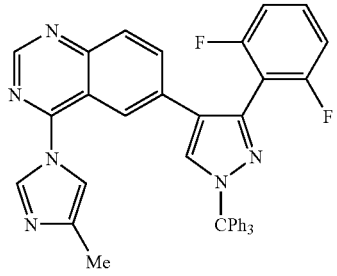

6-[3-(2,6-Difluorophenyl)-1-trityl-1H-pyrazol-4-yl]-4-(4-methylimidazol-1-yl) quinazoline 32 mg of the title compound was obtained as a colorless amorphous by the same reaction as in Example 29 from 97 mg 6-bromo-4-(4-methylimidazol-1-yl)quinazoline (compound in Production Example 423) and 280 mg 3-(2,6-difluorophenyl)-1-trityl-1H-4-pyrazolylboronic acid (compound in Production Example 211).

¹H-NMR (CDCl₃)

δ: 2.26(s, 3H), 6.95(m, 3H), 7.24–7.38(m, 16H), 7.70(s, 1H), 7.80(d, J=1.2 Hz, 1H), 7.85(m, 2H), 8.02(dd, J=8.8, 0.8 Hz, 1H), 9.07(s, 1H)

Example 822

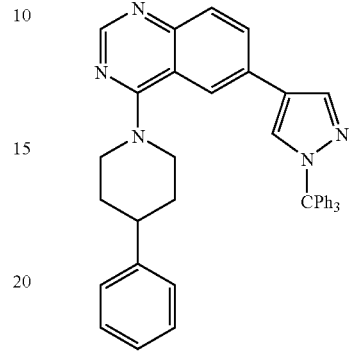

4-(4-Phenylpiperidin-1-yl)-6-(1-trityl-1H-pyrazol-4-yl) quinazoline 167 mg of the title compound was obtained as white crystals by the same reaction as in Example 29 from 112 mg 6-bromo-4-(4-phenylpiperidin-1-yl)quinazoline (compound in Production Example 424) and 162 mg 1-trityl-1H-4-pyrazolylboronic acid.

¹H-NMR (CDCl₃)

δ: 1.87–2.05(m, 4H), 2.88(m, 1H), 3.20(m, 2H), 4.44(m, 2H), 7.18–7.34(m, 18H), 7.38(m, 2H), 7.68(d, J=0.8 Hz, 1H), 7.82(dd, J=8.8, 2.0 Hz, 1H), 7.85(d, J=8.8 Hz, 1H), 7.89(d, J=1.2 Hz, 1H), 8.04(d, J=0.8 Hz, 1H), 8.70(s, 1H)

Example 823

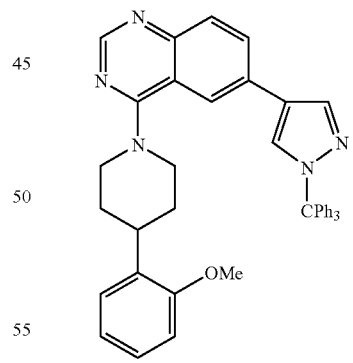

4-[4-(2-Methoxyphenyl)piperidin-1-yl]-6-(1-trityl-1H-pyrazol-4-yl) quinazoline 122 mg of the title compound was obtained as a pale yellowish brown amorphous by the same reaction as in Example 29 from 88 mg 6-bromo-4-[4-(2-methoxyphenyl) piperidin-1-yl]quinazoline (compound in Production Example 425) and 110 mg 1-trityl-1H-4-pyrazolylboronic acid.

¹H-NMR (CDCl₃)

δ: 1.63(m, 2H), 2.79(m, 2H), 3.83(s, 3H), 3.97(m, 2H), 4.40(m, 2H), 5.92(m, 1H), 6.93(dd, J=8.4, 0.8 Hz, 1H), 6.98(ddd, J=7.2, 6.8, 1.2 Hz, 1H), 7.20(m, 6H), 7.31(m, 9H), 7.46(m, 1H), 7.67(m, 2H), 7.79(dd, J=8.4, 2.0 Hz, 1H), 7.84(d, J=8.4 Hz, 1H), 7.96(d, J=1.6 Hz, 1H), 8.03(d, J=1.2 Hz, 1H), 8.67(s, 1H)

Example 824

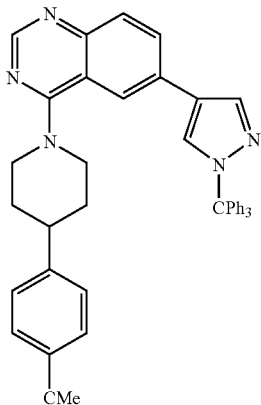

4-[4-(4-Methoxyphenyl)piperidin-1-yl]-6-(1-trityl-1H-pyrazol-4-yl) quinazoline 258 mg of the title compound was obtained as a pale yellow amorphous by the same reaction as in Example 29 from 180 mg 6-bromo-4-[4-(4-methoxyphenyl)piperidin-1-yl]quinazoline (compound in Production Example 426) and 220 mg 1-trityl-1H-4-pyrazolylboronic acid.

¹H-NMR (CDCl₃)

δ: 1.83–2.03(m, 4H), 2.80(m, 1H), 3.18(m, 2H), 3.83(s, 3H), 4.43(m, 2H), 6.92(d, J=8.8 Hz, 2H), 7.18–7.38(m, 15H), 7.46(m, 1H), 7.68(m, 2H), 7.83(m, 2H), 7.89(d, J=1.6 Hz, 1H), 8.03(d, J=0.8 Hz, 1H), 8.69(s, 1H)

Example 825

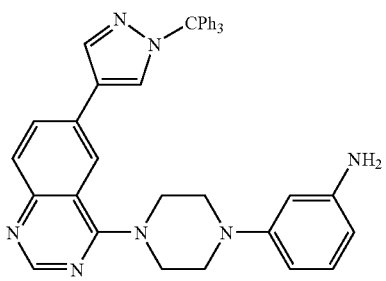

3-{4-[6-(1-Trityl-1H-pyrazol-4-yl)quinazolin-4-yl]-piperazin-1-yl) phenylamine 3.5 g 4-[4-(3-nitrophenyl)piperazin-1-yl]-6-(1-trityl-1H-pyrazol-4-yl) quinazoline obtained from 2.4 g 6-bromo-4-chloroquinazoline, 2.0 g 1-(3-nitrophenyl)piperazine and 4.0 g 1-trityl-1H-4-piperazolylboronic acid by the method described in Example 268 was dissolved in 2 L tetrahydrofuran, then 100 mg of 10% palladium-carbon was added thereto, and the mixture was hydrogenated for 24 hours at normal pressure. The catalyst was filtered off, and the solvent was evaporated, whereby 2.5 g of the title compound was obtained as a brown solid.

¹H-NMR (CDCl₃)

δ: 3.35(m, 4H), 3.79(m, 4H), 6.27–6.33(m, 2H), 6.42(dd, J=1.6, 8.0 Hz, 1H), 7.10(t, J=8.0 Hz, 1H), 7.20–7.38(m, 15H), 7.70(s, 1H), 7.79–7.92(m, 3H), 8.02(s, 1H), 8.71(s, 1H)

Example 826

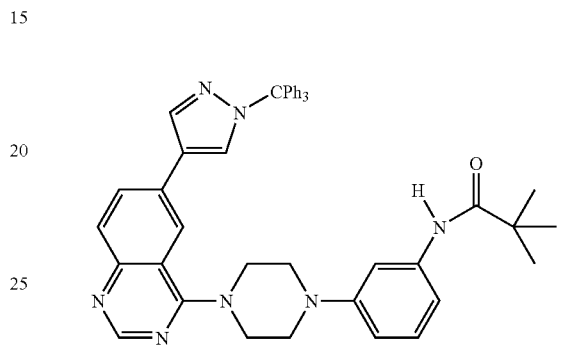

2,2-Dimethyl-N-(3-{4-[6-(1-trityl-1H-pyrazol-4-yl) quinazolin-4-yl]piperazin-1-yl}phenyl) propionamide A mixture of 100 mg 3-{4-[6-(1-trityl-1H-pyrazol-4-yl) quinazolin-4-yl]piperazin-1-yl} phenylamine obtained in Example 825, 30 mg pivaloyl chloride, 50 μl triethylamine and 10 mL N,N-dimethyl formamide was stirred at room temperature for 15 minutes. Water was added to the mixture which was then extracted with ethyl acetate, and the organic layer was washed with brine and dried over anhydrous magnesium sulfate. The solvent was evaporated, and the residue was purified by silica gel column chromatography to give 91 mg of the title compound as a colorless oil.

¹H-NMR (CDCl₃)

δ: 1.31(s, 3H), 3.40(m, 4H), 3.88(m, 4H), 6.72(dd, J=8.0, 2.0 Hz, 1H), 6.83(dd, J=8.0, 2.0 Hz, 1H), 7.20–7.38(m, 16H), 7.56(t, J=2.0 Hz, 1H), 7.68(s, 1H), 7.80(dd, J=9.0, 2.0 Hz, 1H), 7.86(d, 9.0 Hz, 1H), 7.91(d, J=2.0 Hz), 8.02(m, 2H), 8.72(s, 1H)

Example 827

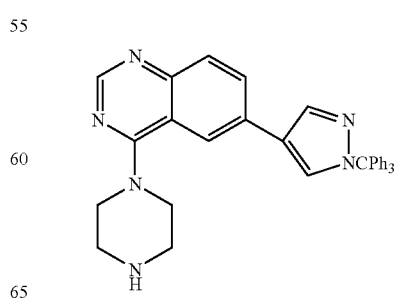

713

4-piperazin-1-yl-6-(1-trityl-1H-pyrazolyl) quinazoline 300 mg of the title compound was obtained in the same manner as in Example 168 from 300 mg 6-bromo-4-piperazin-1-yl-quinazoline (compound in Production Example 364) and 581 mg 1-trityl-1H-4-pyrazolylboronic acid.

$^1$H-NMR (CDCl$_3$)

δ: 3.06–3.09(m, 4H), 3.72–3.74(m, 4H), 7.20–7.23(m, 6H), 7.33–7.36(m, 9H), 7.69(d, J=0.8 Hz, 1H), 7.78(dd, J=8.8, 2.0 Hz, 1H), 7.84(d, J=8.8 Hz, 1H), 7.88(d, J=2.0 Hz, 1H), 8.01(d, J=0.8 Hz, 1H), 8.69(s, 1H)

Example 828

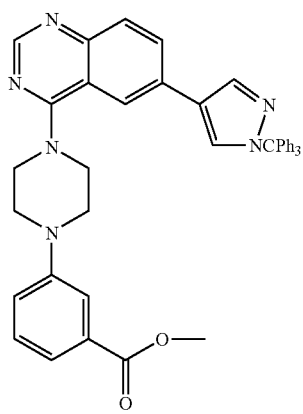

Methyl 3-{4-[6-(1-trityl-1H-4-pyrazolyl)-4-quinazolinyl]-piperazin-1-yl}benzoate 2.0 g of the title compound was obtained in the same manner as in Example 168 from 1.45 g methyl [4-(6-bromo-4-quinazolinyl)piperidino]benzoate and 1.50 g 1-trityl-1H-4-pyrazolylboronic acid.

$^1$H-NMR (CDCl$_3$)

δ: 3.42–3.45(m, 4H), 3.88–3.96(m, 7H), 7.17–7.26(m, 6H), 7.32–7.38(m, 10H), 7.44–7.50(m, 1H), 7.58(m, 1H), 7.64–7.72(m, 3H), 7.83(dd, J=8.8, 2.0 Hz, 1H), 7.88(d, J=8.8 Hz, 1H), 7.92(d, J=2.0 Hz, 1H), 8.73(s, 1H)

Example 829

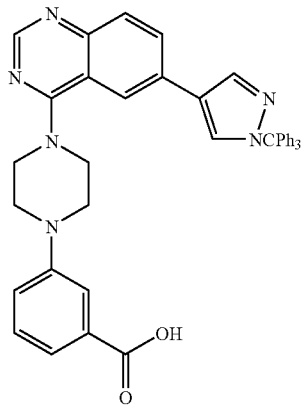

714

3-{4-[6-(1-Trityl-1H-pyrazolyl)-4-quinazolinyl]piperazin-1-yl}benzoic acid

To a solution of 1.0 g methyl 3-[4-(6-bromo-4-quinazolinyl)piperidino]benzoate (compound in Example 828) in tetrahydrofuran/ethanol was added a 15-fold equivalent of 2 N aqueous sodium hydroxide, and the mixture was heated for about 2 hours under reflux. The solution was acidified with 2 N hydrochloric acid, extracted with dichloromethane, dried, and then concentrated to give 900 mg of the title compound.

$^1$H-NMR (CDCl$_3$)

δ: 3.00–3.18(m, 4H), 3.48–3.73(m, 4H), 7.06–7.14(m, 6H), 7.14–7.23(m, 9H), 7.33–7.35(m, 1H), 7.44–7.49(m, 1H), 7.52–7.57(m, 3H), 7.62–7.69(m, 3H), 7.88(s, 1H), 8.48(s, 1H)

Example 830

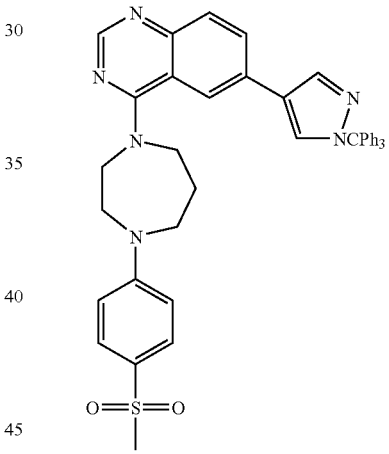

4-[4-(4-Methylsulfonyl)phenyl]-1,4-diazepan-1-yl}-6-(1-trityl-1H-4-pyrazolyl) quinazoline 16 mg of the title compound was obtained in the same manner as in Example 168 from 100 mg 4-[4-(6-bromo-4-quinazolinyl)-1,4-diazepan-1-yl]phenyl methylsulfone (compound in Production Example 348) and 121 mg 1-trityl-1H-4-pyrazolylboronic acid.

$^1$H-NMR (CDCl$_3$)

δ: 1.94–2.00(m, 4H), 3.05(s, 3H), 3.23–3.26(m, 2H), 3.33–3.36(m, 2H), 3.54–3.58(m, 2H), 6.88–6.94(m, 6H), 7.15–7.19(m, 9H), 7.30(d, J=8.0 Hz, 1H), 7.31(d, J=3.2 Hz, 1H), 7.36(d, J=8.0 Hz, 1H), 7.38(d, J=8.0 Hz, 1H), 7.43(s, 1H), 7.45–7.48(m, 2H), 7.62(s, 1H), 7.82(m, 2H)

Example 831

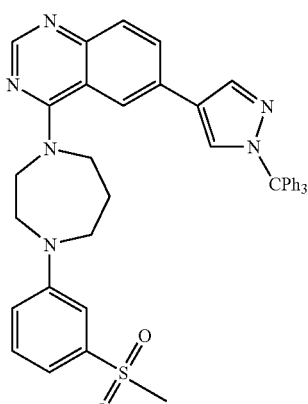

4-{4-(3-Methylsulfonyl)phenyl}-1,4-diazepan-1-yl}-6-(1-trityl-1H-4-pyrazolyl) quinazoline 15 mg of the title compound was obtained in the same manner as in Example 168 from 176 mg 3-[4-(6-bromo-4-quinazolinyl)-1,4-diazepan-1-yl]phenyl methylsulfone (compound in Production Example 349) and 204 mg 1-trityl-1H-4-pyrazolylboronic acid.
$^1$H-NMR (CDCl$_3$)
δ: 2.18–2.21(m, 2H), 3.00(s, 3H), 3.69–3.72(m, 2H), 3.84–3.87(m, 4H), 4.10–4.16(m, 2H), 6.96(dd, J=8.8, 2.4 Hz, 1H), 7.22–7.25 (m, 8H), 7.34–7.38(m, 10H), 7.67(s, 1H), 7.78(dd, J=8.8, 2.0 Hz, 1H), 7.82(d, J=8.8 Hz, 1H), 7.93(d, J=2.0 Hz, 1H), 8.00(s, 1H), 8.59(s, 1H)

Example 832

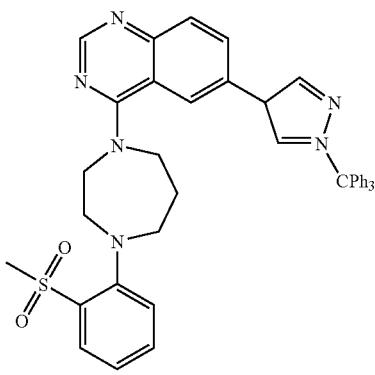

4-{4-[2-(Methylsulfonyl)phenyl]-1,4-diazepan-1-yl}-6-(1-trityl-1H-4-pyrazolyl) quinazoline 166 mg of the title compound was obtained in the same manner as in Example 168 from 191 mg 2-[4-(6-bromo-4-quinazolinyl)-1,4-diazepan-1-ylphenyl] methylsulfone (compound in Production Example 350) and 232 mg 1-trityl-1H-4-pyrazolylboronic acid.
$^1$H-NMR (CDCl$_3$)
δ: 2.24–2.32(m, 2H), 3.25–3.28(m, 2H), 3.28(s, 3H), 3.47(dd, J=5.2, 5.2 Hz, 2H), 4.09–4.12(m, 2H), 4.15–4.20 (m, 2H), 7.19–7.22(m, 6H), 7.30–7.33(m, 9H), 7.34–7.41 (m, 2H), 7.62(ddd, J=8.0, 8.0, 1.6 Hz, 1H), 7.66(s, 1H), 7.77(dd, J=8.8, 1.6 Hz, 1H), 7.83(d, J=8.8 Hz, 1H), 7.98(s, 1H), 8.01(d, J=1.6 Hz, 1H), 8.10(dd, J=8.0, 1.6 Hz, 1H), 8.60(s, 1H)

Example 833

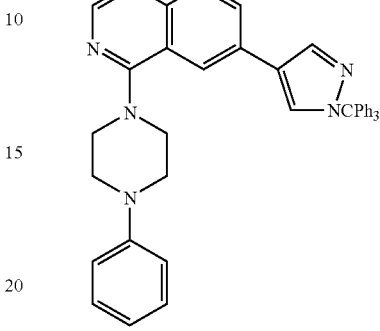

4-(4-Phenyl-piperazin-1-yl)-6-(1-trityl-1H-pyrazol-4-yl)-quinazoline 189 mg of the title compound was obtained in the same manner as in Example 168 from 288 mg 6-bromo-4-(4-phenylpiperazin-1-yl) quinazoline (compound in Production Example 351) and 436 mg 1-trityl-1H-4-pyrazolylboronic acid.
$^1$H-NMR (CDCl$_3$)
δ: 3.38(dd, J=5.2, 5.2 Hz, 2H), 3.38(dd, J=5.2, 5.2 Hz, 2H), 3.91(dd, J=5.2, 5.2 Hz, 2H), 3.91(dd, J=5.2, 5.2 Hz, 2H), 6.94(dd, J=8.4, 8.4 Hz, 1H), 7.00(d, J=8.4 Hz, 2H), 7.20–7.25(m, 6H), 7.38–7.31(m, 11H), 7.71(s, 1H), 7.82(dd, J=8.8, 1.6 Hz, 1H), 7.87(d, J=8.8 Hz, 1H), 7.93(d, J=1.6 Hz, 1H), 8.03(s, 1H), 8.72(s, 1H)

Example 834

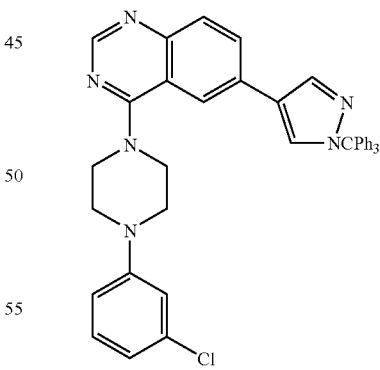

4-[4-(3-Chlorophenyl)piperazin-1-yl]-6-(1-trityl-1H-pyrazolyl) quinazoline 603 mg of the title compound was obtained in the same manner as in Example 168 from 491 mg 6-bromo-4-[4-(3-chlorophenyl)piperazino]quinazoline (compound in Production Example 352) and 708 mg 1-trityl-1H-4-pyrazolylboronic acid.

¹H-NMR (CDCl₃)

δ: 3.36–3.42(m, 4H), 3.86–3.90(m, 4H), 6.86–6.91(m, 2H), 6.96(s, 1H), 7.15–7.25(m, 10H), 7.30–7.40(m, 6H), 7.71(s, 1H), 7.84(d, J=8.8, 2.0 Hz, 1H), 7.89(d, J=8.8 Hz, 1H), 7.92(d, J=2.0 Hz, 1H), 8.04(s, 1H), 8.74(s, 1H)

Example 835

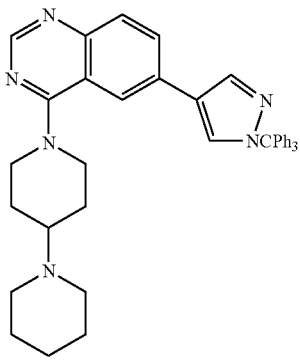

4-1,4'-Bipiperidinyl-1'-yl-6-(1-trityl-1H-pyrazol-4-yl) quinazoline 200 mg of the title compound was obtained in the same manner as in Example 168 from 424 mg 4-1,4'-piperidinyl-1'-yl-6-bromoquinazoline (compound in Production Example 353) and 641 mg 1-trityl-1H-4-pyrazolylboronic acid.

¹H-NMR (CDCl₃)

δ: 1.45–1.55(m, 2H), 1.61–1.70(m, 4H), 1.70–1.82(m, 2H), 1.92–2.00(m, 2H), 2.58(m, 5H), 3.06(dd, J=12.8, 12.8 Hz, 2H), 4.37(d, J=12.8 Hz, 2H), 7.25–7.21(m, 6H), 7.34–7.37(m, 9H), 7.70(s, 1H), 7.79(dd, J=8.8, 1.6 Hz, 1H), 7.83(d, J=8.8 Hz, 1H), 7.87(s, 1H), 8.03(s, 1H), 8.67(s, 1H)

Example 836

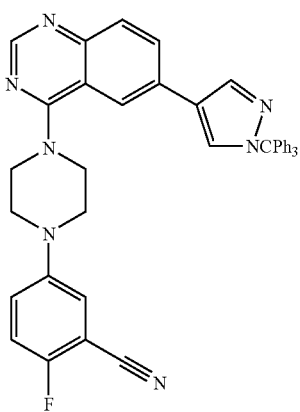

2-Fluoro-5-{4-[6-(1-trityl-1H-4-pyrazolyl)-4-quinazolinyl]piperazin-1-yl} benzonitrile 284 mg of the title compound was obtained in the same manner as in Example 168 from 200 mg 5-[4-(6-bromo-quinazolin-4-yl)piperazin-1-yl]-2-fluorobenzonitrile (compound in Production Example 356) and 275 mg 1-trityl-1H-4-pyrazolylboronic acid.

¹H-NMR (CDCl₃)

δ: 3.33(dd, J=5.2, 5.2 Hz, 2H), 3.33(dd, J=5.2, 5.2 Hz, 2H), 3.90(dd, J=5.2, 5.2 Hz, 2H), 3.90(dd, J=5.2, 5.2 Hz, 2H), 7.10–7.24(m, 9H), 7.34–7.36(m, 9H), 7.72(s, 1H), 7.82(dd, J=8.8, 1.6 Hz, 1H), 7.89(d, J=8.8 Hz, 1H), 7.91(d, J=1.6 Hz, 1H), 8.02(s, 1H), 8.74(s, 1H)

Example 837

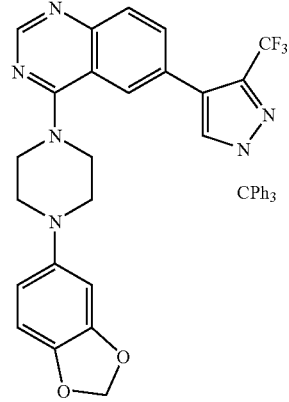

4-[4-(1,3-Benzodioxol-5-yl)piperazin-1-yl]-6-[3-(trifluoromethyl)-1-trityl-1H-4-pyrazolyl] quinazoline 30 mg of the title compound was obtained in the same manner as in Example 168 from 62 mg 4-[4-(1,3-benzo-dioxol-5-yl)piperazin-1-yl]-6-bromoquinazoline (compound in Production Example 359) and 106 mg 3-trifluo-romethyl-1-trityl-1H-4-pyrazolylboronic acid (compound in Production Example 31).

¹H-NMR (CDCl₃)

δ: 3.24–3.30(m, 4H), 3.86–3.92(m, 4H), 5.93(s, 2H), 6.44(dd, J=8.4, 2.0 Hz, 1H), 6.63(d, J=2.0 Hz, 1H), 6.76(d, J=8.4 Hz, 1H), 7.17–7.20(m, 6H), 7.33–7.37(m, 9H), 7.51(s, 1H), 7.67(dd, J=10, 0.8 Hz, 1H), 7.87(d, J=10 Hz, 1H), 8.02(d, J=0.8 Hz, 1H), 8.74(s, 1H)

Example 838

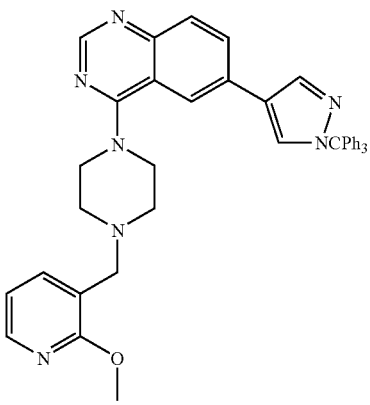

4-{4-[(2-Methoxy-3-pyridyl)methyl]piperazin-1-yl}-6-(1-trityl-1H-4-pyrazolyl) quinazoline 220 mg of the title compound was obtained in the same manner as in Example 168 from 160 mg 3-{[4-(6-bromo-4-quinazolinyl)piperazin-1-yl]methyl}-2-pyridyl methyl ether (compound in Production Example 362) and 273 mg 1-trityl-1H-4-pyrazolylboronic acid.

$^1$H-NMR (CDCl$_3$)

δ: 2.61–2.63(m, 4H), 3.54(s, 2H), 3.71–3.73(m, 4H), 3.91(s, 3H), 6.85(dd, J=7.2, 4.8 Hz, 1H), 7.13–7.17(m, 6H), 7.26–7.29(m, 9H), 7.61(s, 1H), 7.64(dd, J=7.2, 2.0 Hz, 1H), 7.71(dd, J=8.8, 2.0 Hz, 1H), 7.77(d, J=8.8 Hz, 1H), 7.81(d, J=2.0 Hz, 1H), 7.94(s, 1H), 8.04(dd, J=4.8, 2.0 Hz, 1H), 8.61(s, 1H)

Example 839

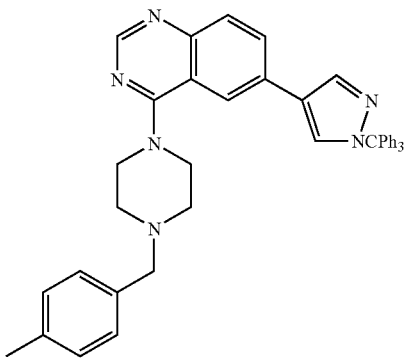

4-[4-(4-Methylbenzyl)piperazin-1-yl]-6-(1-trityl-1H-pyrazolyl) quinazoline 100 mg 4-piperazin-1-yl-6-(1-trityl-1H-pyrazolyl) quinazoline (compound in Example 827) and 54 mg 1-chloromethyl-4-methyl benzene were dissolved in N,N-dimethylformamide, then 79 mg potassium carbonate was added thereto, and the mixture was stirred for about 5 hours at room temperature. The reaction solution was concentrated, and the residue was purified by silica gel column chromatography to give 150 mg of the title compound.

$^1$H-NMR (CDCl$_3$)

δ: 2.58–2.65(m, 4H), 3.57(s, 2H), 3.70–3.80(m, 4H), 4.56(s, 3H), 7.13–7.17(m, 6H), 7.19–7.22(m, 2H), 7.27(d, J=8.0 Hz, 2H), 7.32–7.35(m, 9H), 7.66(d, J=0.8 Hz, 1H), 7.76(dd, J=8.8, 1.2 Hz, 1H), 7.82(d, J=8.8 Hz, 1H), 7.86(d, J=1.2 Hz, 1H), 7.99(d, J=0.8 Hz, 1H), 8.66(s, 1H)

Example 840

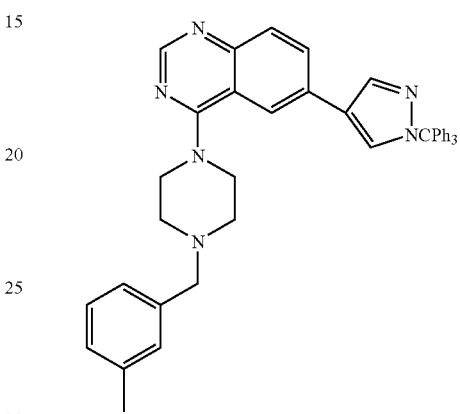

4-[4-(3-Methylphenyl)piperazin-1-yl]-6-(1-trityl-1H-4-pyrazolyl) quinazoline

The title compound was obtained by the same method as in Example 839 from 100 mg 4-piperazin-1-yl-6-(1-trityl-1H-pyrazolyl) quinazoline (compound in Example 827) and 54 mg 1-bromomethyl-3-methylbenzene.

$^1$H-NMR (CDCl$_3$)

δ: 2.62–2.65(m, 4H), 3.57(s, 2H), 3.75–3.78(m, 4H), 4.56(s, 3H), 7.10–7.25(m, 9H), 7.32–7.35(m, 10H), 7.67(d, J=1.2 Hz, 1H), 7.76(dd, J=8.8, 2.0 Hz, 1H), 7.83(d, J=8.8 Hz, 1H), 7.87(d, J=2.0 Hz, 1H), 8.00(d, J=1.2 Hz, 1H), 8.67(s, 1H),

Example 841

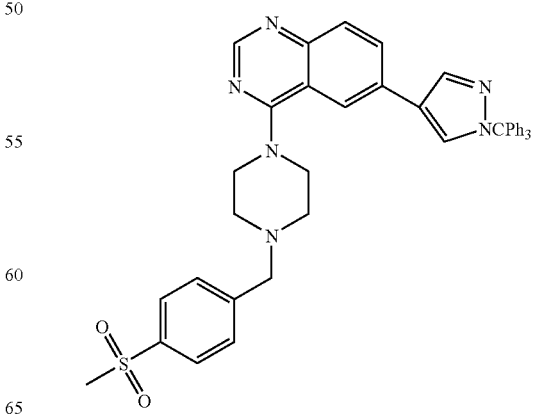

4-{4-[4-(Methylsulfonyl)benzyl)piperazin-1-yl}-6-
(1-trityl-1H-4-pyrazolyl) quinazoline 96 mg of the title compound was obtained by the same method as in Example 839 from 100 mg 4-piperazin-1-yl-6-(1-trityl-1H-4-pyrazolyl) quinazoline (compound in Example 827) and 152 mg 4-(methylsulfonyl)benzyl methanesulfonic acid.

$^1$H-NMR (CDCl$_3$)

δ: 2.65–2.67(m, 4H), 3.08(s, 3H), 3.69(s, 2H), 3.78(bd, 4H), 7.20–7.23(m, 6H), 7.33–7.36(m, 9H), 7.62(d, J=8.8 Hz, 2H), 7.69(s, 1H), 7.77(dd, J=8.8, 2.0 Hz, 1H), 7.84(d, J=8.8 Hz, 1H), 7.88(d, J=2.0 Hz, 1H), 7.94(d, J=8.8 Hz, 2H), 8.00(s, 1H), 8.69(s, 1H),

Example 842

4-{4-[2-(Methylsulfonyl)benzyl]piperazin-1-yl}-6-
(1-trityl-1H-pyrazolyl) quinazoline 96 mg of the title compound was obtained in the same manner as in Example 839 from 100 mg 4-piperazin-1-yl-6-(1-trityl-1H-4-pyrazolyl) quinazoline (compound in Example 827) and 152 mg 2-(methylsulfonyl)benzyl methanesulfonic acid.

$^1$H-NMR (CDCl$_3$)

δ: 2.72–2.78(m, 4H), 3.45(s, 3H), 3.66–3.74(m, 4H), 4.06(s, 2H), 7.21–7.25(m, 6H), 7.34–7.37(m, 9H), 7.46(dd, J=7.6, 1.2 Hz, 1H), 7.53(ddd, J=7.6, 7.6, 1.2 Hz, 1H), 7.62(ddd, J=7.6, 7.6, 1.2 Hz, 1H), 7.70(d, J=0.8 Hz, 1H), 7.78(dd, J=8.8, 2.0 Hz, 1H), 7.85(d, J=8.8 Hz, 1H), 7.88(d, J=2.0 Hz, 1H), 8.01(d, J=0.8 Hz, 1H), 8.15(dd, J=7.6, 1.2 Hz, 1H), 8.69(s, 1H)

Example 843

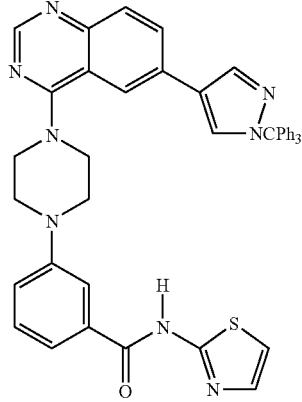

N1-(1,3-Thiazol-2-yl)-3-{4-[6-(1-trityl-1H-4-pyra-zolyl)-4-quinazolinyl]piperazin-1-yl} benzamide 118 mg 3-{4-[6-(1-trityl-1H-4-pyrazolyl)-4-quinazolinyl]piperazin-1-yl}benzoic acid (compound in Example 828), 18 mg 1,3-thiazol-2-amine, 20 mg triethylamine and 89 mg benzotriazol-1-yloxy-tris(dimethylamino)phosphonium hexafluorophosphate were dissolved in dichloromethane and stirred for 12 hours. The reaction solution was concentrated and purified by silica gel column chromatography, to give 150 mg of the title compound.

$^1$H-NMR (CDCl$_3$)

δ: 3.47–3.49(m, 4H), 3.90–3.93(m, 4H), 7.20(d, J=3.6 Hz, 1H), 7.19–7.23(m, 7H), 7.33–7.35(m, 9H), 7.40(d, J=7.6 Hz, 1H), 7.44(d, J=3.6 Hz, 1H), 7.46(dd, J=7.6, 7.6 Hz, 1H), 7.63(m, 1H), 7.71(s, 1H), 7.82(dd, J=8.8, 1.6 Hz, 1H), 7.89(d, J=8.8 Hz, 1H), 7.93(d, J=1.6 Hz, 1H), 8.03(s, 1H), 8.74(s, 1H)

Example 844

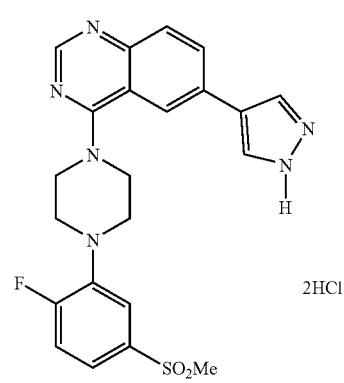

4-[4-(2-Fluoro-5-methylsulfonylphenyl)piperazin-1-yl]-6-(1H-4-pyrazolyl)quinazoline dihydrochloride 211 mg 4-[4-(2-fluoro-5-methylsulfonylphenyl)piperazin-1-yl]-6-(1-trityl-1H-4-pyrazolyl) quinazoline obtained in Example 730 was subjected to deprotection of the trityl group and converted into the corresponding hydrochloride by the same method as in Example 163, to give 108 mg of the title compound as pale yellow crystals.

$^1$H-NMR (DMSO-$d_6$)

δ: 3.25(s, 3H), 3.35–3.54(m, 4H), 4.40–4.50(m, 4H), 7.46–7.61(m, 3H), 7.92(d, J=8.4 Hz, 1H), 8.28–8.37(m, 4H), 8.89(s, 1H)

MS m/e (ESI) 453 (MH$^+$)

Example 845

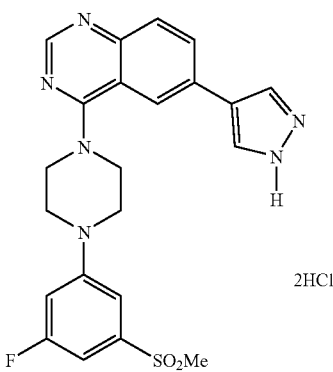

4-[4-(3-Fluoro-5-methylsulfonylphenyl)piperazin-1-yl]-6-(1H-4-pyrazolyl)quinazoline dihydrochloride 130 mg 4-[4-(3-fluoro-5-methylsulfonylphenyl)piperazin-1-yl]-6-(1-trityl-1H-4-pyrazolyl)quinazoline obtained in Example 731 was subjected to deprotection of the trityl group and converted into the corresponding hydrochloride by the same method as in Example 163, to give 62 mg of the title compound as pale yellow crystals. $^1$H-NMR data are those of the salt in a free form.

$^1$H-NMR (CDCl$_3$)

δ: 3.07(s, 3H), 3.50–3.60(m, 4H), 3.90–4.02(m, 4H), 6.81–6.89(m, 1H), 7.06–7.12(m, 1H), 7.24–7.30(m, 2H), 7.90–7.99(m, 3H), 8.01(s, 1H), 8.77(s, 1H)

MS m/e (ESI) 453 (MH$^+$)

Example 846

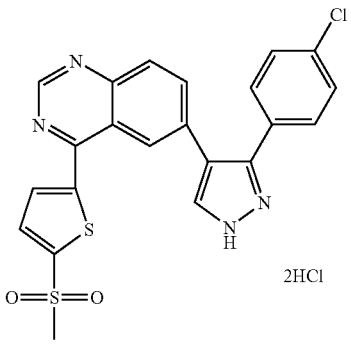

6-[3-(4-Chlorophenyl)-1H-pyrazol-4-yl]-4-(5-methylsulfonylthiophen-2-yl)quinazoline dihydrochloride 31 mg of the title compound was obtained as orange crystals by the same reaction as in Example 67 from 78 mg 6-[3-(4-chlorophenyl)-1-trityl-1H-pyrazol-4-yl]-4-(5-methylsulfonylthiophen-2-yl) quinazoline (compound in Example 733).

$^1$H-NMR (DMSO-$d_6$)

δ: 3.45(s, 3H), 7.42–7.54(m, 5H), 7.73(d, J=4.0 Hz, 1H), 8.02–8.09(m, 2H), 8.16–8.20(m, 1H), 8.27(s, 1H), 9.25(s, 1H)

MS m/e (ESI) 499 (MH$^+$ MeOH adduct)

Example 847

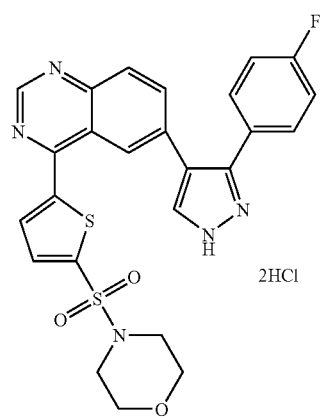

6-[3-(4-Chlorophenyl)-1H-pyrazol-4-yl]-4-[5-(morpholine-4-sulfonyl)thiophen-2-yl]quinazoline dihydrochloride 25 mg of the title compound was obtained as orange crystals by the same reaction as in Example 68 from 86 mg 6-[3-(4-fluorophenyl)-1-trityl-1H-pyrazol-4-yl]-4-[5-(morpholine-4-sulfonyl)thiophen-2-yl] quinazoline (compound in Example 734).

$^1$H-NMR (DMSO-$d_6$)

δ: 2.96–3.04(m, 4H), 3.66–3.74(m, 4H), 7.25–7.32(m, 2H), 7.45–7.58(m, 4H), 8.02–8.10(m, 2H), 8.21(s, 1H), 8.27(s, 1H), 9.23(s, 1H)

MS m/e (ESI) 554 (MH$^+$ MeOH adduct)

Example 848

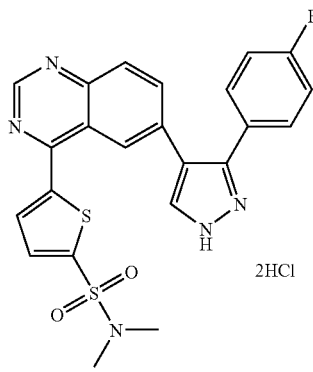

5-{6-[3-(4-Fluorophenyl)-1H-pyrazol-4-yl]quinazo-lin-4-yl}thiophen-2-sulfonic acid dimethylamide dihydrochloride 26 mg of the title compound was obtained as orange crystals by the same reaction as in Example 68 from 74 mg 5-{6-[3-(4-fluorophenyl)-1-trityl-1H-pyrazol-4-yl]-quinazolin-4-yl}thiophen-2-sulfonic acid dimethylamide (compound in Example 735).

$^1$H-NMR (DMSO-$d_6$)

δ: 2.73(s, 6H), 7.23–7.32(m, 2H), 7.45–7.52(m, 3H), 7.54(d, J=4.0 Hz, 1H), 8.05(d, J=8.6 Hz, 1H), 8.09(dd, J=8.6, 1.2 Hz, 1H), 8.20(brs, 1H), 8.27(brs, 1H), 9.22(s, 1H)

MS m/e (ESI) 512 (MH$^+$ MeOH adduct)

Example 849

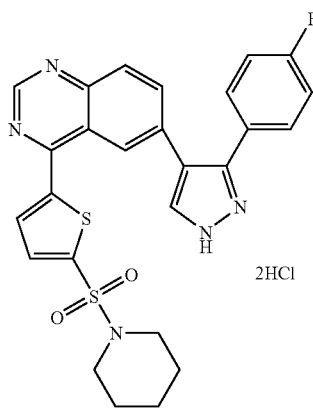

6-[3-(4-Fluorophenyl)-1H-pyrazol-4-yl]-4-[5-(piperidin-1-sulfonyl)thiophen-2-yl]quinazoline dihydrochloride 26 mg of the title compound was obtained as orange crystals by the same reaction as in Example 68 from 79 mg 6-[3-(4-fluorophenyl)-1-trityl-1H-pyrazol-4-yl]-4-[5-(piperidin-1-sulfonyl)thiophen-2-yl] quinazoline (compound in Example 736).

$^1$H-NMR (DMSO-$d_6$)

δ: 1.38–1.46(m, 2H), 1.56–1.64(m, 4H), 2.96–3.04(m, 4H), 7.24–7.33(m, 2H), 7.45–7.53(m, 4H), 8.05(d, J=8.6 Hz, 1H), 8.08(dd, J=8.6, 1.6 Hz, 1H), 8.18–8.22(m, 1H), 8.27(s, 1H), 9.22(s, 1H)

MS m/e (ESI) 552 (MH$^+$ MeOH adduct)

Example 850

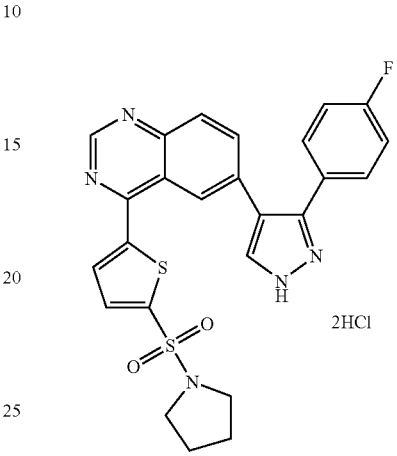

6-[3-(4-Fluorophenyl)-1H-pyrazol-4-yl]-4-[5-(pyrrolidine-1-sulfonyl)thiophen-2-yl]quinazoline dihydrochloride 34 mg of the title compound was obtained as yellow crystals by the same reaction as in Example 68 from 95 mg 6-[3-(4-fluorophenyl)-1-trityl-1H-pyrazol-4-yl]-4-[5-(pyrrolidine-1-sulfonyl)thiophen-2-yl] quinazoline (compound in Example 737).

$^1$H-NMR (DMSO-$d_6$)

δ: 1.68–1.78(m, 4H), 3.18–3.41(m, 4H), 7.22–7.34(m, 2H), 7.42–7.52(m, 3H), 7.58(d, J=4.4 Hz, 1H), 8.02–8.11(m, 2H), 8.19(brs, 1H), 8.27(s, 1H), 9.22(s, 1H)

MS m/e (ESI) 538 (MH$^+$ MeOH adduct)

Example 851

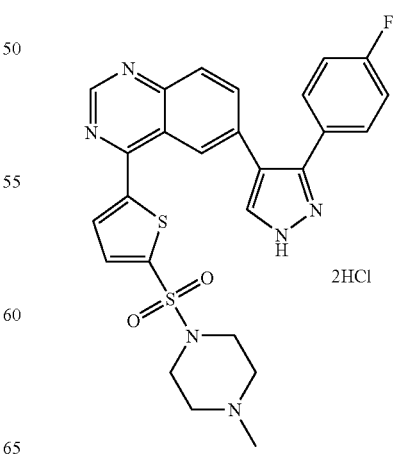

6-[3-(4-Fluorophenyl)-1H-pyrazol-4-yl]-4-[5-(4-methylpiperazine-1-sulfonyl)thiophen-2-yl]quinazoline dihydrochloride 35 mg of the title compound was obtained as orange crystals by the same reaction as in Example 68 from 87 mg 6-[3-(4-fluorophenyl)-1-trityl-1H-pyrazol-4-yl]-4-[5-(4-methylpiperazine-1-sulfonyl)thiophen-2-yl] quinazoline (compound in Example 738).
$^1$H-NMR (DMSO-$d_6$)
δ: 2.40–2.56(m, 1H), 2.77(brs, 3H), 2.85–2.74(m, 1H), 3.16–3.27(m, 2H), 3.47–3.56(m, 2H), 3.80–3.88(m, 2H), 7.26–7.34(m, 2H), 7.44–7.52(m, 2H), 7.55(d, J=4.0 Hz, 1H), 7.62 (d, J=4.0 Hz, 1H), 8.02–8.14(m, 2H), 8.21(br, 1H), 8.28(s, 1H), 9.24(s, 1H)
MS m/e (ESI) 535 (MH$^+$)

Example 852

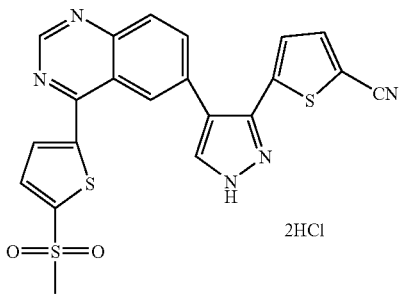

2HCl

5-{4-[4-(5-Methylsulfonylthiophen-2-yl)quinazolin-6-yl]-1H-pyrazol-3-yl}thiophen-2-carbonitrile dihydrochloride 74 mg of the title compound was obtained as yellow crystals by the same reaction as in Example 68 from 180 mg 5-{4-[4-(5-methylsulfonylthiophen-2-yl)quinazolin-6-yl]-1-trityl-1H-pyrazol-3-yl}thiophen-2-carbonitrile (compound in Example 740).
$^1$H-NMR (DMSO-$d_6$)
δ: 3.46(s, 3H), 7.12(brs, 1H), 7.82–7.98(m, 3H), 8.00(dd, J=8.8, 1.6 Hz, 1H), 8.13(d, J=8.8 Hz, 1H), 8.33(brs, 1H), 8.38(s, 1H), 9.30(s, 1H)
MS m/e (ESI) 486 (MH$^+$ MeOH adduct)

Example 853

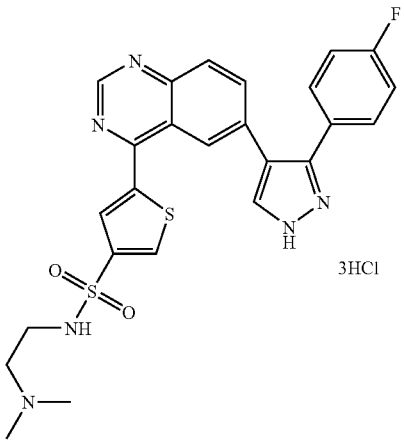

3HCl

5-{6-[3-(4-Fluorophenyl)-1H-pyrazol-4-yl]quinazolin-4-yl}thiophen-3-sulfonic acid (2-dimethylaminoethyl)amide trihydrochloride 14 mg of the title compound was obtained as yellow crystals by the same reaction as in Example 68 from 30 mg 5-{6-[3-(4-fluorophenyl)-1-trityl-1H-pyrazol-4-yl]quinazolin-4-yl}thiophen-3-sulfonic acid (2-dimethylaminoethyl)amide (compound in Example 741).
$^1$H-NMR (DMSO-$d_6$)
δ: 2.72–2.77(m, 6H), 3.15–3.23(m, 2H), 3.50–4.00(m, 2H), 7.14–7.22(m, 2H), 7.40–7.46(m, 2H), 7.85(dd, J=8.8, 1.6 Hz, 1H), 8.01(d, J=8.8 Hz, 1H), 8.17(d, J=1.2 Hz, 1H), 8.26(s, 1H), 8.37 (d, J=1.6 Hz, 1H), 8.56(d, J=1.2 Hz, 1H), 9.25(s, 1H)
MS m/e (ESI) 523 (MH$^+$)

Example 854

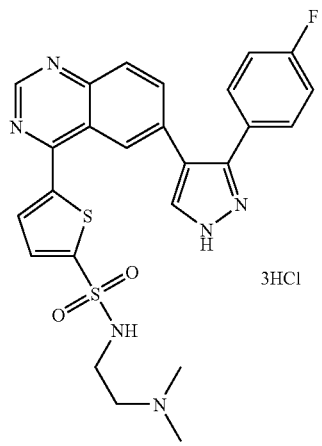

3HCl

5-{6-[3-(4-Fluorophenyl)-1H-pyrazol-4-yl]quinazolin-4-yl}thiophen-2-sulfonic acid (2-dimethylaminoethyl)amide trihydrochloride 61 mg of the title compound was obtained as orange crystals by the same reaction as in Example 68 from 83 mg 5-{6-[3-(4-fluorophenyl)-1-trityl-1H-pyrazol-4-yl]quinazolin-4-yl}thiophen-2-sulfonic acid (2-dimethylaminoethyl)amide (compound in Example 742).
$^1$H-NMR (DMSO-$d_6$)
δ: 2.76(s, 3H), 2.77(s, 3H), 3.16–3.24(m, 2H), 3.25–3.32 (m, 2H), 7.30(t, J=8.8 Hz, 2H), 7.39(d, J=4.2 Hz, 1H), 7.46–7.52(m, 2H), 7.59(d, J=4.2 Hz, 1H), 8.06(brs, 2H), 8.19(s, 1H), 9.26(s, 1H), 9.22(s, 1H)
MS m/e (ESI) 523 (MH$^+$)

Example 855

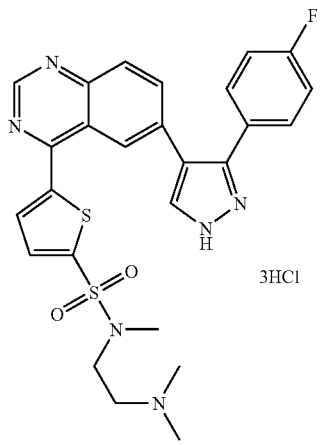

5-{6-[3-(4-Fluorophenyl)-1H-pyrazol-4-yl]quinazolin-4-yl}-thiophen-2-sulfonic acid (2-dimethylaminoethyl)methylamide trihydrochloride 38 mg of the title compound was obtained as pale orange crystals by the same reaction as in Example 68 from 66 mg 5-{6-[3-(4-fluorophenyl)-1-trityl-1H-pyrazol-4-yl]-quinazolin-4-yl}thiophen-2-sulfonic acid (2-dimethylaminoethyl)methylamide (compound in Example 743).

$^1$H-NMR (DMSO-d$_6$)
δ: 2.83(s, 3H), 2.84(s, 6H), 3.33–3.44(m, 4H), 7.25–7.33 (m, 2H), 7.46–7.52(m, 2H), 7.54(d, J=4.0 Hz, 1H), 7.66(d, J=4.0 Hz, 1H), 8.04–8.11(m, 2H), 8.18–8.22(m, 1H), 8.27(s, 1H), 9.24(s, 1H)
MS m/e (ESI) 537 (MH$^+$)

Example 856

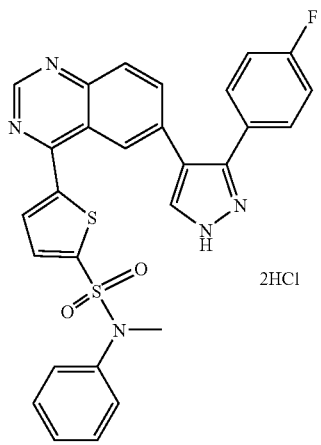

5-{6-[3-(4-Fluorophenyl)-1H-pyrazol-4-yl]quinazolin-4-yl}-thiophen-2-sulfonic acid methylphenylamide dihydrochloride 71 mg mixture of 5-(6-bromoquinazolin-4-yl)-thiophen-2-sulfonic acid methylphenylamide and 5-(6-bromoquinazolin-4-yl)-thiophen-3-sulfonic acid methylphenylamide (compounds in Production Example 378) and 90 mg 3-(4-fluorophenyl)-1-trityl-1H-4-pyrazolylboronic acid (compound in Production Example 25) were reacted in the same manner as in Example 9, to give 114 mg mixture of 5-{6-[3-(4-fluorophenyl)-1-trityl-1H-pyrazol-4-yl]quinazolin-4-yl}thiophen-2-sulfonic acid methylphenylamide and 5-{6-[3-(4-fluorophenyl)-1-trityl-1H-pyrazol-4-yl]quinazolin-4-yl}thiophen-3-sulfonic acid methylphenylamide. The product was subjected to the same reaction as in Example 618, and the positional isomers were separated and purified by silica gel column chromatography, dissolved in dichloromethane/methanol, and recrystallized from ethanol/ether, to give 23 mg of the title compound as orange crystals.

$^1$H-NMR (DMSO-d$_6$)
δ: 3.25(s, 3H), 7.18–7.52(m, 11H), 8.05(d, J=8.8 Hz, 1H), 8.08 (dd, J=8.8, 1.6 Hz, 1H), 8.17(d, J=1.6 Hz, 1H), 8.26(s, 1H), 9.20(s, 1H)
MS m/e (ESI) 486 (MH$^+$ MeOH adduct)

Example 857

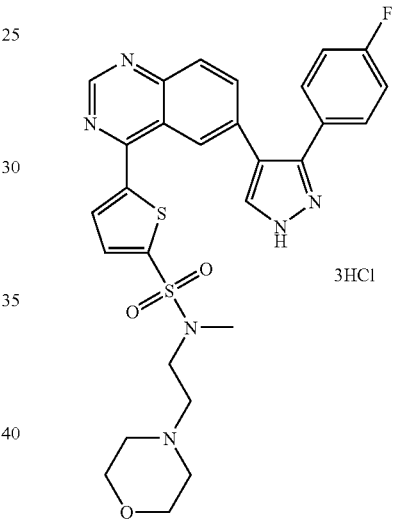

5-{6-[3-(4-Fluorophenyl)-1H-pyrazol-4-yl]quinazolin-4-yl}-thiophen-2-sulfonic acid methyl-(2-morpholin-4-yl-ethyl)amide trihydrochloride 100 mg 5-{6-[3-(4-fluorophenyl)-1-trityl-1H-pyrazol-4-yl]quinazolin-4-yl}thiophen-2-sulfonic acid methylamide (compound in Example 745), 29 mg 4-(2-chloroethyl)morpholine hydrochloride and 21 μL triethylamine were reacted in the same manner as in Example 746, to give 60 mg 5-{6-[3-(4-fluorophenyl)-1-trityl-1H-pyrazol-4-yl]quinazolin-4-yl}thiophen-2-sulfonic acid methyl-(2-morpholin-4-yl-ethyl)amide. This product was subjected to the same reaction as in Example 618, dissolved in dichloromethane/methanol and recrystallized from ethanol/ether, to give 45 mg of the title compound as yellow crystals.

$^1$H-NMR (DMSO-d$_6$)
δ: 2.85(s, 3H), 3.06–3.21(m, 2H), 3.38–3.84(m, 8H), 3.94–4.03(m, 2H), 7.24–7.32(m, 2H), 7.46–7.52(m, 2H), 7.54(d, J=4.0 Hz, 1H), 7.65(d, J=4.0 Hz, 1H), 8.04–8.11(m, 2H), 8.18–8.22(m, 1H), 8.27(s, 1H), 9.23(s, 1H)
MS m/e (ESI) 579 (MH$^+$)

Example 858

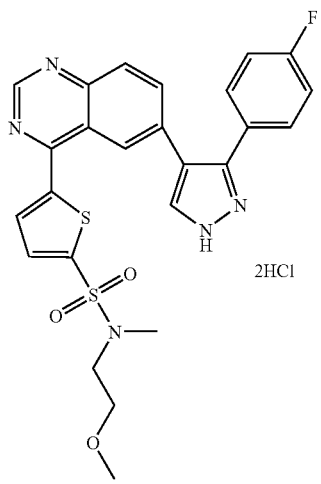

5-{6-[3-(4-Fluorophenyl)-1H-pyrazol-4-yl]quinazolin-4-yl}-thiophen-2-sulfonic acid (2-methoxyethyl)-methylamide dihydrochloride 100 mg 5-{6-[3-(4-fluorophenyl)-1-trityl-1H-pyrazol-4-yl]quinazolin-4-yl}thiophen-2-sulfonic acid methylamide (compound in Example 745) and 15 μL 2-chloroethyl methyl ether were reacted in the same manner as in Example 746, to give 90 mg 5-{6-[3-(4-fluorophenyl)-1-trityl-1H-pyrazol-4-yl]quinazolin-4-yl}thiophen-2-sulfonic acid (2-methoxyethyl)-methylamide. This product was subjected to the same reaction as in Example 618, dissolved in dichloromethane/methanol and recrystallized from ethanol/ether, to give 35 mg of the title compound as orange crystals.

$^1$H-NMR (DMSO-$d_6$)

δ: 2.82(s, 3H), 3.20–3.25(m, 2H), 3.23(s, 3H), 3.47–3.52 (m, 2H), 7.24–7.32(m, 2H), 7.41–7.52(m, 3H), 7.55(d, J=4.2 Hz, 1H), 8.05 (d, J=8.7 Hz, 1H), 8.08(dd, J=8.7, 1.8 Hz, 1H), 8.18–8.22(m, 1H), 8.26(s, 1H), 9.22(s, 1H)

MS m/e (ESI) 556 (MH$^+$)

Example 859

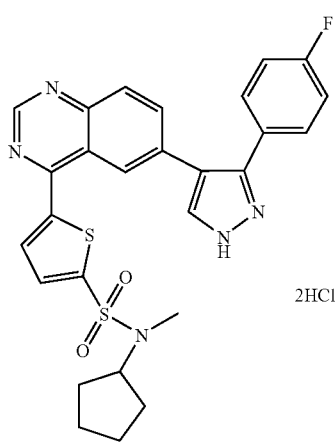

5-{6-[3-(4-Fluorophenyl)-1H-pyrazol-4-yl]quinazolin-4-yl}-thiophen-2-sulfonic acid cyclopentyl-methylamide dihydrochloride 100 mg 5-{6-[3-(4-fluorophenyl)-1-trityl-1H-pyrazol-4-yl]quinazolin-4-yl}thiophen-2-sulfonic acid methylamide (compound in Example 745) and 17 μL cyclopropyl bromide were reacted in the same manner as in Example 746, to give 79 mg 5-{6-[3-(4-fluorophenyl)-1-trityl-1H-pyrazol-4-yl]quinazolin-4-yl}thiophen-2-sulfonic acid cyclopentyl-methylamide. This product was subjected to the same reaction as in Example 618, dissolved in dichloromethane/methanol and recrystallized from ethanol/ether, to give 16 mg of the title compound as yellow crystals.

$^1$H-NMR (DMSO-$d_6$)

δ: 1.35–1.62(m, 8H), 2.74(s, 3H), 7.24–7.32(m, 2H), 7.42(d, J=4.2 Hz, 1H), 7.45–7.52(m, 2H), 7.54(d, J=4.2 Hz, 1H), 8.05(d, J=8.8 Hz, 1H), 8.09(dd, J=8.8, 1.6 Hz, 1H), 8.18(d, J=1.6 Hz, 1H), 8.26(s, 1H), 9.22(s, 1H)

MS m/e (ESI) 566 (MH$^+$ MeOH adduct)

Example 860

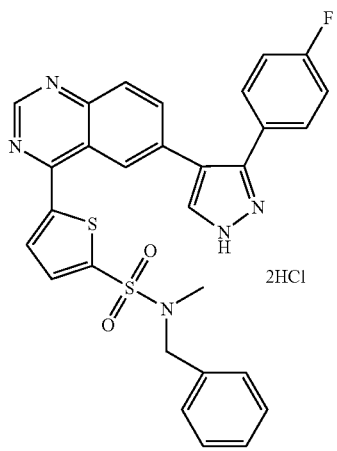

5-{6-[3-(4-Fluorophenyl)-1H-pyrazol-4-yl]quinazolin-4-yl}-thiophen-2-sulfonic acid benzyl-methylamide dihydrochloride 100 mg 5-{6-[3-(4-fluorophenyl)-1-trityl-1H-pyrazol-4-yl]quinazolin-4-yl}thiophen-2-sulfonic acid methylamide (compound in Example 745) and 18 μL benzyl bromide were reacted in the same manner as in Example 746, to give 64 mg 5-{6-[3-(4-fluorophenyl)-1-trityl-1H-pyrazol-4-yl]quinazolin-4-yl}thiophen-2-sulfonic acid benzyl-methylamide. This product was subjected to the same reaction as in Example 618, dissolved in dichloromethane/methanol and recrystallized from ethanol/ether, to give 11 mg of the title compound as orange crystals.

$^1$H-NMR (DMSO-$d_6$)

δ: 2.67(s, 3H), 4.23(s, 2H), 7.25–7.40(m, 7H), 7.46–7.53 (m, 3H), 7.64(d, J=4.0 Hz, 1H), 8.06(d, J=8.4 Hz, 1H), 8.09(dd, J=8.4, 1.2 Hz, 1H), 8.22(d, J=1.2 Hz, 1H), 8.28(s, 1H), 9.24(s, 1H)

MS m/e (ESI) 588 (MH$^+$ MeOH adduct)

Example 861

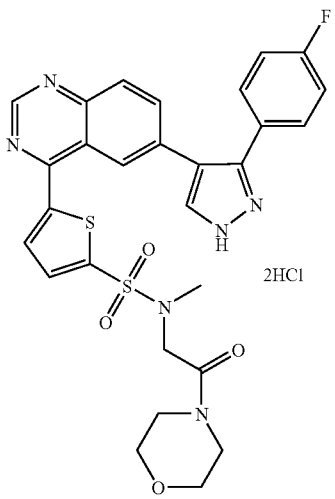

5-{6-[3-(4-Fluorophenyl)-1H-pyrazol-4-yl]quinazo-lin-4-yl}-thiophen-2-sulfonic acid methyl-(2-morpholin-4-yl-2-oxoethyl)amide dihydrochloride 100 mg 5-{6-[3-(4-fluorophenyl)-1-trityl-1H-pyrazol-4-yl]quinazolin-4-yl}thiophen-2-sulfonic acid methylamide (compound in Example 745) and 102 mg 4-(2-chloroacetyl)-morpholine were reacted in the same manner as in Example 746, to give 0.43 g 5-{6-[3-(4-fluorophenyl)-1-trityl-1H-pyrazol-4-yl]quinazolin-4-yl}thiophen-2-sulfonic acid methyl-(2-morpholin-4-yl-2-oxoethyl)amide. This product was subjected to the same reaction as in Example 618, dissolved in dichloromethane/methanol and recrystallized from ethanol/ether, to give 63 mg of the title compound as orange crystals.

$^1$H-NMR (DMSO-$d_6$)

δ: 2.86(s, 3H), 3.35–3.63(m, 8H), 4.16(s, 2H), 7.27–7.34 (m, 2H), 7.44–7.54(m, 3H), 7.63(d, J=4.0 Hz, 1H), 8.05(d, J=9.8 Hz, 1H), 8.09(dd, J=9.8, 1.2 Hz, 1H), 8.23(s, 1H), 8.28(s, 1H), 9.25(s, 1H)

MS m/e (FAB) 593 (MH$^+$ MeOH adduct)

Example 862

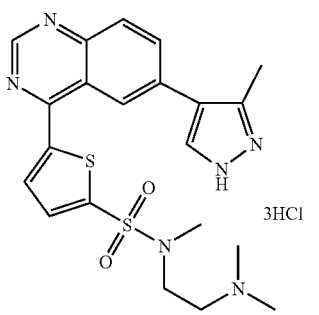

5-[6-(3-Methyl-1H-pyrazol-4-yl)quinazolin-4-yl]
thiophen-2-sulfonic acid (2-dimethylaminoethyl)
methylamide trihydrochloride 43 mg of the title compound was obtained as orange crystals by the same reaction as in Example 68 from 50 mg 5-[6-(3-methyl-1-trityl-1H-pyrazol-4-yl)quinazolin-4-yl] thiophen-2-sulfonic acid (2-dimethylaminoethyl)methylamide (compound in Example 744).

$^1$H-NMR (DMSO-$d_6$)

δ: 2.52(s, 3H), 2.84(s, 3H), 2.85(s, 3H), 2.88(s, 3H), 3.34–3.42(m, 2H), 3.43–3.50(m, 2H), 7.92(d, J=4.2 Hz, 1H), 8.13(s, 1H), 8.16(d, J=4.2 Hz, 1H), 8.28–8.33(m, 2H), 8.46(d, J=2.0 Hz, 1H), 9.27(s, 1H)

MS m/e (ESI) 457 (MH$^+$)

Example 863

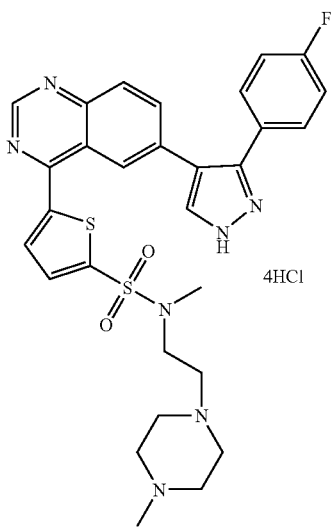

5-{6-[3-(4-Fluorophenyl)-1H-pyrazol-4-yl]quinazo-lin-4-yl}thiophen-2-sulfonic acid methyl-[2-(4-methylpiperazin-1-yl)ethyl]amide tetrahydrochloride A mixture of 100 mg 5-{6-[3-(4-fluorophenyl)-1-trityl-1H-pyrazol-4-yl]quinazolin-4-yl}thiophen-2-sulfonic acid (2-chloroethyl)methylamide (compound in Example 746), 29 μL 1-methyl piperazine, 72 μl triethylamine and 3 mL N,N-dimethylformamide was stirred at 110° C. for 24 hours. Ethyl acetate and water were added to the reaction solution, and the organic layer was separated. The organic layer was washed with water and brine and dried over sodium sulfate, and the solvent was evaporated. The residue was purified by NH silica gel column chromatography (hexane/ethylacetate) to give 41 mg 5-{6-[3-(4-fluorophenyl)-1-trityl-1H-pyrazol-4-yl]quinazolin-4-yl}thio phen-2-sulfonic acid methyl-[2-(4-methylpiperazin-1-yl)ethyl]amide. This product was reacted in the same manner as in Example 68, to give 28 mg of the title compound as yellow crystals.

$^1$H-NMR (DMSO-$d_6$)

δ: 2.80(brs, 3H), 2.87(s, 3H), 3.48–3.90(m, 12H), 7.27–7.34(m, 2H), 7.48–7.56(m, 3H), 7.64(d, J=4.0 Hz, 1H), 8.07–8.10(m, 2H), 8.22(brs, 1H), 8.29(brs, 1H), 9.25(s, 1H)

MS m/e (FAB) 592 (MH$^+$)

Example 864

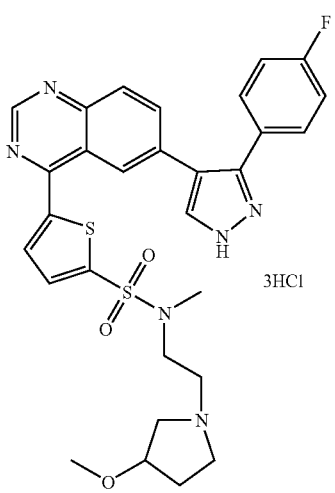

5-{6-[3-(4-Fluorophenyl)-1H-pyrazol-4-yl]quinazo-
lin-4-yl}thiophen-2-sulfonic acid [2-(3-methoxypyr-
rolidin-1-yl)ethyl]methylamide trihydrochloride 23 mg 5-{6-[3-(4-fluorophenyl)-1-trityl-1H-pyrazol-4-yl]quinazolin-4-yl}thiophen-2-sulfonic acid [2-(3-methoxy-pyrrolidin-1-yl)ethyl]methylamide was obtained by the same reaction as in Example 863 from 100 mg 5-{6-[3-(4-fluorophenyl)-1-trityl-1H-pyrazol-4-yl]quinazolin-4-yl}thiophen-2-sulfonic acid (2-chloroethyl)methylamide (compound in Example 746) and 36 mg 3-methoxypyrrolidine hydrochloride. The product was reacted in the same manner as in Example 68, to give 16 mg of the title compound as yellow crystals.

$^1$H-NMR (DMSO-$d_6$)

δ: 2.85(d, J=4.8 Hz, 3H), 3.28(s, 3H), 3.17–4.22(m, 11H), 7.26–7.34(m, 2H), 7.48–7.56(m, 3H), 7.63–7.67(m, 1H), 8.07–8.14 (m, 2H), 8.22(brs, 1H), 8.29(br, 1H), 9.26(s, 1H)

MS m/e (FAB) 593 (MH$^+$)

Example 865

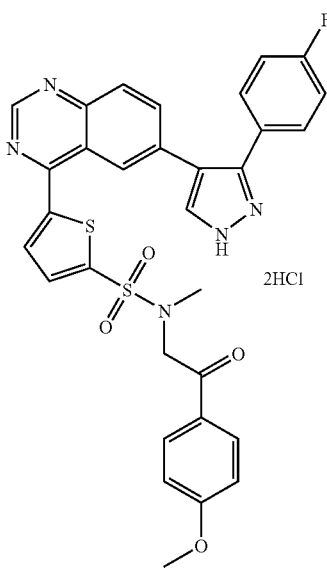

5-{6-[3-(4-Fluorophenyl)-1H-pyrazol-4-yl]quinazo-
lin-4-yl}thiophen-2-sulfonic acid [2-(4-methoxyphe-
nyl) 2-oxoethyl]methylamide dihydrochloride 30 mg of the title compound was obtained as yellow crystals by the same reaction as in Example 618 from 47 mg 5-{6-[3-(4-fluorophenyl)-1-trityl-1H-pyrazol-4-yl]quinazolin-4-yl}thiophen-2-sulfonic acid [2-(4-methoxyphenyl) 2-oxoethyl]methylamide (compound in Example 747).

$^1$H-NMR (DMSO-$d_6$)

δ: 2.92(s, 3H), 3.86(s, 3H), 4.81(s, 2H), 7.04–7.10(m, 2H), 7.26–7.33(m, 2H), 7.48–7.53(m, 3H), 7.67(d, J=4.0 Hz, 1H), 7.97–8.00(m, 2H), 8.04–8.10(m, 2H), 8.25(s, 1H), 8.29(s, 1H), 9.25(s, 1H)

MS m/e (ESI) 646 (MH$^+$ MeOH adduct)

Example 866

5-{6-[3-(4-Fluorophenyl)-1H-pyrazol-4-yl]quinazo-
lin-4-yl}thiophen-2-sulfonic acid [2-(4-fluorophe-
nyl) 2-oxoethyl]methylamide dihydrochloride 7 mg of the title compound was obtained as orange crystals by the same reaction as in Example 618 from 9 mg 5-{6-[3-(4-fluorophenyl)-1-trityl-1H-pyrazol-4-yl]quinazolin-4-yl}thiophen-2-sulfonic acid [2-(4-fluorophenyl) 2-oxoethyl]methylamide (compound in Example 748).

$^1$H-NMR (DMSO-$d_6$)

δ: 2.92(s, 3H), 4.88(s, 2H), 7.26–7.33(m, 2H), 7.36–7.44 (m, 2H), 7.47–7.54(m, 3H), 7.67(d, J=4.0 Hz, 1H), 8.06–8.12(m, 4H), 8.24 (s, 1H), 8.28(brs, 1H), 9.25(s, 1H)

MS m/e (ESI) 634 (MH$^+$ MeOH adduct)

Example 867

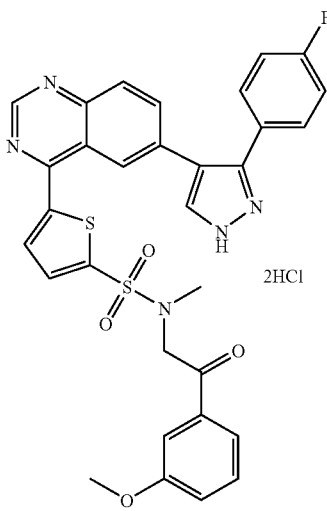

5-[6-[3-(4-Fluorophenyl)-1H-pyrazol-4-yl]quinazolin-4-yl]thiophen-2-sulfonic acid [2-(3-methoxyphenyl) 2-oxoethyl]methylamide dihydrochloride 4 mg of the title compound was obtained as orange crystals by the same reaction as in Example 618 from 17 mg 5-{6-[3-(4-fluorophenyl)-1-trityl-1H-pyrazol-4-yl]quinazolin-4-yl}thiophen-2-sulfonic acid [2-(3-methoxyphenyl) 2-oxoethyl]methylamide (compound in Example 749).

$^1$H-NMR (DMSO-$d_6$)

δ: 2.93(s, 3H), 3.82(s, 3H), 4.88(s, 2H), 7.24–7.34(m, 3H), 7.44–7.54(m, 5H), 7.59(d, J=7.2 Hz, 1H), 7.67(d, J=3.6 Hz, 1H), 8.08(brs, 2H), 8.24(s, 1H), 8.28(s, 1H), 9.25(s, 1H)

MS m/e (ESI) 646 (MH$^+$ MeOH adduct)

Example 868

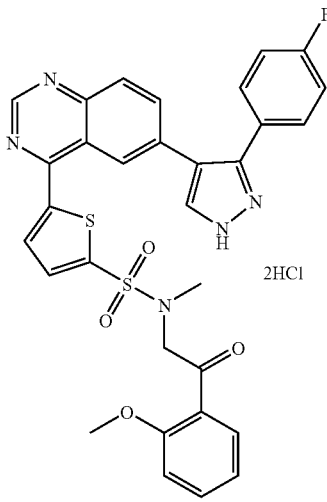

5-{6-[3-(4-Fluorophenyl)-1H-pyrazol-4-yl]quinazolin-4-yl}thiophen-2-sulfonic acid [2-(2-methoxyphenyl) 2-oxoethyl]methylamide dihydrochloride 30 mg 5-{6-[3-(4-fluorophenyl)-1-trityl-1H-pyrazol-4-yl]quinazolin-4-yl}thiophen-2-sulfonic acid [2-(2-methoxyphenyl) 2-oxoethyl]methylamide was obtained by the same reaction as in Example 749 from 50 mg 5-{6-[3-(4-fluorophenyl)-1-trityl-1H-pyrazol-4-yl]quinazolin-4-yl}thiophen-2-sulfonic acid methylamide (compound in Example 745) and 80 mg 2-methoxyphenacyl bromide. The product was reacted in the same manner as in Example 618, to give 2 mg of the title compound as yellow crystals.

$^1$H-NMR (DMSO-$d_6$)

δ: 2.93(s, 3H), 3.95(s, 3H), 4.68(s, 2H), 7.06(t, J=7.5 Hz, 1H), 7.23(d, J=8.0 Hz, 1H), 7.29(t, J=8.0 Hz, 2H), 7.45(d, J=3.4 Hz, 1H), 7.50(t, J=8.0 Hz, 2H), 7.58(d, J=3.4 Hz, 1H), 7.62(t, J=7.5 Hz, 1H), 7.69(d, J=8.0 Hz, 1H), 8.05–8.16(m, 2H), 8.23(brs, 1H), 8.28 (brs, 1H), 9.25(s, 1H)

MS m/e (FAB) 614 (MH$^+$)

Example 869

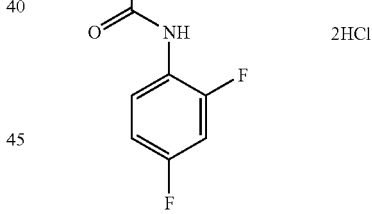

5-[6-(1H-Pyrazol-4-yl)quinazolin-4-yl]thiophen-2-carboxylic acid (2,4-difluorophenyl)amide dihydrochloride 62 mg of the title compound was obtained as pale red crystals by the same reaction as in Example 67 from 122 mg 5-[6-(1-trityl-1H-pyrazol-4-yl)quinazolin-4-yl]thiophen-2-carboxylic acid (2,4-difluorophenyl)amide (compound in Example 750).

$^1$H-NMR (DMSO-$d_6$)

δ: 7.13–7.20(m, 1H), 7.38–7.46(m, 1H), 7.59–7.67(m, 1H), 8.10 (d, J=8.8 Hz, 1H), 8.19(d, J=4.2 Hz, 1H), 8.27(d, J=4.2 Hz, 1H), 8.39(s, 2H), 8.39(dd, J=8.8, 2.0 Hz, 1H), 8.61(d, J=2.0 Hz, 1H), 9.23(s, 1H)

MS m/e (ESI) 466 (MH$^+$ MeOH adduct)

Example 870

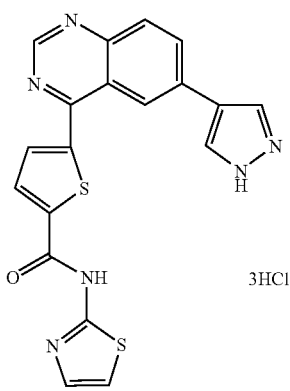

5-[6-(1H-Pyrazol-4-yl)quinazolin-4-yl]thiophen-2-carboxylic acid thiazol-2-ylamide trihydrochloride 15 mg of the title compound was obtained as red crystals by the same reaction as in Example 67 from 38 mg 5-[6-(1-trityl-1H-pyrazol-4-yl)quinazolin-4-yl]thiophen-2-carboxylic acid thiazol-2-ylamide (compound in Example 751).

$^1$H-NMR (DMSO-$d_6$)

δ: 7.33(d, J=4.0 Hz, 1H), 7.60(d, J=4.0 Hz, 1H), 8.10(d, J=8.8 Hz, 1H), 8.29(d, J=4.0 Hz, 1H), 8.36–8.43(m, 4H), 8.61(d, J=1.6 Hz, 1H), 9.24(s, 1H)

MS m/e (ESI) 437 (MH$^+$ MeOH adduct)

Example 871

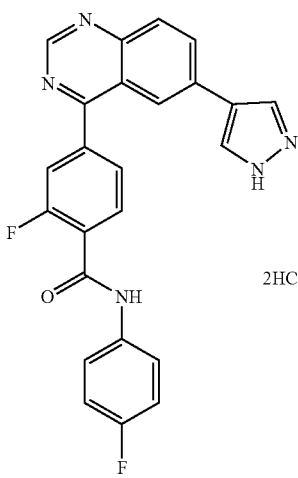

2-Fluoro-N-(4-fluorophenyl)-4-[6-(1H-pyrazol-4-yl)quinazolin-4-yl]benzamide dihydrochloride 62 mg 2-fluoro-N-(4-fluorophenyl)-4-[6-(1-trityl-1H-pyrazol-4-yl)quinazolin-4-yl] benzamide (compound in Example 754) was dissolved in 8.0 mL solvent mixture of tetrahydrofuran and methanol (1:1), then 6.0 mL of 5 N hydrochloric acid was added thereto, and the mixture was heated at 40° C. for 5 minutes and left at room temperature for 3 hours. The reaction solution was neutralized and then extracted with ethyl acetate. 4 N hydrogen chloride solution in ethyl acetate was added thereto, and the solution was concentrated to form the corresponding hydrochloride which was then washed with ether and recrystallized from dichloromethane/methanol/ethyl acetate, to give 17 mg of the title compound as pale yellow crystals.

$^1$H-NMR (DMSO-$d_6$)

δ: 7.20–7.27(m, 2H), 7.77–7.83(m, 3H), 7.85(dd, J=10.8, 1.2 Hz, 1H), 7.91(t, J=7.2 Hz, 1H), 8.13(d, J=8.8 Hz, 1H), 8.17(d, J=1.8 Hz, 1H), 8.23(brs, 2H), 8.38(dd, J=8.8, 1.8 Hz, 1H), 9.34(s, 1H)

MS m/e (ESI) 460 (MH$^+$ MeOH adduct)

Example 872

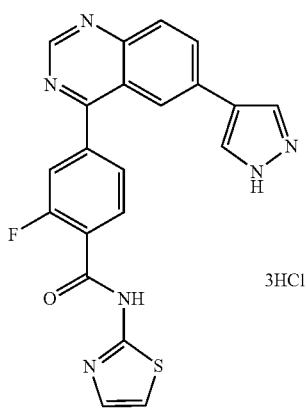

2-Fluoro-N-thiazol-2-yl-4-[6-(1H-pyrazol-4-yl)quinazolin-4-yl]benzamide trihydrochloride 15 mg of the title compound was obtained as pale yellow crystals by the same reaction as in Example 871 from 42 mg 2-fluoro-N-thiazol-2-yl-4-[6-(1-trityl-1H-pyrazol-4-yl)quinazolin-4-yl] benzamide (compound in Example 755).

$^1$H-NMR (DMSO-$d_6$)

δ: 7.37(d, J=3.2 Hz, 1H), 7.60(d, J=3.2 Hz, 1H), 7.81(dd, J=7.6, 1.3 Hz, 1H), 7.85(dd, J=10.8, 1.3 Hz, 1H), 7.99(t, J=7.6 Hz, 1H), 8.14(d, J=8.8 Hz, 1H), 8.15(d, J=2.0 Hz, 1H), 8.23(s, 2H), 8.39 (dd, J=8.8, 2.0 Hz, 1H), 9.34(s, 1H)

MS m/e (ESI) 449 (MH$^+$ MeOH adduct)

Example 873

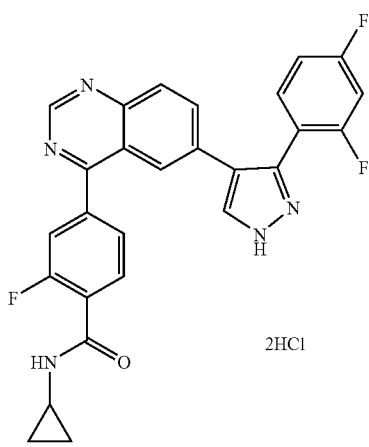

N-Cyclopropyl-4-{6-[3-(2,4-difluorophenyl)-1H-pyrazol-4-yl]quinazolin-4-yl}-2-fluorobenzamide dihydrochloride 6 mg of the title compound was obtained as yellow crystals by the same reaction as in Example 67 from 19 mg N-cyclopropyl-4-{6-[3-(2,4-difluorophenyl)-1-trityl-1H-pyrazol-4-yl]-quinazolin-4-yl}-2-fluorobenzamide (compound in Example 756).

$^1$H-NMR (DMSO-$d_6$)

δ: 0.52–0.78(m, 4H), 2.87–2.94(m, 1H), 7.05–7.27(m, 2H), 7.29–7.35(m, 1H), 7.40–7.50(m, 2H), 7.50–7.63(m, 2H), 8.09(d, J=8.4 Hz, 1H), 7.13(dd, J=8.4, 2.0 Hz, 1H), 8.31(s, 1H), 8.49(d, J=4.0 Hz, 1H), 9.30(s, 1H)

MS m/e (ESI) 518 (MH$^+$ MeOH adduct)

Example 874

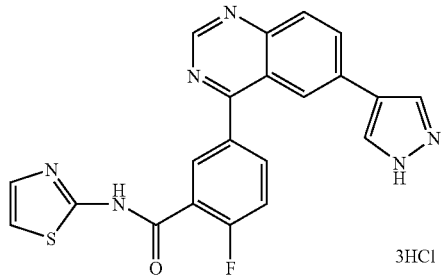

2-Fluoro-N-thiazol-2-yl-5-[6-(1H-pyrazol-4-yl)quinazolin-4-yl]benzamide trihydrochloride 14 mg of the title compound was obtained as orange crystals by the same reaction as in Example 79 from 48 mg 2-fluoro-N-thiazol-2-yl-5-[6-(1-trityl-1H-pyrazol-4-yl)quinazolin-4-yl] benzamide (compound in Example 759).

$^1$H-NMR (DMSO-$d_6$)

δ: 7.34(d, J=3.4 Hz, 1H), 7.57(d, J=3.4 Hz, 1H), 7.65(dd, J=10.0, 8.8 Hz, 1H), 8.12(d, J=8.8 Hz, 1H), 8.10–8.15(m, 1H), 8.20(d, J=2.0 Hz, 1H), 8.22–8.27(m, 3H), 8.38(dd, J=8.8, 2.0 Hz, 1H), 9.32(s, 1H)

MS m/e (ESI) 449 (MH$^+$ MeOH adduct)

Example 875

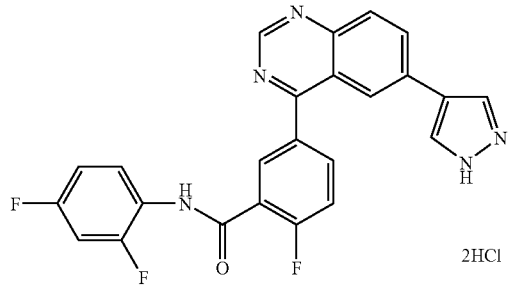

N-(2,4-Difluorophenyl)-2-fluoro-5-[6-(1H-pyrazol-4-yl)quinazolin-4-yl]benzamide dihydrochloride 42 mg of the title compound was obtained as pale yellow crystals by the same reaction as in Example 79 from 68 mg N-(2,4-difluorophenyl)-2-fluoro-5-[6-(1-trityl-1H-pyrazol-4-yl)quinazolin-4-yl] benzamide (compound in Example 760).

$^1$H-NMR (DMSO-$d_6$)

δ: 7.10–7.18(m, 1H), 7.35–7.44(m, 1H), 7.60–7.64(m, 1H), 7.78–7.87(m, 1H), 8.12(d, J=8.8 Hz, 1H), 8.08–8.14(m, 1H), 8.19 (dd, J=6.8, 2.0 Hz, 1H), 8.22(d, J=0.8 Hz, 1H), 8.24(s, 2H), 8.38 (dd, J=8.8, 2.0 Hz, 1H), 9.32(s, 1H)

MS m/e (ESI) 478 (MH$^+$ MeOH adduct)

Example 876

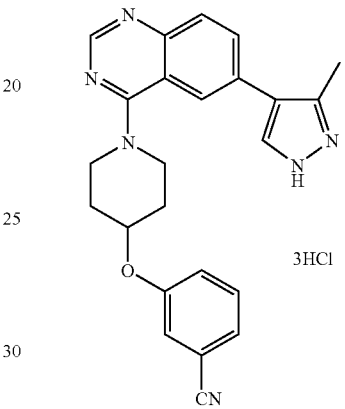

3-{1-[6-(3-Methyl-1H-pyrazol-4-yl)quinazolin-4-yl]piperidin-4-yloxy} benzonitrile trihydrochloride 43 mg of the title compound was obtained as pale yellow crystals by the same reaction as in Example 67 from 93 mg 3-{1-[6-(3-methyl-1-trityl-1H-pyrazol-4-yl)quinazolin-4-yl]piperidin-4-yloxy} benzonitrile (compound in Example 761).

$^1$H-NMR (DMSO-$d_6$)

δ: 1.90–2.07(m, 2H), 2.20–2.30(m, 2H), 2.51(s, 3H), 4.12–4.23(m, 2H), 4.38–4.46(m, 2H), 4.93–5.00(m, 1H), 7.37–7.46(m, 2H), 7.53(t, J=8.0 Hz, 1H), 7.59(d, J=1.6 Hz, 1H), 7.95(d, J=8.8 Hz, 1H), 8.06(s, 1H), 8.09(s, 1H), 8.20 (dd, J=8.8, 1.6 Hz, 1H), 8.85(s, 1H)

MS m/e (ESI) 411 (MH$^+$)

Example 877

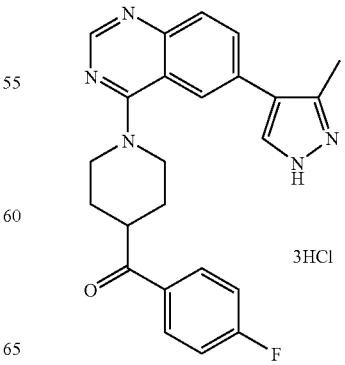

(4-Fluorophenyl)-{1-[6-(3-methyl-1H-pyrazol-4-yl)quinazolin-4-yl]piperidine 4-yl}methanone trihydrochloride 32 mg of the title compound was obtained as pale yellow crystals by the same reaction as in Example 67 from 74 mg (4-fluorophenyl)-{1-[6-(3-methyl-1-trityl-1H-pyrazol-4-yl)quinazolin-4-yl]piperidine 4-yl}methanone (compound in Example 762).

$^1$H-NMR (DMSO-$d_6$)
δ: 1.80–1.92(m, 2H), 2.05–2.14(m, 2H), 2.47(s, 3H), 3.75–3.95(m, 2H), 3.96–4.05(m, 1H), 4.75–4.90(m, 2H), 7.38–7.45(m, 2H), 7.91(d, J=8.4 Hz, 1H), 8.04(s, 1H), 8.07(d, J=1.7 Hz, 1H), 8.13–8.17(m, 2H), 8.18(dd, J=8.4, 1.7 Hz, 1H), 8.83(s, 1H)
MS m/e (ESI) 416 (MH$^+$)

Example 878

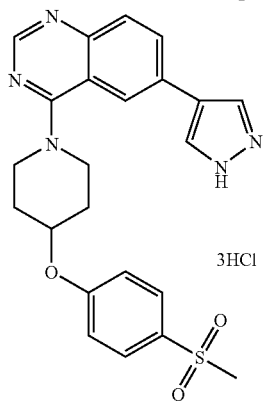

4-[4-(4-Methylsulfonylphenoxy)piperidin-1-yl]-6-(1H-pyrazol-4-yl)quinazoline trihydrochloride 52 mg of the title compound was obtained as colorless crystals by the same reaction as in Example 67 from 102 mg 4-[4-(4-methylsulfonylphenoxy)piperidin-1-yl]-6-(1-trityl-1H-pyrazol-4-yl) quinazoline (compound in Example 763).

$^1$H-NMR (DMSO-$d_6$)
δ: 1.94–2.04(m, 2H), 2.20–2.29(m, 2H), 3.18(s, 3H), 4.17–4.25(m, 2H), 4.35–4.43(m, 2H), 5.00–5.06(m, 1H), 7.28(d, J=9.0 Hz, 2H), 7.88(d, J=9.0 Hz, 2H), 7.91(s, 1H), 8.22–8.34(m, 4H), 8.82(s, 1H)
MS m/e (ESI) 450 (MH$^+$)

Example 879

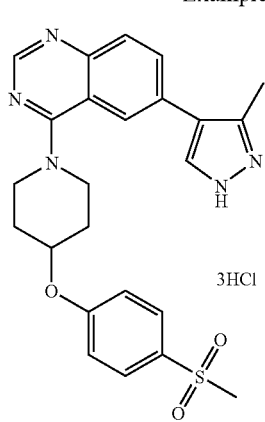

4-[4-(4-Methylsulfonylphenoxy)piperidin-1-yl]-6-(3-methyl-1H-pyrazol-4-yl)quinazoline trihydrochloride 83 mg of the title compound was obtained as colorless crystals by the same reaction as in Example 67 from 126 mg 4-[4-(4-methylsulfonylphenoxy)piperidin-1-yl]-6-(3-methyl-1-trityl-1H-pyrazol-4-yl) quinazoline (compound in Example 764).

$^1$H-NMR (DMSO-$d_6$)
δ: 1.95–2.04(m, 2H), 2.23–2.30(m, 2H), 2.48(s, 3H), 3.18(s, 3H), 4.17–4.25(m, 2H), 4.37–4.44(m, 2H), 5.00–5.04(m, 1H), 7.25–7.30(m, 2H), 7.85–7.90(m, 2H), 7.94(d, J=8.8 Hz, 1H), 8.05 (s, 1H), 8.09(d, J=1.6 Hz, 1H), 8.20(dd, J=8.8, 1.6 Hz, 1H), 8.85(s, 1H)
MS m/e (ESI) 464 (MH$^+$)

Example 880

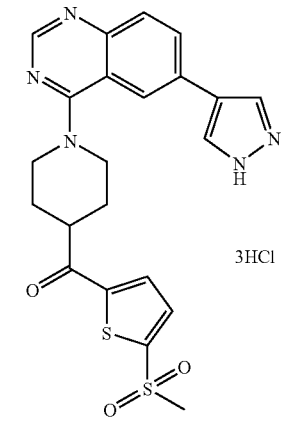

(5-Methylsulfonylthiophen-2-yl)-{1-[6-(1H-pyrazol-4-yl)quinazolin-4-yl]piperidin-4-yl}methanone trihydrochloride 14 mg of the title compound was obtained as yellow crystals by the same reaction as in Example 67 from 87 mg (5-methylsulfonylthiophen-2-yl)-{1-[6-(1-trityl-1H-pyrazol-4-yl)quinazolin-4-yl]piperidin-4-yl} methanone (compound in Example 766).

$^1$H-NMR (DMSO-$d_6$)
δ: 1.85–1.97(m, 2H), 2.10–2.18(m, 2H), 3.45(s, 3H), 3.75–3.88(m, 2H), 3.88–3.97(m, 1H), 4.69–4.82(m, 2H), 7.84(d, J=8.8 Hz, 1H), 7.99(d, J=4.0 Hz, 1H), 8.20–8.34(m, 5H), 8.80(s, 1H)
MS m/e (ESI) 468 (MH$^+$)

Example 881

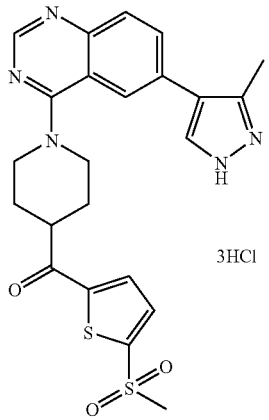

(5-Methylsulfonylthiophen-2-yl)-{1-[6-(3-methyl-1H-pyrazol-4-yl)quinazolin-4-yl]piperidin-4-yl}methanone trihydrochloride 31 mg of the title compound was obtained as yellow crystals by the same reaction as in Example 67 from 59 mg (5-methylsulfonylthiophen-2-yl)-{1-[6-(3-methyl-1-trityl-1H-pyrazol-4-yl)quinazolin-4-yl]piperidin-4-yl} methanone (compound in Example 768).

$^1$H-NMR (DMSO-d$_6$)

δ: 1.85–1.96(m, 2H), 2.10–2.20(m, 2H), 2.47(s, 3H), 3.45(s, 3H), 3.73–3.89(m, 2H), 3.89–3.99(m, 1H), 4.76–4.85(m, 2H), 7.91(d, J=8.8 Hz, 1H), 7.98(d, J=4.0 Hz, 1H), 8.03(brs, 1H), 8.07(d, J=1.6 Hz, 1H), 8.18(dd, J=8.8, 1.6 Hz, 1H), 7.27(d, J=4.0 Hz, 1H), 8.83(s, 1H)

MS m/e (ESI) 482 (MH$^+$)

Example 882

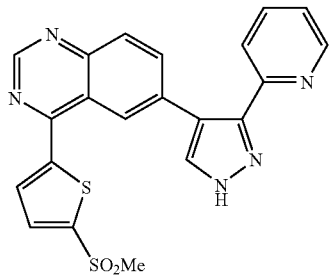

4-(5-Methylsulfonylthiophen-2-yl)-6-[3-(pyridin-2-yl)-1H-pyrazol-4-yl] quinazoline 95 mg of the title compound was obtained as yellow crystals by the same method as in Example 84 from 202 mg 4-(5-methylsulfonylthiophen-2-yl)-6-[3-(pyridin-2-yl)-1-trityl-1H-pyrazol-4-yl] quinazoline (compound in Example 770).

$^1$H-NMR (CDCl$_3$)

δ: 3.26(s, 3H), 7.30(m, 1H), 7.43(d, J=8.0 Hz, 1H), 7.63(m, 2H), 7.71(d, J=4.0 Hz, 1H), 7.80(s, 1H), 8.06(dd, J=8.8, 2.0 Hz, 1H), 8.18(d, J=8.8 Hz, 1H), 8.45(d, J=1.2 Hz, 1H), 8.67(d, J=4.0 Hz, 1H), 9.33(s, 1H)

Example 883

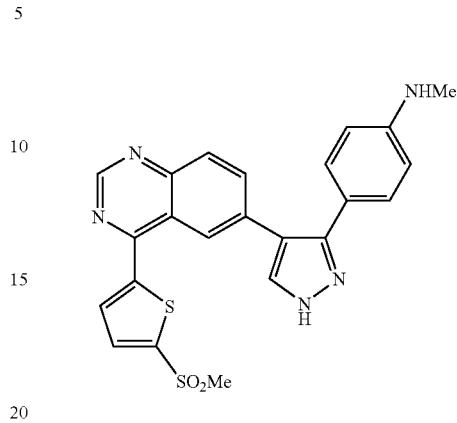

(4-{4-[4-(5-Methylsulfonylthiophen-2-yl)quinazolin-6-yl]-1H-pyrazol-3-yl}phenyl) methylamine 56 mg of the title compound was obtained as yellow crystals by the same method as in Example 84 from 168 mg t-butyl methyl(4-{4-[4-(5-methylsulfonylthiophen-2-yl) quinazolin-6-yl]-1-trityl-1H-pyrazol-3-yl}phenyl) carbaminate (compound in Example 773).

$^1$H-NMR (CDCl$_3$)

δ: 2.90(s, 3H), 3.24(s, 3H), 6.67(d, J=8.4 Hz, 2H), 7.01(d, J=4.0 Hz, 1H), 7.26(d, J=8.4 Hz, 2H), 7.56(d, J=4.0 Hz, 1H), 7.90(s, 1H), 8.11(m, 2H), 8.23(d, J=1.6 Hz, 1H), 9.23(s, 1H)

Example 884

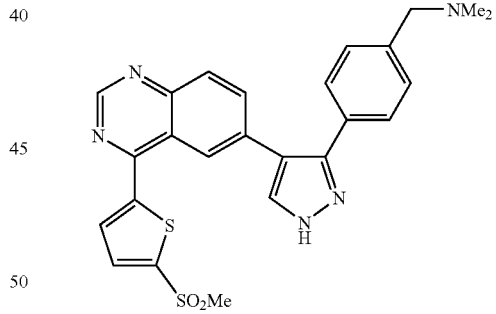

Dimethyl(4-{4-[4-(5-methylsulfonylthiophen-2-yl) quinazolin-6-yl]-1H-pyrazol-3-yl}benzyl)amine 34 mg of the title compound was obtained as yellow crystals by the same method as in Example 84 from 75 mg dimethyl(4-{4-[4-(5-methylsulfonylthiophen-2-yl)quinazolin-6-yl]-1-trityl-1H-pyrazol-3-yl}benzyl)amine (compound in Example 776).

$^1$H-NMR (CDCl$_3$)

δ: 2.28(s, 6H), 3.24(s, 3H), 3.52(s, 2H), 7.03(d, J=4.0 Hz, 1H), 7.40(d, J=8.4 Hz, 2H), 7.43(d, J=8.4 Hz, 2H), 7.56(d, J=4.0 Hz, 1H), 7.88(s, 1H), 8.02(dd, J=8.8, 2.0 Hz, 1H), 8.11(d, J=8.8 Hz, 1H), 8.20(d, J=1.2 Hz, 1H), 9.26(s, 1H)

Example 885

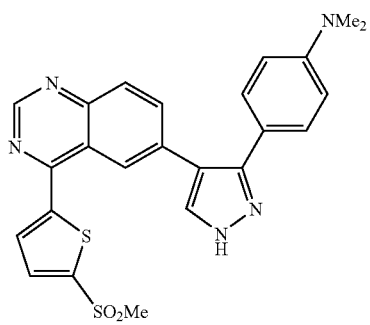

Dimethyl(4-{4-[4-(5-methylsulfonylthiophen-2-yl)quinazolin-6-yl]-1H-pyrazol-3-yl}phenyl)amine 60 mg of the title compound was obtained as yellow crystals by the same method as in Example 84 from 111 mg dimethyl(4-{4-[4-(5-methylsulfonylthiophen-2-yl)quinazolin-6-yl]-1-trityl-1H-pyrazol-3-yl}phenyl)amine (compound in Example 778).

$^1$H-NMR (CDCl$_3$)

δ: 3.06(s, 6H), 3.23(s, 3H), 6.77(d, J=9.2 Hz, 2H), 6.98(d, J=4.0 Hz, 1H), 7.31(d, J=8.8 Hz, 2H), 7.47(d, J=4.0 Hz, 1H), 7.90(s, 1H), 8.10(m, 2H), 8.25(s, 1H), 9.23(s, 1H)

Example 886

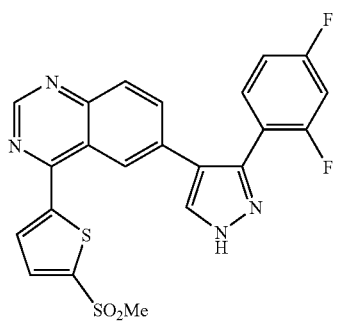

6-[3-(2,4-Difluorophenyl)-1H-pyrazol-4-yl]-4-(5-methylsulfonylthiophen-2-yl) quinazoline 74 mg of the title compound was obtained as pale yellow crystals by the same method as in Example 84 from 201 mg 6-[3-(2,4-difluorophenyl)-1-trityl-1H-pyrazol-4-yl]-4-(5-methylsulfonylthiophen-2-yl) quinazoline (compound in Example 780).

$^1$H-NMR (DMSO-d$_6$)

δ: 3.46(s, 3H), 7.30(m, 3H), 7.59(m, 1H), 7.75(d, J=4.0 Hz, 1H), 8.09(m, 3H), 8.50(brs, 1H), 9.23(s, 1H), 13.48(brs, 1H)

Example 887

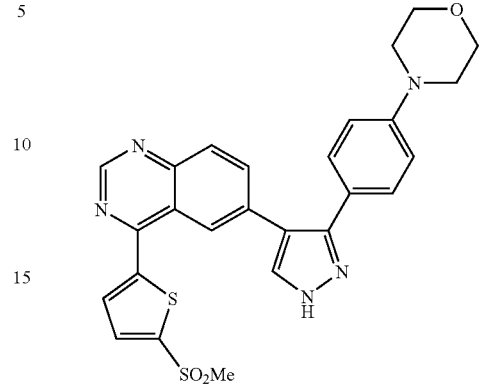

4-(5-Methylsulfonylthiophen-2-yl)-6-[3-(4-morpholin-4-ylphenyl)-1H-pyrazol-4-yl] quinazoline 34 mg of the title compound was obtained as yellow crystals by the same method as in Example 84 from 131 mg 4-(5-methylsulfonylthiophen-2-yl)-6-[3-(4-morpholin-4-ylphenyl)-1-trityl-1H-pyrazol-4-yl] quinazoline (compound in Example 782).

$^1$H-NMR (DMSO-d$_6$)

δ: 3.16(m, 4H), 3.45(s, 3H), 3.75(m, 4H), 7.02(m, 2H), 7.28(m, 3H), 7.70(d, J=4.0 Hz, 1H), 8.00–8.24(m, 4H), 9.21(s, 1H)

Example 888

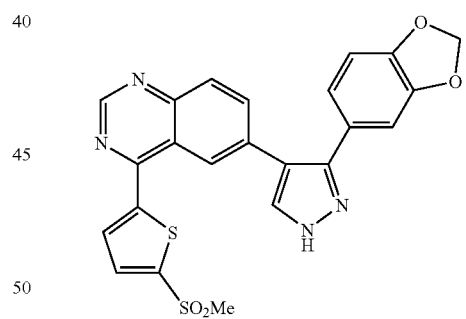

6-(3-Benzo[1,3]dioxol-5-yl-1H-pyrazol-4-yl)-4-(5-methylsulfonylthiophen-2-yl) quinazoline 17 mg of the title compound was obtained as yellow crystals by the same method as in Example 84 from 46 mg 6-(3-benzo[1,3]dioxol-5-yl-1-trityl-1H-pyrazol-4-yl)-4-(5-methylsulfonylthiophen-2-yl) quinazoline (compound in Example 784).

$^1$H-NMR (CDCl$_3$)

δ: 3.25(s, 3H), 6.04(s, 2H), 6.90(m, 2H), 6.96(dd, J=8.0, 2.0 Hz, 1H), 7.18(d, J=4.0 Hz, 1H), 7.65(d, J=4.0 Hz, 1H), 7.89(s, 1H), 8.04(dd, J=8.8, 1.6 Hz, 1H), 8.12(d, J=8.8 Hz, 1H), 8.22(d, J=1.2 Hz, 1H), 9.26(s, 1H)

Example 889

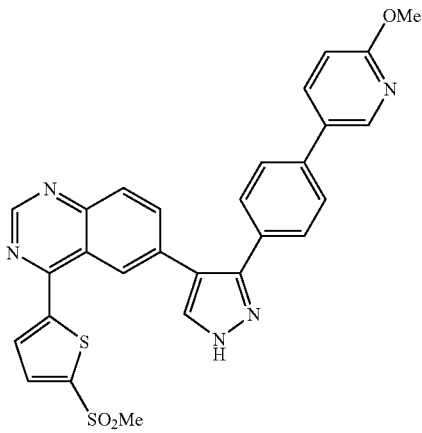

6-{3-[4-(6-Methoxypyridin-3-yl)phenyl]-1H-pyrazol-4-yl}-4-(5-methylsulfonylthiophen-2-yl) quinazoline 86 mg of the title compound was obtained as yellow crystals by the same method as in Example 84 from 157 mg 6-{3-[4-(6-methoxypyridin-3-yl)phenyl]-1-trityl-1H-pyrazol-4-yl}-4-(5-methylsulfonylthiophen-2-yl) quinazoline (compound in Example 786).

$^1$H-NMR (DMSO-$d_6$)

δ: 3.88(s, 3H), 6.91(d, J=8.8 Hz, 1H), 7.44(m, 1H), 7.55(m, 4H), 7.69–7.86(m, 3H), 8.07(m, 4H), 8.25(brs, 1H), 8.36(m, 1H), 8.54(m, 1H), 9.24(s, 1H)

Example 890

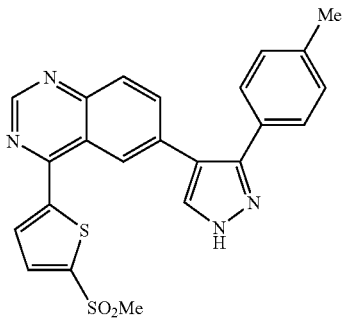

4-(5-Methylsulfonylthiophen-2-yl)-6-(3-p-tolyl-1H-pyrazol-4-yl) quinazoline 125 mg of the title compound was obtained as yellow crystals by the same method as in Example 84 from 248 mg 4-(5-methylsulfonylthiophen-2-yl)-6-(3-p-tolyl-1-trityl-1H-pyrazol-4-yl) quinazoline (compound in Example 788).

$^1$H-NMR (DMSO-$d_6$)

δ: 2.35(s, 3H), 3.44(s, 3H), 7.20–7.40(m, 5H), 7.66(d, J=4.0 Hz, 1H), 8.01–8.20(m, 3H), 8.34(brs, 1H), 9.22(s, 1H)

Example 891

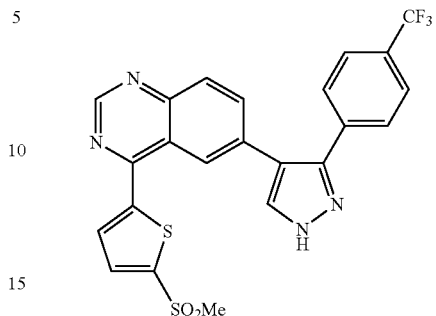

4-(5-Methylsulfonylthiophen-2-yl)-6-[3-(4-trifluoromethylphenyl)-1H-pyrazol-4-yl] quinazoline 88 mg of the title compound was obtained as yellow crystals by the same method as in Example 84 from 260 mg 4-(5-methylsulfonylthiophen-2-yl)-6-[3-(4-trifluoromethylphenyl)-1-trityl-1H-pyrazol-4-yl]quinazoline (compound in Example 790).

$^1$H-NMR (DMSO-$d_6$)

δ: 3.44(s, 3H), 7.55(d, J=4.0 Hz, 1H), 7.69(d, J=4.0 Hz, 1H), 7.70(d, J=8.4 Hz, 2H), 7.81(d, J=8.0 Hz, 2H), 8.05(dd, J=8.8, 2.0 Hz, 1H), 8.11(d, J=8.8 Hz, 1H), 8.25(d, J=1.6 Hz, 1H), 8.33(brs, 1H), 9.28(s, 1H)

Example 892

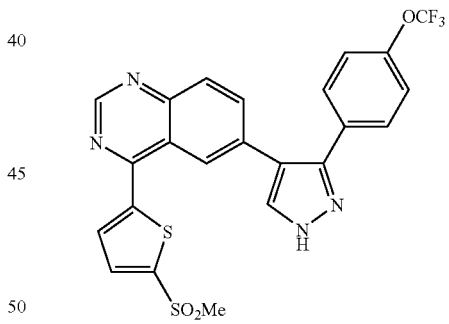

4-(5-Methylsulfonylthiophen-2-yl)-6-[3-(4-trifluoromethoxyphenyl)-1H-pyrazol-4-yl] quinazoline 102 mg of the title compound was obtained as yellow crystals by the same method as in Example 84 from 255 mg 4-(5-methylsulfonylthiophen-2-yl)-6-[3-(4-trifluoromethoxyphenyl)-1-trityl-1H-pyrazol-4-yl] quinazoline (compound in Example 792).

$^1$H-NMR (DMSO-$d_6$)

δ: 3.45(s, 3H), 7.45(m, 2H), 7.54(d, J=4.0 Hz, 1H), 7.59(d, J=8.4 Hz, 2H), 7.72(d, J=4.0 Hz, 1H), 8.06(dd, J=8.8, 1.6 Hz, 1H), 8.10(d, J=8.8 Hz, 1H), 8.24(d, J=1.6 Hz, 1H), 8.26–8.42(br, 1H), 9.27(s, 1H)

Example 893

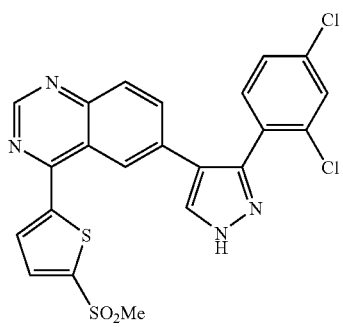

6-[3-(2,4-Dichlorophenyl)-1H-pyrazol-4-yl]-4-(5-methylsulfonylthiophen-2-yl) quinazoline 73 mg of the title compound was obtained as yellow crystals by the same method as in Example 84 from 146 mg 6-[3-(2,4-dichlorophenyl)-1-trityl-1H-pyrazol-4-yl]-4-(5-methylsulfonylthiophen-2-yl) quinazoline (compound in Example 794).

$^1$H-NMR (DMSO-$d_6$)

δ: 3.48(s, 3H), 7.15(brs, 1H), 7.60(m, 2H), 7.80(d, J=4.0 Hz, 1H), 7.95(brs, 1H), 8.08(d, J=8.4 Hz, 2H), 8.20(dd, J=8.8, 1.6 Hz, 1H), 8.56(brs, 1H), 9.23(s, 1H)

Example 894

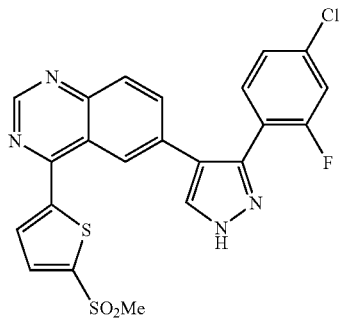

6-[3-(4-Chloro-2-fluorophenyl)-1H-pyrazol-4-yl]-4-(5-methylsulfonylthiophen-2-yl) quinazoline 101 mg of the title compound was obtained as yellow crystals by the same method as in Example 84 from 200 mg 6-[3-(4-chloro-2-fluorophenyl)-1-trityl-1H-pyrazol-4-yl]-4-(5-methylsulfonylthiophen-2-yl) quinazoline (compound in Example 796).

$^1$H-NMR (DMSO-$d_6$)

δ: 3.48(s, 3H), 7.30(d, J=4.0 Hz, 1H), 7.51(m, 2H), 7.60(t, J=8.0 Hz, 1H), 7.76(d, J=4.0 Hz, 1H), 8.12(m, 3H), 8.52(s, 1H), 9.25(s, 1H), 13.54(brs, 1H)

Example 895

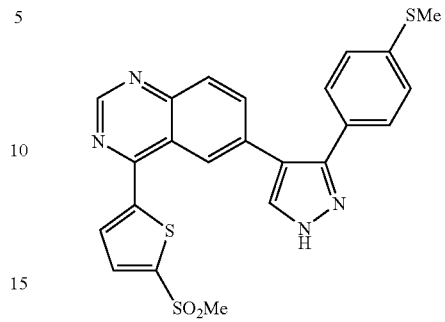

6-[3-(4-Methylsulfanylphenyl)-1H-pyrazol-4-yl]-4-(5-methylsulfonylthiophen-2-yl) quinazoline 107 mg of the title compound was obtained as yellow crystals by the same method as in Example 84 from 298 mg 6-[3-(4-methylsulfanylphenyl)-1-trityl-1H-pyrazol-4-yl]-4-(5-methylsulfonylthiophen-2-yl) quinazoline (compound in Example 797).

$^1$H-NMR (DMSO-$d_6$)

δ: 2.50(s, 3H), 3.46(s, 3H), 7.35(d, J=4.0 Hz, 1H), 7.36–7.44(m, 4H), 7.73(d, J=4.0 Hz, 1H), 8.08(d, J=8.8 Hz, 1H), 8.12(dd, J=8.8, 1.6 Hz, 1H), 8.20(d, J=1.6 Hz, 1H), 8.24(brs, 1H), 9.25(s, 1H)

Example 896

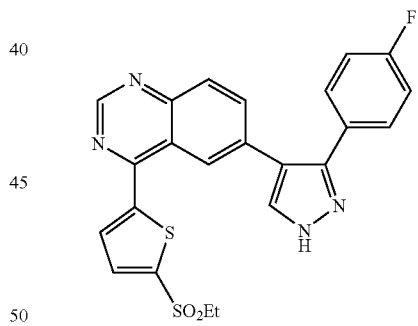

4-(5-Ethanesulfonylthiophen-2-yl)-6-[3-(4-fluorophenyl)-1H-pyrazol-4-yl] quinazoline 128 mg of the title compound was obtained as pale yellow crystals by the same method as in Example 84 from 258 mg 4-(5-ethanesulfonylthiophen-2-yl)-6-[3-(4-fluorophenyl)-1-trityl-1H-pyrazol-4-yl] quinazoline (compound in Example 799).

$^1$H-NMR (CDCl$_3$)

δ: 1.40(t, J=7.2 Hz, 3H), 3.29 (q, J=7.2 Hz, 2H), 7.09(d, J=4.0 Hz, 1H), 7.16(t, J=8.8 Hz, 2H), 7.47(d, J=8.8 Hz, 1H), 7.49(d, J=8.8 Hz, 1H), 7.58(d, J=4.0 Hz, 1H), 7.89(s, 1H), 8.00(dd, J=8.8, 2.0 Hz, 1H), 8.12(d, J=8.8 Hz, 1H), 8.16(d, J=1.6 Hz, 1H), 9.27(s, 1H)

Example 897

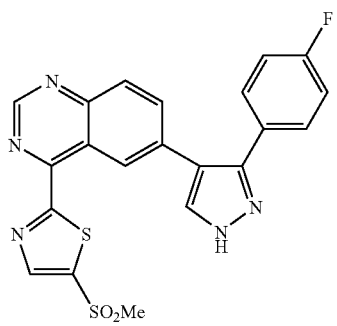

6-[3-(4-Fluorophenyl)-1H-pyrazol-4-yl]-4-(5-methylsulfonylthiazol-2-yl) quinazoline 22 mg of the title compound was obtained as yellow crystals by the same method as in Example 84 from 56 mg 6-[3-(4-fluorophenyl)-1-trityl-1H-pyrazol-4-yl]-4-(5-methylsulfonylthiazol-2-yl) quinazoline (compound in Example 801).

$^1$H-NMR (DMSO-d$_6$)

δ: 3.55(s, 3H), 7.17–7.38(m, 2H), 7.49(m, 2H), 8.10(m, 2H), 8.31(brs, 1H), 8.48(s, 1H), 9.37(s, 1H), 9.42(m, 1H), 13.30–13.50(br, 1H)

MS m/e (ESI) 452 (MH$^+$)

Example 898

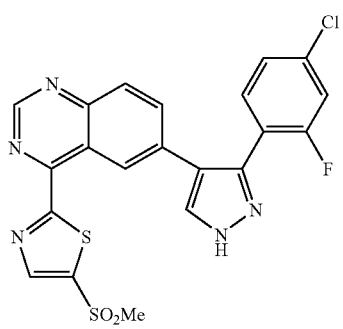

6-[3-(4-Chloro-2-fluorophenyl)-1H-pyrazol-4-yl]-4-(5-methylsulfonylthiazol-2-yl) quinazoline 73 mg of the title compound was obtained as yellow crystals by the same method as in Example 84 from 157 mg 6-[3-(4-chloro-2-fluorophenyl)-1-trityl-1H-pyrazol-4-yl]-4-(5-methylsulfonylthiazol-2-yl) quinazoline (compound in Example 803).

$^1$H-NMR (DMSO-d$_6$)

δ: 3.55(s, 3H), 7.48(m, 2H), 7.59(t, J=8.0 Hz, 1H), 8.10(d, J=8.8 Hz, 1H), 8.26(dd, J=8.8, 1.6 Hz, 1H), 8.35(brs, 1H), 8.50(s, 1H), 9.22(brs, 1H), 9.34(s, 1H), 13.54(brs, 1H)

Example 899

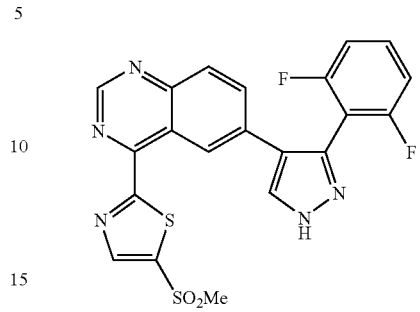

6-[3-(2,6-Difluorophenyl)-1H-pyrazol-4-yl]-4-(5-methylsulfonylthiazol-2-yl) quinazoline 43 mg of the title compound was obtained as yellow crystals by the same method as in Example 84 from 86 mg 6-[3-(2,6-difluorophenyl)-1-trityl-1H-pyrazol-4-yl]-4-(5-methylsulfonylthiazol-2-yl) quinazoline (compound in Example 805).

$^1$H-NMR (DMSO-d$_6$)

δ: 3.58(s, 3H), 7.31(m, 2H), 7.61(m, 1H), 8.11(d, J=9.2 Hz, 1H), 8.31(dd, J=8.8, 2.0 Hz, 1H), 8.39(s, 1H), 9.23(brs, 1H), 9.34(s, 1H), 13.61(brs, 1H)

Example 900

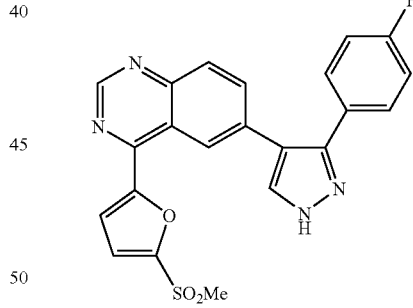

6-[3-(4-Fluorophenyl)-1H-pyrazol-4-yl]-4-(5-methylsulfonylfuran-2-yl) quinazoline 33 mg of the title compound was obtained as yellow crystals by the same method as in Example 84 from 71 mg 6-[3-(4-fluorophenyl)-1-trityl-1H-pyrazol-4-yl]-4-(5-methylsulfonylfuran-2-yl) quinazoline (compound in Example 807).

$^1$H-NMR (DMSO-d$_6$)

δ: 3.40(s, 3H), 7.18–7.36(m, 2H), 7.51(m, 4H), 7.90(m, 1H), 8.03(m, 1H), 8.29(s, 1H), 8.58(s, 1H), 9.34(s, 1H), 13.30–13.50(br, 1H)

Example 901

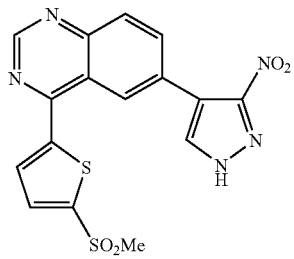

4-(5-Methylsulfonylthiophen-2-yl)-6-(3-nitro-1H-pyrazol-4-yl) quinazoline 3 mg of the title compound was obtained as yellow crystals by the same method as in Example 84 from 8 mg 4-(5-methylsulfonylthiophen-2-yl)-6-(3-nitro-1-trityl-1H-pyrazol-4-yl) quinazoline (compound in Example 809).

MS m/e (ESI) 402 (MH$^+$)

Example 902

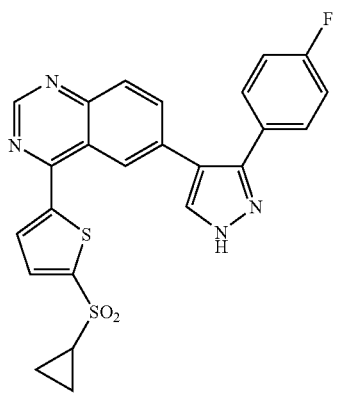

4-(5-Cyclopropanesulfonylthiophen-2-yl)-6-[3-(4-fluorophenyl)-1H-pyrazol-4-yl] quinazoline 124 mg of the title compound was obtained as yellow crystals by the same method as in Example 80 from 269 mg 4-(5-cyclopropanesulfonylthiophen-2-yl)-6-[3-(4-fluorophenyl)-1-trityl-1H-pyrazol-4-yl] quinazoline (compound in Example 810).

$^1$H-NMR (CDCl$_3$)

δ: 1.15(m, 2H), 1.45(m, 2H), 2.66(m, 1H), 7.07(d, J=4.0 Hz, 1H), 7.08(t, J=8.8 Hz, 2H), 7.48(m, 2H), 7.57(d, J=4.0 Hz, 1H), 7.89(s, 1H), 7.99(dd, J=8.8, 2.0 Hz, 1H), 8.12(d, J=8.8 Hz, 1H), 8.18(d, J=2.0 Hz, 1H), 9.27(s, 1H)

MS m/e (ESI) 477 (MH$^+$)

Example 903

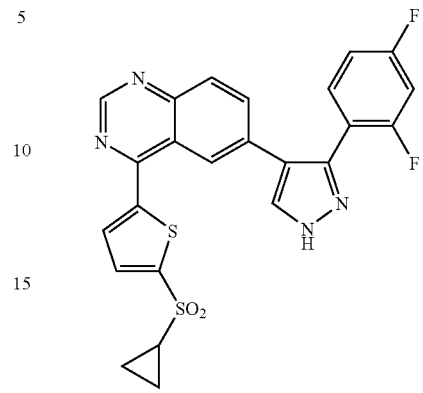

4-(5-Cyclopropanesulfonylthiophen-2-yl)-6-[3-(2,4-difluorophenyl)-1H-pyrazol-4-yl] quinazoline 101 mg of the title compound was obtained as pale yellow crystals by the same method as in Example 80 from 302 mg 4-(5-cyclopropanesulfonylthiophen-2-yl)-6-[3-(2,4-difluorophenyl)-1-trityl-1H-pyrazol-4-yl] quinazoline (compound in Example 811).

$^1$H-NMR (CDCl$_3$)

δ: 1.15(m, 2H), 1.46(m, 2H), 2.66(m, 1H), 6.94(m, 1H), 7.01(m, 1H), 7.16(d, J=4.0 Hz, 1H), 7.48(m, 1H), 7.61(d, J=4.0 Hz, 1H), 7.94(s, 1H), 7.96(dd, J=8.8, 2.0 Hz, 1H), 8.11(d, J=8.4 Hz, 1H), 8.17(d, J=2.0 Hz, 1H), 9.28(s, 1H)

Example 904

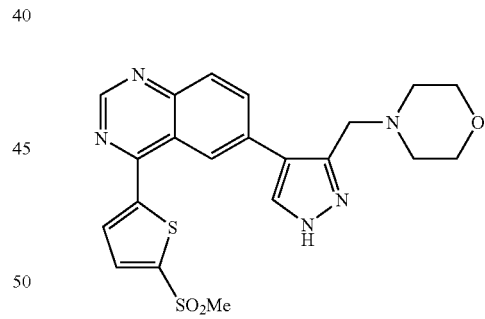

4-(5-Methylsulfonylthiophen-2-yl)-6-(3-morpholin-4-ylmethyl-1H-pyrazol-4-yl) quinazoline 15 mg of the title compound was obtained as pale yellow crystals by the same method as in Example 84 from 35 mg 4-(5-methylsulfonylthiophen-2-yl)-6-(3-morpholin-4-ylmethyl-1-trityl-1H-pyrazol-4-yl) quinazoline (compound in Example 812).

$^1$H-NMR (CDCl$_3$)

δ: 2.52(m, 4H), 3.28(s, 3H), 3.68(m, 4H), 3.73(s, 2H), 7.85(m, 3H), 8.14(dd, J=8.8, 1.6 Hz, 1H), 8.18(d, J=8.8 Hz, 1H), 8.42(brs, 1H), 9.32(s, 1H)

Example 905

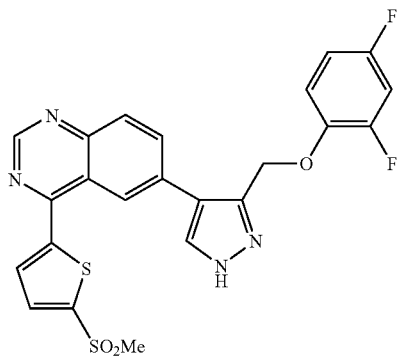

6-[3-(2,4-Difluorophenoxymethyl)-1H-pyrazol-4-yl]-4-(5-methylsulfonylthiophen-2-yl) quinazoline 10 mg of the title compound was obtained as yellow crystals by the same method as in Example 84 from 51 mg 6-[3-(2,4-difluorophenoxymethyl)-1-trityl-1H-pyrazol-4-yl]-4-(5-methylsulfonylthiophen-2-yl) quinazoline (compound in Example 813).

$^1$H-NMR (DMSO-$d_6$)

δ: 3.40(s, 3H), 5.35(s, 2H), 7.03(m, 1H), 7.24(m, 1H), 7.40(m, 1H), 7.46(d, J=4.0 Hz, 1H), 8.10(d, J=4.0 Hz, 1H), 8.14(d, J=9.2 Hz, 1H), 8.36(dd, J=8.8, 2.0 Hz, 1H), 8.45(br, 1H), 8.63(brs, 1H), 9.28(s, 1H)

Example 906

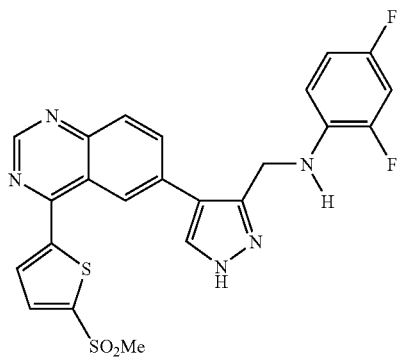

2,4-Difluorophenyl{4-[4-(5-methylsulfonylthiophen-2-yl)quinazolin-6-yl]-1H-pyrazol-3-ylmethyl} amine 15 mg sodium hydride was suspended in 2 mL N,N-dimethylformamide, and 3 mL solution of 41 mg t-butyl (2,4-difluorophenyl)carbaminate in N,N-dimethylformamide was added thereto under cooling with iced water in a stream of nitrogen and stirred for 20 minutes. Then, 3 mL solution of 107 mg 6-(3-bromomethy-1-trityl-1H-pyrazol-4-yl)-(5-methylsulfonylthiophen-2-yl) quinazoline obtained in the synthesis process in Example 812 in N,N-dimethylformamide was added thereto little by little, and the mixture was further stirred for 20 minutes. Water and ethyl acetate were added to the reaction solution, and the organic layer was separated, then washed with water+brine (×2) and brine, and dried over anhydrous sodium sulfate. The drying agent was filtered off, and the filtrate was evaporated. The resulting residue was purified by silica gel column chromatography (ethyl acetate/hexane), to give 23 mg crude product of 2,4-difluorophenyl{4-[4-(5-methylsulfonylthiophen-2-yl)quinazolin-6-yl]-1-trityl-1H-pyrazol-3-ylmethyl] carbaminate as a yellow amorphous. From this compound, 4.8 mg of the title compound was obtained as a pale yellow amorphous by the same method as in Example 84.

$^1$H-NMR (CDCl$_3$)

δ: 3.23(s, 3H), 4.47(s, 2H), 6.67(m, 1H), 6.77(m, 1H), 6.87(m, 1H), 7.39(d, J=4.0 Hz, 1H), 7.74(d, J=4.0 Hz, 1H), 7.92(s, 1H), 8.08(dd, J=8.8, 2.0 Hz, 1H), 8.18(d, J=8.8 Hz, 1H), 8.59(d, J=2.0 Hz, 1H), 9.30(s, 1H)

Example 907

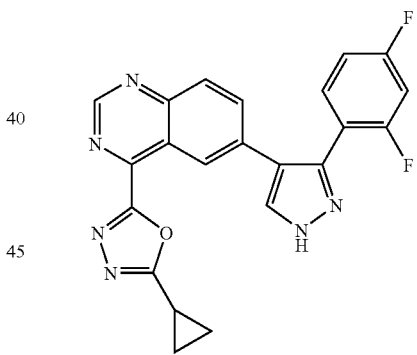

4-(5-Cyclopropyl[1,3,4]oxadiazol-2-yl)-6-[3-(2,4-difluorophenyl)-1H-pyrazol-4-yl] quinazoline 37 mg of the title compound was obtained as yellow crystals by the same method as in Example 84 from 86 mg 4-(5-cyclopropyl[1,3,4]oxadiazol-2-yl)-6-[3-(2,4-difluorophenyl)-1-trityl-1H-pyrazol-4-yl] quinazoline (compound in Example 814).

$^1$H-NMR (CDCl$_3$)

δ: 1.28–1.40(m, 4H), 2.35(m, 1H), 6.87–6.97(m, 2H), 7.45(m, 1H), 7.85(dd, J=8.8, 2.0 Hz, 1H), 8.03(s, 1H), 8.04(d, J=8.8 Hz, 1H), 9.40(d, J=1.6 Hz, 1H), 9.43(s, 1H)

MS m/e (ESI) 417 (MH$^+$)

Example 908

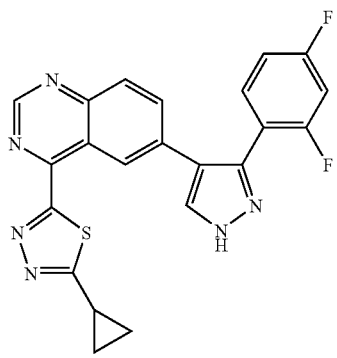

4-(5-Cyclopropyl[1,3,4]thiadiazol-2-yl)-6-[3-(2,4-difluorophenyl)-1H-pyrazol-4-yl] quinazoline 73 mg of the title compound was obtained as pale yellow crystals by the same method as in Example 84 from 193 mg 4-(5-cyclopropyl[1,3,4]thiadiazol-2-yl)-6-[3-(2,4-difluorophenyl)-1-trityl-1H-pyrazol-4-yl] quinazoline (compound in Example 815).

$^1$H-NMR (DMSO-$d_6$)

δ: 1.23(m, 2H), 1.33(m, 2H), 2.66(m, 1H), 7.12–7.32(m, 2H), 7.56(m, 1H), 8.07(d, J=8.8 Hz, 1H), 8.15(d, J=8.8 Hz, 1H), 8.22–8.50(br, 1H), 9.27(brs, 1H), 9.32(s, 1H)

Example 909

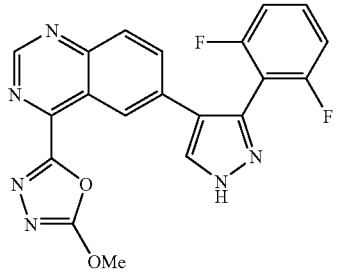

6-[3-(2,6-Difluorophenyl)-1H-pyrazol-4-yl]-4-(5-methoxyl[1,3,4]oxadiazol-2-yl) quinazoline 31 mg of the title compound was obtained as yellow crystals by the same method as in Example 84 from 141 mg 6-[3-(2,6-difluorophenyl)-1-trityl-1H-pyrazol-4-yl]-4-(5-methoxy-[1,3,4]oxadiazol-2-yl) quinazoline (compound in Example 816).

$^1$H-NMR (CDCl$_3$)

δ: 4.33(s, 3H), 7.01(d, J=8.4 Hz, 1H), 7.03(d, J=8.4 Hz, 1H), 7.42(m, 1H), 7.86(dd, J=8.8, 2.0 Hz, 1H), 8.02(d, J=8.8 Hz, 1H), 8.11(s, 1H), 9.33(d, J=2.0 Hz, 1H), 9.39(s, 1H)

Example 910

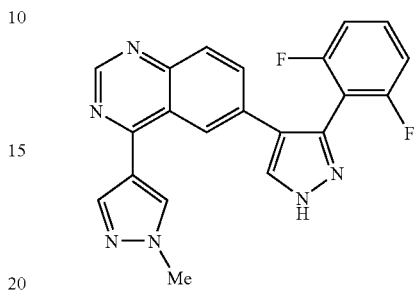

6-[3-(2,6-Difluorophenyl)-1H-pyrazol-4-yl]-4-(1-methyl-1H-pyrazol-4-yl) quinazoline 63 mg of the title compound was obtained as pale yellow crystals by the same method as in Example 80 from 126 mg 6-[3-(2,6-difluorophenyl)-1-trityl-1H-pyrazol-4-yl]-4-(1-methyl-1H-pyrazol-4-yl) quinazoline (compound in Example 817).

$^1$H-NMR (DMSO-$d_6$)

δ: 3.94(s, 3H), 7.24(brs, 2H), 7.38(brs, 1H), 7.66(s, 1H), 7.96(d, J=8.4 Hz, 1H), 8.00(dd, J=8.8, 2.0 Hz, 1H), 8.04(s, 1H), 8.20(s, 1H), 8.42–8.60(br, 1H), 9.11(s, 1H), 13.57(brs, 1H)

Example 911

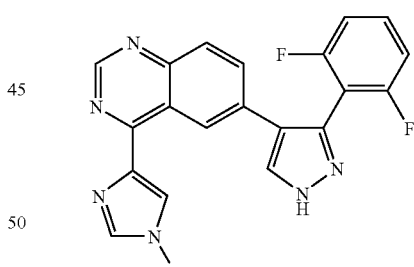

6-[3-(2,6-Difluorophenyl)-1H-pyrazol-4-yl]-4-(1-methyl-1H-imidazol-4-yl) quinazoline 65 mg of the title compound was obtained as pale yellow crystals by the same method as in Example 84 from 214 mg 6-[3-(2,6-difluorophenyl)-1-trityl-1H-pyrazol-4-yl]-4-(1-methyl-1H-imidazol-4-yl) quinazoline (compound in Example 818).

$^1$H-NMR (DMSO-$d_6$)

δ: 3.76(s, 3H), 7.05–7.36(m, 2H), 7.51(m, 1H), 7.66(s, 1H), 7.87(d, J=8.8 Hz, 1H), 8.02(d, J=8.0 Hz, 1H), 8.10(s, 1H), 8.43(s, 1H), 9.03(s, 1H), 9.61(s, 1H), 13.47(brs, 1H)

Example 912

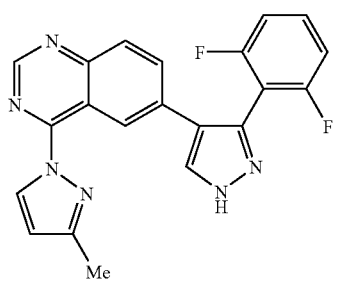

6-[3-(2,6-Difluorophenyl)-1H-pyrazol-4-yl]-4-(3-methylpyrazol-1-yl) quinazoline 33 mg of the title compound was obtained as pale yellow crystals by the same method as in Example 84 from 72 mg 6-[3-(2,6-difluorophenyl)-1-trityl-1H-pyrazol-4-yl]-4-(3-methylpyrazol-1-yl) quinazoline (compound in Example 819).

¹H-NMR (CDCl₃)

δ: 2.36(s, 3H), 6.31(d, J=2.4 Hz, 1H), 6.96(t, J=8.0 Hz, 2H), 7.35(m, 1H), 7.79(dd, J=8.8, 2.0 Hz, 1H), 7.95(d, J=8.8 Hz, 1H), 8.03(s, 1H), 8.63(d, J=2.8 Hz, 1H), 9.00(s, 1H), 9.56(dd, J=1.6 Hz, 1H)

Example 913

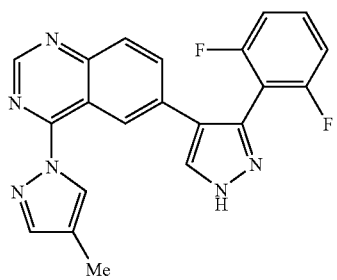

6-[3-(2,6-Difluorophenyl)-1H-pyrazol-4-yl]-4-(4-methylpyrazol-1-yl) quinazoline 12 mg of the title compound was obtained as a white solid by the same method as in Example 84 from 31 mg 6-[3-(2,6-difluorophenyl)-1-trityl-1H-pyrazol-4-yl]-4-(4-methylpyrazol-1-yl) quinazoline (compound in Example 820).

¹H-NMR (CDCl₃)

δ: 2.17(s, 3H), 7.01(t, J=8.0 Hz, 2H), 7.41(m, 1H), 7.52(s, 1H), 7.84(dd, J=8.8, 2.0 Hz, 1H), 7.95(d, J=9.2 Hz, 1H), 8.05(s, 1H), 8.49(s, 1H), 8.99(s, 1H), 9.48(dd, J=2.0 Hz, 1H)

Example 914

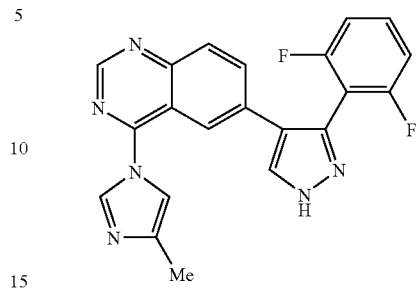

6-[3-(2,6-Difluorophenyl)-1H-pyrazol-4-yl]-4-(4-methylimidazol-1-yl) quinazoline 9 mg of the title compound was obtained as a white solid by the same method as in Example 84 from 32 mg 6-[3-(2,6-difluorophenyl)-1-trityl-1H-pyrazol-4-yl]-4-(4-methylimidazol-1-yl) quinazoline (compound in Example 821).

¹H-NMR (CDCl₃)

δ: 2.32(s, 3H), 7.05(m, 3H), 7.47(m, 1H), 7.87(d, J=1.2 Hz, 1H), 7.97(m, 3H), 8.11(d. J=9.2 Hz, 1H), 9.12(s, 1H)

Example 915

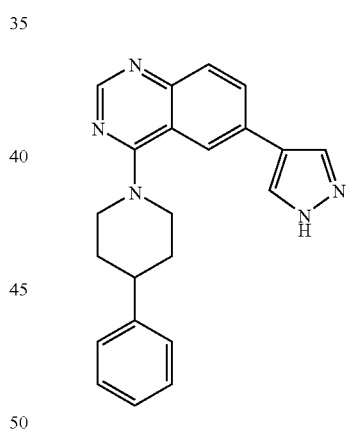

4-(4-Phenylpiperidin-1-yl)-6-(1H-pyrazol-4-yl) quinazoline 93 mg of the title compound was obtained as white crystals by the same method as in Example 80 from 165 mg 4-(4-phenylpiperidin-1-yl)-6-(1-trityl-1H-pyrazol-4-yl) quinazoline (compound in Example 822).

¹H-NMR (CDCl₃)

δ: 2.05(m, 4H), 2.90(m, 1H), 3.28(m, 2H), 4.51(m, 2H), 7.24–7.38(m, 5H), 7.89(dd, J=8.8, 2.0 Hz, 1H), 7.93(dd, J=8.8, 0.4 Hz, 1H), 7.95(brs, 2H), 8.02(dd, J=1.6, 0.4 Hz, 1H), 8.74(s, 1H)

Example 916

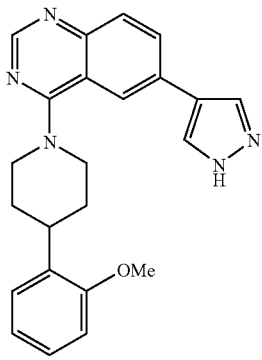

4-[4-(2-Methoxyphenyl)piperidin-1-yl]-6-(1H-pyrazol-4-yl) quinazoline 33 mg of the title compound was obtained as pale yellow crystals by the same method as in Example 80 from 120 mg 4-[4-(2-methoxyphenyl)piperidin-1-yl]-6-(1-trityl-1H-pyrazol-4-yl) quinazoline (compound in Example 823).

$^1$H-NMR (CDCl$_3$)

δ: 1.63(br, 2H), 2.90(m, 2H), 3.88(s, 3H), 4.06(m, 2H), 4.48(m, 2H), 5.93(m, 1H), 6.94(m, 2H), 7.21(dd, J=7.6, 2.0 Hz, 1H), 7.29(dd, J=8.0, 1.6 Hz, 1H), 7.92(m, 4H), 8.06(s, 1H), 8.70(s, 1H)

Example 917

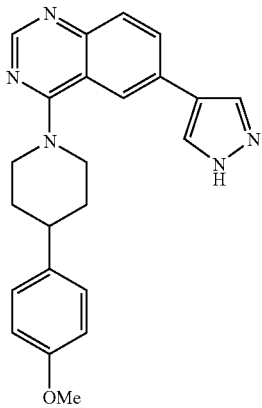

4-[4-(4-Methoxyphenyl)piperidin-1-yl]-6-(1H-pyrazol-4-yl) quinazoline 82 mg of the title compound was obtained as pale yellow crystals by the same method as in Example 80 from 256 mg 4-[4-(4-methoxyphenyl)piperidin-1-yl]-6-(1-trityl-1H-pyrazol-4-yl) quinazoline (compound in Example 824).

$^1$H-NMR (CDCl$_3$)

δ: 1.91–2.10(m, 4H), 2.80(m, 1H), 3.28(m, 2H), 3.80(s, 3H), 4.51(m, 2H), 6.90(d, J=8.8 Hz, 2H), 7.22(d, J=8.8 Hz, 2H), 7.87–7.98(m, 4H), 8.02(s, 1H), 8.73(s, 1H)

Example 918

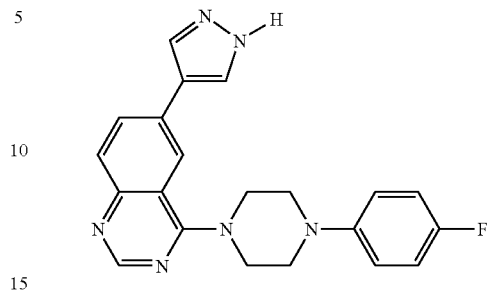

4-[4-(4-Fluorophenyl)piperazin-1-yl]-6-(1H-pyrazol-4-yl) quinazoline

A compound obtained by the same method as in Example 268 from 200 mg 6-bromo-4-chloroquinazoline, 220 mg 1-(4-fluorophenyl)piperazine and 300 mg 1-trityl-1H-4-pyrazolylboronic acid was treated with an aqueous saturated sodiumbicarbonate solution and then extracted with ethyl acetate. The organic layer was washed with brine and then dried over anhydrous magnesium sulfate. The solvent was evaporated, and the residue was purified by silica gel column chromatography to give 120 mg of the title compound as a pale yellow solid.

$^1$H-NMR (DMSO-d$_6$)

δ: 3.40(m, 4H), 4.29(m, 4H), 6.95–7.00(m, 2H), 7.06–7.12(m, 2H), 7.80(d, J=8.6 Hz, 1H), 8.24–8.30(m, 4H), 8.80(s, 1H)

The compounds in Examples 919 to 922 were obtained in the same manner as in Example 918.

Example 919

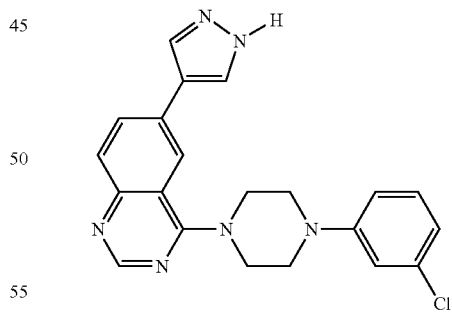

4-[4-(3-Chlorophenyl)piperazin-1-yl]-6-(1H-pyrazol-4-yl) quinazoline $^1$H-NMR (DMSO-d$_6$)

δ: 3.46(m, 4H), 3.88(m, 4H), 6.80(dd, J=2.0, 7.6 Hz, 1H), 6.94(dd, J=2.0, 7.6 Hz, 1H), 6.99(t, J=2.0 Hz, 1H), 7.24(t, J=7.6 Hz, 1H), 7.80(d, J=9.2 Hz, 1H), 8.08–8.12(m, 3H), 8.39(s, 1H), 8.59(s, 1H)

Example 920

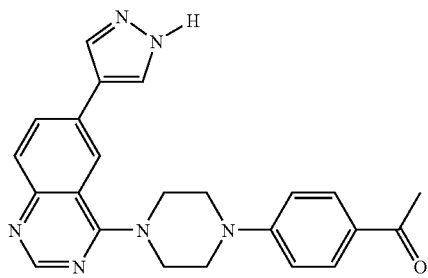

1-(4-{4-[6-(1H-Pyrazol-4-yl)quinazolin-4-yl]piperazin-1-yl} phenylethane $^1$H-NMR (DMSO-$d_6$)

δ: 2.45(s, 3H), 3.65(m, 4H), 3.95(m, 4H), 6.99(d, J=9.0 Hz, 2H), 7.79(d, J=8.6 Hz, 1H), 7.84(d, J=9.0 Hz, 2H), 8.08–8.14(m, 3H), 8.38(s, 1H), 8.59(s, 1H)

Example 921

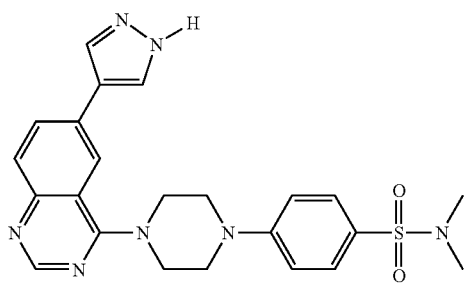

N,N-Dimethyl-4-{4-[6-(1H-pyrazol-4-yl)quinazolin-4-yl]piperazin-1-yl} benzene sulfonamide $^1$H-NMR (DMSO-$d_6$)

δ: 2.54(s, 6H), 3.65(m, 4H), 3.96(m, 4H), 7.09(d, J=8.4 Hz, 2H), 7.56(d, J=8.4 Hz, 2H), 7.80(d, J=8.2 Hz, 1H), 8.08–8.14(m, 3H), 8.38(s, 1H), 8.59(s, 1H)

Example 922

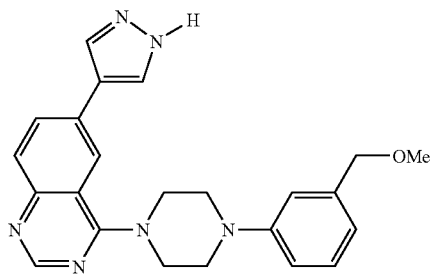

4-[4-(3-Methoxymethylphenyl)piperazin-1-yl]-6-(1H-pyrazol-4-yl) quinazoline $^1$H-NMR (CDCl$_3$)

δ: 3.41(s, 3H), 3.47(m, 4H), 3.95(m, 4H), 4.46(s, 2H), 6.88(d, J=8.0 Hz, 1H), 6.93(d, J=8.0 Hz, 1H), 7.00(s, 1H), 7.28(t, J=8.0 Hz, 1H), 7.88–7.96(m, 4H), 8.02(d, J=1.5 Hz, 1H), 8.75(s, 1H)

Example 923

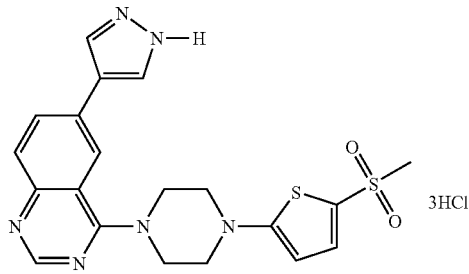

4-[4-(5-Methylsulfonylthiophen-2-yl)piperazin-1-yl]-6-(1H-pyrazol-4-yl)quinazoline trihydrochloride 4-[4-(5-Methylsulfonylthiophen-2-yl)piperazin-1-yl]-6-(1H-pyrazol-4-yl) quinazoline obtained by the same method as in Example 918 from 120 mg 6-bromo-4-chloroquinazoline, 120 mg 1-(5-methylsulfonylthiophen-2-yl) piperazine and 260 mg 1-trityl-1H-4-pyrazolylboronic acid was dissolved in ethyl acetate and then treated with 4 N hydrogen chloride solution in ethyl acetate, and the resulting insolubles were collected to give the title compound as a pale yellow solid.

$^1$H-NMR (DMSO-$d_6$)

δ: 3.19(s, 3H), 3.60(m, 4H), 4.39(m, 4H), 6.29(d, J=4.4 Hz, 1H), 7.48(d, J=4.4 Hz, 1H), 7.90(d, J=8.6, 1H), 8.24–8.32(m, 4H), 8.85(s, 1H)

The compounds in Example 924 to 926 were obtained by the same method as in Example 923.

Example 924

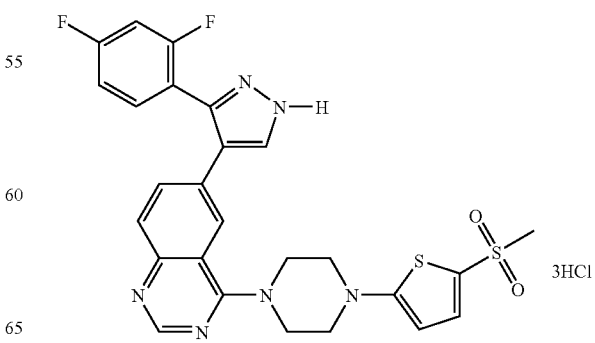

6-[3-(2,4-Difluorophenyl)-1H-pyrazol-4-yl]-4-[4-(5-methylsulfonylthiophen-2-yl)piperazin-1-yl]quinazoline trihydrochloride ¹H-NMR (DMSO-d₆)

δ: 3.20(s, 3H), 3.42(m, 4H), 4.10(m, 4H), 6.25(d, J=4.2 Hz, 1H), 7.26(m, 1H), 7.39(m, 1H), 7.49(d, J=4.2 Hz, 1H), 7.60(m, 1H), 7.85(s, 1H), 7.90–7.96(m, 2H), 8.23(s, 1H), 8.86(s, 1H)

Example 925

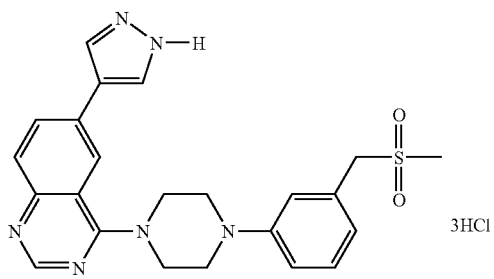

4-[4-(3-Methylsulfonylmethylphenyl)piperazin-1-yl]-6-(1H-pyrazol-4-yl)quinazoline trihydrochloride ¹H-NMR (DMSO-d₆)

δ: 1.97(s, 2H), 2.89(s, 3H), 3.52(m, 4H), 4.41(m, 4H), 6.85(d, J=7.8 Hz, 1H), 6.94–7.00(m, 2H), 7.27(d, J=7.8 Hz, 1H), 7.93(d, J=9.2, 1H), 8.30–8.34(m, 4H), 8.85(s, 1H)

Example 926

4-[4-(3-Cyclopropylphenyl)piperazin-1-yl]-6-(1H-pyrazol-4-yl)quinazoline trihydrochloride

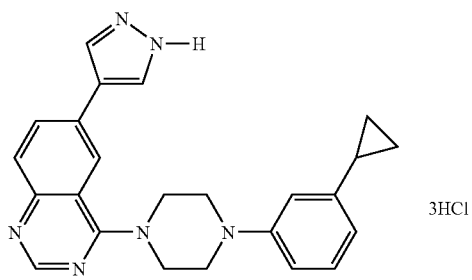

¹H-NMR (DMSO-d₆)

δ: 0.67(m, 2H), 0.91(m, 2H), 1.89(m, 1H), 3.55(m, 4H), 4.47(m, 4H), 6.67(d, J=7.9 Hz, 1H), 6.86–6.96(m, 2H), 7.18(t, J=7.9 Hz, 1H), 7.99(d, J=9.2, 1H), 8.30–8.36(m, 4H), 8.86(s, 1H)

Using 6-bromo-4-chloroquinazoline and a commercial amine or an amine obtained in any one of Production Examples 366 to 368 or Production Examples 427 to 443 as the starting materials, the compounds in Examples 927 to 973 were synthesized by the same method as in Example 268.

Example 927

4-[4-(3-Methoxyphenyl)piperazin-1-yl]-6-(1H-pyrazol-4-yl)quinazoline tri-trifluoroacetate

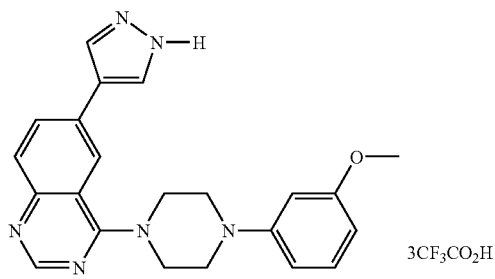

¹H-NMR (DMSO-d₆)

δ: 3.48(m, 4H), 3.72(s, 3H), 4.36(m, 4H), 6.38(dd, J=2.2, 8.1 Hz, 1H), 6.45(m, 1H), 6.52(dd, J=8.1, 2.2 Hz, 1H), 7.14(t, J=8.1 Hz, 1H), 7,81(d, J=9.0 Hz, 1H), 8.27–8.31(m, 4H), 8.83(s, 1H)

Example 928

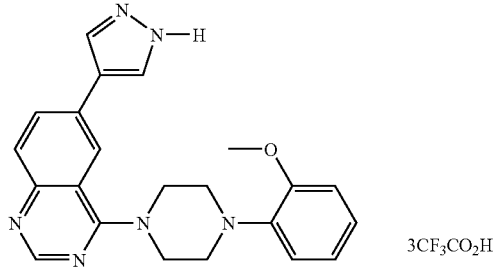

4-[4-(2-Methoxyphenyl)piperazin-1-yl]-6-(1H-pyrazol-4-yl)quinazoline tri-trifluoroacetate ¹H-NMR (DMSO-d₆)

δ: 3.20(m, 4H), 3.82(s, 3H), 4.38(m, 4H), 6.85–7.00(m, 4H), 7.80 (d, J=8.8, 1H), 8.24–8.32(m, 4H), 8.82(s, 1H)

Example 929

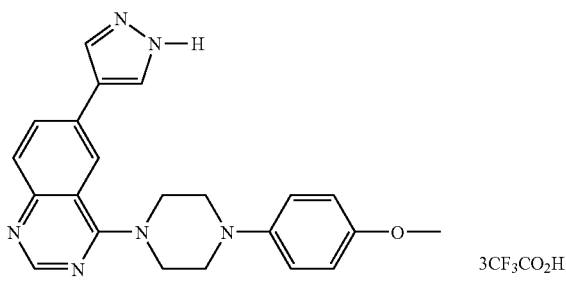

4-[4-(4-Methoxyphenyl)piperazin-1-yl]-6-(1H-pyrazol-4-yl)quinazoline tri-trifluoroacetate ¹H-NMR (CD₃OD)
δ: 3.40(m, 4H), 3.76(s, 3H), 4.57(m, 4H), 6.90(d, J=8.8 Hz, 2H), 7.09(d, J=8.8, 2H), 7.82(d, J=8.8 Hz, 1H), 8.22(s, 2H), 8.29(dd, J=1.8, 8.8 Hz, 1H), 8.35(d, J=1.8, 1H), 8.67(s, 1H)

Example 930

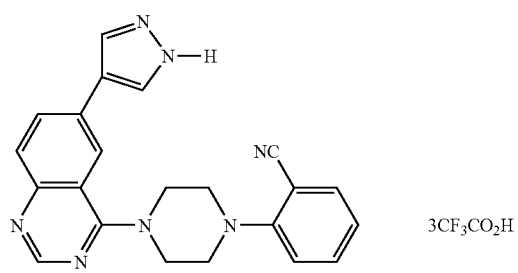

2-{4-[6-(1H-Pyrazol-4-yl)quinazolin-4-yl]piperazin-1-yl}benzonitrile tri-trifluoroacetate ¹H-NMR (CD₃OD)
δ: 3.42(m, 4H), 4.60(m, 4H), 7.12–7.24(m, 2H), 7.58–7.70(m, 2H), 7.83(d, J=8.8, 1H), 8.23(s, 2H), 8.30(dd, J=1.8, 8.8 Hz, 1H), 8.37(d, J=1.8, 1H), 8.68(s, 1H)

Example 931

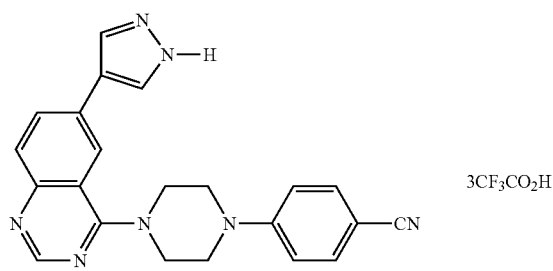

4-{4-[6-(1H-Pyrazol-4-yl)quinazolin-4-yl]piperazin-1-yl}benzonitrile tri-trifluoroacetate ¹H-NMR (DMSO-d₆)
δ: 3.73(m, 4H), 4.40(m, 4H), 6.94(d, J=8.6 Hz, 2H), 7.63(d, J=8.6 Hz, 2H), 7.82(d, J=8.8, 1H), 8.26–8.34(m, 4H), 8.84(s, 1H)

Example 932

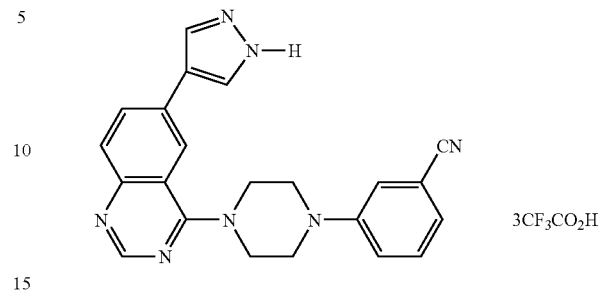

3-{4-[6-(1H-Pyrazol-4-yl)quinazolin-4-yl]piperazin-1-yl}benzonitrile tri-trifluoroacetate ¹H-NMR (DMSO-d₆)
δ: 3.60(m, 4H), 4.32(m, 4H), 7.17(d, J=8.6 Hz, 1H), 7.25(dd, J=1.6, 8.6 Hz, 1H), 7.32(m, 1H), 7.43(t, J=8.6 Hz, 1H), 7.80(d, J=8.8 Hz, 1H), 8.24–8.32(m, 4H), 8.81(s, 1H)

Example 933

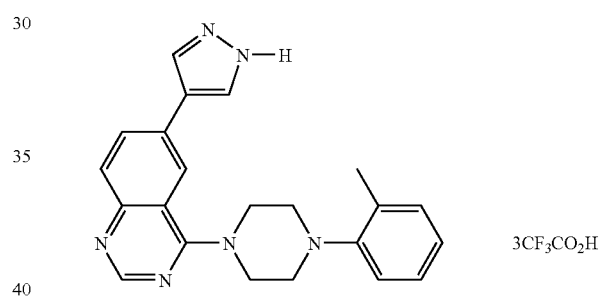

6-(1H-Pyrazol-4-yl)-4-(4-o-tolylpiperazin-1-yl)-quinazoline tri-trifluoroacetate ¹H-NMR (DMSO-d₆)
δ: 2.34(s, 3H), 3.07(m, 4H), 4.38(m, 4H), 6.96–7.04(m, 2H), 7.12–7.22(m, 2H), 7.81(d, J=8.8 Hz, 1H), 8.24–8.32(m, 4H), 8.83(s, 1H)

Example 934

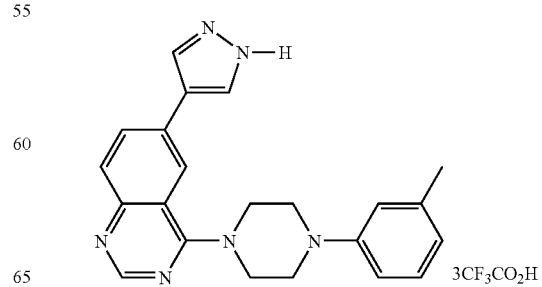

6-(1H-Pyrazol-4-yl)-4-(4-m-tolylpiperazin-1-yl)-
quinazoline tri-trifluoroacetate ¹H-NMR (DMSO-d₆)
δ: 2.26(s, 3H), 3.45(m, 4H), 4.28(m, 4H), 6.62(d, J=8.0, 1H), 6.72–6.78(m, 2H), 7.12(t, J=8.0 Hz, 1H), 7.80(d, J=8.8 Hz, 1H), 8.24–8.32(m, 4H), 8.79(s, 1H)

Example 935

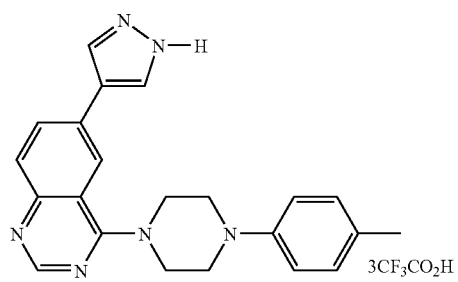

6-(1H-Pyrazol-4-yl)-4-(4-p-tolylpiperazin-1-yl)-
quinazoline tri-trifluoroacetate ¹H-NMR (DMSO-d₆)
δ: 2.20(s, 3H), 3.39(m, 4H), 4.32(m, 4H), 6.86(d, J=8.5 Hz, 2H), 7.06(d, J=8.5 Hz, 2H), 7.80(d, J=8.8 Hz, 1H), 8.24–8.32(m, 4H), 8.80(s, 1H)

Example 936

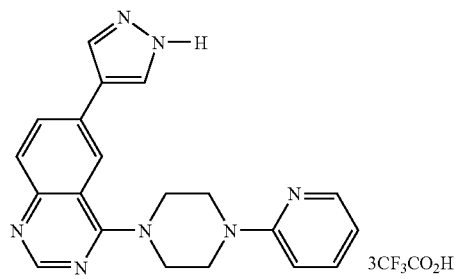

6-(1H-Pyrazol-4-yl)-4-(4-pyridin-2-yl-piperazin-1-
yl)quinazoline tri-trifluoroacetate ¹H-NMR (DMSO-d₆)
δ: 3.90(m, 4H), 4.43(m, 4H), 6.83(t, J=6.2 Hz, 1H), 7.04(d, J=8.6 Hz, 1H), 7.78–7.86(m, 2H), 8.13(d, J=6.2 Hz, 1H), 8.26–8.33(m, 4H), 8.86(s, 1H)

Example 937

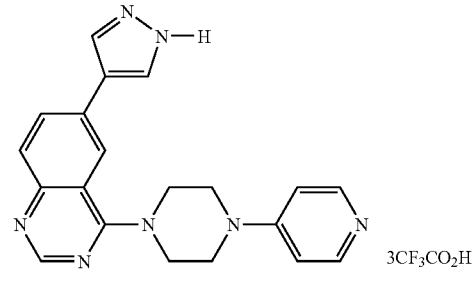

6-(1H-Pyrazol-4-yl)-4-(4-pyridin-4-yl-piperazin-1-
yl)quinazoline tri-trifluoroacetate ¹H-NMR (DMSO-d₆)
δ: 3.98(m, 4H), 4.43(m, 4H), 7.13(d, J=7.7 Hz, 2H), 7.83(d, J=8.6 Hz, 1H), 8.24–8.36(m, 6H), 8.85(s, 1H)

Example 938

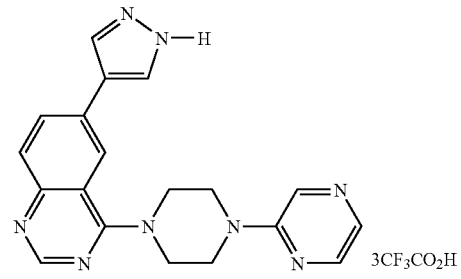

6-(1H-Pyrazol-4-yl)-4-(4-pyrazin-2-yl-piperazin-1-
yl)quinazoline tri-trifluoroacetate ¹H-NMR (DMSO-d₆)
δ: 3.89(m, 4H), 4.33(m, 4H), 7.81(d, J=9.2 Hz, 1H), 7.88(d, J=2.6 Hz, 1H), 8.12(m, 1H), 8.24–8.32(m, 5H), 8.85(s, 1H)

Example 939

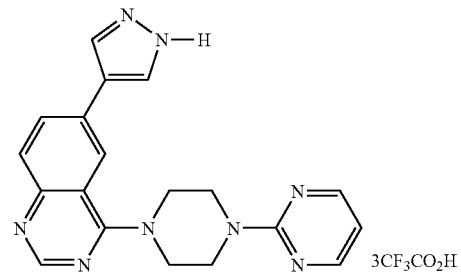

6-(1H-Pyrazol-4-yl)-4-(4-pyrimidin-2-yl-piperazin-1-yl)quinazoline tetra-trifluoroacetate ¹H-NMR (DMSO-d₆)
δ: 4.01(m, 4H), 4.37(m, 4H), 6.71(t, J=4.6 Hz, 1H), 7.81(d, J=9.0 Hz, 1H), 8.26–8.32(m, 4H), 8.42(d, J=4.6 Hz, 2H), 8.84(s, 1H)

Example 940

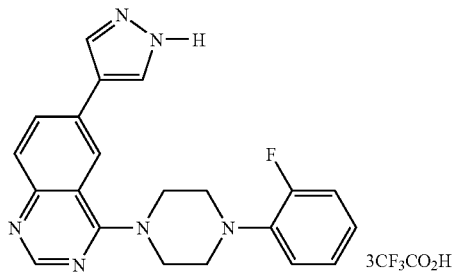

4-[4-(2-Fluorophenyl)piperazin-1-yl]-6-(1H-pyrazol-4-yl)quinazoline tri-trifluoroacetate ¹H-NMR (DMSO-d₆)
δ: 3.28(m, 4H), 4.32(m, 4H), 6.96–7.20(m, 4H), 7.81(d, J=9.0 Hz, 1H), 8.22–8.34(m, 4H), 8.80(s, 1H)

Example 941

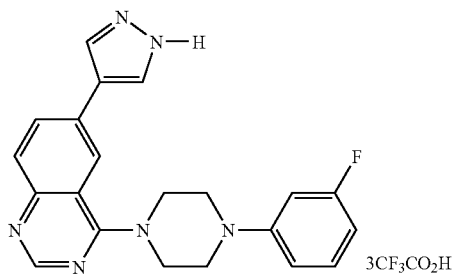

4-[4-(3-Fluorophenyl)piperazin-1-yl]-6-(1H-pyrazol-4-yl)quinazoline tri-trifluoroacetate ¹H-NMR (DMSO-d₆)
δ: 3.54(m, 4H), 4.29(m, 4H), 6.55(t, J=8.0 Hz, 1H), 6.70–6.79(m, 2H), 7.25 (q, J=8.0 Hz, 1H), 7.80(d, J=9.2 Hz), 8.22–8.34(m, 4H), 8.80(s, 1H)

Example 942

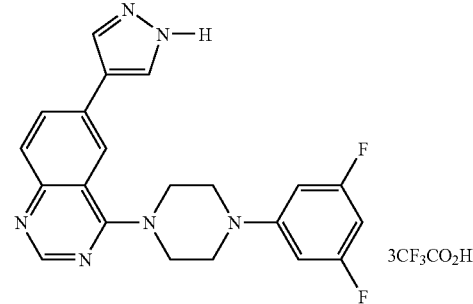

4-[4-(3,5-Difluorophenyl)piperazin-1-yl]-6-(1H-pyrazol-4-yl)quinazoline tri-trifluoroacetate ¹H-NMR (DMSO-d₆)
δ: 3.60(m, 4H), 4.29(m, 4H), 6.49(m, 1H), 6.60(dd, J=2.0, 11.2 Hz, 2H), 7.81(d, J=9.0 Hz, 1H), 8.23–8.34(m, 4H), 8.80(s, 1H)

Example 943

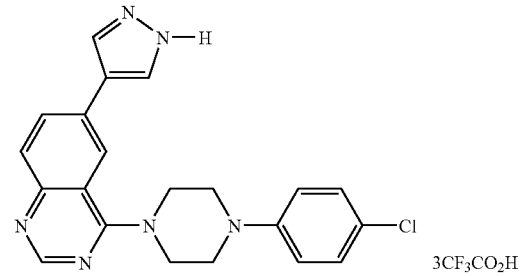

4-[4-(4-Chlorophenyl)piperazin-1-yl]-6-(1H-pyrazol-4-yl)quinazoline tri-trifluoroacetate ¹H-NMR (DMSO-d₆)
δ: 3.45(m, 4H), 4.32(m, 4H), 6.94(d, J=9.0, 2H), 7.27(d, J=9.0 Hz, 2H), 7.80(d, J=9.3 Hz, 1H), 8.24–8.30(m, 4H), 8.81(s, 1H)

Example 944

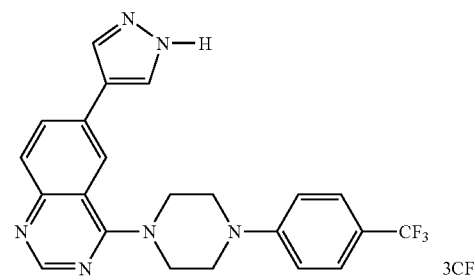

4-[4-(4-Trifluoromethylphenyl)piperazin-1-yl]-6-(1H-pyrazol-4-yl)quinazoline tri-trifluoroacetate ¹H-NMR (DMSO-d₆)
δ: 3.67(m, 4H), 4.36(m, 4H), 7.01(d, J=8.4 Hz, 2H), 7.55(d, J=8.4 Hz, 2H), 7.81(d, J=8.4 Hz, 1H), 8.24–8.30(m, 4H), 8.82(s, 1H)

Example 945

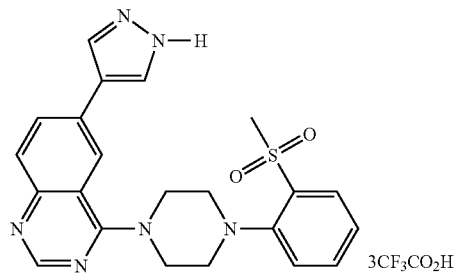

4-[4-(2-Methylsulfonylphenyl)piperazin-1-yl]-6-(1H-pyrazol-4-yl)quinazoline tri-trifluoroacetate ¹H-NMR (DMSO-d₆)
δ: 3.15(s, 3H), 3.20(m, 4H), 4.38(m, 4H), 7.47(t, J=8.0 Hz, 1H), 7.59(d, J=8.0 Hz, 1H), 7.74(t, J=8.0 Hz, 1H), 7.82(d, J=8.8 Hz, 1H), 7.94(d, J=8.0 Hz, 1H), 8.24–8.32(m, 4H), 8.84(s, 1H)

Example 946

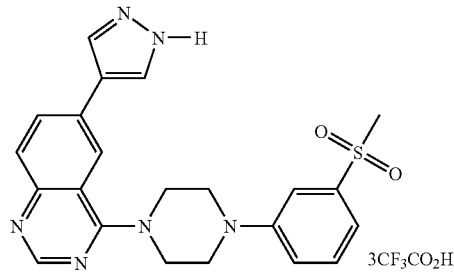

4-[4-(3-Methylsulfonylphenyl)piperazin-1-yl]-6-(1H-pyrazol-4-yl)quinazoline tri-trifluoroacetate ¹H-NMR (DMSO-d₆)
δ: 3.15(s, 3H), 3.64(m, 4H), 4.39(m, 4H), 7.21–7.34(m, 3H), 7.50(t, J=8.0 Hz, 1H), 7.81(d, J=8.4 Hz, 1H), 8.25–8.34 (m, 4H), 8.84(s, 1H)

Example 947

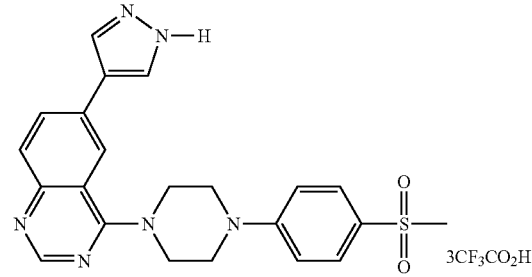

4-[4-(4-Methylsulfonylphenyl)piperazin-1-yl]-6-(1H-pyrazol-4-yl)quinazoline tri-trifluoroacetate ¹H-NMR (DMSO-d₆)
δ: 3.09(s, 3H), 3.73(m, 4H), 4.36(m, 4H), 7.01(d, J=9.0 Hz, 2H), 7.72(d, J=9.0 Hz, 2H), .7.80(d, J=8.6 Hz, 1H), 8.25–8.32(m, 4H), 8.82(s, 1H)

Example 948

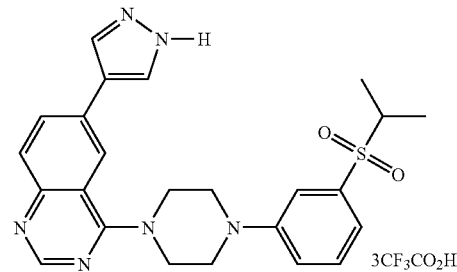

4-[4-(3-Isopropylsulfonylphenyl)piperazin-1-yl]-6-(1H-pyrazol-4-yl)quinazoline tri-trifluoroacetate ¹H-NMR (DMSO-d₆)
δ: 1.15(d, J=7.0, 1H), 3.42(m, 1H), 3.63(m, 4H), 4.36(m, 4H), 7.18–7.28(m, 3H), 7.51(t, J=8.7 Hz, 1H), 7.81(d, J=9.4 Hz, 1H), 8.25–8.34(m, 4H), 8.83(s, 1H)

Example 949

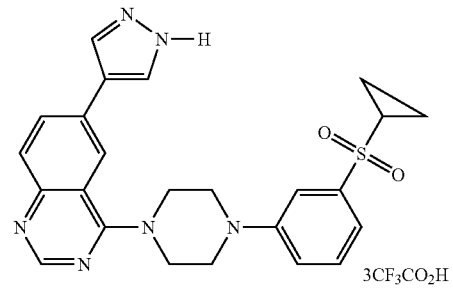

4-[4-(3-Cyclopropylsulfonylphenyl)piperazin-1-yl]-6-(1H-pyrazol-4-yl)quinazoline tri-trifluoroacetate ¹H-NMR (DMSO-d₆)
δ: 0.98–1.12(m, 4H), 2.85(m, 1H), 3.62(m, 4H), 4.32(m, 4H), 7.22–7.31(m, 3H), 7.50(t, J=7.1 Hz, 1H), .7.81(d, J=7.7 Hz, 1H), 8.23–8.32(m, 4H), 8.80(s, 1H)

Example 950

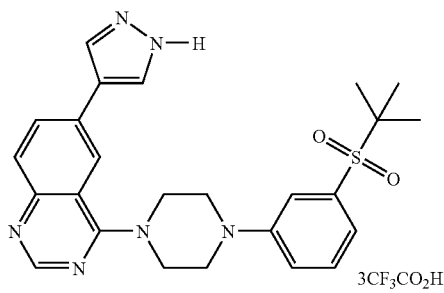

4-[4-(3-t-Butylsulfonylphenyl)piperazin-1-yl]-6-(1H-pyrazol-4-yl)quinazoline tri-trifluoroacetate ¹H-NMR (DMSO-d₆)
δ: 1.23(s, 9H), 3.60(m, 4H), 4.32(m, 4H), 7.16–7.21(m, 2H), 7.29(d, d=8.0 Hz, 1H), 7.51(t, J=8.0 Hz, 1H), .7.80(d, J=8.6 Hz, 1H), 8.23–8.32(m, 4H), 8.80(s, 1H)

Example 951

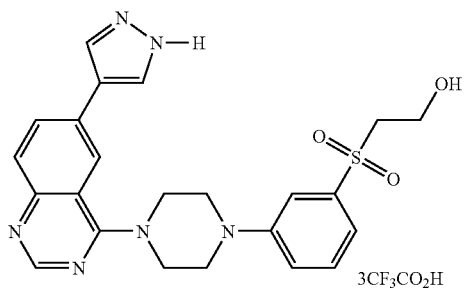

2-(3-{4-[6-(1H-Pyrazol-4-yl)quinazolin-4-yl]piperazin-1-yl}benzenesulfonyl)ethanol tri-trifluoroacetate ¹H-NMR (DMSO-d₆)
δ: 3.43(t, J=6.8 Hz, 2H), 3.60–3.70(m, 6H), 4.37(m, 4H), 7.20–7.32(m, 3H), 7.49(t, J=8.2 Hz, 1H), .7.81(d, J=8.4 Hz, 1H), 8.23–8.32(m, 4H), 8.83(s, 1H)

Example 952

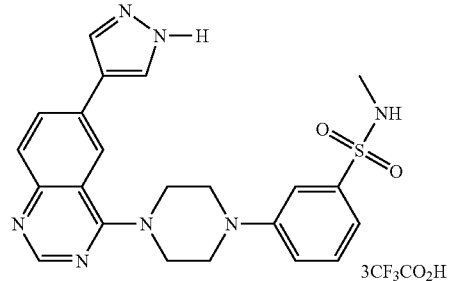

N-Methyl-3-{4-[6-(1H-pyrazol-4-yl)quinazolin-4-yl]piperazin-1-yl}benzene sulfonamide tri-trifluoroacetate ¹H-NMR (CD₃OD)
δ: 2.69(s, 3H), 3.62(m, 4H), 4.56(m, 4H), 7.20–7.50(m, 4H), 7.81(d, J=8.1 Hz, 1H), 8.22(s, 2H), 8.31(d, J=8.5 Hz, 1H), 8.39(s, 1H), 8.68(s, 1H)

Example 953

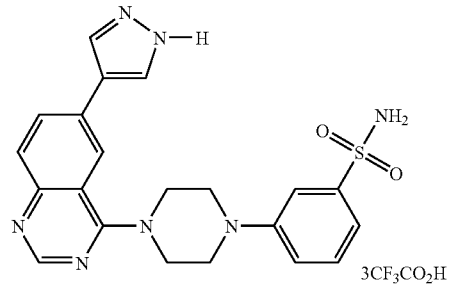

3-{4-[6-(1H-Pyrazol-4-yl)quinazolin-4-yl]piperazin-1-yl}benzene sulfonamide tri-trifluoroacetate ¹H-NMR (DMSO-d₆)
δ: 3.58(m, 4H), 4.33(m, 4H), 7.13(d, J=7.7 Hz, 1H), 7.21(d, J=7.7 Hz, 1H), 7.23(s, 2H), 7.33(s, 1H), 7.42(t, J=7.7 Hz, 1H), 7.81(d, J=9.0 Hz, 1H), 8.24–8.32(m, 4H), 8.81(s, 1H)

Example 954

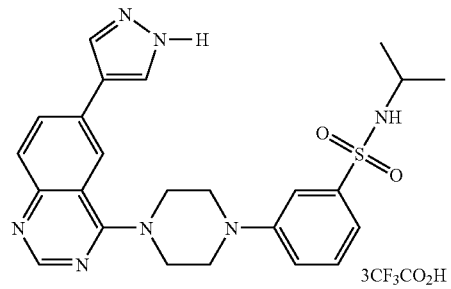

N-Isopropyl-3-{4-[6-(1H-pyrazol-4-yl)quinazolin-4-yl]piperazin-1-yl}benzene sulfonamide tri-trifluoroacetate ¹H-NMR (DMSO-d₆)
δ: 0.93(d, J=6.6 Hz, 6H), 3.21(m, 1H), 3.59(m, 4H), 4.37(m, 4H), 7.13(d, J=7.5 Hz, 1H), 7.18(d, J=7.5 Hz, 1H), 7.27(s, 1H), 7.43(t, J=7.5 Hz, 1H), 7.49(d, J=7.1, 1H), 7.81(d, J=8.6 Hz, 1H), 8.24–8.32(m, 4H), 8.83(s, 1H)

Example 955

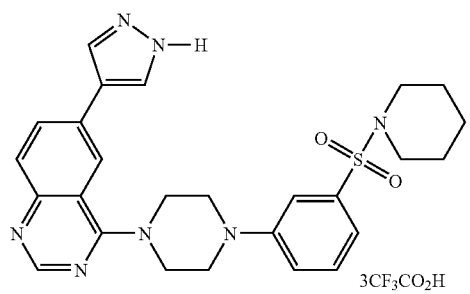

4-{4-[3-(Piperidine-1-sulfonyl)phenyl]piperazin-1-yl}-6-(1H-pyrazol-4-yl)quinazoline tri-trifluoroacetate ¹H-NMR (DMSO-d₆)
δ: 1.30–1.40(m, 2H), 1.50–1.58(m, 4H), 3.59(m, 4H), 4.30(m, 4H), 7.06–7.11(m, 2H), 7.22(d, J=7.9 Hz, 1H), 7.48(t, J=7.9 Hz, 1H), 7.80(d, J=8.6 Hz, 1H), 8.22–8.32(m, 4H), 8.79(s, 1H)

Example 956

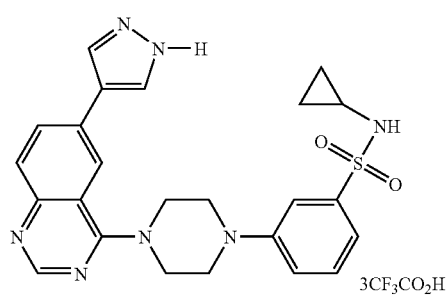

N-Cyclopropyl-3-{4-[6-(1H-pyrazol-4-yl)quinazolin-4-yl]piperazin-1-yl}benzene sulfonamide tri-trifluoroacetate ¹H-NMR (DMSO-d₆)
δ: 0.38–0.48(m, 4H), 2.07(m, 1H), 3.59(m, 4H), 4.33(m, 4H), 7.13–7.28(m, 3H), 7.46(t, J=8.0 Hz, 1H), 7.78–7.84(m, 2H), 8.20–8.30(m, 3H), 8.80(s, 1H)

Example 957

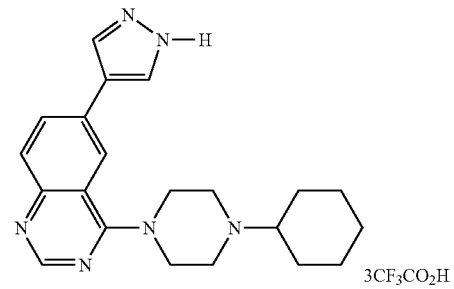

4-(4-Cyclohexylpiperazin-1-yl)-6-(1H-pyrazol-4-yl)quinazoline tri-trifluoroacetate ¹H-NMR (DMSO-d₆)
δ: 1.05–2.15(m, 10H), 3.20–3.80(m, 5H), 4.52(m, 4H), 7.86(d, J=8.8 Hz, 1H), 8.14(s, 1H), 8.22(d, J=8.8 Hz, 1H), 8.30(br.s, 2H), 8.77(s, 1H)

Example 958

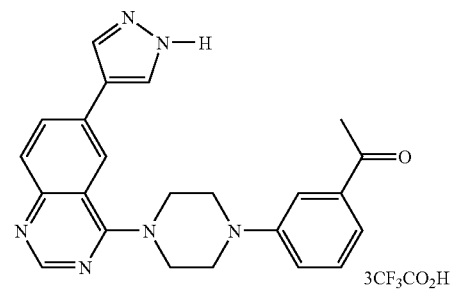

1-(3-{4-[6-(1H-Pyrazol-4-yl)quinazolin-4-yl]piperazin-1-yl}phenylethanone tri-trifluoroacetate ¹H-NMR (DMSO-d₆)
δ: 2.56 (3H, s), 3.57(m, 4H), 4.38(m, 4H), 7.20(m, 1H), 7.38–7.44(m, 3H), 7.82(d, J=9.5 Hz, 1H), 8.26–8.34(m, 4H), 8.84(s, 1H)

Example 959

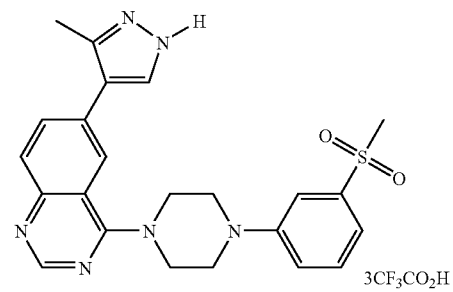

4-[4-(3-Methylsulfonylphenyl)piperazin-1-yl]-6-(3-methyl-1H-pyrazol-4-yl)quinazoline tri-trifluoroacetate ¹H-NMR (DMSO-d₆)
δ: 2.48 (3H, s), 3.19 (3H, s), 3.63(m, 4H), 4.36(m, 4H), 7.23(d, J=7.7 Hz, 1H), 7.28(d, J=7.7 Hz, 1H), 7.50(t, J=7.7 Hz, 1H), 7.85(d, J=8.8 Hz, 1H), 8.02(s, 1H), 8.14–8.19(m, 2H), 8.85(s, 1H)

Example 960

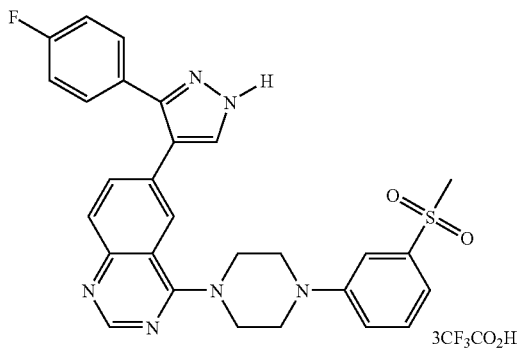

6-[3-(4-Fluorophenyl)-1H-pyrazol-4-yl]-4-[4-(3-methylsulfonylphenyl)piperazin-1-yl]-quinazoline tri-trifluoroacetate ¹H-NMR (DMSO-d₆)
δ: 3.20 (3H, s), 3.42(m, 4H), 4.04(m, 4H), 7.18–7.32(m, 5H), 7.44–7.54(m, 3H), 7.80(d, J=8.8 Hz, 1H), 7.90(s, 1H), 7.94(d, J=8.8 Hz, 1H), 8.12(s, 1H), 8.83(s, 1H)

Example 961

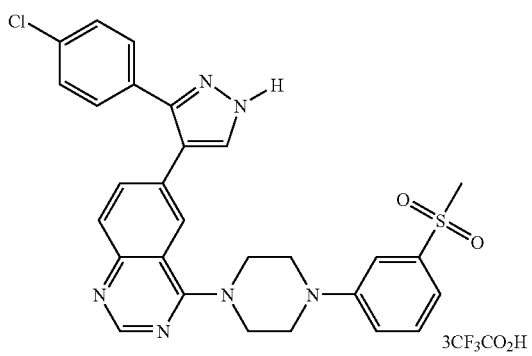

6-[3-(4-Chlorophenyl)-1H-pyrazol-4-yl]-4-[4-(3-methylsulfonylphenyl)piperazin-1-yl]-quinazoline tri-trifluoroacetate ¹H-NMR (DMSO-d₆)
δ: 3.19 (3H, s), 3.38(m, 4H), 3.97(m, 4H), 7.20(d, J=8.0 Hz, 1H), 7.29–7.34(m, 2H), 7.44–7.54(m, 5H), 7.81–7.84 (m, 2H), 7.99(d, J=8.8 Hz, 1H), 8.15(s, 1H), 8.81(s, 1H)

Example 962

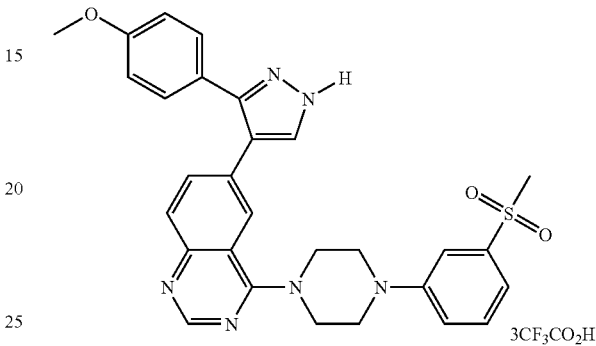

6-[3-(4-Methoxyphenyl)-1H-pyrazol-4-yl]-4-[4-(3-methylsulfonylphenyl)piperazin-1-yl]-quinazoline tri-trifluoroacetate ¹H-NMR (DMSO-d₆)
δ: 3.21 (3H, s), 3.37(m, 4H), 3.72(s, 3H), 3.97(m, 4H), 7.01(d, J=8.8 Hz, 2H), 7.16(d, J=7.9 Hz, 1H), 7.27(s, 1H), 7.30(d, J=7.9 Hz, 1H), 7.36(d, J=8.8 Hz, 2H), 7.53(t, J=7.9 Hz, 1H), 7.81–7.86(m, 2H), 8.01–8.05(m, 2H), 8.82(s, 1H)

Example 963

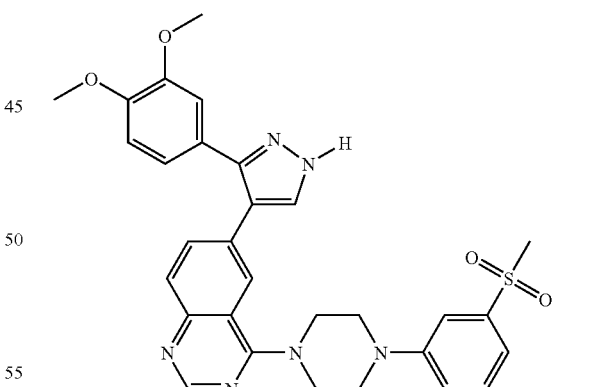

6-[3-(3,4-Dimethoxyphenyl)-1H-pyrazol-4-yl]-4-[4-(3-methylsulfonylphenyl)piperazin-1-yl]-quinazoline tri-trifluoroacetate ¹H-NMR (DMSO-d₆)
δ: 3.22(s, 3H), 3.35(m, 4H), 3.64(s, 3H), 3.72(s, 3H), 3.92(m, 4H), 6.91(d, J=8.2 Hz, 1H), 6.98–7.03(m, 2H), 7.16(d, J=8.0 Hz, 1H), 7.28–7.33(m, 2H), 7.53(t, J=8.2 Hz, 1H), 7.80–7.86(m, 2H), 8.01–8.05(m, 2H), 8.80(s, 1H)

Example 964

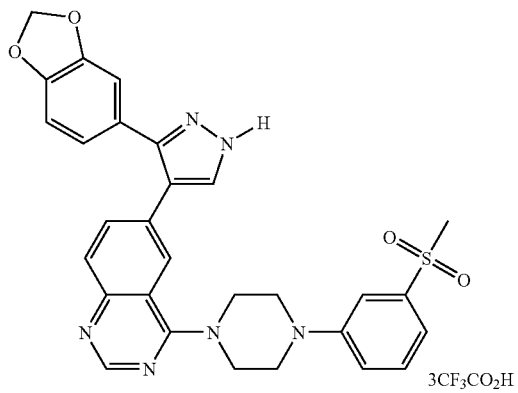

6-(3-Benzo[1,3]dioxol-5-yl-1H-pyrazol-4-yl)-4-[4-(3-methylsulfonylphenyl)piperazin-1-yl]quinazoline tri-trifluoroacetate $^1$H-NMR (DMSO-$d_6$)
δ: 3.21(s, 3H), 3.43(m, 4H), 4.04(m, 4H), 5.99(s, 2H), 6.88(dd, J=1.6, 7.9 Hz, 1H), 6.96(d, J=1.6 Hz, 1H), 6.99(d, J=7.9 Hz, 1H), 7.20(dd, J=2.0, 8.0 Hz, 1H), 7.30–7.34(m, 2H), 7.52(t, J=7.9 Hz, 1H), 7.80(d, J=8.6 Hz, 1H), 7.91(s, 1H), 7.97(d, J=8.6 Hz, 1H), 8.05(s, 1H), 8.82(s, 1H)

Example 965

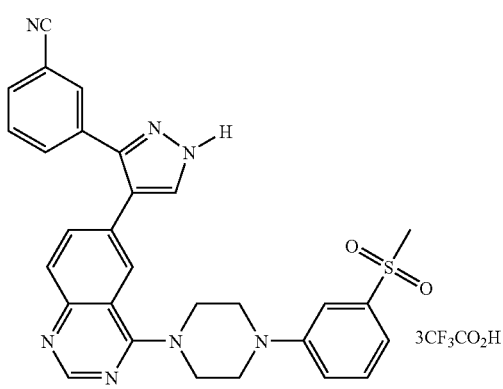

3-(4-{4-[4-(3-Methylsulfonylphenyl)piperazin-1-quinazolin-6-yl}-1H-pyrazol-3-yl)benzonitrile tri-trifluoroacetate $^1$H-NMR (DMSO-$d_6$)
δ: 3.20(s, 3H), 3.40(m, 4H), 4.00(m, 4H), 7.21(d, J=8.2 Hz, 1H), 7.28–7.36(m, 2H), 7.52(t, J=8.2 Hz, 1H), 7.58–7.76(m, 2H), 7.81(d, J=9.2 Hz, 1H), 7.84–7.92(m, 4H), 8.16(s, 1H), 8.81(s, 1H)

Example 966

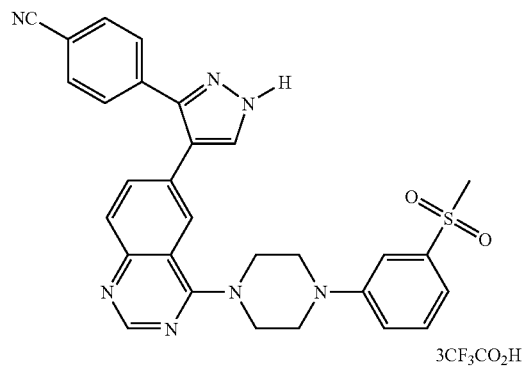

4-(4-{4-[4-(3-Methylsulfonylphenyl)piperazin-1-yl]quinazolin-6-yl}-1H-pyrazol-3-yl)benzonitrile tri-trifluoroacetate $^1$H-NMR (DMSO-$d_6$)
δ: 3.19(s, 3H), 3.41(m, 4H), 4.05(m, 4H), 7.22(d, J=8.2 Hz, 1H), 7.28–7.34(m, 2H), 7.51(t, J=8.2 Hz, 1H), 7.63(d, J=8.4 Hz, 2H), 7.80–7.93(m, 5H), 8.20(s, 1H), 8.83(s, 1H)

Example 967

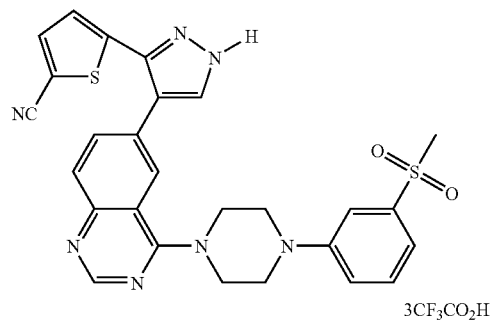

5-(4-{4-[4-(3-Methylsulfonylphenyl)piperazin-1-yl]quinazolin-6-yl}-1H-pyrazol-3-yl)thiophen-2-carbonitrile tri-trifluoroacetate $^1$H-NMR (DMSO-$d_6$)
δ: 3.20(s, 3H), 3.40(m, 4H), 4.15(m, 4H), 7.22(d, J=8.0 Hz, 1H), 7.29(d, J=8.0 Hz, 1H), 7.33(s, 1H), 7.50(t, J=8.0 Hz, 1H), 7.82–7.92(m, 3H), 7.99(d, J=8.6 Hz, 1H), 8.07(s, 1H), 8.23(s, 1H), 8.84(s, 1H)

Example 968

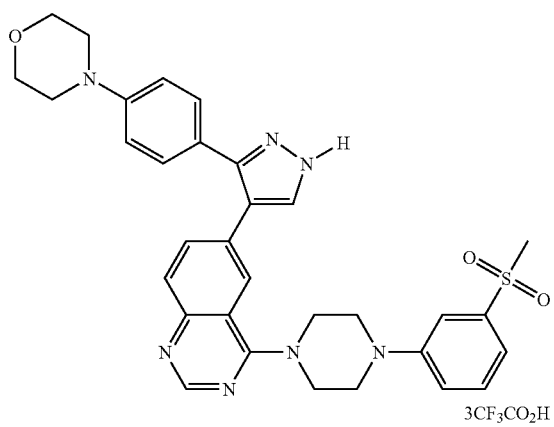

6-[3-(4-Morpholine-4-ylphenyl)-1H-pyrazol-4-yl]-4-[4-(3-methylsulfonylphenyl)piperazin-1-yl]-quinazoline tri-trifluoroacetate $^1$H-NMR (DMSO-$d_6$)

δ: 3.08(m, 4H), 3.20(s, 3H), 3.37(m, 4H), 3.63(m, 4H), 3.99(m, 4H), 7.00(d, J=9.0 Hz, 2H), 7.18(dd, J=2.0, 8.0 Hz, 1H), 7.28–7.34(m, 4H), 7.53(t, J=8.0 Hz, 1H), 7.81(d, J=8.8 Hz, 1H), 7.90(d, J=1.6 Hz, 1H), 8.00–8.08(m, 2H), 8.83(s, 1H)

Example 969

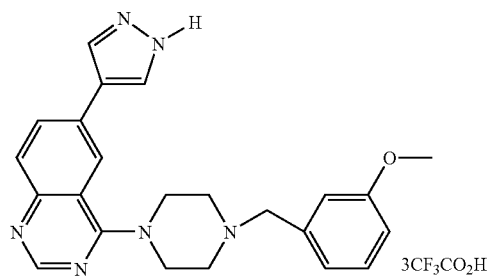

4-[4-(3-Methoxybenzyl)piperazin-1-yl]-6-(1H-pyrazol-4-yl)quinazoline tri-trifluoroacetate $^1$H-NMR (DMSO-$d_6$)

δ: 3.78(s, 3H), 3.60–4.00(m, 8H), 4.34(s, 2H), 7.01–7.13 (m, 3H), 7.40(t, J=8.6 Hz, RH), 7.86(d, J=9.0 Hz, 1H), 8.20–8.30(m, 4H), 8.81(s, 1H)

Example 970

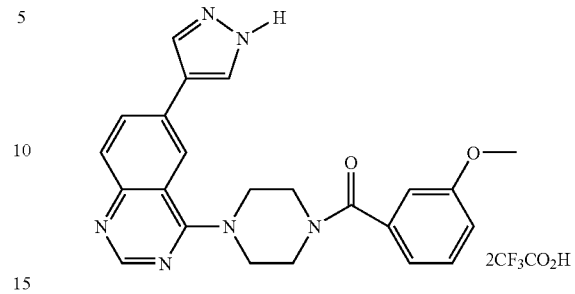

(3-Methoxyphenyl)-{4-[6-(1H-pyrazol-4-yl)quinazolin-4-yl]piperazin-1-yl}methanone di-trifluoroacetate $^1$H-NMR (DMSO-$d_6$)

δ: 3.78(s, 3H), 3.60–3.90(m, 4H), 4.20–4.30(m, 4H), 7.01–7.08(m, 3H), 7.39(t, J=7.9 Hz, 1H), 7.80(d, J=8.6 Hz, 1H), 8.21–8.30(m, 4H), 8.82(s, 1H)

Example 971

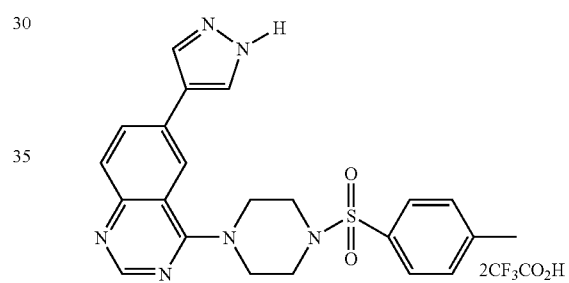

4-[4-(Toluene-4-sulfonyl)piperazin-1-yl]-6-(1H-pyrazol-4-yl)quinazoline di-trifluoroacetate $^1$H-NMR (DMSO-$d_6$)

δ: 2.35(s, 3H), 3.08(m, 4H), 4.21(m, 4H), 7.43(d, J=8.6 Hz, 2H), 7.63(d, J=8.6 Hz, 2H), 7.77(d, J=8.8 Hz, 1H), 8.12–78.27(m, 4H), 8.74(s, 1H)

Example 972

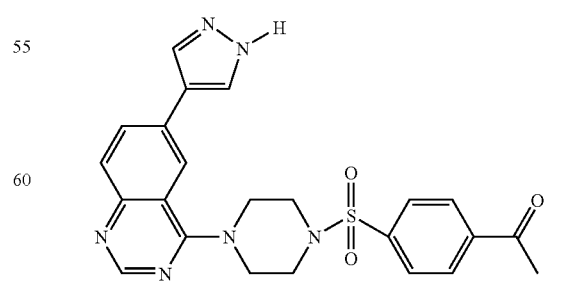

1-(4-{4-[6-(1H-Pyrazol-4-yl)quinazolin-4-yl]piperazine-1-sulfonyl}phenyl)ethanone di-trifluoroacetate ¹H-NMR (DMSO-d₆)
δ: 2.61(s, 3H), 3.22(m, 4H), 4.17(m, 4H), 7.77(d, J=8.7 Hz, 1H), 7.89(d, J=8.4 Hz, 2H), 8.10(s, 1H), 8.15(d, J=8.4, 2H), . 8.21(d, J=8.7 Hz, 1H), 8.24(s, 2H), 8.71 (s, 1H)

Example 973

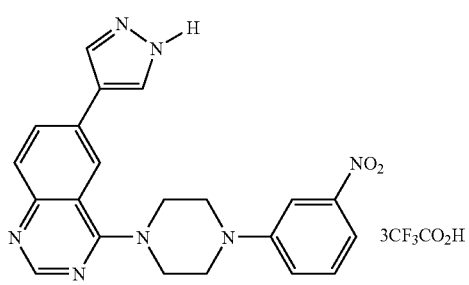

4-[4-(3-Nitrophenyl)piperazin-1-yl]-6-(1H-pyrazol-4-yl)quinazoline tri-trifluoroacetate ¹H-NMR (DMSO-d₆)
δ: 3.66(m, 4H), 4.32(m, 4H), 7.36(m, 1H), 7.51(t, J=8.1 Hz, 1H), 7.57–7.66(m, 2H), 7.81(d, J=9.2 Hz, 1H), 8.22–8.30(m, 4H), 8.81(s, 1H)

Example 974

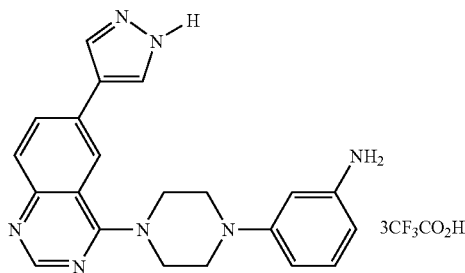

3-{4-[6-(1H-Pyrazol-4-yl)quinazolin-4-yl]piperazin-1-yl}phenylamine 40 mg 3-{4-[6-(1-trityl-1H-pyrazol-4-yl)quinazolin-4-yl]piperazin-1-yl} phenylamine obtained in Example 825 was deprotected and purified by the method described in Example 268 to give 18 mg of the title compound as a brown solid.
¹H-NMR (DMSO-d₆)
δ: 3.49(m, 4H), 4.35(m, 4H), 6.48–6.70(m, 3H), 7.19(t, J=7.8 Hz, 1H), 7.82(d, J=9.2 Hz, 1H), 8.24–8.34(m, 4H), 8.82(s, 1H)

Example 975

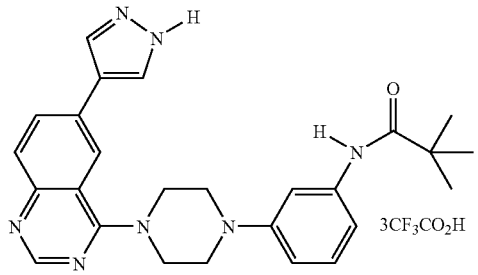

2,2-Dimethyl-N-(3-{4-[6-(1H-pyrazol-4-yl)quinazolin-4-yl]piperazin-1-yl} phenyl)propionamide trifluoroacetate 91 mg 2,2-dimethyl-N-(3-{4-[6-(1-trityl-1H-pyrazol-4-yl)quinazolin-4-yl]piperazin-1-yl}phenyl) propionamide obtained in Example 826 was deprotected and purified by the method described in Example 268 to give 40 mg of the title compound as a pale yellow solid.
¹H-NMR (DMSO-d₆)
δ: 1.21(s, 9H), 3.48(m, 4H), 4.30(m, 4H), 6.62(d, J=7.9 Hz, 1H), 7.09(d, J=7.9 Hz, 1H), 7.14(t, J=7.9 Hz, 1H), 7.37(s, 1H), 7.80(d, J=9.3 Hz, 1H), 8.20–8.28(m, 4H), 8.80(s, 1H), 9.06(s, 1H)

The compounds in Examples 976 to 993 were synthesized in the same manner as in Example 975.

Example 976

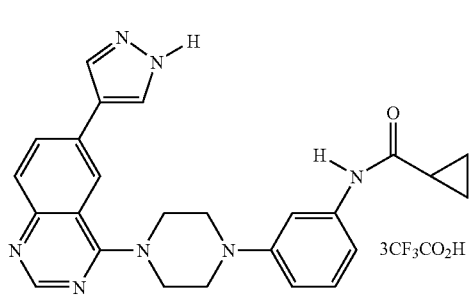

Cyclopropanecarboxylic acid (3-{4-[6-(1H-pyrazol-4-yl)quinazolin-4-yl]piperazin-1-yl}phenyl)amide tri-trifluoroacetate ¹H-NMR (DMSO-d₆)
δ: 0.75(m, 4H), 1.75(m, 1H), 3.46(m, 4H), 4.27(m, 4H), 6.62(d, J=8.4 Hz, 1H), 6.95(d, J=8.4 Hz, 1H), 7.14(t, J=8.4 Hz, 1H), 7.35(s, 1H), 7.78(d, J=9.0 Hz, 1H), 8.20–8.25(m, 4H), 8.77(s, 1H), 10.08(s, 1H)

Example 977

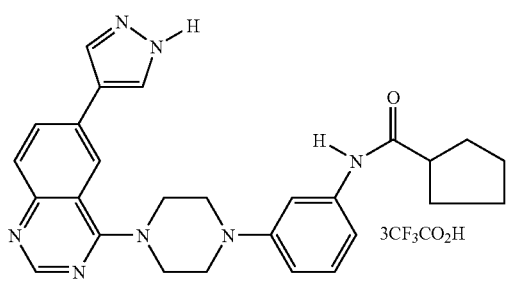

Cyclopentanecarboxylic acid (3-{4-[6-(1H-pyrazol-4-yl)quinazolin-4-yl]piperazin-1-yl}phenyl)amide tri-trifluoroacetate ¹H-NMR (CD₃OD)
δ: 1.50–2.00(m, 8H), 2.80(m, 1H), 3.50(m, 4H), 4.53(m, 4H), 6.76(d, J=8.0 Hz, 1H), 6.91(d, J=8.0 Hz, 1H), 7.20(t, J=8.0 Hz, 1H), 7.44(s, 1H), 7.79(d, J=10.0 Hz, 1H), 8.22(s, 2H), 8.30(dd, J=1.8, 10 Hz, 1H), 8.37(d, J=1.8 Hz, 1H), 8.66(s, 1H), 9.70(s, 1H)

Example 978

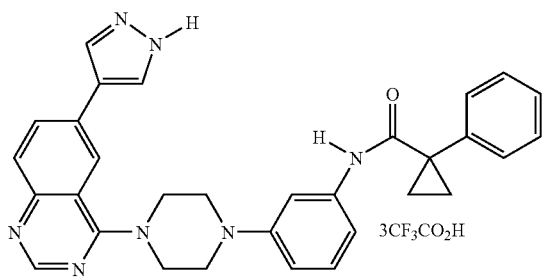

1-Phenylcyclopropanecarboxylic acid (3-{4-[6-(1H-pyrazol-4-yl)quinazolin-4-yl]piperazin-1-yl}phenyl)amide tri-trifluoroacetate ¹H-NMR (DMSO-d₆)
δ: 1.10(m, 2H), 1.41(m, 2H), 3.50(m, 4H), 4.27(m, 4H), 6.62(d, J=8.6 Hz, 1H), 6.97(d, J=8.0 Hz, 1H), 7.12(t, J=8.0 Hz, 1H), 7.20–7.40(m, 6H), 7.79(d, J=9.0 Hz, 1H), 8.20–8.30(m, 4H), 8.78(s, 1H), 8.87(s, 1H)

Example 979

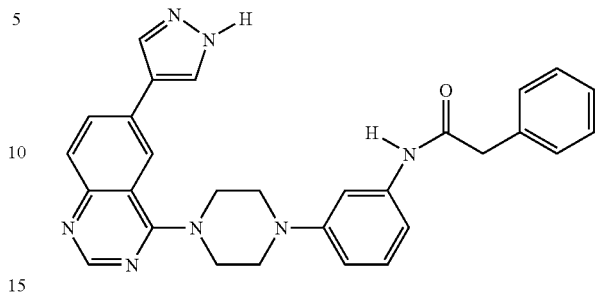

2-Phenyl-N-(3-{4-[6-(1H-pyrazol-4-yl)quinazolin-4-yl]piperazin-1-yl}phenyl)acetamide tri-trifluoroacetate ¹H-NMR (DMSO-d₆)
δ: 3.44(m, 4H), 3.60(s, 2H), 4.29(m, 4H), 6.63(d, J=8.2 Hz, 1H), 6.97(d, J=8.2 Hz, 1H), 7.15(t, J=8.2 Hz, 1H), 7.20–7.40(m, 6H), 7.78(d, J=8.8 Hz, 1H), 8.22–8.32(m, J=4H), 8.79(s, 1H), 10.08(s, 1H)

Example 980

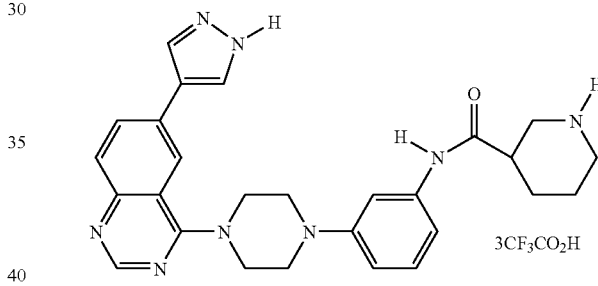

Piperidine-3-carboxylic acid (3-{4-[6-(1H-pyrazol-4-yl)quinazolin-4-yl]piperazin-1-yl}phenyl)amide tri-trifluoroacetate ¹H-NMR (DMSO-d₆)
δ: 1.60–2.05(m, 5H), 2.70–3.35. (m, 4H), 3.45(m, 4H), 4.26 (m, 4H), 6.66(d, J=8.0 Hz, 1H), 6.99(d, J=8.0 Hz, 1H), 7.17(t, J=8.0 Hz, 1H), 7.28(s, 1H), 7.81(d, J=9.1 Hz, 1H), 8.20–8.30(m, 4H), 8.57(s, 1H), 8.78(s, 1H)

Example 981

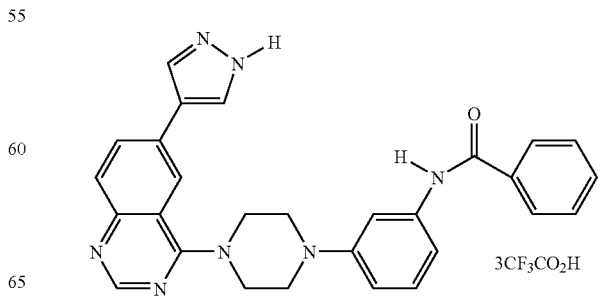

791

N-(3-{4-[6-(1H-Pyrazol-4-yl)quinazolin-4-yl]piperazin-1-yl}phenyl)benzamide tri-trifluoroacetate ¹H-NMR (DMSO-d₆)
δ: 3.48(m, 4H), 4.28(m, 4H), 6.71(m, 1H), 7.18–7.28(m, 3H), 7.50–7.60(m, 3H), 7.80(d, J=9.1 Hz, 1H), 7.92–7.96(m, 2H), 8.20–8.30(m, 4H), 8.78(s, 1H), 10.13(s, 1H)

Example 982

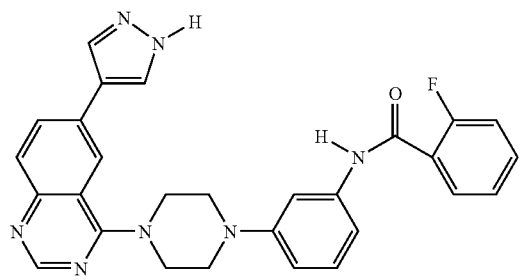

2-Fluoro-N-(3-{4-[6-(1H-pyrazol-4-yl)quinazolin-4-yl]piperazin-1-yl}phenyl)benzamide tri-trifluoroacetate ¹H-NMR (DMSO-d₆)
δ: 3.48(m, 4H), 4.31(m, 4H), 6.71(m, 1H), 7.12(d, J=8.2 Hz, 1H), 7.21(t, J=8.2 Hz, 1H), 7.30(d, J=7.5 Hz, 1H), 7.34(d, J=9.3 Hz, 1H), 7.55(m, 1H), 7.64(m, 1H), 8.20–8.30 (m, 4H), 8.80(s, 1H), 10.30(s, 1H)

Example 983

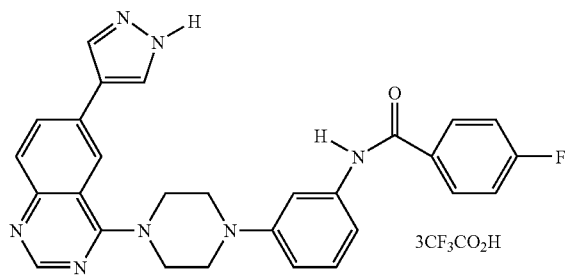

4-Fluoro-N-(3-{4-[6-(1H-pyrazol-4-yl)quinazolin-4-yl]piperazin-1-yl}phenyl)benzamide tri-trifluoroacetate ¹H-NMR (DMSO-d₆)
δ: 3.48(m, 4H), 4.31 (m, 4H), 6.72(m, 1H), 7.20(m, 2H), 7.35(t, J=8.8 Hz, 2H), 7.47(s, 1H), 7.80(d, J=8.4 Hz, 1H), 8.01(m, 2H), 8.20–8.30(m, 4H), 8.79(s, 1H), 10.15(s, 1H)

792

Example 984

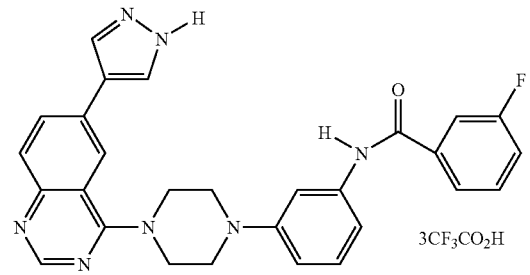

3-Fluoro-N-(3-{4-[6-(1H-pyrazol-4-yl)quinazolin-4-yl]piperazin-1-yl}phenyl)benzamide tri-trifluoroacetate ¹H-NMR (DMSO-d₆)
δ: 3.48(m, 4H), 4.31 (m, 4H), 6.72(m, 1H), 7.21(m, 2H), 7.40–7.48(m, 2H), 7.58(m, 1H), 7.72–7.82(m, 3H), 8.22–8.32(m, 4H), 8.79(s, 1H), 10.20 (s, 1H)

Example 985

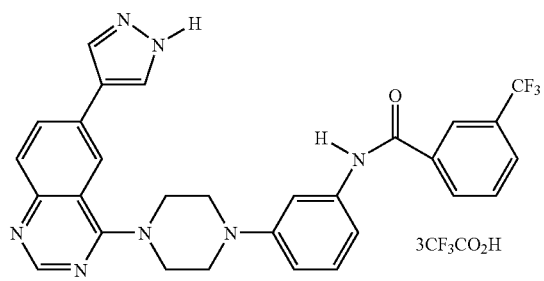

3-Trifluoromethyl-N-(3-{4-[6-(1H-pyrazol-4-yl)quinazolin-4-yl]piperazin-1-yl}phenyl)benzamide tri-trifluoroacetate ¹H-NMR (DMSO-d₆)
δ: 3.48(m, 4H), 4.31 (m, 4H), 6.71(d, J=8.2 Hz, 1H), 7.06(d, J=8.2 Hz, 1H), 7.21(t, J=8.2 Hz, 1H), 7.43(s, 1H), 7.64–7.84(m, 5H), 8.22–8.32(m, 4H), 8.79(s, 1H), 10.44 (s, 1H)

Example 986

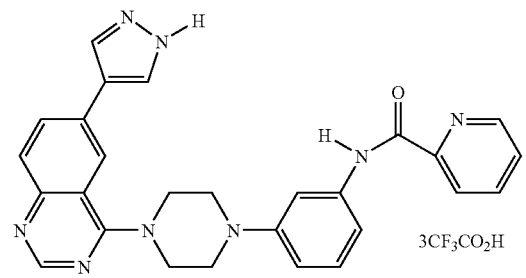

793

Pyridine-2-carboxylic acid (3-{4-[6-(1H-pyrazol-4-yl)quinazolin-4-yl]piperazin-1-yl}phenyl)amide tri-trifluoroacetate ¹H-NMR (DMSO-d₆)

δ: 3.51(m, 4H), 4.30 (m, 4H), 6.73(d, J=8.1 Hz, 1H), 7.23(d, J=8.1 Hz, 1H), 7.39(d, J=8.1 Hz, 1H), 7.59(s, 1H), 7.67(m, 1H), 7.80(d, J=8.4 Hz, 1H), 8.06(m, 1H), 8.14(d, J=7.0 Hz, 1H), 8.22–8.32(m, 4H), 8.73(m, 1H), 8.79(s, 1H), 10.50 (s, 1H)

Example 987

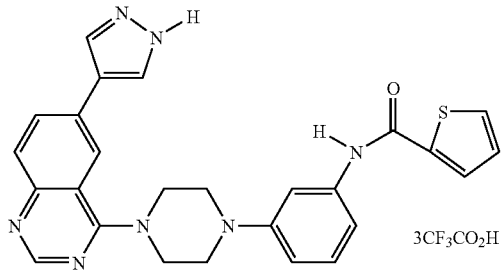

Thiophene-2-carboxylic acid (3-{4-[6-(1H-pyrazol-4-yl)quinazolin-4-yl]piperazin-1-yl}phenyl)amide tri-trifluoroacetate ¹H-NMR (DMSO-d₆)

δ: 3.49(m, 4H), 4.31 (m, 4H), 6.70(d, J=8.0 Hz, 1H), 7.22–7.23(m, 3H), 7.42(s, 1H), 7.81(d, J=8.4 Hz, 1H), 7.84(d, J=4.0, 1H), 8.00(d, J=4.0, 1H), 8.22–8.32(m, 4H), 8.80(m, 1H), 8.79(s, 1H), 10.12 (s, 1H)

Example 988

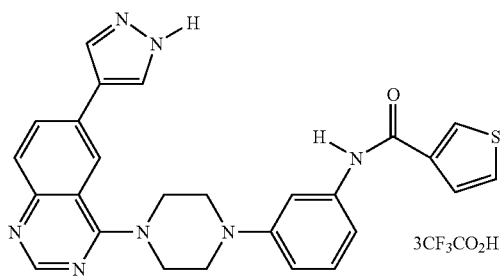

794

Thiophene-3-carboxylic acid (3-{4-[6-(1H-pyrazol-4-yl)quinazolin-4-yl]piperazin-1-yl}phenyl)amide tri-trifluoroacetate ¹H-NMR (DMSO-d₆)

δ: 3.49(m, 4H), 4.31 (m, 4H), 6.70(m, 1H), 7.18–7.22(m, 2H), 7.45(s, 1H), 7.58–7.66(m, 2H), 7.80(d, J=8.8 Hz, 1H), 8.22–8.36(m, 5H), 8.80(m, 1H), 8.79(s, 1H), 9.92 (s, 1H)

Example 989

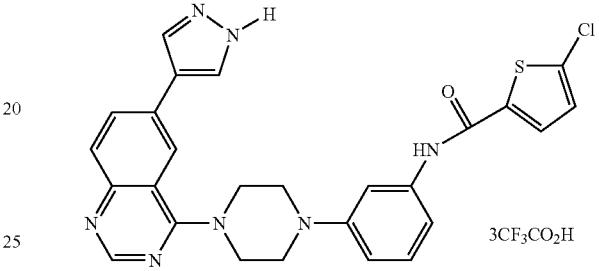

5-Chlorothiophen-2-carboxylic acid (3-{4-[6-(1H-pyrazol-4-yl)quinazolin-4-yl]piperazin-1-yl}phenyl)amide tri-trifluoroacetate ¹H-NMR (DMSO-d₆)

δ: 3.48(m, 4H), 4.31 (m, 4H), 6.71(d, J=8.1 Hz, 1H), 7.11(d, J=8.1 Hz, 1H), 7.19–7.27(m, 2H), 7.38(s, 1H), 7.80(d, J=8.1 Hz, 1H), 7.89(d, J=4.0 Hz, 1H), 8.20–8.32(m, 4H), 8.79(s, 1H), 10.20 (s, 1H)

Example 990

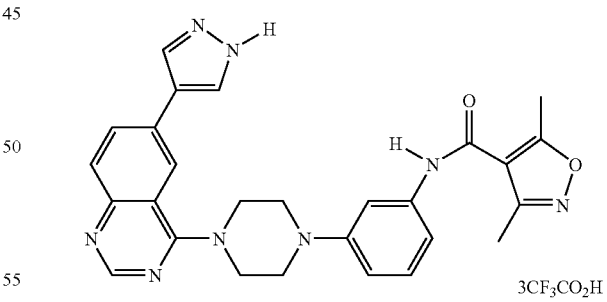

3,5-Dimethylisoxazol-4-carboxylic acid (3-{4-[6-(1H-pyrazol-4-yl)quinazolin-4-yl)piperazin-1-yl}phenyl)amide tri-trifluoroacetate ¹H-NMR (DMSO-d₆)

δ: 2.31(s, 3H), 2.52(s, 3H), 3.46(m, 4H), 4.31 (m, 4H), 6.71(d, J=8.2 Hz, 1H), 7.05(d, J=8.2 Hz, 1H), 7.21(t, J=8.2 Hz, 1H), 7.38(s, 1H), 7.80(d, J=9.1 Hz, 1H), 8.20–8.32(m, 4H), 8.79(s, 1H), 9.95 (s, 1H)

Example 991

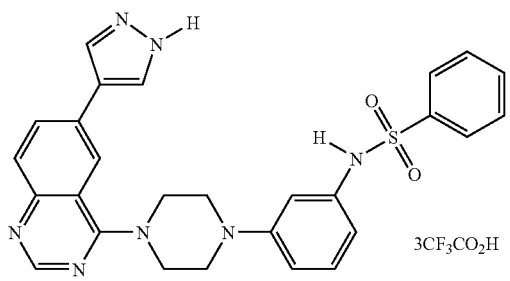

N-(3-{4-[6-(1H-Pyrazol-4-yl)quinazolin-4-yl]piperazin-1-yl}phenyl)benzene sulfonamide tri-trifluoroacetate $^1$H-NMR (DMSO-d$_6$)

δ: 3.46(m, 4H), 4.21 (m, 4H), 6.50(d, J=8.2 Hz, 1H), 6.60(d, J=8.2 Hz, 1H), 6.66(s, 1H), 7.06(t, J=8.2 Hz, 1H), 7.50–7.80(m, 6H), 8.20–8.32(m, 4H), 8.76(s, 1H), 10.12 (s, 1H)

Example 992

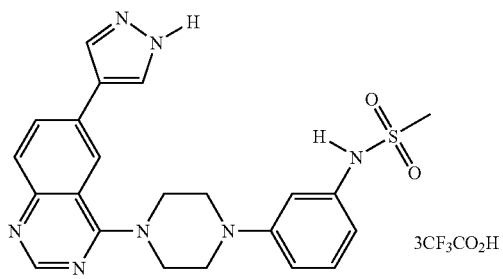

N-(3-{4-[6-(1H-Pyrazol-4-yl)quinazolin-4-yl]piperazin-1-yl}phenyl)methyl sulfonamide tri-trifluoroacetate $^1$H-NMR (DMSO-d$_6$)

δ: 2.96(s, 3H), 3.46(m, 4H), 4.31 (m, 4H), 6.67(m, 2H), 6.75(s, 1H), 7.19(t, J=8.0 Hz, 1H), 7.80(d, J=9.2 Hz, 1H), 8.20–8.33(m, 4H), 8.80(s, 1H), 9.60 (s, 1H)

Example 993

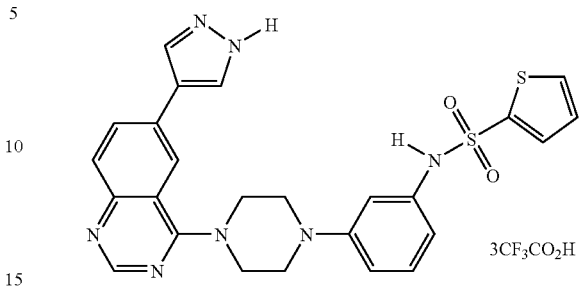

Thiophene-2-sulfonic acid (3-{4-[6-(1H-pyrazol-4-yl)quinazolin-4-yl]piperazin-1-yl}phenyl)amide tri-trifluoroacetate $^1$H-NMR (DMSO-d$_6$)

δ: 3.43(m, 4H), 4.36 (m, 4H), 6.50(d, J=8.2 Hz, 1H), 6.55(d, J=8.6 Hz, 1H), 6.64(d, J=8.6 Hz, 1H), 6.70(s, 1H), 7.08–7.13(m, 2H), 7.4(m, 1H), 7.80(d, J=9.2 Hz, 1H), 7.88(m, 1H), 8.25–8.32(m, 4H), 8.83(s, 1H), 10.31 (s, 1H)

Example 994

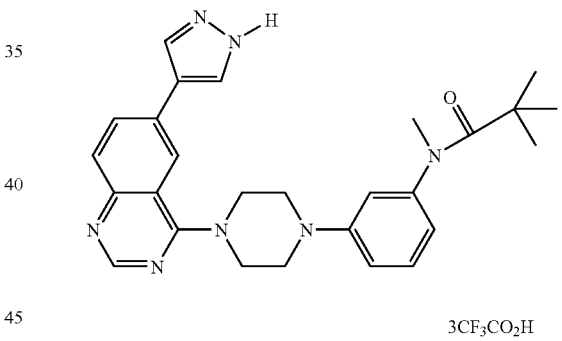

2,2-N-Trimethyl-N-(3-{4-[6-(1H-pyrazol-4-yl)quinazolin-4-yl]piperazin-1-yl}phenyl)propionamide tri-trifluoroacetate A mixture of 20 mg 2,2-dimethyl-N-(3-{4-[6-(1-trityl-1H-pyrazol-4-yl)quinazolin-4-yl]piperazin-1-yl}phenyl)propionamide obtained in Example A59, 10 mg iodomethane, 3 mg (60%) sodium hydride and 5 mL tetrahydrofuran was stirred at room temperature for 15 minutes. Water was added to the reaction solution which was then extracted with ethyl acetate, and the organic layer was washed with brine. The organic layer was dried over anhydrous magnesium sulfate, the solvent was evaporated, and the residue was deprotected and purified by the method described in Example 268 to give 2.5 mg of the title compound as a white solid.

¹H-NMR (DMSO-d₆)

δ: 0.97(s, 9H), 3.15(s, 3H), 3.50(m, 4H), 4.19 (m, 4H), 6.71(d, J=8.0 Hz, 1H), 6.87(s, 1H), 6.94(d, J=8.0 Hz, 1H), 7.28(t, J=8.0 Hz, 1H), 7.79(d, J=9.2 Hz, 1H), 8.20–8.26(m, 4H), 8.74(s, 1H)

Using a carboxylic acid amine or sulfonic acid amine and a halogenated alkyl as the starting materials, the compounds in Examples 995 to 999 were synthesized in the same manner as in Example 994.

Example 995

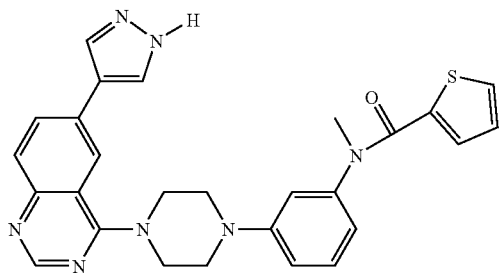

3CF₃CO₂H

Thiophene-2-carboxylic acid methyl-(3-{4-[6-(1H-pyrazol-4-yl)quinazolin-4-yl]piperazin-1-yl}phenyl) amide tri-trifluoroacetate ¹H-NMR (DMSO-d₆)

δ: 3.31(s, 3H), 3.51(m, 4H), 4.27 (m, 4H), 6.67(m, 1H), 6.72(d, J=8.0 Hz, 1H), 6.87(m, 1H), 6.93(s, 1H), 6.97(d, J=8.0 Hz, 1H), 7.30(t, J=8.0 Hz, 1H), 7.61(m, 1H), 7.80(d, J=9.2 Hz, 1H), 8.20–8.30(m, 4H), 8.79(s, 1H)

Example 996

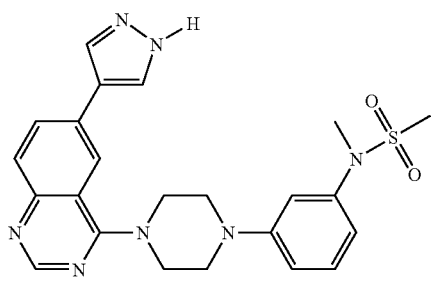

3CF₃CO₂H

N-Methyl-N-(3-{4-[6-(1H-pyrazol-4-yl)quinazolin-4-yl]piperazin-1-yl}phenyl)methyl sulfonamide tri-trifluoroacetate ¹H-NMR (DMSO-d₆)

δ: 2.96(s, 3H), 3.43(m, 4H), 3.52(s, 3H), 4.41 (m, 4H), 6.67(m, 2H), 6.76(s, 1H), 7.19(t, J=8.2 Hz, 1H), 7.91(d, J=9.2 Hz, 1H), 8.28–8.33(m, 4H), 8.84(s, 1H)

Example 997

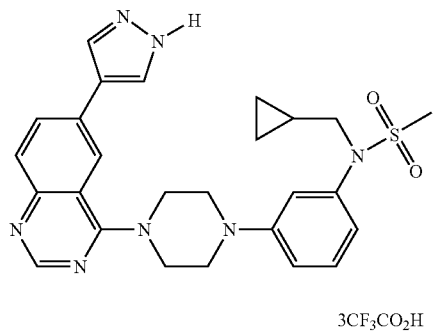

3CF₃CO₂H

N-Cyclopropylmethyl-N-(3-{4-[6-(1H-pyrazol-4-yl) quinazolin-4-yl]piperazin-1-yl}phenyl)methyl sulfonamide tri-trifluoroacetate ¹H-NMR (DMSO-d₆)

δ: 0.02(m, 4H), 0.32(m, 4H), 0.76(m, 1H), 2.89(s, 3H), 3.43(m, 4H), 4.20(m, 4H), 6.77(d, J=7.9 Hz, 1H), 6.85(m, 2H), 7.21(t, J=7.9 Hz, 1H), 7.73(d, J=9.0 Hz, 1H), 8.16–8.23 (m, 4H), 8.71(s, 1H)

Example 998

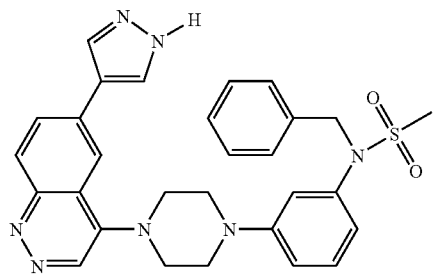

3CF₃CO₂H

N-Benzyl-N-(3-{4-[6-(1H-pyrazol-4-yl)quinazolin-4-yl]piperazin-1-yl}phenyl)methyl sulfonamide tri-trifluoroacetate ¹H-NMR (DMSO-d₆)

δ: 3.07(s, 3H), 3.45(m, 4H), 4.28(m, 4H), 4.84(s, 2H), 6.80(m, 2H), 6.89(s, 1H), 7.14–7.28(m, 6H), 7.80(d, J=9.2 Hz, 1H), 8.23–8.30(m, 4H), 8.80(s, 1H)

Example 999

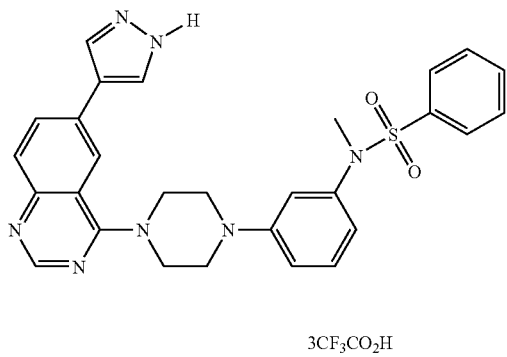

3CF₃CO₂H

N-Methyl-N-(3-{4-[6-(1H-pyrazol-4-yl)quinazolin-4-yl]piperazin-1-yl}phenyl)benzene sulfonamide tri-trifluoroacetate ¹H-NMR (DMSO-d₆)
δ: 3.10(s, 3H), 3.42(m, 4H), 4.28(m, 4H), 6.41(d, J=8.2 Hz, 1H), 6.65(s, 1H), 6.86(d, J=8.2 Hz, 1H), 7.18(t, J=8.2 Hz, 1H), 7.52–7.65(m, 5H), 7.80(d, J=9.2 Hz, 1H), 8.23–8.30(m, 4H), 8.80(s, 1H)

Example 1000

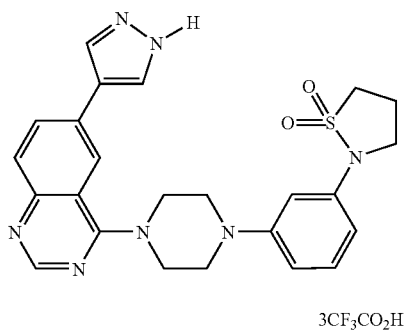

3CF₃CO₂H

4-{4-[3-(1,1-Dioxo-isothiazolidin-2-yl)phenyl]piperazin-1-yl}-6-(1H-pyrazol-4-yl)quinazoline tri-trifluoroacetate A mixture of 50 mg 3-{4-[6-(1-trityl-1H-pyrazol-4-yl)quinazolin-4-yl]piperazin-1-yl} phenylamine obtained in Example 825, 22 mg 3-chloropropyl sulfonyl chloride, 7 mg sodium hydride and 1 mL tetrahydrofuran was stirred at room temperature for 30 minutes. Water was added to the reaction solution which was then extracted with ethyl acetate, and the organic layer was washed with brine and dried over anhydrous magnesium sulfate. The solvent was evaporated, and the residue was deprotected and purified by the method described in Example 268 to give 22 mg of the title compound as a white solid.
¹H-NMR CDCl₃
δ: 2.38(m, 2H), 3.48(m, 6H), 3.73(t, J=6.4 Hz, 2H), 4.32 (m, 4H), 6.62–6.74(m, 3H), 7.22(t, J=8.0 Hz, 1H), 8.23–8.32 (m, 4H), 8.79(s, 1H)

Example 1001

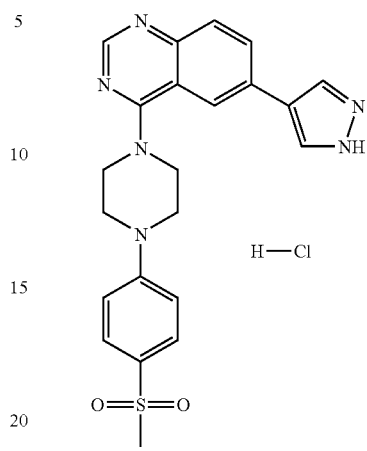

H—Cl

4-[4-(4-Methylsulfonyl)phenyl]-1,4-diazepan-1-yl}-6-(1H-4-pyrazolyl)quinazoline hydrochloride 3 mg of the title compound was obtained from 16 mg 4-[4-(4-methylsulfonyl)phenyl]-1,4-diazepan-1-yl}-6-(1-trityl-1H-4-pyrazolyl) quinazoline (compound in Example 830) by the same manner as in Example 164 (recrystallization solvent: methanol/diethyl ether).
MS m/e(ESI)449(MH⁺)

Example 1002

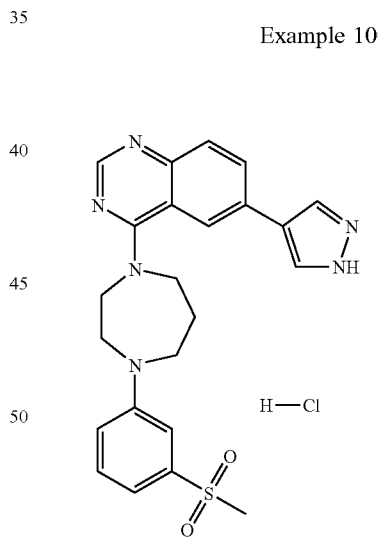

H—Cl

4-{4-(3-Methylsulfonyl)phenyl}-1,4-diazepan-1-yl}-6-(1H-4-pyrazolyl)quinazoline hydrochloride 3 mg of the title compound was obtained from 15 mg 4-{4-(4-methylsulfonyl)phenyl}-1,4-diazepan-1-yl}-6-(1-trityl-1H-4-pyrazolyl) quinazoline (compound in Example 831) by the same manner as in Example 164 (recrystallization solvent: methanol/diethyl ether).
MS m/e(ESI)449(MH⁺)

Example 1003

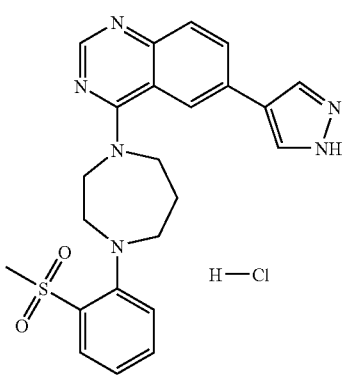

4-{4-[2-(Methylsulfonyl)phenyl]-1,4-diazepan-1-yl}-6-(1H-4-pyrazolyl)quinazoline hydrochloride 58 mg of the title compound was obtained from 166 mg 4-{4-[2-(methylsulfonyl)phenyl]-1,4-diazepan-1-yl}-6-(1-trityl-1H-4-pyrazolyl) quinazoline (compound in Example 832) by the same manner as in Example 164.

MS m/e(ESI)449(MH$^+$)

Example 1004

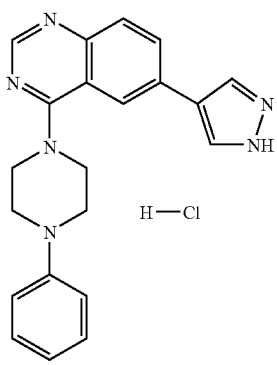

4-(4-Phenylpiperazin-1-yl)-6-(1H-4-pyrazolyl)quinazoline hydrochloride 40 mg of the title compound was obtained from 189 mg 4-(4-phenylpiperazin-1-yl)-6-(1-trityl-1H-4-pyrazolyl)-quinazoline (compound in Example 833) by the same manner as in Example 164.

MS m/e(ESI) 357(MH$^+$)

Example 1005

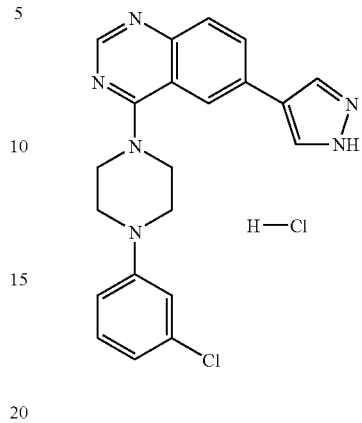

4-[4-(3-Chlorophenyl)piperazin-1-yl]-6-(1H-pyrazolyl)quinazoline hydrochloride 250 mg of the title compound was obtained from 603 mg 4-[4-(3-chlorophenyl)piperazin-1-yl]-6-(1-trityl-1H-4-pyrazol) quinazoline (compound in Example 834) by the same manner as in Example 164.

$^1$H-NMR (CD$_3$OD)

δ: 1.56(dd, J=5.2, 5.2 Hz, 2H), 1.56(dd, J=5.2, 5.2 Hz, 2H), 2.05(dd, J=5.2, 5.2 Hz, 2H), 2.05(dd, J=5.2, 5.2 Hz, 2H), 4.82(dd, J=8.5, 2.4 Hz, 1H), 4.95(dd, J=8.5, 2.4 Hz, 1H), 5.02(dd, J=2.4, 2.4 Hz, 1H), 5.22(dd, J=8.5, 8.5, 2.4 Hz, 1H), 5.83(d, J=8.8 Hz, 1H), 6.10–6.19(m, 4H), 6.57(s, 1H)

Example 1006

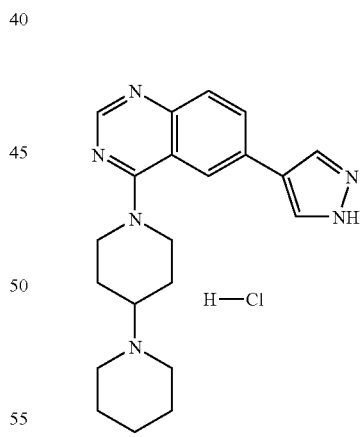

4-1,4'-Bipiperidinyl-1'-yl-6-(1H-pyrazol-4-yl)quinazoline hydrochloride 20 mg of the title compound was obtained from 200 mg 4-1,4'-bipiperidinyl-1'-yl-6-(1-trityl-1H-pyrazol-4-yl) quinazoline (compound in Example 835) by the same manner as in Example 164.

MS m/e(ESI) 363(MH$^+$)

Example 1007

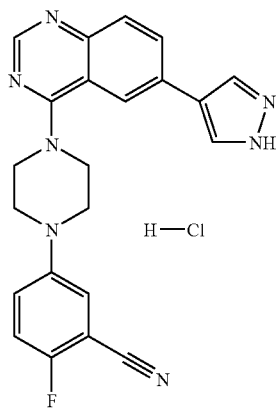

2-Fluoro-5-{4-[6-(1H-4-pyrazolyl)-4-quinazolinyl]piperazin-1-yl}benzonitrile hydrochloride 93 mg of the title compound was obtained from 284 mg 2-fluoro-5-{4-[6-(1-trityl-1H-4-pyrazolyl)-4-quinazolinyl]piperazin-1-yl}benzonitrile (compound in Example 836) by the same manner as in Example 164.
MS m/e(ESI) 400(MH$^+$)

Example 1008

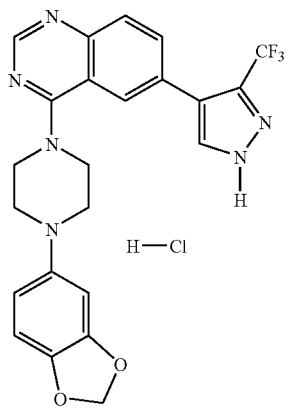

4-[4-(1,3-Benzodioxol-5-yl)piperazin-1-yl]-6-[3-(trifluoromethyl)-1H-4-pyrazolyl]quinazoline hydrochloride 10 mg of the title compound was obtained from 30 mg 4-[4-(1,3-benzodioxol-5-yl)piperazin-1-yl]-6-[3-trifluoromethyl)-1-trityl-1H-4-pyrazolyl] quinazoline (compound in Example 837) by the same manner as in Example 164.
$^1$H-NMR (CD$_3$OD)
δ: 3.22–3.28(m, 4H), 3.96–4.02(m, 4H), 5.88(s, 2H), 6.45–6.50(m, 1H), 6.64–6.70(m, 1H), 6.72–6.75(m, 1H), 7.87(d, J=10 Hz, 1H), 7.93(dd, J=10, 0.8 Hz, 1H), 8.11(d, J=0.8 Hz, 1H), 8.14(s, 1H), 8.63(s, 1H)

Example 1009

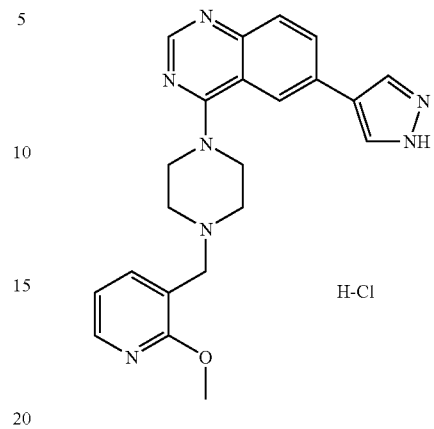

4-{4-[(2-Methoxy-3-pyridyl)methyl]piperazin-1-yl}-6-(1H-4-pyrazolyl)quinazoline hydrochloride 20 mg of the title compound was obtained from 220 mg 4-{4-[(2-methoxy-3-pyridyl)methyl]piperazin-1-yl}-6-(1-trityl-1H-4-pyrazolyl) quinazoline (compound in Example 838) by the same manner as in Example 164.
$^1$H-NMR (CDCl$_3$)
δ: 4.37(s, 2H), 4.48(s, 3H), 6.48–6.52(m, 4H), 7.10–7.13 (m, 4H), 7.60–7.62(m, 1H), 7.92–7.94(m, 2H), 7.97–8.00 (m, 1H), 8.30–8.32(m, 1H), 8.36–8.44(m, 2H), 8.52(s, 1H), 8.83(s, 1H),

Example 1010

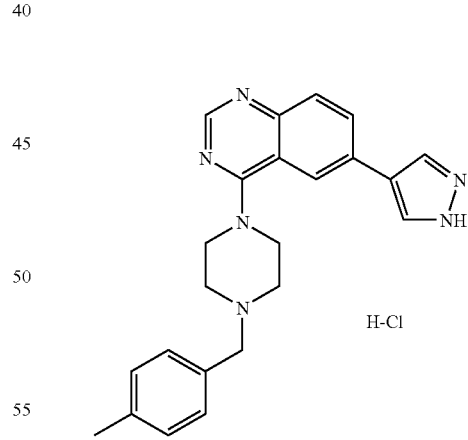

4-[4-(4-Methylbenzyl)piperazin-1-yl]-6-(1H-pyrazolyl)quinazoline hydrochloride 53 mg of the title compound was obtained from 4-[4-(4-methylbenzyl)piperazin-1-yl]-6-(1-trityl-1H-pyrazolyl) quinazoline (compound in Example 839) by the same manner as in Example 164.
MS m/e (ESI) 385(MH$^+$)

Example 1011

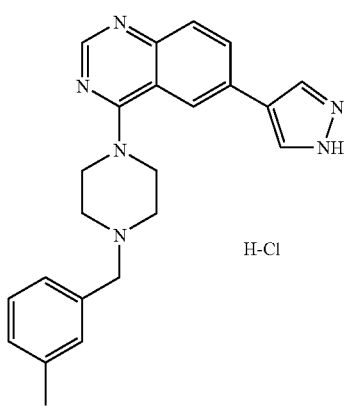

4-[4-(3-Methylphenyl)piperazin-1-yl]-6-(1H-4-pyrazolyl)quinazoline hydrochloride 15 mg of the title compound was obtained from 50 mg 4-[4-(3-methylphenyl)piperazin-1-yl]-6-(1-trityl-1H-4-pyrazolyl) quinazoline (compound in Example 840) by the same manner as in Example 164.
MS m/e(ESI) 385(MH$^+$)

Example 1012

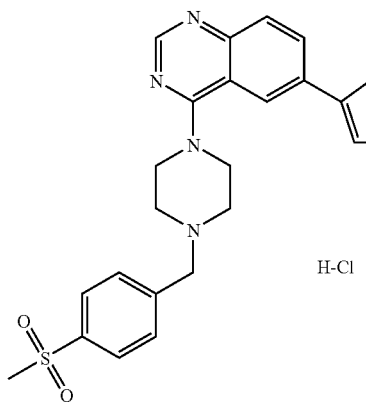

4-{4-[4-(Methylsulfonyl)benzyl]piperazin-1-yl}-6-(1H-4-pyrazolyl)quinazoline hydrochloride 15 mg of the title compound was obtained from 50 mg 4-{4-[4-(methylsulfonyl)benzyl]piperazin-1-yl}-6-(1-trityl-1H-4-pyrazolyl) quinazoline (compound in Example 841) by the same manner as in Example 164.
MS m/e(ESI) 449(MH$^+$)

Example 1013

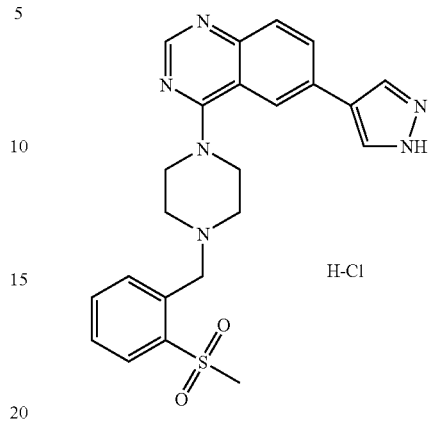

4-{4-[2-(Methylsulfonyl)benzyl]piperazin-1-yl}-6-(1H-pyrazolyl)quinazoline hydrochloride 10 mg of the title compound was obtained from 40 mg 4-{4-[2-(methylsulfonyl)benzyl]piperazin-1-yl}-6-(1-trityl-1H-pyrazolyl) quinazoline (compound in Example 842) by the same manner as in Example 164.
MS m/e(ESI) 449(MH$^+$)

Example 1014

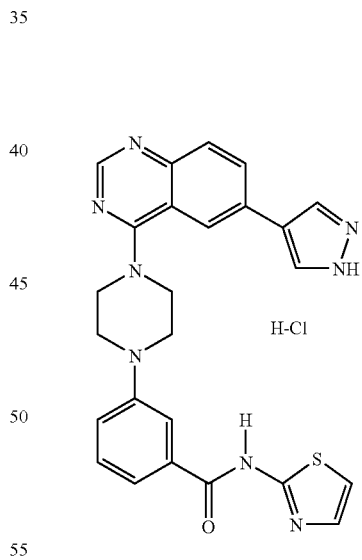

N1-(1,3-Thiazol-2-yl)-3-{4-[6-(1H-4-pyrazolyl)-4-quinazolinyl]piperazin-1-yl}benzamide hydrochloride 20 mg of the title compound was obtained from 150 mg N1-(1,3-thiazol-2-yl)-3-{4-[6-(1-trityl-1H-4-pyrazolyl)-4-quinazolinyl]piperazin-1-yl} benzamide (compound in Example 843) by the same manner as in Example 164.
MS m/e(ESI) 483(MH$^+$).

Example 1015

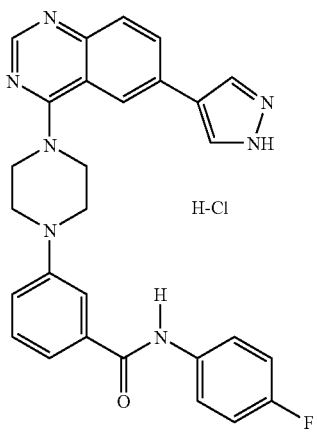

N1-(4-Fluorophenyl)-3-{4-[6-(1H-pyrazolyl)-4-quinazolinyl]piperazin-1-yl}benzamide hydrochloride 200 mg 3-{4-[6-(1-trityl-1H-pyrazolyl)-4-quinazolinyl] piperazin-1-yl} benzoic acid (compound in Example 829), 35 mg 4-fluoroaniline, 46 mg 1-hydroxybenzotriazole and 65 mg 1-ethyl-3-(3-dimethylaminopropyl)-carbodiimide hydrochloride were dissolved in dichloromethane and stirred for about 12 hours, and the reaction solution was concentrated and purified by silica gel column chromatography to give N1-(4-fluorophenyl)-3-{4-[6-(1-trityl-1H-pyrazolyl)-4-quinazolinyl]piperazin-1-yl}benzamide.

From 177 mg of this compound, 98 mg of the title compound was obtained by the same method as in Example 164.

$^1$H-NMR (DMSO)

δ: 3.58–3.66(m, 4H), 4.40–4.50(m, 4H), 7.16–7.22(m, 3H), 7.41(s, 1H), 7.42(dd, J=8.8, 8.8 Hz, 1H), 7.49(bd, 1H), 7.80(d, J=8.8 Hz, 1H), 7.81(d, J=8.8 Hz, 1H), 7.92(d, J=9.2 Hz, 1H), 8.33 (d, J=7.2 Hz, 4H), 8.87(s, 1H), 10.3(s, 1H)

MS m/e(ESI) 494(MH$^+$)

Example 1016

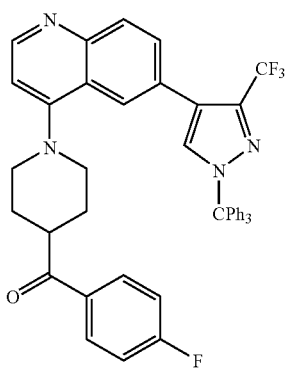

(4-Fluorophenyl)-{1-[6-(3-trifluoromethyl-1-trityl-1H-pyrazol-4-yl)quinolin-4-yl]piperidin-4-yl} methanone 51 mg of the title compound was obtained by the same reaction as in Example 9 from 43 mg [1-(6-bromoquinolin-4-yl)piperidin-4-yl]-(4-fluorophenyl) methanone (compound in Production Example 220) and 57 mg 3-trifluoromethyl-1-trityl-1H-4-pyrazolylboronic acid (compound in Production Example 31).

$^1$H-NMR (CDCl$_3$)

δ: 2.02–2.20(m, 4H), 2.95–3.04(m, 2H), 3.44–3.52(m, 1H), 3.66–3.74(m, 2H), 6.87(d, J=5.0 Hz, 1H), 7.17–7.23(m, 8H), 7.33–7.38(m, 9H), 7.50(d, J=0.8 Hz, 1H), 7.61(dd, J=8.8, 2.0 Hz, 1H), 8.02(d, J=8.8 Hz, 1H), 8.03–8.08(m, 3H), 8.71(d, J=5.0 Hz, 1H)

Example 1017

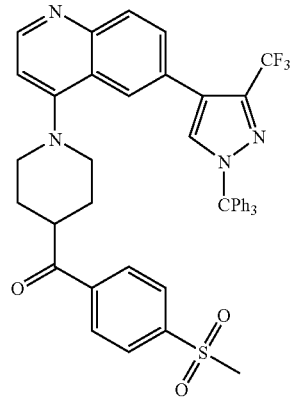

(4-Methylsulfonylphenyl)-{1-[6-(3-trifluoromethyl-1-trityl-1H-pyrazol-4-yl)quinolin-4-yl]piperidin-4-yl} methanone 56 mg [1-(6-bromoquinolin-4-yl)piperidin-4-yl]-(4-methylsulfanylphenyl)methanone (compound in Production Example 225) and 69 mg 3-trifluoromethyl-1-trityl-1H-4-pyrazolylboronic acid (compound in Production Example 31) were reacted in the same manner as in Example 9, to give 80 mg (4-methanesulfanylphenyl)-{1-[6-(3-trifluoromethyl-1-trityl-1H-pyrazol-4-yl)quinolin-4-yl]piperidin-4-yl} methanone as a colorless amorphous. Using this product and 140 mg oxone, 75 mg of the title compound was obtained by the same reaction as in Production Example 43.

$^1$H-NMR (CDCl$_3$)

δ: 2.05–2.21(m, 4H), 2.97–3.05(m, 2H), 3.11(s, 3H), 3.46–3.56(m, 1H), 3.68–3.74(m, 2H), 6.88(d, J=5.2 Hz, 1H), 7.17–7.23(m, 6H), 7.33–7.38(m, 9H), 7.51(d, J=0.8 Hz, 1H), 7.60(dd, J=8.8, 2.0 Hz, 1H), 8.02(d, J=8.8 Hz, 1H), 8.08(d, J=2.0 Hz, 1H), 8.09–8.13(m, 2H), 8.16–8.19(m, 2H), 8.71(d, J=5.2 Hz, 1H)

Example 1018

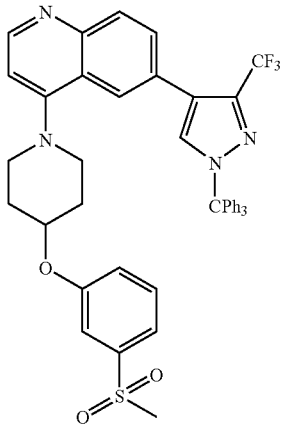

4-[4-(3-Methylsulfonylphenoxy)-piperidin-1-yl]-6-(3-trifluoromethyl-1-trityl-1H-pyrazol-4-yl) quinoline 96 mg 6-bromo-4-[4-(3-methylsulfanylphenoxy)piperidin-1-yl] quinoline (compound in Production Example 229) and 120 mg 3-trifluoromethyl-1-trityl-1H-4-pyrazolylboronic acid (compound in Production Example 31) were reacted in the same manner as in Example 9, to give 139 mg 4-[4-(3-methanesulfanylphenoxy)-piperidin-1-yl]-6-(3-trifluoromethyl-1-trityl-1H-pyrazol-4-yl) quinoline as a colorless amorphous. Using this product and 230 mg oxone, 127 mg of the title compound was obtained by the same reaction as in Production Example 43.

$^1$H-NMR (CDCl$_3$)

δ: 2.07–2.15(m, 2H), 2.24–2.31(m, 2H), 3.08(s, 3H), 3.15–3.24(m, 2H), 3.43–3.52(m, 2H), 4.67–4.73(m, 1H), 6.90(d, J=4.8 Hz, 1H), 7.17–7.27(m, 8H), 7.34–7.39(m, 9H), 7.51–7.56(m, 3H), 7.59(dd, J=8.6, 1.6 Hz, 1H), 8.02(d, J=8.6 Hz, 1H), 8.13(d, J=1.6 Hz, 1H), 8.72(d, J=4.8 Hz, 1H)

Example 1019

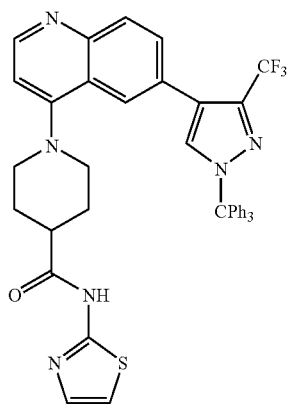

1-[6-(3-Trifluoromethyl-1-trityl-1H-pyrazol-4-yl)quinolin-4-yl]-piperidine-4-carboxylic acid thiazol-2-ylamide 220 mg of the title compound was obtained by the same reaction as in Example 9 from 191 mg 1-(6-bromoquinolin-4-yl)piperidine-4-carboxylic acid thiazol-2-ylamide (compound in Production Example 459) and 250 mg 3-trifluoromethyl-1-trityl-1H-4-pyrazolylboronic acid (compound in Production Example 31).

$^1$H-NMR (CDCl$_3$)

δ: 2.10–2.28(m, 4H), 2.64–2.73(m, 1H), 2.90–2.98(m, 2H), 3.67–3.77(m, 2H), 6.87(d, J=5.0 Hz, 1H), 7.03(d, J=3.6 Hz, 1H), 7.17–7.23(m, 6H), 7.34–7.38(m, 9H), 7.48(d, J=3.6 Hz, 1H), 7.52(d, J=0.8 Hz, 1H), 7.60(dd, J=8.8, 1.8 Hz, 1H), 8.02(d, J=8.8 Hz, 1H), 8.08(d, J=1.8 Hz, 1H), 8.72(d, J=5.0 Hz, 1H)

Example 1020

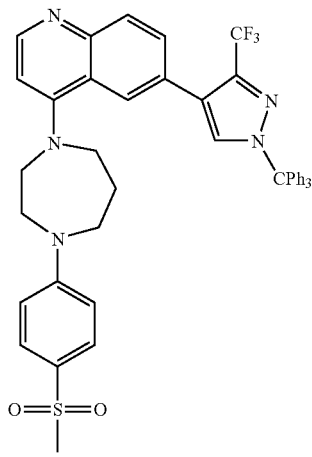

4-{4-[4-(Methylsulfonyl)phenyl]-1,4-diazepan-1-yl}-6-[3-(trifluoromethyl)-1-trityl-1H-4-pyrazolyl]quinoline 205 mg of the title compound was obtained by the same method as in Example 168 from 139 mg 3-trifluoromethyl-1-trityl-1H-4-pyrazolylboronic acid (compound in Production Example 31) and 113 mg 4-[4-(6-bromo-4-quinolyl)-1,4-diazepan-1-yl]phenylmethyl sulfone prepared by the same method as in Production Example 82 using 1-[4-(methylsulfonyl)phenyl]-1,4-diazepan hydrobromide.

$^1$H-NMR (CDCl$_3$)

δ: 2.40–2.60(m, 2H), 3.02(s, 3H), 3.34–3.37(m, 2H), 3.53–3.54(m, 2H), 3.74–3.78(m, 2H), 3.87–3.90(m, 2H), 6.81(d, J=8.8 Hz, 2H), 6.90(d, J=5.2 Hz, 1H), 7.19–7.22(m, 6H), 7.34–7.38(m, 9H), 7.53(s, 1H), 7.63(dd, J=8.4, 2.0 Hz, 1H), 7.77(d, J=8.8 Hz, 2H), 8.03(d, J=8.4 Hz, 1H), 8.12(d, J=2.0 Hz, 1H), 8.68(d, J=5.2 Hz, 1H)

Example 1021

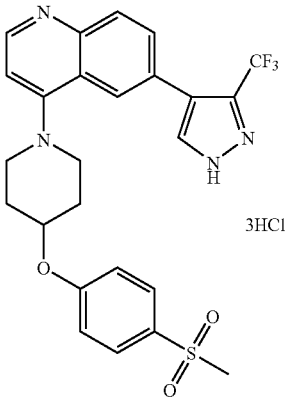

4-[4-(4-Methylsulfonylphenoxy)piperidin-1-yl]-6-(3-trifluoromethyl-1H-pyrazol-4-yl)quinoline trihydrochloride 150 mg 6-bromo-4-{4-[4-(methylsulfonyl)phenoxy]piperidino}quinoline (compound in Production Example 89) and 180 mg 3-trifluoromethyl-1-trityl-1H-4-pyrazolylboronic acid (compound in Production Example 31) were reacted in the same manner as in Example 9, to give 244 mg 4-[4-(4-methylsulfonylphenoxy)piperidin-1-yl]-6-(3-trifluoromethyl-1-trityl-1H-pyrazol-4-yl) quinoline. This product was reacted in the same manner as in Example 67, to give 130 mg of the title compound as pale yellow crystals.

$^1$H-NMR (DMSO-$d_6$)

δ: 1.91–2.01(m, 2H), 2.22–2.29(m, 2H), 3.18(s, 3H), 3.73–3.81(m, 2H), 3.97–4.05(m, 2H), 4.97–5.03(m, 1H), 7.24–7.32(m, 3H), 7.85–7.89(m, 2H), 8.03(dd, J=8.8, 1.6 Hz, 1H), 8.10(d, J=1.6 Hz, 1H), 8.12(d, J=8.8 Hz, 1H), 8.46(s, 1H), 8.72(d, J=6.8 Hz, 1H)

MS m/e (ESI) 517 (MH$^+$)

Example 1022

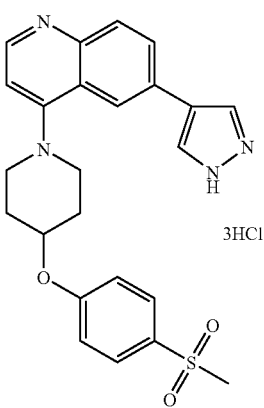

4-[4-(4-Methylsulfonylphenoxy)piperidin-1-yl]-6-(1H-pyrazol-4-yl)quinoline trihydrochloride 80 mg 6-bromo-4-{4-[4-(methylsulfonyl)phenoxy]piperidino}quinoline (compound in Production Example 89) and 80 mg 1-trityl-1H-4-pyrazolylboronic acid were reacted in the same manner as in Example 9, to give 102 mg 4-[4-(4-methylsulfonylphenoxy)piperidin-1-yl]-6-(1-trityl-1H-pyrazol-4-yl) quinoline. This product was reacted in the same manner as in Example 67, to give 52 mg of the title compound as colorless crystals.

$^1$H-NMR (DMSO-$d_6$)

δ: 1.96–2.07(m, 2H), 2.24–2.34(m, 2H), 3.18(s, 3H), 3.80–3.87(m, 2H), 4.02–4.11(m, 2H), 4.97–5.04(m, 1H), 7.25(d, J=7.0 Hz, 1H), 7.26–7.31(m, 2H), 7.85–7.91(m, 2H), 8.04(d, J=8.8 Hz, 1H), 8.21(d, J=1.6 Hz, 1H), 8.26(dd, J=8.8, 1.6 Hz, 1H), 8.30(brs, 2H), 8.63(d, J=7.0 Hz, 1H)

MS m/e (ESI) 449 (MH$^+$)

Example 1023

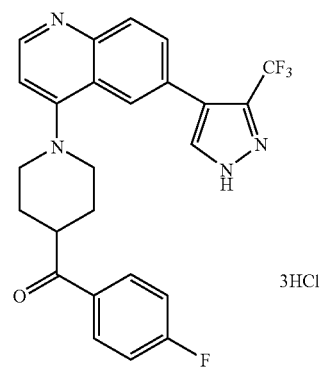

(4-Fluorophenyl)-{1-[6-(3-trifluoromethyl-1H-pyrazol-4-yl)quinolin-4-yl]piperidin-4-yl}methanone trihydrochloride 27 mg of the title compound was obtained as pale yellow crystals by the same reaction as in Example 67 from 51 mg (4-fluorophenyl)-{1-[6-(3-trifluoromethyl-1-trityl-1H-pyrazol-4-yl)quinolin-4-yl]piperidin-4-yl} methanone (compound in Example 1016).

$^1$H-NMR (DMSO-$d_6$)

δ: 1.80–1.94(m, 2H), 1.97–2.08(m, 2H), 3.58–3.69(m, 2H), 3.89–3.99(m, 1H), 4.13–4.25(m, 2H), 7.27(d, J=6.4 Hz, 1H), 7.38–7.45(m, 2H), 8.02(dd, J=8.8, 1.6 Hz, 1H), 8.08(d, J=1.6 Hz, 1H), 8.11(d, J=8.8 Hz, 1H), 8.13–8.19(m, 2H), 8.45(brs, 1H), 8.69(d, J=6.4 Hz, 1H)

MS m/e (ESI) 469 (MH$^+$)

Example 1024

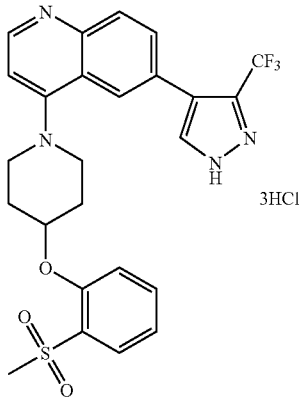

4-[4-(2-Methylsulfonylphenoxy)piperidin-1-yl]-6-(3-trifluoromethyl-1H-pyrazol-4-yl)quinoline trihydrochloride 80 mg 6-bromo-4-[4-(2-methylsulfonylphenoxy)-piperidin-1-yl] quinoline (compound in Production Example 222) and 95 mg 3-trifluoromethyl-1-trityl-1H-4-pyrazolylboronic acid (compound in Production Example 31) were reacted in the same manner as in Example 9, to give 124 mg 4-[4-(2-methylsulfonylphenoxy)piperidin-1-yl]-6-(3-trifluoromethyl-1-trityl-1H-pyrazol-4-yl) quinoline. This product was reacted in the same manner as in Example 67, to give 70 mg of the title compound as colorless crystals.

$^1$H-NMR (DMSO-$d_6$)

δ: 2.03–2.12(m, 2H), 2.20–2.31(m, 2H), 3.30(s, 3H), 3.83–4.01(m, 4H), 5.13–5.20(m, 1H), 7.16–7.22(m, 1H), 7.29(d, J=6.8 Hz, 1H), 7.47(d, J=8.0 Hz, 1H), 7.69–7.75(m, 1H), 7.85(dd, J=8.0, 1.6 Hz, 1H), 8.03(dd, J=8.8, 1.7 Hz, 1H), 8.09(d, J=1.7 Hz, 1H), 8.12(d, J=8.8 Hz, 1H), 8.46(brs, 1H), 8.71(d, J=6.8 Hz, 1H)

MS m/e (ESI) 517 (MH$^+$)

Example 1025

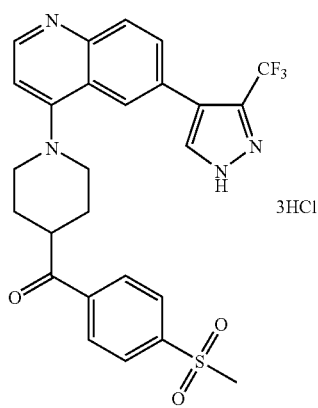

(4-Methylsulfonylphenyl)-{1-[6-(3-trifluoromethyl-1H-pyrazol-4-yl)quinolin-4-yl]piperidin-4-yl}methanone trihydrochloride 46 mg of the title compound was obtained as colorless crystals by the same reaction as in Example 67 from 75 mg (4-methylsulfonylphenyl)-{1-[6-(3-trifluoromethyl-1-trityl-1H-pyrazol-4-yl)quinolin-4-yl]piperidin-4-yl} methanone (compound in Example 1017).

$^1$H-NMR (DMSO-$d_6$)

δ: 1.82–1.95(m, 2H), 2.02–2.11(m, 2H), 3.32(s, 3H), 3.59–3.68(m, 2H), 3.95–4.05(m, 1H), 4.14–4.26(m, 2H), 7.27(d, J=6.8 Hz, 1H), 8.00–8.16(m, 5H), 8.28(d, J=8.0 Hz, 2H), 8.45(brs, 1H), 8.70(d, J=6.8 Hz, 1H)

MS m/e (ESI) 529 (MH$^+$)

Example 1026

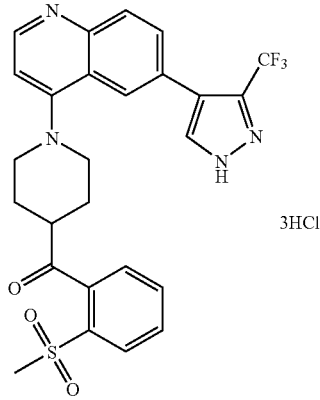

(2-Methylsulfonylphenyl)-{1-[6-(3-trifluoromethyl-1H-pyrazol-4-yl)quinolin-4-yl]piperidin-4-yl}methanone trihydrochloride 70 mg [1-(6-bromoquinolin-4-yl)piperidin-4-yl]-(2-methylsulfanylphenyl) methanone (compound in Production Example 228) and 87 mg 3-trifluoromethyl-1-trityl-1H-4-pyrazolylboronic acid (compound in Production Example 31) were reacted in the same manner as in Example 9, to give 117 mg (2-methanesulfanylphenyl)-{1-[6-(3-trifluoromethyl-1-trityl-1H-pyrazol-4-yl)quinolin-4-yl]piperidin-4-yl}methanone as colorless crystals. This product and 210 mg oxone were reacted in the same manner as in Example 43 to give 48 mg (2-methylsulfonylphenyl)-{1-[6-(3-trifluoromethyl-1-trityl-1H-pyrazol-4-yl)quinolin-4-yl]piperidin-4-yl} methanone. This product was reacted in the same manner as in Example 67 to give 34 mg of the title compound as pale yellow crystals.

$^1$H-NMR (DMSO-$d_6$)

δ: 1.83–1.96(m, 2H), 2.01–2.09(m, 2H), 3.33(s, 3H), 3.16–3.37(m, 1H), 3.43–3.60(m, 2H), 4.12–4.20(m, 2H), 7.23(d, J=6.6 Hz, 1H), 7.76–7.82(m, 2H), 7.86–7.91(m, 1H), 7.98–8.08(m, 4H), 8.44(brs, 1H), 8.69(d, J=6.6 Hz, 1H)

MS m/e (ESI) 529 (MH$^+$)

Example 1027

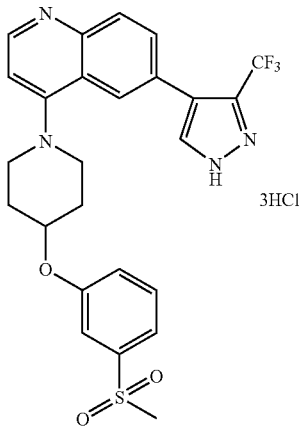

4-[4-(3-Methylsulfonylphenoxy)-piperidin-1-yl]-6-(3-trifluoromethyl-1H-pyrazol-4-yl)quinoline trihydrochloride 86 mg of the title compound was obtained as colorless crystals by the same reaction as in Example 67 from 4-[4-(3-methylsulfonylphenoxy)-piperidin-1-yl]-6-(3-trifluoromethyl-1-trityl-1H-pyrazol-4-yl) quinoline (compound in Example 1018).

$^1$H-NMR (DMSO-d$_6$)

δ: 1.90–2.01(m, 2H), 2.20–2.29(m, 2H), 3.25(s, 3H), 3.75–3.83(m, 2H), 3.98–4.06(m, 2H), 4.96–5.02(m, 1H), 7.29(d, J=7.0 Hz, 1H), 7.39–7.43(m, 1H), 7.50–7.55(m, 2H), 7.58–7.64(m, 1H), 8.03(dd, J=8.8, 1.6 Hz, 1H), 8.11(d, J=11.6 Hz, 1H), 8.13(d, J=8.8 Hz, 1H), 8.47(brs, 1H), 8.72(d, J=7.0 Hz, 1H)

MS m/e (ESI) 517 (MH$^+$)

Example 1028

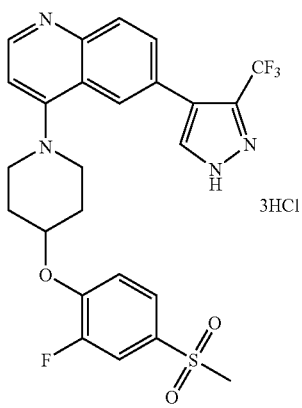

4-[4-(2-Fluoro-9-methylsulfonylphenoxy)-piperidin-1-yl]-6-(3-trifluoromethyl-1H-pyrazol-4-yl)quinoline trihydrochloride 105 mg 6-bromo-4-[4-(2-fluoro-4-methylsulfanylphenoxy)piperidin-1-yl] quinoline (compound in Production Example 448) and 129 mg 3-trifluoromethyl-1-trityl-1H-4-pyrazolylboronic acid (compound in Production Example 31) were reacted in the same manner as in Example 9, to give 128 mg 4-[4-(2-fluoro-4-methanesulfanylphenoxy)-piperidin-1-yl]-6-(3-trifluoromethyl-1-trityl-1H-pyrazol-4-yl) quinoline as a colorless amorphous. This product and 211 mg oxone were reacted in the same manner as in Example 43, to give 91 mg 4-[4-(2-fluoro-4-methanesulfonylphenoxy)-piperidin-1-yl]-6-(3-trifluoromethyl-1-trityl-1H-pyrazol-4-yl) quinoline. This product was reacted in the same manner as in Example 67 to give 47 mg of the title compound as pale yellow crystals.

$^1$H-NMR (DMSO-d$_6$)

δ: 1.93–2.06(m, 2H), 2.20–2.34(m, 2H), 3.24(s, 3H), 3.70–3.83(m, 2H), 3.94–4.05(m, 2H), 5.03–5.09(m, 1H), 7.30(d, J=7.0 Hz, 1H), 7.62(t, J=8.4 Hz, 1H), 7.72–7.77(m, 1H), 7.83(dd, J=10.8, 2.2 Hz, 1H), 8.03(dd, J=8.8, 1.8 Hz, 1H), 8.10–8.13(m, 1H), 8.13(d, J=8.8 Hz, 1H), 8.46(brs, 1H), 8.72(d, J=7.0 Hz, 1H)

MS m/e (ESI) 535 (MH$^+$)

Example 1029

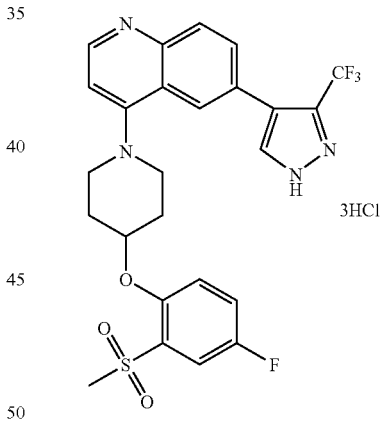

4-[4-(4-Fluoro-2-methylsulfonylphenoxy)-piperidin-1-yl]-6-(3-trifluoromethyl-1H-pyrazol-4-yl)quinoline trihydrochloride 130 mg 6-bromo-4-[4-(4-fluoro-2-methylsulfanylphenoxy)piperidin-1-yl] quinoline (compound in Production Example 449) and 160 mg 3-trifluoromethyl-1-trityl-1H-4-pyrazolylboronic acid (compound in Production Example 31) were reacted in the same manner as in Example 9, to give 182 mg 4-[4-(4-fluoro-2-methanesulfanylphenoxy)-piperidin-1-yl]-6-(3-trifluoromethyl-1-trityl-1H-pyrazol-4-yl) quinoline as a colorless amorphous. This product and 300 mg oxone were reacted in the same manner as in Example 43, to give 77 mg 4-[4-(4-fluoro-2-methylsulfonylphenoxy)- piperidin-1-yl]-6-(3-trifluoromethyl-1-trityl-1H-pyrazol-4-yl) quinoline. This product was reacted in the same manner as in Example 67 to give 46 mg of the title compound as colorless crystals.

$^1$H-NMR (DMSO-d$_6$)

δ: 2.01–2.11(m, 2H), 2.19–2.30(m, 2H), 3.34(s, 3H), 3.80–3.90(m, 2H), 3.90–4.00(m, 2H), 5.10–5.17(m, 1H), 7.28(d, J=6.8 Hz, 1H), 7.53(dd, J=9.0, 3.8 Hz, 1H), 7.58–7.66(m, 2H), 8.00–8.04(m, 1H), 8.09(s, 1H), 8.10(d, J=8.8 Hz, 1H), 8.46(brs, 1H), 8.71(d, J=6.8 Hz, 1H)

MS m/e (ESI) 535 (MH$^+$)

Example 1030

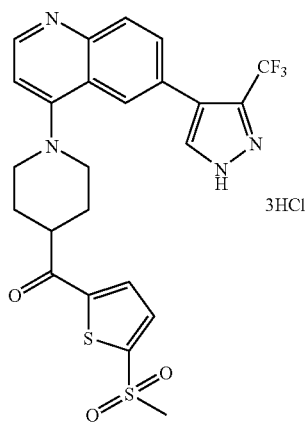

(5-Methylsulfonylthiophen-2-yl)-{1-[6-(3-trifluoromethyl-1H-pyrazol-4-yl)quinolin-4-yl]piperidin-4-yl}methanone trihydrochloride 100 mg [1-(6-bromo-quinolin-4-yl)-piperidin-4-yl]-(5-methylsulfanylthiophen-2-yl)methanone (compound in Production Example 450) and 120 mg 3-trifluoromethyl-1-trityl-1H-4-pyrazolylboronic acid (compound in Production Example 31) were reacted in the same manner as in Example 9, to give 167 mg (5-methanesulfanylthiophen-2-yl)-{1-[6-(3-trifluoromethyl-1-trityl-1H-pyrazol-4-yl)quinolin-4-yl]piperidin-4-yl} methanone as a colorless amorphous. This product and 280 mg oxone were reacted in the same manner as in Example 43, to give 136 mg (5-methylsulfonylthiophen-2-yl)-{1-[6-(3-trifluoromethyl-1-trityl-1H-pyrazol-4-yl)quinolin-4-yl]piperidin-4-yl} methanone. This product was reacted in the same manner as in Example 67 to give 51 mg of the title compound as colorless crystals.

$^1$H-NMR (DMSO-d$_6$)

δ: 1.87–1.98(m, 2H), 2.04–2.13(m, 2H), 3.45(s, 3H), 3.53–3.65(m, 2H), 3.82–3.93(m, 1H), 4.14–4.22(m, 2H), 7.28(d, J=7.0 Hz, 1H), 7.98(d, J=4.0 Hz, 1H), 8.02(dd, J=8.8, 1.6 Hz, 1H), 8.08(s, 1H), 8.10(d, J=8.8 Hz, 1H), 8.26(d, J=4.0 Hz, 1H), 8.45(brs, 1H), 8.70(d, J=7.0 Hz, 1H)

MS m/e (ESI) 535(MH$^{30}$)

Example 1031

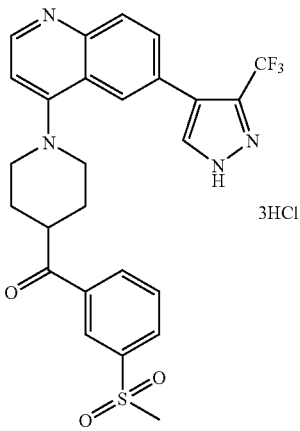

(3-Methylsulfonylphenyl)-{1-[6-(3-trifluoromethyl-1H-pyrazol-4-yl)quinolin-4-yl]piperidin-4-yl}methanone trihydrochloride 66 mg [1-(6-bromoquinolin-4-yl)piperidin-4-yl]-(3-methylsulfanylphenyl) methanone (compound in Production Example 453) and 82 mg 3-trifluoromethyl-1-trityl-1H-4-pyrazolylboronic acid (compound in Production Example 31) were reacted in the same manner as in Example 9, to give 82 mg (3-methanesulfanylphenyl)-{1-[6-(3-trifluoromethyl-1-trityl-1H-pyrazol-4-yl)quinolin-4-yl]piperidin-4-yl}methanone as a colorless amorphous. This product and 136 mg oxone were reacted in the same manner as in Example 43, to give 55 mg (3-methylsulfonylphenyl)-{1-[6-(3-trifluoromethyl-1-trityl-1H-pyrazol-4-yl)quinolin-4-yl]piperidin-4-yl}methanone. This product was reacted in the same manner as in Example 67 to give 33 mg of the title compound as pale yellow crystals.

$^1$H-NMR (DMSO-d$_6$)

δ: 1.84–1.96(m, 2H), 2.02–2.12(m, 2H), 3.32(s, 3H), 3.58–3.70(m, 2H), 3.97–4.07(m, 1H), 4.12–4.24(m, 2H), 7.27(d, J=6.8 Hz, 1H), 7.88(t, J=8.0 Hz, 1H), 7.99–8.03(m, 1H), 8.06–8.11(m, 2H), 8.21–8.25(m, 1H), 8.40–8.48(m, 3H), 8.70(d, J=6.8 Hz, 1H)

MS m/e (ESI) 529 (MH$^+$)

Example 1032

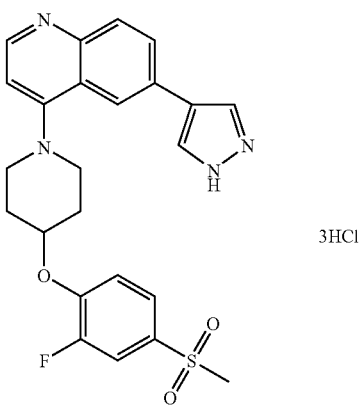

4-[4-(2-Fluoro-4-methylsulfonylphenoxy)-piperidin-1-yl]-6-(1H-pyrazol-4-yl)quinoline trihydrochloride 104 mg 6-bromo-4-[4-(2-fluoro-4-methylsulfanylphenoxy)piperidin-1-yl]quinoline (compound in Production Example 448) and 107 mg 1-trityl-1H-4-pyrazolylboronic acid were reacted in the same manner as in Example 9, to give 108 mg 4-[4-(2-fluoro-4-methanesulfanylphenoxy)-piperidin-1-yl]-6-(1-trityl-1H-pyrazol-4-yl) quinoline as a colorless amorphous. This product and 196 mg oxone were reacted in the same manner as in Example 43, to give 108 mg 4-[4-(2-fluoro-4-methylsulfonylphenoxy)-piperidin-1-yl]-6-(1-trityl-1–1H-pyrazol-4-yl) quinoline. This product was reacted in the same manner as in Example 67 to give 20 mg of the title compound as pale yellow crystals.

$^1$H-NMR (DMSO-$d_6$)

δ: 1.98–2.10(m, 2H), 2.26–2.35(m, 2H), 3.24(s, 3H), 3.78–3.87(m, 2H), 4.00–4.10(m, 2H), 5.03–5.10(m, 1H), 7.26(d, J=6.8 Hz, 1H), 7.62(t, J=8.4 Hz, 1H), 7.72–7.77(m, 1H), 7.84(dd, J=10.6, 2.2 Hz, 1H), 8.05(d, J=8.6 Hz, 1H), 8.22(d, J=1.4 Hz, 1H), 8.26(dd, J=8.6, 1.4 Hz, 1H), 8.30(brs, 2H), 8.64(d, J=6.8 Hz, 1H)

MS m/e (ESI) 467 (MH$^+$)

Example 1033

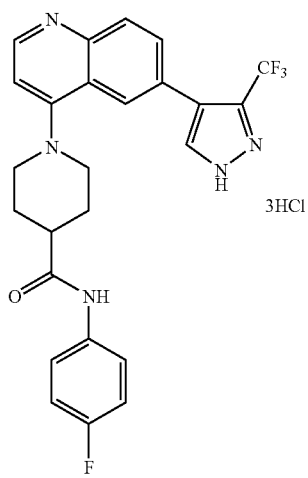

1-[6-(3-Trifluoromethyl-1H-pyrazol-4-yl)quinolin-4-yl]-piperidine-4-carboxylic acid (4-fluorophenyl) amide trihydrochloride 73 mg 1-(6-bromoquinolin-4-yl)piperidine-4-carboxylic acid (4-fluorophenyl)amide (compound in Production Example 457) and 94 mg 3-trifluoromethyl-1-trityl-1H-4-pyrazolylboronic acid (compound in Production Example 31) were reacted in the same manner as in Example 9, to give 54 mg 1-[6-(3-trifluoromethyl-1-trityl-1H-pyrazol-4-yl)quinolin-4-yl]-piperidine-4-carboxylic acid (4-fluorophenyl)amide. This product was reacted in the same manner as in Example 67 to give 54 mg of the title compound as pale gray crystals.

$^1$H-NMR (DMSO-$d_6$)

δ: 1.88–2.10(m, 4H), 2.78–2.85(m, 1H), 3.47–3.57(m, 2H), 4.16–4.25(m, 2H), 7.11–7.19(m, 2H), 7.28(d, J=7.0 Hz, 1H), 7.62–7.69(m, 2H), 8.03(dd, J=8.8, 1.6 Hz, 1H), 8.08 (brs, 1H), 8.13(d, J=8.8 Hz, 1H), 8.46(brs, 1H), 8.70(d, J=7.0 Hz, 1H)

MS m/e (ESI) 484 (MH$^+$)

Example 1034

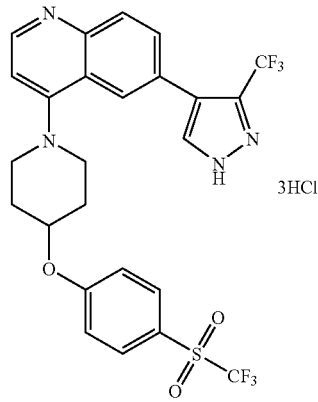

4-[4-(4-Trifluoromethylsulfonylphenoxy)piperidin-1-yl]-6-(3-trifluoromethyl-1H-pyrazol-4-yl)quinoline trihydrochloride 150 mg 6-bromo-4-[4-(4-trifluoromethylsulfonylphenoxy)piperidin-1-yl] quinoline (compound in Production Example 456) and 160 mg 3-trifluoromethyl-1-trityl-1H-4-pyrazolylboronic acid (compound in Production Example 31) were reacted in the same manner as in Example 9, to give 221 mg 4-[4-(4-trifluoromethylsulfonylphenoxy)piperidin-1-yl]-6-(3-trifluoromethyl-1-trityl-1H-pyrazol-4-yl) quinoline. This product was reacted in the same manner as in Example 67, to give 106 mg of the title compound as colorless crystals.

$^1$H-NMR (DMSO-$d_6$)

δ: 1.92–2.06(m, 2H), 2.23–2.34(m, 2H), 3.71–3.82(m, 2H), 3.94–4.05(m, 2H), 5.07–5.13(m, 1H), 7.29(d, J=6.8 Hz, 1H), 7.43–7.48(m, 2H), 8.01–8.14(m, 5H), 8.46(brs, 1H), 8.72(d, J=6.8 Hz, 1H)

MS m/e (ESI) 571 (MH$^+$)

Example 1035

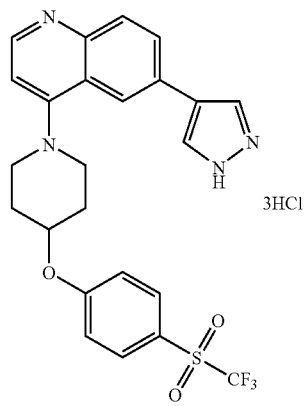

6-(1H-Pyrazol-4-yl)-4-[4-(4-Trifluoromethylsulfonylphenoxy)piperidin-1-yl]quinoline trihydrochloride 150 mg 6-bromo-4-[4-(4-trifluoromethylsulfonylphenoxy)piperidin-1-yl] quinoline (compound in Production Example 456) and 134 mg 1-trityl-1H-4-pyrazolylboronic acid were reacted in the same manner as in Example 9, to give 205 mg 6-(1-trityl-1H-pyrazol-4-yl)-4-[4-(4-trifluoromethylsulfonylphenoxy)piperidin-1-yl] quinoline. This product was reacted in the same manner as in Example 67, to give 90 mg of the title compound as pale yellow crystals.

$^1$H-NMR (DMSO-$d_6$)

δ: 2.13–2.24(m, 2H), 2.37–2.48(m, 2H), 3.90–4.00(m, 2H), 4.09–4.19(m, 2H), 5.07–5.15(m, 1H), 7.24(d, J=6.8 Hz, 1H), 7.36–7.43(m, 2H), 7.94(d, J=8.8 Hz, 1H), 8.01–8.08(m, 2H), 8.20(brs, 2H), 8.23(dd, J=8.8, 1.8 Hz, 1H), 8.30(d, J=1.8 Hz, 1H), 8.72(d, J=6.8 Hz, 1H)

MS m/e (ESI) 503 (MH$^+$)

Example 1036

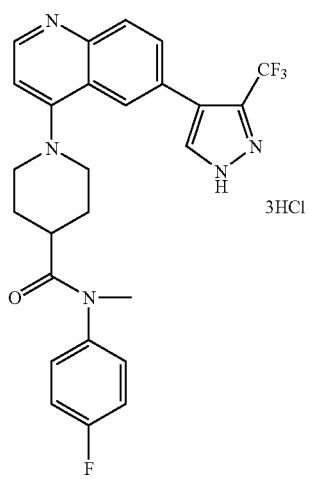

1-[6-(3-Trifluoromethyl-1H-pyrazol-4-yl)quinolin-4-yl]-piperidine-4-carboxylic acid (4-fluorophenyl)methylamide trihydrochloride 92 mg 1-(6-bromoquinolin-4-yl)piperidine-4-carboxylic acid (4-fluorophenyl)methylamide (compound in Production Example 458) and 114 mg 3-trifluoromethyl-1-trityl-1H-4-pyrazolylboronic acid (compound in Production Example 31) were reacted in the same manner as in Example 9, to give 139 mg 1-[6-(3-trifluoromethyl-1-trityl-1H-pyrazol-4-yl)quinolin-4-yl]-piperidine-4-carboxylic acid (4-fluorophenyl)methylamide. This product was reacted in the same manner as in Example 67, to give 80 mg of the title compound as pale yellow crystals.

$^1$H-NMR (DMSO-$d_6$)

δ: 1.73–1.94(m, 4H), 2.52–2.65(m, 1H), 3.15(s, 3H), 3.19–3.35(m, 2H), 4.01–4.11(m, 2H), 7.18(d, J=6.6 Hz, 1H), 7.28–7.38(m, 2H), 7.46–7.55(m, 2H), 7.97–8.04(m, 2H), 8.12(d, J=9.2 Hz, 1H), 8.44(brs, 1H), 8.66(d, J=6.6 Hz, 1H)

MS m/e (ESI) 498 (MH$^+$)

Example 1037

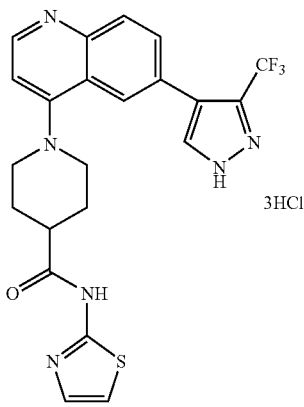

1-[6-(3-Trifluoromethyl-1H-pyrazol-4-yl)quinolin-4-yl]-piperidine-4-carboxylic acid thiazol-2-ylamide trihydrochloride 32 mg of the title compound was obtained as pale yellow crystals by the same reaction as in Example 67 from 220 mg 1-[6-(3-trifluoromethyl-1-trityl-1H-pyrazol-4-yl)quinolin-4-yl]-piperidine-4-carboxylic acid thiazol-2-ylamide (compound in Example 1019).

$^1$H-NMR (DMSO-$d_6$)

δ: 1.89–2.01(m, 2H), 2.03–2.12(m, 2H), 2.93–3.02(m, 1H), 3.41–3.70(m, 2H), 4.17–4.27(m, 2H), 7.23(d, J=3.6 Hz, 1H), 7.29(d, J=6.8 Hz, 1H), 7.49(d, J=3.6 Hz, 1H), 8.04(dd, J=8.8, 1.6 Hz, 1H), 8.08(d, J=1.6 Hz, 1H), 8.12(d, J=8.8 Hz, 1H), 8.44(brs, 1H), 8.71(d, J=6.8 Hz, 1H)

MS m/e (ESI) 473 (MH$^+$)

Example 1038

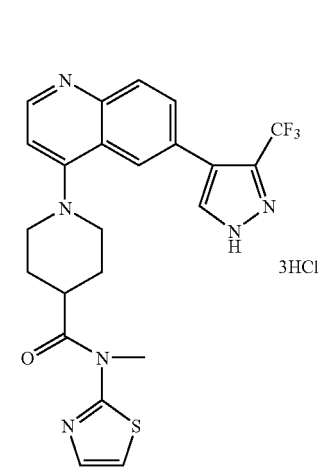

1-[6-(3-Trifluoromethyl-1H-pyrazol-4-yl)quinolin-4-yl]-piperidine-4-carboxylic acid methyl-thiazol-2-ylamide trihydrochloride 100 mg 1-[6-(3-trifluoromethyl-1-trityl-1H-pyrazol-4-yl) quinolin-4-yl]-piperidine-4-carboxylic acid thiazol-2-ylamide (compound in Example 1019) was reacted in the same manner as in Production Example 458, to give 35 mg 1-[6-(3-trifluoromethyl-1-trityl-1H-pyrazol-4-yl)quinolin-4-yl]-piperidine-4-carboxylic acid methyl-thiazol-2-ylamide. This product was reacted in the same manner as in Example 67, to give 9 mg of the title compound as pale yellow crystals.

$^1$H-NMR (DMSO-$d_6$)

δ: 1.88–2.02(m, 2H), 2.04–2.13(m, 2H), 3.44–3.65(m, 3H), 3.80(s, 3H), 4.14–4.24(m, 2H), 7.28(d, J=6.8 Hz, 1H), 7.30(d, J=3.2 Hz, 1H), 7.56(d, J=3.2 Hz, 1H), 8.02(dd, J=8.8, 1.6 Hz, 1H), 8.09(d, J=1.6 Hz, 1H), 8.11(d, J=8.8 Hz, 1H), 8.46(brs, 1H), 8.70(d, J=6.8 Hz, 1H)

MS m/e (ESI) 487 (MH$^+$)

Example 1039

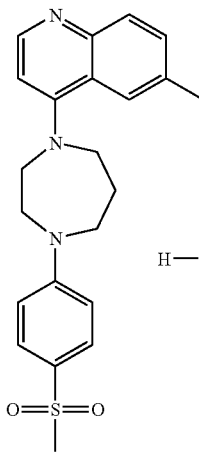

4-{4-[4-(Methylsulfonyl)phenyl]-1,4-diazepan-1-yl}-6-[3-(trifluoromethyl)-1H-4-pyrazolyl]quinoline hydrochloride 100 mg of the title compound was obtained by the same reaction as in Example 164 from 205 mg 4-{4-[4-(methylsulfonyl)phenyl]-1,4-diazepan-1-yl}-6-[3-(trifluoromethyl)-1-trityl-1H-4-pyrazolyl]quinoline (compound in Example 1020).

$^1$H-NMR (DMSO-$d_6$)

δ: 3.30–3.40(m, 4H), 3.48–3.54(m, 2H), 3.74–3.79(m, 2H), 3.88–3.93(m, 2H), 6.97(d, J=9.2 Hz, 2H), 6.98(d, J=4.8 Hz, 1H), 7.64(d, J=9.2 Hz, 2H), 7.70(dd, J=8.4, 2.0 Hz, 1H), 7.89(d, J=8.4 Hz, 1H), 7.94(bd, 1H), 8.01(bd, 1H), 8.55(d, J=4.8 Hz, 1H)

MS m/e(ESI)516(MH$^+$)

Example 1040

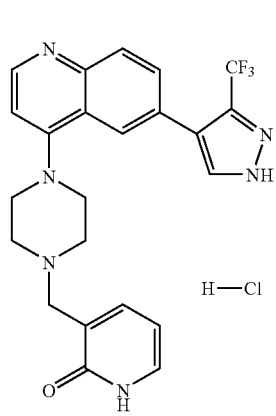

3-[(4-{6-[3-(Trifluoromethyl)-1H-4-pyrazolyl]-4-quinolyl}piperazin-1-yl)methyl]-1,2-dihydro-2-pyridinone hydrochloride 117 mg 4-{4-[(2-methoxy-3-pyridyl)methyl]piperazin-1-yl}-6-(3-(trifluoromethyl)-1-trityl-1H-4-pyrazolyl) quinoline prepared by the same method as in Example 168 from 100 mg 3-{[4-(6-bromo-4-quinolyl)piperazin-1-yl]methyl}-2-pyridyl methyl ether (compound in Production Example 460) and 163 mg 3-trifluoromethyl-1-trityl-1H-4-pyrazolylboronic acid (compound in Production Example 31) was dissolved in acetonitrile, and 100 mg sodium iodide, 330 μl trimethyl silyl chloride and 1.5 μl water were added thereto and stirred at 65° C. for 5 hours. After the reaction was finished, the reaction solution was poured into a 1:1 mixture of 5% aqueous sodium sulfite solution and an aqueous saturated sodium chloride solution and then extracted with ethyl acetate. The solvent was removed, and the resulting residue was purified by silica gel column chromatography, and the resulting solid was dissolved in methanol and converted into the corresponding hydrochloride by 4 N hydrogen chloride solution in ethyl acetate. The product was recrystallized from methanol/diethyl ether, to give 20 mg of the title compound.

$^1$H-NMR (DMSO-$d_6$)δ: 3.47(bd, 4H), 3.88(bd, 2H), 4.23 (bd, 2H), 6.34(dd, J=6.8, 6.8 Hz, 1H), 7.35(d, J=6.8 Hz, 1H), 7.56(bd, 1H), 7.93(dd, J=6.8, 2.0 Hz, 1H), 8.04(d, J=8.8 Hz, 1H), 8.09(d, J=2.0 Hz, 1H), 8.26(d, J=8.8 Hz, 1H), 8.50(s, 1H), 8.85(d, J=6.8 Hz, 1H), 12.1(bd, 1H), 14.1(bd, 1H)

MS m/e(ESI)455(MH$^+$)

The compounds in Examples 1041 to 1059 were synthesized by the same procedure as in Example 268 from starting materials, that is, 6-bromo-4-chloroquinoline, a piperazine derivative which is commercially available or described in the Production Examples and a 1-trityl-1H-4-pyrazolylboronic acid derivative described in the Production Examples. The reaction time for reacting 6-bromo-4-chloroquinoline with the piperazine derivative was from 4 to 14 hours.

Example 1041

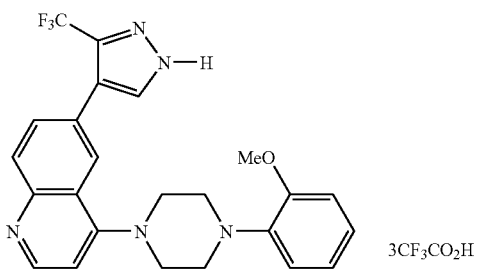

4-{4-[2-(Methoxyphenyl)piperazin-1-yl]-6-[3-(trifluoromethyl-1H-pyrazol-4-yl)quinoline tri-trifluoroacetate $^1$H-NMR (DMSO-$d_6$)
δ: 3.23(m, 4H), 3.81(s, 3H), 3.90(m, 4H), 6.88–7.02(m, 4H), 7.29 (d, J=6.7 Hz, 1H), 8.01(d, J=8.4 Hz, 1H), 8.06(d, J=8.4 Hz, 1H), 8.13(s, 1H), 8.46(s, 1H), 8.74(d, J=6.7 Hz, 1H)

Example 1042

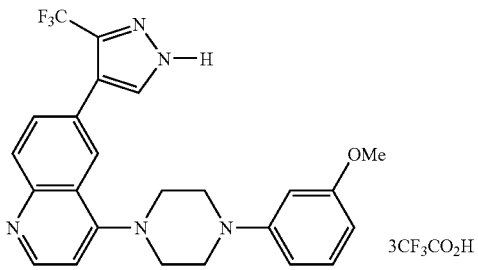

4-{4-[3-(Methoxyphenyl)piperazin-1-yl]-6-(3-trifluoromethyl-1H-pyrazol-4-yl)quinoline tri-trifluoroacetate $^1$H-NMR (DMSO-$d_6$)
δ: 3.45(m, 4H), 3.72(s, 3H), 3.92(m, 4H), 6.40(d, J=8.2 Hz, 1H), 6.48(s, 1H), 6.55(d, J=8.2 Hz, 1H), 7.15(t, J=8.2 Hz, 1H), 7.26 (d, J=6.9 Hz, 1H), 8.01(d, J=8.4 Hz, 1H), 8.06(d, J=8.4 Hz, 1H), 8.16(s, 1H), 8.44(s, 1H), 8.72(d, J=6.9 Hz, 1H)

Example 1043

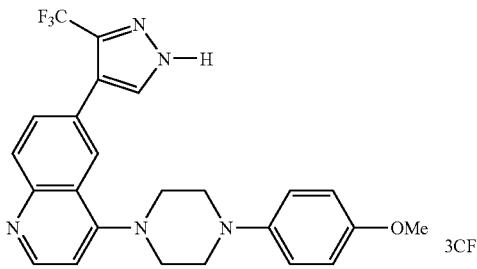

4-[4-(4-Methoxyphenyl)piperazin-1-yl]-6-(3-trifluoromethyl-1H-pyrazol-4-yl)quinoline tri-trifluoroacetate $^1$H-NMR (CD$_3$OD)
δ: 3.38(m, 4H), 3.76(s, 3H), 4.06(m, 4H), 6.89(d, J=9.2 Hz, 2H), 7.04(d, J=9.2 Hz, 2H), 7.31(d, J=6.8 Hz, 1H), 8.00(d, J=8.6 Hz, 1H), 8.08(d, J=8.6 Hz, 1H), 8.20(s, 1H), 8.27(s, 1H), 8.57(d, J=6.8 Hz, 1H)

Example 1044

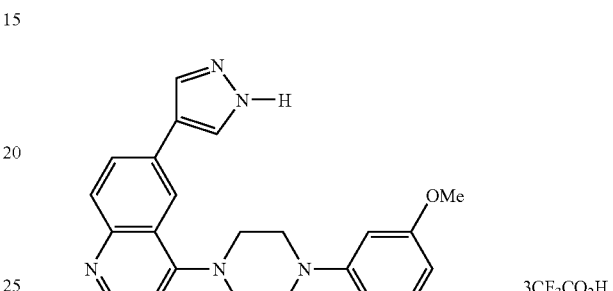

4-[4-(3-Methoxyphenyl)piperazin-1-yl]-6-(1H-pyrazol-4-yl)quinoline tri-trifluoroacetate $^1$H-NMR (DMSO-$d_6$)
δ: 3.50(m, 4H), 3.71(s, 3H), 3.96(m, 4H), 6.40(dd, J=8.4, 2.4 Hz, 1H), 6.49(t, J=2.4 Hz, 1H), 6.56(dd, J=8.4, 2.4 Hz, 1H), 7.15(t, J=8.4 Hz, 1H), 7.20(d, J=6.4 Hz, 1H), 7.95(d, J=8.8 Hz, 1H), 8.20–8.28(m, 4H), 8.63(d, J=6.4 Hz, 1H)

Example 1045

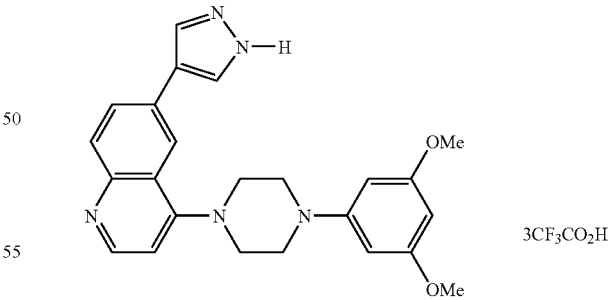

4-[4-(3,5-Dimethoxyphenyl)piperazin-1-yl]-6-(1H-pyrazol-4-yl)quinoline tri-trifluoroacetate $^1$H-NMR (DMSO-$d_6$)
δ: 3.50(m, 4H), 3.72(s, 6H), 4.00(m, 4H), 6.00(m, 1H), 6.10(m, 2H), 7.20(d, J=6.8 Hz, 1H), 7.95(d, J=8.6 Hz, 1H), 8.20–8.28(m, 4H), 8.63(d, J=6.8 Hz, 1H)

Example 1046

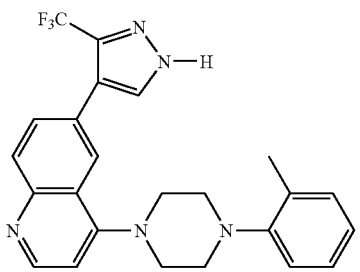

3CF₃CO₂H 4-(4-o-Tolyl-piperazin-1-yl)-6-(3-trifluoromethyl-
1H-pyrazol-4-yl)quinoline tri-trifluoroacetate ¹H-NMR (CD₃OD)
δ: 2.39(s, 3H), 3.20(m, 4H), 4.07(m, 4H), 7.02(t, J=7.6 Hz, 1H), 7.11(d, J=7.6 Hz, 1H), 7.18(t, J=7.6 Hz, 1H), 7.21(d, J=7.6 Hz, 1H), 7.32(d, J=6.9 Hz, 1H), 8.01(d, J=8.6 Hz, 1H), 8.08(dd, J=8.6, 2.0 Hz, 1H), 8.21(s, 1H), 8.28(d, J=2.0 Hz, 1H), 8.56(d, J=6.9 Hz, 1H)

Example 1047

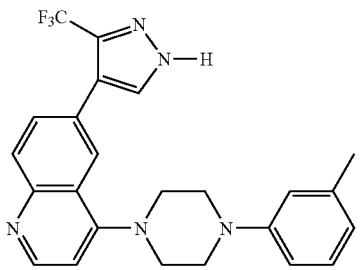

3CF₃CO₂H 4-(4-m-Tolyl-piperazin-1-yl)-6-(3-trifluoromethyl-
1H-pyrazol-4-yl)quinoline tri-trifluoroacetate ¹H-NMR (CD₃OD)
δ: 2.32(s, 3H), 3.48(m, 4H), 4.07(m, 4H), 6.74(d, J=8.2 Hz, 1H), 6.84(d, J=8.2 Hz, 1H), 6.87(s, 1H), 7.16(t, J=8.2 Hz, 1H), 7.30 (d, J=7.0 Hz, 1H), 8.01(d, J=8.8 Hz, 1H), 8.08(dd, J=8.8, 2.0 Hz, 1H), 8.20(s, 1H), 8.28(d, J=2.0 Hz, 1H), 8.56(d, J=7.0 Hz, 1H)

Example 1048

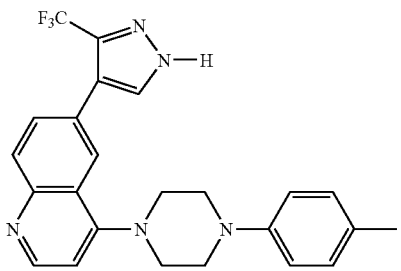

3CF₃CO₂H 4-(4-p-Tolyl-piperazin-1-yl)-6-(3-trifluoromethyl-
1H-pyrazol-4-yl)quinoline tri-trifluoroacetate ¹H-NMR (CD₃OD)
δ: 2.27(s, 3H), 3.46(m, 4H), 4.07(m, 4H), 6.99(d, J=8.7 Hz, 2H), 7.13(d, J=8.7 Hz, 2H), 7.31(d, J=7.0 Hz, 1H), 8.01(d, J=8.6 Hz, 1H), 8.08(dd, J=8.6, 2.0 Hz, 1H), 8.20(s, 1H), 8.28(d, J=2.0 Hz, 1H), 8.57(d, J=7.0 Hz, 1H)

Example 1049

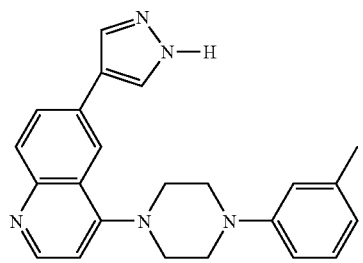

3CF₃CO₂H 4-(4-m-Tolyl-piperazin-1-yl)-6-(1H-pyrazol-4-yl)
quinoline tri-trifluoroacetate ¹H-NMR (DMSO-d₆)
δ: 2.27(s, 3H), 3.48(m, 4H), 3.99(m, 4H), 6.63(d, J=7.7 Hz, 1H), 6.77(d, J=7.7 Hz, 1H), 6.80(s, 1H), 7.14(t, J=7.7 Hz, 1H), 7.22 (d, J=7.0 Hz, 1H), 7.95(d, J=9.1 Hz, 1H), 8.22–8.28(m, 4H), 8.64 (d, J=7.0 Hz, 1H)

Example 1050

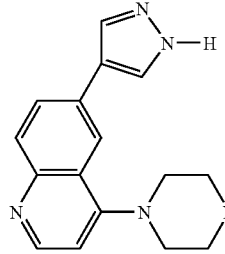

3CF₃CO₂H 4-(4-p-Tolyl-piperazin-1-yl)-6-(1H-pyrazol-4-yl)
quinoline tri-trifluoroacetate ¹H-NMR (DMSO-d₆)
δ: 2.21(s, 3H), 3.42(m, 4H), 3.95(m, 4H), 6.90(d, J=8.5 Hz, 2H), 7.07(d, J=8.5 Hz, 2H), 7.22(d, J=6.7 Hz, 1H), 7.95(d, J=9.3 Hz, 1H), 8.21–8.25(m, 4H), 8.64(d, J=6.7 Hz, 1H)

Example 1051

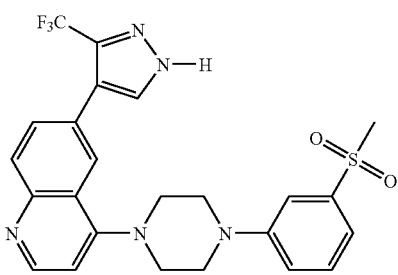

4-[4-(3-Methylsulfonylphenyl)piperazin-1-yl]-6-(3-trifluoromethyl-1H-pyrazol-4-yl) quinoline $^1$H-NMR (CDCl$_3$)
δ: 3.08(s, 3H), 3.42(m, 4H), 3.55(m, 4H), 6.95(d, J=4.9 Hz, 1H), 7.24(m, 1H), 7.42(m, 1H), 7.48(d, J=8.1 Hz, 1H), 7.52(m, 1H), 7.73(dd, J=8.5, 2.0 Hz, 1H), 7.86(s, 1H), 8.13(d, J=8.6 Hz, 1H), 8.21(s, 1H), 8.79(d, J=4.9 Hz, 1H)

Example 1052

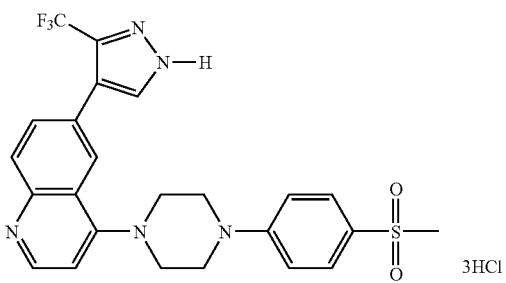

4-[4-(4-Methylsulfonylphenyl)piperazin-1-yl]-6-(3-trifluoromethyl-1H-pyrazol-4-yl)quinoline tri-trihydrochloride $^1$H-NMR (DMSO-d$_6$)
δ: 3.09(s, 3H), 3.70(m, 4H), 4.08(m, 4H), 7.04(d, J=8.6 Hz, 2H), 7.20(d, 7.0 Hz, 1H), 7.72(d, J=8.6 Hz, 2H), 8.03(d, J=9.1 Hz, 1H), 8.16(d, J=9.1 Hz, 1H), 8.21(s, 1H), 8.44(s, 1H), 8.69(d, J=7.0 Hz, 1H)

Example 1053

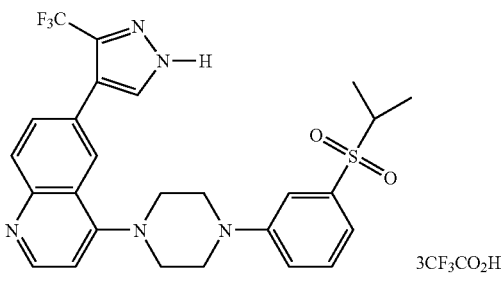

4-[4-(3-Isopropylsulfonylphenyl)piperazin-1-yl]-6-(3-trifluoromethyl-1H-pyrazol-4-yl)quinoline tri-trifluoroacetate $^1$H-NMR (DMSO-d$_6$)
δ: 1.14(d, J=6.8 Hz, 3H), 3.20(m, 1H), 3.58(m, 4H), 3.80(m, 4H), 7.21–7.24(m, 2H), 7.29–7.35(m, 2H), 7.52(t, J=7.5 Hz, 1H), 7.97(m, 1H), 8.05(d, J=9.0 Hz, 1H), 8.17(s, 1H), 8.43(s, 1H), 8.72(d, J=6.4 Hz, 1H)

Example 1054

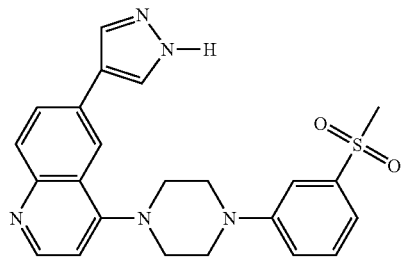

4-[4-(3-Methylsulfonylphenyl)piperazin-1-yl]-6-(1H-pyrazol-4-yl)quinoline tri-trifluoroacetate $^1$H-NMR (DMSO-d$_6$)
δ: 3.20(s, 3H), 365(m, 4H), 4.08(m, 4H), 7.21(d, J=7.0 Hz, 1H), 7.27–7.31(m, 2H), 7.38(s, 1H), 7.51(t, J=8.0 Hz, 1H), 7.98(d, J=8.8 Hz, 1H), 8.23–8.32(m, 4H), 8.65(d, J=7.0 Hz, 1H)

Example 1055

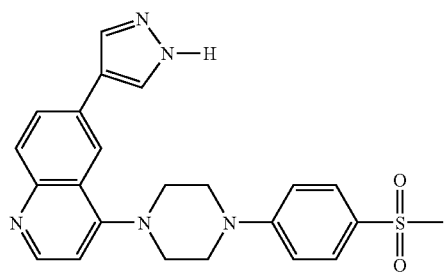

4-[4-(4-Methylsulfonylphenyl)piperazin-1-yl]-6-(1H-pyrazol-4-yl)quinoline tri-trifluoroacetate $^1$H-NMR (DMSO-d$_6$)
δ: 3.09(s, 3H), 3.75(m, 4H), 4.13(m, 4H), 7.03(d, J=9.2 Hz, 2H), 7.15(d, 7.0 Hz, 1H), 7.73(d, J=9.2 Hz, 2H), 7.97(d, J=8.8 Hz, 1H), 8.25(dd, J=8.8, 1.6 Hz, 1H), 8.30(s, 1H), 8.31(d, J=1.6 Hz, 1H), 8.62(d, J=7.0 Hz, 1H)

Example 1056

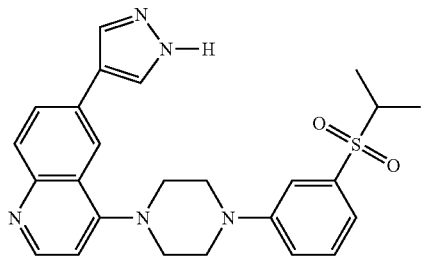

4-[4-(3-Isopropylsulfonylphenyl)piperazin-1-yl]-6-(1H-pyrazol-4-yl)quinoline tri-trihydrochloride ¹H-NMR (DMSO-$d_6$)

δ: 1.01(d, J=6.4 Hz, 3H), 3.58(m, 1H), 3.64(m, 4H), 4.04(m, 4H), 7.18–7.33(m, 4H), 7.52(t, J=8.0 Hz, 1H), 7.96(d, J=8.8 Hz, 1H), 8.20–8.30 (m, 4H), 8.43(s, 1H), 8.64(d, J=6.4 Hz, 1H)

Example 1057

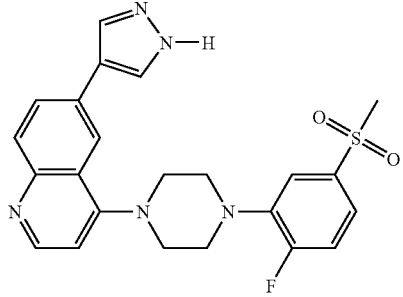

4-[4-(2-Fluoro-5-methylsulfonylphenyl)piperazin-1-yl]-6-(1H-pyrazol-4-yl)quinoline tri-trifluoroacetate ¹H-NMR (DMSO-$d_6$)

δ: 3.23(s, 3H), 347(m, 4H), 3.93(m, 4H), 7.25(d, J=6.4 Hz, 1H), 7.47(m, 1H), 7.55–7.60(m, 2H), 7.97(d, J=8.5 Hz, 1H), 8.20–8.24(m, 4H), 8.68(d, J=6.4 Hz, 1H)

Example 1058

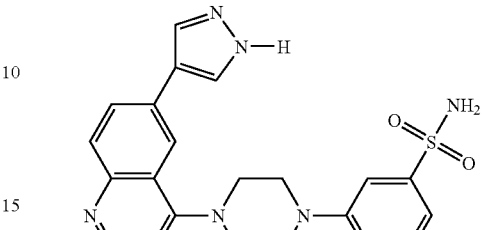

3-{4-[6-(1H-Pyrazol-4-yl)quinolin-4-yl]piperazin-1-yl}benzene sulfonamide tri-trifluoroacetate

¹H-NMR (CD$_3$OD)

δ: 3.66(m, 4H), 4.15(m, 4H), 7.22–7.26(m, 2H), 7.38(d, J=8.1 Hz, 1H), 7.45(t, J=8.1 Hz, 1H), 7.51(s, 1H), 7.96(d, J=8.8 Hz, 1H), 8.23(s, 2H), 8.26(dd, J=8.8, 1.6 Hz, 1H), 8.38(d, J=1.6 Hz, 1H), 8.49(s, 1H)

Example 1059

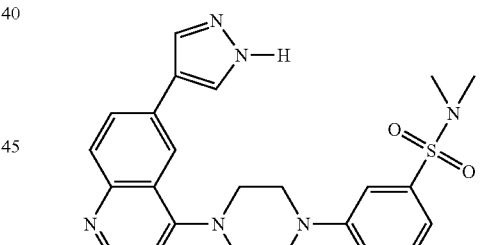

N,N-Dimethyl-3-{4-[6-(1H-pyrazol-4-yl)quinolin-4-yl]piperazin-1-yl}benzene sulfonamide tri-trifluoroacetate ¹H-NMR (DMSO-$d_6$)

δ: 2.61 (6H, s), 3.63(m, 4H), 4.04(m, 4H), 7.12(d, J=8.0 Hz, 1H), 7.15(s, 1H), 7.19(d, J=6.8 Hz, 1H), 7.28(d, J=8.0 Hz, 1H), 7.51(t, J=8.0 Hz, 1H), 7.96(d, J=8.8 Hz, 1H), 8.20–8.30(m, 3H), 8.64(d, J=6.8 Hz, 1H)

Example 1060

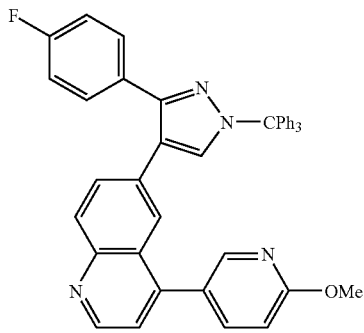

6-[3-(4-Fluorophenyl)-1-trityl-1H-pyrazol-4-yl]-4-(6-methoxypyridin-3-yl) quinoline According to Production Example 90, 510 mg 6-bromo-4-(6-methoxypyridin-3-yl) quinoline obtained by the same method as in Example 154 from 2.0 g 6-bromo-4-quinolyl trifluoromethane sulfonate and 3.4 g 2-methoxy-5-(tri-n-butylstannyl)pyridine was reacted with 3-(4-fluorophenyl)-1-trityl-1H-4-pyrazolylboronic acid (compound in Production Example 25), whereby 680 mg of the title compound was obtained as a pale yellow oil.

$^1$H-NMR (CDCl$_3$)
δ: 4.00(s, 3H), 6.78–6.88(m, 3H), 7.22–7.38(m, 18H), 7.48–7.53(m, 2H), 7.84–7.90(m, 2H), 8.18(d, J=8.4 Hz, 1H), 8.23(d, J=2.0 Hz, 1H), 8.84(d, J=7.2 Hz, 1H)

Example 1061

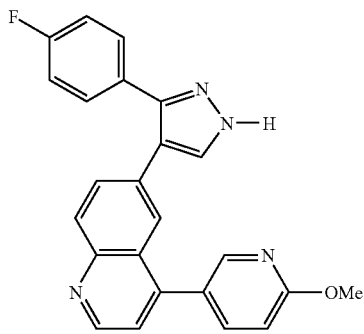

6-[3-(4-Fluorophenyl)-1H-pyrazol-4-yl]-4-(6-methoxypyridin-3-yl) quinoline 70 mg 6-[3-(4-fluorophenyl)-1-trityl-1H-pyrazol-4-yl]-4-(6-methoxypyridin-3-yl) quinoline obtained in Example 1060 was deprotected and purified by the method described in Example 268 to give 16 mg of the title compound as a pale yellow solid.

$^1$H-NMR (CD$_3$OD)
δ: 3.97(s, 3H), 6.90(d, J=8.1 Hz, 1H), 7.03(t, J=8.8 Hz, 2H), 7.41(m, 2H), 7.75(dd, J=8.6, 2.5 Hz, 1H), 7.96(d, J=5.9 Hz, 1H), 8.16(d, J=1.6 Hz, 1H), 8.20(d, J=2.5 Hz, 1H), 8.28–8.30(m, 2H), 8.34(dd, J=8.5, 1.6 Hz, 1H), 9.07(d, J=5.9 Hz, 1H)

Example 1062

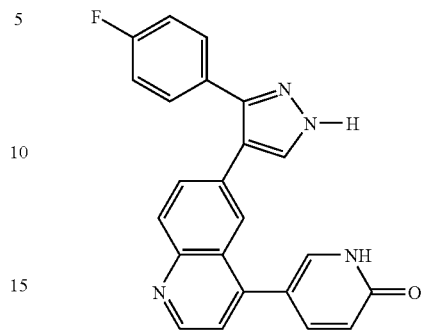

2CF$_3$CO$_2$H

5-{6-[3-(4-Fluorophenyl)-1H-pyrazol-4-yl]quinolin-4-yl} 1H-pyridin-2-one trifluoroacetate A mixture of 70 mg 6-[3-(4-fluorophenyl)-1-trityl-1H-pyrazol-4-yl]-4-(6-methoxypyridin-3-yl) quinoline obtained in Example 1060, 20 mL of 6 N hydrochloric acid and 20 mL ethanol was heated and refluxed for 14 hours under stirring. The reaction mixture was cooled to room temperature, neutralized with an aqueous saturated sodium bicarbonate solution and extracted with ethyl acetate. The organic layer was washed with brine and then dried over anhydrous magnesium sulfate, and the solvent was evaporated. The residue was purified by LC-MS to give 23 mg of the title compound as a pale yellow solid.

$^1$H-NMR (DMSO-d$_6$)
δ: 6.41(d, J=8.8 Hz, 1H), 7.10(t, J=8.0 Hz, 2H), 7.34(m, 2H), 7.42(m, 1H), 7.52(d, J=9.0 Hz, 1H), 7.56–7.62 (m, 2H), 7.83(s, 1H), 8.09–8.14(m, 2H), 8.97(d, J=4.5 Hz, 1H)

The compounds in Examples 1063 and 1064 were synthesized in the same manner as in Example 1060 except that the boronic acid was changed.

Example 1063

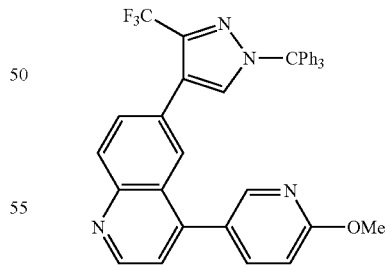

4-(6-Methoxypyridin-3-yl)-6-(3-trifluoromethyl-1-trityl-1H-pyrazol-4-yl) quinoline $^1$H-NMR (CDCl$_3$)
δ: 4.02(s, 3H), 6.92(d, J=8.8 Hz, 1H), 7.14–7.38(m, 16H), 7.47(s, 1H), 7.68(dd, J=8.0, 1.6 Hz, 1H), 7.76(dd, J=8.5, 2.0 Hz, 1H), 7.95(d, J=1.6 Hz, 1H), 8.14(d, J=8.8 Hz, 1H), 8.32(d, J=2.0 Hz, 1H), 8.93(d, J=7.0 Hz, 1H)

Example 1064

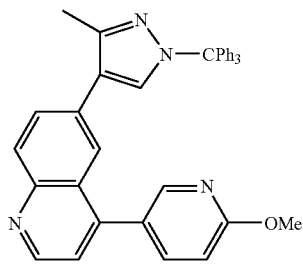

4-(6-Methoxypyridin-3-yl)-6-(3-methyl-1-trityl-1H-pyrazol-4-yl) quinoline $^1$H-NMR (CDCl$_3$)
δ: 2.30(s, 3H), 4.02(s, 3H), 6.86(d, J=8.8 Hz, 1H), 7.20–7.38(m, 16H), 7.52(s, 1H), 7.68(dd, J=8.0, 1.6 Hz, 1H), 7.88(dd, J=8.5, 2.0 Hz, 1H), 7.98(d, J=1.6 Hz, 1H), 8.19(d, J=8.8 Hz, 1H), 8.38(d, J=2.0 Hz, 1H), 8.88(d, J=7.0 Hz, 1H)

Example 1065

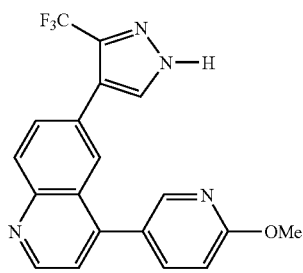

4-(6-Methoxypyridin-3-yl)-6-(3-trifluoromethyl-1H-pyrazol-4-yl) quinoline

A mixture of 210 mg 4-(6-methoxypyridin-3-yl)-6-(3-trifluoromethyl-1-trityl-1H-pyrazol-4-yl) quinoline obtained in Example 1063 and 10 mL trifluoroacetic acid was stirred at room temperature for 1 hour. The trifluoroacetic acid was evaporated, and an aqueous saturated sodiumbicarbonate solution was added to the residue which was then extracted with ethyl acetate. The organic layer was washed with brine and dried over anhydrous magnesium sulfate. The solvent was evaporated, and the residue was purified by silica gel column chromatography to give 110 mg of the title compound as a colorless solid.

$^1$H-NMR (CDCl$_3$)
δ: 4.02(s, 3H), 6.94(d, J=8.2 Hz, 1H), 7.38(d, J=4.4 Hz, 1H), 7.76–7.83(m, 3H), 7.98(d, J=1.8 Hz, 1H), 8.24(d, J=8.8 Hz, 1H), 8.35(d, J=1.8 Hz, 1H), 8.98(d, J=4.4 Hz, 1H)

Example 1066

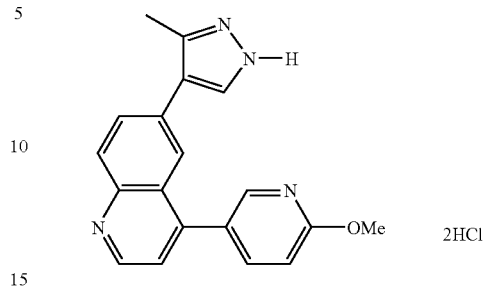

4-(6-Methoxypyridin-3-yl)-6-(3-methyl-1H-pyrazol-4-yl)quinoline dihydrochloride

A free product obtained by the same procedure as in Example 1065 from 210 mg 4-(6-methoxypyridin-3-yl)-6-(3-methyl-1-trityl-1H-pyrazol-4-yl) quinoline obtained in Example 1064 was treated with 4 N hydrogen chloride solution in ethyl acetate to give 16 mg of the title compound as a pale yellow solid.

$^1$H-NMR (CD$_3$OD)
δ: 2.48(s, 3H), 4.18(s, 3H), 7.37(d, J=7.6 Hz, 1H), 8.06(d, J=6.0 Hz, 1H), 8.28(s, 1H), 8.41(d, J=9.0 Hz, 1H), 8.50–8.56(m, 3H), 8.73(d, J=1.8 Hz, 1H), 9.15(d, J=6.0 Hz, 1H)

Example 1067

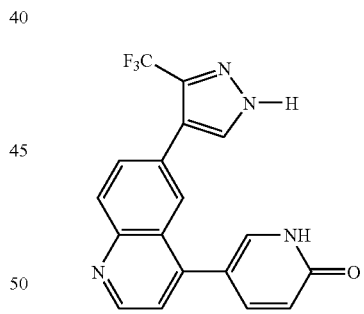

5-[6-(3-Trifluoromethyl-1H-pyrazol-4-yl)quinolin-4-yl]-1H-pyridin-2-one 80 mg 4-(6-methoxypyridin-3-yl)-6-(3-trifluoromethyl-1H-pyrazol-4-yl) quinoline obtained in Example 1065 was treated by the method described in Example 1062 to give 27 mg of the title compound as a colorless solid.

$^1$H-NMR (CD$_3$OD)
δ: 6.73(d, J=8.8 Hz, 1H), 7.53(d, J=4.8 Hz, 1H), 7.72(d, J=2.4 Hz, 1H), 7.84(dd, J=2.4, 8.8 Hz, 1H), 7.93(dd, J=1.6, 8.2 Hz, 1H), 8.06(d, J=1.6 Hz, 1H), 8.12–8.16 (m, 2H), 8.88(d, J=4.8 Hz, 1H)

Example 1068

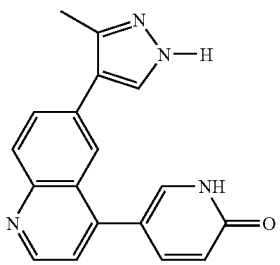

5-[6-(3-Methyl-1H-pyrazol-4-yl)quinolin-4-yl]-1H-pyridin-2-one 85 mg 4-(6-methoxypyridin-3-yl)-6-(3-methyl-1-trityl-1H-pyrazol-4-yl) quinoline obtained in Example 1065 was treated by the method described in Example 1062 to give 16 mg of the title compound as a colorless solid.

¹H-NMR (CD₃OD)

δ: 2.31(s, 3H), 6.67(d, J=9.5 Hz, 1H), 7.47(d, J=4.6 Hz, 1H), 7.81(d, J=2.7 Hz, 1H), 7.96–8.04(m, 4H), 8.14(d, J=8.8 Hz, 1H), 8.83(d, J=4.6 Hz, 1H)

Example 1069

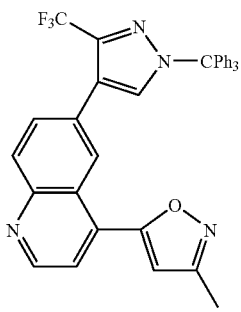

4-(3-Methylisoxazol-5-yl)-6-(3-trifluoromethyl-1-trityl-1H-pyrazol-4-yl) quinoline A mixture of 200 mg 6-(3-trifluoromethyl-1-trityl-1H-pyrazolyl)-4-quinolyl trifluoromethane sulfonate obtained in Production Example 93, 170 mg 5-methyl-3-tri-n-butylstannyl isoxazole, 4 mg tetrakistriphenyl phosphine palladium and 20 mL N,N-dimethylformamide was stirred at 50° C. for 20 hours. The reaction solution was cooled to room temperature, water was added thereto, and the solution was extracted with ethyl acetate. The organic layer was washed with brine and dried over anhydrous magnesium sulfate. The solvent was evaporated, and the residue was purified by silica gel column chromatography to give 16 mg of the title compound as a colorless oil.

¹H-NMR (CDCl₃)

δ: 2.42(s, 3H), 6.66(s, 1H), 7.14–7.40(m, 15H), 7.57(s, 1H), 7.70–7.76(m, 2H), 8.16(d, J=8.4 Hz, 1H), 8.40(d, J=1.6 Hz, 1H), 8.98(d, J=4.6 Hz, 1H)

Example 1070

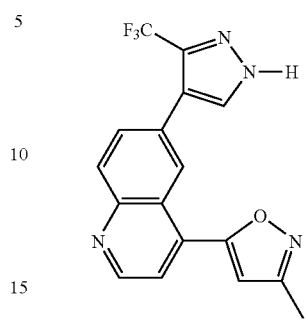

4-(3-Methylisoxazol-5-yl)-6-(3-trifluoromethyl-1H-pyrazol-4-yl) quinoline 2.8 mg of the title compound was obtained as a colorless solid by the same procedure as in Example 1065 from 16 mg 4-(3-methylisoxazol-5-yl)-6-(3-trifluoromethyl-1-trityl-1H-pyrazol-4-yl) quinoline obtained in Production Example 1069.

¹H-NMR (CD₃OD)

δ: 2.44(s, 3H), 6.96(s, 1H), 7.86(d, J=4.6 Hz, 1H), 7.97(dd, J=2.0, 8.5 Hz, 1H), 8.14–8.20(m, 2H), 8.49(d, J=2.0 Hz, 1H), 8.97(d, J=4.6 Hz, 1H)

Example 1071

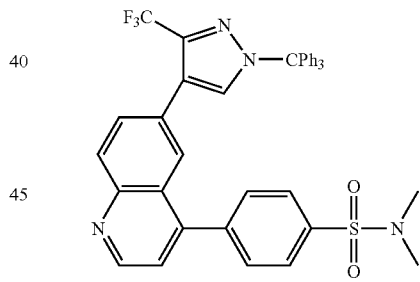

N,N-Dimethyl-4-[6-(3-trifluoromethyl-1-trityl-1H-pyrazol-4-yl)quinolin-4-yl] benzene sulfonamide 120 mg of the title compound was obtained as a colorless oil by the method described in Example 1069 from 300 mg 6-(3-trifluoromethyl-1-trityl-1H-pyrazolyl)-4-quinolyl trifluoromethane sulfonate obtained in Production Example 93 and 320 mg N,N-dimethyl-4-tri-n-butylstannyl benzene sulfonamide.

¹H-NMR (CDCl₃)

δ: 2.80(s, 6H), 7.12–7.40(m, 15H), 7.56(s, 1H), 7.62(d, J=4.6 Hz, 1H), 7.72(d, J=9.0 Hz, 2H), 7.85(m, 1H), 7.98–8.02(m, 3H), 8.32(d, J=8.5 Hz, 1H), 9.45(d, J=4.6 Hz, 1H)

Example 1072

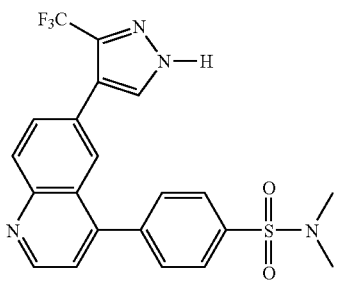

N,N-Dimethyl-4-[6-(3-trifluoromethyl-1H-pyrazol-4-yl)quinolin-4-yl] benzene sulfonamide 62 mg of the title compound was obtained as a colorless solid by the method described in Example 1070 from 120 mg N,N-dimethyl-4-[6-(3-trifluoromethyl-1-trityl-1H-pyrazol-4-yl)quinolin-4-yl] benzene sulfonamide obtained in Production Example 1071.

$^1$H-NMR (DMSO-$d_6$)

δ: 2.67(s, 6H), 7.57(d, J=4.3 Hz, 1H), 7.80–7.83(m, 3H), 7.91–7.95(m, 3H), 8.17(d, J=8.8 Hz, 1H), 8.40(s, 1H), 8.99(d, J=4.3 Hz, 1H)

Example 1073

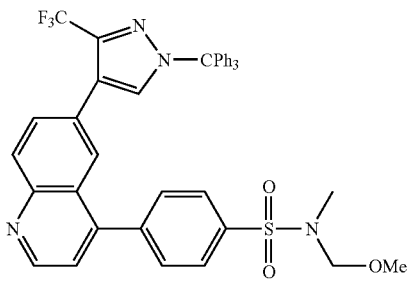

N-Methoxymethyl-N-methyl-4-[6-(3-trifluoromethyl-1-trityl-1H-pyrazol-4-yl)quinolin-4-yl] benzene sulfonamide 120 mg of the title compound was obtained as a colorless oil by the method described in Example 1069 from 300 mg 6-(3-trifluoromethyl-1-trityl-1H-pyrazolyl)-4-quinolyl trifluoromethane sulfonate obtained in Production Example 93 and 200 mg N-methoxymethyl-N-methyl-4-tri-n-butylstannyl benzene sulfonamide.

$^1$H-NMR (CDCl$_3$)

δ: 2.90(s, 3H), 3.37(s, 3H), 4.72(s, 2H), 7.12–7.40(m, 16H), 7.48(s, 1H), 7.66(d, J=9.0 Hz, 2H), 7.70(m, 1H), 7.88(s, 1H), 7.99(d, J=9.0 Hz, 2H), 8.16(d, J=8.5 Hz, 1H), 8.96(d, J=4.6 Hz, 1H)

Example 1074

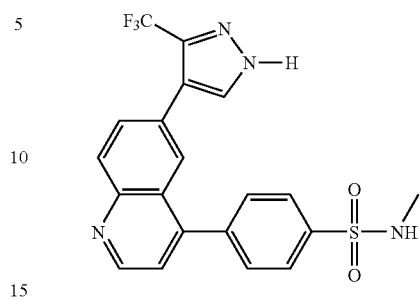

N-Methyl-4-[6-(3-trifluoromethyl-1H-pyrazol-4-yl)quinolin-4-yl] benzene sulfonamide 2.2 mg of the title compound was obtained as a colorless oil by the method described in Example 1070 from 12 mg N-methoxymethyl-N-methyl-4-[6-(3-trifluoromethyl-1-trityl-1H-pyrazol-4-yl)quinolin-4-yl]benzene sulfonamide obtained in Example 1073.

$^1$H-NMR (CD$_3$OD)

δ: 2.61(s, 3H), 3.37(s, 3H), 4.72(s, 2H), 7.56(d, J=4.4 Hz, 1H), 7.76(d, J=8.4 Hz, 2H), 7.92–7.96(m, 2H), 8.04(d, J=8.4 Hz, 2H), 8.17–8.19(m, 2H), 8.93(d, J=4.4 Hz, 1H)

Example 1075

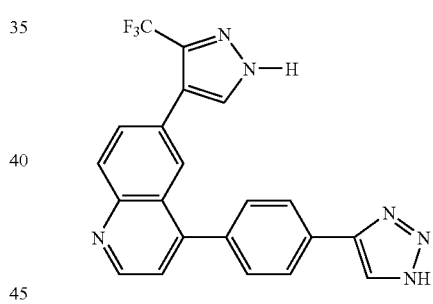

4-[4-(1H-[1,2,3]triazol-4-yl)phenyl]-6-(3-trifluoromethyl-1H-pyrazol-4-yl) quinoline A mixture of 520 mg 6-(3-trifluoromethyl-1-trityl-1H-pyrazol-4-yl)-4-{4-[5-trimethylsilanyl-1-(2-trimethylsilanylethoxymethyl)-1H-[1,2,3]triazol-4-yl]phenyl} quinoline obtained by the method described in Example 1069 from 460 mg 6-(3-trifluoromethyl-1-trityl-1H-pyrazolyl)-4-quinolyl trifluoromethane sulfonate obtained in Production Example 93 and 400 mg 5-trimethylsilanyl-1-(2-trimethylsilanylethoxymethyl)-4-(4-tri-n-butylstannylphenyl)-1H-[1,2,3]triazole, 70 mg potassium fluoride and 5 mL conc. hydrochloric acid was stirred at room temperature for 20 minutes. The reaction mixture was neutralized with an aqueous saturated sodium bicarbonate solution and extracted with ethyl acetate. The organic layer was washed with brine and then dried over anhydrous magnesium sulfate. After the solvent was evaporated, the residue was purified by silica gel column chromatography to give 32 mg of the title compound as a colorless solid.

¹H-NMR (CD₃OD)

δ: 7.53(d, J=4.4 Hz, 1H), 7.65(d, J=8.4 Hz, 2H), 7.90(dd, J=2.0, 8.5 Hz, 1H), 8.02–8.06(m, 3H), 8.09(d, J=2.0 Hz, 1H), 8.15(d, J=8.5 Hz, 1H), 8.28(s, 1H), 8.89(d, J=4.4 Hz, 1H)

Example 1076

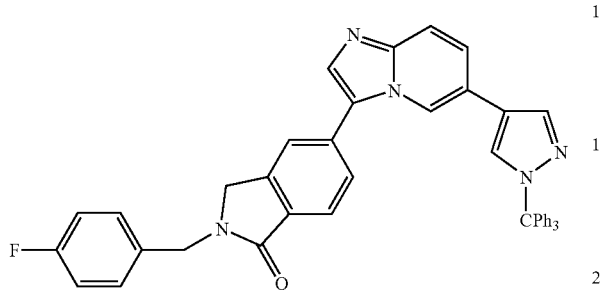

2-(4-Fluorobenzyl)-5-[6-(1-trityl-1H-pyrazol-4-yl) imidazo[1,2-a]pyridin-3-yl]-2,3-dihydroisoindol-1-one 9.3 mg of the title compound was obtained as a colorless amorphous by the same reaction as in Example 21 from 95 mg 3-bromo-6-(1-trityl-1H-4-pyrazolyl)imidazo[1,2-a]pyridine (compound in Production Example 292) and 100 mg 2-(4-fluorobenzyl)-5-tributylstannyl-2,3-dihydroisoindol-1-one (compound in Production Example 464).

¹H-NMR (CDCl₃)

δ: 4.35(s, 2H), 4.83(s, 2H), 7.05(t, J=8.8 Hz, 2H), 7.18(m, 6H), 7.32(m, 12H), 7.58(m, 2H), 7.66(dd, J=9.2, 0.8 Hz, 1H), 7.69(dd, J=8.0, 1.6 Hz, 1H), 7.71(s, 1H), 7.84(d, J=1.2 Hz, 1H), 8.03(dd, J=8.0, 0.8 Hz, 1H), 8.36(dd, J=1.6, 1.2 Hz, 1H)

Example 1077

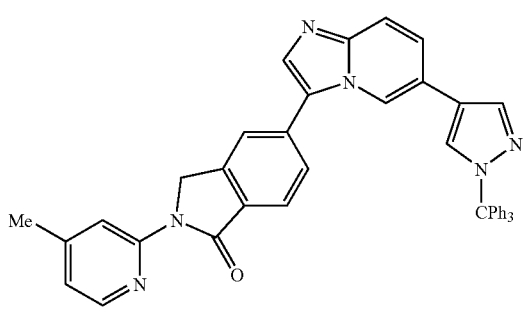

2-(4-Methylpyridin-2-yl)-5-[6-(1-trityl-1H-pyrazol-4-yl)imidazo[1,2-a]pyridin-3-yl]-2,3-dihydroisoindol-1-one 49 mg of the title compound was obtained as a pale yellow amorphous by the same reaction as in Example 21 from 148 mg 3-bromo-6-(1-trityl-1H-4-pyrazolyl)imidazo[1,2-a]pyridine (compound in Production Example 292) and 150 mg 2-(4-methylpyridin-2-yl)-5-tributylstannyl-2,3-dihydroisoindol-1-one (compound in Production Example 465).

¹H-NMR (CDCl₃)

δ: 2.45(s, 3H), 5.18(s, 2H), 6.94(dd, J=4.8, 0.8 Hz, 1H), 7.14–7.40(m, 16H), 7.61(s, 1H), 7.69(m, 2H), 7.73(s, 1H), 7.79(s, 1H), 7.88(d, J=0.4 Hz, 1H), 8.07(d, J=8.4 Hz, 1H), 8.28(d, J=5.2 Hz, 1H), 8.42(s, 1H), 8.53(d, J=0.4 Hz, 1H)

Example 1078

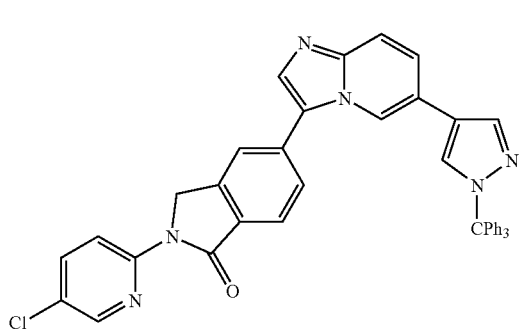

2-(5-Chloropyridin-2-yl)-5-[6-(1-trityl-1H-pyrazol-4-yl)imidazo[1,2-a]pyridin-3-yl]-2,3-dihydroisoindol-1-one 50 mg of the title compound was obtained as a pale yellow amorphous by the same reaction as in Example 21 from 190 mg 3-bromo-6-(1-trityl-1H-4-pyrazolyl)imidazo[1,2-a]pyridine (compound in Production Example 292) and 200 mg 2-(5-chloropyridin-2-yl)-5-tributylstannyl-2,3-dihydroisoindol-1-one (compound in Production Example 466).

¹H-NMR (CDCl₃)

δ: 5.15(s, 2H), 7.14–7.40(m, 16H), 7.47(m, 1H), 7.56(m, 1H), 7.61(s, 1H), 7.69(m, 2H), 7.74(s, 1H), 7.79(s, 1H), 7.88(s, 1H), 8.07(d, J=7.6 Hz, 1H), 8.42(s, 1H), 8.69(d, J=8.8 Hz, 1H)

Example 1079

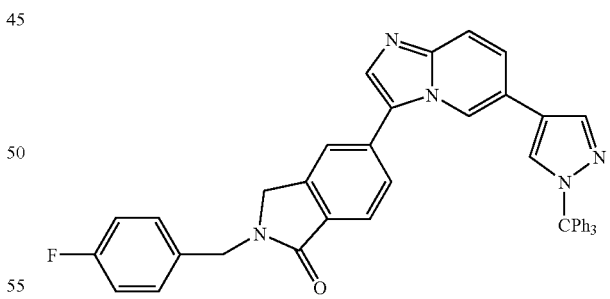

2-(4-Fluorobenzyl)-5-[6-(1H-pyrazol-4-yl)imidazo[1,2-a]pyridin-3-yl]-2,3-dihydroisoindol-1-one 2.4 mg of the title compound was obtained as white crystals by the same method as in Example 80 from 9 mg 2-(4-fluorobenzyl)-5-[6-(1-trityl-1H-pyrazol-4-yl)imidazo[1,2,3]pyridin-3-yl]-2,3-dihydroisoindol-1-one (compound in Production Example 1076).

MS m/e (ESI) 424(MH⁺)

Example 1080

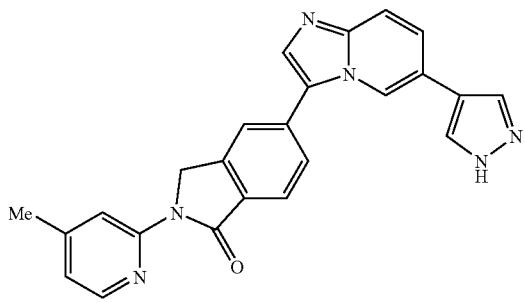

2-(4-Methylpyridin-2-yl)-5-[6-(1H-pyrazol-4-yl)imidazo[1,2-a]pyridin-3-yl]-2,3-dihydroisoindol-1-one 22 mg of the title compound was obtained as pale yellow crystals by the same method as in Example 80 from 47 mg 2-(4-methylpyridin-2-yl)-5-[6-(1-trityl-1H-pyrazol-4-yl)imidazo[1,2-a]pyridin-3-yl]-2,3-dihydroisoindol-1-one (compound in Production Example 1077).

$^1$H-NMR (DMSO-$d_6$)

δ: 2.40(s, 3H), 5.20(s, 2H), 7.04(d, J=4.8 Hz, 1H), 7.66(d, J=9.2 Hz, 1H), 7.73(d, J=9.2 Hz, 1H), 7.84–7.98(m, 3H), 8.07(m, 2H), 8.31(m, 2H), 8.41(s, 1H), 8.77(s, 1H), 13.02 (brs, 1H)

MS m/e (ESI) 407(MH$^+$)

Example 1081

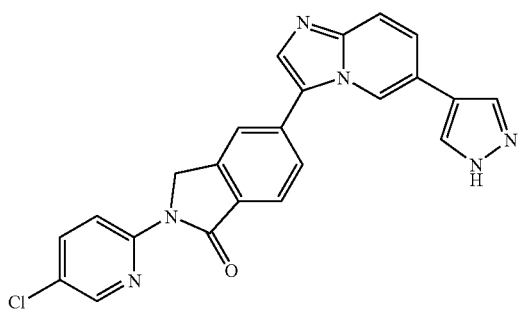

2-(5-Chloropyridin-2-yl)-5-[6-(1H-pyrazol-4-yl)imidazo[1,2-a]pyridin-3-yl]-2,3-dihydroisoindol-1-one 15 mg of the title compound was obtained as pale yellow crystals by the same method as in Example 80 from 47 mg 2-(5-chloropyridin-2-yl)-5-[6-(1-trityl-1H-pyrazol-4-yl)imidazo[1,2-a]pyridin-3-yl]-2,3-dihydroisoindol-1-one (compound in Production Example 1078).

$^1$H-NMR (DMSO-$d_6$)

δ: 5.20(s, 2H), 7.68(d, J=9.2 Hz, 1H), 7.75(d, J=9.2 Hz, 1H), 7.91(m, 2H), 7.98(d, J=8.4, 1H), 8.05(m, 1H), 8.11(s, 1H), 8.20(brs, 2H), 8.53(m, 1H), 8.62(d, J=8.8 Hz, 1H), 8.79(d, J=0.8 Hz, 1H), 13.08(brs, 1H)

MS m/e (ESI) 427(MH$^+$)

Example 1082

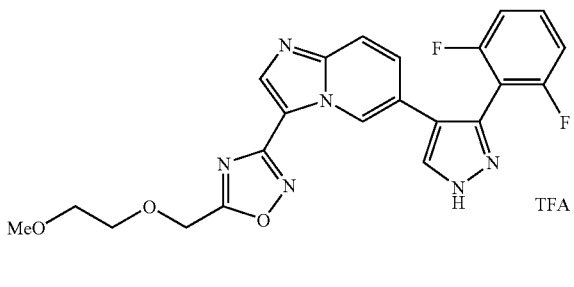

6-[3-(2,6-Difluorophenyl)-1H-4-pyrazolyl]-3-[5-(2-methoxyethoxymethyl)-[1,2,4]oxadiazol-3-yl]-imidazo[1,2-a]pyridine trifluoroacetate 60 mg 6-bromo-3-[5-(2-methoxyethoxymethyl)-[1,2,4]oxadiazol-3-yl]-imidazo[1,2-a]pyridine obtained in Production Example 468 and 158 mg 3-(2,6-difluorophenyl)-1-trityl-1H-4-pyrazolylboronic acid (compound in Production Example 211) were subjected to the same coupling reaction as in Example 29 with 1,2-dimethoxyethane as the solvent. Subsequently, the product was subjected to the reaction for deprotecting the trityl group in the same manner as in Example 68 and then purified by high performance liquid chromatography (WAKO PAK ODS column; solvent, water/acetonitrile/0.1% trifluoroacetic acid) to give 29 mg of the title compound (colorless crystals).

$^1$H-NMR (DMSO-$d_6$)

δ: 3.24(s, 3H), 3.48–3.54(m, 2H), 3.68–3.75(m, 2H), 4.88(s, 2H), 7.14–7.30(m, 2H), 7.48–7.64(m, 3H), 7.81(d, J=9.2 Hz, 1H), 8.27(s, 1H), 8.34–8.50(m, 1H), 8.83(brs, 1H)

MS m/e (ESI) 453 (MH$^+$)

Example 1083

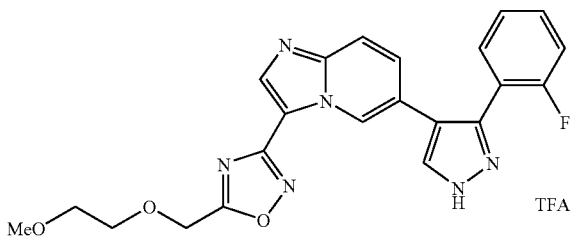

6-[3-(2-Fluorophenyl)-1H-4-pyrazolyl]-3-(5-(2-methoxyethoxymethyl)-[1,2,4]oxadiazol-3-yl]imidazo[1,2-a]-pyridine trifluoroacetate 12 mg of the title compound (colorless crystals) was obtained in the same manner as in Example 1082 from 60 mg 6-bromo-3-[5-(2-methoxyethoxymethyl)-[1,2,4]oxadiazol-3-yl]-imidazo[1,2-a]pyridine (compound in Production Example 468) and 152 mg 3-(2-fluorophenyl)-1-trityl-1H-4-pyrazolylboronic acid (compound in Production Example 197).

MS m/e (ESI) 435 (MH$^+$)

Example 1084

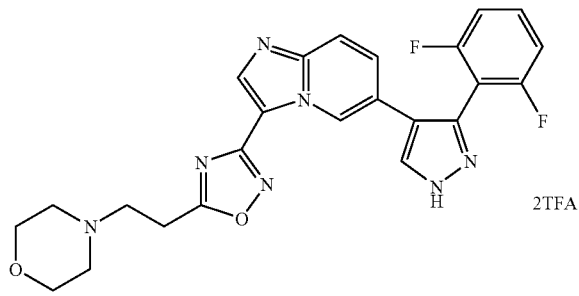

6-[3-(2,6-Difluorophenyl)-1H-4-pyrazolyl]-3-[5-(2-morpholin-4-ylethyl)-[1,2,4]oxadiazol-3-yl]imidazo[1,2-a]-pyridine di-trifluoroacetate 30 mg of the title compound (colorless crystals) was obtained in the same manner as in Example 1082 from 50 mg 6-bromo-3-[5-(2-morpholin-4-ylethyl)-[1,2,4]oxadiazol-3-yl]-imidazo[1,2-a]pyridine (compound in Production Example 469) and 125 mg 3-(2,6-difluorophenyl)-1-trityl-1H-4-pyrazolylboronic acid (compound in Production Example 211).

¹H-NMR (DMSO-d₆)

δ: 3.00–3.33(m, 4H), 3.40–3.59(m, 2H), 3.61–3.76(m, 2H), 3.81–4.20(m, 4H), 7.15–7.28(m, 2H), 7.49–7.66(m, 3H), 7.84(d, J=9.2 Hz, 1H), 8.28(s, 1H), 8.35(brs, 1H), 8.83(s, 1H)

MS m/e (ESI) 478 (MH⁺)

Example 1085

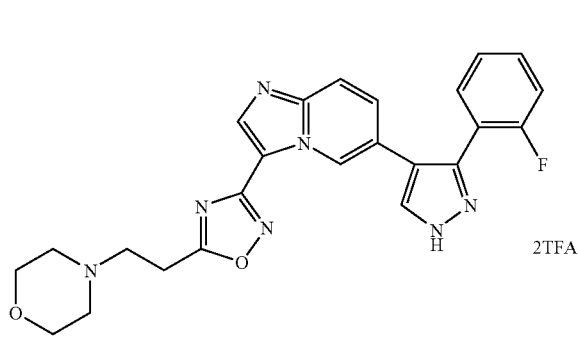

6-[3-(2-Fluorophenyl)-1H-4-pyrazolyl]-3-[5-(2-morpholin-4-ylethyl)-[1,2,4]oxadiazol-3-yl]imidazo[1,2-a]pyridine di-trifluoroacetate 15 mg of the title compound (colorless crystals) was obtained in the same manner as in Example 1082 from 50 mg 6-bromo-3-[5-(2-morpholin-4-ylethyl)-[1,2,4]oxadiazol-3-yl]-imidazo[1,2-a]pyridine (compound in Production Example 469) and 120 mg 3-(2-fluorophenyl)-1-trityl-1H-4-pyrazolylboronic acid (compound in Production Example 197).

MS m/e (ESI) 460 (MH⁺)

Example 1086

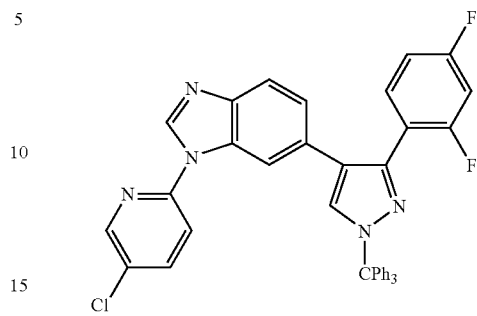

1-(5-Chloropyridin-2-yl)-6-[3-(2,4-difluorophenyl)-1-trityl-1H-4-pyrazolyl]-1H-benzo[d]imidazole 114 mg of the title compound was obtained as a pale purple amorphous by the same reaction as in Example 29 from 70 mg 6-bromo-1-(5-chloropyridin-2-yl)-1H-benzo[d]imidazole (compound in Production Example 473) and 320 mg 3-(2,4-difluorophenyl)-1-trityl-1H-4-pyrazolylboronic acid (compound in Production Example 172).

¹H-NMR (CDCl₃)

δ: 6.80 (td, J=9.2, 2.8 Hz, 1H), 6.89–6.94(m, 1H), 7.18(d, J=8.5 Hz, 1H), 7.23(dd, J=8.5, 1.6 Hz, 1H), 7.25–7.38(m, 15H), 7.41–7.46(m, 1H), 7.59(s, 1H), 7.67(d, J=1.6 Hz, 1H), 7.72(d, J=8.4 Hz, 1H), 7.74(dd, J=8.4, 2.6 Hz, 1H), 8.41(d, J=2.6 Hz, 1H), 8.46(s, 1H)

Example 1087

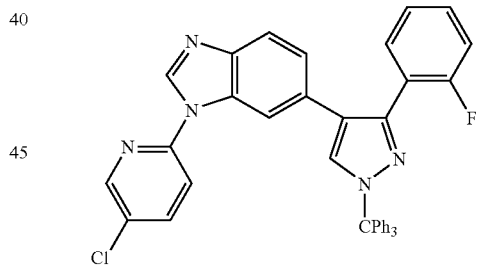

1-(5-Chloropyridin-2-yl)-6-[3-(2-fluorophenyl)-1-trityl-1H-4-pyrazolyl]-1H-benzo[d]imidazole 107 mg of the title compound was obtained as pale purple crystals by the same reaction as in Example 29 from 70 mg 6-bromo-1-(5-chloropyridin-2-yl)-1H-benzo[d]imidazole (compound in Production Example 473) and 132 mg 3-(2-fluorophenyl)-1-trityl-1H-4-pyrazolylboronic acid (compound in Production Example 197).

¹H-NMR (CDCl₃)

δ: 7.05(td, J=9.0, 1.2 Hz, 1H), 7.05(dd, J=8.6, 0.6 Hz, 1H), 7.18(td, J=7.6, 1.2 Hz, 1H), 7.23–7.31(m, 7H), 7.31–7.41(m, 10H), 7.48(td, J=7.6, 2.5 Hz, 1H), 7.60(s, 1H), 7.63(d, J=1.2 Hz, 1H), 7.66(dd, J=8.6, 2.6 Hz, 1H), 7.72(dd, J=8.6, 0.6 Hz, 1H), 8.39(dd, J=2.6, 0.6 Hz, 1H), 8.48(s, 1H)

Example 1088

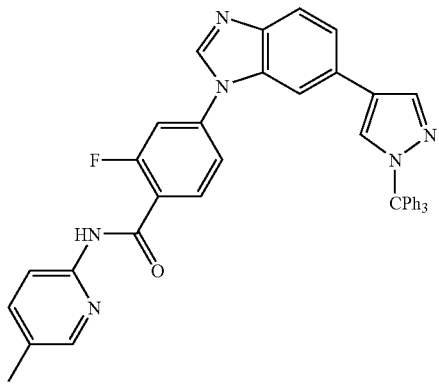

2-Fluoro-N-(5-methylpyridin-2-yl)-4-[6-(1-trityl-1H-4-pyrazolyl)-1H-benzo[d]imidazol-1-yl] benzamide 34 mg of the title compound was obtained as pale pink crystals by the same reaction as in Example 477 from 100 mg 2-fluoro-4-[6-(1-trityl-1H-4-pyrazolyl)-1H-benzo[d]imidazol-1-yl]benzoic acid (compound in Example 720) and 42 mg 2-amino-5-methylpyridine.

$^1$H-NMR (CDCl$_3$)

δ: 2.35(s, 3H), 7.19–7.24(m, 6H), 7.31–7.38(m, 9H), 7.43(dd, J=11.2, 2.0 Hz, 1H), 7.44(dd, J=8.4, 0.6 Hz, 1H), 7.54(dd, J=8.4, 2.0 Hz, 1H), 7.58–7.62(m, 2H), 7.66(d, J=0.8 Hz, 1H), 7.83(d, J=8.4 Hz, 1H), 7.95(d, J=0.8 Hz, 1H), 8.12(s, 1H), 8.18–8.19(m, 1H), 8.29(d, J=8.4 Hz, 1H), 8.40(t, J=8.4 Hz, 1H), 8.98–9.04(m, 1H)

Example 1089

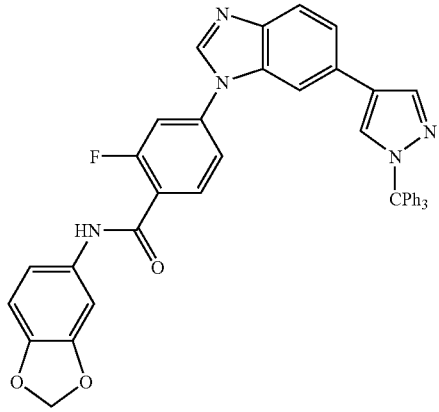

N-Benzo[1,3]dioxol-5-yl-2-fluoro-4-[6-(1-trityl-1H-4-pyrazolyl)-1H-benzo[d]imidazol-1-yl] benzamide 44 mg of the title compound was obtained as pale pink crystals by the same reaction as in Example 477 from 80 mg 2-fluoro-4-[6-(1-trityl-1H-4-pyrazolyl)-1H-benzo[d]imidazol-1-yl]benzoic acid (compound in Example 720) and 43 mg 3,4-methylenedioxyaniline.

$^1$H-NMR (CDCl$_3$)

δ: 6.00(s, 2H), 6.82(d, J=8.4 Hz, 1H), 6.97(dd, J=8.4, 2.0 Hz, 1H), 7.19–7.24(m, 6H), 7.31–7.38(m, 9H), 7.40(dd, J=7.6, 2.0 Hz, 1H), 7.43(d, J=2.0 Hz, 1H), 7.44(dd, J=8.4, 1.4 Hz, 1H), 7.53(dd, J=8.8, 2.0 Hz, 1H), 7.60(d, J=1.4 Hz, 1H), 7.66(d, J=0.6 Hz, 1H), 7.82(d, J=8.4 Hz, 1H), 7.95(d, J=0.6 Hz, 1H), 8.11(s, 1H), 8.31–8.38(m, 1H), 8.42(t, J=8.8 Hz, 1H)

Example 1090

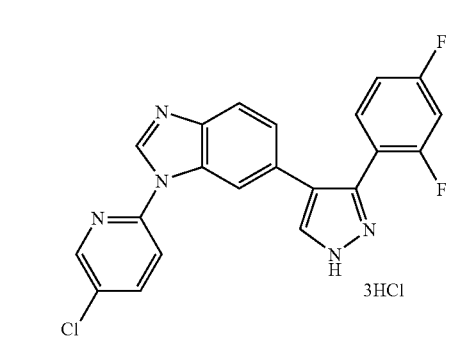

1-(5-Chloropyridin-2-yl)-6-[3-(2,4-difluorophenyl)-1H-4-pyrazolyl]-1H-benzo[d]imidazole trihydrochloride 58 mg of the title compound was obtained as pale purple crystals by the same reaction as in Example 79 from 114 mg 1-(5-chloropyridin-2-yl)-6-[3-(2,4-difluorophenyl)-1-trityl-1H-4-pyrazolyl]-1H-benzo[d]imidazole (compound in Example 1086).

$^1$H-NMR (DMSO-d$_6$)

δ: 7.21–7.27(m, 1H), 7.35(td, J=9.6, 2.4 Hz, 1H), 7.45(dd, J=8.4, 1.4 Hz, 1H), 7.52–7.58(m, 1H), 7.77(d, J=8.4 Hz, 1H), 7.99(dd, J=8.8, 0.4 Hz, 1H), 8.10(d, J=1.4 Hz, 1H), 8.20(s, 1H), 8.27(dd, J=8.8, 2.4 Hz, 1H), 8.49(d, J=2.4 Hz, 1H), 9.51(s, 1H)

MS m/e (ESI) 408 (MH$^+$)

Example 1091

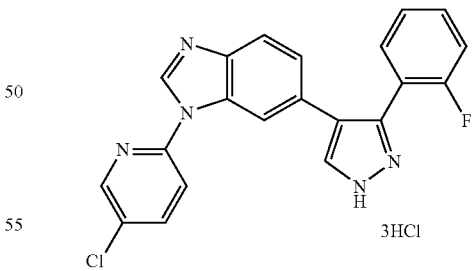

1-(5-Chloropyridin-2-yl)-6-[3-(2-fluorophenyl)-1H-4-pyrazolyl]-1H-benzo[d]imidazole trihydrochloride 43 mg of the title compound was obtained as pale yellow crystals by the same reaction as in Example 79 from 107 mg 1-(5-chloropyridin-2-yl)-6-[3-(2-fluorophenyl)-1-trityl-1H-4-pyrazolyl]-1H-benzo[d]imidazole (compound in Example 1087).

¹H-NMR (DMSO-d₆)

δ: 7.25–7.30(m, 1H), 7.33(td, J=7.6, 1.4 Hz, 1H), 7.43(dd, J=8.4, 1.4 Hz, 1H), 7.48–7.56(m, 2H), 7.75(dd, J=8.4, 0.6 Hz, 1H), 7.91(dd, J=8.80.6 Hz, 1H), 8.10(d, J=1.4 Hz, 1H), 8.17(s, 1H), 8.24(dd, J=8.8, 2.8 Hz, 1H), 8.47(dd, J=2.8, 0.6 Hz, 1H), 9.42(s, 1H)

MS m/e (ESI) 390 (MH⁺)

Example 1092

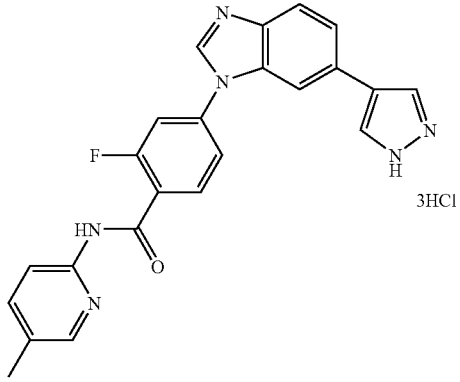

3HCl

2-Fluoro-N-(5-methylpyridin-2-yl)-4-[6-(1H-4-pyrazolyl)-1H-benzo[d]imidazol-1-yl]benzamide trihydrochloride 19 mg of the title compound was obtained as pale pink crystals by the same reaction as in Example 79 from 34 mg 2-fluoro-N-(5-methylpyridin-2-yl)-4-[6-(1-trityl-1H-4-pyrazolyl)-1H-benzo[d]imidazol-1-yl] benzamide (compound in Example 1088).

¹H-NMR (DMSO-d₆)

δ: 2.32(s, 3H), 7.78(dd, J=8.4, 1.2 Hz, 1H), 7.77–7.81(m, 1H), 7.82(dd, J=8.0, 2.2 Hz, 1H), 7.86(d, J=8.4 Hz, 1H), 7.91–7.98(m, 3H), 8.01(t, J=8.0 Hz, 1H), 8.10(d, J=8.4 Hz, 1H), 8.21(s, 2H), 8.25–8.26(m, 1H), 9.26(brs, 1H)

MS m/e (ESI) 413 (MH⁺)

Example 1093

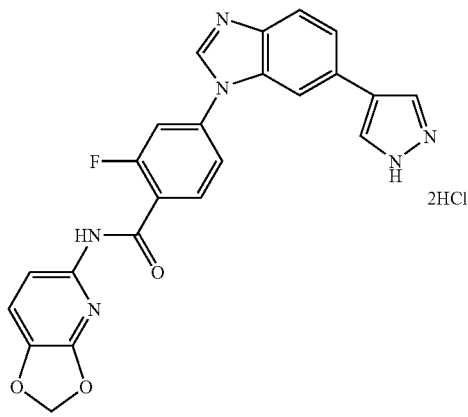

2HCl

N-Benzo[1,3]dioxol-5-yl-2-fluoro-4-[6-(1H-4-pyrazolyl)-1H-benzo[d]imidazol-1-yl]benzamide dihydrochloride 25 mg of the title compound was obtained as pale yellow crystals by the same reaction as in Example 79 from 44 mg N-benzo[1,3]dioxol-5-yl-2-fluoro-4-[6-(1-trityl-1H-4-pyrazolyl)-1H-benzo[d]imidazol-1-yl] benzamide (compound in Example 1089).

¹H-NMR (DMSO-d₆)

δ: 6.03(s, 2H), 6.93(d, J=8.4 Hz, 1H), 7.18(dd, J=8.4, 2.0 Hz, 1H), 7.44(d, J=2.0 Hz, 1H), 7.70–7.85(m, 4H), 7.89–7.97(m, 3H), 8.19(s, 2H), 9.09(brs, 1H)

MS m/e (ESI) 442 (MH⁺)

The invention claimed is:

1. A compound represented by the following formula (I), or a salt thereof or a hydrate thereof:

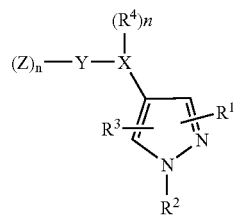

(I)

wherein X represents quinoline, isoquinoline, quinazoline or imidazopyridine, and said X has $(R^4)_n$ as substituent groups whereupon n is 0, 1, 2 or 3, and the substituent groups $(R^4)_n$ independently represent a hydrogen atom, halogen atom, cyano group, hydroxyl group, amino group, $C_{1-6}$ alkyl group, halogenated $C_{1-6}$ alkyl group, $C_{2-6}$ alkenyl group, $C_{1-6}$ alkylsulfonyl group, $C_{1-6}$ alkylsulfonylamino group, $C_{1-6}$ alkylsulfinyl group, N—($C_{1-6}$ alkyl)amino group, N,N-di($C_{1-6}$ alkyl)amino group, $C_{1-6}$ alkoxy group, $C_{1-6}$ alkylsulfanyl group, carbamoyl group, N—($C_{1-6}$ alkyl)carbamoyl group, N,N-di($C_{1-6}$ alkyl)carbamoyl group, sulfamoyl group, phenyl group, heteroaryl group, phenoxy group, heteroallyloxy group, phenyl $C_{1-6}$ alkylamino group or heteroaryl $C_{1-6}$ alkylamino group, which is bound to an atom constituting X;

Y represents a phenyl group, piperazine, pyridine, thiophene, thiazole, oxadiazole or oxathiadiazole;

$(Z)_n$ are n (Z) groups bound to Y, whereupon n is 0, 1, 2 or 3, Z groups are bound to an atom constituting the cyclic group Y and independently represent formula —M¹—M²—M³ wherein:

M¹ and M² each represent a single bond, —(CH₂)ₘ—, —CHR⁵CHR⁶—, —(CH₂)ₘ—CR⁵R⁶—(CH₂)ₙ—, —CR⁵=CR⁶—, —C≡C—, —CR⁵=CR⁶—CO—, —(CH₂)ₘ—O—(CH₂)ₙ—, —O—(CH₂)ₙ—CR⁵R⁶—, —(CH₂)ₘ—S—(CH₂)ₙ—, —SO(CH₂)ₘ—, —SO₂(CH₂)ₘ—, —CO(CH₂)ₘ—, —COO—, —CONR⁷—, —CONR⁷CHR⁸—, —CONR⁷—CR⁵R⁶—, —CONR⁷—(CH₂)ₘ—, —NR⁷—, —NR⁷CO—CR⁵R⁶—, —NR⁷CO—CR⁵R⁶—CO—, —NR⁷CO—(CH₂)ₘ—, —NR⁷SO₂(CH₂)ₘ—, —SO₂NR⁷—(CH₂)ₘ—, —SO₂NR⁷—CR⁵R⁶—, NR⁷CONR⁸—, or —NR⁷CSNR⁸— whereupon n and m are independently 0, 1, 2 or 3, or a group selected from (a) $C_{6-14}$ aromatic hydrocarbon cyclic group, (b) $C_{3-14}$ cycloalkyl group, (c) $C_{4-14}$ cycloalkenyl group, (d) 5- to 14-membered aromatic heterocyclic group, or (e) 4- to 14-membered non-aromatic heterocyclic group, each of which may be substituted with 4 or less groups selected from the substituent group Q, $M^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) —$OR^7$, (xviv) —$NR^7R^8$, (xx) —$NR^7COR^8$, (xxi) —$COR^7$, (xxii) —$CONR^7R^8$, (xxiii) —$SOR^7$, (xxiv) —$SO_2R^7$, (xxv) —$NR^7SO_2R^8$, (xxvi) —$SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

the substituent group Q represents an oxo group, halogen atom, hydroxyl group, amino group, cyano group, nitro group, azido group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$OCH_2CONR^7R^8$, —$NR^7R^8$, —$NR^7COR^8$, —$COR^7$, —$CONR^7R^8$, —$SOR^7$, —$SO_2R^7$, —$NR^7SO_2R^8$, —$SO_2NR^7R^8$, methylene dioxy group or ethylene dioxy group;

$R^1$ represents (1) hydrogen atom, (2) halogen atom, (3) hydroxyl group, (4) nitro group, (5) cyano group, (6) halogenated $C_{1-6}$ alkyl group, (7) $C_{2-6}$ alkyl group substituted with a hydroxyl or cyano group, (8) $C_{2-6}$ alkenyl group, or (9) formula —$L^1$—$L^2$—$L^3$, wherein 1) —$L^1$ represents a single bond, —$(CH_2)_m$—, —$(CH_2)_m$—$CR^5R^6$—$(CH_2)_n$—, —$CR^5$=$CR^6$—, —CH=$CR^5$—CO—, —$(CH_2)_m$—O—$(CH_2)_n$—, —CO$(CH_2)_m$—, —COO—, —$NR^7$—, —CO—$NR^7$—, —$NR^7$CO—, —$NR^7$CO—$(CH_2)_m$—, —$NR^7$CONR$^8$—, whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

2) $L^2$ represents a single bond, —$(CH_2)_m$—, —$CR^5R^6$—, —$(CH_2)_m$—$CR^5R^6$—$(CH_2)_n$—, —$CR^5$=$CR^6$—, —C≡C—, —CR=$CR^5$—CO—, —O—, —S—, —SO—, —$SO_2$—, —$SO_2$—$(CH_2)_m$—, —$(CH_2)_m$—O—$CH_2)_n$—, —O—$(CH_2)_n$—$CR^5R^6$—, —CO—$(CH_2)_m$—, —COO—, —$NR^7$—, —CO—$NR^7$, —CO—$NR^7$$(CH_2)_m$—, —$NR^7$CO—, —$NR^7$CO—$(CH_2)_m$—, —$NR^7SO_2$—, —$SO_2NR^7$—, —$NR^7CONR^8$—, or —$NR^7CSNR^8$— whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group which may be substituted with 4 or less substituent groups selected from the substituent group Q;

3) $L^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) —$OR^7$, (xviv) —$NR^7R^8$, (xx) —$NR^7COR^8$, (xxi) —$COR^7$, (xxii) —$CONR^7R^8$, (xxiii) —$SOR^7$, (xxiv) —$SO_2R^7$, (xxv) —$NR^7SO_2R^8$, (xxvi) —$SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

$R^2$ represents a hydrogen atom or a group for protecting pyrazole nitrogen, $R^3$ represents a hydrogen atom, halogen atom, cyano group, amino group, $C_{1-4}$ alkyl group or halogenated $C_{1-4}$ alkyl group, wherein the above-mentioned $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and the above-mentioned $R^7$ and $R^8$ are the same or different and each represent a hydrogen atom, $C_{1-6}$ alkyl group, halogenated $C_{1-6}$ alkyl group, $C_{3-8}$ cycloalkyl group, phenyl group or 5- to 6-membered aromatic heterocyclic group.

2. The compound according to claim 1, a salt thereof or a hydrate of them, wherein in the formula (I), X is quinoline or isoquinoline.

3. The compound according to claim 1 or 2, a salt thereof or a hydrate of them, wherein in the formula (I), X is quinazoline or imidazopyridine.

4. The compound according to claim 1, a salt thereof or a hydrate of them, wherein in the formula (I), n in the substituent groups $(R^4)_n$ is 0, 1 or 2, and the substituent groups $R^4$ independently represent a hydrogen atom, halogen atom, cyano group, hydroxyl group, amino group, a $C_{1-6}$ alkyl group, a halogenated $C_{1-6}$ alkyl group, an N—($C_{1-6}$ alkyl)amino group or a $C_{1-6}$ alkoxy group.

5. The compound according to claim 1, a salt thereof or a hydrate of them, wherein in the formula (I), Y is thiophene, thiazole, oxadiazole or oxathiadiazole.

6. The compound according to claim 1, a salt thereof or a hydrate of them, wherein in the formula (I), $R^2$ is a hydrogen atom, trityl group, tetrahydropyranyl group, t-butyldimethylsilyl group, t-butoxycarbonyl group or pivaloyloxymethyl group, $R^3$ is a hydrogen atom, and n in the substituent groups $(R^4)_n$ is 0, 1 or 2, and each of the substituent groups $R^4$ independently represents a hydrogen atom, halogen atom, cyano group, carbamoyl group, $C_{1-6}$ alkyl group or halogenated $C_{1-6}$ alkyl group.

7. The compound according to claim 5, a salt thereof or a hydrate thereof, wherein in the formula (I), n in the substituent groups $(R^4)_n$ is 0, 1 or 2, the substituent groups $R^4$ independently represent a hydrogen atom, halogen atom, carbamoyl group or $C_{1-6}$ alkyl group, $R^2$ is a hydrogen atom or trityl group, and $R^3$ is a hydrogen atom.

8. The compound according to any one of claims 5 to 7, a salt thereof or a hydrate thereof, wherein $R^1$ represents (1) hydrogen, (2) halogen atom, (3) nitro group, (4) cyano group, (5) $C_{1-6}$ alkyl group, (6) $C_{2-6}$ alkenyl group, (7) halogenated $C_{1-6}$ alkyl group, (8) $C_{2-6}$ alkenyl group substituted with a hydroxyl or cyano group, (9) —$CONR^7R^8$, (10) —$NR^7R^·$ (11) —$(CH_2)_mR^9$, (12) —$(CH_2)_m$—O—$CH_2)_n$—$R^9$, (13) —$COOR^7$ whereupon n and m independently represent 0, 1, 2 or 3, $R^7$ and $R^8$ are the same or different and each represent a hydrogen atom, $C_{1-6}$ alkyl group or $C_{3-8}$ cycloalkyl group, and $R^9$ groups are the same or different and represent a hydrogen atom, $C_{1-6}$ alkyl group, hydroxyl group, cyano group, or 1) $C_{3-8}$ cycloalkyl group, 2) $C_{4-8}$ cycloalkenyl group, 3) phenyl group, 4) 5- to 10-membered non-aromatic heterocyclic group, 5) 5- to 6-membered aromatic heterocyclic ring, each of which may be substituted with 4 or less groups selected independently from the substituent group $P^1$, or (14) (a) $C_{3-8}$ cycloalkyl group, (b) $C_{3-8}$ cycloalkenyl group, (c) 5- to 10-membered non-aromatic heterocyclic group, (d) phenyl group or (e) 5- to 10-membered aromatic heterocyclic group which may be arbitrarily substittued substituted with 3 or less groups selected independently from the substituent group $P^1$ and with 1 or less group selected independently from the substituent group $P^2$, the above-mentioned substituent group $P^1$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$NR^7R^8$, —$NR^7COR^8$, —$COR^7$, —$CONR^7R^8$, —$SOR^7$, —$SO_2R^7$, —$NR^7SO_2R^8$, or —$SO_2NR^7R^8$, whereupon $R^7$ and $R^8$ are the same or different and each represent a hydrogen atom, $C_{1-6}$ alkyl group or $C_{3-8}$ cycloalkyl group, and the substituent group $P^2$ represents —$CH_2NR^7R^8$, —$OCH_2CONR^7R^8$, —O—$(CH_2)_m$—$R^{10}$, —$NR^7COR^{10}$, —$NR^7COOR^{10}$, $C_{3-7}$ cycloalkyl group, $C_{4-7}$ cycloalkenyl group, phenyl group, 5- to 6-membered aromatic heterocyclic group, 5- to 7-membered non-aromatic heterocyclic group, $C_{3-7}$ cycloalkyloxy group, phenoxy group, heteroallyloxy group, methylene dioxy group or ethylene dioxy group, whereupon m is 0, 1, 2 or 3, $R^7$ and $R^8$ are the same or different and each represent a hydrogen atom, $C_{1-6}$ alkyl group or $C_{3-8}$ cycloalkyl group, $R^{10}$ represents a hydrogen atom, $C_{1-6}$ alkyl group, $C_{3-8}$ cycloalkyl group, phenyl group, 5- to 10-membered non-aromatic heterocyclic group, or 5- to 6-membered aromatic heterocyclic group.

9. The compound according to any one of claims 5 to 7, a salt thereof or a hydrate thereof, wherein in the formula (I), $(Z)n$ represent n $(Z)$ groups bound to Y, n is 0, 1, 2 or 3, Z groups independently represent formula —J—$R^{11}$ wherein J is a single bond, —$(CH_2)_m$—, —$CHR^5CHR^6$—, —$(CH_2)_m$—$CR^5R^6$—$(CH_2)_n$—, —$CR^5$=$CR^6$—, —C≡C—, —$CR^5$=$CR^6$—CO—, —$(CH_2)_m$—O—$(CH_2)_n$—, —O—$(CH_2)_n$—$CR^5R^6$—, —$(CH_2)_m$—S—$(CH_2)_n$—, —$SO(CH_2)_m$—, —$SO_2(CH_2)_m$—, —$CO(CH_2)_m$—, —COO—, —$CONR^7$—, —$CONR^7CHR^5$—, —$CONR^7$—$CR^5R^6$—, $CONR^7$—$(CH_2)_m$—, —$NR^7$—, —$NR^7CO$—$CR^5R^6$—, $NR^7CO$—$CR^5R^6$—CO—, —$NR^7CO$—$(CH_2)_m$—, —$NR^7SO_2(CH_2)_m$—, —$SO_2NR^7$—$(CH_2)_m$—, —$SO_2NR^7$—$CR^5R^6$—, —$NR^7CONR^8$—, or —$NR^7CSNR^8$— whereupon n and m are independently 0, 1, 2 or 3, or $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and $R^7$ and $R^8$ are the same or different and each represent a hydrogen atom, $C_{1-6}$ alkyl group or $C_{3-8}$ cycloalkyl group, $R^{11}$ represents a hydrogen atom, halogen atom, hydroxyl group, cyano group, carboxyl group, $C_{1-6}$ alkyl group, $C_{1-6}$ alkoxy group, halogenated $C_{1-6}$ alkyl group, $C_{3-8}$ cycloalkyl group, $C_{3-8}$ cycloalkenyl group, phenyl group, 5- to 6-membered aromatic heterocyclic group or 5- to 6-membered non-aromatic heterocyclic group, provided that each of the $C_{3-8}$ cycloalkyl group, $C_{3-8}$ cycloalkenyl group, phenyl group, 5- to 6-membered aromatic heterocyclic group and 5- to 6-membered non-aromatic heterocyclic group may be arbitrarily substituted with 3 or less substituent groups selected independently from the substituent group $P^3$ and with 1 or less substituent group selected independently from the substituent group $P^4$, the above-mentioned substituent group $P^3$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$NR^7R^8$, —$NR^7COR^8$, —$COR^7$, —$CONR^7R^8$, —$SOR^7$, —$SO_2R^7$, —$NR^7SO_2R^8$, or —$SO_2NR^7R^8$, whereupon $R^7$ and $R^8$ are the same or different and each represent a hydrogen atom, $C_{1-6}$ alkyl group or $C_{3-8}$ cycloalkyl group, and the substituent group $P^4$ represents a $C_{3-7}$ cycloalkyl group, $C_{4-7}$ cycloalkenyl group, phenyl group, 5- to 6-membered aromatic heterocyclic group, 5- to 7-membered non-aromatic heterocyclic group, $C_{3-7}$ cycloalkyloxy group, phenoxy group, heteroaryloxy group, methylene dioxy group or ethylene dioxy group, each of which is a group binding to the cyclic group Y.

10. The compound according to any one of claims 5 to 7, a salt thereof or a hydrate of them, wherein in the formula (I), $R^1$ is (1) hydrogen, (2) halogen atom, (3) nitro group, (4) cyano group, (5) $C_{1-6}$ alkyl group, (6) $C_{2-6}$ alkenyl group, (7) halogenated $C_{1-6}$ alkyl group, (8) phenyl group, (9) 5- to 6-membered aromatic heterocyclic group, (10) 5- to 7-membered non-aromatic heterocyclic group, provided that (8)

phenyl group, (9) 5- to 6-membered aromatic heterocyclic group and (10) 5- to 7-membered non-aromatic heterocyclic group may be substituted arbitrarily with 3 or less substituent groups selected independently from the substituent group $P^5$ and with 1 or less substituent group selected independently from the substituent group $P^6$, the substituent group $P^5$ represents an oxo group, halogen atom, hydroxyl group, amino group, cyano group, nitro group, azido group, cyano group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$OCH_2CONR^7R^8$, —$NR^7R^8$, —$NR^7COR^8$, —$COR^7$, —$CONR^7R^8$, —$SOR^7$, —$SO_2R^8$, —$NR^7SO_2R^8$ or —$SO_2NR^7R^8$ whereupon $R^7$ and $R^8$ are the same or different and each represent a hydrogen atom, $C_{1-6}$ alkyl group or $C_{3-8}$ cycloalkyl group, the substituent group $P^6$ represents a $C_{3-7}$ cycloalkyl group, $C_{4-7}$ cycloalkenyl group, phenyl group, 5- to 6-membered aromatic heterocyclic group, 5- to 7-membered non-aromatic heterocyclic group, $C_{3-7}$ cycloalkyloxy group, phenoxy group, heteroaryloxy group, methylene dioxy group or ethylene dioxy group; and $R^2$, $R^3$ and $R^4$ are hydrogen atoms.

11. The compound according to claim 1, a salt thereof or a hydrate of them, wherein in the formula (I), X is an imidazo[1,2-a]pyridine cyclic group, and Y is a phenyl group, piperazine, pyridine, thiophene, 1,2,4-thiadiazolyl group, 1,2,4-oxadiazolyl group, or 1,3,4-oxadiazolyl group.

12. The compound according to claim 1, a salt thereof or a hydrate of them, wherein in the formula (I), X is quinazoline and Y is a phenyl group, piperazine, pyridine, thiophene, thiazole or 1,3,4-oxadiazolyl group.

13. The compound according to claim 1 represented by the formula (I), a salt thereof or a hydrate thereof, wherein the compound is the one selected from: 6-[3-(4-fluorophenyl)-1H-4-pyrazolyl]-3-[5-(methylsulfonyl)-2-thienyl]imidazo[1,2-a]pyridine hydrochloride, 6-[3-(2,4-difluorophenyl)-1H-pyrazol-4-yl]-3-(5-methylsulfonylthiophen-2-yl) imidazo [1,2-a]pyridine, 6-[3-(2,6-difluorophenyl)-1H-pyrazol-4-yl]-3-(5-methylsulfonylthiazol-2-yl)imidazo[1,2-a]pyridine, 3-(5-cyclopropyl[1,3,4]oxadiazol-2-yl)-6-[3-(2,4-difluorophenyl)-1H-pyrazol-4-yl]imidazo[1,2-a]pyridine, 6-[3-(2,4-difluorophenyl)-1H-pyrazol-4-yl]-3-(5-methoxy[1,3,4]oxadiazol-2-yl)imidazo[1,2-a]pyridine, 6-[3-(2,6-difluorophenyl)-1H-pyrazol-4-yl]-3-(5-methoxy[1,2,4]oxadiazol-3-yl)imidazo[1,2-a]pyridine, 3-(5-cyclopropyl-[1,2,4]oxadiazol-3-yl)-6-[3-(4-fluorophenyl)-1H-4-pyrazolyl]-imidazo[1,2a]-pyridine hydrochloride, 3-(5-cyclopropyl-[1,2,4]oxadiazol-3-yl)-6-[3-(2,4-difluorophenyl)-1H-4-pyrazolyl]-imidazo[1,2-a]pyridine trihydrochloride, 3-(5-cyclopropyl-[1,2,4]oxadiazol-3-yl)-6-[3-(2-fluoro-4-methoxyphenyl)-1H-4-pyrazolyl]-imidazo[1,2-a]pyridine trihydrochloride, 3-(5-cyclopropyl-[1,2,4]oxadiazol-3-yl)-6-[3-(2-fluorophenyl)-1H-4-pyrazolyl]-imidazo[1,2-a]pyridine trihydrochloride, 6-[3-(4-cyclopentyloxy-2-fluorophenyl)-1H-4-pyrazolyl]-3-(5-cyclopropyl-[1,2,4]oxadiazol-3-yl)-imidazo[1,2-a]pyridine trihydrochloride, 3-(5-cyclopropyl-[1,2,4]oxadiazol-3-yl)-6-[3-(2,6-difluorophenyl)-1H-4-pyrazolyl]-imidazo[1,2-a]pyridine trihydrochloride, 6-[3-(2,4-difluorophenyl)-1H-4-pyrazolyl]-3-(5-difluoromethyl-[1,2,4]oxadiazol-3-yl)-imidazo[1,2-a]pyridine trihydrochloride, 3-(5-difluoromethyl-[1,2,4]oxadiazol-3-yl)-6-[3-(2-fluorophenyl)-1H-4-pyrazolyl]-imidazo[1,2-a]pyridine trihydrochloride, 6-[3-(2,6-difluorophenyl)-1H-4-pyrazolyl]-3-(5-difluoromethyl-[1,2,4]oxadiazol-3-yl)-imidazo[1,2-a]pyridine trihydrochloride, N1-[(1S)-2-(4-fluorophenyl)-1-methyl-2-oxoethyl]-2-fluoro-4-[6-(1H-4-pyrazolyl)imidazo[1,2-a]pyridin-3-yl]benzamide hydrochloride, N1-(2,4-difluorophenyl)-2-fluoro-4-[6-(1H-4-pyrazolyl)imidazo[1,2-a]pyridin-3-yl]benzamide hydrochloride, N1-(5-chloro-2-pyridyl)-2-fluoro-4-[6-(1H-4-pyrazolyl)imidazo[1,2-a]pyridin-3-yl]benzamide dihydrochloride, N1-(4-methyl-2-pyridyl)-2-fluoro-4-[6-(1H-4-pyrazolyl)imidazo[1,2-a]pyridin-3-yl]benzamide dihydrochloride, N1-(2,4-difluorophenyl)-2-chloro-4-[6-(1H-4-pyrazolyl)imidazo[1,2-a]pyridin-3-yl]benzamide hydrochloride, N1-(5-vinyl-2-pyridyl)-2-fluoro-4-[6-(1H-4-pyrazolyl)imidazo[1,2-a]pyridin-3-yl]benzamide dihydrochloride, N1-(5-ethyl-2-pyridyl)-2-fluoro-4-[6-(1H-4-pyrazolyl)imidazo[1,2-a]pyridin-3-yl]benzamide dihydrochloride, 6-[3-(4-fluorophenyl)-1H-4-pyrazolyl]-4-[5-(methylsulfonyl)-2-thienyl]quinazoline dihydrochloride, 6-[3-(2,4-difluorophenyl)-1H-pyrazol-4-yl]-4-(5-methylsulfonylthiophen-2-yl) quinazoline, 6-[3-(4-chloro-2-fluorophenyl)-1H-pyrazol-4-yl]-4-(5-methylsulfonylthiazol-2-yl) quinazoline, 4-(5-cyclopropyl[1,3,4]oxadiazol-2-yl)-6-[3-(2,4-difluorophenyl)-1H-pyrazol-4-yl] quinazoline, 4-(5-cyclopropyl[1,3,4]thiadiazol-2-yl)-6-[3-(2,4-difluorophenyl)-1H-pyrazol-4-yl] quinazoline, 6-[3-(2,6-difluorophenyl)-1H-pyrazol-4-yl]-4-(5-methoxy[1,3,4]oxadiazol-2-yl) quinazoline, 6-(1H-pyrazol-4-yl)-4-(4-m-tolylpiperazin-1-yl)-quinazoline tri-trifluoroacetate, 4-[4-(3-methylsulfonylphenyl)piperazin-1-yl]-6-(1H-pyrazol-4-yl)quinazoline tri-trifluoroacetate, and 4-[4-(3-cyclopropylsulfonylphenyl)piperazin-1-yl]-6-(1H-pyrazol-4-yl)quinazoline tri-trifluoroacetate.

14. A pharmaceutical composition comprising:

a compound represented by the following formula (I), a salt thereof or a hydrate of them, and a pharmaceutically acceptable carrier;

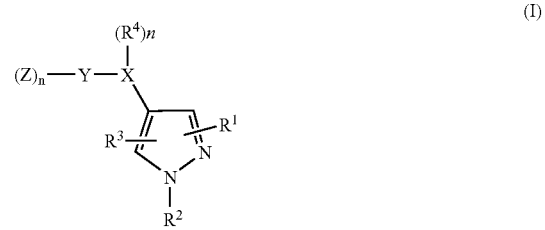

(I)

wherein in the formula, X represents quinoline, isoquinoline, quinazoline or imidazopyridine, and said X has $(R^4)_n$ as substituent groups whereupon n is 0, 1, 2 or 3, and the substituent groups $R^4$ independently represent a hydrogen atom, halogen atom, cyano group, hydroxyl group, amino group, $C_{1-6}$ alkyl group, halogenated $C_{1-6}$ alkyl group, $C_{2-6}$ alkenyl group, $C_{1-6}$ alkylsulfonyl group, $C_{1-6}$ alkylsulfonylamino group, $C_{1-6}$ alkylsulfinyl group, N—($C_{1-6}$ alkyl)amino group, N,N-di($C_{1-6}$ alkyl)amino group, $C_{1-6}$ alkoxy group, $C_{1-6}$ alkylsulfanyl group, carbamoyl group, N—($C_{1-6}$ alkyl)carbamoyl group, N,N-di($C_{1-6}$ alkyl)carbamoyl group, sulfamoyl group, phenyl group, heteroaryl group, phenoxy group, heteroallyloxy group, phenyl $C_{1-6}$ alkylamino group or heteroaryl $C_{1-6}$ alkylamino group, which is bound to an atom constituting X;

Y represents a phenyl group, piperazine, pyridine, thiophene, thiazole, oxadiazole or oxathiadiazole;

(Z)n are n (Z) groups bound to Y, whereupon n is 0, 1, 2 or 3, Z groups are bound to an atom constituting the cyclic group Y and independently represent formula —$M^1$—$M^2$—$M^3$ wherein:

$M^1$ and $M^2$ each represent a single bond, —$(CH_2)_m$—, —$CHR^5CHR^6$—, —$(CH_2)_m$—$CR^5R^6$—$(CH_2)_n$—, —$CR^5$=$CR^6$—, —C≡C—, —$CR^5$=$CR^6$—CO—, $(CH_2)_m$—O—$(CH_2)_n$—, —O—$(CH_2)_n$—$CR^5R^6$—, —$(CH_2)_m$—S—$(CH_2)_n$—, —SO$(CH_2)_m$—, —$SO_2$$(CH_2)_m$—, —CO$(CH_2)_m$—, —COO—, —$CONR^7$—, —$CONR^7CHR^8$—, —$CONR^7$—$CR^5R^6$—, —$CONR^7$—$(CH_2)_m$—, —$NR^7$—, —$NR^7CO$—$CR^5R^6$—, —$NR^7CO$—$CR^5R^6$—CO—, —$NR^7CO$—$(CH_2)_m$—, —$NR^7SO_2(CH_2)_m$—, —$SO_2NR^7$—$(CH_2)_m$—, —$SO_2NR^7$—$CR^5R^6$—, —$NR^7CONR^8$—, or —$NR^7CSNR^8$— whereupon n and m are independently 0, 1, 2 or 3, or a group selected from (a) $C_{6-14}$ aromatic hydrocarbon cyclic group, (b) $C_{3-14}$ cycloalkyl group, (c) $C_{4-14}$ cycloalkenyl group, (d) 5- to 14-membered aromatic heterocyclic group, or (e) 4- to 14-membered non-aromatic heterocyclic group, each of which may be substituted with 4 or less groups selected from the substituent group Q, $M^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) —$OR^7$, (xviv) —$NR^7R^8$, (xx) —$NR^7COR^8$, (xxi) —$COR^7$, (xxii) —$CONR^7R^8$, (xxiii) —$SOR^7$, (xxiv) —$SO_2R^7$, (xxv) —$NR^7SO_2R^8$, (xxvi) —$SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q;

the substituent group Q represents an oxo group, halogen atom, hydroxyl group, amino group, cyano group, nitro group, azido group, carboxyl group, $C_{1-6}$ alkyl group, halogenated $C_{1-4}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$OCH_2CONR^7R^8$, —$NR^7R^8$, —$NR^7COR^8$, —$COR^7$, —$CONR^7R^8$, —$SOR^7$, —$SO_2R^7$, $NR^7SO_2R^8$, —$SO_2NR^7R^8$, methylene dioxy group or ethylene dioxy group (wherein $R^7$ and $R^8$ are the same as or different from each other and each represents a hydrogen atom, a $C_{1-6}$ alkyl group or a $C_{3-8}$ cyloalkyl group);

$R^1$ represents (1) hydrogen atom, (2) halogen atom, (3) hydroxyl group, (4) nitro group, (5) cyano group, (6) halogenated $C_{1-6}$ alkyl group, (7) $C_{2-6}$ alkyl group substituted with a hydroxyl or cyano group, (8) $C_{2-6}$ alkenyl group, or (9) formula —$L^1$—$L^2$—$L^3$,
wherein 1) —$L^1$ represents a single bond, —$(CH_2)_m$—, —$(CH_2)_m$—$CR^5R^6$—$(CH_2)_n$—, —$CR^5$=$CR^6$—, —CH=$CR^5$—CO—, —$(CH_2)_m$—O—$(CH_2)_n$—, —CO$(CH_2)_m$—, —COO—, —$NR^7$—, —CO—$NR^7$—, —$NR^7CO$—, —$NR^7CO$—$(CH_2)_m$—, —$NR^7CONR^8$—, whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

2) $L^2$ represents a single bond, —$(CH_2)_m$—, —$CR^5R^6$—, —$(CH_2)_m$—$CR^5R^6$—$(CH_2)_n$—, —$CR^5$=$CR^6$—, —C≡C—, —CR=$CR^5$—CO—, —O—, —S—, —SO—, —$SO_2$—, —$SO_2$—$(CH_2)_m$—, —$(CH_2)_m$—O—$(CH_2)_n$—, —O—$(CH_2)_n$—$CR^5R^6$—, —CO—$(CH_2)_m$—, —COO—, —$NR^7$, —CO—$NR^7$—, —CO—$NR^7$—$(CH_2)_m$—, —$NR^7CO$—, —$NR^7CO$—$(CH_2)_m$—, —$NR^7SO_2$—, —$SO_2NR^7$—, —$NR^7CONR^8$—, or —$NR^7CSNR^8$— whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

3) $L^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_{2-6}$ alkenyl group, (xv) $C_{2-6}$ alkynyl group, (xvi) halogenated $C_{2-6}$ alkenyl group, (xvii) halogenated $C_{1-6}$ alkoxy group, (xviii) —$OR^7$, (xviv) —$NR^7R^8$, (xx) —$NR^7COR^8$, (xxi) —$COR^7$, (xxii) —$CONR^7R^8$, (xxiii) —$SOR^7$, (xxiv) —$SO_2R^7$, (xxv) —$NR^7SO_2R^8$, (xxvi) —$SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, each of which may be substituted with 4 or less groups selected from the substituent group Q;

$R^2$ represents a hydrogen atom;

$R^3$ represents a hydrogen atom, halogen atom, cyano group, amino group, $C_{1-4}$ alkyl group or halogenated $C_{1-4}$ alkyl group,
wherein the above-mentioned $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and the above-mentioned $R^7$ and $R^8$ are the same or different and each represent a hydrogen atom, $C_{1-6}$ alkyl group, halogenated $C_{1-6}$ alkyl group, $C_{3-8}$ cycloalkyl group, phenyl group or 5- to 6-membered aromatic heterocyclic group.

15. The pharmaceutical composition according to claim 14, wherein in the formula (I), Y is thiophene, thiazole oxadiazole or oxathiadiazole.

16. The compound according to claim 1 represented by the formula (I), a salt thereof or a hydrate thereof, wherein Y is the phenyl group, piperazine or pyridine.

17. A compound represented by the following formula (I), or a salt thereof or a hydrate thereof:

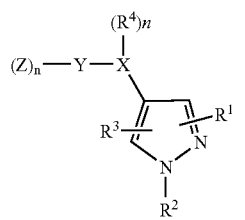

(I)

wherein X represents quinoline, isoquinoline, quinazoline or imidazopyridine, and said X has $(R^4)_n$ as substituent groups whereupon n is 0, 1, 2 or 3, and the substituent groups $(R^4)_n$ independently represent a hydrogen atom, halogen atom, cyano group, hydroxyl group, amino group, $C_{1-6}$ alkyl group, halogenated $C_{1-6}$ alkyl group, $C_{2-6}$ alkenyl group, $C_{1-6}$ alkylsulfonyl group, $C_{1-6}$ alkylsulfonylamino group, $C_{1-6}$ alkylsulfinyl group, N—($C_{1-6}$ alkyl)amino group, N,N-di($C_{1-6}$ alkyl)amino group, $C_{1-6}$ alkoxy group, $C_{1-6}$ alkylsulfanyl group, carbamoyl group, N—($C_{1-6}$ alkyl)carbamoyl group, N,N-di($C_{1-6}$ alkyl)carbamoyl group, sulfamoyl group, phenyl group, heteroaryl group, phenoxy group, heteroallyloxy group, phenyl $C_{1-6}$ alkylamino group or heteroaryl $C_{1-6}$ alkylamino group, which is bound to an atom constituting X;

Y represents a phenyl group, piperazine, pyridine, thiophene, thiazole, oxadiazole or oxathiadiazole;

(Z)n are n (Z) groups bound to Y, whereupon n is 0, 1, 2 or 3, Z groups are bound to an atom constituting the cyclic group Y and independently represent a group selected from the group consisting of (1) hydrogen atom, (2) amino group, (3) halogen atom, (4) hydroxyl group, (5) nitro group, (6) cyano group, (7) azido group, (8) formyl group, (9) hydroxyamino group, (10) sulfamoyl group, (11) guanodino group, (12) oxo group, (13) $C_{2-6}$ alkenyl group, (14) $C_{1-6}$ alkoxy group, (15) $C_{1-6}$ alkylhydroxyamino group, (16) halogenated $C_{1-6}$ alkyl group and (17) halogenated $C_{2-6}$ alkenyl group;

$R^1$ represents (1) hydrogen atom, (2) halogen atom, (3) hydroxyl group, (4) nitro group, (5) cyano group, (6) halogenated $C_{1-6}$ alkyl group, (7) $C_{2-6}$ alkyl group substituted with a hydroxyl or cyano group, (8) $C_{2-6}$ alkenyl group, or (9) formula —$L^1$—$L^2$—$L^3$, wherein 1) —$L^1$ represents a single bond, —$(CH_2)_m$—, —$(CH_2)_m$—$CR^5R^6$—$(CH_2)_n$—, —$CR^5$=$CR^6$—, —CH=$CR^5$—CO—, —$(CH_2)_m$—O—$(CH_2)_n$—, —CO($CH_2)_m$—, —COO—, —$NR^7$—, —CO—$NR^7$—, —$NR^7$CO—, —$NR^7$CO—$(CH_2)_m$—, —$NR^7$CONR$^8$—, whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group, which may be substituted with 4 or less substituent groups selected from the substituent group Q;

2) $L^2$ represents a single bond, —$(CH_2)_m$—, —$CR^5R^6$—, —$(CH_2)_m$—$CR^5R^6$—$(CH_2)_n$—, —$CR^5$=$CR^6$—, —C≡C—, —$CR$=$CR^5$—CO—, —O—, —S—, —SO—, —$SO_2$—, —$SO_2$—$(CH_2)_m$—, —$(CH_2)_m$—O—$(CH_2)_n$—, —O—$(CH_2)_n$—$CR^5R^6$—, —CO—$(CH_2)_m$—, —COO—, —$NR^7$—, —CO—$NR^7$—, —CO—$NR^7$($CH_2)_m$—, —$NR^7$CO—, —$NR^7$CO—$(CH_2)_m$—, —$NR^7SO_2$—, —$SO_2NR^7$—, —$NR^7CONR^8$—, or —$NR^7CSNR^8$— whereupon n and m are independently 0, 1, 2 or 3, or (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group or (e) 5- to 14-membered aromatic heterocyclic group which may be substituted with 4 or less substituent groups selected from the substituent group Q;

3) $L^3$ represents (i) hydrogen atom, (ii) oxo group, (iii) halogen atom, (iv) hydroxyl group, (v) amino group, (vi) cyano group, (vii) nitro group, (viii) azido group, (viv) cyano group, (x) carboxyl group, (xi) $C_{1-6}$ alkyl group, (xii) halogenated $C_{1-6}$ alkyl group, (xiii) $C_{1-6}$ alkyl group substituted with a hydroxyl or cyano group, (xiv) $C_2$ alkenyl group, (xv) $C_{2-6}$ alkynyl group, (xvi) halogenated $C_{2-6}$ alkenyl group, (xvii) halogenated $C_{1-6}$ alkoxy group, (xviii) —$OR^7$, (xviv) —$NR^7R^8$, (xx) —$NR^7COR^8$, (xxi) —$COR^7$, (xxii) —$CONR^7R^8$, (xxiii) —$SOR^7$, (xxiv) —$SO_2R^7$, (xxv) —$NR^7SO_2R^8$, (xxvi) —$SO_2NR^7R^8$, (xxvii) methylene dioxy group, (xxviii) ethylene dioxy group, or (xxviv) (a) $C_{3-8}$ cycloalkyl group, (b) $C_{4-8}$ cycloalkenyl group, (c) 5- to 14-membered non-aromatic heterocyclic group, (d) $C_{6-14}$ aromatic hydrocarbon cyclic group, (e) 5- to 14-membered aromatic heterocyclic group, (f) phenoxy group, (g) heteroallyoxy group or (h) $C_{3-8}$ cycloalkyloxy group, which may be substituted with 4 or less groups selected from the substituent group Q; and the substituent group Q represents an oxo group, halogen atom, hydroxyl group, amino group, cyano group, nitro group, azido group, carboxyl group, $C_{1-6}$ alkyl group, halogenated $C_{1-6}$ alkyl group, $C_{1-6}$ alkyl group substituted with a hydroxyl or cyano group, $C_{2-6}$ alkenyl group, $C_{2-6}$ alkynyl group, halogenated $C_{2-6}$ alkenyl group, halogenated $C_{1-6}$ alkoxy group, —$OR^7$, —$OCH_2CONR^7R^8$, —$NR^7R^8$, —$NR^7COR^8$, —$COR^7$, —$CONR^7R^8$, —$SOR^7$, —$SO_2R^7$, —$NR^7SO_2R^8$, —$SO_2NR^7R^8$, methylene dioxy group or ethylene dioxy group;

$R^2$ represents a hydrogen atom or a group for protecting pyrazole nitrogen, $R^3$ represents a hydrogen atom, halogen atom, cyano group, amino group, $C_{1-4}$ alkyl group or halogenated $C_{1-4}$ alkyl group, wherein the above-mentioned $R^5$ and $R^6$ are the same or different and each represent 1) hydrogen atom, 2) halogen atom, 3) hydroxyl group, 4) cyano group, 5) $C_{1-6}$ alkyl group, 6) $C_{1-6}$ alkyl group substituted with a halogen atom, hydroxy group or cyano group, 7) $C_{3-8}$ cycloalkyl group, 8) phenyl group which may be substituted with 3 or less groups selected from the substituent group Q, 9) 5- to 6-membered aromatic heterocyclic group which may be substituted with 3 or less groups selected from the substituent group Q, or 10) $C_{3-8}$ cycloalkyl group formed by combining $R^5$ with $R^6$, and the above-mentioned $R^7$ and $R^8$ are the same or different and each represent a hydrogen atom, $C_{1-6}$ alkyl group, halogenated $C_{1-6}$ alkyl group, $C_{3-8}$ cycloalkyl group, phenyl group or 5 to 6-membered aromatic heterocyclic group.

* * * * *